(12) United States Patent
Huestis et al.

(10) Patent No.: US 12,187,709 B2
(45) Date of Patent: Jan. 7, 2025

(54) LACTAMS AS CBL-B INHIBITORS SELECTIVE OVER C-CBL

(71) Applicant: Genentech, Inc., South San Francisco, CA (US)

(72) Inventors: Malcolm Huestis, San Francisco, CA (US); Michael John Lambrecht, Burlingame, CA (US); Jun Liang, Los Altos Hills, CA (US); Man Un Ung, San Mateo, CA (US); Xiaojing Wang, Belmont, CA (US); Jason Robert Zbieg, Montara, CA (US); Bing-Yan Zhu, Palo Alto, CA (US); Lisa Marie Barton, Burlingame, CA (US); Fabio Broccatelli, San Diego, CA (US); Georgette Marie Castanedo, South San Francisco, CA (US); Araz Jakalian, Montreal (CA); Robin Larouche-Gauthier, Montreal (CA); Arun Yadav, Montreal (CA)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/052,851

(22) Filed: Nov. 4, 2022

(65) Prior Publication Data

US 2023/0212153 A1 Jul. 6, 2023

Related U.S. Application Data

(60) Provisional application No. 63/276,547, filed on Nov. 5, 2021.

(51) Int. Cl.
*C07D 403/12* (2006.01)
*A61P 35/00* (2006.01)
*C07D 401/14* (2006.01)
*C07D 403/14* (2006.01)
*C07D 405/14* (2006.01)
*C07D 409/14* (2006.01)
*C07D 493/08* (2006.01)

(52) U.S. Cl.
CPC ............ *C07D 403/12* (2013.01); *A61P 35/00* (2018.01); *C07D 401/14* (2013.01); *C07D 403/14* (2013.01); *C07D 405/14* (2013.01); *C07D 409/14* (2013.01); *C07D 493/08* (2013.01)

(58) Field of Classification Search
CPC ................ C07D 403/12; C07D 401/14; C07D 403/14; C07D 405/14; C07D 409/14; C07D 493/08; A61P 35/00
See application file for complete search history.

(56) References Cited

U.S. PATENT DOCUMENTS

| 11,401,267 | B2* | 8/2022 | Sands ............... A61P 37/00 |
| 11,464,802 | B2 | 11/2022 | Sands et al. |
| 11,530,229 | B2 | 12/2022 | Sands et al. |
| 2020/0323904 | A1 | 10/2020 | Sands et al. |
| 2021/0053961 | A1 | 2/2021 | Sands et al. |
| 2021/0053986 | A1 | 2/2021 | Sands et al. |
| 2021/0085717 | A1 | 3/2021 | Gosling et al. |
| 2021/0087529 | A1 | 3/2021 | Gosling et al. |
| 2022/0324835 | A1 | 10/2022 | Barsanti et al. |
| 2023/0079990 | A1 | 3/2023 | Liang et al. |

FOREIGN PATENT DOCUMENTS

| WO | 2019/148005 A1 | 8/2019 |
| WO | 2020/210508 A1 | 10/2020 |
| WO | 2020/236654 A1 | 11/2020 |
| WO | 2020/264398 A1 | 12/2020 |
| WO | 2021/021761 A1 | 2/2021 |
| WO | 2021/061853 A1 | 4/2021 |
| WO | 2021/061870 A1 | 4/2021 |
| WO | 2022/169997 A1 | 8/2022 |
| WO | 2022/169998 A1 | 8/2022 |
| WO | 2022/217123 A2 | 10/2022 |
| WO | 2022/217276 A1 | 10/2022 |
| WO | 2022/221704 A1 | 10/2022 |
| WO | 2022/272248 A1 | 12/2022 |
| WO | 2023/036330 A1 | 3/2023 |

OTHER PUBLICATIONS

Patani et. al. (Dec. 19, 1996) Bioisosterism A rational approach in drug design, Chem. Rev., 96, 3147-3176. (Year: 1996).*
International Search Report with Written Opinion—PCT/US2022/079343 mailed Feb. 20, 2023, pp. 1-11.
"International Preliminary Report on Patentability—PCT/US2022/015152" (Report Issuance Date: Aug. 3, 2023; Chapter I),:pp. 1-10 (Aug. 17, 2023).
"International Preliminary Report on Patentability—PCT/US2022/079343" (Report Issuance Date: Jun. 6, 2024; Chapter II),:pp. 1-84 (Jun. 6, 2024).

(Continued)

*Primary Examiner* — Juliet C Switzer
*Assistant Examiner* — Dawanna Shar-Day White
(74) *Attorney, Agent, or Firm* — Zong-Qiang Bill Tian

(57) ABSTRACT

A compound, of formula (I):

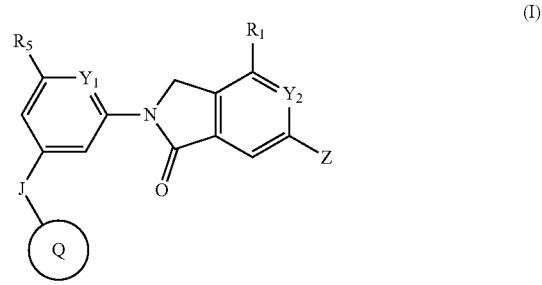

suitable for treating a cancer wherein the cancer is susceptible to inhibition of Cbl-B.

20 Claims, 67 Drawing Sheets

(56) References Cited

OTHER PUBLICATIONS

"International Preliminary Report on Patentability—PCT/US2022/015153" (Report Issuance Date: Aug. 3, 2023; Chapter I),:pp. 1-11 (Aug. 17, 2023).

Schonherr, H., et al., "Profound methyl effects in drug discovery and a call for new C—H methylation reactions" Angew Chem Int Ed Engl 52(47):12256-12267 (Nov. 18, 2013).

Wislicenus, J., Adolph Strecker's Short Text-Book of Organic Chemistry Hodgkinson, et al. ed., London, UK:Kegan Paul Trench & Company,:38-39 ( 1881).

* cited by examiner

*Scheme 1*

*Scheme 2*

Scheme 3

Scheme 4

Scheme 5

Scheme 6

Scheme 7

Scheme 8

Scheme 9

Scheme 10

Scheme 11

Scheme 12

Scheme 13

Scheme 14

Scheme 15

Scheme 16

Scheme 17

Scheme 18

Scheme 19

Scheme 20

Scheme 21

Scheme 22

Scheme 23

Scheme 24

Scheme 25

Scheme 26

Scheme 27

Scheme 28

Scheme 29

Scheme 30

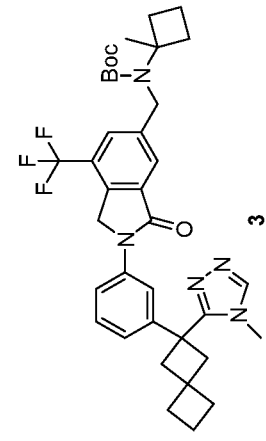
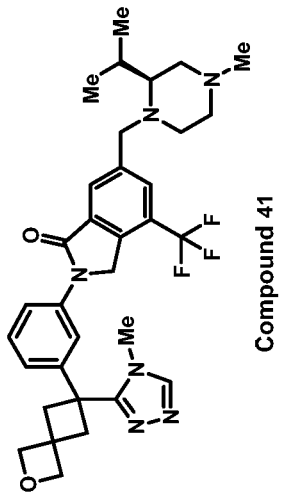
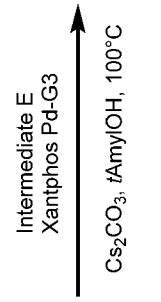
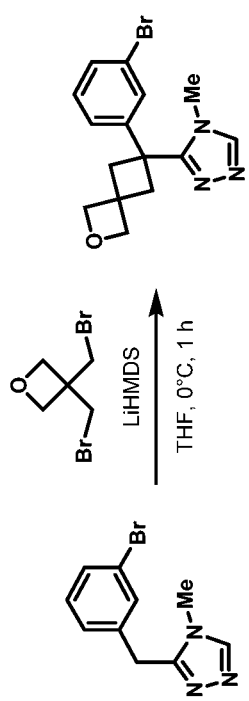
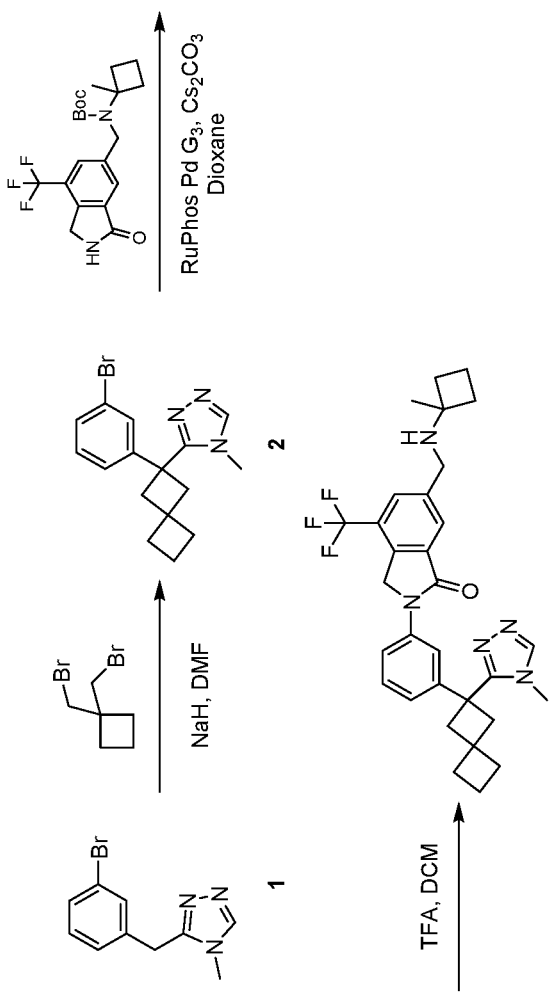
Scheme 31
FIG. 31
Scheme 32
FIG. 32

Scheme 33

Scheme 34

Scheme 35

Scheme 36

Scheme 37

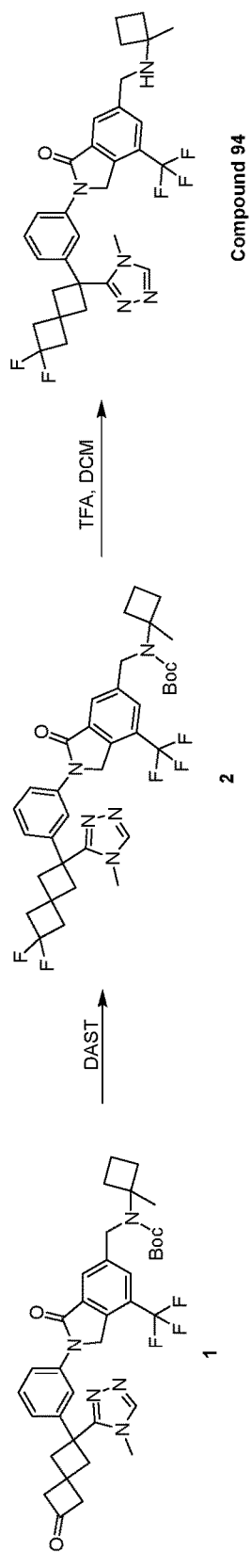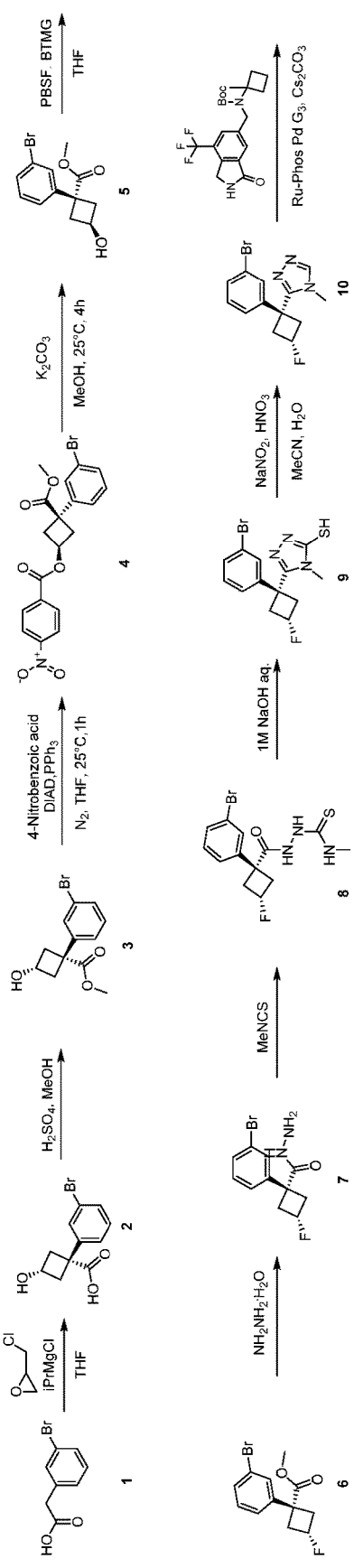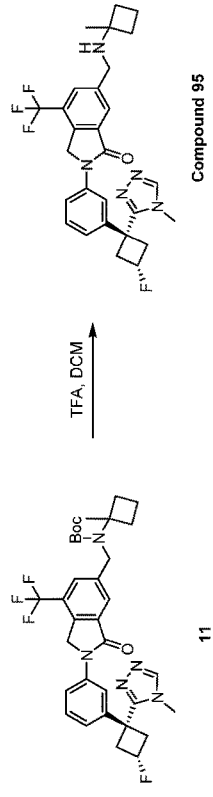
Scheme 38
FIG. 38
Scheme 39
FIG. 39

Compound 96

Scheme 40

Scheme 41

Scheme 42

Scheme 43

Scheme 44

Scheme 45

Scheme 46

Scheme 47

*Scheme 48*

*Scheme 49*

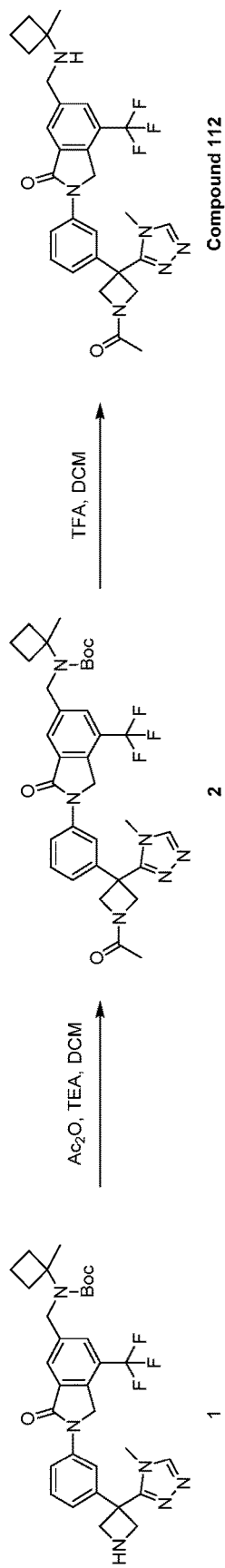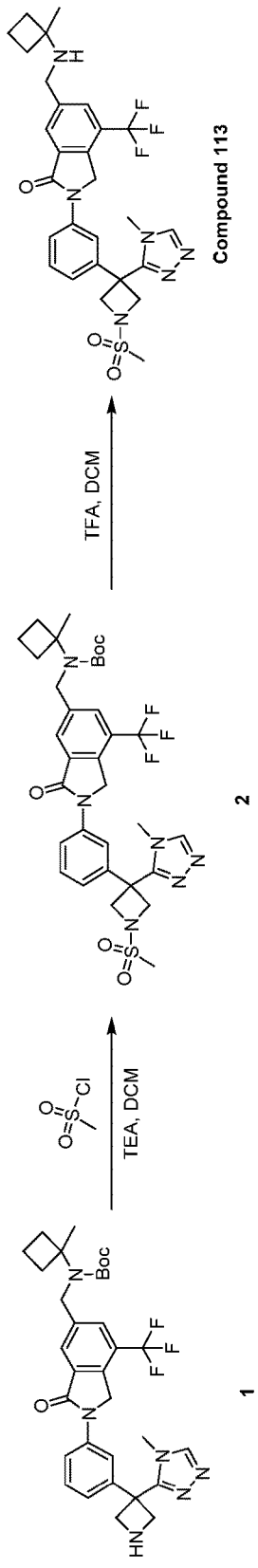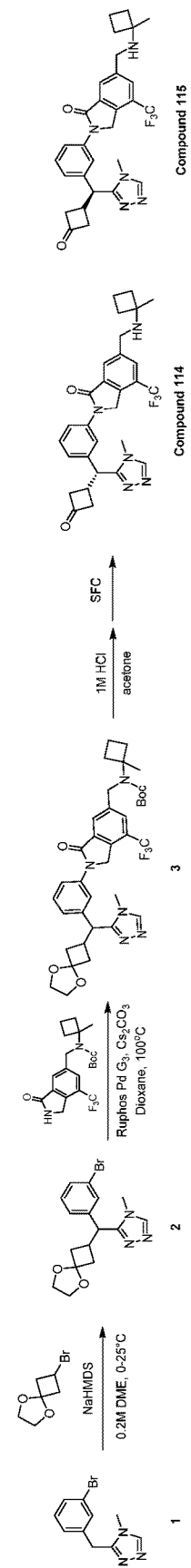
Scheme 50
FIG. 50
Scheme 51
FIG. 51
Scheme 52
FIG. 52

Scheme 53

Scheme 54

Scheme 55

Scheme 56

Scheme 57

Scheme 58

Scheme 59

Scheme 60

Scheme 61

Scheme 62

Scheme 63

Scheme 64

Scheme 65

Scheme 66

Scheme 67

Scheme 68

Scheme 69

Scheme 70

Scheme 71

Scheme 72

Scheme 73

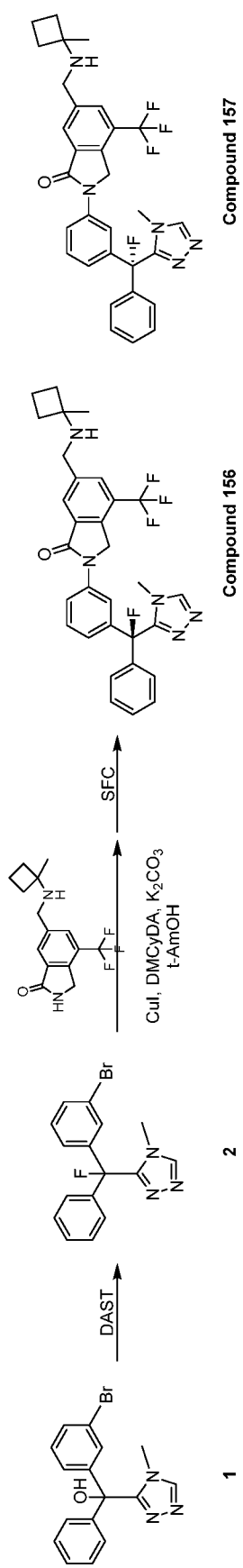
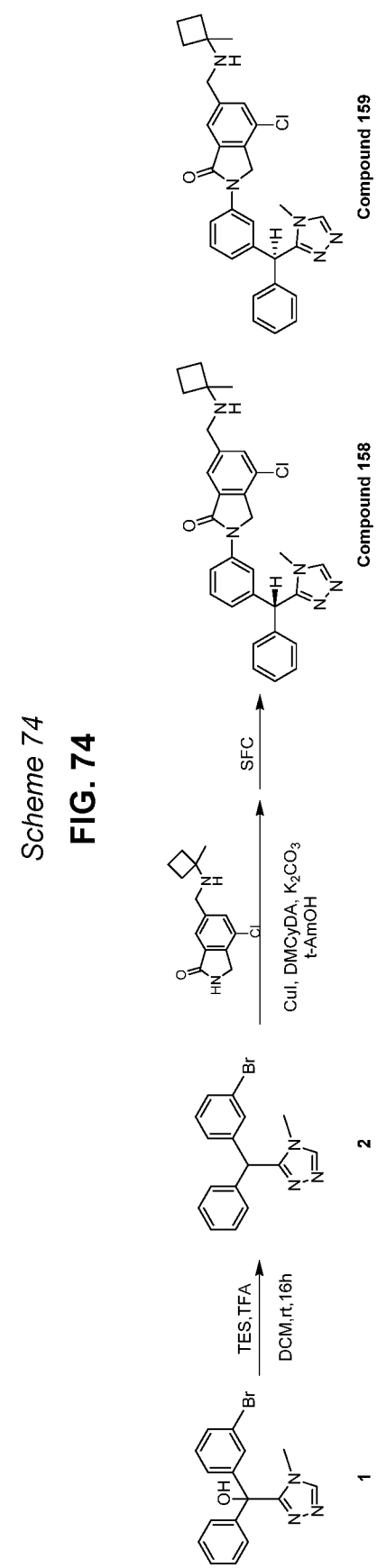
Scheme 74
FIG. 74
Scheme 75
FIG. 75

Scheme 76

Scheme 77

Scheme 78

Scheme 79

Scheme 80

Scheme 81

Scheme 82

Scheme 83

Scheme 84

Scheme 85

Scheme 86

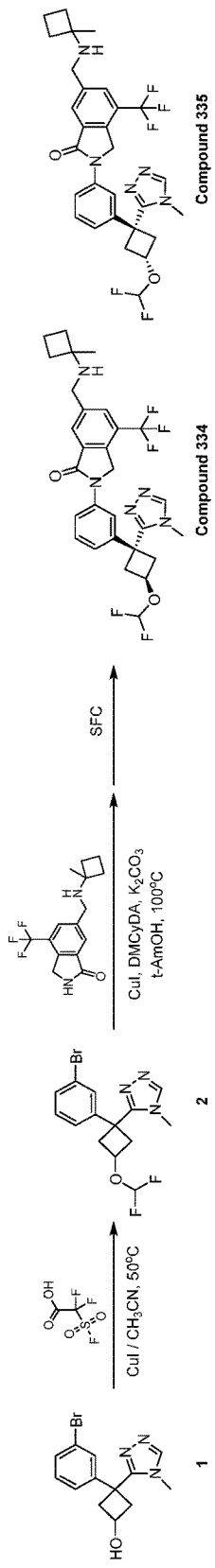
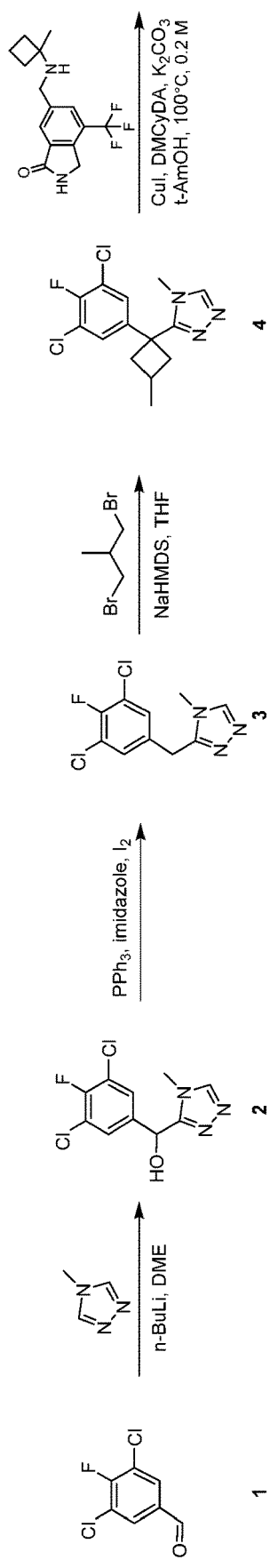
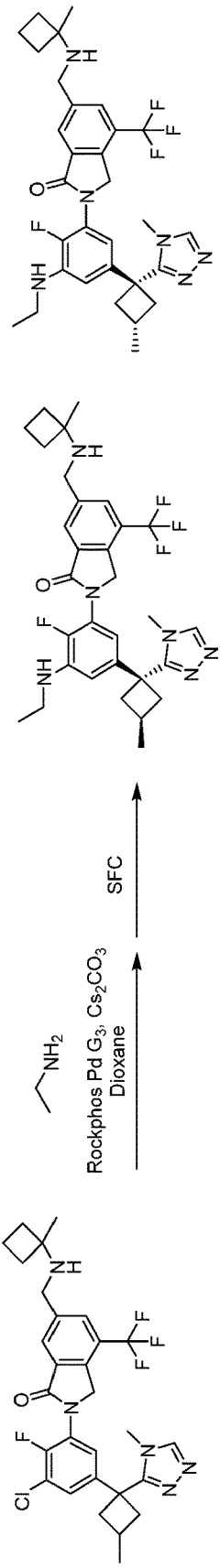
Scheme 87
FIG. 87
Scheme 88
FIG. 88

Scheme 89

Scheme 90

Scheme 91

Scheme 92

Scheme 93

Scheme 94

Scheme 95

Scheme 96

Scheme 97

Scheme 98

Scheme 99

Scheme 100

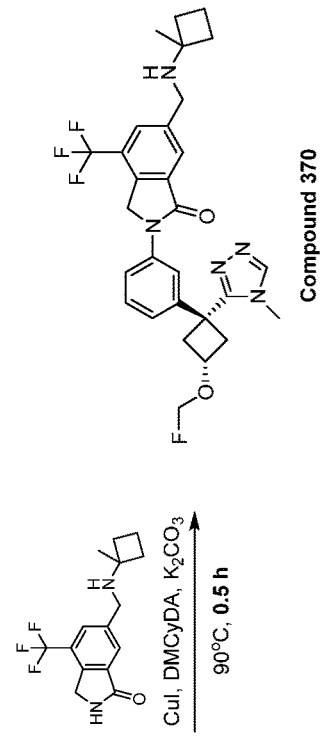
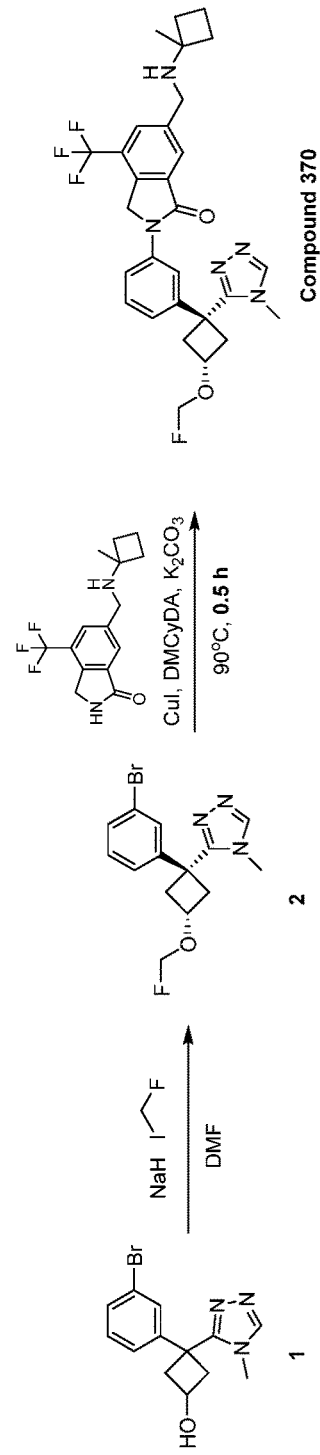
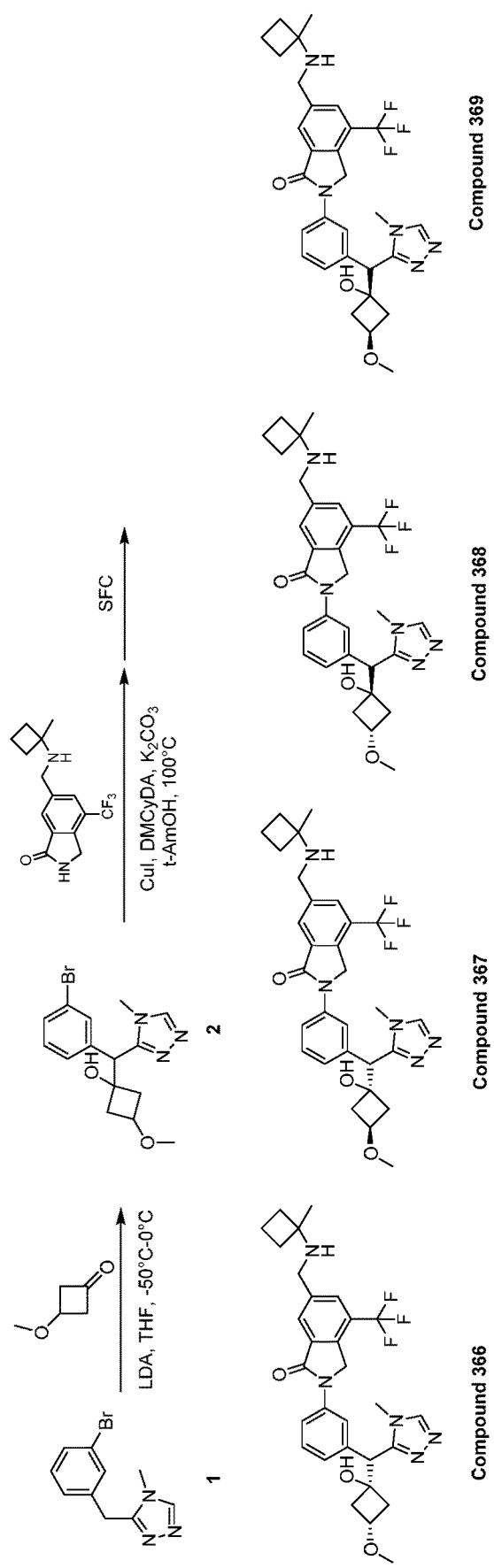
Scheme 101
FIG. 101
Scheme 102
FIG. 102

Scheme 103

Scheme 104

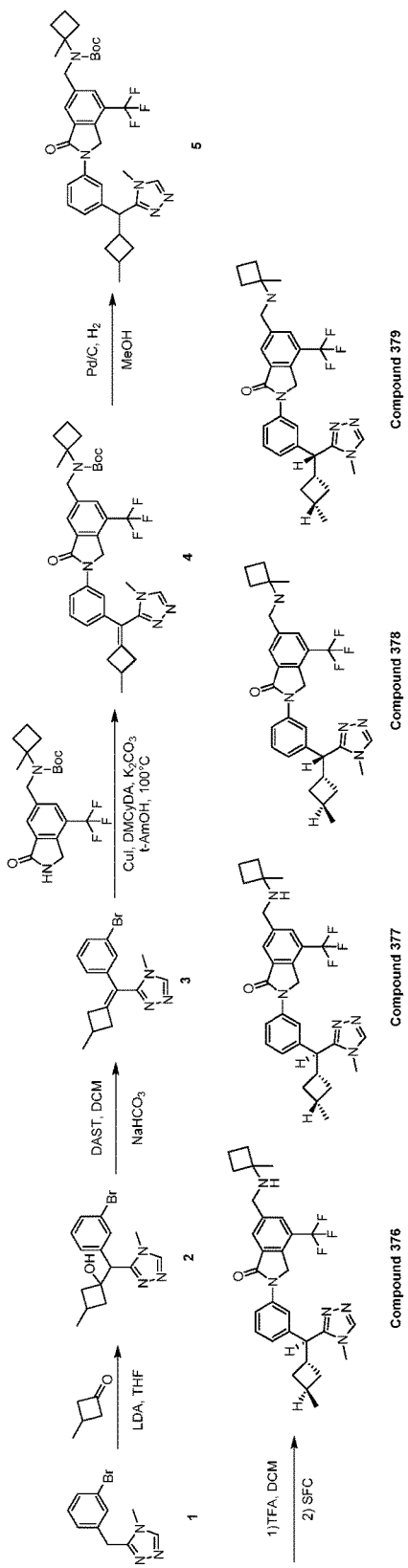
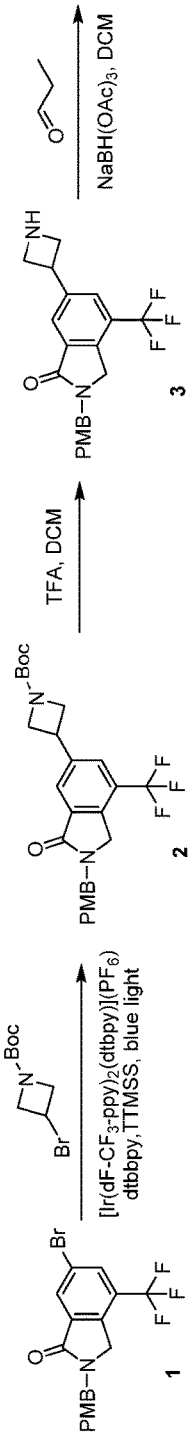
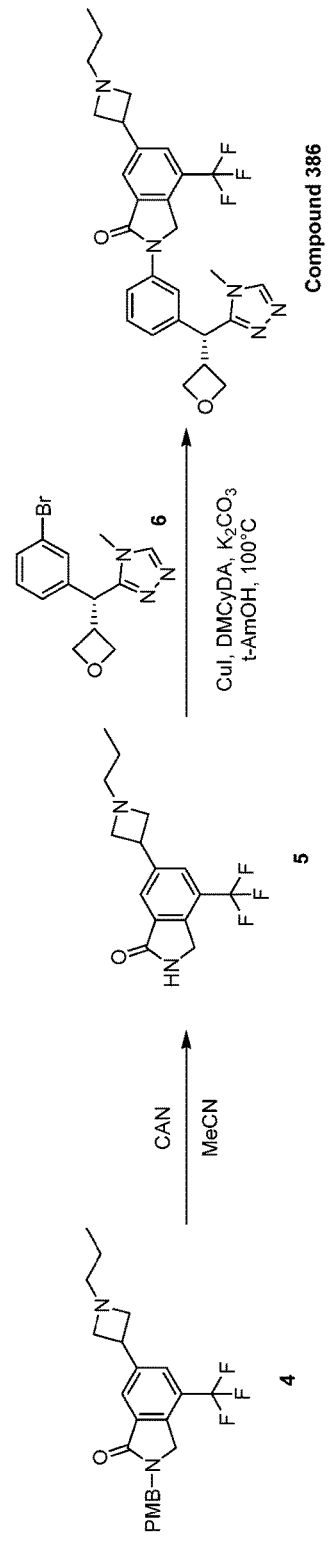
Scheme 105
FIG. 105
Scheme 106
FIG. 106

Scheme 107

Scheme 108

Scheme 109

LACTAMS AS CBL-B INHIBITORS SELECTIVE OVER C-CBL

CLAIM OF PRIORITY

This application claims benefit of priority to U.S. provisional patent application No. 63/276,547, filed Nov. 5, 2021, the contents of which are incorporated by reference herein in their entirety.

TECHNICAL FIELD

The technology described herein generally relates to inhibitors of Cbl-B that are selective for C-Cbl, and more particularly relates to methods of making and using the same.

BACKGROUND

Casitas B-lineage lymphoma-b (Cbl-b) is a member of the Cbl family of RING E3 ubiquitin ligases. A common function of Cbl family proteins is the negative regulation of receptor tyrosine kinase signaling. Since Cbl-b inhibition leads to immune activation, it has been expected that Cbl-b inhibitors could be broadly active in multiple oncology indications.

Cbl proteins comprise three principal domains: a conserved N-terminal tyrosine kinase binding (TKB) domain, a short linker region, and a RING finger (RF) domain. The TKB domain is, in turn, composed of three subdomains: a 4-helix bundle (4H), a calcium-binding domain with an EF-hand fold, and a variant Src homology region 2 (SH2) domain, all three of which are involved in phosphotyrosine binding. The TKB domain binds substrates, such as ZAP70, that contain phosphotyrosine motifs.

The conserved RF domain, which has intrinsic E3 ligase activity, can recruit E2 ubiquitin-conjugating enzymes, and mediate the transfer of ubiquitin to substrates.

Phosphorylation of Cbl-b at Y363 within the linker domain regulates its E3 ubiquitin ligase activity by removing the masking of the RF domain by the TKB domain.

In T-cells, Cbl-b is a key tolerogenic factor that directly regulates the cells' activation. Specifically, Cbl-b is highly expressed in murine and human CD4+ and CD8+ T cells, where it functions as a potent negative regulator of T cell activation by controlling activation thresholds and the requirement for co-stimulation. Mechanistically Cbl-b acts by ubiquitinating multiple substrates downstream of the T cell receptor (TCR), including ZAP70, resulting in TCR internalization and termination of signaling. Loss of Cbl-b in T cells leads to prolonged TCR surface expression, and in combination with TCR stimulation results in increased expression of activation markers, such as CD25, cytokine production and proliferation.

Mouse models have surprisingly demonstrated that the loss of Cbl-b leads to increased adaptive and innate anti-tumor immunity, mediated by enhanced T cell effector function as well as increased natural killer (NK) cell activity. Cbl-b deficient mice spontaneously reject a variety of cancer tumors, including spontaneous solid tumors and hematopoietic malignancies, in a CD8 T cell-dependent manner. Adoptive transfer of Cbl-b−/− CD8+ T cells is sufficient to reject tumors, demonstrating that Cbl-b has a non-redundant role in regulating T-cell-mediated anti-tumor activity.

Consequently, developing a small molecule approach to inhibit Cbl-b is a promising but challenging goal for cancer immunotherapy.

Nevertheless, c-Cbl, a closely related family member to Cbl-b, shares high sequence homology with Cbl-b at the N-terminus, including in the TKB and RING domains. c-Cbl negatively regulates signaling of a number of growth factor receptors, including Flt3 and c-Kit. Among other defects, c-Cbl deficient mice exhibit expansion of hematopoietic stem cells and multipotent progenitors in the bone marrow. In mice that are conditionally deficient in both c-Cbl and Cbl-b this defect is amplified, and the mice develop a rapidly-progressive and lethal myeloproliferative disease accompanied by splenomegaly by around 8 weeks of age. Given a broad spectrum of functions of c-Cbl in growth factor receptor regulation, and a strong amplification in the dysregulation of these pathways in the absence of both c-Cbl and Cbl-b, compounds with selectivity for Cbl-b over c-Cbl are likely to be highly desirable as cancer immunotherapy agents.

Accordingly, there is a need for compounds that both inhibit Cbl-b and exhibit selectivity over binding to c-Cbl.

The discussion of the background herein is included to explain the context of the technology. This is not to be taken as an admission that any of the material referred to was published, known, or part of the common general knowledge as at the priority date of any of the claims found appended hereto.

Throughout the description and claims of the application the word "comprise" and variations thereof, such as "comprising" and "comprises", is not intended to exclude other additives, components, integers or steps.

SUMMARY

The instant disclosure addresses compounds for inhibiting the Cbl-B receptor hat are also selective over the C-Cbl receptor. In particular, the disclosure comprises a number of such compounds and methods for using the same.

The present disclosure provides for compounds of formula (I):

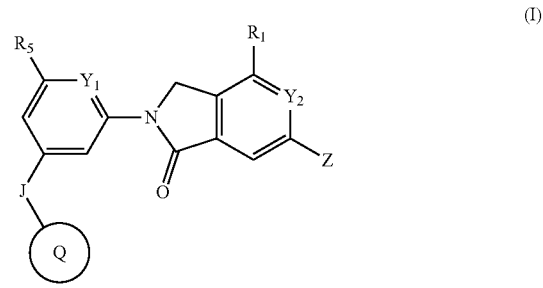

In formula (I), Q is a 5-membered heteroaryl group, optionally substituted by one or more alkyl, cycloalkyl, or haloalkyl groups.

In formula (I), $Y_1$ and $Y_2$ are independently CH, CF, or N;

In formula (I), J is $C(R_3)(R_4)$, wherein: $R_3$, $R_4$ are independently selected from: H, halogen, CN, OH, amino, and $LR_{2a}$, wherein L is O, $NR_0$, $CHR_0$, $C(=O)$, or a bond, wherein $R_0$ is H or alkyl, and $R_{2a}$ is selected from alkyl, alkenyl, alkynyl, alkylcarboxy, cyanoalkyl, aminoalkyl, hydroxyalkyl, haloalkyl, and a 3-14 membered ring moiety, wherein at least one of $R_3$ and $R_4$ is not H; or $R_3$ and $R_4$ together with the carbon atom to which they are both bonded form a 3-14 membered ring moiety, wherein:
if either of $R_3$ or $R_4$ is alkyl, haloalkyl, or hydroxyalkyl, $R_3$ or $R_4$ is optionally substituted by a 3-14 membered ring moiety;
and wherein, if either of $R_3$ or $R_4$ is, or is substituted by, a 3-14 membered ring moiety, or $R_3$ and $R_4$ together are a 3-14 membered ring moiety, the ring moiety is selected from:
a monocyclic ring, a fused bicyclic ring system, a bridged bicyclic ring system, and a spirocyclic ring system, and
wherein the ring moiety:
is optionally substituted by one or more groups independently selected from halogen, CN, amino, oxo, carbenyl, OH, or $L_0R_{2b}$, wherein $L_0$ is $CH_2$, $C(=O)$, NH, O, S, $S(=O)$, $S(=O)_2$, or a bond, and $R_{2b}$ is alkyl, cycloalkyl, heterocyclyl, alkenyl, alkoxy, hydroxyalkyl, haloalkyl, cyanoalkyl, and aminoalkyl;
is saturated, or contains 1 or 2 in-ring double bonds, or is aryl;
is carbocyclic, heterocyclic, or heteroaryl; and
when the ring moiety is heterocyclic or heteroaryl, it comprises 1, 2 or 3 ring atoms that are independently selected from O, N, and S;
$R_5$ is selected from: H, halo, or $L_1$-$R_{10}$, wherein $L_1$ is —$N(R_{11})$—, —$C(=O)N(R_{11})$—, O, S, carbonyl, or a bond, and wherein $R_{10}$ and $R_{11}$ are independently H, alkyl, cycloalkyl, alkenyl, alkynyl, aryl, heteroaryl, or heterocyclyl, and when either of $R_{10}$ and $R_{11}$ are not H, $R_{10}$ or $R_{11}$ is optionally substituted by one or more groups selected from: halo, CN, amino, oxo, OH, alkoxy, alkyl, perhaloalkyl, haloalkyl, heterocyclyl, aryl, and heteroaryl, or $R_{10}$ and $R_{11}$ together form a cycloalkyl or heterocyclyl ring, a spirocyclic ring, a fused bicyclic ring, or a bridged bicyclic ring, wherein the ring formed by $R_{10}$ and $R_{11}$ together is optionally substituted by one or more groups selected from halo, CN, amino, oxo, carbenyl, OH, alkoxy, alkyl, perhaloalkyl, or haloalkyl;
$R_1$ is H, halo, haloalkyl, or cycloalkyl; and
Z is -$L_{2a}NR_7R_8$ or -$L_{2b}CyN$-$R_7$, wherein:
CyN is a 3-8 membered cycloaminoalkyl ring and $R_7$ is bonded to N;
$L_{2a}$ is —$C(H)R_{6a}$—, —$C(=O)$—, or a bond;
$L_{2b}$ is —O—, —$N(R_{6b})$—, —$C(H)R_{6b}$—, —$C(=O)$—, or a bond;
$R_{6a}$=H, alkyl, cycloalkyl, haloalkyl or hydroxyalkyl;
$R_{6b}$=H or alkyl; and
$R_7$ and $R_8$ are independently $L_3R_9$, wherein:
$L_3$=—$(C(H)R_{10})_n$—, —$(C(H)R_{10})_nO$—, or a bond, wherein n=1 or 2;
$R_{10}$ is selected from H and alkyl;
$R_9$ is selected from H, alkyl, haloalkyl, perhaloalkyl, hydroxyalkyl, aminoalkyl, cycloalkyl, hydroxyalkyl, alkoxyalkyl, alkyl alkanoate, heterocyclyl, spirocyclyl ring system, fused ring system, bicyclyl ring system, a 5 or 6 member heteroaromatic ring, or a 3-10 member fused heteroaromatic ring system, and a bridged bicyclyl ring;
and wherein, if Z=CyN-$R_7$ or if any of $R_7$ or $R_8$ is cycloalkyl, heterocyclyl, spirocyclyl, a fused bicyclyl, a bridged bicyclic ring, a 5 or 6 member heteroaromatic ring, or a 3-10 member fused heteroaromatic ring system, said ring or ring system or CyN is optionally substituted with one or more groups selected from: sulfonyl, halo, hydroxyl, alkoxy, alkyl, cycloalkyl, alkoxyalkyl, carbenyl, alkenyl, hydroxyalkyl, cyano, carboxyalkyl, or haloalkyl;

or $R_7$ and $R_8$ together with the nitrogen atom to which they are both bonded form a 3-8 membered ring moiety selected from a monocyclic ring, a fused bicyclic ring, a bridged bicyclic ring, and a spirocyclic ring, wherein the ring moiety:
is optionally substituted with one or more groups independently selected from: sulfonyl, cyano, halo, hydroxyl, alkoxy, alkyl, cycloalkyl, alkoxyalkyl, alkenyl, hydroxyalkyl, oxo, carbenyl, carboxyalkyl, or haloalkyl, and
wherein the ring moiety optionally comprises one or more ring atoms selected from N, O, and S, in addition to the nitrogen atom to which $R_7$ and $R_8$ are bonded;
with the provisos that, when $Y_1$ and $Y_2$ are both CH, $R_5$=H, X=$CF_3$, and Q is 2-methyl triazol-1-yl:
if $R_7$ and $R_8$ together with the nitrogen atom to which they are both bonded form 3-substituted-cyclohexaminyl, then $R_3$ and $R_4$ together are not cyclobutyl, oxetan-4-yl, spiro[2.3]hexan-5-yl, or 3-substituted cyclobutyl, or J is not C(H)(3-substituted cyclobutyl);
if $R_7$ and $R_8$ together with the nitrogen atom to which they are both bonded form 3-substituted morpholinyl, then $R_3$ and $R_4$ together are not 3-substituted cyclobutyl or spiro[2.3]hexan-5-yl, or J is not C(H) (3-substituted cyclobutyl);

An enantiomer, diastereomer or a pharmaceutically acceptable salt or solvate of the structures of Formula (I) are also included.

The present disclosure includes a process for making compounds of formula (I), particularly according to any of the synthetic methods disclosed herein.

The present disclosure further includes a method of treatment comprising administering a compound of formula (I) optionally in combination with another agent, such as a checkpoint inhibitor, to a patient suffering from cancer.

The present disclosure further includes a use or uses of a compound of formula (I) optionally in combination with another agent, such as a checkpoint inhibitor, for the treatment of a type of cancer in an individual suffering therefrom.

DETAILED DESCRIPTION

Figure 1:
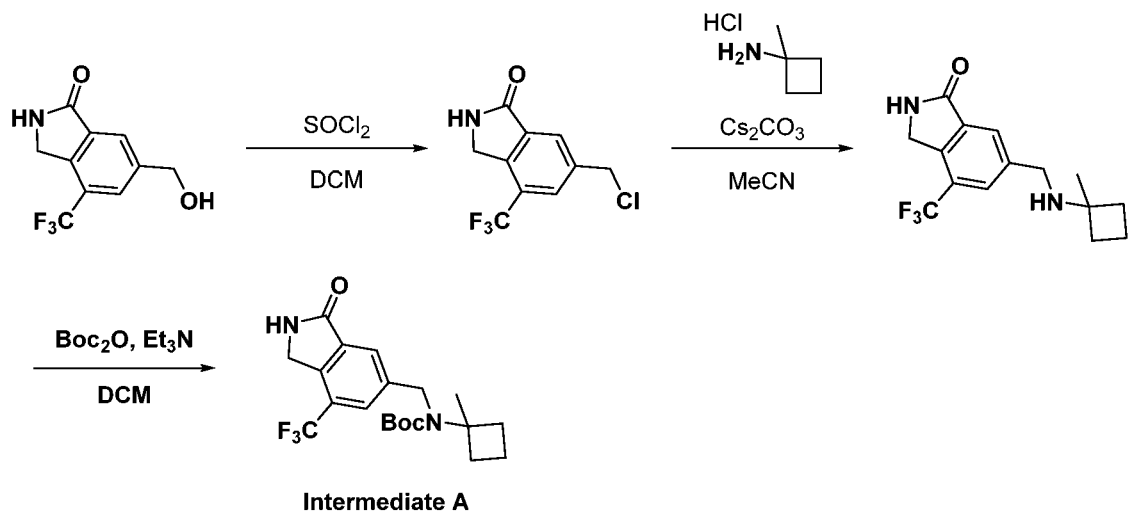
FIGS. 1-7 show, respectively, flow-charts of processes for synthesizing intermediates A-E used in syntheses of compound of formula (I), as further described herein.

The instant disclosure is directed to compounds that bind to the Cbl-b inhibitor and exhibit selectivity over C-Cbl. Methods of making such compounds, as well as assays for assessing their potency and selectivity, as well as metabolic and permeability properties, are also described herein.

Structures

The present disclosure provides for compounds of formula (I):

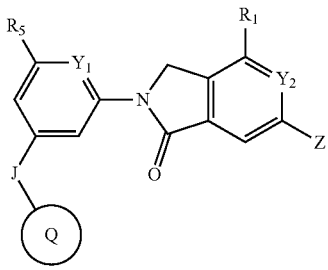

In the following description of substituents and variable positions in formula (I), it would be understood that subsets, including any individual member, of the list of possible substituents at any position can be chosen freely when describing preferred classes of compounds.

In formula (I), Q is a 5-membered heteroaryl group, optionally substituted by one or more alkyl, cycloalkyl, or haloalkyl groups.

In formula (I), $Y_1$ and $Y_2$ are independently CH, CF, or N.

In formula (I), J is $C(R_3)(R_4)$, wherein: $R_3$, $R_4$ are independently selected from: H, halogen, CN, OH, amino, and $LR_{2a}$, wherein L is —O—, —$NR_0$—, —$CHR_0$—, —C(=O)—, or a bond, wherein $R_0$ is H or alkyl, and $R_{2a}$ is selected from alkyl, alkenyl, alkynyl, alkylcarboxy, cyanoalkyl, aminoalkyl, hydroxyalkyl, haloalkyl, and a 3-14 membered ring moiety, wherein at least one of $R_3$ and $R_4$ is not H; or In formula (I), $R_3$ and $R_4$ together with the carbon atom to which they are both bonded form a 3-14 membered ring moiety, wherein:
  if either of $R_3$ or $R_4$ is alkyl, haloalkyl, or hydroxyalkyl, $R_3$ or $R_4$ is optionally substituted by a 3-14 membered ring moiety;
  and wherein, if either of $R_3$ or $R_4$ is, or is substituted by, a 3-14 membered ring moiety, or $R_3$ and $R_4$ together are a 3-14 membered ring moiety, the ring moiety is selected:
    a monocyclic ring, a fused bicyclic ring system, a bridged bicyclic ring system, and a spirocyclic ring system, and
  wherein the ring moiety:
    is optionally substituted by one or more groups independently selected from halogen, CN, amino, oxo, carbenyl, OH, or $L_0R_{2b}$, wherein $L_0$ is $CH_2$, C(=O), NH, O, S, S(=O), S(=O)$_2$, or a bond, and $R_{2b}$ is alkyl, cycloalkyl, heterocyclyl, alkenyl, alkoxy, hydroxyalkyl, haloalkyl, cyanoalkyl, and aminoalkyl;
    is saturated, or contains 1 or 2 in-ring double bonds, or is aryl;
    is carbocyclic, heterocyclic, or heteroaryl; and
  when the ring moiety is heterocyclic or heteroaryl, it comprises 1, 2 or 3 ring atoms that are independently selected from O, N, and S;

In formula (I), $R_5$ is selected from: H, halo, or $L_1$-$R_{10}$, wherein $L_1$ is —$N(R_{11})$—, —C(=O)$N(R_{11})$—, O, S, carbonyl, or a bond, and wherein $R_{10}$ and $R_{11}$ are independently H, alkyl, cycloalkyl, alkenyl, alkynyl, aryl, heteroaryl, or heterocyclyl, and when either of $R_{10}$ and $R_{11}$ are not H, $R_{10}$ or $R_{11}$ is optionally substituted by one or more groups selected from: halo, CN, amino, oxo, OH, alkoxy, alkyl, perhaloalkyl, haloalkyl, heterocyclyl, aryl, and heteroaryl, or $R_{10}$ and $R_{11}$ together form a cycloalkyl or heterocyclyl ring, a spirocyclic ring, a fused bicyclic ring, or a bridged bicyclic ring, wherein the ring formed by $R_{10}$ and $R_{11}$ together is optionally substituted by one or more groups selected from halo, CN, amino, oxo, carbenyl, OH, alkoxy, alkyl, perhaloalkyl, or haloalkyl.

In formula (I), $R_1$ is H, halo, haloalkyl, or cycloalkyl.

In formula (I), Z is -$L_{2a}NR_7R_8$ or -$L_{2b}CyN$-$R_7$, wherein:
  CyN is a 3-8 membered cycloaminoalkyl ring and $R_7$ is bonded to N;
  $L_{2a}$ is —C(H)$R_{6a}$—, —C(=O)—, or a bond;
  $L_{2b}$ is —O—, —$N(R_{6b})$—, —C(H)$R_{6b}$—, —C(=O)—, or a bond;
  $R_{6a}$=H, alkyl, cycloalkyl, haloalkyl or hydroxyalkyl;
  $R_{6b}$=H or alkyl; and
  $R_7$ and $R_8$ are independently $L_3R_9$, wherein:
    $L_3$=—(C(H)$R_{10}$)$_n$—, —(C(H)$R_{10}$)$_n$O—, or a bond, wherein n=1 or 2;
    $R_{10}$ is selected from H and alkyl;
    $R_9$ is selected from H, alkyl, haloalkyl, perhaloalkyl, hydroxyalkyl, aminoalkyl, cycloalkyl, hydroxyalkyl, alkoxyalkyl, alkyl alkanoate, heterocyclyl, spirocyclyl ring system, fused ring system, bicyclyl ring system, a 5 or 6 member heteroaromatic ring, or a 3-10 member fused heteroaromatic ring system, and a bridged bicyclyl ring;
    and wherein, if Z=CyN-$R_7$ or if any of $R_7$ or $R_8$ is cycloalkyl, heterocyclyl, spirocyclyl, a fused bicyclyl, a bridged bicyclic ring, a 5 or 6 member heteroaromatic ring, or a 3-10 member fused heteroaromatic ring system, said ring or ring system or CyN is optionally substituted with one or more groups selected from: sulfonyl, halo, hydroxyl, alkoxy, alkyl, cycloalkyl, alkoxyalkyl, carbenyl, alkenyl, hydroxyalkyl, cyano, carboxyalkyl, or haloalkyl;
  or
  $R_7$ and $R_8$ together with the nitrogen atom to which they are both bonded form a 3-8 membered ring moiety selected from a monocyclic ring, a fused bicyclic ring, a bridged bicyclic ring, and a spirocyclic ring, wherein the ring moiety:
    is optionally substituted with one or more groups independently selected from: sulfonyl, cyano, halo, hydroxyl, alkoxy, alkyl, cycloalkyl, alkoxyalkyl, alkenyl, hydroxyalkyl, oxo, carbenyl, carboxyalkyl, or haloalkyl, and
  wherein the ring moiety optionally comprises one or more ring atoms selected from N, O, and S, in addition to the nitrogen atom to which $R_7$ and $R_8$ are bonded; with the provisos that, when $Y_1$ and $Y_2$ are both CH, $R_5$=H, X=$CF_3$, and Q is 2-methyl triazol-1-yl:
    if $R_7$ and $R_8$ together with the nitrogen atom to which they are both bonded form 3-substituted-cyclohexaminyl, then $R_3$ and $R_4$ together are not cyclobutyl, oxetan-4-yl, spiro[2.3]hexan-5-yl, or 3-substituted cyclobutyl, or J is not C(H)(3-substituted cyclobutyl);
    if $R_7$ and $R_8$ together with the nitrogen atom to which they are both bonded form 3-substituted morpholinyl, then $R_3$ and $R_4$ together are not 3-substituted cyclobutyl or spiro[2.3]hexan-5-yl, or J is not C(H) (3-substituted cyclobutyl);

Enantiomers, diastereomers or pharmaceutically acceptable salts or solvates of the structures of Formula (I) are also included.

The disclosure comprises compounds of formula (I) wherein $R_5$ is H or halogen.

The disclosure comprises compounds of formula (I), wherein $R_5$ is selected from: alkyl, alkoxy, alkylamino, cycloalkylamino, cycloalkyl, and cycloalkyloxy, any of which is optionally substituted by one or more groups independently selected from: halo, alkyl, cyano, hydroxyl, amino, and alkoxy.

The disclosure comprises compounds of formula (I), wherein $R_5$ is $C_{1-6}$alkyl, $C_{1-6}$cycloalkyl, $C_{1-6}$alkylamino, $C_{1-6}$cycloalkylamino, $C_{1-6}$cycloalkyloxy, or $C_{1-6}$alkoxy.

The disclosure comprises compounds of formula (I), wherein $R_5$ is cyclopentylamino or cyclopentyloxy.

The disclosure comprises compounds of formula (I), wherein $R_5$ is $L_1$-$R_{10}$, wherein $L_1$ is a bond, and $R_{10}$ is heterocyclyl.

The disclosure comprises compounds of formula (I), wherein $Y_1$=$Y_2$=CH.

The disclosure comprises compounds of formula (I), wherein $Y_1$=N.

The disclosure comprises compounds of formula (I), wherein $R_1$=$CF_3$.

The disclosure comprises compounds of formula (I), wherein $R_1$=Cl.

The disclosure comprises compounds of formula (I), wherein Q is 2-methyl triazol-1-yl, tetrazolyl, or imidazolyl.

The disclosure comprises compounds of formula (I), wherein Q is 2-methyl triazol-1-yl.

The disclosure comprises compounds of formula (I), wherein Z is —C(H)$R_6$N$R_7R_8$.

The disclosure comprises compounds of formula (I), wherein Z is —C(H)$R_6$N$R_7R_8$, and wherein:
$R_6$ is H or methyl;
$R_7$ and $R_8$ together with the nitrogen atom to which they are both bonded form a saturated monocyclic ring selected from: piperidinyl and piperazinyl; and the saturated monocyclic ring is optionally substituted with alkyl.

The disclosure comprises compounds of formula (I), wherein Z is —C(H)$R_6$N$R_7R_8$, and wherein:
$R_6$ is H or methyl;
$R_7$ is H; and
$R_8$ is cyclobutyl, optionally substituted with alkyl.

The disclosure comprises compounds of formula (I), wherein $R_6$ and $R_7$ are H, and $R_8$ is 1-methylcyclobutyl.

The disclosure comprises compounds of formula (I), wherein Z is —C(H)$R_6$N$R_7R_8$, $R_6$ and $R_7$ are H, and $R_8$ is spirocyclyl.

The disclosure comprises compounds of formula (I), wherein Z is —C(H)$R_6$N$R_7R_8$, $R_6$ and $R_7$ are H, and $R_8$ is selected from isobutyl, 1,1-difluorospiro[2.3]hexan-5-yl, and 6,6-difluorobicyclo[3.1.0]hexan-3-yl.

The disclosure comprises compounds of formula (I), wherein $R_6$ is H or methyl.

The disclosure comprises compounds of formula (I), wherein $R_7$ and $R_8$ together form a piperidinyl or a piperazinyl ring.

The disclosure comprises compounds of formula (I), wherein $R_7$ and $R_8$ are both H and $R_6$ is alkyl.

The disclosure comprises compounds of formula (I), wherein $R_7$ and $R_8$ together form a piperidinyl or a piperazinyl ring substituted by a 2-isopropyl group.

The disclosure comprises compounds of formula (I), wherein Z is H.

The disclosure comprises compounds of formula (I), wherein $R_3$ is H or OH, and $R_4$ is selected from cyclobut-1-amino, 3-oxetanyl, cyclopropyloxy, cyclobutyloxy, cyclopropyl, cyclobutyl, and methoxy, and wherein $R_4$ is optionally substituted by one or more groups selected from: halo, alkyl, hydroxyl, and alkoxyl.

The disclosure comprises compounds of formula (I), wherein $R_3$ is H or OH, and $R_4$ is cyclobutyl, and wherein $R_4$ is optionally substituted by one or more groups selected from: fluoro, methyl, and methoxy.

The disclosure comprises compounds of formula (I), wherein $R_3$ and $R_4$ together with the carbon atom to which they are both bonded form a 3-8 membered ring moiety selected from: cyclobutyl, oxetanyl, cyclobutenyl, spiro[3.3]hept-2-yl, and 2-oxaspiro[3.]hept-6-yl, wherein the ring moiety is optionally substituted by one or more groups independently selected from: halo, carbenyl, oxo, hydroxyl, cyano, alkyl, and alkoxy.

The disclosure comprises compounds of formula (I), wherein $R_3$ and $R_4$ together with the carbon atom to which they are both bonded form an oxetan-3-yl ring.

The disclosure comprises compounds of formula (I), wherein $R_3$ and $R_4$ together with the carbon atom to which they are both bonded form an oxetan-3-yl ring substituted by one or more instances of fluoro.

The disclosure comprises compounds of formula (I), wherein $R_3$ and $R_4$ together with the carbon atom to which they are both bonded form a cyclobutyl ring.

The disclosure comprises compounds of formula (I), wherein $R_3$ and $R_4$ together with the carbon atom to which they are both bonded form a spirocyclic ring moiety having 5
8 ring atoms.

The disclosure comprises compounds of formula (I), wherein $R_3$ and $R_4$ together with the carbon atom to which they are both bonded form 2-oxaspiro[3.3]heptan-6-yl, 1-oxaspiro[3.3]heptan-6-yl, or 6-oxospiro[3.3]heptan-2-yl.

The disclosure comprises compounds of formula (I), wherein $R_3$ and $R_4$ together with the carbon atom to which they are both bonded form a ring moiety twice substituted by fluoro.

The disclosure comprises compounds of formula (I), wherein $R_3$ and $R_4$ together with the carbon atom to which they are both bonded form a cycloalkyl ring substituted by one or more instances of methyl, ethyl, methoxy, acetyl, chloro, fluoro, flurometyl, difluoromethoxy, trifluoromethoxy, methoxy-$d_3$, cyanomethyl, or cyano.

The disclosure comprises compounds of formula (I), where one of $R_3$ and $R_4$ is $C_{1-6}$alkyl and the other is H.

The disclosure comprises a list of compounds of formula (I), as follows, wherein the numerical ordering in the list is arbitrary, but is used consistently herein:

1) (R)-2-(3-(cyclobutyl(hydroxy)(4-methyl-4H-1,2,4-triazol-3-yl)methyl)phenyl)-6-(((1-methylcyclobutyl)amino)methyl)-4-(trifluoromethyl)isoindolin-1-one;

2) (S)-2-(3-(cyclobutyl(hydroxy)(4-methyl-4H-1,2,4-triazol-3-yl)methyl)phenyl)-6-(((1-methylcyclobutyl)amino)methyl)-4-(trifluoromethyl)isoindolin-1-one;

3) 2-(6-ethoxy-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

4) 2-(6-ethoxy-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

5) 2-(6-(ethylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

6) 2-(6-(ethylamino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

7) 2-(6-(ethylamino)-4-(6-(4-methyl-4H-1,2,4-triazol-3-yl)-2-oxaspiro[3.3]heptan-6-yl)pyridin-2-yl)-6-(((1-methylcyclobutyl)amino)methyl)-4-(trifluoromethyl)isoindolin-1-one;

8) 2-(6-(cyclopentylamino)-4-((1s,3s)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

9) 2-(6-(cyclopentylamino)-4-((1r,3r)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

10) 6-(((S)-2-isopropyl-4-methylpiperazin-1-yl)methyl)-2-(3-((R)-(4-methyl-4H-1,2,4-triazol-3-yl)(oxetan-3-yl)methyl)phenyl)-4-(trifluoromethyl)isoindolin-1-one;

11) 6-(((S)-2-isopropyl-4-methylpiperazin-1-yl)methyl)-2-(3-((S)-(4-methyl-4H-1,2,4-triazol-3-yl)(oxetan-3-yl)methyl)phenyl)-4-(trifluoromethyl)isoindolin-1-one;

12) 6-(((S)-2-isopropyl-4-methylpiperazin-1-yl)methyl)-2-(3-((R)-((1r,3R)-3-methoxycyclobutyl)(4-methyl-4H-1,2,4-triazol-3-yl)methyl)phenyl)-4-(trifluoromethyl)isoindolin-1-one;

13) 6-(((S)-2-isopropyl-4-methylpiperazin-1-yl)methyl)-2-(3-((R)-((1s,3S)-3-methoxycyclobutyl)(4-methyl-4H-1,2,4-triazol-3-yl)methyl)phenyl)-4-(trifluoromethyl)isoindolin-1-one;

14) 6-(((S)-2-isopropyl-4-methylpiperazin-1-yl)methyl)-2-(3-((S)-(1s,3R)-3-methoxycyclobutyl)(4-methyl-4H-1,2,4-triazol-3-yl)methyl)phenyl)-4-(trifluoromethyl)isoindolin-1-one;

15) 6-(((S)-2-isopropyl-4-methylpiperazin-1-yl)methyl)-2-(3-((S)-((1r,3S)-3-methoxycyclobutyl)(4-methyl-4H-1,2,4-triazol-3-yl)methyl)phenyl)-4-(trifluoromethyl)isoindolin-1-one;

16) 2-(6-cyclopropyl-4-(3,3-difluoro-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

17) 2-(4-(3,3-difluoro-1-(4-methyl-4H-1,2,4-triazol-3-yl)cyclobutyl)-6-(ethylamino)pyridin-2-yl)-6-(((1-methylcyclobutyl)amino)methyl)-4-(trifluoromethyl)isoindolin-1-one;

18) 2-(3-(1-(4-methyl-4H-1,2,4-triazol-3-yl)-3-methylenecyclobutyl)phenyl)-6-(((1-methylcyclobutyl)amino)methyl)-4-(trifluoromethyl)isoindolin-1-one;

19) 2-(3-(1-(4-methyl-4H-1,2,4-triazol-3-yl)-3-oxocyclobutyl)phenyl)-6-(((1-methylcyclobutyl)amino)methyl)-4-(trifluoromethyl)isoindolin-1-one;

20) 2-(3-((1r,3r)-3-hydroxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

21) 2-(3-((1s,3s)-3-hydroxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

22) 2-(3-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

23) 2-(3-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

24) (1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutanecarbonitrile;

25) (1s,3s)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutanecarbonitrile;

26) 2-(3-((1s,3s)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

27) (2-(3-((1r,3r)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

28) 2-(3-((1r,3r)-3-methoxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

29) (2-(3-((1s,3s)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

30) 2-(3-((1s,3s)-3-fluoro-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

31) 2-(3-((1r,3r)-3-fluoro-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

32) (S)-2-(3-(azetidin-1-yl(4-methyl-4H-1,2,4-triazol-3-yl)methyl)phenyl)-6-(((1-methylcyclobutyl)amino)methyl)-4-(trifluoromethyl)isoindolin-1-one;

33) (R)-2-(3-(azetidin-1-yl(4-methyl-4H-1,2,4-triazol-3-yl)methyl)phenyl)-6-(((1-methylcyclobutyl)amino)methyl)-4-(trifluoromethyl)isoindolin-1-one;

34) 2-(3-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

35) 2-(3-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

36) 2-(3-((1r,3r)-3-fluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one;

37) (S)-6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one;

38) (R)-6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one;

39) 2-(3-(3,3-dimethyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

40) 2-(3-(2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one;

41) (S)-6-((2-isopropyl-4-methylpiperazin-1-yl)methyl)-2-(3-(6-(4-methyl-4H-1,2,4-triazol-3-yl)-2-oxaspiro[3.3]heptan-6-yl)phenyl)-4-(trifluoromethyl)isoindolin-1-one;

42) (R)-2-(3-(methoxy(4-methyl-4H-1,2,4-triazol-3-yl)methyl)phenyl)-6-(((1-methylcyclobutyl)amino)methyl)-4-(trifluoromethyl)isoindolin-1-one;

43) (S)-2-(3-(methoxy(4-methyl-4H-1,2,4-triazol-3-yl)methyl)phenyl)-6-(((1-methylcyclobutyl)amino)methyl)-4-(trifluoromethyl)isoindolin-1-one;

44) (S)-2-(3-(cyclopropoxy(4-methyl-4H-1,2,4-triazol-3-yl)methyl)phenyl)-6-(((1-methylcyclobutyl)amino)methyl)-4-(trifluoromethyl)isoindolin-1-one;

45) (R)-2-(3-(cyclopropoxy(4-methyl-4H-1,2,4-triazol-3-yl)methyl)phenyl)-6-(((1-methylcyclobutyl)amino)methyl)-4-(trifluoromethyl)isoindolin-1-one;

46) (S)-2-(3-(cyclobutoxy(4-methyl-4H-1,2,4-triazol-3-yl)methyl)phenyl)-6-(((1-methylcyclobutyl)amino)methyl)-4-(trifluoromethyl)isoindolin-1-one;

47) (R)-2-(3-(cyclobutoxy(4-methyl-4H-1,2,4-triazol-3-yl)methyl)phenyl)-6-(((1-methylcyclobutyl)amino)methyl)-4-(trifluoromethyl)isoindolin-1-one;

48) 2-(6-((3,3-difluorocyclobutyl)amino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

49) 2-(6-((3,3-difluorocyclobutyl)amino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

50) 2-(6-(cyclohexylamino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

51) 2-(6-(cyclohexylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

52) 2-(6-(cyclopentylamino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

53) 2-(6-(cyclopentylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

54) 2-(6-(cyclopentyloxy)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

55) 2-(6-(cyclopentyloxy)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

56) (S)-2-(3-((3,3-difluoroazetidin-1-yl)(4-methyl-4H-1,2,4-triazol-3-yl)methyl)phenyl)-6-(((1-methylcyclobutyl)amino)methyl)-4-(trifluoromethyl)isoindolin-1-one;

57) (R)-2-(3-((3,3-difluoroazetidin-1-yl)(4-methyl-4H-1,2,4-triazol-3-yl)methyl)phenyl)-6-(((1-methylcyclobutyl)amino)methyl)-4-(trifluoromethyl)isoindolin-1-one;

58) 2-(3-(3-(4-methyl-4H-1,2,4-triazol-3-yl)oxetan-3-yl)phenyl)-6-(((1-methylcyclobutyl)amino)methyl)-4-(trifluoromethyl)isoindolin-1-one;

59) 2-(4-(3,3-difluoro-1-(4-methyl-4H-1,2,4-triazol-3-yl)cyclobutyl)-6-ethylpyridin-2-yl)-6-(((1-methylcyclobutyl)amino)methyl)-4-(trifluoromethyl)isoindolin-1-one;

60) 2-(4-(3,3-difluoro-1-(4-methyl-4H-1,2,4-triazol-3-yl)cyclobutyl)-6-methylpyridin-2-yl)-6-(((1-methylcyclobutyl)amino)methyl)-4-(trifluoromethyl)isoindolin-1-one;

61) 2-(3-(3,3-difluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one;

62) 2-(4-(3,3-difluoro-1-(4-methyl-4H-1,2,4-triazol-3-yl)cyclobutyl)-6-(ethylamino)pyridin-2-yl)-6-(((1-methylcyclobutyl)amino)methyl)-4-(trifluoromethyl)isoindolin-1-one;

63) (1S,3r)-3-(3-(6-(((S)-2-isopropyl-4-methylpiperazin-1-yl)methyl)-1-oxo-4-(trifluoromethyl)isoindolin-2-yl)phenyl)-3-(4-methyl-4H-1,2,4-triazol-3-yl)cyclobutanecarbonitrile;

64) (1R,3s)-3-(3-(6-(((S)-2-isopropyl-4-methylpiperazin-1-yl)methyl)-1-oxo-4-(trifluoromethyl)isoindolin-2-yl)phenyl)-3-(4-methyl-4H-1,2,4-triazol-3-yl)cyclobutanecarbonitrile;

65) 2-(3-(6-(4-methyl-4H-1,2,4-triazol-3-yl)-2-oxaspiro[3.3]heptan-6-yl)phenyl)-6-(((1-methylcyclobutyl)amino)methyl)-4-(trifluoromethyl)isoindolin-1-one;

66) (S)-2-(3-(6-(4-methyl-4H-1,2,4-triazol-3-yl)-2-oxaspiro[3.3]heptan-6-yl)phenyl)-6-((3-methylpiperidin-1-yl)methyl)-4-(trifluoromethyl)isoindolin-1-one;

67) 2-(6-(cyclobutylamino)-4-((1S,3S)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

68) 2-(6-(cyclobutylamino)-4-((1R,3R)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

69) 2-(6-(cyclopentylamino)-4-((1S,3S)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

70) 2-(6-(cyclopentylamino)-4-((1R,3R)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

71) 2-(6-(cyclobutylamino)-4-((S)-3-methyl-1-(4-methyl-4H-1,2,4-triazol-3-yl)cyclobut-2-en-1-yl)pyridin-2-yl)-6-(((S)-2-isopropyl-4-methylpiperazin-1-yl)methyl)-4-(trifluoromethyl)isoindolin-1-one;

72) 2-(6-(cyclopentyloxy)-4-((1S,3R)-3-methyl-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one;

73) 2-(6-(cyclopentyloxy)-4-((1R,3S)-3-methyl-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one;

74) 2-(6-(cyclopentylamino)-4-((1S,3R)-3-methyl-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one;

75) 2-(6-(cyclopentylamino)-4-((1R,3S)-3-methyl-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one;

76) 2-(6-ethoxy-4-((1S,3S)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

77) 2-(6-ethoxy-4-((1R,3R)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

78) 2-(6-(cyclopentyloxy)-4-((1S,3S)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

79) 2-(6-(cyclopentyloxy)-4-((1R,3R)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

80) 2-(6-(ethylamino)-4-((1S,3S)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

81) 2-(6-(ethylamino)-4-((1R,3R)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one;

82) 2-(6-(cyclopentyloxy)-4-((1S,3R)-3-methoxy-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one;

83) 2-(6-(cyclopentyloxy)-4-((1R,3S)-3-methoxy-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one;

84) 2-(6-(cyclopentylamino)-4-((1S,3R)-3-methoxy-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one;

85) 2-(6-(cyclopentylamino)-4-((1R,3S)-3-methoxy-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one;

86) 3-((4-((1S,3S)-3-methoxy-1-(4-methyl-4H-1,2,4-triazol-3-yl)cyclobutyl)-6-(6-(((1-methylcyclobutyl)amino)methyl)-1-oxo-4-(trifluoromethyl)isoindolin-2-yl)pyridin-2-yl)amino)propanenitrile;

87) 3-((4-((1R,3R)-3-methoxy-1-(4-methyl-4H-1,2,4-triazol-3-yl)cyclobutyl)-6-(6-(((1-methylcyclobutyl)amino)methyl)-1-oxo-4-(trifluoromethyl)isoindolin-2-yl)pyridin-2-yl)amino)propanenitrile;

88) 2-((1s,3s)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutyl)acetonitrile;

89) 2-((1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutyl)acetonitrile;

90) 2-(3-(ethylamino)-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

91) 2-(3-(ethylamino)-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

92) 2-(3-(2-(4-methyl-4H-1,2,4-triazol-3-yl)-6-oxospiro[3.3]heptan-2-yl)phenyl)-6-(((1-methylcyclobutyl)amino)methyl)-4-(trifluoromethyl)isoindolin-1-one;

93) 2-(3-(6-hydroxy-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one;

94) 2-(3-(6,6-difluoro-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one;

95) 2-(3-((1s,3s)-3-fluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one;

96) 2-(3-(6-(4-methyl-4H-1,2,4-triazol-3-yl)-2-(2,2,2-trifluoroethyl)-2-azaspiro[3.3]heptan-6-yl)phenyl)-6-(((1-methylcyclobutyl)amino)methyl)-4-(trifluoromethyl)isoindolin-1-one;

97) 2-(3-(2-acetyl-6-(4-methyl-4H-1,2,4-triazol-3-yl)-2-azaspiro[3.3]heptan-6-yl)phenyl)-6-(((1-methylcyclobutyl)amino)methyl)-4-(trifluoromethyl)isoindolin-1-one;

98) 2-(3-(6-(4-methyl-4H-1,2,4-triazol-3-yl)-2-(methylsulfonyl)-2-azaspiro[3.3]heptan-6-yl)phenyl)-6-(((1-methylcyclobutyl)amino)methyl)-4-(trifluoromethyl)isoindolin-1-one;

99) 2-(3-((1s,3s)-3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one formate;

100) 2-(3-((1r,3r)-3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one formate;

101) 2-(3-((1r,3r)-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one;

102) 2-(3-((1s,3s)-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one;

103) 2-(3-((1s,3s)-3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one;

104) 2-(3-((1r,3r)-3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one;

105) 2-(3-((1r,3r)-3-fluoro-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one;

106) (S)-2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one;

107) (R)-2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one;

108) 2-(3-((4r,6r)-6-(4-methyl-4H-1,2,4-triazol-3-yl)-1-oxaspiro[3.3]heptan-6-yl)phenyl)-6-(((1-methylcyclobutyl)amino)methyl)-4-(trifluoromethyl)isoindolin-1-one;

109) 2-(3-((4s,6s)-6-(4-methyl-4H-1,2,4-triazol-3-yl)-1-oxaspiro[3.3]heptan-6-yl)phenyl)-6-(((1-methylcyclobutyl)amino)methyl)-4-(trifluoromethyl)isoindolin-1-one;

110) 2-(3-(3-(4-methyl-4H-1,2,4-triazol-3-yl)-1-(2,2,2-trifluoroethyl)azetidin-3-yl)phenyl)-6-(((1-methylcyclobutyl)amino)methyl)-4-(trifluoromethyl)isoindolin-1-one;

111) 2-(3-(3-(4-methyl-4H-1,2,4-triazol-3-yl)-1-(oxetan-3-yl)azetidin-3-yl)phenyl)-6-(((1-methylcyclobutyl)amino)methyl)-4-(trifluoromethyl)isoindolin-1-one;

112) 2-(3-(1-acetyl-3-(4-methyl-4H-1,2,4-triazol-3-yl)azetidin-3-yl)phenyl)-6-(((1-methylcyclobutyl)amino)methyl)-4-(trifluoromethyl)isoindolin-1-one;

113) 2-(3-(3-(4-methyl-4H-1,2,4-triazol-3-yl)-1-(methylsulfonyl)azetidin-3-yl)phenyl)-6-(((1-methylcyclobutyl)amino)methyl)-4-(trifluoromethyl)isoindolin-1-one;

114) (R)-2-(3-((4-methyl-4H-1,2,4-triazol-3-yl)(3-oxocyclobutyl)methyl)phenyl)-6-(((1-methylcyclobutyl)amino)methyl)-4-(trifluoromethyl)isoindolin-1-one;

115) (S)-2-(3-((4-methyl-4H-1,2,4-triazol-3-yl)(3-oxocyclobutyl)methyl)phenyl)-6-(((1-methylcyclobutyl)amino)methyl)-4-(trifluoromethyl)isoindolin-1-one;

116) 4-(difluoromethyl)-2-(3-((1s,3s)-3-methoxy-1-(4-methyl-4H-1,2,4-triazol-3-yl)cyclobutyl)phenyl)-6-(((1-methylcyclobutyl)amino)methyl)isoindolin-1-one;

117) 4-(difluoromethyl)-2-(3-((1r,3r)-3-methoxy-1-(4-methyl-4H-1,2,4-triazol-3-yl)cyclobutyl)phenyl)-6-(((1-methylcyclobutyl)amino)methyl)isoindolin-1-one;

118) (S)-2-(3-(cyclobutyl(methoxy)(4-methyl-4H-1,2,4-triazol-3-yl)methyl)phenyl)-6-(((1-methylcyclobutyl)amino)methyl)-4-(trifluoromethyl)isoindolin-1-one;

119) (R)-2-(3-(cyclobutyl(methoxy)(4-methyl-4H-1,2,4-triazol-3-yl)methyl)phenyl)-6-(((1-methylcyclobutyl)amino)methyl)-4-(trifluoromethyl)isoindolin-1-one;

120) 2-(3-((1s,3s)-3-hydroxy-1-(4-methyl-4H-1,2,4-triazol-3-yl)-3-(trifluoromethyl)cyclobutyl)phenyl)-6-(((1-methylcyclobutyl)amino)methyl)-4-(trifluoromethyl)isoindolin-1-one;

121) (S)-2-(3-((4-methyl-4H-1,2,4-triazol-3-yl)(2-oxaspiro[3.3]heptan-6-yl)methyl)phenyl)-6-(((1-methylcyclobutyl)amino)methyl)-4-(trifluoromethyl)isoindolin-1-one;

122) (R)-2-(3-((4-methyl-4H-1,2,4-triazol-3-yl)(2-oxaspiro[3.3]heptan-6-yl)methyl)phenyl)-6-(((1-methylcyclobutyl)amino)methyl)-4-(trifluoromethyl)isoindolin-1-one;

123) 2-(3-((2R,4S)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one;

124) 2-(3-((2R,4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one;

125) 2-(3-((2S,4S)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one;

126) 2-(3-((2S,4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one;

127) 2-(3-((S)-((1r,3S)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one;

128) 2-(3-((S)-((1s,3R)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one;

129) 2-(3-((R)-((1r,3R)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one;

130) 2-(3-((R)-((1s,3S)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one;

131) 2-(3-((R)-((1r,3R)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;

132) 2-(3-((R)-((1s,3S)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;

133) 2-(3-((S)-((1r,3S)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;

134) 2-(3-((S)-((1s,3R)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;

135) (R)-2-(3-((5-methyl-1H-1,2,3-triazol-1-yl)(oxetan-3-yl)methyl)phenyl)-6-(((1-methylcyclobutyl)amino)methyl)-4-(trifluoromethyl) isoindolin-1-one;

136) (S)-2-(3-((5-methyl-1H-1,2,3-triazol-1-yl)(oxetan-3-yl)methyl)phenyl)-6-(((1-methylcyclobutyl)amino)methyl)-4-(trifluoro-methyl)isoindolin-1-one;

137) 2-(3-((1r,3r)-3-chloro-1-(4-methyl-4H-1,2,4-triazol-3-yl)cyclobutyl)phenyl)-6-(((1-methylcyclobutyl)amino)methyl)-4-(trifluoromethyl)isoindolin-1-one hydrochloride;

138) 2-(3-((1s,3s)-3-chloro-1-(4-methyl-4H-1,2,4-triazol-3-yl)cyclobutyl)phenyl)-6-(((1-methylcyclobutyl)amino)methyl)-4-(trifluoromethyl)isoindolin-1-one;

139) (1R,3r)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile;

140) (1S,3s)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile;

141) (1R,3s)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile;

142) (1S,3r)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile;

143) (S)-2-(3-(hydroxy(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

144) (R)-2-(3-(hydroxy(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

145) 2-(3-((3,3-difluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one;

146) (R)-2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one;

147) (S)-2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one;

148) (R)-6-(2-hydroxy-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one;

149) (S)-6-(2-hydroxy-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one;

150) (R)-2-(3-(fluoro(4-methyl-4H-1,2,4-triazol-3-yl)(oxetan-3-yl)methyl)phenyl)-6-(((1-methylcyclobutyl)amino)methyl)-4-(trifluoro-methyl)isoindolin-1-one;

151) (S)-2-(3-(fluoro(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

152) (R)-2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

153) (S)-2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

154) (S)-2-(3-(hydroxy(4-methyl-4H-1,2,4-triazol-3-yl)(phenyl)methyl)phenyl)-6-(((1-methylcyclobutyl)amino)methyl)-4-(trifluoromethyl)isoindolin-1-one;

155) (R)-2-(3-(hydroxy(4-methyl-4H-1,2,4-triazol-3-yl)(phenyl)methyl)phenyl)-6-(((1-methylcyclobutyl)amino)methyl)-4-(trifluoromethyl)isoindolin-1-one;

156) (S)-2-(3-(fluoro(4-methyl-4H-1,2,4-triazol-3-yl)(phenyl)methyl)phenyl)-6-(((1-methylcyclobutyl)amino)methyl)-4-(trifluoro-methyl)isoindolin-1-one;

157) (R)-2-(3-(fluoro(4-methyl-4H-1,2,4-triazol-3-yl)(phenyl)methyl)phenyl)-6-(((1-methylcyclobutyl)amino)methyl)-4-(trifluoro-methyl)isoindolin-1-one;

158) (R)-4-chloro-2-(3-((4-methyl-4H-1,2,4-triazol-3-yl)(phenyl)methyl)phenyl)-6-(((1-methylcyclobutyl)amino)methyl)isoindolin-1-one;

159) (S)-4-chloro-2-(3-((4-methyl-4H-1,2,4-triazol-3-yl)(phenyl)methyl)phenyl)-6-(((1-methylcyclobutyl)amino)methyl)isoindolin-1-one;

160) 2-(3-((1 S,3r)-1-(4-methyl-4H-1,2,4-triazol-3-yl)-3-((S)-methylsulfinyl)cyclobutyl)phenyl)-6-(((1-methylcyclobutyl)amino)methyl)-4-(trifluoromethyl)isoindolin-1-one;

161) 2-(3-((1 S,3s)-1-(4-methyl-4H-1,2,4-triazol-3-yl)-3-((R)-methylsulfinyl)cyclobutyl)phenyl)-6-(((1-methylcyclobutyl)amino)methyl)-4-(trifluoromethyl)isoindolin-1-one;

162) 2-(3-((1R,3s)-1-(4-methyl-4H-1,2,4-triazol-3-yl)-3-((S)-methylsulfinyl)cyclobutyl)phenyl)-6-(((1-methylcyclobutyl)amino)methyl)-4-(trifluoromethyl)isoindolin-1-one;

163) 2-(3-((1R,3r)-1-(4-methyl-4H-1,2,4-triazol-3-yl)-3-((R)-methylsulfinyl)cyclobutyl)phenyl)-6-(((1-methylcyclobutyl)amino)methyl)-4-(trifluoromethyl)isoindolin-1-one;

164) (R)-2-(3-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

165) (S)-2-(3-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

166) 2-(3-((2R)-2-(methoxymethyl)-1-(4-methyl-4H-1,2,4-triazol-3-yl)cyclopropyl)phenyl)-6-(((1-methylcyclobutyl)amino)methyl)-4-(trifluoromethyl)isoindolin-1-one;

167) 2-(3-((2S)-2-(methoxymethyl)-1-(4-methyl-4H-1,2,4-triazol-3-yl)cyclopropyl)phenyl)-6-(((1-methylcyclobutyl)amino)methyl)-4-(trifluoromethyl)isoindolin-1-one;

168) 2-(3-((R)-(4-methyl-4H-1,2,4-triazol-3-yl)((S)-tetrahydrofuran-3-yl)methyl)-phenyl)-6-(((1-methylcyclobutyl)amino)methyl)-4-(trifluoromethyl)isoindolin-1-one;

169) 2-(3-((S)-(4-methyl-4H-1,2,4-triazol-3-yl)((R)-tetrahydrofuran-3-yl)methyl)-phenyl)-6-(((1-methylcyclobutyl)amino)methyl)-4-(trifluoromethyl)isoindolin-1-one;

170) (R)-2-(3-(1-(4-methyl-4H-1,2,4-triazol-3-yl)ethyl)phenyl)-6-(((1-methylcyclobutyl)amino)methyl)-4-(trifluoromethyl)isoindolin-1-one;

171) 2-(3-(1-(4-methyl-4H-1,2,4-triazol-3-yl)ethyl)phenyl)-6-(((1-methylcyclobutyl)amino)methyl)-4-(trifluoromethyl)isoindolin-1-one;

172) 6-(((S)-2-isopropyl-4-methylpiperazin-1-yl)methyl)-2-(3-((1s,3R)-3-methoxy-1-(4-methyl-4H-1,2,4-triazol-3-yl)cyclobutyl)phenyl)-4-(trifluoromethyl)isoindolin-1-one;

173) (S)-2-(3-(3,3-difluoro-1-(4-methyl-4H-1,2,4-triazol-3-yl)cyclobutyl)phenyl)-6-(1-((1-methylcyclobutyl)amino)ethyl)-4-(trifluoromethyl)isoindolin-1-one;

174) (R)-2-(3-(3,3-difluoro-1-(4-methyl-4H-1,2,4-triazol-3-yl)cyclobutyl)phenyl)-6-(1-((1-methylcyclobutyl)amino)ethyl)-4-(trifluoromethyl)isoindolin-1-one;

175) 2-(3-((1s,3S)-3-methoxy-1-(4-methyl-4H-1,2,4-triazol-3-yl)cyclobutyl)phenyl)-6-((R)-1-((1-methylcyclobutyl)amino)ethyl)-4-(trifluoromethyl)isoindolin-1-one;

176) 2-(3-((1s,3R)-3-methoxy-1-(4-methyl-4H-1,2,4-triazol-3-yl)cyclobutyl)phenyl)-6-((S)-1-((1-methylcyclobutyl)amino)ethyl)-4-(trifluoromethyl)isoindolin-1-one;

177) 2-(3-(cyclopentylamino)-5-((1s,3s)-3-methyl-1-(4-methyl-4H-1,2,4-triazol-3-yl)-cyclobutyl)phenyl)-6-(((1-methylcyclobutyl)amino)methyl)-4-(trifluoromethyl)isoindolin-1-one;

178) 2-(3-((1s,3s)-3-ethoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

179) 2-(3-((1r,3r)-3-ethoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

180) 6-(((S)-2-isopropyl-4-methylpiperazin-1-yl)methyl)-2-(3-((1r,3S)-3-methoxy-1-(4-methyl-4H-1,2,4-triazol-3-yl)cyclobutyl)phenyl)-4-(trifluoromethyl)isoindolin-1-one;

181) 2-(3-ethoxy-5-((1s,3s)-3-methyl-1-(4-methyl-4H-1,2,4-triazol-3-yl)cyclobutyl)-phenyl)-6-(((1-methylcyclobutyl)amino)methyl)-4-(trifluoromethyl)isoindolin-1-one;

182) 2-(4-(3,3-difluoro-1-(4-methyl-4H-1,2,4-triazol-3-yl)cyclobutyl)-6-ethoxypyridin-2-yl)-6-(((1-methylcyclobutyl)amino)methyl)-4-(trifluoromethyl)isoindolin-1-one;

183) 2-(3-(cyclopentylamino)-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)-isoindolin-1-one;

184) 2-(3-((1r,3R)-3-methoxy-1-(4-methyl-4H-1,2,4-triazol-3-yl)cyclobutyl)phenyl)-6-((R)-1-((1-methylcyclobutyl)amino)ethyl)-4-(trifluoromethyl)isoindolin-1-one;

185) 2-(3-((1r,3S)-3-methoxy-1-(4-methyl-4H-1,2,4-triazol-3-yl)cyclobutyl)phenyl)-6-((S)-1-((1-methylcyclobutyl)amino)ethyl)-4-(trifluoromethyl)isoindolin-1-one;

186) 2-(3-(cyclopentyloxy)-5-((1s,3s)-3-methyl-1-(4-methyl-4H-1,2,4-triazol-3-yl)-cyclobutyl)phenyl)-6-(((1-methylcyclobutyl)amino)methyl)-4-(trifluoromethyl)isoindolin-1-one;

187) 3-((4-(6-(4-methyl-4H-1,2,4-triazol-3-yl)-2-oxaspiro[3.3]heptan-6-yl)-6-(6-(((1-methylcyclobutyl)amino)methyl)-1-oxo-4-(trifluoromethyl)isoindolin-2-yl)pyridin-2-yl)amino)propanenitrile;

188) 2-(6-(cyclopentylamino)-4-(6-(4-methyl-4H-1,2,4-triazol-3-yl)-2-oxaspiro[3.3]heptan-6-yl)pyridin-2-yl)-6-(((1-methylcyclobutyl)amino)methyl)-4-(trifluoromethyl)isoindolin-1-one;

189) 2-(3-ethoxy-5-((1r,3r)-3-methyl-1-(4-methyl-4H-1,2,4-triazol-3-yl)cyclobutyl)-phenyl)-6-(((1-methylcyclobutyl)amino)methyl)-4-(trifluoromethyl)isoindolin-1-one;

190) 2-(3-((1s,3s)-3-methoxy-1-(4-methyl-4H-1,2,4-triazol-3-yl)cyclobutyl)phenyl)-4-(trifluoromethyl)isoindolin-1-one;

191) 2-(3-(6-(4-methyl-4H-1,2,4-triazol-3-yl)-2-oxaspiro[3.3]heptan-6-yl)phenyl)-4-(trifluoromethyl)isoindolin-1-one;

192) (R)-3-((4-(6-(4-methyl-4H-1,2,4-triazol-3-yl)-2-oxaspiro[3.3]heptan-6-yl)-6-(6-(((1-methylcyclobutyl)amino)

methyl)-1-oxo-4-(trifluoromethyl)isoindolin-2-yl)pyridin-2-yl)amino)butanenitrile;
193) (R)-3-((4-(6-(4-methyl-4H-1,2,4-triazol-3-yl)-2-oxaspiro[3.3]heptan-6-yl)-6-(6-(((1-methylcyclobutyl)amino)methyl)-1-oxo-4-(trifluoromethyl)isoindolin-2-yl)pyridin-2-yl)amino)butanenitrile;
194) (S)-3-((4-(6-(4-methyl-4H-1,2,4-triazol-3-yl)-2-oxaspiro[3.3]heptan-6-yl)-6-(6-(((1-methylcyclobutyl)amino)methyl)-1-oxo-4-(trifluoromethyl)isoindolin-2-yl)pyridin-2-yl)amino)butanenitrile;
195) 2-(3-(cyclopentyloxy)-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)-isoindolin-1-one;
196) 2-(3-((1r,3r)-3-methoxy-1-(4-methyl-4H-1,2,4-triazol-3-yl)cyclobutyl)phenyl)-4-(trifluoromethyl)isoindolin-1-one;
197) 4-(difluoromethyl)-2-(3-(6-(4-methyl-4H-1,2,4-triazol-3-yl)-2-oxaspiro[3.3]-heptan-6-yl)phenyl)-6-(((1-methylcyclobutyl)amino)methyl)isoindolin-1-one;
198) (S)-4-(difluoromethyl)-6-((2-isopropyl-4-methylpiperazin-1-yl)methyl)-2-(3-(6-(4-methyl-4H-1,2,4-triazol-3-yl)-2-oxaspiro[3.3]heptan-6-yl)phenyl)isoindolin-1-one formate;
199) 2-(3-(6-(4-methyl-4H-1,2,4-triazol-3-yl)-2-(oxetan-3-yl)-2-azaspiro[3.3]heptan-6-yl)phenyl)-6-(((1-methylcyclobutyl)amino)methyl)-4-(trifluoromethyl)isoindolin-1-one;
200) 2-(3-methoxy-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
201) 2-(3-methoxy-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
202) 2-(3-ethoxy-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
203) 2-(3-ethoxy-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
204) (S)-4-chloro-6-((2-isopropyl-4-methylpiperazin-1-yl)methyl)-2-(3-(6-(4-methyl-4H-1,2,4-triazol-3-yl)-2-oxaspiro[3.3]heptan-6-yl)phenyl)isoindolin-1-one;
205) 2-(3-(allyloxy)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
206) 2-(3-isopropoxy-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
207) 2-(3-isopropoxy-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
208) 2-(3-(cyclopentyloxy)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
209) 2-(3-(cyclopentylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
210) 2-(3-(ethylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
211) 2-(3-(cyclobutylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
212) 2-(3-(cyclopentyloxy)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
213) 2-(3-((R)-but-3-en-2-yloxy)-5-((1s,3S)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
214) 2-(3-(cyclopropylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
215) 2-(3-(isopropylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
216) 3-((3-((1r,3r)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)propanenitrile;
217) 2-(3-(cyclobutylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
218) 2-(3-(cyclopentylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
219) 2-(3-((R)-but-3-en-2-ylamino)-5-((1r,3R)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
220) 2-(3-((S)-but-3-en-2-ylamino)-5-((1r,3S)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
221) (R)-3-((3-((1r,3R)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)butanenitrile;
222) 2-(3-((1s,3s)-3-isopropoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
223) 2-(3-(isopropylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;
224) 3-((3-((1s,3s)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)propanenitrile;
225) (S)-3-((3-((1r,3S)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)butanenitrile;
226) 2-(3-cyclopropyl-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

227) 2-(3-(ethylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

228) (R)-3-((3-((1s,3S)-3-methoxy-1-(4-methyl-4H-1,2,4-triazol-3-yl)cyclobutyl)-5-(6-(((1-methyl¬cyclobutyl)amino)methyl)-1-oxo-4-(trifluoromethyl)isoindolin-2-yl)phenyl)amino)butanenitrile;

229) 2-(3-(6-methoxy-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one;

230) 2-(3-((1r,3r)-3-methoxy-1-(4-methyl-4H-1,2,4-triazol-3-yl)cyclobutyl)-5-methyl-phenyl)-6-(((1-methylcyclobutyl)amino)methyl)-4-(trifluoromethyl)isoindolin-1-one;

231) 2-(3-(cyclopropylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

232) 2-(3-(allylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)-isoindolin-1-one;

233) (S)-3-((3-((1s,3R)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)butanenitrile;

234) 2-(3-((1r,3r)-3-methoxy-1-(4-methyl-4H-1,2,4-triazol-3-yl)cyclobutyl)-5-(oxetan-3-ylamino)phenyl)-6-(((1-methylcyclobutyl)amino)methyl)-4-(trifluoromethyl)isoindolin-1-one;

235) 2-(3-ethyl-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

236) 2-(3-ethyl-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

237) 2-(3-((1s,3s)-3-methoxy-1-(4-methyl-4H-1,2,4-triazol-3-yl)cyclobutyl)-5-methyl-phenyl)-6-(((1-methylcyclobutyl)amino)methyl)-4-(trifluoromethyl)isoindolin-1-one;

238) 2-(3-((1s,3s)-3-methoxy-1-(4-methyl-4H-1,2,4-triazol-3-yl)cyclobutyl)-5-(methylamino)phenyl)-6-(((1-methylcyclobutyl)amino)methyl)-4-(trifluoromethyl)isoindolin-1-one;

239) 2-(3-((1r,3r)-3-methoxy-1-(4-methyl-4H-1,2,4-triazol-3-yl)cyclobutyl)-5-(methylamino)phenyl)-6-(((1-methylcyclobutyl)amino)methyl)-4-(trifluoromethyl)isoindolin-1-one;

240) 2-(3-(allylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one;

241) 2-(3-((1s,3s)-3-methoxy-1-(4-methyl-4H-1,2,4-triazol-3-yl)cyclobutyl)-5-(oxetan-3-yloxy)phenyl)-6-(((1-methylcyclobutyl)amino)methyl)-4-(trifluoromethyl)isoindolin-1-one;

242) 2-(3-((1r,3r)-3-methoxy-1-(4-methyl-4H-1,2,4-triazol-3-yl)cyclobutyl)-5-(oxetan-3-yloxy)phenyl)-6-(((1-methylcyclobutyl)amino)methyl)-4-(trifluoromethyl)isoindolin-1-one;

243) 2-(3-((1s,3s)-3-methoxy-1-(4-methyl-4H-1,2,4-triazol-3-yl)cyclobutyl)-5-(oxetan-3-ylamino)phenyl)-6-(((1-methylcyclobutyl)amino)methyl)-4-(trifluoromethyl)isoindolin-1-one;

244) (S)-2-(3-(1-(4-methyl-4H-1,2,4-triazol-3-yl)-2-(oxetan-3-yl)ethyl)phenyl)-6-(((1-methylcyclobutyl)amino)methyl)-4-(trifluoromethyl)isoindolin-1-one;

245) (R)-2-(3-(1-(4-methyl-4H-1,2,4-triazol-3-yl)-2-(oxetan-3-yl)ethyl)phenyl)-6-(((1-methylcyclobutyl)amino)methyl)-4-(trifluoromethyl)isoindolin-1-one;

246) 4-chloro-2-(3-((1s,3s)-3-fluoro-1-(4-methyl-4H-1,2,4-triazol-3-yl)cyclobutyl)phenyl)-6-(((1-methylcyclobutyl)amino)methyl)isoindolin-1-one;

247) 4-(difluoromethyl)-2-(3-((1s,3s)-3-fluoro-1-(4-methyl-4H-1,2,4-triazol-3-yl)cyclobutyl)phenyl)-6-(((1-methylcyclobutyl)amino)methyl)isoindolin-1-one;

248) (S)-2-(3-(2-cyclopentyl-1-(4-methyl-4H-1,2,4-triazol-3-yl)ethyl)phenyl)-6-(((1-methylcyclobutyl)amino)methyl)-4-(trifluoromethyl)isoindolin-1-one;

249) (R)-2-(3-(2-cyclopentyl-1-(4-methyl-4H-1,2,4-triazol-3-yl)ethyl)phenyl)-6-(((1-methylcyclobutyl)amino)methyl)-4-(trifluoromethyl)isoindolin-1-one;

250) (R)-2-(3-(cyclohexyl(4-methyl-4H-1,2,4-triazol-3-yl)methyl)phenyl)-6-(((1-methylcyclobutyl)amino)methyl)-4-(trifluoromethyl)isoindolin-1-one;

251) (S)-2-(3-(cyclohexyl(4-methyl-4H-1,2,4-triazol-3-yl)methyl)phenyl)-6-(((1-methylcyclobutyl)amino)methyl)-4-(trifluoromethyl)isoindolin-1-one;

252) (R)-2-(3-(1-(4-methyl-4H-1,2,4-triazol-3-yl)-2-(tetrahydro-2H-pyran-4-yl)ethyl)phenyl)-6-(((1-methylcyclobutyl)amino)methyl)-4-(trifluoromethyl)isoindolin-1-one;

253) (S)-2-(3-(1-(4-methyl-4H-1,2,4-triazol-3-yl)-2-(tetrahydro-2H-pyran-4-yl)ethyl)phenyl)-6-(((1-methylcyclobutyl)amino)methyl)-4-(trifluoromethyl)isoindolin-1-one;

254) (R)-2-(3-(1-(4-methyl-4H-1,2,4-triazol-3-yl)-2-(3-methyloxetan-3-yl)ethyl)phenyl)-6-(((1-methylcyclobutyl)amino)methyl)-4-(trifluoromethyl)isoindolin-1-one;

255) (S)-2-(3-(1-(4-methyl-4H-1,2,4-triazol-3-yl)-2-(3-methyloxetan-3-yl)ethyl)phenyl)-6-(((1-methylcyclobutyl)amino)methyl)-4-(trifluoromethyl)isoindolin-1-one;

256) (R)-2-(3-(cyclopentyl(4-methyl-4H-1,2,4-triazol-3-yl)methyl)phenyl)-6-(((1-methylcyclobutyl)amino)methyl)-4-(trifluoromethyl)isoindolin-1-one;

257) (S)-2-(3-(cyclopentyl(4-methyl-4H-1,2,4-triazol-3-yl)methyl)phenyl)-6-(((1-methylcyclobutyl)amino)methyl)-4-(trifluoromethyl)isoindolin-1-one;

258) (R)-2-(3-(cyclobutyl(4-methyl-4H-1,2,4-triazol-3-yl)methyl)phenyl)-6-(((1-methylcyclobutyl)amino)methyl)-4-(trifluoromethyl)isoindolin-1-one;

259) (S)-2-(3-(cyclobutyl(4-methyl-4H-1,2,4-triazol-3-yl)methyl)phenyl)-6-(((1-methylcyclobutyl)amino)methyl)-4-(trifluoromethyl)isoindolin-1-one;

260) 2-(3-((R)-((1r,3R)-3-(2,2-difluoroethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one;

261) 2-(3-((R)-((1s,3S)-3-(2,2-difluoroethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one;

262) 2-(3-((S)-((1s,3R)-3-(2,2-difluoroethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one;

263) 2-(3-((S)-((1r,3S)-3-(2,2-difluoroethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one;

264) 2-(3-((R)-((1r,3R)-3-ethoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;

265) 2-(3-((R)-((1s,3S)-3-ethoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;

266) 2-(3-((S)-((1s,3R)-3-ethoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;

267) 2-(3-((S)-((1r,3S)-3-ethoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;

268) (R)-2-(3-(2-cyclobutyl-1-(4-methyl-4H-1,2,4-triazol-3-yl)ethyl)phenyl)-6-(((1-methylcyclobutyl)amino)methyl)-4-(trifluoromethyl)isoindolin-1-one;

269) (S)-2-(3-(2-cyclobutyl-1-(4-methyl-4H-1,2,4-triazol-3-yl)ethyl)phenyl)-6-(((1-methylcyclobutyl)amino)methyl)-4-(trifluoromethyl)isoindolin-1-one;

270) (R)-4-chloro-2-(3-((4-methyl-4H-1,2,4-triazol-3-yl)(oxetan-3-yl)methyl)phenyl)-6-(((1-methylcyclobutyl)amino)methyl)isoindolin-1-one;

271) (S)-4-chloro-2-(3-((4-methyl-4H-1,2,4-triazol-3-yl)(oxetan-3-yl)methyl)phenyl)-6-(((1-methylcyclobutyl)amino)methyl)isoindolin-1-one;

272) 4-(difluoromethyl)-2-(3-((1r,3r)-3-fluoro-1-(4-methyl-4H-1,2,4-triazol-3-yl)cyclobutyl)phenyl)-6-(((1-methylcyclobutyl)amino)methyl)isoindolin-1-one;

273) 4-chloro-2-(3-((1r,3r)-3-fluoro-1-(4-methyl-4H-1,2,4-triazol-3-yl)cyclobutyl)phenyl)-6-(((1-methylcyclobutyl)amino)methyl)isoindolin-1-one;

274) 4-(difluoromethyl)-2-(6-(ethylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)isoindolin-1-one;

275) 2-(3-((R)-1-(4-methyl-4H-1,2,4-triazol-3-yl)-2-((R)-tetrahydrofuran-3-yl)ethyl)phenyl)-6-(((1-methylcyclobutyl)amino)methyl)-4-(trifluoromethyl)isoindolin-1-one;

276) 2-(3-((S)-1-(4-methyl-4H-1,2,4-triazol-3-yl)-2-((R)-tetrahydrofuran-3-yl)ethyl)phenyl)-6-(((1-methylcyclobutyl)amino)methyl)-4-(trifluoromethyl)isoindolin-1-one;

277) 2-(3-((S)-1-(4-methyl-4H-1,2,4-triazol-3-yl)-2-((S)-tetrahydrofuran-3-yl)ethyl)phenyl)-6-(((1-methylcyclobutyl)amino)methyl)-4-(trifluoromethyl)isoindolin-1-one;

278) 2-(3-((R)-1-(4-methyl-4H-1,2,4-triazol-3-yl)-2-((S)-tetrahydrofuran-3-yl)ethyl)phenyl)-6-(((1-methylcyclobutyl)amino)methyl)-4-(trifluoromethyl)isoindolin-1-one;

279) 2-(3-(1-(4-methyl-4H-1,2,4-triazol-3-yl)cyclobutyl)phenyl)-6-(((1-methylcyclobutyl)amino)methyl)-4-(trifluoromethyl)isoindolin-1-one;

280) 2-((1s,3s)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutoxy)acetonitrile;

281) 2-((1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutoxy)acetonitrile;

282) 2-(3-(4-(4-methyl-4H-1,2,4-triazol-3-yl)tetrahydro-2H-pyran-4-yl)phenyl)-6-(((1-methylcyclobutyl)amino)methyl)-4-(trifluoromethyl)isoindolin-1-one;

283) 2-(3-(1-(4-methyl-4H-1,2,4-triazol-3-yl)cyclopropyl)phenyl)-6-(((1-methylcyclobutyl)amino)methyl)-4-(trifluoromethyl)isoindolin-1-one;

284) 2-(3-((4-methyl-4H-1,2,4-triazol-3-yl)(oxetan-3-yl)methyl)phenyl)-6-((R)-1-((1-methylcyclobutyl)amino)ethyl)-4-(trifluoromethyl)isoindolin-1-one;

285) 2-(3-((4-methyl-4H-1,2,4-triazol-3-yl)(oxetan-3-yl)methyl)phenyl)-6-((S)-1-((1-methylcyclobutyl)amino)ethyl)-4-(trifluoromethyl)isoindolin-1-one;

286) (R)-2-(3-(2-(1,1-dioxidotetrahydro-2H-thiopyran-4-yl)-1-(4-methyl-4H-1,2,4-triazol-3-yl)ethyl)phenyl)-6-(((1-methylcyclobutyl)amino)methyl)-4-(trifluoromethyl)isoindolin-1-one;

287) (S)-2-(3-(2-(1,1-dioxidotetrahydro-2H-thiopyran-4-yl)-1-(4-methyl-4H-1,2,4-triazol-3-yl)ethyl)phenyl)-6-(((1-methylcyclobutyl)amino)methyl)-4-(trifluoromethyl)isoindolin-1-one;

288) 4-chloro-2-(3-((1s,3S)-3-fluoro-1-(4-methyl-4H-1,2,4-triazol-3-yl)cyclobutyl)phenyl)-6-((R)-1-((1-methylcyclobutyl)amino)ethyl)isoindolin-1-one;

289) 4-chloro-2-(3-((1s,3R)-3-fluoro-1-(4-methyl-4H-1,2,4-triazol-3-yl)cyclobutyl)phenyl)-6-((S)-1-((1-methylcyclobutyl)amino)ethyl)isoindolin-1-one;

290) (R)-2-(3-((4-methyl-4H-1,2,4-triazol-3-yl)(tetrahydro-2H-pyran-4-yl)methyl)phenyl)-6-(((1-methylcyclobutyl)amino)methyl)-4-(trifluoromethyl)isoindolin-1-one;

291) (S)-2-(3-((4-methyl-4H-1,2,4-triazol-3-yl)(tetrahydro-2H-pyran-4-yl)methyl)phenyl)-6-(((1-methylcyclobutyl)amino)methyl)-4-(trifluoromethyl)isoindolin-1-one formate;

292) 2-(3-(1-(4-methyl-4H-1,2,4-triazol-3-yl)cyclopentyl)phenyl)-6-(((1-methylcyclobutyl)amino)methyl)-4-(trifluoromethyl)isoindolin-1-one;

293) 2-(3-(2-(4-methyl-4H-1,2,4-triazol-3-yl)-5,8-dioxaspiro[3.4]octan-2-yl)phenyl)-6-(((1-methylcyclobutyl)amino)methyl)-4-(trifluoromethyl)isoindolin-1-one;

294) 2-3-((R)-2-((S)-1,4-dioxan-2-yl)-1-(4-methyl-4H-1,2,4-triazol-3-yl)ethyl)phenyl)-6-(((1-methylcyclobutyl)amino)methyl)-4-(trifluoromethyl)isoindolin-1-one;

295) 2-(3-((S)-2-((S)-1,4-dioxan-2-yl)-1-(4-methyl-4H-1,2,4-triazol-3-yl)ethyl)phenyl)-6-(((1-methylcyclobutyl)amino)methyl)-4-(trifluoromethyl)isoindolin-1-one;

296) 2-(3-((S)-2-((R)-1,4-dioxan-2-yl)-1-(4-methyl-4H-1,2,4-triazol-3-yl)ethyl)phenyl)-6-(((1-methylcyclobutyl)amino)methyl)-4-(trifluoromethyl)isoindolin-1-one;

297) 2-(3-((R)-2-((R)-1,4-dioxan-2-yl)-1-(4-methyl-4H-1,2,4-triazol-3-yl)ethyl)phenyl)-6-(((1-methylcyclobutyl)amino)methyl)-4-(trifluoromethyl)isoindolin-1-one;

298) 2-(3-(1-(4-methyl-4H-1,2,4-triazol-3-yl)cyclohexyl)phenyl)-6-(((1-methylcyclobutyl)amino)methyl)-4-(trifluoromethyl)isoindolin-1-one;

299) (R)-2-(3-((1,1-dioxidotetrahydro-2H-thiopyran-4-yl)(4-methyl-4H-1,2,4-triazol-3-yl)methyl)phenyl)-6-(((1-methylcyclobutyl)amino)methyl)-4-(trifluoromethyl)isoindolin-1-one;

300) (S)-2-(3-((1,1-dioxidotetrahydro-2H-thiopyran-4-yl)(4-methyl-4H-1,2,4-triazol-3-yl)methyl)phenyl)-6-(((1-methylcyclobutyl)amino)methyl)-4-(trifluoromethyl)isoindolin-1-one;

301) (R)-6-(1,2-dihydroxyethyl)-2-(3-(1-(4-methyl-4H-1,2,4-triazol-3-yl)cyclobutyl)phenyl)-4-(trifluoromethyl)isoindolin-1-one;

302) (S)-6-(1,2-dihydroxyethyl)-2-(3-(1-(4-methyl-4H-1,2,4-triazol-3-yl)cyclobutyl)phenyl)-4-(trifluoromethyl)isoindolin-1-one;

303) (R)-4-(difluoromethyl)-2-(3-((4-methyl-4H-1,2,4-triazol-3-yl)(oxetan-3-yl)methyl)phenyl)-6-(((1-methylcyclobutyl)amino)methyl)isoindolin-1-one;

304) (S)-4-(difluoromethyl)-2-(3-((4-methyl-4H-1,2,4-triazol-3-yl)(oxetan-3-yl)methyl)phenyl)-6-(((1-methylcyclobutyl)amino)methyl)isoindolin-1-one;

305) (R)-2-(3-(1-hydroxy-1-(4-methyl-4H-1,2,4-triazol-3-yl)ethyl)phenyl)-6-(((1-methylcyclobutyl)amino)methyl)-4-(trifluoromethyl)isoindolin-1-one;

306) (S)-2-(3-(1-hydroxy-1-(4-methyl-4H-1,2,4-triazol-3-yl)ethyl)phenyl)-6-(((1-methylcyclobutyl)amino)methyl)-4-(trifluoromethyl)isoindolin-1-one;

307) (R)-6-(((1-methylcyclobutyl)amino)methyl)-2-(3-(2,2,2-trifluoro-1-hydroxy-1-(4-methyl-4H-1,2,4-triazol-3-yl)ethyl)phenyl)-4-(trifluoromethyl)isoindolin-1-one;

308) (S)-6-(((1-methylcyclobutyl)amino)methyl)-2-(3-(2,2,2-trifluoro-1-hydroxy-1-(4-methyl-4H-1,2,4-triazol-3-yl)ethyl)phenyl)-4-(trifluoromethyl)isoindolin-1-one;

309) (R)-2-(3-(1-hydroxy-2-methyl-1-(4-methyl-4H-1,2,4-triazol-3-yl)propyl)phenyl)-6-(((1-methylcyclobutyl)amino)methyl)-4-(trifluoromethyl)isoindolin-1-one;

310) (S)-2-(3-(1-hydroxy-2-methyl-1-(4-methyl-4H-1,2,4-triazol-3-yl)propyl)phenyl)-6-(((1-methylcyclobutyl)amino)methyl)-4-(trifluoromethyl)isoindolin-1-one;

311) 4-chloro-2-(3-((1r,3R)-3-fluoro-1-(4-methyl-4H-1,2,4-triazol-3-yl)cyclobutyl)phenyl)-6-((R)-1-((1-methylcyclobutyl)amino)ethyl)isoindolin-1-one;

312) 4-chloro-2-(3-((1r,3S)-3-fluoro-1-(4-methyl-4H-1,2,4-triazol-3-yl)cyclobutyl)phenyl)-6-((S)-1-((1-methylcyclobutyl)amino)ethyl)isoindolin-1-one;

313) 2-(3-((R)-(4-methyl-4H-1,2,4-triazol-3-yl)(oxetan-3-yl)methyl)phenyl)-6-((S)-1-((1-methylcyclobutyl)amino)propyl)-4-(trifluoromethyl)isoindolin-1-one;

314) 2-(3-((R)-(4-methyl-4H-1,2,4-triazol-3-yl)(oxetan-3-yl)methyl)phenyl)-6-((R)-1-((1-methylcyclobutyl)amino)propyl)-4-(trifluoromethyl)isoindolin-1-one;

315) 2-(3-((S)-(4-methyl-4H-1,2,4-triazol-3-yl)(oxetan-3-yl)methyl)phenyl)-6-((S)-1-((1-methylcyclobutyl)amino)propyl)-4-(trifluoromethyl)isoindolin-1-one;

316) 2-(3-((S)-(4-methyl-4H-1,2,4-triazol-3-yl)(oxetan-3-yl)methyl)phenyl)-6-((R)-1-((1-methylcyclobutyl)amino)propyl)-4-(trifluoromethyl)isoindolin-1-one;

317) 4-chloro-2-(3-((R)-((1s,3S)-3-fluorocyclobutyl)(4-methyl-4H-1,2,4-triazol-3-yl)methyl)phenyl)-6-(((1-methylcyclobutyl)amino)methyl)isoindolin-1-one;

318) 4-chloro-2-(3-((R)-((1r,3R)-3-fluorocyclobutyl)(4-methyl-4H-1,2,4-triazol-3-yl)methyl)phenyl)-6-(((1-methylcyclobutyl)amino)methyl)isoindolin-1-one;

319) 4-chloro-2-(3-((S)-((1s,3R)-3-fluorocyclobutyl)(4-methyl-4H-1,2,4-triazol-3-yl)methyl)phenyl)-6-(((1-methylcyclobutyl)amino)methyl)isoindolin-1-one;

320) 4-chloro-2-(3-((S)-((1r,3S)-3-fluorocyclobutyl)(4-methyl-4H-1,2,4-triazol-3-yl)methyl)phenyl)-6-(((1-methylcyclobutyl)amino)methyl)isoindolin-1-one;

321) (S)-4-chloro-2-(3-(fluoro(4-methyl-4H-1,2,4-triazol-3-yl)(phenyl)methyl)phenyl)-6-(((1-methylcyclobutyl)amino)methyl)isoindolin-1-one;

322) (R)-4-chloro-2-(3-(fluoro(4-methyl-4H-1,2,4-triazol-3-yl)(phenyl)methyl)phenyl)-6-(((1-methylcyclobutyl)amino)methyl)isoindolin-1-one;

323) 2-(3-((1r,3r)-1-(4-methyl-4H-1,2,4-triazol-3-yl)-3-(methylthio)cyclobutyl)phenyl)-6-(((1-methylcyclobutyl)amino)methyl)-4-(trifluoromethyl)isoindolin-1-one;

324) 2-(3-((1s,3s)-1-(4-methyl-4H-1,2,4-triazol-3-yl)-3-(methylthio)cyclobutyl)phenyl)-6-(((1-methylcyclobutyl)amino)methyl)-4-(trifluoromethyl)isoindolin-1-one;

325) 2-(3-((1r,3r)-1-(4-methyl-4H-1,2,4-triazol-3-yl)-3-(methylsulfonyl)cyclobutyl)phenyl)-6-(((1-methylcyclobutyl)amino)methyl)-4-(trifluoromethyl)isoindolin-1-one;

326) 2-(3-((1s,3s)-1-(4-methyl-4H-1,2,4-triazol-3-yl)-3-(methylsulfonyl)cyclobutyl)phenyl)-6-(((1-methylcyclobutyl)amino)methyl)-4-(trifluoromethyl)isoindolin-1-one;

327) 2-(3-(1-(4-methyl-4H-1,2,4-triazol-3-yl)cyclobutyl)phenyl)-3-oxo-7-(trifluoromethyl)isoindoline-5-carboxamide;

328) 2-(3-(3-(4-methyl-4H-1,2,4-triazol-3-yl)-1,1-dioxidothietan-3-yl)phenyl)-6-(((1-methylcyclobutyl)amino)methyl)-4-(trifluoromethyl)isoindolin-1-one;

329) 2-(3-(3-(4-methyl-4H-1,2,4-triazol-3-yl)thietan-3-yl)phenyl)-6-(((1-methylcyclobutyl)amino)methyl)-4-(trifluoromethyl)isoindolin-1-one formate;

330) 2-(3-(3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one;

331) 2-(3-(3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one;

332) (R)-2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

333) (S)-2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

334) 2-(3-((1r,3r)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one;

335) 2-(3-((1s,3s)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one;

336) 2-(3-(ethylamino)-2-fluoro-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

337) 2-(3-(ethylamino)-2-fluoro-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;

338) (R)-2-(3-methoxy-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

339) (S)-2-(3-methoxy-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;

340) 2-(3-((2s,4r)-2-(4-methyl-4H-1,2,4-triazol-3-yl)-5-oxaspiro[3.4]octan-2-yl)phenyl)-6-(((1-methylcyclobutyl)amino)methyl)-4-(trifluoromethyl) isoindolin-1-one;

341) 2-(3-((2r,4s)-2-(4-methyl-4H-1, 2, 4-triazol-3-yl)-5-oxaspiro [3.4] octan-2-yl)phenyl)-6-(((1-methylcyclobutyl)amino)methyl)-4-(trifluoromethyl) isoindolin-1-one;

342) (R)-2-(3-(cyclopropyl(4-methyl-4H-1,2,4-triazol-3-yl)methyl)phenyl)-6-(((1-methylcyclobutyl)amino)methyl)-4-(trifluoromethyl)isoindolin-1-one;

343) (S)-2-(3-(cyclopropyl(4-methyl-4H-1,2,4-triazol-3-yl)methyl)phenyl)-6-(((1-methylcyclobutyl)amino)methyl)-4-(trifluoromethyl)isoindolin-1-one;
344) (R)-2-(3-((1H-imidazol-1-yl)(4-methyl-4H-1,2,4-triazol-3-yl)methyl)phenyl)-6-(((1-methylcyclobutyl)amino)methyl)-4-(trifluoromethyl)isoindolin-1-one;
345) (S)-2-(3-((1H-imidazol-1-yl)(4-methyl-4H-1,2,4-triazol-3-yl)methyl)phenyl)-6-(((1-methylcyclobutyl)amino)methyl)-4-(trifluoromethyl)isoindolin-1-one;
346) 2-(3-((1s,3s)-3-acetyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;
347) 2-(3-((1r,3r)-3-acetyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;
348) (R)-2-(3-((1-methyl-1H-tetrazol-5-yl)(oxetan-3-yl)methyl)phenyl)-6-(((1-methylcyclobutyl)amino)methyl)-4-(trifluoromethyl)isoindolin-1-one;
349) (S)-2-(3-((1-methyl-1H-tetrazol-5-yl)(oxetan-3-yl)methyl)phenyl)-6-(((1-methylcyclobutyl)amino)methyl)-4-(trifluoromethyl)isoindolin-1-one;
350) 2-(3-((1s,3s)-1-(4-methyl-4H-1,2,4-triazol-3-yl)-3-(trifluoromethoxy)cyclobutyl)-phenyl)-6-(((1 methylcyclobutyl)amino)methyl)-4-(trifluoromethyl)isoindolin-1-one;
351) 2-(3-((1r,3r)-1-(4-methyl-4H-1,2,4-triazol-3-yl)-3-(trifluoromethoxy)cyclobutyl)-phenyl)-6-(((1-methylcyclobutyl)amino)methyl)-4-(trifluoromethyl)isoindolin-1-one;
352) (R)-2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one;
353) (S)-2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one;
354) 2-(3-((S)-((1s,3R)-3-chlorocyclobutyl)(4-methyl-4H-1,2,4-triazol-3-yl)methyl)-phenyl)-6-(((1-methylcyclobutyl)amino)methyl)-4-(trifluoromethyl)isoindolin-1-one;
355) 2-(3-((S)-((1r,3S)-3-chlorocyclobutyl)(4-methyl-4H-1,2,4-triazol-3-yl)methyl)-phenyl)-6-(((1-methylcyclobutyl)amino)methyl)-4-(trifluoromethyl)isoindolin-1-one;
356) 2-(3-((R)-((1r,3R)-3-chlorocyclobutyl)(4-methyl-4H-1,2,4-triazol-3-yl)methyl)-phenyl)-6-(((1-methylcyclobutyl)amino)methyl)-4-(trifluoromethyl)isoindolin-1-one;
357) 2-(3-((R)-((1s,3S)-3-chlorocyclobutyl)(4-methyl-4H-1,2,4-triazol-3-yl)methyl)-phenyl)-6-(((1-methylcyclobutyl)amino)methyl)-4-(trifluoromethyl)isoindolin-1-one;
358) (R)-4-chloro-2-(3-(1-(4-methyl-4H-1,2,4-triazol-3-yl)propyl)phenyl)-6-(((1-methylcyclobutyl)amino)methyl)isoindolin-1-one;
359) (S)-4-chloro-2-(3-(1-(4-methyl-4H-1,2,4-triazol-3-yl)propyl)phenyl)-6-(((1-methylcyclobutyl)amino)methyl)isoindolin-1-one;
360) 6-((R)-1-amino-2,2-dimethylpropyl)-2-(3-((1r,3R)-3-methoxy-1-(4-methyl-4H-1,2,4-triazol-3-yl)cyclobutyl)phenyl)-4-(trifluoromethyl)isoindolin-1-one;
361) 6-((S)-1-amino-2,2-dimethylpropyl)-2-(3-((1r,3S)-3-methoxy-1-(4-methyl-4H-1,2,4-triazol-3-yl)cyclobutyl)phenyl)-4-(trifluoromethyl)isoindolin-1-one;
362) 2-((1R,3s)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile;
363) 2-((1S,3r)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile;
364) 2-((1R,3r)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile;
365) 2-((1S,3s)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile;
366) 2-(3-((S)-((1r,3S)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;
367) 2-(3-((S)-((1s,3R)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;
368) 2-(3-((R)-((1s,3S)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;
369) 2-(3-((R)-((1r,3R)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;
370) 2-(3-((1s,3s)-3-(fluoromethoxy)-1-(4-methyl-4H-1,2,4-triazol-3-yl)cyclobutyl)-phenyl)-6-(((1-methylcyclobutyl)amino)methyl)-4-(trifluoromethyl)isoindolin-1-one;
371) 2-(3-((1r,3r)-3-(fluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one;
372) 2-(3-((1 S,3S)-3-(methoxy-d3)-1-(4-methyl-4H-1,2,4-triazol-3-yl)cyclobutyl)phenyl)-6-(((1-methylcyclobutyl)amino)methyl)-4-(trifluoromethyl)isoindolin-1-one;
373) 2-(3-((1R,3R)-3-(methoxy-d3)-1-(4-methyl-4H-1,2,4-triazol-3-yl)cyclobutyl)-phenyl)-6-(((1-methylcyclobutyl)amino)methyl)-4-(trifluoromethyl)isoindolin-1-one;
374) 4-chloro-2-(3-((1r,3s)-3-ethyl-1-(4-methyl-4H-1,2,4-triazol-3-yl)cyclobutyl)phenyl)-6-(((1-methylcyclobutyl)amino)methyl)isoindolin-1-one;
375) 4-chloro-2-(3-((1s,3r)-3-ethyl-1-(4-methyl-4H-1,2,4-triazol-3-yl)cyclobutyl)-phenyl)-6-(((1-methylcyclobutyl)amino)methyl)isoindolin-1-one;
376) 2-(3-((S)-(4-methyl-4H-1,2,4-triazol-3-yl)((1r,3S)-3-methylcyclobutyl)methyl)-phenyl)-6-(((1-methylcyclobutyl)amino)methyl)-4-(trifluoromethyl)isoindolin-1-one;
377) 2-(3-((S)-(4-methyl-4H-1,2,4-triazol-3-yl)((1s,3R)-3-methylcyclobutyl)methyl)phenyl)-6-(((1-methylcyclobutyl)amino)methyl)-4-(trifluoromethyl)isoindolin-1-one;
378) 2-(3-((R)-(4-methyl-4H-1,2,4-triazol-3-yl)((1r,3R)-3-methylcyclobutyl)methyl)-phenyl)-6-(((1-methylcyclobutyl)amino)methyl)-4-(trifluoromethyl)isoindolin-1-one;
379) 2-(3-((R)-(4-methyl-4H-1,2,4-triazol-3-yl)((1s,3S)-3-methylcyclobutyl)methyl)phenyl)-6-(((1-methylcyclobutyl)amino)methyl)-4-(trifluoromethyl)isoindolin-1-one;

380) (R)-2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one;
381) (S)-2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one;
382) 2-(3-((R)-((1r,3R)-3-acetylcyclobutyl)(4-methyl-4H-1,2,4-triazol-3-yl)methyl)-phenyl)-6-(((1-methylcyclobutyl)amino)methyl)-4-(trifluoromethyl)isoindolin-1-one;
383) 2-(3-((S)-((1s,3R)-3-acetylcyclobutyl)(4-methyl-4H-1,2,4-triazol-3-yl)methyl)-phenyl)-6-(((1-methylcyclobutyl)amino)methyl)-4-(trifluoromethyl)isoindolin-1-one;
384) 2-(3-((S)-((1r,3S)-3-acetylcyclobutyl)(4-methyl-4H-1,2,4-triazol-3-yl)methyl)-phenyl)-6-(((1-methylcyclobutyl)amino)methyl)-4-(trifluoromethyl)isoindolin-1-one;
385) 2-(3-((R)-((1s,3S)-3-acetylcyclobutyl)(4-methyl-4H-1,2,4-triazol-3-yl)methyl)-phenyl)-6-(((1-methylcyclobutyl)amino)methyl)-4-(trifluoromethyl)isoindolin-1-one;
386) (R)-2-(3-((4-methyl-4H-1,2,4-triazol-3-yl)(oxetan-3-yl)methyl)phenyl)-6-(1-propylazetidin-3-yl)-4-(trifluoromethyl)isoindolin-1-one;
387) 2-(3-((R)-((1r,3R)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one;
388) 2-(3-((R)-((1s,3S)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one;
389) 2-(3-((S)-((1r,3S)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one;
390) 2-(3-((S)-((1s,3R)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one;
391) (S)-2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one;
392) (R)-2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one;
393) (S)-2-(3-(1-fluoro-1-(4-methyl-4H-1,2,4-triazol-3-yl)propyl)phenyl)-6-(((1-methylcyclobutyl)amino)methyl)-4-(trifluoromethyl)isoindolin-1-one;
394) (R)-2-(3-(1-fluoro-1-(4-methyl-4H-1,2,4-triazol-3-yl)propyl)phenyl)-6-(((1-methylcyclobutyl)amino)methyl)-4-(trifluoromethyl)isoindolin-1-one;
395) 2-(3-((R)-(4-methyl-4H-1,2,4-triazol-3-yl)((1r,3R)-3-(trifluoromethoxy)-cyclobutyl)methyl)phenyl)-6-(((1-methylcyclobutyl)amino)methyl)-4-(trifluoromethyl)-isoindolin-1-one;
396) 2-(3-((S)-(4-methyl-4H-1,2,4-triazol-3-yl)((1s,3R)-3-(trifluoromethoxy)-cyclobutyl)methyl)phenyl)-6-(((1-methylcyclobutyl)amino)methyl)-4-(trifluoromethyl)isoindolin-1-one;
397) 2-(3-((R)-(4-methyl-4H-1,2,4-triazol-3-yl)((1s,3S)-3-(trifluoromethoxy)cyclobutyl)methyl)phenyl)-6-(((1-methylcyclobutyl)amino)methyl)-4-(trifluoromethyl)isoindolin-1-one;
398) 2-(3-((S)-(4-methyl-4H-1,2,4-triazol-3-yl)((1r,3S)-3-(trifluoromethoxy)cyclobutyl)methyl)phenyl)-6-(((1-methylcyclobutyl)amino)methyl)-4-(trifluoromethyl)isoindolin-1-one;
399) (R)—N-methyl-N-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)acetamide;
400) (S)—N-methyl-N-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)acetamide;
401) (R)-2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one;
402) (S)-2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one;
403) (S)-2-(3-(fluoro(3-fluorooxetan-3-yl)(4-methyl-4H-1,2,4-triazol-3-yl)methyl)-phenyl)-6-(((1-methylcyclobutyl)amino)methyl)-4-(trifluoromethyl)isoindolin-1-one;
404) (R)-2-(3-(fluoro(3-fluorooxetan-3-yl)(4-methyl-4H-1,2,4-triazol-3-yl)methyl)-phenyl)-6-(((1-methylcyclobutyl)amino)methyl)-4-(trifluoromethyl)isoindolin-1-one;
405) 2-(3-((1s,3s)-3-(difluoromethyl)-3-hydroxy-1-(4-methyl-4H-1,2,4-triazol-3-yl)cyclobutyl)phenyl)-6-(((1-methylcyclobutyl)amino)methyl)-4-(trifluoromethyl)-isoindolin-1-one;
406) 4-(difluoromethyl)-2-(3-((S)-(4-methyl-4H-1,2,4-triazol-3-yl)(oxetan-3-yl)methyl)phenyl)-6-((R)-1-((1-methylcyclobutyl)amino)ethyl)isoindolin-1-one;
407) 4-(difluoromethyl)-2-(3-((S)-(4-methyl-4H-1,2,4-triazol-3-yl)(oxetan-3-yl)methyl)phenyl)-6-((S)-1-((1-methylcyclobutyl)amino)ethyl)isoindolin-1-one;
408) (R)-2-(3-chloro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;
409) (S)-2-(3-chloro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one;
410) (R)-4-chloro-2-(3-(hydroxy(4-methyl-4H-1,2,4-triazol-3-yl)(phenyl)methyl)phenyl)-6-(((1-methylcyclobutyl)amino)methyl)isoindolin-1-one;
411) (S)-4-chloro-2-(3-(hydroxy(4-methyl-4H-1,2,4-triazol-3-yl)(phenyl)methyl)phenyl)-6-(((1-methylcyclobutyl)amino)methyl)isoindolin-1-one;
412) 4-(difluoromethyl)-2-(3-((R)-(4-methyl-4H-1,2,4-triazol-3-yl)(oxetan-3-yl)methyl)phenyl)-6-((R)-1-((1-methylcyclobutyl)amino)ethyl)isoindolin-1-one;
413) 4-(difluoromethyl)-2-(3-((R)-(4-methyl-4H-1,2,4-triazol-3-yl)(oxetan-3-yl)methyl)phenyl)-6-((S)-1-((1-methylcyclobutyl)amino)ethyl)isoindolin-1-one;
414) 6-((cyclobutylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
415) 6-(((cyclopropylmethyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
416) 6-(((cyclobutylmethyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
417) 2-(3-((1r,3r)-3-methoxy-1-(4-methyl-4H-1,2,4-triazol-3-yl)cyclobutyl)phenyl)-6-(morpholinomethyl)-4-(trifluoromethyl)isoindolin-1-one;
418) 2-(3-((1r,3r)-3-methoxy-1-(4-methyl-4H-1,2,4-triazol-3-yl)cyclobutyl)phenyl)-6-(pyrrolidin-1-ylmethyl)-4-(trifluoromethyl)isoindolin-1-one;

419) 6-((isopropylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
420) 2-(3-((1r,3r)-3-methoxy-1-(4-methyl-4H-1,2,4-triazol-3-yl)cyclobutyl)phenyl)-6-(piperidin-1-ylmethyl)-4-(trifluoromethyl)isoindolin-1-one;
421) 6-((isobutylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
422) 6-((3-hydroxyazetidin-1-yl)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
423) 6-(5-azaspiro[2.3]hexan-5-ylmethyl)-2-(3-((1r,3r)-3-methoxy-1-(4-methyl-4H-1,2,4-triazol-3-yl)cyclobutyl)phenyl)-4-(trifluoromethyl)isoindolin-1-one;
424) 6-((2-hydroxy-7-azaspiro[3.5]nonan-7-yl)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
425) methyl 2-(((2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methyl)amino)butanoate;
426) 6-(((1,1-difluorospiro[2.3]hexan-5-yl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
427) 6-(((6,6-difluorobicyclo[3.1.0]hexan-3-yl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;
428) (S)-2-(3-((1-hydroxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;
429) (R)-2-(3-((1-hydroxycyclobutyl)(4-methyl-4H-1,2,4-triazol-3-yl)methyl)phenyl)-6-(((1-methylcyclobutyl)amino)methyl)-4-(trifluoromethyl)isoindolin-1-one;
430) 6-((S)-cyclopropyl((1-methylcyclobutyl)amino)methyl)-2-(3-((R)-(4-methyl-4H-1,2,4-triazol-3-yl)(oxetan-3-yl)methyl)phenyl)-4-(trifluoromethyl)isoindolin-1-one;
431) 6-((R)-cyclopropyl((1-methylcyclobutyl)amino)methyl)-2-(3-((R)-(4-methyl-4H-1,2,4-triazol-3-yl)(oxetan-3-yl)methyl)phenyl)-4-(trifluoromethyl)isoindolin-1-one;
432) 6-((R)-cyclobutyl((1-methylcyclobutyl)amino)methyl)-2-(3-((R)-(4-methyl-4H-1,2,4-triazol-3-yl)(oxetan-3-yl)methyl)phenyl)-4-(trifluoromethyl)isoindolin-1-one;
433) 6-((S)-cyclobutyl((1-methylcyclobutyl)amino)methyl)-2-(3-((R)-(4-methyl-4H-1,2,4-triazol-3-yl)(oxetan-3-yl)methyl)phenyl)-4-(trifluoromethyl)isoindolin-1-one;
434) 6-((R)-cyclobutyl((1-methylcyclobutyl)amino)methyl)-2-(3-((S)-(4-methyl-4H-1,2,4-triazol-3-yl)(oxetan-3-yl)methyl)phenyl)-4-(trifluoromethyl)isoindolin-1-one;
435) 6-((S)-cyclobutyl((1-methylcyclobutyl)amino)methyl)-2-(3-((S)-(4-methyl-4H-1,2,4-triazol-3-yl)(oxetan-3-yl)methyl)phenyl)-4-(trifluoromethyl)isoindolin-1-one;
436) (R)-6-(((1-methylcyclobutyl)amino)methyl)-2-(3-(oxetan-3-yl(1H-1,2,3-triazol-1-yl)methyl)phenyl)-4-(trifluoromethyl)isoindolin-1-one;
437) (S)-6-(((1-methylcyclobutyl)amino)methyl)-2-(3-(oxetan-3-yl(1H-1,2,3-triazol-1-yl)methyl)phenyl)-4-(trifluoromethyl)isoindolin-1-one;
438) 2-(3-((R)-((S)-1,1-dioxidotetrahydrothiophen-3-yl)(4-methyl-4H-1,2,4-triazol-3-yl)methyl)phenyl)-6-(((1-methylcyclobutyl)amino)methyl)-4-(trifluoromethyl)isoindolin-1-one;
439) 2-(3-((S)-((S)-1,1-dioxidotetrahydrothiophen-3-yl)(4-methyl-4H-1,2,4-triazol-3-yl)methyl)phenyl)-6-(((1-methylcyclobutyl)amino)methyl)-4-(trifluoromethyl)isoindolin-1-one;
440) (R)-6-(((1-methylcyclobutyl)amino)methyl)-2-(3-(oxetan-3-yl(4H-1,2,4-triazol-3-yl)methyl)phenyl)-4-(trifluoromethyl)isoindolin-1-one;
441) (S)-6-(((1-methylcyclobutyl)amino)methyl)-2-(3-(oxetan-3-yl(4H-1,2,4-triazol-3-yl)methyl)phenyl)-4-(trifluoromethyl)isoindolin-1-one;
442) 2-(3-((S)-(4-methyl-4H-1,2,4-triazol-3-yl)(oxetan-3-yl)methyl)phenyl)-6-((S)-1-((1-methylcyclobutyl)amino)ethyl)-4-(trifluoromethyl)isoindolin-1-one;
443) 2-(3-((S)-(4-methyl-4H-1,2,4-triazol-3-yl)(oxetan-3-yl)methyl)phenyl)-6-((R)-1-((1-methylcyclobutyl)amino)ethyl)-4-(trifluoromethyl)isoindolin-1-one;
444) 2-(3-((R)-(4-methyl-4H-1,2,4-triazol-3-yl)(oxetan-3-yl)methyl)phenyl)-6-((R)-1-((1-methylcyclobutyl)amino)ethyl)-4-(trifluoromethyl)isoindolin-1-one;
445) 2-(3-((R)-(4-methyl-4H-1,2,4-triazol-3-yl)(oxetan-3-yl)methyl)phenyl)-6-((S)-1-((1-methylcyclobutyl)amino)ethyl)-4-(trifluoromethyl)isoindolin-1-one;
446) 2-(3-((1s,3s)-3-chloro-1-(4-methyl-4H-1,2,4-triazol-3-yl)cyclobutyl)phenyl)-4-(difluoromethyl)-6-(((1-methylcyclobutyl)amino)methyl)isoindolin-1-one;
447) 2-(3-((1r,3r)-3-chloro-1-(4-methyl-4H-1,2,4-triazol-3-yl)cyclobutyl)phenyl)-4-(difluoromethyl)-6-(((1-methylcyclobutyl)amino)methyl)isoindolin-1-one;
448) 2-(3-((1s,3s)-3-methoxy-1-(4-methyl-4H-1,2,4-triazol-3-yl)cyclobutyl)phenyl)-6-(((1-methylcyclobutyl)amino)methyl)isoindolin-1-one;
449) 2-(3-((1r,3r)-3-methoxy-1-(4-methyl-4H-1,2,4-triazol-3-yl)cyclobutyl)phenyl)-6-(((1-methylcyclobutyl)amino)methyl)isoindolin-1-one;
450) 2-(3-((1r,3r)-3-cyclopropoxy-1-(4-methyl-4H-1,2,4-triazol-3-yl)cyclobutyl)-phenyl)-6-(((1-methylcyclobutyl)amino)methyl)-4-(trifluoromethyl)isoindolin-1-one;
451) 4-chloro-2-(3-((1r,3r)-3-chloro-1-(4-methyl-4H-1,2,4-triazol-3-yl)cyclobutyl)phenyl)-6-(((1-methylcyclobutyl)amino)methyl)isoindolin-1-one;
452) 4-chloro-2-(3-((1s,3s)-3-chloro-1-(4-methyl-4H-1,2,4-triazol-3-yl)cyclobutyl)phenyl)-6-(((1-methylcyclobutyl)amino)methyl)isoindolin-1-one;
453) 6-(2-fluoro-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one;
454) 2-(3-((1r,3s)-3-ethyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;
455) 2-(3-((1s,3r)-3-ethyl-1-(4-methyl-4H-1,2,4-triazol-3-yl)cyclobutyl)phenyl)-6-(((1-methylcyclobutyl)amino)methyl)-4-(trifluoromethyl)isoindolin-1-one;
456) 6-((R)-cyclopropyl((1-methylcyclobutyl)amino)methyl)-2-(3-((S)-(4-methyl-4H-1,2,4-triazol-3-yl)(oxetan-3-yl)methyl)phenyl)-4-(trifluoromethyl)isoindolin-1-one;
457) 6-((S)-cyclopropyl((1-methylcyclobutyl)amino)methyl)-2-(3-((S)-(4-methyl-4H-1,2,4-triazol-3-yl)(oxetan-3-yl)methyl)phenyl)-4-(trifluoromethyl)isoindolin-1-one;

458) 4-(difluoromethyl)-2-(3-((R)-((1r,3R)-3-fluorocyclobutyl)(4-methyl-4H-1,2,4-triazol-3-yl)methyl)phenyl)-6-(((1-methylcyclobutyl)amino)methyl)isoindolin-1-one;

459) 4-(difluoromethyl)-2-(3-((R)-((1s,3S)-3-fluorocyclobutyl)(4-methyl-4H-1,2,4-triazol-3-yl)methyl)phenyl)-6-(((1-methylcyclobutyl)amino)methyl)isoindolin-1-one;

460) 4-(difluoromethyl)-2-(3-((S)-((1r,3S)-3-fluorocyclobutyl)(4-methyl-4H-1,2,4-triazol-3-yl)methyl)phenyl)-6-(((1-methylcyclobutyl)amino)methyl)isoindolin-1-one;

461) 4-(difluoromethyl)-2-(3-((S)-((1s,3R)-3-fluorocyclobutyl)(4-methyl-4H-1,2,4-triazol-3-yl)methyl)phenyl)-6-(((1-methylcyclobutyl)amino)methyl)isoindolin-1-one;

462) 2-(3-((3-fluorothietan-3-yl)(4-methyl-4H-1,2,4-triazol-3-yl)methyl)phenyl)-6-(((1-methylcyclobutyl)amino)methyl)-4-(trifluoromethyl)isoindolin-1-one;

463) (R)-6-(((2-fluoro-2-methylpropyl)amino)methyl)-2-(3-((4-methyl-4H-1,2,4-triazol-3-yl)(oxetan-3-yl)methyl)phenyl)-4-(trifluoromethyl)isoindolin-1-one;

464) (R)-6-((isobutylamino)methyl)-2-(3-((4-methyl-4H-1,2,4-triazol-3-yl)(oxetan-3-yl)methyl)phenyl)-4-(trifluoromethyl)isoindolin-1-one;

465) (R)-2-(3-((4-methyl-4H-1,2,4-triazol-3-yl)(oxetan-3-yl)methyl)phenyl)-6-((((1-methylcyclopropyl)methyl)amino)methyl)-4-(trifluoromethyl)isoindolin-1-one;

466) (R)-2-(3-((4-methyl-4H-1,2,4-triazol-3-yl)(oxetan-3-yl)methyl)phenyl)-6-(((1-methylcyclopropyl)amino)methyl)-4-(trifluoromethyl)isoindolin-1-one;

467) 6-((((R)-1-cyclobutylethyl)amino)methyl)-2-(3-((1r,3R)-3-methoxy-1-(4-methyl-4H-1,2,4-triazol-3-yl)cyclobutyl)phenyl)-4-(trifluoromethyl)isoindolin-1-one;

468) (R)-2-(3-((4-methyl-4H-1,2,4-triazol-3-yl)(oxetan-3-yl)methyl)phenyl)-6-((neopentylamino)methyl)-4-(trifluoromethyl)isoindolin-1-one;

469) 6-(((1R,3r,5S)-bicyclo[3.1.0]hexan-3-ylamino)methyl)-2-(3-((R)-(4-methyl-4H-1,2,4-triazol-3-yl)(oxetan-3-yl)methyl)phenyl)-4-(trifluoromethyl)isoindolin-1-one;

470) 6-((((S)-1-cyclobutylethyl)amino)methyl)-2-(3-((1r,3S)-3-methoxy-1-(4-methyl-4H-1,2,4-triazol-3-yl)cyclobutyl)phenyl)-4-(trifluoromethyl)isoindolin-1-one;

471) 6-(((3,3-difluoro-1-methylcyclobutyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

472) 6-(((1R,5S,6r)-3-oxabicyclo[3.1.0]hexan-6-ylamino)methyl)-2-(3-((R)-(4-methyl-4H-1,2,4-triazol-3-yl)(oxetan-3-yl)methyl)phenyl)-4-(trifluoromethyl)isoindolin-1-one;

473) 6-((((1-hydroxycyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

474) 2-(3-((1r,3r)-3-methoxy-1-(4-methyl-4H-1,2,4-triazol-3-yl)cyclobutyl)phenyl)-6-((((1-methylcyclopropyl)methyl)amino)methyl)-4-(trifluoromethyl)isoindolin-1-one;

475) 2-(3-((1r,3r)-3-methoxy-1-(4-methyl-4H-1,2,4-triazol-3-yl)cyclobutyl)phenyl)-6-(((1-methylcyclopropyl)amino)methyl)-4-(trifluoromethyl)isoindolin-1-one;

476) 2-(3-((1r,3r)-3-methoxy-1-(4-methyl-4H-1,2,4-triazol-3-yl)cyclobutyl)phenyl)-6-((oxetan-3-ylamino)methyl)-4-(trifluoromethyl)isoindolin-1-one;

477) 6-((cyclopropylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

478) 6-(((3-hydroxy-3-methylazetidin-1-yl)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

479) 2-(3-((1r,3r)-3-methoxy-1-(4-methyl-4H-1,2,4-triazol-3-yl)cyclobutyl)phenyl)-6-(((3-methyloxetan-3-yl)amino)methyl)-4-(trifluoromethyl)isoindolin-1-one;

480) 6-(azetidin-1-ylmethyl)-2-(3-((1r,3r)-3-methoxy-1-(4-methyl-4H-1,2,4-triazol-3-yl)cyclobutyl)phenyl)-4-(trifluoromethyl)isoindolin-1-one;

481) 2-(3-((1r,3r)-3-methoxy-1-(4-methyl-4H-1,2,4-triazol-3-yl)cyclobutyl)phenyl)-6-((neopentylamino)methyl)-4-(trifluoromethyl)isoindolin-1-one;

482) 6-((((2,2-difluorocyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

483) 6-(((2-fluoro-2-methylpropyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

484) 6-((((1s,3S)-3-hydroxy-1-methylcyclobutyl)amino)methyl)-2-(3-((1r,3R)-3-methoxy-1-(4-methyl-4H-1,2,4-triazol-3-yl)cyclobutyl)phenyl)-4-(trifluoromethyl)isoindolin-1-one;

485) 6-((bicyclo[1.1.1]pentan-1-ylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

486) 6-((((1-fluorocyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

487) 2-(3-((1r,3r)-3-methoxy-1-(4-methyl-4H-1,2,4-triazol-3-yl)cyclobutyl)phenyl)-6-(((1-(methoxymethyl)cyclopropyl)amino)methyl)-4-(trifluoromethyl)isoindolin-1-one;

488) 6-(((3,3-dimethylcyclobutyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

489) 6-((((1-(hydroxymethyl)cyclobutyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

490) 6-(azepan-1-ylmethyl)-2-(3-((1r,3r)-3-methoxy-1-(4-methyl-4H-1,2,4-triazol-3-yl)cyclobutyl)phenyl)-4-(trifluoromethyl)isoindolin-1-one;

491) 6-(((2-(difluoromethoxy)ethyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

492) 6-(((1R,5S,6r)-3-oxabicyclo[3.1.0]hexan-6-ylamino)methyl)-2-(3-((1r,3R)-3-methoxy-1-(4-methyl-4H-1,2,4-triazol-3-yl)cyclobutyl)phenyl)-4-(trifluoromethyl)isoindolin-1-one;

493) 2-(3-((1r,3r)-3-methoxy-1-(4-methyl-4H-1,2,4-triazol-3-yl)cyclobutyl)phenyl)-6-(((1-(2-methoxyethyl)cyclobutyl)amino)methyl)-4-(trifluoromethyl)isoindolin-1-one;

494) 6-(((3-(difluoromethyl)cyclobutyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

495) 2-(3-((1r,3r)-3-methoxy-1-(4-methyl-4H-1,2,4-triazol-3-yl)cyclobutyl)phenyl)-6-(((1-(methoxymethyl)cyclobutyl)amino)methyl)-4-(trifluoromethyl)isoindolin-1-one;

496) 6-((((1-(fluoromethyl)cyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

497) 6-(((3-fluoro-3-methylcyclobutyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

498) 6-((bicyclo[3.1.0]hexan-3-ylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

499) 6-(((2-(2,2-difluorocyclobutyl)ethyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

500) 6-((2-oxabicyclo[2.2.1]heptan-5-ylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

501) 6-((((2,2-difluoro-1-methylcyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

502) 2-(3-((1r,3R)-3-methoxy-1-(4-methyl-4H-1,2,4-triazol-3-yl)cyclobutyl)phenyl)-6-((((1R,2R)-2-methylcyclopropyl)amino)methyl)-4-(trifluoromethyl)isoindolin-1-one;

503) 6-(((((1S,3R)-2,2-difluoro-3-methylcyclopropyl)methyl)amino)methyl)-2-(3-((1r,3S)-3-methoxy-1-(4-methyl-4H-1,2,4-triazol-3-yl)cyclobutyl)phenyl)-4-(trifluoromethyl)isoindolin-1-one;

504) 6-(((1-fluorospiro[2.3]hexan-5-yl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

505) 3-(((2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methyl)amino)cyclobutanecarbonitrile;

506) 6-((((1R,2R)-2-(1,1-difluoroethyl)cyclopropyl)amino)methyl)-2-(3-((1r,3R)-3-methoxy-1-(4-methyl-4H-1,2,4-triazol-3-yl)cyclobutyl)phenyl)-4-(trifluoromethyl)isoindolin-1-one;

507) 6-((((1-(fluoromethyl)cyclobutyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

508) 6-(((1R,5R)-bicyclo[3.1.0]hexan-1-ylamino)methyl)-2-(3-((1r,3R)-3-methoxy-1-(4-methyl-4H-1,2,4-triazol-3-yl)cyclobutyl)phenyl)-4-(trifluoromethyl)isoindolin-1-one;

509) 6-((((3-(hydroxymethyl)bicyclo[3.1.0]hexan-3-yl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one;

510) 6-((((4,4-difluorospiro[2.2]pentan-1-yl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one; and 511) 2-(3-((1r,3r)-3-methoxy-1-(4-methyl-4H-1,2,4-triazol-3-yl)cyclobutyl)phenyl)-6-((propylamino)methyl)-4-(trifluoromethyl)isoindolin-1-one.

The disclosure further comprises a method of treating a cancer, comprising administering to a subject in need thereof, a compound of formula (I), or a pharmaceutically acceptable salt or solvate thereof.

Definitions

It is to be noted that the term "a" or "an" object may refer to one or more of that object. As such, the terms "a" (or "an"), "one or more," and "at least one" can be used interchangeably herein.

All technical and scientific terms used herein have the same meaning as those understood respectively to those skilled in the art, unless otherwise specifically defined herein. Efforts have been made to ensure accuracy with respect to numbers used (e.g. amounts, temperature, etc.) but some experimental errors and deviations should be accounted for when reading this disclosure.

Throughout the specification and the claims, the words "comprise," "comprises," and "comprising" are used in a non-exclusive sense, except where the context requires otherwise. It is to be understood that embodiments described herein include "consisting of" and/or "consisting essentially of" embodiments refer to some aspect as being exclusively defined.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided and unless the context clearly dictates otherwise, it is understood that each intervening value, to the tenth of the unit of the lower limit, between the upper and lower limit of the range, is also disclosed, and that any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

"Geminal" refers to the relationship between two moieties that are attached to the same atom. For example, in the moiety —$CH_2$—$CR^xR^y$—, $R^x$ and $R^y$ are geminal to one another, and $R^x$ may be referred to as a geminal R group to $R^y$.

"Vicinal" refers to the relationship between two moieties that are attached to adjacent atoms. For example, in the residue —$CHR^x$—$CHR^y$—, $R^x$ and $R^y$ are vicinal and $R^x$ may be referred to as a vicinal R group to $R^y$.

"Optionally substituted" unless otherwise specified means that a group may be unsubstituted, or it may be substituted by one or more (e.g., 1, 2, 3, 4 or 5) non-hydrogen atoms or monovalent groups, such that the substituents may be the same or different from one another. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4 or 1 to 5 substituents. In any embodiment in which a group is substituted by two or more substituents, any two such substituents may be situated germinal to one another, as in, e.g., 3,3-difluoro-cyclobutyl.

Structures of molecules herein are typically represented by 2D structure diagrams that embody a number of labeling and layout conventions well understood by synthetic and medicinal chemists. Hydrogen atoms that are bonded to carbon atoms are typically not displayed (principally to reduce clutter) and it is assumed that any depicted carbon has a valency of 4 and that any bonds not explicitly depicted are satisfied by bonds to the number of hydrogen atoms required to satisfy a valency of 4. Correspondingly when structures are depicted in "Markush" form and substituents are presented as lists any "missing" valence is assumed to be completed by a hydrogen atom, in the absence of a specific direction to the contrary.

Heteroatom refers to any atom other than carbon or hydrogen. Typical heteroatoms found in small organic molecules are selected from: nitrogen, oxygen, fluorine, phosphorous, sulfur, chlorine, and bromine. It is understood by those of skill in the art that where the term heteroatom used to denote a member of a ring (e.g., a heteroaromatic ring) then monovalent heteroatoms such as halogen are excluded.

"Alkyl" as used herein refers to a saturated linear (i.e., unbranched) or branched univalent hydrocarbon functional group derived by the removal of one hydrogen atom from one carbon atom of a parent alkane. An alkyl group having n carbon atoms, as a radical, has formula $C_nH_{2n+1}$. Alkyl groups having a given number of carbon atoms can be designated as follows: $C_n$-alkyl to denote any alkyl radical having n carbon atoms, or $C_{n1-n2}$-alkyl to denote any alkyl radical having from n1 to n2 carbon atoms. Thus $C_{1-10}$ means any alkyl radical having from one to ten carbon atoms. Particular alkyl groups of interest herein are those having 1 to 20 carbon atoms (a "$C_{1-20}$-alkyl"), those having 1 to 12 carbon atoms (a "$C_{1-12}$-alkyl"), those having 1 to 6 carbon atoms (a "$C_{1-6}$-alkyl"), having 2 to 6 carbon atoms (a "$C_{2-6}$-alkyl"), or having 1 to 4 carbon atoms (a "$C_{1-4}$-alkyl"). Examples of alkyl groups include, but are not limited to: methyl, ethyl, n-propyl, isopropyl, n-butyl, t-butyl, isobutyl, sec-butyl. It is to be understood that an alkyl group can bond to another group or moiety at any carbon atom in its structure: thus, for example, butan-1-yl (n-butyl) and butan-2-yl (sec-butyl) are contemplated by the definition herein.

"Alkenyl" as used herein refers to an unsaturated linear (i.e., unbranched) or branched univalent hydrocarbon functional group having at least one site of olefinic unsaturation, i.e., having at least one instance of a carbon-carbon double bond (represented by the formula C=C), and having the number of carbon atoms designated. An alkenyl group having n carbon atoms and a single double-bond, as a radical, has formula $C_nH_{2n-1}$ and is derived by the removal of one hydrogen atom from one carbon atom of a parent alkene. Alkenyl groups having a given number of carbon atoms can be designated as follows: $C_n$-alkenyl to denote any alkenyl radical having n carbon atoms, or $C_{n1-n2}$-alkenyl to denote any alkenyl radical having from n1 to n2 carbon atoms. Thus, $C_{2-10}$-alkenyl means an alkenyl group having from two to ten carbon atoms. An alkenyl group may contain constituent carbon atoms that are in "cis" or "trans" configurations, or "E" or "Z" configurations, with respect to a given double bond. Particular alkenyl groups are those having 2 to 20 carbon atoms (a "$C_{2-20}$-alkenyl"), having 2 to 8 carbon atoms (a "$C_{2-8}$-alkenyl"), having 2 to 6 carbon atoms (a "$C_{2-6}$-alkenyl"), or having 2 to 4 carbon atoms (a "$C_{2-4}$-alkenyl"). Preferred alkenyl groups have one double bond. Other alkenyl groups may have two double bonds (and may be referred to as dienyl). In alkenyl groups having more than one double bond, a pair of double bonds may be separated by one carbon-carbon single bond, in which case the arrangement is referred to as "conjugated", or they may be separated by more than one carbon-carbon single bond. Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear (i.e., unbranched) or branched univalent hydrocarbon having at least one site of acetylenic unsaturation, i.e., having at least one instance of a carbon-carbon triple bond (represented by the formula formula C≡C) and having the number of carbon atoms designated. An alkynyl group having n carbon atoms and a single triple-bond, as a radical, has formula $C_nH_{2n-3}$, and is derived by the removal of one hydrogen atom from one carbon atom of a parent alkyne. Alkynyl groups having a given number of carbon atoms can be designated as follows: $C_n$-alkynyl to denote any alkynyl radical having n carbon atoms, or $C_{n1-n2}$-alkynyl to denote any alkynyl radical having from n1 to n2 carbon atoms. Particular alkynyl groups are those having 2 to 20 carbon atoms (a "$C_{2-20}$-alkynyl"), having 2 to 8 carbon atoms (a "$C_{2-8}$-alkynyl"), having 2 to 6 carbon atoms (a "$C_{2-6}$-alkynyl"), or having 2 to 4 carbon atoms (a "$C_{2-4}$-alkynyl"). Examples of alkynyl groups include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkylene" as used herein refers to a saturated linear (i.e., unbranched) or branched bivalent hydrocarbon group having the number of carbon atoms designated. An alkylene group having n carbon atoms, as a radical, has formula —$C_nH_{2n}$—. Particular alkylene groups are those having 1 to 6 carbon atoms (a "$C_{1-6}$-alkylene"), 1 to 5 carbon atoms (a "$C_{1-5}$-alkylene"), having 1 to 4 carbon atoms (a "$C_{1-4}$-alkylene"), or 2 to 3 carbon atoms (a "$C_{2-3}$-alkylene"). Examples of alkylene radicals include, but are not limited to, methylene (—CH$_2$—), ethylene (—CH$_2$—CH$_2$—), propylene (—CH$_2$—CH$_2$—CH$_2$—), butylene (—CH$_2$—CH$_2$—CH$_2$—CH$_2$—), sec-butylene (—CH(CH$_3$)—CH$_2$—CH$_2$—) and the like.

Cyclic (ring-containing) moieties comprise atoms bonded together in a ring, and have one or more substituents other than hydrogen atoms bonded to one or more ring atoms. Each atom in the ring defines a vertex of a polygon.

Two ring atoms are adjacent to one another in that ring if they are bonded to one another in the ring. In rings having 4 or more ring atoms, adjacent atoms are bonded to one another but to no other atom in the same ring. In a three-membered ring, each atom is necessarily bonded to each other atom in the ring. Two adjacent ring atoms define one "edge" of the ring.

Two or more cyclic moieties may join to one another in one of several ways to form ring systems that comprise more than one ring.

Two rings are fused to one another if two ring atoms are adjacent to one another in both rings and are shared by both rings. Such rings are said to share an "edge".

Spirocyclic ring systems comprise a pair of rings that share a single vertex. Such systems contain a ring junction at which the two rings share a single ring atom.

Bridged ring systems contain at least a pair of rings in which two or more non-adjacent ring atoms are shared by two or more rings. The two non-adjacent ring atoms in question are referred to as "bridgehead" atoms and the pair of bridgehead atoms are members of three different rings. Examples of carbocyclic radicals containing bridged bicyclic rings are norbornyl and adamantyl.

Chained ring systems contain two rings that are joined to one another but do not share any ring atom in common: one ring is a substituent of the other, and vice versa. Biphenyl is an example of a chained ring system.

Ring systems may contain pairs of rings that are fused or chained to one another, spiro-joined, or bridged, or in the case of three or more rings, joined in combinations of ways thereof.

"Carbocycle" as used herein refers to aromatic, saturated or unsaturated cyclic univalent hydrocarbon groups having the number of annular (i.e., ring) carbon atoms designated (i.e., $C_{3-10}$ means three to ten annular carbon atoms). Carbocyclic groups have a single ring ("monocycles") or more than one ring ("bicycles", "tricycles", or polycycles, more generally). Two or more carbocyclic rings may be joined to one another by fused, spiro, bridged, or chained connections as further described elsewhere herein.

It is intended herein that the term carbocycle encompasses radicals having one or more adjacent pairs of ring atoms between which are double bonds, and that, where more than one such double bond is present, the double bonds may or may not form a conjugated system within the ring. Thus carbocycles may be more specifically designated according to whether they are fully saturated ("cycloalkyl"), unsaturated at least in part ("cycloalkenyl"), or fully conjugated, ("aromatic" or "aryl"). Cycloalkyl groups are fully saturated radicals and are derived by the removal of one hydrogen atom from one carbon atom of a parent cycloalkane. Particular cycloalkyl groups are those having from 3 to 12 annular carbon atoms ($C_{3-12}$-cycloalkyl). A preferred cycloalkyl is a monocyclic hydrocarbon having from 3 to 8 annular carbon atoms (a "$C_{3-8}$-cycloalkyl"), or having 3 to 6 carbon atoms (a "$C_{3-6}$-cycloalkyl"). Single ring cycloalkyl radicals have formula $C_nH_{2n-1}$. Examples of cycloalkyl groups include, but are not limited to, cyclopropyl, cyclobutyl, cyclopentyl, cyclohexyl, and cycloheptyl. Cycloalkenyl groups have one or more double bonds between adjacent ring carbon atoms. Examples of cycloalkenyl groups include 1-cyclohex-1-enyl, and 1-cyclohex-3-enyl.

"Aryl" as used herein refers to a carbocyclic group having a aromatic single ring (e.g., phenyl) or multiple aromatic rings fused to one another (e.g., naphthyl). Preferably, an aryl group comprises from 6 to 20 carbon atoms, more preferably between 6 to 12 carbon atoms. Particularly preferred aryl groups are those having from 6 to 14 annular carbon atoms (a "$C_{6-14}$-aryl"). The term aromatic is used herein as it is typically used in organic chemistry, meaning, with a few understood exceptions, rings and ring systems in which the annular atoms contribute a total of (4n+2) pi electrons to a set of delocalized molecular orbitals, where n is a non-zero positive integer.

Typical aryl groups include, but are not limited to, groups derived from fused ring systems that comprise one or more aromatic rings, or conjugated ring systems, such as but not limited to aceanthrylene, acenaphthylene, acephenanthrylene, anthracene, azulene, benzene, chrysene, coronene, fluoranthene, heptaphene, hexacene, hexaphene, as-indacene, s-indacene, indene, naphthalene (hexalene), octacene, octaphene, octalene, ovalene, pentacene, pentalene, pentaphene, perylene, phenalene, phenanthrene, picene, pleiadene, pyrene, pyranthrene, rubicene, tetraphenylene, triphenylene, and trinaphthalene.

A "heterocyclic", or "heterocyclyl", group as used herein refers to a saturated or an unsaturated but non-aromatic, cyclic group having one or more rings that comprises at least one carbon atom and one or more heteroatoms. Typically such a group has from 1 to 14 ring carbon atoms and from 1 to 6 ring heteroatoms that can be same or different from each other. Such a group is typically derived by the removal of one hydrogen atom from one ring atom of a parent heterocycle. It is intended herein that the term heterocyclyl encompasses radicals having one or more double bonds between one or more respective adjacent pairs of ring atoms, and that where more than one such double bond is present, the double bonds do not form a conjugated system within the ring.

Particularly preferred heterocyclyl groups are: 3- to 14-membered rings having 1 to 13 annular carbon atoms and 1 to 6 annular heteroatoms independently selected from nitrogen, phosphorus, oxygen and sulfur; 3- to 12-membered rings having 1 to 11 annular carbon atoms and 1 to 6 annular heteroatoms independently selected from nitrogen, phosphorus, oxygen and sulfur; 3- to 10-membered rings having 1 to 9 annular carbon atoms and 1 to 4 annular heteroatoms independently selected from nitrogen, phosphorus, oxygen and sulfur; 3- to 8-membered rings having 1 to 7 annular carbon atoms and 1 to 4 annular heteroatoms independently selected from nitrogen, phosphorus, oxygen and sulfur; and 3- to 6-membered rings having 1 to 5 annular carbon atoms and 1 to 4 annular heteroatoms independently selected from nitrogen, phosphorus, oxygen and sulfur. In one variation, heterocyclyl include monocyclic 3-, 4-, 5-, 6- or 7-membered rings having from 1 to 2, 1 to 3, 1 to 4, 1 to 5 or 1 to 6 annular carbon atoms and 1 to 2, 1 to 3 or 1 to 4 annular heteroatoms independently selected from nitrogen, phosphorus, oxygen and sulfur. In another variation, heterocyclyl includes polycyclic non-aromatic rings having from 1 to 12 annular carbon atoms and 1 to 6 annular heteroatoms independently selected from nitrogen, phosphorus, oxygen and sulfur. Exemplary heterocyclic rings include: oxirane, aziridine, azetidine, pyrrolidine, piperazine, piperidine, oxetane, tetrahydrofuran, and morpholine.

A heterocyclic ring may make fused, spiro, or bridged, connections or make any combination of such connections to one or more other rings.

"Heteroaryl" or "heteroaromatic", as used herein, refers to an aromatic cyclic group having from 1 to 14 ring carbon atoms and at least one ring heteroatom, including but not limited to heteroatoms such as nitrogen, phosphorus, oxygen and sulfur. The term refers to a monovalent heteroaromatic radical derived by the removal of one hydrogen atom from a single ring atom of a parent heteroaromatic ring system. A heteroaryl group may have a single ring (e.g., pyridyl, furyl) or multiple fused rings (e.g., indolizinyl, benzothienyl). Particular heteroaryl groups are 5- to 14-membered rings having 1 to 12 annular (i.e., ring) carbon atoms and 1 to 6 annular (i.e., ring) heteroatoms independently selected from nitrogen, phosphorus, oxygen and sulfur; 5- to 10-membered rings having 1 to 8 annular carbon atoms and 1 to 4 annular heteroatoms independently selected from nitrogen, phosphorus, oxygen and sulfur; and 5-, 6- or 7-membered rings having 1 to 5 annular carbon atoms and 1 to 4 annular heteroatoms independently selected from nitrogen, oxygen and sulfur In one variation, heteroaryl include monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, phosphorus, oxygen and sulfur.

Typical heteroaryl groups include, but are not limited to, groups derived from acridine, arsindole, carbazole, p-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferred heteroaryl groups are thiophene, pyrrole, benzothiophene, benzofuran, indole, pyridine, quinoline, imidazole, oxazole and pyrazine, and those derived therefrom.

Rings of different categories may be connected to one another, such as by fused, spiro, or bridged, connections, or by combinations thereof. Such a ring system can be referred to as a "mixed" ring system.

For example, at least one ring of a multiple ring system can be aromatic on its own, though one or more of the remaining fused rings may be not aromatic. Examples of fused ring systems that contain at least one aromatic ring and at least one partially saturated ring include fluorene, indane, and biphenylene.

A mixed ring system having more than one ring where at least one ring is aromatic and at least one ring is non-aromatic may be connected to another structure by bonding to either an aromatic ring atom or a non-aromatic ring atom.

A heteroaryl group having more than one ring where at least one ring is non-aromatic may be connected to another structure at either an aromatic ring position or at a non-aromatic ring position.

Similarly, carbocyclic and heterocyclic groups may join to one another in one of several ways to form ring systems that comprise more than one ring.

"Halo" or Halogen" refers to fluoro, chloro, bromo, and/or iodo. An alkyl group in which one or more hydrogen atoms is replaced with a halogen is referred to as a "haloalkyl", for example, "$C_{1-6}$-haloalkyl." Where a moiety is substituted with more than one halogen, it may be referred to by using a prefix corresponding to the number of halogen moieties attached, e.g., dihaloaryl, trihaloaryl, refer to aryl groups substituted with two ("di") or three ("tri")halo groups respectively. It is to be understood that, where more than one halo groups are present they are not necessarily the same as one another. Thus 4-chloro-3-fluorophenyl is within the scope of dihaloaryl. An alkyl group in which every hydrogen atom is replaced with a halogen atom is referred to as a "perhaloalkyl." The term haloalkyl thus includes perhaloalkyl unless from context perhaloalkyl is specifically excluded. A preferred perhaloalkyl group is trifluoromethyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C═O.

"Carbenyl", when used as a ring substituent, refers to the moiety ═C, i.e., a carbon atom double-bonded to a carbon atom in a ring. It means that a single carbon atom replaces two hydrogen (or other monovalent) atoms that are bonded to a ring carbon atom and is therefore bonded to the ring carbon atom via a double bond. In general, a carbenyl may be represented as $R_cR_dC$═, where $R_cR_c$ are independently either hydrogen or alkyl.

"Thiocarbonyl" refers to the group C═S.

"Oxo" refers to the moiety ═O, i.e., an oxygen atom double-bonded to a second atom other than oxygen. When used as a ring substituent it means that a ring atom such as a carbon atom is bonded via a double bond to an oxygen atom other than a ring atom.

"Prodrug" refers to a pharmacologically inactive derivative of a drug molecule that requires a transformation within the body, usually a metabolic transformation, to release the active drug.

"Promoiety" refers to a form of protecting group that, when used to mask a functional group within a drug molecule converts the drug into a prodrug. Typically, the promoiety will be attached to the drug via bond(s) that are cleaved by enzymatic or non-enzymatic means in vivo. Ideally, the promoiety is rapidly cleared from the body upon cleavage from the prodrug.

"Protecting group" refers to a grouping of atoms that when attached to a reactive group in a molecule masks, reduces or prevents that reactivity. Examples of protecting groups can be found in Green et al., "Protective Groups in Organic Chemistry", (Wiley, 2nd ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl" ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenyl-methyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

Compounds of Formula (I), described herein, or a salt or solvate thereof may exist in stereoisomeric forms (e.g., such a compound contains one or more asymmetric carbon atoms). The individual stereoisomers (such as purified enantiomers and diastereomers) and mixtures of these or enantiomerically/diastereomerically enriched mixtures are included within the scope of the subject matter disclosed herein. The stereochemistry, as shown in the examples, is arbitrarily assigned.

It is further understood that a compound or salt of Formula (I) may exist in tautomeric forms other than that shown in the formula and these are also included within the scope of the subject matter disclosed herein.

The subject matter disclosed herein also includes isotopically-labelled forms of the compounds described herein, i.e., compounds that have the Formula shown herein but for the fact that one or more constituent atoms are replaced by an atom having an atomic mass or mass number different from the atomic mass or mass number of that atom that is usually found in nature and/or at an abundance not normally found in nature. Examples of isotopes that can be incorporated into compounds described herein and pharmaceutically acceptable salts thereof, at levels that differ from the natural distribution of such isotopes, include isotopes of hydrogen, carbon, nitrogen, oxygen, phosphorous, sulphur, fluorine, iodine, and chlorine, such as $^2H$ (denoted D), $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}C$, $^{123}I$, $^{125}I$, and $^{131}I$. In most instances any hydrogen atom in a molecule disclosed herein may be substituted by a deuterium atom. A given isotopically substituted molecule may then contain a deuterium atom at more than one position. In particular, a methyl group in a molecule may be perdeuterated, denoted CD3. In the case of deuterated molecules, a molecule preferably has an isotopic enrichment factor of at least 3500 (~52.5% deuterium incorporation) at a given position, where an isotopic enrichment factor of 6633 represents 99.5% incorporation.

The subject matter disclosed herein further includes prodrugs, metabolites, and pharmaceutically acceptable salts of compounds of Formula (I). Metabolites of the compounds of Formula (I) include compounds produced by a process comprising contacting a compound of Formula (I) with a mammal for a period of time sufficient to yield a metabolic product thereof.

In some embodiments, the salts of the compounds of the invention are pharmaceutically acceptable salts. "Pharmaceutically acceptable salts" are those salts that retain at least some of the biological activity of the free (non-salt) compound and that can be administered as drugs or pharmaceuticals to a subject. Such salts, for example, include: (1) acid addition salts; (2) salts formed when an acidic proton is replaced by a metal ion; or (3) an acidic proton coordinates with an organic base. Pharmaceutically acceptable salts can be prepared in situ in the manufacturing process, or by separately reacting a purified compound of the invention in its free acid or base form with a suitable organic or inorganic base or acid respectively, and isolating the salt thus formed during subsequent purification.

If the compound of Formula (I) is a base, the desired pharmaceutically acceptable salt may be prepared as an acid addition salt by any suitable method available in the art, for example, treatment of the free base with an inorganic acid, such as hydrochloric acid, hydrobromic acid, sulfuric acid, nitric acid, methanesulfonic acid, phosphoric acid and others of like property, or with an organic acid, such as acetic acid, maleic acid, succinic acid, mandelic acid, fumaric acid, propionic acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, and others of like property.

If the compound of Formula (I) is an acid, one or more acidic protons present may be replaced by a metal ion, e.g., an alkali metal ion, an alkaline earth ion, or an aluminum ion. The desired pharmaceutically acceptable salt may then be prepared by any suitable method, for example, treatment of the free acid with an inorganic or organic base, such as an amine (primary, secondary or tertiary), an alkali metal hydroxide or alkaline earth metal hydroxide, or the like. Examples of suitable salts include, but are not limited to, organic salts derived from amino acids, such as glycine and arginine, ammonia, and cyclic amines, such as piperidine, morpholine and piperazine, alcoholamines such as ethanolamine, diethanolamine, and triethanolamine, and inorganic salts derived from sodium, calcium, potassium, magnesium, manganese, iron, copper, zinc, aluminum and lithium. Acceptable inorganic bases include aluminum hydroxide, calcium hydroxide, potassium hydroxide, sodium carbonate, sodium hydroxide, and the like.

The compounds herein may also be present as solvates, such as crystallized with a corresponding quantity of a solvent molecule, in a ratio that may or may not be stoichiometric.

A compound of Formula (I) can also be in the form of a "prodrug," which includes compounds with moieties that can be metabolized in vivo. Generally, prodrugs are metabolized in vivo by esterases or by other mechanisms to form active drugs inside the patient's body. Examples of prodrugs and their uses are well known in the art (see, e.g., Berge et al. (1977) "Pharmaceutical Salts", *J. Pharm. Sci.*, 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the Formula herein.

It is also to be understood that the subject matter disclosed herein includes combinations and subsets of the particular categories (e.g., salt forms, tautomers, stereoisomeric forms) described herein.

The terms "treat" and "treatment" refer to therapeutic treatment, wherein an object is to slow down, diminish, or attenuate, an undesired physiological change or disorder, such as the development or spread of arthritis or cancer. For purposes of this disclosure, beneficial or desired clinical results include, but are not limited to: alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to a patient's expected survival if not receiving treatment. Those in need of treatment include those with the condition or disorder, and further include those who are only experiencing an early stage of the disorder or disease, in which one or more typical symptoms may yet to manifest.

The phrase "therapeutically effective amount" means an amount of a compound of the present invention (or a salt thereof), that produces a desired therapeutic outcome, such as: (i) treating the particular disease, condition, or disorder, (ii) attenuating, ameliorating, or eliminating one or more symptoms of the particular disease, condition, or disorder, or (iii) preventing or delaying the onset of one or more symptoms of the particular disease, condition, or disorder described herein. In the case of a cancer, the therapeutically effective amount of the drug may reduce the severity or duration of, stabilize the severity of, or eliminate one or more symptoms of the cancer. It may do this by reducing the number of cancer cells; reducing a tumor size or checking its rate of growth; inhibiting (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR). In other therapeutic areas, to be termed a therapeutic use, beneficial or desired results include, e.g., decreasing one or more symptoms resulting from the disease (biochemical, histologic and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients.

The term "cancer" refers to or describe the physiological condition in mammals that is typically characterized by unregulated cell growth and an invasive nature, wherein the cancerous cells are capable of local invasion and/or metastasis to noncontiguous sites. As used herein, "cancer cells," "cancerous cells," or "tumor cells" refer to the cells that are characterized by this unregulated cell growth and invasive property. A "tumor" comprises more than one cancerous cells. Cancers can further be divided into liquid or solid types. The term "cancer" as used herein generally encompasses all types of cancers, subject to specific context. Examples of cancers include, but are not limited to, carcinoma, melanoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, esophageal cancer, endometrial or uterine carcinoma, salivary gland carcinoma, kidney or renal cancer, prostate cancer, vulval cancer, thyroid cancer, hepatic carcinoma, anal carcinoma, penile carcinoma, Ewing's sarcoma, medulloblastomer, as well as head and neck cancer.

A "chemotherapeutic agent" is a chemical compound or biologic useful in the treatment of cancer. A chemotherapeutic agent can be an immunotherapeutic agent. As used herein, an "immunotherapeutic agent" is a compound that enhances the immune system to help fight cancer, specifically or non-specifically. Immunotherapeutics include monoclonal antibodies and non-specific immunotherapies that boost the immune system, As used herein, a "combination therapy" is a therapy that includes two or more different compounds, administered simultaneously or contemporaneously. Typically, each of the two or more different compounds has a different mechanism of action. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances. Combination therapies can comprise two more compounds in a single delivery vehicle such as a tablet, or can comprise doses in separate formulations, such as different tablets, or a tablet and an injectable solution.

As used herein, the term "effective amount" means such an amount of a compound of the invention that, in combination with its parameters of efficacy and toxicity, should be effective in a given administered form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial results may be or is achieved. Suitable doses of any of the co-administered compounds may optionally be lowered due to the combined action (e.g., additive or synergistic effects) of the compounds. In various embodiments, an effective amount of the composition or therapy may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

A "prophylactically effective amount" refers to an amount of a compound, or pharmaceutically acceptable salt thereof, sufficient to prevent or reduce the severity of one or more future symptoms of a disease or disorder when administered to a subject who is susceptible and/or who may develop the disease or disorder. For prophylactic use, beneficial or desired results include, e.g., results such as eliminating or reducing the risk, lessening the severity of future disease, or delaying the onset of the disease (e.g., delaying biochemical, histologic and/or behavioral symptoms of the disease, its complications, and intermediate pathological phenotype presenting during future development of the disease).

It is understood that an effective amount of a compound as disclosed herein, or pharmaceutically acceptable salt thereof, including a prophylactically effective amount, may be given to a subject in the adjuvant setting, which refers to a clinical setting in which a subject has had a history of the disease or disorder, and generally (but not necessarily) has been responsive to therapy, which includes, but is not limited to, surgery (e.g., surgical resection), radiotherapy, and chemotherapy. However, because of their or their family's history of the disease or disorder, these subjects are considered at risk of developing it. Treatment or administration in the "adjuvant setting" refers to a subsequent mode of treatment.

As used herein, "unit dosage form" refers to physically discrete units, suitable as unit dosages, each unit containing a predetermined quantity of active ingredient calculated to produce a desired therapeutic effect, in association with the required pharmaceutical carrier or excipient. Unit dosage forms may contain a single compound or a combination therapy.

As used herein, the term "controlled release" refers to a formulation or fraction thereof containing an active pharmaceutical ingredient in which release of the pharmaceutical is not immediate. Thus, with a "controlled release" formulation, administration to a subject does not result in immediate release of the drug into the subject's circulation. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like), and formulating the mixture according to the desired route of delivery, (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared and updated by the U.S. Food and Drug Administration.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, or xanthan gum. Coatings include, e.g., cellulose acetate phthalate, ethylcellulose, gellan gum, maltodextrin, enteric coatings. Compression/encapsulation aids include, e.g., calcium carbonate, dextrose, fructose dc (dc means "directly compressible"), honey dc, lactose (anhydrate or monohydrate; optionally in combination with aspartame, cellulose, or microcrystalline cellulose), starch dc, sucrose. Disintegrants include, e.g., croscarmellose sodium, gellan gum, sodium starch glycolate. Creams or lotions include, e.g., maltodextrin, carrageenans. Lubricants include, e.g., magnesium stearate, stearic acid, sodium stearyl fumarate. Materials for chewable tablets include, e.g. dextrose, fructose dc, lactose (monohydrate, optionally in combination with aspartame or cellulose). Suspending/gelling agents include, e.g., carrageenan, sodium starch glycolate, xanthan gum. Sweeteners include, e.g., aspartame, dextrose, fructose dc, sorbitol, sucrose dc, etc.; and wet granulation agents include, e.g., calcium carbonate, maltodextrin, microcrystalline cellulose, etc. In some cases, the terms "excipient" and "carrier" are used interchangeably.

The term "subject" or "patient" refers humans, whether adult, juvenile or infant, but may also encompass other higher animals such as mammals, in which case the term may include, but is not limited to, primates, cows, sheep, goats, horses, dogs, cats, rabbits, rats, mice.

The terms "abnormal cell growth," "unregulated cell growth," and "hyperproliferative disorder" are used interchangeably in this application. "Abnormal cell growth", as used herein, unless otherwise indicated, refers to cell growth that is independent of normal regulatory mechanisms (e.g., loss of contact inhibition).

Representative lactam (isoindolin-1-one) compounds according to formula (I) are shown in Table 1. It is understood that individual enantiomers and diastereomers are included in the table below, as applicable. It is further to be understood that inclusion of a single particular enantiomer or diastereomer of a particular molecule does not preclude its partner enantiomer, or another stereoisomer thereof, from being encompassed by the current disclosure.

TABLE 1

| Compound # | Structure | Name |
| --- | --- | --- |
| 1 | 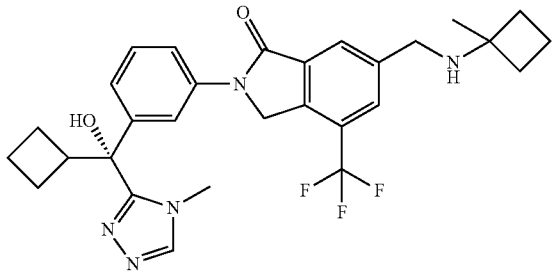 [SMILES: Cn1cnnc1[C@](O)(c1cccc(N2Cc3c(cc(CNC4(C)CCC4)cc3C(F)(F)F)C2=O)c1)C1CCC1] | (R)-2-(3-(cyclobutyl)(hydroxy)(4-methyl-4H-1,2,4-triazol-3-yl)methyl)phenyl)-6-(((1-methylcyclobutyl)amino)methyl)-4-(trifluoromethyl)isoindolin-1-one |
| 2 | 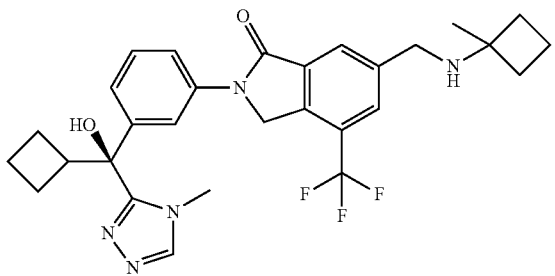 [SMILES: Cn1cnnc1[C@@](O)(c1cccc(N2Cc3c(cc(CNC4(C)CCC4)cc3C(F)(F)F)C2=O)c1)C1CCC1] | (S)-2-(3-(cyclobutyl(hydroxy)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 3 | 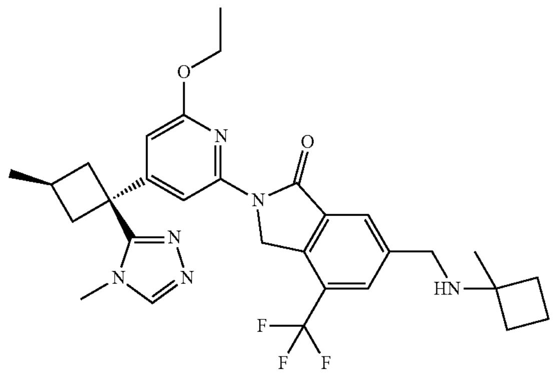 [SMILES: CCOc1cc([C@]2(c3nncn3C)C[C@@H](C)C2)cc(N2Cc3c(cc(CNC4(C)CCC4)cc3C(F)(F)F)C2=O)n1] | 2-(6-ethoxy-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 4 | 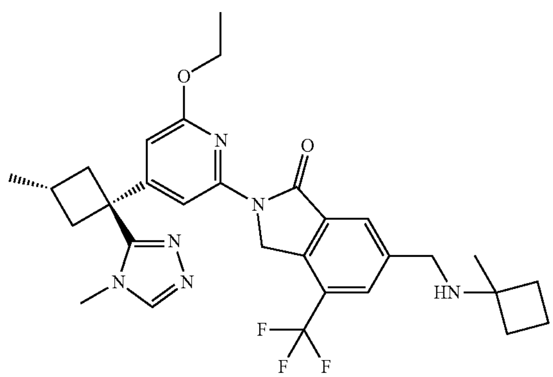 [SMILES: CCOc1cc([C@]2(c3nncn3C)C[C@H](C)C2)cc(N2Cc3c(cc(CNC4(C)CCC4)cc3C(F)(F)F)C2=O)n1] | 2-(6-ethoxy-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 5 | 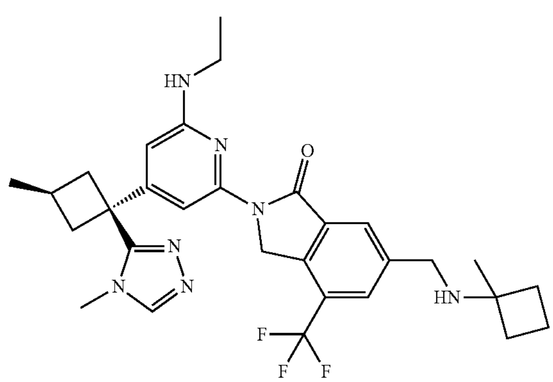 [SMILES: CCNc1cc([C@]2(c3nncn3C)C[C@@H](C)C2)cc(N2Cc3c(cc(CNC4(C)CCC4)cc3C(F)(F)F)C2=O)n1] | 2-(6-(ethylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 6 | 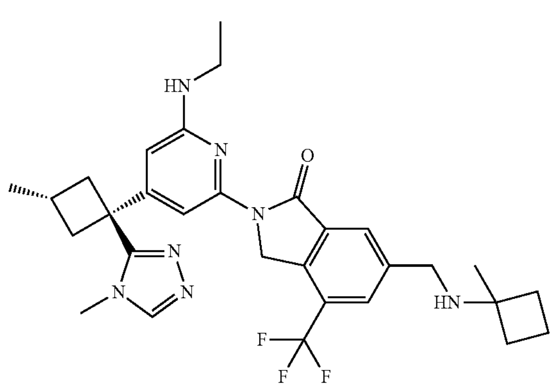 [SMILES: CCNc1cc([C@]2(c3nncn3C)C[C@H](C)C2)cc(N2Cc3c(cc(CNC4(C)CCC4)cc3C(F)(F)F)C2=O)n1] | 2-(6-(ethylamino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |

TABLE 1-continued

| Compound # | Structure | Name |
|---|---|---|
| 7 | 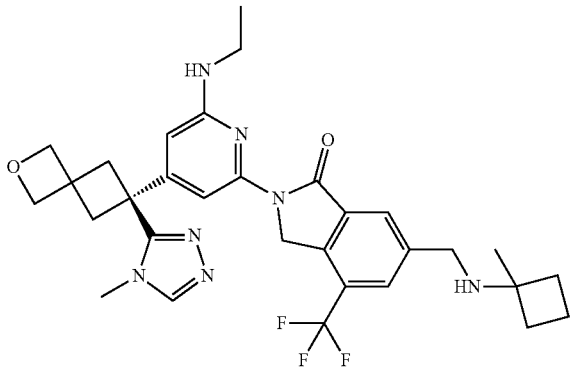 | 2-(6-(ethylamino)-4-(6-(4-methyl-4H-1,2,4-triazol-3-yl)-2-oxaspiro[3.3]heptan-6-yl)pyridin-2-yl)-6-(((1-methylcyclobutyl)amino)methyl)-4-(trifluoromethyl)isoindolin-1-one |
| 8 | 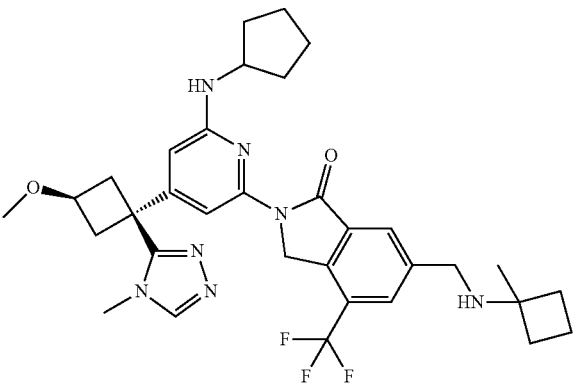 [SMILES: CO[C@H]1C[C@@](c2cc(NC3CCCC3)nc(N3Cc4c(cc(CNC5(C)CCC5)cc4C(F)(F)F)C3=O)c2)(c2nncn2C)C1] | 2-(6-(cyclopentylamino)-4-((1s,3s)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 9 | 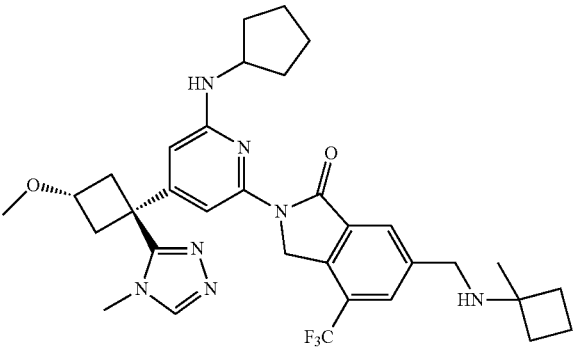 [SMILES: CO[C@H]1C[C@](c2cc(NC3CCCC3)nc(N3Cc4c(cc(CNC5(C)CCC5)cc4C(F)(F)F)C3=O)c2)(c2nncn2C)C1] | 2-(6-(cyclopentylamino)-4-((1r,3r)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 10 | 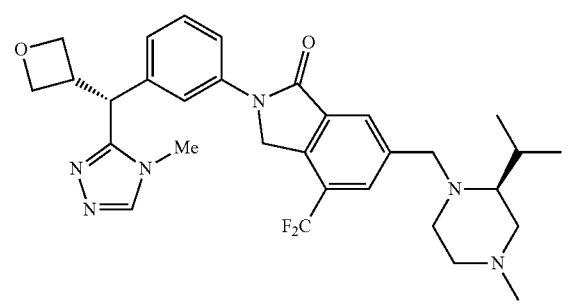 | 6-(((S)-2-isopropyl-4-methylpiperazin-1-yl)methyl)-2-(3-((R)-(4-methyl-4H-1,2,4-triazol-3-yl)(oxetan-3-yl)methyl)phenyl)-4-(trifluoromethyl)isoindolin-1-one |

TABLE 1-continued

| Compound # | Structure | Name |
|---|---|---|
| 11 | 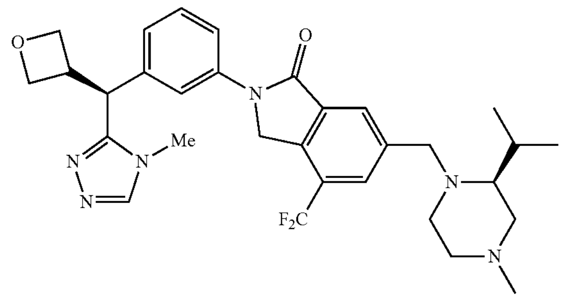 | 6-(((S)-2-isopropyl-4-methylpiperazin-1-yl)methyl)-2-(3-((S)-(4-methyl-4H-1,2,4-triazol-3-yl)(oxetan-3-yl)methyl)phenyl)-4-(trifluoromethyl)isoindolin-1-one |
| 12 | 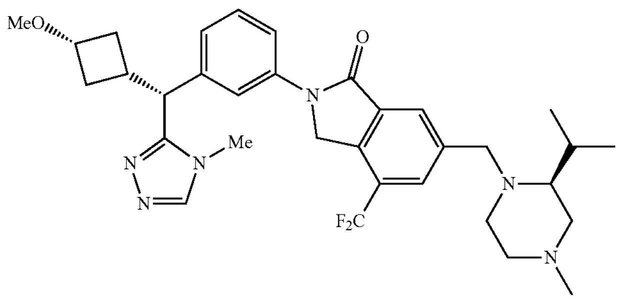 | 6-(((S)-2-isopropyl-4-methylpiperazin-1-yl)methyl)-2-(3-((R)-((1r,3R)-3-methoxycyclobutyl)(4-methyl-4H-1,2,4-triazol-3-yl)methyl)phenyl)-4-(trifluoromethyl)isoindolin-1-one |
| 13 | 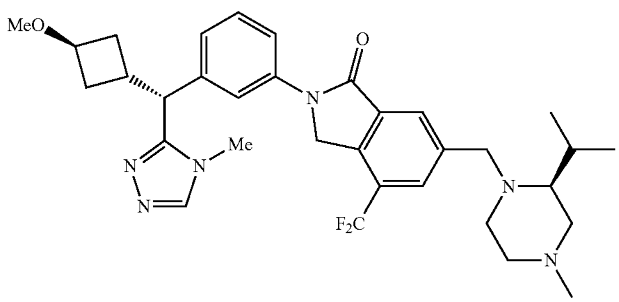 | 6-(((S)-2-isorpropyl-4-methylpiperazin-1-yl)methyl)-2-(3-((R)-((1s,3S)-3-methoxycyclobutyl)(4-methyl-4H-1,2,4-triazol-3-yl)methyl)phenyl)-4-(trifluoromethyl)isoindolin-1-one |
| 14 | 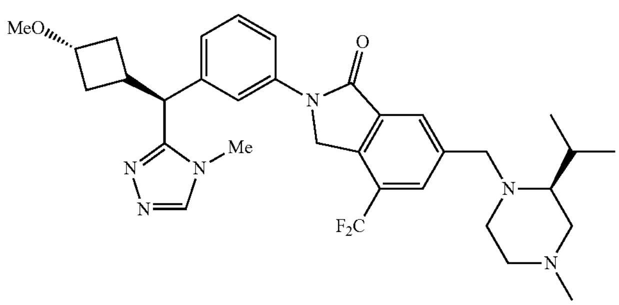 | 6-(((S)-2-isopropyl-4-methylpiperazin-1-yl)methyl)-2-(3-((S)-((1s,3R)-3-methoxycyclobutyl)(4-methyl-4H-1,2,4-triazol-3-yl)methyl)phenyl)-4-(trifluoromethyl)isoindolin-1-one |
| 15 | 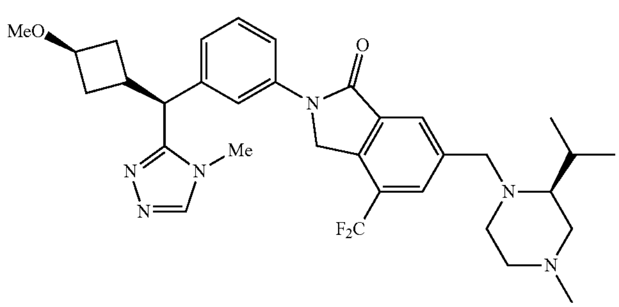 | 6-(((S)-2-isopropyl-4-methylpiperazin-1-yl)methyl)-2-(3-((S)-((1r,3S)-3-methoxycyclobutyl)(4-methyl-4H-1,2,4-triaozl-3-yl)methyl)phenyl)-4-(trifluoromethyl)isoindolin-1-one |

TABLE 1-continued

| Compound # | Structure | Name |
|---|---|---|
| 16 | 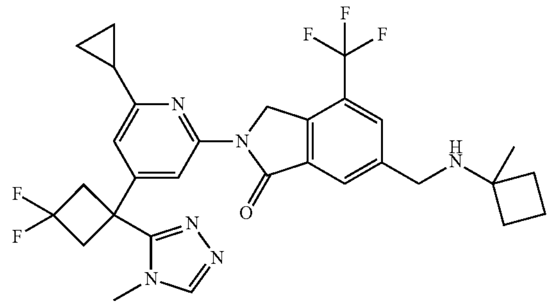 [SMILES: Cn1cnnc1C1(c2cc(C3CC3)nc(N3Cc4c(cc(CNC5(C)CCC5)cc4C(F)(F)F)C3=O)c2)CC(F)(F)C1] | 2-(6-cyclopropyl-4-(3,3-difluoro-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 17 | 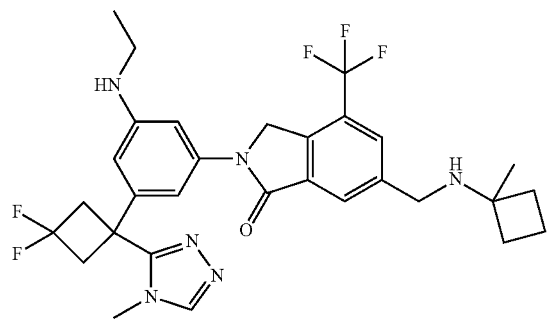 [SMILES: CCNc1cc(N2Cc3c(cc(CNC4(C)CCC4)cc3C(F)(F)F)C2=O)cc(C2(c3nncn3C)CC(F)(F)C2)c1] | 2-(4-(3,3-difluoro-1-(4-methyl-4H-1,2,4-triazol-3-yl)cyclobutyl)-6-(ethylamino)pyridin-2-yl)-6-(((1-methylcyclobutyl)amino)methyl)-4-(trifluoromethyl)isoindolin-1-one |
| 18 | 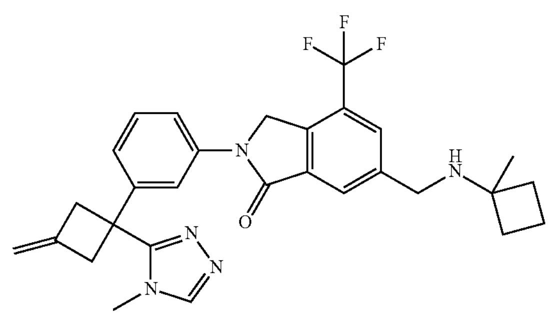 [SMILES: C=C1CC(c2cccc(N3Cc4c(cc(CNC5(C)CCC5)cc4C(F)(F)F)C3=O)c2)(c2nncn2C)C1] | 2-(3-(1-(4-methyl-4H-1,2,4-triazol-3-yl)-3-methylenecyclobutyl)phenyl)-6-(((1-methylcyclobutyl)amino)methyl)-4-(trifluoromethyl)isoindolin-1-one |
| 19 | 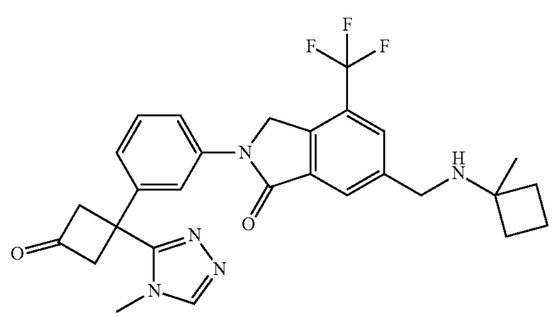 [SMILES: Cn1cnnc1C1(c2cccc(N3Cc4c(cc(CNC5(C)CCC5)cc4C(F)(F)F)C3=O)c2)CC(=O)C1] | 2-(3-(1-(4-methyl-4H-1,2,4-triazol-3-yl)-3-oxocyclobutyl)phenyl)-6-(((1-methylcyclobutyl)amino)methyl)-4-(trifluoromethyl)isoindolin-1-one |
| 20 | 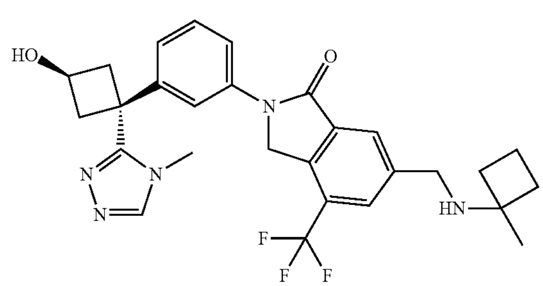 [SMILES: Cn1cnnc1[C@]1(c2cccc(N3Cc4c(cc(CNC5(C)CCC5)cc4C(F)(F)F)C3=O)c2)C[C@@H](O)C1] | 2-(3-((1r,3r)-3-hydroxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 21 | 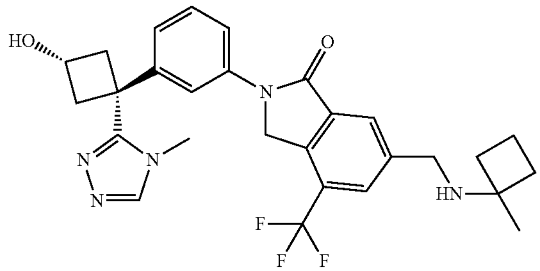 [SMILES: Cn1cnnc1[C@]1(c2cccc(N3Cc4c(cc(CNC5(C)CCC5)cc4C(F)(F)F)C3=O)c2)C[C@H](O)C1] | 2-(3-((1s,3s)-3-hydroxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 22 | 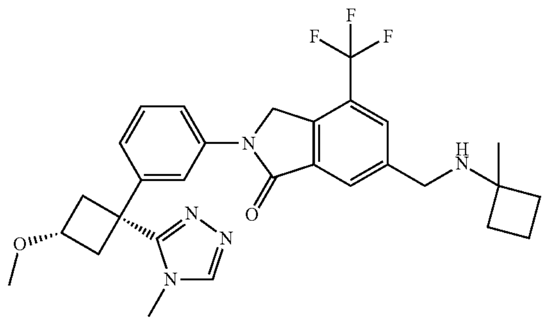 [SMILES: CO[C@H]1C[C@@](c2cccc(N3Cc4c(cc(CNC5(C)CCC5)cc4C(F)(F)F)C3=O)c2)(c2nncn2C)C1] | 2-(3-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 23 | 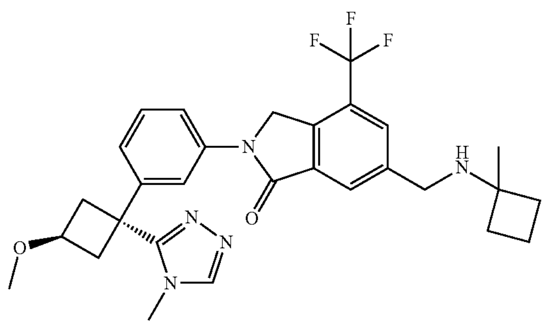 [SMILES: CO[C@H]1C[C@](c2cccc(N3Cc4c(cc(CNC5(C)CCC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 24 | 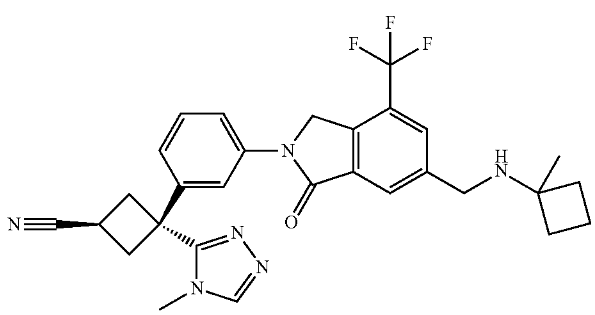 [SMILES: Cn1cnnc1[C@]1(c2cccc(N3Cc4c(cc(CNC5(C)CCC5)cc4C(F)(F)F)C3=O)c2)C[C@@H](C#N)C1] | (1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutanecarbonitrile |
| 25 | 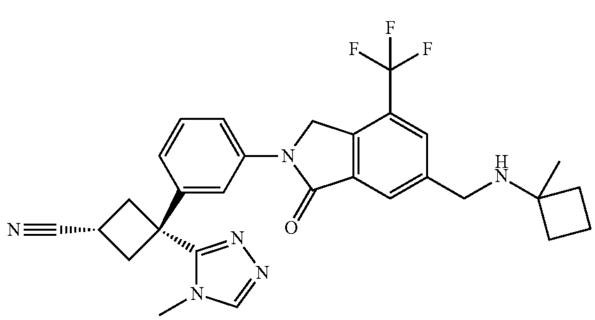 [SMILES: Cn1cnnc1[C@]1(c2cccc(N3Cc4c(cc(CNC5(C)CCC5)cc4C(F)(F)F)C3=O)c2)C[C@H](C#N)C1] | (1s,3s)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutanecarbonitrile |

TABLE 1-continued

| Compound # | Structure | Name |
|---|---|---|
| 26 | 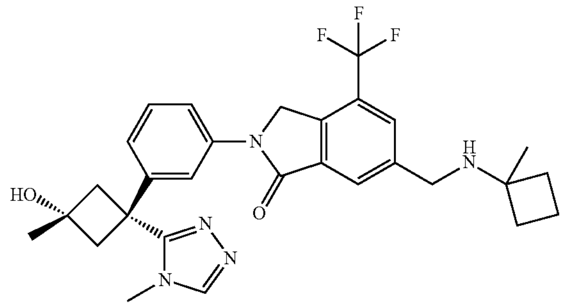 [SMILES: Cn1cnnc1[C@]1(c2cccc(N3Cc4c(cc(CNC5(C)CCC5)cc4C(F)(F)F)C3=O)c2)C[C@](C)(O)C1] | 2-(3-((1s,3s)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 27 | 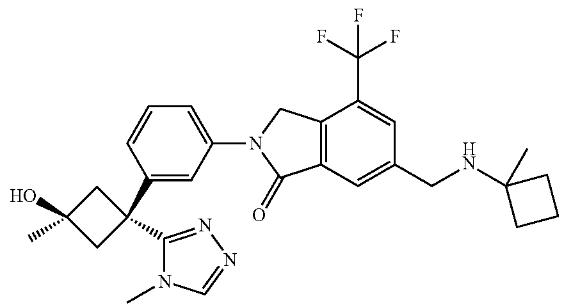 [SMILES: Cn1cnnc1[C@]1(c2cccc(N3Cc4c(cc(CNC5(C)CCC5)cc4C(F)(F)F)C3=O)c2)C[C@@](C)(O)C1] | (2-(3-((1r,3r)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 28 | 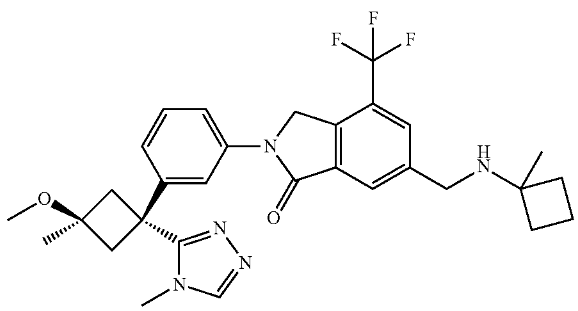 [SMILES: CO[C@]1(C)C[C@@](c2cccc(N3Cc4c(cc(CNC5(C)CCC5)cc4C(F)(F)F)C3=O)c2)(c2nncn2C)C1] | 2-(3-((1r,3r)-3-methoxy-3-methyl-1-(4-methyl-4H-1,2,4-triazol-3-yl)cyclobutyl)phenyl)-6-(((1-methylcyclobutyl)amino)methyl)-4-(trifluromethyl)isoindolin-1-one |
| 29 | 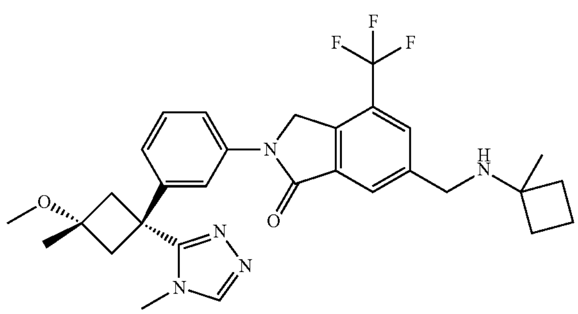 [SMILES: CO[C@]1(C)C[C@](c2cccc(N3Cc4c(cc(CNC5(C)CCC5)cc4C(F)(F)F)C3=O)c2)(c2nncn2C)C1] | (2-(3-((1s,3s)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 30 | 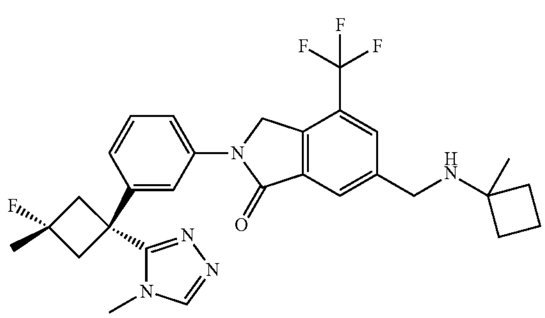 [SMILES: Cn1cnnc1[C@]1(c2cccc(N3Cc4c(cc(CNC5(C)CCC5)cc4C(F)(F)F)C3=O)c2)C[C@](C)(F)C1] | 2-(3-((1s,3s)-3-fluoro-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 31 | 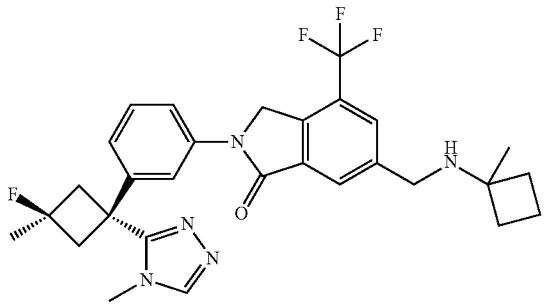 [SMILES: Cn1cnnc1[C@]1(c2cccc(N3Cc4c(cc(CNC5(C)CCC5)cc4C(F)(F)F)C3=O)c2)C[C@@](C)(F)C1] | 2-(3-(((1r,3r)-3-fluoro-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 32 | 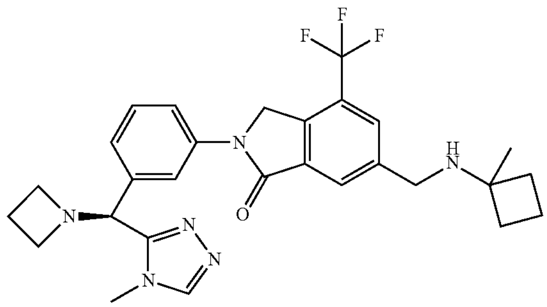 [SMILES: Cn1cnnc1[C@H](c1cccc(N2Cc3c(cc(CNC4(C)CCC4)cc3C(F)(F)F)C2=O)c1)N1CCC1] | (S)-2-(3-(azetidin-1-yl(4-methyl-4H-1,2,4-triazol-3-yl)methyl)phenyl)-6-(((1-methylcyclobutyl)amino)methyl)-4-(trifluoromethyl)isoindolin-1-one |
| 33 | 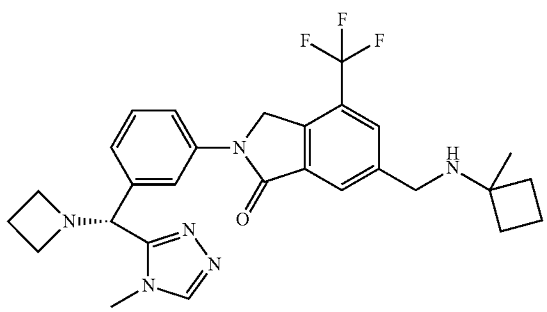 [SMILES: Cn1cnnc1[C@@H](c1cccc(N2Cc3c(cc(CNC4(C)CCC4)cc3C(F)(F)F)C2=O)c1)N1CCC1] | (R)-2-(3-(azetidin-1-yl)(4-methyl-4H-1,2,4-triazol-3-yl)methyl)phenyl)-6-(((1-methylcyclobutyl)amino)methyl)-4-(trifluoromethyl)isoindolin-1-one |
| 34 | 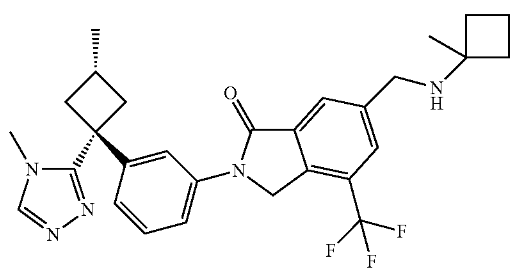 [SMILES: Cn1cnnc1[C@]1(c2cccc(N3Cc4c(cc(CNC5(C)CCC5)cc4C(F)(F)F)C3=O)c2)C[C@H](C)C1] | 2-(3-(((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 35 | 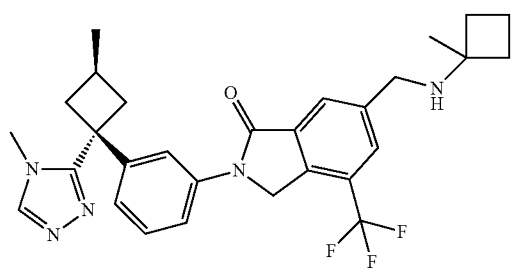 [SMILES: Cn1cnnc1[C@]1(c2cccc(N3Cc4c(cc(CNC5(C)CCC5)cc4C(F)(F)F)C3=O)c2)C[C@@H](C)C1] | 2-(3-(((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 36 | 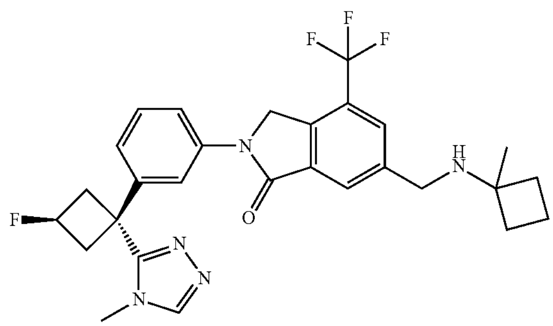 [SMILES: Cn1cnnc1[C@]1(c2cccc(N3Cc4c(cc(CNC5(C)CCC5)cc4C(F)(F)F)C3=O)c2)C[C@@H](F)C1] | 2-(3-((1r,3r)-3-fluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 37 | 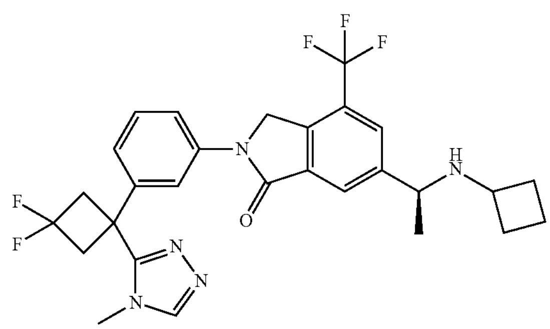 [SMILES: C[C@H](NC1CCC1)c1cc2c(c(C(F)(F)F)c1)CN(c1cccc(C3(c4nncn4C)CC(F)(F)C3)c1)C2=O] | (S)-6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one |
| 38 | 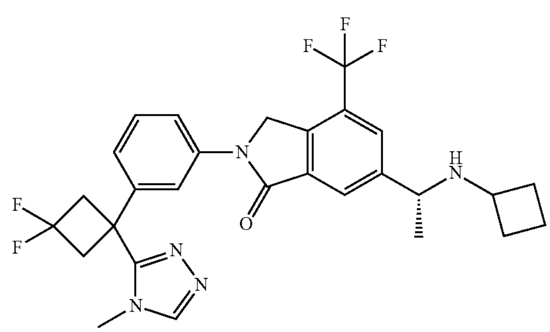 [SMILES: C[C@@H](NC1CCC1)c1cc2c(c(C(F)(F)F)c1)CN(c1cccc(C3(c4nncn4C)CC(F)(F)C3)c1)C2=O] | (R)-6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one |
| 39 | 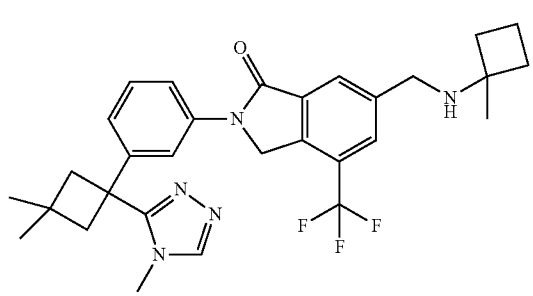 [SMILES: Cn1cnnc1C1(c2cccc(N3Cc4c(cc(CNC5(C)CCC5)cc4C(F)(F)F)C3=O)c2)CC(C)(C)C1] | 2-(3-(3,3-dimethyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 40 | 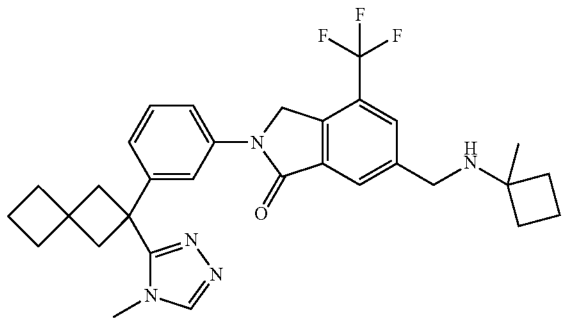 [SMILES: Cn1cnnc1C1(c2cccc(N3Cc4c(cc(CNC5(C)CCC5)cc4C(F)(F)F)C3=O)c2)CC2(CCC2)C1] | 2-(3-(2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one |
| 41 | 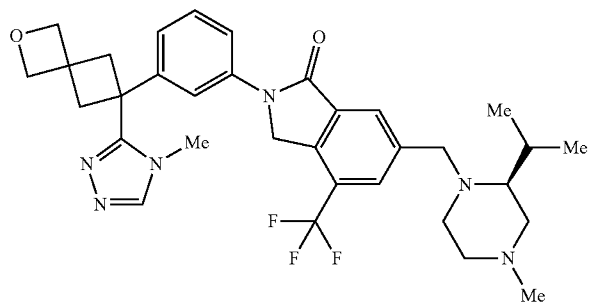 [SMILES: CC(C)[C@H]1CN(C)CCN1Cc1cc2c(c(C(F)(F)F)c1)CN(c1cccc(C3(c4nncn4C)CC4(COC4)C3)c1)C2=O] | (S)-6-((2-isopropyl-4-methylpiperazin-1-yl)methyl)-2-(3-(6-(4-methyl-4H-1,2,4-triazol-3-yl)-2-oxaspiro[3.3]heptan-6-yl)phenyl)-4-(trifluoromethyl)isoindolin-1-one |
| 42 | 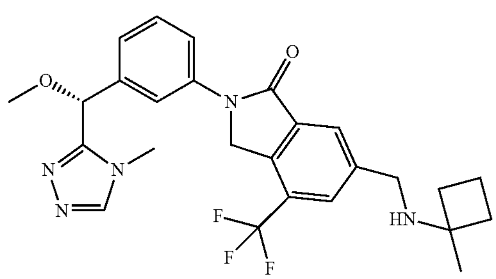 [SMILES: CO[C@H](c1cccc(N2Cc3c(cc(CNC4(C)CCC4)cc3C(F)(F)F)C2=O)c1)c1nncn1C] | (R)-2-(3-(methoxy(4-methyl-4H-1,2,4-triazol-3-yl)methyl)phenyl)-6-(((1-methylcyclobutyl)amino)methyl)-4-(trifluoromethyl)isoindolin-1-one |
| 43 | 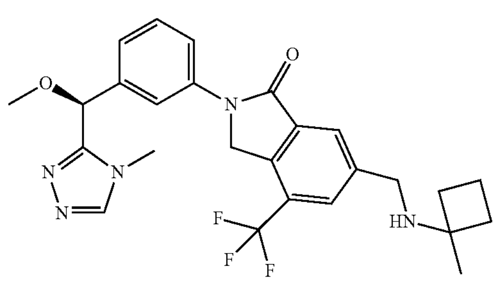 [SMILES: CO[C@@H](c1cccc(N2Cc3c(cc(CNC4(C)CCC4)cc3C(F)(F)F)C2=O)c1)c1nncn1C] | (S)-2-(3-(methoxy(4-methyl-4H-1,2,4-triazol-3-yl)methyl)phenyl)-6-(((1-methylcyclobutyl)amion)methyl)-4-(trifluoromethyl)isoindolin-1-one |
| 44 | 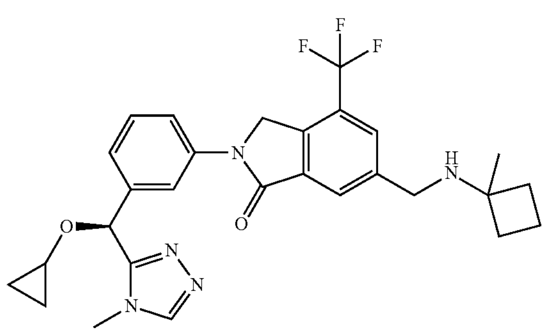 [SMILES: Cn1cnnc1[C@@H](OC1CC1)c1cccc(N2Cc3c(cc(CNC4(C)CCC4)cc3C(F)(F)F)C2=O)c1] | (S)-2-(3-(cyclopropoxy(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 45 | 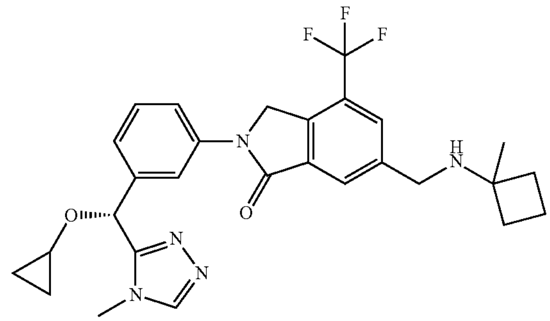 [SMILES: Cn1cnnc1[C@H](OC1CC1)c1cccc(N2Cc3c(cc(CNC4(C)CCC4)cc3C(F)(F)F)C2=O)c1] | (R)-2-(3-(cyclopropoxy(4-methyl-4H-1,2,4-triazol-3-yl)methyl)phenyl)-6-(((1-methylcyclobutyl)amino)methyl)-4-(trifluoromethyl)isoindolin-1-one |
| 46 | 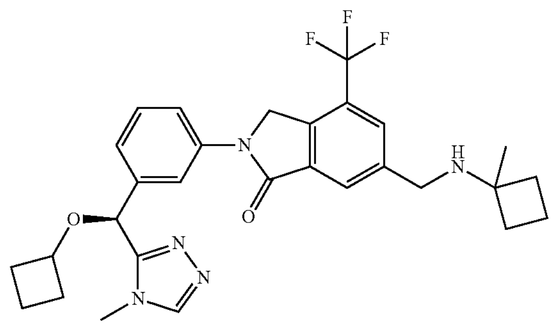 [SMILES: Cn1cnnc1[C@@H](OC1CCC1)c1cccc(N2Cc3c(cc(CNC4(C)CCC4)cc3C(F)(F)F)C2=O)c1] | (S)-2-(3-(cyclobutoxy(4-methyl-4H-1,2,4-triazol-3-yl)methyl)phenyl)-6-(((1-methylcyclobutyl)amino)methyl)-4-(trifluoromethyl)isoindolin-1-one |
| 47 | 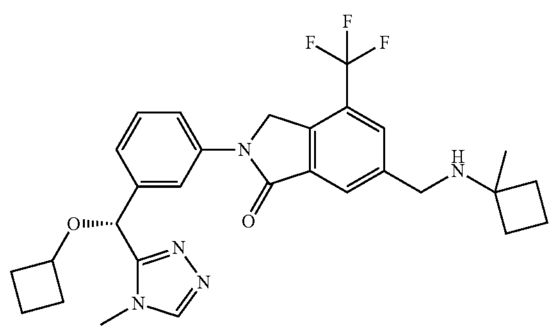 [SMILES: Cn1cnnc1[C@H](OC1CCC1)c1cccc(N2Cc3c(cc(CNC4(C)CCC4)cc3C(F)(F)F)C2=O)c1] | (R)-2-(3-(cyclobutoxy(4-methyl-4H-1,2,4-triazol-3-yl)methyl)phenyl)-6-(((1-methylcyclobutyl)amino)methyl)-4-(trifluoromethyl)isoindolin-1-one |
| 48 | 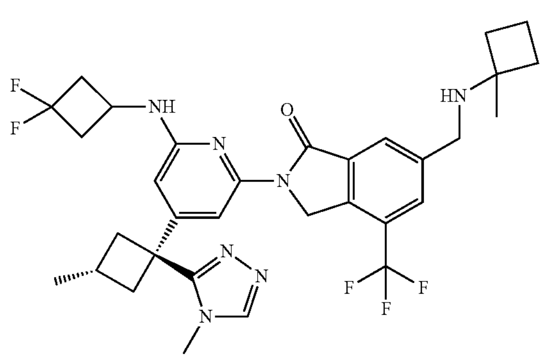 [SMILES: Cn1cnnc1[C@]1(c2cc(NC3CC(F)(F)C3)nc(N3Cc4c(cc(CNC5(C)CCC5)cc4C(F)(F)F)C3=O)c2)C[C@@H](C)C1] | 2-(6-((3,3-difluorocyclobutyl)amino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |

TABLE 1-continued

| Compound # | Structure | Name |
|---|---|---|
| 49 | 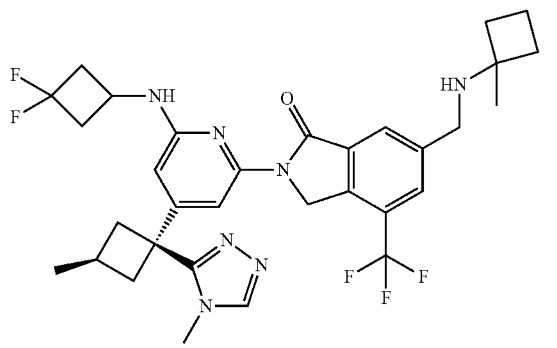 [SMILES: Cn1cnnc1[C@]1(c2cc(NC3CC(F)(F)C3)nc(N3Cc4c(cc(CNC5(C)CCC5)cc4C(F)(F)F)C3=O)c2)C[C@H](C)C1] | 2-(6-((3,3-difluorocyclobutyl)amino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 50 | 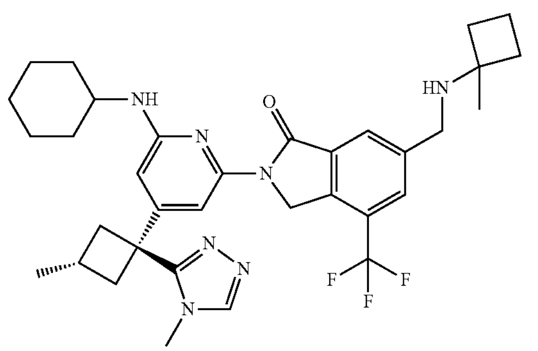 [SMILES: Cn1cnnc1[C@]1(c2cc(NC3CCCCC3)nc(N3Cc4c(cc(CNC5(C)CCC5)cc4C(F)(F)F)C3=O)c2)C[C@@H](C)C1] | 2-(6-(cyclohexylamino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 51 | 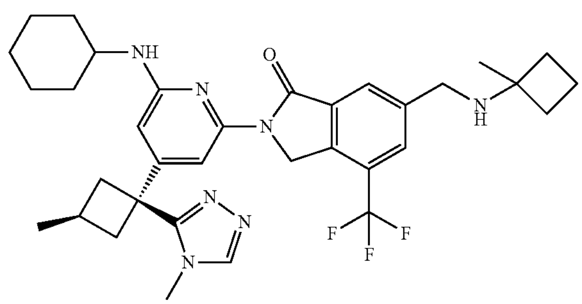 [SMILES: Cn1cnnc1[C@]1(c2cc(NC3CCCCC3)nc(N3Cc4c(cc(CNC5(C)CCC5)cc4C(F)(F)F)C3=O)c2)C[C@H](C)C1] | 2-(6-(cyclohexylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 52 | 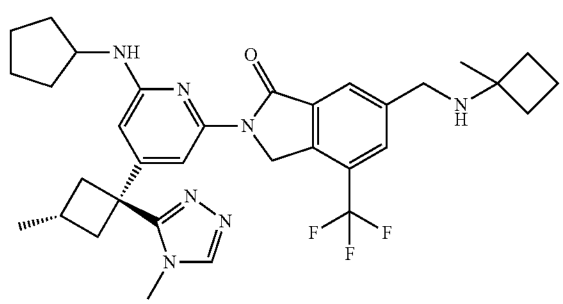 [SMILES: Cn1cnnc1[C@]1(c2cc(NC3CCCC3)nc(N3Cc4c(cc(CNC5(C)CCC5)cc4C(F)(F)F)C3=O)c2)C[C@@H](C)C1] | 2-(6-(cyclopentylamino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |

TABLE 1-continued

| Compound # | Structure | Name |
|---|---|---|
| 53 | 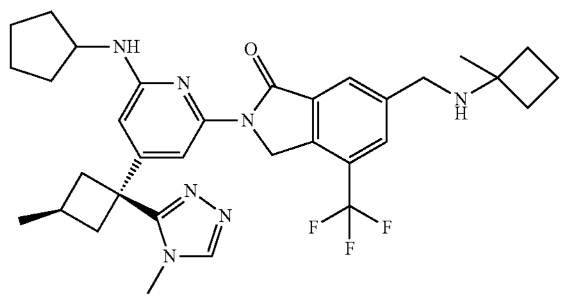 [SMILES: Cn1cnnc1[C@]1(c2cc(NC3CCCC3)nc(N3Cc4c(cc(CNC5(C)CCC5)cc4C(F)(F)F)C3=O)c2)C[C@H](C)C1] | 2-(6-(cyclopentylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 54 | 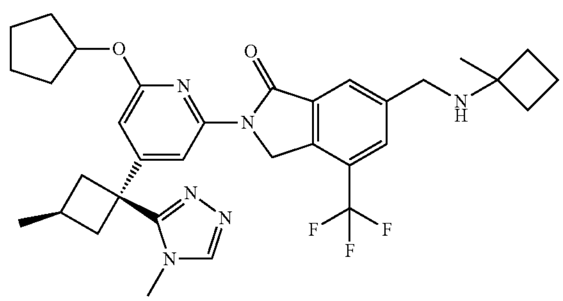 [SMILES: Cn1cnnc1[C@]1(c2cc(OC3CCCC3)nc(N3Cc4c(cc(CNC5(C)CCC5)cc4C(F)(F)F)C3=O)c2)C[C@H](C)C1] | 2-(6-(cyclopentyloxy)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 55 | 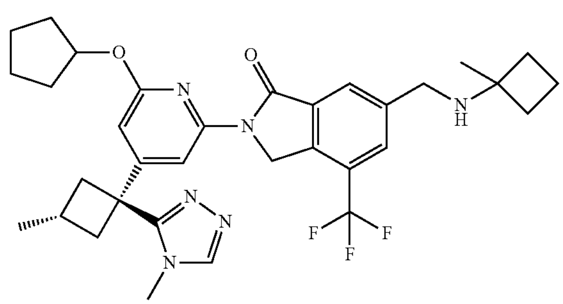 [SMILES: Cn1cnnc1[C@]1(c2cc(OC3CCCC3)nc(N3Cc4c(cc(CNC5(C)CCC5)cc4C(F)(F)F)C3=O)c2)C[C@@H](C)C1] | 2-(6-(cyclopentyloxy)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 56 | 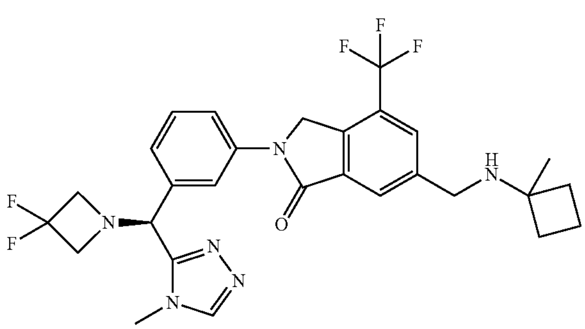 [SMILES: Cn1cnnc1[C@H](c1cccc(N2Cc3c(cc(CNC4(C)CCC4)cc3C(F)(F)F)C2=O)c1)N1CC(F)(F)C1] | (S)-2-(3-((3,3-difluoroazetidin-1-yl)(4-methyl-4H-1,2,4-triazol-3-yl)methyl)phenyl)-6-(((1-methylcyclobutyl)amino)methyl)-4-(trifluoromethyl)isoindolin-1-one |
| 57 | 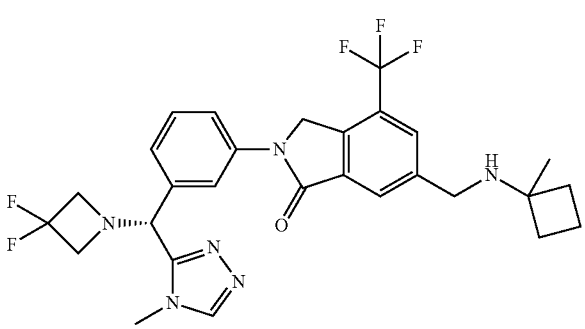 [SMILES: Cn1cnnc1[C@@H](c1cccc(N2Cc3c(cc(CNC4(C)CCC4)cc3C(F)(F)F)C2=O)c1)N1CC(F)(F)C1] | (R)-2-(3-((3,3-difluoroazetidin-1-yl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 58 | 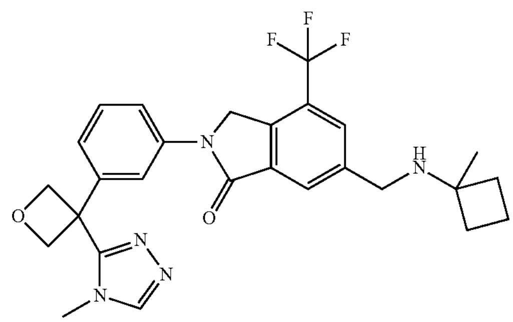 [SMILES: Cn1cnnc1C1(c2cccc(N3Cc4c(cc(CNC5(C)CCC5)cc4C(F)(F)F)C3=O)c2)COC1] | 2-(3-(3-(4-methyl-4H-1,2,4-triazol-3-yl)oxetan-3-yl)phenyl)-6-(((1-methylcyclobutyl)amino)methyl)-4-(trifluoromethyl)isoindolin-1-one |
| 59 | 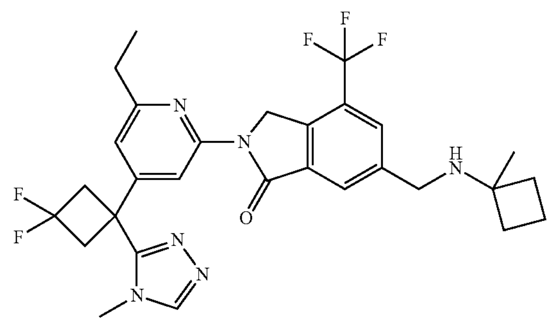 [SMILES: CCc1cc(C2(c3nncn3C)CC(F)(F)C2)cc(N2Cc3c(cc(CNC4(C)CCC4)cc3C(F)(F)F)C2=O)n1] | 2-(4-(3,3-difluoro-1-(4-methyl-4H-1,2,4-triazol-3-yl)cyclobutyl)-6-ethylpyridin-2-yl)-6-(((1-methylcyclobutyl)amino)methyl)-4-(trifluoromethyl)isoindolin-1-one |
| 60 | 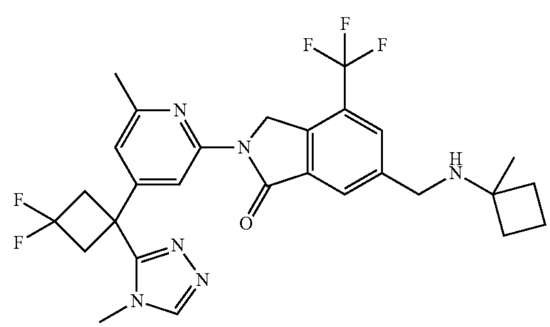 [SMILES: Cc1cc(C2(c3nncn3C)CC(F)(F)C2)cc(N2Cc3c(cc(CNC4(C)CCC4)cc3C(F)(F)F)C2=O)n1] | 2-(4-(3,3-difluoro-1-(4-methyl-4H-1,2,4-triazol-3-yl)cyclobutyl)-6-methylpyridin-2-yl)-6-(((1-methylcyclobutyl)amino)methyl)-4-(trifluoromethyl)isoindolin-1-one |
| 61 | 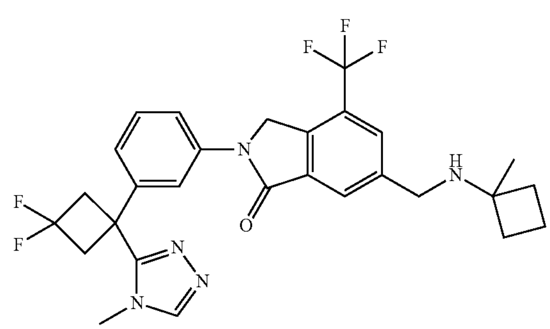 [SMILES: Cn1cnnc1C1(c2cccc(N3Cc4c(cc(CNC5(C)CCC5)cc4C(F)(F)F)C3=O)c2)CC(F)(F)C1] | 2-(3-(3,3-difluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 62 | 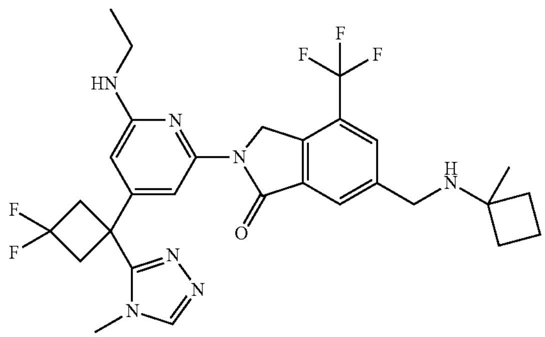 [SMILES: CCNc1cc(C2(c3nncn3C)CC(F)(F)C2)cc(N2Cc3c(cc(CNC4(C)CCC4)cc3C(F)(F)F)C2=O)n1] | 2-(4-(3,3-difluoro-1-(4-methyl-4H-1,2,4-triazol-3-yl)cyclobutyl)-6-(ethylamino)pyridin-2-yl)-6-(((1-methylcyclobutyl)amino)methyl)-4-(trifluoromethyl)isoindolin-1-one |
| 63 | 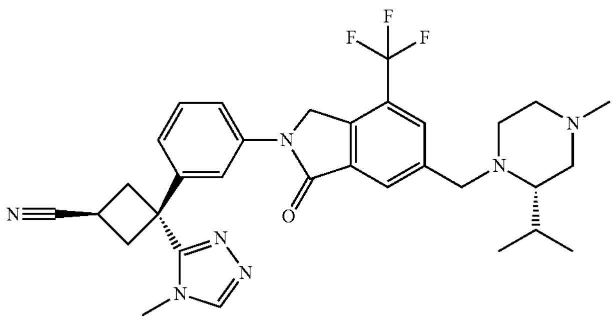 [SMILES: CC(C)[C@H]1CN(C)CCN1Cc1cc2c(c(C(F)(F)F)c1)CN(c1cccc([C@]3(c4nncn4C)C[C@H](C#N)C3)c1)C2=O] | (1S,3r)-3-(3-(6-(((S)-2-isopropyl-4-methylpiperazin-1-yl)methyl)-1-oxo-4-(trifluoromethyl)isoindolin-2-yl)phenyl)-3-(4-methyl-4H-1,2,4-triazol-3-yl)cyclobutanecarbonitrile |
| 64 | 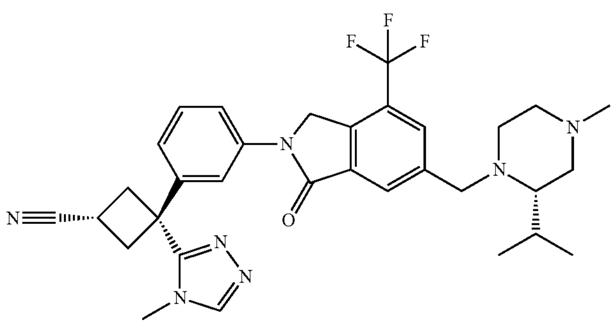 [SMILES: CC(C)[C@H]1CN(C)CCN1Cc1cc2c(c(C(F)(F)F)c1)CN(c1cccc([C@]3(c4nncn4C)C[C@@H](C#N)C3)c1)C2=O] | (1R,3s)-3-(3-(6-(((S)-2-isopropyl-4-methylpiperazin-1-yl)methyl)-1-oxo-4-(trifluoromethyl)isoindolin-2-yl)phenyl)-3-(4-methyl-4H-1,2,4-triazol-3-yl)cyclobutanecarbonitrile |
| 65 | 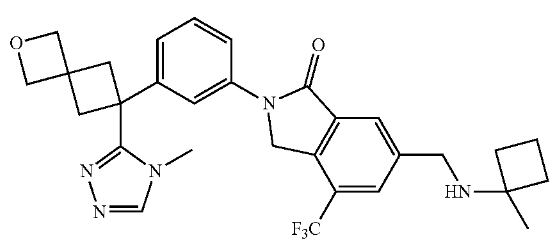 [SMILES: Cn1cnnc1C1(c2cccc(N3Cc4c(cc(CNC5(C)CCC5)cc4C(F)(F)F)C3=O)c2)CC2(COC2)C1] | 2-(3-(6-(4-methyl-4H-1,2,4-triazol-3-yl)-2-oxaspiro[3.3]heptan-6-yl)phenyl)-6-(((1-methylcyclobutyl)amino)methyl)-4-(trifluoromethyl)isoindolin-1-one |
| 66 | 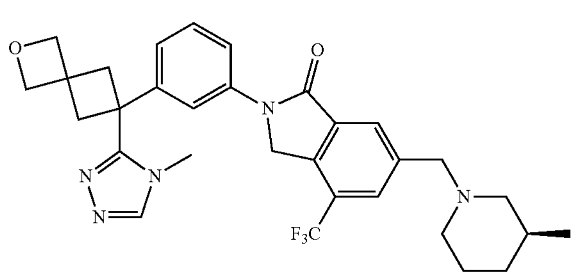 [SMILES: C[C@H]1CCCN(Cc2cc3c(c(C(F)(F)F)c2)CN(c2cccc(C4(c5nncn5C)CC5(COC5)C4)c2)C3=O)C1] | (S)-2-(3-(6-(4-methyl-4H-1,2,4-triazol-3-yl)-2-oxaspiro[3.3]heptan-6-yl)phenyl)-6-((3-methylpiperidin-1-yl)methyl)-4-(trifluoromethyl)isoindolin-1-one |

TABLE 1-continued

| Compound # | Structure | Name |
|---|---|---|
| 67 | 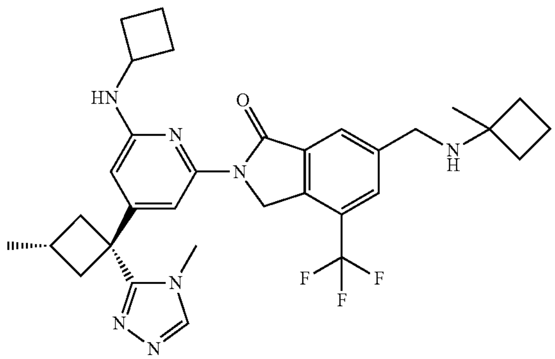 [SMILES: Cn1cnnc1[C@]1(c2cc(NC3CCC3)nc(N3Cc4c(cc(CNC5(C)CCC5)cc4C(F)(F)F)C3=O)c2)C[C@H](C)C1] | 2-(6-(cyclobutylamino)-4-((1S,3S)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 68 | 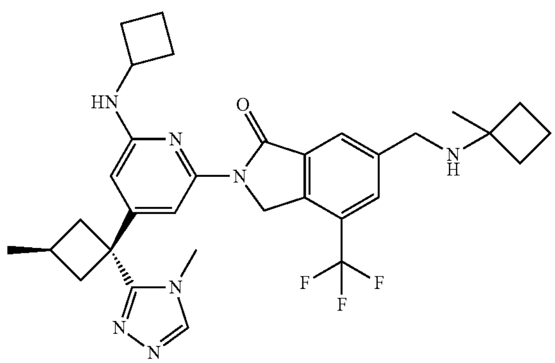 [SMILES: Cn1cnnc1[C@]1(c2cc(NC3CCC3)nc(N3Cc4c(cc(CNC5(C)CCC5)cc4C(F)(F)F)C3=O)c2)C[C@@H](C)C1] | 2-(6-(cyclobutylamino)-4-((1R,3R)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 69 | 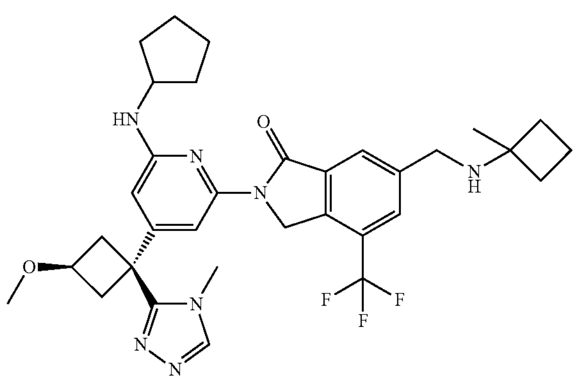 [SMILES: CO[C@H]1C[C@@](c2cc(NC3CCCC3)nc(N3Cc4c(cc(CNC5(C)CCC5)cc4C(F)(F)F)C3=O)c2)(c2nncn2C)C1] | 2-(6-(cyclopentylamino)-4-((1S,3S)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 70 | 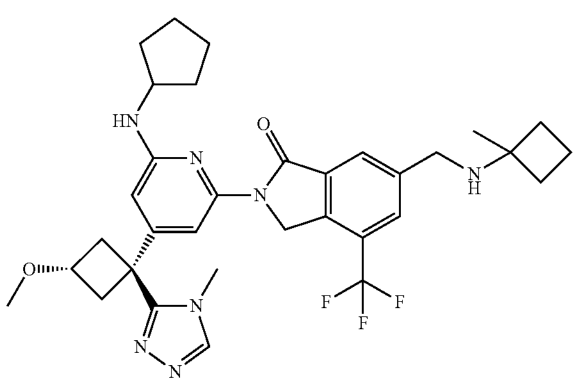 [SMILES: CO[C@H]1C[C@](c2cc(NC3CCCC3)nc(N3Cc4c(cc(CNC5(C)CCC5)cc4C(F)(F)F)C3=O)c2)(c2nncn2C)C1] | 2-(6-(cyclopentylamino)-4-((1R,3R)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |

TABLE 1-continued

| Compound # | Structure | Name |
|---|---|---|
| 71 | 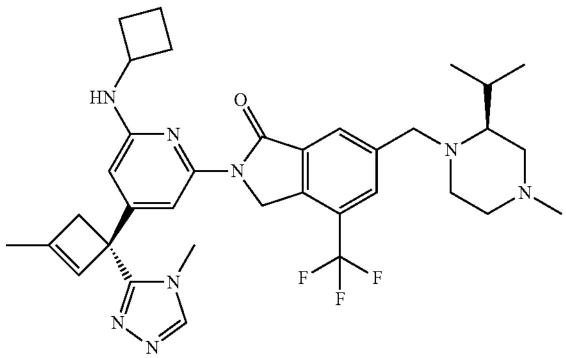 | 2-(6-(cyclobutylamino)-4-((S)-3-methyl-1-(4-methyl-4H-1,2,4-triazol-3-yl)cyclobut-2-en-1-yl)pyridin-2-yl)-6-(((S)-2-isopropyl-4-methylpiperazin-1-yl)methyl)-4-(trifluoromethyl)isoindolin-1-one |
| 72 | 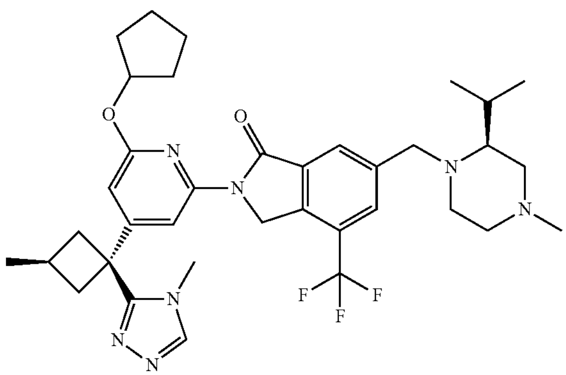 | 2-(6-(cyclopentyloxy)-4-((1S,3R)-3-methyl-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one |
| 73 | 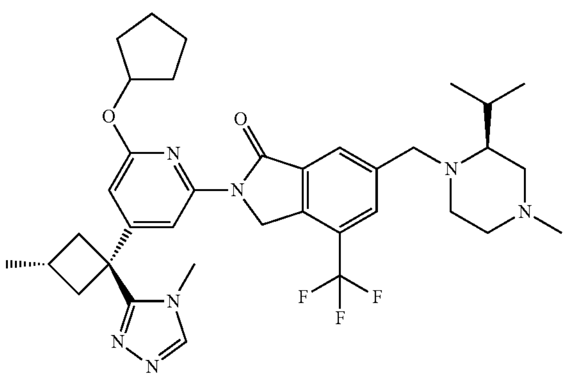 | 2-(6-(cyclopentyloxy)-4-((1R,3S)-3-methyl-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one |
| 74 | 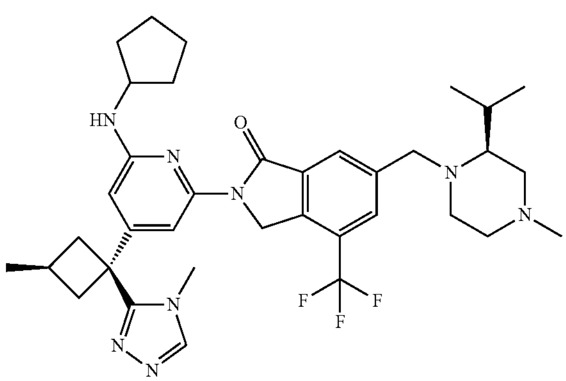 | 2-(6-(cyclopentylamino)-4-((1S,3R)-3-methyl-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one |

TABLE 1-continued

| Compound # | Structure | Name |
|---|---|---|
| 75 | 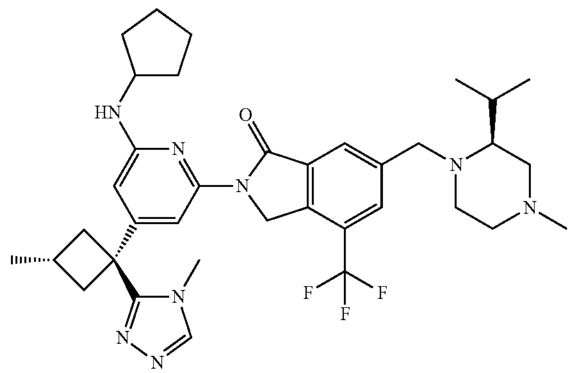 | 2-(6-(cyclopentylamino)-4-((1R,3S)-3-methyl-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one |
| 76 | 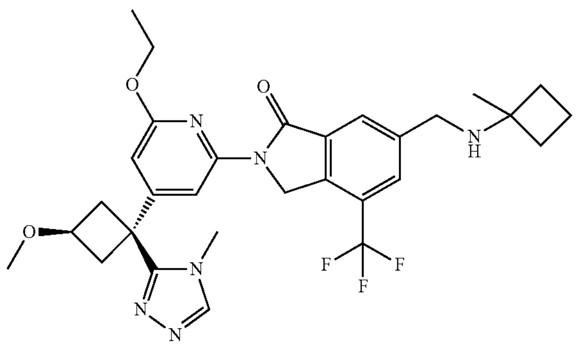 [SMILES: CCOc1cc([C@]2(c3nncn3C)C[C@@H](OC)C2)cc(N2Cc3c(cc(CNC4(C)CCC4)cc3C(F)(F)F)C2=O)n1] | 2-(6-ethoxy-4-((1S,3S)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 77 | 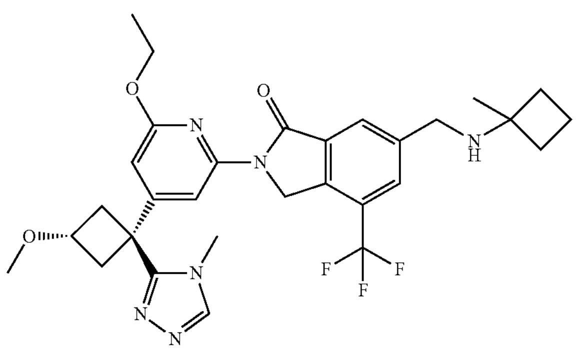 [SMILES: CCOc1cc([C@]2(c3nncn3C)C[C@H](OC)C2)cc(N2Cc3c(cc(CNC4(C)CCC4)cc3C(F)(F)F)C2=O)n1] | 2-(6-ethoxy-4-((1R,3R)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 78 | 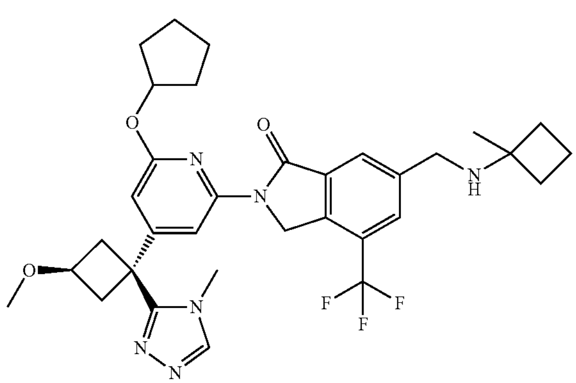 [SMILES: CO[C@H]1C[C@@](c2cc(OC3CCCC3)nc(N3Cc4c(cc(CNC5(C)CCC5)cc4C(F)(F)F)C3=O)c2)(c2nncn2C)C1] | 2-(6-(cyclopentyloxy)-4-((1S,3S)-3-methoxy-1-(4-methyl-4H-1,2,4-triazol-3-yl)cyclobutyl)pyriidn-2-yl)-6-(((1-methylcyclobutyl)amino)methyl)-4-(trifluoromethyl)isoindolin-1-one |

TABLE 1-continued

| Compound # | Structure | Name |
|---|---|---|
| 79 | 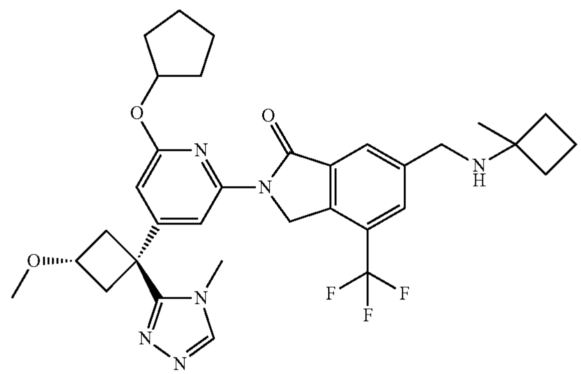 [SMILES: CO[C@H]1C[C@](c2cc(OC3CCCC3)nc(N3Cc4c(cc(CNC5(C)CCC5)cc4C(F)(F)F)C3=O)c2)(c2nncn2C)C1] | 2-(6-(cyclopentyloxy)-4-((1R,3R)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 80 | 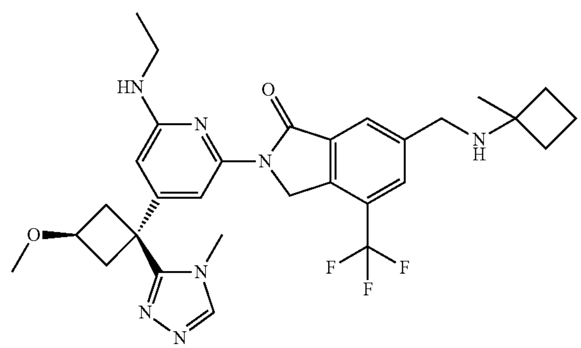 [SMILES: CCNc1cc([C@]2(c3nncn3C)C[C@@H](OC)C2)cc(N2Cc3c(cc(CNC4(C)CCC4)cc3C(F)(F)F)C2=O)n1] | 2-(6-(ethylamino)-4-((1S,3S)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 81 | 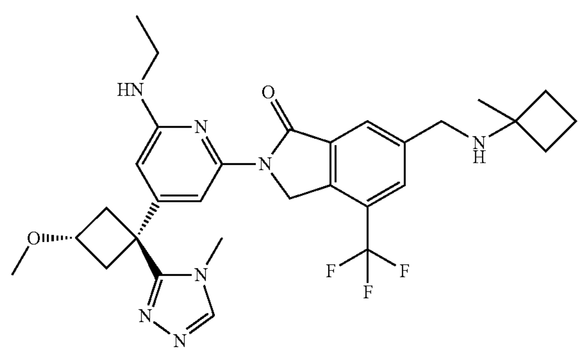 [SMILES: CCNc1cc([C@]2(c3nncn3C)C[C@H](OC)C2)cc(N2Cc3c(cc(CNC4(C)CCC4)cc3C(F)(F)F)C2=O)n1] | 2-(6-(ethylamino)-4-((1R,3R)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one |
| 82 | 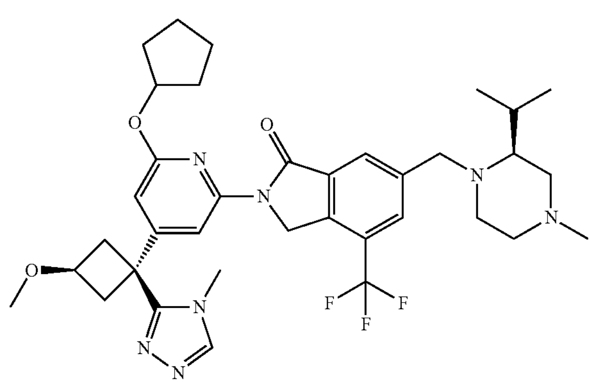 | 2-(6-(cyclopentyloxy)-4-((1S,3R)-3-methoxy-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one |

TABLE 1-continued

| Compound # | Structure | Name |
|---|---|---|
| 83 | 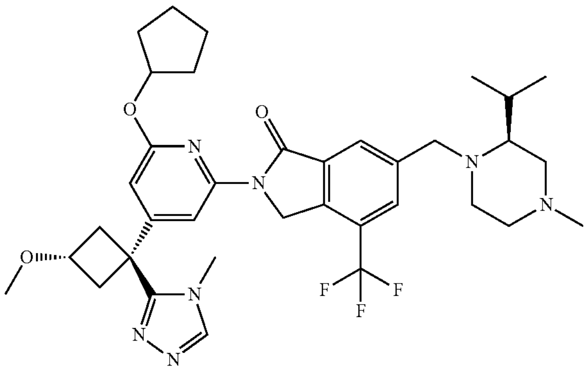 | 2-(6-(cyclopentyloxy)-4-((1R,3S)-3-methoxy-1-(4-methyl-4H-1,2,4-triazol-3-yl)cyclobutyl)pyriidn-2-yl)-6-(((S)-2-isopropyl-4-methylpiperazin-1-yl)methyl)-4-(trifluoromethyl)isoindolin-1-one |
| 84 | 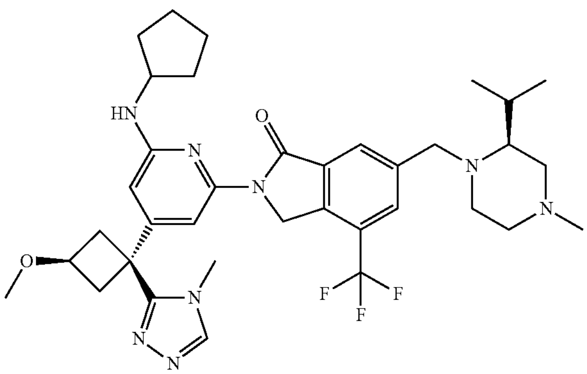 | 2-(6-(cyclopentylamino)-4-((1S,3R)-3-methoxy-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one |
| 85 | 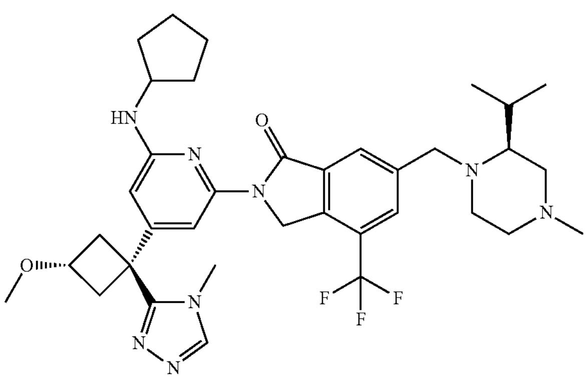 | 2-(6-(cyclopentylamino)-4-((1R,3S)-3-methoxy-1-(4-methyl-4H-1,2,4-triazol-3-yl)cyclobutyl)pyridin-2-yl)-6-(((S)-2-isopropyl-4-methylpiperazin-1-yl)methyl)-4-(trifluoromethyl)isoindolin-1-one |
| 86 | 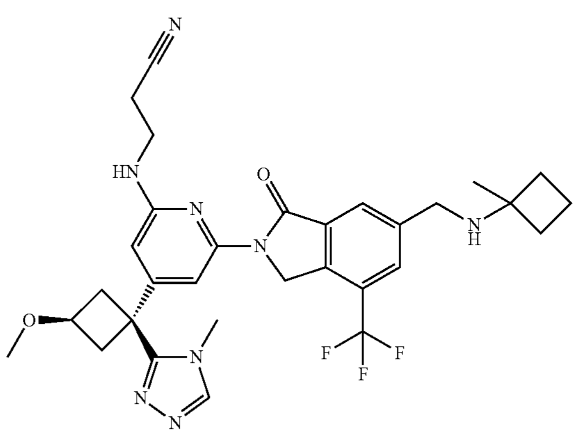 [SMILES: CO[C@H]1C[C@@](c2cc(NCCC#N)nc(N3Cc4c(cc(CNC5(C)CCC5)cc4C(F)(F)F)C3=O)c2)(c2nncn2C)C1] | 3-((4-((1S,3S)-3-methoxy-1-(4-methyl-4H-1,2,4-triazol-3-yl)cyclobutyl)-6-(6-(((1-methylcyclobutyl)amino)methyl)-1-oxo-4-(trifluoromethyl)isoindolin-2-yl)pyridin-2-yl)amino)propanenitrile |

TABLE 1-continued

| Compound # | Structure | Name |
|---|---|---|
| 87 | 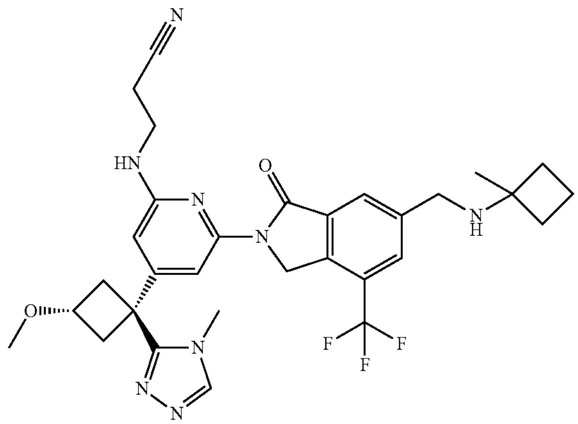 [SMILES: CO[C@H]1C[C@](c2cc(NCCC#N)nc(N3Cc4c(cc(CNC5(C)CCC5)cc4C(F)(F)F)C3=O)c2)(c2nncn2C)C1] | 3-((4-((1R,3R)-3-methoxy-1-(4-methyl-4H-1,2,4-triazol-3-yl)cyclobutyl)-6-(6-(((1-methylcyclobutyl)amino)methyl)-1-oxo-4-(trifluoromethyl)isoindolin-2-yl)pyridin-2-yl)amino)propanenitrile |
| 88 | 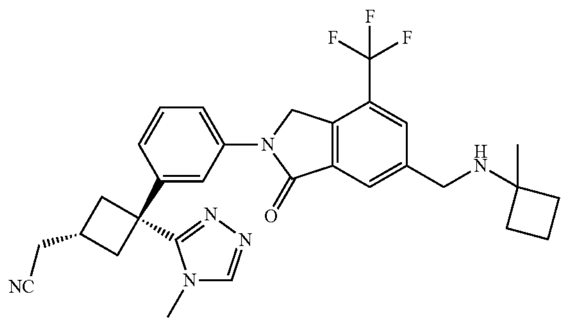 [SMILES: Cn1cnnc1[C@]1(c2cccc(N3Cc4c(cc(CNC5(C)CCC5)cc4C(F)(F)F)C3=O)c2)C[C@H](CC#N)C1] | 2-((1s,3s)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutyl)acetonitrile |
| 89 | 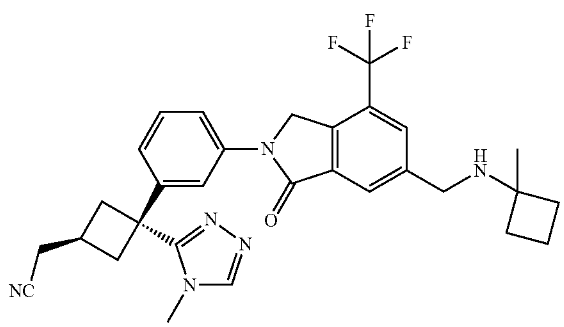 [SMILES: Cn1cnnc1[C@]1(c2cccc(N3Cc4c(cc(CNC5(C)CCC5)cc4C(F)(F)F)C3=O)c2)C[C@@H](CC#N)C1] | 2-((1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutyl)acetonitrile |
| 90 | 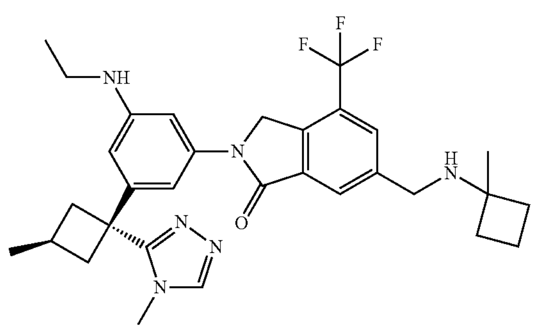 [SMILES: CCNc1cc(N2Cc3c(cc(CNC4(C)CCC4)cc3C(F)(F)F)C2=O)cc([C@]2(c3nncn3C)C[C@H](C)C2)c1] | 2-(3-(ethylamino)-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 91 | 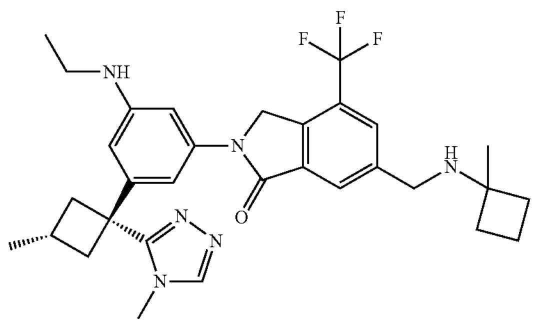 [SMILES: CCNc1cc(N2Cc3c(cc(CNC4(C)CCC4)cc3C(F)(F)F)C2=O)cc([C@]2(c3nncn3C)C[C@@H](C)C2)c1] | 2-(3-(ethylamino)-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 92 | 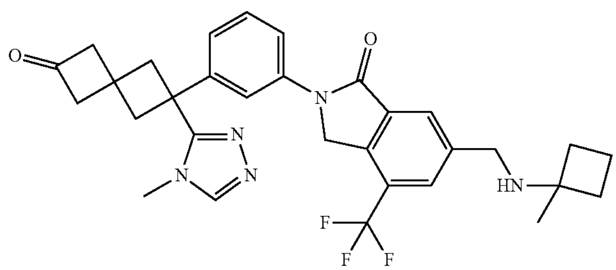 [SMILES: Cn1cnnc1C1(c2cccc(N3Cc4c(cc(CNC5(C)CCC5)cc4C(F)(F)F)C3=O)c2)CC2(CC(=O)C2)C1] | 2-(3-(2-(4-methyl-4H-1,2,4-triazol-3-yl)-6-oxospiro[3.3]heptan-2-yl)phenyl)-6-(((1-methylcyclobutyl)amino)methyl)-4-(trifluoromethyl)isoindolin-1-one |
| 93 | 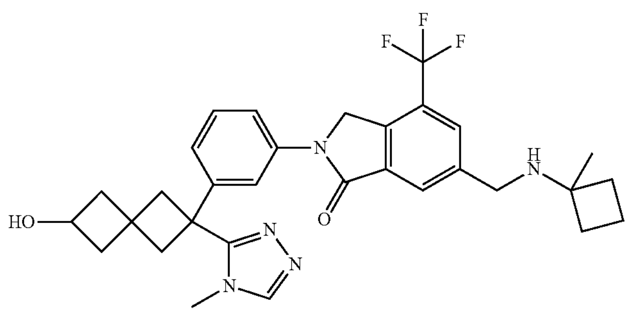 [SMILES: Cn1cnnc1C1(c2cccc(N3Cc4c(cc(CNC5(C)CCC5)cc4C(F)(F)F)C3=O)c2)CC2(CC(O)C2)C1] | 2-(3-(6-hydroxy-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one |
| 94 | 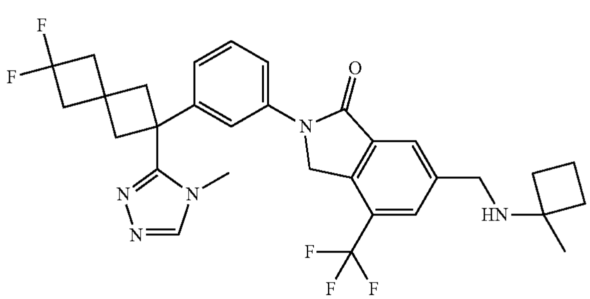 [SMILES: Cn1cnnc1C1(c2cccc(N3Cc4c(cc(CNC5(C)CCC5)cc4C(F)(F)F)C3=O)c2)CC2(CC(F)(F)C2)C1] | 2-(3-(6,6-difluoro-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one |
| 95 | 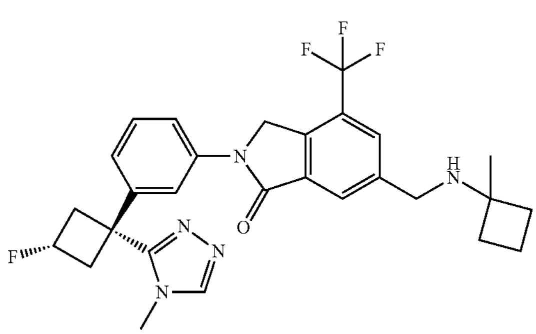 [SMILES: Cn1cnnc1[C@]1(c2cccc(N3Cc4c(cc(CNC5(C)CCC5)cc4C(F)(F)F)C3=O)c2)C[C@H](F)C1] | 2-(3-((1s,3s)-3-fluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 96 | 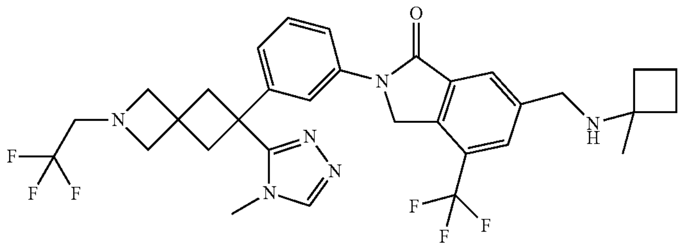 [SMILES: Cn1cnnc1C1(c2cccc(N3Cc4c(cc(CNC5(C)CCC5)cc4C(F)(F)F)C3=O)c2)CC2(CN(CC(F)(F)F)C2)C1] | 2-(3-(6-(4-methyl-4H-1,2,4-triazol-3-yl)-2-(2,2,2-trifluoroethyl)-2-azaspiro[3.3]heptan-6-yl)phenyl)-6-(((1-methylcyclobutyl)amino)methyl)-4-(trifluoromethyl)isoindolin-1-one |
| 97 | 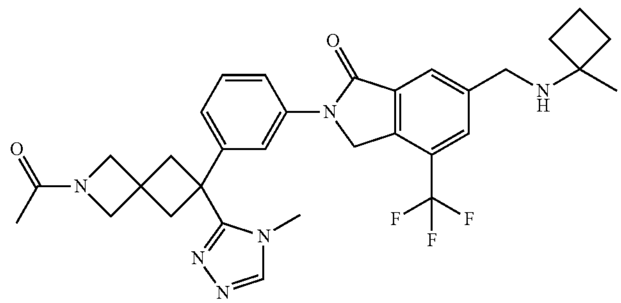 [SMILES: CC(=O)N1CC2(C1)CC(c1cccc(N3Cc4c(cc(CNC5(C)CCC5)cc4C(F)(F)F)C3=O)c1)(c1nncn1C)C2] | 2-(3-(2-acetyl-6-(4-methyl-4H-1,2,4-triazol-3-yl)-2-azaspiro[3.3]heptan-6-yl)phenyl)-6-(((1-methylcyclobutyl)amino)methyl)-4-(trifluoromethyl)isoindolin-1-one |
| 98 | 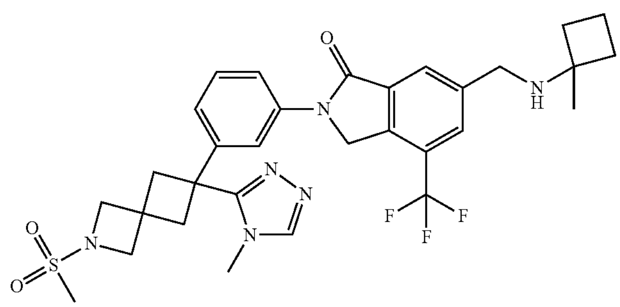 [SMILES: Cn1cnnc1C1(c2cccc(N3Cc4c(cc(CNC5(C)CCC5)cc4C(F)(F)F)C3=O)c2)CC2(CN(S(C)(=O)=O)C2)C1] | 2-(3-(6-(4-methyl-4H-1,2,4-triazol-3-yl)-2-(methylsulfonyl)-2-azaspiro[3.3]heptan-6-yl)phenyl)-6-(((1-methylcyclobutyl)amino)methyl)-4-(trifluoromethyl)isoindolin-1-one |
| 99 | 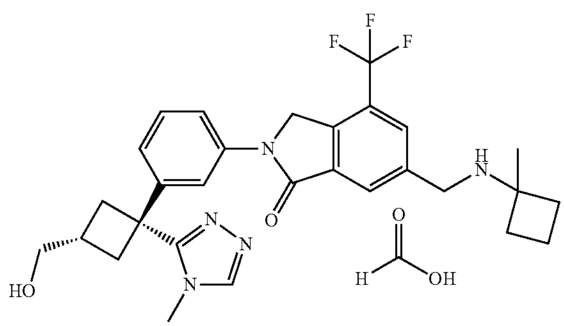 | 2-(3-((1s,3s)-3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one formate |
| 100 | 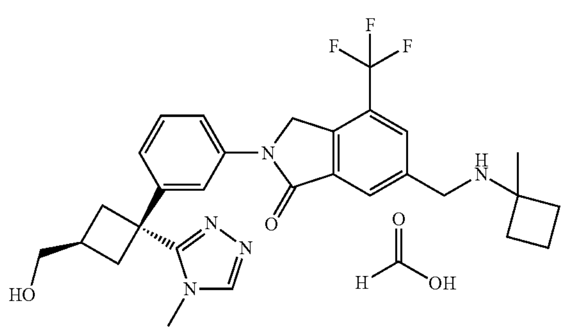 | 2-(3-((1r,3r)-3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one formate |

TABLE 1-continued

| Compound # | Structure | Name |
|---|---|---|
| 101 | 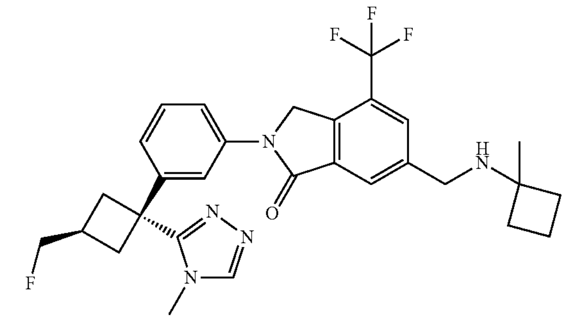 [SMILES: Cn1cnnc1[C@]1(c2cccc(N3Cc4c(cc(CNC5(C)CCC5)cc4C(F)(F)F)C3=O)c2)C[C@@H](CF)C1] | 2-(3-((1r,3r)-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 102 | 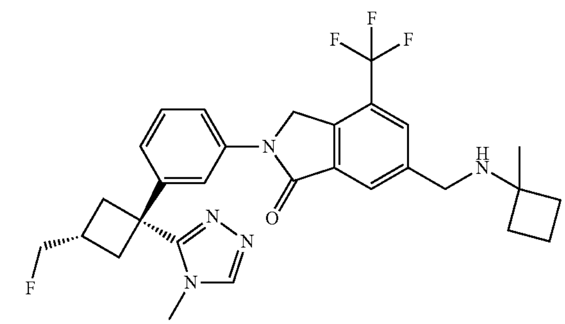 [SMILES: Cn1cnnc1[C@]1(c2cccc(N3Cc4c(cc(CNC5(C)CCC5)cc4C(F)(F)F)C3=O)c2)C[C@H](CF)C1] | 2-(3-((1s,3s)-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 103 | 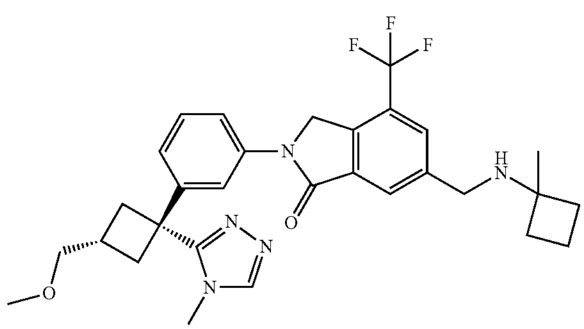 [SMILES: COC[C@H]1C[C@@](c2cccc(N3Cc4c(cc(CNC5(C)CCC5)cc4C(F)(F)F)C3=O)c2)(c2nncn2C)C1] | 2-(3-((1s,3S)-3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 104 | 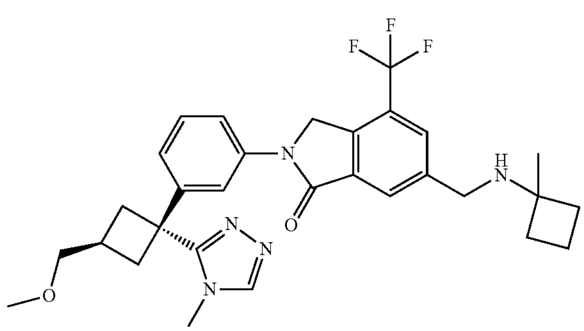 [SMILES: COC[C@H]1C[C@](c2cccc(N3Cc4c(cc(CNC5(C)CCC5)cc4C(F)(F)F)C3=O)c2)(c2nncn2C)C1] | 2-(3-((1r,3r)-3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 105 | 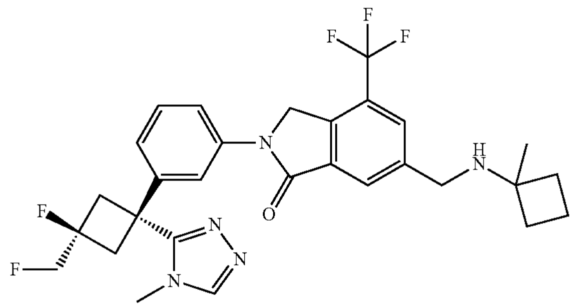 [SMILES: Cn1cnnc1[C@]1(c2cccc(N3Cc4c(cc(CNC5(C)CCC5)cc4C(F)(F)F)C3=O)c2)C[C@](F)(CF)C1] | 2-(3-((1r,3r)-3-fluoro-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 106 | 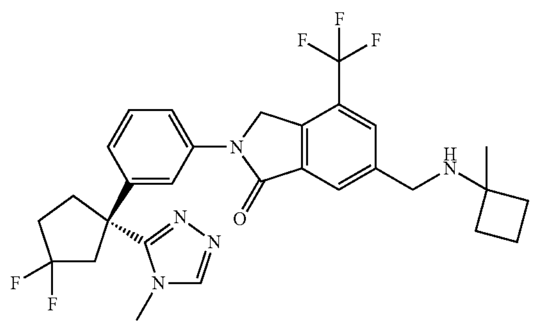 [SMILES: Cn1cnnc1[C@@]1(c2cccc(N3Cc4c(cc(CNC5(C)CCC5)cc4C(F)(F)F)C3=O)c2)CCC(F)(F)C1] | (S)-2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one |
| 107 | 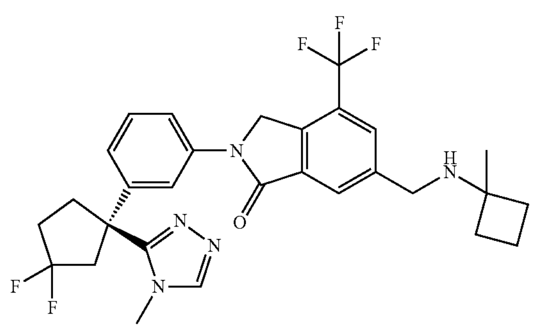 [SMILES: Cn1cnnc1[C@]1(c2cccc(N3Cc4c(cc(CNC5(C)CCC5)cc4C(F)(F)F)C3=O)c2)CCC(F)(F)C1] | (R)-2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one |
| 108 | 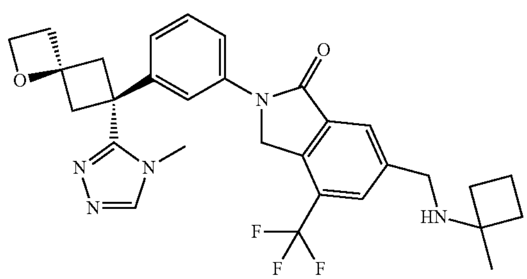 [SMILES: Cn1cnnc1[C@]1(c2cccc(N3Cc4c(cc(CNC5(C)CCC5)cc4C(F)(F)F)C3=O)c2)C[C@]2(CCO2)C1] | 2-(3-((4r,6r)-6-(4-methyl-4H-1,2,4-triazol-3-yl)-1-oxaspiro[3.3]heptan-6-yl)phenyl)-6-(((1-methylcyclobutyl)amino)methyl)-4-(trifluoromethyl)isoindolin-1-one |
| 109 | 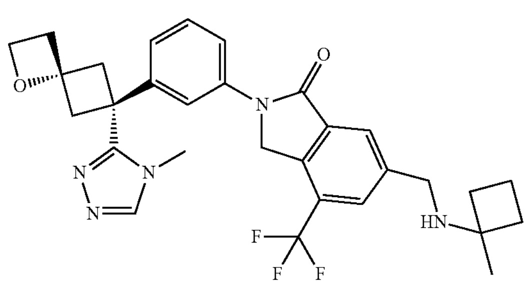 [SMILES: Cn1cnnc1[C@]1(c2cccc(N3Cc4c(cc(CNC5(C)CCC5)cc4C(F)(F)F)C3=O)c2)C[C@@]2(CCO2)C1] | 2-(3-((4s,6s)-6-(4-methyl-4H-1,2,4-triazol-3-yl)-1-oxaspiro[3.3]heptan-6-yl)phenyl)-6-(((1-methylcyclobutyl)amino)methyl)-4-(trifluoromethyl)isoindolin-1-one |

TABLE 1-continued

| Compound # | Structure | Name |
|---|---|---|
| 110 | 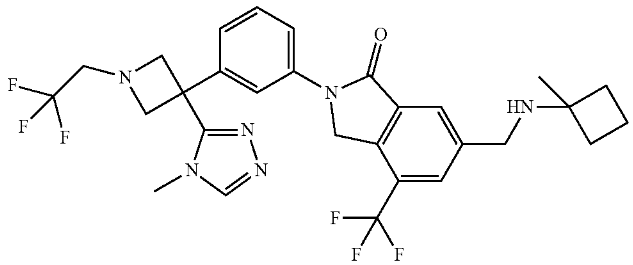 [SMILES: Cn1cnnc1C1(c2cccc(N3Cc4c(cc(CNC5(C)CCC5)cc4C(F)(F)F)C3=O)c2)CN(CC(F)(F)F)C1] | 2-(3-(3-(4-methyl-4H-1,2,4-triazol-3-yl)-1-(2,2,2-trifluoroethyl)azetidin-3-yl)phenyl)-6-(((1-methylcyclobutyl)amino)methyl)-4-(trifluoromethyl)isoindolin-1-one |
| 111 | 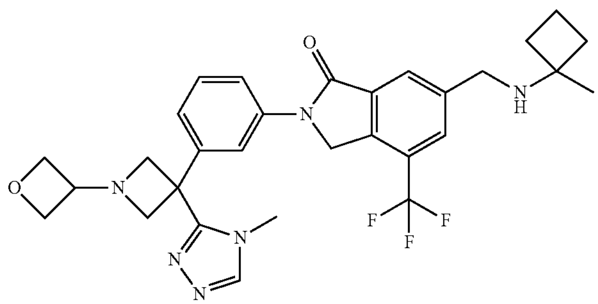 [SMILES: Cn1cnnc1C1(c2cccc(N3Cc4c(cc(CNC5(C)CCC5)cc4C(F)(F)F)C3=O)c2)CN(C2COC2)C1] | 2-(3-(3-(4-methyl-4H-1,2,4-triazol-3-yl)-1-(oxetan-3-yl)azetidin-3-yl)phenyl)-6-(((1-methylcyclobutyl)amino)methyl)-4-(trifluoromethyl)isoindolin-1-one |
| 112 | 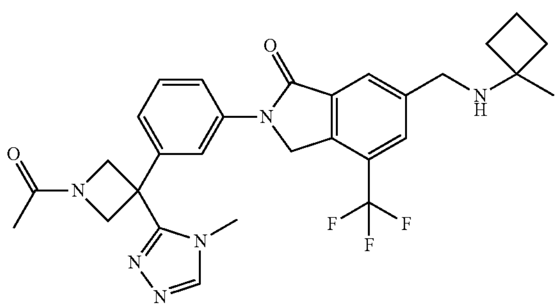 [SMILES: CC(=O)N1CC(c2cccc(N3Cc4c(cc(CNC5(C)CCC5)cc4C(F)(F)F)C3=O)c2)(c2nncn2C)C1] | 2-(3-(1-acetyl-3-(4-methyl-4H-1,2,4-triazol-3-yl)azetidin-3-yl)phenyl)-6-(((1-methylcyclobutyl)amino)methyl)-4-(trilfuoromethyl)isoindolin-1-one |
| 113 | 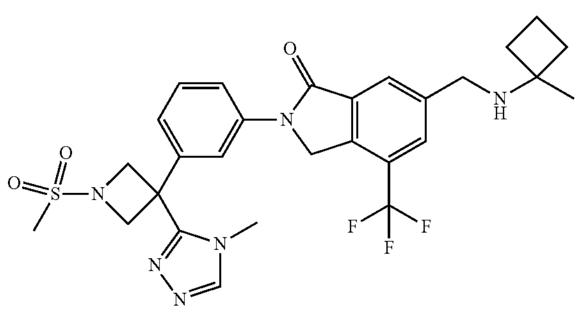 [SMILES: Cn1cnnc1C1(c2cccc(N3Cc4c(cc(CNC5(C)CCC5)cc4C(F)(F)F)C3=O)c2)CN(S(C)(=O)=O)C1] | 2-(3-(3-(4-methyl-4H-1,2,4-triazol-3-yl)-1-(methylsulfonyl)azetidin-3-yl)phenyl)-6-(((1-methylcyclobutyl)amino)methyl)-4-(trifluoromethyl)isoindolin-1-one |
| 114 | 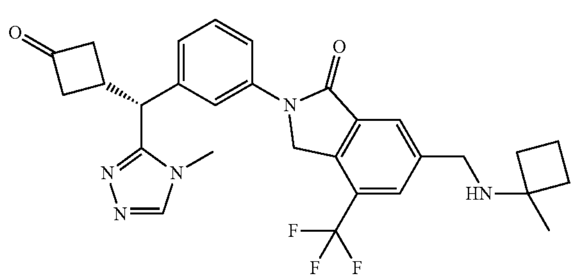 [SMILES: Cn1cnnc1[C@@H](c1cccc(N2Cc3c(cc(CNC4(C)CCC4)cc3C(F)(F)F)C2=O)c1)C1CC(=O)C1] | (R)-2-(3-((4-methyl-4H-1,2,4-triazol-3-yl)(3-oxocyclobutyl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 115 | 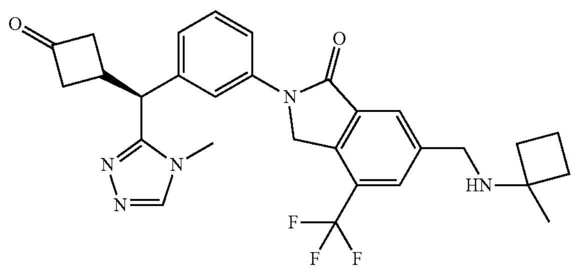 [SMILES: Cn1cnnc1[C@H](c1cccc(N2Cc3c(cc(CNC4(C)CCC4)cc3C(F)(F)F)C2=O)c1)C1CC(=O)C1] | (S)-2-(3-((4-methyl-4H-1,2,4-triazol-3-yl)(3-oxocyclobutyl)methyl)phenyl)-6-(((1-methylcyclobutyl)amino)methyl)-4-(trifluoromethyl)isoindolin-1-one |
| 116 | 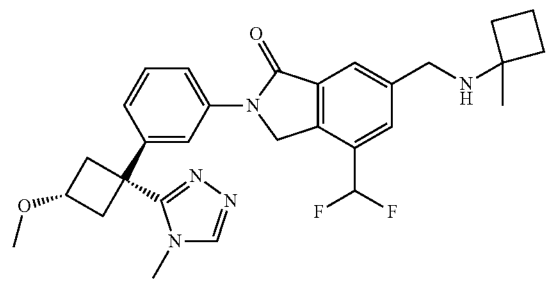 | 4-(difluoromethyl)-2-(3-((1s,3s)-3-methoxy-1-(4-methyl-4H-1,2,4-triazol-3-yl)cyclobutyl)phenyl)-6-(((1-methylcyclobutyl)amino)methyl)isoindolin-1-one |
| 117 | 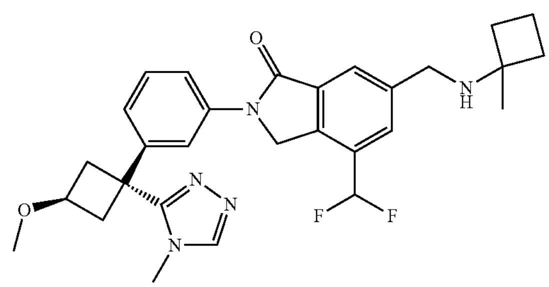 | 4-(difluoromethyl)-2-(3-((1r,3r)-3-methoxy-1-(4-methyl-4H-1,2,4-triazol-3-yl)cyclobutyl)phenyl)-6-(((1-methylcyclobutyl)amino)methyl)isoindolin-1-one |
| 118 | 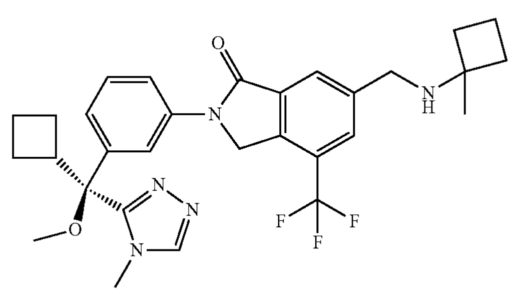 [SMILES: CO[C@@](c1cccc(N2Cc3c(cc(CNC4(C)CCC4)cc3C(F)(F)F)C2=O)c1)(c1nncn1C)C1CCC1] | (S)-2-(3-(cyclobutyl(methoxy)(4-methyl-4H-1,2,4-triazol-3-yl)methyl)phenyl)-6-(((1-methylcyclobutyl)amino)methyl)-4-(trifluoromethyl)isoindolin-1-one |
| 119 | 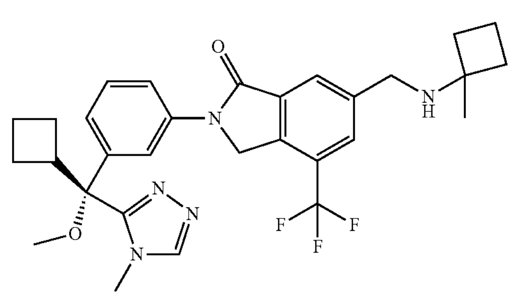 [SMILES: CO[C@](c1cccc(N2Cc3c(cc(CNC4(C)CCC4)cc3C(F)(F)F)C2=O)c1)(c1nncn1C)C1CCC1] | (R)-2-(3-(cyclobutyl(methoxy)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 120 | 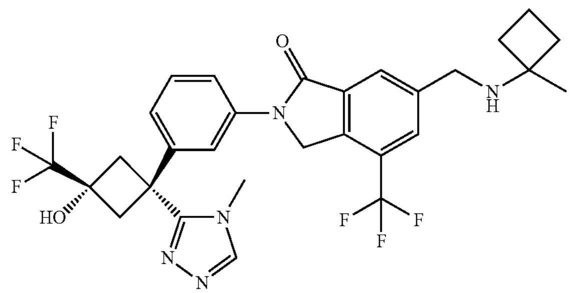 [SMILES: Cn1cnnc1[C@]1(c2cccc(N3Cc4c(cc(CNC5(C)CCC5)cc4C(F)(F)F)C3=O)c2)C[C@@](O)(C(F)(F)F)C1] | 2-(3-((1s,3s)-3-hydroxy-1-(4-methyl-4H-1,2,4-triazol-3-yl)-3-(trifluoromethyl)cyclobutyl)phenyl)-6-(((1-methylcyclobutyl)amino)methyl)-4-(trifluoromethyl)isoindolin-1-one |
| 121 | 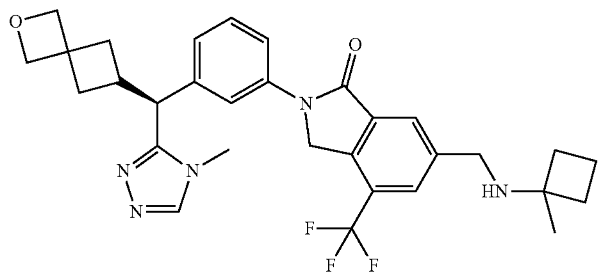 [SMILES: Cn1cnnc1[C@H](c1cccc(N2Cc3c(cc(CNC4(C)CCC4)cc3C(F)(F)F)C2=O)c1)C1CC2(COC2)C1] | (S)-2-(3-((4-methyl-4H-1,2,4-triazol-3-yl)(2-oxaspiro[3.3]heptan-6-yl)methyl)phenyl)-6-(((1-methylcyclobutyl)amino)methyl)-4-(trifluoromethyl)isoindolin-1-one |
| 122 | 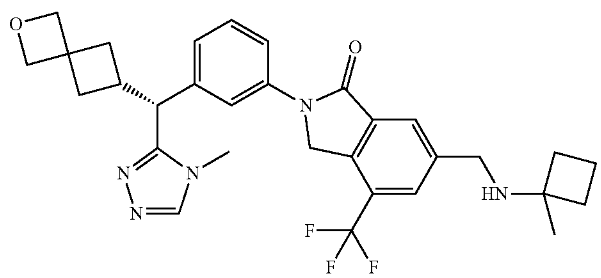 [SMILES: Cn1cnnc1[C@@H](c1cccc(N2Cc3c(cc(CNC4(C)CCC4)cc3C(F)(F)F)C2=O)c1)C1CC2(COC2)C1] | (R)-2-(3-((4-methyl-4H-1,2,4-triazol-3-yl)(2-oxaspiro[3.3]heptan-6-yl)methyl)phenyl)-6-(((1-methylcyclobutyl)amino)methyl)-4-(trifluoromethyl)isoindolin-1-one |
| 123 | 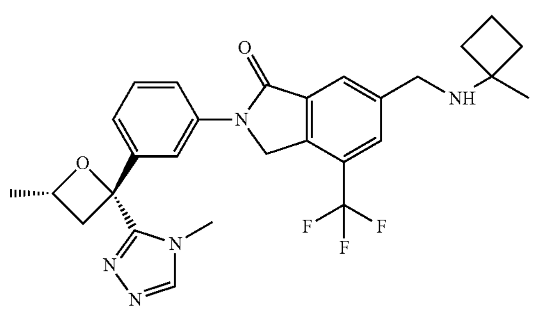 | 2-(3-((2R,4S)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one |
| 124 | 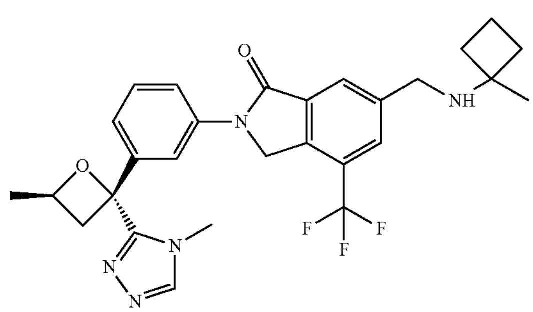 | 2-(3-((2R,4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one |

TABLE 1-continued

| Compound # | Structure | Name |
|---|---|---|
| 125 | 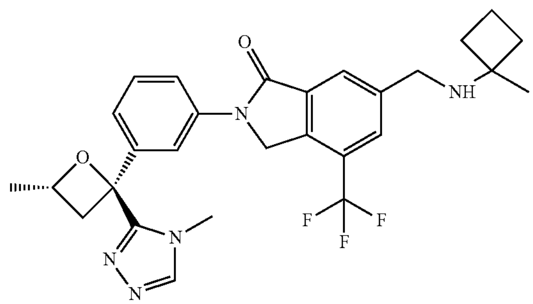 | 2-(3-((2S,3S)-4-methyl-2-(4-methyl-4H-1,2,4-triazol-3-yl)oxetan-2-yl)phenyl)-6-(((1-methylcyclobutyl)amino)methyl)-4-(trifluoroemthyl)isoindolin-1-one |
| 126 | 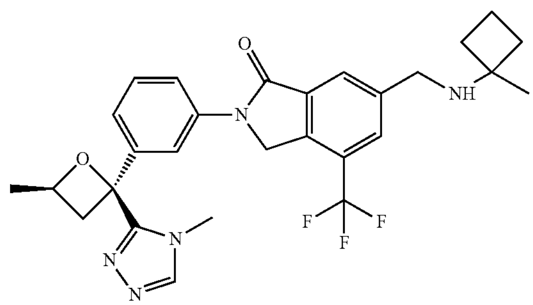 | 2-(3-((2S,4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one |
| 127 | 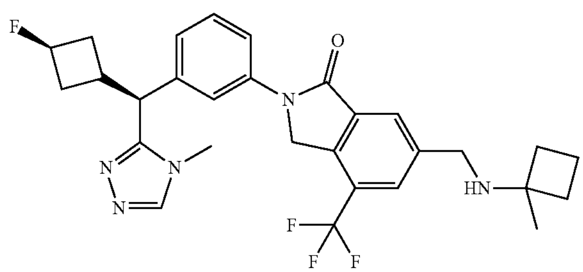 | 2-(3-((S)-((1r,3S)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 128 | 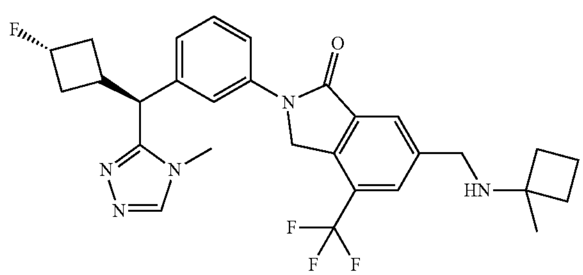 | 2-(3-((S)-((1s,3R)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 129 | 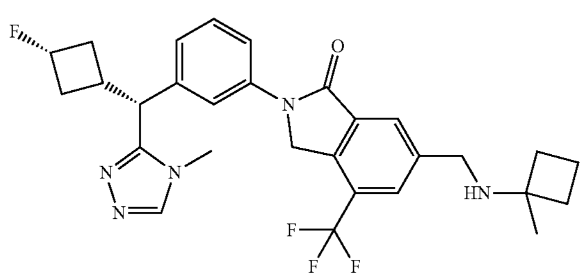 | 2-(3-((R)-((1r,3R)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 130 | 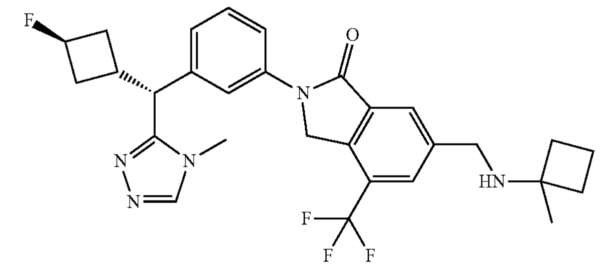 | 2-(3-((R)-((1s,3S)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 131 | 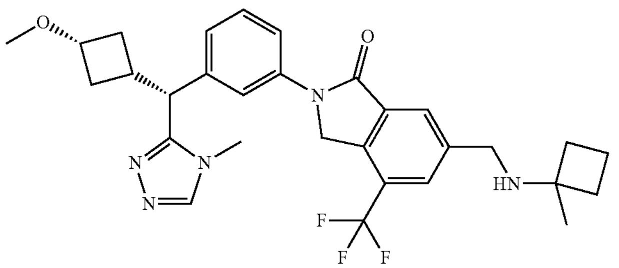 | 2-(3-((R)-((1r,3R)-3-methoxycyclobutyl)(4-methyl-4H-1,2,4-triazol-3-yl)methyl)phenyl)-6-(((1-methylcyclobutyl)amino)methyl)-4-(tifluoromethyl)isoindolin-1-one |
| 132 | 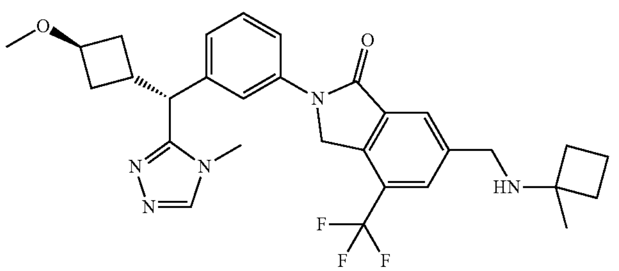 | 2-(3-((R)-((1s,3S)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 133 | 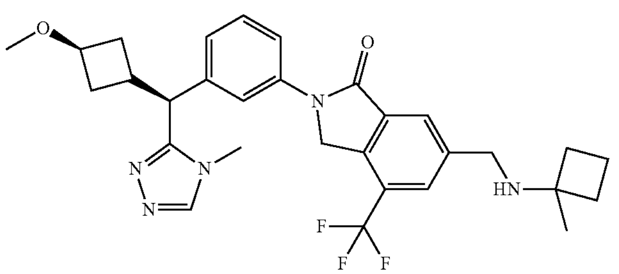 | 2-(3-((S)-((1r,3S)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 134 | 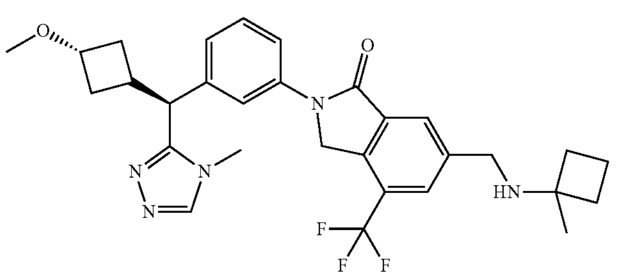 | 2-(3-((S)-((1s,3R)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 135 | 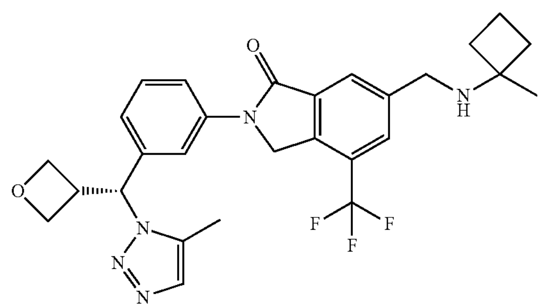 [SMILES: Cc1cnnn1[C@@H](c1cccc(N2Cc3c(cc(CNC4(C)CCC4)cc3C(F)(F)F)C2=O)c1)C1COC1] | (R)-2-(3-((5-methyl-1H-1,2,3-triazol-1-yl)(oxetan-3-yl)methyl)phenyl)-6-(((1-methylcylcobutyl)amino)methyl)-4-(trifluoromethyl)isoindolin-1-one |
| 136 | 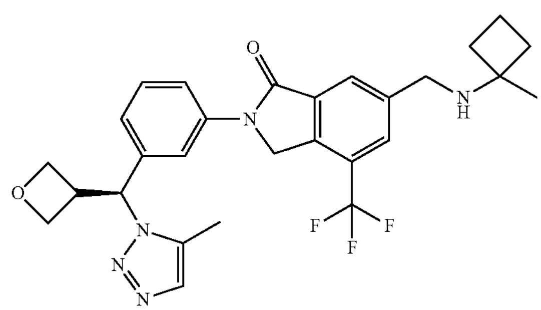 [SMILES: Cc1cnnn1[C@H](c1cccc(N2Cc3c(cc(CNC4(C)CCC4)cc3C(F)(F)F)C2=O)c1)C1COC1] | (S)-2-(3-((5-methyl-1H-1,2,3-triazol-1-yl)(oxetan-3-yl)methyl)phenyl)-6-(((1-methylcyclobutyl)amino)methyl)-4-(trifluoro-methyl)isoindolin-1-one |
| 137 | 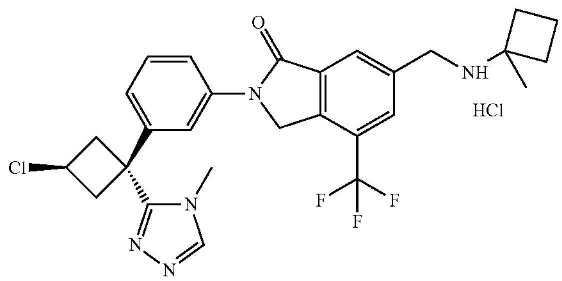 [SMILES: Cn1cnnc1[C@]1(c2cccc(N3Cc4c(cc(CNC5(C)CCC5)cc4C(F)(F)F)C3=O)c2)C[C@@H](Cl)C1 ; Cl] | 2-(3-((1r,3r)-3-chloro-1-(4-methyl-4H-1,2,4-triazol-3-yl)cyclobutyl)phenyl)-6-(((1-methylcyclobutyl)amino)methyl)-4-(trifluoromethyl)isoindolin-1-one hydrochloride |
| 138 | 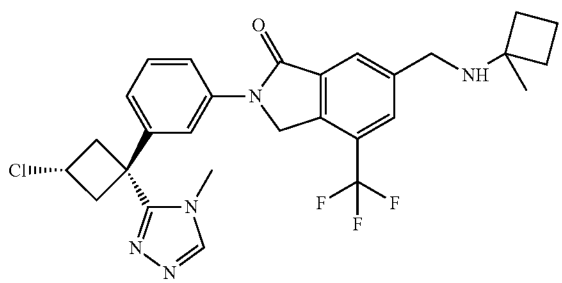 [SMILES: Cn1cnnc1[C@]1(c2cccc(N3Cc4c(cc(CNC5(C)CCC5)cc4C(F)(F)F)C3=O)c2)C[C@H](Cl)C1] | 2-(3-((1s,3s)-3-chloro-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 139 | 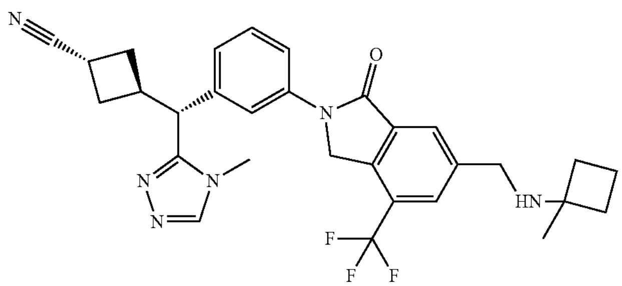 [SMILES: Cn1cnnc1[C@@H](c1cccc(N2Cc3c(cc(CNC4(C)CCC4)cc3C(F)(F)F)C2=O)c1)[C@H]1C[C@H](C#N)C1] | (1R,3r)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile |

TABLE 1-continued

| Compound # | Structure | Name |
|---|---|---|
| 140 | 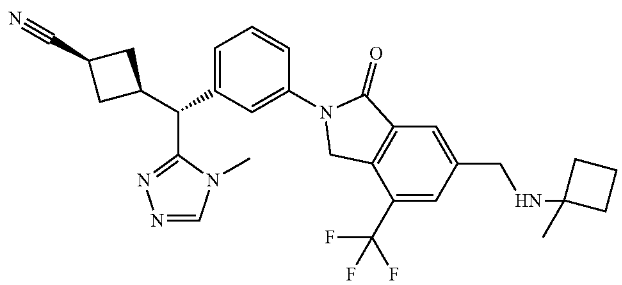 [SMILES: Cn1cnnc1[C@@H](c1cccc(N2Cc3c(cc(CNC4(C)CCC4)cc3C(F)(F)F)C2=O)c1)[C@H]1C[C@@H](C#N)C1] | (1S,3s)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile |
| 141 | 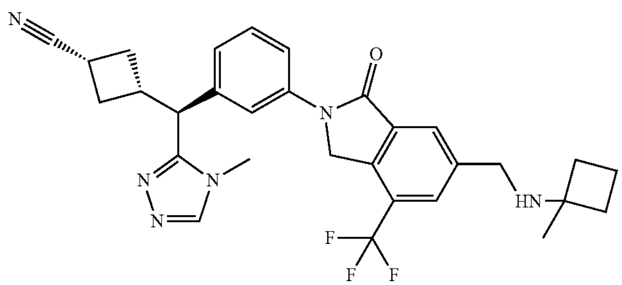 [SMILES: Cn1cnnc1[C@H](c1cccc(N2Cc3c(cc(CNC4(C)CCC4)cc3C(F)(F)F)C2=O)c1)[C@H]1C[C@@H](C#N)C1] | (1R,3s)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile |
| 142 | 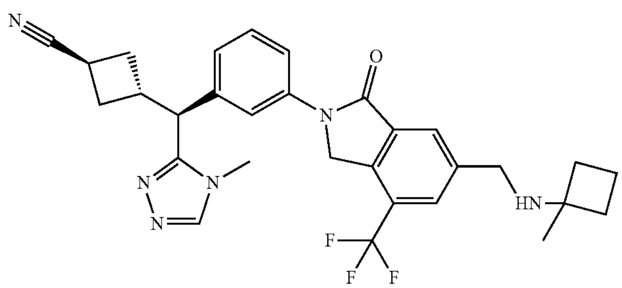 [SMILES: Cn1cnnc1[C@H](c1cccc(N2Cc3c(cc(CNC4(C)CCC4)cc3C(F)(F)F)C2=O)c1)[C@H]1C[C@H](C#N)C1] | (1S,3r)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile |
| 143 | 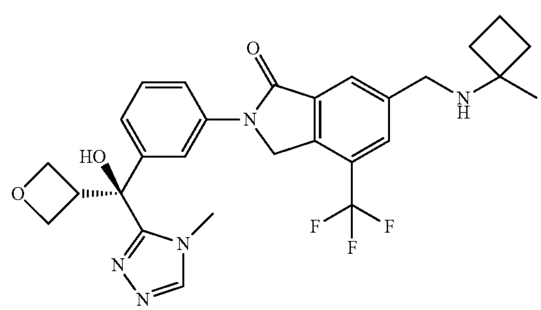 [SMILES: Cn1cnnc1[C@@](O)(c1cccc(N2Cc3c(cc(CNC4(C)CCC4)cc3C(F)(F)F)C2=O)c1)C1COC1] | (S)-2-(3-(hydroxy(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 144 | 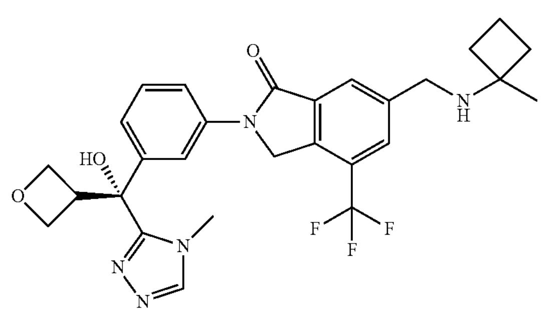 [SMILES: Cn1cnnc1[C@](O)(c1cccc(N2Cc3c(cc(CNC4(C)CCC4)cc3C(F)(F)F)C2=O)c1)C1COC1] | (R)-2-(3-(hydroxy(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 145 | 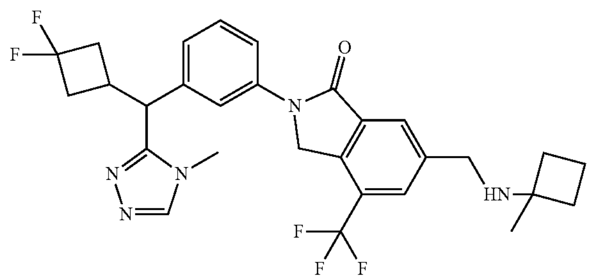 [SMILES: Cn1cnnc1C(c1cccc(N2Cc3c(cc(CNC4(C)CCC4)cc3C(F)(F)F)C2=O)c1)C1CC(F)(F)C1] | 2-(3-((3,3-difluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 146 | 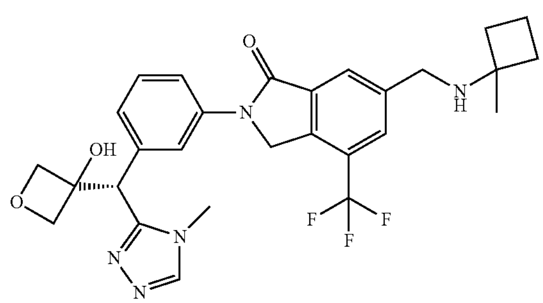 [SMILES: Cn1cnnc1[C@@H](c1cccc(N2Cc3c(cc(CNC4(C)CCC4)cc3C(F)(F)F)C2=O)c1)C1(O)COC1] | (R)-2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 147 | 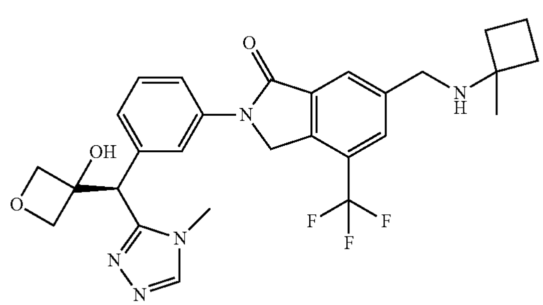 [SMILES: Cn1cnnc1[C@H](c1cccc(N2Cc3c(cc(CNC4(C)CCC4)cc3C(F)(F)F)C2=O)c1)C1(O)COC1] | (S)-2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 148 | 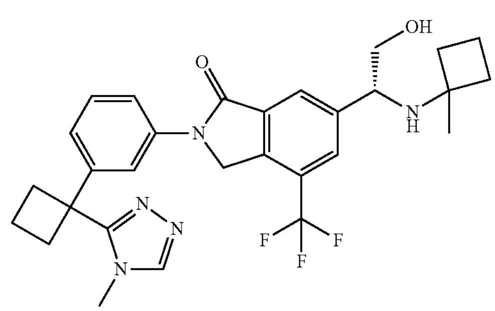 [SMILES: Cn1cnnc1C1(c2cccc(N3Cc4c(cc([C@H](CO)NC5(C)CCC5)cc4C(F)(F)F)C3=O)c2)CCC1] | (R)-6-(2-hydroxy-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one |
| 149 | 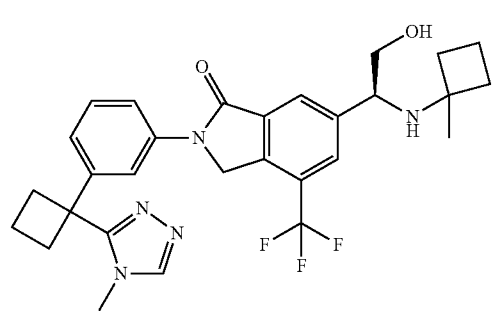 [SMILES: Cn1cnnc1C1(c2cccc(N3Cc4c(cc([C@@H](CO)NC5(C)CCC5)cc4C(F)(F)F)C3=O)c2)CCC1] | (S)-6-(2-hydroxy-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 150 | 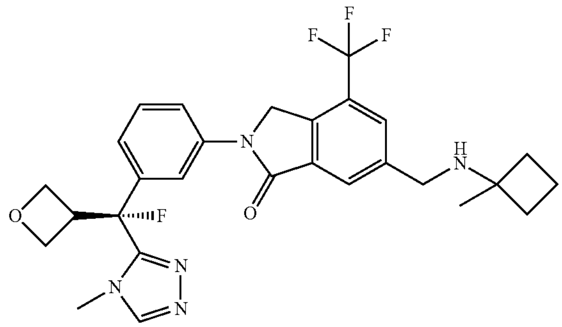 | (R)-2-(3-(fluoro(4-methyl-4H-1,2,4-triazol-3-yl)(oxetan-3-yl)methyl)phenyl)-6-(((1-methylcyclobutyl)amino)methyl)-4-(trifluoro-methyl)isoindolin-1-one |
| 151 | 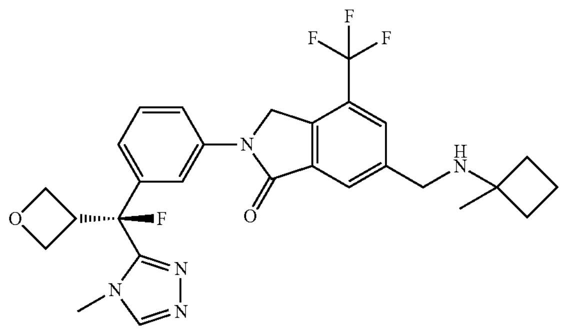 | (S)-2-(3-(fluoro(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 152 | 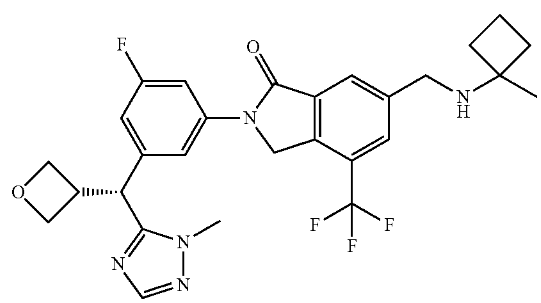 [SMILES: Cn1ncnc1[C@@H](c1cc(F)cc(N2Cc3c(cc(CNC4(C)CCC4)cc3C(F)(F)F)C2=O)c1)C1COC1] | (R)-2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 153 | 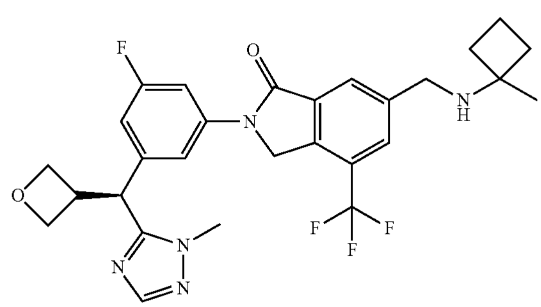 [SMILES: Cn1ncnc1[C@H](c1cc(F)cc(N2Cc3c(cc(CNC4(C)CCC4)cc3C(F)(F)F)C2=O)c1)C1COC1] | (S)-2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 154 | 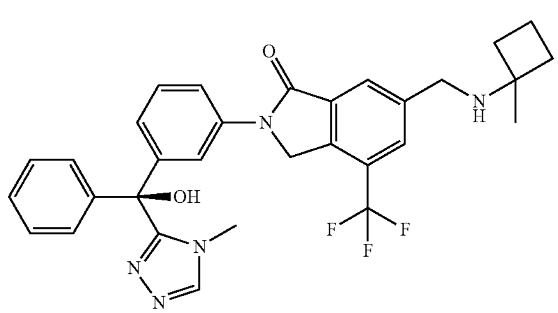 [SMILES: Cn1cnnc1[C@](O)(c1ccccc1)c1cccc(N2Cc3c(cc(CNC4(C)CCC4)cc3C(F)(F)F)C2=O)c1] | (S)-2-(3-(hydroxy(4-methyl-4H-1,2,4-triazol-3-yl)(phenyl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 155 | 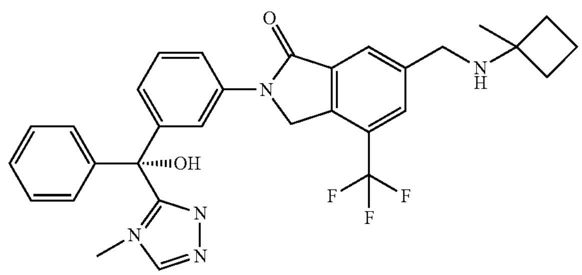 | (R)-2-(3-(hydroxy(4-methyl-4H-1,2,4-triazol-3-yl)(phenyl)methyl)phenyl)-6-(((1-methylcyclobutyl)amino)methyl)-4-(trifluoromethyl)isoindolin-1-one |
| 156 | 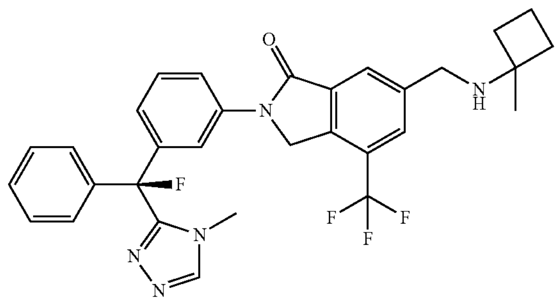 [SMILES: Cn1cnnc1[C@](F)(c1ccccc1)c1cccc(N2Cc3c(cc(CNC4(C)CCC4)cc3C(F)(F)F)C2=O)c1] | (S)-2-(3-(fluoro(4-methyl-4H-1,2,4-triazol-3-yl)(phenyl)methyl)phenyl)-6-(((1-methylcyclobutyl)amino)methyl)-4-(trifluoro-methyl)isoindolin-1-one |
| 157 | 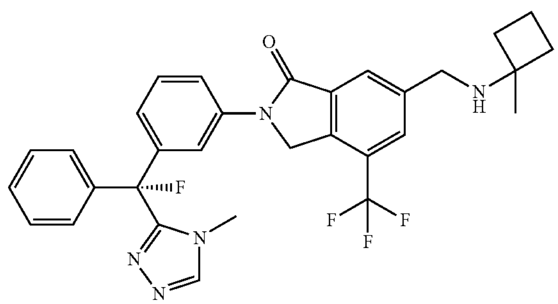 [SMILES: Cn1cnnc1[C@@](F)(c1ccccc1)c1cccc(N2Cc3c(cc(CNC4(C)CCC4)cc3C(F)(F)F)C2=O)c1] | (R)-2-(3-(fluoro(4-methyl-4H-1,2,4-triazol-3-yl)(phenyl)methyl)phenyl)-6-(((1-methylcyclobutyl)amino)methyl)-4-(trifluoro-methyl)isoindolin-1-one |
| 158 | 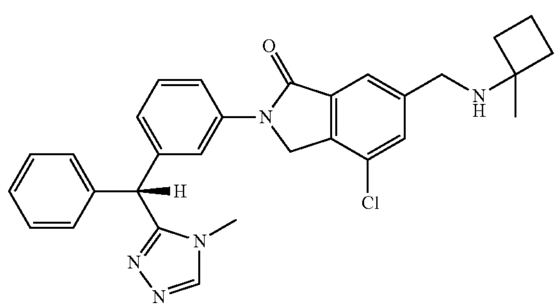 [SMILES: Cn1cnnc1[C@H](c1ccccc1)c1cccc(N2Cc3c(Cl)cc(CNC4(C)CCC4)cc3C2=O)c1] | (R)-4-chloro-2-(3-((4-methyl-4H-1,2,4-triazol-3-yl)(phenyl)methyl)phenyl)-6-(((1-methylcyclobutyl)amino)methyl)isoindolin-1-one |
| 159 | 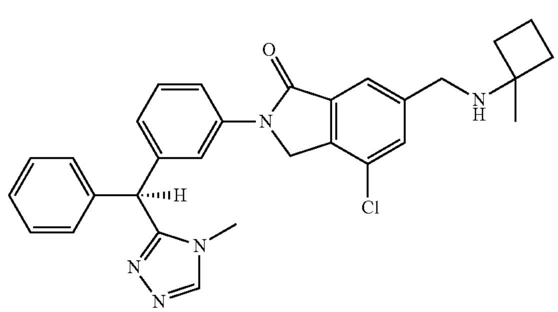 [SMILES: Cn1cnnc1[C@@H](c1ccccc1)c1cccc(N2Cc3c(Cl)cc(CNC4(C)CCC4)cc3C2=O)c1] | (S)-4-chloro-2-(3-((4-methyl-4H-1,2,4-triazol-3-yl)(phenyl)methyl)phenyl)-6-(((1-methylcyclobutyl)amino)methyl)isoindolin-1-one |

TABLE 1-continued

| Compound # | Structure | Name |
|---|---|---|
| 160 | 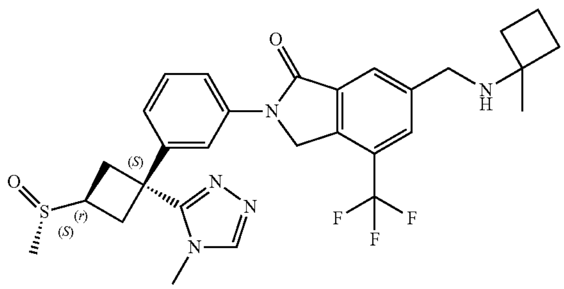 | 2-(3-((1S,3r)-1-(4-methyl-4H-1,2,4-triazol-3-yl)-3-((S)-methylsulfinyl)cyclobutyl)phenyl)-6-(((1-methylcyclobutyl)amino)methyl)-4-(trifluoromethyl)isoindolin-1-one |
| 161 | 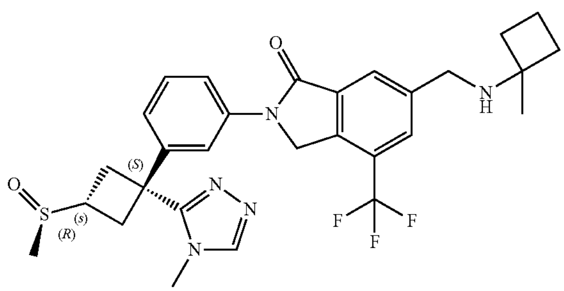 | 2-(3-((1S,3s)-1-(4-methyl-4H-1,2,4-triazol-3-yl)-3-((R)-methylsulfinyl)cyclobutyl)phenyl)-6-(((1-methylcyclobutyl)amino)methyl)-4-(trifluoromethyl)isoindolin-1-one |
| 162 | 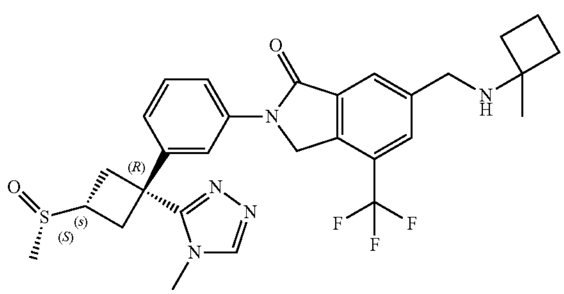 | 2-(3-((1R,3s)-1-(4-methyl-4H-1,2,4-triazol-3-yl)-3-((S)-methylsulfinyl)cyclobutyl)phenyl)-6-(((1-methylcyclobutyl)amino)methyl)-4-(trifluoromethyl)isoindolin-1-one |
| 163 | 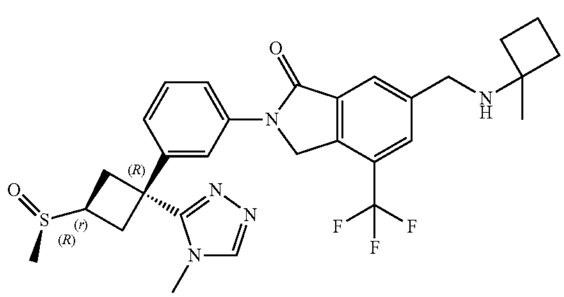 | 2-(3-((1R,3r)-1-(4-methyl-4H-1,2,4-triazol-3-yl)-3-((R)-methylsulfinyl)cyclobutyl)phenyl)-6-(((1-methylcyclobutyl)amino)methyl)-4-(trifluoromethyl)isoindolin-1-one |
| 164 | 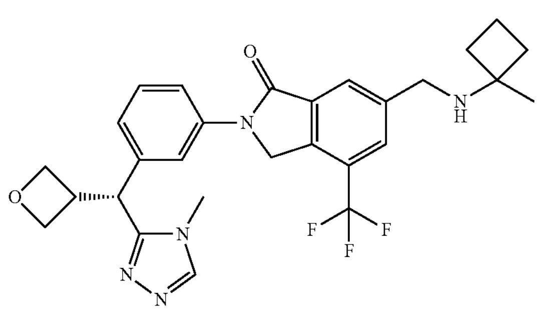 [SMILES: Cn1cnnc1[C@@H](c1cccc(N2Cc3c(cc(CNC4(C)CCC4)cc3C(F)(F)F)C2=O)c1)C1COC1] | (R)-2-(3-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 165 | 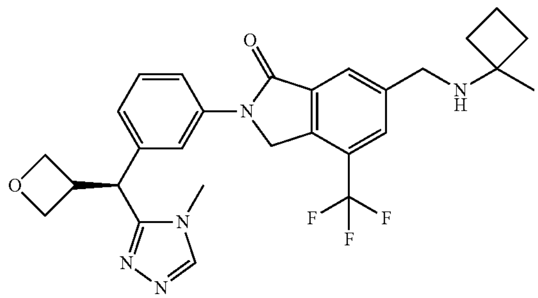 [SMILES: Cn1cnnc1[C@H](c1cccc(N2Cc3c(cc(CNC4(C)CCC4)cc3C(F)(F)F)C2=O)c1)C1COC1] | (S)-2-(3-((4-methyl-4H-1,2,4-triaozl-3-yl)(oxetan-3-yl)methyl)phenyl)-6-(((1-methylcyclobutyl)amino)methyl)-4-(trifluoromethyl)isoindolin-1-one |
| 166 | 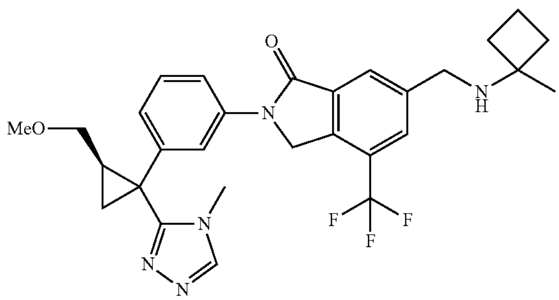 [SMILES: COC[C@@H]1CC1(c1cccc(N2Cc3c(cc(CNC4(C)CCC4)cc3C(F)(F)F)C2=O)c1)c1nncn1C] | 2-(3-((2R)-2-(methoxymethyl)-1-(4-methyl-4H-1,2,4-triazol-3-yl)cyclopropyl)phenyl)-6-(((1-methylcyclobutyl)amino)methyl)-4-(trifluoromethyl)isoindolin-1-one |
| 167 | 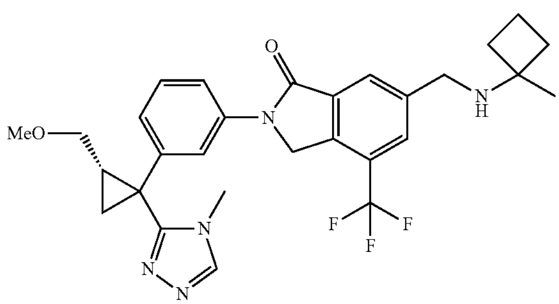 [SMILES: COC[C@H]1CC1(c1cccc(N2Cc3c(cc(CNC4(C)CCC4)cc3C(F)(F)F)C2=O)c1)c1nncn1C] | 2-(3-((2S)-2-(methoxymethyl)-1-(4-methyl-4H-1,2,4-triazol-3-yl)cyclopropyl)phenyl)-6-(((1-methylcyclobutyl)amino)methyl)-4-(trifluoromethyl)isoindolin-1-one |
| 168 | 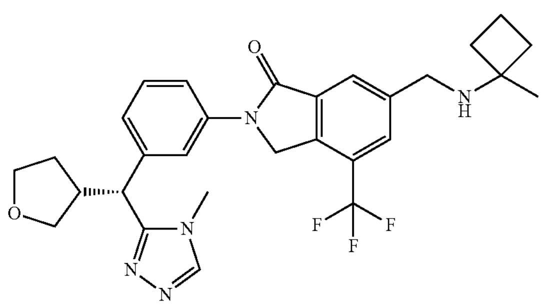 [SMILES: Cn1cnnc1[C@@H](c1cccc(N2Cc3c(cc(CNC4(C)CCC4)cc3C(F)(F)F)C2=O)c1)C1CCOC1] | 2-(3-((R)-(4-methyl-4H-1,2,4-triazol-3-yl)((S)-tetrahydrofuran-3-yl)methyl)phenyl)-6-(((1-methylcyclobutyl)amino)methyl)-4-(trifluoromethyl)isoindolin-1-one |
| 169 | 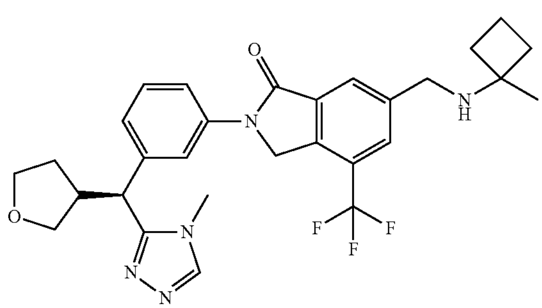 [SMILES: Cn1cnnc1[C@H](c1cccc(N2Cc3c(cc(CNC4(C)CCC4)cc3C(F)(F)F)C2=O)c1)C1CCOC1] | 2-(3-((S)-(4-methyl-4H-1,2,4-triazol-3-yl)((R)-tetrahydrofuran-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 170 | 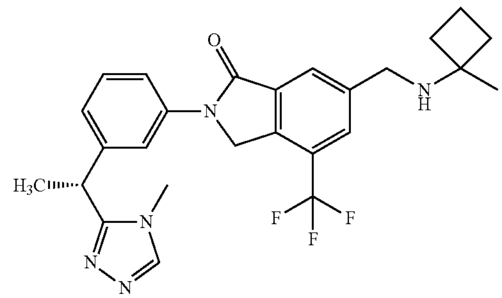 [SMILES: C[C@H](c1cccc(N2Cc3c(cc(CNC4(C)CCC4)cc3C(F)(F)F)C2=O)c1)c1nncn1C] | (R)-2-(3-(1-(4-methyl-4H-1,2,4-triazol-3-yl)ethyl)phenyl)-6-(((1-methylcyclobutyl)amino)methyl)-4-(trifluoromethyl)isoindolin-1-one |
| 171 | 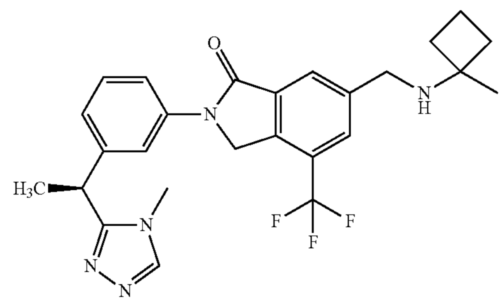 [SMILES: C[C@@H](c1cccc(N2Cc3c(cc(CNC4(C)CCC4)cc3C(F)(F)F)C2=O)c1)c1nncn1C] | 2-(3-(1-(4-methyl-4H-1,2,4-triazol-3-yl)ethyl)phenyl)-6-(((1-methylcyclobutyl)amino)methyl)-4-(trifluoromethyl)isoindolin-1-one |
| 172 | 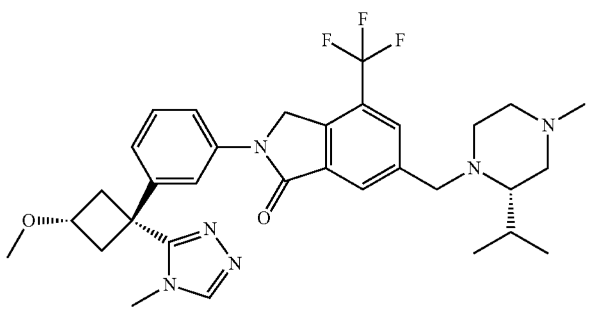 | 6-(((S)-2-isopropyl-4-methylpiperazin-1-yl)methyl)-2-(3-((1s,3R)-3-methoxy-1-(4-methyl-4H-1,2,4-triazol-3-yl)cyclobutyl)phenyl)-4-(trifluoromethyl)isoindolin-1-one |
| 173 | 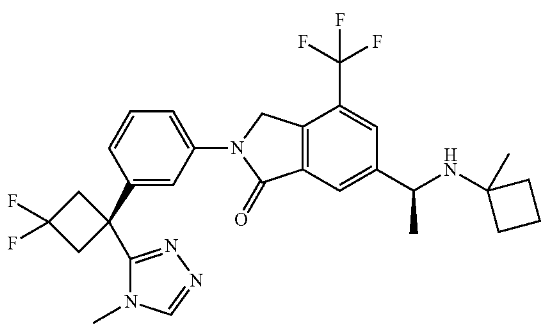 | (S)-2-(3-(3,3-difluoro-1-(4-methyl-4H-1,2,4-triazol-3-yl)cyclobutyl)phenyl)-6-(1-((1-methylcyclobutyl)amino)ethyl)-4-(trifluoromethyl)isoindolin-1-one |
| 174 | 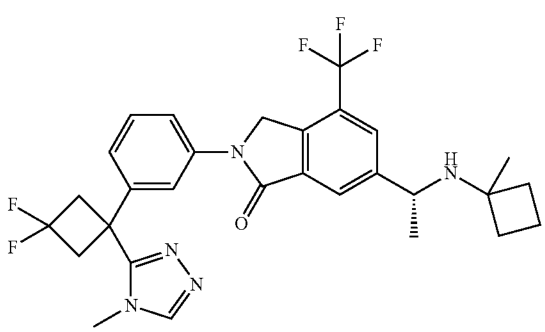 [SMILES: C[C@@H](NC1(C)CCC1)c1cc2c(c(C(F)(F)F)c1)CN(c1cccc(C3(c4nncn4C)CC(F)(F)C3)c1)C2=O] | (R)-2-(3-(3,3-difluoro-1-(4-methyl-4H-1,2,4-triazol-3-yl)cyclobutyl)phenyl)-6-(1-((1-methylcyclobutyl)amino)ethyl)-4-(trifluoromethyl)isoindolin-1-one |

TABLE 1-continued

| Compound # | Structure | Name |
|---|---|---|
| 175 | 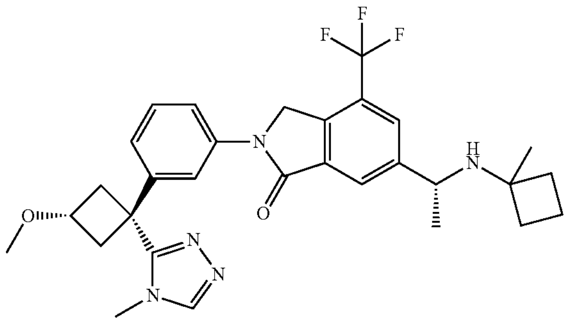 [SMILES: CO[C@H]1C[C@@](c2cccc(N3Cc4c(cc([C@@H](C)NC5(C)CCC5)cc4C(F)(F)F)C3=O)c2)(c2nncn2C)C1] | 2-(3-((1s,3S)-3-methoxy-1-(4-methyl-4H-1,2,4-triazol-3-yl)cyclobutyl)phenyl)-6-((R)-1-((1-methylcyclobutyl)amino)ethyl)-4-(trifluoromethyl)isoindolin-1-one |
| 176 | 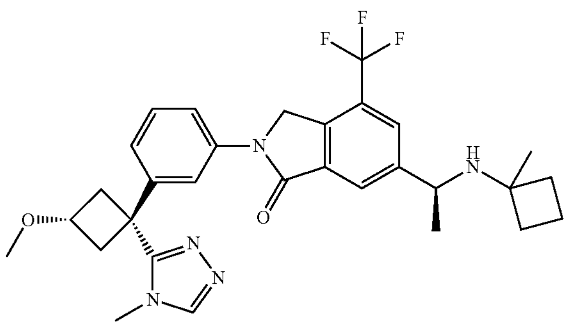 [SMILES: CO[C@H]1C[C@@](c2cccc(N3Cc4c(cc([C@H](C)NC5(C)CCC5)cc4C(F)(F)F)C3=O)c2)(c2nncn2C)C1] | 2-(3-((1s,3R)-3-methoxy-1-(4-methyl-4H-1,2,4-triazol-3-yl)cyclobutyl)phenyl)-6-((S)-1-((1-methylcyclobutyl)amino)ethyl)-4-(trifluoromethyl)isoindolin-1-one |
| 177 | 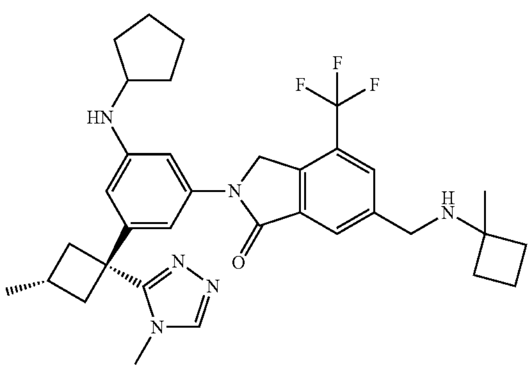 [SMILES: Cn1cnnc1[C@]1(c2cc(NC3CCCC3)cc(N3Cc4c(cc(CNC5(C)CCC5)cc4C(F)(F)F)C3=O)c2)C[C@H](C)C1] | 2-(3-(cyclopentylamino)-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 178 | 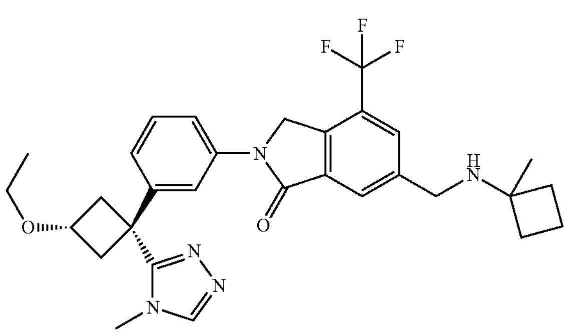 [SMILES: CCO[C@H]1C[C@@](c2cccc(N3Cc4c(cc(CNC5(C)CCC5)cc4C(F)(F)F)C3=O)c2)(c2nncn2C)C1] | 2-(3-((1s,3s)-3-ethoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 179 | 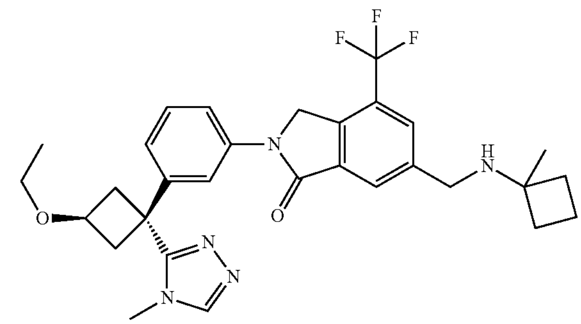 [SMILES: CCO[C@H]1C[C@](c2cccc(N3Cc4c(cc(CNC5(C)CCC5)cc4C(F)(F)F)C3=O)c2)(c2nncn2C)C1] | 2-(3-((1r,3r)-3-ethoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 180 | 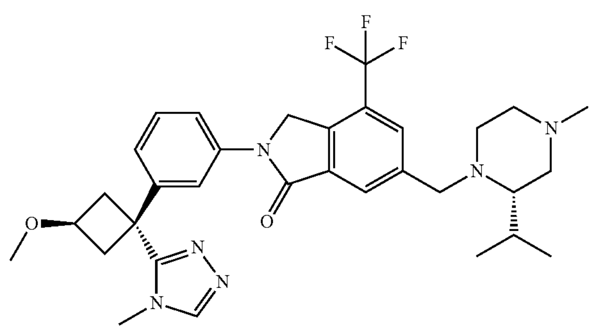 | 6-(((S)-2-isopropyl-4-methylpiperazin-1-yl)methyl)-2-(3-((1r,3S)-3-methoxy-1-(4-methyl-4H-1,2,4-triazol-3-yl)cyclobutyl)phenyl)-4-(trifluoromethyl)isoindolin-1-one |
| 181 | 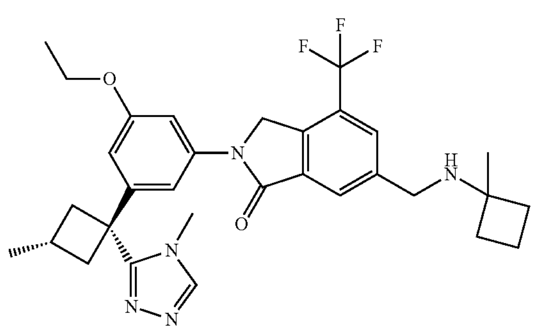 [SMILES: CCOc1cc(N2Cc3c(cc(CNC4(C)CCC4)cc3C(F)(F)F)C2=O)cc([C@]2(c3nncn3C)C[C@@H](C)C2)c1] | 2-(3-ethoxy-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 182 | 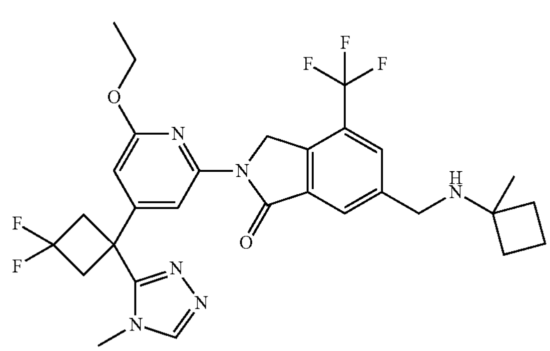 [SMILES: CCOc1cc(C2(c3nncn3C)CC(F)(F)C2)cc(N2Cc3c(cc(CNC4(C)CCC4)cc3C(F)(F)F)C2=O)n1] | 2-(4-(3,3-difluoro-1-(4-methyl-4H-1,2,4-triazol-3-yl)cyclobutyl)-6-ethoxypyridin-2-yl)-6-(((1-methylcyclobutyl)amino)methyl)-4-(trifluoromethyl)isoindolin-1-one |

TABLE 1-continued

| Compound # | Structure | Name |
|---|---|---|
| 183 | 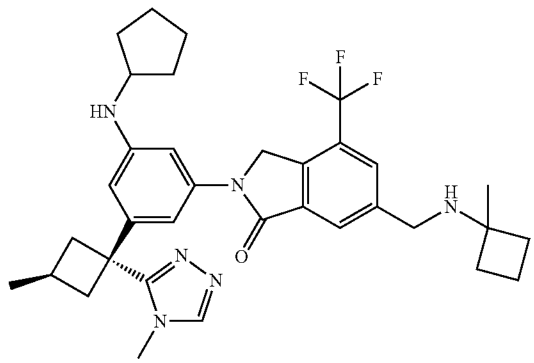 [SMILES: Cn1cnnc1[C@]1(c2cc(NC3CCCC3)cc(N3Cc4c(cc(CNC5(C)CCC5)cc4C(F)(F)F)C3=O)c2)C[C@@H](C)C1] | 2-(3-(cyclopentylamino)-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 184 | 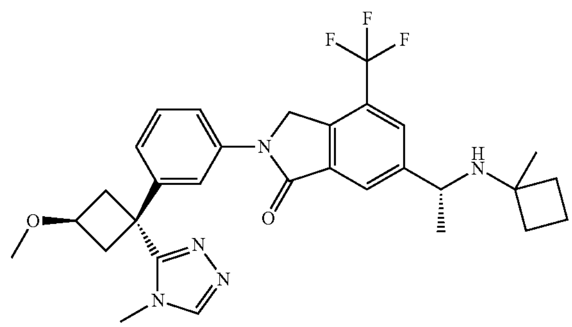 [SMILES: CO[C@H]1C[C@](c2cccc(N3Cc4c(cc([C@@H](C)NC5(C)CCC5)cc4C(F)(F)F)C3=O)c2)(c2nncn2C)C1] | 2-(3-((1r,3R)-3-methoxy-1-(4-methyl-4H-1,2,4-triazol-3-yl)cyclobutyl)phenyl)-6-((R)-1-((1-methylcyclobutyl)amino)ethyl)-4-(trifluoromethyl)isoindolin-1-one |
| 185 | 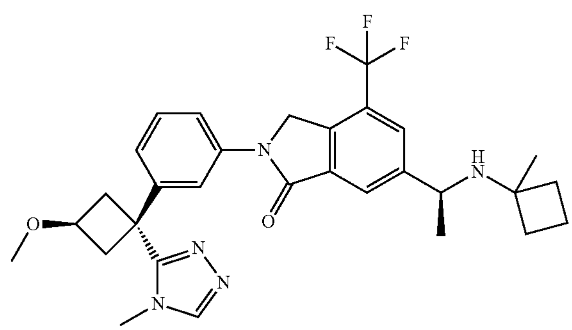 [SMILES: CO[C@H]1C[C@](c2cccc(N3Cc4c(cc([C@H](C)NC5(C)CCC5)cc4C(F)(F)F)C3=O)c2)(c2nncn2C)C1] | 2-(3-((1r,3S)-3-methoxy-1-(4-methyl-4H-1,2,4-triazol-3-yl)cyclobutyl)phenyl)-6-((S)-1-((1-methylcyclobutyl)amino)ethyl)-4-(trifluoromethyl)isoindolin-1-one |
| 186 | 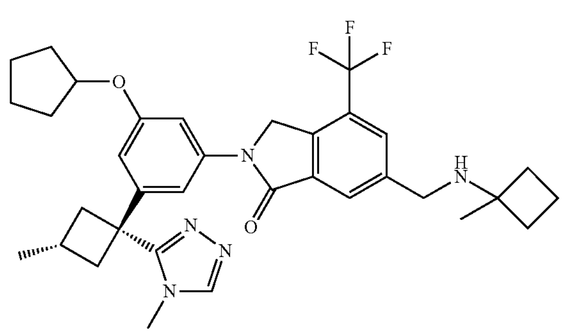 [SMILES: Cn1cnnc1[C@]1(c2cc(OC3CCCC3)cc(N3Cc4c(cc(CNC5(C)CCC5)cc4C(F)(F)F)C3=O)c2)C[C@H](C)C1] | 2-(3-(cyclopentyloxy)-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 187 | 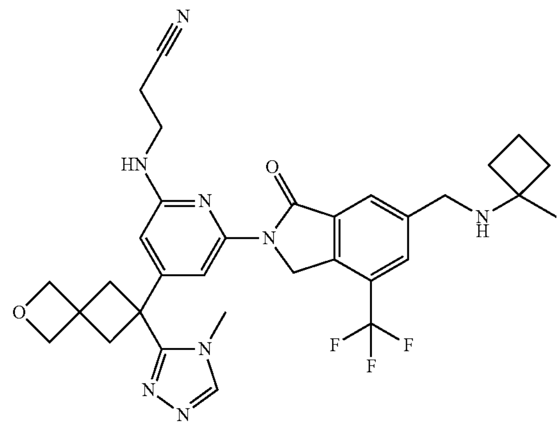 [SMILES: Cn1cnnc1C1(c2cc(NCCC#N)nc(N3Cc4c(cc(CNC5(C)CCC5)cc4C(F)(F)F)C3=O)c2)CC2(COC2)C1] | 3-((4-(6-(4-methyl-4H-1,2,4-triazol-3-yl)-2-oxaspiro[3.3]heptan-6-yl)-6-(6-(((1-methylcyclobutyl)amino)methyl)-1-oxo-4-(trifluoromethyl)isoindolin-2-yl)pyridin-2-yl)amino)propanenitrile |
| 188 | 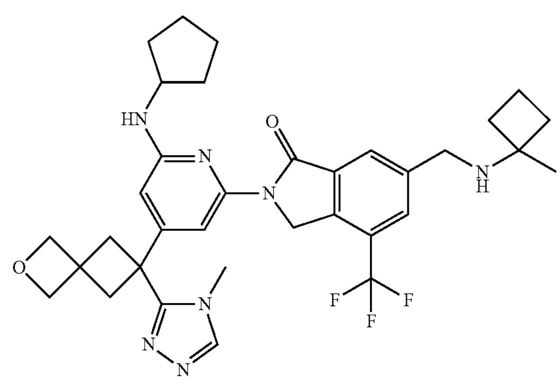 [SMILES: Cn1cnnc1C1(c2cc(NC3CCCC3)nc(N3Cc4c(cc(CNC5(C)CCC5)cc4C(F)(F)F)C3=O)c2)CC2(COC2)C1] | 2-(6-(cyclopentylamino)-4-(6-(4-methyl-4H-1,2,4-triazol-3-yl)-2-oxaspiro[3.3]heptna-6-yl)pyridin-2-yl)-6-(((1-methylcyclobutyl)amino)methyl)-4-(trifluoromethyl)isoindolin-1-one |
| 189 | 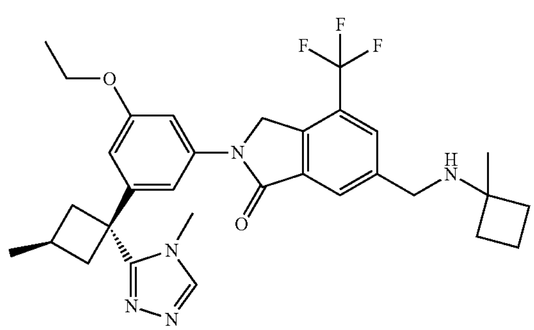 [SMILES: CCOc1cc(N2Cc3c(cc(CNC4(C)CCC4)cc3C(F)(F)F)C2=O)cc([C@]2(c3nncn3C)C[C@H](C)C2)c1] | 2-(3-ethoxy-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 190 | 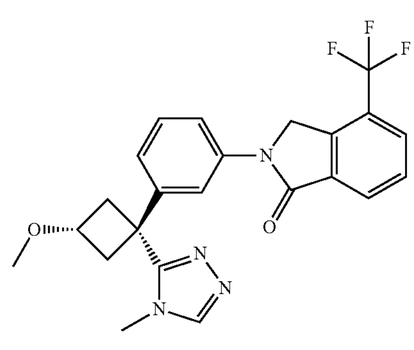 [SMILES: CO[C@H]1C[C@@](c2cccc(N3Cc4c(cccc4C(F)(F)F)C3=O)c2)(c2nncn2C)C1] | 2-(3-((1s,3s)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 191 | 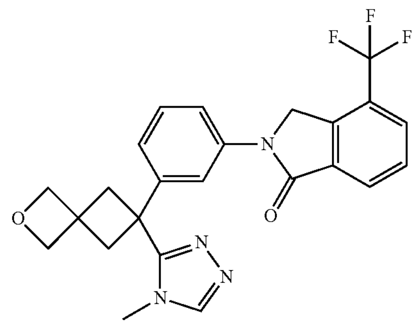 [SMILES: Cn1cnnc1C1(c2cccc(N3Cc4c(cccc4C(F)(F)F)C3=O)c2)CC2(COC2)C1] | 2-(3-(6-(4-methyl-4H-1,2,4-triazol-3-yl)-2-oxaspiro[3.3]heptan-6-yl)phenyl)-4-(trifluoromethyl)isoindolin-1-one |
| 192 | 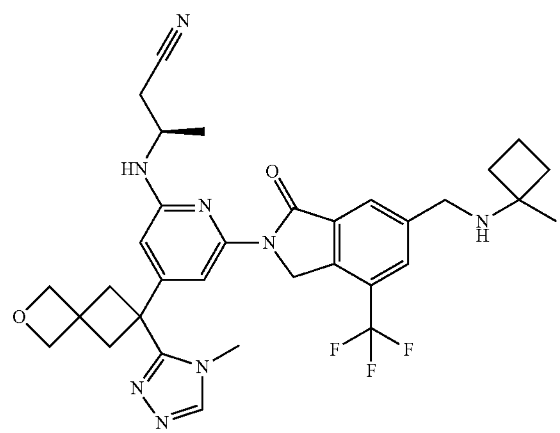 [SMILES: C[C@H](CC#N)Nc1cc(C2(c3nncn3C)CC3(COC3)C2)cc(N2Cc3c(cc(CNC4(C)CCC4)cc3C(F)(F)F)C2=O)n1] | (R)-3-((4-(6-(4-methyl-4H-1,2,4-triazol-3-yl)-2-oxaspiro[3.3]heptan-6-yl)-6-(6-(((1-methylcyclobutyl)amino)methyl)-1-oxo-4-(trifluoromethyl)isonidolin-2-yl)pyridin-2-yl)amino)butanenitrile |
| 193 | 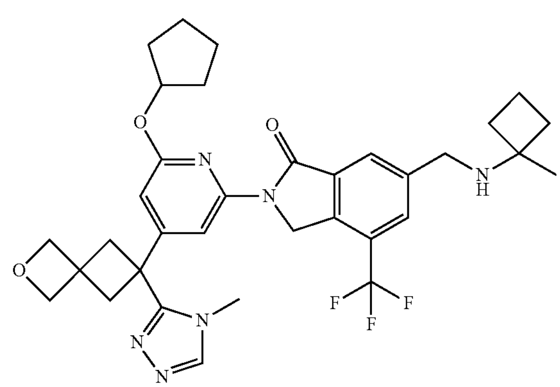 [SMILES: Cn1cnnc1C1(c2cc(OC3CCCC3)nc(N3Cc4c(cc(CNC5(C)CCC5)cc4C(F)(F)F)C3=O)c2)CC2(COC2)C1] | (R)-3-((4-(6-(4-methyl-4H-1,2,4-triazol-3-yl)-2-oxaspiro[3.3]heptan-6-yl)-6-(6-(((1-methylcyclobutyl)amino)methyl)-1-oxo-4-(trifluoromethyl)isoindolin-2-yl)pyridin-2-yl)amino)butanenitrile |
| 194 | 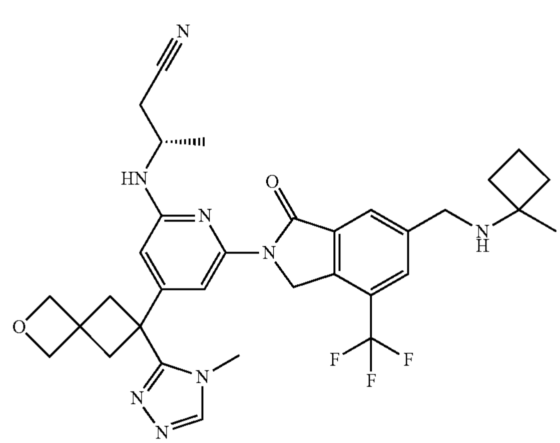 [SMILES: C[C@@H](CC#N)Nc1cc(C2(c3nncn3C)CC3(COC3)C2)cc(N2Cc3c(cc(CNC4(C)CCC4)cc3C(F)(F)F)C2=O)n1] | (S)-3-((4-(6-(4-methyl-4H-1,2,4-triazol-3-yl)-2-oxaspiro[3.3]heptan-6-yl)-6-(6-(((1-methylcyclobutyl)amino)methyl)-1-oxo-4-(trifluoromethyl)isoindolin-2-yl)pyridin-2-yl)amino)butanenitrile |

TABLE 1-continued

| Compound # | Structure | Name |
|---|---|---|
| 195 | 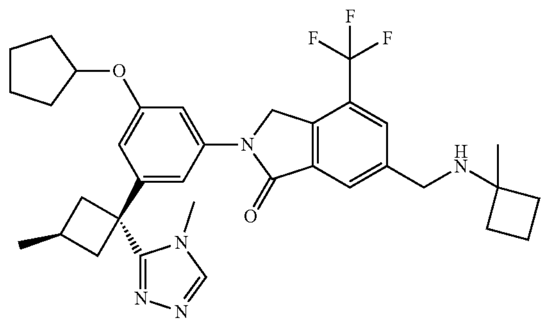 [SMILES: Cn1cnnc1[C@]1(c2cc(OC3CCCC3)cc(N3Cc4c(cc(CNC5(C)CCC5)cc4C(F)(F)F)C3=O)c2)C[C@@H](C)C1] | 2-(3-(cyclopentyloxy)-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 196 | 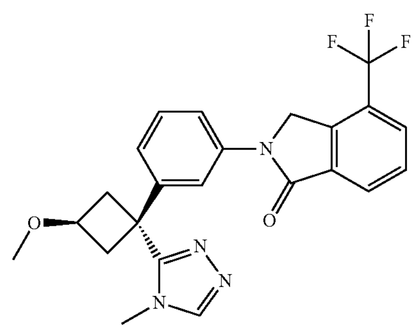 [SMILES: CO[C@H]1C[C@](c2cccc(N3Cc4c(cccc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-4-(trifluoromethyl)isoindolin-1-one |
| 197 | 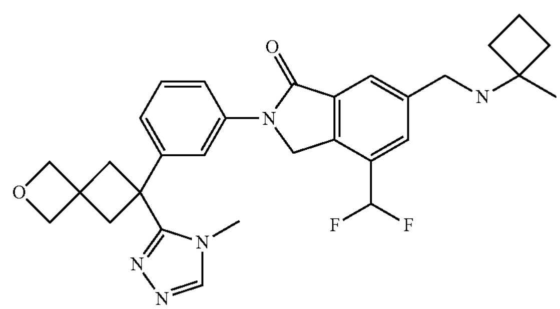 [SMILES: Cn1cnnc1C1(c2cccc(N3Cc4c(cc(CNC5(C)CCC5)cc4C(F)F)C3=O)c2)CC2(COC2)C1] | 4-(difluoromethyl)-2-(3-(6-(4-methyl-4H-1,2,4-triazol-3-yl)-2-oxaspiro[3.3]heptan-6-yl)phenyl)-6-(((1-methylcyclobutyl)amino)methyl)isoindolin-1-one |
| 198 | 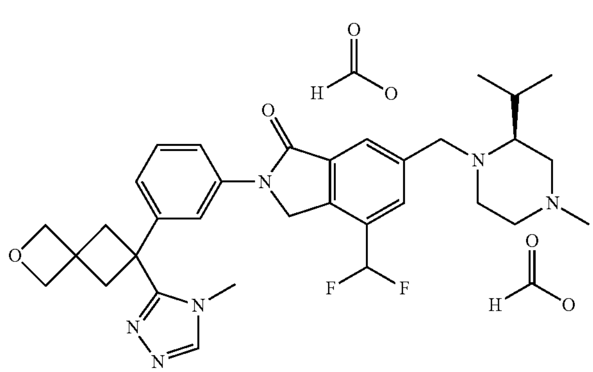 | (S)-4-(difluoromethyl)-6-((2-isopropyl-4-methylpiperazin-1-yl)methyl)-2-(3-(6-(4-methyl-4H-1,2,4-triazol-3-yl)-2-oxaspiro[3.3]heptan-6-yl)phenyl)isoindolin-1-one formate |

| Compound # | Structure | Name |
|---|---|---|
| 199 | 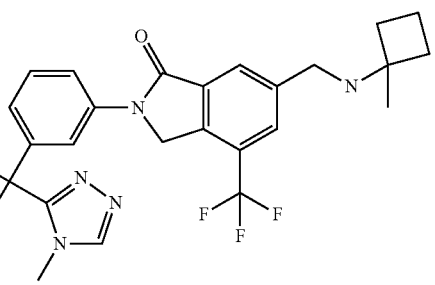 | 2-(3-(6-(4-methyl-4H-1,2,4-triazol-3-yl)-2-(oxetan-3-yl)-2-azaspiro[3.3]heptan-6-yl)phenyl)-6-(((1-methylcyclobutyl)amino)methyl)-4-(trifluoromethyl)isoindolin-1-one |
| 200 | 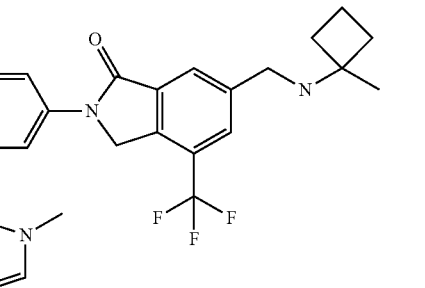 | 2-(3-methoxy-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 201 | 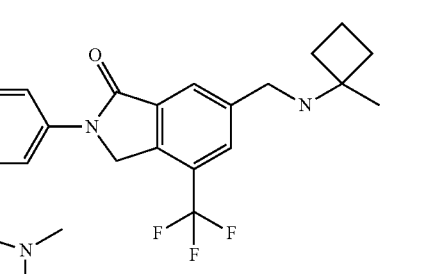 | 2-(3-methoxy-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 202 | 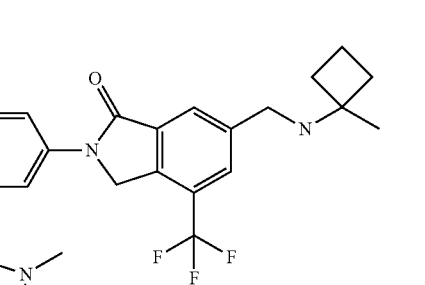 | 2-(3-ethoxy-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 203 | 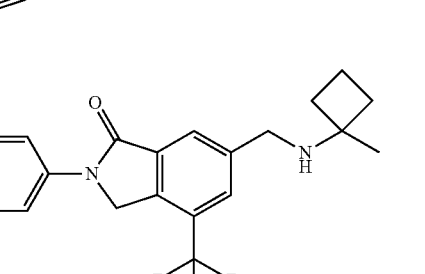 | 2-(3-ethoxy-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 204 | 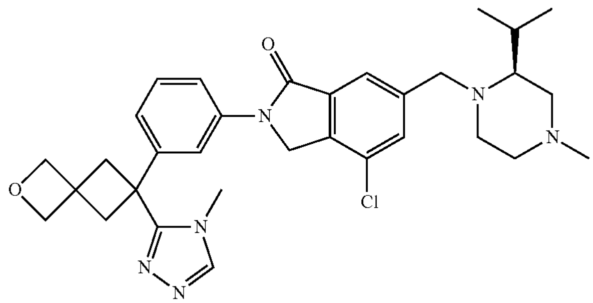 [SMILES: CC(C)[C@H]1CN(C)CCN1Cc1cc(Cl)c2c(c1)C(=O)N(c1cccc(C3(c4nncn4C)CC4(COC4)C3)c1)C2] | (S)-4-chloro-6-((2-isopropyl-4-methylpiperazin-1-yl)methyl)-2-(3-(6-(4-methyl-4H-1,2,4-triazol-3-yl)-2-oxaspiro[3.3]heptan-6-yl)phenyl)isoindolin-1-one |
| 205 | 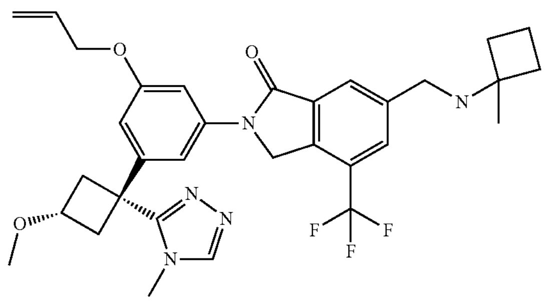 [SMILES: C=CCOc1cc(N2Cc3c(cc(CNC4(C)CCC4)cc3C(F)(F)F)C2=O)cc([C@]2(c3nncn3C)C[C@@H](OC)C2)c1] | 2-(3-(allyloxy)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 206 | 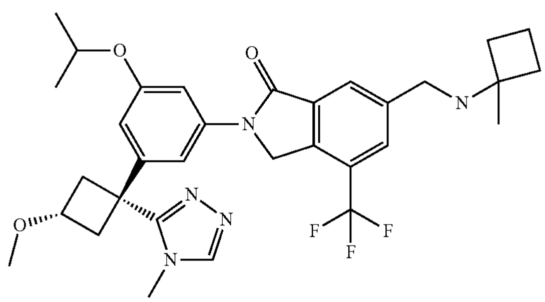 [SMILES: CO[C@H]1C[C@@](c2cc(OC(C)C)cc(N3Cc4c(cc(CNC5(C)CCC5)cc4C(F)(F)F)C3=O)c2)(c2nncn2C)C1] | 2-(3-isopropoxy-5-((1s,3s)-3-methoxy-1-(4-mehtyl-4H-1,2,4-triazol-3-yl)cyclobutyl)phenyl)-6-(((1-methylcyclobutyl)amino)methyl)-4-(trifluoromethyl)isoindolin-1-one |
| 207 | 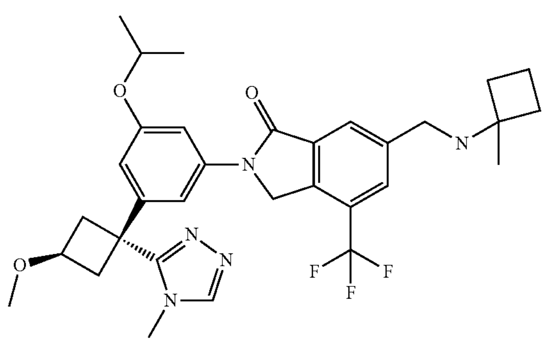 [SMILES: CO[C@H]1C[C@](c2cc(OC(C)C)cc(N3Cc4c(cc(CNC5(C)CCC5)cc4C(F)(F)F)C3=O)c2)(c2nncn2C)C1] | 2-(3-isopropoxy-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 208 | 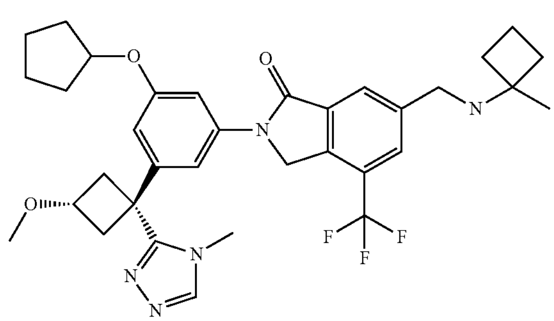 | 2-(3-(cyclopentyloxy)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 209 | 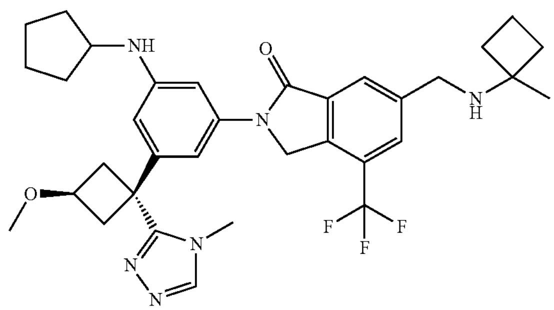 | 2-(3-(cyclopentylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 210 | 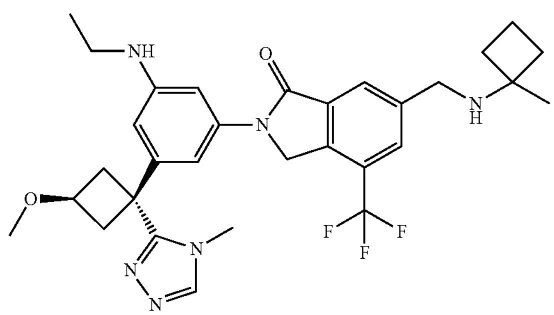 | 2-(3-(ethylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 211 | 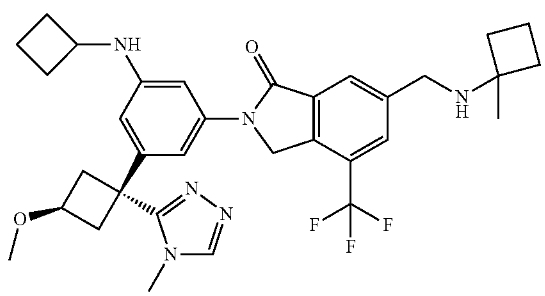 [SMILES: CO[C@H]1C[C@](c2cc(NC3CCC3)cc(N3Cc4c(cc(CNC5(C)CCC5)cc4C(F)(F)F)C3=O)c2)(c2nncn2C)C1] | 2-(3-(cyclobutylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 212 | 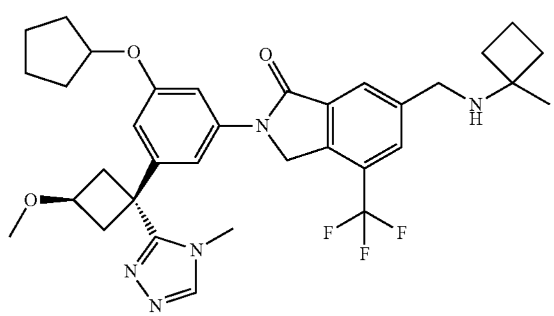 | 2-(3-(cyclopentyloxy)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 213 | 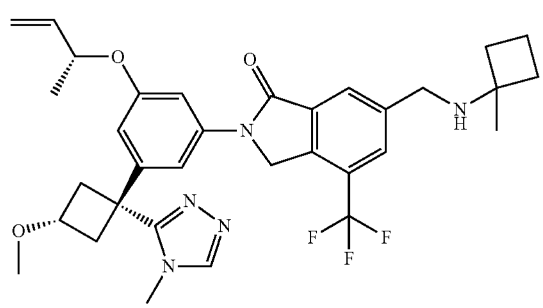 [SMILES: C=C[C@@H](C)Oc1cc(N2Cc3c(cc(CNC4(C)CCC4)cc3C(F)(F)F)C2=O)cc([C@]2(c3nncn3C)C[C@@H](OC)C2)c1] | 2-(3-((R)-but-3-en-2-yloxy)-5-((1s,3S)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 214 | 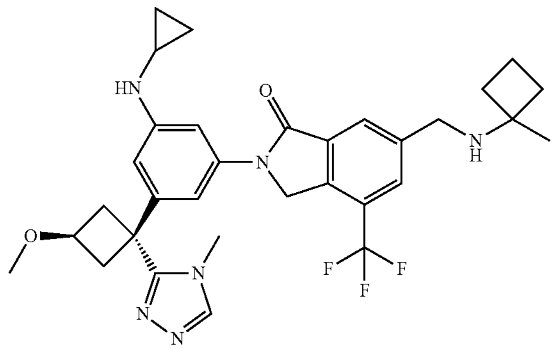 | 2-(3-(cyclopropylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 215 | 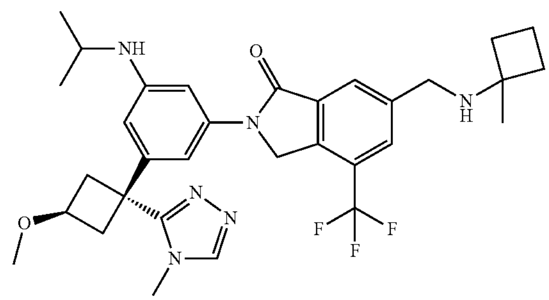 [SMILES: CO[C@H]1C[C@](c2cc(NC(C)C)cc(N3Cc4c(cc(CNC5(C)CCC5)cc4C(F)(F)F)C3=O)c2)(c2nncn2C)C1] | 2-(3-(isopropylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 216 | 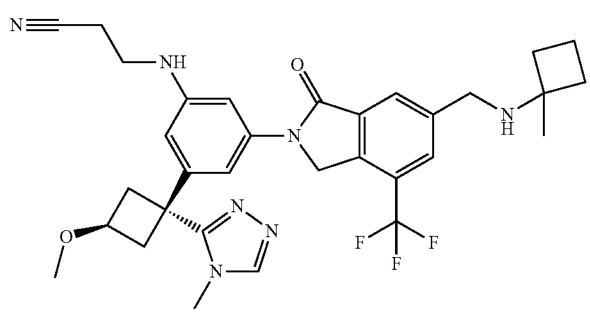 [SMILES: CO[C@H]1C[C@](c2cc(NCCC#N)cc(N3Cc4c(cc(CNC5(C)CCC5)cc4C(F)(F)F)C3=O)c2)(c2nncn2C)C1] | 3-((3-((1r,3r)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)propanenitrile |
| 217 | 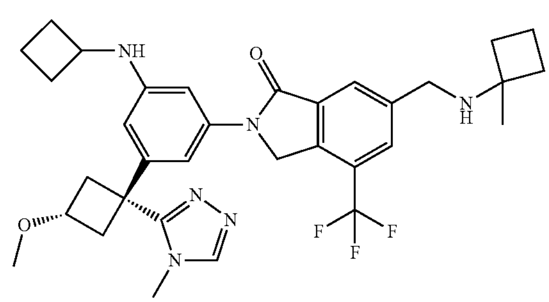 [SMILES: CO[C@H]1C[C@@](c2cc(NC3CCC3)cc(N3Cc4c(cc(CNC5(C)CCC5)cc4C(F)(F)F)C3=O)c2)(c2nncn2C)C1] | 2-(3-(cyclobutylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 218 | 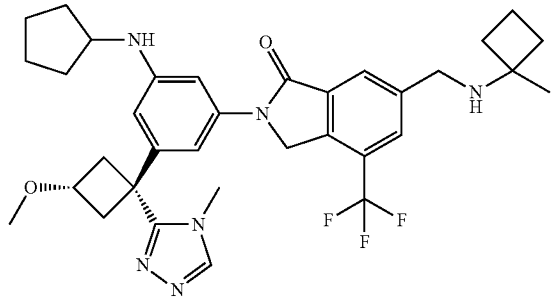 | 2-(3-(cyclopentylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 219 | 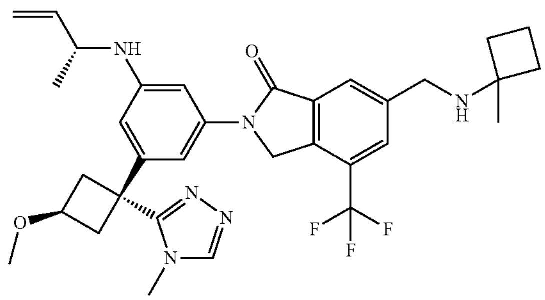 [SMILES: C=C[C@@H](C)Nc1cc(N2Cc3c(cc(CNC4(C)CCC4)cc3C(F)(F)F)C2=O)cc([C@]2(c3nncn3C)C[C@H](OC)C2)c1] | 2-(3-((R)-but-3-en-2-ylamino)-5-((1r,3R)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 220 | 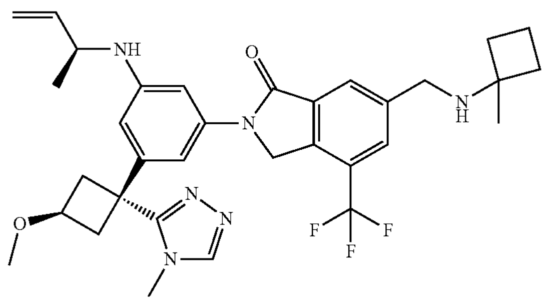 [SMILES: C=C[C@H](C)Nc1cc(N2Cc3c(cc(CNC4(C)CCC4)cc3C(F)(F)F)C2=O)cc([C@]2(c3nncn3C)C[C@H](OC)C2)c1] | 2-(3-((S)-but-3-en-2-ylamino)-5-((1r,3S)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 221 | 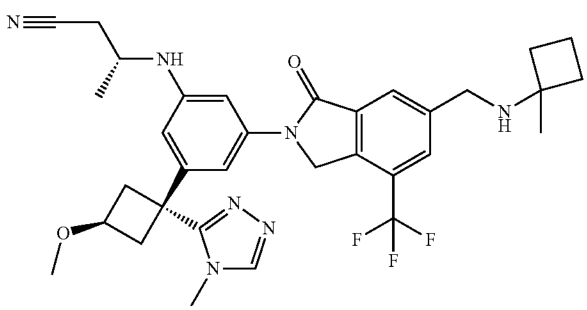 [SMILES: CO[C@H]1C[C@](c2cc(N[C@H](C)CC#N)cc(N3Cc4c(cc(CNC5(C)CCC5)cc4C(F)(F)F)C3=O)c2)(c2nncn2C)C1] | (R)-3-((3-((1r,3R)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)butanenitrile |
| 222 | 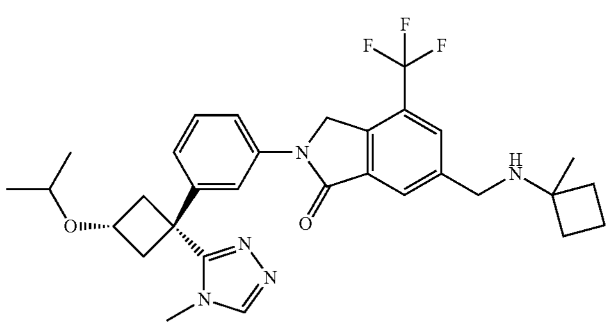 [SMILES: CC(C)O[C@H]1C[C@@](c2cccc(N3Cc4c(cc(CNC5(C)CCC5)cc4C(F)(F)F)C3=O)c2)(c2nncn2C)C1] | 2-(3-((1s,3s)-3-isopropoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 223 | 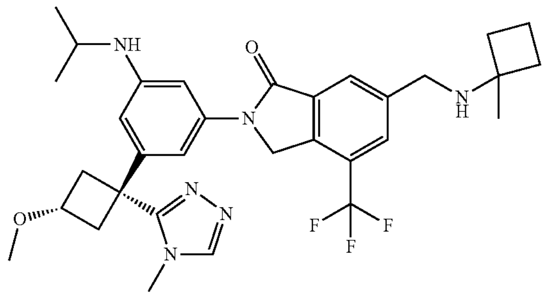 [SMILES: CO[C@H]1C[C@@](c2cc(NC(C)C)cc(N3Cc4c(cc(CNC5(C)CCC5)cc4C(F)(F)F)C3=O)c2)(c2nncn2C)C1] | 2-(3-(isopropylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 224 | 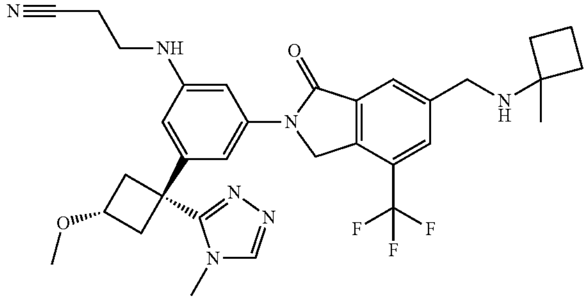 [SMILES: CO[C@H]1C[C@@](c2cc(NCCC#N)cc(N3Cc4c(cc(CNC5(C)CCC5)cc4C(F)(F)F)C3=O)c2)(c2nncn2C)C1] | 3-((3-((1s,3s)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-4-yl)phenyl)amino)propanenitrile |
| 225 | 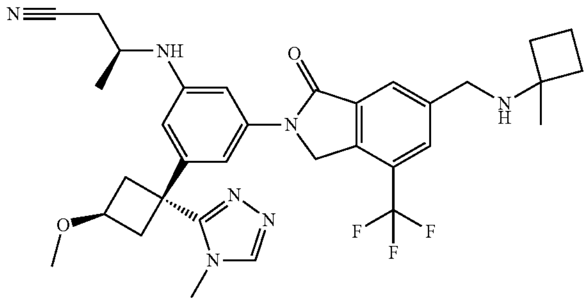 [SMILES: CO[C@H]1C[C@](c2cc(N[C@@H](C)CC#N)cc(N3Cc4c(cc(CNC5(C)CCC5)cc4C(F)(F)F)C3=O)c2)(c2nncn2C)C1] | (S)-3-((3-((1r,3S)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)butanenitrile |
| 226 | 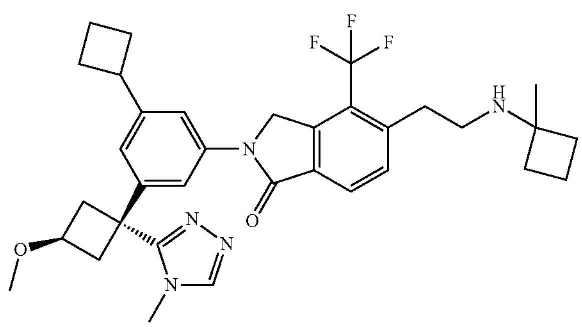 [SMILES: CO[C@H]1C[C@](c2cc(C3CCC3)cc(N3Cc4c(ccc(CCNC5(C)CCC5)c4C(F)(F)F)C3=O)c2)(c2nncn2C)C1] | 2-(3-cyclopropyl-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 227 | 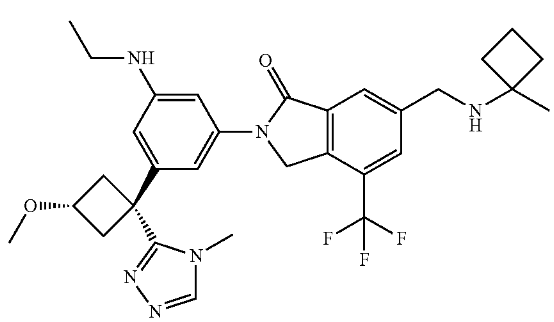 | 2-(3-(ethylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 228 | 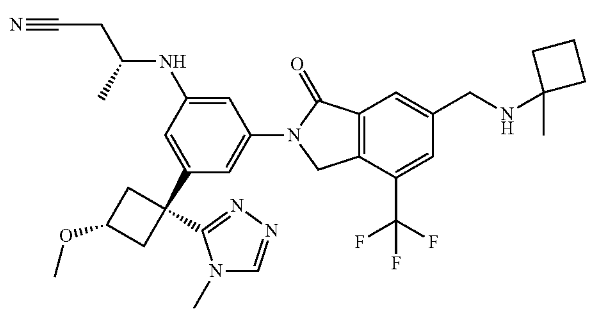 [SMILES: CO[C@H]1C[C@@](c2cc(N[C@H](C)CC#N)cc(N3Cc4c(cc(CNC5(C)CCC5)cc4C(F)(F)F)C3=O)c2)(c2nncn2C)C1] | (R)-3-((3-((1s,3S)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)butanenitrile |
| 229 | 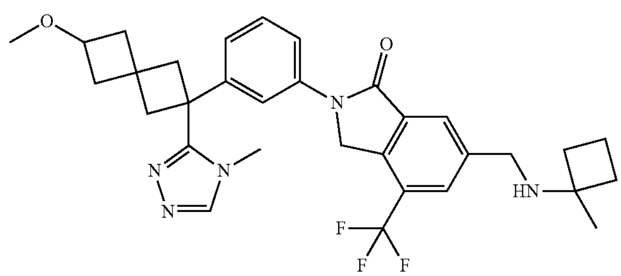 [SMILES: COC1CC2(C1)CC(c1cccc(N3Cc4c(cc(CNC5(C)CCC5)cc4C(F)(F)F)C3=O)c1)(c1nncn1C)C2] | 2-(3-(6-methoxy-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one |
| 230 | 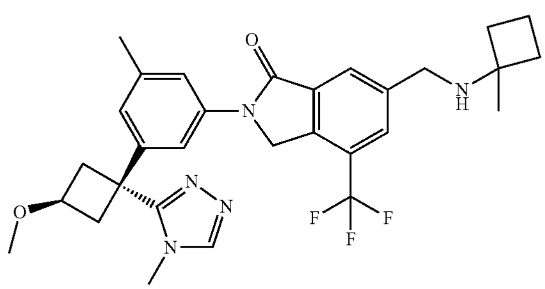 [SMILES: CO[C@H]1C[C@](c2cc(C)cc(N3Cc4c(cc(CNC5(C)CCC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)-5-methylphenyl)-6-(((1-methylcyclobutyl)amino)methyl)-4-(trifluoromethyl)isoindolin-1-one |
| 231 | 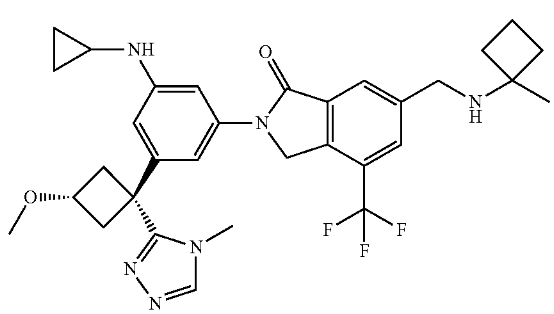 | 2-(3-(cyclopropylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 232 | 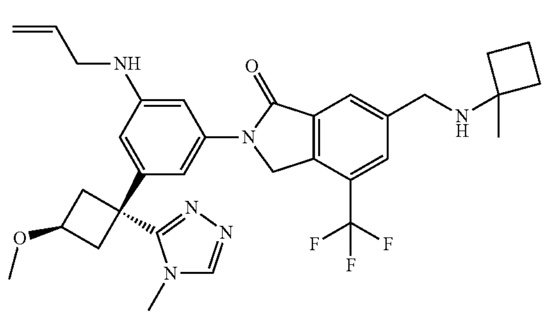 [SMILES: C=CCNc1cc(N2Cc3c(cc(CNC4(C)CCC4)cc3C(F)(F)F)C2=O)cc([C@]2(c3nncn3C)C[C@H](OC)C2)c1] | 2-(3-(allylamino)-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 233 | 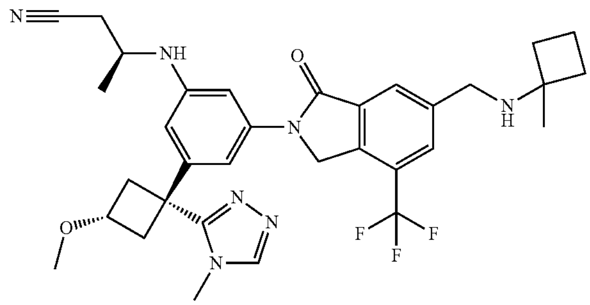 [SMILES: CO[C@H]1C[C@@](c2cc(N[C@@H](C)CC#N)cc(N3Cc4c(cc(CNC5(C)CCC5)cc4C(F)(F)F)C3=O)c2)(c2nncn2C)C1] | (S)-3-((3-((1s,3R)-3-methoxy-1-(4-methyl-4H-1,2,4-triazol-3-yl)cyclobutyl)-5-(6-(((1-methylcyclobutyl)amino)methyl)-1-oxo-4-(trifluoromethyl)isoindolin-2-yl)phenyl)amino)butanenitrile |
| 234 | 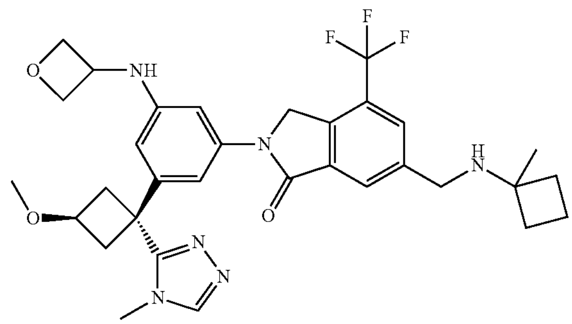 [SMILES: CO[C@H]1C[C@](c2cc(NC3COC3)cc(N3Cc4c(cc(CNC5(C)CCC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)-5-(oxetan-3-ylamino)phenyl)-6-(((1-methylcyclobutyl)amino)methyl)-4-(trifluoromethyl)isoindolin-1-one |
| 235 | 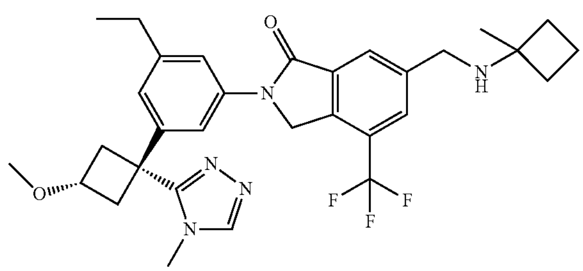 [SMILES: CCc1cc(N2Cc3c(cc(CNC4(C)CCC4)cc3C(F)(F)F)C2=O)cc([C@]2(c3nncn3C)C[C@@H](OC)C2)c1] | 2-(3-ethyl-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 236 | 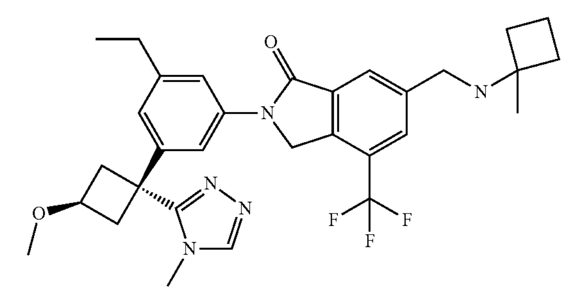 [SMILES: CCc1cc(N2Cc3c(cc(CNC4(C)CCC4)cc3C(F)(F)F)C2=O)cc([C@]2(c3nncn3C)C[C@H](OC)C2)c1] | 2-(3-ethyl-5-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 237 | 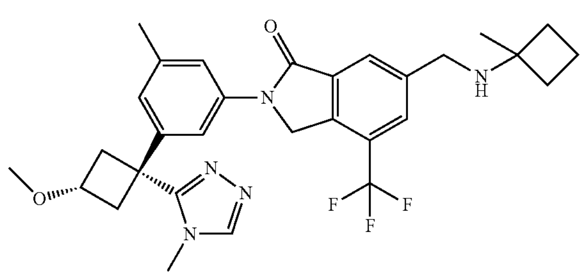 [SMILES: CO[C@H]1C[C@@](c2cc(C)cc(N3Cc4c(cc(CNC5(C)CCC5)cc4C(F)(F)F)C3=O)c2)(c2nncn2C)C1] | 2-(3-((1s,3s)-3-methoxy-1-(4-methyl-4H-1,2,4-triazol-3-yl)cyclobutyl)-5-methylphenyl)-6-(((1-methylcyclobutyl)amino)methyl)-4-(trifluoromethyl)isoindolin-1-one |

TABLE 1-continued

| Compound # | Structure | Name |
|---|---|---|
| 238 | 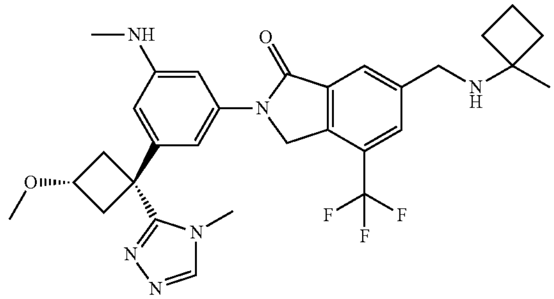 | 2-(3-((1s,3s)-3-methoxy-1-(4-methyl-4H-1,2,4-triazol-3-yl)cyclobutyl)-5-(methylamino)phenyl)-6-(((1-methylcyclobutyl)amino)methyl)-4-(trifluoromethyl)isoindolin-1-one |
| 239 | 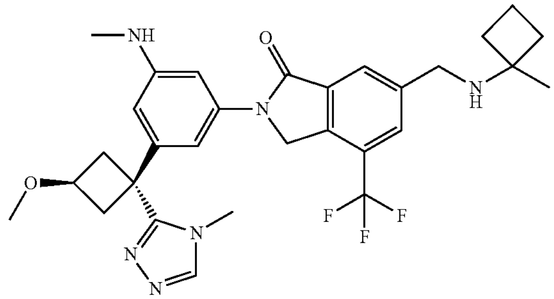 | 2-(3-((1r,3r)-3-methoxy-1-(4-methyl-4H-1,2,4-triazol-3-yl)cyclobutyl)-5-(methylamino)phenyl)-6-(((1-methylcyclobutyl)amino)methyl)-4-(trifluoromethyl)isoindolin-1-one |
| 240 | 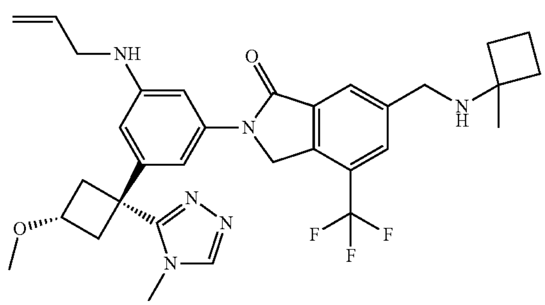 [SMILES: C=CCNc1cc(N2Cc3c(cc(CNC4(C)CCC4)cc3C(F)(F)F)C2=O)cc([C@]2(c3nncn3C)C[C@@H](OC)C2)c1] | 2-(3-(allylamino)-5-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 241 | 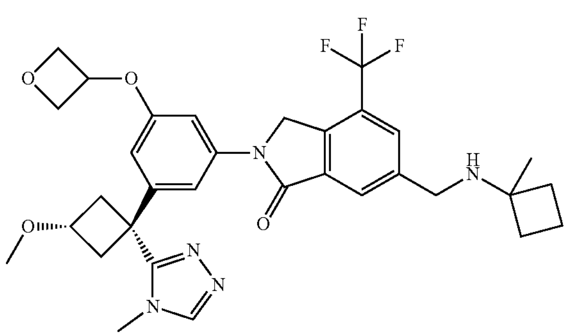 [SMILES: CO[C@H]1C[C@@](c2cc(OC3COC3)cc(N3Cc4c(cc(CNC5(C)CCC5)cc4C(F)(F)F)C3=O)c2)(c2nncn2C)C1] | 2-(3-((1s,3s)-3-methoxy-1-(4-methyl-4H-1,2,4-triazol-3-yl)cyclobutyl)-5-(oxetan-3-yloxy)phenyl)-6-(((1-methylcyclobutyl)amino)methyl)-4-(trifluoromethyl)isoindolin-1-one |
| 242 | 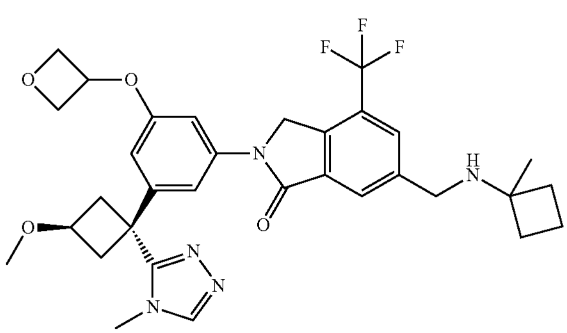 [SMILES: CO[C@H]1C[C@](c2cc(OC3COC3)cc(N3Cc4c(cc(CNC5(C)CCC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)-5-(oxetan-3-yloxy)phenyl)-6-(((1-methylcyclobutyl)amino)methyl)-4-(trifluoromethyl)isoindolin-1-one |

TABLE 1-continued

| Compound # | Structure | Name |
|---|---|---|
| 243 | 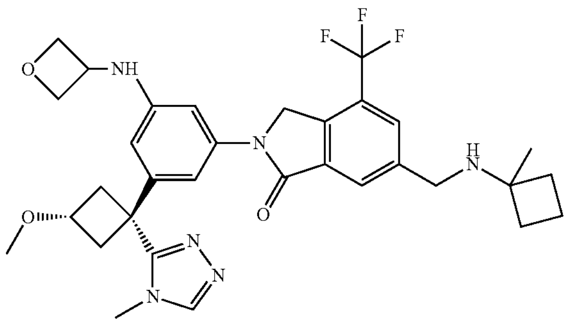 [SMILES: CO[C@H]1C[C@@](c2cc(NC3COC3)cc(N3Cc4c(cc(CNC5(C)CCC5)cc4C(F)(F)F)C3=O)c2)(c2nncn2C)C1] | 2-(3-((1s,3s)-3-methoxy-1-(4-methyl-4H-1,2,4-triazol-3-yl)cyclobutyl)-5-(oxetan-3-ylamino)phenyl)-6-(((1-methylcyclobutyl)amino)methyl)-4-(trifluoromethyl)isoindolin-1-one |
| 244 | 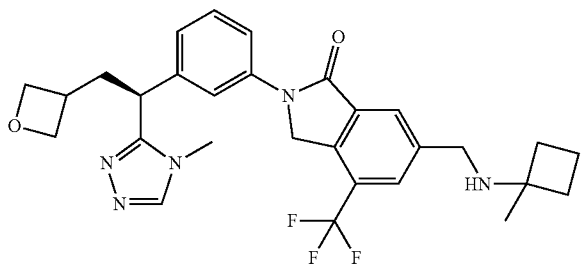 [SMILES: Cn1cnnc1[C@@H](CC1COC1)c1cccc(N2Cc3c(cc(CNC4(C)CCC4)cc3C(F)(F)F)C2=O)c1] | (S)-2-(3-(1-(4-methyl-4H-1,2,4-triazol-3-yl)-2-(oxetan-3-yl)ethyl)phenyl)-6-(((1-methylcyclobutyl)amino)methyl)-4-(trifluoromethyl)isoindolin-1-one |
| 245 | 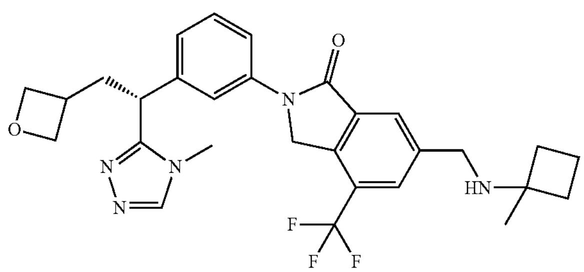 [SMILES: Cn1cnnc1[C@H](CC1COC1)c1cccc(N2Cc3c(cc(CNC4(C)CCC4)cc3C(F)(F)F)C2=O)c1] | (R)-2-(3-(1-(4-methyl-4H-1,2,4-triazol-3-yl)-2-(oxetan-3-yl)ethyl)phenyl)-6-(((1-methylcyclobutyl)amino)methyl)-4-(trifluoromethyl)isoindolin-1-one |
| 246 | 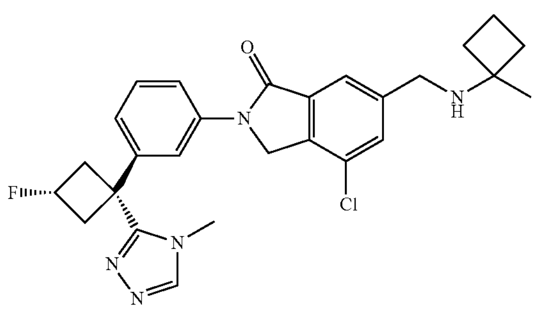 | 4-chloro-2-(3-((1s,3s)-3-fluoro-1-(4-methyl-4H-1,2,4-triazol-3-yl)cyclobutyl)phenyl)-6-(((1-methylcyclobutyl)amino)methyl)isoindolin-1-one |
| 247 | 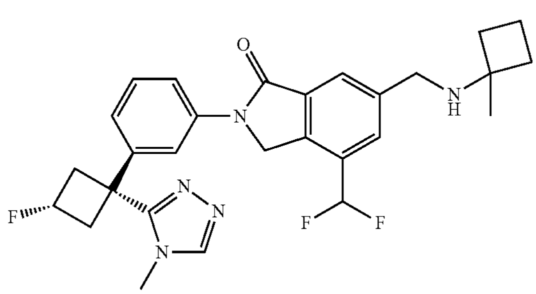 | 4-(difluoromethyl)-2-(3-((1s,3s)-3-fluoro-1-(4-methyl-4H-1,2,4-triazol-3-yl)cyclobutyl)phenyl)-6-(((1-methylcyclobutyl)amino)methyl)isoindolin-1-one; (cf. Compound 272) |

TABLE 1-continued

| Compound # | Structure | Name |
|---|---|---|
| 248 | 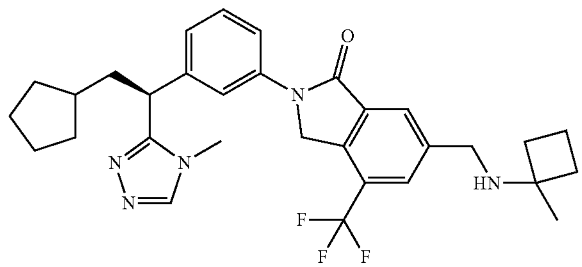 [SMILES: Cn1cnnc1[C@@H](CC1CCCC1)c1cccc(N2Cc3c(cc(CNC4(C)CCC4)cc3C(F)(F)F)C2=O)c1] | (S)-2-(3-(2-cyclopentyl-1-(4-methyl-4H-1,2,4-triazol-3-yl)ethyl)phenyl)-6-(((1-methylcyclobutyl)amino)methyl)-4-(trifluoromethyl)isoindolin-1-one |
| 249 | 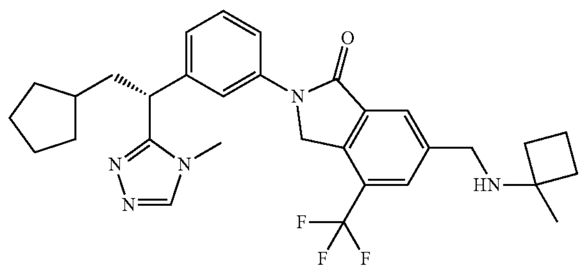 [SMILES: Cn1cnnc1[C@H](CC1CCCC1)c1cccc(N2Cc3c(cc(CNC4(C)CCC4)cc3C(F)(F)F)C2=O)c1] | (R)-2-(3-(2-cyclopentyl-1-(4-methyl-4H-1,2,4-triazol-3-yl)ethyl)phenyl)-6-(((1-methylcyclobutyl)amino)methyl)-4-(trifluoromethyl)isoindolin-1-one |
| 250 | 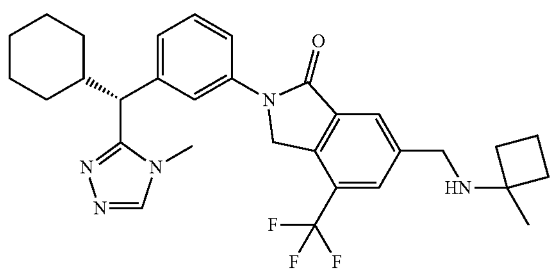 [SMILES: Cn1cnnc1[C@@H](c1cccc(N2Cc3c(cc(CNC4(C)CCC4)cc3C(F)(F)F)C2=O)c1)C1CCCCC1] | (R)-2-(3-(cyclohexyl(4-methyl-4H-1,2,4-triazol-3-yl)methyl)phenyl)-6-(((1-methylcyclobutyl)amino)methyl)-4-(trifluoromethyl)isoindolin-1-one |
| 251 | 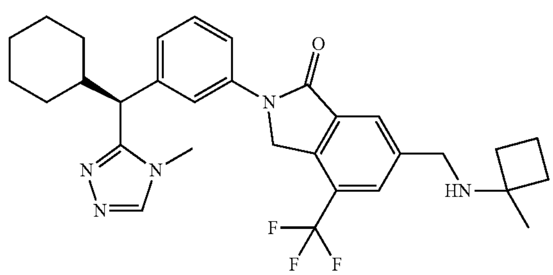 [SMILES: Cn1cnnc1[C@H](c1cccc(N2Cc3c(cc(CNC4(C)CCC4)cc3C(F)(F)F)C2=O)c1)C1CCCCC1] | (S)-2-(3-(cylcohexyl(4-methyl-4H-1,2,4-triazol-3-yl)methyl)phenyl)-6-(((1-methylcyclobutyl)amino)methyl)-4-(trifluoromethyl)isoindolin-1-one |
| 252 | 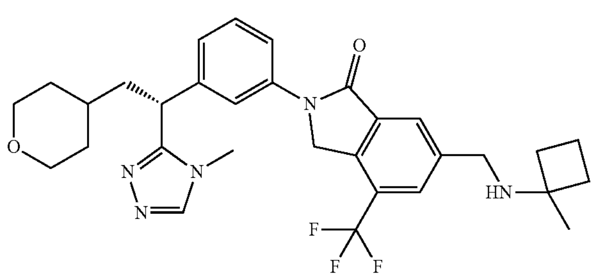 [SMILES: Cn1cnnc1[C@H](CC1CCOCC1)c1cccc(N2Cc3c(cc(CNC4(C)CCC4)cc3C(F)(F)F)C2=O)c1] | (R)-2-(3-(1-(4-methyl-4H-1,2,4-triazol-3-yl)-2-(tetrahydro-2H-pyran-4-yl)ethyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 253 | 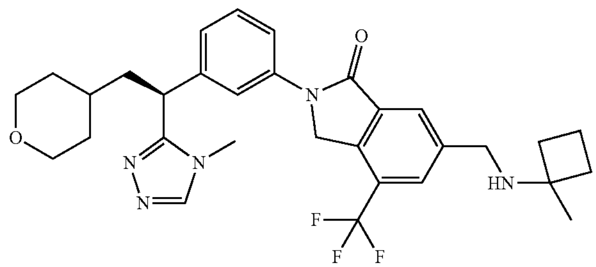 [SMILES: Cn1cnnc1[C@@H](CC1CCOCC1)c1cccc(N2Cc3c(cc(CNC4(C)CCC4)cc3C(F)(F)F)C2=O)c1] | (S)-2-(3-(1-(4-methyl-4H-1,2,4-triazol-3-yl)-2-(tetrahydro-2H-pyran-4-yl)ethyl)phenyl)-6-(((1-methylcyclobutyl)amino)methyl)-4-(trifluoromethyl)isoindolin-1-one |
| 254 | 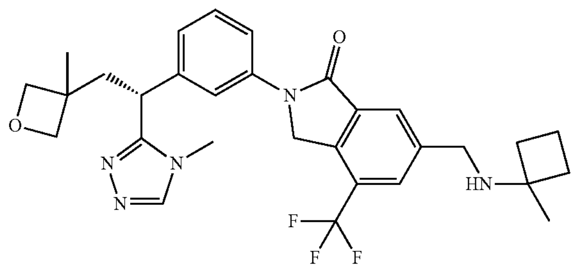 [SMILES: Cn1cnnc1[C@H](CC1(C)COC1)c1cccc(N2Cc3c(cc(CNC4(C)CCC4)cc3C(F)(F)F)C2=O)c1] | (R)-2-(3-(1-(4-methyl-4H-1,2,4-triazol-3-yl)-2-(3-methyloxetan-3-yl)ethyl)phenyl)-6-(((1-methylcyclobutyl)amino)methyl)-4-(trifluoromethyl)isoindolin-1-one |
| 255 | 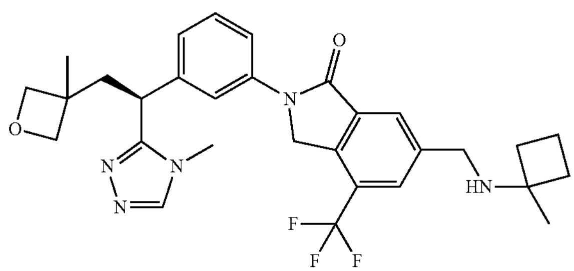 [SMILES: Cn1cnnc1[C@@H](CC1(C)COC1)c1cccc(N2Cc3c(cc(CNC4(C)CCC4)cc3C(F)(F)F)C2=O)c1] | (S)-2-(3-(1-(4-methyl-4H-1,2,4-triazol-3-yl)-2-(3-methyloxetan-3-yl)ethyl)phenyl)-6-(((1-methylcyclobutyl)amino)methyl)-4-(trifluoromethyl)isoindolin-1-one |
| 256 | 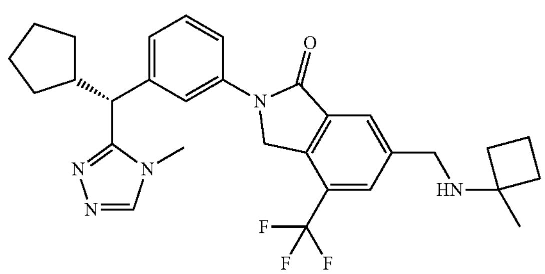 [SMILES: Cn1cnnc1[C@@H](c1cccc(N2Cc3c(cc(CNC4(C)CCC4)cc3C(F)(F)F)C2=O)c1)C1CCCC1] | (R)-2-(3-(cyclopentyl(4-methyl-4H-1,2,4-triazol-3-yl)methyl)phenyl)-6-(((1-methylcyclobutyl)amino)methyl)-4-(trifluoromethyl)isoindolin-1-one |
| 257 | 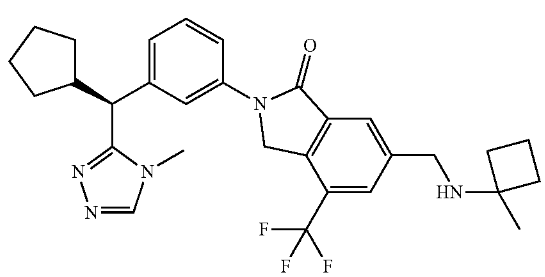 [SMILES: Cn1cnnc1[C@H](c1cccc(N2Cc3c(cc(CNC4(C)CCC4)cc3C(F)(F)F)C2=O)c1)C1CCCC1] | (S)-2-(3-(cyclopentyl(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
| --- | --- | --- |
| 258 | 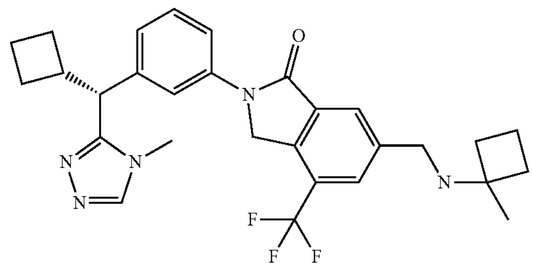 [SMILES: Cn1cnnc1[C@@H](c1cccc(N2Cc3c(cc(CNC4(C)CCC4)cc3C(F)(F)F)C2=O)c1)C1CCC1] | (R)-2-(3-(cyclobutyl(4-methyl-4H-1,2,4-triazol-3-yl)methyl)phenyl)-6-(((1-methylcyclobutyl)amino)methyl)-4-(trifluoromethyl)isoindolin-1-one |
| 259 | 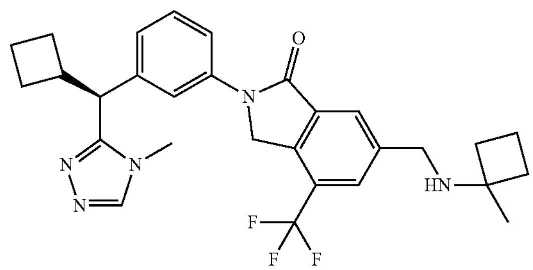 [SMILES: Cn1cnnc1[C@H](c1cccc(N2Cc3c(cc(CNC4(C)CCC4)cc3C(F)(F)F)C2=O)c1)C1CCC1] | (S)-2-(3-(cyclobutyl(4-methyl-4H-1,2,4-triazol-3-yl)methyl)phenyl)-6-(((1-methylcyclobutyl)amino)methyl)-4-(trifluoromethyl)isoindolin-1-one |
| 260 | 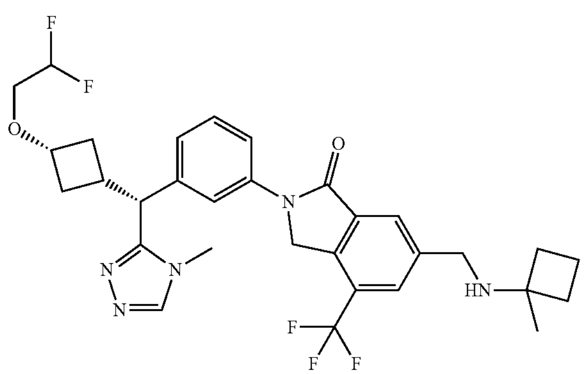 | 2-(3-((R)-((1r,3R)-3-(2,2-difluoroethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 261 | 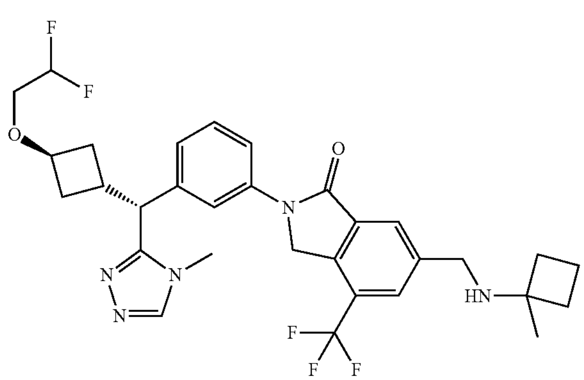 | 2-(3-((R)-((1s,3S)-3-(2,2-difluoroethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 262 | 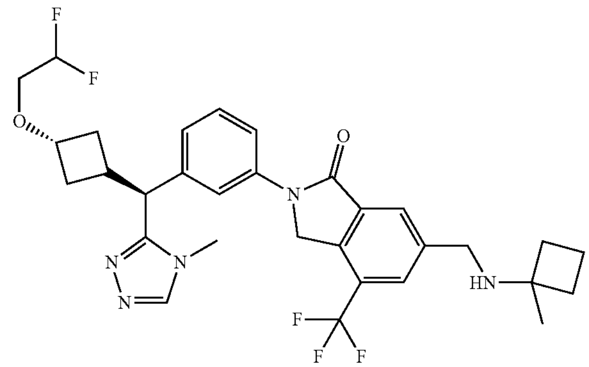 | 2-(3-((S)-((1s,3R)-3-(2,2-difluoroethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 263 | 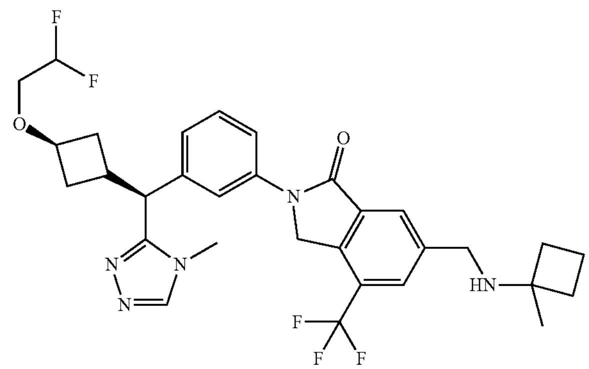 | 2-(3-((S)-((1r,3S)-3-(2,2-difluoroethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 264 | 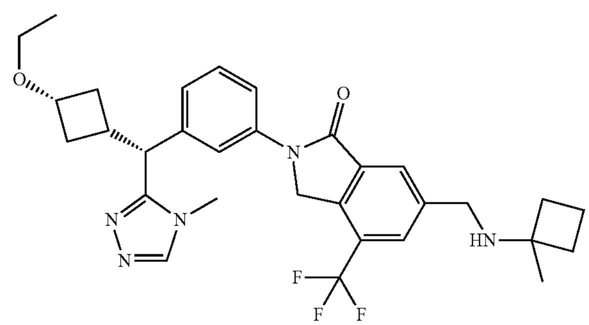 | 2-(3-((R)-((1r,3R)-3-ethoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 265 | 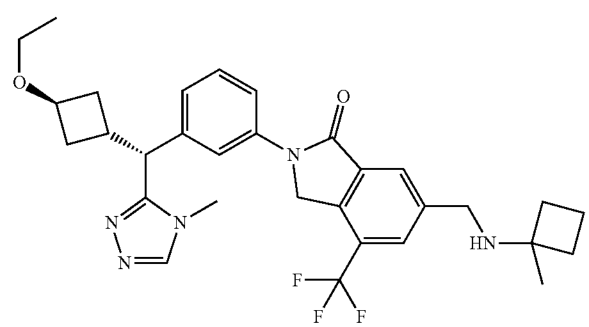 | 2-(3-((R)-((1s,3S)-3-ethoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 266 | 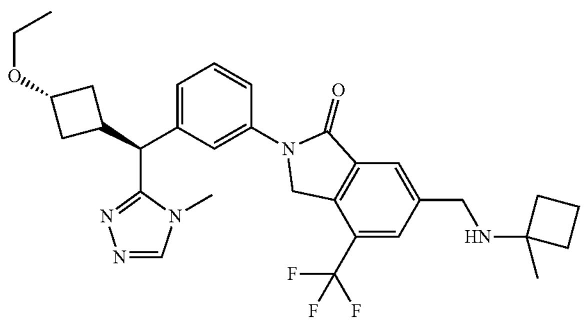 | 2-(3-((S)-((1s,3R)-3-ethoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 267 | 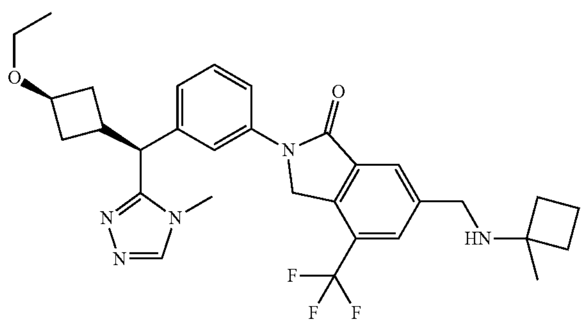 | 2-(3-((S)-((1r,3S)-3-ethoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 268 | 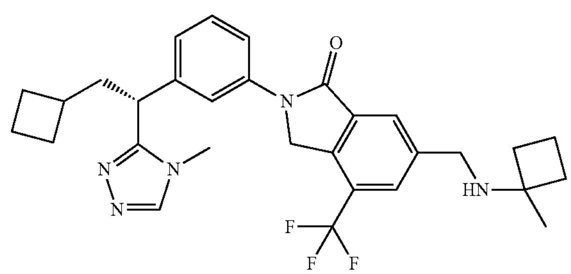 [SMILES: Cn1cnnc1[C@H](CC1CCC1)c1cccc(N2Cc3c(cc(CNC4(C)CCC4)cc3C(F)(F)F)C2=O)c1] | (R)-2-(3-(2-cyclobutyl-1-(4-methyl-4H-1,2,4-triazol-3-yl)ethyl)phenyl)-6-(((1-methylcyclobutyl)amino)methyl)-4-(trifluoromethyl)isoindolin-1-one |
| 269 | 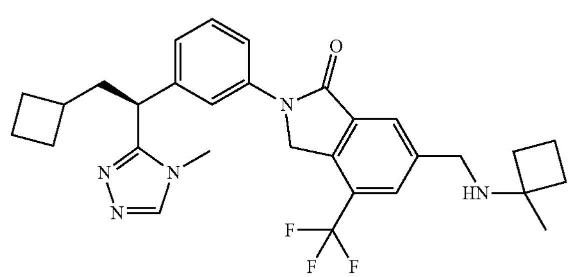 [SMILES: Cn1cnnc1[C@@H](CC1CCC1)c1cccc(N2Cc3c(cc(CNC4(C)CCC4)cc3C(F)(F)F)C2=O)c1] | (S)-2-(3-(2-cyclobutyl-1-(4-methyl-4H-1,2,4-triazol-3-yl)ethyl)phenyl)-6-(((1-methylcyclobutyl)amino)methyl)-4-(trifluoromethyl)isoindolin-1-one |
| 270 | 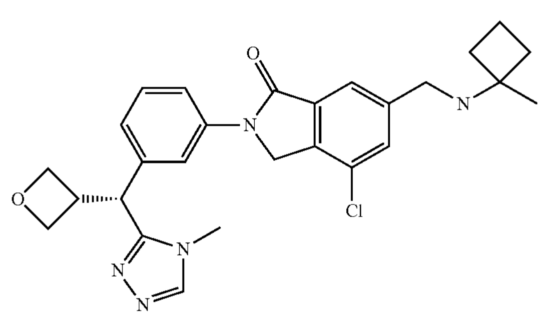 [SMILES: Cn1cnnc1[C@@H](c1cccc(N2Cc3c(Cl)cc(CNC4(C)CCC4)cc3C2=O)c1)C1COC1] | (R)-4-chloro-2-(3-((4-methyl-4H-1,2,4-triazol-3-yl)(oxetan-3-yl)methyl)phenyl)-6-(((1-methylcyclobutyl)amino)methyl)-isoindolin-1-one |

TABLE 1-continued

| Compound # | Structure | Name |
|---|---|---|
| 271 | 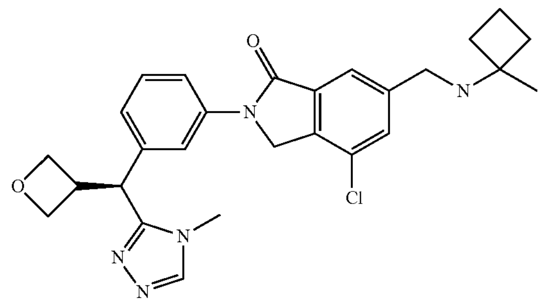 [SMILES: Cn1cnnc1[C@H](c1cccc(N2Cc3c(Cl)cc(CNC4(C)CCC4)cc3C2=O)c1)C1COC1] | (S)-4-chloro-2-(3-((4-methyl-4H-1,2,4-triazol-3-yl)(oxetan-3-yl)methyl)phenyl)-6-(((1-methylcyclobutyl)amino)methyl)-isoindolin-1-one |
| 272 | 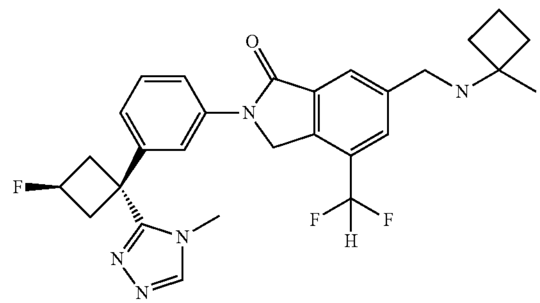 [SMILES: Cn1cnnc1[C@]1(c2cccc(N3Cc4c(cc(CNC5(C)CCC5)cc4C(F)F)C3=O)c2)C[C@@H](F)C1] | 4-(difluoromethyl)-2-(3-((1r,3r)-3-fluoro-1-(4-methyl-4H-1,2,4-triazol-3-yl)cyclobutyl)phenyl)-6-(((1-methylcyclobutyl)amino)methyl)isoindolin-1-one; (cf. Compound 247) |
| 273 | 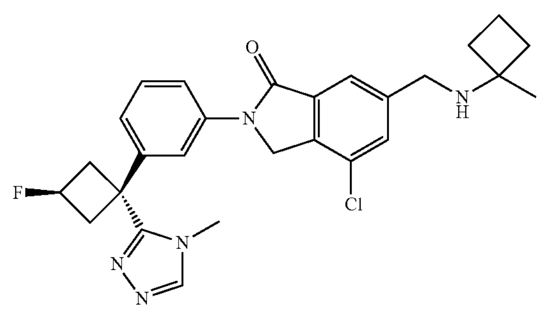 [SMILES: Cn1cnnc1[C@]1(c2cccc(N3Cc4c(Cl)cc(CNC5(C)CCC5)cc4C3=O)c2)C[C@@H](F)C1] | 4-chloro-2-(3-((1r,3r)-3-fluoro-1-(4-methyl-4H-1,2,4-triazol-3-yl)cyclobutyl)phenyl)-6-(((1-methylcyclobutyl)amino)methyl)-isoindolin-1-one |
| 274 | 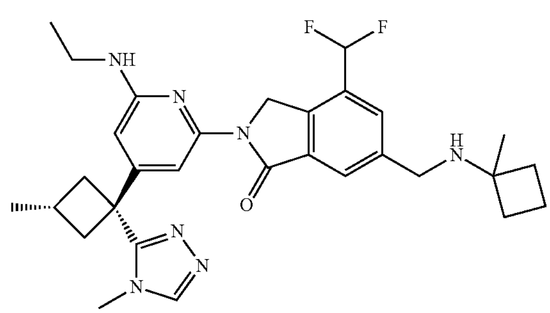 [SMILES: CCNc1cc([C@]2(c3nncn3C)C[C@@H](C)C2)cc(N2Cc3c(cc(CNC4(C)CCC4)cc3C(F)F)C2=O)n1] | 4-(difluoromethyl)-2-(6-(ethylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)isoindolin-1-one |
| 275 | 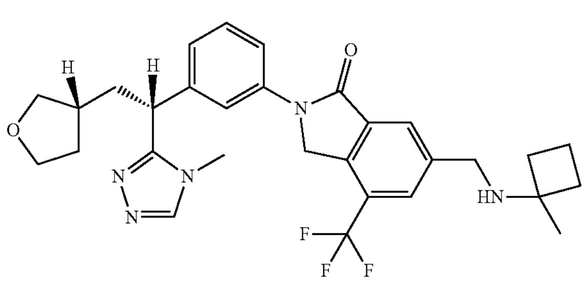 [SMILES: Cn1cnnc1[C@H](C[C@@H]1CCOC1)c1cccc(N2Cc3c(cc(CNC4(C)CCC4)cc3C(F)(F)F)C2=O)c1] | 2-(3-((R)-1-(4-methyl-4H-1,2,4-triazol-3-yl)-2-((R)-tetrahydrofuran-3-yl)ethyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 276 | 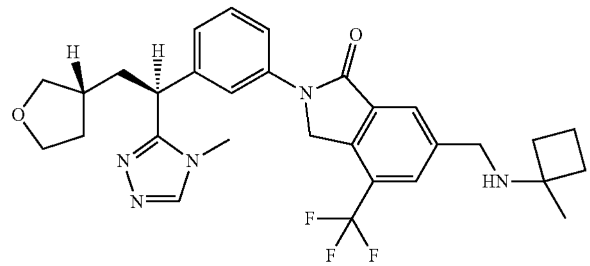 [SMILES: Cn1cnnc1[C@@H](C[C@@H]1CCOC1)c1cccc(N2Cc3c(cc(CNC4(C)CCC4)cc3C(F)(F)F)C2=O)c1] | 2-(3-((S)-1-(4-methyl-4H-1,2,4-triazol-3-yl)-2-((R)-tetrahydrofuran-3-yl)ethyl)phenyl)-6-(((1-methylcyclobutyl)amino)methyl)-4-(trifluoromethyl)isoindolin-1-one |
| 277 | 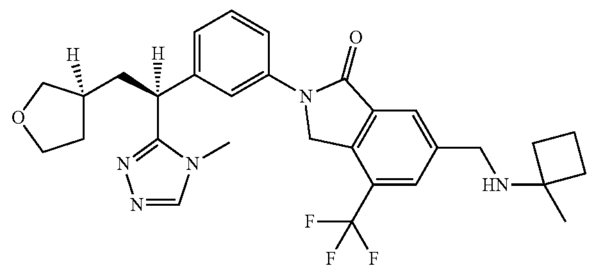 [SMILES: Cn1cnnc1[C@@H](C[C@H]1CCOC1)c1cccc(N2Cc3c(cc(CNC4(C)CCC4)cc3C(F)(F)F)C2=O)c1] | 2-(3-((S)-1-(4-methyl-4H-1,2,4-triazol-3-yl)-2-((S)-tetrahydrofuran-3-yl)ethyl)phenyl)-6-(((1-methylcyclobutyl)amino)methyl)-4-(trifluoromethyl)isoindolin-1-one |
| 278 | 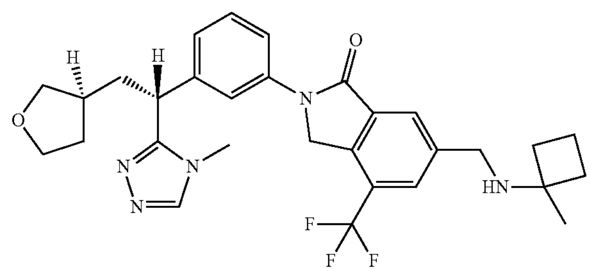 [SMILES: Cn1cnnc1[C@H](C[C@H]1CCOC1)c1cccc(N2Cc3c(cc(CNC4(C)CCC4)cc3C(F)(F)F)C2=O)c1] | 2-(3-((R)-1-(4-methyl-4H-1,2,4-triazol-3-yl)-2-((S)-tetrahydrofuran-3-yl)ethyl)phenyl)-6-(((1-methylcyclobutyl)amino)methyl)-4-(trifluoromethyl)isoindolin-1-one |
| 279 | 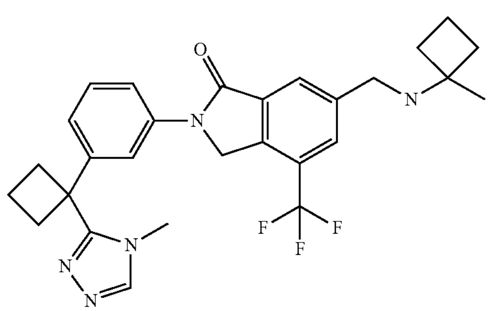 [SMILES: Cn1cnnc1C1(c2cccc(N3Cc4c(cc(CNC5(C)CCC5)cc4C(F)(F)F)C3=O)c2)CCC1] | 2-(3-(1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 280 | 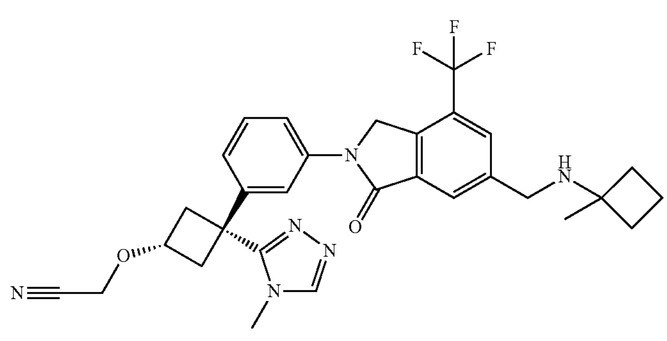 [SMILES: Cn1cnnc1[C@]1(c2cccc(N3Cc4c(cc(CNC5(C)CCC5)cc4C(F)(F)F)C3=O)c2)C[C@H](OCC#N)C1] | 2-((1s,3s)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutoxy)acetonitrile |

TABLE 1-continued

| Compound # | Structure | Name |
|---|---|---|
| 281 | 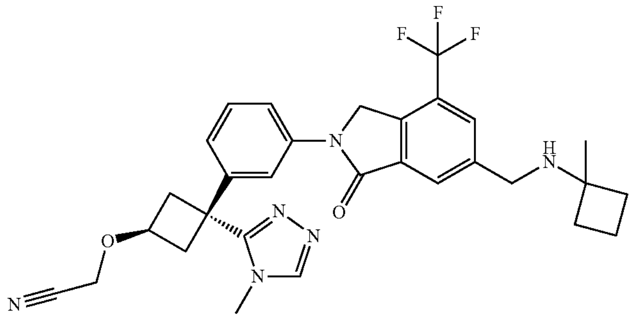 [SMILES: Cn1cnnc1[C@]1(c2cccc(N3Cc4c(cc(CNC5(C)CCC5)cc4C(F)(F)F)C3=O)c2)C[C@@H](OCC#N)C1] | 2-((1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutoxy)acetontrile |
| 282 | 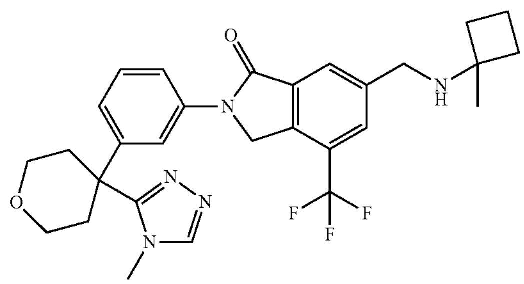 [SMILES: Cn1cnnc1C1(c2cccc(N3Cc4c(cc(CNC5(C)CCC5)cc4C(F)(F)F)C3=O)c2)CCOCC1] | 2-(3-(4-(4-methyl-4H-1,2,4-triazol-3-yl)tetrahydro-2H-pyran-4-yl)phenyl)-6-(((1-methylcyclobutyl)amino)methyl)-4-(trifluoromethyl)isoindolin-1-one |
| 283 | 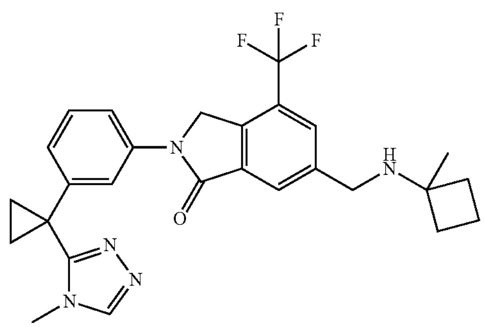 [SMILES: Cn1cnnc1C1(c2cccc(N3Cc4c(cc(CNC5(C)CCC5)cc4C(F)(F)F)C3=O)c2)CC1] | 2-(3-(1-(4-methyl-4H-1,2,4-triazol-3-yl)cyclopropyl)phenyl)-6-(((1-methylcyclobutyl)amino)methyl)-4-(trifluoromethyl)isoindolin-1-one |
| 284 | 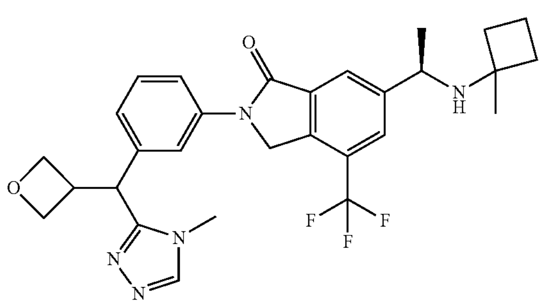 [SMILES: C[C@@H](NC1(C)CCC1)c1cc2c(c(C(F)(F)F)c1)CN(c1cccc(C(c3nncn3C)C3COC3)c1)C2=O] | 2-(3-((4-methyl-4H-1,2,4-triazol-3-yl)(oxetan-3-yl)methyl)phenyl)-6-((R)-1-((1-methylcyclobutyl)amino)ethyl)-4-(trifluoromethyl)isoindolin-1-one |
| 285 | 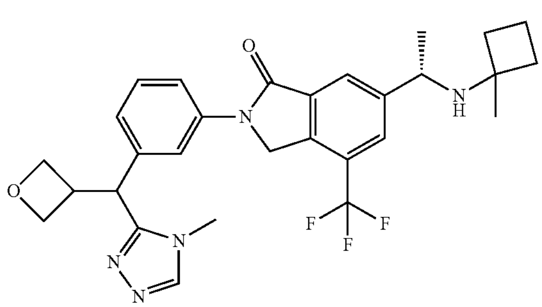 [SMILES: C[C@H](NC1(C)CCC1)c1cc2c(c(C(F)(F)F)c1)CN(c1cccc(C(c3nncn3C)C3COC3)c1)C2=O] | 2-(3-((4-methyl-4H-1,2,4-triazol-3-yl)(oxetan-3-yl)ethyl)phenyl)-6-((S)-1-((1-methylcyclobutyl)amino)methyl)-4-(trifluoromethyl)isoindolin-1-one |

TABLE 1-continued

| Compound # | Structure | Name |
|---|---|---|
| 286 | 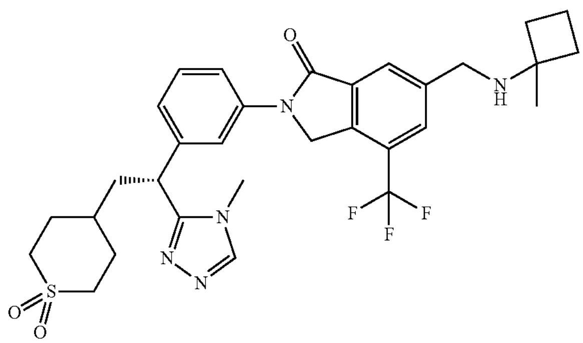 [SMILES: Cn1cnnc1[C@H](CC1CCS(=O)(=O)CC1)c1cccc(N2Cc3c(cc(CNC4(C)CCC4)cc3C(F)(F)F)C2=O)c1] | (R)-2-(3-(2-(1,1-dioxidotetrahydro-2H-thiopyran-4-yl)-1-(4-methyl-4H-1,2,4-triazol-3-yl)ethyl)phenyl)-6-(((1-methylcyclobutyl)amino)methyl)-4-(trifluoromethyl)isoindolin-1-one |
| 287 | 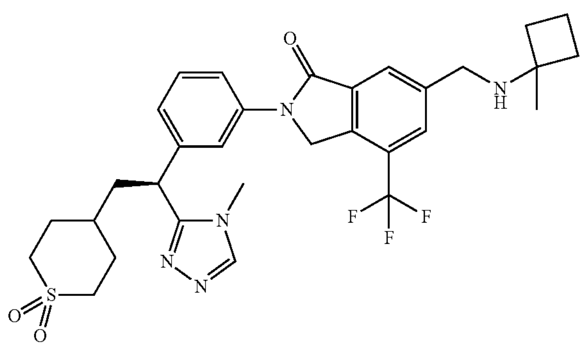 [SMILES: Cn1cnnc1[C@@H](CC1CCS(=O)(=O)CC1)c1cccc(N2Cc3c(cc(CNC4(C)CCC4)cc3C(F)(F)F)C2=O)c1] | (S)-2-(3-(2-(1,1-dioxidotetrahydro-2H-thiopyran-4-yl)-1-(4-methyl-4H-1,2,4-triazol-3-yl)ethyl)phenyl)-6-(((1-methylcyclobutyl)amino)methyl)-4-(trifluoromethyl)isoindolin-1-one |
| 288 | 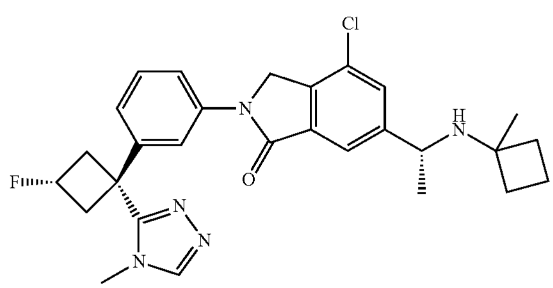 [SMILES: C[C@@H](NC1(C)CCC1)c1cc(Cl)c2c(c1)C(=O)N(c1cccc([C@]3(c4nncn4C)C[C@@H](F)C3)c1)C2] | 4-chloro-2-(3-((1s,3S)-3-fluoro-1-(4-methyl-4H-1,2,4-triazol-3-yl)cyclobutyl)phenyl)-6-((R)-1-((1-methylcyclobutyl)amino)ethyl)isoindolin-1-one |
| 289 | 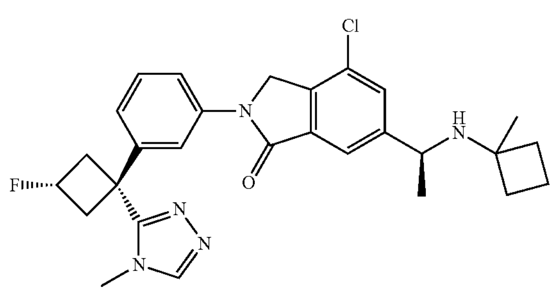 [SMILES: C[C@H](NC1(C)CCC1)c1cc(Cl)c2c(c1)C(=O)N(c1cccc([C@]3(c4nncn4C)C[C@@H](F)C3)c1)C2] | 4-chloro-2-(3-((1s,3R)-3-fluoro-1-(4-methyl-4H-1,2,4-triazol-3-yl)cyclobutyl)phenyl)-6-((S)-1-((1-methylcyclobutyl)amino)ethyl)isoindolin-1-one |
| 290 | 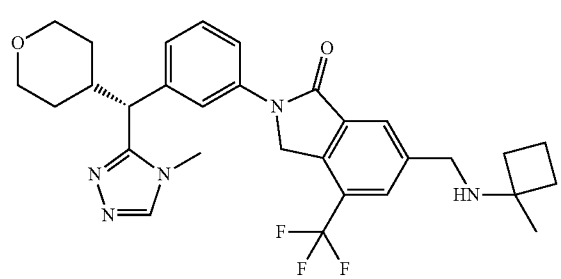 [SMILES: Cn1cnnc1[C@@H](c1cccc(N2Cc3c(cc(CNC4(C)CCC4)cc3C(F)(F)F)C2=O)c1)C1CCOCC1] | (R)-2-(3-((4-methyl-4H-1,2,4-triazol-3-yl)(tetrahydro-2H-pyran-4-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 291 | 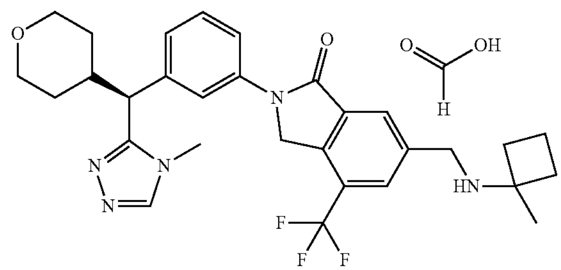 | (S)-2-(3-((4-methyl-4H-1,2,4-triazol-3-yl)(tetrahydro-2H-pyran-4-yl)methyl)phenyl)-6-(((1-methylcyclobutyl)amino)methyl)-4-(trifluoromethyl)isoindolin-1-one formate |
| 292 | 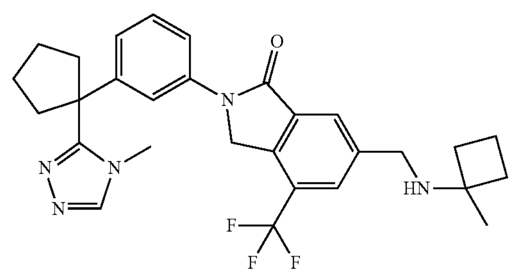 [SMILES: Cn1cnnc1C1(c2cccc(N3Cc4c(cc(CNC5(C)CCC5)cc4C(F)(F)F)C3=O)c2)CCCC1] | 2-(3-(1-(4-methyl-4H-1,2,4-triazol-3-yl)cyclopentyl)phenyl)-6-(((1-methylcyclobutyl)amino)methyl)-4-(trifluoromethyl)isoindolin-1-one |
| 293 | 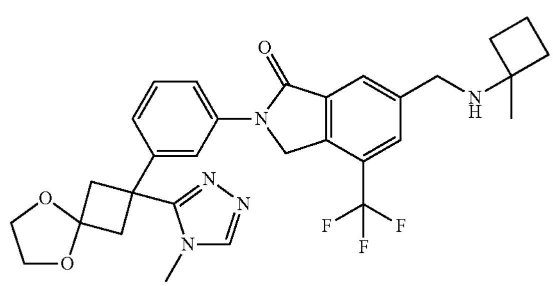 [SMILES: Cn1cnnc1C1(c2cccc(N3Cc4c(cc(CNC5(C)CCC5)cc4C(F)(F)F)C3=O)c2)CC2(C1)OCCO2] | 2-(3-(2-(4-methyl-4H-1,2,4-triazol-3-yl)-5,8-dioxaspiro[3.4]octan-2-yl)phenyl)-6-(((1-methylcyclobutyl)amino)methyl)-4-(trifluoromethyl)isoindolin-1-one |
| 294 | 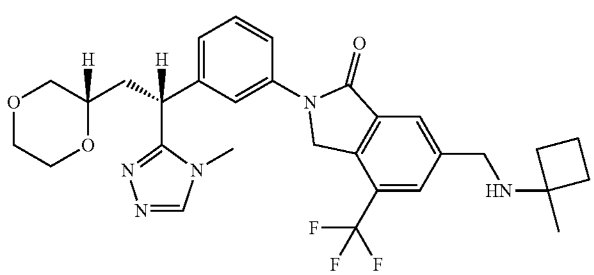 [SMILES: Cn1cnnc1[C@H](C[C@H]1COCCO1)c1cccc(N2Cc3c(cc(CNC4(C)CCC4)cc3C(F)(F)F)C2=O)c1] | 2-(3-((R)-2-((S)-1,4-dioxan-2-yl)-1-(4-methyl-4H-1,2,4-triazol-3-yl)ethyl)phenyl)-6-(((1-methylcyclobutyl)amino)methyl)-4-(trifluoromethyl)isoindolin-1-one |
| 295 | 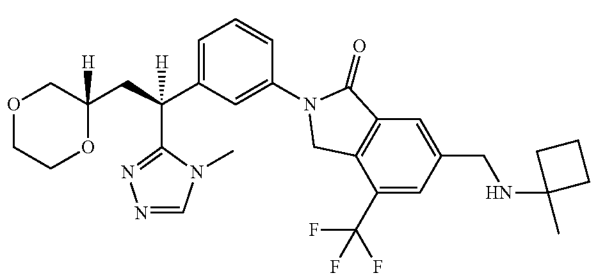 [SMILES: Cn1cnnc1[C@@H](C[C@H]1COCCO1)c1cccc(N2Cc3c(cc(CNC4(C)CCC4)cc3C(F)(F)F)C2=O)c1] | 2-(3-((S)-2-((S)-1,4-dioxan-2-yl)-1-(4-methyl-4H-1,2,4-triazol-3-yl)ethyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 296 | 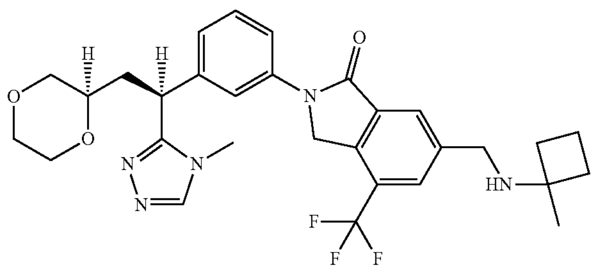 [SMILES: Cn1cnnc1[C@@H](C[C@@H]1COCCO1)c1cccc(N2Cc3c(cc(CNC4(C)CCC4)cc3C(F)(F)F)C2=O)c1] | 2-(3-((S)-2-((R)-1,4-dioxan-2-yl)-1-(4-methyl-4H-1,2,4-triazol-3-yl)ethyl)phenyl)-6-(((1-methylcyclobutyl)amino)methyl)-4-(trifluoromethyl)isoindolin-1-one |
| 297 | 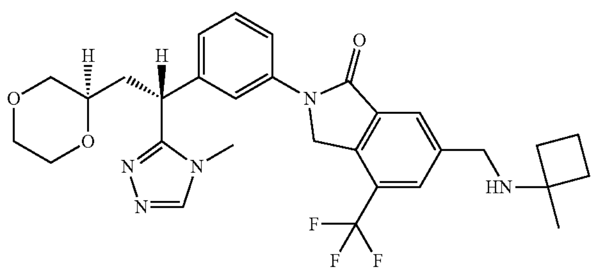 [SMILES: Cn1cnnc1[C@H](C[C@@H]1COCCO1)c1cccc(N2Cc3c(cc(CNC4(C)CCC4)cc3C(F)(F)F)C2=O)c1] | 2-(3-((R)-2-((R)-1,4-dioxan-2-yl)-1-(4-methyl-4H-1,2,4-triazol-3-yl)ethyl)phenyl)-6-(((1-methylcyclobutyl)amino)methyl)-4-(trifluoromethyl)isoindolin-1-one |
| 298 | 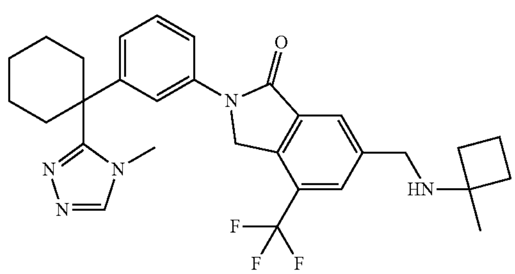 [SMILES: Cn1cnnc1C1(c2cccc(N3Cc4c(cc(CNC5(C)CCC5)cc4C(F)(F)F)C3=O)c2)CCCCC1] | 2-(3-(1-(4-methyl-4H-1,2,4-triazol-3-yl)cyclohexyl)phenyl)-6-(((1-methylcyclobutyl)amino)methyl)-4-(trifluoromethyl)isoindolin-1-one |
| 299 | 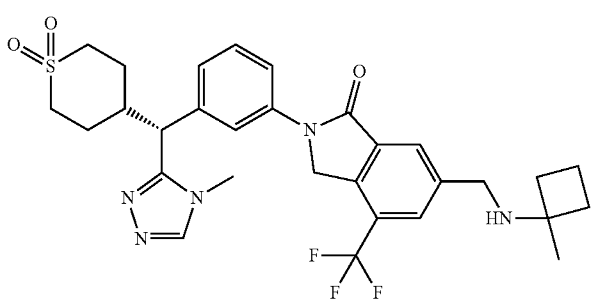 [SMILES: Cn1cnnc1[C@@H](c1cccc(N2Cc3c(cc(CNC4(C)CCC4)cc3C(F)(F)F)C2=O)c1)C1CCS(=O)(=O)CC1] | (R)-2-(3-((1,1-dioxidotetrahydro-2H-thiopyran-4-yl)(4-methyl-4H-1,2,4-triazol-3-yl)methyl)phenyl)-6-(((1-methylcyclobutyl)amino)methyl)-4-(trifluoromethyl)isoindolin-1-one |
| 300 | 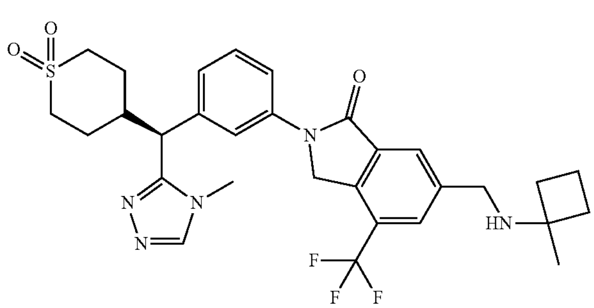 [SMILES: Cn1cnnc1[C@H](c1cccc(N2Cc3c(cc(CNC4(C)CCC4)cc3C(F)(F)F)C2=O)c1)C1CCS(=O)(=O)CC1] | (S)-2-(3-((1,1-dioxidotetrahydro-2H-thiopyran-4-yl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 301 | 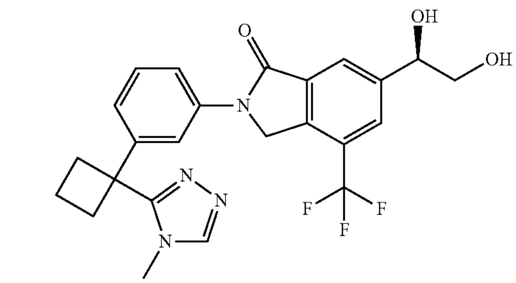 [SMILES: Cn1cnnc1C1(c2cccc(N3Cc4c(cc([C@@H](O)CO)cc4C(F)(F)F)C3=O)c2)CCC1] | (R)-6-(1,2-dihydroxyethyl)-2-(3-(1-(4-methyl-4H-1,2,4-triazol-3-yl)cyclobutyl)phenyl)-4-(trifluoromethyl)isoindolin-1-one |
| 302 | 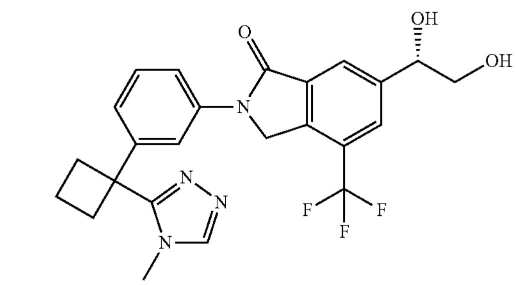 [SMILES: Cn1cnnc1C1(c2cccc(N3Cc4c(cc([C@H](O)CO)cc4C(F)(F)F)C3=O)c2)CCC1] | (S)-6-(1,2-dihydroxyethyl)-2-(3-(1-(4-methyl-4H-1,2,4-triazol-3-yl)cyclobutyl)phenyl)-4-(trifluoromethyl)isoindolin-1-one |
| 303 | 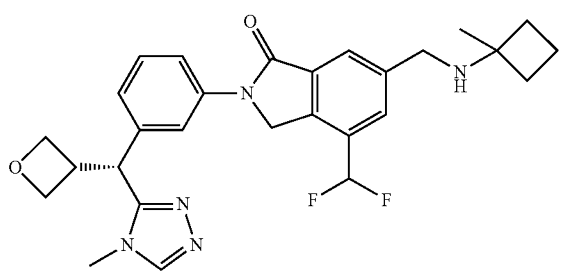 [SMILES: Cn1cnnc1[C@@H](c1cccc(N2Cc3c(cc(CNC4(C)CCC4)cc3C(F)F)C2=O)c1)C1COC1] | (R)-4-(difluoromethyl)-2-(3-((4-methyl-4H-1,2,4-triazol-3-yl)(oxetan-3-yl)methyl)phenyl)-6-(((1-methylcyclobutyl)amino)methyl)isoindolin-1-one |
| 304 | 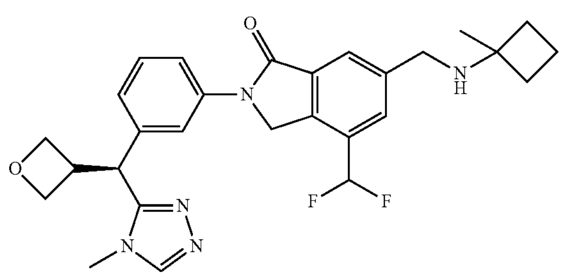 [SMILES: Cn1cnnc1[C@H](c1cccc(N2Cc3c(cc(CNC4(C)CCC4)cc3C(F)F)C2=O)c1)C1COC1] | (S)-4-(difluoromethyl)-2-(3-((4-methyl-4H-1,2,4-triazol-3-yl)(oxetan-3-yl)methyl)phenyl)-6-(((1-methylcyclobutyl)amino)methyl)isoindolin-1-one |
| 305 | 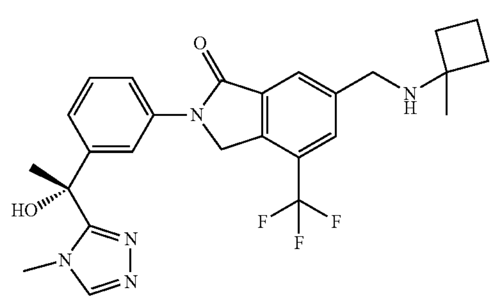 [SMILES: Cn1cnnc1[C@](C)(O)c1cccc(N2Cc3c(cc(CNC4(C)CCC4)cc3C(F)(F)F)C2=O)c1] | (R)-2-(3-(1-hydroxy-1-(4-methyl-4H-1,2,4-triazol-3-yl)ethyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 306 | 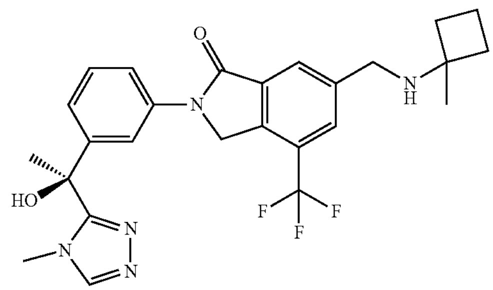 [SMILES: Cn1cnnc1[C@@](C)(O)c1cccc(N2Cc3c(cc(CNC4(C)CCC4)cc3C(F)(F)F)C2=O)c1] | (S)-2-(3-(1-hydroxy-1-(4-methyl-4H-1,2,4-triazol-3-yl)ethyl)phenyl)-6-(((1-methylcyclobutyl)amino)methyl)-4-(trifluoromethyl)isoindolin-1-one |
| 307 | 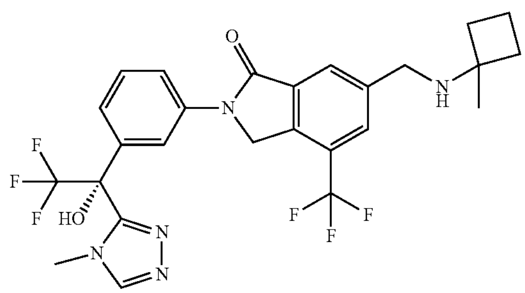 [SMILES: Cn1cnnc1[C@](O)(c1cccc(N2Cc3c(cc(CNC4(C)CCC4)cc3C(F)(F)F)C2=O)c1)C(F)(F)F] | (R)-6-(((1-methylcyclobutyl)amino)methyl)-2-(3-(2,2,2-trifluoro-1-hydroxy-1-(4-methyl-4H-1,2,4-triazol-3-yl)ethyl)phenyl)-4-(trifluoromethyl)isoindolin-1-one |
| 308 | 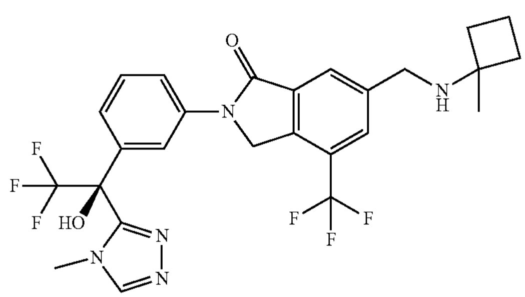 [SMILES: Cn1cnnc1[C@@](O)(c1cccc(N2Cc3c(cc(CNC4(C)CCC4)cc3C(F)(F)F)C2=O)c1)C(F)(F)F] | (S)-6-(((1-methylcyclobutyl)amino)methyl)-2-(3-(2,2,2-trifluoro-1-hydroxy-1-(4-methyl-4H-1,2,4-triazol-3-yl)ethyl)phenyl)-4-(trifluoromethyl)isoindolin-1-one |
| 309 | 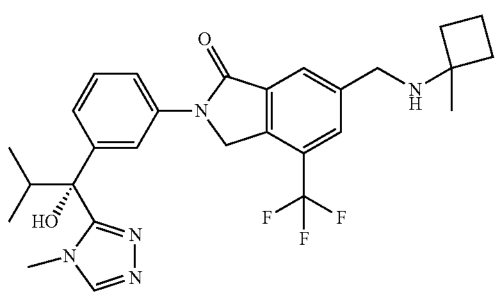 [SMILES: CC(C)[C@@](O)(c1cccc(N2Cc3c(cc(CNC4(C)CCC4)cc3C(F)(F)F)C2=O)c1)c1nncn1C] | (R)-2-(3-(1-hydroxy-2-methyl-1-(4-methyl-4H-1,2,4-triazol-3-yl)propyl)phenyl)-6-(((1-methylcyclobutyl)amino)methyl)-4-(trifluoromethyl)isoindolin-1-one |
| 310 | 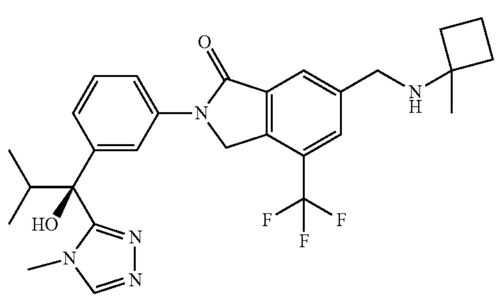 [SMILES: CC(C)[C@](O)(c1cccc(N2Cc3c(cc(CNC4(C)CCC4)cc3C(F)(F)F)C2=O)c1)c1nncn1C] | (S)-2-(3-(1-hydroxy-2-methyl-1-(4-methyl-4H-1,2,4-triazol-3-yl)propyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 311 | 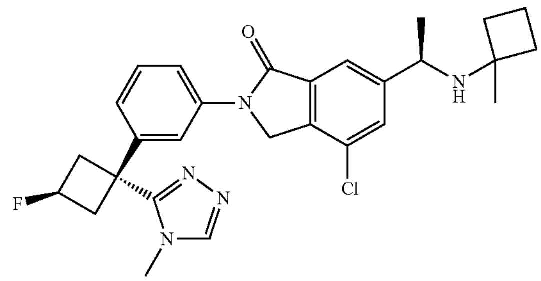 [SMILES: C[C@@H](NC1(C)CCC1)c1cc(Cl)c2c(c1)C(=O)N(c1cccc([C@]3(c4nncn4C)C[C@H](F)C3)c1)C2] | 4-chloro-2-(3-((1r,3R)-3-fluoro-1-(4-methyl-4H-1,2,4-triazol-3-yl)cyclobutyl)phenyl)-6-((R)-1-((1-methylcyclobutyl)amino)ethyl)isoindolin-1-one |
| 312 | 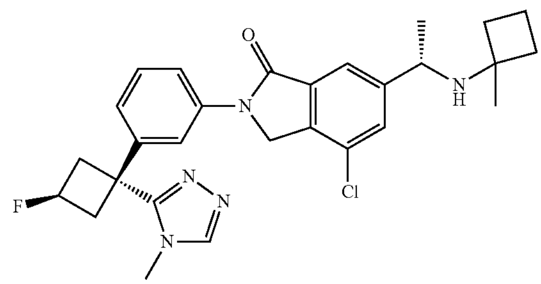 [SMILES: C[C@H](NC1(C)CCC1)c1cc(Cl)c2c(c1)C(=O)N(c1cccc([C@]3(c4nncn4C)C[C@H](F)C3)c1)C2] | 4-chloro-2-(3-((1r,3S)-3-fluoro-1-(4-methyl-4H-1,2,4-triazol-3-yl)cyclobutyl)phenyl)-6-((S)-1-((1-methylcyclobutyl)amino)ethyl)isoindolin-1-one |
| 313 | 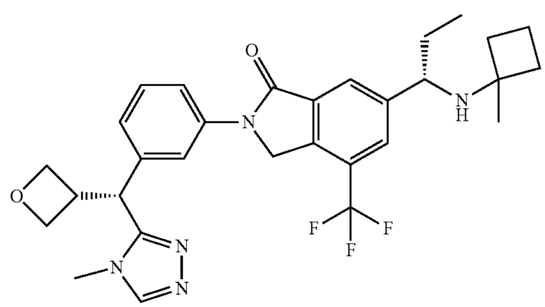 [SMILES: CC[C@H](NC1(C)CCC1)c1cc2c(c(C(F)(F)F)c1)CN(c1cccc([C@H](c3nncn3C)C3COC3)c1)C2=O] | 2-(3-((R)-(4-methyl-4H-1,2,4-triazol-3-yl)(oxetan-3-yl)methyl)phenyl)-6-((S)-1-((1-methylcyclobutyl)amino)propyl)-4-(trifluoromethyl)isoindolin-1-one |
| 314 | 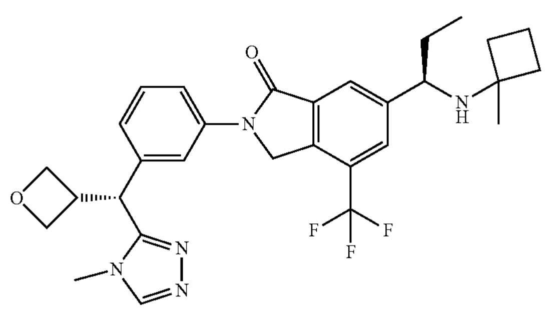 [SMILES: CC[C@@H](NC1(C)CCC1)c1cc2c(c(C(F)(F)F)c1)CN(c1cccc([C@H](c3nncn3C)C3COC3)c1)C2=O] | 2-(3-((R)-(4-methyl-4H-1,2,4-triazol-3-yl)(oxetan-3-yl)methyl)phenyl)-6-((R)-1-((1-methylcyclobutyl)amino)propyl)-4-(trifluoromethyl)isoindolin-1-one |
| 315 | 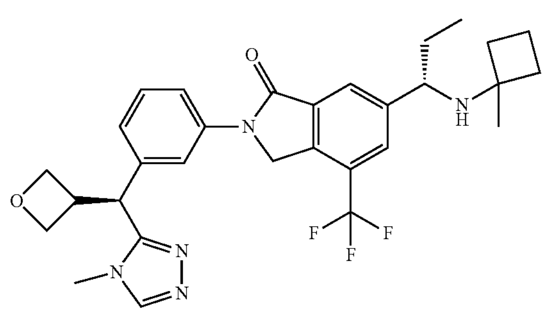 [SMILES: CC[C@H](NC1(C)CCC1)c1cc2c(c(C(F)(F)F)c1)CN(c1cccc([C@@H](c3nncn3C)C3COC3)c1)C2=O] | 2-(3-((S)-(4-methyl-4H-1,2,4-triazol-3-yl)(oxetan-3-yl)methyl)phenyl)-6-((S)-1-((1-methylcyclobutyl)amino)propyl)-4-(trifluoromethyl)isoindolin-1-one |

TABLE 1-continued

| Compound # | Structure | Name |
|---|---|---|
| 316 | 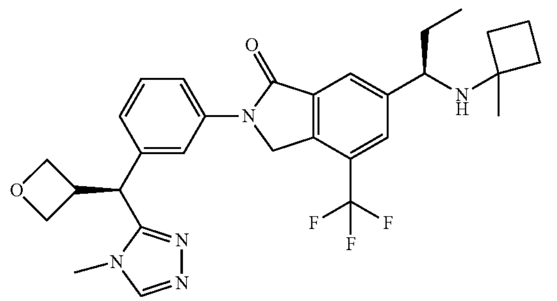 [SMILES: CC[C@@H](NC1(C)CCC1)c1cc2c(c(C(F)(F)F)c1)CN(c1cccc([C@@H](c3nncn3C)C3COC3)c1)C2=O] | 2-(3-((S)-(4-methyl-4H-1,2,4-triazol-3-yl)(oxetan-3-yl)methyl)phenyl)-6-((R)-1-(((1-methylcyclobutyl)amino)propyl)-4-(trifluoromethyl)isoindolin-1-one |
| 317 | 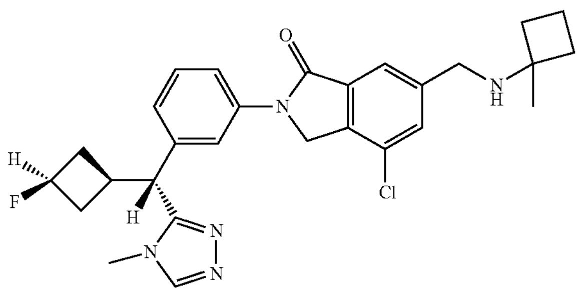 [SMILES: Cn1cnnc1[C@@H](c1cccc(N2Cc3c(Cl)cc(CNC4(C)CCC4)cc3C2=O)c1)[C@H]1C[C@@H](F)C1] | 4-chloro-2-(3-((R)-((1s,3S)-3-fluorocylcobutyl)(4-methyl-4H-1,2,4-triazol-3-yl)methyl)phenyl)-6-(((1-methylcyclobutyl)amino)methyl)isoindolin-1-one |
| 318 | 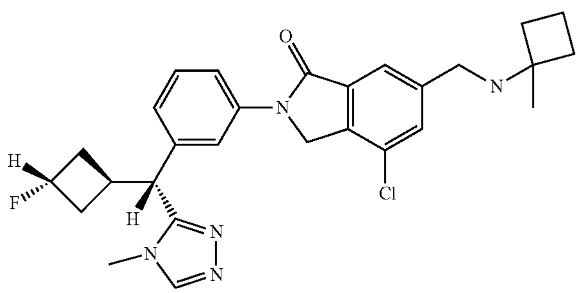 [SMILES: Cn1cnnc1[C@@H](c1cccc(N2Cc3c(Cl)cc(CNC4(C)CCC4)cc3C2=O)c1)[C@H]1C[C@H](F)C1] | 4-chloro-2-(3-((R)-((1r,3R)-3-fluorocyclobutyl)(4-methyl-4H-1,2,4-triazol-3-yl)methyl)phenyl)-6-(((1-methylcyclobutyl)amino)methyl)isoindolin-1-one |
| 319 | 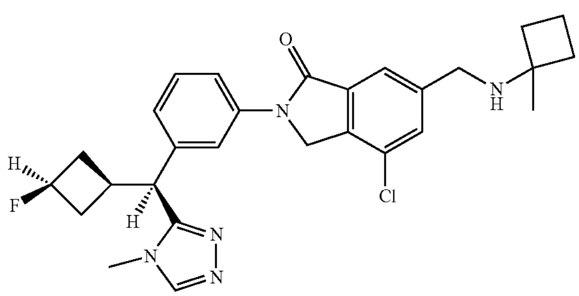 [SMILES: Cn1cnnc1[C@H](c1cccc(N2Cc3c(Cl)cc(CNC4(C)CCC4)cc3C2=O)c1)[C@H]1C[C@@H](F)C1] | 4-chloro-2-(3-((S)-((1s,3R)-3-fluorocyclobutyl)(4-methyl-4H-1,2,4-triazol-3-yl)methyl)phenyl)-6-(((1-methylcyclobutyl)amino)methyl)isoindolin-1-one |
| 320 | 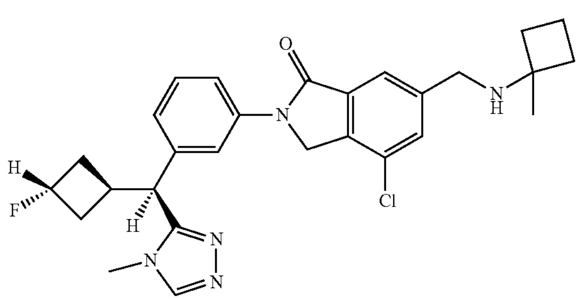 [SMILES: Cn1cnnc1[C@H](c1cccc(N2Cc3c(Cl)cc(CNC4(C)CCC4)cc3C2=O)c1)[C@H]1C[C@H](F)C1] | 4-chloro-2-(3-((S)-((1r,3S)-3-fluorocyclobutyl)(4-methyl-4H-1,2,4-triazol-3-yl)methyl)phenyl)-6-(((1-methylcyclobutyl)amino)methyl)isoindolin-1-one |

TABLE 1-continued

| Compound # | Structure | Name |
|---|---|---|
| 321 | 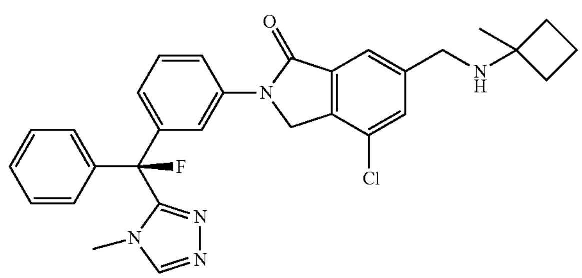 [SMILES: Cn1cnnc1[C@](F)(c1ccccc1)c1cccc(N2Cc3c(Cl)cc(CNC4(C)CCC4)cc3C2=O)c1] | (S)-4-chloro-2-(3-(fluoro(4-methyl-4H-1,2,4-triazol-3-yl)(phenyl)methyl)phenyl)-6-(((1-methylcyclobutyl)amino)methyl)isoindolin-1-one |
| 322 | 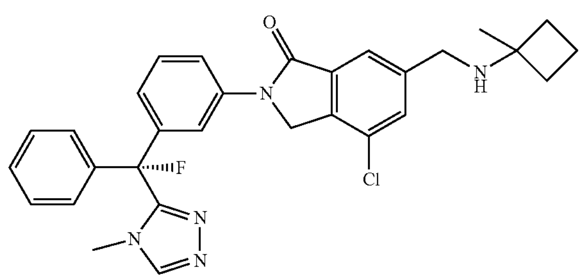 [SMILES: Cn1cnnc1[C@@](F)(c1ccccc1)c1cccc(N2Cc3c(Cl)cc(CNC4(C)CCC4)cc3C2=O)c1] | (R)-4-chloro-2-(3-(fluoro(4-methyl-4H-1,2,4-triazol-3-yl)(phenyl)methyl)phenyl)-6-(((1-methylcyclobutyl)amino)methyl)isoindolin-1-one |
| 323 | 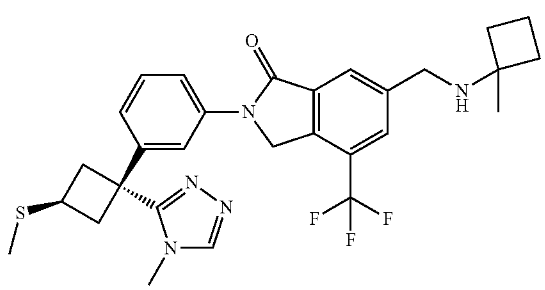 [SMILES: CS[C@H]1C[C@](c2cccc(N3Cc4c(cc(CNC5(C)CCC5)cc4C(F)(F)F)C3=O)c2)(c2nncn2C)C1] | 2-(3-((1r,3r)-1-(4-methyl-4H-1,2,4-triazol-3-yl)-3-(methylthio)cyclobutyl)phenyl)-6-(((1-methylcyclobutyl)amino)methyl)-4-(trifluoromethyl)isoindolin-1-one |
| 324 | 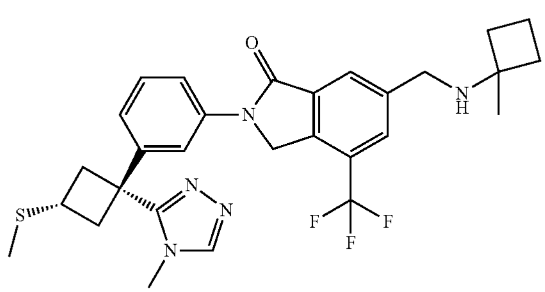 [SMILES: CS[C@H]1C[C@@](c2cccc(N3Cc4c(cc(CNC5(C)CCC5)cc4C(F)(F)F)C3=O)c2)(c2nncn2C)C1] | 2-(3-((1s,3s)-1-(4-methyl-4H-1,2,4-triazol-3-yl)-3-(methylthio)cyclobutyl)phenyl)-6-(((1-methylcyclobutyl)amino)methyl)-4-(trifluoromethyl)isoindolin-1-one |
| 325 | 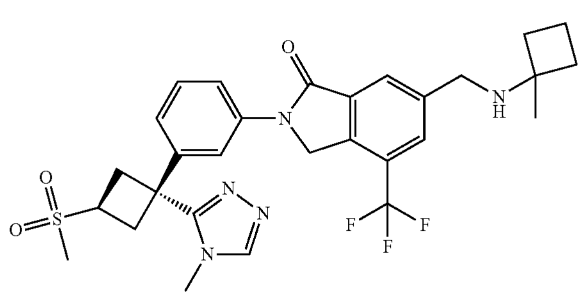 [SMILES: Cn1cnnc1[C@]1(c2cccc(N3Cc4c(cc(CNC5(C)CCC5)cc4C(F)(F)F)C3=O)c2)C[C@@H](S(C)(=O)=O)C1] | 2-(3-((1r,3r)-1-(4-methyl-4H-1,2,4-triazol-3-yl)-3-(methylsulfonyl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 326 | 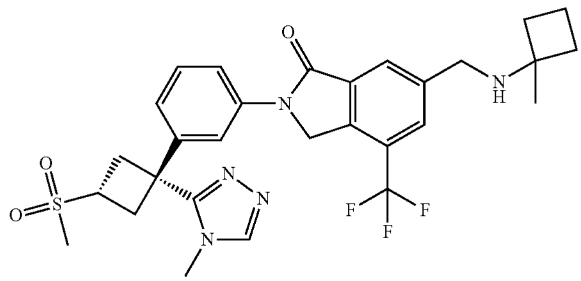 [SMILES: Cn1cnnc1[C@]1(c2cccc(N3Cc4c(cc(CNC5(C)CCC5)cc4C(F)(F)F)C3=O)c2)C[C@H](S(C)(=O)=O)C1] | 2-(3-((1s,3s)-1-(4-methyl-4H-1,2,4-triazol-3-yl)-3-(methylsulfonyl)cyclobutyl)phenyl)-6-(((1-methylcyclobutyl)amino)methyl)-4-(trifluoromethyl)isoindolin-1-one |
| 327 | 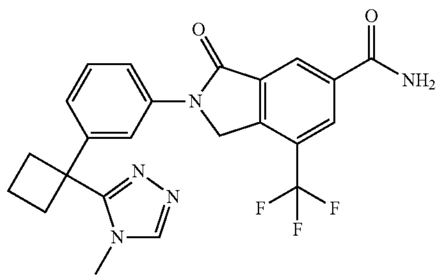 [SMILES: Cn1cnnc1C1(c2cccc(N3Cc4c(cc(C(N)=O)cc4C(F)(F)F)C3=O)c2)CCC1] | 2-(3-(1-(4-methyl-4H-1,2,4-triazol-3-yl)cyclobutyl)phenyl)-3-oxo-7-(trifluoromethyl)isoindoline-5-carboxamide |
| 328 | 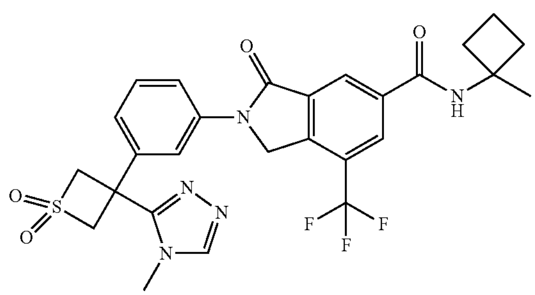 [SMILES: Cn1cnnc1C1(c2cccc(N3Cc4c(cc(C(=O)NC5(C)CCC5)cc4C(F)(F)F)C3=O)c2)CS(=O)(=O)C1] | 2-(3-(3-(4-methyl-4H-1,2,4-triazol-3-yl)-1,1-dioxidothietan-3-yl)phenyl)-6-(((1-methylcyclobutyl)amino)methyl)-4-(trifluoromethyl)isoindolin-1-one |
| 329 | 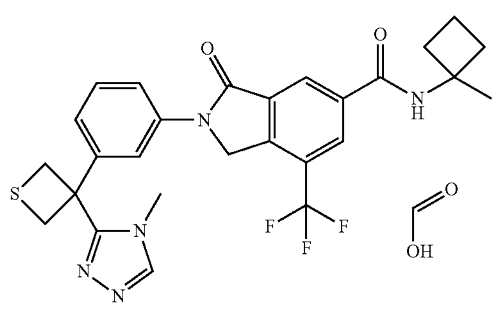 [SMILES: Cn1cnnc1C1(c2cccc(N3Cc4c(cc(C(=O)NC5(C)CCC5)cc4C(F)(F)F)C3=O)c2)CSC1 ; O=CO] | 2-(3-(3-(4-methyl-4H-1,2,4-triazol-3-yl)thietan-3-yl)phenyl)-6-(((1-methylcyclobutyl)amino)methyl)-4-(trifluoromethyl)isoindolin-1-one formate |
| 330 | 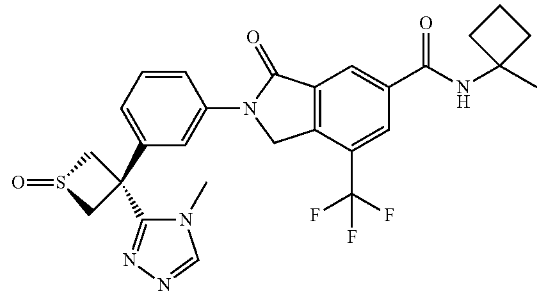 | 2-(3-(3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one |

TABLE 1-continued

| Compound # | Structure | Name |
|---|---|---|
| 331 | 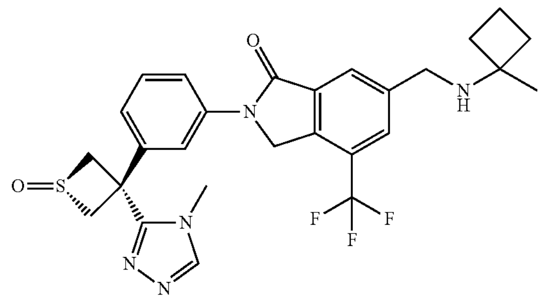 | 2-(3-(3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one |
| 332 | 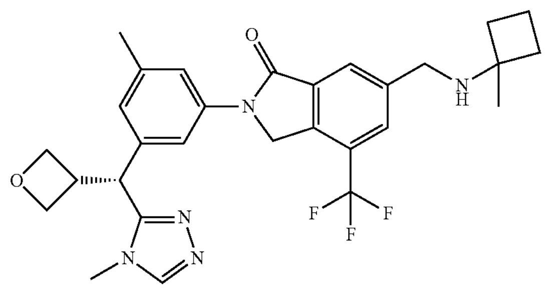 [SMILES: Cc1cc([C@H](c2nncn2C)C2COC2)cc(N2Cc3c(cc(CNC4(C)CCC4)cc3C(F)(F)F)C2=O)c1] | (R)-2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 333 | 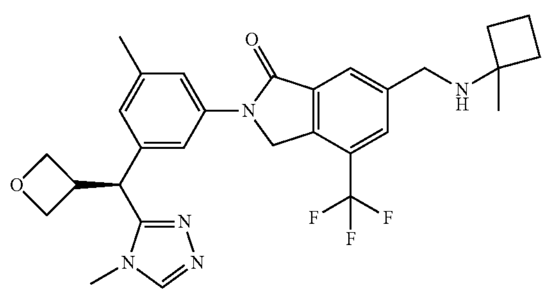 [SMILES: Cc1cc([C@@H](c2nncn2C)C2COC2)cc(N2Cc3c(cc(CNC4(C)CCC4)cc3C(F)(F)F)C2=O)c1] | (S)-2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 334 | 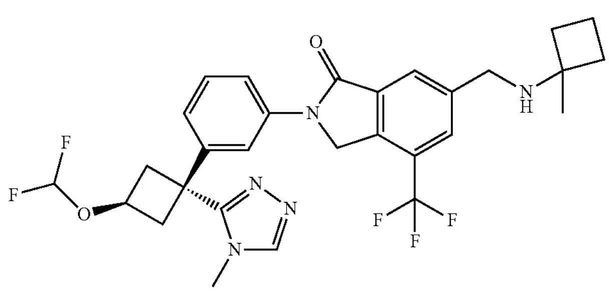 [SMILES: Cn1cnnc1[C@]1(c2cccc(N3Cc4c(cc(CNC5(C)CCC5)cc4C(F)(F)F)C3=O)c2)C[C@@H](OC(F)F)C1] | 2-(3-((1r,3r)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 335 | 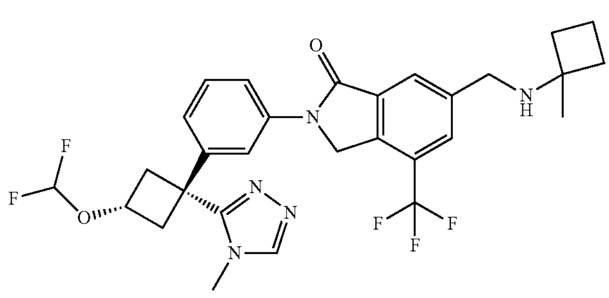 [SMILES: Cn1cnnc1[C@]1(c2cccc(N3Cc4c(cc(CNC5(C)CCC5)cc4C(F)(F)F)C3=O)c2)C[C@H](OC(F)F)C1] | 2-(3-((1s,3s)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 336 | 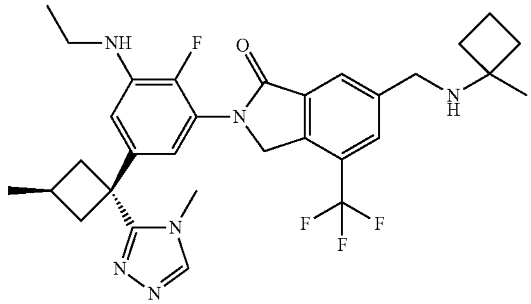 | 2-(3-(ethylamino)-2-fluoro-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 337 | 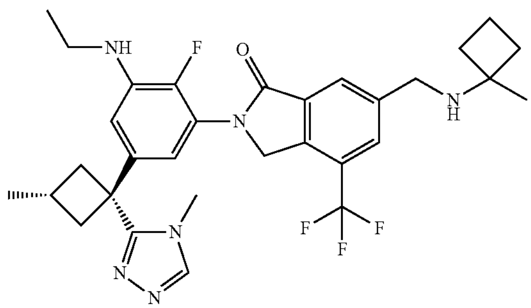 | 2-(3-(ethylamino)-2-fluoro-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 338 | 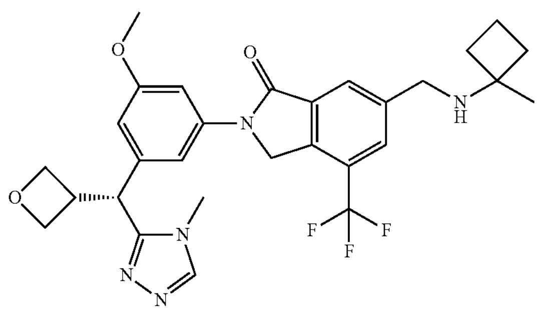 [SMILES: COc1cc([C@H](c2nncn2C)C2COC2)cc(N2Cc3c(cc(CNC4(C)CCC4)cc3C(F)(F)F)C2=O)c1] | (R)-2-(3-methoxy-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 339 | 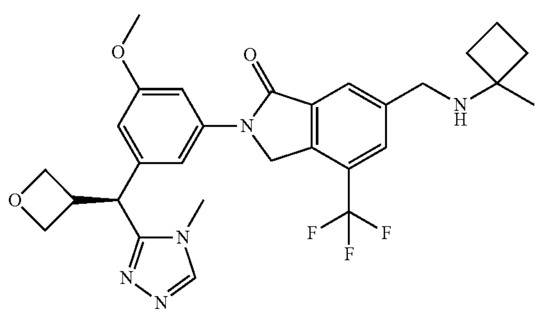 [SMILES: COc1cc([C@@H](c2nncn2C)C2COC2)cc(N2Cc3c(cc(CNC4(C)CCC4)cc3C(F)(F)F)C2=O)c1] | (S)-2-(3-methoxy-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 340 | 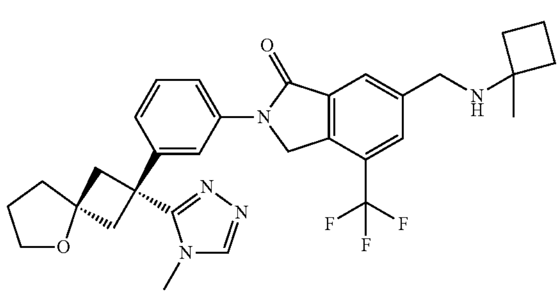 [SMILES: Cn1cnnc1[C@]1(c2cccc(N3Cc4c(cc(CNC5(C)CCC5)cc4C(F)(F)F)C3=O)c2)C[C@]2(CCCO2)C1] | 2-(3-((2s,4r)-2-(4-methyl-4H-1,2,4-triazol-3-yl)-5-oxaspiro[3.4]octan-2-yl)phenyl)-6-(((1-methylcyclobutyl)amino)methyl)-4-(trifluoromethyl)isoindolin-1-one |

TABLE 1-continued

| Compound # | Structure | Name |
|---|---|---|
| 341 | 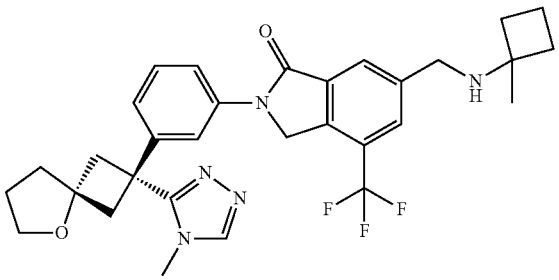 [SMILES: Cn1cnnc1[C@]1(c2cccc(N3Cc4c(cc(CNC5(C)CCC5)cc4C(F)(F)F)C3=O)c2)C[C@@]2(CCCO2)C1] | 2-(3-((2r,4s)-2-(4-methyl-4H-1,2,4-triazol-3-yl)-5-oxaspiro[3.4]octan-2-yl)phenyl)-6-(((1-methylcyclobutyl)amino)methyl)-4-(trifluoromethyl)isoindolin-1-one |
| 342 | 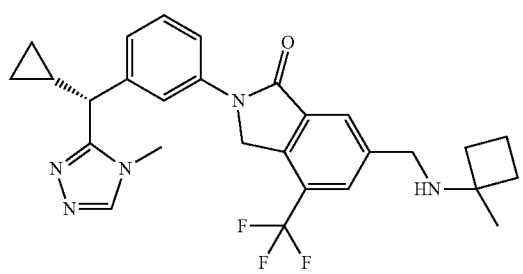 [SMILES: Cn1cnnc1[C@@H](c1cccc(N2Cc3c(cc(CNC4(C)CCC4)cc3C(F)(F)F)C2=O)c1)C1CC1] | (R)-2-(3-(cyclopropyl(4-methyl-4H-1,2,4-triazol-3-yl)methyl)phenyl)-6-(((1-methylcyclobutyl)amino)methyl)-4-(trifluoromethyl)isoindolin-1-one |
| 343 | 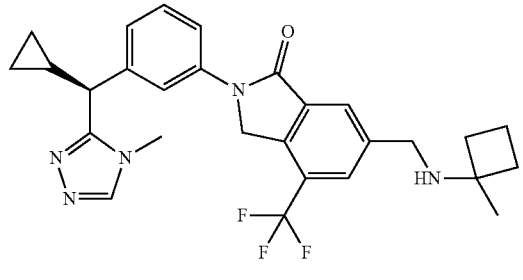 [SMILES: Cn1cnnc1[C@H](c1cccc(N2Cc3c(cc(CNC4(C)CCC4)cc3C(F)(F)F)C2=O)c1)C1CC1] | (S)-2-(3-(cyclopropyl(4-methyl-4H-1,2,4-triazol-3-yl)methyl)phenyl)-6-(((1-methylcyclobutyl)amino)methyl)-4-(trifluoromethyl)isoindolin-1-one |
| 344 | 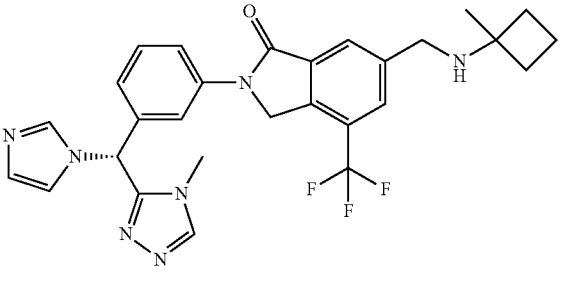 [SMILES: Cn1cnnc1[C@@H](c1cccc(N2Cc3c(cc(CNC4(C)CCC4)cc3C(F)(F)F)C2=O)c1)n1ccnc1] | (R)-2-(3-((1H-imidazol-1-yl)(4-methyl-4H-1,2,4-triazol-3-yl)methyl)phenyl)-6-(((1-methylcyclobutyl)amino)methyl)-4-(trifluoromethyl)isoindolin-1-one |
| 345 | 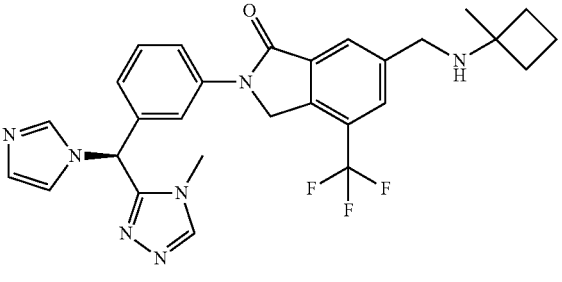 [SMILES: Cn1cnnc1[C@H](c1cccc(N2Cc3c(cc(CNC4(C)CCC4)cc3C(F)(F)F)C2=O)c1)n1ccnc1] | (S)-2-(3-((1H-imidazol-1-yl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 346 | 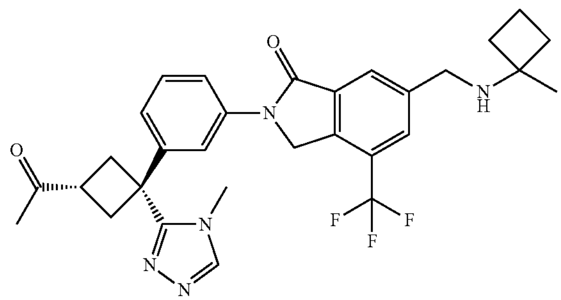 [SMILES: CC(=O)[C@H]1C[C@@](c2cccc(N3Cc4c(cc(CNC5(C)CCC5)cc4C(F)(F)F)C3=O)c2)(c2nncn2C)C1] | 2-(3-((1s,3s)-3-acetyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 347 | 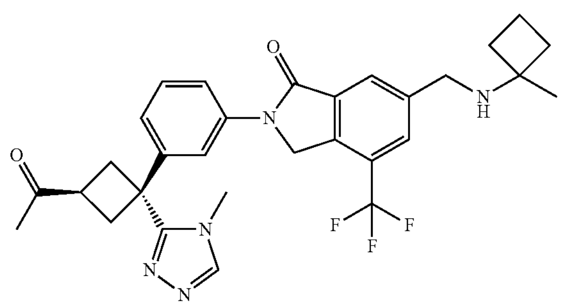 [SMILES: CC(=O)[C@H]1C[C@](c2cccc(N3Cc4c(cc(CNC5(C)CCC5)cc4C(F)(F)F)C3=O)c2)(c2nncn2C)C1] | 2-(3-((1r,3r)-3-acetyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 348 | 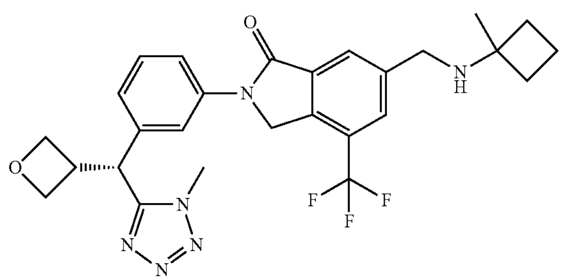 [SMILES: Cn1nnnc1[C@@H](c1cccc(N2Cc3c(cc(CNC4(C)CCC4)cc3C(F)(F)F)C2=O)c1)C1COC1] | (R)-2-(3-((1-methyl-1H-tetrazol-5-yl)(oxetan-3-yl)methyl)phenyl)-6-(((1-methylcyclobutyl)amino)methyl)-4-(trifluoromethyl)isoindolin-1-one |
| 349 | 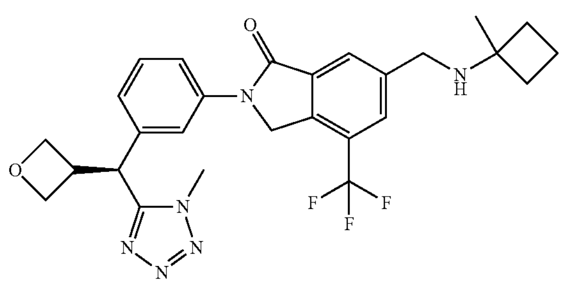 [SMILES: Cn1nnnc1[C@H](c1cccc(N2Cc3c(cc(CNC4(C)CCC4)cc3C(F)(F)F)C2=O)c1)C1COC1] | (S)-2-(3-((1-methyl-1H-tetrazol-5-yl)(oxetan-3-yl)methyl)phenyl)-6-(((1-methylcyclobutyl)amino)methyl)-4-(trifluoromethyl)isoindolin-1-one |
| 350 | 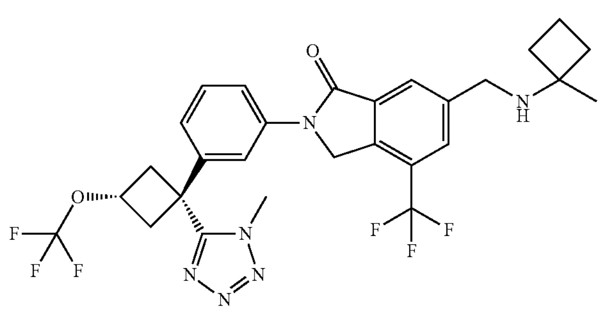 [SMILES: Cn1nnnc1[C@]1(c2cccc(N3Cc4c(cc(CNC5(C)CCC5)cc4C(F)(F)F)C3=O)c2)C[C@H](OC(F)(F)F)C1] | 2-(3-((1s,3s)-1-(4-methyl-4H-1,2,4-triazol-3-yl)-3-(trifluoromethoxy)cyclobutyl)phenyl)-6-(((1-methylcyclobutyl)amino)methyl)-4-(trifluoromethyl)isoindolin-1-one |

| Compound # | Structure | Name |
|---|---|---|
| 351 | 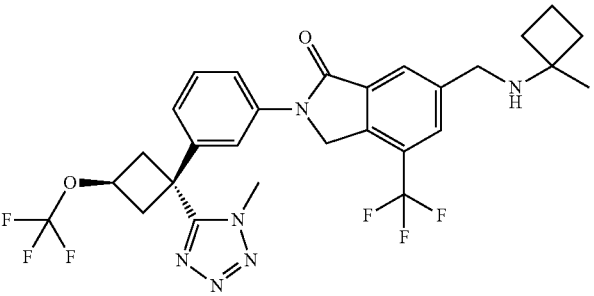 [SMILES: Cn1nnnc1[C@]1(c2cccc(N3Cc4c(cc(CNC5(C)CCC5)cc4C(F)(F)F)C3=O)c2)C[C@@H](OC(F)(F)F)C1] | 2-(3-((1r,3r)-1-(4-methyl-4H-1,2,4-triazol-3-yl)-3-(trifluoromethoxy)cyclobutyl)phenyl)-6-(((1-methylcyclobutyl)amino)methyl)-4-(tifluoromethyl)isoindolin-1-one |
| 352 | 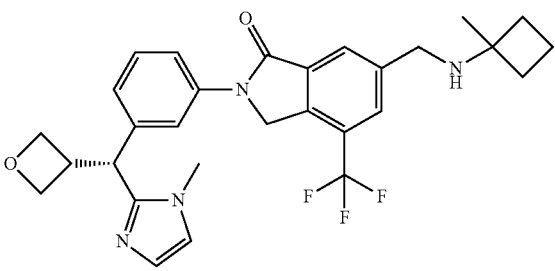 [SMILES: Cn1ccnc1[C@@H](c1cccc(N2Cc3c(cc(CNC4(C)CCC4)cc3C(F)(F)F)C2=O)c1)C1COC1] | (R)-2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one |
| 353 | 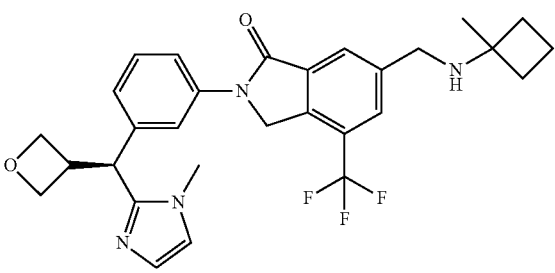 [SMILES: Cn1ccnc1[C@H](c1cccc(N2Cc3c(cc(CNC4(C)CCC4)cc3C(F)(F)F)C2=O)c1)C1COC1] | (S)-2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one |
| 354 | 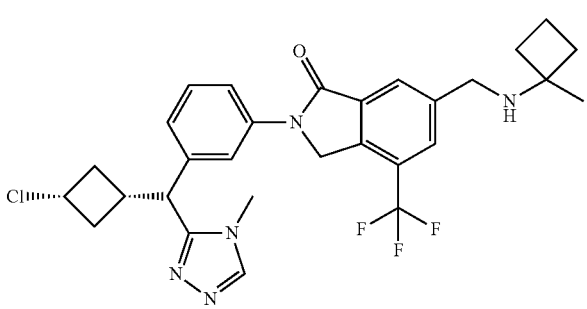 [SMILES: Cn1cnnc1C(c1cccc(N2Cc3c(cc(CNC4(C)CCC4)cc3C(F)(F)F)C2=O)c1)[C@H]1C[C@@H](Cl)C1] | 2-(3-((S)-((1s,3R)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 355 | 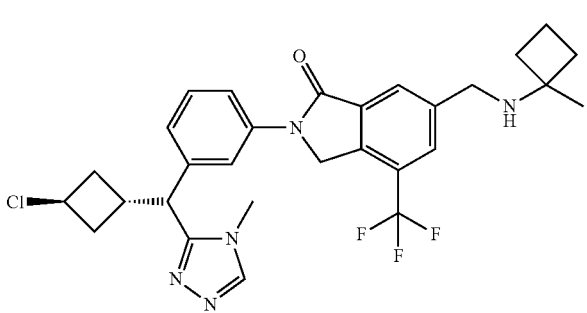 [SMILES: Cn1cnnc1C(c1cccc(N2Cc3c(cc(CNC4(C)CCC4)cc3C(F)(F)F)C2=O)c1)[C@H]1C[C@H](Cl)C1] | 2-(3-((S)-((1r,3S)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 356 | 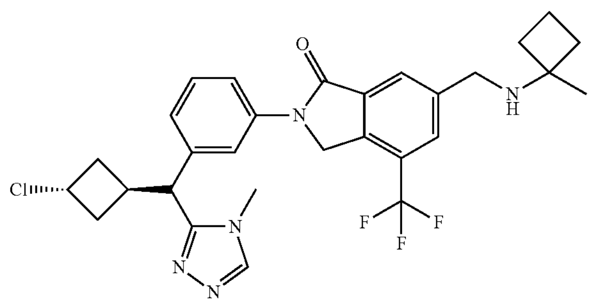 [SMILES: Cn1cnnc1C(c1cccc(N2Cc3c(cc(CNC4(C)CCC4)cc3C(F)(F)F)C2=O)c1)[C@H]1C[C@H](Cl)C1] | 2-(3-((R)-((1r,3R)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 357 | 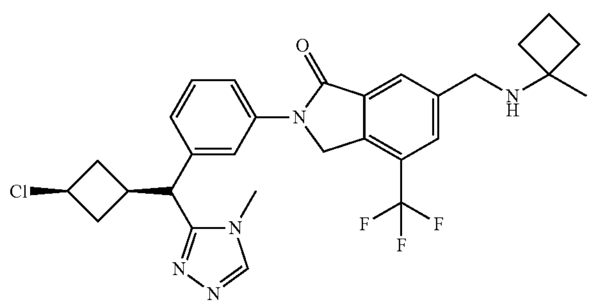 [SMILES: Cn1cnnc1C(c1cccc(N2Cc3c(cc(CNC4(C)CCC4)cc3C(F)(F)F)C2=O)c1)[C@H]1C[C@@H](Cl)C1] | 2-(3-((R)-((1s,3S)-3-chlorocyclobutyl)(4-methyl-4H-1,2,4-triazol-3-yl)phenyl)phenyl)-6-(((1-methylcyclobutyl)amino)methyl)-4-(trifluoromethyl)isoindolin-1-one |
| 358 | 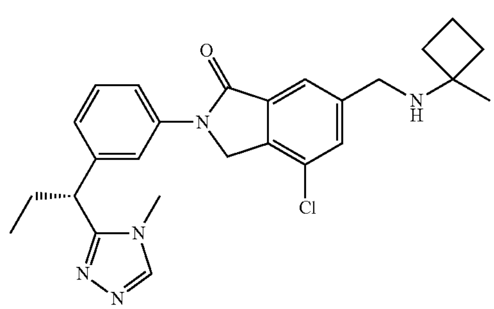 [SMILES: CC[C@H](c1cccc(N2Cc3c(Cl)cc(CNC4(C)CCC4)cc3C2=O)c1)c1nncn1C] | (R)-4-chloro-2-(3-(1-(4-methyl-4H-1,2,4-triazol-3-yl)propyl)phenyl)-6-(((1-methylcyclobtuyl)amino)methyl)isoindolin-1-one |
| 359 | 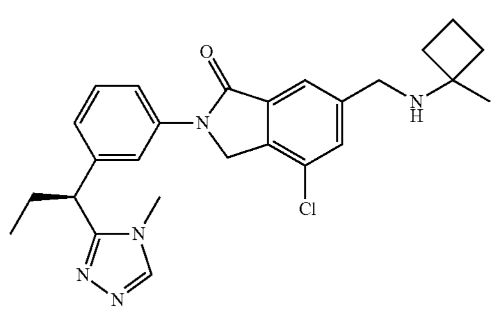 [SMILES: CC[C@@H](c1cccc(N2Cc3c(Cl)cc(CNC4(C)CCC4)cc3C2=O)c1)c1nncn1C] | (S)-4-chloro-2-(3-(1-(4-methyl-4H-1,2,4-triazol-3-yl)propyl)phenyl)-6-(((1-methylcyclobutyl)amino)methyl)isoindolin-1-one |
| 360 | 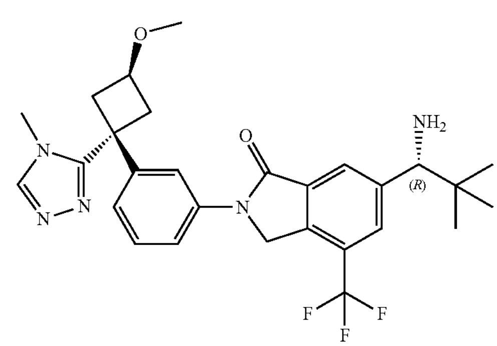 | 6-((R)-1-amino-2,2-dimethylpropyl)-2-(3-((1r,3R)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 361 | 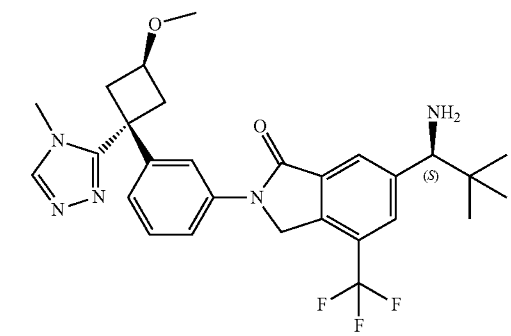 | 6-((S)-1-amino-2,2-dimethylpropyl)-2-(3-((1r,3S)-3-methoxy-1-(4-methyl-4H-1,2,4-triazol-3-yl)cyclobutyl)phenyl)-4-(trifluoromethyl)isoindolin-1-one |
| 362 | 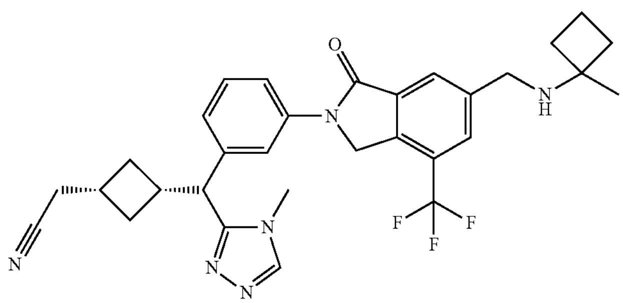 [SMILES: Cn1cnnc1C(c1cccc(N2Cc3c(cc(CNC4(C)CCC4)cc3C(F)(F)F)C2=O)c1)[C@H]1C[C@@H](CC#N)C1] | 2-((1R,3s)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile |
| 363 | 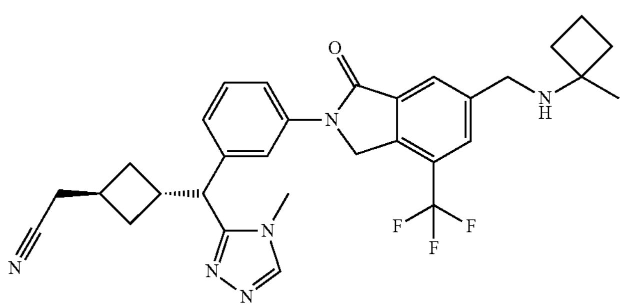 [SMILES: Cn1cnnc1C(c1cccc(N2Cc3c(cc(CNC4(C)CCC4)cc3C(F)(F)F)C2=O)c1)[C@H]1C[C@H](CC#N)C1] | 2-((1S,3r)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile |
| 364 | 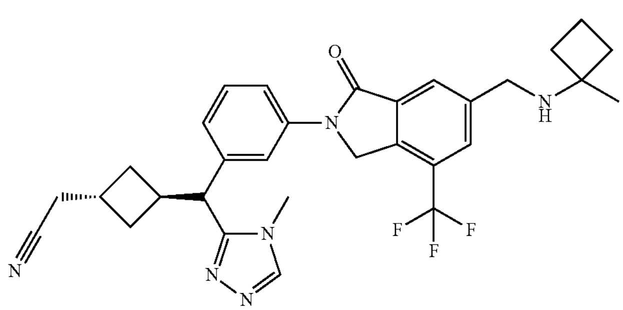 [SMILES: Cn1cnnc1C(c1cccc(N2Cc3c(cc(CNC4(C)CCC4)cc3C(F)(F)F)C2=O)c1)[C@H]1C[C@H](CC#N)C1] | 2-((1R,3r)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile |
| 365 | 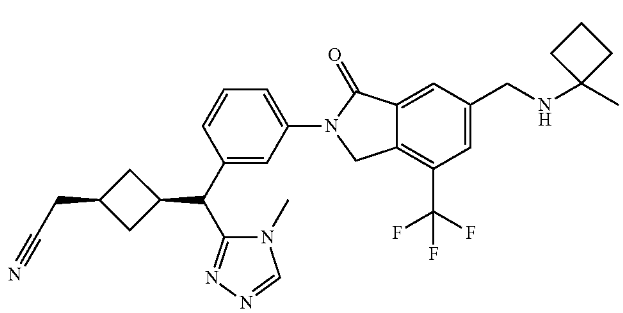 [SMILES: Cn1cnnc1C(c1cccc(N2Cc3c(cc(CNC4(C)CCC4)cc3C(F)(F)F)C2=O)c1)[C@H]1C[C@@H](CC#N)C1] | 2-((1S,3s)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile |

TABLE 1-continued

| Compound # | Structure | Name |
|---|---|---|
| 366 | 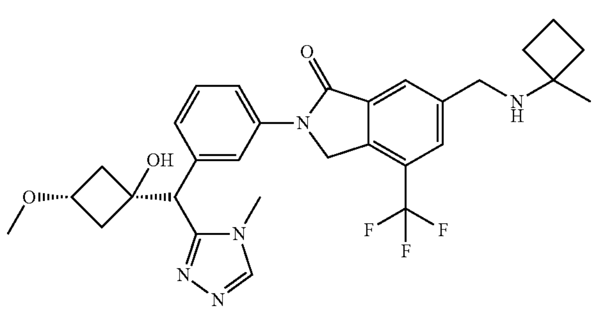 | 2-(3-((S)-((1r,3S)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 367 | 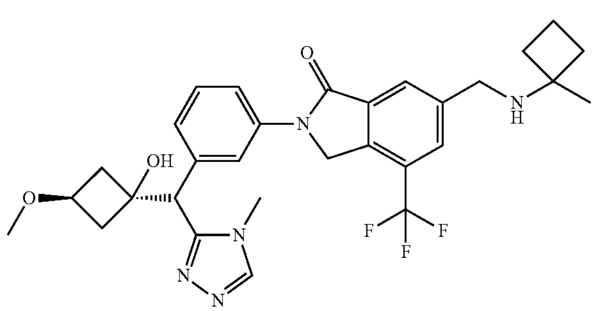 | 2-(3-((S)-((1s,3R)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 368 | 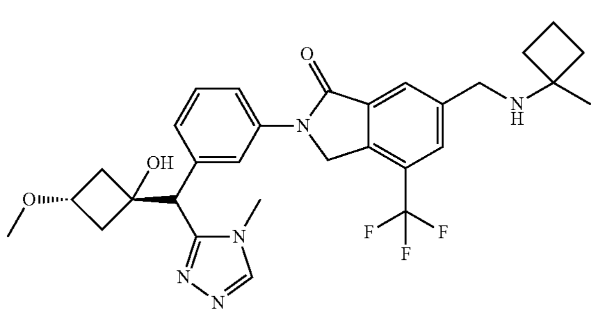 | 2-(3-((R)-((1s,3S)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 369 | 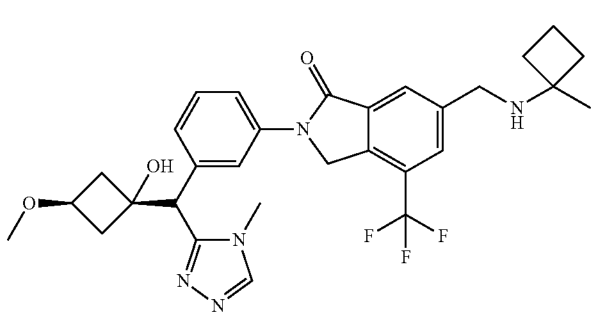 | 2-(3-((R)-((1r,3R)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 370 | 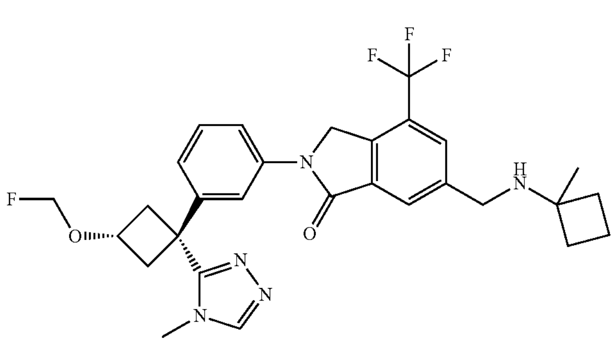 [SMILES: Cn1cnnc1[C@]1(c2cccc(N3Cc4c(cc(CNC5(C)CCC5)cc4C(F)(F)F)C3=O)c2)C[C@H](OCF)C1] | 2-(3-((1s,3s)-3-(fluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 371 | 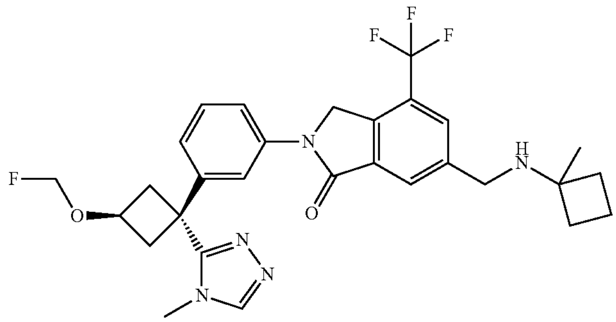 [SMILES: Cn1cnnc1[C@]1(c2cccc(N3Cc4c(cc(CNC5(C)CCC5)cc4C(F)(F)F)C3=O)c2)C[C@@H](OCF)C1] | 2-(3-((1r,3r)-3-(fluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 372 | 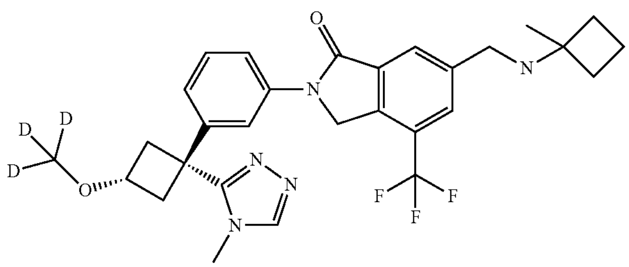 [SMILES: [2H]C([2H])([2H])O[C@H]1C[C@@](c2cccc(N3Cc4c(cc(CNC5(C)CCC5)cc4C(F)(F)F)C3=O)c2)(c2nncn2C)C1] | 2-(3-((1S,3S)-3-(methoxy-$d_3$)-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 373 | 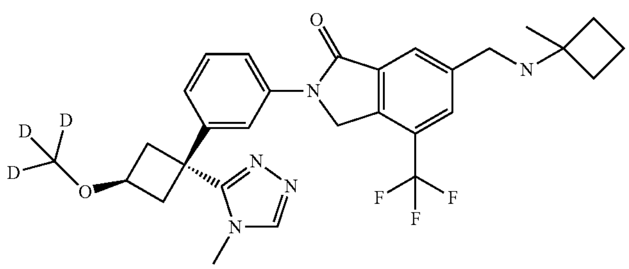 [SMILES: [2H]C([2H])([2H])O[C@H]1C[C@](c2cccc(N3Cc4c(cc(CNC5(C)CCC5)cc4C(F)(F)F)C3=O)c2)(c2nncn2C)C1] | 2-(3-((1R,3R)-3-(methoxy-$d_3$)-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 374 | 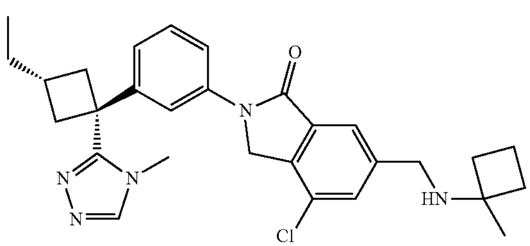 [SMILES: CC[C@H]1C[C@@](c2cccc(N3Cc4c(Cl)cc(CNC5(C)CCC5)cc4C3=O)c2)(c2nncn2C)C1] | 4-chloro-2-(3-((1r,3s)-3-ethyl-1-(4-methyl-4H-1,2,4-triazol-3-yl)cyclobutyl)phenyl)-6-(((1-methylcyclobutyl)amino)methyl)isoindolin-1-one |
| 375 | 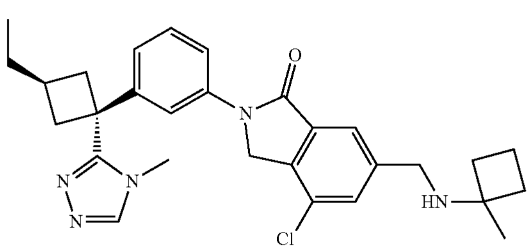 [SMILES: CC[C@H]1C[C@](c2cccc(N3Cc4c(Cl)cc(CNC5(C)CCC5)cc4C3=O)c2)(c2nncn2C)C1] | 4-chloro-2-(3-((1s,3r)-3-ethyl-1-(4-methyl-4H-1,2,4-triazol-3-yl)cyclobutyl)phenyl)-6-(((1-methylcyclobutyl)amino)methyl)isoindolin-1-one |

TABLE 1-continued

| Compound # | Structure | Name |
|---|---|---|
| 376 | 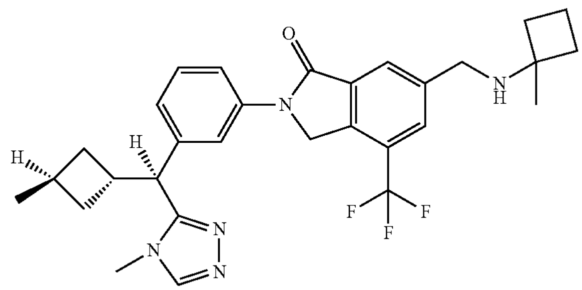 [SMILES: Cn1cnnc1[C@H](c1cccc(N2Cc3c(cc(CNC4(C)CCC4)cc3C(F)(F)F)C2=O)c1)[C@H]1C[C@H](C)C1] | 2-(3-((S)-(4-methyl-4H-1,2,4-triazol-3-yl)((1r,3S)-3-methylcyclobutyl)methyl)phenyl)-6-(((1-methylcyclobutyl)amino)methyl)-4-(trifluoromethyl)isoindolin-1-one |
| 377 | 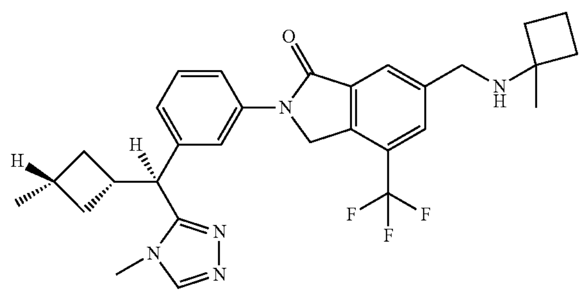 [SMILES: Cn1cnnc1[C@H](c1cccc(N2Cc3c(cc(CNC4(C)CCC4)cc3C(F)(F)F)C2=O)c1)[C@H]1C[C@@H](C)C1] | 2-(3-((S)-(4-methyl-4H-1,2,4-triazol-3-yl)((1s,3R)-3-methylcyclobutyl)methyl)phenyl)-6-(((1-methylcyclobutyl)amino)methyl)-4-(trifluoromethyl)isoindolin-1-one |
| 378 | 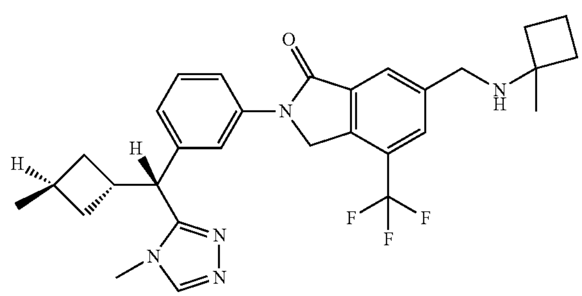 [SMILES: Cn1cnnc1[C@@H](c1cccc(N2Cc3c(cc(CNC4(C)CCC4)cc3C(F)(F)F)C2=O)c1)[C@H]1C[C@H](C)C1] | 2-(3-((R)-(4-methyl-4H-1,2,4-triazol-3-yl)((1r,3R)-3-methylcyclobutyl)methyl)phenyl)-6-(((1-methylcyclobutyl)amino)methyl)-4-(trifluoromethyl)isoindolin-1-one |
| 379 | 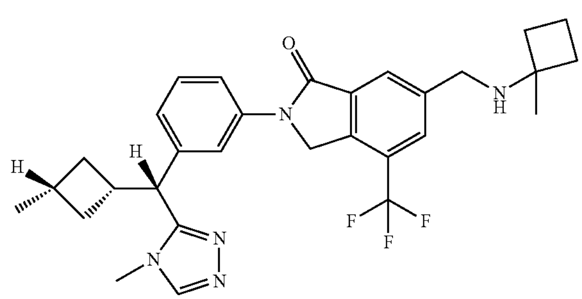 [SMILES: Cn1cnnc1[C@@H](c1cccc(N2Cc3c(cc(CNC4(C)CCC4)cc3C(F)(F)F)C2=O)c1)[C@H]1C[C@@H](C)C1] | 2-(3-((R)-(4-methyl-4H-1,2,4-triazol-3-yl)((1s,3S)-3-methylcyclobutyl)methyl)phenyl)-6-(((1-methylcyclobutyl)amino)methyl)-4-(trifluoromethyl)isoindolin-1-one |
| 380 | 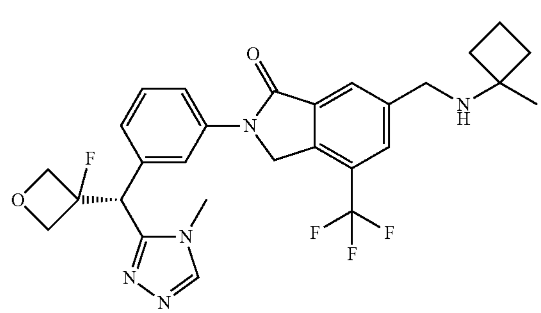 [SMILES: Cn1cnnc1[C@@H](c1cccc(N2Cc3c(cc(CNC4(C)CCC4)cc3C(F)(F)F)C2=O)c1)C1(F)COC1] | (R)-2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 381 | 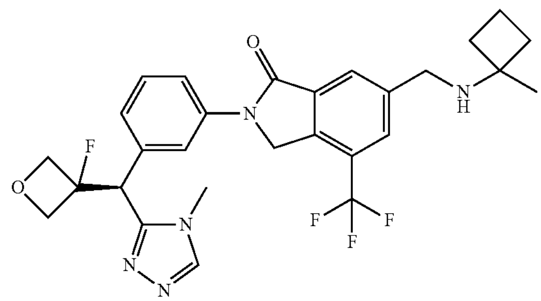 [SMILES: Cn1cnnc1[C@H](c1cccc(N2Cc3c(cc(CNC4(C)CCC4)cc3C(F)(F)F)C2=O)c1)C1(F)COC1] | (S)-2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 382 | 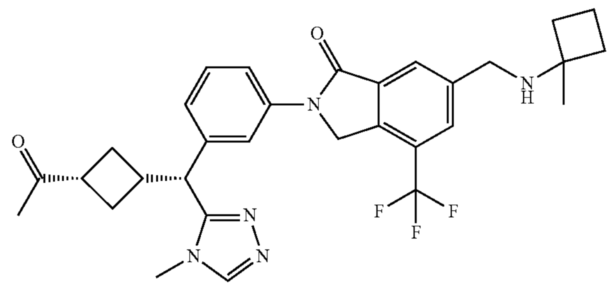 | 2-(3-((R)-((1r,3R)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 383 | 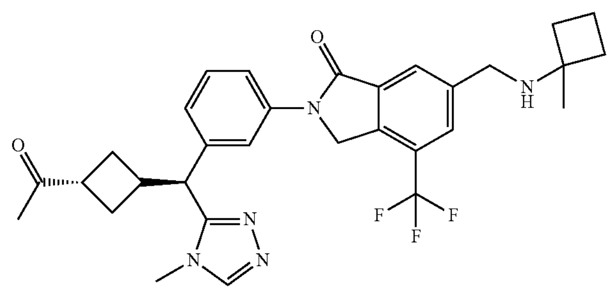 | 2-(3-((S)-((1s,3R)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 384 | 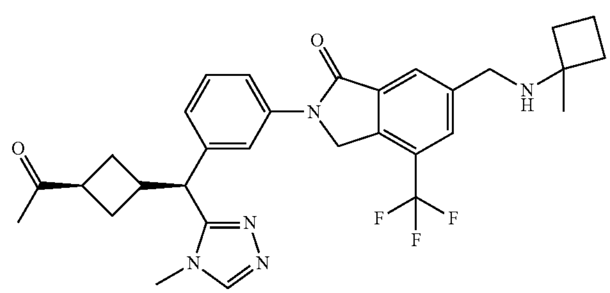 | 2-(3-((S)-((1r,3S)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 385 | 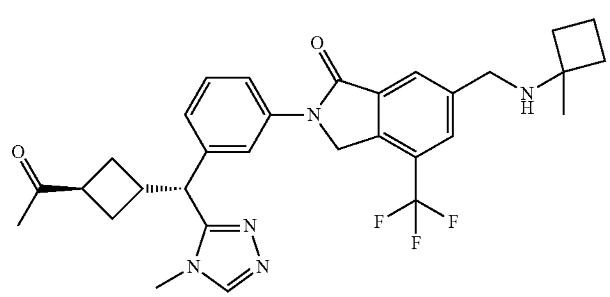 | 2-(3-((R)-((1s,3S)-3-acetylcyclobutyl)(4-methyl-4H-1,2,4-triazol-3-yl)methyl)phenyl)-6-(((1-methylcylcobutyl)amino)methyl)-4-(trifluoromethyl)isoindolin-1-one |

TABLE 1-continued

| Compound # | Structure | Name |
|---|---|---|
| 386 | 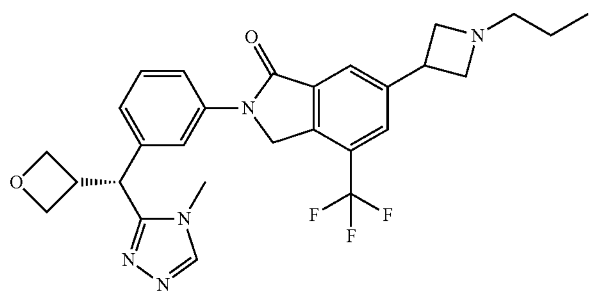 [SMILES: CCCN1CC(c2cc3c(c(C(F)(F)F)c2)CN(c2cccc([C@H](c4nncn4C)C4COC4)c2)C3=O)C1] | (R)-2-(3-((4-methyl-4H-1,2,4-triazol-3-yl)(oxetan-3-yl)methyl)phenyl)-6-(1-propylazetidin-3-yl)-4-(trifluoromethyl)isoindolin-1-one |
| 387 | 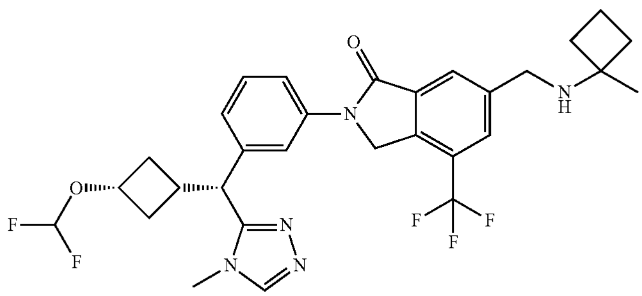 | 2-(3-((R)-((1r,3R)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 388 | 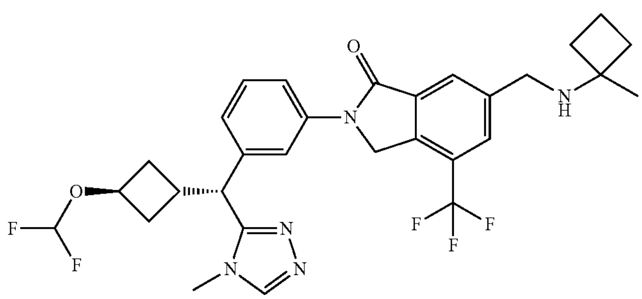 | 2-(3-((R)-((1s,3S)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 389 | 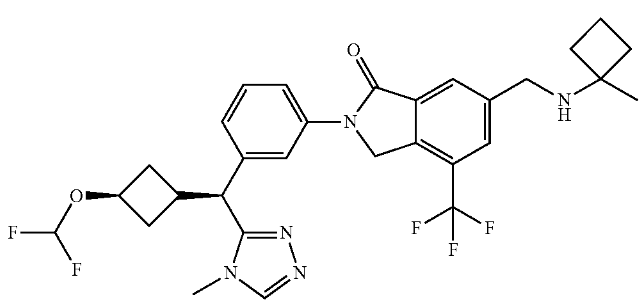 | 2-(3-((S)-((1r,3S)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 390 | 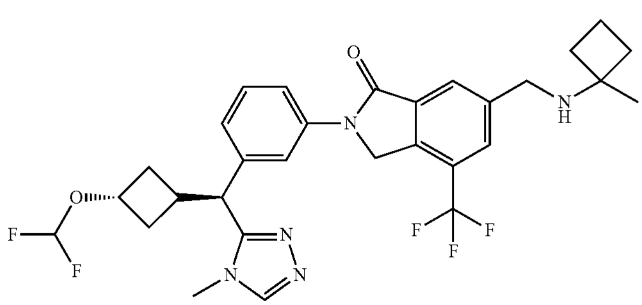 | 2-(3-((S)-((1s,3R)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 391 | 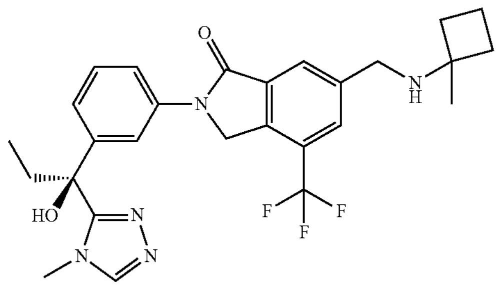 [SMILES: CC[C@](O)(c1cccc(N2Cc3c(cc(CNC4(C)CCC4)cc3C(F)(F)F)C2=O)c1)c1nncn1C] | (S)-2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one |
| 392 | 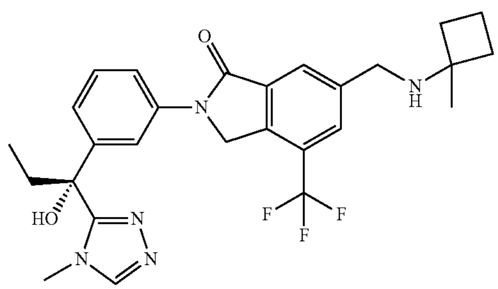 [SMILES: CC[C@@](O)(c1cccc(N2Cc3c(cc(CNC4(C)CCC4)cc3C(F)(F)F)C2=O)c1)c1nncn1C] | (R)-2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one |
| 393 | 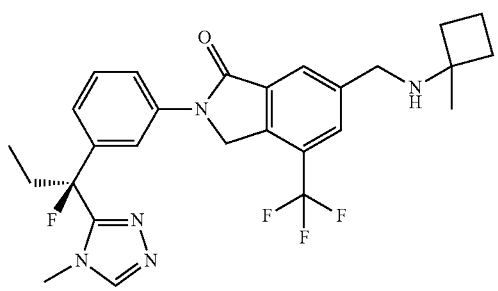 [SMILES: CC[C@](F)(c1cccc(N2Cc3c(cc(CNC4(C)CCC4)cc3C(F)(F)F)C2=O)c1)c1nncn1C] | (S)-2-(3-(1-fluoro-1-(4-methyl-4H-1,2,4-triazol-3-yl)propyl)phenyl)-6-(((1-methylcyclobutyl)amino)methyl)-4-(trifluoromethyl)isoindolin-1-one |
| 394 | 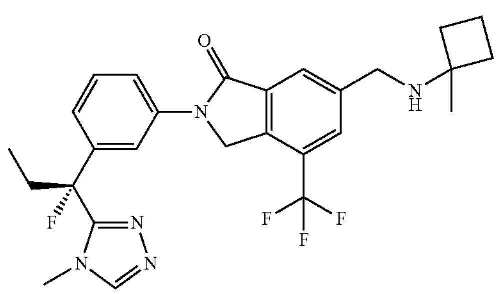 [SMILES: CC[C@@](F)(c1cccc(N2Cc3c(cc(CNC4(C)CCC4)cc3C(F)(F)F)C2=O)c1)c1nncn1C] | (R)-2-(3-(1-fluoro-1-(4-methyl-4H-1,2,4-triazol-3-yl)propyl)phenyl)-6-(((1-methylcyclobutyl)amino)methyl)-4-(trifluoromethyl)isoindolin-1-one |
| 395 | 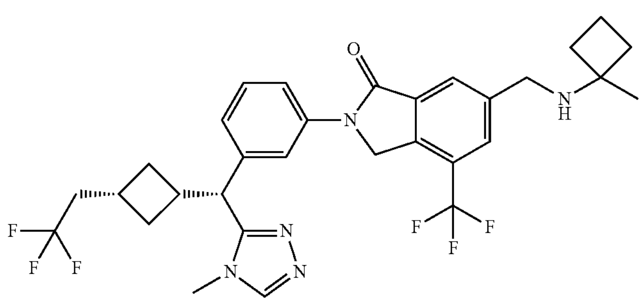 | 2-(3-((R)-(4-methyl-4H-1,2,4-triazol-3-yl)((1r,3R)-3-(trifluoromethoxy)-cyclobutyl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 396 | 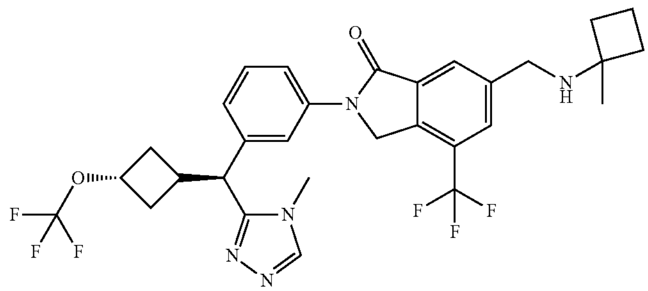 | 2-(3-((S)-(4-methyl-4H-1,2,4-triazol-3-yl)((1s,3R)-3-(trifluoromethoxy)-cyclobutyl)methyl)phenyl)-6-(((1-methylcyclobutyl)amino)methyl)-4-(trifluoromethyl)isoindolin-1-one |
| 397 | 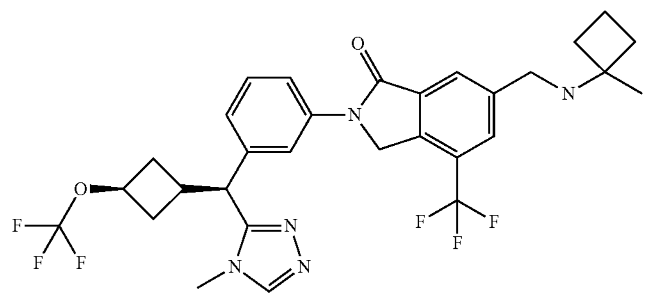 | 2-(3-((R)-(4-methyl-4H-1,2,4-triazol-3-yl)((1s,3S)-3-(trifluoromethoxy)-cyclobutyl)methyl)phenyl)-6-(((1-methylcyclobutyl)amino)methyl)-4-(trifluoromethyl)isoindolin-1-one |
| 398 | 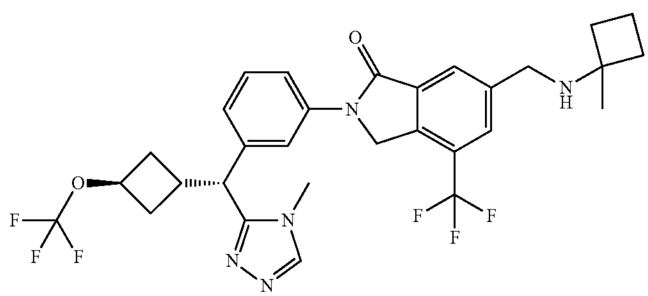 | 2-(3-((S)-(4-methyl-4H-1,2,4-triazol-3-yl)((1r,3S)-3-(trifluoromethoxy)-cyclobutyl)methyl)phenyl)-6-(((1-methylcyclobutyl)amino)methyl)-4-(trifluoromethyl)isoindolin-1-one |
| 399 | 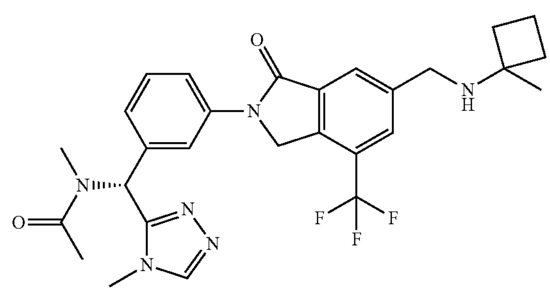 [SMILES: CC(=O)N(C)[C@H](c1cccc(N2Cc3c(cc(CNC4(C)CCC4)cc3C(F)(F)F)C2=O)c1)c1nncn1C] | (R)-N-methyl-N-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)acetamide |
| 400 | 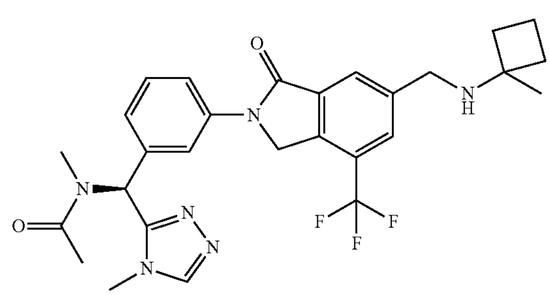 [SMILES: CC(=O)N(C)[C@@H](c1cccc(N2Cc3c(cc(CNC4(C)CCC4)cc3C(F)(F)F)C2=O)c1)c1nncn1C] | (S)-N-methyl-N-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)acetamide |

TABLE 1-continued

| Compound # | Structure | Name |
|---|---|---|
| 401 | 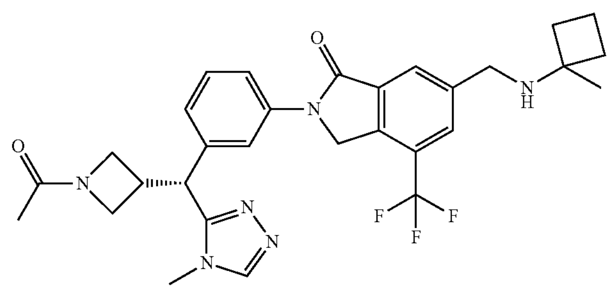 [SMILES: CC(=O)N1CC([C@H](c2cccc(N3Cc4c(cc(CNC5(C)CCC5)cc4C(F)(F)F)C3=O)c2)c2nncn2C)C1] | (R)-2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 402 | 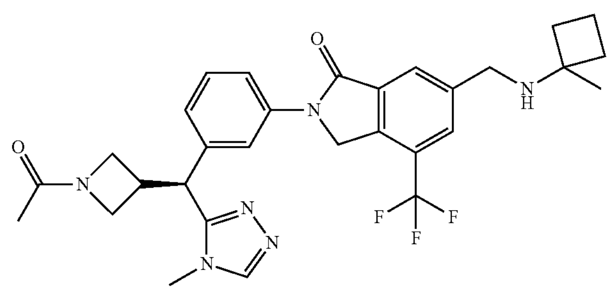 [SMILES: CC(=O)N1CC([C@@H](c2cccc(N3Cc4c(cc(CNC5(C)CCC5)cc4C(F)(F)F)C3=O)c2)c2nncn2C)C1] | (S)-2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 403 | 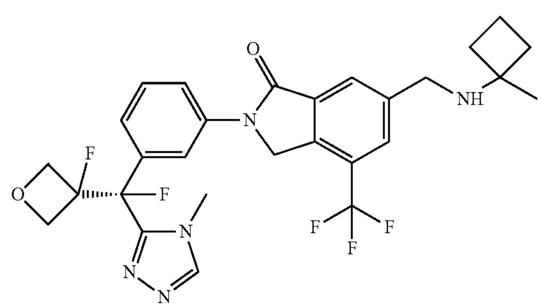 [SMILES: Cn1cnnc1[C@](F)(c1cccc(N2Cc3c(cc(CNC4(C)CCC4)cc3C(F)(F)F)C2=O)c1)C1(F)COC1] | (S)-2-(3-(fluoro(3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 404 | 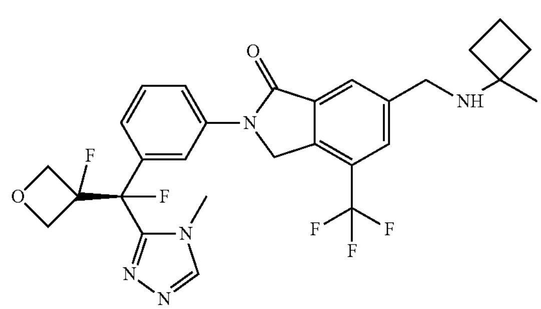 [SMILES: Cn1cnnc1[C@@](F)(c1cccc(N2Cc3c(cc(CNC4(C)CCC4)cc3C(F)(F)F)C2=O)c1)C1(F)COC1] | (R)-2-(3-(fluoro(3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 405 | 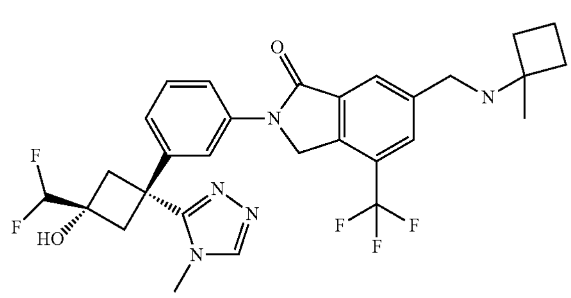 [SMILES: Cn1cnnc1[C@]1(c2cccc(N3Cc4c(cc(CNC5(C)CCC5)cc4C(F)(F)F)C3=O)c2)C[C@@](O)(C(F)F)C1] | 2-(3-((1s,3s)-3-(difluoromethyl)-3-hydroxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 406 | 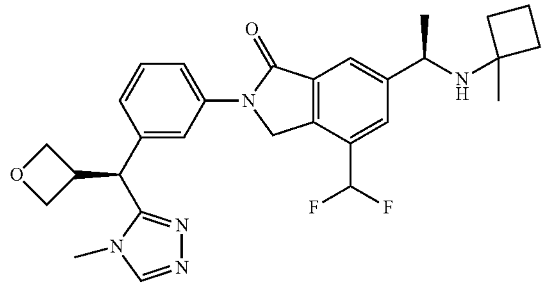 [SMILES: C[C@@H](NC1(C)CCC1)c1cc2c(c(C(F)F)c1)CN(c1cccc([C@@H](c3nncn3C)C3COC3)c1)C2=O] | 4-(difluoromethyl)-2-(3-((S)-(4-methyl-4H-1,2,4-triazol-3-yl)(oxetan-3-yl)methyl)phenyl)-6-((R)-1-((1-methylcyclobutyl)amino)ethyl)isoindolin-1-one |
| 407 | 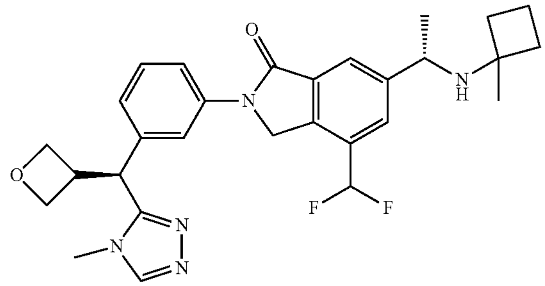 [SMILES: C[C@H](NC1(C)CCC1)c1cc2c(c(C(F)F)c1)CN(c1cccc([C@@H](c3nncn3C)C3COC3)c1)C2=O] | 4-(difluoromethyl)-2-(3-((S)-(4-methyl-4H-1,2,4-triazol-3-yl)(oxetan-3-yl)methyl)phenyl)-6-((S)-1-((1-methylcyclobutyl)amino)ethyl)isoindolin-1-one |
| 408 | 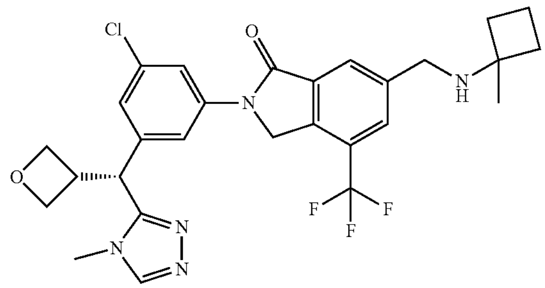 [SMILES: Cn1cnnc1[C@@H](c1cc(Cl)cc(N2Cc3c(cc(CNC4(C)CCC4)cc3C(F)(F)F)C2=O)c1)C1COC1] | (R)-2-(3-chloro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 409 | 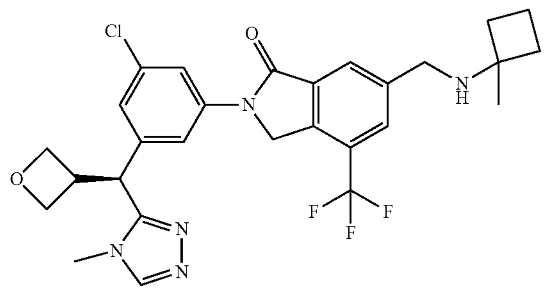 [SMILES: Cn1cnnc1[C@H](c1cc(Cl)cc(N2Cc3c(cc(CNC4(C)CCC4)cc3C(F)(F)F)C2=O)c1)C1COC1] | (S)-2-(3-chloro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one |
| 410 | 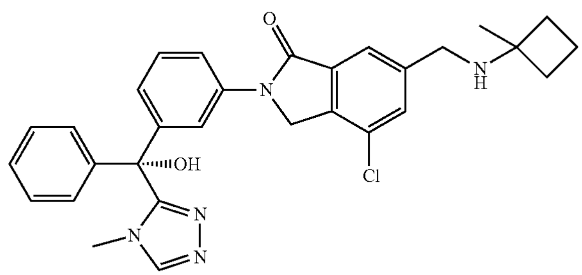 | (R)-4-chloro-2-(3-(hydroxy(4-methyl-4H-1,2,4-triazol-3-yl)(phenyl)methyl)phenyl)-6-(((1-methylcyclobutyl)amino)methyl)isoindolin-1-one |

TABLE 1-continued

| Compound # | Structure | Name |
|---|---|---|
| 411 | 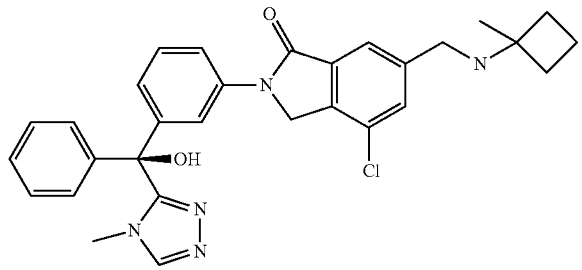 [SMILES: Cn1cnnc1[C@](O)(c1ccccc1)c1cccc(N2Cc3c(Cl)cc(CNC4(C)CCC4)cc3C2=O)c1] | (S)-4-chloro-2-(3-(hydroxy(4-methyl-4H-1,2,4-triazol-3-yl)(phenyl)methyl)phenyl)-6-(((1-methylcyclobutyl)amino)methyl)-isoindolin-1-one |
| 412 | 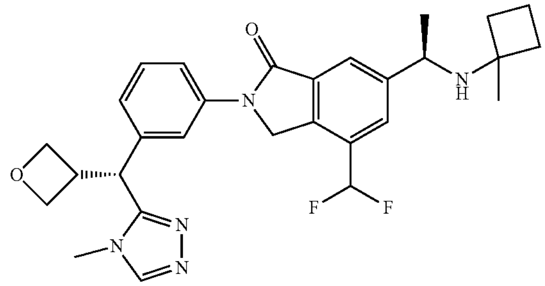 [SMILES: C[C@@H](NC1(C)CCC1)c1cc2c(c(C(F)F)c1)CN(c1cccc([C@H](c3nncn3C)C3COC3)c1)C2=O] | 4-(difluoromethyl)-2-(3-((R)-(4-methyl-4H-1,2,4-triazol-3-yl)(oxetan-3-yl)methyl)phenyl)-6-((R)-1-((1-methylcyclobutyl)amino)methyl)isoindolin-1-one |
| 413 | 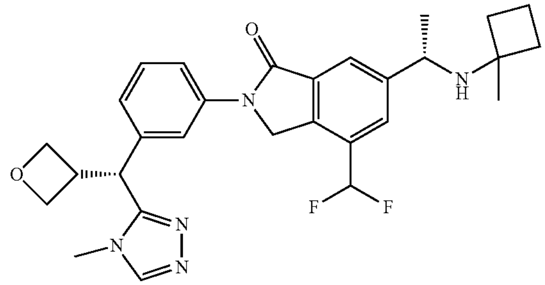 [SMILES: C[C@H](NC1(C)CCC1)c1cc2c(c(C(F)F)c1)CN(c1cccc([C@H](c3nncn3C)C3COC3)c1)C2=O] | 4-(difluoromethyl)-2-(3-((R)-(4-methyl-4H-1,2,4-triazol-3-yl)(oxetan-3-yl)methyl)phenyl)-6-((S)-1-((1-methylcyclobutyl)amino)ethyl)isoindolin-1-one |
| 414 | 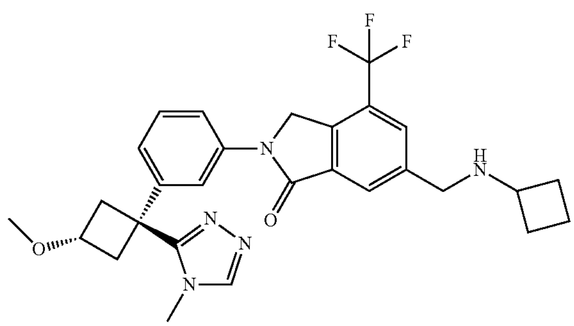 [SMILES: CO[C@H]1C[C@](c2cccc(N3Cc4c(cc(CNC5CCC5)cc4C(F)(F)F)C3=O)c2)(c2nncn2C)C1] | 6-((cyclobutylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 415 | 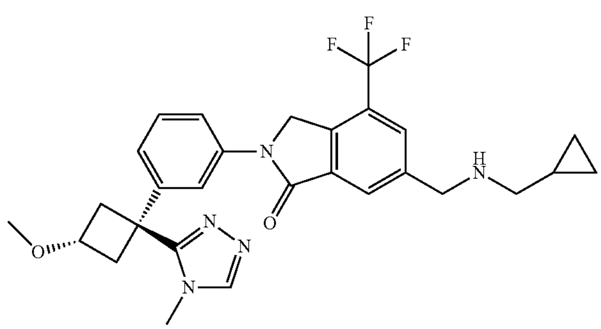 [SMILES: CO[C@H]1C[C@](c2cccc(N3Cc4c(cc(CNCC5CC5)cc4C(F)(F)F)C3=O)c2)(c2nncn2C)C1] | 6-(((cyclopropylmethyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
| --- | --- | --- |
| 416 | 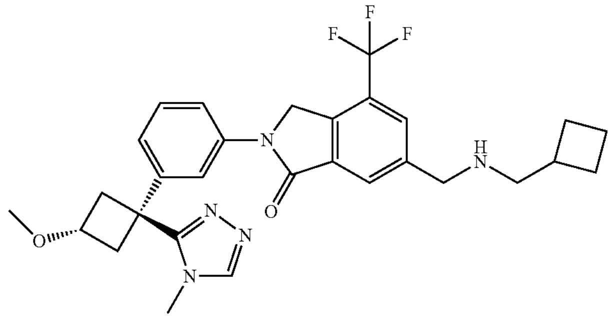 [SMILES: CO[C@H]1C[C@](c2cccc(N3Cc4c(cc(CNCC5CCC5)cc4C(F)(F)F)C3=O)c2)(c2nncn2C)C1] | 6-(((cyclobutylmethyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 417 | 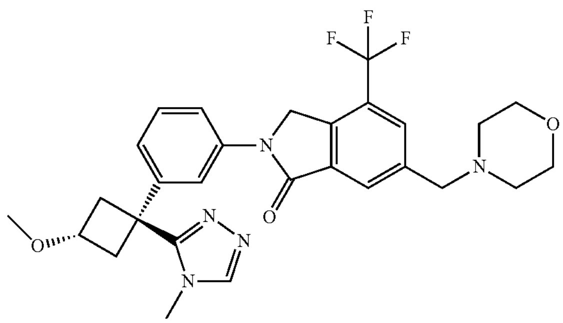 [SMILES: CO[C@H]1C[C@](c2cccc(N3Cc4c(cc(CN5CCOCC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-6-(morpholinomethyl)-4-(trifluoromethyl)isoindolin-1-one |
| 418 | 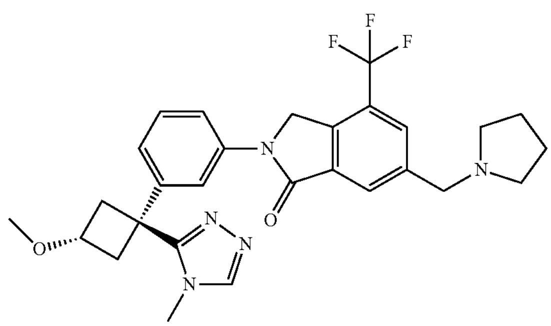 [SMILES: CO[C@H]1C[C@](c2cccc(N3Cc4c(cc(CN5CCCC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-6-(pyrrolidin-1-ylmethyl)-4-(trifluoromethyl)isoindolin-1-one |
| 419 | 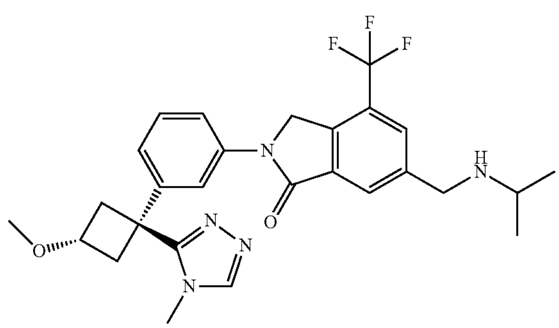 [SMILES: CO[C@H]1C[C@](c2cccc(N3Cc4c(cc(CNC(C)C)cc4C(F)(F)F)C3=O)c2)(c2nncn2C)C1] | 6-((isopropylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 420 | 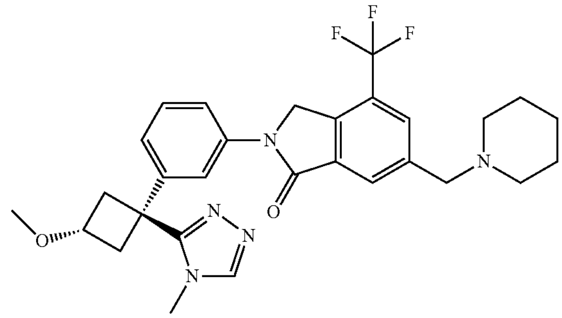 [SMILES: CO[C@H]1C[C@](c2cccc(N3Cc4c(cc(CN5CCCCC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-6-(piperidin-1-ylmethyl)-4-(trifluoromethyl)isoindolin-1-one |
| 421 | 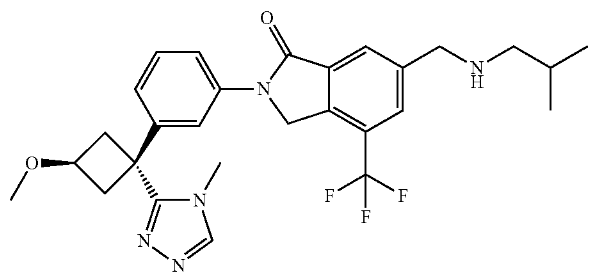 [SMILES: CO[C@H]1C[C@](c2cccc(N3Cc4c(cc(CNCC(C)C)cc4C(F)(F)F)C3=O)c2)(c2nncn2C)C1] | 6-((isobutylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 422 | 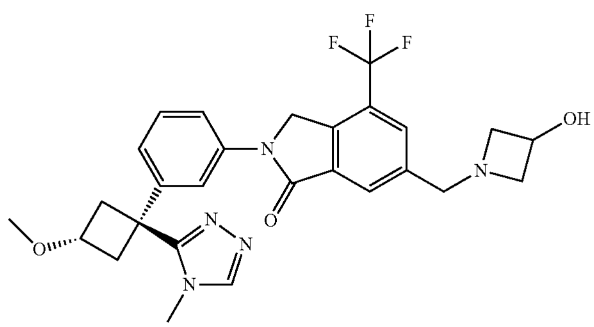 [SMILES: CO[C@H]1C[C@](c2cccc(N3Cc4c(cc(CN5CC(O)C5)cc4C(F)(F)F)C3=O)c2)(c2nncn2C)C1] | 6-((3-hydroxyazetidin-1-yl)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 423 | 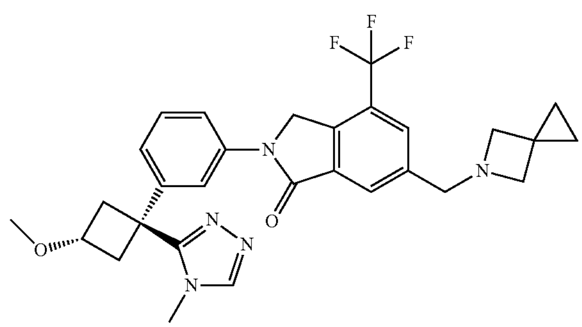 [SMILES: CO[C@H]1C[C@](c2cccc(N3Cc4c(cc(CN5CC6(CC6)C5)cc4C(F)(F)F)C3=O)c2)(c2nncn2C)C1] | 6-(5-azaspiro[2.3]hexan-5-ylmethyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 424 | 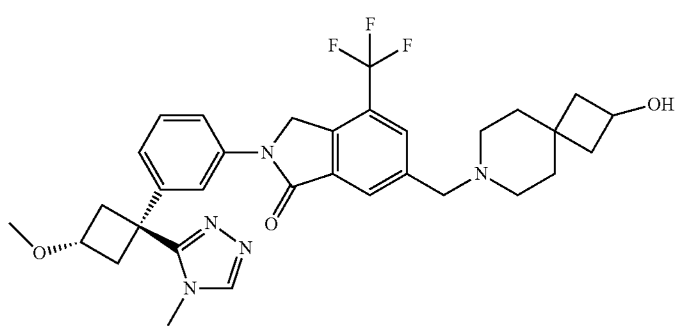 [SMILES: CO[C@H]1C[C@](c2cccc(N3Cc4c(cc(CN5CCC6(CC5)CC(O)C6)cc4C(F)(F)F)C3=O)c2)(c2nncn2C)C1] | 6-((2-hydroxy-7-azaspiro[3.5]nonan-7-yl)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 425 | 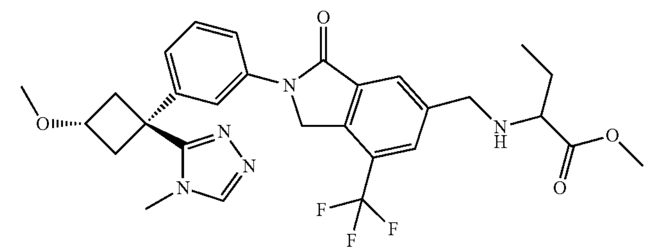 | methyl 2-(((2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methyl)amino)butanoate |
| 426 | 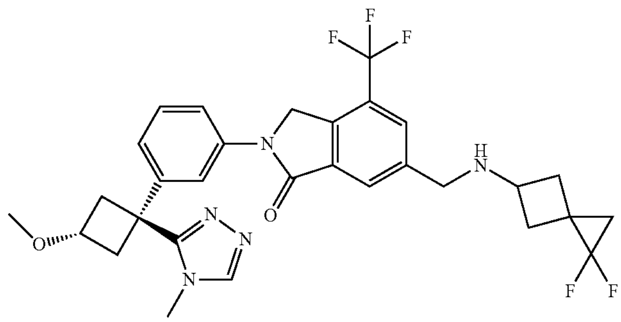 [SMILES: CO[C@H]1C[C@](c2cccc(N3Cc4c(cc(CNC5CC6(C5)CC6(F)F)cc4C(F)(F)F)C3=O)c2)(c2nncn2C)C1] | 6-(((1,1-difluorospiro[2.3]hexan-5-yl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 427 | 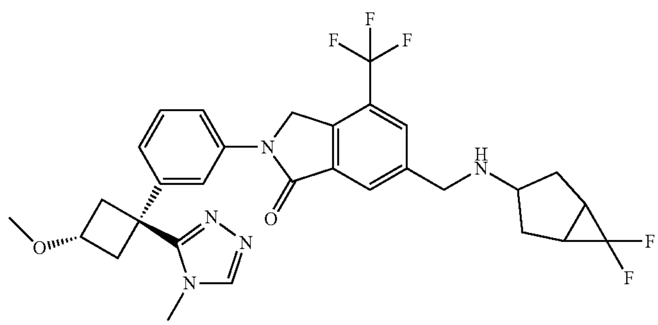 [SMILES: CO[C@H]1C[C@](c2cccc(N3Cc4c(cc(CNC5CC6C(C5)C6(F)F)cc4C(F)(F)F)C3=O)c2)(c2nncn2C)C1] | 6-(((6,6-difluorobicyclo[3.1.0]hexan-3-y)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 428 | 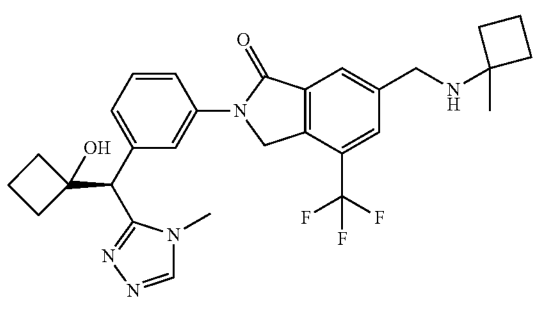 [SMILES: Cn1cnnc1[C@H](c1cccc(N2Cc3c(cc(CNC4(C)CCC4)cc3C(F)(F)F)C2=O)c1)C1(O)CCC1] | (S)-2-(3-((1-hydroxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |
| 429 | 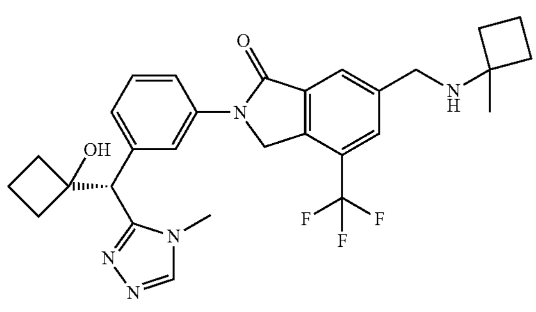 [SMILES: Cn1cnnc1[C@@H](c1cccc(N2Cc3c(cc(CNC4(C)CCC4)cc3C(F)(F)F)C2=O)c1)C1(O)CCC1] | (R)-2-(3-((1-hydroxycyclobutyl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 430 | 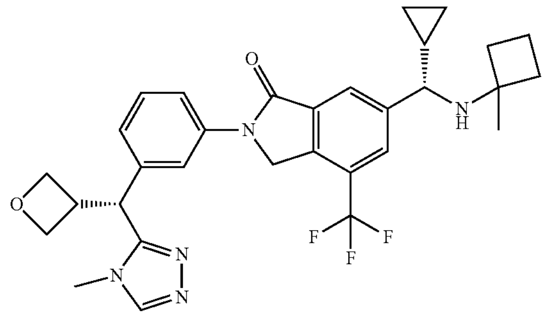 [SMILES: Cn1cnnc1[C@@H](c1cccc(N2Cc3c(cc([C@@H](NC4(C)CCC4)C4CC4)cc3C(F)(F)F)C2=O)c1)C1COC1] | 6-((S)-cyclopropyl((1-methylcyclobutyl)amino)methyl)-2-(3-((R)-(4-methyl-4H-1,2,4-triazol-3-yl)(oxetan-3-yl)methyl)phenyl)-4-(trifluoromethyl)isoindolin-1-one |
| 431 | 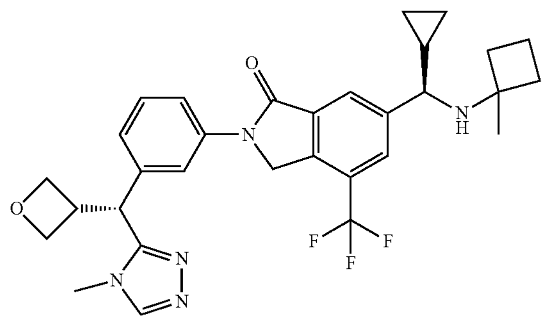 [SMILES: Cn1cnnc1[C@@H](c1cccc(N2Cc3c(cc([C@H](NC4(C)CCC4)C4CC4)cc3C(F)(F)F)C2=O)c1)C1COC1] | 6-((R)-cyclopropyl((1-methylcyclobutyl)amino)methyl)-2-(3-((R)-(4-methyl-4H-1,2,4-triazol-3-yl)(oxetan-3-yl)methyl)phenyl)-4-(trifluoromethyl)isoindolin-1-one |
| 432 | 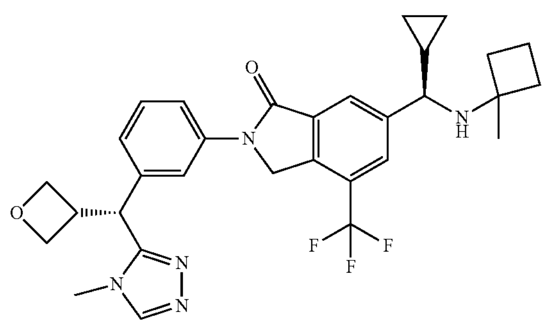 [SMILES: Cn1cnnc1[C@@H](c1cccc(N2Cc3c(cc([C@H](NC4(C)CCC4)C4CC4)cc3C(F)(F)F)C2=O)c1)C1COC1] | 6-((R)-cyclobutyl((1-methylcyclobutyl)amino)methyl)-2-(3-((R)-(4-methyl-4H-1,2,4-triazol-3-yl)(oxetan-3-yl)methyl)phenyl)-4-(trifluoromethyl)isoindolin-1-one |
| 433 | 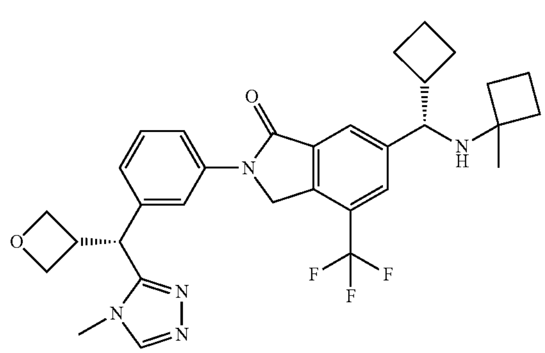 [SMILES: Cn1cnnc1[C@@H](c1cccc(N2Cc3c(cc([C@@H](NC4(C)CCC4)C4CCC4)cc3C(F)(F)F)C2=O)c1)C1COC1] | 6-((S)-cyclobutyl((1-methylcyclobutyl)amino)methyl)-2-(3-((R)-(4-methyl-4H-1,2,4-triazol-3-yl)(oxetan-3-yl)methyl)phenyl)-4-(trifluoromethyl)isoindolin-1-one |

TABLE 1-continued

| Compound # | Structure | Name |
|---|---|---|
| 434 | 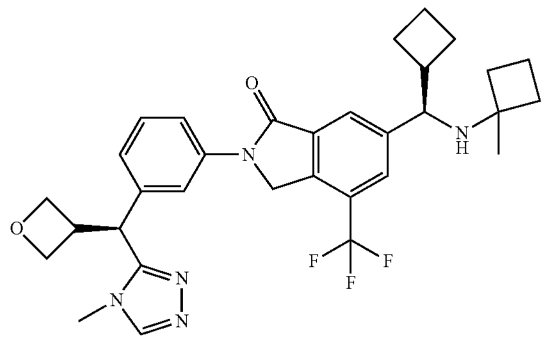 [SMILES: Cn1cnnc1[C@H](c1cccc(N2Cc3c(cc([C@H](NC4(C)CCC4)C4CCC4)cc3C(F)(F)F)C2=O)c1)C1COC1] | 6-((R)-cyclobutyl((1-methylcyclobutyl)amino)methyl)-2-(3-((S)-(4-methyl-4H-1,2,4-triazol-3-yl)(oxetan-3-yl)methyl)phenyl)-4-(trifluoromethyl)isoindolin-1-one |
| 435 | 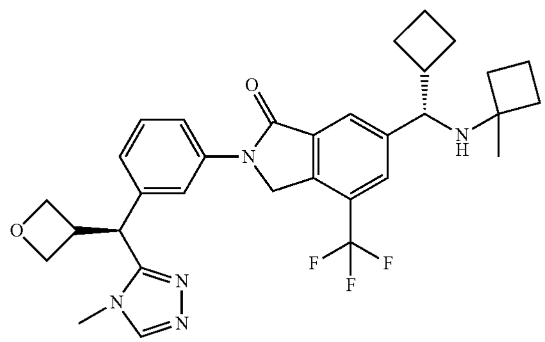 [SMILES: Cn1cnnc1[C@H](c1cccc(N2Cc3c(cc([C@@H](NC4(C)CCC4)C4CCC4)cc3C(F)(F)F)C2=O)c1)C1COC1] | 6-((S)-cyclobutyl((1-methylcyclobutyl)amino)methyl)-2-(3-((S)-(4-methyl-4H-1,2,4-triazol-3-yl)(oxetan-3-yl)methyl)phenyl)-4-(trifluoromethyl)isoindolin-1-one |
| 436 | 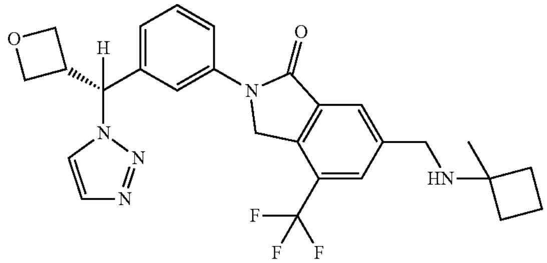 [SMILES: CC1(NCc2cc3c(c(C(F)(F)F)c2)CN(c2cccc([C@@H](C4COC4)n4ccnn4)c2)C3=O)CCC1] | (R)-6-(((1-methylcyclobutyl)amino)methyl)-2-(3-(oxetan-3-yl(1H-1,2,3-triazol-1-yl)methyl)phenyl)-4-(trifluoromethyl)isoindolin-1-one |
| 437 | 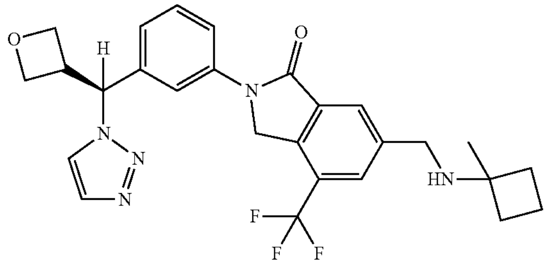 [SMILES: CC1(NCc2cc3c(c(C(F)(F)F)c2)CN(c2cccc([C@H](C4COC4)n4ccnn4)c2)C3=O)CCC1] | (S)-6-(((1-methylcyclobutyl)amino)methyl)-2-(3-(oxetan-3-yl(1H-1,2,3-triazol-1-yl)methyl)phenyl)-4-(trifluoromethyl)isoindolin-1-one |
| 438 | 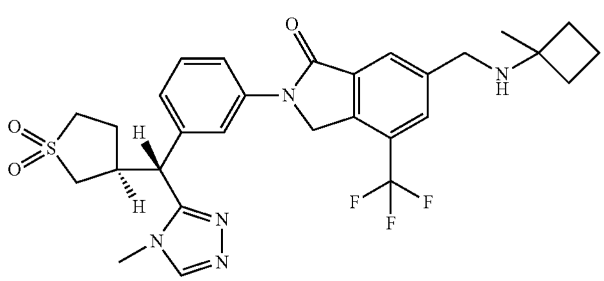 [SMILES: Cn1cnnc1[C@@H](c1cccc(N2Cc3c(cc(CNC4(C)CCC4)cc3C(F)(F)F)C2=O)c1)[C@@H]1CCS(=O)(=O)C1] | 2-(3-((R)-((S)-1,1-dioxidotetrahydrothiophen-3-yl)(4-methyl-4H-1,2,4-triazol-3-yl)methyl)phenyl)-6-(((1-methylcyclobutyl)amino)methyl)-4-(trifluoromethyl)isoindolin-1-one |

TABLE 1-continued

| Compound # | Structure | Name |
|---|---|---|
| 439 | 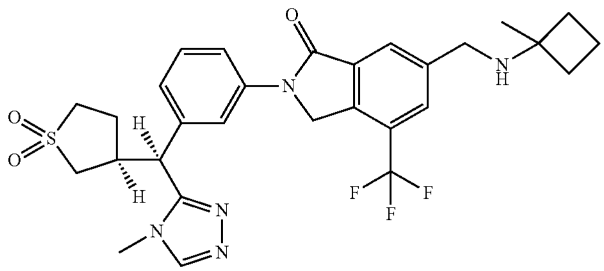 [SMILES: Cn1cnnc1[C@H](c1cccc(N2Cc3c(cc(CNC4(C)CCC4)cc3C(F)(F)F)C2=O)c1)[C@@H]1CCS(=O)(=O)C1] | 2-(3-((S)-((S)-1,1-dioxidotetrahydrothiophen-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 440 | 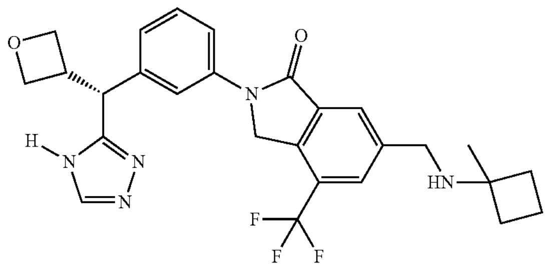 [SMILES: CC1(NCc2cc3c(c(C(F)(F)F)c2)CN(c2cccc([C@H](c4nnc[nH]4)C4COC4)c2)C3=O)CCC1] | (R)-6-(((1-methylcyclobutyl)amino)methyl)-2-(3-(oxetan-3-yl(4H-1,2,4-triazol-3-yl)methyl)phenyl)-4-(trifluoromethyl)isoindolin-1-one |
| 441 | 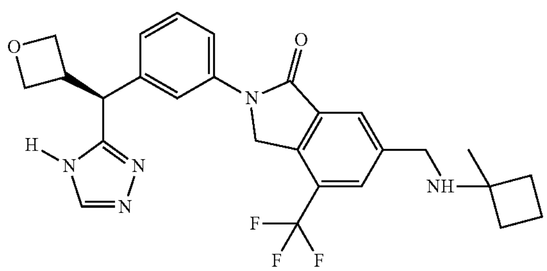 [SMILES: CC1(NCc2cc3c(c(C(F)(F)F)c2)CN(c2cccc([C@@H](c4nnc[nH]4)C4COC4)c2)C3=O)CCC1] | (S)-6-(((1-methylcyclobutyl)amino)methyl)-2-(3-(oxetan-3-yl(4H-1,2,4-triazol-3-yl)methyl)phenyl)-4-(trifluoromethyl)isoindolin-1-one |
| 442 | 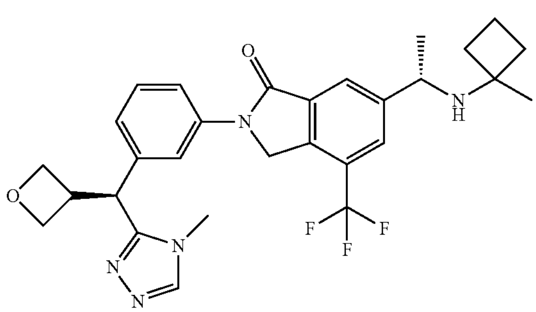 [SMILES: C[C@H](NC1(C)CCC1)c1cc2c(c(C(F)(F)F)c1)CN(c1cccc([C@@H](c3nncn3C)C3COC3)c1)C2=O] | 2-(3-((S)-(4-methyl-4H-1,2,4-triazol-3-yl)(oxetan-3-yl)methyl)phenyl)-6-((S)-1-((1-methylcyclobutyl)amino)ethyl)-4-(trifluoromethyl)isoindolin-1-one |
| 443 | 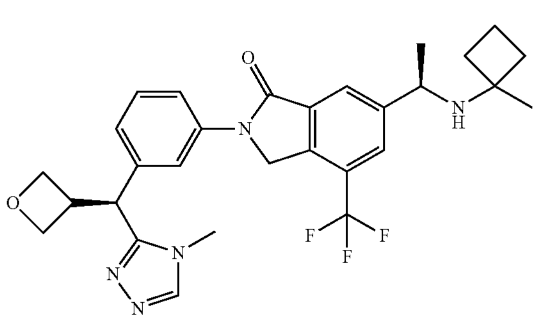 [SMILES: C[C@@H](NC1(C)CCC1)c1cc2c(c(C(F)(F)F)c1)CN(c1cccc([C@@H](c3nncn3C)C3COC3)c1)C2=O] | 2-(3-((S)-(4-methyl-4H-1,2,4-triazol-3-yl)(oxetan-3-yl)methyl)phenyl)-6-((R)-1-((1-methylcyclobutyl)amino)ethyl)-4-(trifluoromethyl)isoindolin-1-one |

TABLE 1-continued

| Compound # | Structure | Name |
|---|---|---|
| 444 | 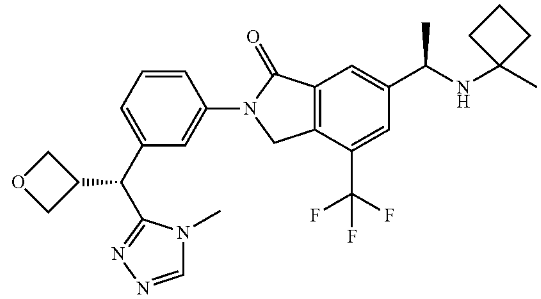 [SMILES: C[C@@H](NC1(C)CCC1)c1cc2c(c(C(F)(F)F)c1)CN(c1cccc([C@H](c3nncn3C)C3COC3)c1)C2=O] | 2-(3-((R)-(4-methyl-4H-1,2,4-triazol-3-yl)(oxetan-3-yl)methyl)phenyl)-6-((R)-1-((1-methylcyclobutyl)amino)ethyl)-4-(trifluoromethyl)isoindolin-1-one |
| 445 | 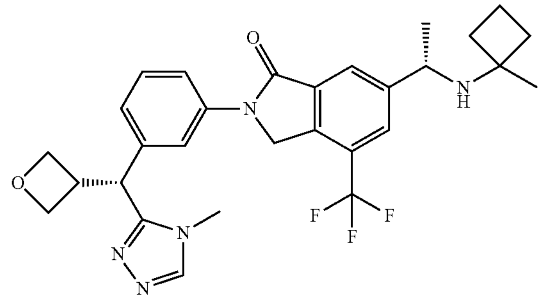 [SMILES: C[C@H](NC1(C)CCC1)c1cc2c(c(C(F)(F)F)c1)CN(c1cccc([C@H](c3nncn3C)C3COC3)c1)C2=O] | 2-(3-((R)-(4-methyl-4H-1,2,4-triazol-3-yl)(oxetan-3-yl)methyl)phenyl)-6-((S)-1-((1-methylcyclobutyl)amino)ethyl)-4-(trifluoromethyl)isoindolin-1-one |
| 446 | 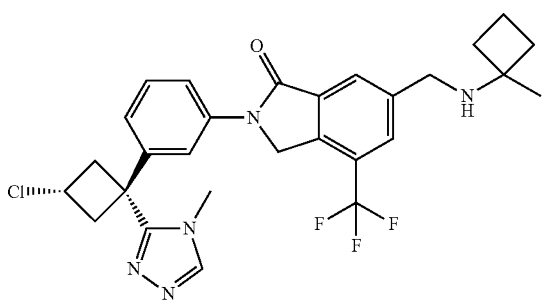 [SMILES: Cn1cnnc1[C@]1(c2cccc(N3Cc4c(cc(CNC5(C)CCC5)cc4C(F)(F)F)C3=O)c2)C[C@H](Cl)C1] | 2-(3-((1s,3s)-3-chloro-1-(4-methyl-4H-1,2,4-triazol-3-yl)cyclobutyl)phenyl)-4-(difluoromethyl)-6-(((1-methylcyclobutyl)amino)methyl)isoindolin-1-one |
| 447 | 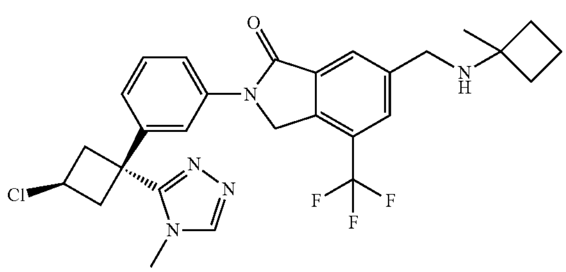 [SMILES: Cn1cnnc1[C@]1(c2cccc(N3Cc4c(cc(CNC5(C)CCC5)cc4C(F)(F)F)C3=O)c2)C[C@@H](Cl)C1] | 2-(3-((1r,3r)-3-chloro-1-(4-methyl-4H-1,2,4-triazol-3-yl)cyclobutyl)phenyl)-4-(difluoromethyl)-6-(((1-methylcyclobutyl)amino)methyl)isoindolin-1-one |
| 448 | 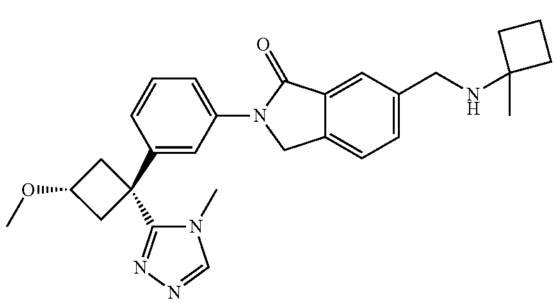 [SMILES: CO[C@H]1C[C@@](c2cccc(N3Cc4ccc(CNC5(C)CCC5)cc4C3=O)c2)(c2nncn2C)C1] | 2-(3-((1s,3s)-3-methoxy-1-(4-methyl-4H-1,2,4-triazol-3-yl)cyclobutyl)phenyl)-6-(((1-methylcyclobutyl)amino)methyl)isoindolin-1-one |

TABLE 1-continued

| Compound # | Structure | Name |
|---|---|---|
| 449 | 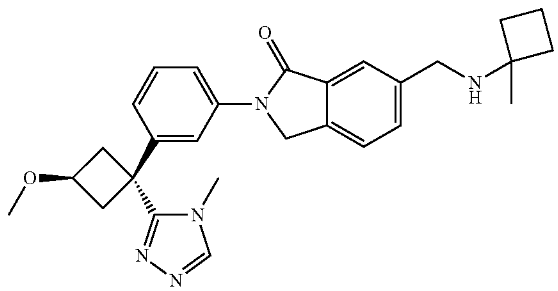 [SMILES: CO[C@H]1C[C@](c2cccc(N3Cc4ccc(CNC5(C)CCC5)cc4C3=O)c2)(c2nncn2C)C1] | 2-(3-((1r,3r)-3-methoxy-1-(4-methyl-4H-1,2,4-triazol-3-yl)cyclobutyl)phenyl)-6-(((1-methylcyclobutyl)amino)methyl)isoindolin-1-one |
| 450 | 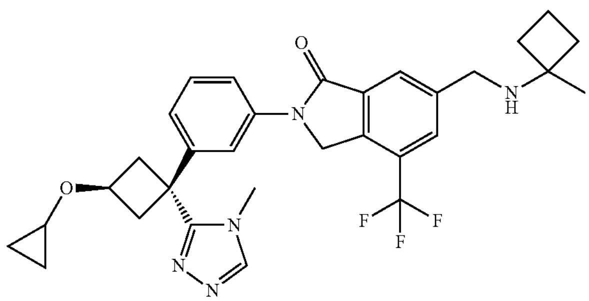 [SMILES: Cn1cnnc1[C@]1(c2cccc(N3Cc4c(cc(CNC5(C)CCC5)cc4C(F)(F)F)C3=O)c2)C[C@@H](OC2CC2)C1] | 2-(3-((1r,3r)-3-cyclopropoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 451 | 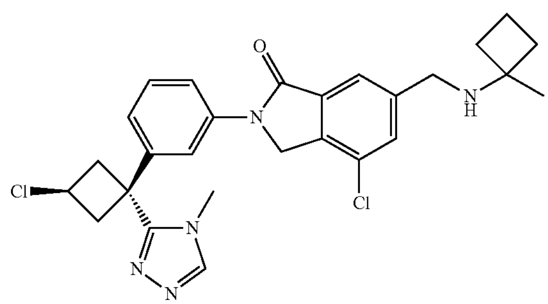 [SMILES: Cn1cnnc1[C@]1(c2cccc(N3Cc4c(Cl)cc(CNC5(C)CCC5)cc4C3=O)c2)C[C@@H](Cl)C1] | 4-chloro-2-(3-((1r,3r)-3-chloro-1-(4-methyl-4H-1,2,4-triazol-3-yl)cyclobutyl)phenyl)-6-(((1-methylcyclobutyl)amino)-methyl)isoindolin-1-one |
| 452 | 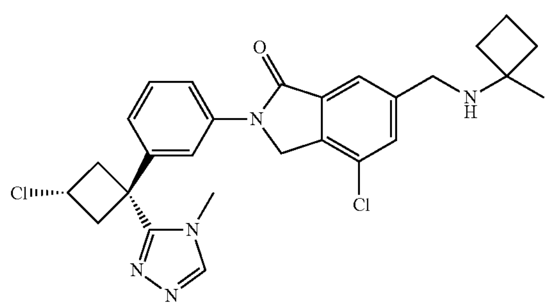 [SMILES: Cn1cnnc1[C@]1(c2cccc(N3Cc4c(Cl)cc(CNC5(C)CCC5)cc4C3=O)c2)C[C@H](Cl)C1] | 4-chloro-2-(3-((1s,3s)-3-chloro-1-(4-methyl-4H-1,2,4-triazol-3-yl)cyclobutyl)phenyl)-6-(((1-methylcyclobutyl)amino)methyl)isoindolin-1-one |
| 453 | 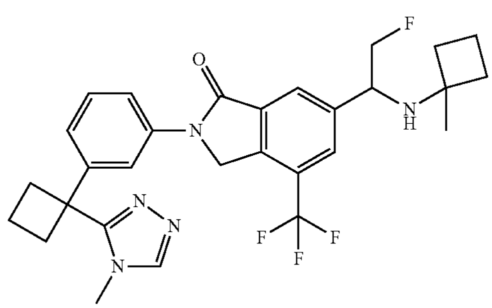 [SMILES: Cn1cnnc1C1(c2cccc(N3Cc4c(cc(C(CF)NC5(C)CCC5)cc4C(F)(F)F)C3=O)c2)CCC1] | 6-(2-fluoro-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 454 | 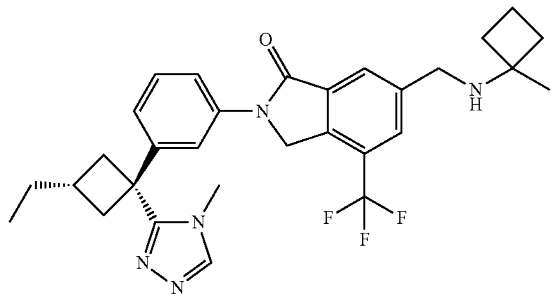 [SMILES: CC[C@H]1C[C@@](c2cccc(N3Cc4c(cc(CNC5(C)CCC5)cc4C(F)(F)F)C3=O)c2)(c2nncn2C)C1] | 2-(3-((1r,3s)-3-ethyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 455 | 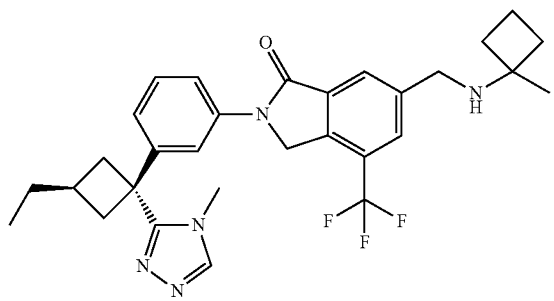 [SMILES: CC[C@H]1C[C@](c2cccc(N3Cc4c(cc(CNC5(C)CCC5)cc4C(F)(F)F)C3=O)c2)(c2nncn2C)C1] | 2-(3-((1s,3r)-3-ethyl-1-(4-methyl-4H-1,2,4-triazol-3-yl)cyclobutyl)phenyl)-6-(((1-methylcyclobutyl)amino)methyl)-4-(trifluoromethyl)isoindolin-1-one |
| 456 | 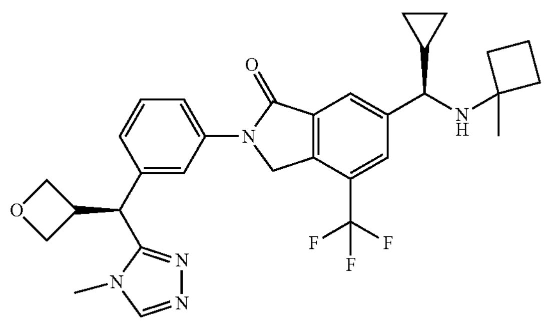 [SMILES: Cn1cnnc1[C@H](c1cccc(N2Cc3c(cc([C@H](NC4(C)CCC4)C4CC4)cc3C(F)(F)F)C2=O)c1)C1COC1] | 6-((R)-cyclopropyl((1-methylcyclobutyl)amino)methyl)-2-(3-((S)-(4-methyl-4H-1,2,4-triazol-3-yl)(oxetan-3-yl)methyl)phenyl)-4-(trifluoromethyl)isoindolin-1-one |
| 457 | 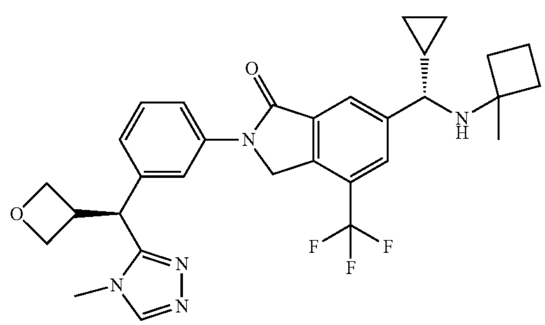 [SMILES: Cn1cnnc1[C@H](c1cccc(N2Cc3c(cc([C@@H](NC4(C)CCC4)C4CC4)cc3C(F)(F)F)C2=O)c1)C1COC1] | 6-((S)-cyclopropyl((1-methylcyclobutyl)amino)methyl)-2-(3-((S)-(4-methyl-4H-1,2,4-triazol-3-yl)(oxetan-3-yl)methyl)phenyl)-4-(trifluoromethyl)isoindolin-1-one |
| 458 | 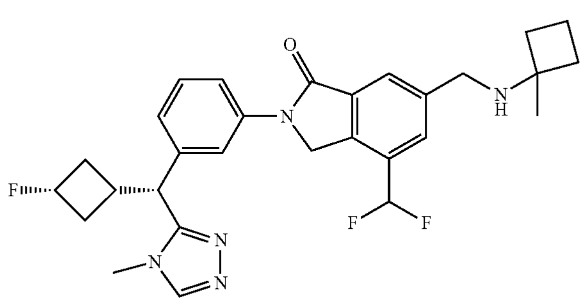 | 4-(difluoromethyl)-2-(3-((R)-((1r,3R)-3-fluorocyclobutyl)(4-methyl-4H-1,2,4-triazol-3-yl)methyl)phenyl)-6-(((1-methylcyclobutyl)amino)methyl)isoindolin-1-one |

TABLE 1-continued

| Compound # | Structure | Name |
|---|---|---|
| 459 | 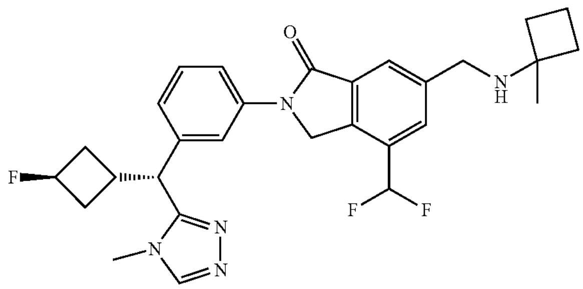 | 4-(difluoromethyl)-2-(3-((R)-((1s,3S)-3-fluorocyclobutyl)(4-methyl-4H-1,2,4-triazol-3-yl)methyl)phenyl)-6-(((1-methylcyclobutyl)amino)methyl)isoindolin-1-one |
| 460 | 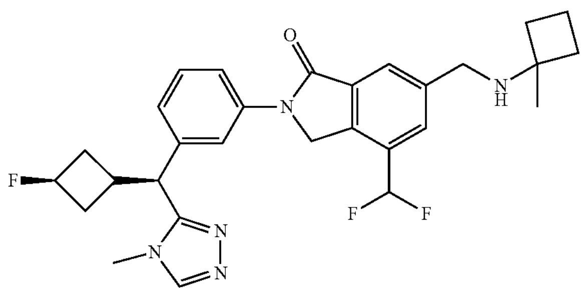 | 4-(difluoromethyl)-2-(3-((S)-((1r,3S)-3-fluorocyclobutyl)(4-methyl-4H-1,2,4-triazol-3-yl)methyl)phenyl)-6-(((1-methylcyclobutyl)amino)methyl)isoindolin-1-one |
| 461 | 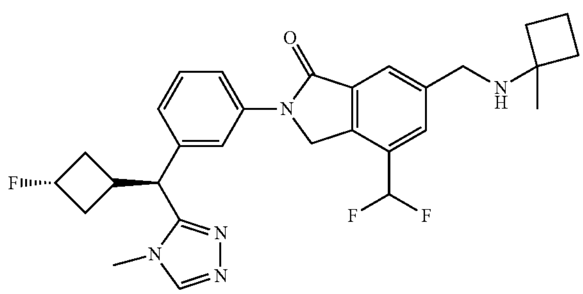 | 4-(difluoromethyl)-2-(3-((S)-((1s,3R)-3-fluorocyclobutyl)(4-methyl-4H-1,2,4-triazol-3-yl)methyl)phenyl)-6-(((1-methylcyclobutyl)amino)methyl)isoindolin-1-one |
| 462 | 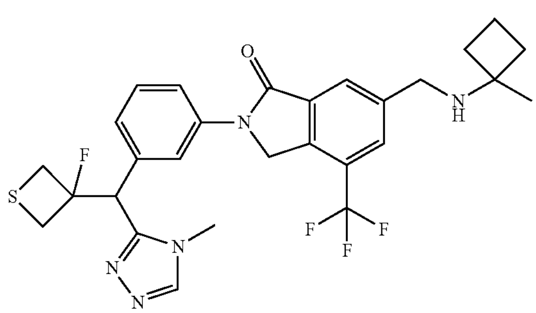 [SMILES: Cn1cnnc1C(c1cccc(N2Cc3c(cc(CNC4(C)CCC4)cc3C(F)(F)F)C2=O)c1)C1(F)CSC1] | 2-(3-((3-fluorothietan-3-yl)(4-methyl-4H-1,2,4-triazol-3-yl)methyl)phenyl)-6-(((1-methylcyclobutyl)amino)methyl)-4-(trifluoromethyl)isoindolin-1-one |
| 463 | 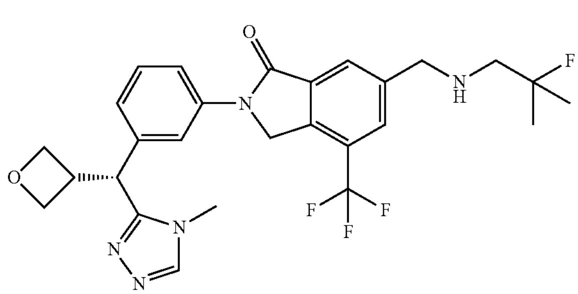 [SMILES: Cn1cnnc1[C@@H](c1cccc(N2Cc3c(cc(CNCC(C)(C)F)cc3C(F)(F)F)C2=O)c1)C1COC1] | (R)-6-(((2-fluoro-2-methylpropyl)amino)methyl)-2-(3-((4-methyl-4H-1,2,4-triazol-3-yl)(oxetan-3-yl)methyl)phenyl)-4-(trifluoromethyl)isoindolin-1-one |

TABLE 1-continued

| Compound # | Structure | Name |
|---|---|---|
| 464 | 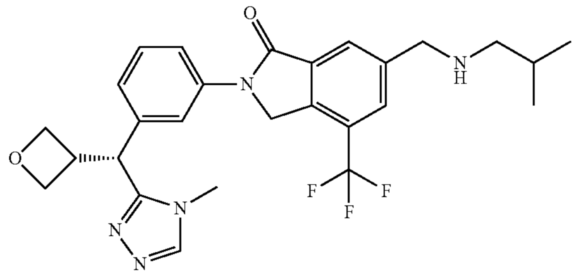 [SMILES: CC(C)CNCc1cc2c(c(C(F)(F)F)c1)CN(c1cccc([C@H](c3nncn3C)C3COC3)c1)C2=O] | (R)-6-((isobutylamino)methyl)-2-(3-((4-methyl-4H-1,2,4-triazol-3-yl)(oxetan-3-yl)methyl)phenyl)-4-(trifluoromethyl)isoindolin-1-one |
| 465 | 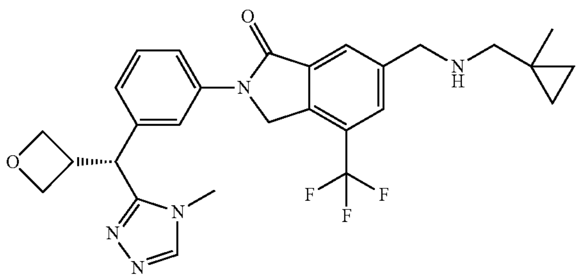 [SMILES: Cn1cnnc1[C@@H](c1cccc(N2Cc3c(cc(CNCC4(C)CC4)cc3C(F)(F)F)C2=O)c1)C1COC1] | (R)-2-(3-((4-methyl-4H-1,2,4-triazol-3-yl)(oxetan-3-yl)methyl)phenyl)-6-((((1-methylcyclopropyl)methyl)amino)methyl)-4-(trifluoromethyl)isoindolin-1-one |
| 466 | 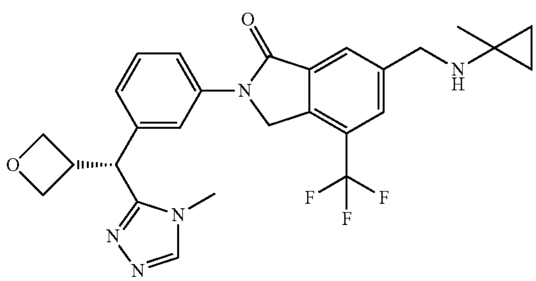 [SMILES: Cn1cnnc1[C@@H](c1cccc(N2Cc3c(cc(CNC4(C)CC4)cc3C(F)(F)F)C2=O)c1)C1COC1] | (R)-2-(3-((4-methyl-4H-1,2,4-triazol-3-yl)(oxetan-3-yl)methyl)phenyl)-6-(((1-methylcyclopropyl)amino)methyl)-4-(trifluoromethyl)isoindolin-1-one |
| 467 | 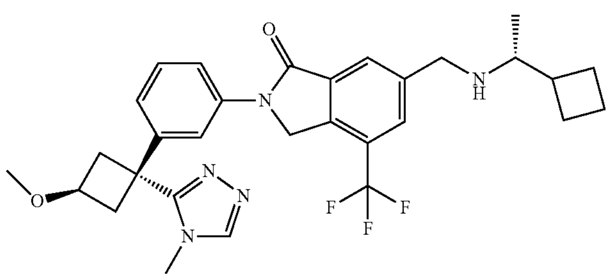 [SMILES: CO[C@H]1C[C@](c2cccc(N3Cc4c(cc(CN[C@H](C)C5CCC5)cc4C(F)(F)F)C3=O)c2)(c2nncn2C)C1] | 6-((((R)-1-cyclobutylethyl)amino)methyl)-2-(2-((1r,3R)-3-methoxy-1-(4-methyl-4H-1,2,4-triazol-3-yl)cyclobutyl)pehnyl)-4-(trifluoromethyl)isoindolin-1-one |
| 468 | 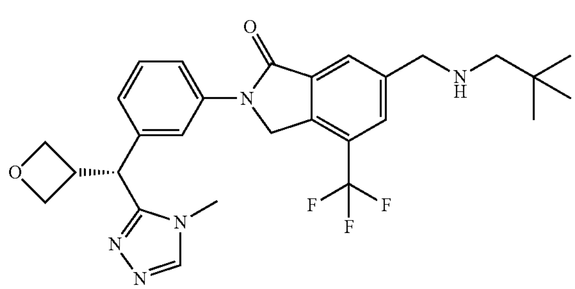 [SMILES: Cn1cnnc1[C@@H](c1cccc(N2Cc3c(cc(CNCC(C)(C)C)cc3C(F)(F)F)C2=O)c1)C1COC1] | (R)-2-(3-((4-methyl-4H-1,2,4-triazol-3-yl)(oxetan-3-yl)methyl)phenyl)-6-((neopentylamino)methyl)-4-(trifluoromethyl)isoindolin-1-one |

TABLE 1-continued

| Compound # | Structure | Name |
|---|---|---|
| 469 | 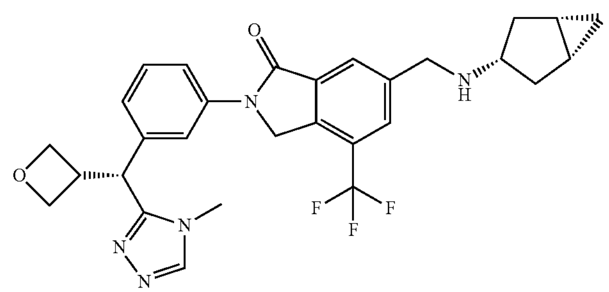 [SMILES: Cn1cnnc1[C@@H](c1cccc(N2Cc3c(cc(CN[C@@H]4C[C@@H]5C[C@@H]5C4)cc3C(F)(F)F)C2=O)c1)C1COC1] | 6-(((1R,3r,5S)-bicyclo[3.1.0]hexan-3-ylamino)methyl)-2-(3-((R)-(4-methyl-4H-1,2,4-triazol-3-yl)(oxetan-3-yl)methyl)phenyl)-4-(trifluoromethyl)isoindolin-1-one |
| 470 | 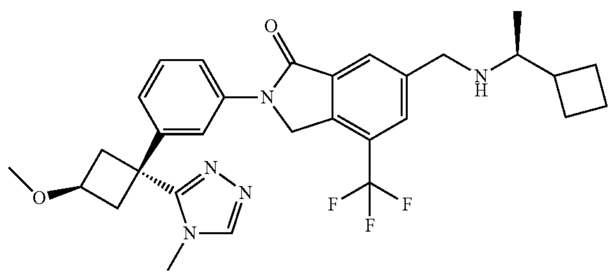 [SMILES: CO[C@H]1C[C@](c2cccc(N3Cc4c(cc(CN[C@@H](C)C5CCC5)cc4C(F)(F)F)C3=O)c2)(c2nncn2C)C1] | 6-((((S)-1-cyclobutylethyl)amino)methyl)-2-(3-((1r,3S)-3-methoxy-1-(4-methyl-4H-1,2,4-triazol-3-yl)cyclobutyl)phenyl)-4-(trifluoromethyl)isoindolin-1-one |
| 471 | 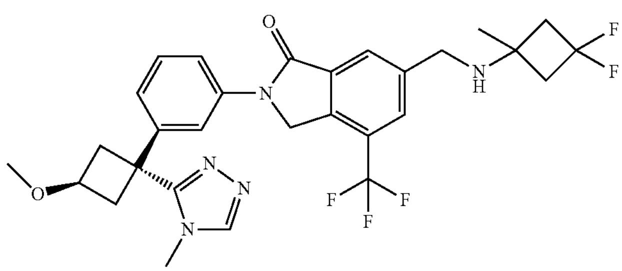 | 6-(((3,3-difluoro-1-methylcyclobutyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 472 | 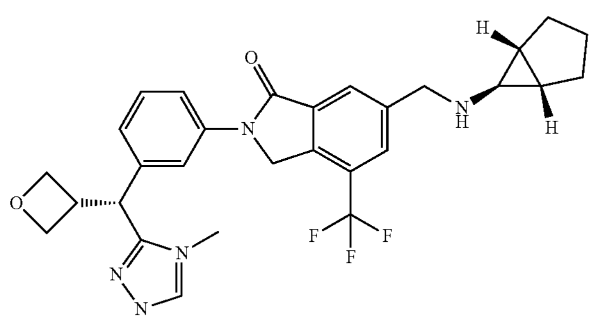 | 6-(((1R,5S,6r)-3-oxabicyclo[3.1.0]hexan-6-ylamino)methyl)-2-(3-((R)-(4-methyl-4H-1,2,4-triazol-3-yl)(oxetan-3-yl)methyl)phenyl)-4-(trifluoromethyl)isoindolin-1-one |
| 473 | 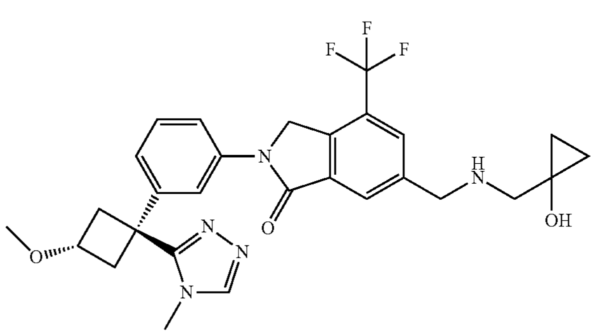 | 6-((((1-hydroxycyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 474 | 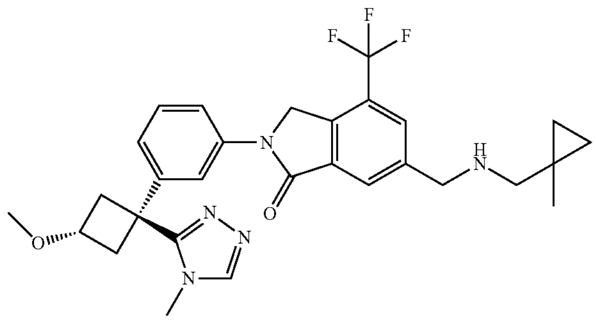 | 2-(3-((1r,3r)-3-methoxy-1-(4-methyl-4H-1,2,4-triazol-3-yl)cyclobutyl)phenyl)-6-((((1-methylcyclopropyl)methyl)amino)methyl)-4-(trifluoromethyl)isoindolin-1-one |
| 475 | 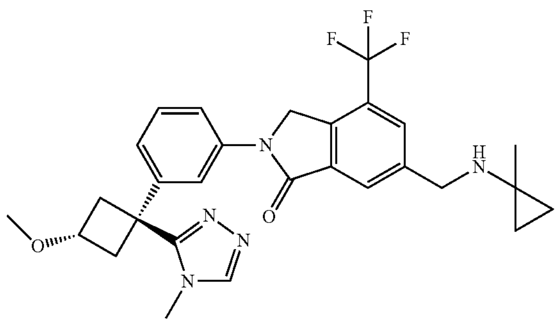 [SMILES: CO[C@H]1C[C@](c2cccc(N3Cc4c(cc(CNC5(C)CC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-6-(((1-methylcyclopropyl)amino)methyl)-4-(trifluoromethyl)isoindolin-1-one |
| 476 | 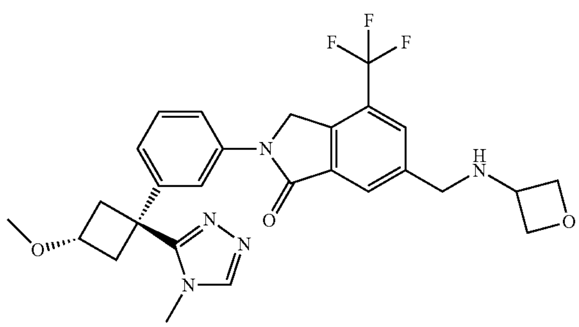 [SMILES: CO[C@H]1C[C@](c2cccc(N3Cc4c(cc(CNC5COC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-6-((oxetan-3-ylamino)methyl)-4-(trifluoromethyl)isoindolin-1-one |
| 477 | 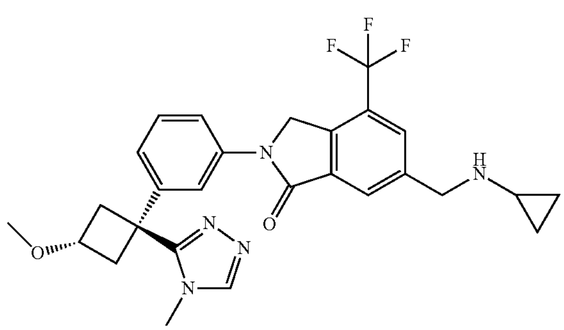 [SMILES: CO[C@H]1C[C@](c2cccc(N3Cc4c(cc(CNC5CC5)cc4C(F)(F)F)C3=O)c2)(c2nncn2C)C1] | 6-((cyclopropylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 478 | 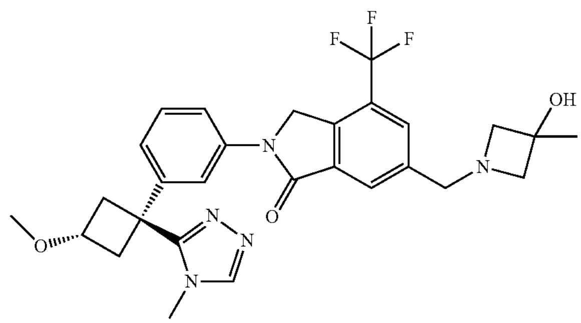 | 6-((3-hydroxy-3-methylazetidin-1-yl)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 479 | 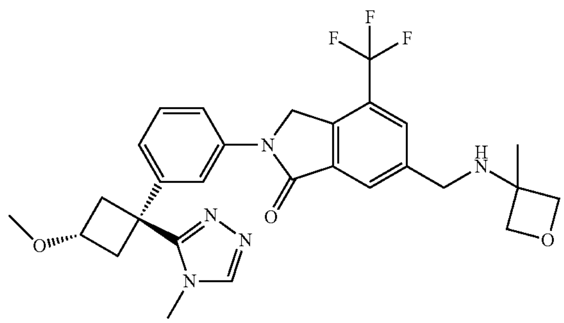 [SMILES: CO[C@H]1C[C@](c2cccc(N3Cc4c(cc(CNC5(C)COC5)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-6-(((3-methyloxetan-3-yl)amino)methyl)-4-(trifluoromethyl)isoindolin-1-one |
| 480 | 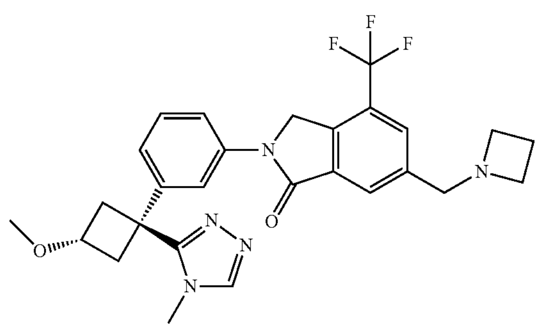 [SMILES: CO[C@H]1C[C@](c2cccc(N3Cc4c(cc(CN5CCC5)cc4C(F)(F)F)C3=O)c2)(c2nncn2C)C1] | 6-(azetidin-1-ylmethyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 481 | 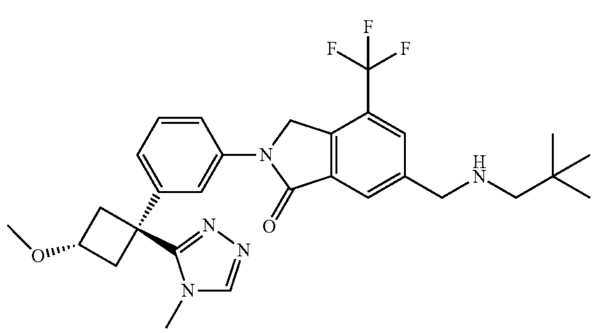 [SMILES: CO[C@H]1C[C@](c2cccc(N3Cc4c(cc(CNCC(C)(C)C)cc4C(F)(F)F)C3=O)c2)(c2nncn2C)C1] | 2-(3-((1r,3r)-3-methoxy-1-(4-methyl-4H-1,2,4-triazol-3-yl)cyclobutyl)phenyl)-6-((neopentylamino)methyl)-4-(trifluoromethyl)isoindolin-1-one |

TABLE 1-continued

| Compound # | Structure | Name |
|---|---|---|
| 482 | 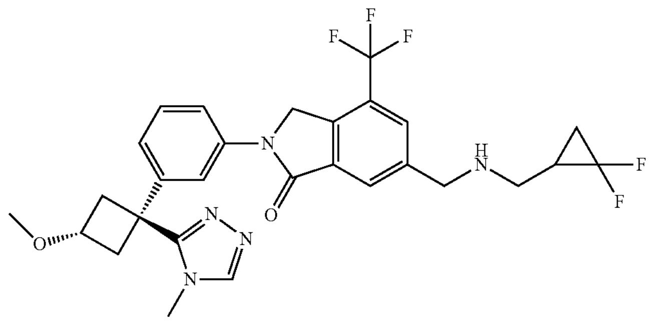 [SMILES: CO[C@H]1C[C@](c2cccc(N3Cc4c(cc(CNCC5CC5(F)F)cc4C(F)(F)F)C3=O)c2)(c2nncn2C)C1] | 6-((((2,2-difluorocyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 483 | 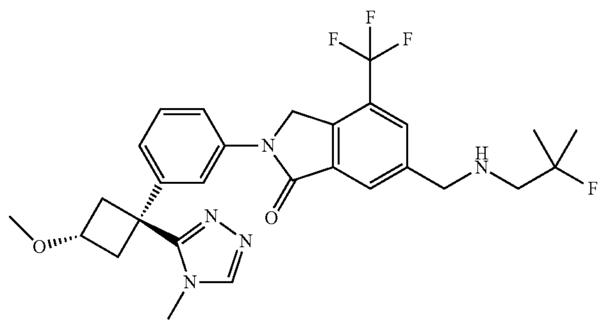 [SMILES: CO[C@H]1C[C@](c2cccc(N3Cc4c(cc(CNCC(C)(C)F)cc4C(F)(F)F)C3=O)c2)(c2nncn2C)C1] | 6-(((2-fluoro-2-methylpropyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 484 | 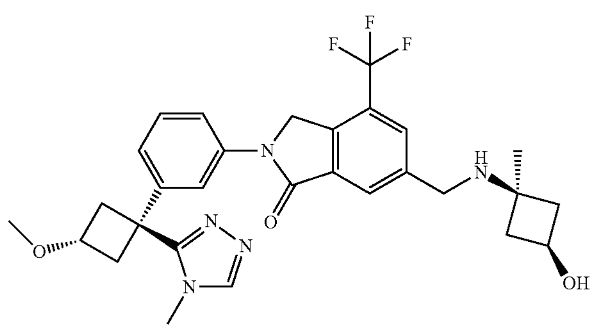 [SMILES: CO[C@H]1C[C@](c2cccc(N3Cc4c(cc(CN[C@]5(C)C[C@H](O)C5)cc4C(F)(F)F)C3=O)c2)(c2nncn2C)C1] | 6-((((1s,3S)-3-hydroxy-1-methylcyclobutyl)amino)methyl)-2-(3-((1r,3R)-3-methoxy-1-(4-methyl-4H-1,2,4-triazol-3-yl)cyclobutyl)phenyl)-4-(trifluoromethyl)isoindolin-1-one |
| 485 | 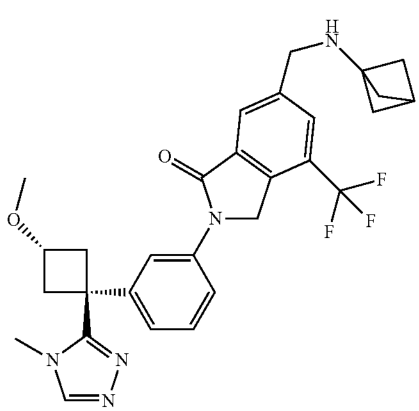 [SMILES: CO[C@H]1C[C@](c2cccc(N3Cc4c(cc(CNC56CC(C5)C6)cc4C(F)(F)F)C3=O)c2)(c2nncn2C)C1] | 6-((bicyclo[1.1.1]pentan-1-ylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 486 | 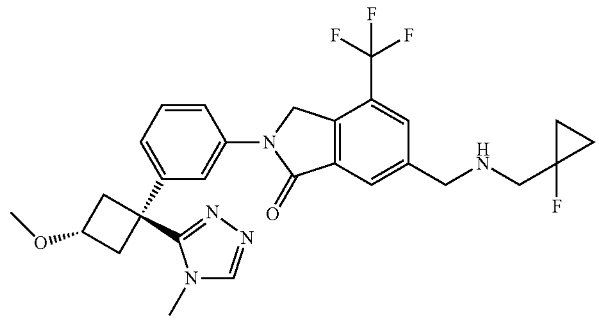 [SMILES: CO[C@H]1C[C@](c2cccc(N3Cc4c(cc(CNCC5(F)CC5)cc4C(F)(F)F)C3=O)c2)(c2nncn2C)C1] | 6-((((1-fluorocyclopropyl)-methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 487 | 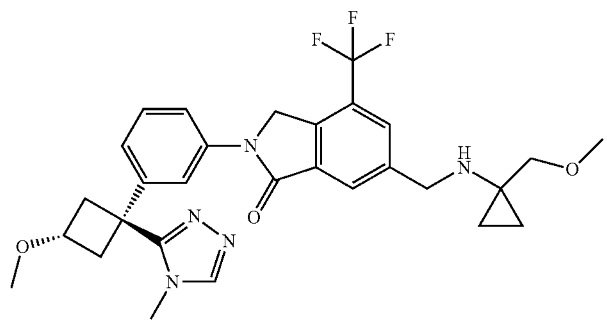 | 2-(3-((1r,3r)-3-methoxy-1-(4-methyl-4H-1,2,4-triazol-3-yl)cyclobutyl)phenyl)-6-(((1-(methoxymethyl)cyclopropyl)amino)methyl)-4-(trifluoromethyl)isoindolin-1-one |
| 488 | 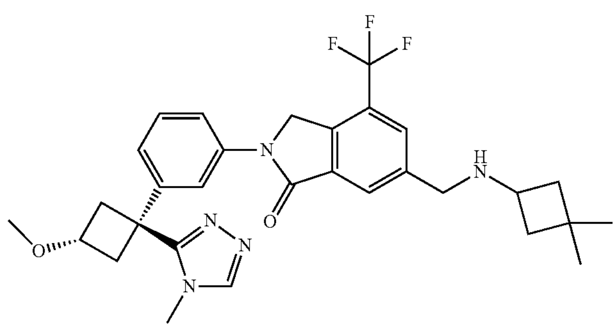 | 6-(((3,3-dimethylcyclobutyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 489 | 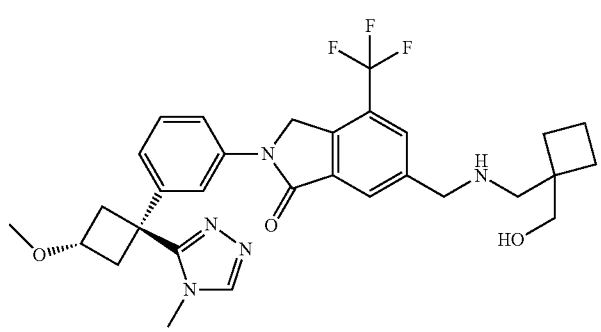 [SMILES: CO[C@H]1C[C@](c2cccc(N3Cc4c(cc(CNCC5(CO)CCC5)cc4C(F)(F)F)C3=O)c2)(c2nncn2C)C1] | 6-((((1-(hydroxymethyl)cyclobutyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 490 | 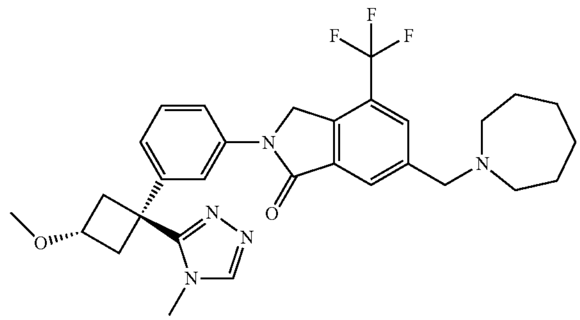 [SMILES: CO[C@H]1C[C@](c2cccc(N3Cc4c(cc(CN5CCCCCC5)cc4C(F)(F)F)C3=O)c2)(c2nncn2C)C1] | 6-(azepan-1-ylmethyl)-2-(3-((1r,3r)-3-methxoy-1-(4-methyl-4H-1,2,4-triazol-3-yl)cyclobutyl)phenyl)-4-(trifluoromethyl)isoindolin-1-one |
| 491 | 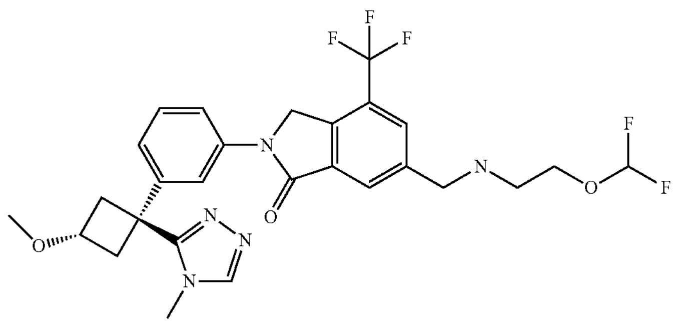 [SMILES: CO[C@H]1C[C@](c2cccc(N3Cc4c(cc(CNCCOC(F)F)cc4C(F)(F)F)C3=O)c2)(c2nncn2C)C1] | 6-(((2-(difluoromethoxy)ethyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 492 | 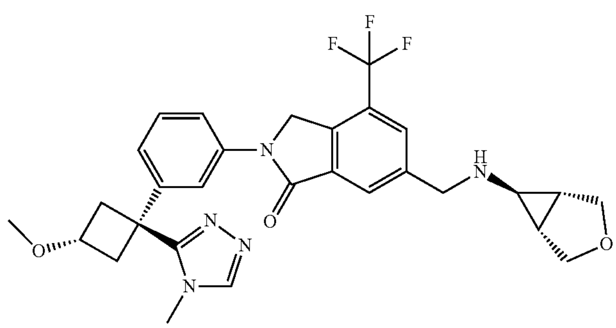 [SMILES: CO[C@H]1C[C@](c2cccc(N3Cc4c(cc(CN[C@H]5[C@@H]6COC[C@@H]65)cc4C(F)(F)F)C3=O)c2)(c2nncn2C)C1] | 6-(((1R,5S,6r)-3-oxabicyclo[3.1.0]hexan-6-ylamino)methyl)-2-(3-((1r,3R)-3-methoxy-1-(4-methyl-4H-1,2,4-triazol-3-yl)cyclobutyl)phenyl)-4-(trifluoromethyl)isoindolin-1-one |
| 493 | 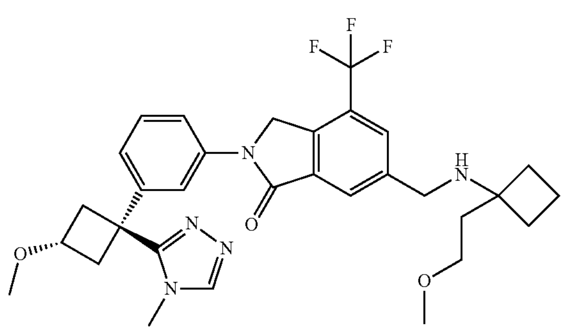 [SMILES: COCCC1(NCc2cc3c(c(C(F)(F)F)c2)CN(c2cccc([C@]4(c5nncn5C)C[C@H](OC)C4)c2)C3=O)CCC1] | 2-(3-((1r,3r)-3-methoxy-1-(4-methyl-4H-1,2,4-triazol-3-yl)cyclobutyl)phenyl)-6-(((1-(2-methoxyethyl)cyclobutyl)amino)methyl)-4-(trifluoromethyl)isoindolin-1-one |

TABLE 1-continued

| Compound # | Structure | Name |
|---|---|---|
| 494 | 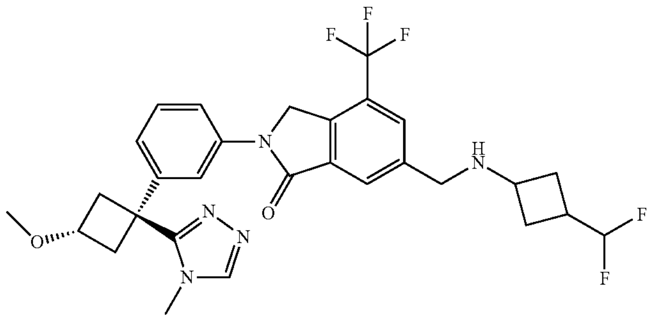 [SMILES: CO[C@H]1C[C@](c2cccc(N3Cc4c(cc(CNC5CC(C(F)F)C5)cc4C(F)(F)F)C3=O)c2)(c2nncn2C)C1] | 6-(((3-(difluoromethyl)cyclobutyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 495 | 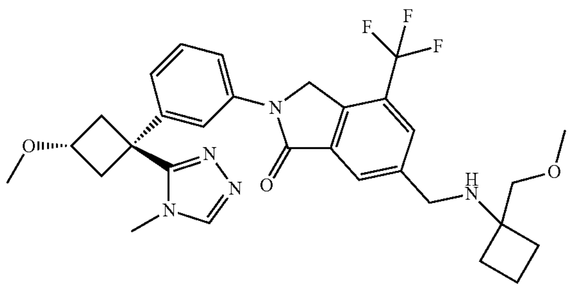 | 2-(3-((1r,3r)-3-methoxy-1-(4-methyl-4H-1,2,4-triazol-3-yl)cyclobutyl)phenyl)-6-(((1-(methoxymethyl)cyclobutyl)amino)methyl)-4-(trifluoromethyl)isoindolin-1-one |
| 496 | 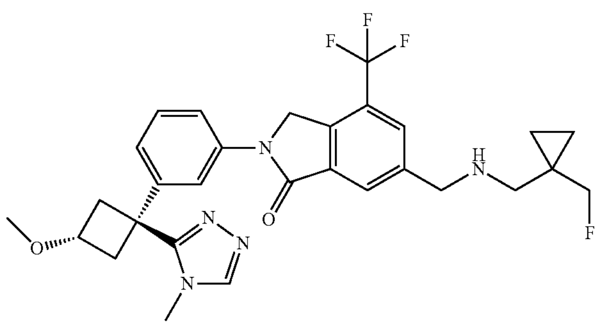 [SMILES: CO[C@H]1C[C@](c2cccc(N3Cc4c(cc(CNCC5(CF)CC5)cc4C(F)(F)F)C3=O)c2)(c2nncn2C)C1] | 6-((((1-(fluoromethyl)cyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 497 | 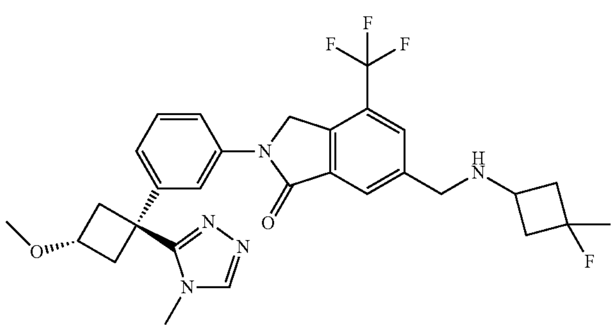 | 6-(((3-fluoro-3-methylcyclobutyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 498 | 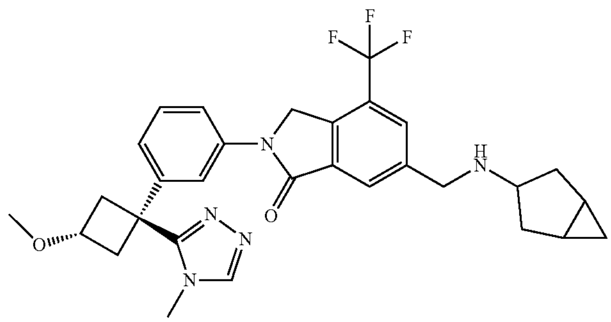 [SMILES: CO[C@H]1C[C@](c2cccc(N3Cc4c(cc(CNC5CC6CC6C5)cc4C(F)(F)F)C3=O)c2)(c2nncn2C)C1] | 6-((bicyclo[3.1.0]hexan-3-ylamino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 499 | 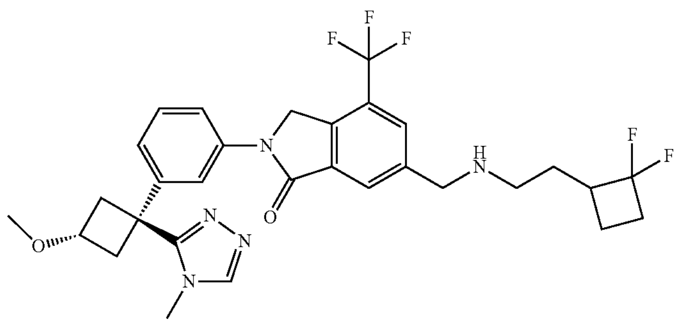 [SMILES: CO[C@H]1C[C@](c2cccc(N3Cc4c(cc(CNCCC5CCC5(F)F)cc4C(F)(F)F)C3=O)c2)(c2nncn2C)C1] | 6-(((2-(2,2-difluorocyclobutyl)ethyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 500 | 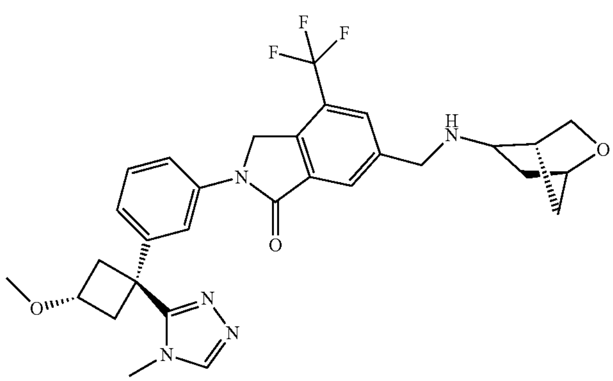 [SMILES: CO[C@H]1C[C@](c2cccc(N3Cc4c(cc(CNC5C[C@@H]6C[C@H]5CO6)cc4C(F)(F)F)C3=O)c2)(c2nncn2C)C1] | 6-((2-oxabicyclo[2.2.1]heptan-5-ylamino)methyl)-2-(3-((1r,3r)-3-methoxy-1-(4-methyl-4H-1,2,4-triazol-3-y)cyclobutyl)phenyl)-4-(trifluoromethyl)isoindolin-1-one |
| 501 | 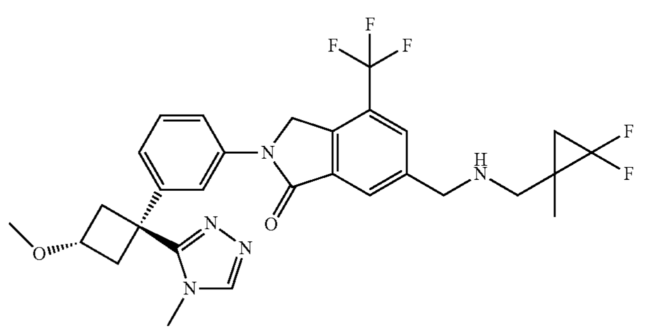 [SMILES: CO[C@H]1C[C@](c2cccc(N3Cc4c(cc(CNCC5(C)CC5(F)F)cc4C(F)(F)F)C3=O)c2)(c2nncn2C)C1] | 6-((((2,2-difluoro-1-methylcyclopropyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 502 | 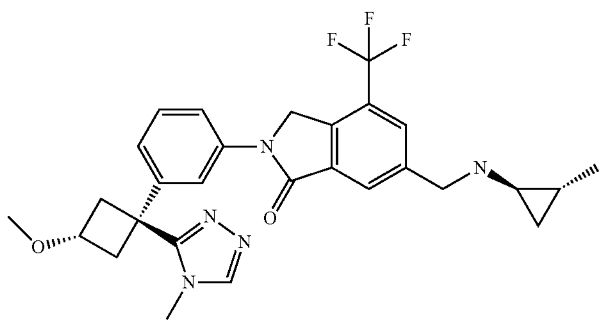 | 2-(3-((1r,3R)-3-methoxy-1-(4-methyl-4H-1,2,4-triazol-3-yl)cyclobutyl)phenyl)-6-(((((1R,2R)-2-methylcyclopropyl)amino)methyl)-4-(trifluoromethyl)isoindolin-1-one |
| 503 | 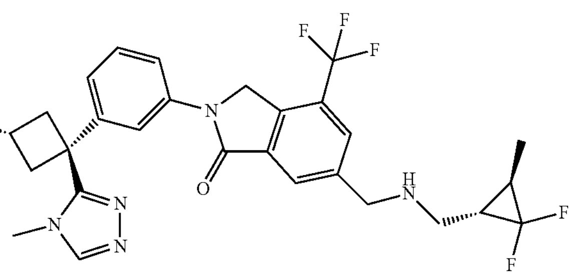 | 6-(((((1S,3R)-2,2-difluoro-3-methylcyclopropyl)methyl)amino)methyl)-2-(3-((1r,3S)-3-methoxy-1-(4-methyl-4H-1,2,4-triazol-3-yl)cyclobutyl)phenyl)-4-(trifluoromethyl)isoindolin-1-one |
| 504 | 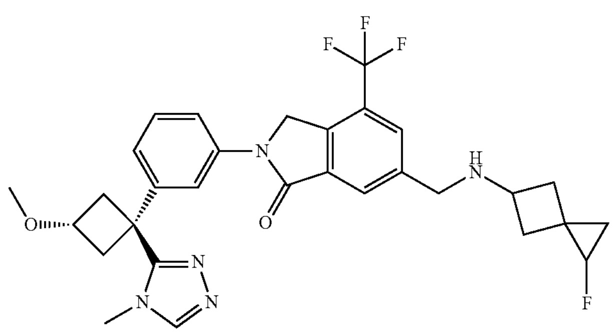 [SMILES: CO[C@H]1C[C@](c2cccc(N3Cc4c(cc(CNC5CC6(C5)CC6F)cc4C(F)(F)F)C3=O)c2)(c2nncn2C)C1] | 6-(((1-fluorospiro[2.3]hexan-5-yl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 505 | 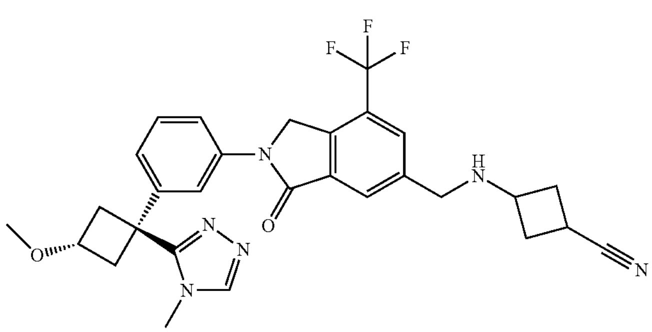 [SMILES: CO[C@H]1C[C@](c2cccc(N3Cc4c(cc(CNC5CC(C#N)C5)cc4C(F)(F)F)C3=O)c2)(c2nncn2C)C1] | 3-(((2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methyl)amino)cyclobutanecarbonitrile |

TABLE 1-continued

| Compound # | Structure | Name |
|---|---|---|
| 506 | 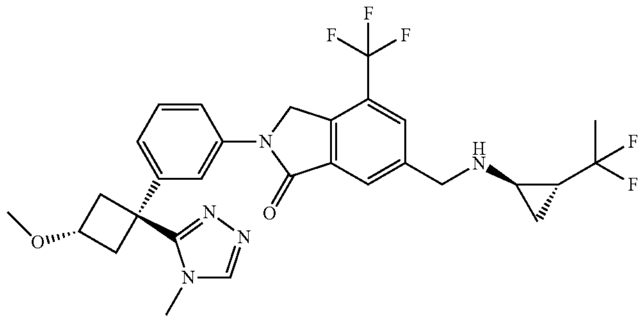 [SMILES: CO[C@H]1C[C@](c2cccc(N3Cc4c(cc(CN[C@@H]5C[C@H]5C(C)(F)F)cc4C(F)(F)F)C3=O)c2)(c2nncn2C)C1] | 6-((((1R,2R)-2-(1,1-difluoroethyl)cyclopropyl)amino)methyl)-2-(3-((1r,3R)-3-methoxy-1-(4-methyl-4H-1,2,4-triazol-3-yl)cyclobutyl)phenyl)-4-(trifluoromethyl)isoindolin-1-one |
| 507 | 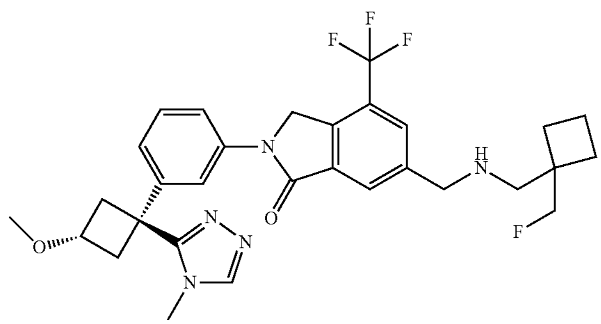 [SMILES: CO[C@H]1C[C@](c2cccc(N3Cc4c(cc(CNCC5(CF)CCC5)cc4C(F)(F)F)C3=O)c2)(c2nncn2C)C1] | 6-((((1-(fluoromethyl)cyclobutyl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 508 | 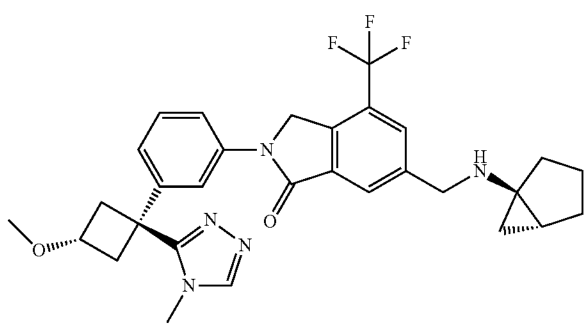 [SMILES: CO[C@H]1C[C@](c2cccc(N3Cc4c(cc(CN[C@@]56CCC[C@@H]5C6)cc4C(F)(F)F)C3=O)c2)(c2nncn2C)C1] | 6-(((1R,5R)-bicyclo[3.1.0]hexan-1-ylamino)methyl)-2-(3-((1r,3R)-3-methoxy-1-(4-methyl-4H-1,2,4-triazol-3-yl)cyclobutyl)phenyl)-4-(trifluoromethyl)isoindolin-1-one |
| 509 | 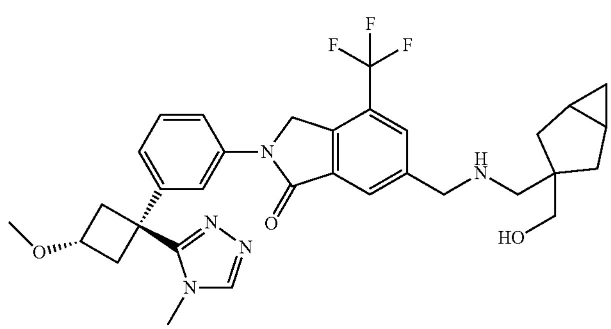 [SMILES: CO[C@H]1C[C@](c2cccc(N3Cc4c(cc(CNCC5(CO)CC6CC6C5)cc4C(F)(F)F)C3=O)c2)(c2nncn2C)C1] | 6-((((3-(hydroxymethyl)bicyclo[3.1.0]hexan-3-yl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |

TABLE 1-continued

| Compound # | Structure | Name |
|---|---|---|
| 510 | 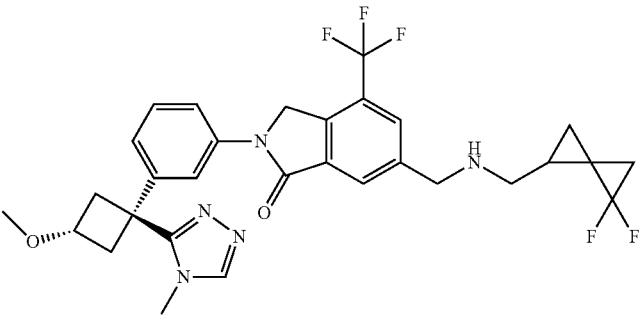 [SMILES: CO[C@H]1C[C@](c2cccc(N3Cc4c(cc(CNCC5CC56CC6(F)F)cc4C(F)(F)F)C3=O)c2)(c2nncn2C)C1] | 6-((((4,4-difluorospiro[2.2]heptan-1-yl)methyl)amino)methyl)-2-(3-((1r,3r)-3-methoxy-1-(4-methyl-4H-1,2,4-triazol-3-yl)cyclobutyl)phenyl)-4-(trifluoromethyl)isoindolin-1-one |
| 511 | 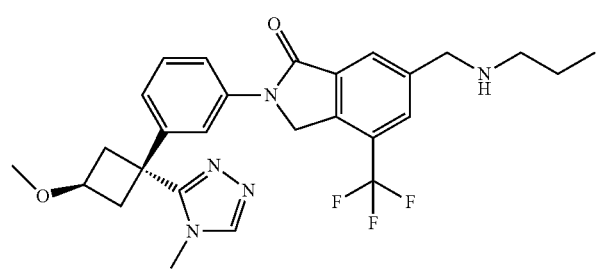 [SMILES: CCCNCc1cc2c(c(C(F)(F)F)c1)CN(c1cccc([C@]3(c4nncn4C)C[C@H](OC)C3)c1)C2=O] | 2-(3-((1r,3r)-3-methoxy-1-(4-methyl-4H-1,2,4-triazol-3-yl)cyclobutyl)phenyl)-6-((propylamino)methyl)-4-(trifluoromethyl)isoindolin-1-one |

Pharmaceutical Compositions and Formulations

The presently disclosed compounds can be formulated into pharmaceutical compositions along with a pharmaceutically acceptable carrier or excipient.

Compounds of Formula (I), can be formulated in accordance with standard pharmaceutical practice as a pharmaceutical composition. According to this aspect, there is provided a pharmaceutical composition comprising a compound of Formula (I) in association with a pharmaceutically acceptable excipient, diluent or carrier.

A typical formulation is prepared by mixing a compound of Formula (I), and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of Formula (I), is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of Formula (I), or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula (I), or stabilized form of the Compound of Formula (I), (e.g., complex with a cyclodextrin derivative or other known complexation agent) is dissolved in a suitable solvent in the presence of one or more of the excipients described above. The compound of Formula (I) is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations may be prepared for various routes and types of administration. For example, a compound of Formula (I) having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable excipients or carriers, i.e., excipients or carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compounds of Formula (I) can be sterile. In particular, formulations to be used for in vivo administration should be sterile. Such sterilization is readily accomplished by filtration through sterile filtration membranes.

The compound of Formula (I) ordinarily can be stored as a solid composition, a lyophilized formulation or as an aqueous solution.

The pharmaceutical compositions comprising a compound of Formula (I) can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. In some embodiments, the amount is below the amount that is toxic to the host or renders the host more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of Formula (I) compounds may be prepared. Suitable examples of sustained-release preparations include semipermeable matrices of solid hydrophobic polymers containing a compound of formula (I), which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the excipient or carrier which constitutes one or more accessory ingredients. In general the formulations are prepared by uniformly and intimately bringing into association the active ingredient with liquid excipients or carriers or finely divided solid excipients or carriers or both, and then, if necessary, shaping the product.

Formulations of a compound of Formula (I) suitable for oral administration may be prepared as discrete units such as pills, capsules, cachets or tablets each containing a predetermined amount of a compound of Formula (I).

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula (I) intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400), and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise solely an emulsifier, it may also comprise a mixture of at least one emulsifier and a fat or oil, or both a fat and an oil. A hydrophilic emulsifier included together with a lipophilic emulsifier may act as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of Formula (I) compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula (I), may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the excipient or carrier material to produce a single dosage form will vary depending upon the host treated and the particular mode of administration. For example, a time-release formulation intended for oral administration to humans may contain approximately 1 to 1000 mg of active material compounded with an appropriate and convenient amount of excipient or carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable excipient or carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of disorders as described below.

Formulations suitable for vaginal administration may be presented as pessaries, tampons, creams, gels, pastes, foams or spray formulations containing in addition to the active ingredient such excipients or carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid excipient or carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary excipient or carrier therefore. Veterinary excipients or carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent. In some of these embodiments, the chemotherapeutic agent is an immunotherapeutic agent.

Kits

Further provided are kits for carrying out the methods detailed herein, which kits comprise one or more compounds described herein or a pharmaceutical composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of a disorder such as cancer. In some embodiments, the kit contains instructions for use in the treatment of a cancer.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for a disorder (e.g., cancer) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and may be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to a subject.

Methods of Use

The presently disclosed compounds find use in inhibiting the activity of Cbl-B. The compounds additionally do so with an inhibitory effect that is greater than that for C-cbl.

In one embodiment, the subject matter disclosed herein is directed to a method of inhibiting Cbl-B, the method comprising contacting one or more cells containing active Cbl-B proteins with an effective amount of a compound of formula (I), or a pharmaceutical composition described herein. By "contacting" is meant, bringing the compound within close enough proximity to an isolated Cbl-B enzyme or a cell expressing Cbl-B (e.g., T cell, B cell, dendritic cell) such that the compound is able to bind to and inhibit the activity of Cbl-B. The compound can be contacted with Cbl-B in vitro or in vivo via administration of the compound to a subject.

In an embodiment, the subject matter disclosed herein is directed to a method for enhancing an immune response in a subject in need thereof, wherein the method comprises administering to said subject an effective amount of a compound of Formula (I), or variations thereof such as Formula (I)), or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of y-IFN+ CDS T cells, an elevated frequency of y-IFN+CD4 T cells, or enhanced levels of IL-2 or granzyme B production by T cells, relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CDS T cell. In certain aspects of this embodiment, the T cell is an antigen specific CD4 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells. In some aspects, compounds of Formula (I), or variations thereof, or a pharmaceutical composition thereof provides general priming of the immune response (i.e., vaccines) to tumors or viruses for boosting/generating anti-viral/tumor immunity.

In another embodiment, the subject matter disclosed herein is directed to a method for treating a cancer, the method comprising administering to a subject in need thereof an effective amount of a compound of formula (I), or a pharmaceutical composition thereof as further described herein. It is understood that the compound functions by inhibiting Cbl-B in a manner that leads to activated T cells that are able to kill cancer cells, regardless of their origin in the body. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In the methods described herein, the method can further comprise administering a therapeutic, or chemotherapeutic agent to said subject. For example, such an agent may be an inhibitor of PD-1/PD-1. In certain aspects of this embodiment, the therapeutic or chemotherapeutic agent is administered to the subject simultaneously with the compound or the composition. In certain aspects of this embodiment, the therapeutic or chemotherapeutic agent is administered to the subject prior to administration of the compound or the composition. In certain aspects of this embodiment, the therapeutic or chemotherapeutic agent is administered to the subject after administration of the compound or said composition.

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CDS T cells), enhanced T cell (e.g., CD4 T cell, CDS T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CDS T cells.

In some embodiments, the CDS T cells in the subject have enhanced priming, activation, proliferation and/or cytolytic activity relative to prior to the administration of the compound of Formula (I), or variations thereof such as Formula (IA), (IB) and (IC), or a pharmaceutically acceptable salt, prodrug, metabolite, or derivative thereof. In some embodiments, the CDS T cell priming is characterized by elevated CD44 expression and/or enhanced cytolytic activity in CDS T cells. In some embodiments, the CDS T cell activation is characterized by an elevated frequency of y-IFN+CDS T cells. In some embodiments, the CDS T cell is an antigen-specific T-cell.

In some embodiments, the CD4 T cells in the subject have enhanced priming, activation, proliferation and/or cytolytic activity relative to prior to the administration of the compound of Formula (I), or variations thereof such as Formula (IA), (IB) and (IC), or a pharmaceutically acceptable salt, prodrug, metabolite, or derivative thereof. In some embodiments, the CD4 T cell priming is characterized by elevated CD44 expression and/or enhanced cytolytic activity in CD4 T cells. In some embodiments, the CD4 T cell activation is characterized by an elevated frequency of y-IFN+CD4 T cells. In some embodiments, the CD4 T cell is an antigen-specific T-cell.

Accordingly, the presently disclosed compounds of Formula (I), or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation.

Thus, the presently disclosed compounds can be used in treating conditions where enhanced immunogenicity is desired, such as increasing tumor immunogenicity for the treatment of cancer.

"Immunogenicity" refers to the ability of a particular substance to provoke an immune response. Tumors are immunogenic and enhancing tumor immunogenicity aids in the clearance of the tumor cells by the immune response. Viruses may also be immunogenic and enhancing/activating immunogenicity may aid in clearance of viral particles by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In some embodiments, the compound is administered to the subject at a dose of between about 0.001 µg/kg and about 1000 mg/kg, including but not limited to about 0.001 µg/kg, about 0.01 µg/kg, about 0.05 µg/kg, about 0.1 µg/kg, about 0.5 µg/kg, about 1 µg/kg, about 10 µg/kg, about 25 µg/kg, about 50 µg/kg, about 100 µg/kg, about 250 µg/kg, about 500 µg/kg, about 1 mg/kg, about 5 mg/kg, about 10 mg/kg, about 25 mg/kg, about 50 mg/kg, about 100 mg/kg, and about 200 mg/kg.

EXAMPLES

Compounds of the invention may be synthesized according to the following exemplary synthetic procedures. Unless otherwise indicated, absolute configuration was arbitrarily assigned to each enantiomer or diastereomer where a pair of (or more than two) such stereoisomeric compounds was synthesized or isolated. In an instance in which only one member of a stereoisomerically related pair was identified, the absolute stereochemistry of such a final product was assigned arbitrarily.

Example 1: Intermediate A

Intermediate A (tert-butyl (1-methylcyclobutyl)((3-oxo-7-(trifluoromethyl)isoindolin-5-yl)methyl)carbamate) may be synthesized according to a 3-step scheme (FIG. 1).

Step 1

To a solution of 6-(hydroxymethyl)-4-(trifluoromethyl) isoindolin-1-one (3.50 g, 15.14 mmol) in DCM (75.7 mL) was added thionyl chloride (2.75 mL, 37.85 mmol). The reaction was stirred at rt for 2 days. The reaction was cooled to 0° C. and a few drops of MeOH was added. After 10 minutes, the reaction was diluted with saturated aqueous NaHCO$_3$ solution, extracted with DCM, dried over sodium sulfate, filtered and evaporated to afford 6-(chloromethyl)-4-(trifluoromethyl)isoindolin-1-one (3.705 g, 98% yield). Product was used crude as such in next step. LCMS (ESI) m/z: 250.4 [M+H]$^+$.

Step 2

To a solution of 1-methylcyclobutanamine hydrochloride (2.253 g, 18.53 mmol) in MeCN (37.1 mL) was added cesium carbonate (9.719 g, 29.65 mmol). The reaction was stirred at 60° C. for 5 minutes before 6-(chloromethyl)-4-(trifluoromethyl)isoindolin-1-one (1.850 g, 7.41 mmol) was added. The reaction was stirred at 60° C. for 16 h. The reaction was cooled down to rt and water was added, extracted with EtOAc, combined organic phases were dried over sodium sulfate, filtered and evaporated. The residue was purified by chromatography on silica gel (0-10% MeOH in DCM) to give 6-(((1-methylcyclobutyl)amino)methyl)-4-(trifluoromethyl)isoindolin-1-one (1.230 g, 56% yield). LCMS (ESI) m/z: 299.4 [M+H]$^+$ Step 3

To a solution of 6-(((1-methylcyclobutyl)amino)methyl)-4-(trifluoromethyl)-isoindolin-1-one (0.64 g, 2.15 mmol) and di-tert-butyl dicarbonate (0.54 mL, 2.36 mmol) in DCM (7.2 mL) was added triethylamine (0.45 mL, 3.22 mmol). The reaction was stirred at rt for 16 h. The reaction was diluted with saturated aqueous NaHCO$_3$ solution, extracted with EtOAc, dried over sodium sulfate, filtered and evaporated. The residue was purified by chromatography on silica gel (0-5% MeOH in DCM) to give tert-butyl (1-methylcyclobutyl)-((3-oxo-7-(trifluoromethyl)isoindolin-5-yl)methyl)carbamate (Intermediate A; 745 mg, 87% yield). LCMS (ESI) m/z: 397.4 [M+H]+.

Example 2: Alternative Route to Intermediate A

Figure 2:
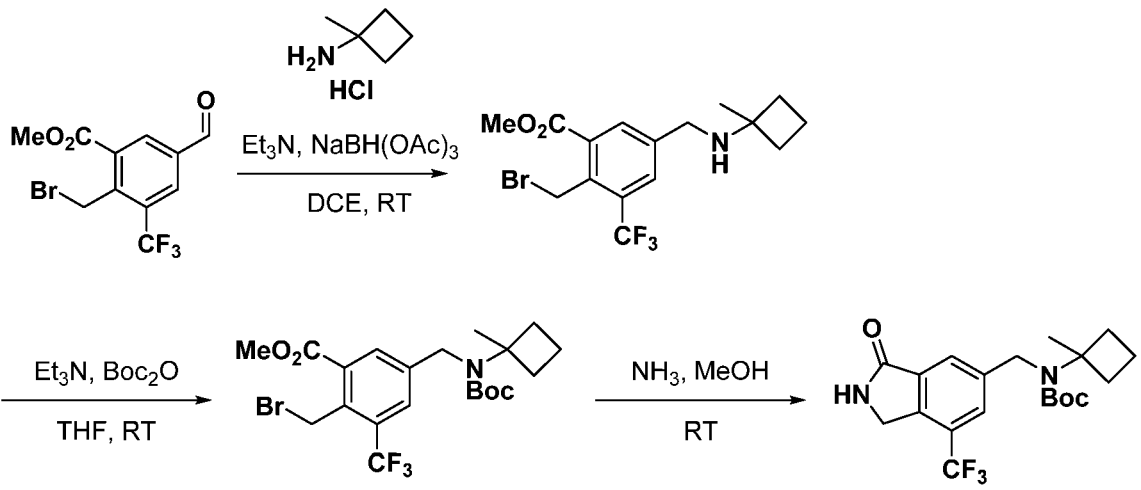

Intermediate A may also be synthesized according to a 4-step scheme (Scheme 2, FIG. 2).

Step 1

To a stirred solution of methyl 2-(bromomethyl)-5-formyl-3-(trifluoromethyl)-benzoate (12.0 g, 36.9 mmol) and (1-methylcyclobutyl)ammonium chloride (4.49 g, 36.9 mmol) in DCE (100 mL) was added triethylamine (5.15 mL, 36.9 mmol) followed by sodium triacetoxyborohydride (23.47 g, 110.74 mmol) portion-wise over 20 minutes. The suspension was stirred at rt for 16 h. The reaction was then quenched with addition of saturated aqueous NaHCO$_3$ solution and extracted with DCM (3×150 mL). The organics were combined, dried over sodium sulfate, filtered and concentrated to afford methyl 2-(bromomethyl)-5-(((1-methylcyclobutyl)amino)methyl)-3-(trifluoromethyl)benzoate (16.2 g, 111% yield) as an amber oil and used in the next step without further purification.

Step 2

To a solution of methyl 2-(bromomethyl)-5-(((1-methylcyclobutyl)amino)methyl)-3-(trifluoromethyl)benzoate (16.5 g, 31.4 mmol) in THF (150 mL) was added triethylamine (13.1 mL, 94.2 mmol) followed by di-tert-butyl dicarbonate (10.8 mL, 47.09 mmol). The reaction was stirred at rt for 18 h. Saturated aqueous NaHCO$_3$ solution (150 mL) was added to the reaction and the product was extracted with EtOAc (3×250 mL). The organic layers were combined, dried over sodium sulfate, filtered and concentrated to afford methyl 2-(bromomethyl)-5-(((tert-butoxycarbonyl)(1-methylcyclobutyl)amino)methyl)-3-(trifluoromethyl)benzoate (18.2 g, 117% yield). Used in the next step without further purification.

Step 3

A solution of methyl 2-(bromomethyl)-5-(((tert-butoxycarbonyl)(1-methylcyclobutyl)amino)methyl)-3-(trifluoromethyl)benzoate (18 g, 16.4 mmol) in ammonia (7 M in MeOH) (100 mL, 700 mmol) was stirred at rt for 16 h. The reaction was concentrated and the residue was purified by chromatography on silica gel (0-100% EtOAc in heptanes). The product obtained was not pure enough so a second purification was made by chromatography on C18 silica gel (40-100% acetonitrile in ammonium formate buffer, pH=3.7). Appropriate fractions were concentrated, frozen and lyophilized to provide tert-butyl (1-methylcyclobutyl)((3-oxo-7-(trifluoromethyl)isoindolin-5-yl)methyl)carbamate (Intermediate A; 2.55 g, 39% yield). LCMS (ESI) m/z: 299.2 [M+H]+.

Example 3: Intermediate B

Figure 3:
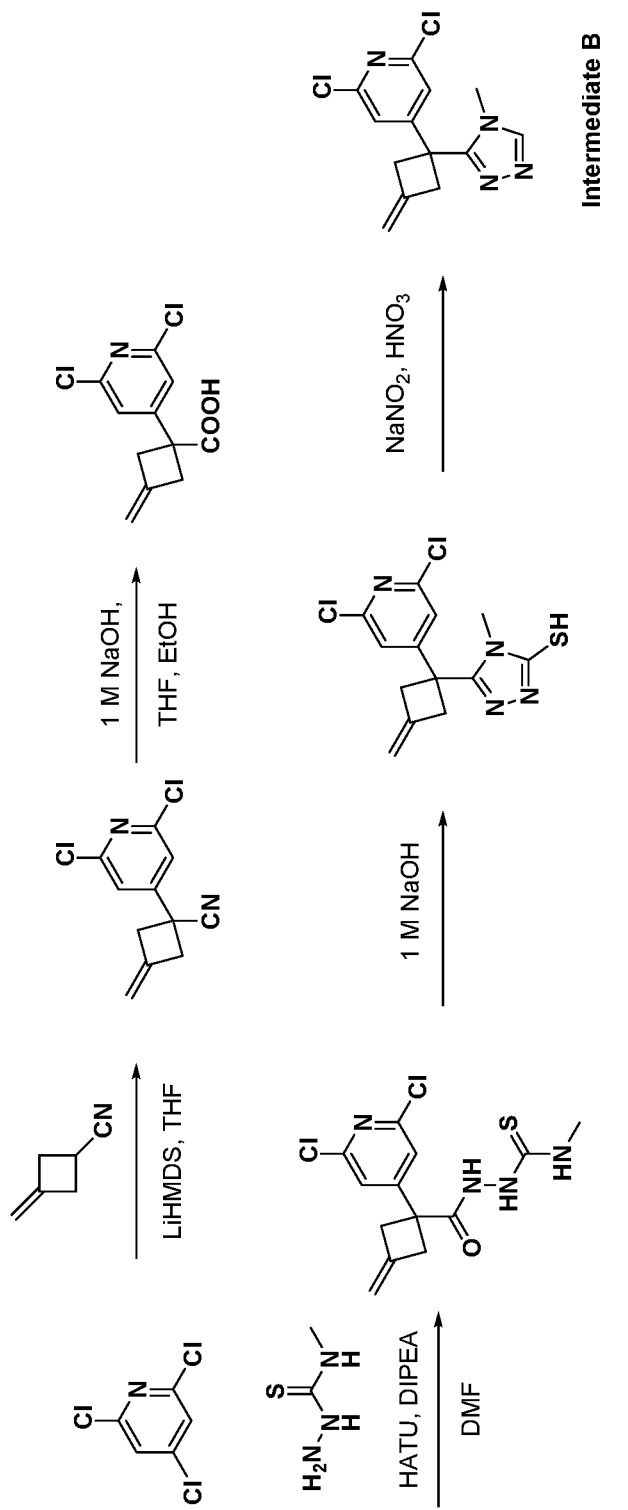

Intermediate B (2,6-dichloro-4-(1-(4-methyl-4H-1,2,4-triazol-3-yl)-3-methylene-cyclobutyl)pyridine) can be synthesized according to a 5-step scheme (Scheme 3, FIG. 3).

Step 1: 1-(2,6-dichloropyridin-4-yl)-3-methylenecyclobutanecarbonitrile 2,4,6-trichloropyridine (7.5 g, 41.11 mmol) and 3-methylenecyclobutanecarbo-nitrile (4.02 g, 43.16 mmol) was dissolved in THF (82.2 mL). The mixture was cooled to −78° C. and LiHMDS 1 M in THF (45.2 mL, 45.22 mmol) was added dropwise over 10 minutes. The reaction mixture was allowed to warm to 0° C. over 4-5 h. After completion, the reaction was quenched by addition of saturated aqueous solution of NH$_4$Cl, extracted with DCM (3×), the combined organic phases were washed with brine, dried over sodium sulfate, filtered and concentrated. The crude product was purified by chromatography on silica gel (0-10% EtOAc in heptanes) to obtain 1-(2,6-dichloropyridin-4-yl)-3-methylenecyclobutanecarbonitrile (4.92 g, 50% yield). LCMS (ESI) m/z: 239.3, 241.2 [M+H]+

Step 2: 1-(2,6-dichloropyridin-4-yl)-3-methylenecyclobutanecarboxylic acid

To a stirred solution of 1-(2,6-dichloropyridin-4-yl)-3-methylenecyclobutanecarbo-nitrile (4.2 g, 17.57 mmol) in ethanol (80 mL) was added 1 M NaOH solution (87.8 mL, 87.83 mmol). The resulting reaction mixture was heated at 100° C. for 20 h. The reaction was cooled down to rt and most of ethanol was removed. The mixture was slowly quenched by the addition of 1 M HCl solution to pH 4-5 and concentrated again. The crude residue was purified by chromatography on C18 silica gel (0-100% acetonitrile in ammonium formate buffer, pH=3.8). Appropriate fractions were concentrated, frozen and lyophilized to obtain 1-(2,6-dichloropyridin-4-yl)-3-methylenecyclobutanecarboxylic acid (3.4 g, 75% yield). LCMS (ESI) m/z: 258.4, 260.4 [M+H]+.

Step 3: 2-(1-(2,6-dichloropyridin-4-yl)-3-methylene-cyclobutanecarbonyl)-N-methylhydrazinecarbothioamide A mixture of 1-(2,6-dichloropyridin-4-yl)-3-methylene-cyclobutanecarboxylic acid (3.1 g, 12 mmol), N-methylhydrazinecarbothioamide (1.89 g, 18 mmol), HATU (6.84 g, 18 mmol) and DIPEA (6.3 mL, 36 mmol) was dissolved in DMF (60 mL) and was stirred at rt for 2 h. The reaction mixture was quenched with saturated aqueous solution of NH$_4$Cl and extracted with CHCl$_3$:IPA (9:1). The combined organic layers were dried over sodium sulfate, filtered and concentrated to obtain 2-(1-(2,6-dichloropyridin-4-yl)-3-methylene-cyclobutanecarbonyl)-N-methylhydrazinecarbothioamide (4.5 g, 109% yield) which was used in next step without any further purification. LCMS (ESI) m/z: 345.3, 347.3 [M+H]+

Step 4: 5-(1-(2,6-dichloropyridin-4-yl)-3-methylenecyclobutyl)-4-methyl-4H-1,2,4-triazole-3-thiol The product of the preceding step (2-(1-(2,6-dichloropyridin-4-yl)-3-methylenecyclobutanecarbonyl)-N-methylhydrazinecarbothioamide, 4.14 g, 12 mmol) was dissolved in 1 M NaOH solution (60 mL, 60 mmol) and was stirred at 50° C. for 5 h then cooled down to rt and acidified with 1 N HCl solution to pH 4. The resulting mixture was extracted with CHCl$_3$:IPA (9:1). The organics were combined, dried over sodium sulfate, filtered and concentrated to afford 5-(1-(2,6-dichloropyridin-4-yl)-3-methylenecyclobutyl)-4-methyl-4H-1,2,4-triazole-3-thiol (3.28 g, 84% yield) which was used in next step without any further purification. LCMS (ESI) m/z: 327.4, 329.4 [M+H]+.

Step 5: 2,6-dichloro-4-(1-(4-methyl-4H-1,2,4-triazol-3-yl)-3-methylenecyclo-butyl)pyridine At 0° C. and to 5-(1-(2,6-dichloropyridin-4-yl)-3-methylenecyclobutyl)-4-methyl-4H-1,2,4-triazole-3-thiol (3.27 g, 10 mmol) and sodium nitrite (3.45 g, 50 mmol) in THF (50 mL)/water (50 mL) was added nitric acid 1 M solution (60 mL, 60 mmol). The resulting reaction mixture was stirred at 0° C. for 1 h. The reaction was then quenched with addition of saturated aqueous NaHCO$_3$ solution and extracted with mixture of CHCl$_3$:IPA (9:1). Combined organic layers were washed with brine, dried over sodium sulfate and concentrated. The crude product was purified by chromatography on silica gel (0-10% MeOH in DCM) to obtain 2,6-dichloro-4-(1-(4-methyl-4H-1,2,4-triazol-3-yl)-3-methylenecyclobutyl)pyridine (2.4 g, 81% yield). LCMS (ESI) m/z: 295.2, 297.2 [M+H]$^+$.

Example 4: Intermediate C

Figure 4:
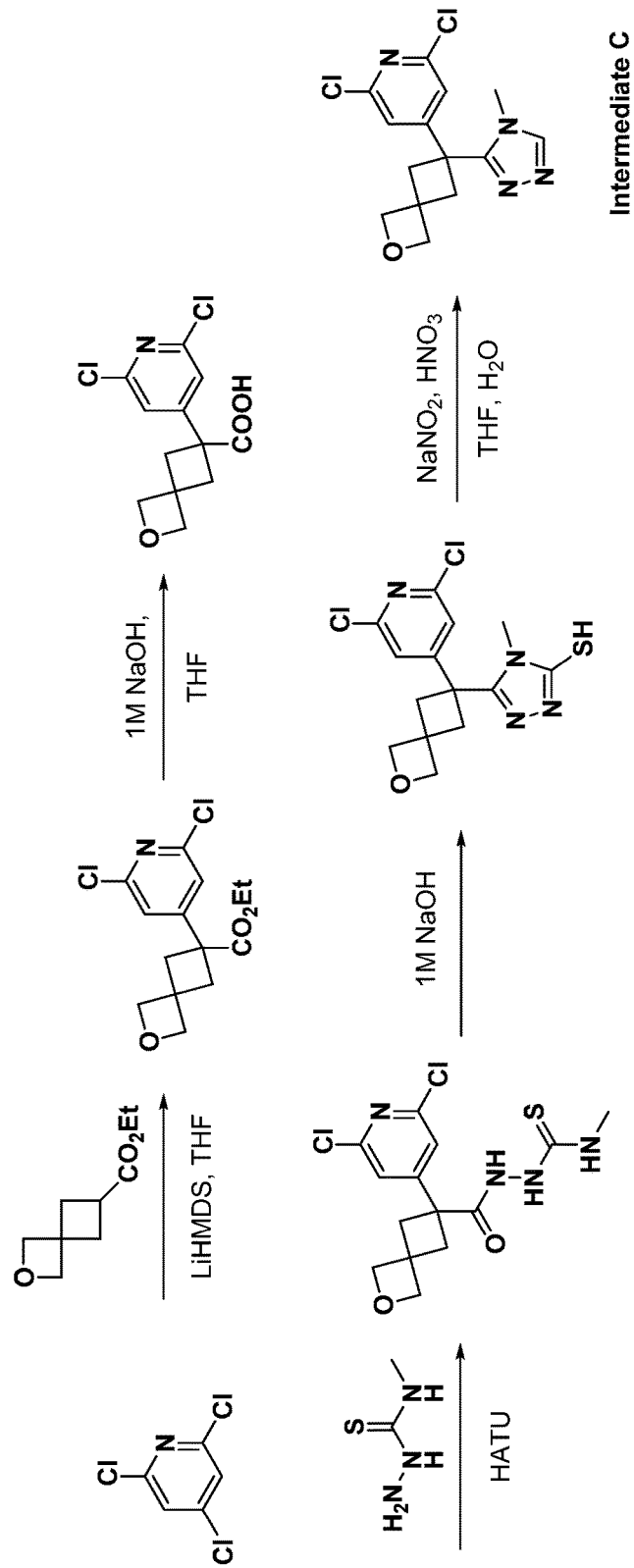

Intermediate C (2,6-dichloro-4-(6-(4-methyl-4H-1,2,4-triazol-3-yl)-2-oxaspiro[3.3]heptan-6-yl)pyridine) can be synthesized according to a 5-step scheme shown in FIG. 4 (Scheme 4).

Step 1: Ethyl 6-(2,6-dichloropyridin-4-yl)-2-oxaspiro[3.3]heptane-6-carboxylate 2,4,6-trichloropyridine (500 mg, 2.74 mmol) and ethyl 2-oxaspiro[3.3]heptane-6-carboxylate (466.5 mg, 2.74 mmol) was dissolved in THF (30 mL) and cooled to −78° C. 1 M LiHMDS solution in THF (3.3 mL, 3.29 mmol) was added dropwise over 10 minutes at −78° C. and the reaction mixture was allowed to warm to 0° C. over 4-5 h. After completion, the reaction was quenched by addition of saturated aqueous solution of NH$_4$Cl, extracted with DCM (3×), the combined organic phases were washed with brine, dried over sodium sulfate, filtered and concentrated. The crude product was purified by chromatography on silica gel (0-10 EtOAc in heptanes) to obtain ethyl 6-(2,6-dichloropyridin-4-yl)-2-oxaspiro[3.3]heptane-6-carboxylate (320 mg, 37% yield). LCMS (ESI) m/z: 316.3 [M+H]$^+$.

Step 2: 6-(2,6-dichloropyridin-4-yl)-2-oxaspiro[3.3]heptane-6-carboxylic acid

Ethyl 6-(2,6-dichloropyridin-4-yl)-2-oxaspiro[3.3]heptane-6-carboxylate (1.4 g, 4.43 mmol) was dissolved in THF (10 mL). 2 M NaOH solution (11.07 mL, 22.14 mmol) was added and the reaction mixture was stirred for 4 h. After completion, it was quenched by addition of 0.5 M KHSO$_4$ solution and 1 N HCl and extracted with IPA/CHCl$_3$ (1:4) and combined organic layers were washed with brine and dried over sodium sulfate, filtered and concentrated to get 6-(2,6-dichloropyridin-4-yl)-2-oxaspiro[3.3]heptane-6-carboxylic acid (1.25 g, 98% yield) which was used in next step without any further purification. LCMS (ESI) m/z: 288.4 [M+H]$^+$.

Step 3: 2-(6-(2,6-dichloropyridin-4-yl)-2-oxaspiro[3.3]heptane-6-carbonyl)-N-methylhydrazinecarbothioamide A mixture of 6-(2,6-dichloropyridin-4-yl)-2-oxaspiro[3.3]heptane-6-carboxylic acid (500 mg, 1.74 mmol), N-methylhydrazinecarbothioamide (237.2 mg, 2.26 mmol), HATU (989.8 mg, 2.6 mmol), and DIPEA (0.91 mL, 5.21 mmol) was dissolved in DMF (5 mL) and the reaction was stirred at room temperature for 2 h. Solvent was evaporated and the crude was purified by chromatography on C18 silica gel (0-100% acetonitrile in ammonium bicarbonate buffer, pH=10). Appropriate fractions were concentrated, frozen and lyophilized to obtain 2-(6-(2,6-dichloropyridin-4-yl)-2-oxaspiro[3.3]heptane-6-carbonyl)-N-methylhydrazinecarbothioamide (155 mg, 24% yield). LCMS (ESI) m/z: 373.3 [M+H]$^+$ Step 4: 5-(6-(2,6-dichloropyridin-4-yl)-2-oxaspiro[3.3]heptan-6-yl)-4-methyl-4H-1,2,4-triazole-3-thiol The product of the preceding step (2-(6-(2,6-dichloropyridin-4-yl)-2-oxaspiro[3.3]heptane-6-carbonyl)-N-methylhydrazine carbothioamide, 155 mg, 0.41 mmol) was dissolved in 1 M NaOH solution (5 mL, 5 mmol) and the mixture was stirred at 45° C. for 4 h. After completion, it was quenched by addition of 0.5 M KHSO$_4$ solution and 1 N HCl and extracted with IPA/CHCl$_3$ (1:4) and combined organic layers were washed with brine and dried over sodium sulfate, filtered and concentrated to get 5-(6-(2,6-dichloropyridin-4-yl)-2-oxaspiro[3.3]heptan-6-yl)-4-methyl-4H-1,2,4-triazole-3-thiol (125 mg, 85% yield) which was used in next step without any further purification. LCMS (ESI) m/z: 355.3, 357.3 [M+H]$^+$ Step 5: 2,6-dichloro-4-(6-(4-methyl-4H-1,2,4-triazol-3-yl)-2-oxaspiro[3.3]heptan-6-yl)pyridine At 0° C., to a solution of 5-(6-(2,6-dichloropyridin-4-yl)-2-oxaspiro[3.3]heptan-6-yl)-4-methyl-4H-1,2,4-triazole-3-thio (125 mg, 0.35 mmol) and NaNO$_2$ (120.7 mg, 1.75 mmol) in THF (2 mL)/water (2 mL) was added 1 M HNO$_3$ solution (2.1 mL, 2.1 mmol). The resulting reaction mixture was stirred at 0° C. for 1 h. After completion, it was quenched with saturated aqueous NaHCO$_3$ solution, extracted with mixture of CHCl$_3$:IPA (4:1). Combined organic layers were washed with brine, dried over sodium sulfate, filtered and concentrated to obtain Intermediate D (2,6-dichloro-4-(6-(4-methyl-4H-1,2,4-triazol-3-yl)-2-oxaspiro[3.3]heptan-6-yl)pyridine, 105 mg, 92% yield). LCMS (ESI) m/z: 325.4 [M+H]$^+$.

Example 5: Intermediate D

Figure 5:
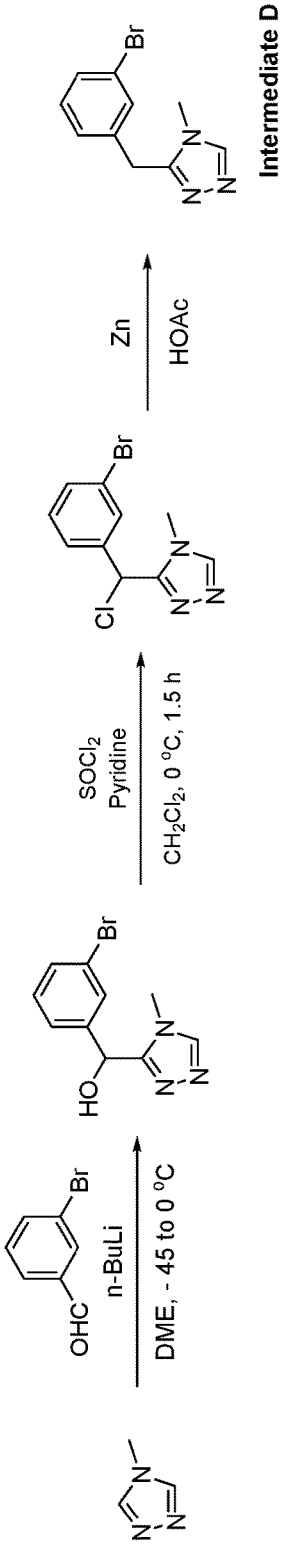

Intermediate D (3-(3-bromobenzyl)-4-methyl-4H-1,2,4-triazole) can be synthesized according to Scheme 5 (FIG. 5).

Step 1: (3-bromophenyl)(4-methyl-4H-1,2,4-triazol-3-yl)methanol

To a −45° C. solution of 4-methyl-1,2,4-triazole (250 mg, 3.009 mmol) in 1,2-dimethoxyethane (0.1 M) was added N-butyl lithium (1.6 mol/L) in hexanes (1 equiv., 3.009 mmol, 1.6 mol/L). The reaction was stirred at −45° C. for 30 min at which point 3-bromobenzaldehyde (1 equiv., 3.009 mmol) was added in a small amount of DME. The reaction was immediately warmed to 0° C. and stirred for 1 h at which point it was quenched with saturated aqueous sodium bicarbonate, extracted three times with methylene chloride, dried over sodium sulfate and concentrated. Purification by silica column chromatography (using a gradient of 0-10% MeOH in CH$_2$Cl$_2$) gave the desired product (359 mg, 1.33 mmol, 44% yield). $^1$H NMR (400 MHz, DMSO-d$_6$) δ 8.41 (s, 1H), 7.57 (dd, J=2.1, 1.1 Hz, 1H), 7.50 (dtd, J=6.1, 4.1, 3.6, 1.9 Hz, 1H), 7.38-7.29 (m, 2H), 6.61 (d, J=4.9 Hz, 1H), 6.03 (d, J=4.6 Hz, 1H), 3.55 (s, 3H).

Step 2: 3-((3-bromophenyl)chloromethyl)-4-methyl-4H-1,2,4-triazole

To a 0° C. solution of (3-bromophenyl)-(4-methyl-1,2,4-triazol-3-yl)methanol (345 mg, 1.29 mmol) in dichloromethane (0.2 M) was added pyridine (5.0 equiv., 6.4339 mmol) followed by thionyl chloride (3 equiv., 3.8604 mmol) and the reaction was stirred at 0° C. for 2 h. After 2 h, the reaction was judged to be complete and saturated aqueous sodium bicarbonate was added to quench the reaction. The solution was subsequently poured into saturated aqueous sodium bicarbonate and ice, extracted three times with methylene chloride, dried over sodium sulfate, concentrated and purified by silica column chromatography using a methylene chloride/methanol gradient to give the desired product (Intermediate D, 263 mg, 0.918 mmol, 71% yield). $^1$H NMR (400 MHz, DMSO-d$_6$) δ 8.56 (s, 1H), 7.86 (t, J=1.9 Hz, 1H), 7.72-7.56 (m, 2H), 7.42 (t, J=7.9 Hz, 1H), 6.77 (s, 1H), 3.72 (s, 3H).

Step 3:
3-(3-bromobenzyl)-4-methyl-4H-1,2,4-triazole

To a room temperature solution of 3-[(3-bromophenyl)-chloro-methyl]-4-methyl-1,2,4-triazole (60 mg, 0.20938 mmol) in acetic acid (0.1 M, 36.54 mmol) was added zinc (10 equiv., 2.0938 mmol). The reaction was stirred at room temperature for 2 h at which point the zinc was filtered and the filtrate was poured into saturated aqueous sodium bicarbonate. The solution was extracted three times with methylene chloride, dried over sodium sulfate, concentrated and purified by silica column chromatography using a methylene chloride/methanol gradient to give the desired product (34 mg, 64% Yield). $^1$H NMR (400 MHz, DMSO-d$_6$) δ 8.38 (s, 1H), 7.47-7.43 (m, 2H), 7.29 (dd, J=8.7, 7.5 Hz, 1H), 7.22 (dt, J=7.7, 1.5 Hz, 1H), 4.16 (s, 2H), 3.51 (s, 3H).

Example 6: Alternative Route to Intermediate D

Figure 6:
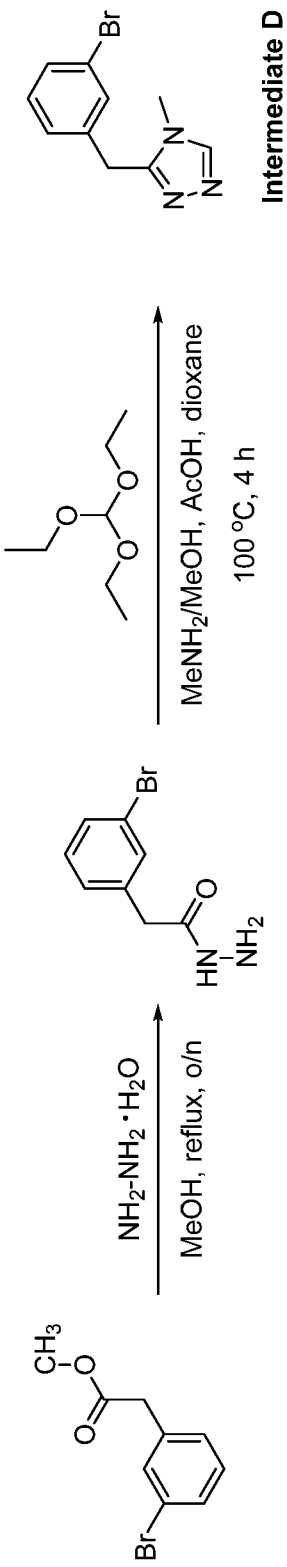

Intermediate D can also be synthesized according to the 2-step approach of Scheme 6 (FIG. 6).

Step 1: 2-(3-bromophenyl)acetohydrazide

To a solution of methyl 2-(3-bromophenyl)acetate (300 g, 1.31 mol) in MeOH (6.6 L) was added dropwise hydrazine hydrate solution (80%, 162 g, 2.6 mol) at room temperature. Then the mixture was stirred at 65° C. under N$_2$ overnight. TLC analysis showed the reaction was complete. The mixture was concentrated under reduced pressure. The residue was washed with petroleum ether to give the crude desired product (310 g).

Step 2:
3-(3-bromobenzyl)-4-methyl-4H-1,2,4-triazole

To a solution of 2-(3-bromophenyl)acetohydrazide (310 g, crude) in 1,4-dioxane (2.5 L) was added triethoxymethane (300.6 g, 2.0 mol) at room temperature. The mixture was stirred at 100° C. for 2 h. Then the reaction was cooled to room temperature, and AcOH (135 mL) and methylamine/MeOH (852 g, 9.0 mol) was added. The mixture was stirred at 100° C. for 2 h. TLC showed ~40% of starting material was remained. The mixture was concentrated under reduced pressure. The residue was dissolved in 1,4-dioxane (2.5 L) and triethoxymethane 4 (300.6 g, 2.0 mol) was added at room temperature. The mixture was stirred at 100° C. for 2 h. The reaction was cooled to room temperature, and then AcOH (135 mL) and Methylamine/MeOH (852 g, 9.0 mol) was added. The mixture was stirred at 100° C. for 2 h. TLC showed the reaction was complete. The mixture was concentrated under reduced pressure. The residue was purified by column chromatography on silica gel (DCM/MeOH 50/1) to the desired product (117 g, 35% for 2 steps) as a white solid. LCMS: [M+H]$^+$=254, $^1$H NMR (400 MHz, DMSO-d$_6$) δ 8.39 (s, 1H), 7.45 (m, 2H), 7.33-7.20 (m, 2H), 4.17 (s, 2H), 3.52 (s, 3H).

Example 7: Intermediate E

Figure 7:
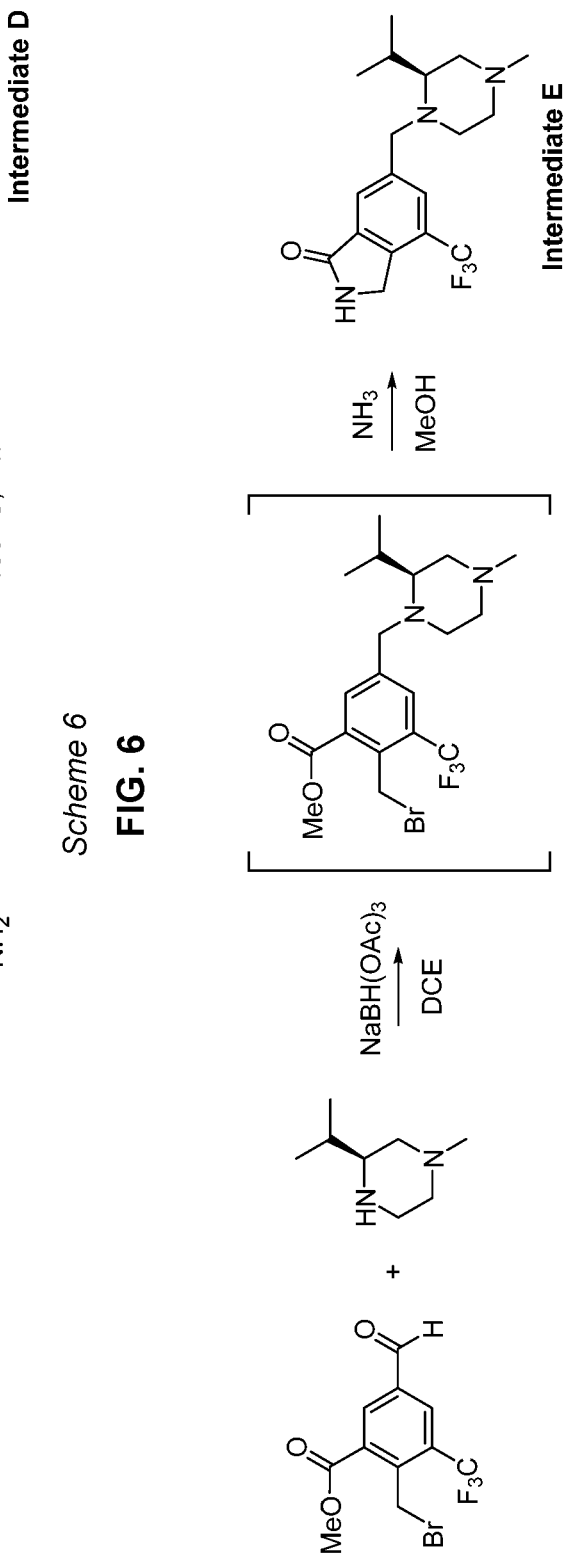

Intermediate E ((S)-6-((2-isopropyl-4-methylpiperazin-1-yl)methyl)-4-(trifluoromethyl)isoindolin-1-one) can be synthesized according to the scheme in Scheme 7 (FIG. 7).

To a solution of methyl 2-(bromomethyl)-5-formyl-3-(trifluoromethyl)benzoate (1.64 g, 5.05 mmol) and (S)-3-isopropyl-1-methylpiperazine (718 mg, 5.05 mmol) in 1,2-dichloroethane (25 mL) was added sodium triacetoxyborohydride (3.21 g, 15.1 mmol). The reaction mixture was stirred for 18.5 h before being quenched by the addition of saturated aq sodium bicarbonate and extracted with dichloromethane. The organic layer was dried with magnesium sulfate and concentrated to dryness. The crude benzyl amine was dissolved in methanol (5 mL) and ammonia (18.0 mL, 7 M in MeOH, 126 mmol) was added. The reaction mixture was stirred for 21 h and concentrated to dryness. The residue thus obtained was purified by flash column chromatography (0-10% MeOH in CH$_2$Cl$_2$) to afford the desired product as a white solid (1.15 g, 64% yield); $^1$H NMR (400 MHz, CDCl$_3$) δ 8.06 (s, 1H), 7.75 (s, 1H), 6.69 (br s, 1H), 4.61 (s, 2H), 4.31 (d, J=13.9 Hz, 1H), 3.27 (d, J=13.9 Hz, 1H), 3.19 (d, J=11.7 Hz, 1H), 3.10 (d, J=11.4 Hz, 1H), 2.91-2.85 (m, 1H), 2.76-2.67 (m, 2H), 2.63 (s, 3H), 2.60-2.53 (m, 1H), 2.51-2.45 (m, 1H), 2.40-2.32 (m, 1H), 1.03 (d, J=6.9 Hz, 3H), 0.97 (d, J=6.9 Hz, 3H).

Example 8: Compounds 1 and 2

Figure 8:
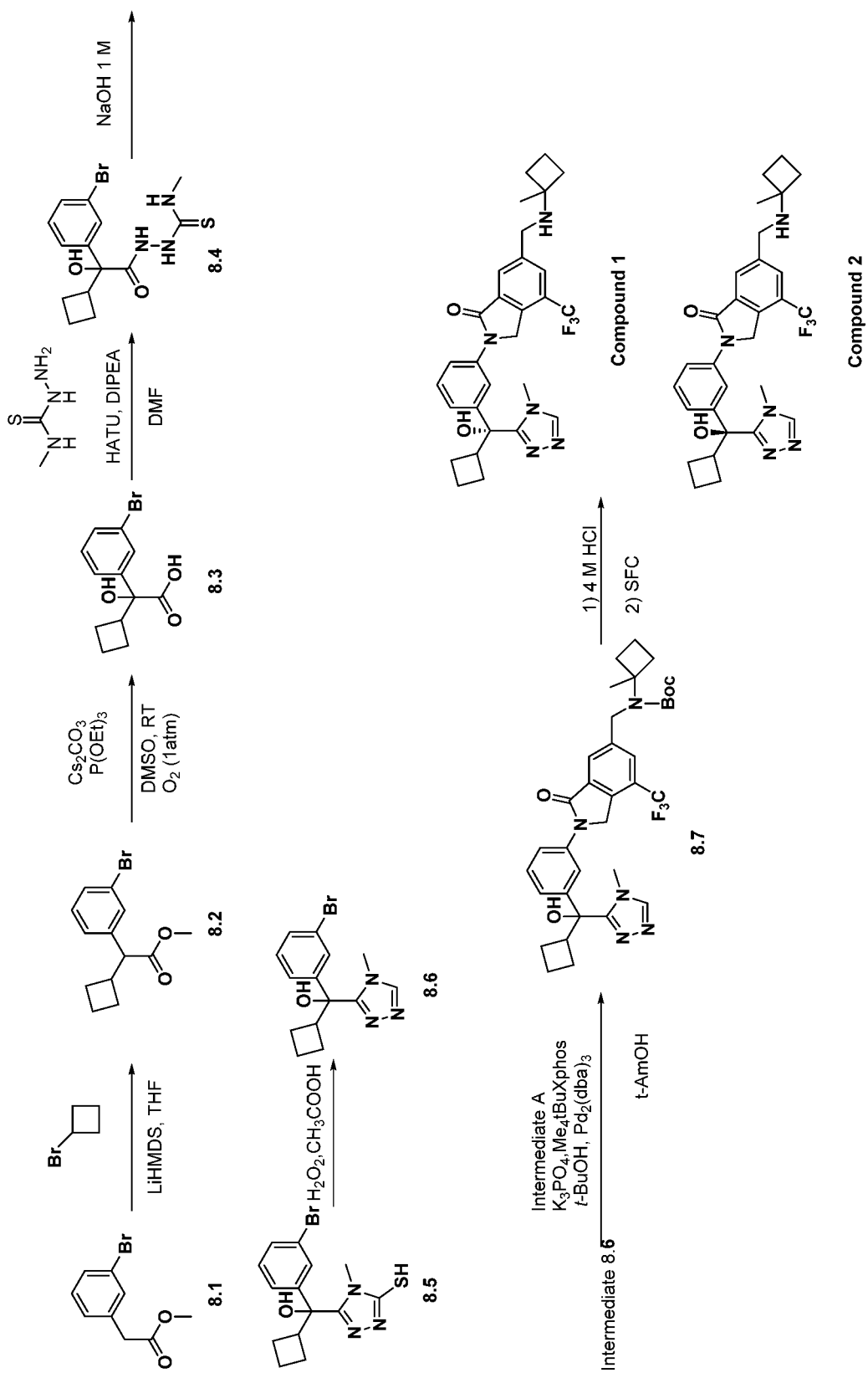
FIGS. 8-109 show respectively, flow-charts of processes for synthesizing various exemplary compounds according to formula (I), as further described herein.

Compound 1 ((R)-2-(3-(cyclobutyl(hydroxy)(4-methyl-4H-1,2,4-triazol-3-yl)methyl)phenyl)-6-(((1-methylcyclobutyl)amino)methyl)-4-(trifluoromethyl)isoindolin-1-one) and Compound 2 ((S)-2-(3-(cyclobutyl(hydroxy)(4-methyl-4H-1,2,4-triazol-3-yl)methyl)phenyl)-6-(((1-methylcyclobutyl)amino)methyl)-4-(trifluoromethyl) isoindolin-1-one) can be synthesized as follows, as shown in Scheme 8, FIG. 8.

Intermediate 8.2 (Methyl 2-(3-bromophenyl)-2-cyclobutylacetate)

In a round bottom flask, potassium tert-butoxide (2.69 g, 24.01 mmol) were suspended in dry DMF (87.1 mL) at 0° C. under an argon gas atmosphere and methyl 2-(3-bromophenyl)acetate (5 g, 21.83 mmol) was added. After 10 minutes of stirring, bromocyclobutane (2.26 mL, 24.01 mmol) was added and it was allowed to warm to rt and stirred for 2 h. Water (50 mL) was added and the solution was extracted with DCM (2×100 mL). Combined organic layers were washed with saturated aqueous solution of NH$_4$Cl (100 mL) and water (100 mL), dried over magnesium sulfate filtered and concentrated. The crude product was purified by chromatography on silica gel (Hexane: EtOAc (9:1)) to afford methyl 2-(3-bromophenyl)-2-cyclobutylacetate (3.2 g, 52% yield) as a colorless oil. LCMS (ESI) m/z: 283.1, 285.1 [M+H]$^+$. $^1$H NMR (400 MHz, CDCl$_3$): δ 7.43 (t, J=1.6 Hz, 1H), 7.37 (ddd, J=11.6, 6.7, 4.9 Hz, 1H), 7.23-7.19 (m, 1H), 7.17 (t, J=7.6 Hz, 1H), 3.65 (s, 3H), 3.50 (d, J=11.0 Hz, 1H), 3.02-2.85 (m, 1H), 2.23-2.12 (m, 1H), 1.89-1.73 (m, 4H), 1.63-1.56 (m, 1H)

Intermediate 8.3
(2-(3-bromophenyl)-2-cyclobutyl-2-hydroxyacetic acid)

Cesium carbonate (230.1 mg, 0.71 mmol), triethyl phosphite (1.21 mL, 7.06 mmol), methyl 2-(3-bromophenyl)-2-cyclobutylacetate (1 g, 3.53 mmol) were added to a 100 mL flask under oxygen atmosphere. DMSO (20 mL) was added and then the mixture was stirred at rt under oxygen atmosphere for 72 h. The solution was then diluted with water (100 mL), extracted with EtOAc (3×100 mL), dried over sodium sulfate, filtered, and concentrated. The crude product was purified by chromatography on silica gel to afford methyl 2-(3-bromophenyl)-2-cyclobutyl-2-hydroxyacetate (250 mg, 24% yield). The aqueous layer was acidified with 1 M HCl solution to pH 5 and extracted with a mixture of $CHCl_3$:IPA (9:1), the combined organic phases were dried over sodium sulfate, filtered and concentrated to get 2-(3-bromophenyl)-2-cyclobutyl-2-hydroxy-acetic acid (450 mg, 45% yield) which was used in next step without any further purification. LCMS (ESI) m/z: 283.3, 285.3 $[M+H]^+$.

Intermediate 8.4 (2-(2-(3-bromophenyl)-2-cyclobutyl-2-hydroxyacetyl)-N-methylhydrazinecarbothioamide)

A mixture of 2-(3-bromophenyl)-2-cyclobutyl-2-hydroxyacetic acid (550 mg, 1.93 mmol), N-methylhydrazinecarbothioamide (0.3 g, 2.89 mmol), HATU (1.1 g, 2.89 mmol) and DIPEA (1 mL, 5.79 mmol) was dissolved in DMF (19.3 mL) and was stirred at rt for 20 h. The reaction mixture was quenched with saturated aqueous solution of $NH_4Cl$ and extracted with $CHCl_3$:IPA (9:1). The combined organic layers were dried over sodium sulfate, filtered and concentrated. The crude residue was purified by chromatography on C18 silica gel (0-100% acetonitrile in ammonium bicarbonate buffer, pH=10) to obtain 2-(2-(3-bromophenyl)-2-cyclobutyl-2-hydroxyacetyl)-N-methylhydrazinecarbothioamide (580 mg, 81% yield). LCMS (ESI) m/z: 372.3, 374.2 $[M+H]^+$

Intermediate 8.5 ((3-bromophenyl)(cyclobutyl)(5-mercapto-4-methyl-4H-1,2,4-triazol-3-yl)methanol)

A solution of 2-(2-(3-bromophenyl)-2-cyclobutyl-2-hydroxyacetyl)-N-methylhydrazine carbothioamide (580 mg, 1.56 mmol) in 1 M NaOH solution (4.9 mL, 4.86 mmol) was stirred at 50° C. for 20 h. The reaction mixture was acidified with 1 N HCl solution to pH 4. The resulting mixture was extracted with $CHCl_3$:IPA (9:1). Combined organic layers were dried over sodium sulfate, filtered and concentrated to obtain (3-bromophenyl)(cyclobutyl)(5-mercapto-4-methyl-4H-1,2,4-triazol-3-yl)methanol (490 mg, 89% yield) which was used in next step without any further purification. LCMS (ESI) m/z: 354.2, 356.2 $[M+H]^+$

Intermediate 8.6 ((3-bromophenyl)(cyclobutyl)(4-methyl-4H-1,2,4-triazol-3-yl)methanol)

To a solution of (3-bromophenyl)(cyclobutyl)(5-mercapto-4-methyl-4H-1,2,4-triazol-3-yl)methanol (490 mg, 1.38 mmol) in DCM (10 mL) and acetic acid (2.5 mL) was added hydrogen peroxide, 30% (0.57 mL, 5.53 mmol). The reaction mixture was stirred at rt for 1 h then was quenched with saturated aqueous $NaHCO_3$ solution and extracted with DCM (3×). The combined organic layer was dried over sodium sulfate, filtered and evaporated to afford (3-bromophenyl)(cyclobutyl)(4-methyl-4H-1,2,4-triazol-3-yl)methanol (402 mg, 90% yield) which was used in next step without any further purification. LCMS (ESI) m/z: 322.4, 324.4 $[M+H]^+$

Intermediate 8.7 (tert-butyl ((2-(3-(cyclobutyl(hydroxy)(4-methyl-4H-1,2,4-triazol-3-yl)methyl)phenyl)-3-oxo-7-(trifluoromethyl)isoindolin-5-yl)methyl)(1-methylcyclobutyl)carbamate)

To a screw capped vial (3-bromophenyl)(cyclobutyl)(4-methyl-4H-1,2,4-triazol-3-yl)methanol (100 mg, 0.31 mmol), tert-butyl (1-methylcyclobutyl)((3-oxo-7-(trifluoromethyl)isoindolin-5-yl)methyl)carbamate (Intermediate A, 160.8 mg, 0.40 mmol), XantPhos Pd G3 (29.4 mg, 0.03 mmol) and cesium carbonate (303.5 mg, 0.93 mmol) was added degassed tert-amyl alcohol (1.6 mL) under nitrogen atmosphere. The reaction was heated at 110° C. for 20 h. The reaction mixture was cooled down to rt, filtered through Celite and concentrated. The crude product was purified by chromatography on silica gel (0-10% MeOH in DCM) to obtain tert-butyl ((2-(3-(cyclobutyl(hydroxy)(4-methyl-4H-1,2,4-triazol-3-yl)methyl)phenyl)-3-oxo-7-(trifluoromethyl)isoindolin-5-yl)methyl)(1-methylcyclobutyl)carbamate (80 mg, 40% yield). LCMS (ESI) m/z: 640.6 $[M+H]^+$

Example 8: Compounds 1 and 2

To a stirred solution tert-butyl ((2-(3-(cyclobutyl(hydroxy)(4-methyl-4H-1,2,4-triazol-3-yl)methyl)phenyl)-3-oxo-7-(trifluoromethyl)isoindolin-5-yl)methyl)(1-methylcyclo-butyl)carbamate (80 mg, 0.13 mmol) in methanol (0.5 mL) was added 4 M HCl in dioxane (0.63 mL, 2.5 mmol) at rt for 1 h. The reaction was concentrated and crude was purified by chromatography on C18 silica gel (acetonitrile in ammonium formate buffer, pH=3.8). Appropriate fractions were concentrated, frozen and lyophilized to provide (28 mg, 42% yield) the desired product as a mixture of diastereoisomers.

The above racemate was further purified by chiral SFC (Column=AS; Column dimensions=250 mm×10 mm×5 μm; Flow rate=10 mL/min; Run time=6 min; Column temperature=40° C.) with 0.1% ammonium hydroxide-40% IPA-carbon dioxide) to afford:

(R)-2-(3-(cyclobutyl(hydroxy)(4-methyl-4H-1,2,4-triazol-3-yl)methyl)phenyl)-6-(((1-methylcyclobutyl)amino)methyl)-4-(trifluoromethyl)isoindolin-1-one (peak 1) (Compound 1; 8.2 mg, 12% yield). LCMS (ESI) m/z: 540.5 $[M+H]^+$ $^1$H NMR (400 MHz, DMSO-$d_6$) δ 8.33 (s, 1H), 8.02 (s, 1H), 7.97 (s, 1H), 7.90 (s, 1H), 7.74 (d, J=8.1 Hz, 1H), 7.36 (t, J=8.0 Hz, 1H), 6.93 (d, J=7.8 Hz, 1H), 6.09 (s, 1H), 5.11 (s, 2H), 3.80 (s, 2H), 3.45 (m, 1H), 3.28 (s, 3H), 2.15-1.93 (m, 5H), 1.66 (m, 6H), 1.38 (m, 1H), 1.21 (s, 3H).

(S)-2-(3-(cyclobutyl(hydroxy)(4-methyl-4H-1,2,4-triazol-3-yl)methyl)phenyl)-6-(((1-methylcyclobutyl)amino)methyl)-4-(trifluoromethyl)isoindolin-1-one (peak 2) (Compound 2; 8.4 mg, 12% yield). LCMS (ESI) m/z: 540.5 $[M+H]^+$ $^1$HNMR (400 MHz, DMSO-$d_6$) δ 8.33 (s, 1H), 8.02 (s, 1H), 7.97 (s, 1H), 7.91 (s, 1H), 7.74 (dd, J=8.1, 1.5 Hz, 1H), 7.36 (t, J=8.0 Hz, 1H), 6.93 (d, J=7.8 Hz, 1H), 6.09 (s, 1H), 5.13 (s, 2H), 3.80 (s, 2H), 3.46 (m, 1H), 3.28 (s, 3H), 2.19-1.90 (m, 5H), 1.77-1.52 (m, 6H), 1.38 (m, 1H), 1.21 (s, 3H).

Example 9: Compound 3 and Compound 4

Figure 9:
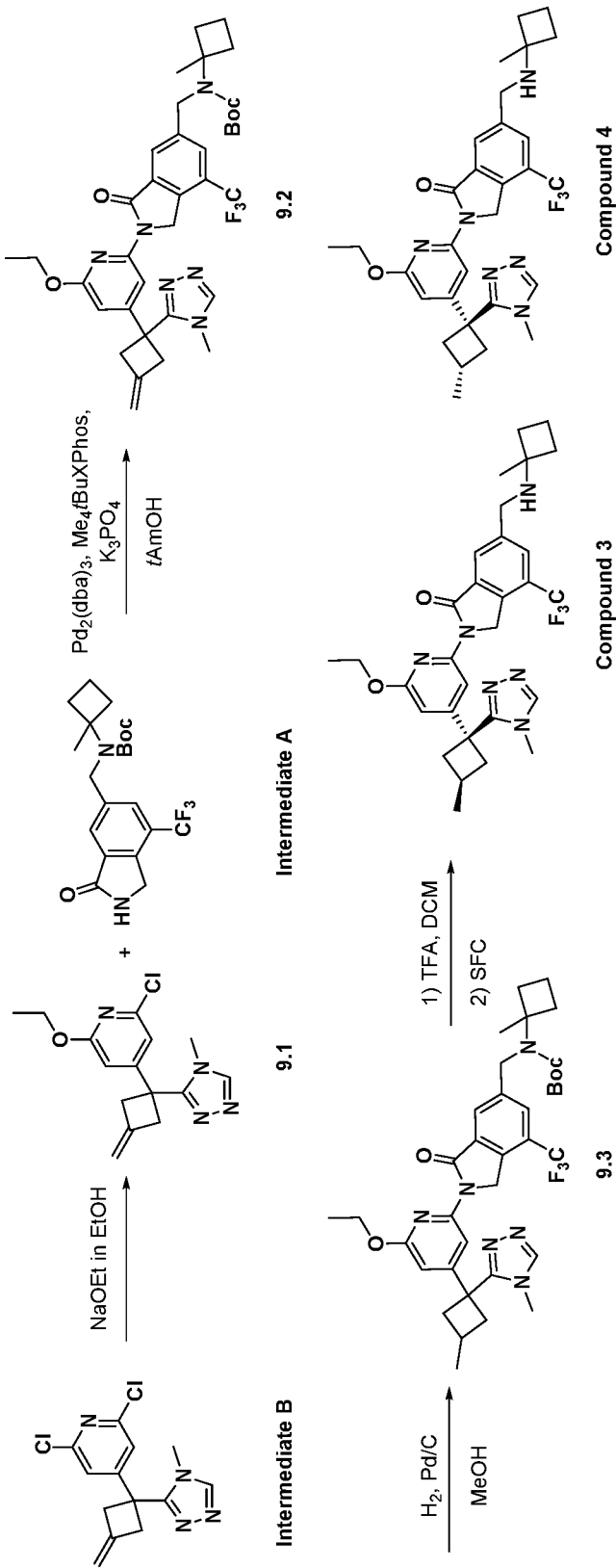

Compound 3 (2-(6-ethoxy-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one), and Compound 4 (2-(6-ethoxy-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one) can be synthesized according to Scheme 9, FIG. 9.

Intermediate 1: (2-chloro-6-ethoxy-4-(1-(4-methyl-4H-1,2,4-triazol-3-yl)-3-methylenecyclobutyl)pyridine)

2,6-dichloro-4-(1-(4-methyl-4H-1,2,4-triazol-3-yl)-3-methylenecyclobutyl)pyridine (100 mg, 0.34 mmol) was dissolved in sodium ethoxide (21% wt in EtOH) (2.5 mL, 6.78 mmol) in a sealed tube. The resulting mixture was stirred at 80° C. for 25 minutes, then cooled to rt and concentrated. The crude mixture was purified by chromatography on silica gel (0-50% EtOAc in heptanes) to afford 2-chloro-6-ethoxy-4-(1-(4-methyl-4H-1,2,4-triazol-3-yl)-3-methylenecyclobutyl)pyridine (58.9 mg, 57% yield). LCMS (ESI) m/z: 305.4/307.4 [M+H]$^+$ Intermediate 2: (tert-butyl ((2-(6-ethoxy-4-(1-(4-methyl-4H-1,2,4-triazol-3-yl)-3-methylenecyclobutyl)pyridin-2-yl)-3-oxo-7-(trifluoromethyl)isoindolin-5-yl)methyl)(1-methylcyclobutyl)carbamate)

A microwave vial equipped with a stir bar was charged with 2-chloro-6-ethoxy-4-(1-(4-methyl-4H-1,2,4-triazol-3-yl)-3-methylenecyclobutyl)pyridine (58.9 mg, 0.19 mmol), tert-butyl (1-methylcyclobutyl)((3-oxo-7-(trifluoromethyl)isoindolin-5-yl)methyl)carbamate (84.7 mg, 0.21 mmol), tris(dibenzylideneacetone)dipalladium(0) (7.1 mg, 0.01 mmol), Me$_4$tButylXphos (9.3 mg, 0.02 mmol), flame dried K$_3$PO$_4$ (82.1 mg, 0.39 mmol) and 4 Å MS (not weighed). The vial was then flushed with nitrogen for several minutes and degassed tert-amyl alcohol (0.97 mL) was added via syringe. The vial was capped and the reaction mixture was stirred at 110° C. for 18 h then cooled down to rt and adsorbed on silica gel. The crude mixture was purified by chromatography on silica gel (50-100% EtOAc in heptanes then 0-25% iPrOH/EtOAc) to afford tert-butyl ((2-(6-ethoxy-4-(1-(4-methyl-4H-1,2,4-triazol-3-yl)-3-methylenecyclobutyl)pyridin-2-yl)-3-oxo-7-(trifluoromethyl)isoindolin-5-yl)methyl)(1-methylcyclobutyl)carbamate (48.5 mg, 38% yield). LCMS (ESI) m/z: 667.5 [M+H]$^+$.

Intermediate 3: (tert-butyl ((2-(6-ethoxy-4-(3-methyl-1-(4-methyl-4H-1,2,4-triazol-3-yl)cyclobutyl)pyridin-2-yl)-3-oxo-7-(trifluoromethyl)isoindolin-5-yl)methyl)(1-methylcyclobutyl)carbamate)

A solution of tert-butyl ((2-(6-ethoxy-4-(1-(4-methyl-4H-1,2,4-triazol-3-yl)-3-methylenecyclobutyl)pyridin-2-yl)-3-oxo-7-(trifluoromethyl)isoindolin-5-yl)methyl)(1-methylcyclobutyl)carbamate (48.5 mg, 0.07 mmol) in methanol (0.73 mL) was degassed by bubbling nitrogen, then Pd/C, 10% (7.74 mg, 0.01 mmol) was added. The mixture was saturated with hydrogen by bubbling through the solution, then stirred at rt under 1 atmosphere of hydrogen for 17 h. The reaction mixture was degassed again by bubbling nitrogen, filtered through a 45 μm PTFE filter and evaporated to dryness to afford tert-butyl ((2-(6-ethoxy-4-(3-methyl-1-(4-methyl-4H-1,2,4-triazol-3-yl)cyclobutyl)pyridin-2-yl)-3-oxo-7-(trifluoromethyl)isoindolin-5-yl)methyl)(1-methylcyclobutyl)carbamate (46.4 mg, 95% yield), which was used in next step without any further purification. LCMS (ESI) m/z: 669.5 [M+H]$^+$ Compound 3 and Compound 4

Trifluroroacetic acid (0.35 mL) was added to a solution of tert-butyl ((2-(6-ethoxy-4-(3-methyl-1-(4-methyl-4H-1,2,4-triazol-3-yl)cyclobutyl)pyridin-2-yl)-3-oxo-7-(trifluoromethyl)isoindolin-5-yl)methyl)(1-methylcyclobutyl)carbamate (46.4 mg, 0.07 mmol) in DCM (0.35 mL) and the solution was stirred at rt for 1 h. The reaction mixture was diluted with toluene and concentrated to dryness, then basified with 1 N NaOH solution and extracted with a 4:1 mixture of CHCl$_3$/IPA (3×). The organics were combined, dried with over sodium sulfate, filtered and concentrated to afford 39.8 mg of the desired product as a mixture of diastereoisomers.

The above racemate was further purified by chiral SFC (Column=IA; Column dimensions=250 mm×10 mm×5 μm; Detection wavelength=310 nm; Flow rate=10 mL/min; Run time=10 min; Column temperature=40° C.) with 0.1% ammonium hydroxide-40% IPA/carbon dioxide) to afford:

2-(6-ethoxy-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one (Compound 3, Peak 1, retention time=5.71 min) (15.8 mg, 40% yield). LCMS (ESI) m/z: 569.5 [M+H]$^+$ $^1$H NMR (400 MHz, DMSO-d$_6$) δ 8.41 (s, 1H), 8.03 (d, J=7.1 Hz, 2H), 7.88 (d, J=1.1 Hz, 1H), 6.42 (d, J=1.1 Hz, 1H), 5.18 (s, 2H), 4.34 (q, J=7.0 Hz, 2H), 3.81 (s, 2H), 3.26 (s, 3H), 3.13-3.04 (m, 2H), 2.42-2.29 (m, 1H), 2.29-2.19 (m, 2H), 2.01-1.92 (m, 2H), 1.76-1.61 (m, 4H), 1.36 (t, J=7.0 Hz, 3H), 1.22 (s, 3H), 1.10 (d, J=6.5 Hz, 3H).

2-(6-ethoxy-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one (Compound 4, Peak 2, retention time=7.86 min) (4.8 mg, 12% yield). LCMS (ESI) m/z: 569.5 [M+H]$^+$. $^1$H NMR (400 MHz, DMSO-d$_6$) δ 8.34 (s, 1H), 8.05-8.01 (m, 3H), 6.55 (d, J=1.2 Hz, 1H), 5.19 (s, 2H), 4.35 (q, J=7.1 Hz, 2H), 3.81 (s, 2H), 3.23 (s, 3H), 2.87-2.75 (m, 2H), 2.60-2.54 (m, 3H), 2.01-1.92 (m, 2H), 1.77-1.62 (m, 4H), 1.36 (t, J=7.0 Hz, 3H), 1.22 (s, 3H), 1.08 (d, J=5.4 Hz, 3H).

Example 10: Compound 5 and Compound 6

Figure 10:
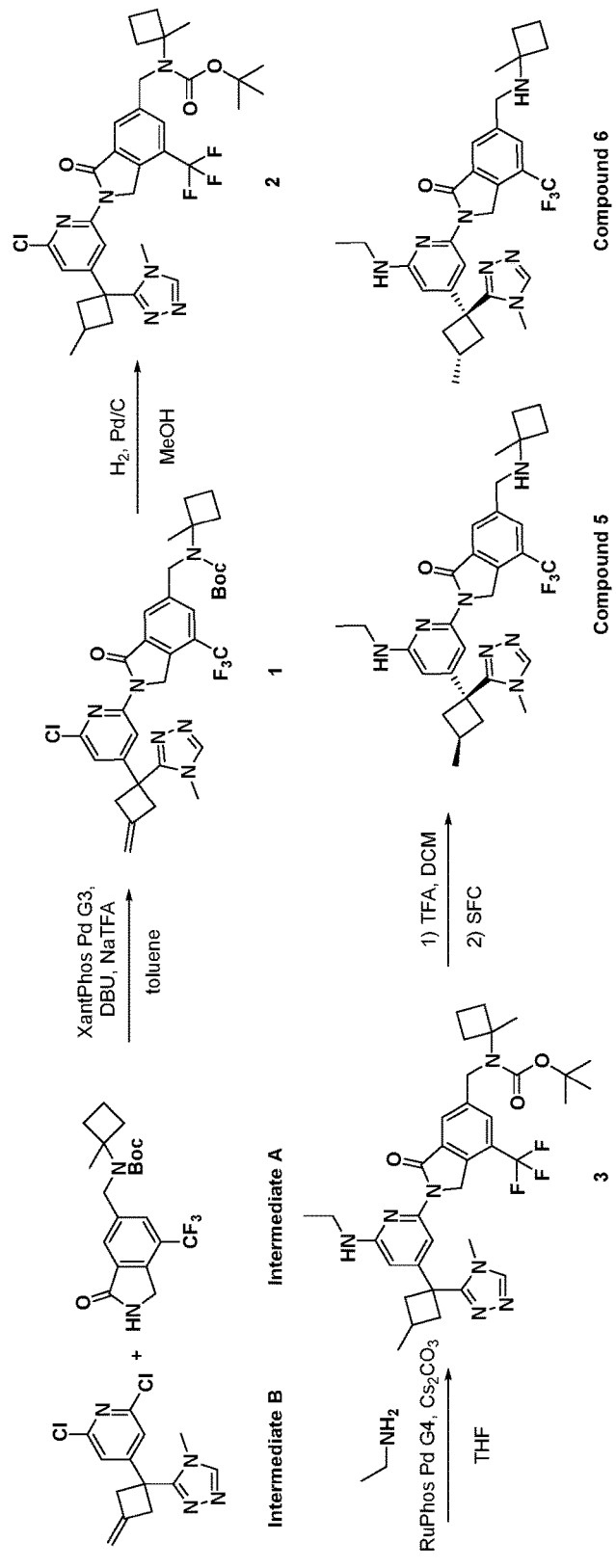

Compound 5 (2-(6-(ethylamino)-4-((1s,3s)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)-isoindolin-1-one), and Compound 6 (2-(6-(ethylamino)-4-((1r,3r)-3-methyl-1-(4-methyl-4H-1,2,4-triazol-3-yl)cyclobutyl)pyridin-2-yl)-6-(((1-methylcyclobutyl)amino)methyl)-4-(trifluoromethyl)-isoindolin-1-one), can be synthesized according to Scheme 10 (FIG. 10).

Intermediate 1: (tert-butyl ((2-(6-chloro-4-(1-(4-methyl-4H-1,2,4-triazol-3-yl)-3-methylenecyclobutyl)pyridin-2-yl)-3-oxo-7-(trifluoromethyl)isoindolin-5-yl)methyl)(1-methylcyclobutyl)carbamate)

A microwave vial equipped with a stir bar was charged with 2,6-dichloro-4-(1-(4-methyl-4H-1,2,4-triazol-3-yl)-3-methylenecyclobutyl)pyridine (15 mg, 0.05 mmol), tert-butyl (1-methylcyclobutyl)((3-oxo-7-(trifluoromethyl)isoindolin-5-yl)methyl)carbamate (22.3 mg, 0.06 mmol), sodium trifluoroacetate (13.8 mg, 0.10 mmol) and XantPhos Pd G3

(4.8 mg, 0.01 mmol). The vial was flushed with nitrogen for several minutes, then degassed toluene (0.51 mL) was added via syringe, followed by DBU (30.4 µl, 0.20 mmol). The vial was capped and the reaction mixture was stirred at 120° C. for 20 h. The reaction was cooled down to rt and the solvent was evaporated under an air flow. The crude mixture was purified by chromatography on silica gel (0-6% MeOH in DCM) to afford tert-butyl ((2-(6-chloro-4-(1-(4-methyl-4H-1,2,4-triazol-3-yl)-3-methylenecyclobutyl)pyridin-2-yl)-3-oxo-7-(trifluoromethyl)isoindolin-5-yl)methyl)(1-methyl-cyclobutyl)carbamate (23.8 mg, 71% yield), not completely clean, 36% yield when accounting for purity. Used as is in the next step. LCMS (ESI) m/z: 657.4 [M+H]$^+$.

Intermediate 2: (tert-butyl ((2-(6-chloro-4-(3-methyl-1-(4-methyl-4H-1,2,4-triazol-3-yl)cy-clobutyl)pyridin-2-yl)-3-oxo-7-(trifluoromethyl) isoindolin-5-yl)methyl)(1-methylcyclobutyl) carbamate A solution of tert-butyl ((2-(6-chloro-4-(1-(4-methyl-4H-1,2,4-triazol-3-yl)-3-methylenecyclobutyl)pyridin-2-yl)-3-oxo-7-(trifluoromethyl)isoindolin-5-yl)methyl)(1-methyl-cyclobutyl)carbamate (117.3 mg, 0.18 mmol) in methanol (1.8 mL) was degassed by bubbling nitrogen, then Pd/C, 10% (19 mg, 0.02 mmol) was added. The mixture was saturated with hydrogen by bubbling through the solution, then stirred at rt under 1 atmosphere of hydrogen for 28 h (more Pd/C was added after 16 h to get to completion). The reaction mixture was degassed by bubbling nitrogen, filtered through a 45 µm PTFE filter and evaporated to dryness. The crude mixture was purified by chromatography on silica gel (50-100% EtOAc in heptanes) to afford tert-butyl ((2-(6-chloro-4-(3-methyl-1-(4-methyl-4H-1,2,4-triazol-3-yl)cy-clobutyl)pyridin-2-yl)-3-oxo-7-(trifluoromethyl)isoindolin-5-yl)methyl)(1-methylcyclobutyl)carbamate (69.8 mg, 56% yield). LCMS (ESI) m/z: 659.7 [M+H]$^+$.

Intermediate 3: (tert-butyl ((2-(6-(ethylamino)-4-(3-methyl-1-(4-methyl-4H-1,2,4-triazol-3-yl)cy-clobutyl)pyridin-2-yl)-3-oxo-7-(trifluoromethyl) isoindolin-5-yl)methyl)(1-methylcyclobutyl) carbamate)

A microwave vial equipped with a stir bar was charged with tert-butyl ((2-(6-chloro-4-(3-methyl-1-(4-methyl-4H-1,2,4-triazol-3-yl)cyclobutyl)pyridin-2-yl)-3-oxo-7-(trifluo-romethyl)isoindolin-5-yl)methyl)(1-methylcyclobutyl)car-bamate (104.7 mg, 0.16 mmol), cesium carbonate (103.5 mg, 0.32 mmol) and RuPhos Pd G4 (13.5 mg, 0.02 mmol). The vial was flushed with nitrogen for several minutes, then degassed THF (1.6 mL) was added via syringe, followed by ethylamine, 2 M in THF (0.12 mL, 0.24 mmol). The vial was capped and the reaction mixture was stirred at 120° C. for 17 h. The reaction was cooled down to rt and the solvent was evaporated under an air flow. The crude residue was purified by chromatography on C18 silica gel (60-85% acetonitrile in ammonium formate buffer, pH=3.8). Appropriate fractions were concentrated, frozen and lyophilized to provide tert-butyl ((2-(6-(ethylamino)-4-(3-methyl-1-(4-methyl-4H-1,2, 4-triazol-3-yl)cyclobutyl)pyridin-2-yl)-3-oxo-7-(trifluorom-ethyl)isoindolin-5-yl)methyl)(1-methylcyclobutyl) carbamate (69.7 mg, 66% yield). LCMS (ESI) m/z: 668.8 [M+H]$^+$.

Compound 5 and Compound 6

Trifluoroacetic acid (0.52 mL) was added to a solution of tert-butyl ((2-(6-(ethylamino)-4-(3-methyl-1-(4-methyl-4H-1,2,4-triazol-3-yl)cyclobutyl)pyridin-2-yl)-3-oxo-7-(trifluo-romethyl)isoindolin-5-yl)methyl)(1-methylcyclobutyl)car-bamate (69.7 mg, 0.10 mmol) in DCM (0.52 mL) and the solution was stirred at rt for 1 h. The reaction mixture was diluted with toluene and concentrated to dryness, then basified with 1 N NaOH solution and extracted with a 4:1 mixture of CHCl$_3$/IPA (3×). The organics were combined, dried with over sodium sulfate, filtered and concentrated to afford 54.9 mg of the desired product as a mixture of diastereoisomers.

The above racemate was further purified by chiral SFC (Column=ID; Column dimensions=250 mm×10 mm×5 µm; Detection wavelength=320 nm; Flow rate=10 mL/min; Run time=14 min; Column temperature=40° C.) with 0.1% ammonium hydroxide-5 0% IPA/carbon dioxide) to afford:

2-(6-(ethylamino)-4-((1s,3s)-3-methyl-1-(4-methyl-4H-1,2,4-triazol-3-yl)cyclobutyl)-pyridin-2-yl)-6-(((1-methyl-cyclobutyl)amino)methyl)-4-(trifluoromethyl)isoindolin-1-one (Compound 5, Peak 1, retention time=4.3 min) (23.5 mg, 40% yield). LCMS (ESI) m/z: 568.5 [M+H]$^+$ $^1$H NMR (400 MHz, DMSO-d$_6$) δ 8.40 (s, 1H), 8.01 (s, 1H), 7.99 (s, 1H), 7.57 (s, 1H), 6.68 (t, J=5.1 Hz, 1H), 5.98 (s, 1H), 5.13 (s, 2H), 3.80 (s, 2H), 3.30-3.20 (m, 5H), 3.06 (t, J=9.6 Hz, 2H), 2.33 (dt, J=15.3, 7.7 Hz, 1H), 2.17 (t, J=10.2 Hz, 2H), 2.03-1.90 (m, 2H), 1.77-1.60 (m, 4H), 1.22 (s, 3H), 1.14 (t, J=7.2 Hz, 3H), 1.10 (d, J=6.6 Hz, 3H).

2-(6-(ethylamino)-4-((1r,3r)-3-methyl-1-(4-methyl-4H-1, 2,4-triazol-3-yl)cyclobutyl)-pyridin-2-yl)-6-(((1-methylcy-clobutyl)amino)methyl)-4-(trifluoromethyl)isoindolin-1-one (Compound 6, Peak 2, retention time=5.8 min) (7.1 mg, 12% yield). LCMS (ESI) m/z: 568.5 [M+H]$^+$ $^1$H NMR (400 MHz, DMSO-d$_6$) δ 8.34 (s, 1H), 8.01 (s, 1H), 7.99 (s, 1H), 7.70 (d, J=0.9 Hz, 1H), 6.68 (t, J=5.3 Hz, 1H), 6.12 (d, J=0.9 Hz, 1H), 5.15 (s, 2H), 3.81 (s, 2H), 3.30-3.21 (m, 5H), 2.79-2.71 (m, 2H), 2.63-2.52 (m, 3H), 2.03-1.92 (m, 2H), 1.70 (ddd, J=20.3, 10.1, 4.9 Hz, 4H), 1.23 (s, 3H), 1.15 (t, J=7.1 Hz, 3H), 1.08 (d, J=5.9 Hz, 3H).

Example 11: Compound 7

Figure 11:
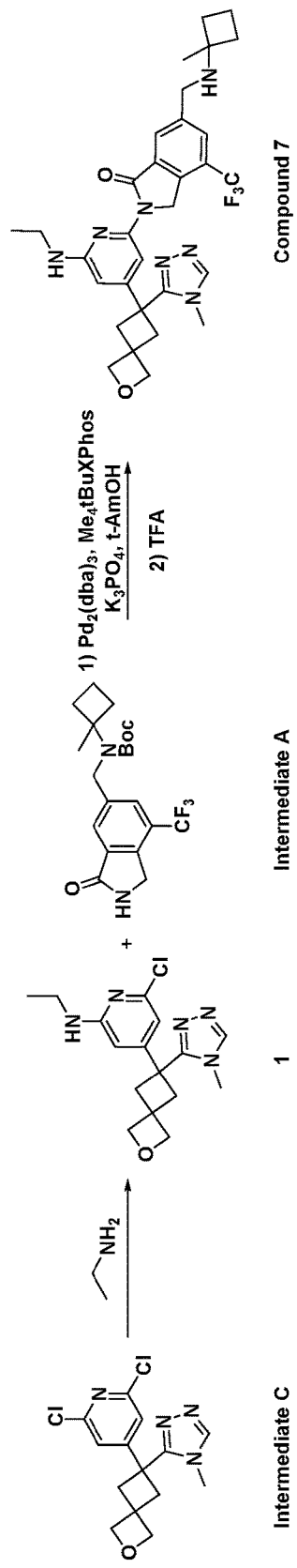

Compound 7 can be synthesized according to Scheme 11 (FIG. 11).

Intermediate 1: (6-chloro-N-ethyl-4-(6-(4-methyl-4H-1,2,4-triazol-3-yl)-2-oxaspiro[3.3]heptan-6-yl) pyridin-2-amine)

Ethylamine solution (1 mL, 19.14 mmol) was added to 2,6-dichloro-4-(6-(4-methyl-4H-1,2,4-triazol-3-yl)-2-oxas-piro[3.3]heptan-6-yl)pyridine (50 mg, 0.15 mmol) and reac-tion was stirred at 80° C. for 16 h. Reaction was concen-trated and the crude residue was purified by chromatography on C18 silica gel (acetonitrile in ammonium formate buffer, pH=3.8). Appropriate fractions were concentrated, frozen and lyophilized to provide 6-chloro-N-ethyl-4-(6-(4-methyl-4H-1,2,4-triazol-3-yl)-2-oxaspiro[3.3]heptan-6-yl)pyridin-2-amine (42 mg, 82% yield). LCMS (ESI) m/z: 334.5 [M+H]$^+$.

Compound 7

A microwave vial equipped with a stir bar was charged with 6-chloro-N-ethyl-4-(6-(4-methyl-4H-1,2,4-triazol-3-yl)-2-oxaspiro[3.3]heptan-6-yl)pyridin-2-amine (35 mg, 0.10 mmol), tert-butyl (1-methylcyclobutyl)((3-oxo-7-(trif-luoromethyl)isoindolin-5-yl)methyl)-carbamate (45.9 mg, 0.12 mmol), tris(dibenzylideneacetone)dipalladium(0) (9.6 mg, 0.01 mmol), Me$_4$tButylXphos (10.1 mg, 0.02 mmol) and flame dried K$_3$PO$_4$ (44.5 mg, 0.21 mmol). The vial was then flushed with nitrogen for several minutes and degassed t-AmOH (1 mL) was added via syringe. The vial was capped and the reaction mixture was stirred at 110° C. for 16 h, then cooled down to rt and adsorbed on silica. The crude mixture was purified by chromatography on silica gel (5-30% MeOH in DCM) to afford 17 mg of Boc-protected intermediate. The intermediate was dissolved in DCM (2 mL), trifluoroacetic acid (1 mL) was added and stirred for 1 h. Solvent was evaporated and the crude mixture was dissolved in MeOH (2 mL), saturated aqueous NaHCO$_3$ solution was added and stirred for 10 minutes. Solvent was evaporated and crude was purified by chromatography on C18 silica gel (acetonitrile in 0.5% formic acid buffer). Appropriate fractions were concentrated, frozen and lyophilized to obtain 2-(6-(ethylamino)-4-(6-(4-methyl-4H-1,2,4-triazol-3-yl)-2-oxaspiro[3.3]heptan-6-yl)pyridin-2-yl)-6-(((1-methylcyclobutyl)amino)methyl)-4-(trifluoro-methyl)isoindolin-1-one (8 mg, 13% yield). LCMS (ESI) m/z: 596.5 [M+H]$^+$. $^1$H NMR (400 MHz, DMSO-d$_6$) δ 9.14 (s, 1H), 8.40 (s, 1H), 8.30-8.21 (m, 2H), 7.50 (s, 1H), 6.79-6.72 (m, 1H), 6.03 (s, 1H), 5.21 (s, 2H), 4.63 (s, 2H), 4.48 (s, 2H), 4.36-4.28 (m, 2H), 3.28-3.16 (m, 7H), 2.87-2.78 (m, 2H), 1.97-1.80 (m, 6H), 1.56 (s, 3H), 1.15 (t, J=7.2 Hz, 3H).

Example 12: Compound 8 and Compound 9

Figure 12:
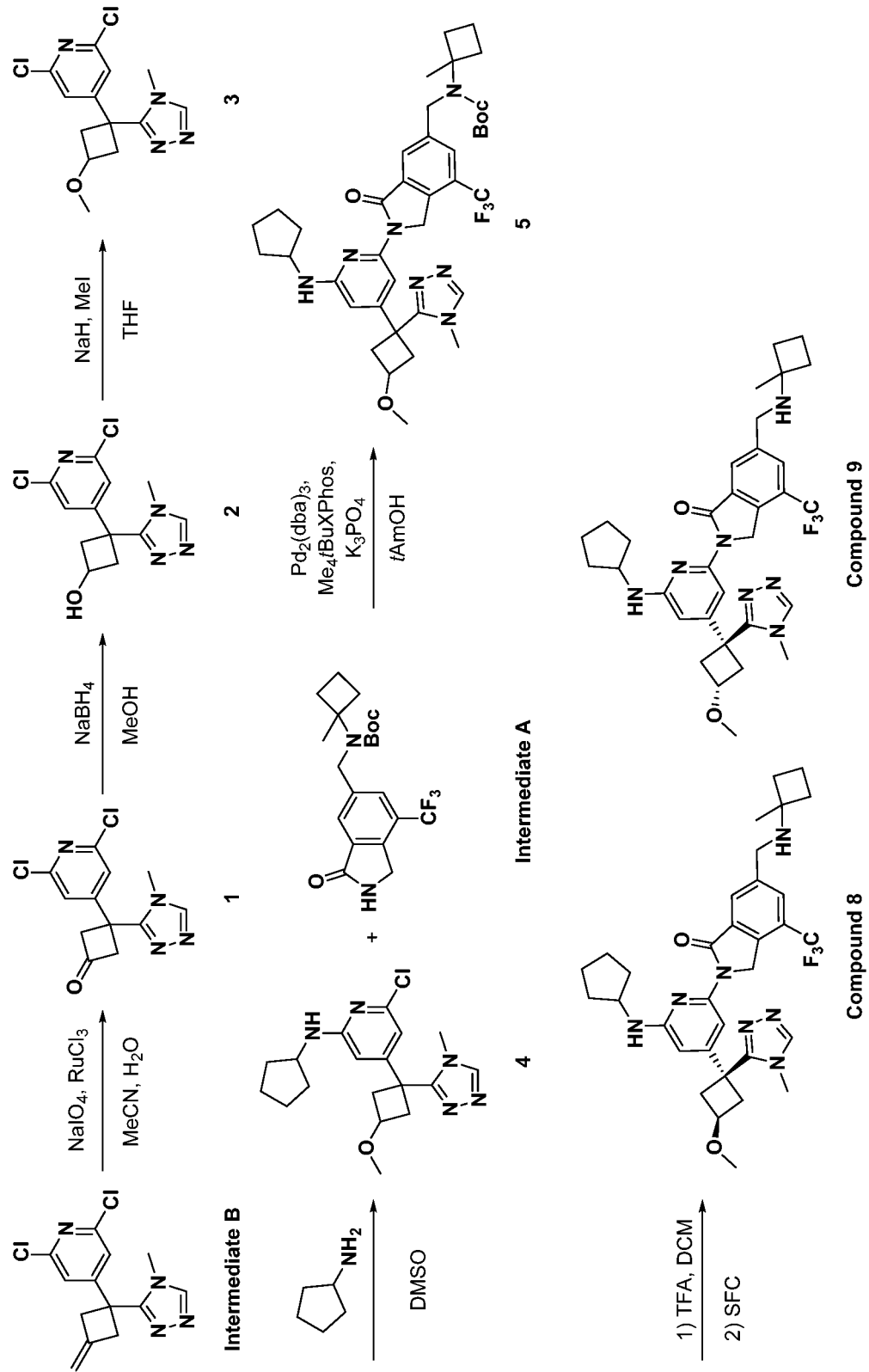

Compound 8 (2-(6-(cyclopentylamino)-4-((1s,3s)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one) and
Compound 9 (2-(6-(cyclopentylamino)-4-((1r,3r)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one), can be synthesized according to Scheme 12 (FIG. 12).

Intermediate 1: (3-(2,6-dichloropyridin-4-yl)-3-(4-methyl-4H-1,2,4-triazol-3-yl)cyclobutanone)

NaIO$_4$ (1.014 mg, 4.74 mmol) was added to a solution of 2,6-dichloro-4-(1-(4-methyl-4H-1,2,4-triazol-3-yl)-3-methylenecyclobutyl)pyridine (700 mg, 2.37 mmol) and RuCl$_3$ (19.7 mg, 0.09 mmol) in 49 mL of a 6:1 mixture of MeCN:H$_2$O. The solution was stirred at room temperature for 5 h. The reaction mixture was quenched with a 10% aqueous solution of Na$_2$S$_2$O$_3$ and extracted with CHCl$_3$:IPA (9:1). The organic layers were collected and washed with saturated aqueous NaCl solution, dried over sodium sulfate, filtered and concentrated. The crude mixture was purified by chromatography on silica gel (0-15% MeOH in DCM) to afford 3-(2,6-dichloropyridin-4-yl)-3-(4-methyl-4H-1,2,4-triazol-3-yl)cyclobutanone (254 mg, 36% yield) as a white solid. LCMS (ESI) m/z: 297.3, 299.3 [M+H]$^+$.

Intermediate 2: (3-(2,6-dichloropyridin-4-yl)-3-(4-methyl-4H-1,2,4-triazol-3-yl)cyclobutanol)

To a stirred solution of 3-(2,6-dichloropyridin-4-yl)-3-(4-methyl-4H-1,2,4-triazol-3-yl)cyclobutanone (250 mg, 0.84 mmol) in methanol (4.2 mL) was added sodium borohydride (38.2 mg, 1.01 mmol) at 0° C. After completion, the reaction was quenched with saturated aqueous NH$_4$Cl solution and extracted with CHCl$_3$:IPA (9:1). The combined extract was dried over sodium sulfate and concentrated to obtain 3-(2,6-dichloropyridin-4-yl)-3-(4-methyl-4H-1,2,4-triazol-3-yl) cyclobutanol (230 mg, 91% yield) which was used in next step without any further purification. LCMS (ESI) m/z: 299.3, 301.3 [M+H]$^+$.

Intermediate 3: (2,6-dichloro-4-(3-methoxy-1-(4-methyl-4H-1,2,4-triazol-3-yl)cyclobutyl)pyridine)

To a cooled solution of 3-(2,6-dichloropyridin-4-yl)-3-(4-methyl-4H-1,2,4-triazol-3-yl)cyclobutanol (180 mg, 0.60 mmol) in THF (0.5 mL) was added sodium hydride (48.1 mg, 1.2 mmol) at 0° C. After stirring for 10 minutes at 0° C., it was warm to rt and stirred for additional 1 h. The reaction was once again cooled to 0° C. and methyl iodide (74.9 µL, 1.2 mmol) was added to reaction and allowed to stir for 20 h. Solvent was evaporated and crude was purified by chromatography on C18 silica gel (0-50% acetonitrile in ammonium formate buffer, pH=3.8). Appropriate fractions were concentrated, frozen and lyophilized to obtain 2,6-dichloro-4-(3-methoxy-1-(4-methyl-4H-1,2,4-triazol-3-yl)cyclobutyl)pyridine (80 mg, 42% yield) LCMS (ESI) m/z: 313.3, 315.2 [M+H]$^+$.

Intermediate 4: (6-chloro-N-cyclopentyl-4-(3-methoxy-1-(4-methyl-4H-1,2,4-triazol-3-yl)cyclobutyl)pyridin-2-amine)

A mixture of 2,6-dichloro-4-(3-methoxy-1-(4-methyl-4H-1,2,4-triazol-3-yl)cyclobutyl)pyridine (80 mg, 0.26 mmol) and cyclopentylamine (0.25 mL, 2.55 mmol) in DMSO (1.3 mL) was heated to 120° C. for 4 h. Solvent was evaporated and crude was purified by chromatography on C18 silica gel (0-100% acetonitrile in ammonium formate buffer, pH=3.8). Appropriate fractions were concentrated, frozen and lyophilized to obtain 6-chloro-N-cyclopentyl-4-(3-methoxy-1-(4-methyl-4H-1,2,4-triazol-3-yl)cyclobutyl)pyridin-2-amine (80 mg, 875% yield). LCMS (ESI) m/z: 362.3, 364.3 [M+H]$^+$.

Intermediate 5: (tert-butyl ((2-(6-(cyclopentylamino)-4-(3-methoxy-1-(4-methyl-4H-1,2,4-triazol-3-yl)cyclobutyl)pyridin-2-yl)-3-oxo-7-(trifluoromethyl)isoindolin-5-yl)methyl)(1-methylcyclobutyl)carbamate)

Microwave vial was charged with obtain 6-chloro-N-cyclopentyl-4-(3-methoxy-1-(4-methyl-4H-1,2,4-triazol-3-yl)cyclobutyl)pyridin-2-amine (50 mg, 0.14 mmol), tert-butyl (1-methylcyclobutyl)((3-oxo-7-(trifluoromethyl)isoindolin-5-yl)methyl)carbamate (60.7 mg, 0.15 mmol), Me$_4$tButylXphos (6.6 mg, 0.01 mmol), Pd$_2$(dba)$_3$ (6.3 mg, 0.01 mmol) and K$_3$PO$_4$ (88.0 mg, 0.41 mmol). The vial was purged with nitrogen before degassed anhydrous tert-Amyl alcohol (1.6 mL) was added and the vial was sealed. The reaction mixture was stirred at 120° C. for 15 h. Solvent was evaporated and crude was purified by chromatography on C18 silica gel (0-100% acetonitrile in ammonium formate buffer, pH=3.8). Appropriate fractions were concentrated, frozen and lyophilized to obtain tert-butyl ((2-(6-(cyclopentylamino)-4-(3-methoxy-1-(4-methyl-4H-1,2,4-triazol-3-yl)cyclobutyl)pyridin-2-yl)-3-oxo-7-(trifluoromethyl)isoindolin-5-yl)methyl)(1-methylcyclobutyl)carbamate (90 mg, 90% yield) as a white solid. LCMS (ESI) m/z: 724.7 [M+H]$^+$.

To a stirred solution of tert-butyl ((2-(6-(cyclopentylamino)-4-(3-methoxy-1-(4-methyl-4H-1,2,4-triazol-3-yl)cyclobutyl)pyridin-2-yl)-3-oxo-7-(trifluoromethyl)isoindolin-5-yl)methyl)(1-methylcyclobutyl)carbamate (90.5 mg, 0.13 mmol) in methanol (0.5 mL) was added 4 M HCl solution in dioxane (0.63 mL, 2.5 mmol). After completion, the reaction was concentrated and the crude product was purified by semi-prep. LCMS (70-90% gradient of acetonitrile in ammonium bicarbonate buffer, pH=10). Appropriate fractions were concentrated, frozen and lyophilized to provide 77 mg.

The above racemate was further purified by chiral SFC (Column=ID; Column dimensions=250 mm×10 mm×5 µm; Flow rate=10 mL/min; Run time=9 min; Column temperature=40° C.) with 0.1% ammonium hydroxide-40% IPA/MeCN-carbon dioxide) to afford:

2-(6-(cyclopentylamino)-4-((1 s,3s)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one (peak 1) (Compound 8, 19 mg, 24%). LCMS (ESI) m/z: 624.5 [M+H]$^+$ $^1$H NMR (400 MHz, DMSO-d$_6$) δ 8.41 (s, 1H), 8.02-7.94 (m, 2H), 7.52 (d, J=1.1 Hz, 1H), 6.72 (d, J=5.9 Hz, 1H), 5.98 (s, 1H), 5.12 (s, 2H), 4.06-3.96 (m, 1H), 3.84-3.73 (m, 3H), 3.28-3.19 (m, 5H), 3.15 (s, 3H), 2.40-2.32 (m, 1H), 2.06-1.85 (m, 5H), 1.73-1.60 (m, 6H), 1.58-1.39 (m, 4H), 1.20 (s, 3H).

2-(6-(cyclopentylamino)-4-((1r,3r)-3-methoxy-1-(4-methyl-4H-1,2,4-triazol-3-yl)cyclobutyl)pyridin-2-yl)-6-(((1-methylcyclobutyl)amino)methyl)-4-(trifluoromethyl)isoindolin-1-one (peak 2) (Compound 9, 6 mg, 8%). LCMS (ESI) m/z: 624.5 [M+H]$^+$ $^1$H NMR (400 MHz, DMSO-d$_6$) δ 8.36 (s, 1H), 8.03-7.98 (m, 2H), 7.63 (s, 1H), 6.75 (d, J=5.9 Hz, 1H), 6.12 (s, 1H), 5.15 (s, 2H), 4.15-3.99 (m, 1H), 3.81 (s, 2H), 3.27 (s, 2H), 3.17 (s, 3H), 2.98-2.89 (m, 2H), 2.81-2.78 (m, 2H), 2.08 (d, J=8.7 Hz, 1H), 2.02-1.81 (m, 4H), 1.76-1.62 (m, 6H), 1.60-1.41 (m, 5H), 1.23 (s, 3H).

Example 13: Compound 10 and Compound 11

Figure 13:
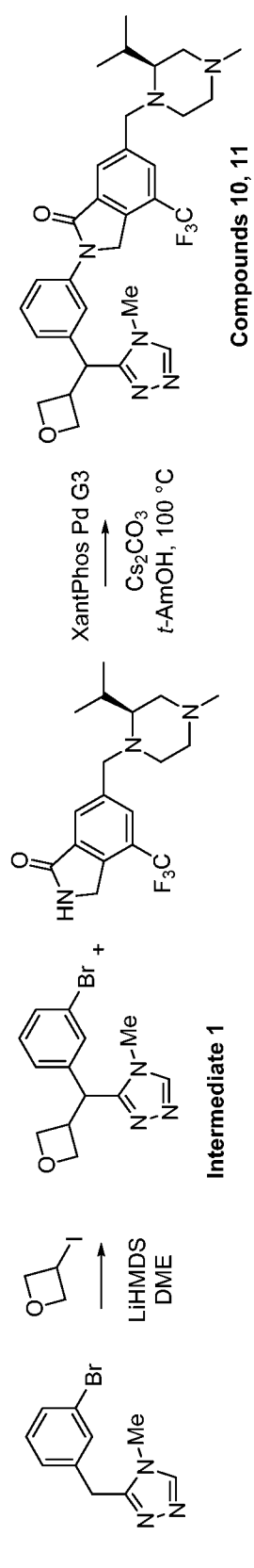

Compounds 10 and 11 can be synthesized according to Scheme 13, FIG. 13.

Intermediate 1: (3-((3-bromophenyl)(oxetan-3-yl)methyl)-4-methyl-4H-1,2,4-triazole)

To a solution of 3-(3-bromobenzyl)-4-methyl-4H-1,2,4-triazole (100 mg, 0.397 mmol) in anhydrous 1,2-dimethoxyethane (1.3 mL) under nitrogen and at −10° C. added lithium bis(trimethylsilyl)amide (0.6 mL, 1.0 M in THF, 0.6 mmol). The stirring mixture was allowed to warm to room temperature and stirring continued for 48 h. Additional lithium bis(trimethylsilyl)amide (0.6 mL, 1.0 M in THF) was added and stirred for 1 h, then the reaction was quenched by the addition of saturated aq NH$_4$Cl and extracted with CH$_2$Cl$_2$. The organic layer was dried over MgSO$_4$, filtered and concentrated. The crude mixture was purified by chromatography on silica gel (0-100% 80:15:2.5 CH$_2$Cl$_2$/MeOH/NH$_4$OH in heptane) to afford 3-((3-bromophenyl)(oxetan-3-yl)methyl)-4-methyl-4H-1,2,4-triazole as a colorless liquid (43.6 mg, 36% yield); $^1$H NMR (400 MHz, CDCl$_3$) δ 8.06 (s, 1H), 7.46-7.38 (m, 1H), 7.38-7.31 (m, 1H), 7.21 (dd, J=7.8 Hz, 7.8 Hz, 1H), 7.19-7.07 (m, 1H), 5.06-4.99 (m, 1H), 4.73-4.61 (m, 1H), 4.51-4.43 (m, 1H), 4.37 (d, J=7.0 Hz, 7.0 Hz, 1H), 4.35-4.24 (m, 1H), 4.04-3.88 (m, 1H), 3.39 (s, 3H); LCMS (ESI) m/z: 308, 310 [M+H]$^+$.

Compound 10 and Compound 11

Into a vial was weighed 3-((3-bromophenyl)(oxetan-3-yl)methyl)-4-methyl-4H-1,2,4-triazole (43.6 mg, 0.141 mmol), (S)-6-((2-isopropyl-4-methylpiperazin-1-yl)methyl)-4-(trifluoromethyl)isoindolin-1-one (55.3 mg, 0.156 mmol), [(4,5-bis(diphenylphosphino)-9,9-dimethylxanthene)-2-(2'-amino-1,1'-biphenyl)]palladium(II) methanesulfonate (13.6 mg, 0.014 mmol), and cesium carbonate (138 mg, 0.424 mmol). Under a stream of nitrogen gas, the vessel was charged with anhydrous 2-methyl-2-butanol (0.7 mL) and the vial was sealed. The reaction mixture was stirred at 100° C. for 5 h. After cooling to rt, the mixture was concentrated and purified by flash column chromatography (0-100% 80:15:2.5 CH$_2$Cl$_2$/MeOH/NH$_4$OH in CH$_2$Cl$_2$), HPLC, and chiral SFC to afford:

6-(((S)-2-isopropyl-4-methylpiperazin-1-yl)methyl)-2-(3-((S)-(4-methyl-4H-1,2,4-triazol-3-yl)(oxetan-3-yl)methyl)phenyl)-4-(trifluoromethyl)isoindolin-1-one (peak 1) (Compound 10, 7.3 mg, 9%), and 6-(((S)-2-isopropyl-4-methylpiperazin-1-yl)methyl)-2-(3-((R)-(4-methyl-4H-1,2,4-triazol-3-yl)(oxetan-3-yl)methyl)phenyl)-4-(trifluoromethyl)isoindolin-1-one (peak 2) (Compound 11, 6.7 mg, 8%); LCMS (ESI) m/z: 583.3 [M+H]$^+$; $^1$H NMR (500 MHz, DMSO-d$_6$) δ 8.36 (s, 1H), 7.98 (s, 1H), 7.91 (s, 2H), 7.82 (dd, J=8.1, 2.1 Hz, 1H), 7.40 (t, J=7.9 Hz, 1H), 7.02 (d, J=7.7 Hz, 1H), 5.17 (s, 2H), 4.81-4.71 (m, 2H), 4.54-4.43 (m, 2H), 4.32-4.26 (m, 1H), 4.21 (d, J=14.4 Hz, 1H), 3.94-3.82 (m, 1H), 3.43-3.32 (m, 5H), 2.69-2.54 (m, 2H), 2.32-2.18 (m, 3H), 2.14 (s, 3H), 2.01-1.86 (m, 2H), 0.93 (d, J=6.6 Hz, 3H), 0.88 (d, J=6.7 Hz, 3H).

Example 14: Compound 12, Compound 13, Compound 14, and Compound 15

Figure 14:
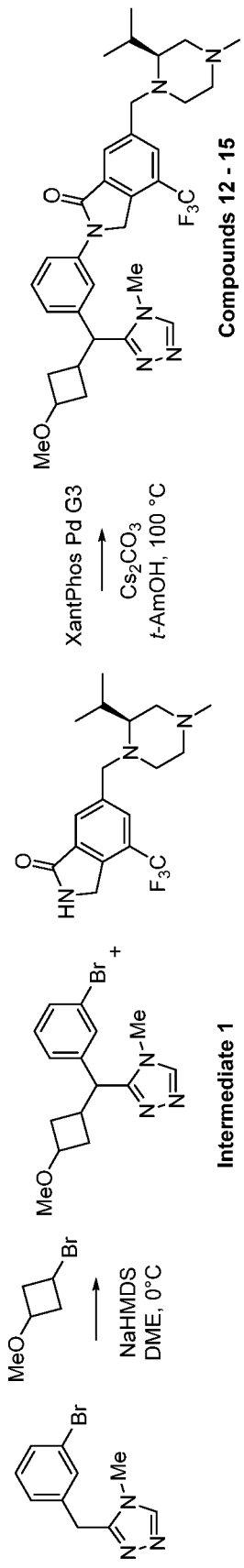

Compounds 12-15 can be synthesized according to Scheme 14, FIG. 14.

Intermediate 1: (3-((3-bromophenyl)(3-methoxycyclobutyl)methyl)-4-methyl-4H-1,2,4-triazole)

To a solution of 3-(3-bromobenzyl)-4-methyl-4H-1,2,4-triazole (300 mg, 1.19 mmol) in anhydrous 1,2-dimethoxyethane (2.4 mL) under nitrogen and at 0° C. added sodium bis(trimethylsilyl)amide (1.4 mL, 1.0 M in THF [untitrated], 1.4 mmol). After 1.5 h, the reaction was quenched by the addition of saturated aq NH$_4$Cl and extracted with CH$_2$Cl$_2$. The organic layer was dried over MgSO$_4$, filtered and concentrated. The crude residue was purified by chromatography on silica gel (0-100% 3:1 iPrOH/MeOH in heptane) to afford 3-((3-bromophenyl)(3-methoxycyclobutyl)methyl)-4-methyl-4H-1,2,4-triazole as a colorless liquid (210 mg, 53% yield); LCMS (ESI) m/z: 336, 338 [M+H]$^+$.

Compound 12, Compound 13, Compound 14, and Compound 15

Into a vial was weighed 3-((3-bromophenyl)(3-methoxycyclobutyl)methyl)-4-methyl-4H-1,2,4-triazole (97.9 mg, 0.291 mmol), (S)-6-((2-isopropyl-4-methylpiperazin-1-yl)methyl)-4-(trifluoromethyl)isoindolin-1-one (114 mg, 0.320 mmol), [(4,5-bis(diphenylphosphino)-9,9-dimethylxanthene)-2-(2'-amino-1,1'-biphenyl)]palladium(II) methanesulfonate (27.9 mg, 0.0195 mmol), and cesium carbonate (285 mg, 0.874 mmol). Under a stream of nitrogen gas, the vessel was charged with anhydrous 2-methyl-2-butanol (1.5 mL) and the vial was sealed. The reaction mixture was stirred at 100° C. for 18 h. After cooling to rt, the mixture was concentrated and purified by flash column chromatography (0-100% 80:15:2.5 CH$_2$Cl$_2$/MeOH/NH$_4$OH in CH$_2$Cl$_2$), HPLC, and chiral SFC to afford:

6-(((S)-2-isopropyl-4-methylpiperazin-1-yl)methyl)-2-(3-((S)-((1R,3S)-3-methoxycyclobutyl)(4-methyl-4H-1,2,4-triazol-3-yl)methyl)phenyl)-4-(trifluoromethyl)isoindolin-1-one (peak 1) (Compound 12, 3.7 mg, 2%), 6-(((S)-2-isopropyl-4-methylpiperazin-1-yl)methyl)-2-(3-((S)-((1

S,3S)-3-methoxycyclobutyl)(4-methyl-4H-1,2,4-triazol-3-yl)methyl)phenyl)-4-(trifluoromethyl)isoindolin-1-one (peak 2) (Compound 13, 1511.8 mg, 7%), 6-(((S)-2-isopropyl-4-methylpiperazin-1-yl)methyl)-2-(3-((S)-((1 S,3R)-3-methoxycyclobutyl)(4-methyl-4H-1,2,4-triazol-3-yl)methyl)phenyl)-4-(trifluoromethyl)isoindolin-1-one (Compound 14, peak 3) and (5.7 mg, 3%), and 6-(((S)-2-isopropyl-4-methylpiperazin-1-yl)methyl)-2-(3-((S)-((1R,3S)-3-methoxycyclobutyl)(4-methyl-4H-1,2,4-triazol-3-yl)methyl)phenyl)-4-(trifluoromethyl)isoindolin-1-one (Compound 15, peak 4) (11.9 mg, 7%); LCMS (ESI) m/z: 611.3 [M+H]$^+$; $^1$H NMR (500 MHz, DMSO-d$_6$) δ 8.32 (s, 1H), 7.98 (s, 1H), 7.90 (d, J=8.1 Hz, 2H), 7.77 (d, J=8.2 Hz, 1H), 7.38 (dd, J=7.9 Hz, 7.9 Hz, 1H), 7.03 (d, J=7.4 Hz, 1H), 5.16 (s, 2H), 4.27-4.15 (m, 2H), 3.71 (p, J=7.4 Hz, 1H), 3.45-3.32 (m, 5H), 3.09 (s, 3H), 2.78-2.66 (m, 1H), 2.66-2.56 (m, 2H), 2.45-2.33 (m, 1H), 2.31-2.17 (m, 3H), 2.14 (s, 3H), 2.11-2.00 (m, 1H), 1.99-1.86 (m, 2H), 1.72-1.50 (m, 2H), 0.93 (d, J=6.7 Hz, 3H), 0.88 (d, J=6.7 Hz, 3H).

Example 15: Compound 16

Figure 15:
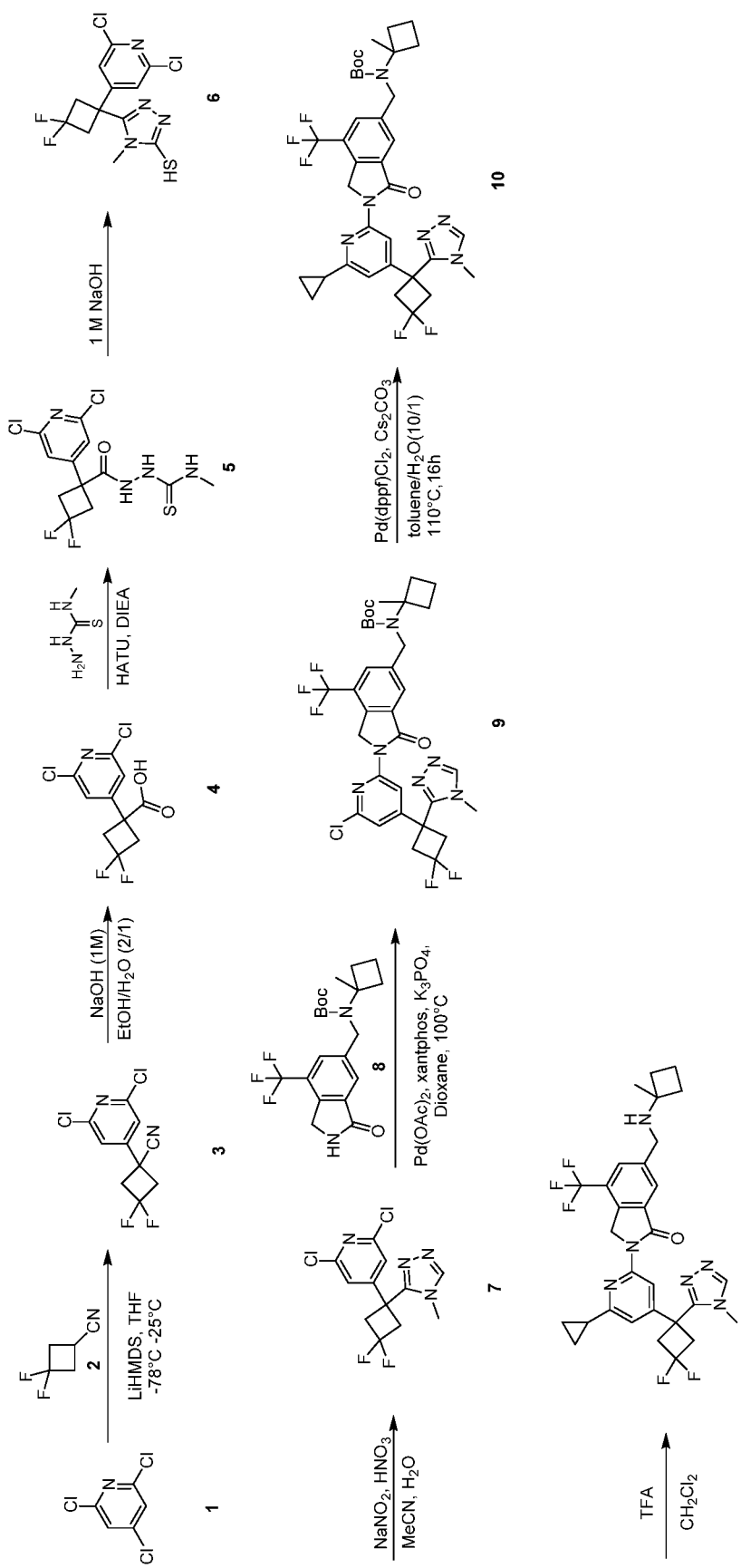

Compound 16 can be synthesized according to Scheme 15, FIG. 15.

Intermediate 3: (1-(2,6-dichloropyridin-4-yl)-3,3-difluorocyclobutanecarbonitrile)

To a solution of 2,4,6-trichloropyridine (5 g, 27.4 mmol) in tetrahydrofuran (80 mL) was added 3,3-difluorocyclobutanecarbonitrile (3.37 g, 28.8 mmol), followed by lithiumbis(trimethylsilyl)amide (1.0 M in tetrahydrofuran, 30.2 mL, 30.2 mmol)) at −78° C. over 10 min. The mixture was stirred at 20° C. for 2 h. The mixture was quenched with saturated aqueous ammonium chloride (30 mL), then extracted with ethyl acetate (3×100 mL), The combined organic phases were washed with brine (50 mL), dried and concentrated under reduced pressure. The residue was purified by silica gel chromatography (mobile phase: ethyl acetate/petroleum ether, gradient 0% to 10%) to afford 1-(2,6-dichloropyridin-4-yl)-3,3-difluorocyclobutanecarbonitrile (5.2 g, 72% yield) as a white solid. $^1$H NMR (400 MHz, CDCl$_3$) δ 7.40 (s, 2H), 3.58-3.54 (m, 2H), 3.23-3.20 (m, 2H).

Intermediate 4: (1-(2,6-dichloropyridin-4-yl)-3,3-difluorocyclobutanecarboxylic acid)

To a mixture of 1-(2,6-dichloropyridin-4-yl)-3,3-difluorocyclobutanecarbonitrile (4.5 g, 17.1 mmol) in ethanol (35 mL) and water (15 mL) was added sodium hydroxide (2.0 g, 51.3 mmol). The mixture was stirred at 80° C. for 2 h. After cooling to 0° C., the mixture was adjusted to pH=5 with aqueous hydrochloric acid (1 M) and diluted with water (100 mL). The solution was extracted with dichloromethane (3×100 mL). The combined organic layers were washed with brine (40 mL), dried and concentrated under reduced pressure to afford crude 1-(2,6-dichloropyridin-4-yl)-3,3-difluorocyclobutanecarboxylic acid (4.5 g, 93% yield) as a yellow solid. LCMS [M+H]$^+$=282.0 and 284.0.

Intermediate 5: (2-(1-(2,6-dichloropyridin-4-yl)-3,3-difluorocyclobutanecarbonyl)-N-methylhydrazinecarbothioamide To a mixture of 1-(2,6-dichloropyridin-4-yl)-3,3-difluorocyclobutanecarboxylic acid (4.5 g, 16.0 mmol), N-methylhydrazinecarbothioamide (2.5 g, 23.9 mmol) and N-ethyl-N-isopropylpropan-2-amine (5.5 g, 47.9 mmol) in N,N-dimethylformamide (50 mL) was added 2-(7-azabenzotriazol-1-yl)-N,N,N',N'-tetramethyluronium hexafluorophosphate (9.1 g, 23.9 mmol). The mixture was stirred at 25° C. for 16 h. The reaction mixture was diluted with water (100 mL) and then extracted with dichloromethane (3×100 mL). The combined organic layers were washed with brine (3×50 mL), dried and concentrated under reduced pressure. The residue was purified by silica gel chromatography (mobile phase: ethyl acetate/petroleum ether, gradient 0% to 50%) to afford the crude product (4.1 g). It was triturated with ethyl acetate (10 mL) to afford 2-(1-(2,6-dichloropyridin-4-yl)-3,3-difluorocyclobutanecarbonyl)-N-methylhydrazinecarbothioamide (1.5 g, 26% yield) as a white solid. LCMS [M+H]$^+$=369.0 and 371.0.

Intermediate 6: (5-(1-(2,6-dichloropyridin-4-yl)-3,3-difluorocyclobutyl)-4-methyl-4H-1,2,4-triazole-3-thiol A mixture of 2-(1-(2,6-dichloropyridin-4-yl)-3,3-difluorocyclobutanecarbonyl)-N-methylhydrazinecarbothioamide (1.3 g, 3.52 mmol) in aqueous sodium hydroxide (1 M, 28.9 mL, 28.9 mmol) was stirred at 25° C. for 12 h. After cooled to 0° C., the mixture was adjusted to pH=5 by addition of aqueous hydrochloric acid (1 M) and filtered. The filter cake was washed with water (2×10 mL) and dried to afford 5-(1-(2,6-dichloropyridin-4-yl)-3,3-difluorocyclobutyl)-4-methyl-4H-1,2,4-triazole-3-thiol (1.0 g, 81% yield) as a white solid. LCMS [M+H]$^+$=351.1 and 353.0.

Intermediate 7: (2,6-dichloro-4-(3,3-difluoro-1-(4-methyl-4H-1,2,4-triazol-3-yl)cyclobutyl)pyridine To a solution of 5-(1-(2,6-dichloropyridin-4-yl)-3,3-difluorocyclobutyl)-4-methyl-4H-1,2,4-triazole-3-thiol (1.3 g, 3.7 mmol) in water (30 mL) and acetonitrile (10 mL) was added sodium nitrite (1.3 g, 18.5 mmol), followed by aqueous nitric acid (1 M, 18.5 mL, 18.5 mmol) at 0° C. The mixture was stirred at 20° C. for 5 h and quenched with saturated aqueous sodium bicarbonate (50 mL). The resulting mixture was extracted with dichloromethane (3×50 mL). The combined organic layers were washed with brine (50 mL), dried and concentrated under reduced pressure. The residue was purified by silica gel chromatography (mobile phase: methanol/dichloromethane, gradient 0% to 5%) to afford 2,6-dichloro-4-(3,3-difluoro-1-(4-methyl-4H-1,2,4-triazol-3-yl)cyclobutyl)pyridine (600 mg, 51% yield) as a brown oil. $^1$H NMR (400 MHz, CDCl$_3$) δ 8.23 (s, 1H), 7.15 (s, 2H), 3.84-3.70 (m, 2H), 3.35 (s, 3H), 3.33-3.22 (m, 2H). LCMS [M+H]$^+$=319.1 and 321.1.

Intermediate 9: (tert-butyl ((2-(6-chloro-4-(3,3-difluoro-1-(4-methyl-4H-1,2,4-triazol-3-yl)cyclobutyl)pyridin-2-yl)-3-oxo-7-(trifluoromethyl)isoindolin-5-yl)methyl)(1-methylcyclobutyl)carbamate)

To a solution of tert-butyl (1-methylcyclobutyl)((3-oxo-7-(trifluoromethyl)isoindolin-5-yl)methyl)carbamate (562 mg, 1.4 mmol) and 2,6-dichloro-4-(3,3-difluoro-1-(4-methyl-4H-1,2,4-triazol-3-yl)cyclobutyl)pyridine (450 mg, 1.4 mmol) in 1,4-dioxane (40 mL) was added potassium phosphate (599 mg, 2.8 mmol), (9,9-dimethyl-9H-xanthene-4,5-diyl)bis(diphenyl-phosphine) (82 mg, 0.14 mmol) and palladium(II) acetate (31.7 mg, 0.14 mmol). The mixture was stirred at 100° C. for 16 h under nitrogen protection. After cooled, the mixture was diluted with dichloromethane (50 mL). The separated organic layer was washed with brine (20 mL), dried and concentrated under reduced pressure. The residue was purified by silica gel chromatography (mobile phase: methanol/dichloromethane, gradient 0% to 6%) to afford tert-butyl ((2-(6-chloro-4-(3,3-difluoro-1-(4-methyl-4H-1,2,4-triazol-3-yl)cyclobutyl)-pyridin-2-yl)-3-oxo-7-(trifluoromethyl)isoindolin-5-yl)methyl)(1-methyl-cyclobutyl)carbamate (900 mg, 94% yield) as a yellow solid. LCMS [M+H]$^+$=681.3 and 683.3.

Intermediate 10: (tert-butyl ((2-(6-cyclopropyl-4-(3, 3-difluoro-1-(4-methyl-4H-1,2,4-triazol-3-yl)cy-clobutyl)pyridin-2-yl)-3-oxo-7-(trifluoromethyl) isoindolin-5-yl)methyl)(1-methylcyclobutyl) carbamate)

A mixture of tert-butyl ((2-(6-chloro-4-(3,3-difluoro-1-(4-methyl-4H-1,2,4-triazol-3-yl)cyclobutyl)pyridin-2-yl)-3-oxo-7-(trifluoromethyl)isoindolin-5-yl)methyl)(1-methyl-cyclobutyl)carbamate (150 mg, 0.22 mmol), cyclopropyl boronic acid (37.8 mg, 0.44 mmol), [1,1'-Bis(diphenylphos-phino)ferrocene]dichloropalladium(II) (18.0 mg, 0.02 mmol) and cesium carbonate (215.3 mg, 0.66 mmol) in toluene (5 mL) and water (0.5 mL) was stirred at 110° C. for 16 h under nitrogen protection. After cooled, the mixture was diluted with water (30 mL) and extracted with dichloromethane (3×20 mL). The combined organic layers were dried and concentrated under reduced pressure. The residue was purified by preparative TLC (solvent gradient: 10% methanol in dichloromethane) to afford tert-butyl ((2-(6-cyclopropyl-4-(3,3-difluoro-1-(4-methyl-4H-1,2,4-triazol-3-yl)cyclobutyl)pyridin-2-yl)-3-oxo-7-(trifluoromethyl) isoindolin-5-yl)methyl)(1-methylcyclobutyl)carbamate (70.0 mg, 46% yield) as a yellow solid. LCMS [M+H]$^+$=687.1.

Compound 16

A mixture of tert-butyl ((2-(6-chloro-4-(3,3-difluoro-1-(4-methyl-4H-1,2,4-triazol-3-yl)cyclobutyl)pyridin-2-yl)-3-oxo-7-(trifluoromethyl)isoindolin-5-yl)methyl)(1-methyl-cyclobutyl)carbamate (60.0 mg, 0.09 mmol) and trifluoroacetic acid (0.03 mL, 0.4 mmol) in dichloromethane (1 mL) was stirred at 20° C. for 2 h and concentrated under reduced pressure. The residue was purified by RP-HPLC (60% to 90% ACN/(0.05% $NH_3H_2O$+10 mM $NH_4HCO_3$ in water)) to afford 2-(6-cyclopropyl-4-(3,3-difluoro-1-(4-methyl-4H-1,2,4-triazol-3-yl)cyclobutyl)pyridin-2-yl)-6-(((1-methylcyclobutyl)amino)methyl)-4-(trifluoromethyl) isoindolin-1-one (Compound 16, 20.6 mg, 38% yield). $^1$H NMR (400 MHz, methanol-d$_4$) δ 8.44 (s, 1H), 8.30 (s, 1H), 8.09 (s, 1H), 8.02 (s, 1H), 7.04 (s, 1H), 5.20 (s, 2H), 3.88 (s, 2H), 3.76-3.69 (m, 2H), 3.48-3.44 (m, 2H), 3.42 (s, 3H), 2.13-2.08 (m, 3H), 1.91-1.80 (m, 4H), 1.39 (s, 3H), 1.08-1.01 (m, 4H). LCMS [M+H]$^+$=587.1.

Example 16: Compound 17

Figure 16:
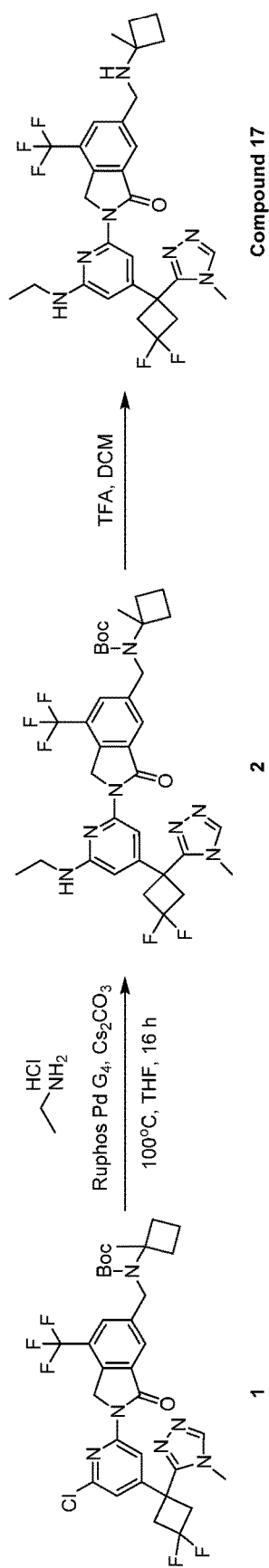

Compound 17 can be synthesized according to Scheme 16, FIG. 16.

Intermediate 2: (tert-butyl ((2-(4-(3,3-difluoro-1-(4-methyl-4H-1,2,4-triazol-3-yl)cyclobutyl)-6-(ethyl-amino)pyridin-2-yl)-3-oxo-7-(trifluoromethyl)isoin-dolin-5-yl)methyl)(1-methylcyclobutyl)carbamate)

A mixture of tert-butyl ((2-(6-chloro-4-(3,3-difluoro-1-(4-methyl-4H-1,2,4-triazol-3-yl)cyclobutyl)pyridin-2-yl)-3-oxo-7-(trifluoromethyl)isoindolin-5-yl)methyl)(1-methyl-cyclobutyl)carbamate (200.0 mg, 0.29 mmol), Ruphos Pd G4 (24.5 mg, 0.03 mmol, CAS #: 1599466-85-9), ethanamine hydrochloride (28.2 mg, 0.35 mmol) and cesium carbonate (281.2 mg, 0.86 mmol) in tetrahydrofuran (6 mL) was stirred at 100° C. for 16 h under nitrogen protection and concentrated under reduced pressure. The residue was purified by preparative TLC (solvent gradient: 10% methanol in dichloromethane) to afford tert-butyl ((2-(4-(3,3-difluoro-1-(4-methyl-4H-1,2,4-triazol-3-yl)cyclobutyl)-6-(ethyl-amino)-pyridin-2-yl)-3-oxo-7-(trifluoromethyl)isoindolin-5-yl)methyl)(1-methylcyclobutyl)carbamate (70.0 mg, 35% yield) as a yellow solid. LCMS [M+H]$^+$=690.0.

Compound 17

A mixture of tert-butyl ((2-(4-(3,3-difluoro-1-(4-methyl-4H-1,2,4-triazol-3-yl)cyclo-butyl)-6-(ethylamino)pyridin-2-yl)-3-oxo-7-(trifluoromethyl)isoindolin-5-yl)methyl)(1-methylcyclobutyl)carbamate (70.0 mg, 0.10 mmol) and trifluoroacetic acid (0.6 mL, 8.19 mmol) in dichloromethane (5 mL) was stirred at 25° C. for 2 h and concentrated under reduced pressure. The residue was purified by RP-HPLC (50 to 80% ACN/(0.05% $NH_3H_2O$+10 mM $NH_4HCO_3$ in water)) to afford 2-(4-(3,3-difluoro-1-(4-methyl-4H-1,2,4-triazol-3-yl)cyclobutyl)-6-(ethylamino)pyridin-2-yl)-6-(((1-methylcyclobutyl)amino)methyl)-4-(trifluoromethyl)isoin-dolin-1-one (30.0 mg, 50% yield). $^1$H NMR (400 MHz, methanol-d$_4$) δ 8.43 (s, 1H), 8.07 (s, 1H), 8.00 (s, 1H), 7.69 (s, 1H), 6.11 (d, J=1.2 Hz, 1H), 5.22 (s, 2H), 3.85 (s, 2H), 3.72-3.65 (m, 2H), 3.44 (s, 3H), 3.41-3.33 (m, 4H), 2.12-2.08 (m, 2H), 1.90-1.77 (m, 4H), 1.38 (s, 3H), 1.23 (t, J=7.2 Hz, 3H). LCMS [M+H]$^+$=590.3.

Example 18: Compound 18

Figure 17:
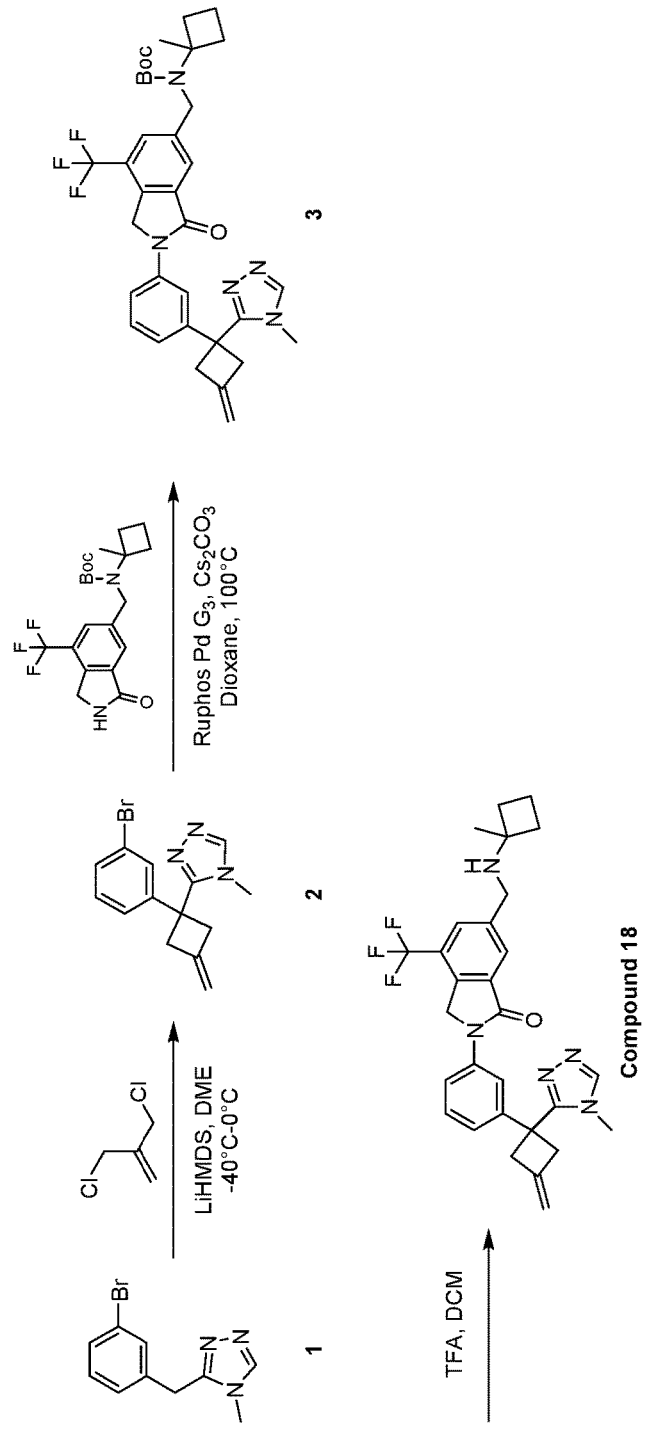

Compound 18 can be synthesized according to Scheme 17, FIG. 17.

Intermediate 2: (3-(1-(3-bromophenyl)-3-methylene-cyclobutyl)-4-methyl-4H-1,2,4-triazole)

To a solution of 3-(3-bromobenzyl)-4-methyl-4H-1,2,4-triazole (500.0 mg, 1.98 mmol) in 1,2-dimethoxyethane (20 mL) was added 3-chloro-2-(chloromethyl)prop-1-ene (0.28 mL, 2.38 mmol) and lithium bis(trimethylsilyl)amide (1.0 M in tetrahydrofuran, 3.97 mL, 3.97 mmol) at −40° C. The mixture was stirred at −40° C. for 20 min, then another portion of lithium bis(trimethylsilyl)amide (1.0 M in tetrahydrofuran, 3.97 mL, 3.97 mmol) was added at −40° C. The resulting mixture was stirred at 0° C. for another 1 h and quenched with water (15 mL). The mixture was extracted with dichloromethane (3×30 mL). The combined organic phases was washed with brine (10 mL), dried and concentrated under reduced pressure. The residue was purified by silica gel chromatography (mobile phase: methanol/dichloromethane, gradient 0% to 10%) to afford 3-(1-(3-brom-ophenyl)-3-methylenecyclobutyl)-4-methyl-4H-1,2,4-triaz-ole (100.0 mg, 17% yield) as a white solid. 1H NMR (400 MHz, DMSO-d$_6$) δ 8.40 (s, 1H), 7.51-7.45 (m, 1H), 7.38-7.29 (m, 2H), 7.21-7.19 (m, 1H), 4.91 (t, J=2.4 Hz, 2H), 3.70-3.59 (m, 2H), 3.31-3.29 (m, 2H), 3.21 (s, 3H).

Intermediate 3: (tert-butyl ((2-(3-(1-(4-methyl-4H-1, 2,4-triazol-3-yl)-3-methylenecyclobutyl)phenyl)-3-oxo-7-(trifluoromethyl)isoindolin-5-yl)methyl)(1-methylcyclobutyl)carbamate)

In a glove box, a mixture of 3-(1-(3-bromophenyl)-3-methylenecyclobutyl)-4-methyl-4H-1,2,4-triazole (30.0 mg, 0.10 mmol), tert-butyl (1-methylcyclobutyl)((3-oxo-7-(trifluoromethyl)isoindolin-5-yl)methyl)carbamate (43.2 mg, 0.11 mmol), cesium carbonate (96.4 mg, 0.30 mmol) and (2-Dicyclohexylphosphino-2',6'-diisopropoxy-1,1'-biphenyl)[2-(2'-amino-1,1'biphenyl)]palladium(II) methanesulfonate (8.3 mg, 0.01 mmol, CAS #: 1445085-77-7) in 1,4-dioxane (2 mL) was stirred at 100° C. for 16 h and concentrated under reduced pressure. The residue was purified by preparative TLC (solvent gradient: 10% methanol in dichloromethane) to afford tert-butyl ((2-(3-(1-(4-methyl-4H-1,2,4-triazol-3-yl)-3-methylenecyclobutyl)phenyl)-3-oxo-7-(trifluoromethyl)isoindolin-5-yl)methyl)(1-methylcyclobutyl)carbamate (50.0 mg, 82% yield) as a yellow oil. LCMS [M+H]⁺=622.3.

Compound 18

A mixture of tert-butyl ((2-(3-(1-(4-methyl-4H-1,2,4-triazol-3-yl)-3-methylenecyclobutyl)phenyl)-3-oxo-7-(trifluoromethyl)isoindolin-5-yl)methyl)(1-methylcyclobutyl)carbamate (50.0 mg, 0.08 mmol) and trifluoroacetic acid (0.5 mL, 6.49 mmol) in dichloromethane (5 mL) was stirred at 20° C. for 16 h and concentrated under reduced pressure. The residue was purified by RP-HPLC (55% to 85% ACN/(0.05% NH₃H₂O+10 mM NH₄HCO₃ in water)) to afford 2-(3-(1-(4-methyl-4H-1,2,4-triazol-3-yl)-3-methylenecyclobutyl)phenyl)-6-(((1-methylcyclobutyl)amino)methyl)-4-(trifluoromethyl)-isoindolin-1-one (Compound 18, 12.0 mg, 29% yield). ¹H NMR (400 MHz, methanol-d₄) δ 8.41 (s, 1H), 8.08 (s, 1H), 8.01 (s, 1H), 7.96 (s, 1H), 7.68 (d, J=9.2 Hz, 1H), 7.48 (t, J=8.0 Hz, 1H), 7.16 (d, J=6.8 Hz, 1H), 5.14 (s, 2H), 4.98 (s, 2H), 3.88 (s, 2H), 3.77-3.72 (m, 2H), 3.49-3.46 (m, 2H), 3.39 (s, 3H), 2.15-2.09 (m, 2H), 1.90-1.86 (m, 2H), 1.82-1.78 (m, 2H), 1.39 (s, 3H). LCMS [M+H]⁺=522.3.

Example 19: Compound 19

Figure 18:
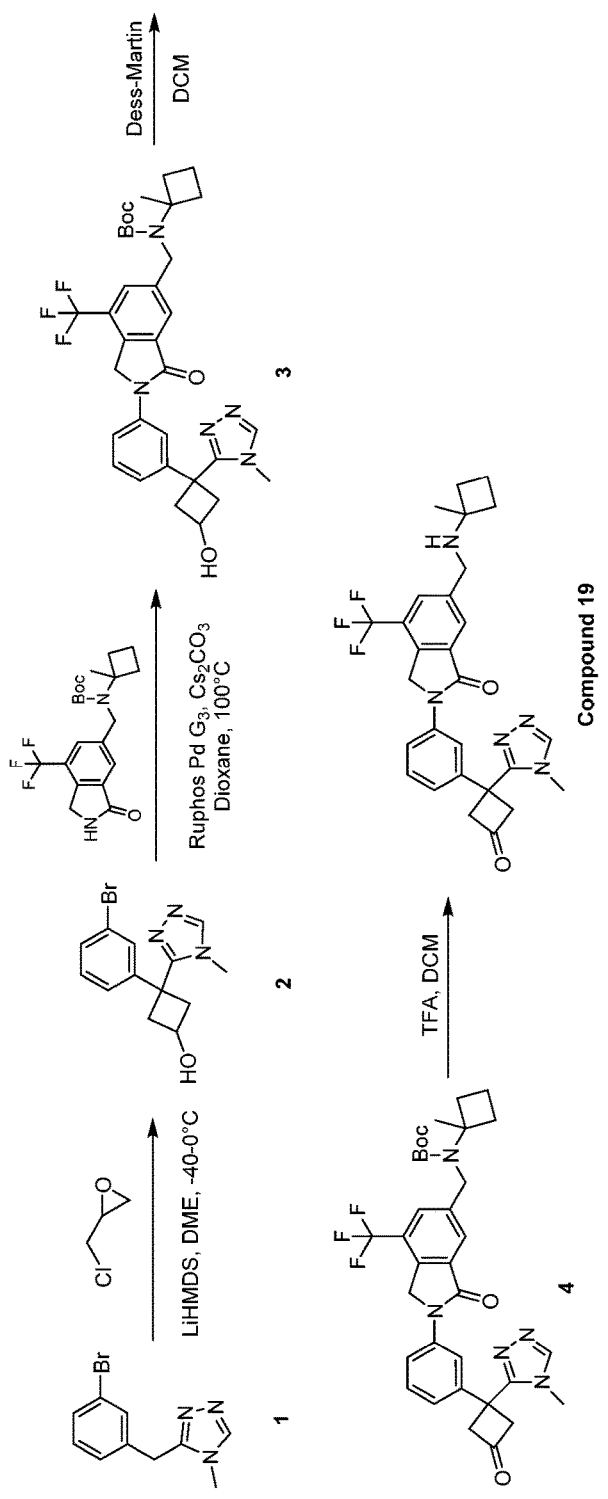

Compound 19 can be synthesized according to Scheme 18, FIG. 18.

Intermediate 2: (3-(3-bromophenyl)-3-(4-methyl-4H-1,2,4-triazol-3-yl)cyclobutanol)

A solution of 3-(3-bromobenzyl)-4-methyl-4H-1,2,4-triazole (500 mg, 1.98 mmol) in tetrahydrofuran (20 mL) was added epichlorohydrin (202 mg, 2.18 mmol) and isopropylmagnesium chloride (2.0 M in tetrahydrofuran, 3.97 mL, 7.94 mmol) at −40° C. The reaction mixture was stirred at −40° C. for 30 min, then stirred at 20° C. for 16 h. The mixture was quenched by addition of water (30 mL) and extracted with dichloromethane (3×50 mL). The combined organic layers were washed with brine (50 mL), dried and concentrated under reduced pressure. The residue was purified by silica gel chromatography (mobile phase: methanol/dichloromethane, gradient 0% to 10%) to afford 3-(3-bromophenyl)-3-(4-methyl-1,2,4-triazol-3-yl)cyclobutanol (300 mg, 49% yield). ¹H NMR (400 MHz, DMSO-d₆) δ 8.29 (s, 1H), 7.47-7.43 (m, 1H), 7.40 (s, 1H), 7.33 (s, 2H), 5.31 (d, J=6.8 Hz, 1H), 4.27-4.17 (m, 1H), 3.18 (s, 3H), 3.03-2.98 (m, 2H), 2.77-2.62 (m, 2H).

Intermediate 3: (tert-butyl ((2-(3-(3-hydroxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate)

In a glove box, a mixture of 3-(3-bromophenyl)-3-(4-methyl-4H-1,2,4-triazol-3-yl)cyclobutanol (50.0 mg, 0.16 mmol), tert-butyl (1-methylcyclobutyl)((3-oxo-7-(trifluoromethyl)isoindolin-5-yl)methyl)carbamate (71.1 mg, 0.18 mmol), cesium carbonate (158.6 mg, 0.49 mmol) and (2-Dicyclohexylphosphino-2',6'-diisopropoxy-1,1'-biphenyl)[2-(2'-amino-1,1'biphenyl)]palladium(II) methanesulfonate (13.6 mg, 0.02 mmol, CAS #: 1445085-77-7) in 1,4-dioxane (2 mL) was stirred at 100° C. for 16 h and concentrated under reduced pressure. The residue was purified by preparative TLC (solvent gradient: 10% methanol in dichloromethane) to afford tert-butyl ((2-(3-(3-hydroxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (40.0 mg, 39% yield) as a yellow oil. LCMS [M+H]⁺=626.3.

Intermediate 5: (tert-butyl ((2-(3-(1-(4-methyl-4H-1,2,4-triazol-3-yl)-3-oxocyclobutyl)phenyl)-3-oxo-7-(trifluoromethyl)isoindolin-5-yl)methyl)(1-methylcyclobutyl)carbamate)

To a solution of tert-butyl ((2-(3-(3-hydroxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (40.0 mg, 0.06 mmol) in dichloromethane (2 mL) was added Dess-Martin periodinane (54.2 mg, 0.13 mmol) at 0° C. The mixture was stirred at 25° C. for 16 h, diluted with dichloromethane (20 mL), washed with saturated aqueous sodium sulfite (3×10 mL), saturated aqueous sodium bicarbonate (10 mL), brine (10 mL), dried and concentrated under reduced pressure. The residue was purified by preparative TLC (solvent gradient: 10% methanol in dichloromethane) to afford tert-butyl ((2-(3-(1-(4-methyl-4H-1,2,4-triazol-3-yl)-3-oxocyclobutyl)phenyl)-3-oxo-7-(trifluoromethyl)isoindolin-5-yl)methyl)(1-methylcyclobutyl)carbamate (35 mg, 88% yield) as a white solid.

Compound 19

A mixture of tert-butyl ((2-(3-(1-(4-methyl-4H-1,2,4-triazol-3-yl)-3-oxocyclobutyl)-phenyl)-3-oxo-7-(trifluoromethyl)isoindolin-5-yl)methyl)(1-methylcyclobutyl)carbamate (50.0 mg, 0.08 mmol) and trifluoroacetic acid (0.5 mL, 6.49 mmol) in dichloromethane (5 mL) was stirred at 20° C. for 2 h and concentrated under reduced pressure. The residue was purified by RP-HPLC (45% to 75% ACN/(0.05% NH₃H₂O+10 mM NH₄HCO₃ in water)) to afford 2-(3-(1-(4-methyl-4H-1,2,4-triazol-3-yl)-3-oxocyclobutyl)phenyl)-6-(((1-methylcyclobutyl)-amino)methyl)-4-(trifluoromethyl)isoindolin-1-one (9.0 mg, 21% yield). ¹H NMR (400 MHz, CDCl₃) δ 8.13 (d, J=2.4 Hz, 2H), 8.10 (s, 1H), 7.93 (s, 1H), 7.54-7.45 (m, 2H), 7.13 (d, J=7.6 Hz, 1H), 4.95 (s, 2H), 4.29-4.23 (m, 2H), 3.91-3.82 (m, 4H), 3.43 (s, 3H), 2.25-2.00 (m, 2H), 2.00-1.92 (m, 2H), 1.82-1.80 (m, 2H), 1.38 (s, 3H). LCMS: [M+H]⁺=524.3.

Example 20: Compounds 20 and 21

Figure 19:
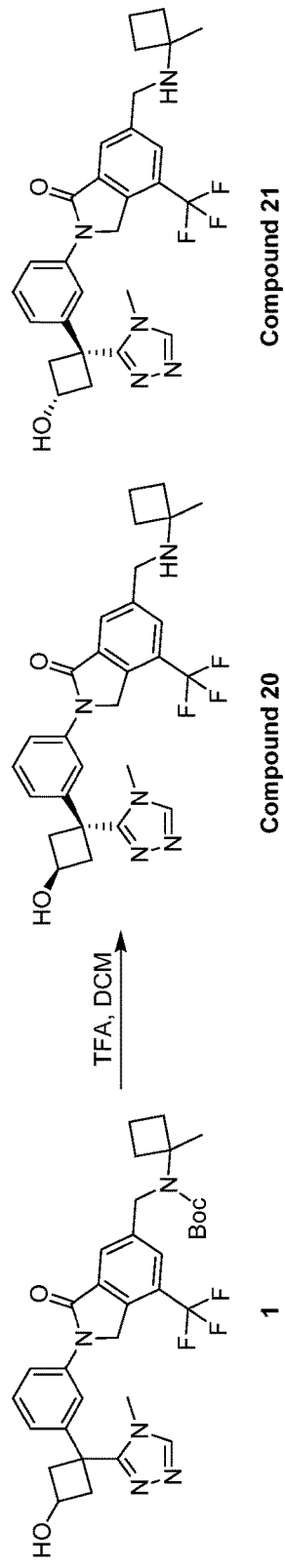

Compounds 20 and 21, can be synthesized according to Scheme 19 (FIG. 19).

A mixture of tert-butyl ((2-(3-(3-hydroxy-1-(4-methyl-4H-1,2,4-triazol-3-yl)cyclo-butyl)phenyl)-3-oxo-7-(trifluoromethyl)isoindolin-5-yl)methyl)(1-methylcyclobutyl)carbamate (109 mg, 0.17 mmol) and trifluoroacetic acid (0.5 mL, 6.49 mmol) in dichloromethane (5 mL) was stirred at 20° C. for 2 h and concentrated under reduced pressure. The residue was purified by RP-HPLC (45% to 75% ACN/(0.05% NH₃H₂O+10 mM NH₄HCO₃ in water)) to afford ((2-(3-(3-hydroxy-1-(4-methyl-4H-1,2,4-triazol-3-yl)cyclobutyl)phenyl)-3-6-((1-methyl cyclobutyl)amino)methyl)-4-(trifluoromethyl)isoindolin-1-one (50 mg, 55% yield).

The above racemate (46 mg, 0.09 mmol) was further purified by chiral SFC (Column=Daicel ChiralPAK IG; Column dimensions=250 mm×30 mm×10 μm; Detection wavelength=220 nM; Flow rate=80 mL/min; Run time=4.0 min; Column temperature=25° C.) with 0.1% ammonium hydroxide-30% ethanol-carbon dioxide) to afford:

2-(3-((1r,3r)-3-hydroxy-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1, retention time=2.552 min) (Compound 20, 4.1 mg, 9% yield). $^1$H NMR (400 MHz, methanol-$d_4$) δ 8.29 (s, 1H), 8.07 (s, 1H), 8.04 (t, J=8.0 Hz, 1H), 7.99 (s, 1H), 7.65 (d, J=8.4 Hz, 1H), 7.46 (t, J=8.0 Hz, 1H), 7.20 (d, J=9.2 Hz, 1H), 5.13 (s, 2H), 4.47-4.41 (m, 1H), 3.86 (s, 2H), 3.33 (s, 3H), 3.20-3.16 (m, 2H), 2.87-2.83 (m, 2H), 2.10-2.07 (m, 2H), 1.88-1.74 (m, 4H), 1.37 (s, 3H). LCMS: [M+H]$^+$=526.3; and 2-(3-((1s,3s)-3-hydroxy-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2, retention time=2.808 min) (Compound 21, 19.9 mg, 43% yield). $^1$H NMR (400 MHz, methanol-$d_4$) δ$^1$H NMR (400 MHz, methanol-$d_4$) δ 8.36 (s, 1H), 8.07 (s, 1H), 7.99 (s, 1H), 7.87 (s, 1H), 7.65 (d, J=8.0 Hz, 1H), 7.45 (t, J=8.0 Hz, 1H), 7.06 (d, J=7.6 Hz, 1H), 5.13 (s, 2H), 4.27 (t, J=7.2 Hz, 1H), 3.87 (s, 2H), 3.36-3.31 (m, 5H), 2.65-2.59 (m, 2H), 2.11-2.08 (m, 2H), 1.88-1.76 (m, 4H), 1.38 (s, 3H). LCMS: [M+H]$^+$=526.3.

Example 21: Compound 22

Figure 20:
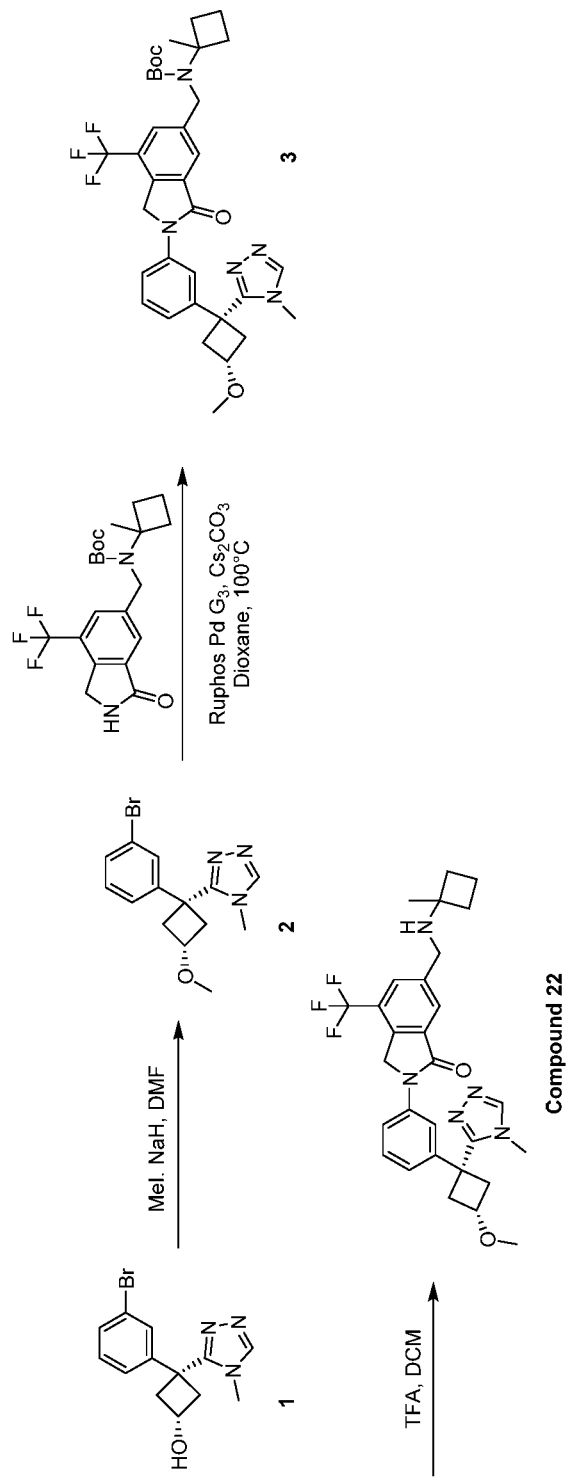

Compound 22 can be synthesized according to Scheme 20, FIG. 20.

Intermediate 2: (3-((1s,3s)-1-(3-bromophenyl)-3-methoxycyclobutyl)-4-methyl-4H-1,2,4-triazole)

To a solution of methyl (1s,3s)-3-(3-bromophenyl)-3-(4-methyl-4H-1,2,4-triazol-3-yl)cyclobutanol (300 mg, 0.97 mmol) in N,N-dimethylformamide (10 mL) was added sodium hydride (60%, 47 mg, 1.2 mmol) at 0° C. The mixture was stirred at 0° C. for 30 min and then methyl iodide (0.09 mL, 1.46 mmol) was added. The resulting mixture was stirred at 25° C. for 16 h. After cooled, the mixture was quenched by addition of water (10 mL) and extracted with ethyl acetate (3×30 mL). The combined organic phases were washed with brine (2×10 mL), dried and concentrated under reduced pressure. The residue was purified by preparative TLC (solvent gradient: 10% methanol in dichloromethane) to afford 3-((1s,3s)-1-(3-bromophenyl)-3-methoxycyclobutyl)-4-methyl-4H-1,2,4-triazole (90 mg, 29% yield) as a colorless oil. LCMS [M+H]$^+$=322.0.

Intermediate 3: (tert-butyl ((2-(3-((1s,3s)-3-methoxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate)

In a glove box, a mixture of 3-((1s,3s)-1-(3-bromophenyl)-3-methoxycyclobutyl)-4-methyl-4H-1,2,4-triazole (90.0 mg, 0.16 mmol), tert-butyl (1-methylcyclobutyl)((3-oxo-7-(trifluoromethyl)isoindolin-5-yl)methyl)carbamate (122 mg, 0.31 mol), cesium carbonate (273 mg, 0.84 mmol) and (2-Dicyclohexylphosphino-2',6'-diisopropoxy-1,1'-biphenyl)[2-(2'-amino-1,1'biphenyl)]palladium(II) methanesulfonate (23.4 mg, 0.03 mmol, CAS #1445085-77-7) in 1,4-dioxane (2 mL) was stirred at 100° C. for 16 h and concentrated under reduced pressure. The residue was purified by preparative TLC (solvent gradient: 10% methanol in dichloromethane) to afford tert-butyl ((2-(3-((1s,3s)-3-methoxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (30 mg, 17% yield) as a yellow oil. LCMS [M+H]$^+$=640.0.

Compound 22

A mixture of tert-butyl ((2-(3-((1s,3s)-3-methoxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (30.0 mg, 0.05 mmol) and trifluoroacetic acid (0.3 mL, 3.89 mmol) in dichloromethane (5 mL) was stirred at 20° C. for 2 h and concentrated under reduced pressure. The residue was purified by RP-HPLC (50% to 80% ACN/(0.05% NH$_3$H$_2$O+10 mM NH$_4$HCO$_3$ in water)) to afford 2-(3-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one (9.0 mg, 21% yield). $^1$H NMR (400 MHz, methanol-$d_4$) δ 8.32 (s, 1H), 8.08 (s, 1H), 8.06 (t, J=2.0 Hz, 1H), 8.01 (s, 1H), 7.70-7.67 (m, 1H), 7.49 (t, J=8.0 Hz, 1H), 7.23-7.20 (m, 1H), 5.15 (s, 2H), 4.22-4.15 (m, 1H), 3.86 (s, 2H), 3.36 (s, 3H), 3.29 (s, 3H), 3.22-3.17 (m, 2H), 2.93-2.83 (m, 2H), 2.15-2.04 (m, 2H), 1.91-1.76 (m, 4H), 1.38 (s, 3H). LCMS: [M+H]$^+$=540.1.

Example 22: Compound 23

Figure 21:
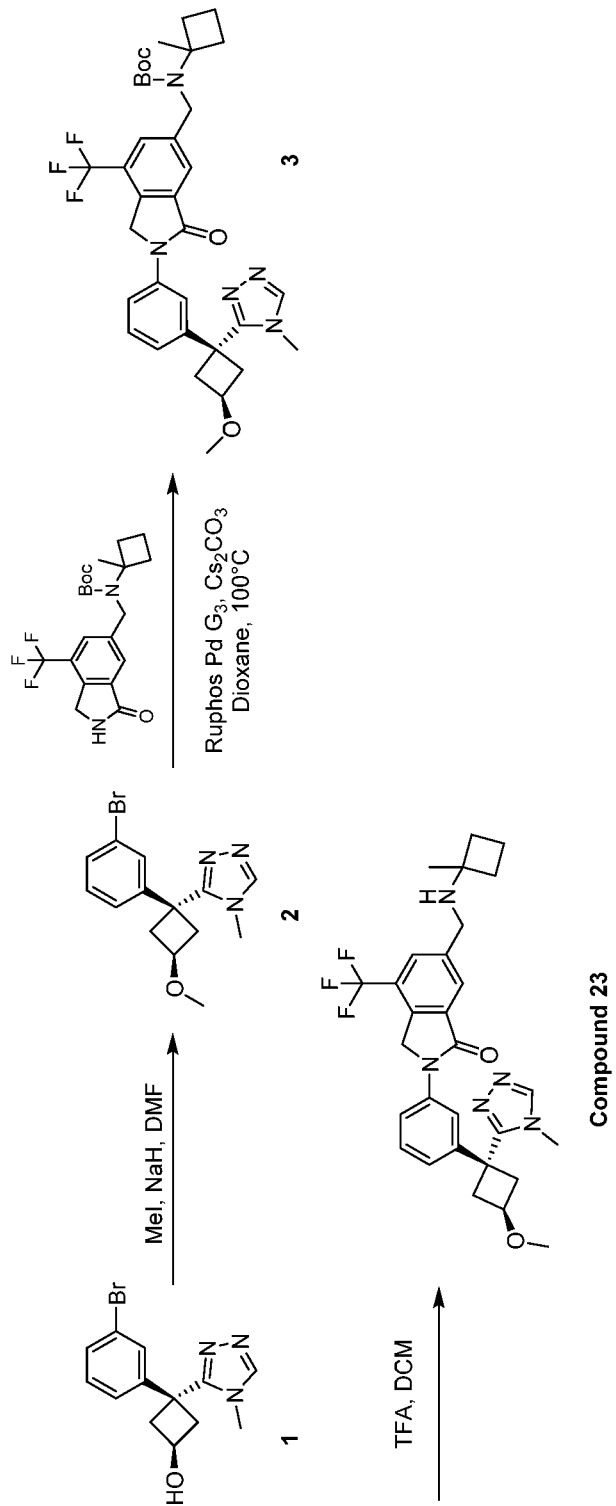

Compound 23 can be synthesized according to Scheme 21 (FIG. 21).

Intermediate 2: (3-((1r,3r)-1-(3-bromophenyl)-3-methoxycyclobutyl)-4-methyl-4H-1,2,4-triazole)

To a solution of methyl (1r,3r)-3-(3-bromophenyl)-3-(4-methyl-4H-1,2,4-triazol-3-yl)cyclobutanol (250 mg, 0.81 mmol) in N,N-dimethylformamide (10 mL) was added sodium hydride (60%, 38.9 mg, 0.97 mmol) at 0° C. The mixture was stirred at 0° C. for 30 min and then methyl iodide (0.08 mL, 1.22 mmol) was added. The resulting mixture was stirred at 25° C. for 16 h. After cooled, the mixture was quenched by addition of water (10 mL) and extracted with ethyl acetate (3×30 mL). The combined organic phases were washed with brine (2×10 mL), dried and concentrated under reduced pressure. The residue was purified by preparative TLC (solvent gradient: 10% methanol in dichloromethane) to afford 3-((1r,3r)-1-(3-bromophenyl)-3-methoxycyclobutyl)-4-methyl-4H-1,2,4-triazole (170 mg, 65% yield) as a colorless oil. LCMS [M+H]$^+$=322.0.

Intermediate 3: (tert-butyl ((2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate)

In a glove box, a mixture of 3-((1r,3r)-1-(3-bromophenyl)-3-methoxycyclobutyl)-4-methyl-4H-1,2,4-triazole (170 mg, 0.53 mmol), tert-butyl (1-methylcyclobutyl)((3-oxo-7-(trifluoromethyl)isoindolin-5-yl)methyl)carbamate (231 mg, 0.58 mmol), cesium carbonate (516 mg, 1.58 mmol) and (2-Dicyclohexylphosphino-2',6'-diisopropoxy-1,1'-biphenyl)[2-(2'-amino-1,1'biphenyl)]palladium(II) methanesulfonate (44.1 mg, 0.05 mmol, CAS #: 1445085-77-7) in 1,4-dioxane (5 mL) was stirred at 110° C. for 16 h and concentrated under reduced pressure. The residue was purified by preparative TLC (solvent gradient: 10% methanol in dichloromethane) to afford tert-butyl ((2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (150 mg, 44% yield) as a yellow oil. LCMS [M+H]$^+$=640.0.

Compound 23

A mixture of tert-butyl ((2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (150 mg, 0.23 mmol) and trifluoroacetic acid (0.58 mL, 7.49 mmol) in dichloromethane (5 mL) was stirred at 20° C. for 2 h and concentrated under reduced pressure. The residue was purified by RP-HPLC (50% to 80% ACN/(0.05% $NH_3H_2O$+10 mM $NH_4HCO_3$ in water)) to afford 2-(3-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl)isoindolin-1-one (Compound 23, 9.0 mg, 21% yield). $^1$H NMR (400 MHz, DMSO-$d_6$) δ 8.39 (s, 1H), 8.07 (s, 1H), 8.03 (s, 1H), 7.88 (s, 1H), 7.72 (dd, J=1.2, 8.0 Hz, 1H), 7.42 (t, J=8.0 Hz, 1H), 6.96 (d, J=7.6 Hz, 1H), 5.20 (s, 2H), 3.88-3.82 (m, 3H), 3.24 (s, 3H), 3.18 (s, 3H), 2.53-2.49 (m 4H), 2.10-1.90 (m, 2H), 1.74-1.67 (m, 4H), 1.27 (s, 3H). LCMS: [M+H]$^+$=540.4.

Example 23: Compounds 24 and 25

Figure 22:
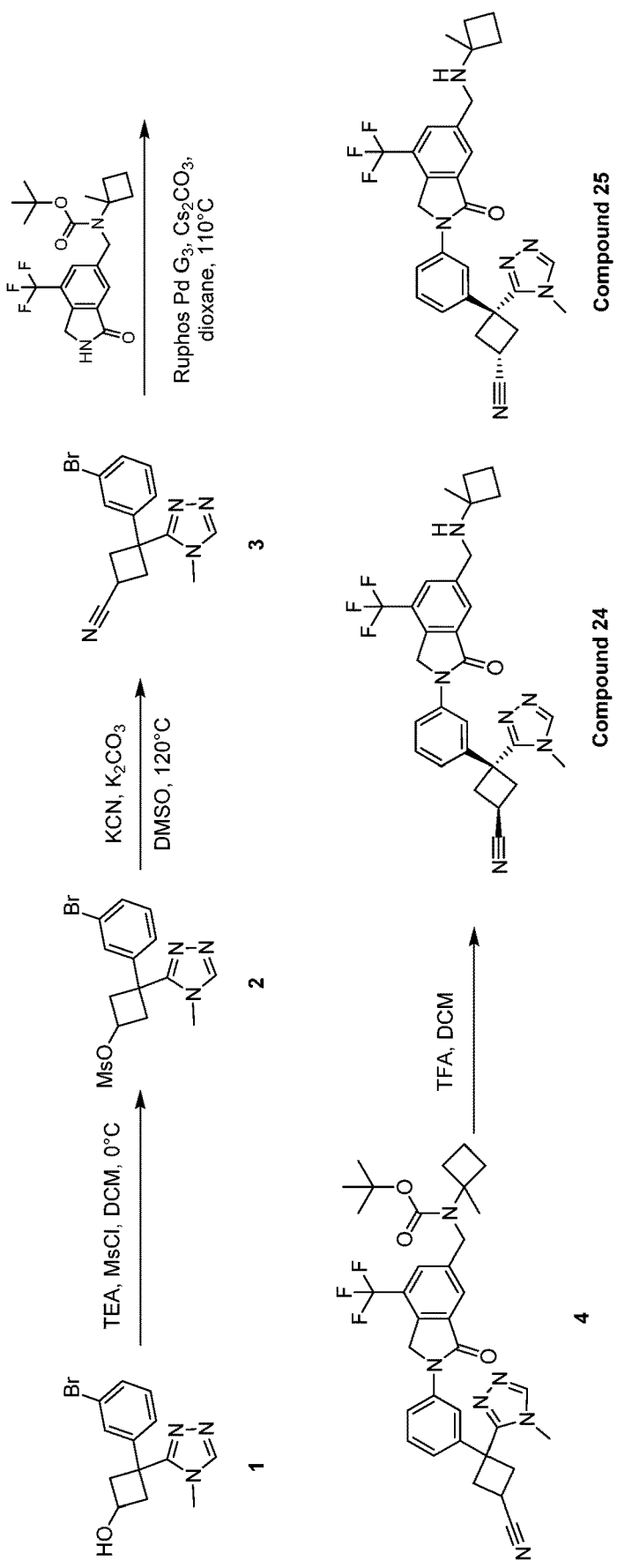

Compounds 24 and 25 can be synthesized according to Scheme 22, FIG. 22.

Intermediate 2: (3-(3-bromophenyl)-3-(4-methyl-4H-1,2,4-triazol-3-yl)cyclobutyl methanesulfonate)

To a mixture of 3-(3-bromophenyl)-3-(4-methyl-4H-1,2,4-triazol-3-yl)cyclobutanol (1.00 g, 3.24 mmol) in dichloromethane (20 mL) was added triethylamine (2.26 mL, 16.2 mmol) and mesyl chloride (1.23 mL, 15.9 mmol) at 0° C. The mixture was stirred at 25° C. for 3 h then quenched with saturated aqueous sodium bicarbonate (10 mL). The resulting mixture was extracted with dichloromethane (3×20 mL). The combined organic layers were washed with brine (50 mL), dried and concentrated under reduced pressure to afford 3-(3-bromophenyl)-3-(4-methyl-4H-1,2,4-triazol-3-yl)cyclobutyl methanesulfonate (1.20 g, 96% yield) as a yellow oil.

Intermediate 3: (3-(3-bromophenyl)-3-(4-methyl-4H-1,2,4-triazol-3-yl)cyclobutanecarbonitrile)

To a solution of 3-(3-bromophenyl)-3-(4-methyl-4H-1,2,4-triazol-3-yl)cyclobutyl methanesulfonate (1.2 g, 3.11 mmol) in dimethyl sulfoxide (15 mL). was added potassium carbonate (2.15 g, 15.53 mmol) and potassium cyanide (1.16 g, 17.8 mmol), the mixture was stirred at 120° C. for 16 hours and diluted with water (10 mL). The resulting mixture was extracted with dichloromethane (3×20 mL). The combined organic layers were washed with brine (20 mL), dried and concentrated under reduced pressure. The residue was purified by silica gel chromatography (mobile phase: methanol/dichloromethane, gradient 0% to 4%) to afford 3-(3-bromophenyl)-3-(4-methyl-4H-1,2,4-triazol-3-yl)cyclobutanecarbonitrile (750 mg, 76% yield) as a yellow oil. LCMS [M+H]$^+$=319.1 and 320.1.

Intermediate 4: (tert-butyl ((2-(3-(3-cyano-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate)

To a solution of tert-butyl (1-methylcyclobutyl)((3-oxo-7-(trifluoromethyl)isoindolin-5-yl)methyl)carbamate (180 mg, 0.45 mmol) and 3-(3-bromophenyl)-3-(4-methyl-4H-1,2,4-triazol-3-yl)cyclobutanecarbonitrile (130 mg, 0.4 mmol) in 1,4-dioxane (5 mL) was added cesium carbonate (401 mg, 1.2 mmol), (2-Dicyclohexylphosphino-2',6'-diisopropoxy-1,1'-biphenyl)[2-(2'-amino-1,1'biphenyl)]palladium(II) methanesulfonate (34 mg, 0.04 mmol, CAS #: 1445085-77-7). The mixture was stirred at 110° C. for 16 h under nitrogen protection. After cooled, the mixture was diluted with dichloromethane (5 mL). The separated organic layer was washed with brine (5 mL), dried and concentrated under reduced pressure. The residue was purified by silica gel chromatography (mobile phase: methanol/dichloro-methane, gradient 0% to 6%) to afford tert-butyl ((2-(3-(3-cyano-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (150 mg, 58% yield) as a yellow solid. LCMS [M+H]$^+$=635.3.

Compounds 24 and 25

A mixture of tert-butyl ((2-(3-(3-cyano-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (150 mg, 0.23 mmol) and trifluoroacetic acid (0.5 mL, 27.6 mmol) in dichloromethane (5 mL) was stirred at 20° C. for 2 h and concentrated under reduced pressure. The residue was purified by RP-HPLC (60% to 90% ACN/(0.05% $NH_3H_2O$+10 mM $NH_4HCO_3$ in water)) to afford 3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutane-carbonitrile (60 mg, 48% yield).

The above racemate (60 mg, 0.57 mmol) was further purified by chiral SFC (Column=Daicel Chiralcel OD; Column dimensions=250 mm×30 mm×10 μm; Detection wavelength=220 nM; Flow rate=70 mL/min; Run time=4.0 min; Column temperature=25° C.) with 0.1% ammonium hydroxide-30% ethanol-carbon dioxide) to afford:

(1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutanecarbonitrile (Peak 2, retention time=4.550 min) (39 mg, 69% yield). $^1$H NMR (400 MHz, DMSO-$d_6$) δ 8.43 (s, 1H), 8.26 (s, 1H), 8.21 (s, 1H), 7.86-7.82 (m, 2H), 7.51-7.46 (m, 1H), 7.08 (d, J=8.0 Hz, 1H), 5.28 (s, 2H), 4.26 (s, 2H), 3.43-3.38 (m, 3H), 3.23 (s, 3H), 3.08-3.01 (m, 2H), 2.38-2.32 (m, 3H), 1.90-1.83 (m, 4H), 1.52 (s, 3H). LCMS: [M+H]$^+$=535.3.

(1s,3s)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutanecarbonitrile (Peak 1, retention time=4.233 min) (2 mg, 4% yield). $^1$H NMR (400 MHz, DMSO-$d_6$) δ 8.38 (s, 1H), 8.05 (s, 1H), 8.01 (s, 1H), 7.89 (s, 1H), 7.81 (d, J=8.0 Hz, 1H), 7.47 (t, J=8.0 Hz, 1H), 7.12 (d, J=8.4 Hz, 1H), 5.20 (s, 2H), 3.82 (s, 2H), 3.70-3.50 (m, 1H), 3.26 (s, 3H), 3.26-3.12 (m, 4H), 2.02-1.94 (m, 2H), 1.76-1.62 (m, 4H), 1.23 (s, 3H). LCMS: [M+H]$^+$=535.3.

Example 24: Compounds 26 and 27

Figure 23:
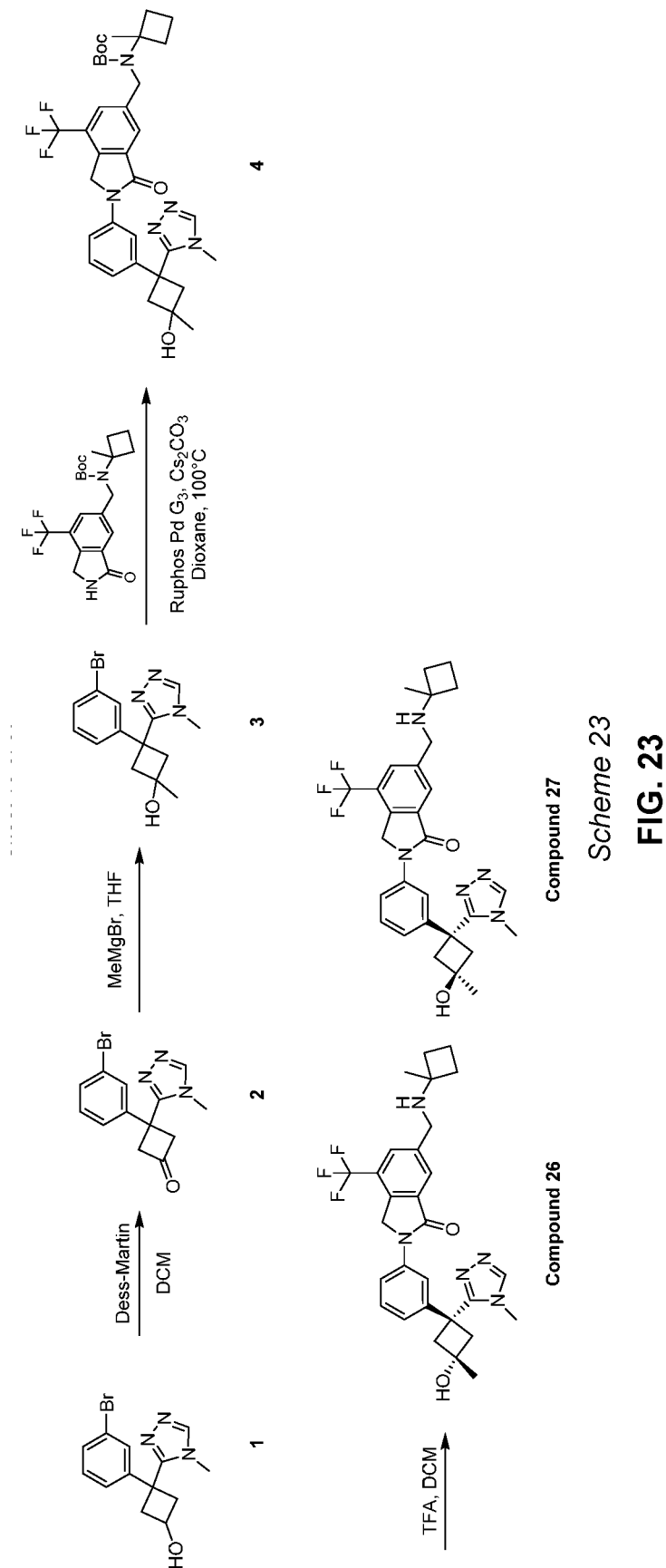

Compounds 26 and 27 (2-(3-((1s,3s)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one), and (2-(3-((1r,3r)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one) can be synthesized according to Scheme 23 (FIG. 23).

Intermediate 2: (3-(3-bromophenyl)-3-(4-methyl-4H-1,2,4-triazol-3-yl)cyclobutanone To a solution of 3-(3-bromophenyl)-3-(4-methyl-4H-1,2,4-triazol-3-yl)cyclobutanol (4.0 g, 13.0 mmol) in ethyl acetate (100 mL) was added 2-iodoxybenzoicacid (10.9 g, 38.94 mmol) at 25° C. The mixture was stirred at 80° C. for 16 h and filtered. The filtrate was concentrated under reduced pressure and the residue was purified by silica gel chromatography (mobile phase: methanol/dichloromethane, gradient 0% to 10%) to afford 3-(3-bromophenyl)-3-(4-methyl-4H-1,2,4-triazol-3-yl)cyclobutanone (3.5 g, 88% yield) as a yellow solid. LCMS: [M+H]$^+$=306.

Intermediate 3: (3-(3-bromophenyl)-1-methyl-3-(4-methyl-4H-1,2,4-triazol-3-yl)cyclobutanol A solution of 3-(3-bromophenyl)-3-(4-methyl-4H-1,2,4-triazol-3-yl)cyclobutan-1-one (2.0 g, 6.53 mmol) in tetrahydrofuran (30 mL) was added methylmagnesium bromide (3M in tetrahydrofuran, 8.71 mL, 26.13 mmol) at 0° C. The reaction mixture was stirred at 20° C. for 16 h. The reaction was quenched with water (20 mL) then extracted with dichloromethane (3×50 mL). The combined organic phases were washed with brine (50 mL), dried and concentrated under reduced pressure. The resulting residue was purified by silica gel chromatography (mobile phase: methanol/dichloromethane, gradient 0% to 10%) to afford 3-(3-bromophenyl)-1-methyl-3-(4-methyl-4H-1,2,4-triazol-3-yl)cyclobutanol (900 mg, 45% yield) as a yellow oil. LCMS: [M+H]$^+$=324.0.

Intermediate 4: (tert-butyl ((2-(3-(3-hydroxy-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glove box, a mixture of 3-(3-bromophenyl)-1-methyl-3-(4-methyl-4H-1,2,4-triazol-3-yl)cyclobutan-1-ol (150 mg, 0.47 mmol), tert-butyl (1-methylcyclobutyl)((3-oxo-7-(trifluoromethyl)isoindolin-5-yl)methyl)carbamate (204 mg, 0.51 mmol), cesium carbonate (455 mg, 1.40 mmol) and (2-Dicyclohexylphosphino-2',6'-diisopropoxy-1,1'-biphenyl)[2-(2'-amino-1,1'biphenyl)]palladium(II) methanesulfonate (38.9 mg, 0.05 mmol, CAS No.: 1445085-77-7) in 1,4-dioxane (4 mL) was stirred at 110° C. for 16 h and concentrated under reduced pressure. The residue was purified by preparative TLC (solvent gradient: 10% methanol in dichloromethane) to afford tert-butyl ((2-(3-(3-hydroxy-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (130 mg, 44% yield) as a yellow solid. LCMS [M+H]$^+$=640.1.

Compounds 26 and 27

To a mixture of tert-butyl ((2-(3-(3-hydroxy-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (130 mg, 0.20 mmol) in dichloromethane (5 mL) was added trifluoroacetic acid (0.5 mL, 6.49 mmol). The mixture was stirred at 20° C. for 2 h and concentrated under reduced pressure. The residue was purified by RP-HPLC (45% to 75% ACN/(0.05% NH$_3$H$_2$O+ 10 mM NH$_4$HCO$_3$ in water)) to afford tentatively assigned:

2-(3-((1s,3s)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1) (5 mg, 5% yield). $^1$H NMR (400 MHz, methanol-d$_4$) δ 8.39 (s, 1H), 8.13 (s, 1H), 8.05 (s, 1H), 7.90 (s, 1H), 7.69 (d, J=6.8 Hz, 1H), 7.53-7.41 (m, 1H), 7.17 (d, J=7.2 Hz, 1H), 5.17 (s, 2H), 4.02 (s, 2H), 3.40 (s, 3H), 3.24-3.21 (m, 2H), 2.94 (d, J=12.8 Hz, 2H), 2.25-2.19 (m, 2H), 1.97-1.84 (m, 4H), 1.47 (s, 3H), 1.29 (s, 3H). LCMS [M+H]$^+$=540.2.

2-(3-((1r,3r)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2) (5 mg, 5% yield). $^1$H NMR (400 MHz, methanol-d$_4$) δ 8.28 (s, 1H), 8.13 (s, 1H), 8.10 (s, 1H) 8.02 (s, 1H), 7.69 (d, J=8.0 Hz, 1H), 7.49 (t, J=8.0 Hz, 1H), 7.33 (d, J=7.6 Hz, 1H), 5.16 (s, 2H), 3.89 (s, 2H), 3.46 (s, 3H), 3.21-3.14 (m, 2H), 3.12-3.04 (m, 2H), 2.17-2.07 (m, 2H), 1.92-1.78 (m, 4H), 1.40 (s, 3H), 1.30 (s, 3H). LCMS [M+H]$^+$=540.2.

Example 25: Compounds 28 and 29

Figure 24:
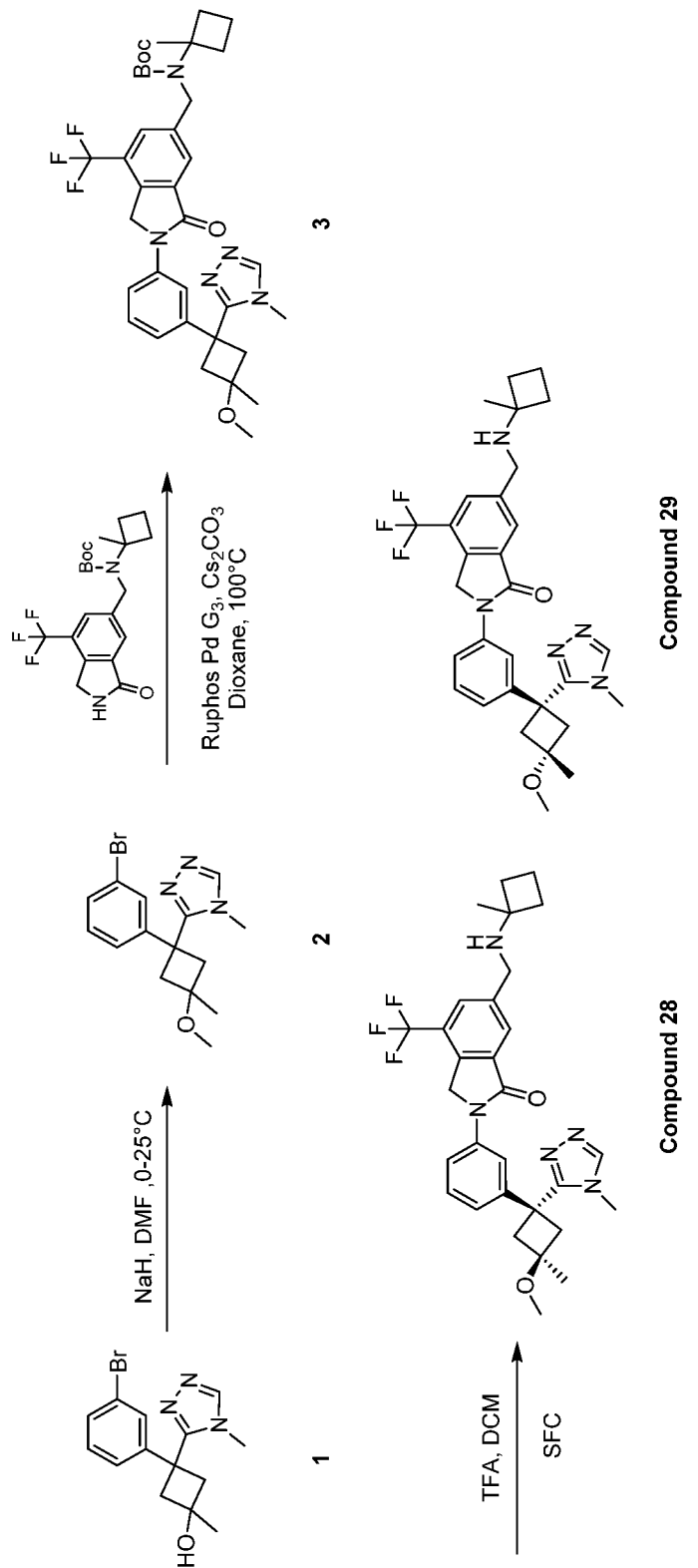

Compound 28 (2-(3-((1r,3r)-3-methoxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one), and
Compound 29 (2-(3-((1s,3s)-3-hydroxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to Scheme 24 (FIG. 24).

Intermediate 2: (3-(1-(3-bromophenyl)-3-methoxy-3-methylcyclobutyl)-4-methyl-4H-1,2,4-triazole To a solution of 3-(3-bromophenyl)-1-methyl-3-(4-methyl-4H-1,2,4-triazol-3-yl)cyclobutanol (300 mg, 0.93 mmol) in N,N-dimethylacetamide (5 mL) was added sodium hydride (60%, 44.7 mg, 1.12 mmol) at 0° C. The mixture was stirred for 1 h and then methyl iodide (0.09 mL, 1.40 mmol) was added. The reaction mixture was stirred at 25° C. for another 16 h and quenched by addition of water (5 mL). The solution was concentrated under reduced pressure and the residue was purified by preparative TLC (solvent gradient: 10% methanol in dichloromethane) to afford 3-(1-(3-bromophenyl)-3-methoxy-3-methylcyclobutyl)-4-methyl-4H-1,2,4-triazole (200 mg, 64% yield) as a yellow oil. LCMS [M+H]$^+$=336.3.

Intermediate 3: (tert-butyl ((2-(3-(3-methoxy-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glove box, a mixture of 3-(1-(3-bromophenyl)-3-methoxy-3-methylcyclobutyl)-4-methyl-4H-1,2,4-triazole (200 mg, 0.59 mmol), tert-butyl (1-methylcyclobutyl)((3-oxo-7-(trifluoromethyl)isoindolin-5-yl)methyl)carbamate (261 mg, 0.65 mmol), cesium carbonate (581 mg, 1.78 mmol) and (2-Dicyclohexylphosphino-2',6'-diisopropoxy-1,1'-biphenyl)[2-(2'-amino-1,1'biphenyl)]palladium(II) methanesulfonate (49.8 mg, 0.06 mmol, CAS No.: 1445085-77-7) in 1,4-dioxane (5 mL) was stirred at 110° C. for 16 h and concentrated under reduced pressure. The residue was purified by preparative TLC (solvent gradient: 10% methanol in dichloromethane) to afford tert-butyl ((2-(3-(3-methoxy-3- methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (180 mg, 46% yield) as a yellow oil. LCMS [M+H]$^+$=654.3.

Compounds 28 and 29

A mixture of tert-butyl ((2-(3-(3-methoxy-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (180 mg, 0.28 mmol) and trifluoroacetic acid (0.68 mL, 8.79 mmol) in dichloromethane (5 mL) was stirred at 20 C for 2 h and concentrated under reduced pressure. The residue was purified by RP-HPLC (50% to 80% ACN/(0.05% NH$_3$H$_2$O+10 mM NH$_4$HCO$_3$ in water)) to afford 2-(3-(3-methoxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (50 mg, 33% yield).

The above racemate (50 mg, 0.09 mmol) was purified by chiral SFC (Column=Daicel Chiralcel AD; Column dimensions=250 mm×30 mm×10 μm; Detection wavelength=220 nM; Flow rate=70 mL/min; Run time=4.0 min; Column temperature=25° C.) with 0.1% ammonium hydroxide-40% ethanol-carbon dioxide) to afford tentatively assigned:

2-(3-((1s,3s)-3-methoxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1, retention time=1.653 min) (22.7 mg, 45% yield). $^1$H NMR (400 MHz, methanol-d$_4$) δ 8.40 (s, 1H), 8.09 (s, 1H), 8.02 (s, 1H), 7.95 (s, 1H), 7.68 (d, J=8.0 Hz, 1H), 7.47 (t, J=8.0 Hz, 1H), 7.11 (d, J=8.8 Hz, 1H), 5.15 (s, 2H), 3.89 (s, 2H), 3.40 (s, 3H), 3.23 (s, 3H), 3.13-3.09 (m, 2H), 2.98-2.94 (m, 2H), 2.17-2.10 (m, 2H), 1.92-1.78 (m, 4H), 1.40 (s, 3H), 1.30 (s, 3H). LCMS [M+H]$^+$=554.3.

2-(3-((1r,3r)-3-methoxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2, retention time=2.243 min) (11.9 mg, 23% yield). $^1$H NMR (400 MHz, methanol-d$_4$) δ 8.29 (s, 1H), 8.11 (s, 1H), 8.09 (s, 1H), 8.02 (s, 1H), 7.68 (d, J=9.2 Hz, 1H), 7.49 (t, J=8.0 Hz, 1H), 7.29 (d, J=6.8 Hz, 1H), 5.16 (s, 2H), 3.88 (s, 2H), 3.44 (s, 3H), 3.24-3.20 (m, 2H), 3.20 (s, 3H), 2.95-2.91 (m, 2H), 2.12-2.07 (m, 2H), 1.91-1.78 (m, 4H), 1.39 (s, 3H), 1.32 (s, 3H). LCMS [M+H]$^+$=554.3.

Example 26: Compounds 30 and 31

Figure 25:
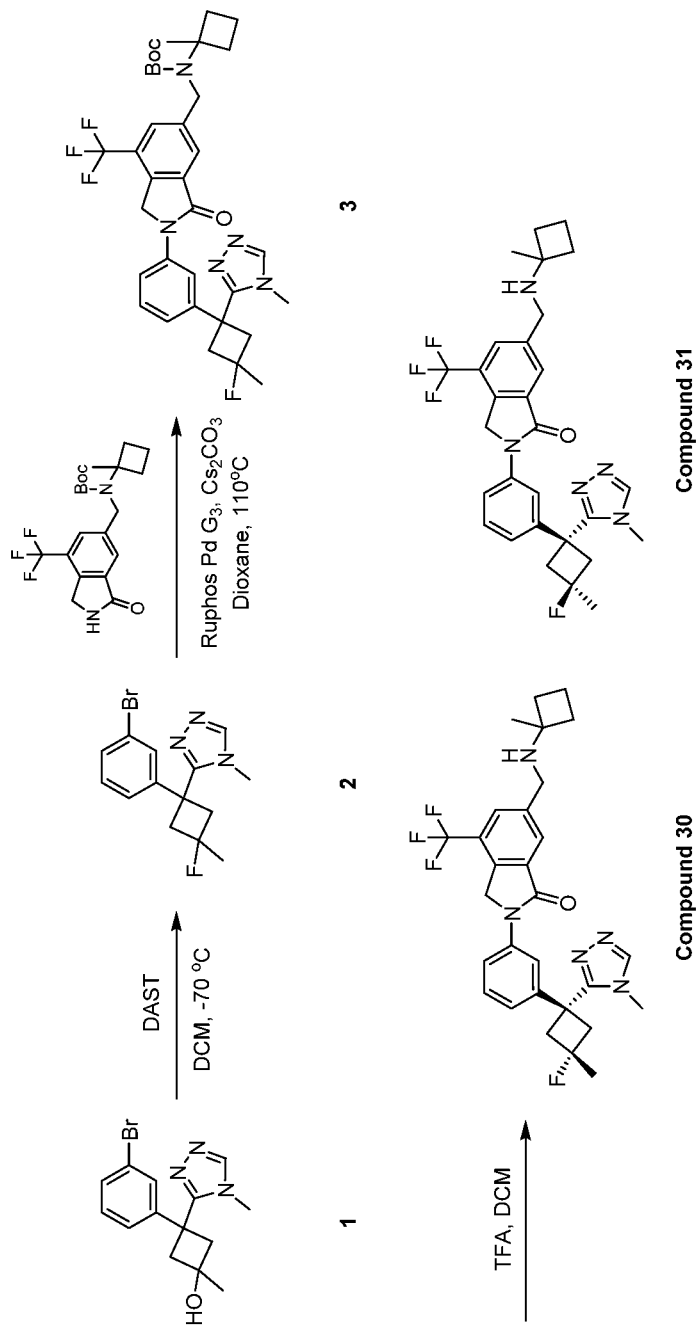

Compound 30 (2-(3-((1s,3s)-3-fluoro-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one) and Compound 31 (2-(3-((1r,3r)-3-fluoro-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to Scheme 25 (FIG. 25).

Intermediate 2: (3-(1-(3-bromophenyl)-3-fluoro-3-methylcyclobutyl)-4-methyl-4H-1,2,4-triazole To a solution of 3-(3-bromophenyl)-1-methyl-3-(4-methyl-4H-1,2,4-triazol-3-yl)cyclobutanol (500 mg, 1.62 mmol) in dichloromethane (10 mL) was added diethylaminosulfur trifluoride (0.64 mL, 4.87 mmol) at 0° C. The mixture was stirred at 25° C. for 16 h under nitrogen and quenched by addition of saturated aqueous ammonium chloride (20 mL). The resulting solution was extracted with dichloromethane (3×50 ml). The combined organic layers were washed with brine (50 mL), dried and concentrated under reduced pressure. The residue was purified by silica gel chromatography (mobile phase: methanol/dichloromethane, gradient 0% to 4%) to afford 3-(1-(3-bromophenyl)-3-fluoro-3-methylcyclobutyl)-4-methyl-4H-1,2,4-triazole (430 mg, 82% yield) as a colorless oil.

Intermediate 3: (tert-butyl ((2-(3-(3-fluoro-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glove box, a mixture of 3-(1-(3-bromophenyl)-3-fluoro-3-methylcyclobutyl)-4-methyl-4H-1,2,4-triazole (350 mg, 1.08 mmol), tert-butyl (1-methylcyclobutyl)((3-oxo-7-(trifluoromethyl)isoindolin-5-yl)methyl)carbamate (473 mg, 1.19 mmol), cesium carbonate (879 mg, 2.7 mmol) and (2-Dicyclohexylphosphino-2',6'-diisopropoxy-1,1'-biphenyl)[2-(2'-amino-1,1'biphenyl)]palladium(II) methanesulfonate (72.2 mg, 0.09 mmol, CAS No.: 1445085-77-7) in 1,4-dioxane (10 mL) was stirred at 110° C. for 16 h and concentrated under reduced pressure. The residue was purified by silica gel chromatography (mobile phase: methanol/dichloromethane, gradient 0% to 4%) to afford tert-butyl ((2-(3-(3-fluoro-3-methyl-1-(4-methyl-4H-1,2,4-triazol-3-yl)cyclobutyl)phenyl)-3-oxo-7-(trifluoromethyl)-isoindolin-5-yl)methyl)(1-methylcyclobutyl)carbamate (300 mg, 43% yield) as a yellow oil. LCMS [M+H]$^+$=642.3.

Compounds 30 and 31

To a mixture of tert-butyl ((2-(3-(3-fluoro-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (300 mg, 0.47 mmol) in dichloromethane (5 mL) was added trifluoroacetic acid (0.68 mL, 8.79 mmol). The mixture was stirred at 20 C for 2 h and concentrated under reduced pressure. The residue was purified by RP-HPLC (55% to 85% ACN/(0.05% NH$_3$H$_2$O+10 mM NH$_4$HCO$_3$ in water)) to afford 2-(3-(3-methoxy-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (80 mg, 21% yield).

The above racemate (80 mg, 0.15 mmol) was purified by chiral SFC (Column=Daicel Chiralcel AD; Column dimensions=250 mm×30 mm×10 μm; Detection wavelength=220 nM; Flow rate=70 mL/min; Run time=4.0 min; Column temperature=25° C.) with 0.1% ammonium hydroxide-35% ethanol-carbon dioxide) to afford:

2-(3-((1r,3r)-3-fluoro-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1, retention time=1.608 min) (25.2 mg, 32% yield). $^1$H NMR (400 MHz, methanol-d$_4$) δ 8.41 (s, 1H), 8.14 (s, 1H), 8.07 (s, 1H), 7.96 (s, 1H), 7.68 (d, J=8.4 Hz, 1H), 7.51 (t, J=8.0 Hz, 1H), 7.19 (d, J=7.6 Hz, 1H), 5.19 (s, 2H), 4.07 (s, 2H), 3.39 (s, 3H), 3.39-3.35 (m, 2H), 3.21-3.15 (m, 2H), 2.27-2.21 (m, 2H), 2.01-1.88 (m, 4H), 1.51 (s, 3H), 1.43 (d, J=22.4 Hz, 3H). LCMS [M+H]$^+$=542.4.

2-(3-((1s,3s)-3-fluoro-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2, retention time=2.244 min) (22.3 mg, 28% yield). $^1$H NMR (400 MHz, methanol-d$_4$) δ 8.31 (s, 1H), 8.13 (s, 1H), 8.10 (s, 1H), 8.06 (s, 1H), 7.70 (d, J=8.4 Hz, 1H), 7.51 (t, J=8.0 Hz, 1H), 7.30 (d, J=7.6 Hz, 1H), 5.19 (s, 2H), 4.02 (s, 2H), 3.43 (s, 3H), 3.41-3.34 (m, 2H), 3.19-3.14 (m, 2H), 2.23-

2.18 (m, 2H), 1.98-1.88 (m, 4H), 1.48 (s, 3H), 1.45 (d, J=20.4 Hz, 3H). LCMS [M+H]$^+$=542.3.

Example 27: Compounds 32 and 33

Figure 26:
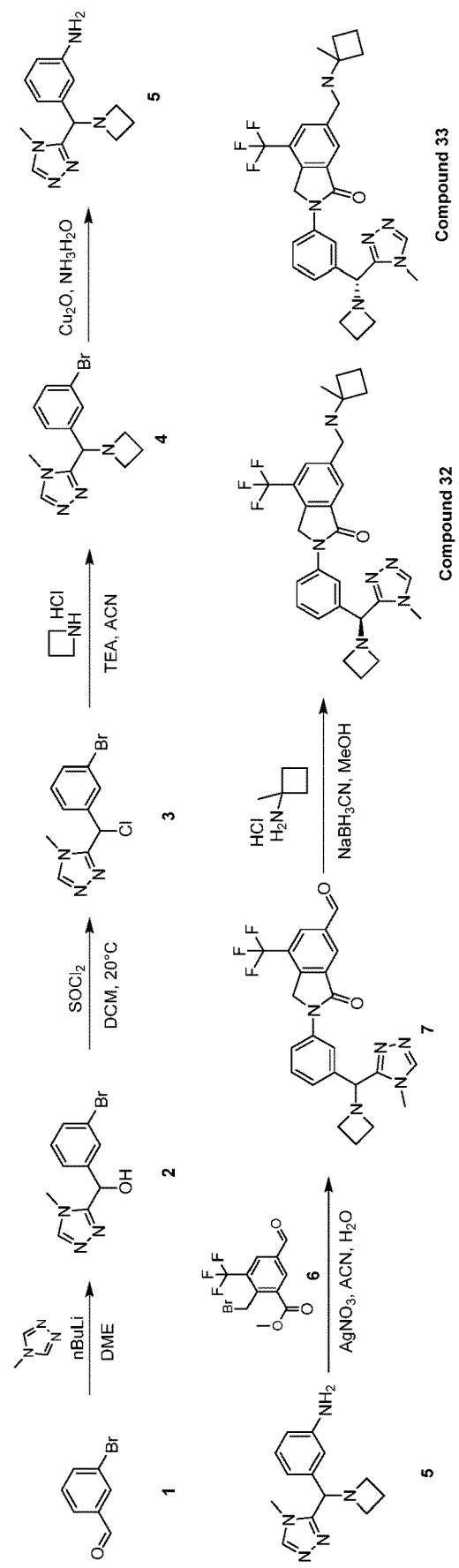

Compound 32 (S)-2-(3-(azetidin-1-yl(4-methyl-4H-1,2,4-triazol-3-yl)methyl)phenyl)-6-(((1-methylcyclobutyl)amino)methyl)-4-(trifluoromethyl)isoindolin-1-one and Compound 33 (R)-2-(3-(azetidin-1-yl(4-methyl-4H-1,2,4-triazol-3-yl)methyl)phenyl)-6-(((1-methylcyclobutyl)amino)methyl)-4-(trifluoromethyl)isoindolin-1-one, can be synthesized according to Scheme 26 (FIG. 26).

Intermediate 2: ((3-bromophenyl)(4-methyl-4H-1,2,4-triazol-3-yl)methanol

Under nitrogen, to a solution of 4-methyl-4H-1,2,4-triazole (1.35 g, 16.2 mmol) in 1,2-dimethoxyethane (100 mL) was added n-butyllithium (2.5 M in hexanes, 6.5 mL, 16.2 mmol) at −50° C. over 5 min. The resulting mixture was stirred for 1.5 h at −50° C., then a solution of 3-bromobenzaldehyde (1.3 mL, 10.8 mmol) in 1,2-dimethoxyethane (10 mL) was added dropwise. The reaction mixture was warmed to 0° C. and stirred for another 1 h. The mixture was quenched with water (1 mL) and concentrated under reduced pressure. The residue was purified by silica gel chromatography (mobile phase: methanol/dichloro-methane, gradient 0% to 10%) to afford (3-bromophenyl)(4-methyl-4H-1,2,4-triazol-3-yl)-methanol (2.2 g, 76% yield) as a yellow solid. LCMS: [M+H]$^+$=268.1.

Intermediate 3: (3-((3-bromophenyl)chloromethyl)-4-methyl-4H-1,2,4-triazole To a solution of (3-bromophenyl)(4-methyl-4H-1,2,4-triazol-3-yl)methanol (1.7 g, 6.3 mmol) in dichloromethane (10 mL) was added thionyl chloride (1.4 mL, 19.0 mmol) and N,N-dimethylformamide (0.05 mL) at 0° C. The mixture was stirred at 25° C. for 20 h then concentrated under reduced pressure to afford crude 3-((3-bromophenyl)chloromethyl)-4-methyl-4H-1,2,4-triazole (1.8 g, 99% yield) as a white solid. LCMS: [M+H]$^+$=286.0 and 288.0.

Intermediate 4: (3-(azetidin-1-yl(3-bromophenyl)methyl)-4-methyl-4H-1,2,4-triazole To a mixture of 3-((3-bromophenyl)chloromethyl)-4-methyl-4H-1,2,4-triazole (1.0 g, 3.5 mmol) and azetidine hydrochloride (1.6 g, 17.5 mmol) in acetonitrile (15 mL) was added triethylamine (2.4 mL, 17.5 mmol). The reaction mixture was stirred at 20° C. for 2 h and diluted with water (30 mL). The resulting solution was extracted with dichloromethane (3×30 mL). The combined organic layers were washed with brine (40 mL), dried and concentrated under reduced pressure to afford crude 3-(azetidin-1-yl(3-bromophenyl)methyl)-4-methyl-4H-1,2,4-triazole (1.0 g, 93% yield) as a yellow solid. LCMS: [M+H]$^+$=307.0 and 309.1.

Intermediate 5: (3-(azetidin-1-yl(4-methyl-4H-1,2,4-triazol-3-yl)methyl)aniline To a mixture of 3-(azetidin-1-yl(3-bromophenyl)methyl)-4-methyl-4H-1,2,4-triazole (500 mg, 1.63 mmol) and 30% ammonia water (5.3 mL, 49.4 mmol) in acetonitrile (5 mL) was added copper(I) oxide (466 mg, 3.3 mmol). The sealed tube was stirred at 100° C. for 18 h and cooled. The mixture was diluted with water (30 mL) and extracted with dichloromethane (3×30 mL). The combined organic phases were dried and concentrated under reduced pressure to crude afford 3-(azetidin-1-yl(4-methyl-4H-1,2,4-triazol-3-yl)methyl)aniline (390 mg, 98% yield) as a yellow solid. LCMS: [M+H]$^+$=244.1.

Intermediate 7: (2-(3-(azetidin-1-yl(4-methyl-4H-1,2,4-triazol-3-yl)methyl)phenyl)-3-oxo-7-(trifluoromethyl)isoindoline-5-carbaldehyde To a mixture of 3-(azetidin-1-yl(4-methyl-4H-1,2,4-triazol-3-yl)methyl)aniline (290 mg, 1.2 mmol) in acetonitrile (12 mL) and water (6 mL) was added methyl 2-(bromomethyl)-5-formyl-3-(trifluoromethyl)benzoate (426 mg, 1.3 mmol) and silver nitrate (304 mg, 1.8 mmol). The mixture was stirred at 25° C. for 16 h and diluted with water (30 mL). The resulting solution was extracted with dichloromethane (3×30 mL). The combined organic layers were dried and concentrated under reduced pressure. The residue was purified by silica gel chromatography (mobile phase: methanol/dichloromethane, gradient 0% to 8%) to afford 2-(3-(azetidin-1-yl(4-methyl-4H-1,2,4-triazol-3-yl)methyl)phenyl)-3-oxo-7-(trifluoromethyl)isoindoline-5-carbaldehyde (300 mg, 55% yield) as a light yellow oil. LCMS: [M+H]$^+$=456.2.

Compounds 32 and 33

A mixture of 2-(3-(azetidin-1-yl(4-methyl-4H-1,2,4-triazol-3-yl)methyl)phenyl)-3-oxo-7-(trifluoromethyl)isoindoline-5-carbaldehyde (250 mg, 0.55 mmol), 1-methylcyclobutan-1-amine hydrochloride (134 mg, 1.1 mmol) and triethylamine (0.14 mL, 1.0 mmol) in methanol (10 mL) was stirred at 100° C. for 2 min under microwave conditions and cooled, then sodium cyanoborohydride (69.0 mg, 1.1 mmol) was added. The solution was stirred at 80° C. under microwave conditions for 1 h and concentrated under reduced pressure. The residue was purified by RP-HPLC (37% to 67% ACN/(0.05% NH$_3$H$_2$O+10 mM NH$_4$HCO$_3$ in water)) to afford 2-(3-(azetidin-1-yl(4-methyl-4H-1,2,4-triazol-3-yl)methyl)phenyl)-6-(((1-methylcyclobutyl)amino)methyl)-4-(trifluoromethyl)isoindolin-1-one (130 mg, 45.1% yield). LCMS: [M+H]$^+$=525.1.

The above racemate was further purified by chiral SFC (Column=Daicel Chiralcel AD; Column dimensions=250 mm×30 mm×10 μm; Detection wavelength=220 nm; Flow rate=70 mL/min; Run time=4.0 min; Column temperature=25° C.) with 0.1% ammonium hydroxide-30% ethanol-carbon dioxide) to afford tentatively assigned:

(S)-2-(3-(azetidin-1-yl(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=4.495 min) (43.5 mg, 32% yield). $^1$H NMR (400 MHz, CD3CN) δ 8.14 (s, 1H), 8.02 (s, 1H), 8.00 (s, 1H), 7.94 (s, 1H), 7.70-7.67 (m, 1H), 7.41 (t, J=8.0 Hz, 1H), 7.25 (d, J=8.0 Hz, 1H), 5.04 (s, 2H), 4.94 (s, 1H), 3.86 (s, 2H), 3.63 (s, 3H), 3.33-3.27 (m, 2H), 3.19-3.15 (m, 2H), 2.10-1.99 (m, 4H), 1.80-1.74 (m, 4H), 1.29 (s, 3H). LCMS: [M+H]$^+$=525.1.

(R)-2-(3-(azetidin-1-yl(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=3.983 min) (47.0 mg, 34% yield). $^1$H NMR (400 MHz, CD3CN) δ 8.14 (s, 1H), 8.02 (s, 1H), 8.00 (s, 1H), 7.94 (s, 1H), 7.70-7.67 (m, 1H), 7.41 (t, J=8.0 Hz, 1H), 7.25 (d, J=7.6 Hz, 1H), 5.04 (s, 2H), 4.94 (s, 1H), 3.86 (s, 2H), 3.63 (s, 3H), 3.33-3.27 (m, 2H), 3.19-3.13 (m, 2H), 2.10-1.99 (m, 4H), 1.84-1.74 (m, 4H), 1.29 (s, 3H). LCMS: [M+H]$^+$=525.1.

Example 28: Compounds 34 and 35

Figure 27:
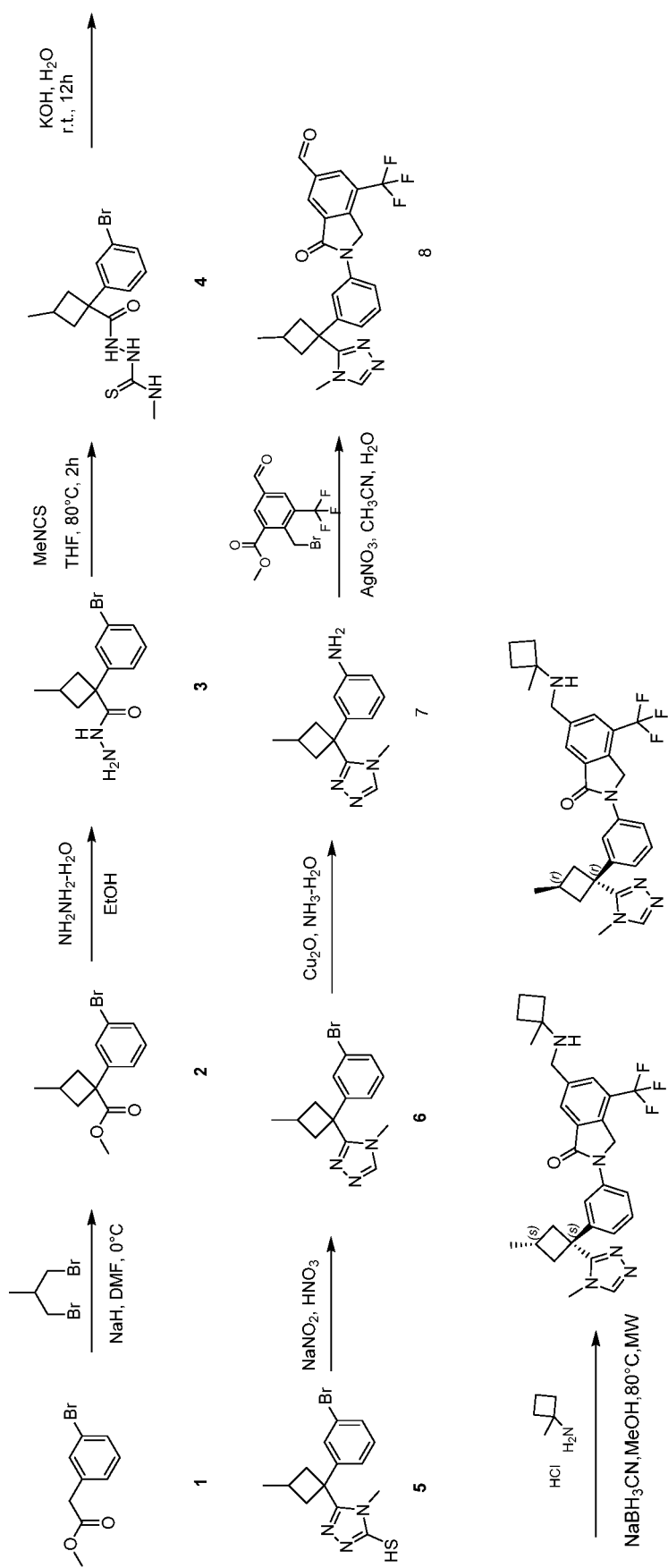

Compound 34 2-(3-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one and Compound 35 2-(3-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one, can be synthesized according to Scheme 27 (FIG. 27).

Intermediate 2: (methyl 1-(3-bromophenyl)-3-methylcyclobutanecarboxylate

To a solution of methyl 2-(3-bromophenyl)acetate (20.0 g, 87.3 mmol, CAS #: 150529-73-0) in N,N-dimethylformamide (100 mL) was added sodium hydride (60%, 6.3 g, 261.9 mmol) at 0° C. The mixture was stirred at 0° C. for 30 min and then 1,3-dibromo-2-methylpropane (22.6 g, 104.8 mmol) was added. The resulting mixture was stirred at 60° C. for 16 h. After cooled, the mixture was quenched by addition of water (100 mL) and extracted with ethyl acetate (2×150 mL). The combined organic phases were washed with water (2×100 mL), dried and concentrated under reduced pressure. The residue was purified by silica gel chromatography (mobile phase: ethyl acetate/petroleum ether, gradient 0% to 10%) to afford methyl 1-(3-bromophenyl)-3-methylcyclobutanecarboxylate (14.0 g, 57% yield) as a colorless oil. LCMS [M+H]$^+$=283.1 and 285.1.

Intermediate 3: 1-(3-bromophenyl)-3-methylcyclobutanecarbohydrazide

To a solution of methyl 1-(3-bromophenyl)-3-methylcyclobutanecarboxylate (14.0 g, 49.4 mmol) in ethanol (200 mL) was added hydrazine hydrate (85%, 70.0 mL, 1.2 mol). The reaction mixture was stirred at 100° C. for 16 h and concentrated under reduced pressure to afford crude 1-(3-bromophenyl)-3-methyl-cyclobutanecarbohydrazide (14.0 g, 100% yield) as a yellow solid. LCMS [M+H]$^+$=283.1 and 285.1.

Intermediate 4: 2-(1-(3-bromophenyl)-3-methylcyclobutanecarbonyl)-N-methylhydrazinecarbothioamide To a solution of 1-(3-bromophenyl)-3-methylcyclobutanecarbohydrazide (14.0 g, 49.4 mmol) in tetrahydrofuran (200 mL) was added methyl isothiocyanate (4.7 g, 64.3 mmol). The solution was stirred at room temperature for 16 h and concentrated under reduced pressure to afford crude 2-(1-(3-bromophenyl)-3-methylcyclobutanecarbonyl)-N-methylhydrazinecarbothioamide (17.0 g, 100% yield) as a yellow oil. LCMS [M+H]$^+$=356.1 and 358.1.

Intermediate 5: (5-(1-(3-bromophenyl)-3-methylcyclobutyl)-4-methyl-4H-1,2,4-triazole-3-thiol A mixture of 2-(1-(3-bromophenyl)-3-methylcyclobutanecarbonyl)-N-methylhydrazinecarbothioamide (17.0 g, 47.72 mmol) in aqueous sodium hydroxide (1 M, 200 mL) was stirred at 25° C. for 16 h. The reaction mixture was adjusted to pH=5 by addition of aqueous hydrochloric acid (1 M) at 0° C. The precipitate was collected by filtration and dried to afford 5-(1-(3-bromophenyl)-3-methylcyclobutyl)-4-methyl-4H-1,2,4-triazole-3-thiol (16.0 g, 99% yield) as a yellow solid.

Intermediate 6: (3-(1-(3-bromophenyl)-3-methylcyclobutyl)-4-methyl-4H-1,2,4-triazole To a solution of 5-(1-(3-bromophenyl)-3-methylcyclobutyl)-4-methyl-4H-1,2,4-triazole-3-thiol (10.0 g, 29.5 mmol) in water (120 mL) and acetonitrile (40 mL) was added sodium nitrite (10.2 g, 147.8 mmol), followed by a solution of aqueous nitric acid (1 M, 147 mL, 147 mmol) dropwise at 0° C. The mixture was stirred at 20° C. for 2 h and quenched by addition of saturated aqueous sodium bicarbonate (100 mL). The mixture was extracted with dichloromethane (3×100 mL). The combined organic layers were washed with brine (100 mL), dried and concentrated under reduced pressure. The residue was purified by silica gel chromatography (mobile phase: methanol/dichloromethane, gradient 0% to 5%) to afford 3-(1-(3-bromophenyl)-3-methylcyclobutyl)-4-methyl-4H-1,2,4-triazole (6.0 g, 66% yield) as a yellow solid. LCMS [M+H]$^+$=306.1 and 308.0.

Intermediate 7: (3-(3-methyl-1-(4-methyl-4H-1,2,4-triazol-3-yl)cyclobutyl)aniline To a mixture of 3-(1-(3-bromophenyl)-3-methylcyclobutyl)-4-methyl-4H-1,2,4-triazole (3 g, 9.8 mmol) and 30% ammonia water (15 mL, 413 mmol) in acetonitrile (15 mL) was added copper(I) oxide (701 mg, 4.9 mmol). The sealed tube was stirred at 100° C. for 18 h. After cooled, the mixture was diluted with water (50 mL) and extracted with dichloromethane (3×30 mL). The combined organic phases were dried and concentrated under reduced pressure to afford crude 3-(3-methyl-1-(4-methyl-4H-1,2,4-triazol-3-yl)cyclobutyl)aniline (2 g, 84% yield) as a yellow solid. LCMS: [M+H]$^+$=243.2.

Intermediate 8: (2-(3-(3-methyl-1-(4-methyl-4H-1,2,4-triazol-3-yl)cyclobutyl)phenyl)-3-oxo-7-(trifluoromethyl)isoindoline-5-carbaldehyde To a mixture of 3-(3-methyl-1-(4-methyl-4H-1,2,4-triazol-3-yl)cyclobutyl)aniline (1.7 g, 7.0 mmol) in acetonitrile (60 mL) and water (18 mL) was added methyl 2-(bromomethyl)-5-formyl-3-(trifluoromethyl)benzoate (2.5 g, 7.7 mmol) and silver nitrate (1.8 g, 10.5 mmol). The mixture was stirred at 25° C. for 16 h and diluted with water (30 mL). The mixture was extracted with dichloromethane (3×50 mL). The combined organic layers were dried and concentrated under reduced pressure. The residue was purified by silica gel chromatography (mobile phase: methanol/dichloromethane, gradient 0% to 6%) to afford 2-(3-(3-methyl-1-(4-methyl-4H-1,2,4-triazol-3-yl)cyclobutyl)phenyl)-3-oxo-7-(trifluoromethyl)isoindoline-5-carbaldehyde (2.2 g, 69% yield) as a yellow solid. LCMS: [M+H]$^+$=455.2.

Compounds 34 and 35:

A mixture of 2-(3-(3-methyl-1-(4-methyl-4H-1,2,4-triazol-3-yl)cyclobutyl)phenyl)-3-oxo-7-(trifluoromethyl)isoindoline-5-carbaldehyde (300 mg, 0.7 mmol), 1-methylcyclobutan-1-amine hydrochloride (161 mg, 1.32 mmol) and triethylamine (0.17 mL, 1.2 mmol) in methanol (10 mL) was stirred at 100° C. for 2 min under microwave conditions. After cooled, sodium cyanoborohydride (83 mg, 1.3 mmol) was added and the mixture was stirred at 80° C. under microwave for another 45 min. The reaction mixture was concentrated under reduced pressure and the residue was purified by silica gel chromatography (mobile phase: methyl alcohol/dichloromethane, gradient 0% to 8%) to afford 2-(3-(3-methyl-1-(4-methyl-4H-1,2,4-triazol-3-yl)cyclobutyl)

phenyl)-6-(((1-methylcyclobutyl)amino)methyl)-4-(trifluoromethyl)isoindolin-1-one (300 mg, 87% yield).

The above racemate (300 mg, 0.57 mmol) was further purified by chiral SFC (Column=Daicel Chiralcel OD; Column dimensions=250 mm×30 mm×10 μm; Detection wavelength=220 nM; Flow rate=70 mL/min; Run time=4.0 min; Column temperature=25° C.) with 0.1% ammonium hydroxide-30% ethanol-carbon dioxide) to afford tentatively assigned:

2-(3-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1, retention time=4.292 min) (80.9 mg, 26% yield). $^1$H NMR (400 MHz, methanol-$d_4$) δ 8.30 (s, 1H), 8.08 (d, J=2.0 Hz, 2H), 7.87 (s, 1H), 7.70-7.67 (m, 1H), 7.49 (t, J=8.0 Hz, 1H), 7.24 (d, J=8.0 Hz, 1H), 5.15 (s, 2H), 3.86 (s, 2H), 3.35 (s, 3H), 3.00-2.94 (m, 2H), 2.69-2.57 (m, 3H), 2.12-2.08 (m, 2H), 1.89-1.77 (m, 4H), 1.38 (s, 3H), 1.16 (d, J=6.4 Hz, 3H). LCMS: $[M+H]^+$=524.3.

2-(3-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2, retention time=4.37 min) (28.8 mg, 9% yield). $^1$H NMR (400 MHz, methanol-$d_4$) δ 8.37 (s, 1H), 8.08 (s, 1H), 8.00 (s, 1H), 7.91 (s, 1H), 7.64 (d, J=8.0 Hz, 1H), 7.45 (t, J=8.0 Hz, 1H), 7.07 (d, J=7.6 Hz, 1H), 5.15 (s, 2H), 3.87 (s, 2H), 3.35 (s, 3H), 3.18-3.12 (m, 2H), 2.42-2.38 (m, 3H), 2.12-2.08 (m, 2H), 1.91-1.78 (m, 4H), 1.38 (s, 3H), 1.17 (d, J=7.6 Hz, 3H). LCMS: $[M+H]^+$=524.3.

Example 29: Compound 36

Figure 28:
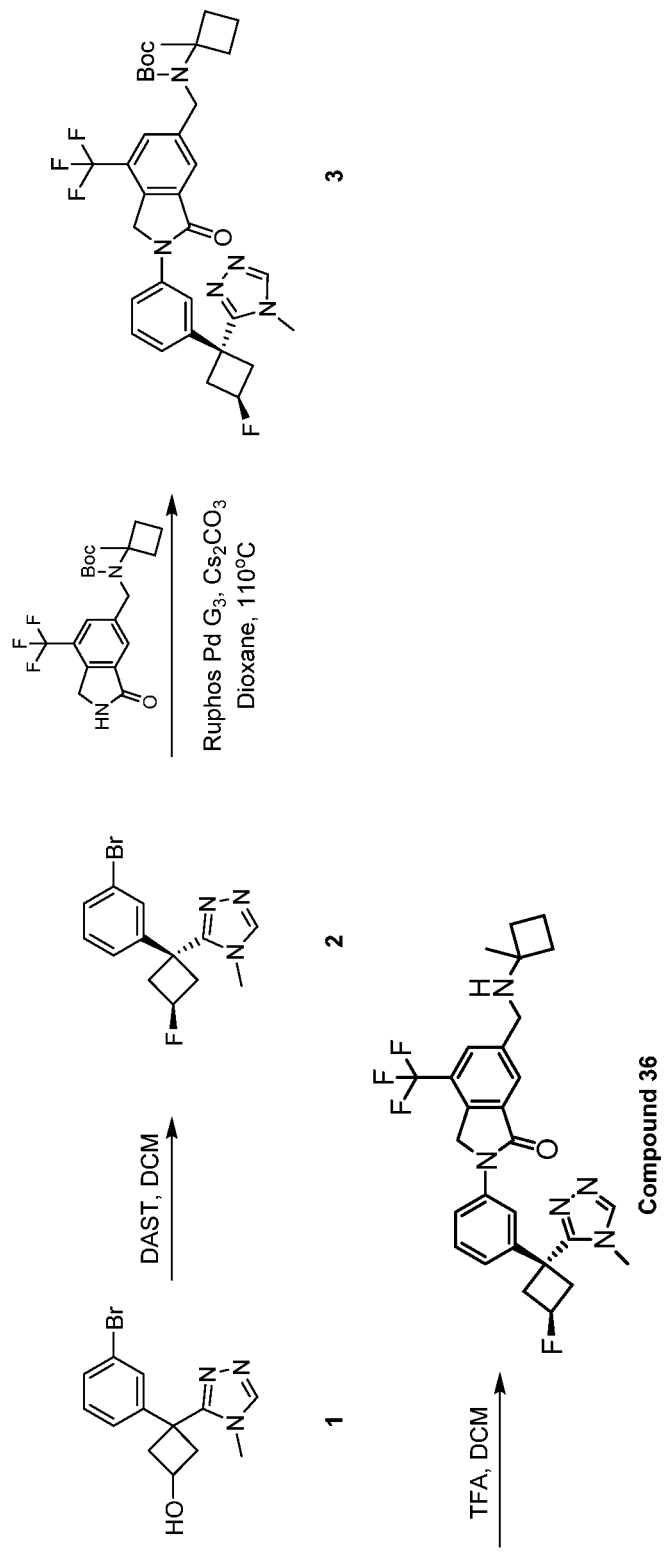

Compound 36, 2-(3-((1r,3r)-3-fluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one, can be synthesized according to Scheme 28 (FIG. 28).

Intermediate 2: (3-((1r,3r)-1-(3-bromophenyl)-3-fluorocyclobutyl)-4-methyl-4H-1,2,4-triazole)

To a solution of 3-(3-bromophenyl)-3-(4-methyl-4H-1,2,4-triazol-3-yl)cyclobutanol (300 mg, 0.97 mmol) in dichloromethane (6 mL) was added diethylaminosulphur trifluoride (0.39 mL, 2.92 mmol) at 0° C. The reaction mixture was stirred at 0° C. for 2 h and quenched by addition of saturated aqueous sodium bicarbonate (20 mL). The mixture was extracted with dichloromethane (3×50 ml). The combined organic layers were washed with brine (50 mL), dried and concentrated under reduced pressure. The residue was purified by silica gel chromatography (mobile phase: ethyl acetate/petroleum ether, gradient 0% to 15%) to afford 3-((1r,3r)-1-(3-bromophenyl)-3-fluorocyclobutyl)-4-methyl-4H-1,2,4-triazole (90 mg, 30% yield) as a colorless oil. LCMS: $[M+H]^+$=310.0 and 312.0.

Intermediate 3: (tert-butyl ((2-(3-((1r,3r)-3-fluoro-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glove box, a mixture of 3-((1r,3r)-1-(3-bromophenyl)-3-fluorocyclobutyl)-4-methyl-4H-1,2,4-triazole (70.0 mg, 0.23 mmol), tert-butyl (1-methylcyclobutyl)((3-oxo-7-(trifluoromethyl)isoindolin-5-yl)methyl)carbamate (98.9 mg, 0.25 mmol), cesium carbonate (221 mg, 0.68 mmol) and (2-Dicyclohexylphosphino-2',6'-diisopropoxy-1,1'-biphenyl)[2-(2'-amino-1,1'-biphenyl)]palladium(II) methanesulfonate (18.9 mg, 0.02 mmol, CAS #: 1445085-77-7) in 1,4-dioxane (5 mL) was stirred at 100° C. for 16 h and concentrated under reduced pressure. The residue was purified by silica gel chromatography (mobile phase: methanol/dichloromethane, gradient 0% to 6%) to afford tert-butyl ((2-(3-((1r,3r)-3-fluoro-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (80 mg, 56% yield) as a yellow solid. LCMS: $[M+H]^+$=628.3.

Compound 36

A mixture of tert-butyl ((2-(3-((1r,3r)-3-fluoro-1-(4-methyl-4H-1,2,4-triazol-3-yl)cyclobutyl)phenyl)-3-oxo-7-(trifluoromethyl)isoindolin-5-yl)methyl)(1-methyl-cyclobutyl)carbamate (80.5 mg, 0.13 mmol) and trifluoroacetic acid (0.8 mL, 10.35 mmol) in dichloromethane (5 mL) was stirred at 20° C. for 2 h and concentrated under reduced pressure. The residue was purified by RP-HPLC (40% to 70% ACN/(0.05% $NH_3H_2O$+10 mM $NH_4HCO_3$ in water)) to afford 2-(3-((1r,3r)-3-fluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one (31.9 mg, 44% yield). $^1$H NMR (400 MHz, methanol-$d_4$) δ 8.39 (s, 1H), 8.10 (s, 1H), 8.02 (s, 1H), 7.94 (d, J=2.0 Hz, 1H), 7.70 (t, J=8.4 Hz, 1H), 7.51 (t, J=8.0 Hz, 1H), 7.13 (d, J=8.8 Hz, 1H), 5.17 (s, 2H), 5.03 (t, J=6.8 Hz, 1H), 3.92 (s, 2H), 3.52-3.47 (m, 2H), 3.34 (s, 3H), 2.95-2.94 (m, 2H), 2.16-2.12 (m, 2H), 1.93-1.81 (m, 4H), 1.41 (s, 3H). LCMS: $[M+H]^+$=528.2.

Example 30: Compounds 37 and 38

Figure 29:
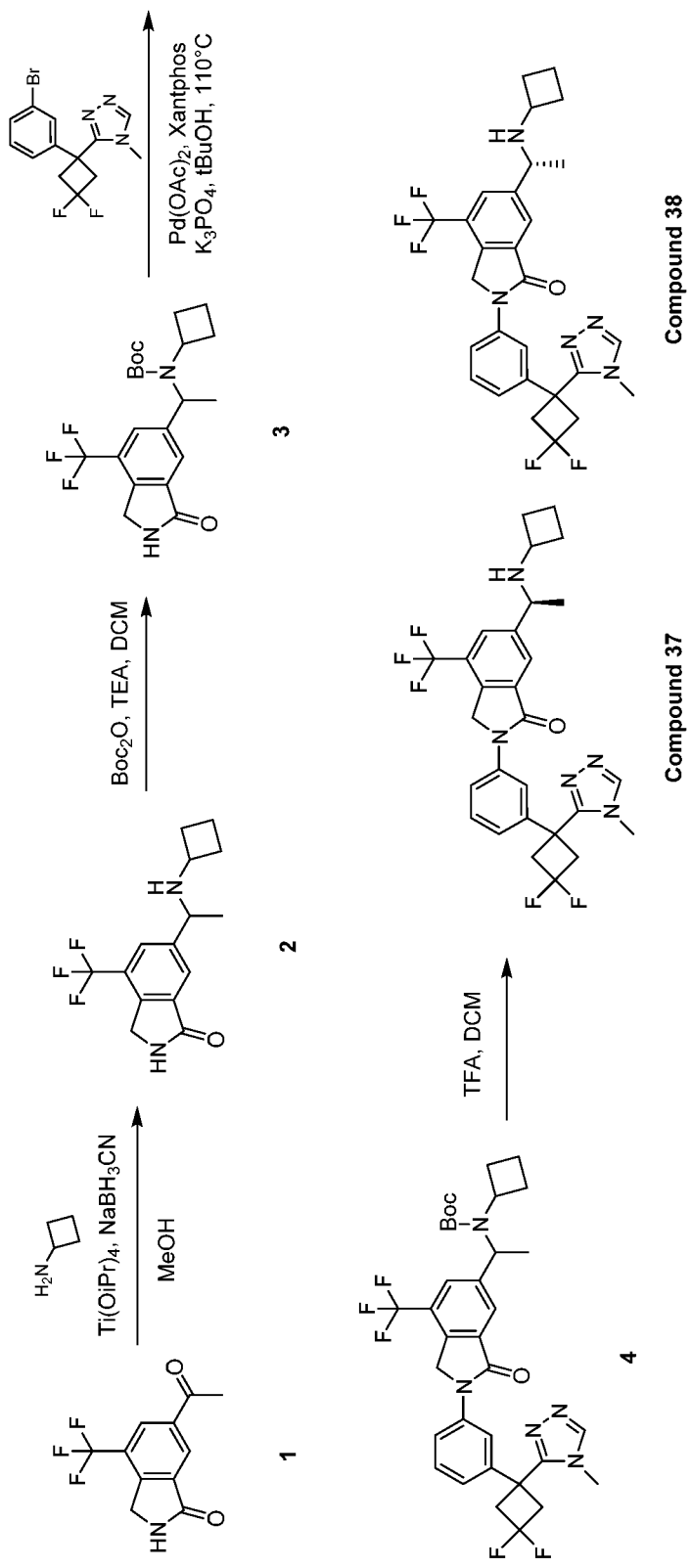

Compound 37 (S)-6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one,
and Compound 38 (R)-6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one, can be synthesized according to Scheme 29 (FIG. 29).

Intermediate 2: (6-(1-(cyclobutylamino)ethyl)-4-(trifluoromethyl)isoindolin-1-one To a solution of 6-acetyl-4-(trifluoromethyl)isoindolin-1-one (400 mg, 1.64 mmol) in methanol (8 mL) was added cyclobutanamine (0.28 mL, 3.29 mmol) and Titanium(IV) isopropoxide (0.63 mL, 2.14 mmol). The mixture was stirred at 25° C. for 16 h and then sodium cyanoborohydride (254 mg, 4.05 mmol) was added. The resulting mixture was stirred for another 6 h and concentrated under reduced pressure to afford crude 6-[1-(cyclobutylamino)ethyl]-4-(trifluoromethyl)isoindolin-1-one (170 mg, 70% yield) as a yellow oil. LCMS $[M+H]^+$=299.0.

Intermediate 3: (tert-butyl cyclobutyl(1-(3-oxo-7-(trifluoromethyl)isoindolin-5-yl)ethyl)carbamate To a solution of 6-(1-(cyclobutylamino)ethyl)-4-(trifluoromethyl)isoindolin-1-one (170 mg, 0.57 mmol) in dichloromethane (5 mL) was added di-tert-butyl dicarbonate (146.8 mg, 0.68 mmol) and triethylamine (0.24 mL, 1.71 mmol). The mixture was stirred at 25° C. for 16 h and concentrated under reduced pressure. The residue was purified by preparative TLC (solvent gradient: 10% methanol in dichloromethane) to afford tert-butyl cyclobutyl(1-(3-oxo-7-(trifluoromethyl)isoindolin-5-yl)ethyl)carbamate (60 mg, 26% yield) as a yellow solid. LCMS: $[M+H-56]^+$=343.1.

Intermediate 4: (tert-butyl cyclobutyl(1-(2-(3-(3,3-difluoro-1-(4-methyl-4H-1,2,4-triazol-3-yl)cyclobutyl)phenyl)-3-oxo-7-(trifluoromethyl)isoindolin-5-yl)ethyl)carbamate A mixture of 3-(1-(3-bromophenyl)-3,3-difluorocyclobutyl)-4-methyl-4H-1,2,4-triazole (120 mg, 0.37 mmol), tert-butyl cyclobutyl(1-(3-oxo-7-(trifluoromethyl)isoindolin-5-yl)ethyl)carbamate (218 mg, 0.55 mmol), Palladium (II) acetate (16 mg, 0.07 mmol), 4,5-Bis(DiphenylPhosphino)-9,9-dimethylxanthene (85 mg, 0.15 mmol) and potassium phosphate (232 mg, 1.1 mmol) in 2-methyl-2-propanol (5 mL) was stirred at 110° C. for 3 h under nitrogen protection and concentrated under reduced pressure. The residue was purified by preparative TLC (solvent gradient: 10% methanol in dichloromethane) to afford tert-butyl cyclobutyl(1-(2-(3-(3,3-difluoro-1-(4-methyl-4H-1,2,4-triazol-3-yl)cyclobutyl)phenyl)-3-oxo-7-(trifluoromethyl)isoindolin-5-yl)ethyl)carbamate (106 mg, 48% yield) as a yellow oil. LCMS [M+H]$^+$=646.3.

Compounds 37 and 38

A mixture of tert-butyl cyclobutyl(1-(2-(3-(3,3-difluoro-1-(4-methyl-4H-1,2,4-triazol-3-yl)cyclobutyl)phenyl)-3-oxo-7-(trifluoromethyl)isoindolin-5-yl)ethyl)carbamate (106 mg, 0.16 mmol) and trifluoroacetic acid (0.8 mL, 10.35 mmol) in dichloromethane (5 mL) was stirred at 20° C. for 2 h and concentrated under reduced pressure to afford 6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one (89.0 mg, 44% yield). The racemate was further purified by chiral SFC (Column=Daicel Chiralcel OD; Column dimensions=250 mm×30 mm×10 μm; Detection wavelength=220 nM; Flow rate=70 mL/min; Run time=4.0 min; Column temperature=25° C.) with 0.1% ammonium hydroxide-30% ethanol-carbon dioxide) to afford tentatively assigned:

(S)-6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one (Peak 1, retention time=3.188 min) (20 mg, 22% yield). $^1$H NMR (400 MHz, methanol-d$_4$) δ 8.38 (s, 1H), 8.06 (s, 1H), 7.98 (s, 2H), 7.71 (d, J=6.8 Hz, 1H), 7.51 (t, J=8.0 Hz, 1H), 7.21 (d, J=8.0 Hz, 1H), 5.16 (s, 2H), 4.14-4.10 (m, 1H), 3.72-3.65 (m, 2H), 3.50-3.42 (m, 2H), 3.39 (s, 3H), 3.29-3.20 (m, 1H), 2.26-2.20 (m, 1H), 1.93-1.87 (m, 2H), 1.75-1.66 (m, 3H), 1.45 (d, J=6.4 Hz, 3H). LCMS: [M+H]$^+$=546.2.

(R)-6-(1-(cyclobutylamino)ethyl)-2-(3-(3,3-difluoro-1-(4-methyl-4H-1,2,4-triazol-3-yl)cyclobutyl)phenyl)-4-(trifluoromethyl)isoindolin-1-one (Peak 2, retention time=3.368 min) (20 mg, 22% yield). $^1$H NMR (400 MHz, methanol-d$_4$) δ 8.38 (s, 1H), 8.10 (s, 1H), 8.02 (s, 1H), 7.98 (s, 1H), 7.72 (d, J=8.4 Hz, 1H), 7.51 (t, J=8.0 Hz, 1H), 7.23 (d, J=7.6 Hz, 1H), 5.17 (s, 2H), 4.35-4.30 (m, 1H), 3.72-3.65 (m, 2H), 3.49-3.42 (m, 3H), 3.39 (s, 3H), 2.26-2.20 (m, 1H), 2.04-2.00 (m, 2H), 2.00-1.87 (m, 1H), 1.78-1.70 (m, 2H), 1.55 (d, J=6.8 Hz, 3H). LCMS: [M+H]$^+$=546.2.

Example 31: Compound 39

Figure 30:
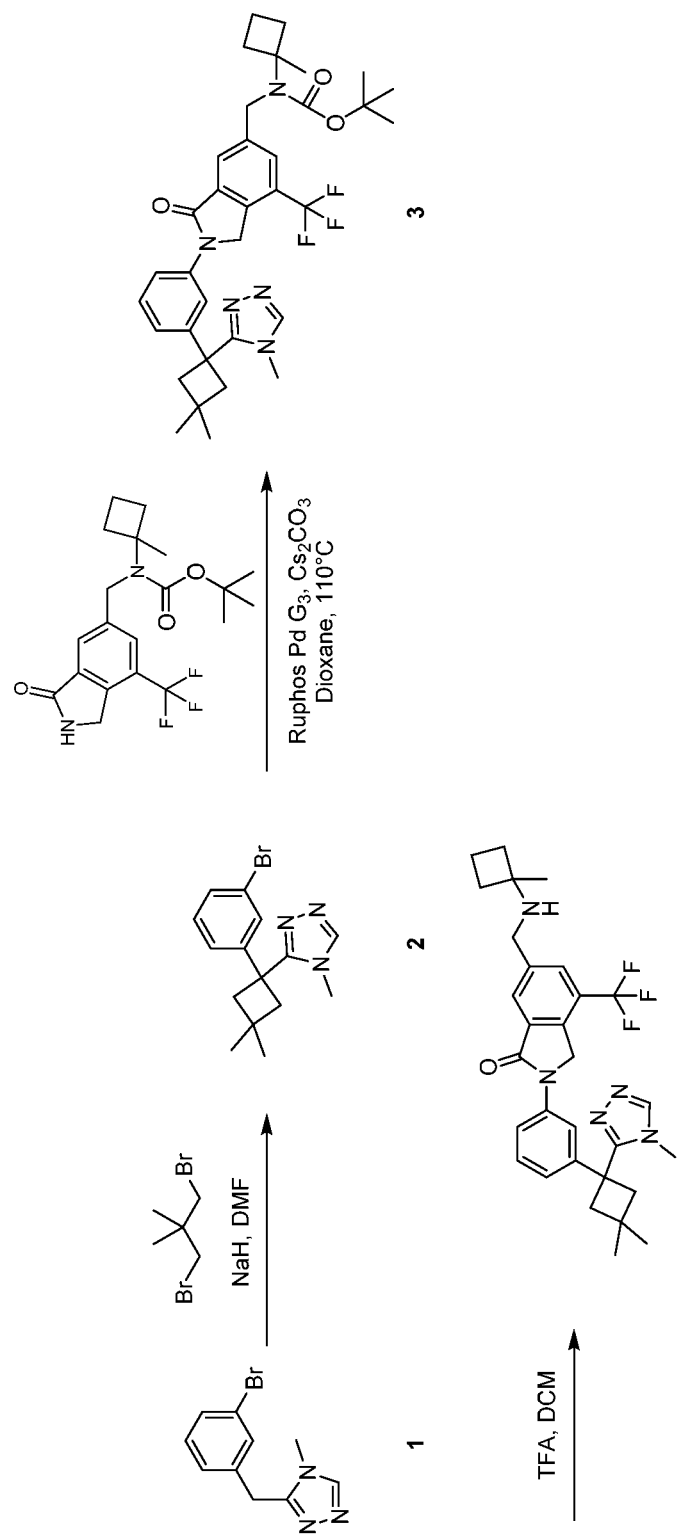

Compound 39 can be synthesized according to Scheme 30 (FIG. 30).

Intermediate 2: (3-(1-(3-bromophenyl)-3,3-dimethylcyclobutyl)-4-methyl-4H-1,2,4-triazole To a solution of 3-(3-bromobenzyl)-4-methyl-4H-1,2,4-triazole (200.0 mg, 0.79 mmol) in N,N-dimethylformamide (2.5 mL) was added sodium hydride (60%, 95.2 mg, 2.38 mmol) at 0° C. After 30 min, 1,3-dibromo-2,2-dimethylpropane (0.14 mL, 0.95 mmol) was added and the reaction mixture was heated at 60° C. for 16 h. The reaction was quenched with water (30 mL) and extracted with dichloromethane (2×20 mL). The combined organic phases were washed with brine (20 mL), dried and concentrated under reduced pressure. The residue was purified by silica gel chromatography (mobile phase: methanol/dichloromethane, gradient 0% to 10%) to afford 3-(1-(3-bromophenyl)-3,3-dimethylcyclobutyl)-4-methyl-4H-1,2,4-triazole (120.0 mg, 47% yield) as a colorless oil. LCMS [M+H]$^+$=320.0 and 322.0.

Intermediate 3: (tert-butyl ((2-(3-(3,3-dimethyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glove box, a mixture of 3-(1-(3-bromophenyl)-3,3-dimethylcyclobutyl)-4-methyl-4H-1,2,4-triazole (80.0 mg, 0.25 mmol), tert-butyl (1-methylcyclobutyl)((3-oxo-7-(trifluoromethyl)isoindolin-5-yl)methyl)carbamate (109.0 mg, 0.27 mmol), cesium carbonate (244 mg, 0.75 mmol) and (2-Dicyclohexylphosphino-2',6'-diisopropoxy-1,1'-biphenyl)[2-(2'-amino-1,1'biphenyl)]palladium(II) methanesulfonate (41.8 mg, 0.05 mmol) in 1,4-dioxane (4 mL) was stirred at 100° C. for 16 h and concentrated under reduced pressure. The residue was purified by preparative TLC (solvent gradient: 10% methanol in dichloromethane) to afford tert-butyl ((2-(3-(3,3-dimethyl-1-(4-methyl-4H-1,2,4-triazol-3-yl)cyclobutyl)phenyl)-3-oxo-7-(trifluoromethyl)isoindolin-5-yl)methyl)(1-methylcyclobutyl) carbamate (60 mg, 38% yield) as a yellow oil. LCMS [M+H]$^+$=638.3.

Compound 39

A mixture of tert-butyl ((2-(3-(3,3-dimethyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (60.0 mg, 0.09 mmol) and trifluoroacetic acid (0.4 mL, 5.67 mmol) in dichloromethane (5 mL) was stirred at 20° C. for 2 h and concentrated under reduced pressure. The residue was purified by RP-HPLC (65% to 95% ACN/(0.05% NH$_3$H$_2$O+10 mM NH$_4$HCO$_3$ in water)) to afford 2-(3-(3,3-dimethyl-1-(4-methyl-4H-1,2,4-triazol-3-yl)cyclobutyl)phenyl)-6-(((1-methylcyclobutyl)amino)methyl)-4-(trifluoromethyl)-isoindolin-1-one (24.0 mg, 47% yield). $^1$H NMR (400 MHz, methanol-d$_4$) δ 8.33 (s, 1H), 8.09 (s, 1H), 8.06 (s, 2H), 7.71 (d, J=6.8 Hz, 1H), 7.51 (t, J=8.0 Hz, 1H), 7.21 (d, J=8.0 Hz, 1H), 5.16 (s, 2H), 3.87 (s, 2H), 3.40 (s, 3H), 2.96 (d, J=13.2 Hz, 2H), 2.76 (d, J=12.8 Hz, 2H), 2.12-2.08 (m, 2H), 1.90-1.86 (m, 2H), 1.82-1.78 (m, 2H), 1.38 (s, 3H), 1.20 (s, 3H), 1.14 (s, 3H). LCMS [M+H]$^+$=538.3.

Example 32: Compound 40

Compound 40 can be synthesized according to Scheme 31 (FIG. 31).

Intermediate 2: (3-(2-(3-bromophenyl)spiro[3.3]heptan-2-yl)-4-methyl-4H-1,2,4-triazole To a solution of 3-(3-bromobenzyl)-4-methyl-4H-1,2,4-triazole (50.0 mg, 0.2 mmol) in N,N-dimethylformamide (1 mL) was added sodium hydride (60%, 14.3 mg, 0.59 mmol) at 0° C. After 30 min, 1,1-bis(bromomethyl)cyclobutane (0.04 mL, 0.24 mmol) was added and the reaction mixture was stirred at 60° C. for 16 h. The reaction was quenched with water (10 mL) and extracted with dichloromethane (2×20 mL). The combined organic layers were washed with brine (20 mL), dried and concentrated under reduced pressure. The residue was purified by silica gel chromatography (mobile phase: methanol/dichloro-methane, gradient 0% to 6%) to afford 3-(2-(3-bromophenyl)spiro[3.3]heptan-2-yl)-4-methyl-4H-1,2,4-triazole (25.0 mg, 42% yield) as a colorless oil. LCMS [M+H]$^+$=332.1 and 334.1.

Intermediate 3: (tert-butyl ((2-(3-(2-(4-methyl-4H-1,2,4-triazol-3-yl)spiro[3.3]heptan-2-yl)phenyl)-3-oxo-7-(trifluoromethyl)isoindolin-5-yl)methyl)(1-methylcyclobutyl)carbamate In a glove box, a mixture of 3-(2-(3-bromophenyl)spiro[3.3]heptan-2-yl)-4-methyl-4H-1,2,4-triazole (50.0 mg, 0.15 mmol), tert-butyl ((2-(3-(2-(4-methyl-4H-1,2,4-triazol-3-yl)spiro[3.3]heptan-2-yl)phenyl)-3-oxo-7-(trifluoromethyl)isoindolin-5-yl)methyl)(1-methylcyclobutyl)carbamate (66.0 mg, 0.17 mmol), cesium carbonate (147 mg, 0.45 mmol) and (2-Dicyclohexylphosphino-2',6'-diisopropoxy-1,1'-biphenyl)[2-(2'-amino-1,1'biphenyl)]palladium(II) methanesulfonate (12.6 mg, 0.02 mmol) in 1,4-dioxane (3 mL) was stirred at 100° C. for 16 h and concentrated under reduced pressure. The residue was purified by preparative TLC (solvent gradient: 10% methanol in dichloromethane) to afford tert-butyl ((2-(3-(2-(4-methyl-4H-1,2,4-triazol-3-yl)spiro[3.3]heptan-2-yl)phenyl)-3-oxo-7-(trifluoromethyl)isoindolin-5-yl)methyl)(1-methylcyclobutyl)carbamate (140 mg, 46% yield) as a yellow oil. LCMS [M+H]$^+$=650.3.

Compound 40

A mixture of tert-butyl ((2-(3-(2-(4-methyl-4H-1,2,4-triazol-3-yl)spiro[3.3]heptan-2-yl)phenyl)-3-oxo-7-(trifluoromethyl)isoindolin-5-yl)methyl)(1-methylcyclobutyl)carbamate (100 mg, 0.06 mmol) and trifluoroacetic acid (0.4 mL, 5.67 mmol) in dichloromethane (5 mL) was stirred at 20° C. for 2 h and concentrated under reduced pressure. The residue was purified by RP-HPLC (55% to 85% ACN/(0.05% NH$_3$H$_2$O+10 mM NH$_4$HCO$_3$ in water)) to afford 2-(3-(2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one (5.4 mg, 17% yield). 1H NMR (400 MHz, DMSO-d$_6$) δ 8.32 (s, 1H), 8.05 (s, 1H), 8.01-7.97 (m, 2H), 7.66 (d, J=8.4 Hz, 1H), 7.40 (t, J=8.0 Hz, 1H), 6.98 (d, J=8.4 Hz, 1H), 5.17 (s, 2H), 3.83 (s, 2H), 3.25 (s, 3H), 3.07 (d, J=12.4 Hz, 2H), 2.76 (d, J=12.4 Hz, 2H), 2.03-1.90 (m, 7H), 1.79-1.69 (m, 6H), 1.23 (s, 3H). LCMS [M+H]$^+$=550.3.

Example 33: Compound 41

Compound 41 (S)-6-((2-isopropyl-4-methylpiperazin-1-yl)methyl)-2-(3-(6-(4-methyl-4H-1,2,4-triazol-3-yl)-2-oxaspiro[3.3]heptan-6-yl)phenyl)-4-(trifluoromethyl)isoindolin-1-one, can be synthesized according to Scheme 32 (FIG. 32).

Intermediate: 3-(6-(3-bromophenyl)-2-oxaspiro[3.3]heptan-6-yl)-4-methyl-4H-1,2,4-triazole To a 0° C. solution of 3-(3-bromobenzyl)-4-methyl-4H-1,2,4-triazole (50 mg, 0.20 mmol) and 3,3-bis(bromomethyl)oxetane (56 mg, 1.1 equiv., 0.22 mmol) in tetrahydrofuran (0.1 M) was added lithium hexamethyldisilazide (0.40 mL of 1M THF solution, 0.40 mmol, 2.0 eq). The reaction was stirred at 0° C. for 1 h at which point saturated aqueous sodium bicarbonate was added. The reaction was poured into saturated aqueous sodium bicarbonate, extracted three times with methylene chloride, dried over sodium sulfate, concentrated and purified by silica column chromatography using a methylene chloride/methanol gradient to give desired product (42 mg, 63% yield). $^1$H NMR (400 MHz, DMSO-d$_6$) δ 8.38 (d, J=9.0 Hz, 1H), 7.46 (ddd, J=7.9, 2.0, 1.0 Hz, 1H), 7.39-7.26 (m, 2H), 7.26-7.14 (m, 1H), 4.52 (s, 2H), 4.44 (s, 2H), 3.20-3.15 (m, 5H), 2.96-2.85 (m, 2H).

Compound 41

To a vial containing 3-[6-(3-bromophenyl)-2-oxaspiro[3.3]heptan-6-yl]-4-methyl-1,2,4-triazole (20 mg, 0.060 mmol, 1 eq) and 6-[[(2S)-2-isopropyl-4-methyl-piperazin-1-yl]methyl]-4-(trifluoromethyl)isoindolin-1-one (32 mg, 0.090 mmol, 1.5) was added cesium carbonate (39 mg, 0.1197 mmol, 2 eq) and XantPhos Pd G3 (3.0 mg, 0.0030 mmol, 0.05 eq). The reaction was dissolved in t-amyl alcohol (0.2 M) and heated to 100° C. for 21 h. The reaction was poured into saturated aqueous sodium bicarbonate, extracted three times with methylene chloride, dried over sodium sulfate, and concentrated. The product was purified by silica column chromatography using a methylene chloride/methanol gradient followed by HPLC purification to afford the desired product (6.3 mg, 17% yield). $^1$H NMR (400 MHz, DMSO-d$_6$) δ 8.35 (s, 1H), 7.99 (s, 1H), 7.92 (dd, J=4.0, 1.9 Hz, 2H), 7.67 (ddd, J=8.2, 2.2, 0.9 Hz, 1H), 7.42 (t, J=8.0 Hz, 1H), 6.98 (ddd, J=7.9, 1.9, 0.9 Hz, 1H), 5.18 (s, 2H), 4.58 (s, 2H), 4.48 (s, 2H), 4.21 (d, J=14.4 Hz, 1H), 3.38 (d, J=14.2 Hz, 1H), 3.24 (d, J=13.0 Hz, 2H), 3.23 (s, 3H), 2.97-2.88 (m, 2H), 2.67-2.51 (m, 3H), 2.24 (ddt, J=21.6, 11.3, 4.2 Hz, 3H), 2.14 (s, 3H), 2.01-1.87 (m, 2H), 0.91 (dd, J=19.5, 6.7 Hz, 6H); LCMS 609.3.

Example 34: Compounds 42 and 43

Figure 33:
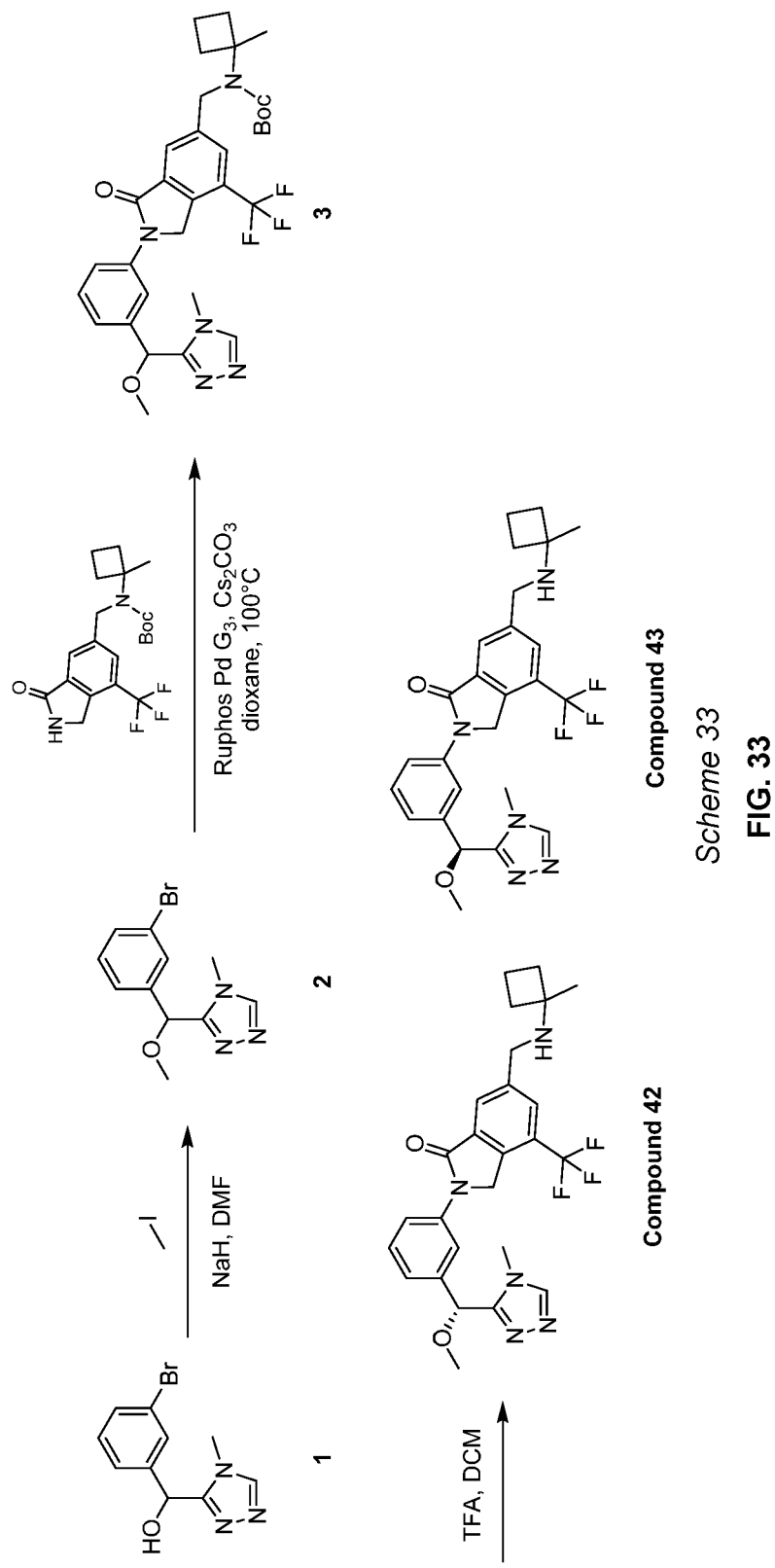

Compound 42 ((R)-2-(3-(methoxy(4-methyl-4H-1,2,4-triazol-3-yl)methyl)phenyl)-6-(((1-methylcyclobutyl)amino)methyl)-4-(trifluoromethyl)isoindolin-1-one) and Compound 43 ((S)-2-(3-(methoxy(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 33 (FIG. 33).

Intermediate 2: (3-((3-bromophenyl)(methoxy)methyl)-4-methyl-4H-1,2,4-triazole

To a solution of (3-bromophenyl)(4-methyl-4H-1,2,4-triazol-3-yl)methanol (500 mg, 1.86 mmol) in N,N-dimethylformamide (10 mL) was added sodium hydride (60%, 90 mg, 2.24 mmol) at 0° C. The mixture was stirred at 0° C. for 1 h and then methyl iodide (0.52 mL, 8.39 mmol) was added. The resulting mixture was stirred at 25° C. for 2 h. The mixture was quenched by addition of water (10 mL) and extracted with ethyl acetate (3×20 mL). The combined organic phases were washed with water (2×10 mL), dried and concentrated under reduced pressure. The residue was purified by RP-HPLC (25% to 55% ACN/(0.05% NH$_3$H$_2$O+10 mM NH$_4$HCO$_3$ in water)) to afford 3-((3-bromophenyl)(methoxy)-4-methyl-4H-1,2,4-triazole (260 mg, 49% yield) as a colorless oil. $^1$H NMR (400 MHz, DMSO-d$_6$) δ 8.51 (s, 1H), 7.57-7.55 (m, 2H), 7.40-7.35 (m, 2H), 5.75 (s, 1H), 3.57 (s, 3H), 3.32 (s, 3H). LCMS [M+H]$^+$=282.0 and 284.0.

Intermediate 3: (tert-butyl ((2-(3-(methoxy(4-methyl-4H-1,2,4-triazol-3-yl)methyl)phenyl)-3-oxo-7-(trifluoromethyl)isoindolin-5-yl)methyl)(1-methylcyclobutyl)carbamate In a glove box, a mixture of 3-((3-bromophenyl)(methoxy)methyl)-4-methyl-4H-1,2,4-triazole (50.0 mg, 0.18 mmol), tert-butyl N-(1-methylcyclobutyl)-N-[[3-oxo-7-(trifluoromethyl)isoindolin-5-yl]methyl]carbamate (77.7 mg, 0.19 mmol), cesium carbonate (173 mg, 0.53 mmol), (2-Dicyclohexylphosphino-2′,6′-diisopropoxy-1,1′-biphenyl)[2-(2′-amino-1,1′biphenyl)]palladium(II) methanesulfonate (14.8 mg, 0.02 mmol, CAS #: 1445085-77-7) in 1,4-Dioxane (2 mL) was stirred at 100° C. for 16 h and concentrated under reduced pressure. The residue was purified by preparative TLC (solvent gradient: 10% methanol in dichloromethane) to afford tert-butyl ((2-(3-(methoxy(4-methyl-4H-1,2,4-triazol-3-yl)methyl)phenyl)-3-oxo-7-(trifluoromethyl)isoindolin-5-yl)methyl)(1-methylcyclobutyl)carbamate (40 mg, 38% yield). LCMS [M+H]$^+$=600.3.
Compounds 42 and 43

To a mixture of tert-butyl ((2-(3-(methoxy(4-methyl-4H-1,2,4-triazol-3-yl)methyl)phenyl)-3-oxo-7-(trifluoromethyl) isoindolin-5-yl)methyl)(1-methyl-cyclobutyl)carbamate (40.0 mg, 0.07 mmol) in dichloromethane (2 mL) was added trifluoroacetic acid (0.3 mL, 4.15 mmol), the mixture was stirred at 20° C. for 2 h and concentrated under reduced pressure. The residue was purified by RP-HPLC (38% to 68% ACN/(0.05% NH$_3$H$_2$O+10 mM NH$_4$HCO$_3$ in water)) to afford 2-[3-[methoxy-(4-methyl-1,2,4-triazol-3-yl) methyl]phenyl]-6-[[(1-methylcyclobutyl)amino]methyl]-4-(trifluoromethyl)isoindolin-1-one (30 mg, 90% yield). LCMS [M+H]$^+$500.2.

The above racemate was further purified by chiral SFC (Column=DAICEL CHIRALPAK AD; Column dimensions=250 mm×30 mm×10 µm; Detection wavelength=220 nM; Flow rate=70 mL/min; Run time=4.0 min; Column temperature=25° C.) with 0.05% DEA-45% ethanol-carbon dioxide) to afford tentatively assigned:

(S)-2-(3-(methoxy(4-methyl-4H-1,2,4-triazol-3-yl) methyl)phenyl)-6-(((1-methylcyclo-butyl)amino)methyl)-4-(trifluoromethyl)isoindolin-1-one (Peak 1, retention time=2.072 min) (56.2 mg, 37% yield). $^1$H NMR (400 MHz, DMSO-d$_6$) δ 8.46 (s, 1H), 8.05 (s, 1H), 8.03 (s, 1H), 8.00 (s, 1H), 7.84 (d, J=8.0 Hz, 1H), 7.48 (t, J=8.0 Hz, 1H), 7.17 (d, J=7.6 Hz, 1H), 5.79 (s, 1H), 5.18 (s, 2H), 3.82 (s, 2H), 3.58 (s, 3H), 3.36 (s, 3H), 2.02-1.96 (m, 2H), 1.74-1.66 (m, 4H), 1.23 (s, 3H). LCMS [M+H]$^+$=500.2.

(R)-2-(3-(methoxy(4-methyl-4H-1,2,4-triazol-3-yl) methyl)phenyl)-6-(((1-methyl-cyclobutyl)amino)methyl)-4-(trifluoromethyl)isoindolin-1-one (Peak 2, retention time=2.258 min) (62.5 mg, 42% yield). $^1$H NMR (400 MHz, DMSO-d$_6$) δ 8.46 (s, 1H), 8.06 (s, 1H), 8.04 (s, 1H), 8.00 (s, 1H), 7.85-7.83 (m, 1H), 7.48 (t, J=8.0 Hz, 1H), 7.17 (d, J=7.6 Hz, 1H), 5.79 (s, 1H), 5.19 (s, 2H), 3.82 (s, 2H), 3.58 (s, 3H), 3.36 (s, 3H), 2.00-1.97 (m, 2H), 1.73-1.67 (m, 4H), 1.23 (s, 3H). LCMS [M+H]$^+$=500.2.

Example 35: Compounds 88 and 89

Figure 34:
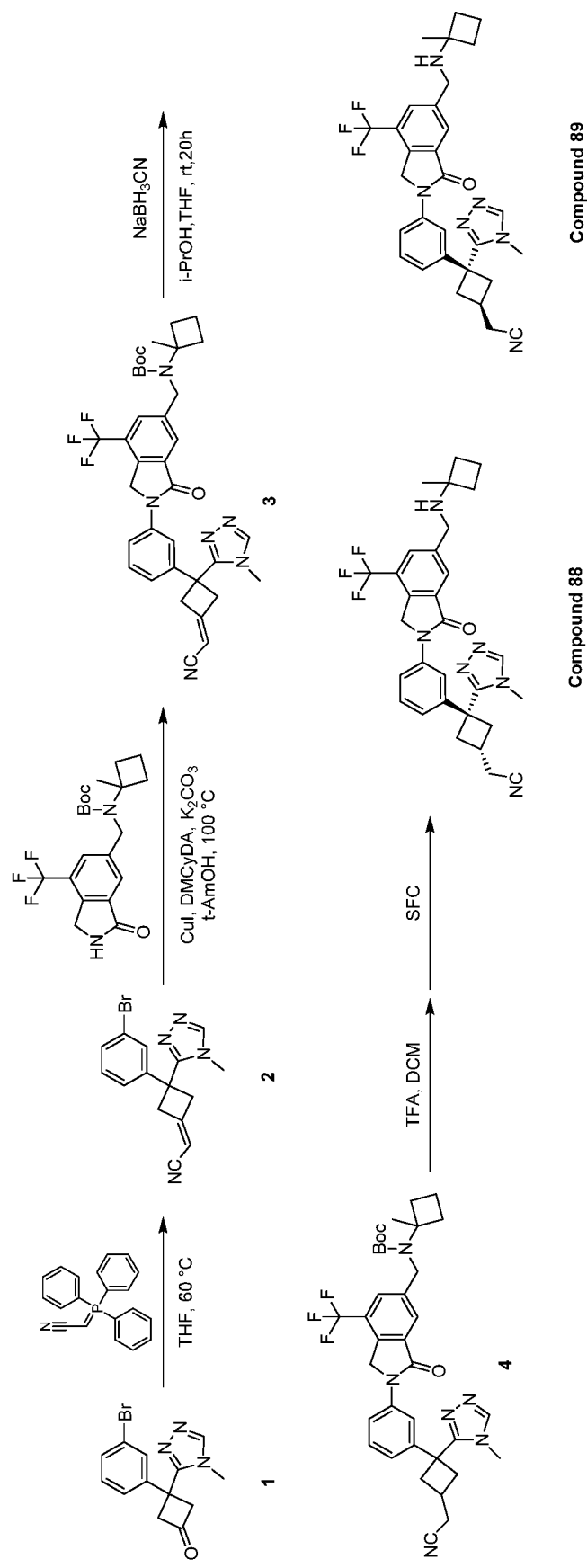

Compound 88 (2-((1s,3s)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)-cyclobutyl)acetonitrile)
and Compound 89 (2-((1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)-cyclobutyl)acetonitrile) can be synthesized according to Scheme 34 (FIG. 34).

Intermediate 2: (2-(3-(3-bromophenyl)-3-(4-methyl-4H-1,2,4-triazol-3-yl)cyclobutylidene)acetonitrile)

To a solution of 3-(3-bromophenyl)-3-(4-methyl-4H-1,2,4-triazol-3-yl)cyclobutanone (1 g, 3.27 mmol) in anhydrous tetrahydrofuran (40 mL) was added 2-(triphenylphosphoranylidene)acetonitrile (1.97 g, 6.53 mmol). The mixture was stirred at 60° C. for 12 h and concentrated to dryness. The residue was purified by silica gel chromatography (mobile phase: ethyl acetate/petroleum ether, gradient 0% to 4%) to afford 2-(3-(3-bromophenyl)-3-(4-methyl-4H-1,2,4-triazol-3-yl)cyclobutylidene)acetonitrile (945 mg, 88% yield) as a yellow solid.

Intermediate 3: (tert-butyl ((2-(3-(3-(cyanomethylene)-1-(4-methyl-4H-1,2,4-triazol-3-yl)cyclobutyl) phenyl)-3-oxo-7-(trifluoromethyl)isoindolin-5-yl) methyl)(1-methylcyclobutyl)carbamate A mixture of 2-(3-(3-bromophenyl)-3-(4-methyl-4H-1,2, 4-triazol-3-yl)cyclobutylidene)acetonitrile (250.0 mg, 0.79 mmol), tert-butyl (1-methylcyclobutyl)((3-oxo-7-(trifluoromethyl)isoindolin-5-yl)methyl)carbamate (344.4 mg, 0.86 mmol), copper(I) iodide (29.9 mg, 0.16 mmol), (1S,2S)—N$^1$,N$^2$-dimethylcyclohexane-1,2-diamine (44.7 mg, 0.31 mmol) and potassium carbonate (325.8 mg, 2.36 mmol) in tert-amyl alcohol (5 mL) was stirred at 100° C. for 10 h under N$_2$. After cooled, the reaction was diluted with water (25 mL) and extracted with dichloromethane (3×25 mL). The combined organic phases were washed with brine (2×25 mL), dried over sodium sulfate and concentrated to dryness. The residue was purified by silica gel chromatography (mobile phase: methanol/dichloromethane, gradient 0% to 5%) to afford tert-butyl N-[[2-[6-chloro-4-[3,3-difluoro-1-(4-methyl-1,2,4-triazol-3-yl)cyclobutyl]-2-pyridyl]-3-oxo-7-(trifluoromethyl)isoindolin-5-yl]methyl]-N-(1-methylcyclobutyl)carbamate (350 mg, 65% yield) as a white solid. LCMS [M+H]$^+$=647.4.

Intermediate 4: (tert-butyl ((2-(3-(3-(cyanomethyl)-1-(4-methyl-4H-1,2,4-triazol-3-yl)cyclobutyl)phenyl)-3-oxo-7-(trifluoromethyl)isoindolin-5-yl) methyl)(1-methylcyclobutyl)carbamate To a solution of tert-butyl ((2-(3-(3-(cyanomethylene)-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (300.0 mg, 0.46 mmol) in tetrahydrofuran (10 mL) and propan-2-ol (2 mL) was added sodium cyanoborohydride (58.3 mg, 0.93 mmol). The mixture was stirred at 25° C. for 12 h, diluted with water (15 mL) and extracted with ethyl acetate (3×15 mL). The combined organics were washed with brine (2×15 mL), dried over sodium sulfate and concentrated to give tert-butyl ((2-(3-(3-(cyanomethyl)-1-(4-methyl-4H-1,2,4-triazol-3-yl) cyclobutyl)phenyl)-3-oxo-7-(trifluoromethyl)isoindolin-5-yl)methyl)(1-methylcyclobutyl)-carbamate (250 mg, 83% yield) as a yellow solid. LCMS [M+H]$^+$649.2.
Compounds 88 and 89

To a solution of tert-butyl ((2-(3-(3-(cyanomethyl)-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (240.0 mg, 0.37 mmol) in dichloromethane (5 mL) was added trifluoroacetic acid (210.9 mg, 1.85 mmol). The reaction was stirred at 25° C. for 2 h and concentrated to give 2-(3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutyl)acetonitrile (85 mg, 42% yield).

The above mixture was further purified by chiral SFC (Column=Daicel Chiralpak IG; Column dimensions=250 mm×30 mm×10 µm; Detection wavelength=220 nM; Flow rate=80 mL/min; Mobile phase: A: CO$_2$ B: ethanol (0.05% DEA); Isocratic: 40% B) with 0.1% ammonium hydroxide) to afford tentatively assigned:

2-((1s,3s)-3-(4-methyl-4H-1,2,4-triazol-3-yl)-3-(3-(6-(((1-methylcyclobutyl)amino)-methyl)-1-oxo-4-(trifluoromethyl)isoindolin-2-yl)phenyl)cyclobutyl)acetonitrile (Peak 1, retention time=4.528 min) (36.4 mg, 43% yield). $^1$H NMR (400 MHz, methanol-d$_4$) δ 8.41 (s, 1H), 8.11 (s, 1H), 8.03 (s, 1H), 7.91 (s, 1H), 7.72-7.69 (m, 1H), 7.51-7.47 (m, 1H), 7.11 (d, J=8.0 Hz, 1H), 5.17 (s, 2H), 3.95 (s, 2H), 3.36 (s, 3H), 3.23-3.22 (m, 2H), 2.70-2.66 (m, 5H), 2.18-2.15 (m, 2H), 1.94-1.83 (m, 4H), 1.43 (s, 3H). LCMS [M+H]$^+$=549.7.

2-((1r,3r)-3-(4-methyl-4H-1,2,4-triazol-3-yl)-3-(3-(6-(((1-methylcyclobutyl)-amino)methyl)-1-oxo-4-(trifluoromethyl)isoindolin-2-yl)phenyl)cyclobutyl)acetonitrile (Peak 2, retention time=5.412 min) (11.2 mg, 13% yield). $^1$H NMR (400 MHz, methanol-d$_4$) δ 8.33 (s, 1H), 8.12 (s, 1H), 8.09 (s, 1H), 8.04 (s, 1H), 7.73-7.71 (m, 1H), 7.54-7.50 (m, 1H), 7.28 (d, J=8.0 Hz, 1H), 5.18 (s, 2H), 3.97 (s, 2H), 3.36 (s, 3H), 3.06-3.04 (m, 2H), 2.91-2.86 (m, 3H), 2.67 (d, J=6.0 Hz, 2H), 2.18-2.16 (m, 2H), 1.95-1.83 (m, 4H), 1.45 (s, 3H). LCMS [M+H]$^+$=549.7.

Example 36: Compound 90

Figure 35:
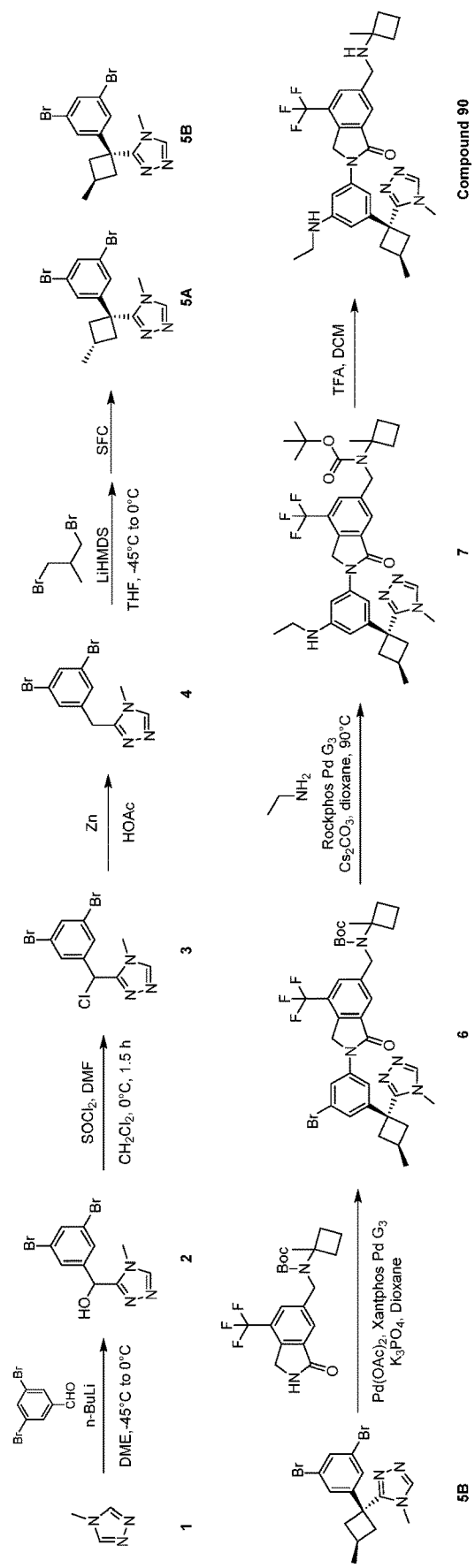

Compound 90 (2-(3-(ethylamino)-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one) can be synthesized according to Scheme 35 (FIG. 35).

Intermediate 2: ((3,5-dibromophenyl)(4-methyl-4H-1,2,4-triazol-3-yl)methanol

To a solution of 4-methyl-4H-1,2,4-triazole (4.72 g, 56.8 mmol) in 1,2-dimethoxyethane (250 mL) was added n-butyl lithium (2.5 M in hexanes, 22.74 mL, 56.84 mmol) at −50° C. over 15 min. The resulting mixture was stirred for 1 h at −50° C., then a solution of 3,5-dibromobenzaldehyde (10.0 g, 37.9 mmol) in 1,2-dimethoxyethane (30 mL) was added dropwise to the mixture. The reaction mixture was warmed to 0° C. slowly and stirred for another 1 h. The reaction was quenched with water (20 mL) and extracted with dichloromethane (3×25 mL). The combined organics were washed with brine (2×25 mL), dried over sodium sulfate and concentrated to give crude (3,5-dibromophenyl)(4-methyl-4H-1,2,4-triazol-3-yl)methanol (8.0 g, 61% yield) as a white solid which was used directly without further purification. $^1$H NMR (400 MHz, methanol-d$_4$) δ 8.41 (s, 1H), 7.70 (d, J=1.2 Hz, 1H), 7.57 (d, J=1.6 Hz, 2H), 6.11 (s, 1H), 3.67 (s, 3H).

Intermediate 3: (3-(chloro(3,5-dibromophenyl)methyl)-4-methyl-4H-1,2,4-triazole

To a solution of (3,5-dibromophenyl)(4-methyl-4H-1,2,4-triazol-3-yl)methanol (20.0 g, 57.6 mmol) in dichloromethane (200 mL) was added N,N-dimethylformamide (1 mL) and thionyl chloride (12.5 mL, 172.9 mmol) at 0° C. The reaction mixture was stirred at 25° C. for 4 h. The mixture was then quenched with water (200 mL) and extracted with dichloromethane (3×200 mL). The combined organic layers were washed with saturated sodium bicarbonate (200 mL), brine (200 mL) and concentrated to dryness. The residue was purified by silica gel chromatography (mobile phase: methanol/dichloromethane, gradient 0% to 10%) to afford 3-(chloro(3,5-dibromophenyl)methyl)-4-methyl-4H-1,2,4-triazole (18.0 g, 86% yield) as a white solid.

Intermediate 4: (3-(3,5-dibromobenzyl)-4-methyl-4H-1,2,4-triazole

To a solution of 3-(chloro(3,5-dibromophenyl)methyl)-4-methyl-4H-1,2,4-triazole (9.0 g, 24.6 mmol) in acetic acid (100 mL) was added Zinc powder (16.1 g, 246.3 mmol). The mixture was stirred at 25° C. for 16 h and filtered. The filtrate was diluted with water (50 mL) and extracted with ethyl acetate (3×100 mL). The combined organic layers were washed with brine (100 mL), dried over sodium sulfate and concentrated to afford crude 3-(3,5-dibromobenzyl)-4-methyl-4H-1,2,4-triazole (8 g, 98% yield) as a yellow solid. $^1$H NMR (400 MHz, methanol-d$_4$) δ 8.08 (s, 1H), 7.56 (d, J=1.6 Hz, 1H), 7.19 (d, J=8.0 Hz, 2H), 4.14 (s, 2H), 3.51 (s, 3H).

Intermediate 5A and 5B: (3-((1s,3s)-1-(3,5-dibromophenyl)-3-methylcyclobutyl)-4-methyl-4H-1,2,4-triazole and 3-((1r,3r)-1-(3,5-dibromophenyl)-3-methylcyclobutyl)-4-methyl-4H-1,2,4-triazole To a solution of 3-(3,5-dibromobenzyl)-4-methyl-4H-1,2,4-triazole (3.5 g, 10.6 mmol) and 1,3-dibromo-2-methylpropane (1.52 mL, 12.7 mmol) in tetrahydrofuran (100 mL) was added lithium hexamethyldisilazide (1.0 M in tetrahydrofuran, 21.2 mL, 21.2 mmol) at −40° C. The mixture was stirred at −40° C. for 20 min, then another batch of lithium hexamethyldisilazide (1.0 M in tetrahydrofuran, 21.2 mL, 21.2 mmol) was added. The reaction mixture was stirred at 0° C. for 1 h and then quenched by addition of saturated aqueous ammonium chloride (100 mL). The mixture was extracted with ethyl acetate (3×100 mL). The combined organic layers were washed with brine (2×50 mL), dried and concentrated to dryness. The residue was purified by silica gel chromatography (mobile phase: ethyl acetate/petroleum ether, gradient 0% to 25%) to afford 3-[1-(3,5-dibromophenyl)-3-methyl-cyclobutyl]-4-methyl-1,2,4-triazole (2.1 g, 52% yield) as a yellow oil.

The above product was purified by RP-HPLC (water (NH$_3$H$_2$O+NH$_4$HCO$_3$)-ACN 40% to 70%) to afford:

3-((1s,3s)-1-(3,5-dibromophenyl)-3-methylcyclobutyl)-4-methyl-4H-1,2,4-triazole (1.4 g, 67% yield). $^1$H NMR (400 MHz, methanol-d$_4$) δ 8.32 (s, 1H), 7.67 (t, J=1.2 Hz, 1H), 7.51 (d, J=2.0 Hz, 2H), 3.30 (s, 3H), 2.91-2.85 (m, 2H), 2.60-2.53 (m, 3H), 1.13 (d, J=6.0 Hz, 3H).

3-((1r,3r)-1-(3,5-dibromophenyl)-3-methylcyclobutyl)-4-methyl-4H-1,2,4-triazole (300 mg, 14% yield) as a yellow oil. $^1$H NMR (400 MHz, methanol-d$_4$) δ 8.38 (s, 1H), 7.63 (t, J=1.6 Hz, 1H), 7.34 (d, J=1.6 Hz, 2H), 3.32 (s, 3H), 3.13-3.06 (m, 2H), 2.50-2.38 (m, 1H), 2.33-2.25 (m, 2H), 1.13 (d, J=6.4 Hz, 3H).

Intermediate 6: (tert-butyl ((2-(3-bromo-5-((1r,3r)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate To a solution of 3-((1r,3r)-1-(3,5-dibromophenyl)-3-methylcyclobutyl)-4-methyl-4H-1,2,4-triazole (200 mg, 0.52 mmol) and tert-butyl (1-methylcyclobutyl)((3-oxo-7-(trifluoromethyl)isoindolin-5-yl)methyl)carbamate (186.2 mg, 0.47 mmol) in toluene (4 mL) was added [4,5-Bis(diphenylphosphino)-9,9-dimethylxanthene][2'-amino-2-biphenylyl]-[(methylsulfonyl)oxy]palladium(II) (44.4 mg, 0.05 mmol, CAS No.: 1445085-97-1) and potassium carbonate (144 mg, 1.04 mmol). The mixture was stirred at 100° C. for 16 h under nitrogen atmosphere and concentrated under vacuum. The residue was purified by silica gel chromatography (mobile phase: methanol/dichloromethane, gradient 0% to 10%) to afford tert-butyl ((2-(3-bromo-5-((1r,3r)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (180 mg, 49% yield) as a yellow oil. LCMS [M+H]$^+$=702.2.

Intermediate 7: (tert-butyl ((2-(3-(ethylamino)-5-((1r,3r)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glovebox, to a vial was added tert-butyl ((2-(3-bromo-5-((1r,3r)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (180.0 mg, 0.26 mmol), 1,4-dioxane (2 mL), ethylamine (5 mL, 75.4 mmol), methanesulfonato[2-(di-t-butylphosphino)-3-methoxy-6-methyl-2',4',6'-tri-i-propylbiphenyl](2'-amino-2-biphenylyl)palladium(II) (43.8 mg, 0.05 mmol) and cesium carbonate (250.4 mg, 0.77 mmol). The mixture was sealed then stirred at 90° C. for 5 h. The mixture was then concentrated to dryness and the residue was purified by preparative TLC (solvent gradient: 10% methanol in dichloromethane) to afford tert-butyl ((2-(3-(ethylamino)-5-((1r,3r)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (100.0 mg, 59% yield) as a yellow oil.
Compound 90
To a solution of tert-butyl ((2-(3-(ethylamino)-5-((1r,3r)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (110.0 mg, 0.16 mmol) in dichloromethane (3 mL) was added trifluoroacetic acid (0.4 mL, 5.19 mmol). The mixture was stirred at 25° C. for 2 h and concentrated to dryness. The residue was purified by RP-HPLC (0.05% FA in water/ACN 18% to 48%) to afford 2-(3-(ethylamino)-5-((1r,3r)-3-methyl-1 (4-methyl-4H-1,2,4-triazol-3-yl)cyclobutyl)phenyl)-6-(((1-methylcyclobutyl)amino)methyl)-4-(trifluoromethyl)isoindolin-1-one (86.6 mg, 90% yield)$^1$H NMR (400 MHz, methanol-d$_4$) δ 8.36 (s, 1H), 8.16 (s, 1H), 8.09 (s, 1H), 6.97 (d, J=11.6 Hz, 2H), 6.33 (s, 1H), 5.14 (s, 2H), 4.20 (s, 2H), 3.38 (s, 3H), 3.15-3.05 (m, 4H), 2.51-2.40 (m, 1H), 2.39-2.30 (m, 4H), 2.09-1.90 (m, 4H), 1.59 (s, 3H), 1.22 (t, J=7.2 Hz, 3H), 1.15 (d, J=6.4 Hz, 3H). LCMS [M+H]$^+$=567.

Example 37: Compound 91

Figure 36:
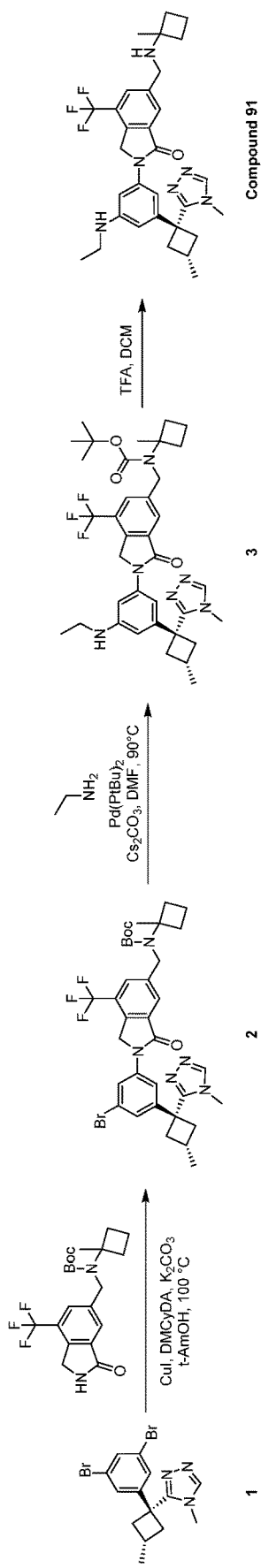

Compound 91, (2-(3-(ethylamino)-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)-isoindolin-1-one) can be synthesized according to Scheme 36 (FIG. 36).

Intermediate 2: (tert-butyl ((2-(3-bromo-5-((1s,3s)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glovebox, a mixture of 3-((1s,3s)-1-(3,5-dibromophenyl)-3-methylcyclobutyl)-4-methyl-4H-1,2,4-triazole (200.0 mg, 0.52 mmol), tert-butyl (1-methylcyclobutyl)((3-oxo-7-(trifluoromethyl)isoindolin-5-yl)methyl)carbamate (227.6 mg, 0.57 mmol), copper(I) iodide (19.8 mg, 0.10 mmol), (1S,2S)—N$^1$,N$^2$-dimethylcyclohexane-1,2-diamine (29.5 mg, 0.2 mmol) and potassium carbonate (215.0 mg, 1.56 mmol) in tert-amyl alcohol (5 mL) was stirred in a sealed vial at 100° C. for 16 h. The mixture was concentrated under vacuum and the residue was purified by preparative TLC (solvent gradient: 10% methanol in dichloromethane) to afford tert-butyl ((2-(3-bromo-5-((1s,3s)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (200.0 mg, 55% yield) as a yellow oil. LCMS [M+H]$^+$=702.2.

Intermediate 3: (tert-butyl ((2-(3-(ethylamino)-5-((1s,3s)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glovebox, a mixture of tert-butyl ((2-(3-bromo-5-((1s,3s)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (80.0 mg, 0.11 mmol), ethylamine hydrochloride (13.6 mg, 0.17 mmol), cesium carbonate (108.8 mg, 0.33 mmol) and bis(tri-tert-butylphosphine)-palladium(0) (5.7 mg, 0.01 mmol) in N,N-dimethylformamide (2 mL) was stirred at 90° C. for 16 h under nitrogen atmosphere and concentrated under reduced pressure. The residue was purified by preparative TLC (solvent gradient: 10% methanol in dichloromethane) to afford tert-butyl ((2-(3-(ethylamino)-5-((1s,3s)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (40.0 mg, 53% yield) as a white solid.
Compound 91
A mixture of tert-butyl ((2-(3-(ethylamino)-5-((1s,3s)-3-methyl-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (40.0 mg, 0.06 mmol) and trifluoroacetic acid (0.02 mL, 0.30 mmol) in dichloromethane (2 mL) was stirred for 2 h at 25° C. and concentrated under reduced pressure. The residue was purified by RP-HPLC (water(NH$_3$H$_2$O+NH$_4$HCO$_3$)-ACN 55% to 85%) to afford 2-(3-(ethylamino)-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (5.5 mg, 16% yield). $^1$H NMR (400 MHz, DMSO-d$_6$) δ 8.28 (s, 1H), 8.02 (s, 1H), 7.98 (s, 1H), 7.20 (s, 1H), 6.94 (s, 1H), 6.27 (s, 1H), 5.79-5.74 (m, 1H), 5.11 (s, 2H), 3.81 (s, 2H), 3.38-3.35 (m, 1H), 3.31-3.28 (m, 3H), 3.23 (s, 3H), 3.05-2.96 (m, 2H), 2.83-2.76 (m, 2H), 2.03-1.94 (m, 2H), 1.76-1.65 (m, 4H), 1.23 (s, 3H), 1.13 (t, J=7.2 Hz, 3H), 1.07 (d, J=6.0 Hz, 3H). LCMS [M+H]$^+$=567.3.

Example 38: Compound 92

Figure 37:
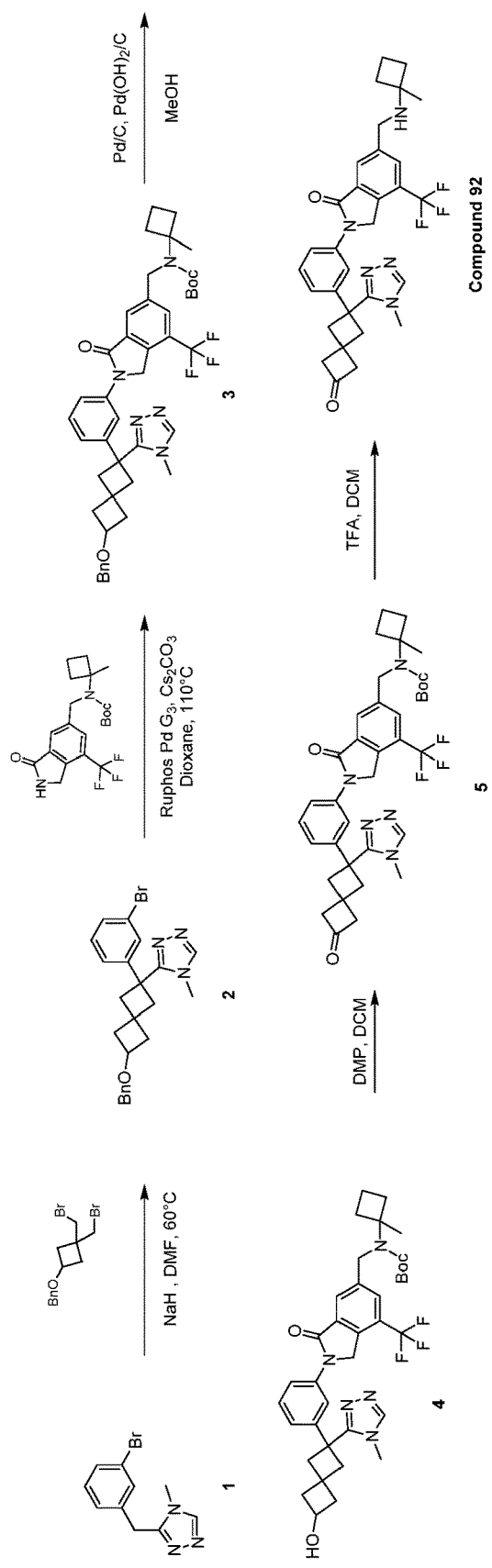

Compound 92 (2-(3-(2-(4-methyl-4H-1,2,4-triazol-3-yl)-6-oxospiro[3.3]heptan-2-yl)phenyl)-6-(((1-methylcyclobutyl)amino)methyl)-4-(trifluoromethyl)isoindolin-1-one) can be synthesized according to Scheme 37 (FIG. 37).

Intermediate 2: (3-(6-(benzyloxy)-2-(3-bromophenyl)spiro[3.3]heptan-2-yl)-4-methyl-4H-1,2,4-triazole To a mixture of 3-[(3-bromophenyl)methyl]-4-methyl-1,2,4-triazole (2.8 g, 11.1 mmol) in N,N-dimethylformamide (35 mL) was added sodium hydride (60%, 1.78 g, 44.43 mmol) at 0° C. The mixture was stirred at 0° C. for 30 min, and then [3,3-((3,3-bis(bromomethyl)cyclobutoxy)methyl) benzene (5.8 g, 16.7 mmol) was added. The resulting mixture was heated to 60° C. and stirred for 16 h. After cooled, the mixture was quenched by addition of water (50 mL) and extracted with dichloromethane (3×100 mL). The combined organic layers were washed with brine (100 mL), dried and concentrated to dryness. The residue was purified by silica gel chromatography (mobile phase: methanol/ dichloromethane, gradient 0% to 2%) to afford 3-(6-(benzyloxy)-2-(3-bromophenyl)spiro[3.3]heptan-2-yl)-4-methyl-4H-1,2,4-triazole (4.8 g, 98% yield) as a yellow oil. $^1$H NMR (400 MHz, MeCN-d$_3$) δ 8.05 (s, 1H), 7.44-7.40 (m, 2H), 7.36-7.27 (m, 6H), 7.23-7.20 (m, 1H), 4.35 (s, 2H), 3.99-3.91 (m, 1H), 3.19 (s, 3H), 3.17-3.12 (m, 1H), 3.06-3.01 (m, 1H), 2.78-2.72 (m, 2H), 2.35-2.25 (m, 2H), 2.02-1.98 (m, 1H), 1.95-1.91 (m, 1H). LCMS [M+H]$^+$=438.1.

Intermediate 3: (tert-butyl ((2-(3-(6-(benzyloxy)-2-(4-methyl-4H-1,2,4-triazol-3-yl)spiro[3.3]heptan-2-yl)phenyl)-3-oxo-7-(trifluoromethyl)isoindolin-5-yl) methyl)(1-methylcyclobutyl)carbamate A mixture of tert-butyl (1-methylcyclobutyl)((3-oxo-7-(trifluoromethyl)isoindolin-5-yl)methyl)carbamate (1.09 g, 2.74 mmol), 3-(6-(benzyloxy)-2-(3-bromophenyl)spiro[3.3] hept-an-2-yl)-4-methyl-4H-1,2,4-triazole (1.0 g, 2.28 mmol), dicyclohexylphosphino-2',6'-diisopropoxy-1,1'-biphenyl)[2-(2'-amino-1,1'biphenyl)]palladium(II) methanesulfonate (190.8 mg, 0.23 mmol) and cesium carbonate (2.2 g, 6.84 mmol) in 1,4-dioxane (20 mL) was stirred at 110° C. for 16 h under nitrogen atmosphere and concentrated under reduced pressure. The residue was purified by silica gel chromatography (mobile phase: methanol/dichloromethane, gradient 0% to 4%) to give tert-butyl ((2-(3-(6-(benzyloxy)-2-(4-methyl-4H-1,2,4-triazol-3-yl)spiro[3.3]heptan-2-yl) phenyl)-3-oxo-7-(trifluoromethyl)isoindolin-5-yl)methyl) (1-methylcyclobutyl)carbamate (1.15 g, 67% yield) as a yellow oil. LCMS [M+H]$^+$=756.3.

Intermediate 4: (tert-butyl ((2-(3-(6-hydroxy-2-(4-methyl-4H-1,2,4-triazol-3-yl)spiro[3.3]heptan-2-yl) phenyl)-3-oxo-7-(trifluoromethyl)isoindolin-5-yl) methyl)(1-methylcyclobutyl)carbamate A mixture of tert-butyl ((2-(3-(6-(benzyloxy)-2-(4-methyl-4H-1,2,4-triazol-3-yl)spiro[3.3]heptan-2-yl)phenyl)-3-oxo-7-(trifluoromethyl)isoindolin-5-yl)methyl)(1-methylcyclobutyl)carbamate (300.0 mg, 0.40 mmol), palladium hydroxide (55.6 mg, 0.08 mmol) and palladium (10% on carbon, 84.1 mg, 0.08 mmol) in methanol (8 mL) was stirred at 25° C. under H$_2$ (15 Psi) for 16 h and then filtered. The filtrate was concentrated to give crude tert-butyl ((2-(3-(6-hydroxy-2-(4-methyl-4H-1,2,4-triazol-3-yl)spiro [3.3]heptan-2-yl)phenyl)-3-oxo-7-(trifluoromethyl)isoindolin-5-yl)methyl)(1-methylcyclobutyl)carbamate (250.0 mg, 95% yield) as a yellow solid. LCMS [M+H]$^+$=666.4.

Intermediate 5: (tert-butyl ((2-(3-(2-(4-methyl-4H-1, 2,4-triazol-3-yl)-6-oxospiro[3.3]heptan-2-yl)phenyl)-3-oxo-7-(trifluoromethyl)isoindolin-5-yl)methyl)(1-methylcyclobutyl)carbamate To a solution of tert-butyl ((2-(3-(6-hydroxy-2-(4-methyl-4H-1,2,4-triazol-3-yl)spiro[3.3]heptan-2-yl)phenyl)-3-oxo-7-(trifluoromethyl)isoindolin-5-yl)methyl)(1-methylcy-clobutyl)carbamate (150 mg, 0.23 mmol) in dichloromethane (5 mL) was added Dess-Martin periodinane (19 mg, 0.45 mmol). The mixture was stirred at 25° C. for 16 h and then quenched with saturated aqueous sodium sulfite (5 mL). The mixture was extracted with dichloromethane (2×10 mL). The combined organic layers were washed with saturated aqueous sodium bicarbonate (5 mL), brine (5 mL), dried and concentrated to dryness. The residue was purified by preparative TLC (10% methanol in dichloromethane) to give tert-butyl ((2-(3-(2-(4-methyl-4H-1,2,4-triazol-3-yl)-6-oxospiro[3.3]heptan-2-yl)phenyl)-3-oxo-7-(trifluoromethyl)isoindolin-5-yl)methyl)(1-methylcyclobutyl)carbamate (100.0 mg, 67% yield) as a yellow oil. LCMS [M+H]$^+$=664.4.

Compound 92

To a solution of tert-butyl ((2-(3-(2-(4-methyl-4H-1,2,4-triazol-3-yl)-6-oxospiro[3.3]heptan-2-yl)phenyl)-3-oxo-7-(trifluoromethyl)isoindolin-5-yl)methyl)(1-methylcyclobutyl)carbamate (100 mg, 0.15 mmol) in dichloromethane (3 mL) was added trifluoroacetic acid (0.3 mL, 3.89 mmol) at 0° C. The mixture was stirred for 1 h and then concentrated to dryness. The residue was purified by RP-HPLC (0.2% NH$_4$OH in water/ACN 65% to 95%) to afford 2-(3-(2-(4-methyl-4H-1,2,4-triazol-3-yl)-6-oxospiro [3.3]heptan-2-yl)phenyl)-6-(((1-methylcyclobutyl)amino) methyl)-4-(trifluoromethyl)isoindolin-1-one (Compound 92, 14.4 mg, 16% yield). $^1$H NMR (400 MHz, CDCl$_3$) δ 8.27 (s, 1H), 8.10 (s, 1H), 8.03 (s, 1H), 7.91 (s, 1H), 7.49-7.45 (m, 1H), 7.44-7.39 (m, 1H), 7.06 (d, J=7.6 Hz, 1H), 4.99 (s, 2H), 3.88 (s, 2H), 3.42 (d, J=12.8 Hz, 2H), 3.33 (s, 3H), 3.19-3.17 (m, 4H), 3.12 (d, J=12.4 Hz, 2H), 2.02-1.88 (m, 4H), 1.83-1.75 (m, 2H), 1.35 (s, 3H). LCMS [M+H]$^+$=564.2.

Example 39: Compound 93

Compound 93 (2-(3-(6-hydroxy-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one) can be synthesized as follows.

A solution of 2-(3-(2-(4-methyl-4H-1,2,4-triazol-3-yl)-6-oxospiro[3.3]heptan-2-yl)phenyl)-6-(((1-methylcyclobutyl) amino)methyl)-4-(trifluoromethyl)isoindolin-1-one (60.0 mg, 0.09 mmol) in dichloromethane (2 mL) was added trifluoroacetic acid (0.2 mL, 2.6 mmol) at 0° C. The mixture was stirred at 25° C. for 3 h and concentrated to dryness. The residue was purified by RP-HPLC (0.2% NH$_4$OH in water/ ACN 65% to 95%) to afford 2-(3-(6-hydroxy-2-(4-methyl-4H-1,2,4-triazol-3-yl)spiro[3.3]heptan-2-yl)phenyl)-6-(((1-methylcyclobutyl)amino)methyl)-4-(trifluoromethyl) isoindolin-1-one (13.7 mg, 26% yield). $^1$H NMR (400 MHz, CDCl$_3$) δ 8.09 (s, 2H), 8.00 (s, 1H), 7.90 (s, 1H), 7.50 (d, J=9.2 Hz, 1H), 7.39 (t, J=8.0 Hz, 1H), 7.04 (d, J=8.0 Hz, 1H), 4.98 (s, 2H), 4.27-4.19 (m, 1H), 3.87 (s, 2H), 3.30-3.25 (m, 4H), 3.08 (d, J=12.4 Hz, 1H), 2.91 (d, J=12.0 Hz, 1H), 2.82 (d, J=11.2 Hz, 1H), 2.50-2.43 (m, 2H), 2.06-1.90 (m, 6H), 1.83-1.74 (m, 2H), 1.34 (s, 3H). LCMS [M+H]$^+$=566.3.

Example 40: Compound 94

Compound 94 (2-(3-(6,6-difluoro-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one) can be synthesized according to Scheme 38 (FIG. 38).

Intermediate 2: (tert-butyl ((2-(3-(6,6-difluoro-2-(4-methyl-4H-1,2,4-triazol-3-yl)spiro[3.3]heptan-2-yl) phenyl)-3-oxo-7-(trifluoromethyl)isoindolin-5-yl) methyl)(1-methylcyclobutyl)carbamate To a solution of tert-butyl ((2-(3-(2-(4-methyl-4H-1,2,4-triazol-3-yl)-6-oxospiro[3.3]heptan-2-yl)phenyl)-3-oxo-7-

(trifluoromethyl)isoindolin-5-yl)methyl)(1-methylcyclobutyl)carbamate (273.0 mg, 0.41 mmol) in dichloromethane (3 mL) was added diethylaminosulphur trifluoride (0.2 mL, 2.06 mmol) at 0° C. The mixture was warmed to 25° C. and stirred for 16 h under nitrogen atmosphere. The reaction mixture was quenched with water (10 mL) and then extracted with dichloromethane (3×10 mL). The combined organic layers were washed with brine (10 mL), dried over sodium sulfate and concentrated to dryness. The residue was purified by preparative TLC (solvent gradient: 10% methanol in dichloromethane) to give tert-butyl ((2-(3-(6,6-difluoro-2-(4-methyl-4H-1,2,4-triazol-3-yl)spiro[3.3]heptan-2-yl)phenyl)-3-oxo-7-(trifluoromethyl)isoindolin-5-yl)methyl)(1-methyl-cyclobutyl)carbamate (30 mg, 11% yield) as a yellow solid. LCMS [M+H]$^+$=686.2.

Compound 94

To a solution of tert-butyl ((2-(3-(6,6-difluoro-2-(4-methyl-4H-1,2,4-triazol-3-yl)spiro[3.3]heptan-2-yl)phenyl)-3-oxo-7-(trifluoromethyl)isoindolin-5-yl)methyl)(1-methylcyclobutyl)carbamate (30 mg, 0.04 mmol) in dichloromethane (3 mL) was added trifluoroacetic acid (0.3 mL, 3.89 mmol). The mixture was stirred for 1 h at 25° C. and concentrated to dryness. The residue was purified by RP-HPLC (0.2% NH$_4$OH in water/65%-95% ACN) to afford 2-(3-(6,6-difluoro-2-(4-methyl-4H-1,2,4-triazol-3-yl)spiro[3.3]heptan-2-yl)phenyl)-6-(((1-methylcyclobutyl)amino)methyl)-4-(trifluoromethyl)isoindolin-1-one (2.8 mg, 11% yield). $^1$H NMR (400 MHz, methanol-d$_4$) δ 8.35 (s, 1H), 8.09 (s, 1H), 8.04 (t, J=1.6 Hz, 1H), 8.01 (s, 1H), 7.68-7.64 (m, 1H), 7.48 (t, J=8.0 Hz, 1H), 7.14 (d, J=7.6 Hz, 1H), 5.15 (s, 2H), 3.88 (s, 2H), 3.36 (s, 3H), 3.22 (d, J=12.8 Hz, 2H), 3.03 (d, J=12.8 Hz, 2H), 2.68-2.55 (m, 4H), 2.16-2.07 (m, 2H), 1.92-1.78 (m, 4H), 1.39 (s, 3H). LCMS [M+H]$^+$=586.3.

Example 41: Compound 95

Compound 95 (2-(3-((1s,3s)-3-fluoro-1-(4-methyl-4H-1,2,4-triazol-3-yl)cyclobutyl)-phenyl)-6-(((1-methylcyclobutyl)amino)methyl)-4-(trifluoromethyl)isoindolin-1-one) can be synthesized according to Scheme 39 (FIG. 39).

Intermediate 2: ((1s,3s)-1-(3-bromophenyl)-3-hydroxycyclobutanecarboxylic acid

To a solution of 2-(3-bromophenyl)acetic acid (10.0 g, 46.5 mmol) in tetrahydrofuran (100 mL) was added isopropyl magnesium chloride (2.0 M in tetrahydrofuran, 50.1 mL, 102.3 mmol) at 0° C. The mixture was stirred at 20° C. for 1 h and then 2-(chloromethyl)oxirane (7.3 mL, 93.0 mmol) was added. The resulting mixture was stirred at 0° C. for 1.5 h, and another portion of isopropyl magnesium chloride (2.0 M in tetrahydrofuran, 50.1 mL, 102.3 mmol) was added. The mixture was stirred at 20° C. for another 16 h and then adjusted to pH=4 by addition of aqueous hydrochloric acid (1.0 M). The solution was diluted with water (100 mL) and extracted with ethyl acetate (3×100 mL). The combined organic layers were washed with brine (100 mL), dried over anhydrous sodium sulfate and concentrated under vacuum. The residue was purified by silica gel chromatography (mobile phase: ethyl acetate/petroleum ether, gradient: 0% to 60%) to afford (1s,3s)-1-(3-bromophenyl)-3-hydroxycyclobutanecarboxylic acid (4.3 g, 34% yield) as a yellow solid. $^1$H NMR (400 MHz, DMSO-d$_6$): δ 12.40 (s, 1H), 7.52-7.49 (m, 1H), 7.47-7.44 (m, 1H), 7.40-7.37 (m, 1H), 7.34-7.29 (m, 1H), 5.19 (d, J=6.4 Hz, 1H), 3.91-3.81 (m, 1H), 2.77-2.71 (m, 2H), 2.53-2.52 (m, 2H).

Intermediate 3: ((1s,3s)-methyl 1-(3-bromophenyl)-3-hydroxycyclobutane-carboxylate A solution of (1s,3s)-1-(3-bromophenyl)-3-hydroxycyclobutanecarboxylic acid (4.3 g, 15.86 mmol) and sulfuric acid (0.08 mL, 1.59 mmol) in methanol (45 mL) was stirred at 60° C. for 16 h and concentrated under vacuum. The residue was dissolved with dichloromethane (300 mL), washed with saturated aqueous sodium bicarbonate (100 mL), brine (300 mL), dried over anhydrous sodium sulfate and concentrated under vacuum to afford crude (1s,3s)-methyl 1-(3-bromophenyl)-3-hydroxycyclobutanecarboxylate (4.0 g, 88% yield) as a yellow solid. $^1$H NMR (400 MHz, DMSO-d$_6$): δ 7.53-7.50 (m, 1H), 7.49-7.45 (m, 1H), 7.41-7.36 (m, 1H), 7.35-7.29 (m, 1H), 5.24 (d, J=6.0 Hz, 1H), 3.90-3.80 (m, 1H), 3.56 (s, 3H), 2.85-2.74 (m, 2H), 2.56-2.52 (m, 2H).

Intermediate 4: ((1s,3s)-3-(3-bromophenyl)-3-(methoxycarbonyl)cyclobutyl 4-nitrobenzoate To a solution of (1s,3s)-methyl 1-(3-bromophenyl)-3-hydroxycyclobutane-carboxylate (2.00 g, 7.01 mmol) and 4-nitrobenzoic acid (1.49 g, 9.12 mmol) in tetrahydrofuran (20 mL) was added triphenylphosphine (2.76 g, 10.5 mmol) and diisopropyl azodicarboxylate (2.07 mL, 10.5 mmol) under nitrogen. The reaction mixture was stirred at 20° C. for 1 h then diluted with water (35 mL). The resulting mixture was extracted with ethyl acetate (3×35 mL). The combined organic layers were washed with brine (35 mL), dried over sodium sulfate and concentrated to dryness. The residue was purified by silica gel chromatography (mobile phase: ethyl acetate/petroleum ether, gradient 0% to 10%) to afford (1s,3s)-3-(3-bromophenyl)-3-(methoxycarbonyl)cyclobutyl 4-nitrobenzoate (2.70 g, 89% yield) as a white solid.

Intermediate 5: ((1r,3r)-methyl 1-(3-bromophenyl)-3-hydroxycyclobutane-carboxylate A mixture of (1s,3s)-3-(3-bromophenyl)-3-(methoxycarbonyl)cyclobutyl 4-nitrobenzoate (2.7 g, 6.22 mmol) and potassium carbonate (4.3 g, 31.1 mmol) in methanol (10 mL) was stirred at 20° C. for 2 h and filtered. The filtrate was concentrated under reduced pressure and the residue was purified by silica gel chromatography (mobile phase: ethyl acetate/petroleum ether, gradient 0% to 15%) to afford (1r,3r)-methyl 1-(3-bromophenyl)-3-hydroxycyclobutanecarboxylate (1.60 g, 90% yield) as a colorless oil. $^1$H NMR (400 MHz, CDCl$_3$) δ 7.39-7.36 (m, 2H), 7.20-7.15 (m, 2H), 4.51-4.43 (m, 1H), 3.66 (s, 3H), 3.26-3.20 (m, 2H), 2.38-2.32 (m, 2H).

Intermediate 6: ((1s,3s)-methyl 1-(3-bromophenyl)-3-fluorocyclobutane-carboxylate To a solution of (1r,3r)-methyl 1-(3-bromophenyl)-3-hydroxycyclobutanecarboxylate (500 mg, 1.75 mmol) and 2-tert-butyl-1,1,3,3-tetramethylguanidine (541 mg, 3.16 mmol) in dichloromethane (10 mL) was added Perfluoro-1-butanesulfonyl Fluoride (795 mg, 2.63 mmol) at 25° C. The mixture was stirred for 1 h then diluted with water (15 mL). The solution was extracted with ethyl acetate (3×15 mL). The combined organic layers were washed with brine (2×15 mL), dried over sodium sulfate and concentrated to dryness. The residue was purified by silica gel chromatography (mobile phase: ethyl acetate/petroleum ether, gradient 0% to 4%) to afford (1s,3s)-methyl 1-(3-bromophenyl)-3-fluorocyclobutanecarboxylate (400 mg, 79% yield) as a white solid.

Intermediate 7: ((1s,3s)-1-(3-bromophenyl)-3-fluorocyclobutanecarbohydrazide

To a solution of (1s,3s)-methyl 1-(3-bromophenyl)-3-fluorocyclobutanecarboxylate (400 mg, 1.42 mmol) in methanol (4.0 mL) was added hydrazine hydrate (0.89 mL, 15.5 mmol). The reaction mixture was stirred at 80° C. for 2 h and concentrated to afford 1-(3-bromophenyl)-3-methylene-cyclobutanecarbohydrazide (395 mg, 99% yield) as a white solid.

Intermediate 8: (2-((1s,3s)-1-(3-bromophenyl)-3-fluorocyclobutanecarbonyl)-N-methylhydrazinecarbothioamide To a solution of (1s,3s)-1-(3-bromophenyl)-3-fluorocyclobutanecarbohydrazide (400 mg, 1.4 mmol) in tetrahydrofuran (20 mL) was added methyl isothiocyanate (0.15 g, 2.11 mmol). The solution was stirred at 25° C. for 1 h and concentrated under vacuum to afford crude 2-((1s,3s)-1-(3-bromophenyl)-3-fluorocyclobutanecarbonyl)-N-methylhydrazinecarbothioamide (475 mg, 95% yield) as a yellow oil.

Intermediate 9: (5-((1s,3s)-1-(3-bromophenyl)-3-fluorocyclobutyl)-4-methyl-4H-1,2,4-triazole-3-thiol A mixture of 2-((1s,3s)-1-(3-bromophenyl)-3-fluorocyclobutanecarbonyl)-N-methylhydrazinecarbothioamide (0.48 g, 1.32 mmol) in aqueous sodium hydroxide (1.0 M, 6.91 mL, 6.91 mmol) was stirred at 25° C. for 2 h and then adjusted to pH=5 with aqueous hydrochloric acid (1.0 M). The solid was collected by filtration, washed with water (20 mL) and dried under vacuum to give 5-((1s,3s)-1-(3-bromophenyl)-3-fluorocyclobutyl)-4-methyl-4H-1,2,4-triazole-3-thiol (0.38 g, 84% yield) as a light yellow solid.

Intermediate 10: (3-((1s,3s)-1-(3-bromophenyl)-3-fluorocyclobutyl)-4-methyl-4H-1,2,4-triazole To a solution of 5-((1s,3s)-1-(3-bromophenyl)-3-fluorocyclobutyl)-4-methyl-4H-1,2,4-triazole-3-thiol (0.38 g, 1.11 mmol) in water (10 mL) and acetonitrile (2 mL) was added sodium nitrite (0.23 g, 3.33 mmol) and nitric acid (1 M, 3.33 mL, 3.33 mmol) at 0° C. The reaction mixture was stirred for 2 h at 20° C. and extracted with dichloromethane (2×50 mL). The combined organic layers were washed with saturated sodium bicarbonate (30 mL), brine (30 mL), dried over sodium sulfate and concentrated. The residue was purified by silica gel chromatography (mobile phase: methanol/dichloromethane, gradient 0% to 4%) to afford 3-((1s,3s)-1-(3-bromophenyl)-3-fluorocyclobutyl)-4-methyl-4H-1,2,4-triazole (320 mg, 93% yield) as a colorless oil. LCMS [M+H]$^+$=310.0.

Intermediate 11: (tert-butyl ((2-(3-((1s,3s)-3-fluoro-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glove box, a mixture of dicyclohexylphosphino-2',6'-diisopropoxy-1,1'-biphenyl)[2-(2'-amino-1,1'biphenyl)] palladium(II) methanesulfonate (4.9 mg, 0.01 mmol), 3-((1s,3s)-1-(3-bromophenyl)-3-fluorocyclobutyl)-4-methyl-4H-1,2,4-triazole (12.0 mg, 0.04 mmol), cesium carbonate (37.8 mg, 0.12 mmol), tert-butyl (1-methylcyclobutyl)((3-oxo-7-(trifluoromethyl)isoindolin-5-yl)methyl)carbamate (17.0 mg, 0.04 mmol) in 1,4-dioxane (1 mL) was stirred at 110° C. in a sealed vail for 16 h. The mixture was concentrated under vacuum and the residue was purified by preparative TLC (solvent gradient: 10% methanol in dichloromethane) to afford tert-butyl ((2-(3-((1s,3s)-3-fluoro-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (20.0 mg, 82% yield) as a yellow solid. LCMS [M+H]$^+$=628.3.

Compound 95

To a mixture of tert-butyl ((2-(3-((1s,3s)-3-fluoro-1-(4-methyl-4H-1,2,4-triazol-3-yl)cyclobutyl)phenyl)-3-oxo-7-(trifluoromethyl)isoindolin-5-yl)methyl)(1-methylcyclobutyl)-carbamate (20 mg, 0.03 mmol) in dichloromethane (1 mL) was added trifluoroacetic acid (0.13 mL, 0.50 mmol). The mixture was stirred at 25° C. for 16 h and concentrated under vacuum. The residue was purified by RP-HPLC (water(NH$_3$H$_2$O+NH$_4$HCOs)/ACN 43% to 73%) to afford 2-(3-((1s,3s)-3-fluoro-1-(4-methyl-4H-1,2,4-triazol-3-yl)cyclobutyl)phenyl)-6-(((1-methylcyclobutyl)amino)methyl)-4-(trifluoromethyl)isoindolin-1-one (2.4 mg, 14% yield). $^1$H NMR (400 MHz, methanol-d$_4$) δ 8.35 (s, 1H), 8.14 (s, 1H), 8.06 (s, 1H), 8.01 (s, 1H), 7.74-7.69 (m, 1H), 7.51 (t, J=8.0 Hz, 1H), 7.23 (d, J=7.6 Hz, 1H), 5.39-5.21 (m, 1H), 5.19 (s, 2H), 4.03 (s, 2H), 3.37 (s, 3H), 3.35-3.31 (m, 2H), 3.26-3.12 (m, 2H), 2.27-2.18 (m, 2H), 2.00-1.85 (m, 4H), 1.48 (s, 3H). LCMS [M+H]$^+$=528.2.

Example 42: Compound 96

Figure 40:
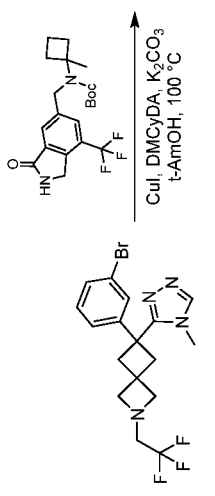
Figure 40:
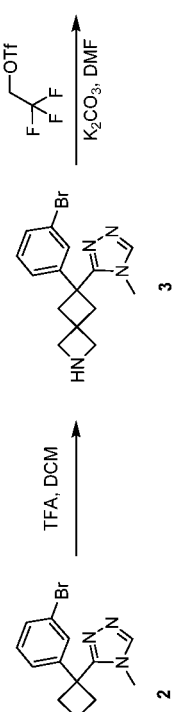
Figure 40:
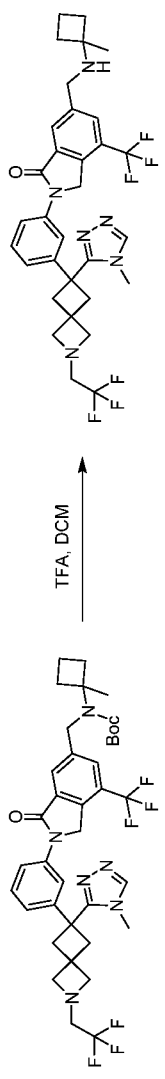
Figure 40:

Compound 96 (2-(3-(6-(4-methyl-4H-1,2,4-triazol-3-yl)-2-(2,2,2-trifluoroethyl)-2-azaspiro[3.3]heptan-6-yl)phenyl)-6-(((1-methylcyclobutyl)amino)methyl)-4-(trifluoromethyl)-isoindolin-1-one) can be synthesized according to Scheme 40 (FIG. 40).

Intermediate 2: (tert-butyl 6-(3-bromophenyl)-6-(4-methyl-4H-1,2,4-triazol-3-yl)-2-azaspiro[3.3]heptane-2-carboxylate To a mixture of 3-(3-bromobenzyl)-4-methyl-4H-1,2,4-triazole (2.00 g, 7.93 mmol) in N,N-dimethylformamide (30 mL) was added sodium hydride (60%, 1.27 g, 31.73 mmol) at 0° C. The mixture was stirred at 0° C. for 30 min and then tert-butyl 3,3-bis(bromomethyl)-azetidine-1-carboxylate (5.44 g, 15.87 mmol) was added. The resulting mixture was first warmed to 25° C. and stirred for 5 min, then heated at 60° C. for another 16 h. After cooled, the mixture was quenched by water (20 mL) and extracted with dichloromethane (3×50 mL). The combined organic layers were washed with brine (50 mL), dried over sodium sulfate and concentrated. The residue was purified by silica gel chromatography (mobile phase: methanol/dichloromethane, gradient 0% to 10%) to afford tert-butyl 6-(3-bromophenyl)-6-(4-methyl-4H-1,2,4-triazol-3-yl)-2-azaspiro[3.3]heptane-2-carboxylate (3.10 g, 90% yield) as a yellow oil. LCMS [M+H]$^+$=433.0.

Intermediate 3: (6-(3-bromophenyl)-6-(4-methyl-4H-1,2,4-triazol-3-yl)-2-azaspiro[3.3]heptane To a solution of tert-butyl 6-(3-bromophenyl)-6-(4-methyl-4H-1,2,4-triazol-3-yl)-2-azaspiro[3.3]heptane-2- carboxylate (650 mg, 1.5 mmol) in dichloromethane (10 mL) was added trifluoroacetic acid (1.0 mL, 12.98 mmol). The mixture was stirred at 25° C. for 2 h and concentrated under vacuum. The residue was purified by RP-HPLC (water (NH$_3$H$_2$O+NH$_4$HCO)/ACN 35% to 65%) to afford 6-(3-bromophenyl)-6-(4-methyl-4H-1,2,4-triazol-3-yl)-2-azaspiro[3.3]heptane (250 mg, 50% yield) as a yellow oi.

Intermediate 4: (6-(3-bromophenyl)-6-(4-methyl-4H-1,2,4-triazol-3-yl)-2-(2,2,2-trifluoroethyl)-2-azaspiro[3.3]heptane To a solution of 6-(3-bromophenyl)-6-(4-methyl-4H-1,2,4-triazol-3-yl)-2-azaspiro[3.3]heptane (50.0 mg, 0.15 mmol) in N,N-dimethylformamide (2 mL) was added potassium carbonate (82.9 mg, 0.60 mmol) and 2,2,2-trifluoroethyl trifluoromethanesulfonate (69.7 mg, 0.30 mmol). The reaction mixture was stirred at 25° C. for 2 h and then concentrated under vacuum. The resulting residue was purified by preparative TLC (solvent gradient: 10% methanol in dichloromethane) to afford 6-(3-bromophenyl)-6-(4-methyl-4H-1,2,4-triazol-3-yl)-2-(2,2,2-trifluoroethyl)-2-azaspiro[3.3]heptane (40 mg, 64% yield) as a yellow oil. LCMS [M+H]$^+$=415.1.

Intermediate 5: (tert-butyl ((2-(3-(6-(4-methyl-4H-1,2,4-triazol-3-yl)-2-(2,2,2-trifluoroethyl)-2-azaspiro[3.3]heptan-6-yl)phenyl)-3-oxo-7-(trifluoromethyl)isoindolin-5-yl)methyl)(1-methylcyclobutyl) carbamate A mixture of tert-butyl N-(1-methylcyclobutyl)-N-[[3-oxo-7-(trifluoromethyl)isoindolin-5-yl]methyl]carbamate (31.7 mg, 0.08 mmol), 6-(3-bromophenyl)-6-(4-methyl-4H-1,2,4-triazol-3-yl)-2-(2,2,2-trifluoroethyl)-2-azaspiro[3.3]heptane (30.0 mg, 0.07 mmol), (1S,2S)—N$^1$,N$^2$-dimethylcyclohexane-1,2-diamine (4.1 mg, 0.03 mmol), potassium carbonate (30.0 mg, 0.22 mmol) and copper(I) iodide (5.5 mg, 0.03 mmol) in tert-amyl alcohol (2 mL) was heated at 100° C. for 2 h under nitrogen atmosphere and concentrated to dryness. The residue was purified by preparative TLC (solvent gradient: 10% methanol in dichloromethane) to afford tert-butyl ((2-(3-(6-(4-methyl-4H-1,2,4-triazol-3-yl)-2-(2,2,2-trifluoroethyl)-2-azaspiro[3.3]heptan-6-yl)phenyl)-3-oxo-7-(trifluoromethyl)-isoindolin-5-yl)methyl)(1-methylcyclobutyl)carbamate (30.0 mg, 57% yield) as a yellow oil. LCMS [M+H]$^+$=733.2.

Compound 96

To a solution of tert-butyl ((2-(3-(6-(4-methyl-4H-1,2,4-triazol-3-yl)-2-(2,2,2-trifluoroethyl)-2-azaspiro[3.3]heptan-6-yl)phenyl)-3-oxo-7-(trifluoromethyl)isoindolin-5-yl)methyl)(1-methylcyclobutyl)carbamate (30.0 mg, 0.04 mmol) in dichloromethane (2 mL) was added trifluoroacetic acid (0.2 mL, 2.6 mmol). The mixture was stirred at 25° C. for 2 h then concentrated under vacuum. The residue was purified by RP-HPLC (water(NH$_3$H$_2$O+NH$_4$HCO$_3$)/CAN 50% to 80%) to afford 2-(3-(6-(4-methyl-4H-1,2,4-triazol-3-yl)-2-(2,2,2-trifluoroethyl)-2-azaspiro[3.3]heptan-6-yl)phenyl)-6-(((1-methylcyclobutyl)-amino)methyl)-4-(trifluoromethyl)isoindolin-1-one (2.6 mg 10% yield). $^1$H NMR (400 MHz, methanol-d$_4$) δ 8.35 (s, 1H), 8.09 (s, 1H), 8.00 (d, J=2.0 Hz, 2H), 7.67-7.65 (m, 1H), 7.47 (t, J=8.0 Hz, 1H), 7.11 (d, J=8.4 Hz, 1H), 5.15 (s, 2H), 3.87 (s, 2H), 3.47 (s, 2H), 3.39 (s, 2H), 3.36 (s, 3H), 3.23-3.20 (m, 2H), 3.12-2.98 (m, 4H), 2.15-2.05 (m, 2H), 1.92-1.85 (m, 2H), 1.84-1.76 (m, 2H), 1.38 (s, 3H). LCMS [M+H]$^+$=633.2.

Example 43: Compound 97

Figure 41:
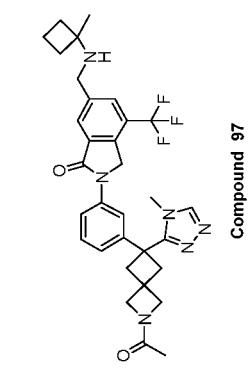
Figure 41:
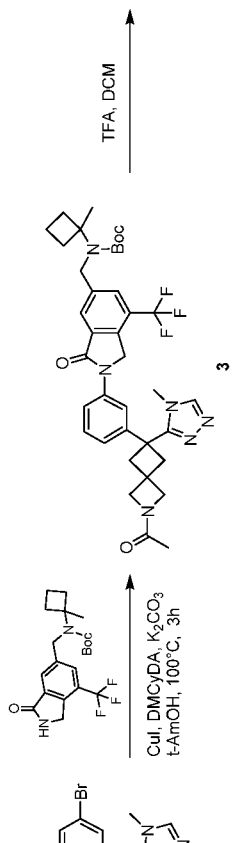
Figure 41:
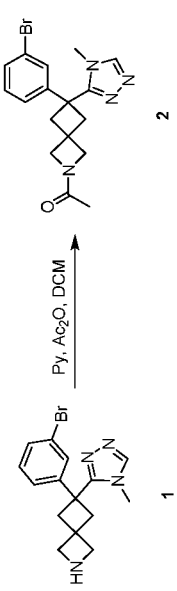

Compound 97 (2-(3-(2-acetyl-6-(4-methyl-4H-1,2,4-triazol-3-yl)-2-azaspiro[3.3]heptan-6-yl)phenyl)-6-(((1-methylcyclobutyl)amino)methyl)-4-(trifluoromethyl)isoindolin-1-one) can be synthesized according to Scheme 41 (FIG. 41).

Intermediate 2: (1-(6-(3-bromophenyl)-6-(4-methyl-4H-1,2,4-triazol-3-yl)-2-azaspiro[3.3]heptan-2-yl) ethanone To a solution of 6-(3-bromophenyl)-6-(4-methyl-4H-1,2,4-triazol-3-yl)-2-azaspiro[3.3]heptane (70.0 mg, 0.21 mmol) in dichloromethane (2 mL) was added pyridine (0.08 mL, 1.05 mmol) and acetic anhydride (0.04 mL, 0.42 mmol). The mixture was stirred at 25° C. for 16 h then concentrated under vacuum. The resulting residue was purified by preparative TLC (solvent gradient: 10% methanol in dichloromethane) to afford 1-(6-(3-bromophenyl)-6-(4-methyl-4H-1,2,4-triazol-3-yl)-2-azaspiro[3.3]heptan-2-yl) ethanone (30.0 mg, 38.1% yield) as a yellow oil. LCMS [M+H]$^+$=375.1.

Intermediate 3: (tert-butyl ((2-(3-(2-acetyl-6-(4-methyl-4H-1,2,4-triazol-3-yl)-2-azaspiro[3.3]heptan-6-yl)phenyl)-3-oxo-7-(trifluoromethyl)isoindolin-5-yl)methyl)(1-methylcyclobutyl)carbamate In a glove box, a mixture of tert-butyl (1-methylcyclobutyl)((3-oxo-7-(trifluoromethyl)isoindolin-5-yl)methyl) carbamate (35.0 mg, 0.09 mmol), 1-(6-(3-bromophenyl)-6-(4-methyl-4H-1,2,4-triazol-3-yl)-2-azaspiro[3.3]heptan-2-yl)ethanone (30.0 mg, 0.08 mmol), (1S,2S)—N$^1$,N$^2$-dimethylcyclohexane-1,2-diamine (4.6 mg, 0.03 mmol), potassium carbonate (33.2 mg, 0.24 mmol) and copper(I) iodide (6.1 mg, 0.03 mmol), in tert-amyl alcohol (2 mL) was heated at 100° C. in sealed vail for 2 h and concentrated under vacuum. The residue was purified by preparative TLC (solvent gradient: 10% methanol in dichloromethane) to afford tert-butyl ((2-(3-(2-acetyl-6-(4-methyl-4H-1,2,4-triazol-3-yl)-2-azaspiro[3.3]heptan-6-yl)phenyl)-3-oxo-7-(trifluoromethyl)isoindolin-5-yl)methyl)(1-methylcyclobutyl) carbamate (30.0 mg, 54% yield) as a yellow solid. LCMS [M+H]$^+$=693.0.

Compound 97

To a solution of tert-butyl ((2-(3-(2-acetyl-6-(4-methyl-4H-1,2,4-triazol-3-yl)-2-azaspiro[3.3]heptan-6-yl)phenyl)-3-oxo-7-(trifluoromethyl)isoindolin-5-yl)methyl)(1-methylcyclobutyl)carbamate (30.0 mg, 0.04 mmol) in dichloromethane (1 mL) was added trifluoroacetic acid (0.1 mL, 1.3 mmol). The mixture was stirred at 25° C. for 2 h and concentrated under vacuum. The residue was purified by RP-HPLC (water(NH$_3$H$_2$O+NH$_4$HCO$_3$)/CAN 36% to 66%) to afford 2-(3-(2-acetyl-6-(4-methyl-4H-1,2,4-triazol-3-yl)-2-azaspiro[3.3]heptan-6-yl)phenyl)-6-(((1-methylcyclobutyl)amino)methyl)-4-(trifluoromethyl)isoindolin-1-one (14.0 mg, 52% yield). $^1$H NMR (400 MHz, methanol-d$_4$) δ 8.37 (d, J=6.0 Hz, 1H), 8.09 (s, 1H), 8.06-8.00 (m, 2H), 7.68 (d, J=8.0 Hz, 1H), 7.49 (t, J=8.0 Hz, 1H), 7.17-7.09 (m, 1H), 5.16 (s, 2H), 4.25 (s, 1H), 4.18 (s, 1H), 3.99 (s, 1H), 3.95 (s, 1H), 3.87 (s, 2H), 3.36 (d, J=1.2 Hz, 3H), 3.35 (s, 1H), 3.27 (s, 1H), 3.11-3.06 (m, 2H), 2.16-2.06 (m, 2H), 1.93-1.86 (m, 2H), 1.85-1.76 (m, 5H), 1.38 (s, 3H). LCMS [M+H]$^+$=593.2.

Example 44: Compound 98

Compound 98 (2-(3-(6-(4-methyl-4H-1,2,4-triazol-3-yl)-2-(methylsulfonyl)-2-azaspiro[3.3]heptan-6-yl)phenyl)-6-

Figure 42:
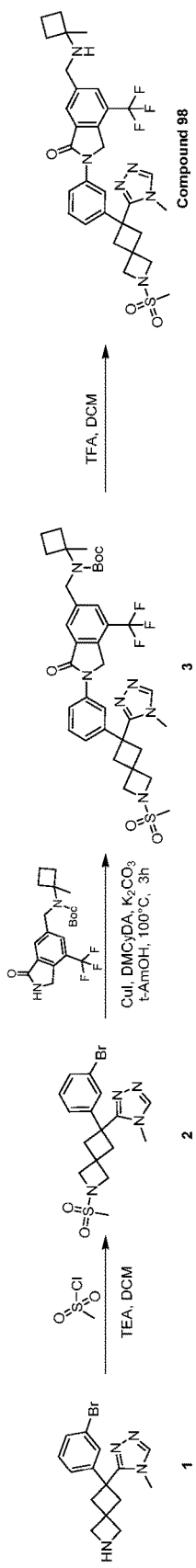

(((1-methylcyclobutyl)amino)methyl)-4-(trifluoromethyl) isoindolin-1-one) can be synthesized according to Scheme 42 (FIG. 42).

Intermediate 2: (6-(3-bromophenyl)-6-(4-methyl-4H-1,2,4-triazol-3-yl)-2-(methylsulfonyl)-2-azaspiro[3.3]heptane To a solution of 6-(3-bromophenyl)-6-(4-methyl-4H-1,2,4-triazol-3-yl)-2-azaspiro[3.3]heptane (70.0 mg, 0.21 mmol) in dichloromethane (4 mL) was added triethylamine (0.12 mL, 0.84 mmol) and methanesulfonyl chloride (0.07 mL, 0.87 mmol) at 0° C. The mixture was stirred at 25° C. for 2 h and quenched by addition of saturated aqueous sodium bicarbonate (10 mL). The resulting solution was extracted with dichloromethane (3×20 mL). The combined organic layers were washed with brine (30 mL), dried over sodium sulfate and concentrated under vacuum. The residue was purified by preparative TLC (solvent gradient: 10% methanol in dichloromethane) to afford 6-(3-bromophenyl)-6-(4-methyl-4H-1,2,4-triazol-3-yl)-2-(methylsulfonyl)-2-azaspiro[3.3]heptane (70.0 mg, 81% yield) as a yellow oil. LCMS $[M+H]^+$=411.2.

Intermediate 3: (tert-butyl ((2-(3-(6-(4-methyl-4H-1,2,4-triazol-3-yl)-2-(methylsulfonyl)-2-azaspiro[3.3]heptan-6-yl)phenyl)-3-oxo-7-(trifluoromethyl)isoindolin-5-yl)methyl)(1-methylcyclobutyl)carbamate In a glove box, a mixture of tert-butyl (1-methylcyclobutyl)((3-oxo-7-(trifluoromethyl)isoindolin-5-yl)methyl)carbamate (74.6 mg, 0.19 mmol), 6-(3-bromophenyl)-2-methylsulfonyl-6-(4-methyl-1,2,4-triazol-3-yl)-2-azaspiro[3.3]heptane (70.0 mg, 0.17 mmol), (1S,2S)—$N^1,N^2$-dimethylcyclohexane-1,2-diamine (9.7 mg, 0.07 mmol), potassium carbonate (70.6 mg, 0.51 mmol) and copper(I) iodide (13.0 mg, 0.07 mmol) in tert-amyl alcohol (4 mL) was heated at 100° C. in sealed via for 2 h under nitrogen atmosphere and concentrated to dryness. The residue was purified by preparative TLC (solvent gradient: 10% methanol in dichloromethane) to afford tert-butyl ((2-(3-(6-(4-methyl-4H-1,2,4-triazol-3-yl)-2-(methylsulfonyl)-2-azaspiro[3.3]heptan-6-yl)phenyl)-3-oxo-7-(trifluoromethyl)isoindolin-5-yl)methyl)(1-methylcyclobutyl)carbamate (40.0 mg, 32% yield) as a yellow oil. LCMS $[M+H]^+$=729.0. Compound 98

To a solution of tert-butyl ((2-(3-(6-(4-methyl-4H-1,2,4-triazol-3-yl)-2-(methylsulfonyl)-2-azaspiro[3.3]heptan-6-yl)phenyl)-3-oxo-7-(trifluoromethyl)isoindolin-5-yl)methyl)(1-methylcyclobutyl)carbamate (40.0 mg, 0.05 mmol) in dichloromethane (2 mL) was added trifluoroacetic acid (0.20 mL, 2.60 mmol). The mixture was stirred at 25° C. for 16 h and concentrated under vacuum. The residue was purified by RP-HPLC (water(NH$_3$H$_2$O+NH$_4$HCO$_3$)-ACN (35%-65%)) to afford 2-(3-(6-(4-methyl-4H-1,2,4-triazol-3-yl)-2-(methylsulfonyl)-2-azaspiro[3.3]heptan-6-yl)phenyl)-6-(((1-methylcyclobutyl)-amino)methyl)-4-(trifluoromethyl)isoindolin-1-one (15.3 mg, 43% yield). $^1$H NMR (400 MHz, methanol-d$_4$) δ 8.36 (s, 1H), 8.10 (s, 1H), 8.04-8.00 (m, 2H), 7.71-7.64 (m, 1H), 7.48 (t, J=8.0 Hz, 1H), 7.12 (d, J=8.0 Hz, 1H), 5.15 (s, 2H), 3.95 (s, 2H), 3.89 (s, 2H), 3.86 (s, 2H), 3.36 (s, 3H), 3.27 (s, 2H), 3.09-3.06 (m, 2H), 2.90 (s, 3H), 2.15-2.06 (m, 2H), 1.91-1.76 (m, 4H), 1.38 (s, 3H). LCMS $[M+H]^+$=629.1.

Example 45: Compounds 99 and 100

Figure 43:
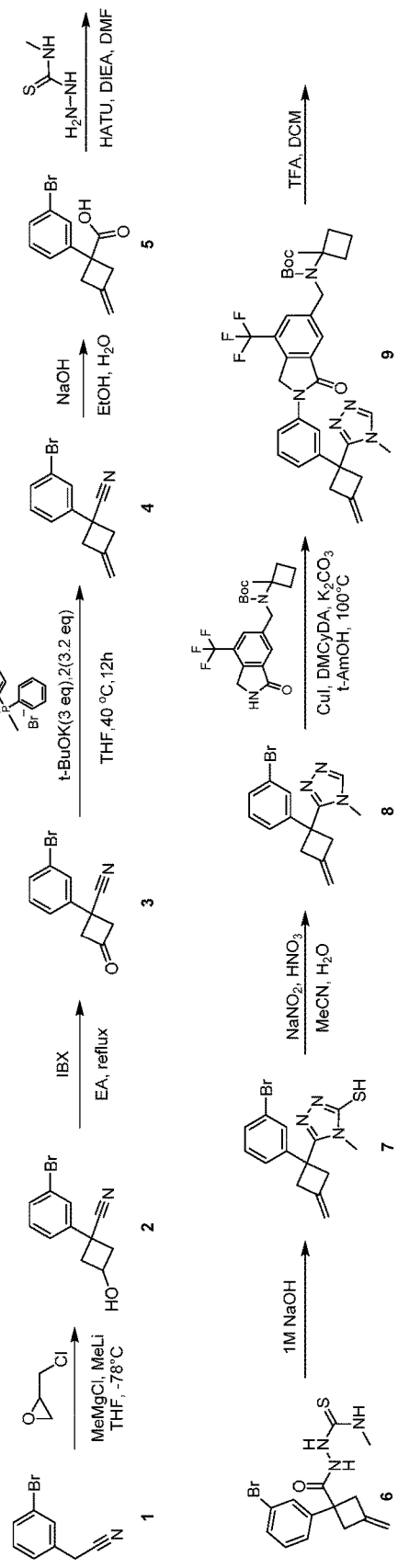
Figure 43:
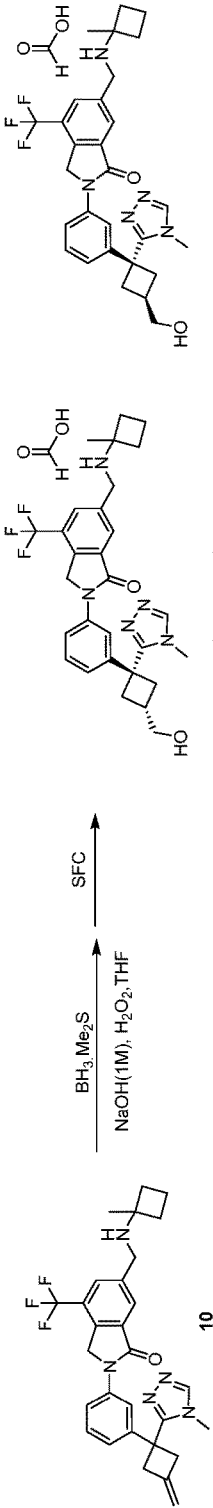

Compound 99 (2-(3-((1s,3s)-3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one formate), and Compound 100 (2-(3-((1r,3r)-3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one formate), can be synthesized according to Scheme 43 (FIG. 43).

Intermediate 2: (1-(3-bromophenyl)-3-hydroxycyclobutanecarbonitrile)

To a solution of 2-(3-bromophenyl)acetonitrile (6.05 mL, 45.9 mmol) in tetrahydrofuran (50 mL) was added methyllithium (1.6 M in diethyl ether, 28.7 mL, 45.91 mmol) at −78° C. dropwise. The mixture was stirred at −78° C. for 1 h and a solution of epichlorohydrin (3.59 mL, 45.91 mmol) in tetrahydrofuran (12 mL) was added. The mixture was stirred at −78° C. for another 1 h and then methyl magnesium bromide (3.0 M in diethyl ether, 50.0 mL, 150.0 mmol) was added dropwise. The resulting mixture was stirred at room temperature for 16 h and quenched by water (100 mL). The solution was extracted with ethyl acetate (3×100 mL). The combined organic layers were washed with brine (100 mL), dried over sodium sulfate and concentrated under vacuum. The residue was purified by silica gel chromatography (mobile phase: ethyl acetate/petroleum ether, gradient 0% to 33%) to afford 1-(3-bromophenyl)-3-hydroxycyclobutanecarbonitrile (11.0 g, 95% yield) as a yellow oil. LCMS $[M+H]^+$=252.1.

Intermediate 3: (1-(3-bromophenyl)-3-oxocyclobutanecarbonitrile

To a solution of 1-(3-bromophenyl)-3-hydroxycyclobutanecarbonitrile (10.0 g, 39.67 mmol) in ethyl acetate (300 mL) was added 1-2-iodoxybenzoic acid (33.3 g, 119 mmol) in portions. The mixture was stirred at 80° C. for 4 h and filtered through a pad of Celite. The filtrate was concentrated under reduced pressure and the residue was purified by silica gel chromatography (mobile phase: ethyl acetate/petroleum ether, gradient 0% to 15%) to afford 1-(3-bromophenyl)-3-oxo-cyclobutanecarbonitrile (8.0 g, 80% yield) as a white solid. $^1$H NMR (400 MHz, CDCl$_3$) δ 7.65 (t, J=2.0 Hz, 1H), 7.58-7.51 (m, 1H), 7.44-7.43 (m, 1H), 7.39-7.31 (m, 1H), 4.11-4.08 (m, 1H), 4.07-4.03 (m, 1H), 3.76-3.72 (m, 1H), 3.71-3.67 (m, 1H).

Intermediate 4: (1-(3-bromophenyl)-3-methylenecyclobutanecarbonitrile

Under nitrogen, to a solution of methyltriphenylphosphonium bromide (20.6 g, 57.6 mmol) in tetrahydrofuran (80 mL) was added potassium t-butoxide (1.0 M in tetrahydrofuran, 54.0 mL, 54.0 mmol) at 0° C. The mixture was stirred at 40° C. for 1 h, and then a solution of 1-(3-bromophenyl)-3-oxocyclobutanecarbonitrile (4.5 g, 18.0 mmol) in tetrahydrofuran (10 ml) was added. The mixture was stirred at 40° C. for another 5 h and quenched with water (100 mL). The resulting solution was extracted with ethyl acetate (3×100 mL). The combined organic layers were washed with brine (2×100 mL), dried over sodium sulfate and concentrated to dryness. The residue was purified by silica gel chromatography (mobile phase: ethyl acetate/petroleum ether, gradient 0% to 2%) to afford 1-(3-bromophenyl)-3-methylenecyclobutanecarbonitrile (2.9 g, 65% yield) as yellow oil. $^1$H NMR (400 MHz, CDCl$_3$) δ 7.57 (d, J=1.6 Hz, 1H), 7.56-7.36 (m, 2H), 7.23-7.19 (m, 1H), 5.00-4.98 (s, 2H), 3.56-3.52 (m, 2H), 3.23-3.17 (m, 2H).

Intermediate 5: (1-(3-bromophenyl)-3-methylenecyclobutanecarboxylic acid

A mixture of 1-(3-bromophenyl)-3-methylenecyclobutanecarbonitrile (2.9 g, 11.7 mmol) and sodium hydroxide (1.9 g, 46.8 mmol) in ethanol (30 mL) and water (10 mL) was stirred at 80° C. for 2 h. The mixture was adjusted to pH=3 with aqueous hydrochloric acid (1 M) and extracted with dichloromethane (3×40 mL). The combined organic layers were washed with brine (30 mL), dried over sodium sulfate and concentrated to give crude 1-(3-bromophenyl)-3-methylenecyclobutanecarboxylic acid (2.7 g, 86% yield) as a white solid.

Intermediate 6: (2-(1-(3-bromophenyl)-3-methylenecyclobutanecarbonyl)-N-methylhydrazinecarbothioamide To a mixture of 1-(3-bromophenyl)-3-methylenecyclobutanecarboxylic acid (2.7 g, 10.11 mmol) in N,N-dimethylformamide (50 mL) was added N-methyl hydrazinecarbothioamide (1.6 g, 15.16 mmol), N,N-diisopropylethylamine (5.28 mL, 30.32 mmol) and 2-(7-azabenzotriazol-1-yl)-N,N,N',N'-tetramethyluronium hexafluorophosphate (5.8 g, 15.16 mmol). The reaction mixture was stirred for 1 h at 25° C. and diluted with water (35 mL). The solution was extracted with ethyl acetate (3×75 mL). The combined organic layers were washed with brine (2×75 mL), dried over sodium sulfate and concentrated to dryness. The residue was purified by silica gel chromatography ((mobile phase: ethyl acetate/petroleum ether, gradient 0% to 35%) to afford 2-(1-(3-bromophenyl)-3-methylenecyclobutanecarbonyl)-N-methylhydrazinecarbothioamide (3.0 g, 84% yield) as a yellow solid. LCMS [M+H]$^+$=356.1.

Intermediate 7: (5-(1-(3-bromophenyl)-3-methylenecyclobutyl)-4-methyl-4H-1,2,4-triazole-3-thiol A solution of 2-(1-(3-bromophenyl)-3-methylenecyclobutanecarbonyl)-N-methylhydrazinecarbothioamide (2.9 g, 8.19 mmol) in aqueous sodium hydroxide (1.0 M, 41.4 mL, 41.4 mmol) was stirred at 25° C. for 12 h. After cooled to 0° C., the reaction mixture was adjusted to pH=5 with aqueous hydrochloric acid (1 M). The solid was collected by filtration and dried to afford crude 5-(1-(3-bromophenyl)-3-methylenecyclobutyl)-4-methyl-4H-1,2,4-triazole-3-thiol (1.2 g, 44% yield) as a white solid. LCMS [M+H]$^+$=336.0.

Intermediate 8: (3-(1-(3-bromophenyl)-3-methylenecyclobutyl)-4-methyl-4H-1,2,4-triazole To a solution of 5-(1-(3-bromophenyl)-3-methylenecyclobutyl)-4-methyl-4H-1,2,4-triazole-3-thiol (1.2 g, 3.57 mmol) in water (10 mL) and acetonitrile (2 mL) was added sodium nitrite (0.7 g, 10.7 mmol) and nitric acid (1 M, 10 mL, 10 mmol). The reaction mixture was stirred for 1 h at 20° C. and then quenched with saturated aqueous sodium bicarbonate (20 mL). The solution was extracted with dichloromethane (3×20 mL). The combined organic layers were washed with brine (30 mL), dried over sodium sulfate and concentrated to dryness. The residue was purified by silica gel chromatography (mobile phase: methanol/dichloromethane, gradient 0% to 5%) to afford 3-(1-(3-bromophenyl)-3-methylenecyclobutyl)-4-methyl-4H-1,2,4-triazole (555 mg, 51% yield) as a brown oil. $^1$H NMR (400 MHz, CDCl$_3$) δ 8.09 (s, 1H), 7.43-7.39 (m, 2H), 7.25-7.22 (m, 1H), 7.19-7.15 (m, 1H), 5.00-4.96 (m, 2H), 3.80-3.74 (m, 2H), 3.36-3.30 (m, 2H), 3.25 (s, 3H).

Intermediate 9: (tert-butyl ((2-(3-(1-(4-methyl-4H-1,2,4-triazol-3-yl)-3-methylenecyclobutyl)phenyl)-3-oxo-7-(trifluoromethyl)isoindolin-5-yl)methyl)(1-methylcyclobutyl)carbamate In a glove box, a mixture of 3-(1-(3-bromophenyl)-3-methylenecyclobutyl)-4-methyl-4H-1,2,4-triazole (130 mg, 0.43 mmol), tert-butyl (1-methylcyclobutyl)((3-oxo-7-(trifluoromethyl)isoindolin-5-yl)methyl)carbamate (187.3 mg, 0.47 mmol), copper(I) iodide (16.3 mg, 0.09 mmol), (1 S,2S)—N$^1$,N$^2$-dimethylcyclohexane-1,2-diamine (24.3 mg, 0.17 mmol) and potassium carbonate (0.18 g, 1.28 mmol) in tert-amyl alcohol (5 mL) was heated at 100° C. in sealed vial for 2 h and concentrated to dryness. The residue was purified by silica gel chromatography (mobile phase: methanol/dichloromethane, gradient 0% to 3%) to afford tert-butyl ((2-(3-(1-(4-methyl-4H-1,2,4-triazol-3-yl)-3-methylenecyclobutyl)phenyl)-3-oxo-7-(trifluoromethyl)isoindolin-5-yl)methyl)(1-methylcyclobutyl)carbamate (245 mg, 92% yield) as a light green solid. LCMS [M+H]$^+$=622.3.

Intermediate 10: (2-(3-(1-(4-methyl-4H-1,2,4-triazol-3-yl)-3-methylenecyclobutyl)phenyl)-6-(((1-methylcyclobutyl)amino)methyl)-4-(trifluoromethyl)isoindolin-1-one To a solution of tert-butyl ((2-(3-(1-(4-methyl-4H-1,2,4-triazol-3-yl)-3-methylenecyclobutyl)phenyl)-3-oxo-7-(trifluoromethyl)isoindolin-5-yl)methyl)(1-methylcyclobutyl) carbamate (245 mg, 0.39 mmol) in dichloromethane (5 mL) was added trifluoroacetic acid (2.0 mL, 25.96 mmol). The mixture was stirred at 20° C. for 1 h and concentrated to give crude 2-(3-(1-(4-methyl-4H-1,2,4-triazol-3-yl)-3-methylene-cyclobutyl)phenyl)-6-(((1-methylcyclobutyl)amino) methyl)-4-(trifluoromethyl)isoindolin-1-one (190 mg, 92% yield) as a yellow solid. LCMS [M+H]$^+$=522.5.

Compounds 99 and 100

To a solution of 2-(3-(1-(4-methyl-4H-1,2,4-triazol-3-yl)-3-methylenecyclobutyl)-phenyl)-6-(((1-methylcyclobutyl) amino)methyl)-4-(trifluoromethyl)isoindolin-1-one (110 mg, 0.21 mmol) in tetrahydrofuran (4 mL) was added borane dimethyl sulfide complex (10.0 M, 0.17 mL, 1.70 mmol) dropwise at −10° C. The reaction mixture was stirred at 20° C. for 2 h and cooled to −20° C., then aqueous sodium hydroxide (1 M, 2.0 mL, 2.0 mmol), followed by aqueous hydrogen peroxide (30%, 1.0 mL, 9.79 mmol) were added. The resulting mixture was stirred at 20° C. for another 2 h and quenched with saturated aqueous sodium sulfite (15 mL). The solution was extracted with ethyl acetate (3×15 mL). The combined organic layers were washed with brine (15 mL), dried over sodium sulfate and concentrated to dryness. The residue was purified by RP-HPLC (NH$_3$H$_2$O+ NH$_4$HCO$_3$)/ACN 41% to 71%) to afford 2-(3-(3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one (25.0 mg, 22% yield).

The above product was purified by chiral SFC (Column=Daicel Chiralcel OD-H; Column dimensions=250 mm×30 mm×5 μm; Detection wavelength=220 nM; Flow rate=80 mL/min; Mobile phase: A: CO$_2$ B: ethanol; Isocratic: 40% B with 0.1% ammonium hydroxide), then by RP-HPLC (water(FA)-ACN 7%-37%) to afford tentatively assigned:

2-(3-((1s,3s)-3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one formate (Peak 1, retention time=4.252 min) (2.9 mg, 11% yield). $^1$H NMR (400 MHz, methanol-$d_4$) δ 8.51 (br s, 1H), 8.33 (s, 1H), 8.17 (s, 1H), 8.10 (s, 1H), 8.06 (s, 1H), 7.71 (d, J=6.8 Hz, 1H), 7.52 (t, J=8.0 Hz, 1H), 7.31 (d, J=7.6 Hz, 1H), 5.21 (s, 2H), 4.16 (s, 2H), 3.58 (d, J=5.6 Hz, 2H), 3.35 (s, 3H), 2.91-2.69 (m, 5H), 2.39-2.26 (m, 2H), 2.07-1.87 (m, 4H), 1.56 (s, 3H). LCMS [M+H]$^+$=540.2.

2-(3-((1r,3r)-3-(hydroxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one formate (Peak 2, retention time=4.647 min) (2.7 mg, 11% yield). $^1$H NMR (400 MHz, methanol-$d_4$) δ 8.49 (br s, 1H), 8.40 (s, 1H), 8.18 (s, 1H), 8.12 (s, 1H), 7.89 (s, 1H), 7.72-7.66 (m, 1H), 7.49 (t, J=8.0 Hz, 1H), 7.17 (d, J=8.4 Hz, 1H), 5.21 (s, 2H), 4.22 (s, 2H), 3.59 (d, J=5.2 Hz, 2H), 3.37 (s, 3H), 3.09-3.02 (m, 2H), 2.72-2.52 (m, 3H), 2.44-2.29 (m, 2H), 2.09-1.92 (m, 4H), 1.59 (s, 3H). LCMS [M+H]$^+$=540.2.

Example 46: Compounds 101 and 102

Figure 44:
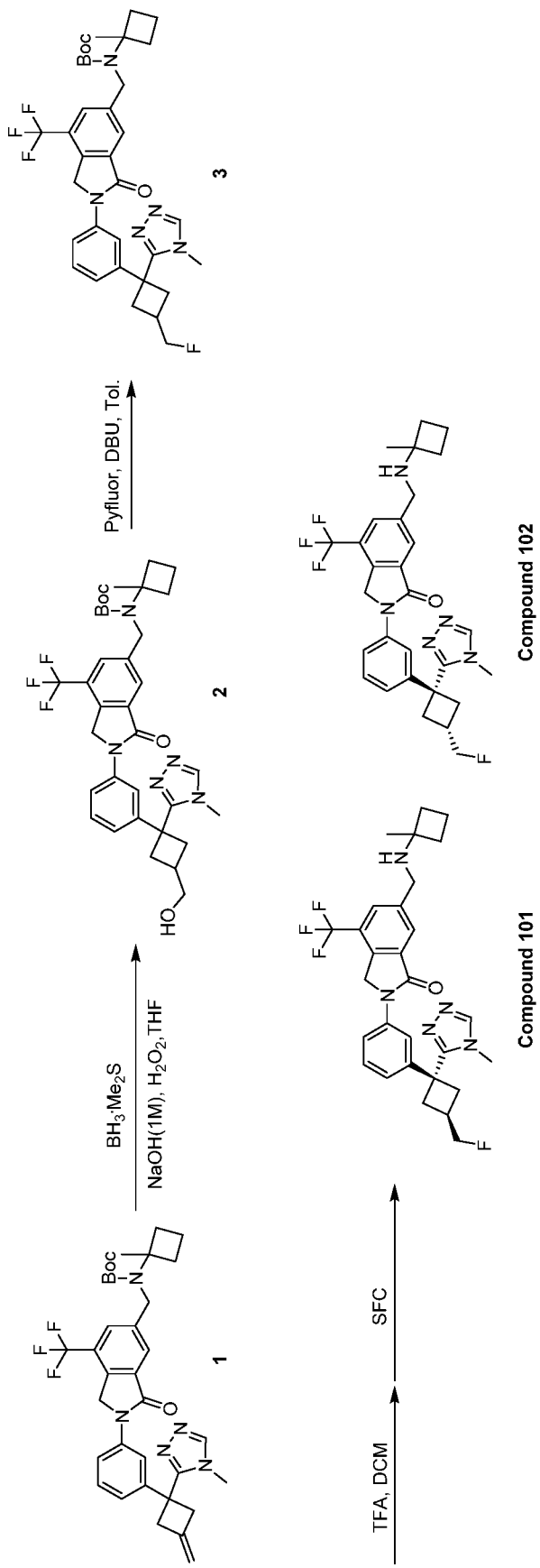

Compound 101 (2-(3-((1r,3r)-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one) and Compound 102 (2-(3-((1s,3s)-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to Scheme 44 (FIG. 44).

Intermediate 2: (tert-butyl ((2-(3-(3-(hydroxymethyl)-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate To a solution of tert-butyl ((2-(3-(1-(4-methyl-4H-1,2,4-triazol-3-yl)-3-methylenecyclobutyl)phenyl)-3-oxo-7-(trifluoromethyl)isoindolin-5-yl)methyl)(1-methylcyclobutyl)carbamate (1.5 g, 2.41 mmol) in tetrahydrofuran (24 mL) was added borane dimethyl sulfide complex (10.0 M, 1.2 mL, 12.00 mmol) dropwise at −10° C. The reaction mixture was stirred at 20° C. for 2 h and cooled to −20° C., then aqueous sodium hydroxide (1 M, 14.4 mL, 14.4 mmol), followed by aqueous hydrogen peroxide (30%, 12.0 mL, 117.48 mmol) were added. The resulting mixture was stirred at 20° C. for another 2 h and quenched with saturated aqueous sodium sulfite (15 mL). The solution was extracted with ethyl acetate (3×25 mL). The combined organic layers were washed with brine (25 mL), dried over sodium sulfate and concentrated to dryness. The residue was purified by silica gel chromatography (mobile phase: methanol/dichloromethane, gradient 0% to 8%) to afford tert-butyl ((2-(3-(3-(hydroxymethyl)-1-(4-methyl-4H-1,2,4-triazol-3-yl)cyclobutyl)-phenyl)-3-oxo-7-(trifluoromethyl)isoindolin-5-yl)methyl)(1-methylcyclobutyl)carbamate (700 mg, 45% yield) as a colorless oil. LCMS [M+H]$^+$=640.3.

Intermediate 3: (tert-butyl ((2-(3-(3-(fluoromethyl)-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate To a solution of tert-butyl ((2-(3-(3-(hydroxymethyl)-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (300 mg, 0.47 mmol) in toluene (5.0 mL) was added pyridine-2-sulfonyl fluoride (90.7 mg, 0.56 mmol) and 1,8-diazabicyclo[5.4.0]undec-7-ene (0.14 mL, 0.94 mmol) at −25° C. The resulting mixture was stirred at 100° C. for 1 h. After cooled, the reaction was quenched with water (15 mL) and extracted with ethyl acetate (3×15 mL). The combined organic layers were washed with brine (2×15 mL), dried over sodium sulfate and concentrated. The residue was purified by silica gel chromatography (mobile phase: methanol/dichloromethane, gradient 0% to 10%) to afford tert-butyl ((2-(3-(3-(fluoromethyl)-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (180 mg, 60% yield) as yellow oil. LCMS [M+H]$^+$=642.3.

Compound 101 and 102

To a solution of tert-butyl 4-[[2-[3-[3-[(4-methyl-1,2,4-triazol-3-yl)methyl]oxetan-3-yl]phenyl]-3-oxo-7-(trifluoromethyl)isoindolin-5-yl]methyl]piperazine-1-carboxylate (180 mg, 0.29 mmol) in dichloromethane (2 mL) was added trifluoroacetic acid (0.36 mL, 4.67 mmol). The mixture was stirred at 25° C. for 1 h and concentrated under vacuum. The residue was purified by preparative TLC (solvent gradient: 10% methanol in dichloromethane) to give 2-(3-(3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one (80 mg, 53% yield).

The above product was further purified by chiral SFC (Column=Daicel Chiralpak AD; Column dimensions=250 mm×30 mm×10 μm; Detection wavelength=220 nM; Flow rate=70 mL/min; Mobile phase: A: $CO_2$ B: ethanol (0.05% DEA); Isocratic: 35% B) with 0.1% ammonium hydroxide) to afford:

2-(3-((1r,3r)-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1, retention time=1.779 min) (9.5 mg, 12% yield). $^1$H NMR (400 MHz, methanol-$d_4$) δ 8.41 (s, 1H), 8.08 (s, 1H), 8.01 (s, 1H), 7.93 (t, J=2.0 Hz, 1H), 7.67 (dd, J=8.0, 1.6 Hz, 1H), 7.48 (t, J=8.0 Hz, 1H), 7.11 (d, J=8.4 Hz, 1H), 5.15 (s, 2H), 4.52-4.36 (m, 2H), 3.86 (s, 2H), 3.37 (s, 3H), 3.13-3.05 (m, 2H), 2.78-2.69 (m, 3H), 2.16-2.06 (m, 2H), 1.94-1.77 (m, 4H), 1.38 (s, 3H). LCMS [M+H]$^+$=542.3.

2-(3-((1s,3s)-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2, retention time=1.977 min) (16.2 mg, 21% yield). $^1$H NMR (400 MHz, methanol-$d_4$) δ 8.33 (s, 1H), 8.14 (s, 1H), 8.07 (s, 2H), 7.72 (d, J=6.0 Hz, 1H), 7.52 (t, J=8.0 Hz, 1H), 7.30 (d, J=8.4 Hz, 1H), 5.20 (s, 2H), 4.52-4.33 (m, 2H), 4.07 (s, 2H), 3.35 (s, 3H), 2.99-2.84 (m, 5H), 2.29-2.20 (m, 2H), 2.02-1.86 (m, 4H), 1.50 (s, 3H). LCMS [M+H]$^+$=542.3.

Example 47: Compounds 103 and 104

Figure 45:
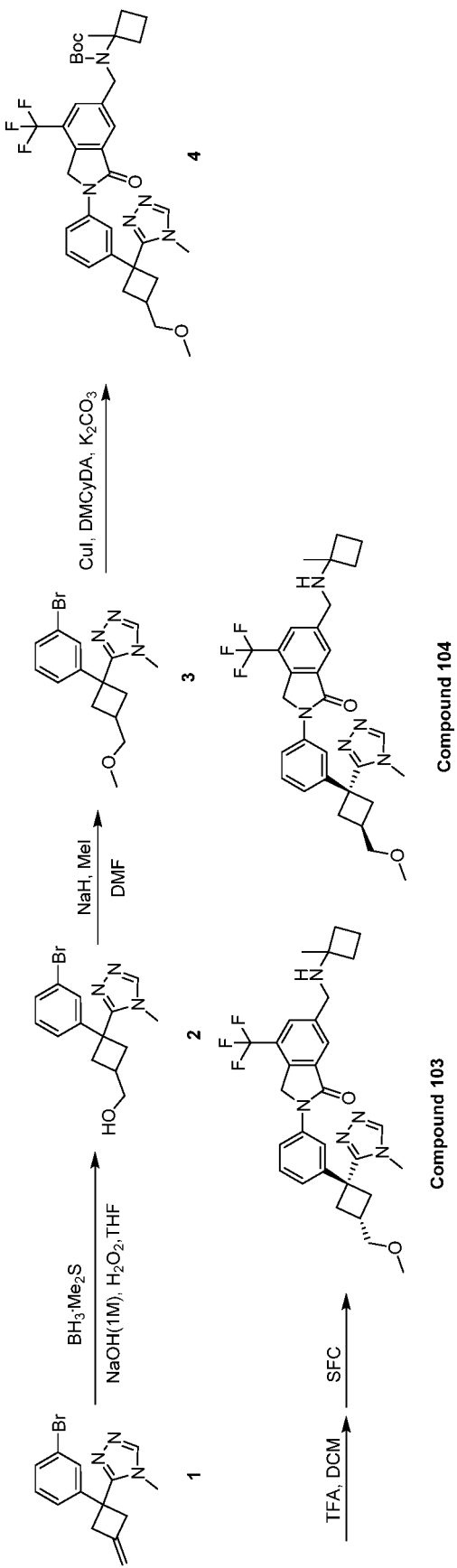

Compound 103 (2-(3-((1s,3s)-3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one) and Compound 104 (2-(3-((1r,3r)-3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one) can be synthesized according to Scheme 45 (FIG. 45).

Intermediate 2: ((3-(3-bromophenyl)-3-(4-methyl-4H-1,2,4-triazol-3-yl)cyclobutyl)methanol To a solution of 3-(1-(3-bromophenyl)-3-methylenecyclobutyl)-4-methyl-4H-1,2,4-triazole (1.0 g, 3.29 mmol) in tetrahydrofuran (24 mL) was added borane dimethyl sulfide complex (10.0 M, 1.64 mL, 16.40 mmol) dropwise at −10° C. The reaction mixture was stirred at 20° C. for 2 h and cooled to −20° C., then aqueous sodium hydroxide (1 M, 19.7 mL, 19.7 mmol), followed by aqueous hydrogen peroxide (30%, 8.0 mL, 78.32 mmol) were added. The resulting mixture was stirred at 20° C. for another 2 h and quenched with saturated aqueous sodium sulfite (10 mL). The solution was extracted with ethyl acetate (3×25 mL). The combined organic layers were washed with brine (25 mL), dried over sodium sulfate and concentrated to dryness. The residue was purified by silica gel chromatography (mobile phase: methanol/dichloromethane, gradient 0% to 8%) to afford (3-(3-bromophenyl)-3-(4-methyl-4H-1,2,4-triazol-3-yl)cyclobutyl)methanol (600 mg, 57% yield) as a white solid. LCMS [M+H]$^+$=322.0.

Intermediate 3: (3-(1-(3-bromophenyl)-3-(methoxymethyl)cyclobutyl)-4-methyl-4H-1,2,4-triazole To a solution of (3-(3-bromophenyl)-3-(4-methyl-4H-1,2,4-triazol-3-yl)cyclobutyl)-methanol (200 mg, 0.62 mmol) in N,N-dimethylformamide (5 mL) was added sodium hydride (60%, 37.2 mg, 0.93 mmol) at 0° C. The mixture was stirred for 0.5 h at 0° C., and then iodomethane (176 mg, 1.24 mmol) was added. The resulting mixture was stirred at 25° C. for 1 h and quenched with saturated aqueous ammonium chloride (1 mL). The mixture was concentrated under vacuum and the residue was purified by silica gel chromatography (mobile phase: methanol/dichloromethane, gradient 0% to 2%) to afford 3-(1-(3-bromophenyl)-3-(methoxymethyl)cyclobutyl)-4-methyl-4H-1,2,4-triazole (150 mg, 72% yield) as a colorless oil. LCMS [M+H]$^+$=336.1.

Intermediate 4: (tert-butyl ((2-(3-(3-(methoxymethyl)-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate In a glove box, a mixture of tert-butyl (1-methylcyclobutyl)((3-oxo-7-(trifluoromethyl)isoindolin-5-yl)methyl)carbamate (143 mg, 0.36 mmol), (1 S,2S)—N$^1$,N$^2$-dimethylcyclohexane-1,2-diamine (18.6 mg, 0.13 mmol), potassium carbonate (113 mg, 0.82 mmol), 3-(1-(3-bromophenyl)-3-(methoxymethyl)cyclobutyl)-4-methyl-4H-1,2,4-triazole (110 mg, 0.33 mmol) and copper(I) iodide (12.5 mg, 0.07 mmol) in tert-amyl alcohol (4 mL) was heated at 100° C. in sealed vial for 4 h. After cooled, the mixture was poured into water (50 mL) and extracted with dichloromethane (3×50 mL). The combined organic layers were concentrated. The residue was purified by silica gel chromatography (mobile phase: methanol/dichloromethane, gradient 0% to 5%) to afford tert-butyl ((2-(3-(3-(methoxymethyl)-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (160 mg, 75% yield) as a light green solid. LCMS [M+H]$^+$=654.3.

Compounds 103 and 104

A mixture of tert-butyl ((2-(3-(3-(methoxymethyl)-1-(4-methyl-4H-1,2,4-triazol-3-yl)cyclobutyl)phenyl)-3-oxo-7-(trifluoromethyl)isoindolin-5-yl)methyl)(1-methylcyclobutyl)carbamate (160 mg, 0.24 mmol) and trifluoroacetic acid (1.0 mL, 13.0 mmol) in dichloromethane (2 mL) was stirred at 25° C. for 1 h and concentrated to dryness. The residue was purified by RP-HPLC (water(NH$_3$H$_2$O+NH$_4$HCO$_3$)-ACN 50%-80%) to afford 2-(3-(3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one (70 mg, 52% yield). The above mixture was further purified by chiral SFC (Column=Phenomenex-Cellulose-2; Column dimensions=250 mm×30 mm×10 μm; Detection wavelength=220 nM; Flow rate=80 mL/min; Mobile phase: A: CO$_2$ B: methanol (0.05% DEA); Isocratic: 40% B) with 0.1% ammonium hydroxide) to afford tentatively assigned:

2-(3-((1s,3s)-3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1, retention time=3.670 min) (11.1 mg, 15% yield). $^1$H NMR (400 MHz, methanol-d$_4$) δ 8.32 (s, 1H), 8.10-8.06 (m, 2H), 8.01 (s, 1H), 7.70 (dd, J=8.0, 1.2 Hz, 1H), 7.50 (t, J=8.0 Hz, 1H), 7.15 (d, J=7.6 Hz, 1H), 5.16 (s, 2H), 3.87 (s, 2H), 3.43 (d, J=4.0 Hz, 2H), 3.34 (s, 3H), 3.33 (s, 3H), 2.93-2.80 (m, 5H), 2.16-2.05 (m, 2H), 1.93-1.75 (m, 4H), 1.39 (s, 3H). LCMS [M+H]$^+$=554.2.

2-(3-((1r,3r)-3-(methoxymethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2, retention time=4.659 min) (15.7 mg, 21% yield). $^1$H NMR (400 MHz, methanol-d$_4$) δ 8.40 (s, 1H), 8.09 (s, 1H), 8.01 (s, 1H), 7.92 (s, 1H), 7.68 (d, J=8.0 Hz, 1H), 7.46 (t, J=8.0 Hz, 1H), 7.08 (d, J=7.2 Hz, 1H), 5.17 (s, 2H), 3.88 (s, 2H), 3.44 (d, J=4.0 Hz, 2H), 3.36 (s, 6H), 3.11-3.01 (m, 2H), 2.68-2.61 (m, 3H), 2.17-2.06 (m, 2H), 1.93-1.75 (m, 4H), 1.39 (s, 3H). LCMS [M+H]$^+$=554.2.

Example 48: Compounds 105, 106, 107

Figure 46:
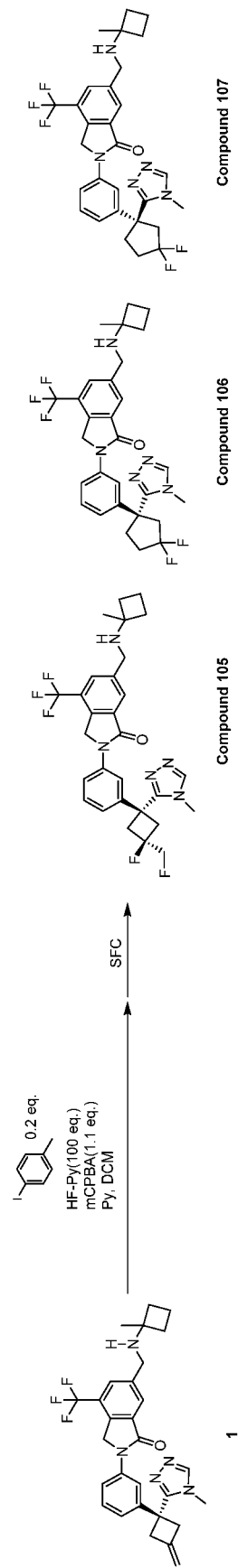

Compound 105 (2-(3-((1r,3r)-3-fluoro-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one), Compound 106 ((S)-2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one), and Compound 107 ((R)-2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one), can be synthesized according to Scheme 46 (FIG. 46).

To a 75 mL low-density-polyethylene tube equipped with a stir bar was charged with 1-iodo-4-methylbenzene (16.7 mg, 0.08 mmol), 3-chlorobenzenecarboperoxoic acid (85.6 mg, 0.42 mmol) and dichloromethane (4 mL). The resulting mixture was vigorously stirred while pyridine hydrofluoride (1.2 mL, 38.4 mmol) was added via plastic syringe. After addition, the tube was sealed with a low density polyethylene snap top, and a solution of the 2-(3-(1-(4-methyl-4H-1,2,4-triazol-3-yl)-3-methylenecyclobutyl)phenyl)-6-(((1-methylcyclobutyl)amino)methyl)-4-(trifluoromethyl)isoindolin-1-one (200.0 mg, 0.38 mmol) in dichloromethane (2 mL) was added dropwise through a low density polyethylene snap top by syringe pump over 30 min. The mixture was stirred for 6 h and diluted with water (25 mL). The solution was extracted with ethyl acetate (3×25 mL). The combined organic layers were washed with saturated aqueous sodium bicarbonate (15 mL), dried over sodium sulfate and concentrated to dryness. The residue was purified by RP-HPLC (water(NH₃H₂O+NH₄HCO)/ACN 55%-85%) to afford:

2-(3-((1r,3r)-3-fluoro-3-(fluoromethyl)-1-(4-methyl-4H-1,2,4-triazol-3-yl)cyclobutyl)phenyl)-6-(((1-methylcyclobutyl)amino)methyl)-4-(trifluoromethyl)isoindolin-1-one (Compound 105, 13.0 mg, 5.6% yield). $^1$H NMR (400 MHz, methanol-d₄) δ 8.41 (s, 1H), 8.13 (s, 1H), 8.06 (s, 1H), 7.98 (t, J=1.6 Hz, 1H), 7.70 (dd, J=8.0, 1.6 Hz, 1H), 7.52 (t, J=8.0 Hz, 1H), 7.20 (d, J=7.6 Hz, 1H), 5.18 (s, 2H), 4.53-4.33 (m, 2H), 4.03 (s, 2H), 3.54-3.45 (m, 2H), 3.38 (s, 3H), 3.20-3.08 (m, 2H), 2.23-2.20 (m, 2H), 2.01-1.84 (m, 4H), 1.48 (s, 3H). LCMS [M+H]⁺=560.2 and 2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one (30.0 mg, 14% yield).

The latter racemate was further purified by chiral SFC (Column=Daicel Chiralpak AD; Column dimensions=250 mm×30 mm×10 µm; Detection wavelength=220 nM; Flow rate=80 mL/min; Mobile phase: A: CO₂ B: ethanol (0.05% DEA); Isocratic: 50% B) with 0.1% ammonium hydroxide) to afford tentatively assigned:

(S)-2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one (Peak 1, retention time=1.976 min) (5.3 mg, 21% yield). $^1$H NMR (400 MHz, methanol-d₄) δ 8.38 (s, 1H), 8.08 (s, 1H), 8.01 (s, 1H), 7.96 (s, 1H), 7.72 (d, J=8.0 Hz, 1H), 7.49 (t, J=8.0 Hz, 1H), 7.10 (d, J=7.6 Hz, 1H), 5.15 (s, 2H), 3.86 (s, 2H), 3.31 (s, 3H), 3.19-3.10 (m, 2H), 3.03-2.94 (m, 1H), 2.58-2.49 (m, 1H), 2.45-2.27 (m, 2H), 2.16-2.05 (m, 2H), 1.93-1.78 (m, 4H), 1.38 (s, 3H). LCMS [M+H]⁺=560.2.

(R)-2-(3-(3,3-difluoro-1-(4-methyl-4H-1,2,4-triazol-3-yl)cyclopentyl)phenyl)-6-(((1-methylcyclobutyl)amino)methyl)-4-(trifluoromethyl)isoindolin-1-one (Peak 2, retention time=3.141 min) (4.7 mg, 18% yield). $^1$H NMR (400 MHz, methanol-d₄) δ 8.38 (s, 1H), 8.08 (s, 1H), 8.01 (s, 1H), 7.95 (d, J=2.0 Hz, 1H), 7.74-7.69 (m, 1H), 7.49 (t, J=8.0 Hz, 1H), 7.10 (d, J=8.0 Hz, 1H), 5.15 (s, 2H), 3.86 (s, 2H), 3.32 (s, 3H), 3.18-3.10 (m, 2H), 3.03-2.93 (m, 1H), 2.60-2.49 (m, 1H), 2.41-2.31 (m, 2H), 2.15-2.05 (m, 2H), 1.91-1.76 (m, 4H), 1.38 (s, 3H). LCMS [M+H]⁺=560.2.

Example 49: Compounds 108 and 109

Figure 47:
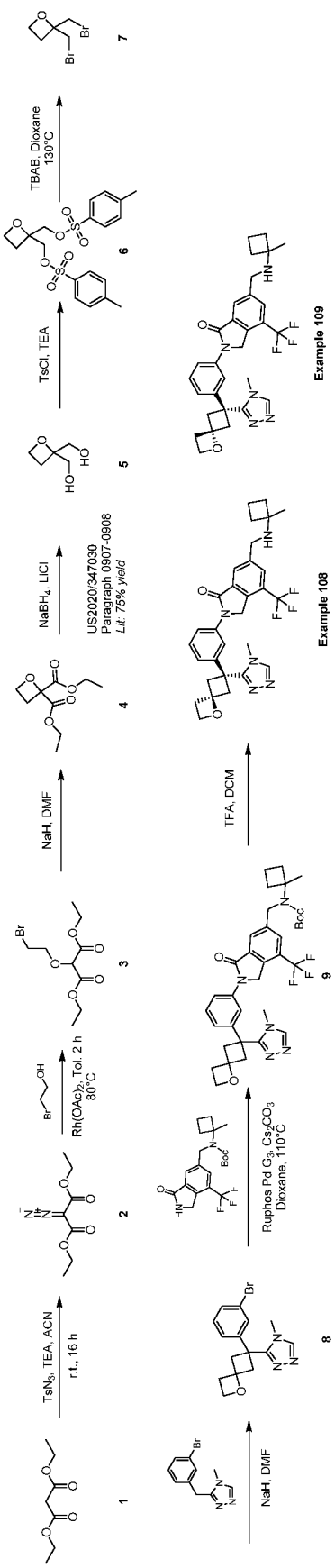

Compound 108 (2-(3-((4r,6r)-6-(4-methyl-4H-1,2,4-triazol-3-yl)-1-oxaspiro[3.3]heptan-6-yl)phenyl)-6-(((1-methylcyclobutyl)amino)methyl)-4-(trifluoromethyl)isoindolin-1-one) and Compound 109 (2-(3-((4s,6s)-6-(4-methyl-4H-1,2,4-triazol-3-yl)-1-oxaspiro[3.3]heptan-6-yl)phenyl)-6-(((1-methylcyclobutyl)amino)methyl)-4-(trifluoromethyl)isoindolin-1-one) can be synthesized according to Scheme 47 (FIG. 47).

Intermediate 2: (diethyl 2-diazomalonate

To a solution of diethyl malonate (15.0 g, 93.6 mmol) in acetonitrile (200 mL) was added p-toluene sulfonylazide (75% in ethyl acetate, 32.0 g, 121.8 mmol) and triethylamine (17.0 mL, 121.8 mmol) at 0° C. The reaction mixture was stirred at 25° C. for 16 h and quenched with saturated aqueous sodium bicarbonate (60 mL). The solution was extracted with ethyl acetate (3×100 mL). The combined organic layers were washed with brine (80 mL), dried over sodium sulfate and concentrated. The residue was purified by silica gel chromatography (mobile phase: ethyl acetate/petroleum ether, gradient 0% to 5%) to give diethyl 2-diazomalonate (16.0 g, 92% yield) as a yellow oil.

Intermediate 3: (diethyl 2-(2-bromoethoxy)malonate

To a solution of 2-bromoethanol (6.1 mL, 85.94 mmol) and diethyl 2-diazomalonate (16.0 g, 85.9 mmol) in toluene (250 mL) was added Rhodium(II) acetate dimer (189.9 mg, 0.43 mmol). The reaction mixture was stirred for 3 h at 80° C. and quenched with water (200 mL). The solution was extracted with ethyl acetate (3×200 mL). The combined organic layers were washed with brine (50 mL), dried over sodium sulfate and concentrated under reduced pressure. The residue was purified by silica gel chromatography (mobile phase: ethyl acetate/petroleum ether, gradient 0% to 10%) to afford diethyl 2-(2-bromoethoxy)malonate (20.0 g, 82% yield) as a colorless oil. $^1$H NMR (400 MHz, CDCl₃) δ 4.55 (s, 1H), 4.29-4.23 (m, 4H), 3.96-3.91 (m, 2H), 3.53-3.48 (m, 2H), 1.30-1.27 (m, 6H).

Intermediate 4: (diethyl oxetane-2,2-dicarboxylate

Under nitrogen, to a slurry of sodium hydride (60%, 4.1 g, 101.7 mmol) in N,N-dimethylformamide (2 L) was added a solution of diethyl 2-(2-bromoethoxy)propanedioate (24.0 g, 84.8 mmol) in N,N-dimethylformamide (10 mL) at 0° C. The reaction mixture was stirred for 5 h at 0° C. and then quenched with saturate aqueous ammonium chloride (30 mL). The mixture was concentrated to remove most of the solvent and the residue was diluted with water (300 mL). The resulting solution was extracted with ethyl acetate (3×150 mL). The combined organic layers were washed with brine (100 mL), dried over sodium sulfate and concentrated to dryness. The residue was purified by silica gel chromatography (mobile phase: ethyl acetate/petroleum ether, gradient 0% to 25%) to afford diethyl oxetane-2,2-dicarboxylate (11.7 g, 68% yield) as a colorless oil. $^1$H NMR (400 MHz, CDCl₃) δ 4.63 (t, J=7.8 Hz, 2H), 4.32-4.23 (m, 4H), 3.06 (t, J=7.8 Hz, 2H), 1.28 (t, J=7.2 Hz, 6H).

Intermediate 5: (oxetane-2,2-diyldimethanol

To a solution of diethyl oxetane-2,2-dicarboxylate (5.00 g, 21.7 mmol) in tetrahydrofuran (200 mL) was added lithium borohydride (1.23 g, 32.6 mmol) at 0° C. The reaction mixture was stirred at 25° C. for 16 h and quenched with sodium sulfate decahydrate. The resulting mixture was stirred for 10 min and filtered. The filtrate was concentrated to give crude oxetane-2,2-diyldimethanol (1.55 g, 60% yield) as a yellow oil.

Intermediate 6: (oxetane-2,2-diylbis(methylene) bis(4-methylbenzenesulfonate)

To a mixture of oxetane-2,2-diyldimethanol (1.50 g, 12.7 mmol) in dichloro-methane (50 mL) was added p-toluenesulfonyl chloride (7.26 g, 38.1 mmol) and triethylamine (7.08 mL, 50.8 mmol) at 0° C. The mixture was stirred at 25° C. for 3 h and concentrated. The residue was purified by silica gel chromatography (mobile phase: ethyl acetate/petroleum ether, gradient 0% to 30%) to afford oxetane-2,2-diylbis(methylene) bis(4-methylbenzenesulfonate) (3.00 g, 55% yield) as a white solid. LCMS [M+Na]⁺=449.1.

Intermediate 7: (2,2-bis(bromomethyl)oxetane

To a solution of oxetane-2,2-diylbis(methylene) bis(4-methylbenzenesulfonate) (3.0 g, 7.03 mmol) in 1,4-dioxane (40 mL) was added tetrabutylammonium bromide (6.6 mL, 21.1 mmol) at 25° C. The mixture was heated at 130° C. for 12 h and concentrated under vacuum. The residue was purified by silica gel chromatography (mobile phase: ethyl acetate/petroleum ether, gradient 0% to 5%) to afford 2,2-bis(bromomethyl)oxetane (660 mg, 39% yield) as yellow oil. $^1$H NMR (400 MHz, CDCl$_3$) δ 4.50 (t, J=8.0 Hz, 2H), 3.81-3.73 (m, 4H), 2.68 (t, J=8.0 Hz, 2H).

Intermediate 8: (3-(6-(3-bromophenyl)-1-oxaspiro [3.3]heptan-6-yl)-4-methyl-4H-1,2,4-triazole To a mixture of 3-(3-bromobenzyl)-4-methyl-4H-1,2,4-triazole (450.0 mg, 1.78 mmol) in N,N-dimethylformamide (8 mL) was added sodium hydride (60%, 285.6 mg, 7.14 mmol) at 0° C. The reaction mixture was stirred at 0° C. for 30 min, then 2,2-bis(bromomethyl)oxetane (653.1 mg, 2.68 mmol) was added. The mixture was stirred at 60° C. for 16 h and quenched by water (5 mL). The resulting solution was extracted with dichloromethane (3×10 mL). The combined organic layers were washed with brine (10 mL), dried over sodium sulfate and concentrated to dryness. The residue was purified by preparative TLC (solvent gradient: 10% methanol in dichloromethane) to give 3-(6-(3-bromophenyl)-1-oxaspiro[3.3]heptan-6-yl)-4-methyl-4H-1,2,4-triazole (465.0 mg, 78% yield) as a yellow oil. LCMS [M+H]$^+$=336.1.

Intermediate 9: (tert-butyl ((2-(3-(6-(4-methyl-4H-1, 2,4-triazol-3-yl)-1-oxaspiro[3.3]heptan-6-yl)phenyl)-3-oxo-7-(trifluoromethyl)isoindolin-5-yl)methyl)(1-methylcyclobutyl)carbamate In a glovebox, a mixture of 3-(6-(3-bromophenyl)-1-oxaspiro[3.3]heptan-6-yl)-4-methyl-4H-1,2,4-triazole (100.0 mg, 0.30 mmol), tert-butyl (1-methylcyclobutyl)((3-oxo-7-(trifluoromethyl)isoindolin-5-yl)methyl)carbamate (143.1 mg, 0.36 mmol), dicyclohexyl-phosphino-2',6'-diisopropoxy-1,1'-biphenyl)[2-(2'-amino-1,1'-biphenyl)]palladium(II) methanesulfonate (50.1 mg, 0.06 mmol) and cesium carbonate (292.5 mg, 0.90 mmol) in 1,4-dioxane (5 mL) was heated at 110° C. in sealed vial for 3 h and concentrated to dryness. The residue was purified by preparative TLC (solvent gradient: 10% methanol in dichloromethane) to afford tert-butyl ((2-(3-(6-(4-methyl-4H-1,2,4-triazol-3-yl)-1-oxaspiro[3.3]heptan-6-yl)phenyl)-3-oxo-7-(trifluoromethyl)isoindolin-5-yl)methyl)(1-methylcyclobutyl)carbamate (175.0 mg, 90% yield) as a white solid. LCMS [M+H]$^+$=652.3.

Compounds 108 and 109

To a solution of tert-butyl ((2-(3-(6-(4-methyl-4H-1,2,4-triazol-3-yl)-1-oxaspiro[3.3]heptan-6-yl)phenyl)-3-oxo-7-(trifluoromethyl)isoindolin-5-yl)methyl)(1-methylcyclobutyl)carbamate (175.0 mg, 0.27 mmol) in dichloromethane (5 mL) was added trifluoroacetic acid (0.5 mL, 6.49 mmol). The mixture was stirred for 1 h at 0° C. and concentrated to dryness. The residue was purified by RP-HPLC (0.2% NH$_3$·H$_2$O in water/ACN 65% to 95%) to afford 2-(3-(6-(4-methyl-4H-1,2,4-triazol-3-yl)-1-oxaspiro[3.3] heptan-6-yl)phenyl)-6-(((1-methylcyclobutyl)amino) methyl)-4-(trifluoromethyl)isoindolin-1-one (88.0 mg, 59% yield).

The above mixture was further purified by chiral SFC (Column=Daicel Chiralpak AD; Column dimensions=250 mm×30 mm×10 μm; Detection wavelength=220 nM; Flow rate=80 mL/min; Mobile phase: A: CO$_2$ B: ethanol (0.05% DEA); Isocratic: 40% B) with 0.1% ammonium hydroxide) to afford:

2-(3-((4r,6r)-6-(4-methyl-4H-1,2,4-triazol-3-yl)-1-oxaspiro[3.3]heptan-6-yl)phenyl)-6-(((1-methylcyclobutyl) amino)methyl)-4-(trifluoromethyl)isoindolin-1-one (Peak 1, retention time=1.740 min) (38.4 mg, 42% yield). $^1$H NMR (400 MHz, methanol-d$_4$) δ 8.39 (s, 1H), 8.08 (s, 1H), 8.00 (s, 1H), 7.88 (s, 1H), 7.70-7.66 (m, 1H), 7.46 (t, J=8.0 Hz, 1H), 7.07 (d, J=8.0 Hz, 1H), 5.14 (s, 2H), 4.54 (t, J=7.6 Hz, 2H), 3.86 (s, 2H), 3.51-3.46 (m, 2H), 3.37 (s, 3H), 3.10-2.90 (m, 2H), 2.70-2.65 (m, 2H), 2.14-2.06 (m, 2H), 1.91-1.77 (m, 4H), 1.38 (s, 3H). LCMS [M+H]$^+$=552.3.

2-(3-((4s,6s)-6-(4-methyl-4H-1,2,4-triazol-3-yl)-1-oxaspiro[3.3]heptan-6-yl)phenyl)-6-(((1-methylcyclobutyl) amino)methyl)-4-(trifluoromethyl)isoindolin-1-one (Peak 2, retention time=2.317 min) (11.4 mg, 13% yield). $^1$H NMR (400 MHz, methanol-d$_4$) δ 8.31 (s, 1H), 8.12 (s, 1H), 8.10 (s, 1H), 8.02 (s, 1H), 7.67 (d, J=8.0 Hz, 1H), 7.47 (t, J=8.0 Hz, 1H), 7.18 (d, J=6.8 Hz, 1H), 5.16 (s, 2H), 4.54 (t, J=7.6 Hz, 2H), 3.87 (s, 2H), 3.37 (s, 3H), 3.35-3.30 (m, 2H), 3.25-3.19 (m, 2H), 2.78 (t, J=7.6 Hz, 2H), 2.15-2.07 (m, 2H), 1.92-1.78 (m, 4H), 1.39 (s, 3H). LCMS [M+H]$^+$=552.3.

Example 50: Compound 110

Figure 48:
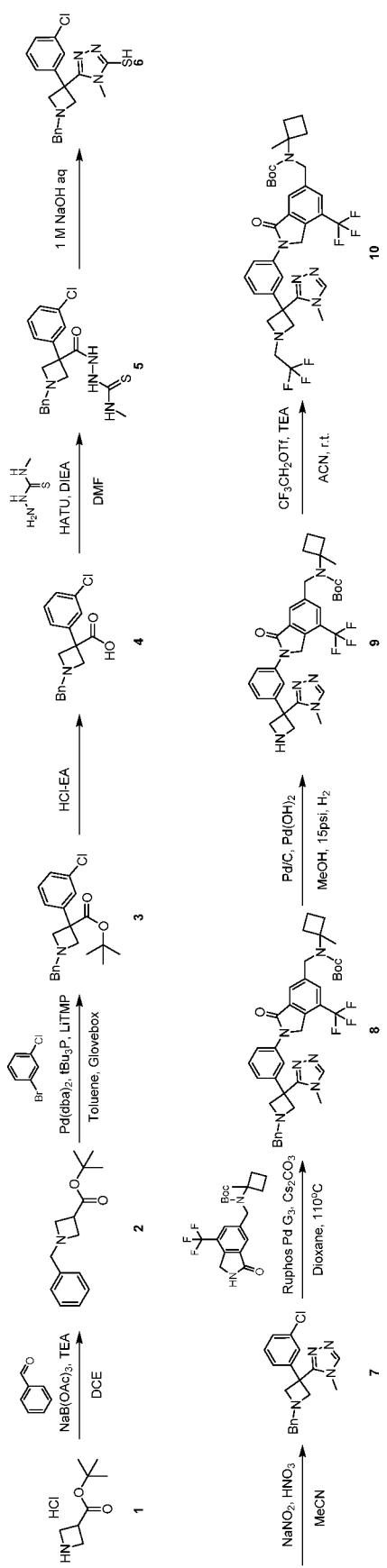

Compound 110 (2-(3-(3-(4-methyl-4H-1,2,4-triazol-3-yl)-1-(2,2,2-trifluoroethyl)azetidin-3-yl)phenyl)-6-(((1-methylcyclobutyl)amino)methyl)-4-(trifluoromethyl)isoindolin-1-one) can be synthesized according to Scheme 48 (FIG. 48).

Intermediate 2: (tert-butyl 1-benzylazetidine-3-carboxylate

To a solution of tert-butyl azetidine-3-carboxylate hydrochloride (4.00 g, 20.7 mmol) in 1,2-dichloroethane (50 mL) was added triethylamine (2.89 mL, 20.7 mmol). The mixture was stirred for 5 min and then benzaldehyde (2.52 mL, 24.78 mmol) and acetic acid (0.59 mL, 10.3 mmol) was added. The mixture was stirred at 25° C. for 2 h, and sodium triacetoxyborohydride (6.57 g, 31.0 mmol) was added in portions. The resulting mixture was stirred at 25° C. for another 3 h and concentrated under vacuum. The residue was purified by silica gel chromatography (mobile phase: methanol/dichloromethane, gradient 0% to 10%) to afford tert-butyl 1-benzylazetidine-3-carboxylate (4.75 g, 93% yield) as a colorless oil. $^1$H NMR (400 MHz, CDCl$_3$) δ 7.36-7.25 (m, 5H), 3.63 (s, 2H), 3.59-3.49 (m, 2H), 3.34-3.22 (m, 3H), 1.47 (s, 9H). LCMS [M+H]$^+$=248.1.

Intermediate 3: (tert-butyl 1-benzyl-3-(3-chlorophenyl)azetidine-3-carboxylate

A mixture of (2,2,6,6-tetramethyl-1-piperidyl)lithium (1.54 g, 10.47 mmol) was added to a solution of tert-butyl 1-benzylazetidine-3-carboxylate (1.94 g, 7.85 mmol), 1-bromo-3-chlorobenzene (0.61 mL, 5.24 mmol), bis(dibenzylideneacetone)palladium (301.1 mg, 0.52 mmol) and tri-tert-butylphosphine (1.06 g, 0.52 mmol) in toluene (16 mL) was heated at 50° C. under nitrogen atmosphere for 16 h and concentrated under vacuum. The residue was purified by silica gel chromatography (mobile phase: ethyl acetate/petroleum ether, gradient 0% to 30%) to afford tert-butyl 1-benzyl-3-(3-chlorophenyl)azetidine-3-carboxylate (1.00 g, 53% yield) as a yellow oil. LCMS [M+H]$^+$=358.2.

Intermediate 4: (1-benzyl-3-(3-chlorophenyl)azetidine-3-carboxylic acid

A mixture of tert-butyl 1-benzyl-3-(3-chlorophenyl)azetidine-3-carboxylate (3.5 g, 9.8 mmol) and hydrochloric acid (aq., 4 M, 40.0 mL, 160.0 mmol) in ethyl acetate (40 mL) was stirred at 25° C. for 5 h and concentrated under vacuum to afford crude tert-butyl 1-benzyl-3-(3-chlorophenyl)azetidine-3-carboxylate (2.9 g, 98% yield) as a yellow solid. LCMS [M+H]$^+$=302.1.

Intermediate 5: (2-(1-benzyl-3-(3-chlorophenyl)azetidine-3-carbonyl)-N-methylhydrazinecarbothioamide To a solution of N-methyl hydrazinecarbothioamide (1.1 g, 10.6 mmol) and 1-benzyl-3-(3-chlorophenyl)azetidine-3-carboxylic acid (2.9 g, 9.6 mmol) in N,N-dimethylformamide (30 mL) was added 2-(7-Azabenzotriazol-1-yl)-N,N,N',N'-tetramethyluronium hexafluorophosphate (5.5 g, 14.4 mmol) and N,N-diisopropylethylamine (5.02 mL, 28.8 mmol). The mixture was stirred at 25° C. for 16 h and concentrated under vacuum to afford crude 2-(1-benzyl-3-(3-chlorophenyl)azetidine-3-carbonyl)-N-methylhydrazinecarbothioamide (3.7 g, 99% yield) as a yellow solid. LCMS [M+H]$^+$=389.1.

Intermediate 6: (5-(1-benzyl-3-(3-chlorophenyl)azetidin-3-yl)-4-methyl-4H-1,2,4-triazole-3-thiol A mixture of 2-(1-benzyl-3-(3-chlorophenyl)azetidine-3-carbonyl)-N-methylhydrazinecarbothioamide (3.7 g, 9.51 mmol) in aqueous sodium hydroxide (1.0 M, 25.6 mL, 25.6 mmol) and water (30 mL) was heated at 45° C. for 16 h. After cooled, the mixture was adjusted to pH=5 by aqueous hydrochloric acid (1 M). The precipitate was collected by filtration to afford crude 5-(1-benzyl-3-(3-chlorophenyl)azetidin-3-yl)-4-methyl-4H-1,2,4-triazole-3-thiol (3.5 g, 99% yield) as a gray solid. LCMS [M+H]$^+$=371.1.

Intermediate 7: (3-(1-benzyl-3-(3-chlorophenyl)azetidin-3-yl)-4-methyl-4H-1,2,4-triazole To a solution of 5-(1-benzyl-3-(3-chlorophenyl)azetidin-3-yl)-4-methyl-4H-1,2,4-triazole-3-thiol (3.5 g, 9.44 mmol) in water (20 mL) and acetonitrile (20 mL) was added sodium nitrite (6.5 g, 94.37 mmol) and nitric acid (4.0 g, 63.5 mmol). The reaction mixture was stirred for 1 h at 20° C. and then quenched with saturated aqueous sodium bicarbonate (20 mL). The solution was extracted with ethyl acetate (3×50 mL). The combined organic layers were washed with brine (30 mL), dried over sodium sulfate and concentrated to dryness. The residue was purified by silica gel chromatography (mobile phase: ethyl acetate/petroleum ether, gradient 0% to 15%) to afford 3-(1-benzyl-3-(3-chlorophenyl)azetidin-3-yl)-4-methyl-4H-1,2,4-triazole (1.6 g, 50% yield) as a white solid. LCMS [M+H]$^+$=339.1.

Intermediate 8: (tert-butyl ((2-(3-(1-benzyl-3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate In a glovebox, a mixture of dicyclohexylphosphino-2',6'-diisopropoxy-1,1'-biphenyl)[2-(2'-amino-1,1'biphenyl)]palladium(II) methane sulfonate (351.8 mg, 0.42 mmol), 3-(1-benzyl-3-(3-chlorophenyl)azetidin-3-yl)-4-methyl-4H-1,2,4-triazole (950 mg, 2.8 mmol), cesium carbonate (2.74 g, 8.41 mmol) and tert-butyl (1-methylcyclobutyl)((3-oxo-7-(trifluoromethyl)isoindolin-5-yl)methyl)carbamate (1.23 g, 3.08 mmol) in 1,4-dioxane (10 mL) was heated at 110° C. in sealed vial for 16 h and concentrated to dryness. The residue was purified by silica gel chromatography (mobile phase: methanol/dichloromethane, gradient 0% to 15%) to afford tert-butyl ((2-(3-(1-benzyl-3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate (1.0 g, 51% yield) as a yellow solid. LCMS [M+H]$^+$=701.3.

Intermediate 9: (tert-butyl ((2-(3-(3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate A mixture of tert-butyl ((2-(3-(1-benzyl-3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate (1.0 g, 1.43 mmol), palladium (10% on carbon, 302.5 mg, 0.29 mmol) and palladium hydroxide (200 mg, 0.29 mmol) in ethanol (20 mL) was stirred at 25° C. under hydrogen (15 psi) for 16 h and filtered. The filtrate was concentrated to give crude tert-butyl ((2-(3-(3-(4-methyl-4H-1,2,4-triazol-3-yl)azetidin-3-yl)phenyl)-3-oxo-7-(trifluoromethyl) isoindolin-5-yl)methyl)(1-methylcyclobutyl)carbamate (770 mg, 88% yield) as a yellow solid. LCMS [M+H]$^+$=611.3.

Intermediate 10: (tert-butyl ((2-(3-(3-(4-methyl-4H-1,2,4-triazol-3-yl)-1-(2,2,2-trifluoroethyl)azetidin-3-yl)phenyl)-3-oxo-7-(trifluoromethyl)isoindolin-5-yl)methyl)(1-methylcyclobutyl)carbamate To a solution of tert-butyl ((2-(3-(3-(4-methyl-4H-1,2,4-triazol-3-yl)azetidin-3-yl)phenyl)-3-oxo-7-(trifluoromethyl) isoindolin-5-yl)methyl)(1-methylcyclobutyl)carbamate (80.0 mg, 0.13 mmol) in N,N-dimethylformamide (2 mL) was added potassium carbonate (72.4 mg, 0.52 mmol) and 2,2,2-trifluoroethyl trifluoromethanesulfonate (0.04 mL, 0.26 mmol). The mixture was stirred at 25° C. for 2 h and concentrated under vacuum. The mixture was purified by preparative TLC (solvent gradient: 10% methanol in dichloromethane) to afford tert-butyl ((2-(3-(3-(4-methyl-4H-1,2,4-triazol-3-yl)-1-(2,2,2-trifluoroethyl)azetidin-3-yl)phenyl)-3-oxo-7-(trifluoromethyl)isoindolin-5-yl)methyl)(1-methylcyclobutyl)carbamate (50.0 mg, 55% yield) as a yellow oil. LCMS [M+H]$^+$=693.3.

Compound 110

A mixture of tert-butyl ((2-(3-(3-(4-methyl-4H-1,2,4-triazol-3-yl)-1-(2,2,2-trifluoroethyl)azetidin-3-yl)phenyl)-3-oxo-7-(trifluoromethyl)isoindolin-5-yl)methyl)(1-methylcyclobutyl)carbamate (50.0 mg, 0.07 mmol) and trifluoroacetic acid (0.16 mL, 0.63 mmol) in dichloromethane (2 mL) was stirred at 25° C. for 16 h and concentrated under vacuum. The residue was purified by RP-HPLC (water(NH$_3$H$_2$O+NH$_4$HCO$_3$)/ACN 43% to 73%) to afford 2-(3-(3-(4-methyl-4H-1,2,4-triazol-3-yl)-1-(2,2,2-trifluoroethyl)azetidin-3-yl)phenyl)-6-(((1-methylcyclobutyl)amino)methyl)-4-(trifluoromethyl)isoindolin-1-one (12.9 mg, 30% yield). $^1$H NMR (400 MHz, methanol-d$_4$) δ 8.43 (s, 1H), 8.09 (s, 1H), 8.02 (d, J=5.2 Hz, 2H), 7.78 (d, J=8.4 Hz, 1H), 7.51 (t, J=8.0 Hz, 1H), 7.23 (d, J=8.0 Hz, 1H), 5.16 (s, 2H), 4.26 (d, J=7.6 Hz, 2H), 4.12 (d, J=7.6 Hz, 2H), 3.88 (s, 2H), 3.39 (s, 3H), 3.28-3.22 (m, 2H), 2.15-2.07 (m, 2H), 1.92-1.77 (m, 4H), 1.39 (s, 3H). LCMS [M+H]⁺=593.3.

Example 51: Compound 111

Figure 49:
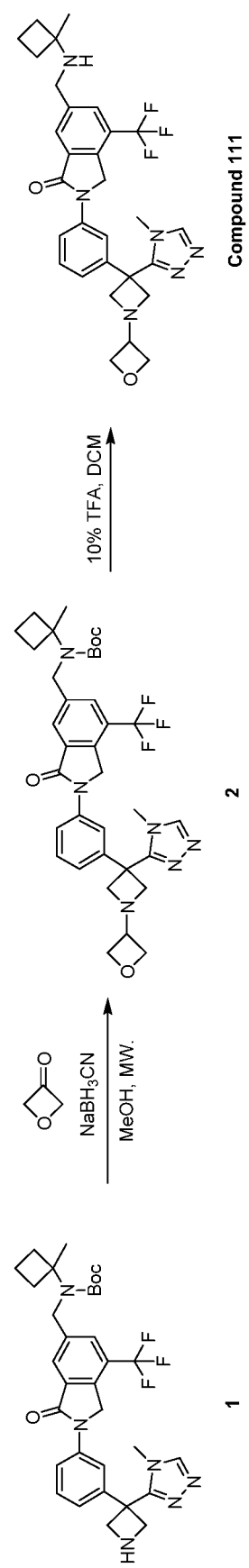

Compound 111 (2-(3-(3-(4-methyl-4H-1,2,4-triazol-3-yl)-1-(oxetan-3-yl)azetidin-3-yl)phenyl)-6-(((1-methylcyclobutyl)amino)methyl)-4-(trifluoromethyl)isoindolin-1-one) can be synthesized according to Scheme 49 (FIG. 49).

a. Intermediate 2: (tert-butyl ((2-(3-(3-(4-methyl-4H-1,2,4-triazol-3-yl)-1-(oxetan-3-yl)azetidin-3-yl)phenyl)-3-oxo-7-(trifluoromethyl)isoindolin-5-yl)methyl)(1-methylcyclobutyl)carbamate To a solution of tert-butyl ((2-(3-(3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate (80.0 mg, 0.13 mmol) and oxetan-3-one (28.3 mg, 0.39 mmol) in methanol (2 mL) was added sodium cyanoborohydride (16.5 mg, 0.26 mmol). The mixture was stirred at 25° C. for 2 h and concentrated under vacuum. The residue was purified by preparative TLC (solvent gradient: 10% methanol in dichloromethane) to afford tert-butyl ((2-(3-(3-(4-methyl-4H-1,2,4-triazol-3-yl)-1-(oxetan-3-yl)azetidin-3-yl)phenyl)-3-oxo-7-(trifluoromethyl)isoindolin-5-yl)methyl)(1-methylcyclobutyl)carbamate (30.0 mg, 34% yield) as a white solid. LCMS [M+H]⁺=248.1.
Compound 111

A mixture of tert-butyl ((2-(3-(3-(4-methyl-4H-1,2,4-triazol-3-yl)-1-(oxetan-3-yl)azetidin-3-yl)phenyl)-3-oxo-7-(trifluoromethyl) isoindolin-5-yl)methyl)(1-methyl-cyclobutyl)carbamate (30.0 mg, 0.05 mmol) and trifluoroacetic acid (0.16 mL, 0.63 mmol) in dichloromethane (2 mL) was stirred at 25° C. for 2 h and concentrated under vacuum. The residue was purified by RP-HPLC (0.05% NH₄OH in water/ACN 40% to 70%) to afford 2-(3-(3-(4-methyl-4H-1,2,4-triazol-3-yl)-1-(oxetan-3-yl)azetidin-3-yl)phenyl)-6-(((1-methyl-cyclobutyl)amino)methyl)-4-(trifluoromethyl) isoindolin-1-one (7.1 mg, 28% yield). ¹H NMR (400 MHz, methanol-d₄) δ 8.43 (s, 1H), 8.09 (s, 1H), 8.06 (s, 1H), 8.02 (s, 1H), 7.75 (dd, J=8.0, 1.2 Hz, 1H), 7.52 (t, J=8.0 Hz, 1H), 7.25 (d, J=8.0 Hz, 1H), 5.18 (s, 2H), 4.75 (t, J=6.8 Hz, 2H), 4.58-4.52 (m, 2H), 4.19 (d, J=8.0 Hz, 2H), 4.04 (d, J=8.0 Hz, 2H), 3.94-3.88 (m, 3H), 3.40 (s, 3H), 2.16-2.07 (m, 2H), 1.94-1.77 (m, 4H), 1.40 (s, 3H).

Example 52: Compound 112

Compound 112 (2-(3-(1-acetyl-3-(4-methyl-4H-1,2,4-triazol-3-yl)azetidin-3-yl)phenyl)-6-(((1-methylcyclobutyl)amino)methyl)-4-(trifluoromethyl)isoindolin-1-one) can be synthesized according to Scheme 50 (FIG. 50).

a. Intermediate 2: (tert-butyl ((2-(3-(1-acetyl-3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate To a solution of tert-butyl ((2-(3-(3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate (80.0 mg, 0.13 mmol) in dichloromethane (2 mL) was added pyridine (0.05 mL, 0.66 mmol) and acetic anhydride (0.02 mL, 0.26 mmol). The reaction mixture was stirred at 25° C. for 16 h and concentrated under vacuum. The crude was purified by preparative TLC (solvent gradient: 10% methanol in dichloromethane) to afford tert-butyl ((2-(3-(1-acetyl-3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate (60 mg, 70% yield) as a yellow oil. LCMS [M+H]⁺=653.3.
Compound 112

A mixture of tert-butyl ((2-(3-(1-acetyl-3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate (60.0 mg, 0.09 mmol) and trifluoroacetic acid (0.2 mL, 0.80 mmol) in dichloromethane (2 mL) was stirred at 25° C. for 16 h and concentrated to dryness. The residue was purified by RP-HPLC (water(NH₃H₂O+NH₄HCO₃)/ACN 43% to 73%) to afford 2-(3-(1-acetyl-3-(4-methyl-4H-1,2,4-triazol-3-yl)azetidin-3-yl)phenyl)-6-(((1-methylcyclobutyl)amino)methyl)-4-(trifluoromethyl)isoindolin-1-one (16.5 mg, 33% yield). ¹H NMR (400 MHz, methanol-d₄) δ 8.50 (s, 1H), 8.09 (s, 1H), 8.02 (s, 2H), 7.74 (d, J=8.0 Hz, 1H), 7.55 (t, J=8.0 Hz, 1H), 7.16 (d, J=7.6 Hz, 1H), 5.22-5.15 (m, 3H), 4.85-4.78 (m, 2H), 4.67-4.62 (m, 1H), 3.87 (s, 2H), 3.41 (s, 3H), 2.15-2.06 (m, 2H), 1.98 (s, 3H), 1.92-1.74 (m, 4H), 1.38 (s, 3H). LCMS [M+H]⁺=528.2.

Example 53: Compound 113

Compound 113 (2-(3-(3-(4-methyl-4H-1,2,4-triazol-3-yl)-1-(methylsulfonyl)azetidin-3-yl)phenyl)-6-(((1-methylcyclobutyl)amino)methyl)-4-(trifluoromethyl)isoindolin-1-one) can be synthesized according to Scheme 51 (FIG. 51).

Intermediate 2: (tert-butyl ((2-(3-(3-(4-methyl-4H-1,2,4-triazol-3-yl)-1-(methylsulfonyl)azetidin-3-yl)phenyl)-3-oxo-7-(trifluoromethyl)isoindolin-5-yl)methyl)(1-methylcyclobutyl)carbamate To a solution of tert-butyl ((2-(3-(3-(4-methyl-4H-1,2,4-triazol-3-yl)azetidin-3-yl)phenyl)-3-oxo-7-(trifluoromethyl)isoindolin-5-yl)methyl)(1-methylcyclobutyl)carbamate (80.0 mg, 0.13 mmol) in dichloromethane (2 mL) was added triethylamine (0.07 mL, 0.52 mmol) and methanesulfonyl chloride (0.04 mL, 0.52 mmol) at 0° C. The mixture was stirred at 25° C. for 2 h and quenched with saturated aqueous sodium bicarbonate (10 mL). The solution was extracted with dichloromethane (3×20 mL). The combined organic layers were washed with brine (30 mL), dried and concentrated under vacuum. The residue was purified by preparative TLC (solvent gradient: 10% methanol in dichloromethane) to afford tert-butyl ((2-(3-(3-(4-methyl-4H-1,2,4-triazol-3-yl)-1-(methylsulfonyl)azetidin-3-yl)phenyl)-3-oxo-7-(trifluoromethyl)isoindolin-5-yl)methyl)(1-methylcyclobutyl)carbamate (55.0 mg, 61% yield) as a yellow solid. LCMS [M+H]⁺=689.3.
Compound 113

A mixture of tert-butyl ((2-(3-(3-(4-methyl-4H-1,2,4-triazol-3-yl)-1-(methylsulfonyl)azetidin-3-yl)phenyl)-3-oxo-7-(trifluoromethyl)isoindolin-5-yl)methyl)(1-methylcyclobutyl)carbamate (55.0 mg, 0.08 mmol) and trifluoroacetic acid (0.2 mL, 0.80 mmol) in dichloromethane (2 mL) was stirred at 25° C. for 16 h and concentrated to dryness. The residue was purified by RP-HPLC (water(NH₃H₂O+NH₄HCO₃)/ACN 40% to 70%) to afford 2-(3-(3-(4-methyl-4H-1,2,4-triazol-3-yl)-1-(methylsulfonyl)azetidin-3-yl)phenyl)-6-(((1-methylcyclobutyl)amino)methyl)-4-(trifluoromethyl)isoindolin-1-one (17.2 mg, 37% yield). 1H NMR (400 MHz, methanol-d₄) δ 8.49 (s, 1H), 8.08 (s, 1H), 8.06 (s, 1H), 8.02 (s, 1H), 7.77 (d, J=8.0 Hz, 1H), 7.56 (t, J=8.0 Hz, 1H), 7.22 (d, J=7.6 Hz, 1H), 5.18 (s, 2H), 4.88-4.83 (m, 2H), 4.54 (d, J=8.4 Hz, 2H), 3.87 (s, 2H), 3.39 (s, 3H), 3.02 (s, 3H), 2.15-2.06 (m, 2H), 1.91-1.76 (m, 4H), 1.38 (s, 3H).

Example 54: Compounds 114 and 115

Compound 114 ((R)-2-(3-((4-methyl-4H-1,2,4-triazol-3-yl)(3-oxocyclobutyl)methyl)phenyl)-6-(((1-methylcyclobutyl)amino)methyl)-4-(trifluoromethyl)isoindolin-1-one) and
Compound 115 ((S)-2-(3-((4-methyl-4H-1,2,4-triazol-3-yl)(3-oxocyclobutyl)methyl)phenyl)-6-(((1-methylcyclobutyl)amino)methyl)-4-(trifluoromethyl)isoindolin-1-one) can be synthesized according to Scheme 52 (FIG. 52).

Intermediate 2: (3-((3-bromophenyl)(5,8-dioxaspiro[3.4]octan-2-yl)methyl)-4-methyl-4H-1,2,4-triazole To a solution of 3-(3-bromobenzyl)-4-methyl-4H-1,2,4-triazole (1.3 g, 5.16 mmol) in 1,2-dimethoxyethane (25 mL) was added sodium bis(trimethylsilyl)amide (1.0 M in tetrahydrofuran, 7.73 mL, 7.73 mmol) at 0° C. The mixture was stirred at 0° C. for 1 h, and 2-bromo-5,8-dioxaspiro[3.4]octane (1.7 g, 8.77 mmol) was added. The resulting mixture was stirred at 25° C. for 1 h and quenched by water (30 mL). The solution was extracted with dichloromethane (3×50 mL). The combined organic layers were dried over sodium sulfate and concentrated under vacuum. The residue was purified by silica gel chromatography (mobile phase: methanol/dichloromethane, gradient 0% to 10%) to afford 3-((3-bromophenyl)(5,8-dioxaspiro[3.4]octan-2-yl)methyl)-4-methyl-4H-1,2,4-triazole (450 mg, 24% yield) as a white solid. LCMS [M+H]$^+$=364.2.

Intermediate 3: (tert-butyl ((2-(3-((4-methyl-4H-1,2,4-triazol-3-yl)(5,8-dioxaspiro[3.4]octan-2-yl)methyl)phenyl)-3-oxo-7-(trifluoromethyl)isoindolin-5-yl)methyl)(1-methylcyclobutyl)carbamate In a glovebox, a mixture of dicyclohexylphosphino-2',6'-diisopropoxy-1,1'-biphenyl)[2-(2'-amino-1,1'biphenyl)]palladium(II) methanesulfonate (34.4 mg, 0.04 mmol), 3-[(3-bromophenyl)-(5,8-dioxaspiro[3.4]octan-2-yl)methyl]-4-methyl-1,2,4-triazole (100.0 mg, 0.27 mmol), cesium carbonate (268.4 mg, 0.82 mmol) and tert-butyl N-(1-methylcyclobutyl)-N-[[3-oxo-7-(trifluoromethyl)isoindolin-5-yl]methyl]carbamate (120.32 mg, 0.30 mmol) in 1,4-Dioxane (3 mL) was heated at 110° C. in sealed tube for 5 h and concentrated under vacuum. The residue was purified by preparative TLC (solvent gradient: 10% methanol in dichloromethane) to afford tert-butyl N-[[2-[3-[5,8-dioxaspiro[3.4]octan-2-yl-(4-methyl-1,2,4-triazol-3-yl)methyl]phenyl]-3-oxo-7-(trifluoromethyl)isoindolin-5-yl]methyl]-N-(1-methylcyclobutyl)carbamate (120.0 mg, 64% yield) as a yellow solid.

Compounds 114 and 115

To a solution of tert-butyl ((2-(3-((4-methyl-4H-1,2,4-triazol-3-yl)(5,8-dioxaspiro[3.4]octan-2-yl)methyl)phenyl)-3-oxo-7-(trifluoromethyl)isoindolin-5-yl)methyl)(1-methylcyclobutyl)carbamate (100.0 mg, 0.15 mmol) in acetone (1 mL) was added aqueous hydrochloric acid (1.0 M, 0.59 mL, 0.59 mmol). The mixture was stirred at 25° C. for 2 h and adjusted to pH=7 by addition of saturated aqueous sodium bicarbonate. The resulting solution was extracted with dichloromethane (3×50 mL). The combined organic layers were washed with brine (50 mL), dried over sodium sulfate and concentrated under vacuum. The residue was purified by preparative TLC (solvent gradient: 10% methanol in dichloromethane) to afford 2-(3-((4-methyl-4H-1,2,4-triazol-3-yl)(3-oxocyclobutyl)-methyl)phenyl)-6-(((1-methylcyclobutyl)amino)methyl)-4-(trifluoromethyl)isoindolin-1-one (50.0 mg, 63% yield) as a yellow oil.

The above mixture was further purified by chiral SFC (Column=Daicel Chiralpak OD; Column dimensions=250 mm×30 mm×10 μm; Detection wavelength=220 nM; Flow rate=80 mL/min; Mobile phase: A: $CO_2$ B: ethanol (0.05% DEA); Isocratic: 40% B) with 0.1% ammonium hydroxide), then by RP-HPLC (water($NH_3H_2O+NH_4HCO_3$)/ACN 48% to 78%) to afford tentatively assigned:

(R)-2-(3-((4-methyl-4H-1,2,4-triazol-3-yl)(3-oxocyclobutyl)methyl)phenyl)-6-(((1-methylcyclobutyl)amino) methyl)-4-(trifluoromethyl)isoindolin-1-one (Peak 1, Retention time=1.103 min) (5.5 mg, 11% yield). $^1$H NMR (400 MHz, DMSO-$d_6$) δ 8.36 (s, 1H), 8.05 (s, 1H), 8.00 (s, 1H), 7.96 (s, 1H), 7.86 (d, J=8.0 Hz, 1H), 7.41 (t, J=8.0 Hz, 1H), 7.09 (d, J=8.0 Hz, 1H), 5.18 (s, 2H), 4.47 (d, J=10.4 Hz, 1H), 3.82 (s, 2H), 3.42 (s, 3H), 3.33-3.31 (m, 1H), 3.23-3.15 (m, 1H), 2.99-2.75 (m, 3H), 2.02-1.97 (m, 2H), 1.75-1.65 (m, 4H), 1.23 (s, 3H). LCMS [M+H]$^+$=538.2.

(S)-2-(3-((4-methyl-4H-1,2,4-triazol-3-yl)(3-oxocyclobutyl)methyl)phenyl)-6-(((1-methylcyclobutyl)amino) methyl)-4-(trifluoromethyl)isoindolin-1-one (Peak 2, Retention time=1.6993) (8.5 mg, 15% yield). $^1$H NMR (400 MHz, DMSO-$d_6$) δ 8.36 (s, 1H), 8.05 (s, 1H), 8.00 (s, 1H), 7.96 (s, 1H), 7.86 (d, J=8.4 Hz, 1H), 7.41 (t, J=8.0 Hz, 1H), 7.09 (d, J=8.0 Hz, 1H), 5.18 (s, 2H), 4.47 (d, J=10.8 Hz, 1H), 3.82 (s, 2H), 3.42 (s, 3H), 3.33-3.31 (m, 1H), 3.23-3.15 (m, 1H), 2.99-2.75 (m, 3H), 2.02-1.96 (m, 2H), 1.75-1.65 (m, 4H), 1.23 (s, 3H). LCMS [M+H]$^+$=538.3.

Example 55: Compound 116

Figure 53:
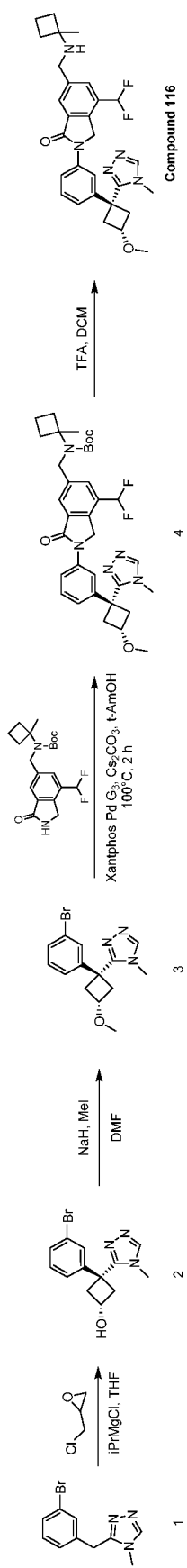

Compound 116 (4-(difluoromethyl)-2-(3-((1s,3s)-3-methoxy-1-(4-methyl-4H-1,2,4-triazol-3-yl)cyclobutyl)phenyl)-6-(((1-methylcyclobutyl)amino)methyl)isoindolin-1-one) can be synthesized according to Scheme 53 (FIG. 53).

Intermediate 2: ((1s,3s)-3-(3-bromophenyl)-3-(4-methyl-4H-1,2,4-triazol-3-yl)cyclobutanol To a solution of 3-(3-bromobenzyl)-4-methyl-4H-1,2,4-triazole (5.0 g, 19.83 mmol) and epichlorohydrin (3.1 mL, 39.67 mmol) in tetrahydrofuran (100 mL) was added isopropyl magnesium chloride (2.0 M in tetrahydrofuran, 39.7 mL, 79.33 mmol) at −40° C. dropwise. The mixture was stirred at −40° C. for 30 min and at 20° C. for 16 h. The mixture was quenched by water (10 mL) and saturated aqueous sodium bicarbonate (50 mL). The solution was extracted with ethyl acetate (2×100 mL) and dichloromethane (2×100 ml). The combined organic layers were dried over sodium sulfate and concentrated under vacuum. The residue was purified by silica gel chromatography (mobile phase: methanol/dichloromethane, gradient 0% to 6%) to afford (1s,3s)-3-(3-bromophenyl)-3-(4-methyl-4H-1,2,4-triazol-3-yl)cyclobutanol (4 g, 62% yield) as a yellow solid.

Intermediate 3: (3-((1s,3s)-1-(3-bromophenyl)-3-methoxycyclobutyl)-4-methyl-4H-1,2,4-triazole To a solution of (1s,3s)-3-(3-bromophenyl)-3-(4-methyl-4H-1,2,4-triazol-3-yl)cyclobutanol (1.0 g, 3.24 mmol) in N,N-dimethylformamide (10 mL) was added sodium hydride (60%, 194.7 mg, 4.87 mmol). The mixture was stirred at 25° C. for 20 min and then iodomethane (0.4 mL, 6.49 mmol) was added. The mixture was stirred at 25° C. for 1 h and quenched with water (10 mL). The resulting solution was extracted with dichloromethane (3×50 mL). The combined organic layers were concentrated. The residue was purified by silica gel chromatography (mobile phase: methanol/dichloromethane, gradient 0% to 10%) to afford 3-((1s,3s)-1-(3-bromophenyl)-3-methoxycyclobutyl)-4-methyl-4H-1,2,4-triazole (860.0 mg, 82% yield) as a yellow oil. LCMS [M+H]$^+$=324.0.

Intermediate 4: (tert-butyl ((7-(difluoromethyl)-2-(3-((1s,3s)-3-methoxy-1-(4-methyl-4H-1,2,4-triazol-3-yl)cyclobutyl)phenyl)-3-oxoisoindolin-5-yl)methyl)(1-methylcyclobutyl)carbamate In a glovebox, a mixture of 3-((1s,3s)-1-(3-bromophenyl)-3-methoxycyclobutyl)-4-methyl-4H-1,2,4-triazole (55.9 mg, 0.17 mmol), tert-butyl ((7-(difluoromethyl)-3-oxoisoindolin-5-yl)methyl)(1-methylcyclobutyl)carbamate (60.0 mg, 0.16 mmol), cesium carbonate (154.2 mg, 0.47 mmol) and [4,5-Bis(diphenylphosphino)-9,9-dimethylxanthene][2'-amino-2-biphenylyl][(methylsulfonyl)oxy]palladium(II) (32.6 mg, 0.03 mmol) in 2-methyl-2-butanol (1.5 mL) was heated at 100° C. in sealed tube for 2 h and concentrated. The residue was purified by preparative TLC (solvent gradient: 10% methanol in dichloromethane) to afford tert-butyl ((7-(difluoromethyl)-2-(3-((1s,3s)-3-methoxy-1-(4-methyl-4H-1,2,4-triazol-3-yl)cyclobutyl)phenyl)-3-oxoisoindolin-5-yl)methyl)(1-methylcyclobutyl) carbamate (30.0 mg, 31% yield) as a yellow solid. LCMS [M+H]$^+$=622.3.

Compound 116

A mixture of tert-butyl ((7-(difluoromethyl)-2-(3-((1s,3s)-3-methoxy-1-(4-methyl-4H-1,2,4-triazol-3-yl)cyclobutyl)phenyl)-3-oxoisoindolin-5-yl)methyl)(1-methylcyclobutyl) carbamate (30.0 mg, 0.05 mmol) and trifluoroacetic acid (0.2 mL, 2.6 mmol) in dichloromethane (2 mL) was stirred at 25° C. for 2 h and concentrated under reduce pressure. The residue was purified by RP-HPLC (water(NH$_3$H$_2$O+NH$_4$HCO$_3$)/ACN 47% to 77%) to afford 4-(difluoromethyl)-2-(3-((1s,3s)-3-methoxy-1-(4-methyl-4H-1,2,4-triazol-3-yl)cyclobutyl)phenyl)-6-(((1-methylcyclobutyl)amino)methyl)isoindolin-1-one (12.6 mg, 50% yield). $^1$H NMR (400 MHz, methanol-d$_4$) δ 8.30 (s, 1H), 8.04 (s, 1H), 7.96 (s, 1H), 7.82 (s, 1H), 7.70-7.65 (m, 1H), 7.47 (t, J=8.0 Hz, 1H), 7.19 (d, J=8.4 Hz, 1H), 7.03 (t, J=55.6 Hz, 1H), 5.11 (s, 2H), 4.21-4.12 (m, 1H), 3.82 (s, 2H), 3.34 (s, 3H), 3.27 (s, 3H), 3.21-3.14 (m, 2H), 2.89-2.83 (m, 2H), 2.13-2.04 (m, 2H), 1.90-1.74 (m, 4H), 1.37 (s, 3H). LCMS [M+H]$^+$=522.3.

Example 56: Compound 117

Figure 54:
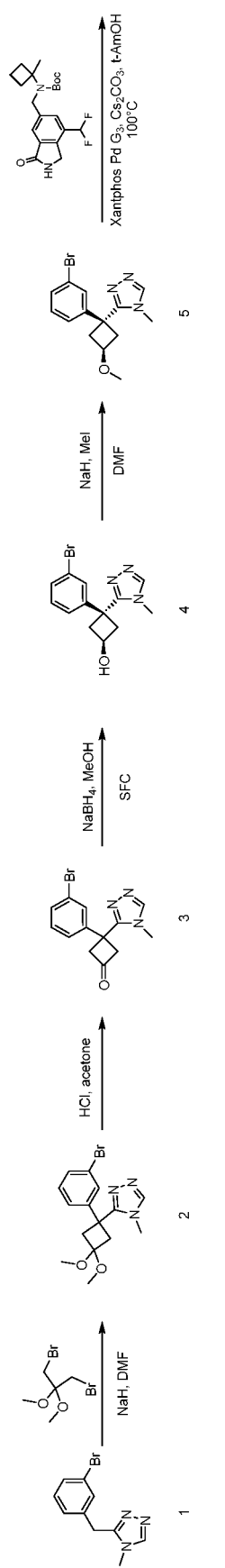

Compound 117 (4-(difluoromethyl)-2-(3-((1r,3r)-3-methoxy-1-(4-methyl-4H-1,2,4-triazol-3-yl)cyclobutyl)phenyl)-6-(((1-methylcyclobutyl)amino)methyl)isoindolin-1-one) can be synthesized according to Scheme 54 (FIG. 54).

Intermediate 2: (3-(1-(3-bromophenyl)-3,3-dimethoxycyclobutyl)-4-methyl-4H-1,2,4-triazole To a solution of 3-(3-bromobenzyl)-4-methyl-4H-1,2,4-triazole (5.0 g, 19.8 mmol) in N,N-dimethylformamide (100 mL) was added sodium hydride (60%, 2.4 g, 59.5 mmol) at 0° C. The mixture was stirred at 0° C. for 30 min and then 1,3-dibromo-2,2-dimethoxypropane (6.2 g, 23.8 mmol) was added. The mixture was then heated at 60° C. for 16 h. After cooled, the mixture was quenched with water (100 mL) and extracted with dichloromethane (2×100 mL). The combined organic layers were concentrated and the residue was purified by silica gel chromatography (mobile phase: methanol/dichloromethane, gradient 0% to 10%) to afford 3-(1-(3-bromophenyl)-3,3-dimethoxycyclobutyl)-4-methyl-4H-1,2,4-triazole (3.5 g, 50% yield) as yellow solid. LCMS [M+H]$^+$=460.1.

Intermediate 3: (3-(3-bromophenyl)-3-(4-methyl-4H-1,2,4-triazol-3-yl)cyclobutanone A mixture of 3-(1-(3-bromophenyl)-3,3-dimethoxycyclobutyl)-4-methyl-4H-1,2,4-triazole (3.4 g, 7.4 mmol) and aqueous hydrochloric acid (6.0 M, 68.0 mL, 408.0 mmol) in acetone (70 mL) was stirred at 25° C. for 16 hr and concentrated to remove acetone. The residue was diluted with water (20 mL) and extracted with ethyl acetate (3×80 mL). The combined organic layers were dried over sodium sulfate and concentrated. The residue was purified by silica gel chromatography (mobile phase: ethyl acetate/petroleum ether, gradient 0% to 15%) to afford 3-(3-bromophenyl)-3-(4-methyl-4H-1,2,4-triazol-3-yl)cyclobutanone (5.4 g, 89% yield) as a light yellow solid.

Intermediate 4: ((1r,3r)-3-(3-bromophenyl)-3-(4-methyl-4H-1,2,4-triazol-3-yl)cyclobutanol To a solution of 3-(3-bromophenyl)-3-(4-methyl-4H-1,2,4-triazol-3-yl)cyclobutanone (8.5 g, 27.7 mmol) in methanol (150 mL) was added sodium borohydride (2.1 g, 51.6 mmol) at 0° C. The mixture was stirred at 25° C. for 24 hr and quenched with saturated aqueous ammonium chloride (20 mL). The resulting mixture was extracted with dichloromethane (3×50 mL). The combined organic layers were washed with brine (50 mL), dried over with sodium sulfate and concentrated under vacuum. The residue was purified by silica gel chromatography (mobile phase: methanol/dichloromethane, gradient 0% to 10%) to afford 3-(3-bromophenyl)-3-(4-methyl-4H-1,2,4-triazol-3-yl)cyclobutanol (6.5 g, 60% yield) as a yellow solid.

The above product was purified by chiral SFC (Column=Daicel Chiralpak AS; Column dimensions=250 mm×30 mm×10 μm; Detection wavelength=220 nM; Flow rate=80 mL/min; Mobile phase: A: CO$_2$ B: ethanol (0.05% DEA); Isocratic: 40% B) with 0.1% ammonium hydroxide) to afford:

(1r,3r)-3-(3-bromophenyl)-3-(4-methyl-4H-1,2,4-triazol-3-yl)cyclobutanol (Peak 1, retention time=3.290 min) (3.0 g, 46% yield) as a yellow solid. $^1$H NMR (400 MHz, DMSO-d$_6$) δ 8.38 (s, 1H), 7.45 (d, J=7.8 Hz, 1H), 7.35-7.27 (m, 2H), 7.11 (d, J=7.8 Hz, 1H), 5.30 (d, J=7.2 Hz, 1H), 4.01 (t, J=7.2 Hz, 1H), 3.27-3.20 (m, 2H), 3.18 (s, 3H), 2.45-2.40 (m, 2H).

(1s,3s)-3-(3-bromophenyl)-3-(4-methyl-4H-1,2,4-triazol-3-yl)cyclobutanol (Peak 2, retention time=3.771 min) (2.5 g, 39% yield) as a yellow solid. $^1$H NMR (400 MHz, DMSO-d$_6$) δ 8.30 (s, 1H), 7.50-7.44 (m, 1H), 7.42-7.38 (m, 1H), 7.35-7.30 (m, 2H), 5.31 (d, J=7.2 Hz, 1H), 4.28-4.12 (m, 1H), 3.21-3.14 (m, 3H), 3.07-2.95 (m, 2H), 2.76-2.62 (m, 2H).

Intermediate 5: (3-((1r,3r)-1-(3-bromophenyl)-3-methoxycyclobutyl)-4-methyl-4H-1,2,4-triazole To a solution of (1r,3r)-3-(3-bromophenyl)-3-(4-methyl-4H-1,2,4-triazol-3-yl)cyclobutanol (1.0 g, 3.24 mmol) in N,N-dimethylformamide (10 mL) was added sodium hydride (60%, 194.7 mg, 4.87 mmol). The mixture was stirred at 25° C. for 20 min and iodomethane (0.4 mL, 6.49 mmol) was added. The resulting mixture was stirred at 25° C. for 1 h and then quenched by water (15 mL). The mixture was extracted with dichloromethane (3×75 mL). The combined organic layers were concentrated to dryness. The residue was purified by silica gel chromatography (mobile phase: methanol/dichloromethane, gradient 0% to 10%) to afford 3-((1r,3r)-1-(3-bromophenyl)-3-methoxycyclobutyl)-4-methyl-4H-1,2,4-triazole (601 mg, 58% yield) as a yellow oil.

Intermediate 6: (tert-butyl ((7-(difluoromethyl)-2-(3-((1r,3r)-3-methoxy-1-(4-methyl-4H-1,2,4-triazol-3-yl)cyclobutyl)phenyl)-3-oxoisoindolin-5-yl)methyl)(1-methylcyclobutyl)carbamate In a glovebox, a mixture of 3-((1r,3r)-1-(3-bromophenyl)-3-methoxycyclobutyl)-4-methyl-4H-1,2,4-triazole (46.6 mg, 0.14 mmol), tert-butyl ((7-(difluoromethyl)-3-oxoisoindolin-5-yl)methyl)(1-methylcyclobutyl)carbamate (50.0 mg, 0.13 mmol), cesium carbonate (128.5 mg, 0.39 mmol) and [4,5-Bis(diphenylphosphino)-9,9-dimethylxanthene][2'-amino-2-biphenylyl][(methylsulfonyl)oxy]palladium(II) (27.2 mg, 0.03 mmol) in 2-methyl-2-butanol (1.5 mL) was heated at 100° C. in sealed tube for 2 h and concentrated. The residue was purified by preparative TLC (solvent gradient: 10% methanol in dichloromethane) to give tert-butyl ((7-(difluoromethyl)-2-(3-((1r,3r)-3-methoxy-1-(4-methyl-4H-1,2,4-triazol-3-yl)cyclobutyl)phenyl)-3-oxoisoindolin-5-yl)methyl)(1-methylcyclobutyl)carbamate (45.0 mg, 55% yield) as a yellow oil. LCMS [M+H]$^+$=622.3.

Compound 117

A mixture of tert-butyl ((7-(difluoromethyl)-2-(3-((1r,3r)-3-methoxy-1-(4-methyl-4H-1,2,4-triazol-3-yl)cyclobutyl)phenyl)-3-oxoisoindolin-5-yl)methyl)(1-methylcyclobutyl)carbamate (45.0 mg, 0.07 mmol) and trifluoroacetic acid (0.2 mL, 2.6 mmol) in dichloromethane (2 mL) was stirred at 25° C. for 2 h and concentrated. The crude product was purified by RP-HPLC (water (NH$_3$H$_2$O+NH$_4$HCO$_3$)-ACN 47%-77%) to afford 4-(difluoromethyl)-2-(3-((1r,3r)-3-methoxy-1-(4-methyl-4H-1,2,4-triazol-3-yl)cyclobutyl)phenyl)-6-(((1-methylcyclobutyl)amino)methyl)isoindolin-1-one (23.0 mg, 60% yield). $^1$H NMR (400 MHz, methanol-d$_4$) δ 8.37 (s, 1H), 7.94 (s, 1H), 7.89 (t, J=1.6 Hz, 1H), 7.80 (s, 1H), 7.67 (dd, J=8.0, 2.0 Hz, 1H), 7.45 (t, J=8.0 Hz, 1H), 7.02 (t, J=55.6 Hz, 1H), 7.05 (d, J=8.4 Hz, 1H), 5.09 (s, 2H), 4.05-3.92 (m, 1H), 3.80 (s, 2H), 3.39-3.34 (m, 2H), 3.33 (s, 3H), 3.28 (s, 3H), 2.66-2.59 (m, 2H), 2.12-2.02 (m, 2H), 1.91-1.73 (m, 4H), 1.36 (s, 3H). LCMS [M+H]$^+$=522.3.

Example 57: Compound 118 and Compound 119

Figure 55:
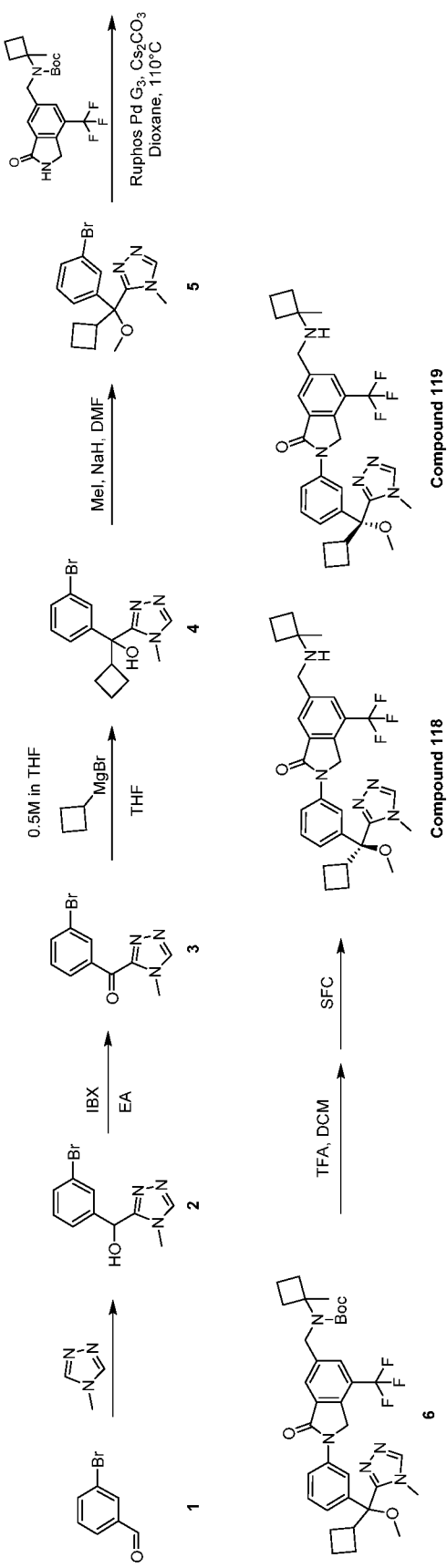

Compound 118 ((S)-2-(3-(cyclobutyl(methoxy)(4-methyl-4H-1,2,4-triazol-3-yl)methyl)phenyl)-6-(((1-methylcyclobutyl)amino)methyl)-4-(trifluoromethyl)isoindolin-1-one) and Compound 119 ((R)-2-(3-(cyclobutyl(methoxy)(4-methyl-4H-1,2,4-triazol-3-yl)methyl)phenyl)-6-(((1-methylcyclobutyl)amino)methyl)-4-(trifluoromethyl)isoindolin-1-one) can be synthesized according to Scheme 55 (FIG. 55).

Intermediate 2: ((3-bromophenyl)(4-methyl-4H-1,2,4-triazol-3-yl)methanol

Under nitrogen, to a solution of 4-methyl-4H-1,2,4-triazole (6.7 g, 81.07 mmol) in 1,2-dimethoxyethane (300 mL) was added n-butyl lithium (2.5 M in hexane, 28.11 mL, 70.26 mmol) at −50° C. over 5 min. The mixture was stirred at −50° C. for 1.5 h. and a solution of 3-bromobenzaldehyde (10.0 g, 54.10 mmol) in 1,2-dimethoxyethane (30 mL) was added dropwise. After addition, the reaction mixture was stirred at 0° C. for 1 h and then quenched with water (5 mL). The mixture was adjusted to pH=7 with hydrochloric acid (1 M) and diluted with water (100 mL). The resulting solution was extracted with dichloromethane (3×100 mL). The combined organic layers were washed with brine (100 mL), dried over sodium sulfate and concentrated. The residue was purified by silica gel chromatography (mobile phase: methanol/dichloromethane, gradient 0% to 10%) to afford (3-bromophenyl)(4-methyl-4H-1,2,4-triazol-3-yl)methanol (10 g, 69% yield) as a yellow solid.

Intermediate 3: ((3-bromophenyl)(4-methyl-4H-1,2,4-triazol-3-yl)methanone

To a solution of (3-bromophenyl)(4-methyl-4H-1,2,4-triazol-3-yl)methanol (5.0 g, 18.65 mmol) in ethyl acetate (150 mL) was added 2-iodoxybenzoic acid (15.7 g, 55.95 mmol). The mixture was stirred at 80° C. for 16 h and filtered. The filtrate was concentrated. The residue was purified by silica gel chromatography (mobile phase: methanol/dichloromethane, gradient 0% to 10%) to afford (3-bromophenyl)(4-methyl-4H-1,2,4-triazol-3-yl)methanone (4.7 g, 95% yield) as a white solid.

Intermediate 4: ((3-bromophenyl)(cyclobutyl)(4-methyl-4H-1,2,4-triazol-3-yl)methanol A solution of (3-bromophenyl)(4-methyl-4H-1,2,4-triazol-3-yl)methanone (4.5 g, 16.9 mmol) in tetrahydrofuran (20 mL) was added cyclobutyl magnesium bromide (0.5 M in tetrahydrofuran, 90.0 mL, 45.0 mmol). The mixture was stirred at 25° C. for 16 h and quenched with saturated aqueous ammonium chloride (100 mL). The solution was extracted with dichloromethane (3×100 mL). The combined organic layers were washed with brine (100 mL), dried over sodium sulfate and concentrated. The residue was purified by silica gel chromatography (mobile phase: methanol/dichloromethane, gradient 0% to 6%) to give (3-bromophenyl)(cyclobutyl)(4-methyl-4H-1,2,4-triazol-3-yl)methanol (2.0 g, 37% yield) as a yellow solid. $^1$H NMR (400 MHz, methanol-d$_4$) δ 8.34 (s, 1H), 7.51 (t, J=1.6 Hz, 1H), 7.43-7.40 (m, 1H), 7.26-7.21 (m, 1H), 7.18-7.13 (m, 1H), 3.51-3.44 (m, 1H), 3.42 (s, 3H), 2.17-2.09 (m, 2H), 2.04-1.96 (m, 1H), 1.89-1.81 (m, 1H), 1.68 (q, J=9.6 Hz, 1H), 1.50-1.41 (m, 1H).

Intermediate 5: (3-((3-bromophenyl)(cyclobutyl)(methoxy)methyl)-4-methyl-4H-1,2,4-triazole To a solution of (3-bromophenyl)(cyclobutyl)(4-methyl-4H-1,2,4-triazol-3-yl)methanol (500 mg, 1.55 mmol) in N,N-dimethylformamide (10 mL) was added sodium hydride (60%, 124 mg, 3.1 mmol) at 0° C. The mixture was stirred at 0° C. for 30 min and iodomethane (0.14 mL, 2.33 mmol) was added. The mixture was stirred at 25° C. for another 16 h and quenched with saturated ammonia chloride (50 mL). The solution was extracted with dichloromethane (3×50 mL). The combined organic layers were washed with brine (50 mL), dried over sodium sulfate and concentrated. The residue was purified by silica gel chromatography (mobile phase: methanol/dichloromethane, gradient 0% to 6%) to give 3-((3-bromophenyl)(cyclobutyl)(methoxy)

methyl)-4-methyl-4H-1,2,4-triazole (267 mg, 51% yield) as a yellow oil. $^1$H NMR (400 MHz, methanol-d$_4$) δ 8.45 (s, 1H), 7.55-7.52 (m, 1H), 7.43 (t, J=1.6 Hz, 1H), 7.30 (t, J=8.0 Hz, 1H), 6.97 (d, J=8.0 Hz, 1H), 3.81-3.71 (m, 1H), 3.22 (s, 3H), 3.20-3.18 (m, 1H), 3.19 (s, 3H), 2.24-2.14 (m, 1H), 1.99-1.90 (m, 1H), 1.88-1.77 (m, 2H), 1.73-1.62 (m, 1H), 1.44-1.35 (m, 1H).

Intermediate 6: (tert-butyl ((2-(3-(cyclobutyl (methoxy)(4-methyl-4H-1,2,4-triazol-3-yl)methyl) phenyl)-3-oxo-7-(trifluoromethyl)isoindolin-5-yl) methyl)(1-methylcyclobutyl)carbamate In a glovebox, a mixture of 3-((3-bromophenyl)(cyclobutyl)(methoxy)methyl)-4-methyl-4H-1,2,4-triazole (150.0 mg, 0.45 mmol), tert-butyl (1-methylcyclobutyl)((3-oxo-7-(trifluoromethyl)isoindolin-5-yl)methyl)carbamate (195.5 mg, 0.49 mmol), dicyclohexylphosphino-2',6'-diisopropoxy-1,1'-biphenyl)[2-(2'-amino-1,1'biphenyl)]-palladium(II) methanesulfonate (74.6 mg, 0.09 mmol) and cesium carbonate (436.1 mg, 1.34 mmol) in 1,4-dioxane (5 mL) was heated at 110° C. in sealed tube for 3 h and concentrated. The residue was purified by preparative TLC (solvent gradient: 10% methanol in dichloromethane) to afford tert-butyl ((2-(3-(cyclobutyl(methoxy)(4-methyl-4H-1,2,4-triazol-3-yl)methyl)phenyl)-3-oxo-7-(trifluoromethyl) isoindolin-5-yl)methyl)(1-methylcyclobutyl)carbamate (220.0 mg, 75% yield) as a colorless oil.
Compound 118 and Compound 119

A mixture of tert-butyl ((2-(3-(cyclobutyl(methoxy)(4-methyl-4H-1,2,4-triazol-3-yl)methyl)phenyl)-3-oxo-7-(trifluoromethyl) isoindolin-5-yl)methyl)(1-methylcyclobutyl)carbamate (264.0 mg, 0.41 mmol) and trifluoroacetic acid (1.2 mL, 12.98 mmol) in dichloromethane (10 mL) was stirred at 25° C. for 1 h and concentrated under vacuum. The residue was purified by RP-HPLC (0.2% NH$_3$·H$_2$O in water/ACN 65% to 95%) to afford 2-(3-(cyclobutyl(methoxy)(4-methyl-4H-1,2,4-triazol-3-yl)methyl)phenyl)-6-(((1-methylcyclobutyl)amino)methyl)-4-(trifluoromethyl)isoindolin-1-one (75 mg, 35% yield).

The above mixture was purified by chiral SFC (Column=Daicel Chiralpak AS; Column dimensions=250 mm×30 mm×10 μm; Detection wavelength=220 nM; Flow rate=80 mL/min; Mobile phase: A: CO$_2$ B: ethanol (0.05% DEA); Isocratic: 40% B) with 0.1% ammonium hydroxide) to afford tentatively assigned:

(S)-2-(3-(cyclobutyl(methoxy)(4-methyl-4H-1,2,4-triazol-3-yl)methyl)phenyl)-6-(((1-methylcyclobutyl)amino) methyl)-4-(trifluoromethyl)isoindolin-1-one (Peak 1, retention time=0.922 min) (32.1 mg, 41% yield). $^1$H NMR (400 MHz, methanol-d$_4$) δ 8.45 (s, 1H), 8.09 (s, 1H), 8.02 (s, 1H), 7.90 (s, 1H), 7.78 (d, J=8.0 Hz, 1H), 7.50 (t, J=8.0 Hz, 1H), 6.97 (d, J=8.0 Hz, 1H), 5.17 (s, 2H), 3.92 (s, 2H), 3.87-3.77 (m, 1H), 3.25 (s, 3H), 3.21 (s, 3H), 2.24-2.11 (m, 3H), 2.01-1.78 (m, 9H), 1.42 (s, 3H). LCMS [M+H]$^+$=553.3.

(R)-2-(3-(cyclobutyl(methoxy)(4-methyl-4H-1,2,4-triazol-3-yl)methyl)phenyl)-6-(((1-methylcyclobutyl)amino) methyl)-4-(trifluoromethyl)isoindolin-1-one (Peak 2, retention time=1.254 min) (33.8 mg, 43% yield). $^1$H NMR (400 MHz, methanol-d$_4$) δ 8.45 (s, 1H), 8.09 (s, 1H), 8.02 (s, 1H), 7.90 (s, 1H), 7.78 (d, J=8.0 Hz, 1H), 7.50 (t, J=8.0 Hz, 1H), 6.97 (d, J=8.0 Hz, 1H), 5.17 (s, 2H), 3.92 (s, 2H), 3.87-3.77 (m, 1H), 3.25 (s, 3H), 3.21 (s, 3H), 2.24-2.11 (m, 3H), 2.01-1.78 (m, 9H), 1.42 (s, 3H). LCMS [M+H]$^+$=553.3.

Example 58: Compound 120

Figure 56:
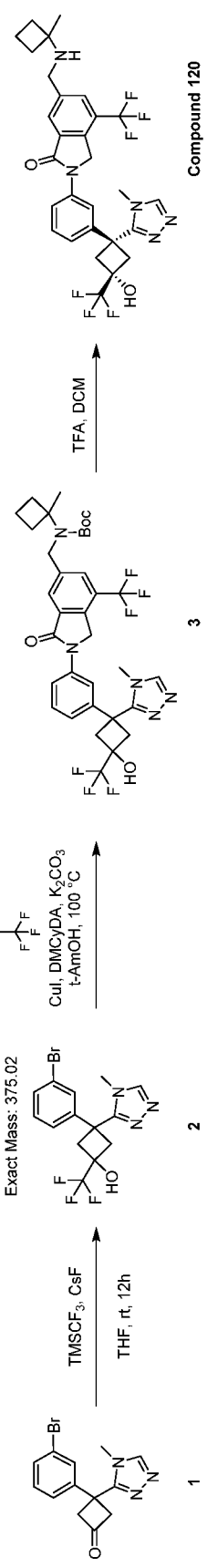

Compound 120 (2-(3-((1s,3s)-3-hydroxy-1-(4-methyl-4H-1,2,4-triazol-3-yl)-3-(trifluoromethyl)cyclobutyl)phenyl)-6-(((1-methylcyclobutyl)amino)methyl)-4-(trifluoromethyl)isoindolin-1-one) can be synthesized according to Scheme 56 (FIG. 56).

Intermediate 2: (3-(3-bromophenyl)-3-(4-methyl-4H-1,2,4-triazol-3-yl)-1-(trifluoromethyl)cyclobutanol To a solution of 3-(3-bromophenyl)-3-(4-methyl-4H-1,2,4-triazol-3-yl)cyclobutanone (300.0 mg, 0.98 mmol) and trimethyl(trifluoromethyl)silane (167.2 mg, 1.18 mmol) in tetrahydrofuran (4 mL) was added cesium fluoride (446.5 mg, 2.94 mmol). The mixture was stirred at 25° C. for 12 h and diluted with water (15 mL). The mixture was extracted with dichloromethane (3×15 mL). The combined organic layers were washed with brine (2×15 mL), dried over sodium sulfate and concentrated. The residue was purified by silica gel chromatography (mobile phase: methanol/dichloromethane, gradient 0% to 6%) to afford 3-(3-bromophenyl)-3-(4-methyl-4H-1,2,4-triazol-3-yl)-1-(trifluoromethyl)cyclobutanol (100.0 mg, 27% yield) as a white solid. LCMS [M+H]$^+$=376.0.

Intermediate 3: (tert-butyl ((2-(3-(3-hydroxy-1-(4-methyl-4H-1,2,4-triazol-3-yl)-3-(trifluoromethyl) cyclobutyl)phenyl)-3-oxo-7-(trifluoromethyl)isoindolin-5-yl)methyl)(1-methylcyclobutyl)carbamate In a glovebox, a mixture of tert-butyl (1-methylcyclobutyl)((3-oxo-7-(trifluoromethyl)isoindolin-5-yl)methyl) carbamate (79.4 mg, 0.20 mmol), (1 S,2S)—N$^1$,N$^2$-dimethylcyclohexane-1,2-diamine (11.3 mg, 0.08 mmol), potassium carbonate (68.9 mg, 0.50 mmol), 3-(3-bromophenyl)-3-(4-methyl-4H-1,2,4-triazol-3-yl)-1-(trifluoromethyl) cyclobutanol (75.0 mg, 0.20 mmol) and copper(I) iodide (7.6 mg, 0.04 mmol) in tert-amyl alcohol (3 mL) was heated at 100° C. in sealed tube for 2 h and concentrated. The residue was purified by silica gel chromatography (mobile phase: methanol/dichloromethane, gradient 0% to 6%) to afford tert-butyl ((2-(3-(3-hydroxy-1-(4-methyl-4H-1,2,4-triazol-3-yl)-3-(trifluoromethyl)cyclobutyl)phenyl)-3-oxo-7-(trifluoromethyl)isoindolin-5-yl)methyl)(1-methylcyclobutyl) carbamate (80.0 mg, 58% yield) as a light green solid. LCMS [M+H]$^+$=694.3.
Compound 120

A mixture of tert-butyl N-[[2-[3-[3-hydroxy-1-(4-methyl-1,2,4-triazol-3-yl)-3-(trifluoromethyl)cyclobutyl]phenyl]-3-oxo-7-(trifluoromethyl)isoindolin-5-yl]methyl]-N-(1-methylcyclobutyl)carbamate (85.0 mg, 0.12 mmol) and trifluoroacetic acid (1.0 mL, 12.98 mmol) in dichloromethane (2 mL) was stirred at 25° C. for 1 h and concentrated. The residue was purified by RP-HPLC (water(NH$_3$H$_2$O+NH$_4$HCO$_3$)/ACN 45% to 75%) to afford tentatively assigned 2-(3-((1s,3s)-3-hydroxy-1-(4-methyl-4H-1,2,4-triazol-3-yl)-3-(trifluoromethyl)cyclobutyl)phenyl)-6-(((1-methylcyclobutyl)amino)methyl)-4-(trifluoromethyl)isoindolin-1-one (15.1 mg, 20% yield). $^1$H NMR (400 MHz, methanol-d$_4$) δ 8.27 (s, 1H), 7.99 (s, 1H), 7.91 (d, J=3.2 Hz, 2H), 7.60 (d, J=8.4 Hz, 1H), 7.39 (t, J=8.0 Hz, 1H), 7.10 (d, J=7.6 Hz, 1H), 5.05 (s, 2H), 3.77 (s, 2H), 3.36 (s, 3H), 3.26-3.22 (m, 2H), 3.18-3.16 (m, 2H), 2.06-1.97 (m, 2H), 1.83-1.76 (m, 2H), 1.74-1.64 (m, 2H), 1.29 (s, 3H). LCMS [M+H]$^+$=594.2.

Example 59: Compounds 121 and 122

Figure 57:
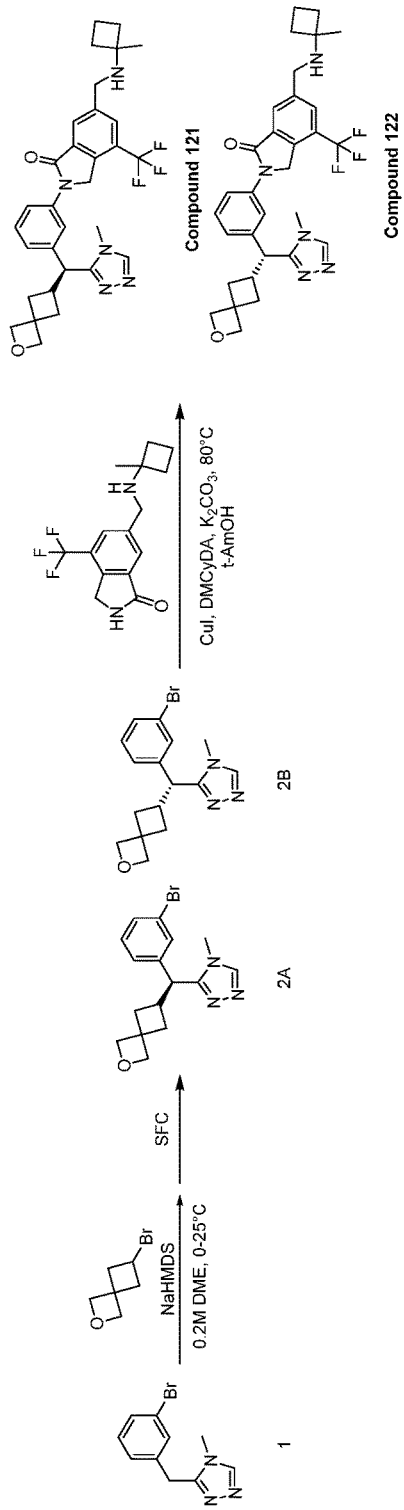

Compound 121 ((S)-2-(3-((4-methyl-4H-1,2,4-triazol-3-yl)(2-oxaspiro[3.3]heptan-6-yl)methyl)phenyl)-6-(((1- methylcyclobutyl)amino)methyl)-4-(trifluoromethyl)isoindolin-1-one), and Compound 122 ((R)-2-(3-((4-methyl-4H-1,2,4-triazol-3-yl)(2-oxaspiro[3.3]heptan-6-yl)methyl)phenyl)-6-(((1-methylcyclobutyl)amino)methyl)-4-(trifluoromethyl)isoindolin-1-one) can be synthesized according to Scheme 57 (FIG. 57).

Intermediate 2A and 2B: ((S)-3-((3-bromophenyl)(2-oxaspiro[3.3]heptan-6-yl)methyl)-4-methyl-4H-1,2,4-triazole, and (R)-3-((3-bromophenyl)(2-oxaspiro[3.3]heptan-6-yl)methyl)-4-methyl-4H-1,2,4-triazole To a solution of 3-(3-bromobenzyl)-4-methyl-4H-1,2,4-triazole (300.0 mg, 1.19 mmol) in 1,2-dimethoxyethane (10 mL) was added sodium bis(trimethylsilyl)amide (1.0 M in tetrahydrofuran, 1.78 mL, 1.78 mmol) at 0° C. The mixture was stirred at 0° C. for 1 h and then 6-bromo-2-oxaspiro[3.3]heptane (0.24 mL, 2.14 mmol) was added. The resulting mixture was stirred at 25° C. for 1 h and quenched with water (10 mL). The solution was extracted with dichloromethane (3×50 mL). The combined organic layers were dried over sodium sulfate and concentrated under vacuum. The residue was purified by silica gel chromatography (mobile phase: methanol/dichloromethane, gradient 0% to 10%) to afford 3-[(3-bromophenyl)-(2-oxaspiro[3.3]heptan-6-yl)methyl]-4-methyl-1,2,4-triazole (400.0 mg, 96% yield) as a yellow oil.

The above product was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: methanol (0.05% DEA); Isocratic: 35% B) with 0.1% ammonium hydroxide) to afford tentatively assigned: (S)-3-((3-bromophenyl)(2-oxaspiro[3.3]heptan-6-yl)methyl)-4-methyl-4H-1,2,4-triazole (Peak 1, Retention time=3.916 min) (150.0 mg, 43% yield) as a yellow oil and (R)-3-((3-bromophenyl)(2-oxaspiro[3.3]heptan-6-yl)methyl)-4-methyl-4H-1,2,4-triazole (Peak 2, Retention time=4.311 min) (150.0 mg, 43% yield) as a yellow oil.

Compound 121

In a glovebox, a mixture of 6-(((1-methylcyclobutyl)amino)methyl)-4-(trifluoromethyl)isoindolin-1-one (42.8 mg, 0.14 mmol), (S)-3-((3-bromophenyl)(2-oxaspiro[3.3]heptan-6-yl)methyl)-4-methyl-4H-1,2,4-triazole (50.0 mg, 0.14 mmol), (1 S,2S)—$N^1,N^2$-dimethyl cyclohexane-1,2-diamine (8.2 mg, 0.06 mmol), potassium carbonate (59.5 mg, 0.43 mmol) and copper(I) iodide (10.9 mg, 0.06 mmol) in tert-amyl alcohol (2 mL was heated at 100° C. in sealed vial for 2 h and concentrated. The residue was first purified by preparative TLC (solvent gradient: 10% methanol in dichloromethane), then by RP-HPLC (water($NH_3H_2O$+$NH_4HCO_3$)/ACN 52% to 82%) to afford (S)-2-(3-((4-methyl-4H-1,2,4-triazol-3-yl)(2-oxaspiro[3.3]heptan-6-yl)methyl)phenyl)-6-(((1-methylcyclobutyl)amino)methyl)-4-(trifluoromethyl)isoindolin-1-one (3.0 mg, 4% yield). $^1$H NMR (400 MHz, DMSO-$d_6$) δ 8.33 (s, 1H), 8.05 (s, 1H), 8.00 (s, 1H), 7.87 (s, 1H), 7.78 (d, J=8.4 Hz, 1H), 7.38 (t, J=8.0 Hz, 1H), 7.00 (d, J=7.6 Hz, 1H), 5.15 (s, 2H), 4.61-4.55 (m, 2H), 4.47-4.42 (m, 2H), 4.12 (d, J=10.8 Hz, 1H), 3.82 (s, 2H), 3.39 (s, 3H), 3.01-2.92 (m, 1H), 2.42-2.37 (m, 1H), 2.11-1.87 (m, 6H), 1.78-1.61 (m, 4H), 1.23 (s, 3H). LCMS [M+H]$^+$=566.

Compound 122

In a glovebox, a mixture of 6-(((1-methylcyclobutyl)amino)methyl)-4-(trifluoromethyl)isoindolin-1-one (47.1 mg, 0.16 mmol), (R)-3-((3-bromophenyl)(2-oxaspiro[3.3]heptan-6-yl)methyl)-4-methyl-4H-1,2,4-triazole (50.0 mg, 0.14 mmol), (1 S,2S)—$N^1,N^2$-dimethyl cyclohexane-1,2-diamine (8.2 mg, 0.06 mmol), potassium carbonate (59.5 mg, 0.43 mmol) and copper(I) iodide (10.9 mg, 0.06 mmol) in 2-methyl-2-butanol (2 mL) was heated at 100° C. in sealed tube for 2 h and concentrated under vacuum. The residue was first purified by preparative TLC (solvent gradient: 10% methanol in dichloromethane), then by RP-HPLC (water($NH_3H_2O$+$NH_4HCO_3$)/ACN 43% to 73%) to afford (R)-2-(3-((4-methyl-4H-1,2,4-triazol-3-yl)(2-oxaspiro[3.3]heptan-6-yl)methyl)phenyl)-6-(((1-methylcyclobutyl)amino)methyl)-4-(trifluoromethyl)isoindolin-1-one (10.0 mg, 12% yield). $^1$H NMR (400 MHz, DMSO-$d_6$) δ 8.33 (s, 1H), 8.04 (s, 1H), 8.00 (s, 1H), 7.87 (s, 1H), 7.78 (d, J=8.0 Hz, 1H), 7.37 (t, J=8.0 Hz, 1H), 7.00 (d, J=7.6 Hz, 1H), 5.15 (s, 2H), 4.61-4.55 (m, 2H), 4.47-4.42 (m, 2H), 4.12 (d, J=10.8 Hz, 1H), 3.82 (s, 2H), 3.39 (s, 3H), 3.01-2.92 (m, 1H), 2.42-2.37 (m, 1H), 2.11-1.84 (m, 6H), 1.77-1.60 (m, 4H), 1.23 (s, 3H). LCMS [M+H]$^+$=566.

Example 60: Compound 123

Figure 58:
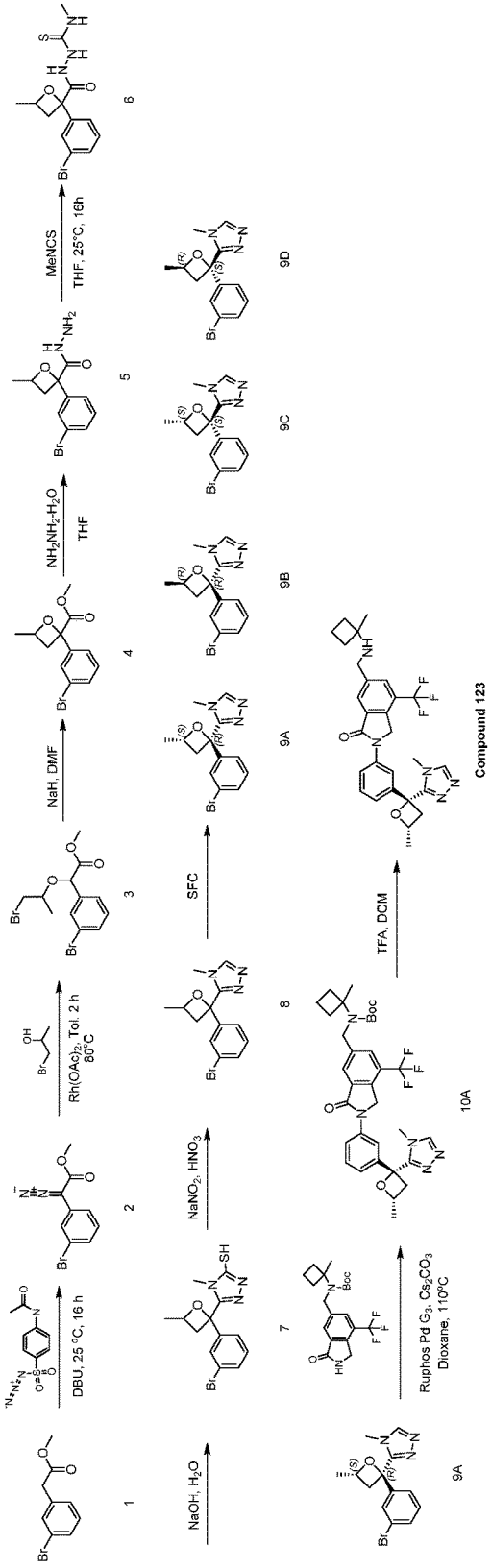

Compound 123 (2-(3-((2R,4S)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one) can be synthesized according to Scheme 58 (FIG. 58).

Intermediate 2: (methyl 2-(3-bromophenyl)-2-diazoacetate

To a solution of methyl 2-(3-bromophenyl)acetate (10.0 g, 43.65 mmol) and 4-acetamidobenzenesulfonyl azide (15.7 g, 65.48 mmol) in acetonitrile (100 mL) was added 1,8-diazabicyclo[5.4.0]undec-7-ene (9.8 mL, 65.48 mmol). The reaction mixture was stirred for 16 h at 25° C. and quenched with saturated aqueous ammonium chloride (100 mL). The mixture was extracted with ethyl acetate (3×100 mL). The combined organic layers were dried over sodium sulfate and concentrated under vacuum. The residue was purified by silica gel chromatography (mobile phase: ethyl acetate/petroleum ether, gradient 0% to 5%) to afford methyl 2-(3-bromophenyl)-2-diazoacetate (10.8 g, 97% yield) as a yellow solid.

Intermediate 3: (methyl 2-(3-bromophenyl)-2-((1-bromopropan-2-yl)oxy)acetate

To a solution of 1-bromopropan-2-ol (1.0 mL, 8.63 mmol) and methyl 2-(3-bromophenyl)-2-diazoacetate (2.0 g, 7.84 mmol) in toluene (20 mL) was added Rhodium(II) acetate dimer (8.6 mg, 0.02 mmol). The reaction mixture was stirred at 80° C. for 1 h then quenched with water (200 mL). The solution was extracted with ethyl acetate (3×200 mL). The combined organic layers were dried over sodium sulfate and concentrated under reduced pressure. The residue was purified by silica gel chromatography (mobile phase: ethyl acetate/petroleum ether, gradient 0% to 5%) to afford methyl 2-(3-bromophenyl)-2-((1-bromopropan-2-yl)oxy)acetate (2.2 g, 77% yield) as a colorless oil.

Intermediate 4: (methyl 2-(3-bromophenyl)-4-methyloxetane-2-carboxylate

Under nitrogen, to a slurry of sodium hydride (60%, 710.3 mg, 17.76 mmol) in N,N-dimethylformamide (30 mL) and tetrahydrofuran (180 mL) was added a solution of methyl 2-(3-bromophenyl)-2-((1-bromopropan-2-yl)oxy)acetate (5.0 g, 13.66 mmol) in N,N-dimethylformamide (30 mL)

dropwise at 0° C. The reaction mixture was stirred at 0° C. for 1 h and at 25° C. for 1 h. The reaction was quenched with saturated aqueous ammonium chloride (30 mL) and water (100 mL). The solution was extracted with ethyl acetate (3×150 mL). The combined organic layers were washed with brine (100 mL), dried over sodium sulfate and concentrated. The residue was purified by silica gel chromatography (mobile phase: ethyl acetate/petroleum ether, gradient 0% to 15%) to afford methyl 2-(3-bromophenyl)-4-methyloxetane-2-carboxylate (800.0 mg, 21% yield) as a yellow oil.

Intermediate 5: (2-(3-bromophenyl)-4-methyloxetane-2-carbohydrazide

A solution of hydrazine hydrate (214.8 mg, 3.65 mmol) and methyl 2-(3-bromophenyl)-4-methyloxetane-2-carboxylate (800.0 mg, 2.81 mmol) in tetrahydrofuran (10 mL) was stirred at 25° C. for 16 h and concentrated under reduce pressure to afford crude 2-(3-bromophenyl)-4-methyl-oxetane-2-carbohydrazide (800.0 mg, 100% yield) as a yellow oil. LCMS [M+H]$^+$=285.1.

Intermediate 6: (2-(2-(3-bromophenyl)-4-methyl-oxetane-2-carbonyl)-N-methylhydrazinecarbothioamide A solution of isothiocyanatomethane (266.7 mg, 3.65 mmol) and 2-(3-bromophenyl)-4-methyloxetane-2-carbohydrazide (800.0 mg, 2.81 mmol) in tetrahydrofuran (10 mL) was stirred at 25° C. for 16 h and concentrated under reduce pressure to afford crude 2-(2-(3-bromophenyl)-4-methyl-oxetane-2-carbonyl)-N-methylhydrazinecarbothioamide (1.0 g, 99% yield) as a yellow oil.

Intermediate 7: (5-(2-(3-bromophenyl)-4-methyl-oxetan-2-yl)-4-methyl-4H-1,2,4-triazole-3-thiol A solution of 2-(2-(3-bromophenyl)-4-methyloxetane-2-carbonyl)-N-methylhydrazinecarbothioamide (1.0 g, 2.79 mmol) in aqueous sodium hydroxide (1.0 M, 26.67 mL, 26.67 mmol) was stirred at 25° C. for 16 h. The mixture was cooled to 0° C. and adjusted to pH=5 with aqueous hydrochloric acid (1 M). The solid was collected by filtration and dried to afford crude 5-(2-(3-bromophenyl)-4-methyloxetan-2-yl)-4-methyl-4H-1,2,4-triazole-3-thiol (949.0 mg, 99% yield) as a yellow solid. LCMS [M+H]$^+$=342.0.

Intermediate 8: (3-(2-(3-bromophenyl)-4-methyl-oxetan-2-yl)-4-methyl-4H-1,2,4-triazole To a solution of 5-(2-(3-bromophenyl)-4-methyloxetan-2-yl)-4-methyl-4H-1,2,4-triazole-3-thiol (900.0 mg, 2.65 mmol) in water (10 mL) and acetonitrile (10 mL) was added sodium nitrite (365.0 mg, 5.29 mmol) and nitric acid (1.0 M, 13.54 mL, 13.54 mmol) at 0° C. The mixture was stirred at 20° C. for 5 h and quenched with saturated aqueous sodium bicarbonate (30 mL). The solution was extracted with dichloromethane (3×30 mL). The combined organic layers were washed with brine (30 mL), dried over sodium sulfate and concentrated. The residue was purified by silica gel chromatography (mobile phase: methanol/dichloromethane, gradient 0% to 5%) to afford 3-(2-(3-bromophenyl)-4-methyloxetan-2-yl)-4-methyl-4H-1,2,4-triazole (300.0 mg, 37% yield) as a brown oil. LCMS [M+H]$^+$=310.1.

Intermediate 9: (3-((2R,4S)-2-(3-bromophenyl)-4-methyloxetan-2-yl)-4-methyl-4H-1,2,4-triazole 3-[2-(3-bromophenyl)-4-methyl-oxetan-2-yl]-4-methyl-1,2,4-triazole (400.0 mg, 1.3 mmol) was purified by chiral SFC (Column=Daicel Chiralpak IG; Column dimensions=250 mm×30 mm×10 μm; Detection wavelength=220 nM; Flow rate=70 mL/min; Mobile phase: A: $CO_2$ B: methanol (0.05% DEA); Isocratic: 25% B) with 0.1% ammonium hydroxide) to afford two tentatively assigned fractions: 4-methyl-3-[rac-(2R)-2-(3-bromophenyl)-4-methyl-oxetan-2-yl]-1,2,4-triazole (Fraction 1, Retention time=2.688 and 2.744 min) (120 mg, 30% yield) and 4-methyl-3-[rac-(2S)-2-(3-bromophenyl)-4-methyl-oxetan-2-yl]-1,2,4-triazole (Fraction 2, Retention time=2.917 and 2.976 min) (84 mg, 21% yield) both as colorless oil.

4-methyl-3-[rac-(2R)-2-(3-bromophenyl)-4-methyl-oxetan-2-yl]-1,2,4-triazole (120.0 mg, 0.39 mmol) was further purified by chiral SFC (Column=Daicel Chiralpak AS; Column dimensions=250 mm×30 mm×10 μm; Detection wavelength=220 nM; Flow rate=60 mL/min; Mobile phase: A: $CO_2$ B: ethanol (0.05% DEA); Isocratic: 25% B) with 0.1% ammonium hydroxide) to afford tentatively assigned: 3-((2R,4S)-2-(3-bromophenyl)-4-methyloxetan-2-yl)-4-methyl-4H-1,2,4-triazole (Peak 1, Retention time=2.465 min) (40 mg, 33% yield) as a colorless oil and 3-((2R,4R)-2-(3-bromophenyl)-4-methyloxetan-2-yl)-4-methyl-4H-1,2,4-triazole (Peak 1, Retention time=2.790 min) (30 mg, 25% yield) as a colorless oil.

4-methyl-3-[rac-(2S)-2-(3-bromophenyl)-4-methyl-oxetan-2-yl]-1,2,4-triazole (84.0 mg, 0.27 mmol) was further purified by chiral SFC (Column=Daicel Chiralpak IC; Column dimensions=250 mm×30 mm×10 μm; Detection wavelength=220 nM; Flow rate=60 mL/min; Mobile phase: A: $CO_2$ B: ethanol (0.05% IPA); Isocratic: 45% B) with 0.1% ammonium hydroxide) to afford tentatively assigned: 3-((2S,4S)-2-(3-bromophenyl)-4-methyloxetan-2-yl)-4-methyl-4H-1,2,4-triazole (Peak 1, Retention time=3.614 min) (40 mg, 48% yield) as a colorless oil and 3-((2S,4R)-2-(3-bromophenyl)-4-methyloxetan-2-yl)-4-methyl-4H-1,2,4-triazole (Peak 2, Retention time=4.473 min) (30 mg, 36% yield) as a colorless oil.

Intermediate 10A: (tert-butyl ((2-(3-((2R,4S)-4-methyl-2-(4-methyl-4H-1,2,4-triazol-3-yl)oxetan-2-yl)phenyl)-3-oxo-7-(trifluoromethyl)isoindolin-5-yl)methyl)(1-methylcyclobutyl)carbamate In a glovebox, a mixture of 3-((2R,4S)-2-(3-bromophenyl)-4-methyloxetan-2-yl)-4-methyl-4H-1,2,4-triazole (40.0 mg, 0.13 mmol), tert-butyl (1-methylcyclobutyl)((3-oxo-7-(trifluoromethyl)isoindolin-5-yl)methyl)carbamate (56.7 mg, 0.14 mmol), dicyclohexyl-phosphino-2',6'-diisopropoxy-1,1'-biphenyl)[2-(2'-amino-1,1'biphenyl)]palladium(II) methanesulfonate (21.7 mg, 0.03 mmol) and cesium carbonate (126.9 mg, 0.39 mmol) in 1,4-dioxane (1 mL) was heated at 110° C. in sealed tube for 3 h and concentrated. The residue was purified by preparative TLC (solvent gradient: 10% methanol in dichloromethane) to afford tert-butyl ((2-(3-((2R,4S)-4-methyl-2-(4-methyl-4H-1,2,4-triazol-3-yl)oxetan-2-yl)phenyl)-3-oxo-7-(trifluoromethyl)isoindolin-5-yl)methyl)(1-methylcyclobutyl)-carbamate (40.0 mg, 49% yield) as a yellow oil.

Compound 123

A mixture of tert-butyl ((2-(3-((2R,4S)-4-methyl-2-(4-methyl-4H-1,2,4-triazol-3-yl)oxetan-2-yl)phenyl)-3-oxo-7-(trifluoromethyl)isoindolin-5-yl)methyl)(1-methylcyclobutyl)-carbamate (40.0 mg, 0.06 mmol) and trifluoroacetic acid (0.2 mL, 2.6 mmol) in dichloro-methane (2 mL) was stirred at 25° C. for 1 h and concentrated under vacuum. The residue was purified by RP-HPLC (0.2% $NH_3H_2O$ in water/ACN 65% to 95%) to afford 2-(3-((2R, 4S)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one (8.7 mg, 26% yield). $^1$H NMR (400 MHz, methanol-d$_4$) δ 8.43 (s, 1H), 8.14 (s, 1H), 8.09 (s, 1H), 8.01 (s, 1H), 7.78 (d, J=8.4 Hz, 1H), 7.51 (t, J=8.0 Hz, 1H), 7.18 (d, J=7.6 Hz, 1H), 5.16 (s, 2H), 5.03-4.95 (m, 1H), 4.02-3.97 (m, 1H), 3.88 (s, 2H), 3.42 (s, 3H), 2.69-2.64 (m, 1H), 2.15-2.07 (m, 2H), 1.92-1.78 (m, 4H), 1.56 (d, J=6.0 Hz, 3H), 1.39 (s, 3H). LCMS [M+H]$^+$=526.3.

Example 61: Compound 124

Figure 59:
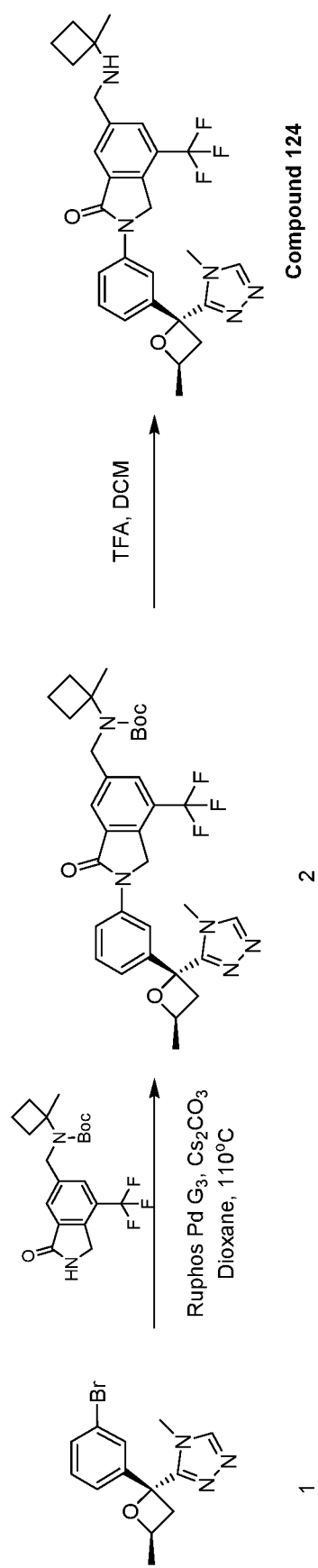

Compound 124 (2-(3-((2R,4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one), can be synthesized according to Scheme 59 (FIG. 59).

Intermediate 2: (tert-butyl ((2-(3-((2R,4R)-4-methyl-2-(4-methyl-4H-1,2,4-triazol-3-yl)oxetan-2-yl)phenyl)-3-oxo-7-(trifluoromethyl)isoindolin-5-yl) methyl)(1-methylcyclobutyl)carbamate In a glovebox, a mixture of 3-((2R,4R)-2-(3-bromophenyl)-4-methyloxetan-2-yl)-4-methyl-4H-1,2,4-triazole (30.0 mg, 0.10 mmol), tert-butyl (1-methylcyclobutyl)((3-oxo-7-(trifluoromethyl)isoindolin-5-yl)methyl)carbamate (42.7 mg, 0.11 mmol), dicyclohexylphosphino-2',6'-diisopropoxy-1,1'-biphenyl)[2-(2'-amino-1,1'biphenyl)]palladium(II) methanesulfonate (16.3 mg, 0.02 mmol) and cesium carbonate (95.2 mg, 0.29 mmol) in 1,4-dioxane (1 mL) was heated at 110° C. for 3 h and concentrated. The residue was purified by preparative TLC (solvent gradient: 10% methanol in dichloromethane) to afford 2-(3-((2R,4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one (30.0 mg, 49% yield) as a yellow oil. LCMS [M+H]$^+$=626.3.
Compound 124

A mixture of tert-butyl ((2-(3-((2R,4R)-4-methyl-2-(4-methyl-4H-1,2,4-triazol-3-yl)oxetan-2-yl)phenyl)-3-oxo-7-(trifluoromethyl)isoindolin-5-yl)methyl)(1-methylcyclobutyl)-carbamate (27.0 mg, 0.04 mmol) and trifluoroacetic acid (0.27 mL, 3.5 mmol) in dichloromethane (1 mL) was stirred at 25° C. for 1 h and concentrated under vacuum. The residue was purified by RP-HPLC (0.2% $NH_3H_2O$ in water/ACN 65% to 95%) to afford 2-(3-((2R, 4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one (4.1 mg, 18% yield). $^1$H NMR (400 MHz, methanol-d$_4$) δ 8.40 (s, 1H), 8.12-8.08 (m, 2H), 8.01 (s, 1H), 7.80 (t, J=6.4 Hz, 1H), 7.53 (t, J=8.0 Hz, 1H), 7.22 (d, J=8.0 Hz, 1H), 5.17 (s, 2H), 5.16-5.10 (m, 1H), 3.87 (s, 2H), 3.84-3.58 (m, 1H), 3.42 (s, 3H), 3.09-3.03 (m, 1H), 2.15-2.07 (m, 2H), 1.91-1.78 (m, 4H), 1.44 (d, J=6.4 Hz, 3H), 1.38 (s, 3H). LCMS [M+H]$^+$=526.3.

Example 62: Compound 125

Figure 60:
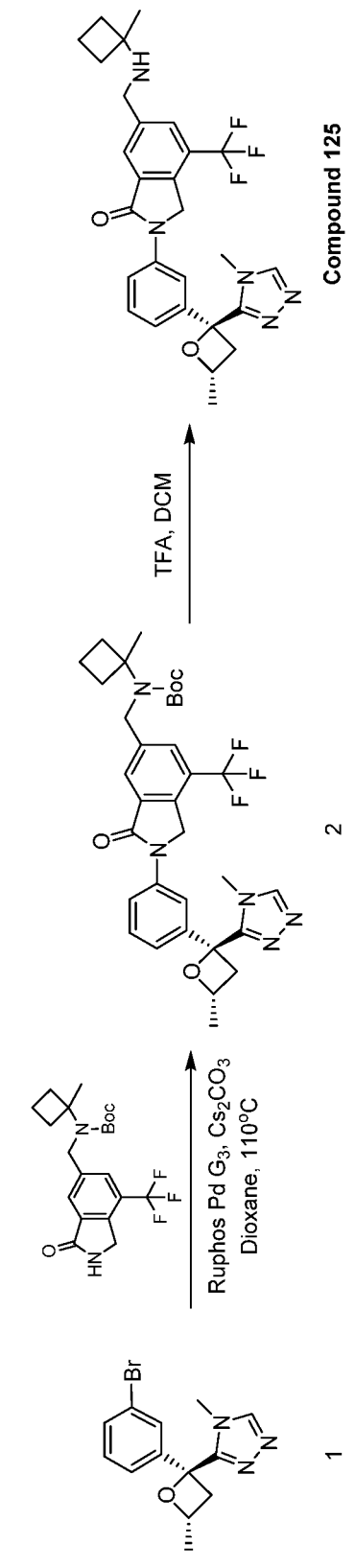

Compound 125 (2-(3-((2S,4S)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one), can be synthesized according to Scheme 60 (FIG. 60).

Intermediate 2: (tert-butyl ((2-(3-((2S,4S)-4-methyl-2-(4-methyl-4H-1,2,4-triazol-3-yl)oxetan-2-yl)phenyl)-3-oxo-7-(trifluoromethyl)isoindolin-5-yl) methyl)(1-methylcyclobutyl)carbamate In a glovebox, a mixture of 3-((2S,4S)-2-(3-bromophenyl)-4-methyloxetan-2-yl)-4-methyl-4H-1,2,4-triazole (20.0 mg, 0.06 mmol), tert-butyl (1-methylcyclobutyl)((3-oxo-7-(trifluoromethyl)isoindolin-5-yl)methyl)carbamate (28.4 mg, 0.07 mmol), dicyclohexyl-phosphino-2',6'-diisopropoxy-1,1'-biphenyl)[2-(2'-amino-1,1'biphenyl)]palladium(II) methanesulfonate (10.9 mg, 0.01 mmol) and cesium carbonate (63.4 mg, 0.19 mmol) in 1,4-dioxane (1 mL) was heated at 110° C. in sealed tube for 3 h and concentrated. The residue was purified by preparative TLC (solvent gradient: 10% methanol in dichloromethane) to afford tert-butyl ((2-(3-((2S,4S)-4-methyl-2-(4-methyl-4H-1,2,4-triazol-3-yl)oxetan-2-yl)phenyl)-3-oxo-7-(trifluoromethyl)isoindolin-5-yl)methyl)(1-methylcyclobutyl)carbamate (20.0 mg, 49% yield) as a colorless solid. LCMS [M+H]$^+$=626.3.

b. Compound 125

A mixture of tert-butyl ((2-(3-((2S,4S)-4-methyl-2-(4-methyl-4H-1,2,4-triazol-3-yl)oxetan-2-yl)phenyl)-3-oxo-7-(trifluoromethyl)isoindolin-5-yl)methyl)(1-methylcyclobutyl)-carbamate (30.0 mg, 0.05 mmol) and trifluoroacetic acid (0.3 mL, 3.89 mmol) in dichloromethane (1 mL) was stirred at 25° C. for 1 h and concentrated under vacuum. The residue was purified by RP-HPLC (0.2% $NH_3H_2O$ in water/ACN 65% to 95%) to afford 2-(3-((2S, 4S)-4-methyl-2-(4-methyl-4H-1,2,4-triazol-3-yl)oxetan-2-yl)phenyl)-6-(((1-methyl-cyclobutyl)amino)methyl)-4-(trifluoromethyl)isoindolin-1-one (4.4 mg, 17% yield). $^1$H NMR (400 MHz, methanol-d$_4$) δ 8.41 (s, 1H), 8.12 (s, 1H), 8.09 (s, 1H), 8.01 (s, 1H), 7.81 (d, J=7.2 Hz, 1H), 7.53 (t, J=8.0 Hz, 1H), 7.22 (d, J=8.0 Hz, 1H), 5.18 (s, 2H), 5.14 (d, J=7.2 Hz, 1H), 3.87 (s, 2H), 3.63-3.58 (m, 1H), 3.42 (s, 3H), 3.09-3.03 (m, 1H), 2.16-2.05 (m, 2H), 1.91-1.76 (m, 4H), 1.44 (d, J=6.0 Hz, 3H), 1.38 (s, 3H).

Example 63: Compound 126

Figure 61:
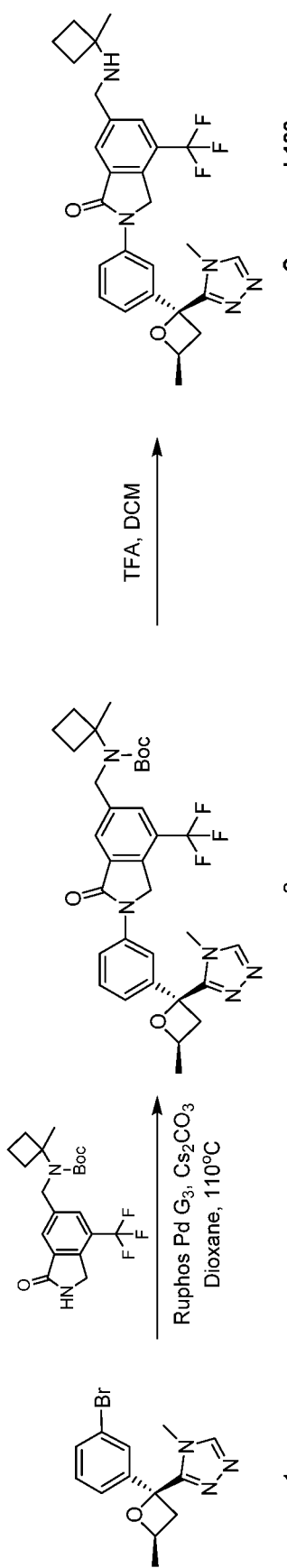

Compound 126 (2-(3-((2S,4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one), can be synthesized according to Scheme 61 (FIG. 61).

Intermediate 2: (tert-butyl ((2-(3-((2S,4R)-4-methyl-2-(4-methyl-4H-1,2,4-triazol-3-yl)oxetan-2-yl)phenyl)-3-oxo-7-(trifluoromethyl)isoindolin-5-yl) methyl)(1-methylcyclobutyl)carbamate In a glovebox, a mixture of 3-((2S,4R)-2-(3-bromophenyl)-4-methyloxetan-2-yl)-4-methyl-4H-1,2,4-triazole (30.0 mg, 0.10 mmol), tert-butyl (1-methylcyclobutyl)((3-oxo-7-(trifluoromethyl)isoindolin-5-yl)methyl)carbamate (42.7 mg, 0.11 mmol), dicyclohexyl-phosphino-2',6'-diisopropoxy-1,1'-biphenyl)[2-(2'-amino-1,1'biphenyl)]palladium(II) methane-sulfonate (16.3 mg, 0.02 mmol) and cesium carbonate (95.2 mg, 0.29 mmol) in 1,4-dioxane (1 mL) was heated at 110° C. for 3 h and concentrated. The residue was purified by preparative TLC (solvent gradient: 10% methanol in dichloromethane) to afford tert-butyl ((2-(3-((2S,4R)-4-methyl-2-(4-methyl-4H-1,2,4-triazol-3-yl)

oxetan-2-yl)phenyl)-3-oxo-7-(trifluoromethyl)isoindolin-5-yl)methyl)(1-methylcyclobutyl)carbamate (34.0 mg, 56% yield) as a yellow oil.

Compound 126

A mixture of tert-butyl ((2-(3-((2S,4R)-4-methyl-2-(4-methyl-4H-1,2,4-triazol-3-yl)oxetan-2-yl)phenyl)-3-oxo-7-(trifluoromethyl)isoindolin-5-yl)methyl)(1-methylcyclobutyl)carbamate (34.0 mg, 0.06 mmol) and trifluoroacetic acid (0.35 mL, 4.54 mmol) in dichloromethane (1 mL) was stirred at 25° C. for 1 h and concentrated under vacuum. The residue was purified by RP-HPLC (0.2% NH$_3$H$_2$O in water/ACN 65% to 95%) to afford 2-(3-((2S,4R)-4-methyl-2-(4-methyl-4H-1,2,4-triazol-3-yl)oxetan-2-yl)phenyl)-6-(((1-methylcyclobutyl)amino)methyl)-4-(trifluoromethyl)isoindolin-1-one (9.2 mg, 31% yield). $^1$H NMR (400 MHz, methanol-d$_4$) δ 8.44 (s, 1H), 8.15 (s, 1H), 8.09 (s, 1H), 8.02 (s, 1H), 7.78 (d, J=7.8 Hz, 1H), 7.51 (t, J=8.4 Hz, 1H), 7.17 (d, J=8.5 Hz, 1H), 5.17 (s, 2H), 5.01-4.95 (m, 2H), 4.02-3.96 (m, 1H), 3.88 (s, 2H), 3.42 (s, 3H), 2.69-2.64 (m, 1H), 2.11 (d, J=9.0 Hz, 2H), 1.91-1.79 (m, 4H), 1.56 (d, J=6.0 Hz, 3H), 1.39 (s, 3H). LCMS [M+H]$^+$=526.3.

Example 64: Compounds 127, 128, 129, 130

Figure 62:
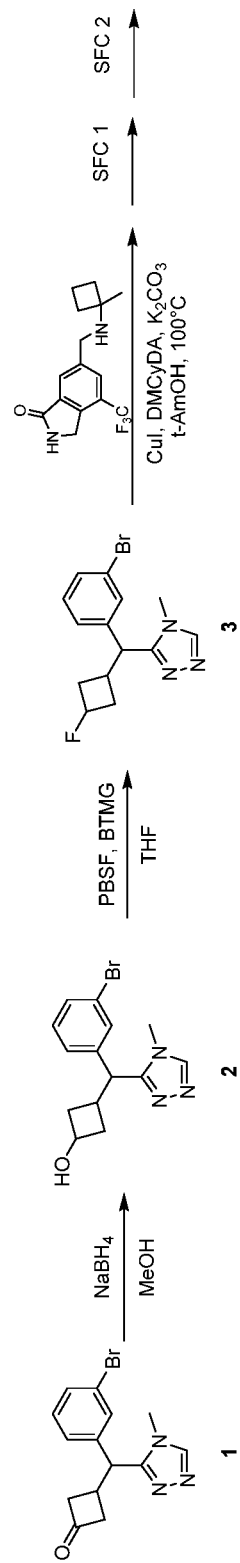

Compound 127 (2-(3-((S)-((1r,3S)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one),
Compound 128 (2-(3-((S)-((1s,3R)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one),
Compound 129 (2-(3-((R)-((1r,3R)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one),
and Compound 130 (2-(3-((R)-((1s,3S)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 62 (FIG. 62).

Intermediate 2: (3-((3-bromophenyl)(4-methyl-4H-1,2,4-triazol-3-yl)methyl)cyclobutanol To a solution of 3-((3-bromophenyl)(4-methyl-4H-1,2,4-triazol-3-yl)methyl)cyclobutanone (1.6 g, 4.99 mmol) in methanol (20 mL) was added sodium borohydride (450 mg, 2.38 mmol). The mixture was stirred at 25° C. for 2 h then quenched with saturated aqueous ammonium chloride (20 mL), extracted with dichloromethane (3×50 mL). The combined organic layers were washed with brine (50 mL), dried over with sodium sulfate, filtered and concentrated to dryness. The residue was purified by silica gel chromatography (mobile phase: methanol/dichloromethane, gradient 0% to 10%) to afford 3-((3-bromophenyl)(4-methyl-4H-1,2,4-triazol-3-yl)methyl)cyclobutanol (1.1 g, 68% yield) as a white solid.

Intermediate 3: (3-((3-bromophenyl)(3-fluorocyclobutyl)methyl)-4-methyl-4H-1,2,4-triazole To a solution of 3-((3-bromophenyl)(4-methyl-4H-1,2,4-triazol-3-yl)methyl)cyclobutanol (850 mg, 2.63 mmol) and 2-tert-butyl-1,1,3,3-tetramethylguanidine (813 mg, 4.74 mmol) in tetrahydrofuran (20 mL) was added perfluoro-1-butanesulfonyl fluoride (1.2 g, 3.95 mmol) at 25° C. The mixture was stirred for 1 h then diluted with water (15 mL), extracted with ethyl acetate (3×40 mL). The combined organic layers were washed with brine (2×20 mL), dried over sodium sulfate and concentrated to dryness. The residue was purified by silica gel chromatography (mobile phase: methanol/dichloro-methane, gradient 0% to 10%) to afford 3-((3-bromophenyl)(3-fluorocyclobutyl)methyl)-4-methyl-4H-1,2,4-triazole (700 mg, 82% yield) as a yellow oil.

Compounds 127, 128, 129, 130

In a glove box, a mixture of 3-((3-bromophenyl)(3-fluorocyclobutyl)methyl)-4-methyl-4H-1,2,4-triazole (130 mg, 2.15 mmol), 6-(((1-methylcyclobutyl)amino)methyl)-4-(trifluoromethyl)isoindolin-1-one (708 mg, 2.37 mmol), copper (I) iodide (164 mg, 0.86 mmol), (1S,2S)—N$^1$,N$^2$-dimethylcyclohexane-1,2-diamine (122 mg, 0.86 mmol) and potassium carbonate (895 mg, 6.47 mmol) in tert-amyl alcohol (20 mL) was heated at 100° C. in sealed vial for 2 h then concentrated to dryness. The residue was purified by silica gel chromatography (mobile phase: methanol/dichloromethane, gradient 0% to 10%) to afford a crude product which was purified by RP-HPLC (0.2% NH$_3$·H$_2$O in water/ACN 50% to 80%) to give 2-(3-((3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one (550 mg, 47% yield).

The above mixture was purified by chiral SFC (Column=Daicel Chiralpak IG; Column dimensions=250 mm×30 mm×10 μm; Detection wavelength=220 nm; Flow rate=80 mL/min; Mobile phase: A: CO$_2$ B: ethanol (0.05% DEA); Isocratic: 50% B) with 0.1% ammonium hydroxide) to afford product A and product B.

The product A was further separated by chiral SFC (Column=Daicel Chiralpak IG; Column dimensions=250 mm×30 mm×10 μm; Detection wavelength=220 nm; Flow rate=80 mL/min; Mobile phase: A: CO$_2$ B: ethanol (0.05% DEA); Isocratic: 45% B) with 0.1% ammonium hydroxide) to afford structure tentatively:

2-(3-((S)-((1r,3S)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=4.253 min) (15.0 mg, 6% yield). $^1$H NMR (400 MHz, methanol-d$_4$) δ 8.38 (s, 1H), 8.17 (s, 1H), 8.10 (s, 1H), 7.85 (s, 1H), 7.78 (d, J=8.0 Hz, 1H), 7.46 (t, J=8.0 Hz, 1H), 7.13 (d, J=8.0 Hz, 1H), 5.19 (s, 2H), 4.99-4.82 (m, 1H), 4.28 (d, J=10.4 Hz, 1H), 4.16 (s, 2H), 3.51 (s, 3H), 2.81-2.61 (m, 2H), 2.37-2.26 (m, 3H), 2.09-1.89 (m, 6H), 1.56 (s, 3H). LCMS [M+H]$^+$=542.3.

and 2-((1r,3r)-3-(4-methyl-4H-1,2,4-triazol-3-yl)-3-(3-(6-(((1-methylcyclobutyl)amino)methyl)-1-oxo-4-(trifluoromethyl)isoindolin-2-yl)phenyl)cyclobutyl)acetonitrile (Peak 2, retention time=5.196 min) (150.0 mg, 62% yield). $^1$H NMR (400 MHz, methanol-d$_4$) δ 8.36 (s, 1H), 8.08 (s, 1H), 8.00 (s, 1H), 7.88 (t, J=1.6 Hz, 1H), 7.77 (dd, J=1.6, 8.0 Hz, 1H), 7.44 (t, J=7.6 Hz, 1H), 7.11 (d, J=7.6 Hz, 1H), 5.29-5.21 (m, 0.5H), 5.14 (s, 2H), 5.11-5.07 (m, 0.5H), 4.26 (d, J=11.2 Hz, 1H), 3.86 (s, 2H), 3.52 (s, 3H), 3.39-3.36 (m, 1H), 2.61-2.46 (m, 1H), 2.34-2.08 (m, 5H), 1.91-1.75 (m, 4H), 1.38 (s, 3H). LCMS [M+H]$^+$=542.3.

The product B was further purified by chiral SFC (Column=Daicel Chiralpak IG; Column dimensions=250 mm×30 mm×10 μm; Detection wavelength=220 nm; Flow rate=80 mL/min; Mobile phase: A: CO$_2$ B: ethanol (0.05% DEA); Isocratic: 45% B) with 0.1% ammonium hydroxide) to afford structure tentatively:

2-(3-((R)-((1r,3R)-3-fluorocyclobutyl)(4-methyl-4H-1,2,4-triazol-3-yl)methyl)phenyl)-6-(((1-methylcyclobutyl)

amino)methyl)-4-(trifluoromethyl)isoindolin-1-one (Peak 1, retention time=3.090 min) (30 mg, 12% yield). $^1$H NMR (400 MHz, methanol-d$_4$) δ 8.37 (s, 1H), 8.08 (s, 1H), 8.00 (s, 1H), 7.85 (s, 1H), 7.81-7.73 (m, 1H), 7.44 (t, J=7.6 Hz, 1H), 7.10 (d, J=7.6 Hz, 1H), 5.13 (s, 2H), 5.02-4.94 (m, 0.5H), 4.82-4.80 (m, 0.5H), 4.27 (d, J=10.4 Hz, 1H), 3.86 (s, 2H), 3.51 (s, 3H), 2.79-2.63 (m, 2H), 2.33-2.24 (m, 1H), 2.14-2.04 (m, 3H), 1.97-1.76 (m, 5H), 1.38 (s, 3H). LCMS [M+H]$^+$=542.3.

2-(3-((R)-((1s,3S)-3-fluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=3.767 min) (150.0 mg, 62% yield). $^1$H NMR (400 MHz, methanol-d$_4$) δ 8.36 (s, 1H), 8.08 (s, 1H), 8.00 (s, 1H), 7.88-7.87 (m, 1H), 7.78-7.76 (m, 1H), 7.44 (t, J=7.6 Hz, 1H), 7.11 (d, J=7.6 Hz, 1H), 5.28-5.21 (m, 0.5H), 5.14 (s, 2H), 5.11-5.06 (m, 0.5H), 4.26 (d, J=11.6 Hz, 1H), 3.86 (s, 2H), 3.52 (s, 3H), 3.40-3.36 (m, 1H), 2.61-2.47 (m, 1H), 2.29-2.06 (m, 5H), 1.92-1.76 (m, 4H), 1.38 (s, 3H). LCMS [M+H]$^+$=542.3.

Example 65: Compounds 131, 132, 133, 134

Figure 63:
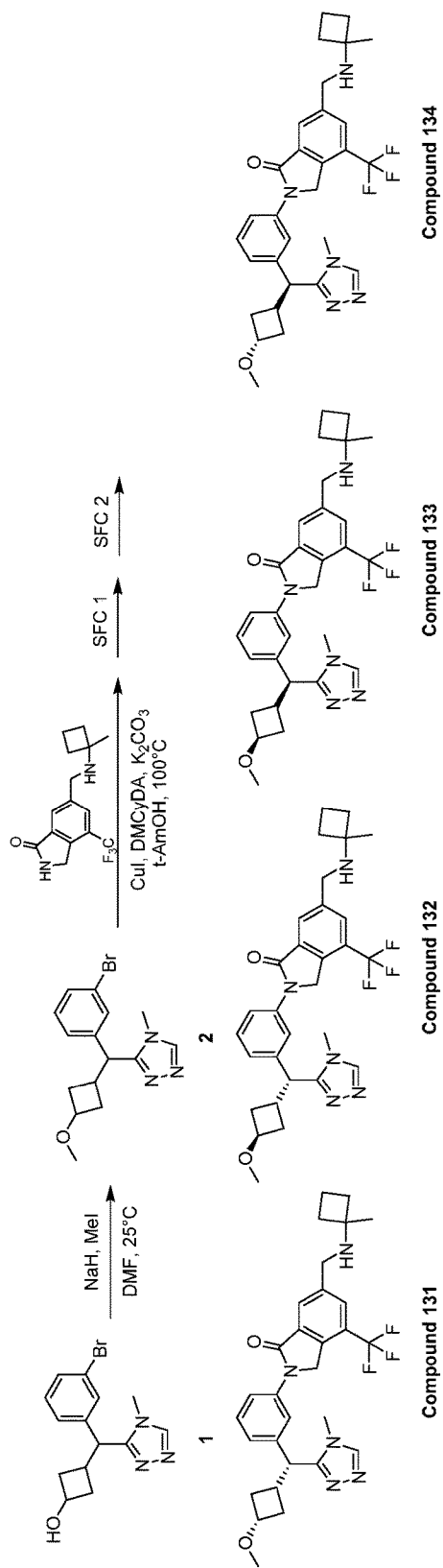

Compound 131 (2-(3-((R)-((1r,3R)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one),
Compound 132 (2-(3-((R)-((1s,3S)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one),
Compound 133 (2-(3-((S)-((1r,3S)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one), and
Compound 134 (2-(3-((S)-((1s,3R)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 63 (FIG. 63).

Intermediate 2: (3-((3-bromophenyl)(3-methoxycyclobutyl)methyl)-4-methyl-4H-1,2,4-triazole To a solution of 3-((3-bromophenyl)(4-methyl-4H-1,2,4-triazol-3-yl)methyl)-cyclobutanol (400 mg, 1.24 mmol) in N,N-dimethylformamide (2 mL) was added sodium hydride (60%, 74.5 mg, 1.50 mmol) at 25° C. and the mixture was stirred for 1 h. iodomethane (0.14 mL, 2.23 mmol) was added and the mixture was stirred for another 1 h then quenched with water (5 mL), concentrated to dryness. The residue was purified by silica gel chromatography (mobile phase: methanol/dichloromethane, gradient 0% to 10%) to afford 3-((3-bromophenyl)(3-methoxycyclobutyl)methyl)-4-methyl-4H-1,2,4-triazole (270 mg, 65% yield) as a yellow solid.
Compounds 131, 132, 133, 134
In a glove box, a mixture of 3-((3-bromophenyl)(3-methoxycyclobutyl)methyl)-4-methyl-4H-1,2,4-triazole (270 mg, 0.81 mmol), 6-(((1-methylcyclobutyl)amino)methyl)-4-(trifluoromethyl)isoindolin-1-one (264 mg, 0.88 mmol), copper(I) iodide (61 mg, 0.40 mmol), (1S,2S)—N$^1$,N$^2$-dimethylcyclohexane-1,2-diamine (46 mg, 0.40 mmol) and potassium carbonate (334 mg, 2.42 mmol) in tert-amyl alcohol (6 mL) was heated at 100° C. in sealed vial for 2 h and concentrated to dryness. The residue was purified by silica gel chromatography (mobile phase: methanol/dichloromethane, gradient 0% to 10%) to afford a crude product which was purified by RP-HPLC (0.2% NH$_3$·H$_2$O in water/ACN 55% to 85%) to afford 2-(3-((3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (150 mg, 34% yield).

The above mixture was purified by chiral SFC (Column=Daicel Chiralpak OD; Column dimensions=250 mm×30 mm×10 μm; Detection wavelength=220 nm; Flow rate=100 mL/min; Mobile phase: A: CO$_2$ B: ethanol (0.05% DEA); Isocratic: 25% B) with 0.1% ammonium hydroxide) to afford product A and product B.

The product A was further separation by chiral SFC (Column=Daicel Chiralpak AS; Column dimensions=250 mm×30 mm×10 μm; Detection wavelength=220 nm; Flow rate=150 mL/min; Mobile phase: A: CO$_2$ B: ethanol; Isocratic: 25% B) with 0.1% ammonium hydroxide) to afford structure tentatively:

2-(3-((R)-((1r,3R)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=2.536 min) (26.3 mg, 41% yield). $^1$H NMR (400 MHz, methanol-d$_4$) δ 8.37 (s, 1H), 8.09 (s, 1H), 8.01 (s, 1H), 7.84 (d, J=2.4 Hz, 1H), 7.77 (dd, J=2.4, 8.4 Hz, 1H), 7.43 (t, J=8.0 Hz, 1H), 7.09 (d, J=8.0 Hz, 1H), 5.14 (s, 2H), 4.19 (d, J=10.4 Hz, 1H), 3.86 (s, 2H), 3.85-3.81 (m, 1H), 3.51 (s, 3H), 3.22 (s, 3H), 2.81-2.70 (m, 1H), 2.60-2.50 (m, 1H), 2.25-2.20 (m, 1H), 2.20-2.00 (m, 2H), 1.90-1.85 (m, 2H), 1.80-1.77 (m, 3H), 1.70-1.55 (m, 1H), 1.38 (s, 3H). LCMS [M+H]$^+$=554.4.

and 2-(3-((R)-((1s,3S)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=2.789 min) (21.1 mg, 30% yield). $^1$H NMR (400 MHz, methanol-d$_4$) δ 8.36 (s, 1H), 8.09 (s, 1H), 8.01 (s, 1H), 7.88 (s, 1H), 7.77 (d, J=8.4 Hz, 1H), 7.44 (t, J=7.6 Hz, 1H), 7.12 (d, J=7.6 Hz, 1H), 5.15 (s, 2H), 4.27 (d, J=11.2 Hz, 1H), 4.10-4.06 (m, 1H), 3.87 (s, 2H), 3.53 (s, 3H), 3.22 (s, 3H), 2.35-2.26 (m, 1H), 2.20-2.05 (m, 3H), 2.05-2.00 (m, 2H), 2.00-1.75 (m, 5H), 1.38 (s, 3H). LCMS [M+H]$^+$=554.4.

The product B was further purified by chiral SFC (Column=Daicel Chiralpak AS; Column dimensions=250 mm×30 mm×10 μm; Detection wavelength=220 nm; Flow rate=150 mL/min; Mobile phase: A: CO$_2$ B: ethanol; Isocratic: 25% B) with 0.1% ammonium hydroxide) to afford structure tentatively:

2-(3-((S)-((1r,3S)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=2.641 min) (31.32 mg, 44% yield). $^1$H NMR (400 MHz, methanol-d$_4$) δ 8.37 (s, 1H), 8.09 (s, 1H), 8.01 (s, 1H), 7.85 (s, 1H), 7.84 (d, J=2.0 Hz, 1H), 7.43 (t, J=8.0 Hz, 1H), 7.09 (d, J=8.0 Hz, 1H), 5.14 (s, 2H), 4.20 (d, J=10.8 Hz, 1H), 3.86 (s, 2H), 3.85-3.79 (m, 1H), 3.51 (s, 3H), 3.22 (s, 3H), 2.85-2.75 (m, 1H), 2.65-2.55 (m, 1H), 2.30-2.20 (m, 1H), 2.20-2.00 (m, 2H), 1.90-1.76 (m, 5H), 1.70-1.60 (m, 1H), 1.38 (s, 3H). LCMS [M+H]$^+$=554.4.

and 2-(3-((S)-((1s,3R)-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=2.841 min) (15.1 mg, 21% yield). 1H NMR (400 MHz, methanol-d$_4$) δ 8.36 (s, 1H), 8.09 (s, 1H), 8.01 (s, 1H), 7.89 (s, 1H), 7.77 (d, J=9.2 Hz, 1H), 7.44 (t, J=8.0 Hz, 1H), 7.12 (d, J=7.6 Hz, 1H), 5.15 (s, 2H), 4.27 (d, J=11.2 Hz, 1H), 4.10-4.06 (m, 1H), 3.87 (s, 2H), 3.53 (s, 3H), 3.22 (s, 3H), 2.35-2.25 (m, 1H), 2.20-2.10 (m, 3H), 2.10-1.95 (m, 2H), 1.90-1.70 (m, 5H), 1.39 (s, 3H). LCMS [M+H]$^+$=554.4.

Example 66: Compounds 135, 136

Figure 64:
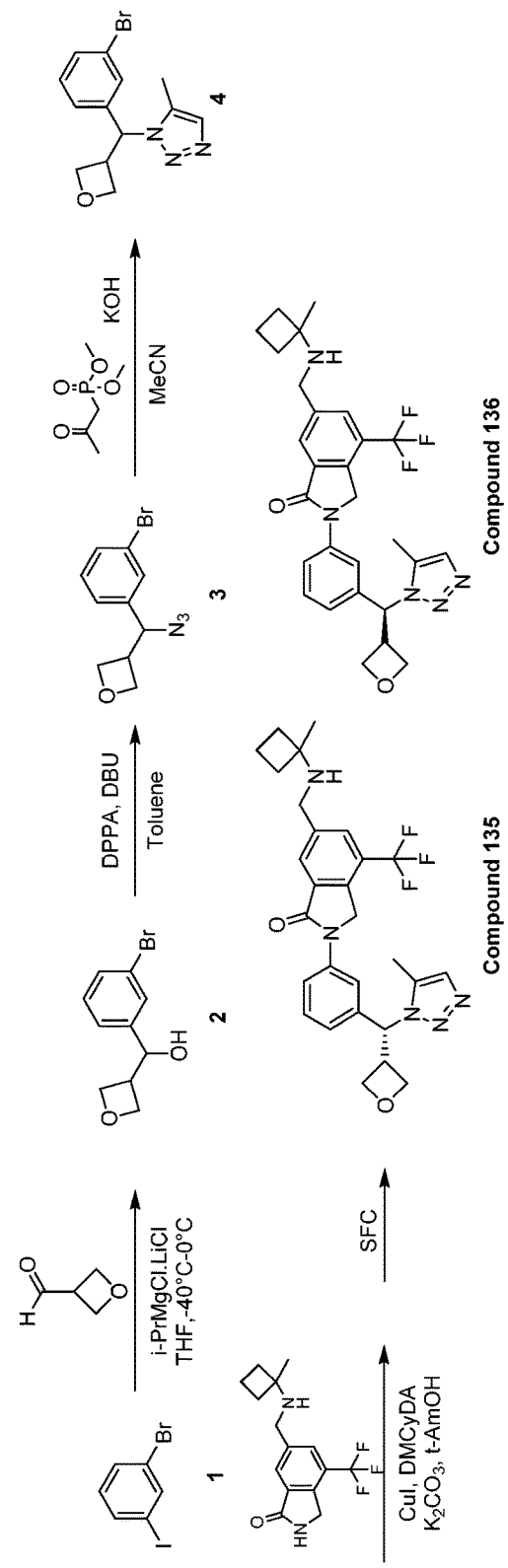

Compound 135 ((R)-2-(3-((5-methyl-1H-1,2,3-triazol-1-yl)(oxetan-3-yl)methyl)phenyl)-6-(((1-methylcyclobutyl)amino)methyl)-4-(trifluoromethyl)isoindolin-1-one) and Compound 136 ((S)-2-(3-((5-methyl-1H-1,2,3-triazol-1-yl)(oxetan-3-yl)methyl)phenyl)-6-(((1-methylcyclobutyl)amino)methyl)-4-(trifluoromethyl)isoindolin-1-one), can be synthesized according to Scheme 64 (FIG. 64).

Intermediate 2: ((3-bromophenyl)(oxetan-3-yl)methanol

To a mixture of 1-bromo-3-iodobenzene (1.64 g, 5.80 mmol) in tetrahydrofuran (25 mL) was added isopropylmagnesium chloride lithium chloride complex (4.02 mL, 5.23 mmol, 1.3 M in tetrahydrofuran) in one portion at −40° C. under nitrogen protection. The mixture was stirred at 0° C. for 30 min, then oxetane-3-carbaldehyde (0.5 g, 5.81 mmol) in THF (5 mL) was added at 0° C. and the resulting mixture was stirred for another 30 min. The mixture was quenched with saturated aqueous ammonium chloride (50 mL), extracted with ethyl acetate (3×50 mL), combined the organic layers and washed with brine (100 mL), dried over anhydrous sodium sulfate, filtered and concentrated. The residue was purified by silica gel chromatography (mobile phase: methyl tert-butyl ether/petroleum ether, gradient 0% to 38%) to give (3-bromophenyl)(oxetan-3-yl)methanol (1.1 g, 78% yield) as a white solid. $^1$H NMR (400 MHz, CDCl$_3$) δ 7.50 (s, 1H), 7.44 (dd, J=2.0, 8.8 Hz, 1H), 7.27-7.20 (m, 2H), 5.00-4.90 (m, 1H), 4.84-4.79 (m, 1H), 4.75-4.73 (m, 1H), 4.66-4.62 (m, 1H), 4.44 (t, J=6.4 Hz, 1H), 3.34-3.22 (m, 1H).

Intermediate 3: (3-(azido(3-bromophenyl)methyl)oxetane

To a mixture of (3-bromophenyl)(oxetan-3-yl)methanol (1.4 g, 5.76 mmol) in toluene (20 mL) was added diphenyl azidophosphate (1.90 g, 6.91 mmol, CAS: 26386-88-9) and 1,8-diazabicyclo[5.4.0]undec-7-ene (1.05 g, 6.91 mmol) in one portion at 0° C. under nitrogen protection. The mixture was stirred at 0° C. for 2 h then heated to 70° C. and stirred for another 16 h. The reaction mixture was quenched with water (50 mL), extracted with ethyl acetate (3×50 mL), combined the organic phase and washed with brine (50 mL), dried over anhydrous sodium sulfate, filtered and concentrated to dryness. The residue was purified by silica gel chromatography (mobile phase: methyl tert-butyl ether/petroleum ether, gradient 0% to 25%) to give 3-(azido(3-bromophenyl)methyl)oxetane (1.5 g, 97% yield) as a white solid.

Intermediate 4: (1-((3-bromophenyl)(oxetan-3-yl)methyl)-5-methyl-1H-1,2,3-triazole To a mixture of 3-(azido(3-bromophenyl)methyl)oxetane (1.5 g, 5.59 mmol) in acetonitrile (25 mL) was added potassium hydroxide (784.7 mg, 13.99 mmol) and dimethyl (2-oxopropyl)phosphonate (929.3 mg, 5.59 mmol) at 20° C. The mixture was stirred at 60° C. for 16 h then quenched with water (50 mL), extracted with ethyl acetate (3×50 mL), the combined the organic layers was washed with brine (100 mL), dried over sodium sulfate. Filtered and concentrated to dryness, the residue was purified by silica gel chromatography (mobile phase: methyl tert-butyl ether/petroleum ether, gradient 0% to 80%) to give 1-((3-bromophenyl)(oxetan-3-yl)methyl)-5-methyl-1H-1,2,3-triazole (0.8 g, 46% yield) as a white solid. $^1$H NMR (400 MHz, CDCl$_3$) δ 7.47 (s, 1H), 7.46 (s, 1H), 7.38 (s, 1H), 7.23 (t, J=8.0 Hz, 1H), 7.20-7.16 (m, 1H), 5.61 (d, J=10.4 Hz, 1H), 4.96-4.94 (m, 1H), 4.78 (t, J=7.2 Hz, 1H), 4.48 (t, J=6.4 Hz, 1H), 4.30-4.25 (m, 2H), 2.18 (s, 3H).

Compounds 135, 136

In a glove box, a mixture of 1-((3-bromophenyl)(oxetan-3-yl)methyl)-5-methyl-1H-1,2,3-triazole (200 mg, 0.65 mmol), 6-(((1-methylcyclobutyl)amino)methyl)-4-(trifluoromethyl)isoindolin-1-one (212.9 mg, 0.71 mmol), copper (I) iodide (49 mg, 0.26 mmol), (1S,2S)—N$^1$,N$^2$-dimethylcyclohexane-1,2-diamine (37 mg, 0.26 mmol) and potassium carbonate (269 mg, 1.95 mmol) in tert-amyl alcohol (4 mL) was heated at 100° C. in sealed vial for 2 h and concentrated to dryness. The residue was purified by RP-HPLC (0.2% NH$_4$HCO$_3$ in water/ACN 30% to 70%) to afford 2-(3-((5-methyl-1H-1,2,3-triazol-1-yl)(oxetan-3-yl)methyl)phenyl)-6-(((1-methylcyclobutyl)amino)methyl)-4-(trifluoromethyl)isoindolin-1-one (140 mg, 41% yield).

The above product was further separation by chiral SFC (Column=Daicel Chiralpak AD; Column dimensions=250 mm×30 mm×10 μm; Detection wavelength=220 nm; Flow rate=150 mL/min; Mobile phase: A: CO$_2$ B: ethanol; Isocratic: 50% B) with 0.1% ammonium hydroxide) to afford structure tentatively:

(R)-2-(3-((5-methyl-1H-1,2,3-triazol-1-yl)(oxetan-3-yl)methyl)phenyl)-6-(((1-methylcyclobutyl)amino)methyl)-4-(trifluoromethyl) isoindolin-1-one (Peak 1, retention time=1.344 min) (36 mg, 26% yield). $^1$H NMR (400 MHz, methanol-d$_4$) δ 8.09 (s, 1H), 8.01 (d, J=2.8 Hz, 2H), 7.81 (dd, J=1.2, 8.0 Hz, 1H), 7.52 (s, 1H), 7.48 (t, J=8.0 Hz, 1H), 7.12 (d, J=7.6 Hz, 1H), 6.08 (d, J=10.0 Hz, 1H), 5.14 (s, 2H), 4.90-4.88 (m, 1H), 4.77-4.75 (m, 1H), 4.74-4.69 (m, 1H), 4.47-4.42 (m, 1H), 4.41-4.32 (m, 1H), 3.86 (s, 2H), 2.25 (s, 3H), 2.16-2.04 (m, 2H), 1.93-1.85 (m, 2H), 1.85-1.73 (m, 2H), 1.38 (s, 3H). LCMS [M+H]$^+$=526.4.

and (S)-2-(3-((5-methyl-1H-1,2,3-triazol-1-yl)(oxetan-3-yl)methyl)phenyl)-6-(((1-methylcyclobutyl)amino)methyl)-4-(trifluoro-methyl)isoindolin-1-one (Peak 2, retention time=1.709 min) (50 mg, 36% yield). $^1$H NMR (400 MHz, methanol-d$_4$) δ 8.09 (s, 1H), 8.04-7.98 (m, 2H), 7.80 (dd, J=1.2, 8.4 Hz, 1H), 7.52 (s, 1H), 7.48 (t, J=8.0 Hz, 1H), 7.12 (d, J=7.6 Hz, 1H), 6.08 (d, J=10.4 Hz, 1H), 5.14 (s, 2H), 4.91-4.87 (m, 1H), 4.78-4.73 (m, 1H), 4.72-4.67 (m, 1H), 4.46-4.42 (m, 1H), 4.41-4.32 (m, 1H), 3.86 (s, 2H), 2.25 (s, 3H), 2.15-2.04 (m, 2H), 1.93-1.84 (m, 2H), 1.84-1.73 (m, 2H), 1.38 (s, 3H). LCMS [M+H]$^+$=526.3.

Example 67: Compounds 137, 138

Figure 65:
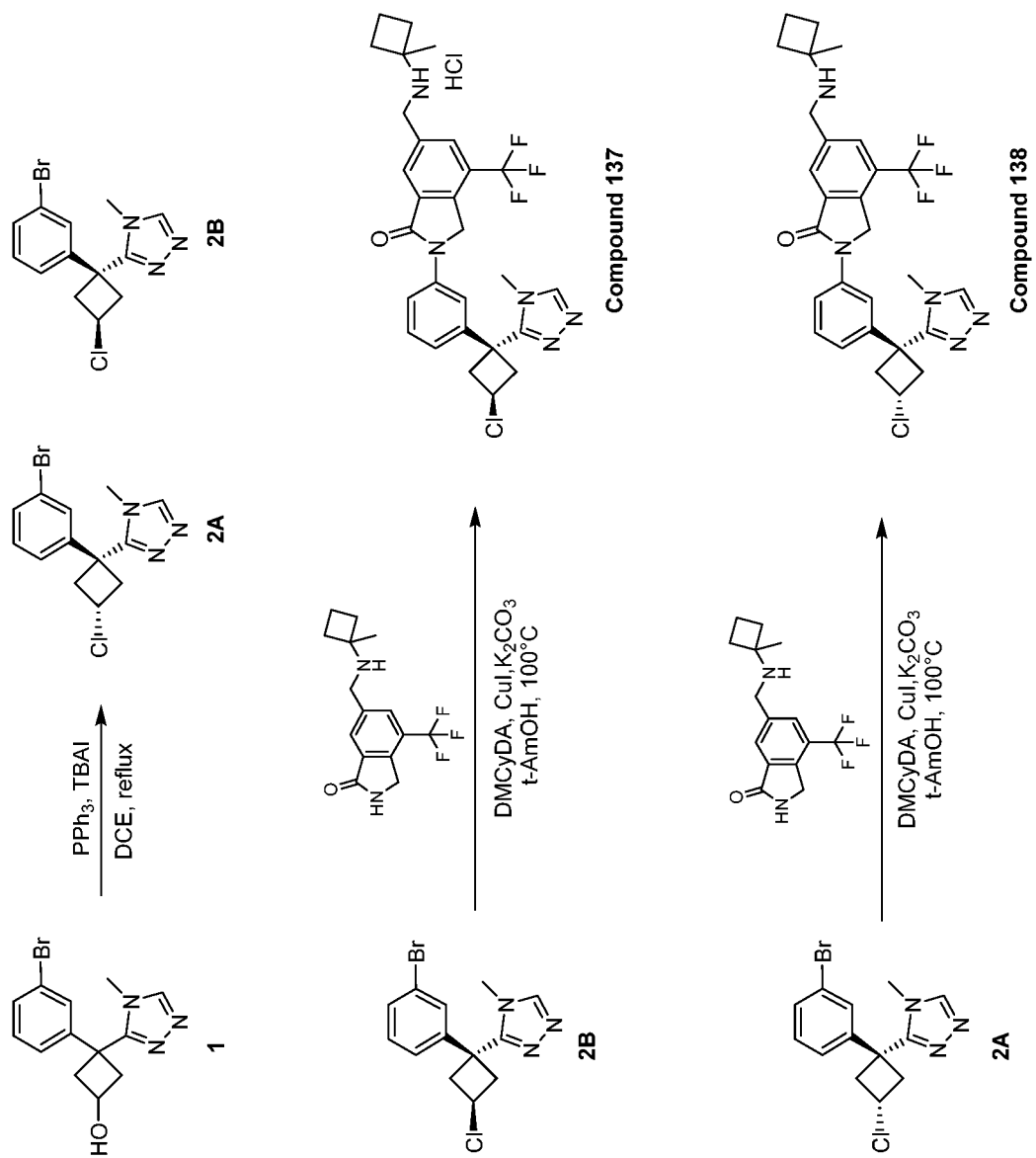

Compound 137 (2-(3-((1r,3r)-3-chloro-1-(4-methyl-4H-1,2,4-triazol-3-yl)cyclobutyl)phenyl)-6-(((1-methylcyclobutyl)amino)methyl)-4-(trifluoromethyl)isoindolin-1-one hydrochloride), and Compound 138 (2-(3-((1s,3s)-3-chloro-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to Scheme 65 (FIG. 65).

Intermediates 2A and 2B: (3-((1s,3s)-1-(3-bromophenyl)-3-chlorocyclobutyl)-4-methyl-4H-1,2,4-triazole and 3-((1r,3r)-1-(3-bromophenyl)-3-chlorocyclobutyl)-4-methyl-4H-1,2,4-triazole To a solution of 3-(3-bromophenyl)-3-(4-methyl-4H-1,2,4-triazol-3-yl)cyclobutan-1-ol (550 mg, 1.76 mmol) in 1,2- dichloroethane (50 mL) was added triphenylphosphine (1.63 g, 6.27 mmol) and tetrabutylammonium iodide (2.30 g, 6.27 mmol) at 25° C. The reaction mixture was refluxed for 3 h then concentrated to dryness. The crude product was purified by RP-HPLC (TFA in water/ACN 15% to 55%) to afford:

3-((1s,3s)-1-(3-bromophenyl)-3-chlorocyclobutyl)-4-methyl-4H-1,2,4-triazole (100 mg, 17% yield). $^1$H NMR (400 MHz, DMSO-$d_6$) δ 8.62 (s, 1H), 7.53-7.50 (m, 2H), 7.36-7.34 (m, 2H), 4.80-4.71 (m, 1H), 3.41-3.40 (m, 2H), 3.22 (s, 3H), 3.21-3.14 (m, 2H).

and 3-((1r,3r)-1-(3-bromophenyl)-3-chlorocyclobutyl)-4-methyl-4H-1,2,4-triazole (100 mg, 17% yield). $^1$H NMR (400 MHz, DMSO-$d_6$) δ 8.72 (s, 1H), 7.51 (d, J=8.0 Hz, 1H), 7.40-7.33 (m, 2H), 7.25-7.24 (m, 1H), 4.54-4.48 (m, 1H), 3.64-3.60 (m, 2H), 3.23 (s, 3H), 2.95-2.90 (m, 2H).

Compound 137

In a glove box, a mixture of 3-((1r,3r)-1-(3-bromophenyl)-3-chlorocyclobutyl)-4-methyl-4H-1,2,4-triazole (140 mg, 0.43 mmol), 6-(((1-methylcyclobutyl)amino)methyl)-4-(trifluoromethyl)isoindolin-1-one (153.4 mg, 0.51 mmol), copper(I) iodide (32.7 mg, 0.17 mmol), (1S,2S)—$N^1$,$N^2$-dimethylcyclohexane-1,2-diamine e (24.4 mg, 0.26 mmol) and potassium carbonate (177.7 mg, 1.29 mmol) in tert-amyl alcohol (4 mL) was heated at 110° C. in sealed vial for 2 h and concentrated. Ammonia (4 mL) and water (20 mL) were added then the mixture was extracted with ethyl acetate (2×10 mL), the combined organic phase washed with brine (1×10 mL), dried over anhydrous sodium sulfate, filtered and concentrated to dryness. The residue was purified by RP-HPLC (water (HCl)-ACN 15% to 35%) to afford 2-(3-((1r,3r)-3-chloro-1-(4-methyl-4H-1,2,4-triazol-3-yl)cyclobutyl)phenyl)-6-(((1-methylcyclobutyl)amino)methyl)-4-(trifluoromethyl)isoindolin-1-one hydrochloride (14.9 mg, 6.4% yield). $^1$H NMR (400 MHz, DMSO-$d_6$) δ 9.76 (br s, 2H), 9.25 (s, 1H), 8.37 (d, J=4.4 Hz, 2H), 7.94-7.80 (m, 2H), 7.50 (t, J=8.0 Hz, 1H), 7.10 (d, J=7.6 Hz, 1H), 5.29 (s, 2H), 4.58 (t, J=7.6 Hz, 1H), 4.34-4.23 (m, 2H), 3.73-3.67 (m, 2H), 3.35 (s, 3H), 3.06-2.93 (m, 2H), 2.57-2.51 (m, 2H), 1.95-1.78 (m, 4H), 1.59 (s, 3H). LCMS [M+H]$^+$=544.3.

Compound 138

In a glove box, a mixture of 3-((1s,3s)-1-(3-bromophenyl)-3-chlorocyclobutyl)-4-methyl-4H-1,2,4-triazole (60 mg, 0.18 mmol), 6-(((1-methylcyclobutyl)amino)methyl)-4-(trifluoromethyl)isoindolin-1-one (65.8 mg, 0.22 mmol), copper(I) iodide (14 mg, 0.07 mmol), (1S,2S)—$N^1$,$N^2$-dimethylcyclohexane-1,2-diamine (10.5 mg, 0.07 mmol) and potassium carbonate (76.1 mg, 0.55 mmol) in tert-amyl alcohol (1 mL) was heated at 110° C. in sealed vial for 2 h and concentrated. Ammonia (4 mL) and water (20 mL) were added then the mixture was extracted with ethyl acetate (2×10 mL), combined the organic phase washed with brine (10 mL), dried over with anhydrous sodium sulfate, filtered and concentrated to dryness. The residue was purified by RP-HPLC ((0.2% NH$_4$HCO$_3$ in water)/ACN 50% to 80%) to afford 2-(3-((1s,3s)-3-chloro-1-(4-methyl-4H-1,2,4-triazol-3-yl)cyclobutyl)phenyl)-6-(((1-methylcyclobutyl)amino)methyl)-4-(trifluoromethyl)isoindolin-1-one (18.8 mg, 19% yield). $^1$H NMR (400 MHz, methanol-$d_4$) δ 8.35 (s, 1H), 8.05 (s, 1H), 8.01 (s, 1H), 7.92 (s, 1H), 7.81 (dd, J=1.2, 8.0 Hz, 1H), 7.45 (t, J=8.0 Hz, 1H), 7.12 (d, J=7.6 Hz, 1H), 5.21 (s, 2H), 4.79 (t, J=8.0 Hz, 1H), 3.82 (s, 2H), 3.45-3.38 (m, 2H), 3.28-3.23 (m, 2H), 3.22 (s, 3H), 2.03-1.93 (m, 2H), 1.75-1.64 (m, 4H), 1.23 (s, 3H). LCMS [M+H]$^+$=544.3.

Example 68: Compound 139, 140, 141, 142

Figure 66:
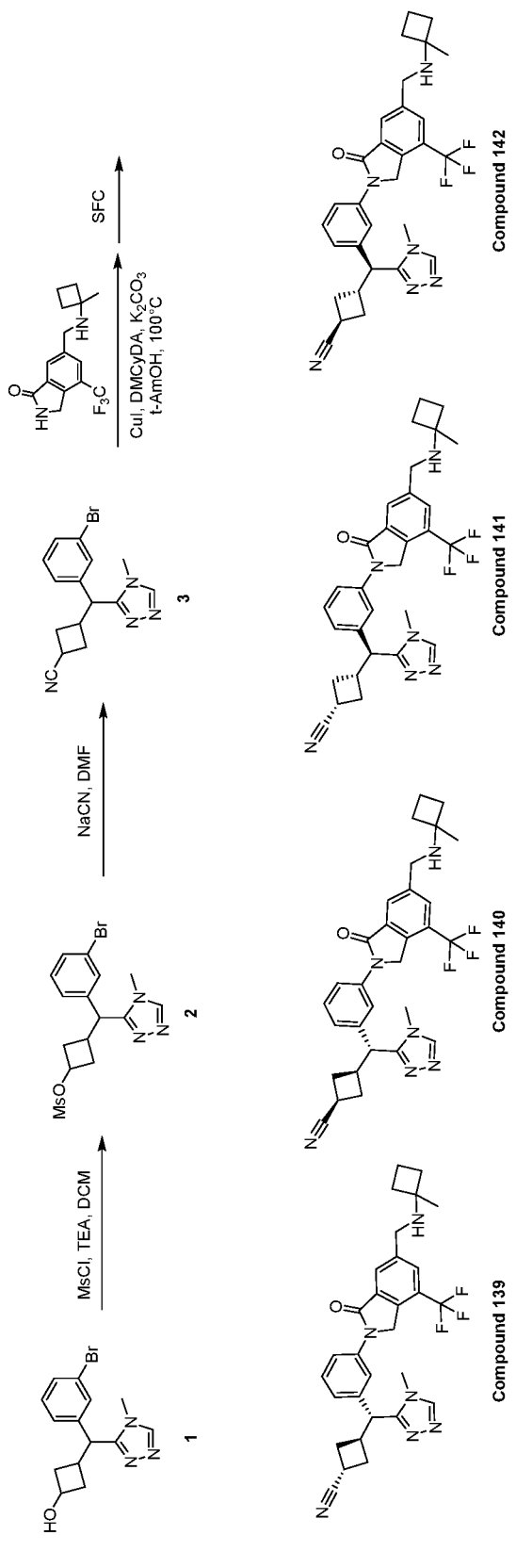

Compound 139 ((1R,3r)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile), Compound 140 ((1 S,3s)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile), Compound 141 ((1R,3s)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile), and Compound 142 ((1 S,3r)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile) can be synthesized according to Scheme 66 (FIG. 66).

Intermediate 2: (3-((3-bromophenyl)(4-methyl-4H-1,2,4-triazol-3-yl)methyl)cyclobutyl methanesulfonate To a solution of 3-((3-bromophenyl)(4-methyl-4H-1,2,4-triazol-3-yl)methyl)cyclobutan-1-ol (200 mg, 0.62 mmol) in dichloromethane (4 mL) was added methanesulfonyl chloride (50 mg, 0.44 mmol) and triethylamine (188 mg, 1.86 mmol). The mixture was stirred at 25° C. for 1 h then quenched with water (10 mL), extracted with dichloromethane (3×20 mL), combined the organic layers and washed with brine (50 mL), dried over sodium sulfate, filtered and concentrated to dryness. The residue was purified by silica gel chromatography (mobile phase: methanol/dichloromethane, gradient 0% to 10%) to afford 3-((3-bromophenyl)(4-methyl-4H-1,2,4-triazol-3-yl)methyl)cyclobutyl methanesulfonate (230 mg, 93% yield) as a white solid.

Intermediate 3: (3-((3-bromophenyl)(4-methyl-4H-1,2,4-triazol-3-yl)methyl)cyclobutane-1-carbonitrile To a solution of 3-((3-bromophenyl)(4-methyl-4H-1,2,4-triazol-3-yl)methyl)cyclobutyl methanesulfonate (230 mg, 0.62 mmol) in dimethyl sulfoxide (2 mL) was added sodium cyanide (100 mg, 3.55 mmol). The mixture was stirred at 120° C. for 16 h then quenched with water (10 mL), extracted with ethyl acetate (3×20 mL). The combined organic layers were washed with brine (50 mL), dried over sodium sulfate, filtered and concentrated under vacuum. The residue was purified by silica gel chromatography (mobile phase: methanol/dichloromethane, gradient 0% to 10%) to afford 3-((3-bromophenyl)(4-methyl-4H-1,2,4-triazol-3-yl)methyl)cyclobutane-1-carbonitrile (130 mg, 68% yield) as a yellow oil.

Compounds 139, 140, 141, 142

In a glove box, a mixture of 3-((3-bromophenyl)(4-methyl-4H-1,2,4-triazol-3-yl)methyl)cyclobutane-1-carbonitrile (130 mg, 0.39 mmol), 6-(((1-methylcyclobutyl)amino)methyl)-4-(trifluoromethyl)isoindolin-1-one (129 mg, 0.43 mmol), copper(I) iodide (30 mg, 0.4 mmol), (1S,2S)—$N^1$,$N^2$-dimethylcyclohexane-1,2-diamine (22 mg, 0.4 mmol) and potassium carbonate (163 mg, 1.17 mmol) in tert-amyl alcohol (4 mL) was heated at 100° C. in sealed vial for 2 h and concentrated to dryness. The residue was purified by silica gel chromatography (mobile phase: methanol/dichloromethane, gradient 0% to 10%) to afford a crude product which was further purified by RP-HPLC ((0.2%

NH$_3$·H$_2$O in water)/ACN 37% to 67%) to afford 3-((4-methyl-4H-1,2,4-triazol-3-yl)(3-(6-(((1-methylcyclobutyl)-amino)methyl)-1-oxo-4-(trifluoromethyl)isoindolin-2-yl)phenyl)methyl)cyclobutane-1-carbonitrile (70 mg, 33% yield).

The above sample was purified by chiral SFC (Column=Daicel Chiralpak IG; Column dimensions=250 mm×30 mm×10 µm; Detection wavelength=220 nm; Flow rate=80 mL/min; Mobile phase: A: CO$_2$ B: ethanol (0.05% DEA); Isocratic: 35% B) with 0.1% ammonium hydroxide) to afford product A, product B and product C.

The product A was further purified by chiral SFC (Column=Daicel Chiralpak IG; Column dimensions=250 mm×30 mm×10 µm; Detection wavelength=220 nm; Flow rate=80 mL/min; Mobile phase: A: CO$_2$ B: ethanol (0.05% DEA); Isocratic: 45% B) with 0.1% ammonium hydroxide) to afford structure tentatively:

(1R,3r)-3-((R)-(4-methyl-4H-1,2,4-triazol-3-yl)(3-(6-(((1-methylcyclobutyl)-amino)methyl)-1-oxo-4-(trifluoromethyl)isoindolin-2-yl)phenyl)methyl)cyclobutane-1-carbonitrile (Peak 1, retention time=2.847 min) (15.0 mg, 19% yield). $^1$H NMR (400 MHz, methanol-d$_4$) δ 8.39 (s, 1H), 8.10 (s, 1H), 8.02 (s, 1H), 7.86 (s, 1H), 7.79-7.77 (m, 1H), 7.45 (t, J=8.0 Hz, 1H), 7.09 (d, J=7.6 Hz, 1H), 5.15 (s, 2H), 4.36 (d, J=10.8 Hz, 1H), 3.90 (s, 2H), 3.51 (s, 3H), 3.21-3.11 (m, 1H), 2.71-2.69 (m, 1H), 2.32-2.30 (m, 2H), 2.25-2.08 (m, 4H), 1.93-1.78 (m, 4H), 1.41 (s, 3H). LCMS [M+H]$^+$=549.3.

(1 S,3s)-3-((R)-(4-methyl-4H-1,2,4-triazol-3-yl)(3-(6-(((1-methylcyclobutyl)-amino)methyl)-1-oxo-4-(trifluoromethyl)isoindolin-2-yl)phenyl)methyl)cyclobutane-1-carbonitrile (Peak 2, retention time=3.649 min) (7.0 mg, 10% yield). $^1$H NMR (400 MHz, methanol-d$_4$) δ 8.38 (s, 1H), 8.10 (s, 1H), 8.02 (s, 1H), 7.88 (s, 1H), 7.78 (d, J=8.4 Hz, 1H), 7.45 (t, J=7.6 Hz, 1H), 7.10 (d, J=7.6 Hz, 1H), 5.15 (s, 2H), 4.37 (d, J=11.2 Hz, 1H), 3.89 (s, 2H), 3.57-3.55 (m, 1H), 3.51 (s, 3H), 2.67-2.61 (m, 1H), 2.41-2.34 (m, 1H), 2.43-2.18 (m, 3H), 2.17-2.07 (m, 2H), 1.92-1.76 (m, 4H), 1.40 (s, 3H). LCMS [M+H]$^+$=549.3.

The product B was tentatively assigned as (1R,3s)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile (Peak 3, retention time=5.473 min) (7 mg, 10% yield). $^1$H NMR (400 MHz, methanol-d$_4$) δ 8.38 (s, 1H), 8.09 (s, 1H), 8.01 (s, 1H), 7.89 (s, 1H), 7.78 (d, J=8.0 Hz, 1H), 7.45 (t, J=8.0 Hz, 1H), 7.09 (d, J=7.6 Hz, 1H), 5.15 (s, 2H), 4.37 (d, J=10.0 Hz, 1H), 3.87 (s, 2H), 3.60-3.53 (m, 1H), 3.51 (s, 3H), 2.63 (s, 1H), 2.42-2.33 (m, 1H), 2.29-2.23 (m, 2H), 2.15-1.99 (m, 3H), 1.91-1.77 (m, 4H), 1.38 (s, 3H). LCMS [M+H]$^+$=549.3.

The product C was tentatively assigned as (1 S,3r)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile (Peak 4, retention time=5.852 min) (20.0 mg, 29% yield). $^1$H NMR (400 MHz, methanol-d$_4$) δ 8.38 (s, 1H), 8.10 (s, 1H), 8.02 (s, 1H), 7.86 (s, 1H), 7.78 (d, J=8.4 Hz, 1H), 7.45 (t, J=8.0 Hz, 1H), 7.09 (d, J=7.6 Hz, 1H), 5.15 (s, 2H), 4.35 (d, J=10.0 Hz, 1H), 3.90 (s, 2H), 3.50 (s, 3H), 3.21-3.11 (m, 1H), 2.72-2.67 (m, 1H), 2.36-2.25 (m, 2H), 2.25-2.09 (m, 4H), 1.93-1.78 (m, 4H), 1.41 (s, 3H). LCMS [M+H]$^+$=549.3.

Example 69: Compounds 143, 144

Figure 67:
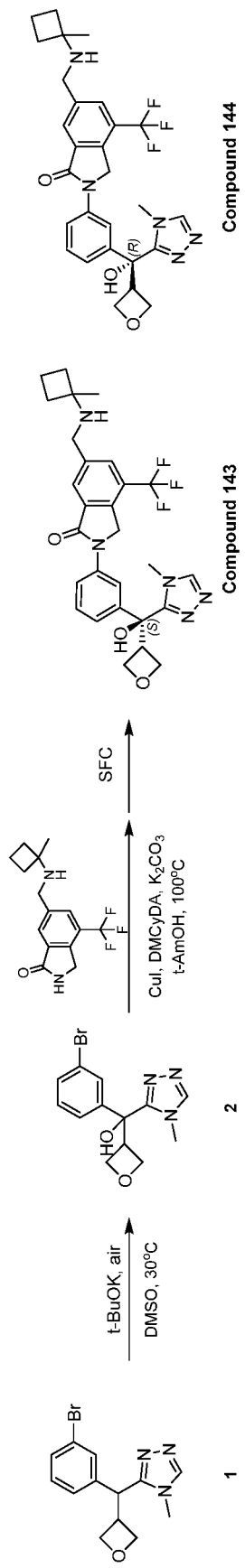

Compound 143 ((S)-2-(3-(hydroxy(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one) and Compound 144 ((R)-2-(3-(hydroxy(4-methyl-4H-1,2,4-triazol-3-yl)(oxetan-3-yl)methyl)phenyl)-6-(((1-methyl-cyclobutyl)amino)methyl)-4-(trifluoromethyl)isoindolin-1-one), can be synthesized according to Scheme 67 (FIG. 67).

Intermediate 2: ((3-bromophenyl)(4-methyl-4H-1,2,4-triazol-3-yl)(oxetan-3-yl)methanol To a solution of potassium tert-butoxide (1.09 g, 9.73 mmol) in dimethyl sulfoxide (10 mL) was added 3-((3-bromophenyl)(oxetan-3-yl)methyl)-4-methyl-4H-1,2,4-triazole (1 g, 3.24 mmol) then the mixture was stirred at 25° C. for 1 h. The mixture was diluted with ethyl acetate (30 mL), washed with water (3×10 mL), dried over with sodium sulfate, filtered, and concentrated to dryness. The residue was purified by chromatography on silica (solvent gradient: 0-50% methanol in dichloromethane) to afford (3-bromophenyl)(4-methyl-4H-1,2,4-triazol-3-yl)(oxetan-3-yl)methanol (357 mg, 34% yield) as white solid. LCMS [M+H]$^+$=324.0.

Compounds 143 and 144

In a glove box, a mixture of (3-bromophenyl)(4-methyl-4H-1,2,4-triazol-3-yl)(oxetan-3-yl)methanol (100 mg, 0.31 mmol), 6-(((1-methylcyclobutyl)amino)methyl)-4-(trifluoromethyl)isoindolin-1-one (101 mg, 0.31 mmol), copper(I) iodide (23.5 mg, 0.12 mmol), (1S,2S)—N$^1$,N$^2$-dimethylcyclohexane-1,2-diamine (18 mg, 0.12 mmol) and potassium carbonate (128 mg, 0.93 mmol) in tert-amyl alcohol (2 mL) was heated at 100° C. in sealed vial for 2 h and concentrated to dryness. The mixture was diluted with dichloromethane (10 mL), washed with 5% ammonia (3×5 mL), dried over sodium sulfate, filtered and concentrated to dryness. The residue was purified by preparative TLC (solvent gradient: 10% methanol in dichloromethane) to afford 2-(3-(hydroxy(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (150 mg, 90% yield).

The above mixture was further purified by chiral SFC (Column=Daicel Chiralcel OD; Column dimensions=250 mm×30 mm×10 µm; Detection wavelength=220 nm; Flow rate=120 mL/min; Mobile phase: A: CO$_2$ B: ethanol (0.05% DEA); Isocratic: 40% B) with 0.1% ammonium hydroxide) to afford tentatively assigned:

(S)-2-(3-(hydroxy(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 1, retention time=0.996 min) (41 mg, 27% yield). $^1$H NMR (400 MHz, methanol-d$_4$) δ 8.39 (s, 1H), 8.08 (s, 1H), 8.03 (s, 1H), 8.00 (s, 1H), 7.77 (dd, J=2.0, 8.4 Hz, 1H), 7.47 (t, J=8.0 Hz, 1H), 7.15 (d, J=7.6 Hz, 1H), 5.15 (s, 2H), 5.01-4.95 (m, 1H), 4.85-4.77 (m, 2H), 4.48-4.45 (m, 1H), 4.28-4.20 (m, 1H), 3.85 (s, 2H), 3.44 (s, 3H), 2.14-2.04 (m, 2H), 1.92-1.76 (m, 4H), 1.38 (s, 3H). LCMS [M+H]$^+$=542.4.

(R)-2-(3-(hydroxy(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 2, retention time=1.605 min) (31 mg, 21% yield). $^1$H NMR (400 MHz, methanol-d$_4$) δ 8.39 (s, 1H), 8.08 (s, 1H), 8.03 (s, 1H), 8.01 (s, 1H), 7.77 (dd, J=2.0, 8.0 Hz, 1H), 7.47 (t, J=8.0 Hz, 1H), 7.15 (d, J=8.0 Hz, 1H), 5.15 (s, 2H), 4.99-4.96 (m, 1H), 4.84-4.78 (m, 2H), 4.87-4.45 (m, 1H), 4.27-4.20 (m, 1H), 3.86 (s, 2H), 3.44 (s, 3H), 2.15-2.06 (m, 2H), 1.91-1.76 (m, 4H), 1.38 (s, 3H). LCMS [M+H]$^+$=542.4.

Example 70: Compound 145

Figure 68:
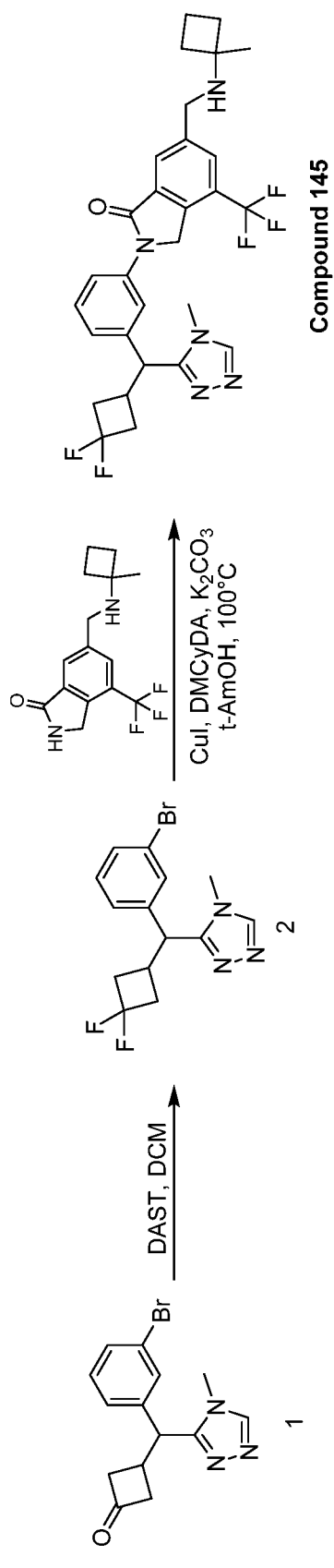

Compound 145 (2-(3-((3,3-difluorocyclobutyl)(4-methyl-4H-1,2,4-triazol-3-yl)methyl)phenyl)-6-(((1-methylcyclobutyl)amino)methyl)-4-(trifluoromethyl)isoindolin-1-one) can be synthesized according to Scheme 68 (FIG. 68).

Intermediate 2: (3-((3-bromophenyl)(3,3-difluorocyclobutyl)methyl)-4-methyl-4H-1,2,4-triazole)

To a solution of 3-((3-bromophenyl)(4-methyl-4H-1,2,4-triazol-3-yl)methyl)cyclobutan-1-one (300.0 mg, 0.93 mmol, such as may be obtained from the first step of Scheme 23) in dichloromethane (6 mL) was added bis(2-methoxyethyl)amino)sulfur trifluoride (0.9 mL, 4.68 mmol) at 0° C. Then the mixture was warmed to 25° C. and stirred for 16 h under nitrogen atmosphere. The reaction mixture was quenched with water (10 mL) and extracted with dichloromethane (3×20 mL). The combined organic layers were washed with brine (10 mL), dried over sodium sulfate and concentrated to dryness. The residue was purified by preparative TLC (solvent gradient: 10% methanol in dichloromethane) to give 3-((3-bromophenyl)(3,3-difluorocyclobutyl)methyl)-4-methyl-4H-1,2,4-triazole (90 mg, 28% yield) as a yellow oil.
Compound 145

In a glove box, a mixture of 3-((3-bromophenyl)(3,3-difluorocyclobutyl)methyl)-4-methyl-4H-1,2,4-triazole (110 mg, 0.32 mmol), 6-(((1-methylcyclobutyl)amino)methyl)-4-(trifluoromethyl)isoindolin-1-one (105 mg, 0.35 mmol), copper(I) iodide (25 mg, 0.12 mmol), (1S,2S)—$N^1,N^2$-dimethylcyclohexane-1,2-diamine (18 mg, 0.12 mmol) and potassium carbonate (133 mg, 0.96 mmol) in tert-amyl alcohol (3 mL) was heated at 100° C. in sealed vial for 2 h and concentrated to dryness. The residue was purified by silica gel chromatography (mobile phase: methanol/dichloromethane, gradient 0% to 10%) to afford 50 mg crude product which was further purified by RP-HPLC ((0.2% $NH_3·H_2O$ in water)/ACN 47% to 77%) to give 3-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutane-1-carbonitrile (2.8 mg, 2% yield) which was delivered as a mixture of enantiomer. $^1$H NMR (400 MHz, methanol-$d_4$) δ 8.38 (s, 1H), 8.09 (s, 1H), 8.01 (s, 1H), 7.91 (s, 1H), 7.79 (d, J=7.6 Hz, 1H), 7.46 (t, J=8.0 Hz, 1H), 7.12 (d, J=7.6 Hz, 1H), 5.15 (s, 2H), 4.30 (d, J=10.8 Hz, 1H), 3.86 (s, 2H), 3.50 (s, 3H), 3.20-3.10 (m, 1H), 2.95-2.80 (m, 1H), 2.55-2.43 (m, 2H), 2.42-2.30 (m, 1H), 2.14-2.04 (m, 2H), 1.90-1.76 (m, 4H), 1.38 (s, 3H). LCMS [M+H]$^+$=560.3.

Example 71: Compounds 146, 147

Figure 69:
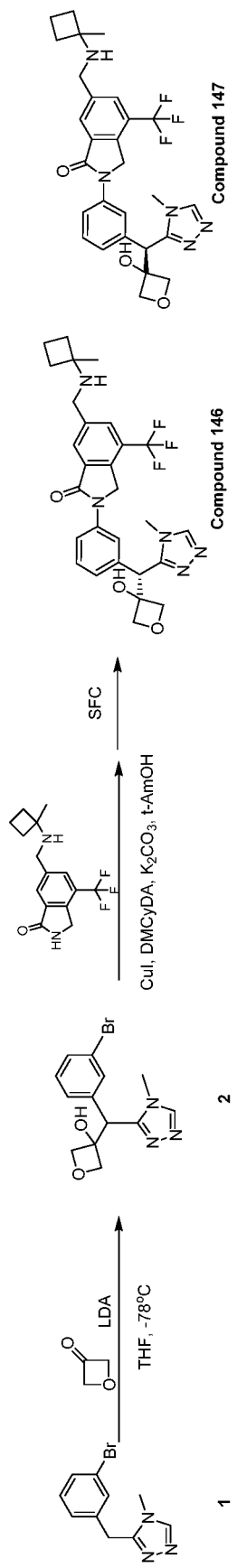

Compound 146 ((R)-2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one) and Compound 147 ((S)-2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 69 (FIG. 69).

Intermediate 2: (3-((3-bromophenyl)(4-methyl-4H-1,2,4-triazol-3-yl)methyl)oxetan-3-ol To a solution of 3-(3-bromobenzyl)-4-methyl-4H-1,2,4-triazole (200.0 mg, 0.79 mmol) in 1,2-dimethoxyethane (6 mL) was added lithium diisopropylamide (1.19 mL, 1.19 mmol, 1 M in tetrahydrofuran) at −40° C., the solution was stirred at −40° C. for 20 min then oxetan-3-one (0.09 mL, 1.59 mmol) was added. The resulting mixture was stirred at −40° C. for 1 h and quenched with saturated aqueous ammonium chloride (30 mL), extracted with dichloromethane (3×20 mL). The combined organic phase was washed with brine (20 mL) then dried over sodium sulfate and concentrated to dryness. The residue was purified by silica gel chromatography (mobile phase: methanol/dichloromethane, gradient 0% to 10%) to afford 3-((3-bromophenyl)(4-methyl-4H-1,2,4-triazol-3-yl)methyl)oxetan-3-ol (110 mg, 43% yield) as a yellow oil. LCMS [M+H]$^+$=324.0 and 326.0.
Compounds 146, 147

In a glove box, a mixture of 3-((3-bromophenyl)(4-methyl-4H-1,2,4-triazol-3-yl)methyl)oxetan-3-ol (110 mg, 0.34 mmol), 6-(((1-methylcyclobutyl)amino)methyl)-4-(trifluoromethyl)isoindolin-1-one (110 mg, 0.34 mmol), copper (I) iodide (26 mg, 0.14 mmol), (1S,2S)—$N^1,N^2$-dimethylcyclohexane-1,2-diamine (19 mg, 0.14 mmol) and potassium carbonate (133 mg, 0.96 mmol) in tert-amyl alcohol (3 mL) was heated at 100° C. in sealed vial for 2 h and concentrated to dryness. The residue was purified by silica gel chromatography (mobile phase: methanol/dichloromethane, gradient 0% to 10%) to afford 2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one (89 mg, 48% yield) as a yellow oil.

The above mixture was further purified by chiral SFC (Column=Daicel Chiralcel OJ; Column dimensions=250 mm×30 mm×10 μm; Detection wavelength=220 nm; Flow rate=70 mL/min; Mobile phase: A: $CO_2$ B: ethanol (0.05% DEA); Isocratic: 25% B) with 0.1% ammonium hydroxide) to afford tentatively assigned:

(R)-2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=0.922 min) (32.1 mg, 41% yield). $^1$H NMR (400 MHz, methanol-$d_4$) δ 8.40 (s, 1H), 8.11-8.07 (m, 1H), 8.01 (s, 1H), 7.98 (s, 1H), 7.82 (dd, J=1.6, 8.4 Hz, 1H), 7.47 (t, J=8.0 Hz, 1H), 7.22 (d, J=8.0 Hz, 1H), 5.15 (d, J=2.8 Hz, 2H), 4.94 (s, 2H), 4.72-4.66 (m, 2H), 4.55 (d, J=7.2 Hz, 1H), 3.86 (s, 2H), 3.45 (s, 3H), 2.15-2.06 (m, 2H), 1.92-1.86 (m, 2H), 1.84-1.76 (m, 2H), 1.38 (s, 3H). LCMS [M+H]$^+$=542.3.
and (S)-2-(3-((3-hydroxyoxetan-3-yl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=1.254 min) (33.8 mg, 43% yield). $^1$H NMR (400 MHz, methanol-$d_4$) δ 8.40 (s, 1H), 8.08 (s, 1H), 8.00 (s, 1H), 7.97 (s, 1H), 7.81 (dd, J=1.2, 8.0 Hz, 1H), 7.47 (t, J=7.6 Hz, 1H), 7.21 (d, J=8.0 Hz, 1H), 5.14 (d, J=3.6 Hz, 2H), 4.94-4.91 (m, 2H), 4.71-4.65 (m, 2H), 4.55 (d, J=7.2 Hz, 1H), 3.86 (s, 2H), 3.45 (s, 3H), 2.14-2.06 (m, 2H), 1.91-1.85 (m, 2H), 1.84-1.76 (m, 2H), 1.38 (s, 3H). LCMS [M+H]$^+$=542.3.

Example 72: Compounds 148, 149

Figure 70:
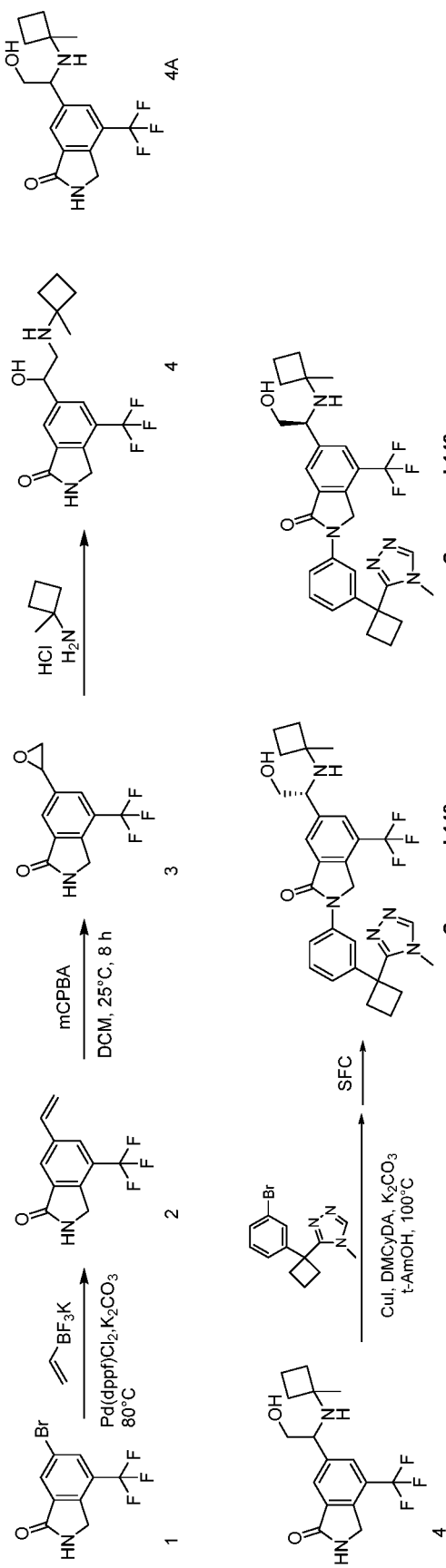

Compound 148 ((R)-6-(2-hydroxy-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one) and
Compound 149 ((S)-6-(2-hydroxy-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one), can be synthesized according to Scheme 70 (FIG. 70).

Intermediate 2: (4-(trifluoromethyl)-6-vinylisoindolin-1-one

A mixture of 6-bromo-4-(trifluoromethyl)isoindolin-1-one (2.0 g, 7.14 mmol), potassium vinyltrifluoroborate (1.15 g, 8.57 mmol), potassium carbonate (2.96 g, 21.43 mmol) and 1,1'-bis(diphenylphosphino)ferrocene dichloropalladium(II) (313.54 mg, 0.43 mmol) in 1,4-dioxane (15 mL) and water (1.5 mL) was stirred at 80° C. for 16 hours under nitrogen atmosphere. The reaction solution was diluted with ethyl acetate (100 mL), washed with water (2×25 mL), dried over sodium sulfate and concentrated to dryness. The residue was purified by silica gel chromatography (mobile phase: methanol/dichloro-methane, gradient 0% to 5%) to afford 4-(trifluoromethyl)-6-vinylisoindolin-1-one (1 g, 62% yield) as a yellow solid. $^1$H NMR (400 MHz, CDCl$_3$) δ 8.10 (s, 1H), 7.82 (s, 1H), 7.11 (s, 1H), 6.83 (dd, J=10.8, 17.6 Hz, 1H), 5.94 (d, J=17.6 Hz, 1H), 5.47 (d, J=10.8 Hz, 1H), 4.63 (s, 2H).

Intermediate 3: (6-(oxiran-2-yl)-4-(trifluoromethyl) isoindolin-1-one

A mixture of 4-(trifluoromethyl)-6-vinylisoindolin-1-one (800.0 mg, 3.52 mmol) and 3-chloroperbenzoic acid (85%, 1.21 g, 7.04 mmol) in Dichloromethane (20 mL) was stirred at 20° C. for 12 h. The mixture was quenched with saturated sodium sulfite aqueous (20 mL), extracted with dichloromethane (2×50 mL), dried over sodium sulfate and concentrated to dryness. The residue was purified by silica gel chromatography (mobile phase: methanol/dichloromethane, gradient 0% to 5%) to give 6-(oxiran-2-yl)-4-(trifluoromethyl)isoindolin-1-one (650 mg, 76% yield) as a yellow oil. $^1$H NMR (400 MHz, CDCl$_3$) δ 8.01 (s, 1H), 7.73 (s, 1H), 7.03-6.90 (m, 1H), 4.63 (s, 2H), 4.03 (dd, J=2.4, 4.0 Hz, 1H), 3.25 (dd, J=4.0, 5.2 Hz, 1H), 2.83 (dd, J=2.4, 5.2 Hz, 1H).

Intermediate 4A: (6-(1-hydroxy-2-((1-methylcyclobutyl)amino)ethyl)-4-(trifluoromethyl)isoindolin-1-one and 6-(2-hydroxy-1-((1-methylcyclobutyl)-amino)ethyl)-4-(trifluoromethyl)isoindolin-1-one To a solution of 6-(oxiran-2-yl)-4-(trifluoromethyl)isoindolin-1-one (300.0 mg, 1.23 mmol), 1-methylcyclobutan-1-amine hydro-chloride (1.5 g, 12.34 mmol) in 2-propanol (20 mL) was added potassium carbonate (2.56 g, 18.5 mmol), the mixture was stirred at 20° C. for 12 h then diluted with ethyl acetate (100 mL), washed with water (3×30 mL), dried over with sodium sulfate and concentrated. The residue was purified by silica gel chromatography (mobile phase: methanol/dichloromethane, gradient 0% to 15%) to afford:

6-[2-hydroxy-1-[(1-methylcyclobutyl)amino]ethyl]-4-(trifluoromethyl)isoindolin-1-one (100 mg, 25% yield). $^1$H NMR (400 MHz, CDCl$_3$) δ 8.14 (s, 1H), 7.83 (s, 1H), 7.07-6.58 (m, 1H), 4.63 (s, 2H), 4.09 (dd, J=4.8, 8.4 Hz, 1H), 3.75-3.67 (m, 1H), 3.56 (s, 1H), 2.02 (s, 1H), 1.94-1.81 (m, 2H), 1.75-1.63 (m, 3H), 1.23 (s, 3H).
and
6-[1-hydroxy-2-[(1-methylcyclobutyl)amino]ethyl]-4-(trifluoromethyl)isoindolin-1-one (80 mg, 20% yield). $^1$H NMR (400 MHz, CDCl$_3$) δ 8.07 (s, 1H), 7.95 (s, 1H), 7.09-6.86 (m, 1H), 5.10 (d, J=8.4 Hz, 1H), 4.55 (s, 2H), 3.06 (dd, J=2.8, 12.4 Hz, 1H), 2.77-2.64 (m, 1H), 2.36-2.11 (m, 2H), 1.97-1.71 (m, 4H), 1.41 (s, 3H).
Compounds 148, 149
In a glove box, a mixture of 3-(1-(3-bromophenyl)cyclobutyl)-4-methyl-4H-1,2,4-triazole (97.9 mg, 0.34 mmol), 6-(2-hydroxy-1-((1-methylcyclobutyl)amino)ethyl)-4-(trifluoromethyl)isoindolin-1-one (80 mg, 0.24 mmol), copper (I) iodide (50 mg, 0.26 mmol), (1S,2S)—N$^1$,N$^2$-dimethylcyclohexane-1,2-diamine (30 mg, 0.21 mmol) and potassium carbonate (126 mg, 0.91 mmol) in tert-amyl alcohol (2 mL) was heated at 100° C. in sealed vial for 2 h and concentrated to dryness. The residue was purified by RP-HPLC (0.05% FA in water/ACN 15% to 45%) to afford 6-(2-hydroxy-1-((1-methylcyclobutyl)amino)ethyl)-2-(3-(1-(4-methyl-4H-1,2,4-triazol-3-yl)cyclobutyl)phenyl)-4-(trifluoromethyl)isoindolin-1-one (100 mg, 61% yield).

The above mixture was further purified by chiral SFC (Column=Phenomenex-Cellulose-2 (250 mm×30 mm×10 um); Detection wavelength=220 nm; Flow rate=80 mL/min; Mobile phase: A: CO$_2$ B: ethanol (0.05% DEA); Isocratic: 45% B) with 0.1% ammonium hydroxide to afford tentatively assigned:

(R)-6-(2-hydroxy-1-((1-methylcyclobutyl)amino)ethyl)-2-(3-(1-(4-methyl-4H-1,2,4-triazol-3-yl)cyclobutyl)phenyl)-4-(trifluoro-methyl)isoindolin-1-one (Peak 1, retention time=4.350 min) (35 mg, 18% yield). $^1$H NMR (400 MHz, methanol-d$_4$) δ 8.36 (s, 1H), 8.13 (s, 1H), 8.07 (s, 1H), 7.99 (t, J=1.6 Hz, 1H), 7.68 (dd, J=1.6, 8.0 Hz, 1H), 7.48 (t, J=8.0 Hz, 1H), 7.16 (d, J=8.8 Hz, 1H), 5.15 (s, 2H), 4.07 (t, J=6.4 Hz, 1H), 3.68-3.60 (m, 1H), 3.59-3.52 (m, 1H), 3.33 (s, 3H), 3.06-2.96 (m, 2H), 2.88-2.75 (m, 2H), 2.23-2.07 (m, 2H), 2.06-1.97 (m, 1H), 1.93-1.80 (m, 2H), 1.74-1.57 (m, 3H), 1.14 (s, 3H). LCMS [M+H]$^+$=540.3.

(S)-6-(2-hydroxy-1-((1-methylcyclobutyl)amino)ethyl)-2-(3-(1-(4-methyl-4H-1,2,4-triazol-3-yl)cyclobutyl)phenyl)-4-(trifluoro methyl)isoindolin-1-one (Peak 2, retention time=6.241 min) (35 mg, 18% yield). $^1$H NMR (400 MHz, methanol-d$_4$) δ 8.36 (s, 1H), 8.13 (s, 1H), 8.07 (s, 1H), 7.99 (t, J=2.0 Hz, 1H), 7.68 (dd, J=1.6, 8.0 Hz, 1H), 7.48 (t, J=8.0 Hz, 1H), 7.17 (d, J=7.6 Hz, 1H), 5.15 (s, 2H), 4.07 (t, J=6.4 Hz, 1H), 3.68-3.61 (m, 1H), 3.59-3.51 (m, 1H), 3.33 (s, 3H), 3.07-2.96 (m, 2H), 2.86-2.76 (m, 2H), 2.22-2.07 (m, 2H), 2.02 (m, 1H), 1.93-1.82 (m, 2H), 1.75-1.58 (m, 3H), 1.14 (s, 3H). LCMS [M+H]$^+$=540.2.

Example 73: Compound 150 and 151

Figure 71:
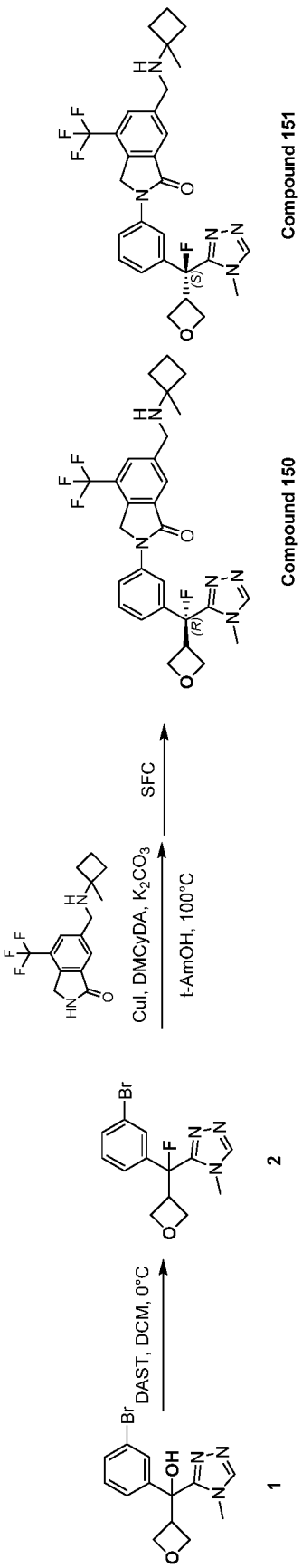

Compound 150 ((R)-2-(3-(fluoro(4-methyl-4H-1,2,4-triazol-3-yl)(oxetan-3-yl)methyl)phenyl)-6-(((1-methylcyclobutyl)amino)methyl)-4-(trifluoro-methyl)isoindolin-1-one) and Compound 151 ((S)-2-(3-(fluoro(4-methyl-4H-1,2,4-triazol-3-yl)(oxetan-3-yl)methyl)phenyl)-6-(((1-methylcyclobutyl)amino)methyl)-4-(trifluoromethyl) isoindolin-1-one), can be synthesized according to Scheme 71 (FIG. 71).

Intermediate 2: (3-((3-bromophenyl)fluoro(oxetan-3-yl)methyl)-4-methyl-4H-1,2,4-triazole To a solution of (3-bromophenyl)(4-methyl-4H-1,2,4-triazol-3-yl)(oxetan-3-yl)methanol (110 mg, 0.34 mmol) in dichloromethane (4 mL) was added diethylaminosulphur trifluoride (188 uL, 1.02 mmol) and a drop of hydrogen fluoride-pyridine at 25° C., the mixture was stirred at 25° C. for 2 h. The reaction mixture was quenched with saturated aqueous sodium bicarbonate (5 mL), extracted with dichloromethane (3×5 mL), dried over with sodium sulfate and concentrated. The residue was purified by preparative TLC (solvent gradient: 10% methanol in dichloromethane) to afford 3-((3-bromophenyl)-fluoro(oxetan-3-yl)methyl)-4-methyl-4H-1,2,4-triazole (80 mg, 72% yield) as a colorless oil.
Compounds 150 and 151
In a glove box, a mixture of 3-((3-bromophenyl)fluoro (oxetan-3-yl)methyl)-4-methyl-4H-1,2,4-triazole (80 mg, 0.25 mmol), 6-(((1-methylcyclobutyl)amino)methyl)-4-(trifluoromethyl)isoindolin-1-one (80.5 mg, 0.27 mmol), copper(I) iodide (19 mg, 0.10 mmol), (1S,2S)—N$^1$,N$^2$-dimethylcyclohexane-1,2-diamine (14 mg, 0.1 mmol) and potassium carbonate (102 mg, 0.74 mmol) in tert-amyl alcohol (2 mL) was heated at 100° C. in sealed vial for 2 h and concentrated to dryness. The residue was dissolved with dichloromethane (10 mL), washed with 1% ammonia aqueous (3×5 mL), dried over sodium sulfate and concentrated. The residue was purified by preparative TLC (solvent gradient: 10% methanol in dichloromethane) to afford 2-(3-(fluoro(4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (130 mg, 98% yield).

The above mixture was further purified by chiral SFC (Column=REGIS(S,S)WHELK-O1; Column dimensions=250 mm×25 mm×10 µm; Detection wavelength=220 nm; Flow rate=80 mL/min; Mobile phase: A: CO$_2$ B: ethanol (0.05% DEA); Isocratic: 55% B) with 0.1% ammonium hydroxide) to afford tentatively assigned:

(R)-2-(3-(fluoro(4-methyl-4H-1,2,4-triazol-3-yl)(oxetan-3-yl)methyl)phenyl)-6-(((1-methylcyclobutyl)amino)methyl)-4-(trifluoro-methyl)isoindolin-1-one (Peak 1, retention time=2.730 min) (37.4 mg, 29% yield). $^1$H NMR (400 MHz, methanol-d$_4$) δ 8.48 (s, 1H), 8.09-8.06 (m, 2H), 8.01 (s, 1H), 7.80 (dd, J=2.0, 8.4 Hz, 1H), 7.55 (t, J=8.0 Hz, 1H), 7.15 (d, J=8.0 Hz, 1H), 5.17 (s, 2H), 5.03-4.97 (m, 1H), 4.79-4.76 (m, 2H), 4.58-4.54 (m, 1H), 4.48-4.32 (m, 1H), 3.86 (s, 2H), 3.48 (s, 3H), 2.14-2.06 (m, 2H), 1.90-1.77 (m, 4H), 1.38 (s, 3H). LCMS [M+H]$^+$=544.4.

(S)-2-(3-(fluoro(4-methyl-4H-1,2,4-triazol-3-yl)(oxetan-3-yl)methyl)phenyl)-6-(((1-methylcyclobutyl)amino)methyl)-4-(trifluoro-methyl)isoindolin-1-one (Peak 2, retention time=3.413 min) (37.8 mg, 29% yield) as a yellow solid. $^1$H NMR (400 MHz, methanol-d$_4$) δ 8.48 (s, 1H), 8.09-8.07 (m, 2H), 8.01 (s, 1H), 7.80 (dd, J=1.6, 8.0 Hz, 1H), 7.55 (t, J=8.0 Hz, 1H), 7.15 (d, J=7.6 Hz, 1H), 5.17 (s, 2H), 5.02-4.97 (m, 1H), 4.80-4.76 (m, 2H), 4.59-4.55 (m, 1H), 4.48-4.33 (m, 1H), 3.86 (s, 2H), 3.48 (s, 3H), 2.13-2.05 (m, 2H), 1.90-1.77 (m, 4H), 1.38 (s, 3H). LCMS [M+H]$^+$=544.3.

Example 74: Compound 152 and 153

Figure 72:
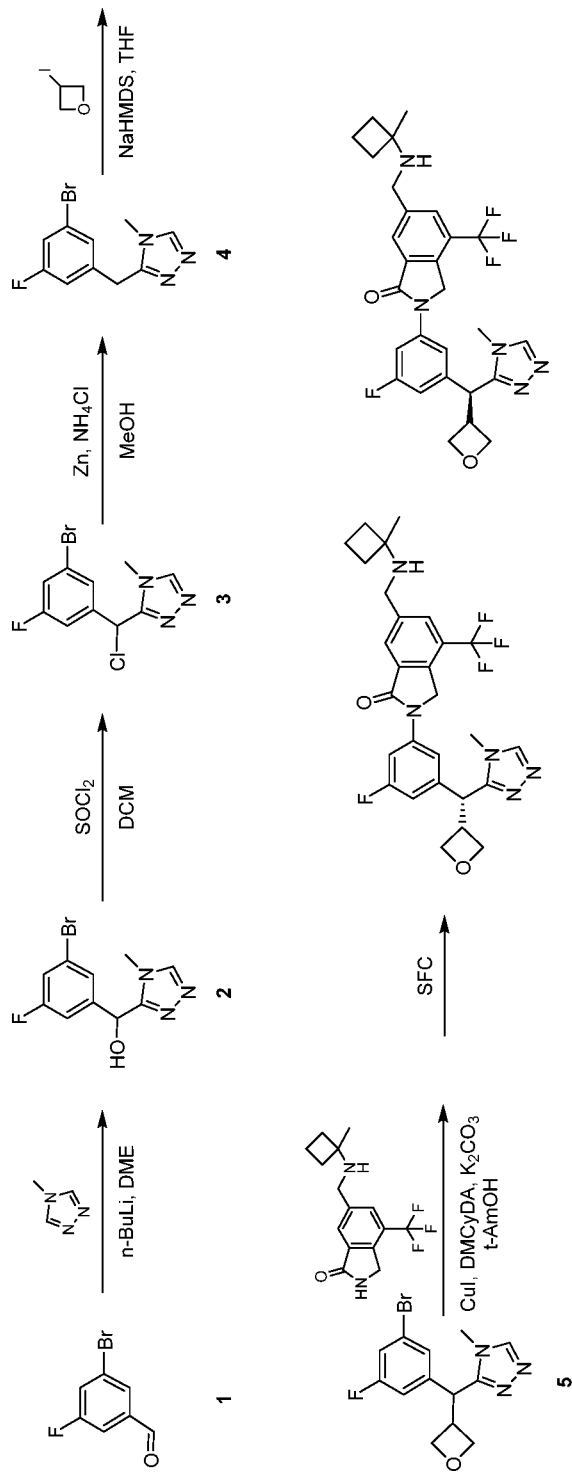

Compound 152 ((R)-2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one) and Compound 153 ((S)-2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one), can be synthesized according to Scheme 72 (FIG. 72).

Intermediate 2: ((3-bromo-5-fluorophenyl)(4-methyl-4H-1,2,4-triazol-3-yl)methanol To a solution of 4-methyl-4H-1,2,4-triazole (0.41 g, 4.93 mmol) in 1,2-dimethoxyethane (30 mL) was added n-butyl lithium (2.5 M in hexane, 2.27 mL, 5.66 mmol) at −50° C. The resulting mixture was stirred for 1 h at −50° C., then a solution of 3-bromo-5-fluorobenzaldehyde (1.0 g, 4.93 mmol) in 1,2-dimethoxyethane (10 mL) was added dropwise to the mixture. The reaction mixture was warmed to 0° C. slowly and stirred for another 1 h. The reaction was quenched with water (5 mL) and extracted with dichloromethane (3×25 mL). The combined organics were washed with brine (30 mL), dried over sodium sulfate and concentrated. The residue was purified by silica gel chromatography (mobile phase: methanol/dichloromethane, gradient 0% to 5%) to give (3-bromo-5-fluorophenyl)(4-methyl-4H-1,2,4-triazol-3-yl)methanol (340 mg, 24% yield) as a white solid. $^1$H NMR (400 MHz, methanol-d$_4$) δ 8.41 (s, 1H), 7.41 (s, 1H), 7.33-7.29 (m, 1H), 7.21-7.16 (m, 1H), 6.12 (s, 1H), 3.66 (s, 3H). LCMS [M+H]$^+$=285.7 and 287.7.

Intermediate 3: (3-((3-bromo-5-fluorophenyl)chloromethyl)-4-methyl-4H-1,2,4-triazole To a solution of (3-bromo-5-fluorophenyl)(4-methyl-4H-1,2,4-triazol-3-yl)methanol (340.0 mg, 1.19 mmol) in dichloromethane (4 mL) was added thionyl chloride (0.17 mL, 2.38 mmol) and a drop of N,N-dimethylformamide at 0° C. The mixture was stirred at 25° C. for 16 h then adjusted to pH 8 with saturated aqueous sodium bicarbonate, extracted with dichloromethane (3×15 mL), combined the organic layers and dried over sodium sulfate. Filtered and concentrated to afford a crude product 3-((3-bromo-5-fluorophenyl)-chloromethyl)-4-methyl-4H-1,2,4-triazole (200 mg, 55% yield) as a yellow solid which was used directly without further purification. LCMS [M+H]$^+$=303.8 and 305.8

Intermediate 4: (3-(3-bromo-5-fluorobenzyl)-4-methyl-4H-1,2,4-triazole

To a solution of 3-((3-bromo-5-fluorophenyl)chloromethyl)-4-methyl-4H-1,2,4-triazole (200 mg, 0.66 mmol) in methanol (5 mL) was added ammonium chloride (123 mg, 2.3 mmol) and zinc powder (160 mg, 2.45 mmol), then the mixture was stirred at 25° C. for 16 h. The reaction mixture was filtrated and the filtrate was adjusted to pH 8 with ammonia hydroxide, extracted with dichloromethane (3×10 mL). The combined organic layer was dried over sodium sulfate and concentrated to afford 3-[(3-bromo-5-fluorophenyl)methyl]-4-methyl-1,2,4-triazole (80 mg, 45% yield) as a yellow solid. LCMS [M+H]$^+$=269.2 and 271.2.

Intermediate 5: (3-((3-bromo-5-fluorophenyl)(oxetan-3-yl)methyl)-4-methyl-4H-1,2,4-triazole To a solution of 3-[(3-bromo-5-fluoro-phenyl)methyl]-4-methyl-1,2,4-triazole (80 mg, 0.30 mmol) in 1,2-dimethoxyethane (1.5 mL) was added sodium bis(trimethylsilyl)amide (0.44 mL, 0.44 mmol, 1.0 M in tetrahydrofuran) at 0° C., the mixture was stirred at 0° C. for 30 mins, then 3-iodooxetane (0.05 mL, 0.53 mmol) was added and the mixture was stirred at 25° C. for another 2 h. The mixture was quenched with water (2 mL), extracted with dichloromethane (3×10 mL), the combined organic phase washed with brine (10 mL), dried over sodium sulfate and concentrated under vacuum. The residue was purified by preparative TLC (solvent gradient: 10% methanol in dichloromethane) to afford 3-((3-bromo-5-fluorophenyl)(oxetan-3-yl)methyl)-4-methyl-4H-1,2,4-triazole (30 mg, 31% yield) as a yellow solid. LCMS [M+H]$^+$=325.7 and 327.7.

Compounds 152 and 153

In a glove box, a mixture of 3-((3-bromo-5-fluorophenyl)(oxetan-3-yl)methyl)-4-methyl-4H-1,2,4-triazole (30 mg, 0.09 mmol), 6-(((1-methylcyclobutyl)amino)methyl)-4-(trifluoromethyl)isoindolin-1-one (30.2 mg, 0.10 mmol), copper(I) iodide (7 mg, 0.04 mmol), (1S,2S)—N$^1$,N$^2$-dimethylcyclohexane-1,2-diamine (4 mg, 0.03 mmol) and potassium carbonate (38 mg, 0.28 mmol) in tert-amyl alcohol (1 mL) was heated at 100° C. in sealed vial for 2 h and concentrated to dryness. The residue was purified by preparative TLC (solvent gradient: 10% methanol in dichloromethane) to afford 2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (40 mg, 80% yield). LCMS [M+H]$^+$ =544.2.

The above mixture was further purified by chiral SFC (Column=Daicel Chiralpak IG; Column dimensions=250 mm×30 mm×10 μm; Detection wavelength=220 nm; Flow rate=80 mL/min; Mobile phase: A: $CO_2$ B: ethanol (0.05% DEA); Isocratic: 40% B) with 0.1% ammonium hydroxide) to afford tentatively assigned:

(R)-2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 1, retention time=4.612 min) (3.6 mg, 9% yield). $^1$H NMR (400 MHz, methanol-d$_4$) δ 8.41 (s, 1H), 8.09 (s, 1H), 8.02 (s, 1H), 7.80 (d, J=11.2 Hz, 1H), 7.68 (s, 1H), 6.85 (d, J=8.8 Hz, 1H), 5.14 (s, 2H), 4.94-4.90 (m, 1H), 4.82-4.75 (m, 1H), 4.70-4.65 (m, 2H), 4.41 (t, J=6.4 Hz, 1H), 4.05-3.94 (m, 1H), 3.86 (s, 2H), 3.54 (s, 3H), 2.13-2.04 (m, 2H), 1.90-1.85 (m, 2H), 1.84-1.77 (m, 2H), 1.38 (s, 3H). LCMS [M+H]$^+$= 544.2.

(S)-2-(3-fluoro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 2, retention time=5.120 min) (3.8 mg, 10% yield). $^1$H NMR (400 MHz, methanol-d$_4$) δ 8.41 (s, 1H), 8.09 (s, 1H), 8.02 (s, 1H), 7.80 (d, J=11.2 Hz, 1H), 7.68 (s, 1H), 6.85 (d, J=8.4 Hz, 1H), 5.15 (s, 2H), 4.94-4.90 (m, 1H), 4.82-4.75 (m, 1H), 4.70-4.65 (m, 2H), 4.41 (t, J=6.4 Hz, 1H), 4.05-3.94 (m, 1H), 3.85 (s, 2H), 3.54 (s, 3H), 2.13-2.04 (m, 2H), 1.90-1.85 (m, 2H), 1.84-1.77 (m, 2H), 1.37 (s, 3H). LCMS [M+H]$^+$= 544.2.

Example 75: Compound 154 and 155

Figure 73:
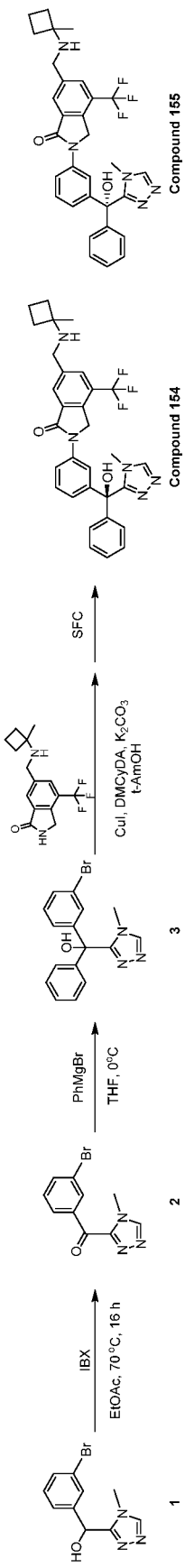

Compound 154 ((S)-2-(3-(hydroxy(4-methyl-4H-1,2,4-triazol-3-yl)(phenyl)methyl)phenyl)-6-(((1-methylcyclobutyl)amino)methyl)-4-(trifluoromethyl)isoindolin-1-one) and Compound 155 ((R)-2-(3-(hydroxy(4-methyl-4H-1,2,4-triazol-3-yl)(phenyl)methyl)phenyl)-6-(((1-methylcyclobutyl)amino)methyl)-4-(trifluoromethyl)isoindolin-1-one), can be synthesized according to Scheme 73 (FIG. 73).

Intermediate 2: ((3-bromophenyl)(4-methyl-4H-1,2,4-triazol-3-yl)methanone

To a solution of (3-bromophenyl)(4-methyl-4H-1,2,4-triazol-3-yl)methanol (10.0 g, 37.3 mmol) in ethyl acetate (200 mL) was added 2-iodoxybenzoic acid (29.91 g, 106.81 mmol). The mixture was refluxed for 16 h then filtered. The filtrate was concentrated to dryness and the residue was purified by silica gel chromatography (mobile phase: methanol/dichloromethane, gradient 0% to 10%) to afford (3-bromophenyl)(4-methyl-4H-1,2,4-triazol-3-yl)methanone (8.7 g, 88% yield) as a white solid. LCMS [M+H]$^+$=265.9 and 267.9.

Intermediate 3: ((3-bromophenyl)(4-methyl-4H-1,2,4-triazol-3-yl)(phenyl)-methanol To a solution of (3-bromophenyl)(4-methyl-4H-1,2,4-triazol-3-yl)methanone (0.6 g, 2.25 mmol) in THF (10 mL) was added dropwise phenylmagnesium bromide (2.37 mL, 2.37 mmol, 3M in ethyl ether) at 0° C. The reaction was slowly warmed to 25° C. and stirred for 2 hours. The reaction was quenched with ammonium chloride solution (3 mL), extracted with dichloromethane (3×50 mL). The combined organic phase was washed with brine (50 mL), dried over sodium sulfate and concentrated. The residue was purified by silica gel chromatography (mobile phase: ethyl acetate/petroleum ether, gradient 0% to 4%) to afford (3-bromophenyl)(4-methyl-4H-1,2,4-triazol-3-yl)(phenyl)methanol (600 mg, 77% yield) as a white solid. $^1$H NMR (400 MHz, DMSO-d$_6$) δ 8.49 (s, 1H), 7.52 (d, J=1.6 Hz, 1H), 7.50-7.46 (m, 1H), 7.39-7.34 (m, 2H), 7.33-7.27 (m, 2H), 7.25-7.20 (m, 4H), 3.35 (s, 3H).

Compounds 154 and 155

In a glove box, a mixture of (3-bromophenyl)(4-methyl-4H-1,2,4-triazol-3-yl)(phenyl)methanol (50 mg, 0.15 mmol), 6-(((1-methylcyclobutyl)amino)methyl)-4-(trifluoromethyl)isoindolin-1-one (47.7 mg, 0.16 mmol), copper(I) iodide (9 mg, 0.06 mmol), (1S,2S)—N$^1$,N$^2$-dimethylcyclohexane-1,2-diamine (8.3 mg, 0.06 mmol) and potassium carbonate (60 mg, 0.44 mmol) in tert-amyl alcohol (2 mL) was heated at 100° C. in sealed vial for 6 h and concentrated to dryness. The residue was purified by preparative TLC (solvent gradient: 10% methanol in dichloromethane) to afford 2-(3-(hydroxy(4-methyl-4H-1,2,4-triazol-3-yl)(phenyl)methyl)phenyl)-6-(((1-methyl-cyclobutyl)amino)methyl)-4-(trifluoromethyl)isoindolin-1-one (30 mg, 37% yield). LCMS [M+H]$^+$=562.3.

The above mixture was further purified by chiral SFC (Column=Daricel Chiralpark AD; Column dimensions=250 mm×30 mm×10 μm; Detection wavelength=220 nm; Flow rate=80 mL/min; Mobile phase: A: $CO_2$ B: IPA; Isocratic: 45% B) with 0.1% ammonium hydroxide) to afford tentatively assigned:

(S)-2-(3-(hydroxy(4-methyl-4H-1,2,4-triazol-3-yl)(phenyl)methyl)phenyl)-6-(((1-methylcyclobutyl)amino)methyl)-4-(trifluoro-methyl)isoindolin-1-one (Peak 1, retention time=3.626 min) (13.3 mg, 14% yield). $^1$H NMR (400 MHz, methanol-d$_4$) δ 8.46 (s, 1H), 8.12 (s, 1H), 8.06 (s, 1H), 7.95 (s, 1H), 7.85 (d, J=9.6 Hz, 1H), 7.45 (t, J=8.0 Hz, 1H), 7.40-7.34 (m, 5H), 7.16 (d, J=8.4 Hz, 1H), 5.15 (s, 2H), 4.07 (s, 2H), 3.56 (s, 3H), 2.30-2.20 (m, 2H), 2.01-1.87 (m, 4H), 1.51 (s, 3H). LCMS [M+H]$^+$=562.3.

(R)-2-(3-(hydroxy(4-methyl-4H-1,2,4-triazol-3-yl)(phenyl)methyl)phenyl)-6-(((1-methylcyclobutyl)amino)methyl)-4-(trifluoro-methyl)isoindolin-1-one (Peak 2, retention time=5.196 min) (14.7 mg, 16% yield). $^1$H NMR (400 MHz, methanol-d$_4$) δ 8.45 (s, 1H), 8.08 (s, 1H), 8.01 (s, 1H), 7.95 (d, J=2.0 Hz, 1H), 7.87-7.83 (m, 1H), 7.44 (t, J=8.0 Hz, 1H), 7.39-7.33 (m, 5H), 7.14 (d, J=8.8 Hz, 1H), 5.13 (s, 2H), 3.92 (s, 2H), 3.56 (s, 3H), 2.20-2.10 (m, 2H), 1.97-1.78 (m, 4H), 1.41 (s, 3H). LCMS [M+H]$^+$=562.3.

Example 76: Compound 156 and 157

Compound 156 ((S)-2-(3-(fluoro(4-methyl-4H-1,2,4-triazol-3-yl)(phenyl)methyl)phenyl)-6-(((1-methylcyclobutyl)amino)methyl)-4-(trifluoromethyl)isoindolin-1-one) and Compound 157 ((R)-2-(3-(fluoro(4-methyl-4H-1,2,4-triazol-3-yl)(phenyl)methyl)phenyl)-6-(((1-methylcyclobutyl)amino)methyl)-4-(trifluoromethyl)isoindolin-1-one), can be synthesized according to Scheme 74 (FIG. 74).

Intermediate 2: (3-((3-bromophenyl)fluoro(phenyl)methyl)-4-methyl-4H-1,2,4-triazole To a solution of (3-bromophenyl)(4-methyl-4H-1,2,4-triazol-3-yl)(phenyl)methanol (350 mg, 1.02 mmol) in dichloromethane (2 mL) was added diethylaminosulfur trifluoride (0.27 mL, 2.03 mmol) at 0° C. The mixture was stirred at 0°

C. for 2 h then quenched with saturated aqueous sodium bicarbonate (20 mL), extracted with dichloromethane (3×50 mL), washed with brine (50 mL), dried over sodium sulfate, filtrated and concentrated to dryness. The residue was purified by silica gel chromatography (mobile phase: methanol/dichloromethane, gradient 0% to 10%) to afford 3-((3-bromophenyl)-fluoro(phenyl)methyl)-4-methyl-4H-1,2,4-triazole (300 mg, 85% yield) as a light yellow oil. LCMS [M+H]$^+$=345.9 and 347.9.

Compound 156 and 157

In a glove box, a mixture of 3-((3-bromophenyl)fluoro(phenyl)methyl)-4-methyl-4H-1,2,4-triazole (200 mg, 0.58 mmol), 6-(((1-methylcyclobutyl)amino)methyl)-4-(trifluoromethyl)isoindolin-1-one (189 mg, 0.64 mmol), copper(I) iodide (43 mg, 0.23 mmol), (1S,2S)—N$^1$,N$^2$-dimethylcyclohexane-1,2-diamine (32.9 mg, 0.23 mmol) and potassium carbonate (240 mg, 1.73 mmol) in tert-amyl alcohol (4 mL) was heated at 100° C. in sealed vial for 6 h and concentrated to dryness. The residue was purified by preparative TLC (solvent gradient: 10% methanol in dichloromethane) to afford 2-(3-(fluoro(4-methyl-4H-1,2,4-triazol-3-yl)(phenyl) methyl)phenyl)-6-(((1-methylcyclobutyl)amino)methyl)-4-(trifluoromethyl)isoindolin-1-one (90 mg, 28%) as light yellow oil.

The above product was purified by chiral SFC (Column=Daicel Chiralpak AD; Column dimensions=250 mm×30 mm×10 µm; Detection wavelength=220 nm; Flow rate=80 mL/min; Mobile phase: A: CO$_2$ B: ethanol (0.05% DEA); Isocratic: 50% B) with 0.1% ammonium hydroxide) to afford tentatively assigned:

(S)-2-(3-(fluoro(4-methyl-4H-1,2,4-triazol-3-yl)(phenyl) methyl)phenyl)-6-(((1-methylcyclobutyl)amino)methyl)-4-(trifluoro-methyl)isoindolin-1-one (Peak 1, retention time=2.450 min) (17.5 mg, 19% yield). $^1$H NMR (400 MHz, methanol-d$_4$) δ 8.58 (s, 1H), 8.18 (s, 1H), 8.12 (s, 1H), 8.04 (s, 1H), 7.87 (d, J=6.8 Hz, 1H), 7.54 (t, J=8.4 Hz, 1H), 7.49-7.44 (m, 3H), 7.29 (dd, J=2.4, 7.2 Hz, 2H), 7.13 (d, J=8.8 Hz, 1H), 5.22 (s, 2H), 4.28 (s, 2H), 3.57 (s, 3H), 2.42-2.34 (m, 2H), 2.10-1.96 (m, 4H), 1.63 (s, 3H). LCMS [M+H]$^+$=564.1.

(R)-2-(3-(fluoro(4-methyl-4H-1,2,4-triazol-3-yl)(phenyl) methyl)phenyl)-6-(((1-methylcyclobutyl)amino)methyl)-4-(trifluoro-methyl)isoindolin-1-one (Peak 2, retention time=4.478 min) (24.1 mg, 26% yield). $^1$H NMR (400 MHz, methanol-d$_4$) δ 8.57 (s, 1H), 8.06 (s, 1H), 8.01 (d, J=8.4 Hz, 2H), 7.86 (d, J=6.4 Hz, 1H), 7.53 (t, J=8.4 Hz, 1H), 7.48-7.45 (m, 3H), 7.35-7.25 (m, 2H), 7.10 (d, J=7.2 Hz, 1H), 5.14 (s, 2H), 3.86 (s, 2H), 3.58 (s, 3H), 2.12-2.03 (m, 2H), 1.90-1.77 (m, 4H), 1.38 (s, 3H). LCMS [M+H]$^+$=564.1.

Example 77: Compound 158 and 159

Compound 158 ((R)-4-chloro-2-(3-((4-methyl-4H-1,2,4-triazol-3-yl)(phenyl)methyl)phenyl)-6-(((1-methylcyclobutyl)amino)methyl)isoindolin-1-one) and Compound 159 ((S)-4-chloro-2-(3-((4-methyl-4H-1,2,4-triazol-3-yl)(phenyl)methyl)phenyl)-6-(((1-methylcyclobutyl)amino)methyl)isoindolin-1-one), can be synthesized according to Scheme 75 (FIG. 75).

Intermediate 2: (3-((3-bromophenyl)(phenyl) methyl)-4-methyl-4H-1,2,4-triazole

To a mixture of (3-bromophenyl)-(4-methyl-1,2,4-triazol-3-yl)-phenyl-methanol (300.0 mg, 0.87 mmol), triethylsilane (0.7 mL, 4.36 mmol) and trifluoroacetic acid (5.37 mL, 69.72 mmol) in dichloromethane (1.5 mL) was added trifluoromethanesulfonic acid (0.3 mL, 0.35 mmol) at 0° C. Then the mixture was stirred at 40° C. for 16 h, then adjust pH to 8 by saturated sodium bicarbonate aqueous, extracted with dichloromethane (3×30 mL), the combined organics phase was washed with brine (2×20 mL), dried over sodium sulfate and concentrated. The residue was purified by silica gel chromatography (mobile phase: methanol/dichloromethane, gradient 0% to 10%) to afford 3-((3-bromophenyl) (phenyl)-methyl)-4-methyl-4H-1,2,4-triazole (210 mg, 73% yield) as a light yellow oil. LCMS [M+H]$^+$=328.0 and 330.0.

Compounds 158 and 159

In a glove box, a mixture of 3-((3-bromophenyl)(phenyl) methyl)-4-methyl-4H-1,2,4-triazole (100 mg, 0.30 mmol), 4-chloro-6-(((1-methylcyclobutyl)amino)methyl)isoindolin-1-one (89 mg, 0.34 mmol), copper(I) iodide (22 mg, 0.12 mmol), trans-N,N'-dimethyl-cyclohexane-1,2-diamine (17 mg, 0.12 mmol) and potassium carbonate (126 mg, 0.91 mmol) in tert-amyl alcohol (2 mL) was heated at 100° C. in sealed vial for 6 h and concentrated to dryness. The residue was purified by preparative TLC (solvent gradient: 10% methanol in dichloromethane) to afford 4-chloro-2-(3-((4-methyl-4H-1,2,4-triazol-3-yl)(phenyl)methyl)phenyl)-6-(((1-methylcyclobutyl)amino)methyl)-isoindolin-1-one (100 mg, 64%) as light yellow oil.

The above product was purified by chiral SFC (Column=Daicel Chiralpak AD; Column dimensions=250 mm×30 mm×10 µm; Detection wavelength=220 nm; Flow rate=80 mL/min; Mobile phase: A: CO$_2$ B: ethanol (0.05% DEA); Isocratic: 50% B) with 0.1% ammonium hydroxide) to afford tentatively assigned:

(R)-4-chloro-2-(3-((4-methyl-4H-1,2,4-triazol-3-yl)(phenyl)methyl)phenyl)-6-(((1-methylcyclobutyl)amino) methyl)isoindolin-1-one (Peak 1, retention time=1.795 min) (27.5 mg, 31% yield). $^1$H NMR (400 MHz, methanol-d$_4$) δ 8.46 (s, 1H), 7.86 (s, 1H), 7.81-7.75 (m, 2H), 7.71 (s, 1H), 7.44 (t, J=7.6 Hz, 1H), 7.40-7.35 (m, 2H), 7.31 (d, J=7.2 Hz, 1H), 7.26 (d, J=7.2 Hz, 2H), 7.09 (d, J=7.2 Hz, 1H), 5.86 (s, 1H), 4.94 (s, 2H), 3.78 (s, 2H), 3.56 (s, 3H), 2.11-2.08 (m, 2H), 1.91-1.78 (m, 4H), 1.37 (s, 3H). LCMS [M+H]$^+$=512.1.

(S)-4-chloro-2-(3-((4-methyl-4H-1,2,4-triazol-3-yl)(phenyl)methyl)phenyl)-6-(((1-methylcyclobutyl)amino) methyl)isoindolin-1-one (Peak 2, retention time=2.722 min) (29.2 mg, 33% yield). $^1$H NMR (400 MHz, methanol-d$_4$) δ 8.46 (s, 1H), 7.86 (s, 1H), 7.81-7.75 (m, 2H), 7.71 (s, 1H), 7.44 (t, J=8.0 Hz, 1H), 7.39-7.35 (m, 2H), 7.31 (d, J=7.2 Hz, 1H), 7.28-7.25 (m, 2H), 7.09 (d, J=8.0 Hz, 1H), 5.86 (s, 1H), 4.94 (s, 2H), 3.77 (s, 2H), 3.56 (s, 3H), 2.14-2.05 (m, 2H), 1.88-1.77 (m, 4H), 1.37 (s, 3H). LCMS [M+H]$^+$=512.3.

Example 78: Compounds 160, 161, 162, 163

Figure 76:
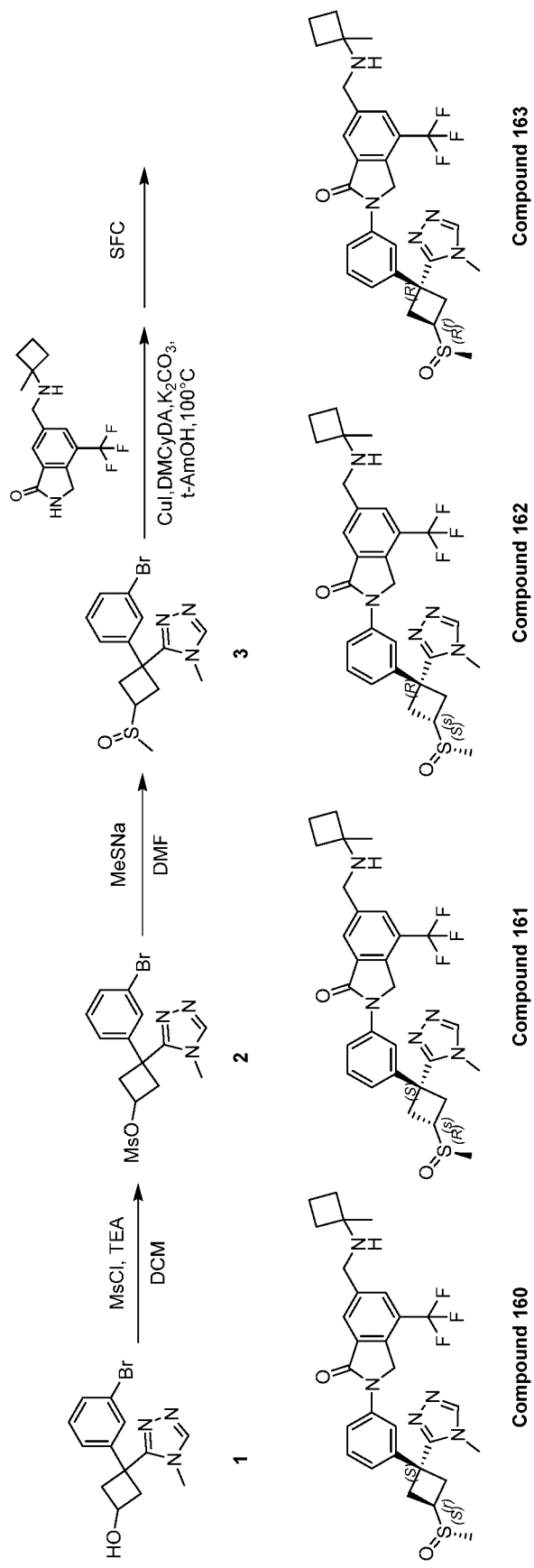

Compound 160 (2-(3-((1 S,3r)-1-(4-methyl-4H-1,2,4-triazol-3-yl)-3-((S)-methylsulfinyl)cyclobutyl)phenyl)-6-(((1-methylcyclobutyl)amino)methyl)-4-(trifluoromethyl)isoindolin-1-one), Compound 161 (2-(3-((1 S,3s)-1-(4-methyl-4H-1,2,4-triazol-3-yl)-3-((R)-methylsulfinyl)cyclobutyl)phenyl)-6-(((1-methylcyclobutyl)amino)methyl)-4-(trifluoromethyl)isoindolin-1-one), Compound 162 (2-(3-((1R,3s)-1-(4-methyl-4H-1,2,4-triazol-3-yl)-3-((S)-methylsulfinyl)cyclobutyl)phenyl)-6-(((1-methylcyclobutyl)amino)methyl)-4-(trifluoromethyl)isoindolin-1-one) and Compound 163 (2-(3-((1R,3r)-1-(4-methyl-4H-1,2,4-triazol-3-yl)-3-((R)-methylsulfinyl)cyclobutyl)phenyl)-6-(((1- methylcyclobutyl)amino)methyl)-4-(trifluoromethyl)isoindolin-1-one), can be synthesized according to Scheme 76 (FIG. 76).

Intermediate 2: (3-(3-bromophenyl)-3-(4-methyl-4H-1,2,4-triazol-3-yl)cyclobutyl methanesulfonate To a solution of 3-(3-bromophenyl)-3-(4-methyl-4H-1,2,4-triazol-3-yl)cyclobutan-1-ol (1.5 g, 4.87 mmol) in dichloromethane (25 mL) was added triethylamine (2.05 mL, 14.6 mmol) and methanesulfonyl chloride (1.59 mL, 20.6 mmol) at 0° C., then the mixture was stirred at 25° C. for 3 h, quenched with water (25 mL), extracted with dichloromethane (3×25 mL). The combined organic phase was washed with saturated aqueous sodium bicarbonate (20 mL), brine (2×25 mL), dried over with sodium sulfate, filtered, and concentrated to dryness. The residue was purified by silica gel chromatography (mobile phase: methanol/dichloromethane, gradient 0% to 10%) to afford 3-(3-bromophenyl)-3-(4-methyl-4H-1,2,4-triazol-3-yl)cyclobutyl methanesulfonate (1.8 g, 96% yield) as a white solid. LCMS [M+H]$^+$=386.0.

Intermediate 3: (3-(1-(3-bromophenyl)-3-(methylsulfinyl)cyclobutyl)-4-methyl-4H-1,2,4-triazole To a solution of 3-(3-bromophenyl)-3-(4-methyl-4H-1,2,4-triazol-3-yl)cyclobutyl methanesulfonate (1.8 g, 4.68 mmol) in N,N-dimethylformamide (60 mL) was added sodium methanethiolate (0.98 g, 14.03 mmol) at 0° C., the mixture was stirred at 25° C. for 1 h then quenched with water (20 mL), extracted with dichloromethane (2×60 mL), the combined organic phase was washed with saturated aqueous sodium bicarbonate (60 mL), brine (60 mL), dried over sodium sulfate and concentrated to dryness. The residue was purified by silica gel chromatography (mobile phase: methanol/dichloromethane, gradient 0% to 10%) to afford 3-(1-(3-bromophenyl)-3-(methylsulfinyl)cyclobutyl)-4-methyl-4H-1,2,4-triazole (1 g, 60% yield) as a white solid. LCMS [M+H]$^+$=354.0 and 356.0.

Compounds 160, 161, 162, 163

In a glove box, a mixture of 3-(1-(3-bromophenyl)-3-(methylsulfinyl)cyclobutyl)-4-methyl-4H-1,2,4-triazole (300 mg, 0.93 mmol), 6-(((1-methylcyclobutyl)amino)methyl)-4-(trifluoromethyl)isoindolin-1-one (89 mg, 0.34 mmol), copper(I) iodide (71 mg, 0.37 mmol), (1S,2S)—N$^1$,N$^2$-dimethylcyclohexane-1,2-diamine (53 mg, 0.37 mmol) and potassium carbonate (386 mg, 2.79 mmol) in tert-amyl alcohol (9 mL) was heated at 100° C. in sealed vial for 2 h. The mixture was filtrated and concentrated to dryness. The residue was purified by silica gel chromatography (mobile phase: methanol/dichloromethane, gradient 0% to 10%) to afford 2-(3-(1-(4-methyl-4H-1,2,4-triazol-3-yl)-3-(methylsulfinyl)cyclobutyl)-phenyl)-6-(((1-methylcyclobutyl)amino)methyl)-4-(trifluoromethyl)isoindolin-1-one (470 mg, 88% yield).

The above product was purified by chiral SFC (Column=Daicel Chiralcel OD-H; Column dimensions=250 mm×30 mm×10 μm; Detection wavelength=220 nm; Flow rate=80 mL/min; Mobile phase: A: CO$_2$ B: ethanol; Isocratic: 40% B with 0.1% ammonium hydroxide) to afford Product A, Product B and Product C:

Product A was tentatively assigned as 2-(3-((1 S,3r)-1-(4-methyl-4H-1,2,4-triazol-3-yl)-3-((S)-methylsulfinyl)cyclobutyl)phenyl)-6-(((1-methylcyclobutyl)amino)methyl)-4-(trifluoromethyl)isoindolin-1-one (Peak 1, retention time=2.101 min) (41.9 mg, 10% yield). $^1$H NMR (400 MHz, methanol-d$_4$) δ 8.47 (s, 1H), 8.08 (s, 1H), 8.01 (s, 1H), 7.87 (s, 1H), 7.74 (d, J=8.0 Hz, 1H), 7.50 (t, J=8.0 Hz, 1H), 7.15 (d, J=8.0 Hz, 1H), 5.16 (s, 2H), 4.60 (s, 3H), 3.86 (s, 2H), 3.64 (m, 1H), 3.39 (s, 3H), 3.34 (s, 1H), 3.29-3.15 (m, 2H), 3.07-2.98 (m, 1H), 2.50 (s, 3H), 2.17-2.05 (m, 2H), 1.94-1.84 (m, 2H), 1.84-1.71 (m, 2H), 1.38 (s, 3H). LCMS [M+H]$^+$=572.3.

Product B was tentatively assigned as 2-(3-((1 S,3s)-1-(4-methyl-4H-1,2,4-triazol-3-yl)-3-((R)-methylsulfinyl)cyclobutyl)phenyl)-6-(((1-methylcyclobutyl)amino)methyl)-4-(trifluoromethyl)isoindolin-1-one (Peak 2, retention time=2.772 min) (56.1 mg, 14% yield). $^1$H NMR (400 MHz, methanol-d$_4$) δ 8.48 (s, 1H), 8.08 (s, 1H), 8.01 (s, 1H), 7.87 (s, 1H), 7.74 (d, J=8.0 Hz, 1H), 7.50 (m, 1H), 7.15 (d, J=7.6 Hz, 1H), 5.16 (s, 2H), 3.87 (s, 2H), 3.64 (m, 1H), 3.39 (s, 3H), 3.37-3.33 (m, 1H), 3.28-3.16 (m, 2H), 3.07-3.00 (m, 1H), 2.50 (s, 3H), 2.16-2.05 (m, 2H), 1.93-1.85 (m, 2H), 1.85-1.75 (m, 2H), 1.38 (s, 3H). LCMS [M+H]$^+$=572.3

Then the mixture product C was further purified by chiral SFC (Column=Daicel Chiralcel OD-H; Column dimensions=250 mm×30 mm×10 μm; Detection wavelength=220 nm; Flow rate=80 mL/min; Mobile phase: A: CO$_2$ B: ethanol; Isocratic: 25% B with 0.1% ammonium hydroxide) to afford tentatively assigned:

2-(3-((1R,3s)-1-(4-methyl-4H-1,2,4-triazol-3-yl)-3-((S)-methylsulfinyl)cyclobutyl)-phenyl)-6-(((1-methylcyclobutyl)amino)methyl)-4-(trifluoromethyl)isoindolin-1-one (Peak 3, retention time=4.054 min) (53.3 mg, 12% yield). $^1$H NMR (400 MHz, methanol-d$_4$) δ 8.35 (s, 1H), 8.13-8.08 (m, 2H), 8.02 (s, 1H), 7.76 (m, 1H), 7.54 (m, 1H), 7.33-7.28 (m, 1H), 5.18 (s, 2H), 3.87 (s, 2H), 3.86-3.79 (m, 1H), 3.51 (m, 1H), 3.40 (s, 3H), 3.29-3.23 (m, 1H), 3.10-3.02 (m, 2H), 2.50 (s, 3H), 2.15-2.06 (m, 2H), 1.91-1.86 (m, 2H), 1.84-1.76 (m, 2H), 1.38 (s, 3H). LCMS [M+H]$^+$=572.3.

2-(3-((1R,3r)-1-(4-methyl-4H-1,2,4-triazol-3-yl)-3-((R)-methylsulfinyl)cyclobutyl)-phenyl)-6-(((1-methylcyclobutyl)amino)methyl)-4-(trifluoromethyl)isoindolin-1-one (Peak 4, retention time=4.529 min) (24.6 mg, 6% yield). $^1$H NMR (400 MHz, methanol-d$_4$) δ 8.35 (s, 1H), 8.10 (d, J=8.0 Hz, 2H), 8.01 (s, 1H), 7.75 (d, J=8.0 Hz, 1H), 7.54 (m, 1H), 7.31 (d, J=8.4 Hz, 1H), 5.17 (s, 2H), 3.89-3.81 (m, 3H), 3.51 (m, 1H), 3.40 (s, 3H), 3.29-3.21 (m, 1H), 3.10-3.02 (m, 2H), 2.51 (s, 3H), 2.14-2.05 (m, 2H), 1.91-1.85 (m, 2H), 1.84-1.75 (m, 2H), 1.38 (s, 3H). LCMS [M+H]$^+$=572.3.

Example 79: Compounds 164 and 165

Figure 77:
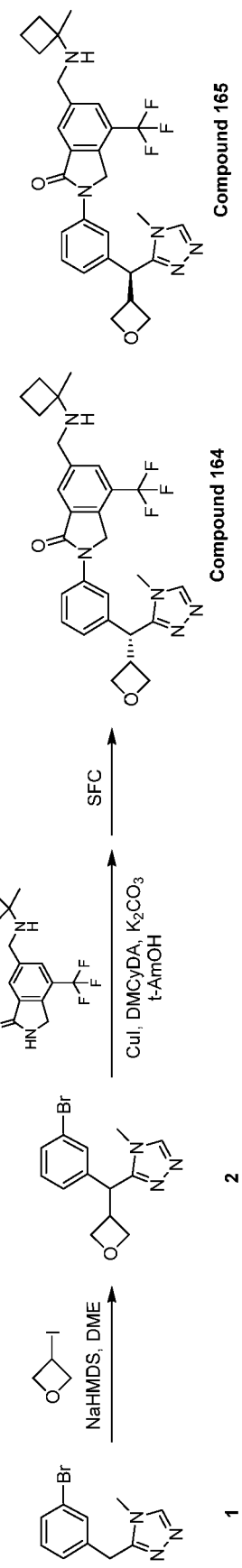

Compounds 164 and 165 can be synthesized according to Scheme 77 (FIG. 77).

Intermediate 2: (3-((3-bromophenyl)(oxetan-3-yl)methyl)-4-methyl-4H-1,2,4-triazole To a solution of 3-(3-bromobenzyl)-4-methyl-4H-1,2,4-triazole (10.0 g, 39.7 mmol) in 1,2-dimethoxyethane (200 mL) was added sodium bis(trimethylsilyl)amide (59.5 mL, 59.5 mmol, 1.0 M in tetrahydrofuran) at 0° C. The mixture was stirred at 0° C. for 30 min and 3-iodooxetane (6.14 mL, 71.4 mmol) was added. The resulting mixture was stirred at 25° C. for 2 h and quenched by water (100 mL) then extracted with dichloromethane (3×200 mL). The combined organic layers were dried over sodium sulfate and concentrated under vacuum. The residue was purified by silica gel chromatography (mobile phase: methanol/dichloromethane, gradient 0% to 10%) to afford 3-((3-bromophenyl)(oxetan-3-yl)methyl)-4-methyl-4H-1,2,4-triazole (10 g, 82% yield). LCMS [M+H]$^+$=307.9 and 309.9.

Compounds 164 and 165

A mixture of 3-((3-bromophenyl)(oxetan-3-yl)methyl)-4-methyl-4H-1,2,4-triazole (3 g, 9.73 mmol), 6-(((1-methylcyclobutyl)amino)methyl)-4-(trifluoromethyl)isoindolin-1-one (2.90 g, 9.73 mmol), copper(I) iodide (0.74 g, 3.89 mmol), (1S,2S)—$N^1$,$N^2$-dimethylcyclohexane-1,2-diamine (0.69 g, 4.87 mmol) and potassium carbonate (4.04 g, 29.2 mmol) in tert-amyl alcohol (100 mL) was stirred at 100° C. for 3 h under $N_2$. The mixture was concentrated then water (120 mL) was added. Extracted with ethyl acetate (3×120 mL), the combined organic phase was washed with brine (3×120 mL), dried over sodium sulfate, filtered and concentrated to dryness. The residue was purified by RP-HPLC (water($NH_3H_2O+NH_4HCO_3$)-ACN 25% to 55%) to afford 2-(3-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (4 g, 39% yield).

The above mixture was further purified by chiral SFC (Column=Daicel Chiralpak AD; Column dimensions=250 mm×50 mm×10 μm; Detection wavelength=220 nM; Flow rate=70 mL/min; Mobile phase: A: $CO_2$ B: ethanol (0.05% DEA); Isocratic: 45% B) with 0.1% ammonium hydroxide) to afford:

(R)-2-(3-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 1, retention time=1.408 min) (1.7 g, 43% yield). $^1$H NMR (400 MHz, DMSO) δ 8.37 (s, 1H), 8.05 (s, 1H), 8.00 (s, 1H), 7.91 (s, 1H), 7.85 (dd, J=1.6, 8.4 Hz, 1H), 7.40 (t, J=8.0 Hz, 1H), 7.01 (d, J=8.0 Hz, 1H), 5.17 (s, 2H), 4.79-4.72 (m, 2H), 4.51-4.46 (m, 2H), 4.29 (t, J=6.4 Hz, 1H), 3.90-3.87 (m, 1H), 3.82 (s, 2H), 3.38 (s, 3H), 2.02-1.94 (m, 2H), 1.81-1.52 (m, 4H), 1.23 (s, 3H). LCMS [M+H]$^+$=526.4.

(S)-2-(3-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one. (Peak 2, retention time=1.577 min) (1.7 g, 43% yield). $^1$H NMR (400 MHz, DMSO) δ 8.37 (s, 1H), 8.05 (s, 1H), 8.00 (s, 1H), 7.91 (s, 1H), 7.85 (dd, J=1.2, 8.4 Hz, 1H), 7.40 (t, J=8.0 Hz, 1H), 7.01 (d, J=8.0 Hz, 1H), 5.17 (s, 2H), 4.80-4.71 (m, 2H), 4.51-4.46 (m, 2H), 4.29 (t, J=6.4 Hz, 1H), 3.93-3.84 (m, 1H), 3.82 (s, 2H), 3.38 (s, 3H), 2.02-1.94 (m, 2H), 1.89-1.51 (m, 4H), 1.23 (s, 3H). LCMS [M+H]$^+$=526.4.

Example 80: Compound 166 and 167

Figure 78:
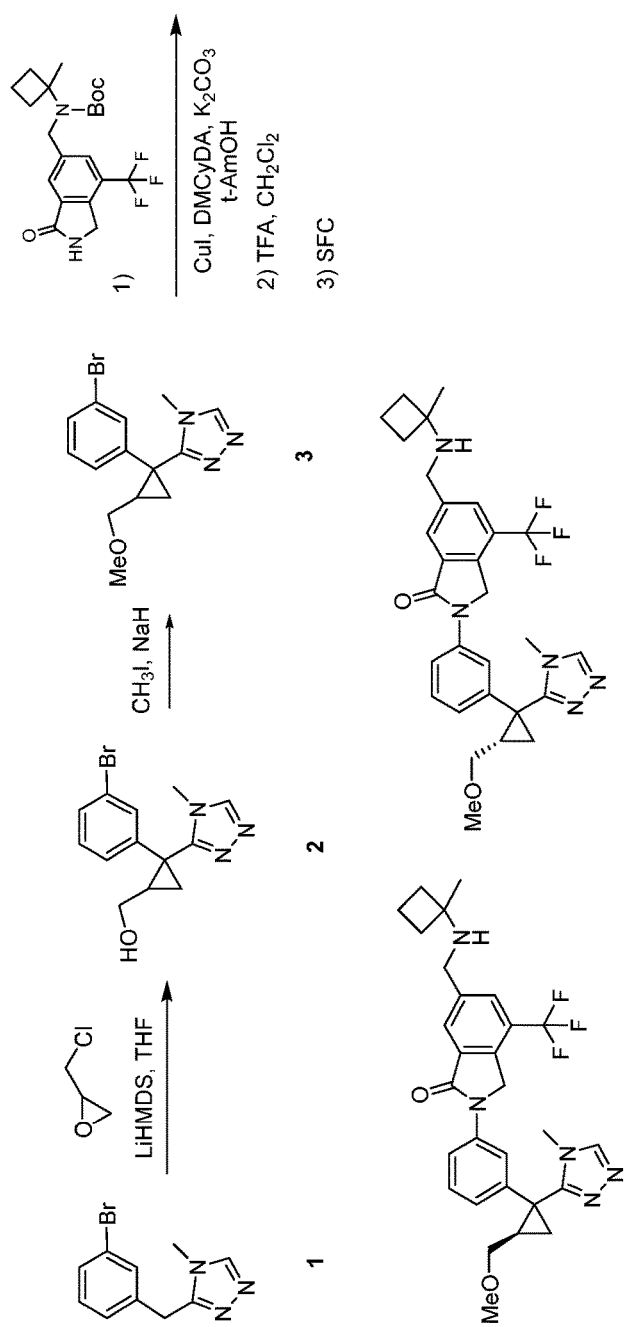

Compounds 166 and 167 can be synthesized according to Scheme 78 (FIG. 78).

Intermediate 2: ((2-(3-bromophenyl)-2-(4-methyl-4H-1,2,4-triazol-3-yl)cyclopropyl)methanol To a solution of 3-(3-bromobenzyl)-4-methyl-4H-1,2,4-triazole (250 mg, 0.99 mmol, 1 eq) and epichlorohydrin (100 mg, 1.09 mmol, 1.1 eq) in tetrahydrofuran (5.0 mL, 0.2M) at 0° C. was added lithium bis(trimethylsilyl)amide (3.0 mL of a 1 M solution, 3.0 mmol, 3 eq). The solution was stirred at 0° C. for 1.5 h at which point it was quenched with saturated aqueous sodium bicarbonate and diluted with water. The solution was extracted three times with methylene chloride, dried over sodium sulfate and concentrated. Purification of the residue by flash column chromatography (methylene chloride/methanol gradient) afforded the title compound (78 mg, 25%).

Intermediate 3: (3-(1-(3-bromophenyl)-2-(methoxymethyl)cyclopropyl)-4-methyl-4H-1,2,4-triazole To a room temperature suspension of sodium hydride (7.8 mg of 60% in mineral oil, 0.19 mmol, 1.2 eq) in DMF (1.6 mL) was added (2-(3-bromophenyl)-2-(4-methyl-4H-1,2,4-triazol-3-yl)cyclopropyl)methanol (50 mg, 0.16 mmol, 1 eq) in a minimal amount of DMF. Next, methyl iodide (25 mg, 0.18 mmol, 1.1 eq) was added and the reaction was stirred at room temperature for 2 h. After 2 h the reaction was added to saturated aqueous sodium bicarbonate, extracted three times with methylene chloride, dried over sodium sulfate and concentrated. Purification of the residue by flash column chromatography (methylene chloride/methanol gradient) afforded the title compound (29 mg, 55%).

Compounds 166 and 167

To a vial containing 3-(1-(3-bromophenyl)-2-(methoxymethyl)cyclopropyl)-4-methyl-4H-1,2,4-triazole (46 mg, 0.14 mmol, 1 eq), tert-butyl N-(1-methylcyclobutyl)-N-[[3-oxo-7-(trifluoromethyl)isoindolin-5-yl]methyl]carbamate (68 mg, 0.17 mmol, 1.2 eq), tBuBrettPhos G3 (13 mg, 0.014 mmol, 0.1 eq), and cesium carbonate (92 mg, 0.28 mmol, 2 eq) was added DMF (0.70 mL). The solution was heated at 100° C. for 22 h at which point it was diluted with water, extracted three times with methylene chloride, dried over sodium sulfate and concentrated. Purification of the residue by flash column chromatography (methylene chloride/methanol gradient) afforded the desired product (37 mg, 41%).

To a 0° C. solution of tert-butyl ((2-(3-(2-(methoxymethyl)-1-(4-methyl-4H-1,2,4-triazol-3-yl)cyclopropyl)phenyl)-3-oxo-7-(trifluoromethyl)isoindolin-5-yl)methyl)(1-methylcyclobutyl)carbamate (37 mg, 0.058 mmol, 1 eq) in methylene chloride (0.58 mL) was added trifluoroacetic acid (0.58 mL). The reaction was stirred at 0° C. for 2.5 h at which point the volatiles were evaporated. The crude mixture was purified by preparative HPLC and chiral SFC to give 5.8 mg isomer 1 and 5.3 mg isomer 2.

2-(3-((2R)-2-(methoxymethyl)-1-(4-methyl-4H-1,2,4-triazol-3-yl)cyclopropyl)phenyl)-6-(((1-methylcyclobutyl)amino)methyl)-4-(trifluoromethyl)isoindolin-1-one (Peak 1, 5.8 mg). $^1$H NMR (400 MHz, DMSO) δ 8.45 (s, 1H), 8.04 (s, 1H), 7.99 (s, 1H), 7.74 (t, J=2.0 Hz, 1H), 7.72-7.66 (m, 1H), 7.38 (t, J=8.0 Hz, 1H), 6.90 (dt, J=7.8, 1.3 Hz, 1H), 5.17 (s, 2H), 3.82 (s, 2H), 3.41 (s, 3H), 3.35-3.31 (m, 1H), 3.14 (s, 3H), 2.82 (dd, J=10.5, 8.3 Hz, 1H), 2.36 (tt, J=8.4, 6.0 Hz, 1H), 2.04-1.90 (m, 2H), 1.83-1.60 (m, 5H), 1.34 (dd, J=9.0, 4.8 Hz, 1H), 1.23 (s, 3H). LCMS [M+H]$^+$=540.2.

2-(3-((2S)-2-(methoxymethyl)-1-(4-methyl-4H-1,2,4-triazol-3-yl)cyclopropyl)phenyl)-6-(((1-methylcyclobutyl)amino)methyl)-4-(trifluoromethyl)isoindolin-1-one (Peak 2, 5.3 mg). $^1$H NMR (400 MHz, DMSO) δ 8.45 (s, 1H), 8.04 (s, 1H), 7.99 (s, 1H), 7.74 (d, J=2.0 Hz, 1H), 7.72-7.66 (m, 1H), 7.38 (t, J=7.9 Hz, 1H), 6.93-6.86 (m, 1H), 5.17 (s, 2H), 3.82 (s, 2H), 3.41 (s, 3H), 3.34 (d, J=5.6 Hz, 1H), 3.14 (s, 3H), 2.82 (dd, J=10.5, 8.3 Hz, 1H), 2.42-2.31 (m, 1H), 2.04-1.91 (m, 2H), 1.79 (dd, J=6.5, 4.8 Hz, 1H), 1.77-1.61 (m, 4H), 1.34 (dd, J=9.0, 4.8 Hz, 1H), 1.23 (s, 3H). LCMS [M+H]$^+$=540.2.

Example 81: Compound 168 and 169

Figure 79:
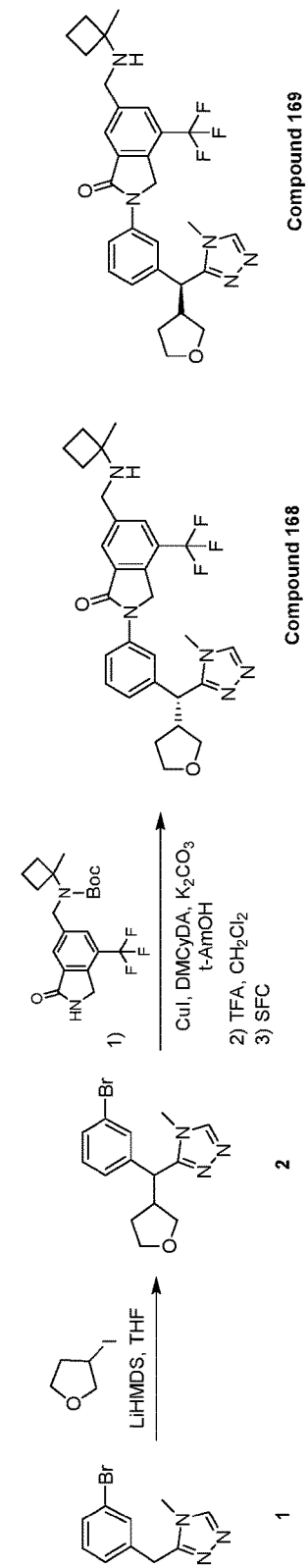

Compounds 168 and 169 can be synthesized according to Scheme 79 (FIG. 79).

Intermediate 2: (3-((3-bromophenyl)(tetrahydrofuran-3-yl)methyl)-4-methyl-4H-1,2,4-triazole To a solution of 3-(3-bromobenzyl)-4-methyl-4H-1,2,4-triazole (30 mg, 0.12 mmol, 1 eq) and 3-iodotetrahydrofuran (26 mg, 0.13 mmol, 1.1 eq) in tetrahydrofuran (0.60 mL) was added lithium bis(trimethylsilyl)amide (0.12 mL of a 1

M solution in tetrahydrofuran, 0.12 mmol, 1 eq). The solution was stirred at 0° C. for 1 h and at room temperature for an additional 1 h. The reaction was poured into saturated aqueous sodium bicarbonate, extracted three times with methylene chloride, dried over sodium sulfate and concentrated. The crude material was used without additional purification.

Compounds 168 and 169

To a vial containing tert-butyl (1-methylcyclobutyl)((3-oxo-7-(trifluoromethyl)-isoindolin-5-yl)methyl)carbamate (57 mg, 0.14 mmol, 1 eq), 3-((3-bromophenyl)-(tetrahydrofuran-3-yl)methyl)-4-methyl-4H-1,2,4-triazole (38 mg, 0.12 mmol, 1 eq) cesium carbonate (78 mg, 0.24 mmol, 2 eq), and tBuBrettPhos Pd G3 (5.3 mg, 0.0059 mmol, 0.05 eq) was added N,N-dimethylformamide (0.59 mL). The solution was heated at 100° C. for 21 h at which point it was cooled to room temperature, diluted with water and extracted three times with methylene chloride. The combined organic extracts were dried over sodium sulfate and concentrated. The crude material was used without further purification.

To a 0° C. solution of tert-butyl ((2-(3-((4-methyl-4H-1,2,4-triazol-3-yl)(tetrahydrofuran-3-yl)methyl)phenyl)-3-oxo-7-(trifluoromethyl)isoindolin-5-yl)methyl)(1-methylcyclobutyl)carbamate (76 mg, 0.12 mmol, 1 eq) in dichloromethane (0.59 mL) was added trifluoroacetic acid (0.59 mL). The solution was stirred at 0° C. for 90 min at which point it was carefully quenched with saturated aqueous sodium bicarbonate, extracted three times with methylene chloride, dried over sodium sulfate and concentrated. The crude material was purified by reverse phase HPLC and SFC.

2-(3-((R)-(4-methyl-4H-1,2,4-triazol-3-yl)((S)-tetrahydrofuran-3-yl)methyl)phenyl)-6-(((1-methylcyclobutyl)amino)methyl)-4-(trifluoromethyl)isoindolin-1-one (Peak 1, 2.1 mg). LCMS [M+H]$^+$=540.2.

2-(3-((S)-(4-methyl-4H-1,2,4-triazol-3-yl)((R)-tetrahydrofuran-3-yl)methyl)phenyl)-6-(((1-methylcyclobutyl)amino)methyl)-4-(trifluoromethyl)isoindolin-1-one (Peak 2, 3.5 mg). $^1$H NMR (400 MHz, DMSO) δ 8.32 (d, J=2.1 Hz, 1H), 8.06 (s, 1H), 8.01 (s, 1H), 7.94 (dt, J=3.7, 1.8 Hz, 1H), 7.84 (dt, J=8.4, 2.6 Hz, 1H), 7.40 (td, J=7.9, 5.1 Hz, 1H), 7.12 (d, J=8.2 Hz, 1H), 5.16 (s, 2H), 4.17 (dd, J=21.4, 10.7 Hz, 1H), 3.99-3.90 (m, 1H), 3.86-3.75 (m, 3H), 3.74-3.58 (m, 1H), 3.56-3.35 (m, 4H), 2.00 (q, J=8.3, 6.5 Hz, 2H), 1.79-1.64 (m, 4H), 1.64-1.48 (m, 1H), 1.46-1.29 (m, 1H), 1.24 (d, J=3.4 Hz, 5H), 0.92-0.80 (m, 1H). LCMS [M+H]$^+$=540.2.

Example 82: Compounds 323 and 324

Figures 80, 81, 82:
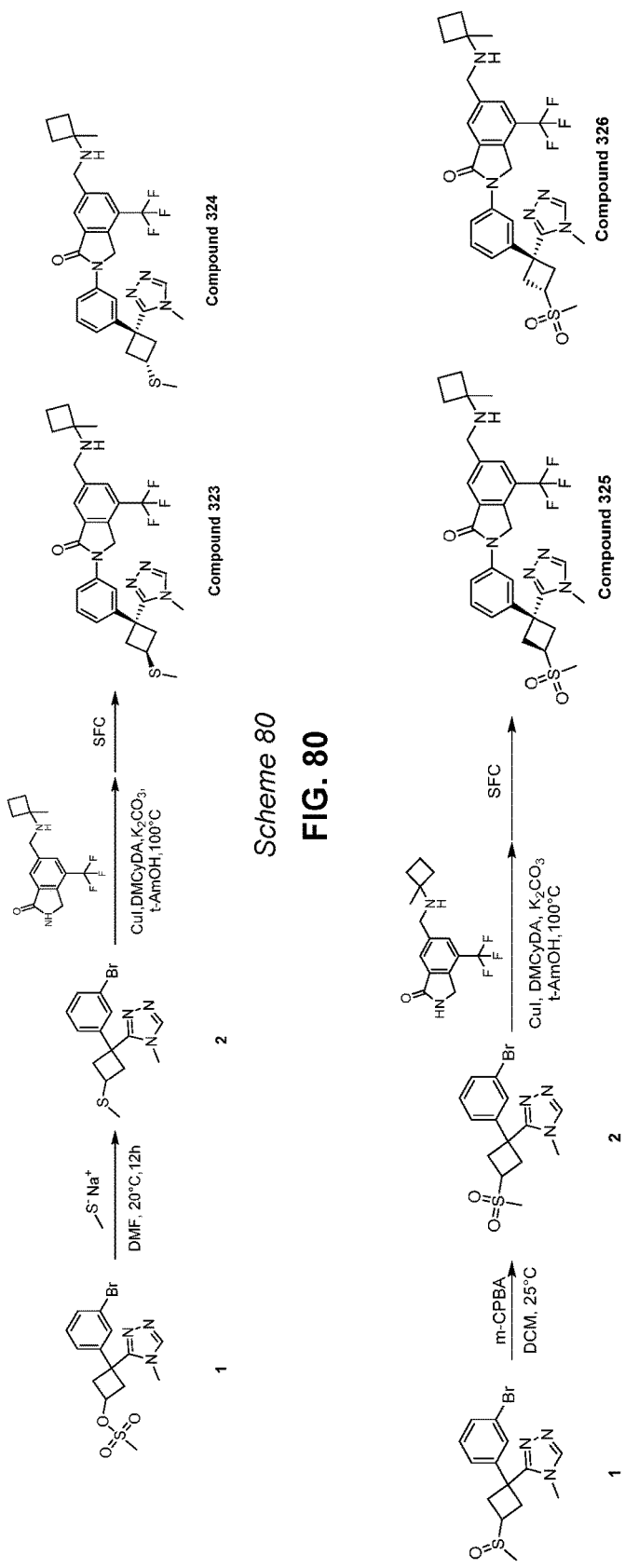

2-(3-((1r,3r)-1-(4-methyl-4H-1,2,4-triazol-3-yl)-3-(methylthio)cyclobutyl)phenyl)-6-(((1-methylcyclobutyl)amino)methyl)-4-(trifluoromethyl)isoindolin-1-one and 2-(3-((1s,3s)-1-(4-methyl-4H-1,2,4-triazol-3-yl)-3-(methylthio)cyclobutyl)phenyl)-6-(((1-methylcyclobutyl)amino)methyl)-4-(trifluoromethyl)isoindolin-1-one), can be synthesized according to Scheme 80 (FIG. 80)

Intermediate 2: 3-(1-(3-bromophenyl)-3-(methylthio)cyclobutyl)-4-methyl-4H-1,2,4-triazole To a solution of 3-(3-bromophenyl)-3-(4-methyl-4H-1,2,4-triazol-3-yl)cyclobutyl methanesulfonate (1.2 g, 3.11 mmol) in N,N-dimethylformamide (30 mL) was added sodium methanethiolate (0.65 g, 9.32 mmol) at 0° C., the mixture was stirred at 25° C. for 1 h then quenched by water (20 mL), extracted with dichloromethane (3×20 mL), the organic phase was washed with saturated sodium bicarbonate solution (20 ml) and brine (20 ml), dried over sodium sulfate, filtrated and concentrated under vacuum. The residue was purified by silica gel chromatography (mobile phase: methanol/dichloromethane, gradient 0% to 5%) to afford 3-(1-(3-bromophenyl)-3-(methylthio)cyclobutyl)-4-methyl-4H-1,2,4-triazole (1 g, 95% yield). LCMS [M+H]$^+$= 338.0 and 340.0.

Compounds 323 and 324

In a glove box, a mixture of 3-(1-(3-bromophenyl)-3-(methylthio)cyclobutyl)-4-methyl-4H-1,2,4-triazole (500 mg, 1.48 mmol), 6-[[(1-methylcyclobutyl)amino]methyl]-4-(trifluoromethyl)isoindolin-1-one (485 mg, 1.63 mmol), copper(I) iodide (113 mg, 0.59 mmol), (1S,2S)—N$^1$,N$^2$-dimethylcyclohexane-1,2-diamine (84 mg, 0.59 mmol) and potassium carbonate (613 mg, 4.43 mmol) in tert-amyl alcohol (14 mL) was heated at 100° C. in sealed vial for 2 h and concentrated to dryness. The residue was purified by silica gel chromatography (mobile phase: methanol/dichloromethane, gradient 0% to 10%) to afford a crude product which was further purified by RP-HPLC (water/NH$_3$H$_2$O+ NH$_4$HCO$_3$)-ACN 55% to 85%) to afford tentatively assigned:

2-(3-((1r,3r)-1-(4-methyl-4H-1,2,4-triazol-3-yl)-3-(methylthio)cyclobutyl)phenyl)-6-(((1-methylcyclobutyl)amino)methyl)-4-(trifluoromethyl)isoindolin-1-one (61 mg, 7% yield). $^1$H NMR (400 MHz, methanol-d$_4$) δ 8.33 (s, 1H), 8.09 (s, 2H), 8.01 (s, 1H), 7.71 (d, J=8.0 Hz, 1H), 7.51 (t, J=8.0 Hz, 1H), 7.24 (d, J=8.4 Hz, 1H), 5.16 (s, 2H), 3.86 (s, 2H), 3.72-3.69 (m, 1H), 3.34 (s, 3H), 3.20-3.16 (m, 2H), 3.03-2.99 (m, 2H), 2.12-2.00 (m, 5H), 1.90-1.85 (m, 2H), 1.82-1.78 (m, 2H), 1.38 (s, 3H). LCMS [M+H]$^+$=556.3.

and 2-(3-((1s,3s)-1-(4-methyl-4H-1,2,4-triazol-3-yl)-3-(methylthio)cyclobutyl)phenyl)-6-(((1-methylcyclobutyl)amino)methyl)-4-(trifluoromethyl)isoindolin-1-one (34.5 mg, 4% yield). $^1$H NMR (400 MHz, methanol-d$_4$) δ 8.40 (s, 1H), 8.08 (s, 1H), 8.01 (s, 1H), 7.94 (s, 1H), 7.68 (d, J=8.0 Hz, 1H), 7.48 (t, J=8.0 Hz, 1H), 7.08 (d, J=7.6 Hz, 1H), 5.15 (s, 2H), 3.87 (s, 2H), 3.55-3.45 (m, 1H), 3.42-3.41 (m, 2H), 3.34 (s, 3H), 2.79-2.75 (m, 2H), 2.12-2.00 (m, 5H), 1.90-1.85 (m, 2H), 1.82-1.78 (m, 2H), 1.38 (s, 3H). LCMS [M+H]$^+$=556.3.

Example 83: Compound 325, 326

2-(3-((1r,3r)-1-(4-methyl-4H-1,2,4-triazol-3-yl)-3-(methylsulfonyl)cyclobutyl)phenyl)-6-(((1-methylcyclobutyl)amino)methyl)-4-(trifluoromethyl)isoindolin-1-one, and 2-(3-((1s,3s)-1-(4-methyl-4H-1,2,4-triazol-3-yl)-3-(methylsulfonyl)cyclobutyl)phenyl)-6-(((1-methylcyclobutyl)amino)methyl)-4-(trifluoromethyl)isoindolin-1-one), can be synthesized according to Scheme 81 (FIG. 81)

Intermediate 2: 3-(1-(3-bromophenyl)-3-(methylsulfonyl)cyclobutyl)-4-methyl-4H-1,2,4-triazole To a solution of 3-(1-(3-bromophenyl)-3-(methylsulfinyl)cyclobutyl)-4-methyl-4H-1,2,4-triazole (200 mg, 0.57 mmol) in dichloromethane (5 mL) was added 3-chlorobenzoperoxoic acid (85%, 172 mg, 0.85 mmol). The solution was stirred at 25° C. for 1.5 h then quenched with saturated sodium sulfite solution (2 mL), then the mixture was filtered and the filtrate was concentrated to dryness. The residue was purified by preparative TLC (solvent gradient: 10% methanol in dichloromethane) to afford 3-(1-(3-bromophenyl)-3-

(methylsulfonyl)cyclobutyl)-4-methyl-4H-1,2,4-triazole (200 mg, 96% yield) as a light yellow solid. LCMS [M+H]$^+$=370.1.

Compounds 325, 326

In a glove box, a mixture of 3-(1-(3-bromophenyl)-3-(methylsulfonyl)cyclobutyl)-4-methyl-4H-1,2,4-triazole (250 mg, 0.67 mmol), 6-(((1-methylcyclobutyl)amino)methyl)-4-(trifluoromethyl)isoindolin-1-one (201 mg, 0.67 mmol), copper(I) iodide (51 mg, 0.27 mmol), (1S,2S)—N$^1$,N$^2$-dimethylcyclohexane-1,2-diamine (38 mg, 0.27 mmol) and potassium carbonate (280 mg, 2 mmol) in tert-amyl alcohol (6.5 mL) was heated at 100° C. in sealed vial for 2 h and concentrated to dryness. The residue was purified by silica gel chromatography (mobile phase: methanol/dichloromethane, gradient 0% to 10%) to afford a crude product which was purified by chiral SFC (Column=Daicel Chiralcel OD-H; Column dimensions=250 mm×30 mm×10 μm; Detection wavelength=220 nM; Flow rate=40 mL/min; Mobile phase: A: CO$_2$ B: ethanol; Isocratic: 40% B with 0.1% ammonium hydroxide) to afford tentatively assigned:

2-(3-((1r,3r)-1-(4-methyl-4H-1,2,4-triazol-3-yl)-3-(methylsulfonyl)cyclobutyl)phenyl)-6-(((1-methylcyclobutyl)amino)methyl)-4-(trifluoromethyl)isoindolin-1-one (Peak 1, retention time=0.527 min) (57 mg, 14% yield). $^1$H NMR (400 MHz, methanol-d$_4$) δ 8.36 (s, 1H), 8.09 (s, 2H), 8.01 (s, 1H), 7.75 (d, J=8.8 Hz, 1H), 7.54 (t, J=8.0 Hz, 1H), 7.27 (d, J=7.6 Hz, 1H), 5.17 (s, 2H), 4.32-4.27 (m, 1H), 3.86 (s, 2H), 3.50-3.40 (m, 2H), 3.38 (s, 3H), 3.20-3.13 (m, 2H), 2.92 (m, 3H), 2.14-2.00 (m, 2H), 1.90-1.85 (m, 2H), 1.82-1.77 (m, 2H), 1.38 (s, 3H). LCMS [M+H]$^+$=588.3.

2-(3-((1s,3s)-1-(4-methyl-4H-1,2,4-triazol-3-yl)-3-(methylsulfonyl)cyclobutyl)phenyl)-6-(((1-methylcyclobutyl)amino)methyl)-4-(trifluoromethyl)isoindolin-1-one (Peak 2, retention time=1.118 min) (73.5 mg, 18% yield). $^1$H NMR (400 MHz, methanol-d$_4$) δ 8.45 (s, 1H), 8.08 (s, 1H), 8.01 (s, 1H), 7.92 (s, 1H), 7.75 (d, J=8.4 Hz, 1H), 7.51 (t, J=8.0 Hz, 1H), 7.14 (d, J=8.4 Hz, 1H), 5.16 (s, 2H), 4.13-4.07 (m, 1H), 3.87 (s, 2H), 3.55-3.34 (m, 5H), 3.22-3.18 (m, 2H), 2.93 (s, 3H), 2.12-2.08 (m, 2H), 1.90-1.85 (m, 2H), 1.82-1.77 (m, 2H), 1.38 (s, 3H). LCMS [M+H]$^+$=588.3.

Example 84: Compound 327

2-(3-(1-(4-methyl-4H-1,2,4-triazol-3-yl)cyclobutyl)phenyl)-3-oxo-7-(trifluoromethyl)isoindoline-5-carboxamide), can be synthesized according to Scheme 82 (FIG. 82).

Intermediate 2: 3-(1-(4-methyl-4H-1,2,4-triazol-3-yl)cyclobutyl)aniline

A mixture of 3-[1-(3-bromophenyl)cyclobutyl]-4-methyl-1,2,4-triazole (1.8 g, 6.21 mmol) ammonia hydrate (14.5 mL, 401.64 mmol) and copper(I) oxide (0.3 mL, 12.41 mmol) in acetonitrile (15 mL) was stirred at 100° C. for 16 h in a sealed tube. The reaction was filtered and concentrated to give a crude product 3-(1-(4-methyl-4H-1,2,4-triazol-3-yl)cyclobutyl)aniline (1 g, 70% yield) as a yellow solid. LCMS [M+H]$^+$=229.1.

Intermediate 3: 2-(3-(1-(4-methyl-4H-1,2,4-triazol-3-yl)cyclobutyl)phenyl)-3-oxo-7-(trifluoromethyl) isoindoline-5-carbaldehyde To a mixture of 3-oxo-7-(trifluoromethyl)isoindoline-5-carbaldehyde (0.5 g, 2.19 mmol) and 3-[1-(4-methyl-1,2,4-triazol-3-yl)cyclobutyl]aniline (0.5 g, 2.19 mmol) in acetonitrile (12 mL) and Water (4 mL) was added a solution of silver(I) nitrate (0.5 g, 3.08 mmol) in water (1 mL) at 0° C., the mixture was stirred at 25° C. for 16 h. The reaction mixture was concentrated under vacuum. The residue was purified by flash chromatography on silica gel eluting with (10% methanol in dichloromethane) to afford 2-(3-(1-(4-methyl-4H-1,2,4-triazol-3-yl)cyclobutyl)phenyl)-3-oxo-7-(trifluoromethyl)isoindoline-5-carbaldehyde (430 mg, 44% yield) as a yellow solid. LCMS [M+H]$^+$=441.1.

Intermediate 4: 2-(3-(1-(4-methyl-4H-1,2,4-triazol-3-yl)cyclobutyl)phenyl)-3-oxo-7-(trifluoromethyl) isoindoline-5-carboxylic acid To a mixture of 2-(3-(1-(4-methyl-4H-1,2,4-triazol-3-yl)cyclobutyl)phenyl)-3-oxo-7-(trifluoromethyl)isoindoline-5-carbaldehyde (150 mg, 0.34 mmol), a hydrogen peroxide (30%, 0.42 mL, 0.37 mmol) aqueous solution, sodium dihydrogen phosphate (45 mg, 0.37 mmol), acetonitrile (2 mL), and water (1 mL) was added a solution of sodium chlorite (34 mg, 0.37 mmol) in water (1 mL). The mixture was stirred for 3 h at 25° C. Then quenched with sodium hydrogen sulfite solution. After an extractive work-up with dichloromethane (3×25 mL), the organic layer was washed with brine (20 mL), dried over magnesium sulfate, and concentrated to give a colorless solid of the desired product of 2-(3-(1-(4-methyl-4H-1,2,4-triazol-3-yl)cyclobutyl)phenyl)-3-oxo-7-(trifluoromethyl)isoindoline-5-carboxylic acid (150 mg, 96% yield). LCMS [M+H]$^+$=457.1.

Compound 327

To a solution of 2-(3-(1-(4-methyl-4H-1,2,4-triazol-3-yl)cyclobutyl)phenyl)-3-oxo-7-(trifluoromethyl)isoindoline-5-carboxylic acid (150 mg, 0.33 mmol), 2-(3H-[1,2,3]triazolo[4,5-b]pyridin-3-yl)-1,1,3,3-tetramethylisouronium hexafluorophosphate(V) (187 mg, 0.49 mmol) in N,N-dimethylformamide (3 mL) was added N-ethyl-N-isopropylpropan-2-amine (0.2 mL, 0.99 mmol) and ammonium hydroxide (26.3 mg, 0.49 mmol) at 25° C. The mixture was stirred at 25° C. for 12 h then concentrated under reduced pressure to remove most solvent, ethyl acetate (60 mL) was added and the mixture was washed with brine (20 mL), dried over anhydrous sodium sulfate and filtered. The filtrate was concentrated and the residue was purified by silica gel chromatography (mobile phase: ethyl acetate/petroleum ether, gradient 0% to 50%) and was purified by RP-HPLC (water(NH$_3$H$_2$O+NH$_4$HCO$_3$)-ACN 30% to 60%) to afford 2-(3-(1-(4-methyl-4H-1,2,4-triazol-3-yl)cyclobutyl)phenyl)-3-oxo-7-(trifluoromethyl)-isoindoline-5-carboxamide (66 mg, 44% yield). $^1$H NMR (400 MHz, methanol-d$_4$) δ 8.56 (s, 1H), 8.48 (s, 1H), 8.35 (s, 1H), 8.00 (d, J=2.0 Hz, 1H), 7.69 (dd, J=2.0, 0.8.4 Hz, 1H), 7.49 (t, J=8.0 Hz, 1H), 7.18 (d, J=8.0 Hz, 1H), 5.24 (s, 2H), 3.34 (s, 3H), 3.05-2.98 (m, 2H), 2.85-2.78 (m, 2H), 2.21-2.10 (m, 2H). LCMS [M+H]$^+$=456.2.

Example 85: Compound 328

Figure 83:
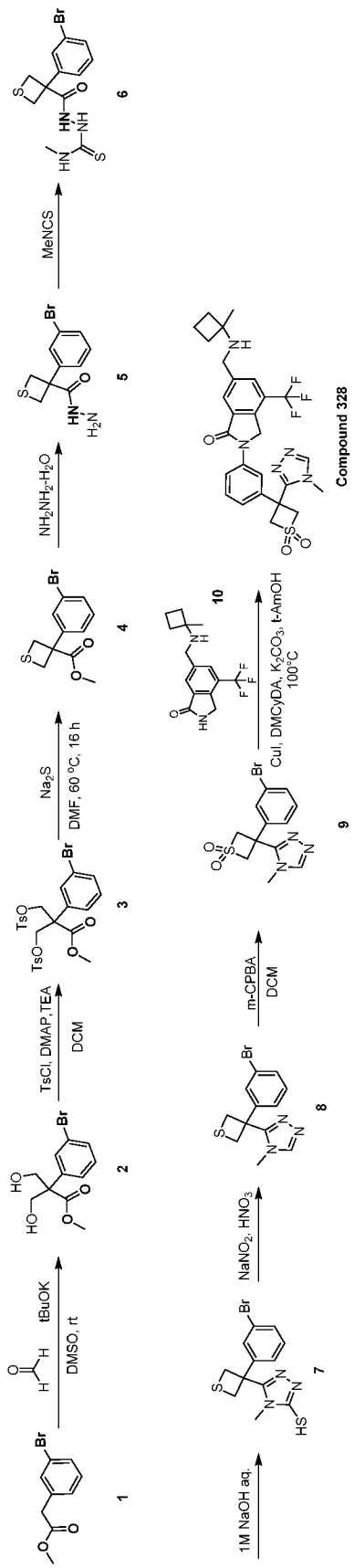

2-(3-(3-(4-methyl-4H-1,2,4-triazol-3-yl)-1,1-dioxidothietan-3-yl)phenyl)-6-(((1-methylcyclobutyl)amino)methyl)-4-(trifluoromethyl)isoindolin-1-one), can be synthesized according to Scheme 83 (FIG. 83).

Intermediate 2: methyl 2-(3-bromophenyl)-3-hydroxy-2-(hydroxymethyl)propanoate

To the mixture of paraformaldehyde (5.24 g, 174.62 mmol) and methyl 2-(3-bromophenyl)acetate (10.0 g, 43.65 mmol) in dimethyl sulfoxide (100 mL) was added potassium tert-butoxide (1 M in tetrahydrofuran, 8.73 mL, 8.73 mmol) under nitrogen atmosphere. The reaction mixture was stirred at 25° C. for 16 h then quenched by water (200 mL), extracted with ethyl acetate (2×200 mL), combined the organic phase and washed with brine (2×100 mL), dried over sodium sulfate, filtered and concentrated. The crude product was purified by silica gel chromatography (mobile phase: ethyl acetate/petroleum ether, gradient 30-40%) to give methyl 2-(3-bromophenyl)-3-hydroxy-2-(hydroxymethyl)propanoate (12 g, 95% yield) as a colorless oil. $^1$H NMR (400 MHz, DMSO-$d_6$) δ 7.45 (dd, J=0.8, 7.2 Hz, 1H), 7.32 (t, J=2.0 Hz, 1H), 7.28 (t, J=8.0 Hz, 1H), 7.21-7.16 (m, 1H), 4.87 (t, J=5.2 Hz, 2H), 3.97-3.94 (m, 2H), 3.92 (d, J=5.2 Hz, 2H), 3.59 (s, 3H).

Intermediate 3: methyl 2-(3-bromophenyl)-3-(tosyloxy)-2-((tosyloxy)methyl)propanoate To the mixture of methyl 2-(3-bromophenyl)-3-hydroxy-2-(hydroxymethyl)propanoate (4.5 g, 15.56 mmol) in dichloromethane (50 mL) was added triethylamine (8.68 mL, 62.26 mmol) and 4-dimethylaminopyridine (950 mg, 7.78 mmol) at 0° c. p-Toluenesulfonylchloride (7.42 g, 38.91 mmol) was added in portions and the mixture was stirred at 25° C. for 16 h. The mixture was concentrated and the residue was purified by silica gel chromatography (mobile phase: 100% dichloromethane, 220 nm monitored) to afford methyl 2-(3-bromophenyl)-3-(tosyloxy)-2-((tosyloxy)methyl)propanoate (4.7 g, 50% yield) as colorless oil. $^1$H NMR (400 MHz, CDCl$_3$) δ 7.66 (d, J=8.4 Hz, 4H), 7.41 (dd, J=1.2, 8.0 Hz, 1H), 7.33 (d, J=8.0 Hz, 4H), 7.14 (t, J=8.0 Hz, 1H), 7.06 (t, J=1.2 Hz, 1H), 6.98 (dd, J=1.2, 8.0 Hz, 1H), 4.55 (d, J=9.6 Hz, 2H), 4.41 (d, J=9.6 Hz, 2H), 2.47 (s, 6H).

Intermediate 4: methyl 3-(3-bromophenyl)thietane-3-carboxylate

A mixture of sodium sulfide (2.3 g, 17.57 mmol) and methyl 2-(3-bromophenyl)-3-(tosyloxy)-2-((tosyloxy)methyl)propanoate (7.0 g, 11.72 mmol) in N,N-dimethylformamide (100 mL) was stirred at 60° C. under N$_2$ for 16 h. The mixture was diluted with ethyl acetate (100 mL) and washed with water (50 mL×3). The organic was dried over sodium sulfate, filtered and concentrated. The residue was purified by silica gel chromatography (mobile phase: ethyl acetate/petroleum ether, gradient 0-10%) to afford methyl 3-(3-bromophenyl)thietane-3-carboxylate (1.4 g, 42% yield) as colorless oil. $^1$H NMR (400 MHz, CDCl$_3$) δ 7.47-7.38 (m, 2H), 7.26-7.22 (m, 1H), 7.22-7.17 (m, 1H), 3.93-3.87 (m, 2H), 3.77 (s, 3H), 3.76-3.74 (m, 2H).

Intermediate 5: 3-(3-bromophenyl)thietane-3-carbohydrazide

To a mixture of methyl 3-(3-bromophenyl)thietane-3-carboxylate (1.2 g, 4.18 mmol) in methanol (20 mL) was added hydrazine hydrate (85%, 6 mL, 122.37 mmol), the mixture was stirred at 80° C. for 16 h then concentrated to afford 3-(3-bromophenyl)thietane-3-carbohydrazide (1.1 g, 92% yield) as white solid which was used directly for next step. LCMS [M+H]$^+$=287.0 and 289.0.

Intermediate 6: 2-(3-(3-bromophenyl)thietane-3-carbonyl)-N-methylhydrazine-1-carbothioamide To a mixture of 3-(3-bromophenyl)thietane-3-carbohydrazide (1.2 g, 4.18 mmol) in tetrahydrofuran (10 mL) was added methyl isothiocyanate (611 mg, 8.36 mmol) at 25° c. The resulting mixture was stirred for 4 h then concentrated to afford 2-(3-(3-bromophenyl)thietane-3-carbonyl)-N-methylhydrazine-1-carbothioamide (1 g, 66% yield) as a white solid which was used directly for next step. LCMS [M+H]$^+$=360.0 and 362.0.

Intermediate 7: 5-(3-(3-bromophenyl)thietan-3-yl)-4-methyl-4H-1,2,4-triazole-3-thiol A mixture of 2-(3-(3-bromophenyl)thietane-3-carbonyl)-N-methylhydrazine-1-carbothioamide (1.0 g, 2.82 mmol) in 1M sodium hydroxide solution (15 mL, 15 mmol) was stirred at 25° C. for 16 h. The mixture was diluted with water (5 mL), then adjusted pH to 5 with 1M hydrochloric acid solution. The precipitate was filtered to afford 5-(3-(3-bromophenyl)thietan-3-yl)-4-methyl-4H-1,2,4-triazole-3-thiol (800 mg, 84% yield) as a yellow solid which was used directly for next step without further purification. LCMS [M+H]$^+$=341.0 and 343.0.

Intermediate 8: 3-(3-(3-bromophenyl)thietan-3-yl)-4-methyl-4H-1,2,4-triazole

To a solution of 5-(3-(3-bromophenyl)thietan-3-yl)-4-methyl-4H-1,2,4-triazole-3-thiol (1.1 g, 3.21 mmol) in water (10 mL) and acetonitrile (10 mL) was added sodium nitrite (2.22 g, 32.14 mmol), followed by the addition of 1M nitric acid aqueous (34.51 mL, 34.51 mmol) dropwise with stirring at 0° C. and stirred for another 1 h at 20° C. The mixture was quenched with saturated sodium bicarbonate solution (5 mL) then extracted with dichloromethane (3×20 mL). The combined organic phase was washed with brine (10 mL), dried over sodium sulfate, filtered and concentrated. The residue was purified by silica gel chromatography (mobile phase: methanol/dichloromethane, gradient 0% to 10%) to afford 3-(3-(3-bromophenyl)thietan-3-yl)-4-methyl-4H-1,2,4-triazole (360 mg, 36% yield) as a white solid. LCMS [M+H]$^+$=310.0 and 312.0.

Intermediate 9: 3-(3-bromophenyl)-3-(4-methyl-4H-1,2,4-triazol-3-yl)thietane 1,1-dioxide To a solution of 3-(3-(3-bromophenyl)thietan-3-yl)-4-methyl-4H-1,2,4-triazole (100.0 mg, 0.32 mmol) in dichloromethane (5 mL) was added 3-chloroperoxybenzoic acid (85%, 112 mg, 0.64 mmol). The mixture was stirred at 20° C. for 4 h then quenched with saturated sodium bicarbonate solution (5 mL), the mixture was extracted with dichloromethane (3×10 mL) and the organic layer was washed with brine (10 mL), dried over sodium sulfate, filtered and concentrated. The residue was purified by silica gel chromatography (mobile phase: methanol/dichloromethane, gradient 0% to 10%) to afford 3-(3-bromophenyl)-3-(4-methyl-4H-1,2,4-triazol-3-yl)thietane 1,1-dioxide (70 mg, 64% yield) as white solid. $^1$H NMR (400 MHz, DMSO-$d_6$) δ 8.51 (s, 1H), 7.63-7.52 (m, 2H), 7.40 (t, J=8.0 Hz, 1H), 7.34-7.27 (m, 1H), 5.35 (d, J=15.2 Hz, 2H), 5.08 (d, J=15.2 Hz, 2H), 3.21 (s, 3H).

Compound 328

A mixture of 3-(3-bromophenyl)-3-(4-methyl-4H-1,2,4-triazol-3-yl)thietane 1,1-dioxide (50.0 mg, 0.15 mmol), 6-[[(1-methylcyclobutyl)amino]methyl]-4-(trifluoromethyl)-isoindolin-1-one (50.6 mg, 0.17 mmol), copper(I) iodide (11.7 mg, 0.06 mmol), potassium carbonate (63.9 mg, 0.46 mmol) and (1S,2S)—N$^1$,N$^2$-dimethylcyclohexane-1,2-diamine (8.7 mg, 0.06 mmol) in tert-amyl alcohol (3 mL)

was stirred at 100° C. for 16 h under $N_2$. After cooled, the reaction was diluted with water (25 mL) and extracted with dichloromethane (3×25 mL). The combined organic phases were washed with brine (2×25 mL), dried over sodium sulfate, filtered and concentrated to dryness. The residue was purified by RP-HPLC (water($NH_3H_2O+NH_4HCO_3$)-ACN 50% to 80%) to afford 2-(3-(3-(4-methyl-4H-1,2,4-triazol-3-yl)-1,1-dioxidothietan-3-yl)phenyl)-6-(((1-methylcyclobutyl)amino)methyl)-4-(trifluoromethyl)isoindolin-1-one (27 mg, 55% yield). $^1$H NMR (400 MHz, methanol-$d_4$) δ 8.50 (s, 1H), 8.10 (s, 1H), 8.05 (t, J=2.0 Hz, 1H), 8.03 (s, 1H), 7.83 (dd, J=1.6, 8.4 Hz, 1H), 7.58 (t, J=8.0 Hz, 1H), 7.29 (dd, J=1.6, 8.0 Hz, 1H), 5.36 (d, J=14.8 Hz, 2H), 5.18 (s, 2H), 5.01 (d, J=14.8 Hz, 2H), 3.88 (s, 2H), 3.40 (s, 3H), 2.19-2.04 (m, 2H), 1.96-1.75 (m, 4H), 1.40 (s, 3H). LCMS [M+H]=560.2.

Example 86: Compound 329

Figure 84:
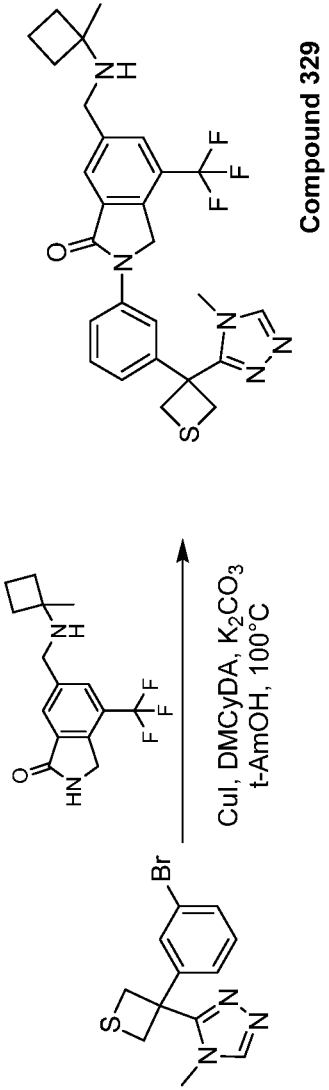

Compound 329 (2-(3-(3-(4-methyl-4H-1,2,4-triazol-3-yl)thietan-3-yl)phenyl)-6-(((1-methylcyclobutyl)amino)methyl)-4-(trifluoromethyl)isoindolin-1-one formate), can be synthesized according to Scheme 84 (FIG. 84).

A mixture of 3-(3-(3-bromophenyl)thietan-3-yl)-4-methyl-4H-1,2,4-triazole (50.0 mg, 0.15 mmol), 6-(((1-methylcyclobutyl)amino)methyl)-4-(trifluoromethyl)isoindolin-1-one (50.6 mg, 0.17 mmol), copper(I) iodide (11.7 mg, 0.06 mmol), potassium carbonate (63.9 mg, 0.46 mmol) and (1S,2S)—$N^1,N^2$-dimethylcyclohexane-1,2-diamine (8.78 mg, 0.06 mmol) in tert-amyl alcohol (3 mL) was stirred at 100° C. under $N_2$ for 16 h. After cooled, the reaction was diluted with water (25 mL) and extracted with dichloromethane (3×25 mL). The combined organic phases were washed with brine (2×25 mL), dried over sodium sulfate, filtered and concentrated to dryness. The residue was purified by RP-HPLC (water(FA)-ACN 15% to 45%) to afford 2-(3-(3-(4-methyl-4H-1,2,4-triazol-3-yl)thietan-3-yl)phenyl)-6-(((1-methylcyclobutyl)amino)methyl)-4-(trifluoromethyl)isoindolin-1-one formate (30 mg, 70% yield). $^1$H NMR (400 MHz, DMSO-$d_6$) δ 8.45 (s, 1H), 8.21 (s, 1H), 8.07 (s, 1H), 8.01 (d, J=7.2 Hz, 2H), 7.80 (dd, J=1.6, 8.0 Hz, 1H), 7.50 (t, J=8.0 Hz, 1H), 7.14 (d, J=7.6 Hz, 1H), 5.21 (s, 2H), 4.19 (d, J=9.6 Hz, 2H), 3.85 (s, 2H), 3.80 (d, J=9.6 Hz, 2H), 3.21 (s, 3H), 2.07-1.97 (m, 2H), 1.77-1.66 (m, 4H), 1.25 (s, 3H). LCMS [M+H]$^+$=528.2.

Example 87: Compounds 330, 331

Figure 85:
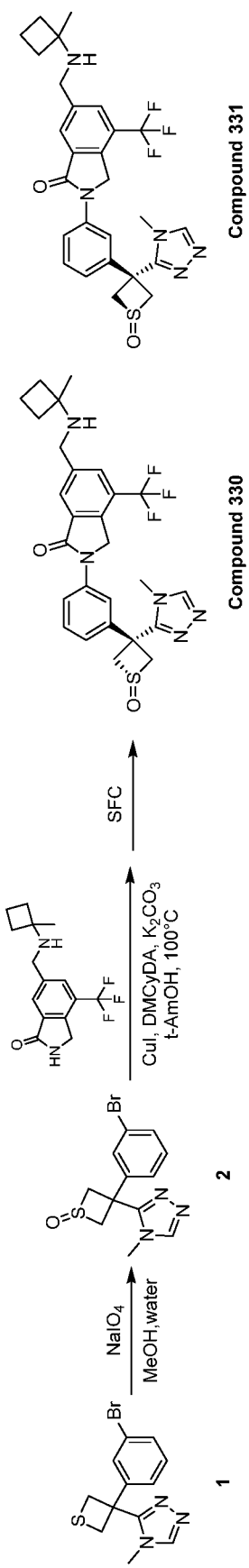

Compound 330 (2-(3-((1s,3s)-3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one), and Compound 331 (2-(3-((1r,3r)-3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one), can be synthesized according to Scheme 85 (FIG. 85).

Intermediate 2: 3-(3-bromophenyl)-3-(4-methyl-4H-1,2,4-triazol-3-yl)thietane 1-oxide To a solution of 3-(3-bromophenyl)-3-(4-methyl-4H-1,2,4-triazol-3-yl)thietane 1-oxide (500 mg, 1.61 mmol) in methanol (10 mL) and water (2 mL) was added sodium periodate (345 mg, 1.61 mmol) at 0° C. The mixture was stirred at 20° C. for 12 h then diluted with water (30 mL), extracted with dichloromethane (3×20 mL). The organic layer was washed with brine (20 mL), dried over sodium sulfate, filtered and concentrated. The residue was purified by silica gel chromatography (mobile phase: methanol/dichloro-methane, gradient 0% to 10%) to afford 3-(3-bromophenyl)-3-(4-methyl-4H-1,2,4-triazol-3-yl)thietane 1-oxide (200 mg, 38% yield). LCMS [M+H]$^+$=325.9 and 327.9.

Compounds 330, 331

A mixture of 3-(3-bromophenyl)-3-(4-methyl-4H-1,2,4-triazol-3-yl)thietane 1-oxide (100.0 mg, 0.31 mmol), 6-(((1-methylcyclobutyl)amino)methyl)-4-(trifluoromethyl)isoindolin-1-one (91.4 mg, 0.31 mmol), copper(I) iodide (23.3 mg, 0.12 mmol), (1S,2S)—$N^1,N^2$-dimethylcyclohexane-1,2-diamine (17.4 mg, 0.12 mmol) and potassium carbonate (84.7 mg, 0.61 mmol) in tert-amyl alcohol (3 mL) was stirred at 100° C. for 10 h under $N_2$. After cooled, the reaction was diluted with water (25 mL) and extracted with dichloromethane (3×25 mL). The combined organic phases were washed with brine (2×25 mL), dried over sodium sulfate, filtered and concentrated to dryness. The residue was purified by RP-HPLC (water($NH_3H_2O+NH_4HCO_3$)-ACN 43% to 73%) to afford 2-(3-(3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one (75.0 mg, 45% yield).

The above product was further purified by chiral SFC (Column=Daicel Chiralpak AD; Column dimensions=250 mm×30 mm×10 μm; Detection wavelength=220 nM; Flow rate=80 mL/min; Mobile phase: A: $CO_2$ B: ethanol; Isocratic: 40% B with 0.1% ammonium hydroxide) to afford tentatively assigned:

2-(3-((1s,3s)-3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one (Peak 1, Retention time=2.425 min) (32.4 mg, 43% yield). $^1$H NMR (400 MHz, DMSO-$d_6$) δ 8.45 (s, 1H), 8.05-8.00 (m, 2H), 7.88 (d, J=7.6 Hz, 1H), 7.83 (s, 1H), 7.48 (t, J=8.4 Hz, 1H), 6.98 (d, J=7.2 Hz, 1H), 5.23 (s, 2H), 4.73 (d, J=8.0 Hz, 2H), 3.85-3.78 (m, 4H), 3.21 (s, 3H), 2.02-1.95 (m, 2H), 1.75-1.64 (m, 4H), 1.22 (s, 3H). LCMS [M+H]$^+$=544.2.

2-(3-((1r,3r)-3-(4-methyl-4H-1,2,4-triazol-3-yl)-1-oxidothietan-3-yl)phenyl)-6-(((1-methylcyclobutyl)amino)methyl)-4-(trifluoromethyl)isoindolin-1-one (Peak 2, Retention time=2.481 min) (21.4 mg, 28% yield). $^1$H NMR (400 MHz, DMSO-$d_6$) δ 8.39 (s, 1H), 8.05-8.00 (m, 2H), 7.89 (s, 1H), 7.87-7.79 (m, 1H), 7.55-7.44 (m, 1H), 7.24-7.13 (m, 1H), 5.18 (s, 2H), 4.59 (d, J=8.8 Hz, 2H), 4.06 (d, J=8.8 Hz, 2H), 3.81 (s, 2H), 3.21 (s, 3H), 2.01-1.93 (m, 2H), 1.77-1.63 (m, 4H), 1.22 (s, 3H). LCMS [M+H]$^+$=544.2.

Example 88: Compound 332, 333

Figure 86:
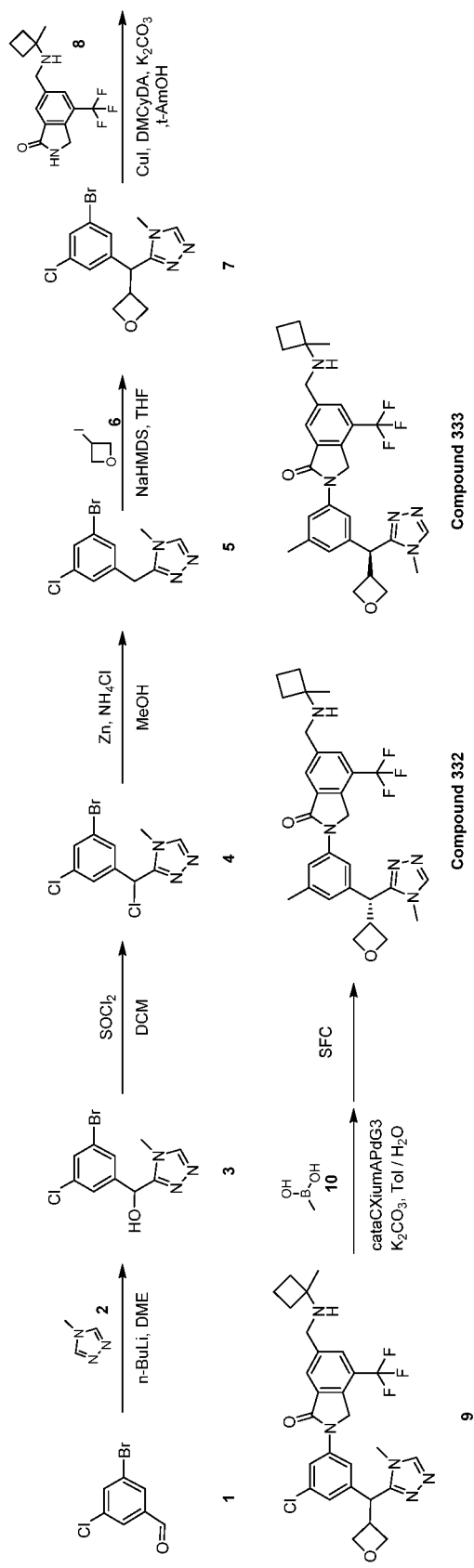

(R)-2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one and (S)-2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one), can be synthesized according to Scheme 86 (FIG. 86).

Intermediate 3: (3-bromo-5-chlorophenyl)(4-methyl-4H-1,2,4-triazol-3-yl)methanol To a solution of 4-methyl-4H-1,2,4-triazole (2.46 g, 22.8 mmol) in 1,2-dimethoxyethane (70 mL) was added n-butyl lithium (2.5 M in hexanes, 11.85 mL, 29.62 mmol) at −50° C. over 15 min. The mixture was stirred for 1 h at −50° C., then a solution of 3-bromo-5-chlorobenzaldehyde (5.0 g, 22.78 mmol) in 1,2-dimethoxyethane (15 mL) was added dropwise. The resulting mixture was warmed to 0° C. and stirred for another 1 h. The reaction was quenched with water (10 mL) and extracted with dichloromethane (3×50 mL). The combined organics were washed with brine (2×50 mL), dried over sodium sulfate and concentrated to give crude (3-bromo-5-chlorophenyl)(4-methyl-4H-1,2,4-triazol-3-yl)methanol (6.8 g, 100% yield) as a white solid which was used directly without further purification. LCMS [M+H]$^+$=301.9 and 303.9.

Intermediate 4: 3-((3-bromo-5-chlorophenyl)chloromethyl)-4-methyl-4H-1,2,4-triazole To a solution of (3-bromo-5-chlorophenyl)(4-methyl-4H-1,2,4-triazol-3-yl)methanol (6.8 g, 22.77 mmol) in dichloromethane (130 mL) was added N,N-dimethylformamide (1 mL) and thionyl chloride (3.3 mL, 45.55 mmol) at 0° C. The reaction mixture was stirred at 25° C. for 16 h. The mixture was then quenched with water (50 mL) and extracted with dichloromethane (3×50 mL). The combined organic layers were washed with saturated sodium bicarbonate (50 mL), brine (50 mL) and concentrated to dryness. The residue was purified by silica gel chromatography (mobile phase: methanol/dichloromethane, gradient 0% to 10%) to afford 3-((3-bromo-5-chlorophenyl)chloromethyl)-4-methyl-4H-1,2,4-triazole (6.0 g, 84% yield) as a yellow solid. LCMS [M+H]$^+$=320.0 and 321.9 and 323.9.

Intermediate 5: 3-(3-bromo-5-chlorobenzyl)-4-methyl-4H-1,2,4-triazole

To a solution of 3-((3-bromo-5-chlorophenyl)chloromethyl)-4-methyl-4H-1,2,4-triazole (6.0 g, 18.7 mmol) in methanol (50 mL) was added Zinc powder (4.43 g, 67.8 mmol) and ammonium chloride (3.50 g, 65.4 mmol). The mixture was stirred at 25° C. for 16 h and filtered. The filtrate was adjusted to pH 8 with ammonia aqueous, diluted with water (50 mL) and extracted with dichloromethane (3×50 mL). The combined organic layers were washed with brine (50 mL), dried over sodium sulfate and concentrated. The residue was purified by silica gel chromatography (mobile phase: methanol/dichloromethane, gradient 0% to 10%) to afford 3-(3-bromo-5-chlorobenzyl)-4-methyl-4H-1,2,4-triazole (2.5 g, 47% yield) as a yellow solid. LCMS [M+H]$^+$=286.0 and 288.0.

Intermediate 7: 3-((3-bromo-5-chlorophenyl)(oxetan-3-yl)methyl)-4-methyl-4H-1,2,4-triazole To a solution of 3-(3-bromo-5-chlorobenzyl)-4-methyl-4H-1,2,4-triazole (2.4 g, 8.38 mmol) in tetrahydrofuran (40 mL) was added sodium bis(trimethylsilyl)amide (1.0 M in tetrahydrofuran, 10.9 mL, 10.9 mmol) at 0° C. The mixture was stirred at 0° C. for 1 h then 3-iodooxetane (1.1 g, 12.56 mmol) was added. The resulting mixture was stirred at 25° C. for 2 h and quenched by water (30 mL), extracted with dichloromethane (3×30 mL). The combined organic layers were dried over sodium sulfate and concentrated under vacuum. The residue was purified by silica gel chromatography (mobile phase: methanol/dichloro-methane, gradient 0% to 10%) to afford 3-((3-bromo-5-chlorophenyl)(oxetan-3-yl)methyl)-4-methyl-4H-1,2,4-triazole (1.7 g, 59% yield) as a white solid. LCMS [M+H]$^+$=344.0.

Intermediate 9: 2-(3-chloro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one A mixture of 3-((3-bromo-5-chlorophenyl)(oxetan-3-yl)methyl)-4-methyl-4H-1,2,4-triazole (650.0 mg, 1.90 mmol), 6-(((1-methylcyclobutyl)amino)methyl)-4-(trifluoromethyl)-isoindolin-1-one (565.9 mg, 1.90 mmol), copper(I) iodide (144.5 mg, 0.76 mmol), (1S,2S)—N$^1$,N$^2$-dimethylcyclohexane-1,2-diamine (107.9 mg, 0.76 mmol) and potassium carbonate (786.6 mg, 5.69 mmol) in tert-amyl alcohol (10 mL) was stirred at 100° C. for 16 h under N$_2$. After cooled, the reaction was diluted with water (25 mL) and extracted with dichloro-methane (3×25 mL). The combined organic phases were washed with brine (2×25 mL), dried over sodium sulfate, filtered and concentrated to dryness. The residue was purified by silica gel chromatography (mobile phase: methanol/dichloromethane, gradient 0% to 5%) to afford 2-(3-chloro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (480 mg, 45% yield) as a white solid. LCMS [M+H]$^+$=560.2 and 562.2.

Compounds 332, 333

A mixture of 2-(3-chloro-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (250.0 mg, 0.45 mmol), methylboronic acid (133.6 mg, 2.23 mmol), Mesylate[(di(1-adamantyl)-n-butylphosphine)-2-(2'-amino-1,1'-biphenyl)]palladium(II) (32.5 mg, 0.04 mmol, CAS NO.: 1651823-59-4) and potassium carbonate (185.1 mg, 1.34 mmol) in toluene (3 mL) and water (0.03 mL) was stirred at 100° C. for 16 h under N$_2$. After cooled, the reaction was diluted with water (25 mL) and extracted with dichloromethane (3×25 mL). The combined organic phases were washed with brine (2×25 mL), dried over sodium sulfate, filtered and concentrated to dryness. The residue was purified by RP-HPLC (NH$_3$H$_2$O+NH$_4$HCO$_3$)/ACN 38% to 68%) to afford 2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (40 mg, 17% yield). LCMS [M+H]$^+$=540.0. The above racemate was further purified by chiral SFC (Column=Daicel Chiralcel OD; Column dimensions=250 mm×30 mm×10 μm; Detection wavelength=220 nM; Flow rate=90 mL/min; Run time=4.0 min; Column temperature=25° C.; A: CO$_2$ B: ethanol; Isocratic: 60% B with 0.1% ammonium hydroxide) to afford tentatively assigned:

(R)-2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 1, retention time=1.642 min) (8.5 mg, 19% yield). $^1$H NMR (400 MHz, methanol-d$_4$) δ 8.39 (s, 1H), 8.09 (s, 1H), 8.01 (s, 1H), 7.70 (s, 1H), 7.61 (s, 1H), 6.93 (s, 1H), 5.13 (s, 2H), 4.97-4.93 (m, 1H), 4.73 (d, J=11.2 Hz, 1H), 4.67-4.63 (m, 2H), 4.42 (t, J=6.4 Hz, 1H), 3.98 (d, J=11.6 Hz, 1H), 3.89 (s, 2H), 3.51 (s, 3H), 2.37 (s, 3H), 2.16-2.08 (m, 2H), 1.92-1.79 (m, 4H), 1.40 (s, 3H). LCMS [M+H]$^+$=540.3.

(S)-2-(3-methyl-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 2, retention time=3.687 min) (10.5 mg, 25% yield). $^1$H NMR (400 MHz, methanol-d$_4$) δ 8.39 (s, 1H), 8.09 (s, 1H), 8.01

(s, 1H), 7.70 (s, 1H), 7.61 (s, 1H), 6.93 (s, 1H), 5.13 (s, 2H), 4.97-4.93 (m, 1H), 4.73 (d, J=11.2 Hz, 1H), 4.67-4.63 (m, 2H), 4.42 (t, J=6.4 Hz, 1H), 3.98 (d, J=11.6 Hz, 1H), 3.89 (s, 2H), 3.51 (s, 3H), 2.37 (s, 3H), 2.16-2.08 (m, 2H), 1.92-1.79 (m, 4H), 1.40 (s, 3H). LCMS [M+H]$^+$=540.3.

Example 89: Compounds 334, 335

2-(3-((1r,3r)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one, and
2-(3-((1s,3s)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to Scheme 87 (FIG. 87).

Intermediate 2: 3-(1-(3-bromophenyl)-3-(difluoromethoxy)cyclobutyl)-4-methyl-4H-1,2,4-triazole To a solution of 3-(3-bromophenyl)-3-(4-methyl-4H-1,2,4-triazol-3-yl)cyclobutan-1-ol (1.0 g, 3.24 mmol) in acetonitrile (5 mL) was added copper(I) iodide (1.24 g, 6.49 mmol) at 0° C., the mixture was stirred for 1 h at 0° C. Then difluoro(fluorosulfonyl)acetic acid (1.73 g, 9.73 mmol) was added at 0° C. over 15 min and the resulting mixture was stirred at 50° C. for 1 h. The reaction was diluted with water (15 mL) and extracted with ethyl acetate (3×15 mL), combined the organic layers and washed with brine (2×15 mL), dried over sodium sulfate, filtered and concentrated. The resulting residue was purified by reverse phase chromatography (water (NH$_3$H$_2$O+NH$_4$HCO$_3$)-ACN 42-72%) to afford 3-(1-(3-bromophenyl)-3-(difluoromethoxy)cyclobutyl)-4-methyl-4H-1,2,4-triazole (50 mg, 4.3% yield) as white solid. LCMS [M+H]$^+$=358.0 and 360.0.
Compounds 334, 335
In a glove box, a mixture of 3-(1-(3-bromophenyl)-3-(difluoromethoxy)cyclobutyl)-4-methyl-4H-1,2,4-triazole (50 mg, 0.14 mmol), 6-(((1-methylcyclobutyl)amino)methyl)-4-(trifluoromethyl)isoindolin-1-one (45.8 mg, 0.15 mmol), copper(I) iodide (10.6 mg, 0.06 mmol), (1S,2S)—N$^1$,N$^2$-dimethylcyclohexane-1,2-diamine (7.9 mg, 0.06 mmol) and potassium carbonate (57.9 mg, 0.42 mmol) in tert-amyl alcohol (5 mL) was heated at 100° C. in sealed vial for 2 h then concentrated to dryness. The residue was purified by silica gel chromatography (mobile phase: methanol/dichloromethane, gradient 0% to 10%) to afford a crude product which was purified by RP-HPLC (water(NH$_3$H$_2$O+NH$_4$HCO$_3$)-ACN 70%-100%) to give 2-(3-(3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one (30 mg, 37% yield).
The above mixture was purified by chiral SFC (Column=REGIS(S,S)WHELK-O1, Column dimensions=250 mm×25 mm×10 μm; Detection wavelength=220 nM; Flow rate=80 mL/min; Mobile phase: A: CO$_2$ B: ethanol; Isocratic: 55% B with 0.1% ammonium hydroxide) to afford:
2-(3-((1r,3r)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1, retention time=6.810 min) (6.9 mg, 23% yield). $^1$H NMR (400 MHz, methanol-d$_4$) δ 8.39 (s, 1H), 8.08 (s, 1H), 8.01 (s, 1H), 7.93 (s, 1H), 7.69 (dd, J=1.2, 8.0 Hz, 1H), 7.49 (t, J=8.0 Hz, 1H), 7.10 (d, J=8.4 Hz, 1H), 6.39 (t, J=75.2 Hz, 1H), 5.15 (s, 2H), 4.75-4.65 (m, 1H), 3.87 (s, 2H), 3.48-3.43 (m, 2H), 3.34 (s, 3H), 2.93-2.86 (m, 2H), 2.16-2.05 (m, 2H), 1.92-1.75 (m, 4H), 1.38 (s, 3H). LCMS [M+H]$^+$=576.2

2-(3-((1s,3s)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2, retention time=7.915 min) (3.0 mg, 10% yield). $^1$H NMR (400 MHz, methanol-d$_4$) δ 8.34 (s, 1H), 8.11 (s, 1H), 8.09 (t, J=1.6 Hz, 1H), 8.03 (s, 1H), 7.73 (dd, J=1.2, 8.0 Hz, 1H), 7.53 (t, J=8.0 Hz, 1H), 7.27 (d, J=8.8 Hz, 1H), 6.39 (t, J=75.2 Hz, 1H), 5.18 (s, 2H), 4.95-4.89 (m, 1H), 3.90 (s, 2H), 3.38 (s, 3H), 3.32-3.26 (m, 2H), 3.19-3.10 (m, 2H), 2.18-2.07 (m, 1H), 2.18-2.07 (m, 2H), 1.93-1.77 (m, 4H), 1.41 (s, 3H). LCMS [M+H]$^+$=576.2.

Example 90: Compounds 336, 337

Compound 336 (2-(3-(ethylamino)-2-fluoro-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one) and
Compound 337 2-(3-(ethylamino)-2-fluoro-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to Scheme 88 (FIG. 88).

Intermediate 2: (3,5-dichloro-4-fluorophenyl)(4-methyl-4H-1,2,4-triazol-3-yl)methanol Under nitrogen, to a solution of 4-methyl-4H-1,2,4-triazole (7 g, 93.9 mmol) in distilled 1,2-dimethoxyethane (300 mL) was added n-butyllithium (2.5M in tetrahydrofuran, 32.2 mL, 80.44 mmol) at −50° C. and stirred for 0.5 h at −50° C. Then a solution of 3,5-dichloro-4-fluorobenzaldehyde (13.5 g, 70.0 mmol) in 1,2-dimethoxyethane (30 mL) was added dropwise. The resulting mixture was warmed to 0° C. and stirred for 1 h then quenched with water (100 mL), concentrated to remove most solvent then adjusted to pH=5 by 1M hydrochloride solution, extracted with dichloromethane (3×100 mL). The combined organic phase was washed with brine (100 mL), dried over sodium sulfate, filtrated and concentrated to afford (3,5-dichloro-4-fluorophenyl)(4-methyl-4H-1,2,4-triazol-3-yl)methanol (13 g, 67% yield) as yellow solid.

Intermediate 3: 3-(3,5-dichloro-4-fluorobenzyl)-4-methyl-4H-1,2,4-triazole

A solution of (3,5-dichloro-4-fluorophenyl)(4-methyl-4H-1,2,4-triazol-3-yl)methanol (13.0 g, 47.1 mmol) in tetrahydrofuran (400 mL) was added 1H-imidazole (19.2 g, 282.5 mmol), iodine (47.8 g, 188.3 mmol) and triphenylphosphane (49.4 g, 188.3 mmol) under nitrogen. The mixture was stirred at 80° C. for 3 h then cooled to room temperature. The mixture was washed with saturate the sodium sulfite solution (2×100 ml), saturated sodium bicarbonate solution (100 ml) and brine (100 ml), dried over sodium sulfate, filtrated and concentrated under vacuum. The residue was purified by silica gel chromatography (mobile phase: methanol/dichloromethane, gradient 0% to 10%) to afford 3-(3,5-dichloro-4-fluorobenzyl)-4-methyl-4H-1,2,4-triazole (11 g, 90%). $^1$H NMR (400 MHz, CDCl$_3$) δ 8.15 (s, 1H), 7.18 (d, J=12.0 Hz, 2H), 4.12 (s, 2H), 3.54 (s, 3H).

Intermediate 4: 3-(1-(3,5-dichloro-4-fluorophenyl)-3-methylcyclobutyl)-4-methyl-4H-1,2,4-triazole To a solution of 3-(3,5-dichloro-4-fluorobenzyl)-4-methyl-4H-1,2,4-triazole (480.0 mg, 1.9 mmol) in tetrahydrofuran (8 mL) was added sodium bis(trimethylsilyl)amide (1.0 M in tetrahydrofuran, 3.7 mL, 3.7 mmol) at −40° C. The mixture was stirred at −40° C. for 30 min, and 1,3-dibromo-2-methyl-propane (0.27 mL, 2.21 mmol) was added. The resulting mixture was stirred at 0° C. for 1 h and quenched by water (5 mL) then extracted with dichloromethane (3×10 mL). The combined organic layers were dried over sodium sulfate and concentrated under vacuum. The residue was purified by silica gel chromatography (mobile phase: methanol/dichloromethane, gradient 0% to 10%) to afford 3-(1-(3,5-dichloro-4-fluorophenyl)-3-methylcyclobutyl)-4-methyl-4H-1,2,4-triazole (500 mg, 86% yield) as a yellow solid. $^1$H NMR (400 MHz, methanol-$d_4$) δ 8.34 (s, 1H), 7.46 (d, J=6.0 Hz, 2H), 3.34 (s, 3H), 2.94-2.87 (m, 2H), 2.63-2.55 (m, 3H), 1.15 (d, J=6.0 Hz, 3H). LCMS [M+H]$^+$=314.1 and 316.0

Intermediate 5: 2-(3-chloro-2-fluoro-5-(3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one A mixture of 6-(((1-methylcyclobutyl)amino)methyl)-4-(trifluoromethyl)isoindolin-1-one (425.9 mg, 1.4 mmol), 3-(1-(3,5-dichloro-4-fluorophenyl)-3-methylcyclobutyl)-4-methyl-4H-1,2,4-triazole (400.0 mg, 1.3 mmol), (1S,2S)—N$^1$,N$^2$-dimethylcyclohexane-1,2-diamine (73.9 mg, 0.5 mmol), potassium carbonate (538.2 mg, 3.9 mmol) and copper(I) iodide (98.9 mg, 0.5 mmol) in tert-amyl alcohol (6 mL) was stirred at 100° C. for 2 h under nitrogen. The reaction mixture was diluted with dichloromethane (50 mL), washed with 5% ammonia aqueous (3×30 mL), dried over sodium sulfate, filtered and concentrated to dryness. The residue was purified by silica gel chromatography (mobile phase: methanol/dichloro-methane, gradient 0% to 10%) to afford 2-(3-chloro-2-fluoro-5-(3-methyl-1-(4-methyl-4H-1,2,4-triazol-3-yl)cyclobutyl)phenyl)-6-(((1-methylcyclobutyl)amino)methyl)-4-(trifluoro-methyl)isoindolin-1-one (180 mg, 26% yield) as a yellow solid. LCMS [M+H]$^+$=576.2.

Compounds 336, 337

To a solution of 2-(3-chloro-2-fluoro-5-(3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (160.0 mg, 0.28 mmol) was added ethylamine (0.18 mL, 2.78 mmol), cesium carbonate (271.5 mg, 0.83 mmol) and methanesulfonato[2-(di-t-butylphosphino)-3-methoxy-6-methyl-2',4',6'-tri-i-propylbiphenyl](2'-amino-2-biphenylyl)palladium(II) (23.73 mg, 0.03 mmol CAS No.: 2009020-38-4). The mixture was stirred at 90° C. for 3 h then concentrated under vacuum. The residue was purified by preparative TLC (solvent gradient: 10% methanol in dichloromethane) to afford crude product which was further purified by RP-HPLC (water(NH$_3$H$_2$O+NH$_4$HCO$_3$)-ACN 65% to 95%) to afford 2-(3-(ethylamino)-2-fluoro-5-(3-methyl-1-(4-methyl-4H-1,2,4-triazol-3-yl)cyclobutyl)phenyl)-6-(((1-methylcyclobutyl)-amino)methyl)-4-(trifluoromethyl)isoindolin-1-one (30 mg, 19% yield).

The above mixture was further purified by chiral SFC (Column=Daicel Chiralpak AD; Column dimensions=250 mm×30 mm×10 μm; Detection wavelength=220 nM; Flow rate=70 mL/min; Mobile phase: A: CO$_2$ B: ethanol; Isocratic: 30% B with 0.1% ammonium hydroxide) to afford:

2-(3-(ethylamino)-2-fluoro-5-((1r,3r)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 1, retention time=1.542 min) (2.7 mg, 9% yield). $^1$H NMR (400 MHz, methanol-$d_4$) δ 8.37 (s, 1H), 8.10 (s, 1H), 8.02 (s, 1H), 6.73 (dd, J=2.4, 6.4 Hz, 1H), 6.40 (dd, J=2.0, 7.6 Hz, 1H), 5.04 (s, 2H), 3.87 (s, 2H), 3.40 (s, 3H), 3.16-3.05 (m, 4H), 2.50-2.29 (m, 3H), 2.15-2.04 (m, 2H), 1.92-1.76 (m, 4H), 1.38 (s, 3H), 1.20 (t, J=7.2 Hz, 3H), 1.14 (d, J=6.4 Hz, 3H). LCMS [M+H]$^+$=585.4.

2-(3-(ethylamino)-2-fluoro-5-((1s,3s)-3-methyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (Peak 2, retention time=1.694 min) (17.2 mg, 57% yield). $^1$H NMR (400 MHz, methanol-$d_4$) δ 8.30 (s, 1H), 8.10 (s, 1H), 8.03 (s, 1H), 6.92 (dd, J=2.0, 6.0 Hz, 1H), 6.58 (dd, J=2.0, 7.6 Hz, 1H), 5.06 (s, 2H), 3.88 (s, 2H), 3.38 (s, 3H), 3.15-3.06 (m, 2H), 2.97-2.87 (m, 2H), 2.71-2.60 (m, 1H), 2.57-2.50 (m, 2H), 2.15-2.06 (m, 2H), 1.92-1.77 (m, 4H), 1.38 (s, 3H), 1.20 (t, J=7.2 Hz, 3H), 1.13 (d, J=6.4 Hz, 3H). LCMS [M+H]$^+$=585.4.

Example 91: Compound 338, 339

Figure 89:
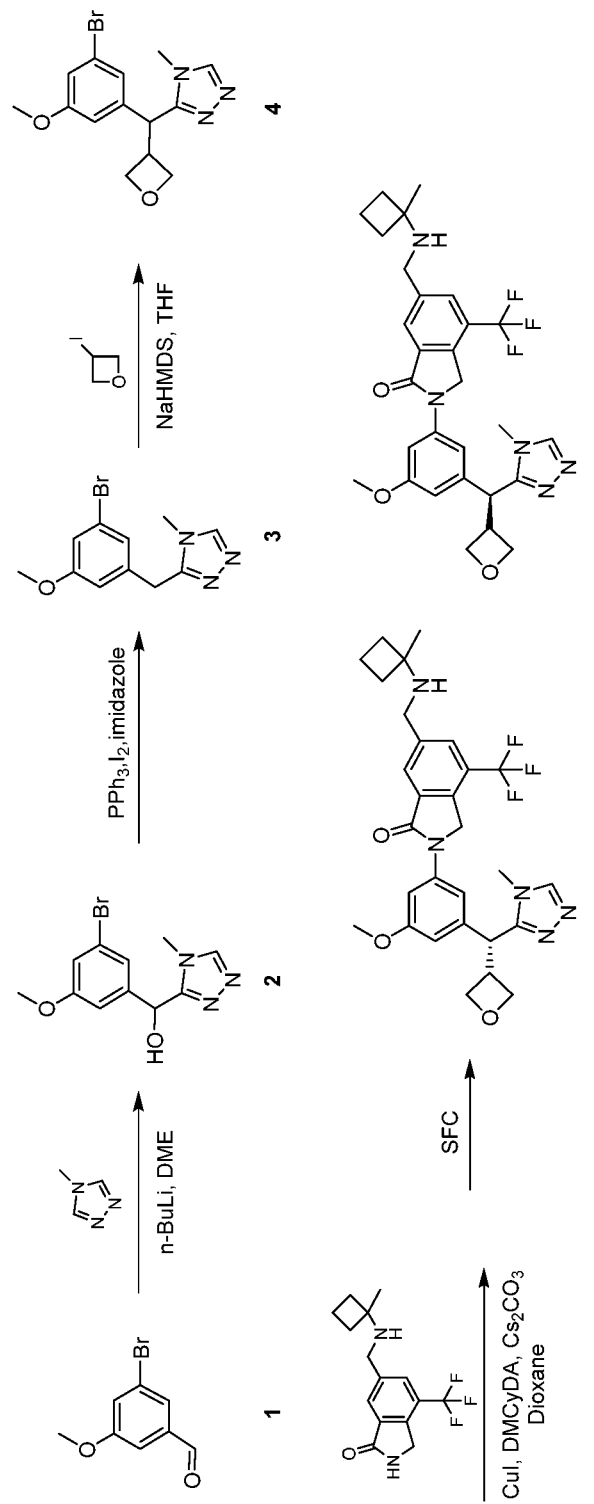

(R)-2-(3-methoxy-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one), and ((S)-2-(3-methoxy-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one), can be synthesized according to Scheme 89 (FIG. 89).

Intermediate 2: (3-bromo-5-methoxyphenyl)(4-methyl-4H-1,2,4-triazol-3-yl)methanol Under nitrogen, to a solution of 4-methyl-4H-1,2,4-triazole (1.16 g, 13.95 mmol) in 1,2-dimethoxyethane (60 mL) was added n-butyl lithium (2.5 M in hexane, 6.4 mL, 16.05 mmol) at −50° C. over 5 min. The mixture was stirred at −50° C. for 1 h then a solution of 3-bromo-5-methoxybenzaldehyde (3.0 g, 13.95 mmol) in 1,2-dimethoxyethane (10 mL) was added dropwise. The resulting reaction mixture was stirred at 0° C. for 1 h and quenched with water (5 mL). The mixture was adjusted to pH=7 with 1M hydrochloric acid solution and diluted with water (30 mL), extracted with dichloromethane (3×50 mL). The combined organic layers were washed with brine (50 mL), dried over sodium sulfate, filtered and concentrated. The residue was purified by silica gel chromatography (mobile phase: methanol/dichloromethane, gradient 0% to 10%) to afford (3-bromo-5-methoxyphenyl)(4-methyl-4H-1,2,4-triazol-3-yl)methanol (500 mg, 12% yield) as a yellow solid.

Intermediate 3: 3-(3-bromo-5-methoxybenzyl)-4-methyl-4H-1,2,4-triazole

To a solution of (3-bromo-5-methoxyphenyl)(4-methyl-4H-1,2,4-triazol-3-yl)methanol (500 mg, 1.68 mmol) in tetrahydrofuran (30 mL) was added iodide (1.70 g, 6.73 mmol), imidazole (0.69 g, 10.10 mmol) and triphenylphosphine (1.77 g, 6.73 mmol), the mixture was stirred at 80° C. for 24 h then concentrated. The residue was dissolved with dichloromethane (30 mL), washed with saturated sodium bicarbonate solution (2×10 mL), brine (10 mL), dried over sodium sulfate, filtered and concentrated. The residue was purified by silica gel chromatography (mobile phase: methanol/dichloromethane, gradient 0% to 10%) to afford 3-((3-bromo-5-methoxyphenyl)chloromethyl)-4-methyl-4H-1,2,4-triazole (230 mg, 54% yield) as a white solid. LCMS [M+H]$^+$=282.0 and 284.0.

Intermediate 4: 3-((3-bromo-5-methoxyphenyl)
(oxetan-3-yl)methyl)-4-methyl-4H-1,2,4-triazole To a solution of 3-((3-bromo-5-methoxyphenyl)chloromethyl)-4-methyl-4H-1,2,4-triazole (190 mg, 0.67 mmol) in 1,2-dimethoxyethane (3 mL) was added sodium bis(trimethylsilyl)amide (1 M in tetrahydrofuran, 1 mL, 1 mmol) at 0° C., the mixture was stirred for 30 min, then 3-iodooxetane (0.10 mL, 1.21 mmol) was added and the resulting mixture was stirred at 25° C. for another 2 h. Quenched with water (2 mL), extracted with dichloromethane (3×10 mL), combined the organic layers and washed with brine (10 mL), dried over sodium sulfate, filtered and concentrated. The residue was purified by silica gel chromatography (mobile phase: methanol/dichloromethane, gradient 0% to 6%) to give 3-((3-bromo-5-methoxyphenyl)(oxetan-3-yl)methyl)-4-methyl-4H-1,2,4-triazole (130 mg, 57% yield) as a yellow solid. LCMS [M+H]$^+$=338.0 and 340.0.
Compounds 338, 339

A mixture of 3-((3-bromo-5-methoxyphenyl)(oxetan-3-yl)methyl)-4-methyl-4H-1,2,4-triazole (130 mg, 57% yield), copper(I) iodide (29.3 mg, 0.15 mmol), (1S,2S)—N$^1$,N$^2$-dimethylcyclohexane-1,2-diamine (21.9 mg, 0.15 mmol) and potassium carbonate (159.4 mg, 0.15 mmol) in tert-amyl alcohol (2 mL) was stirred at 100° C. for 2 h under N$_2$. After cooled, the reaction was diluted with water (5 mL) and extracted with dichloromethane (3×10 mL). The combined organic phases were washed with brine (2×10 mL), dried over sodium sulfate, filtered and concentrated to dryness. The residue was purified by silica gel chromatography (mobile phase: methanol/dichloromethane, gradient 0% to 5%) to afford 2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one (100 mg, 47% yield). LCMS [M+H]$^+$=556.3.

The above mixture was purified by chiral SFC (Column=Daicel Chiralpak AS; Column dimensions=250 mm×30 mm×10 μm; Detection wavelength=220 nM; Flow rate=80 mL/min; Mobile phase: A: CO$_2$ B: ethanol; Isocratic: 40% B with 0.1% ammonium hydroxide) to afford tentatively assigned:

(R)-2-(3-methoxy-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 1, retention time=4.162 min) (39.6 mg, 40% yield). $^1$H NMR (400 MHz, methanol-d$_4$) δ 8.41 (s, 1H), 8.10 (s, 1H), 8.03 (s, 1H), 7.54 (t, J=2.0 Hz, 1H), 7.41-7.36 (m, 1H), 6.72-6.64 (m, 1H), 5.15 (s, 2H), 4.99-4.96 (m, 1H), 4.77 (d, J=12.0 Hz, 1H), 4.68 (dd, J=6.4, 8.0 Hz, 2H), 4.43 (t, J=6.4 Hz, 1H), 4.06-3.97 (m, 1H), 3.88 (s, 2H), 3.84 (s, 3H), 3.55 (s, 3H), 2.16-2.07 (m, 2H), 1.94-1.87 (m, 2H), 1.86-1.77 (m, 2H), 1.40 (s, 3H). LCMS [M+H]$^+$=556.3.

(S)-2-(3-methoxy-5-((4-methyl-4H-1,2,4-triazol-3-yl)(oxetan-3-yl)methyl)phenyl)-6-(((1-methylcyclobutyl)amino)methyl)-4-(trifluoromethyl)isoindolin-1-one (Peak 2, retention time=5.071 min) (39.1 mg, 39% yield). $^1$H NMR (400 MHz, methanol-d$_4$) δ 8.40 (s, 1H), 8.09 (s, 1H), 8.01 (s, 1H), 7.55-7.50 (m, 1H), 7.37 (s, 1H), 6.70-6.64 (m, 1H), 5.13 (s, 2H), 4.97-4.95 (m, 1H), 4.75 (d, J=12 Hz, 1H), 4.67 (dd, J=4.8, 6.0 Hz, 2H), 4.42 (t, J=6.4 Hz, 1H), 4.04-3.96 (m, 1H), 3.87 (s, 2H), 3.82 (s, 3H), 3.53 (s, 3H), 2.15-2.06 (m, 2H), 1.92-1.85 (m, 2H), 1.84-1.75 (m, 2H), 1.38 (s, 3H). LCMS [M+H]$^+$=556.3.

Example 92: Compound 340

Figure 90:
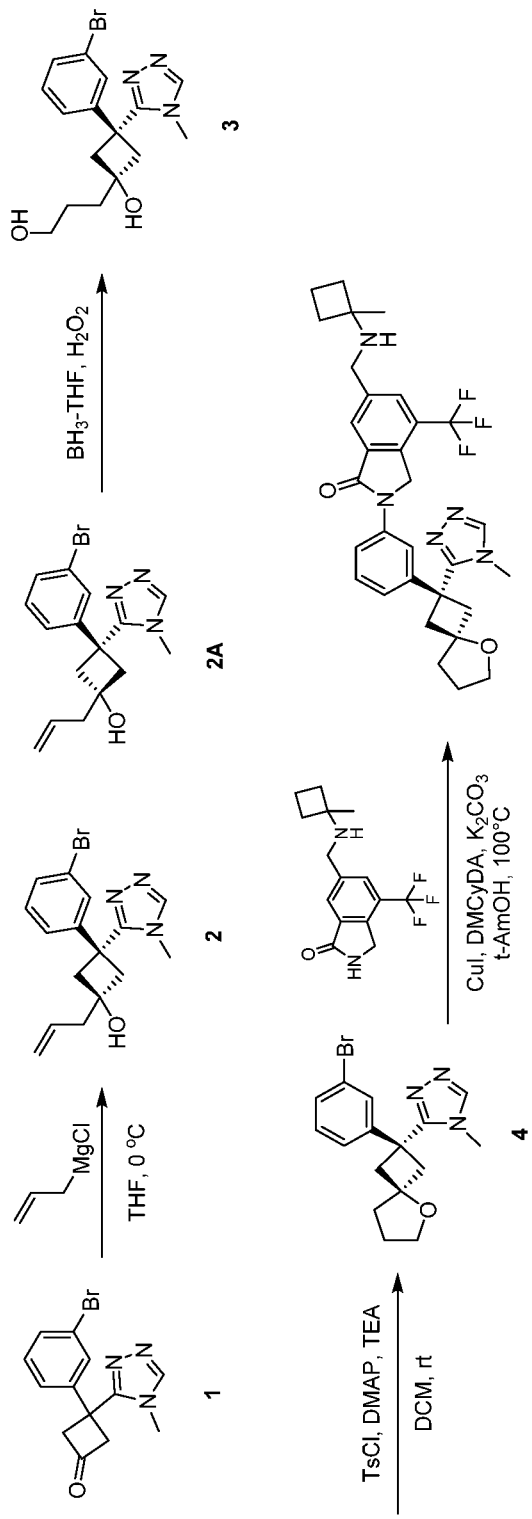

2-(3-((2s, 4r)-2-(4-methyl-4H-1,2,4-triazol-3-yl)-5-oxaspiro[3.4]octan-2-yl)phenyl)-6-(((1-methylcyclobutyl)amino)methyl)-4-(trifluoromethyl) isoindolin-1-one), can be synthesized according to Scheme 90 (FIG. 90).

Intermediate 2: (1r, 3s)-1-allyl-3-(3-bromophenyl)-3-(4-methyl-4H-1,2,4-triazol-3-yl)cyclobutan-1-ol, and (1s, 3r)-1-allyl-3-(3-bromophenyl)-3-(4-methyl-4H-1,2,4-triazol-3-yl)cyclobutan-1-ol To a solution of 3-(3-bromophenyl)-3-(4-methyl-4H-1, 2, 4-triazol-3-yl)cyclobutan-1-one (500.0 mg, 1.63 mmol) in tetrahydrofuran (10 mL) was added allyl magnesium chloride (2M in tetrahydrofuran, 2.04 mL, 4.08 mmol) at −40° C., the mixture was stirred at 25° C. for 16 h then filtrated and concentrated under vacuum. The crude was purified by silica gel chromatography (mobile phase: methanol/dichloromethane, gradient 0% to 10%) to afford (1r, 3s)-1-allyl-3-(3-bromophenyl)-3-(4-methyl-4H-1,2,4-triazol-3-yl)cyclobutan-1-ol (200 mg, 35% yield) and (1s, 3r)-1-allyl-3-(3-bromophenyl)-3-(4-methyl-4H-1, 2, 4-triazol-3-yl)cyclobutan-1-ol (300 mg, 52% yield) as a yellow solid. LCMS [M+H]$^+$=347.9 and 349.9.

Intermediate 3: (1r, 3s)-3-(3-bromophenyl)-1-(3-hydroxypropyl)-3-(4-methyl-4H-1, 2, 4-triazol-3-yl) cyclobutan-1-ol To a solution of (1r,3s)-1-allyl-3-(3-bromophenyl)-3-(4-methyl-4H-1,2,4-triazol-3-yl)cyclobutan-1-ol (400.0 mg, 1.15 mmol) in tetrahydrofuran (10 mL) was added dropwise borane (1 M in tetrahydrofuran, 2.9 mL, 2.9 mmol) at 0° C., the resulting mixture was allowed to warm to 20° C. and stirred for 1 h. Then a solution of 1 M sodium hydroxide (7 mL, 7 mmol) was added and stirred for 15 min, then hydrogen peroxide (4.3 mL, 42.16 mmol) was added dropwise at 0° C. The resulting mixture was stirred at 20° C. for 16 hr then quenched by saturated sodium sulfite solution (20 mL). The resulting solution was extracted with ethyl acetate (3×40 mL), combined the organic layers and concentrated. The residue was purified by silica gel chromatography (mobile phase: methanol/dichloromethane, gradient 0% to 10%) to give (1r, 3s)-3-(3-bromophenyl)-1-(3-hydroxypropyl)-3-(4-methyl-4H-1, 2, 4-triazol-3-yl)cyclobutan-1-ol (200 mg, 47% yield) as a white solid. LCMS [M+H]$^+$=365.9 and 367.9.

Intermediate 4: 3-((2s, 4r)-2-(3-bromophenyl)-5-oxaspiro [3.4] octan-2-yl)-4-methyl-4H-1, 2, 4-triazole To a solution of (1r, 3s)-3-(3-bromophenyl)-1-(3-hydroxypropyl)-3-(4-methyl-4H-1, 2, 4-triazol-3-yl)cyclobutan-1-ol (150.0 mg, 0.41 mmol) in dichloromethane (20 mL) was added trimethylamine (0.34 mL, 2.46 mmol), 4-dimethylaminopyridine (10 mg, 0.08 mmol) and 4-methylbenzenesulfonyl chloride (150 mg, 0.79 mmol). The resulting mixture was stirred at 26° C. for 16 h then concentrated to dryness, the residue was purified by preparative TLC (solvent gradient: 10% methanol in dichloromethane) to afford 3-((2s, 4r)-2-(3-bromophenyl)-5-oxaspiro [3.4] octan-2-yl)-4-methyl-4H-1, 2, 4-triazole (60 mg, 42% yield) as colorless oil. LCMS [M+H]$^+$=347.9 and 349.9.
Compound 340

To a solution of 6-(((1-methylcyclobutyl)amino)methyl)-4-(trifluoromethyl)isoindolin-1-one (66.8 mg, 0.22 mmol) and 3-((2s, 4r)-2-(3-bromophenyl)-5-oxaspiro [3.4] octan-2-yl)-4-methyl-4H-1, 2, 4-triazole (60 mg, 0.17 mmol) in tert-amyl alcohol (2 mL) was added (1S,2S)—N$^1$,N$^2$-dimethylcyclohexane-1,2-diamine (9.8 mg, 0.07 mmol) and potassium carbonate (47.6 mg, 0.34 mmol) and copper(I) iodide (13.1 mg, 0.07 mmol). The mixture was stirred at 100° C. for 2 h under nitrogen atmosphere. After cooled, the reaction was diluted with water (25 mL) and extracted with dichloromethane (3×25 mL). The combined organic phases were washed with brine (2×25 mL), dried over sodium sulfate, filtered and concentrated to dryness. The residue was purified by silica gel chromatography (mobile phase: methanol/dichloromethane, gradient 0% to 5%) to afford 2-(3-((2s,4r)-2-(4-methyl-4H-1, 2, 4-triazol-3-yl)-5-oxaspiro[3.4]octan-2-yl)phenyl)-6-(((1-methylcyclobutyl)amino)methyl)-4-(trifluoromethyl) isoindolin-1-one (30.3 mg, 30% yield). $^1$H NMR (400 MHz, methanol-$d_4$) δ 8.43 (s, 1H), 8.10 (s, 1H), 8.03 (s, 1H), 7.93 (s, 1H), 7.71 (d, J=8.0 Hz, 1H), 7.48 (t, J=8.0 Hz, 1H), 7.13 (d, J=8.0 Hz, 1H), 5.16 (s, 2H), 3.90 (s, 2H), 3.83 (t, J=6.8 Hz, 2H), 3.41 (s, 3H), 3.26 (d, J=13.2 Hz, 2H), 3.01 (d, J=13.2 Hz, 2H), 2.20-2.08 (m, 2H), 1.98-1.78 (m, 8H), 1.41 (s, 3H). LCMS [M+H]$^+$=566.4.

Example 93: Compound 341

Figure 91:
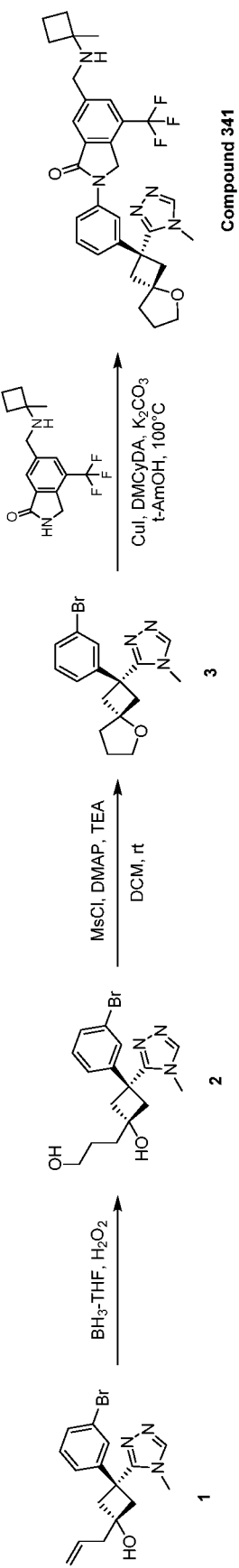

2-(3-((2r, 4s)-2-(4-methyl-4H-1, 2, 4-triazol-3-yl)-5-oxaspiro [3.4] octan-2-yl)phenyl)-6-(((1-methylcyclobutyl)amino)methyl)-4-(trifluoromethyl) isoindolin-1-one), can be synthesized according to Scheme 91 (FIG. 91).

Intermediate 2: (1s, 3r)-3-(3-bromophenyl)-1-(3-hydroxypropyl)-3-(4-methyl-4H-1,2,4-triazol-3-yl) cyclobutan-1-ol To a solution of (1s,3r)-1-allyl-3-(3-bromophenyl)-3-(4-methyl-4H-1,2,4-triazol-3-yl)cyclobutan-1-ol (300.0 mg, 0.86 mmol) in tetrahydrofuran (10 mL) was added dropwise borane (1 M in tetrahydrofuran, 2.2 mL, 2.2 mmol) at 0° C., the resulting mixture was allowed to warm to 20° C. and stirred for 1 h. Then a solution of 1 M sodium hydroxide aqueous (4.3 mL, 4.31 mmol) was added and stirred for 15 minutes, hydrogen peroxide (4.6 mL, 45.69 mmol) was added dropwise at 0° C. The resulting mixture was stirred at 20° C. for 16 h and quenched by saturated sodium sulfite solution (20 mL). The resulting solution was extracted with ethyl acetate (3×40 mL), combined the organic layers and concentrated. The residue was purified by silica gel chromatography (mobile phase: methanol/dichloromethane, gradient 0% to 10%) to give (1s,3r)-3-(3-bromophenyl)-1-(3-hydroxypropyl)-3-(4-methyl-4H-1,2,4-triazol-3-yl) cyclobutan-1-ol (210 mg, 66% yield) as a white solid. LCMS [M+H]$^+$=365.9 and 367.9.

Intermediate 3: 3-((2r, 4s)-2-(3-bromophenyl)-5-oxaspiro[3.4]octan-2-yl)-4-methyl-4H-1,2,4-triazole To a solution of (1s, 3r)-3-(3-bromophenyl)-1-(3-hydroxypropyl)-3-(4-methyl-4H-1,2,4-triazol-3-yl)cyclobutan-1-ol (110.0 mg, 0.30 mmol) in dichloromethane (20 mL) was added dropwise triethylamine (0.25 mL, 1.8 mmol), 4-dimethylaminopyridine (6.6 mg, 0.05 mmol) and methane sulfonic anhydride (78.5 mg, 0.45 mmol). The resulting mixture was stirred at 26° C. for 16 h then concentrated to dryness and the residue was purified by preparative TLC (solvent gradient: 10% methanol in dichloromethane) to afford 3-((2r, 4s)-2-(3-bromophenyl)-5-oxaspiro[3.4]octan-2-yl)-4-methyl-4H-1,2,4-triazole (15 mg, 14% yield) as colorless oil. LCMS [M+H]$^+$=347.9 and 349.9.

Compound 341

To a solution of 6-(((1-methylcyclobutyl)amino)methyl)-4-(trifluoromethyl)-isoindolin-1-one (33.4 mg, 0.11 mmol) and 3-((2r, 4s)-2-(3-bromophenyl)-5-oxaspiro [3.4]octan-2-yl)-4-methyl-4H-1, 2, 4-triazole (30.0 mg, 0.09 mmol) in tert-amyl alcohol (2 mL) was added ((1S,2S)—N$^1$,N$^2$-dimethylcyclohexane-1,2-diamine (4.9 mg, 0.03 mmol), potassium carbonate (23.8 mg, 0.17 mmol) and copper(I) iodide (6.6 mg, 0.03 mmol). The mixture was stirred at 100° C. for 2 h under nitrogen atmosphere. After cooled, the reaction was diluted with water (25 mL) and extracted with dichloromethane (3×25 mL). The combined organic phases were washed with brine (2×25 mL), dried over sodium sulfate, filtered and concentrated to dryness. The residue was purified by silica gel chromatography (mobile phase: methanol/dichloromethane, gradient 0% to 5%) to afford 2-(3-((2r, 4s)-2-(4-methyl-4H-1,2,4-triazol-3-yl)-5-oxaspiro[3.4]octan-2-yl)phenyl)-6-(((1-methylcyclobutyl)amino)methyl)-4-(trifluoromethyl) isoindolin-1-one (12.5 mg, 24% yield). $^1$H NMR (400 MHz, methanol-$d_4$) δ 8.28 (s, 1H), 8.15 (s, 1H), 8.09 (s, 1H), 8.01 (s, 1H), 7.69 (d, J=8.0 Hz, 1H), 7.49 (t, J=8.0 Hz, 1H), 7.29 (d, J=8.0 Hz, 1H), 5.16 (s, 2H), 3.88 (s, 2H), 3.78 (t, J=6.4 Hz, 2H), 3.42 (s, 3H), 3.23 (d, J=13.2 Hz, 2H), 3.13-3.06 (m, 2H), 2.18-2.05 (m, 2H), 1.93-1.85 (m, 6H), 1.83-1.76 (m, 2H), 1.39 (s, 3H). LCMS [M+H]$^+$=566.3.

Example 94: Compound 342, 343

Figure 92:
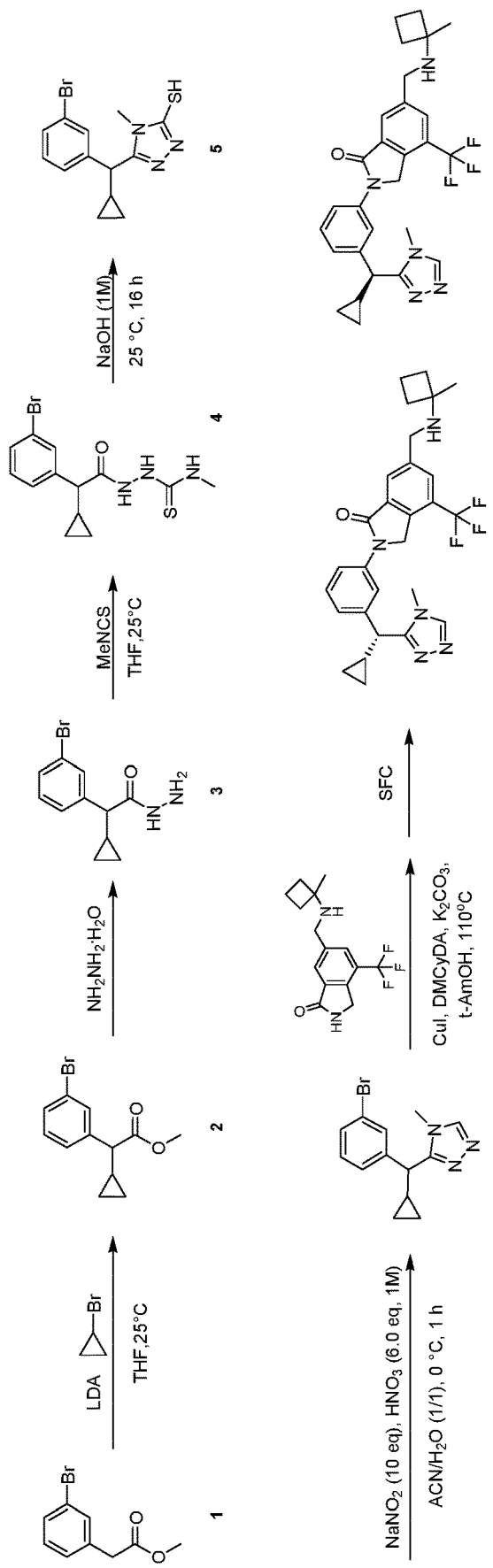

Compound 342 ((R)-2-(3-(cyclopropyl(4-methyl-4H-1,2,4-triazol-3-yl)methyl)phenyl)-6-(((1-methylcyclobutyl) amino)methyl)-4-(trifluoromethyl)isoindolin-1-one) and Compound 343 ((S)-2-(3-(cyclopropyl(4-methyl-4H-1,2,4-triazol-3-yl)methyl)phenyl)-6-(((1-methylcyclobutyl) amino)methyl)-4-(trifluoromethyl)isoindolin-1-one), can be synthesized according to Scheme 92 (FIG. 92).

Intermediate 2: methyl 2-(3-bromophenyl)-2-cyclopropylacetate

To a solution of methyl 2-(3-bromophenyl)acetate (3 g, 13.1 mmol) in dichloromethane (10 mL) was added in tetrahydrofuran (50 mL) was added lithium diisopropylamide (2M in tetrahydrofuran, 13.1 mL, 26.2 mmol) at 0° C., the reaction was stirred for 30 min then bromocyclopropane (1.89 mL, 23.6 mmol) was added. The resulting mixture was stirred at 25° C. for 2 h then quenched by ammonium chloride solution (30 mL), extracted with ethyl acetate (3×50 mL), the combined organic phase was washed with brine (1×50 mL), dried over sodium sulfate, filtered and concentrated to dryness. The crude was purified by silica gel chromatography (mobile phase: ethyl acetate/petroleum ether, gradient 0% to 20%) to give the crude product which was further purified by RP-HPLC (water(NH$_3$H$_2$O+NH$_4$HCO$_3$)-ACN 46% to 76%) to afford methyl 2-(3-bromophenyl)-2-cyclopropylacetate (1.2 g, 34% yield) as a colorless oil. $^1$H NMR (400 MHz, CDCl$_3$) δ 7.35 (s, 1H), 7.24 (d, J=8.0 Hz, 1H), 7.16-7.08 (m, 1H), 7.07-6.99 (m, 1H), 3.53 (s, 3H), 2.60 (d, J=10.4 Hz, 1H), 1.37-1.19 (m, 1H), 0.57-0.47 (m, 1H), 0.45-0.36 (m, 1H), 0.23-0.19 (m, 1H), 0.04-0.07 (m, 1H).

Intermediate 3: 2-(3-bromophenyl)-2-cyclopropylacetohydrazide

To a solution of methyl 2-(3-bromophenyl)-2-cyclopropylacetate (1.26 g, 4.68 mmol) in methanol (15 mL) was added hydrazine hydrate (6.87 mL, 140.2 mmol). The reaction mixture was stirred at 80° C. for 2 h and concentrated to afford 2-(3-bromophenyl)-2-cyclopropylacetohydrazide (1.25 g, 99% yield) as a white solid which was used directly without further purification.

Intermediate 4: 2-(2-(3-bromophenyl)-2-cyclopropylacetyl)-N-methylhydrazine-1-carbothioamide To a solution of 2-(3-bromophenyl)-2-cyclopropylacetohydrazide (1.25 g, 4.68 mmol) in tetrahydrofuran (15 mL) was added methyl isothiocyanate (0.68 g, 4.67 mmol). The solution was stirred at 25° C. for 1 h and concentrated under vacuum to afford crude 2-(2-(3-bromophenyl)-2-cyclopropylacetyl)-N-methylhydrazine-1-carbothioamide (1.6 g, 99% yield) as a yellow oil.

Intermediate 5: 5-((3-bromophenyl)(cyclopropyl)methyl)-4-methyl-4H-1,2,4-triazole-3-thiol A mixture of 2-(2-(3-bromophenyl)-2-cyclopropylacetyl)-N-methylhydrazine-1-carbothioamide (1.60 g, 4.67 mmol) in aqueous sodium hydroxide (1.0 M, 24 mL, 24 mmol) was stirred at 25° C. for 2 h and then adjusted to pH=5 with 1M hydrochloric acid solution. The precipitate was filtered and washed with water (20 mL), dried under vacuum to give 5-((3-bromophenyl)(cyclopropyl)methyl)-4-methyl-4H-1,2,4-triazole-3-thiol (1.49 g, 98% yield) as a light yellow solid.

Intermediate 6: 3-((3-bromophenyl)(cyclopropyl)methyl)-4-methyl-4H-1,2,4-triazole To a solution of 5-((3-bromophenyl)(cyclopropyl)methyl)-4-methyl-4H-1,2,4-triazole-3-thiol (0.50 g, 1.54 mmol) in water (2 mL) and acetonitrile (2 mL) was added sodium nitrite (1.06 g, 15.4 mmol) and nitric acid (1 M, 16.56 mL, 16.56 mmol) at 0° C. The reaction mixture was stirred for 2 h at 20° C. and extracted with dichloromethane (2×20 mL). The combined organic layers were washed with saturated sodium bicarbonate (30 mL), brine (30 mL), dried over sodium sulfate, filtered and concentrated. The residue was purified by silica gel chromatography (mobile phase: methanol/dichloromethane, gradient 0% to 4%) to afford 3-((3-bromophenyl)(cyclopropyl)methyl)-4-methyl-4H-1,2,4-triazole (160 mg, 36% yield) as a colorless oil. LCMS [M+H]$^+$=292.0 and 294.0.

Compounds 342, 343

A mixture of 3-((3-bromophenyl)(cyclopropyl)methyl)-4-methyl-4H-1,2,4-triazole (150.0 mg, 0.51 mmol), 6-(((1-methylcyclobutyl)amino)methyl)-4-(trifluoromethyl)isoindolin-1-one (153.1 mg, 0.51 mmol), copper(I) iodide (19.6 mg, 0.10 mmol), (1S,2S)—N$^1$,N$^2$-dimethylcyclohexane-1,2-diamine (29.2 mg, 0.21 mmol) and potassium carbonate (212.9 mg, 1.54 mmol) in tert-amyl alcohol (2 mL) was stirred at 100° C. for 10 h under N$_2$. After cooled, the reaction was diluted with water (25 mL) and extracted with dichloromethane (3×25 mL). The combined organic phases were washed with brine (2×25 mL), dried over sodium sulfate, filtered and concentrated to dryness. The residue was purified by preparative TLC (solvent gradient: 10% methanol in dichloromethane) to afford 2-(3-(cyclopropyl(4-methyl-4H-1,2,4-triazol-3-yl)methyl)phenyl)-6-(((1-methylcyclobutyl)-amino)methyl)-4-(trifluoromethyl)isoindolin-1-one (166 mg, 64% yield). LCMS [M+H]$^+$=510.3.

The above mixture was further purified by chiral SFC (Column=Regis(S,S)Whelk-O1; Column dimensions=250 mm×25 mm×10 μm; Detection wavelength=220 nM; Flow rate=80 mL/min; Mobile phase: A: CO$_2$ B: ethanol; Isocratic: 55% B with 0.1% ammonium hydroxide) to afford tentatively assigned:

(R)-2-(3-(cyclopropyl(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=2.679 min) (37 mg, 45% yield). $^1$H NMR (400 MHz, methanol-d$_4$) δ 8.41 (s, 1H), 8.10 (s, 1H), 8.02 (s, 1H), 7.90 (s, 1H), 7.77 (d, J=7.6 Hz, 1H), 7.49-7.45 (m, 1H), 7.15 (d, J=7.6 Hz, 1H), 5.16 (s, 2H), 3.88 (s, 2H), 3.61 (d, J=9.6 Hz, 1H), 3.49 (s, 3H), 2.15-2.09 (m, 2H), 1.91-1.88 (m, 2H), 1.86-1.78 (m, 2H), 1.73-1.69 (m, 1H), 1.40 (s, 3H), 0.79-0.77 (m, 1H), 0.71-0.68 (m, 1H), 0.51-0.49 (m, 1H), 0.42-0.40 (m, 1H). LCMS [M+H]$^+$=510.1.

(S)-2-(3-(cyclopropyl(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=3.258 min) (48 mg, 58% yield). $^1$H NMR (400 MHz, methanol-d$_4$) δ 8.41 (s, 1H), 8.10 (s, 1H), 8.02 (s, 1H), 7.90-7.89 (s, 1H), 7.79-7.76 (m, 1H), 7.47 (t, J=8.0 Hz, 1H), 7.15 (d, J=7.6 Hz, 1H), 5.16 (s, 2H), 3.88 (s, 2H), 3.61 (d, J=9.6 Hz, 1H), 3.49 (s, 3H), 2.15-2.08 (m, 2H), 1.92-1.88 (m, 2H), 1.85-1.78 (m, 2H), 1.75-1.68 (m, 1H), 1.40 (s, 3H), 0.80-0.74 (m, 1H), 0.72-0.67 (m, 1H), 0.52-0.48 (m, 1H), 0.44-0.39 (m, 1H). LCMS [M+H]$^+$=510.1.

Example 95: Compound 344, 345

Figure 93:
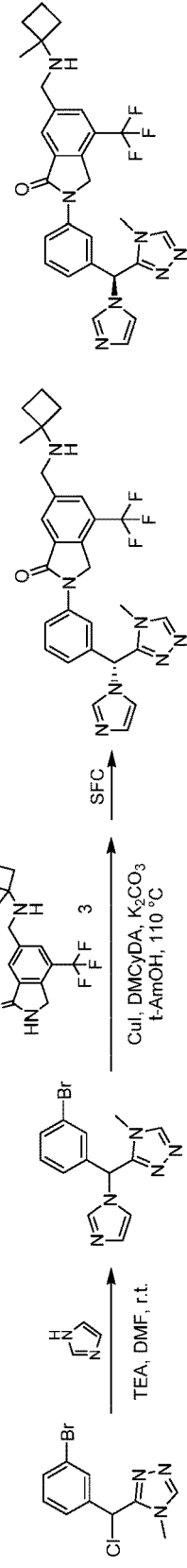

Compound 344 ((R)-2-(3-((1H-imidazol-1-yl)(4-methyl-4H-1,2,4-triazol-3-yl)methyl)phenyl)-6-(((1-methylcyclobutyl)amino)methyl)-4-(trifluoromethyl)isoindolin-1-one), and Compound 345 ((S)-2-(3-((1H-imidazol-1-yl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 93 (FIG. 93).

Intermediate 2: 3-((3-bromophenyl)(1H-imidazol-1-yl)methyl)-4-methyl-4H-1,2,4-triazole To a solution of 3-((3-bromophenyl)chloromethyl)-4-methyl-4H-1,2,4-triazole (600.0 mg, 2.09 mmol) in N,N-dimethylformamide (10 mL) was added 1H-imidazole (213.8 mg, 3.14 mmol) and triethylamine (0.87 mL, 6.28 mmol). The mixture was stirred at 90° C. for 2 h. After cooled, the reaction was diluted with water (25 mL) and extracted with ethyl acetate (3×25 mL). The combined organic phases were washed with brine (2×30 mL), dried over sodium sulfate, filtered and concentrated to dryness. The residue was purified by preparative TLC (solvent gradient: 20% methanol in dichloromethane) to afford 3-((3-bromophenyl)(1H-imidazol-1-yl)methyl)-4-methyl-4H-1,2,4-triazole (280.0 mg, 42% yield) as a yellow oil. LCMS [M+H]$^+$=318.0 and 320.0.

Compounds 344, 345

A mixture of 3-((3-bromophenyl)(1H-imidazol-1-yl)methyl)-4-methyl-4H-1,2,4-triazole (280.0 mg, 0.96 mmol), 6-(((1-methylcyclobutyl)amino)methyl)-4-(trifluoromethyl)-isoindolin-1-one (288.4 mg, 0.10 mmol), (1S,2S)—N$^1$,N$^2$-dimethylcyclohexane-1,2-diamine (134.1 mg, 0.88 mmol), potassium carbonate (364.9 mg, 2.65 mmol) and copper(I) iodide (167.6 mg, 0.88 mmol) in tert-amyl alcohol (3 mL) was heated at 100° C. for 2 h under nitrogen atmosphere and concentrated to dryness. The residue was purified by preparative TLC (solvent gradient: 10% methanol in dichloromethane) to afford 2-(3-((1H-imidazol-1-yl)(4-methyl-4H-1,2,4-triazol-3-yl)methyl)phenyl)-6-(((1- methylcyclobutyl)amino)methyl)-4-(trifluoromethyl) isoindolin-1-one (110.0 mg, 21% yield) as a yellow oil.

The above product was further purified by chiral SFC (Column=Daicel Chiralcel OD-H; Column dimensions=250 mm×30 mm×5 μm; Detection wavelength=220 nM; Flow rate=60 mL/min; Mobile phase: A: $CO_2$ B: ethanol; Isocratic: 55% B with 0.1% ammonium hydroxide) to afford tentatively assigned:

(R)-2-(3-((1H-imidazol-1-yl)(4-methyl-4H-1,2,4-triazol-3-yl)methyl)phenyl)-6-(((1-methylcyclobutyl)amino) methyl)-4-(trifluoromethyl)isoindolin-1-one (Peak 1, retention time=5.495 min) (30.1 mg, 27% yield). $^1$H NMR (400 MHz, DMSO-$d_6$) δ 8.55 (s, 1H), 8.05 (s, 2H), 8.00 (s, 1H), 7.89 (dd, J=1.2, 6.8 Hz, 1H), 7.83 (s, 1H), 7.48 (t, J=8.0 Hz, 1H), 7.28 (s, 1H), 7.24 (s, 1H), 7.12 (d, J=7.6 Hz, 1H), 6.96 (s, 1H), 5.16 (s, 2H), 3.82 (s, 2H), 3.52 (s, 3H), 3.31-3.29 (m, 1H), 1.99-1.97 (m, 2H), 1.74-1.65 (m, 4H), 1.23 (s, 3H). LCMS [M+H]$^+$=536.1.

(S)-2-(3-((1H-imidazol-1-yl)(4-methyl-4H-1,2,4-triazol-3-yl)methyl)phenyl)-6-(((1-methylcyclobutyl)amino) methyl)-4-(trifluoromethyl)isoindolin-1-one (Peak 2, retention time=5.479 min) (34.1 mg, 31% yield). $^1$H NMR (400 MHz, DMSO-$d_6$) δ 8.55 (s, 1H), 8.05 (s, 2H), 8.00 (s, 1H), 7.89 (dd, J=1.6, 6.4 Hz, 1H), 7.83 (s, 1H), 7.48 (t, J=8.0 Hz, 1H), 7.28 (s, 1H), 7.24 (s, 1H), 7.12 (d, J=8.0 Hz, 1H), 6.96 (s, 1H), 5.16 (s, 2H), 3.81 (s, 2H), 3.52 (s, 3H), 3.31-3.29 (m, 1H); 2.01-1.97 (m, 2H), 1.74-1.65 (m, 4H), 1.23 (s, 3H). LCMS [M+H]$^+$=536.1.

Example 96: Compounds 346, 347

Compound 346 (2-(3-((1s,3s)-3-acetyl-1-(4-methyl-4H-1,2,4-triazol-3-yl)cyclobutyl)phenyl)-6-(((1-methylcyclobutyl)amino)methyl)-4-(trifluoromethyl)isoindolin-1-one, and Compound 347 (2-(3-((1r,3r)-3-acetyl-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to the following steps.

Intermediate: 1-(3-(3-bromophenyl)-3-(4-methyl-4H-1,2,4-triazol-3-yl)cyclobutyl)ethan-1-one To a solution of 3-(3-bromophenyl)-3-(4-methyl-4H-1,2,4-triazol-3-yl)cyclobutane-1-carbonitrile (60 mg, 0.19 mmol) in tetrahydrofuran (2 mL) was added methyl magnesium bromide (3 M in tetrahydrofuran, 0.2 mL, 0.60 mmol). The mixture was stirred at 0° C. for 2 h under $N_2$ then quenched with saturated ammonium chloride aqueous (10 mL), extracted with ethyl acetate (3×40 mL), washed with water (30 mL) and dried over sodium sulfate, filtered and concentrated to give 1-(3-(3-bromophenyl)-3-(4-methyl-4H-1,2,4-triazol-3-yl)cyclobutyl)ethan-1-one (61 mg, 68% yield) as a brown solid which was used directly for next step. LCMS [M+H]$^+$=334.0 and 336.0.
Compounds 346, 347

A mixture of 1-(3-(3-bromophenyl)-3-(4-methyl-4H-1,2,4-triazol-3-yl)cyclobutyl)ethan-1-one (100 mg, 0.21 mmol), 6-(((1-methylcyclobutyl)amino)methyl)-4-(trifluoromethyl) isoindolin-1-one (cf. Scheme 1; 68.7 mg, 0.23 mmol), copper(I) iodide (16 mg, 0.08 mmol), potassium carbonate (86.8 mg, 0.63 mmol) and (1S,2S)—$N^1$,$N^2$-dimethylcyclohexane-1,2-diamine (11.9 mg, 0.08 mmol) in tert-amyl alcohol (2 mL) was stirred at 100° C. under nitrogen protection for 2 hrs. The resulting reaction was concentrated and the residue was dissolved with dichloromethane (30 mL), washed with 5% ammonia aqueous (2×10 mL) and brine (10 mL), dried over anhydrous sodium sulfate, filtrated and concentrated under vacuum. The residue was purified by RP-HPLC (($NH_3H_2O$+$NH_4HCO_3$)-ACN 46%-76%) to afford 2-(3-(3-acetyl-1-(4-methyl-4H-1,2,4-triazol-3-yl)cyclobutyl)phenyl)-6-(((1-methylcyclobutyl)amino)methyl)-4-(trifluoromethyl)isoindolin-1-one (40 mg, 35% yield). LCMS [M+H]$^+$=552.3.

The above mixture was further purified by chiral SFC (Column=Daicel Chiralpak OD; Column dimensions=250 mm×30 mm×10 μm; Detection wavelength=220 nM; Flow rate=120 mL/min; Mobile phase: A: $CO_2$ B: ethanol; Isocratic: 35% B with 0.1% ammonium hydroxide) to afford tentatively assigned:

2-(3-((1s,3s)-3-acetyl-1-(4-methyl-4H-1,2,4-triazol-3-yl) cyclobutyl)phenyl)-6-(((1-methylcyclobutyl)amino) methyl)-4-(trifluoromethyl)isoindolin-1-one (Peak 1, retention time=4.879 min) (6.5 mg, 16% yield). $^1$H NMR (400 MHz, methanol-$d_4$) δ 8.33 (s, 1H), 8.09 (s, 1H), 8.07 (s, 1H), 8.01 (s, 1H), 7.72 (d, J=8.0 Hz, 1H), 7.52 (t, J=8.0 Hz, 1H), 7.24 (d, J=7.2 Hz, 1H), 5.17 (s, 2H), 3.87 (s, 2H), 3.59-3.52 (m, 1H), 3.36 (s, 3H), 3.23-3.17 (m, 2H), 3.05-2.98 (m, 2H), 2.15 (s, 3H), 2.10 (d, J=10.4 Hz, 2H), 1.91-1.86 (m, 2H), 1.82-1.76 (m, 2H), 1.38 (s, 3H). LCMS [M+H]$^+$=552.3.

2-(3-((1r,3r)-3-acetyl-1-(4-methyl-4H-1,2,4-triazol-3-yl) cyclobutyl)phenyl)-6-(((1-methylcyclobutyl)amino) methyl)-4-(trifluoromethyl)isoindolin-1-one (Peak 2, retention time=6.144 min) (9.7 mg, 23% yield). $^1$H NMR (400 MHz, methanol-$d_4$) δ 8.44 (s, 1H), 8.10 (s, 1H), 8.03 (s, 1H), 7.90 (s, 1H), 7.71 (d, J=8.8 Hz, 1H), 7.49 (t, J=8.0 Hz, 1H), 7.10 (d, J=7.6 Hz, 1H), 5.17 (s, 2H), 3.89 (s, 2H), 3.47-3.42 (m, 1H), 3.38 (s, 3H), 3.25-3.20 (m, 2H), 2.99-2.93 (m, 2H), 2.17 (s, 3H), 2.12 (d, J=10.4 Hz, 2H), 1.92-1.88 (m, 2H), 1.84-1.78 (m, 2H), 1.40 (s, 3H). LCMS [M+H]$^+$=552.3.

Example 97: Compound 348, 349

Figure 94:
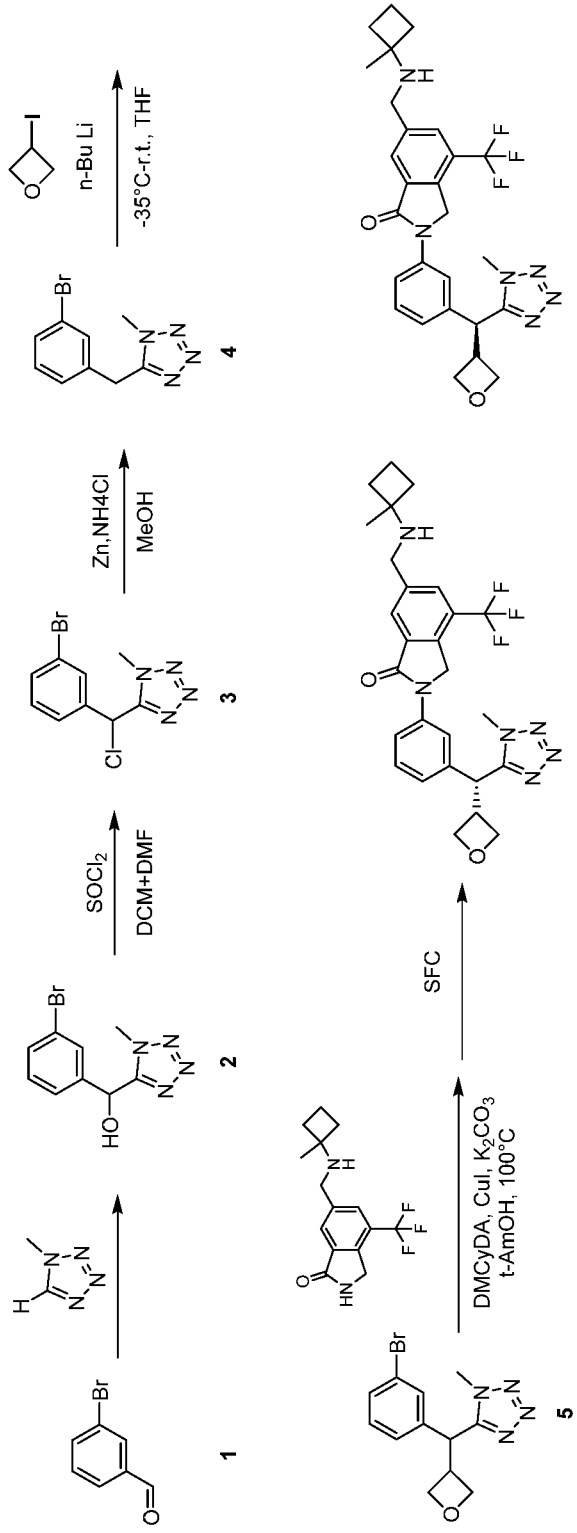

Compound 348 ((R)-2-(3-((1-methyl-1H-tetrazol-5-yl) (oxetan-3-yl)methyl)phenyl)-6-(((1-methylcyclobutyl) amino)methyl)-4-(trifluoromethyl)isoindolin-1-one), and Compound 349 ((S)-2-(3-((1-methyl-1H-tetrazol-5-yl) (oxetan-3-yl)methyl)phenyl)-6-(((1-methylcyclobutyl) amino)methyl)-4-(trifluoromethyl)isoindolin-1-one), can be synthesized according to Scheme 94 (FIG. 94).

Intermediate 2: (3-bromophenyl)(1-methyl-1H-tetrazol-5-yl)methanol

To a solution of 1-methyltetrazole (330 mg, 3.9 mmol) in 1,2-dimethoxyethane (10 mL) was added n-butyl lithium (2.5 M in tetrahydrofuran, 2 mL, 5.0 mmol) at −50° C. The reaction mixture was stirred for 1.5 h at −50° C. under $N_2$. Then a solution of 3-bromobenzaldehyde in 1,2-dimethoxyethane (3 mL) was added dropwise and the resulting mixture was warmed to 0° C. and stirred for another 1 h. The reaction mixture was quenched with water (5 mL), adjusted to pH=5 by 1 M hydrochloride aqueous, extracted with dichloromethane (3×20 mL), the combined organic layers was washed with brine (20 mL), dried over sodium sulfate, filtered and concentrated. The residue was purified by silica gel chromatography (mobile phase: methyl alcohol/dichloromethane, gradient 0%-5%) to afford (3-bromophenyl)(1-methyl-1H-tetrazol-5-yl)methanol (640 mg, 61% yield) as yellow oil. LCMS [M+H]$^+$=269.0 and 271.0.

Intermediate 3: 5-((3-bromophenyl)chloromethyl)-1-methyl-1H-tetrazole

To a solution of (3-bromophenyl)(1-methyl-1H-tetrazol-5-yl)methanol (520 mg, 1.9 mmol) in dichloromethane (5 mL) was added thionyl chloride (0.4 mL, 5.8 mmol) and N,N-dimethylformamide (1 mL) at 0° C. Then the mixture was stirred at 25° C. for 16 h adjusted to pH=8 with saturated sodium bicarbonate aqueous. The reaction mixture was diluted with dichloromethane (80 mL), washed with brine (3×50 mL), dried over sodium sulfate, filtered and concentrated to dryness. The mixture was concentrated to give 5-((3-bromophenyl)chloromethyl)-1-methyl-1H-tetrazole (500 mg, 90% yield) as a yellow oil which was used for the next step directly. LCMS [M+H]$^+$=287.2.

Intermediate 4:
5-(3-bromobenzyl)-1-methyl-1H-tetrazole

To a solution of 5-[(3-bromophenyl)-chloro-methyl]-1-methyl-tetrazole (500 mg, 1.7 mmol) and ammonium chloride (325 mg, 6.1 mmol) in methanol (10 mL) was added zinc powder (398 mg, 6.1 mmol), then the mixture was stirred at 25° C. for 4 h. Filtered and the filtrate was concentrated to dryness, adjusted to pH=7 by addition of saturated sodium bicarbonate solution then extracted with dichloromethane (3×30 mL), washed with brine (30 mL), dried over sodium sulfate, filtered and concentrated to dryness. The residue was purified by silica gel chromatography (mobile phase: methyl alcohol/dichloromethane, gradient 0% to 10%) to give 5-(3-bromobenzyl)-1-methyl-1H-tetrazole (310 mg, 70% yield) as a colorless oil. LCMS [M+H]$^+$=253.1 and 255.1.

Intermediate 5: 5-((3-bromophenyl)(oxetan-3-yl) methyl)-1-methyl-1H-tetrazole

To a solution of 5-(3-bromobenzyl)-1-methyl-1H-tetrazole (200 mg, 0.8 mmol) in tetrahydrofuran (10 mL) was added n-butyllithium (2.5 M solution in tetrahydrofuran 0.5 mL, 1.2 mmol) at 0° C. and stirred for 30 mins, 3-iodooxetane (0.1 mL, 1.2 mmol) in tetrahydrofuran (1 mL) was added, the mixture was stirred at 25° C. for 2 h then quenched by water (20 mL), extracted with dichloromethane (2×20 mL), washed with brine (20 mL), dried with sodium sulfate, filtrated and concentrated. The mixture was purified silica gel chromatography (mobile phase: methanol/dichloromethane, gradient 4% to 6%) to afford 5-((3-bromophenyl)(oxetan-3-yl)methyl)-1-methyl-1H-tetrazole (200 mg, 82% yield) as a yellow solid. LCMS [M+H]$^+$=309.1 and 311.1.

Compounds 348, 349
To a solution of 5-((3-bromophenyl)(oxetan-3-yl) methyl)-1-methyl-1H-tetrazole (250 mg, 0.8 mmol), 6-(((1-methylcyclobutyl)amino)methyl)-4-(trifluoromethyl)isoindolin-1-one (289 mg, 1 mmol) and potassium carbonate (279 mg, 2 mmol) in tert-amyl alcohol (3 mL), was added (1S,2S)—N$^1$,N$^2$-dimethylcyclohexane-1,2-diamine (46 mg, 0.3 mmol) and copper(I) iodide (62 mg, 0.3 mmol). The mixture was stirred at 100° C. for 2 h under nitrogen atmosphere then concentrated to dryness, purified by RP-HPLC (water (NH$_3$H$_2$O+NH$_4$HCO$_3$)-ACN 42% to 72%) to afford 2-(3-(((1-methyl-1H-tetrazol-5-yl)(oxetan-3-yl) methyl)phenyl)-6-(((1-methylcyclobutyl)amino)methyl)-4-(trifluoromethyl)isoindolin-1-one. The above mixture was further purified by chiral SFC (Column=Daicel Chiralpak IG; Column dimensions=250 mm×30 mm×10 µm; Detection wavelength=220 nM; Flow rate=80 mL/min; Mobile phase: A: CO$_2$ B: ethanol; Isocratic: 40% B with 0.1% ammonium hydroxide) to afford tentatively assigned:

(R)-2-(3-(((1-methyl-1H-tetrazol-5-yl)(oxetan-3-yl) methyl)phenyl)-6-(((1-methylcyclobutyl)amino)methyl)-4-(trifluoromethyl)isoindolin-1-one (Peak 1, retention time=0.453 min) (38 mg, 9% yield). $^1$H NMR (400 MHz, methanol-d$_4$) δ 8.08 (s, 1H), 8.01 (s, 1H), 7.97 (s, 1H), 7.81-7.74 (m, 1H), 7.48 (t, J=8.0 Hz, 1H), 7.09 (d, J=7.6 Hz, 1H), 5.16 (s, 2H), 4.98-4.90 (m, 2H), 4.71-4.62 (m, 2H), 4.44 (t, J=8.0 Hz, 1H), 4.11-3.98 (m, 1H), 3.88-3.83 (m, 5H), 2.16-2.04 (m, 2H), 1.94-1.85 (m, 2H), 1.84-1.75 (m, 2H), 1.38 (s, 3H). LCMS [M+H]$^+$=527.1.

(S)-2-(3-(((1-methyl-1H-tetrazol-5-yl)(oxetan-3-yl) methyl)phenyl)-6-(((1-methylcyclobutyl)amino)methyl)-4-(trifluoromethyl)isoindolin-1-one (Peak 2, retention time=1.292 min) (33 mg, 8% yield). $^1$H NMR (400 MHz, methanol-d$_4$) δ 8.09 (s, 1H), 8.01 (m, 1H), 7.97 (s, 1H), 7.78 (dd, J=2.0, 8.0 Hz, 1H), 7.47 (t, J=8.0 Hz, 1H), 7.09 (d, J=7.6 Hz, 1H), 5.16 (s, 2H), 4.97-4.89 (m, 2H), 4.71-4.63 (m, 2H), 4.47-4.41 (m, 1H), 4.09-3.99 (m, 1H), 3.89-3.82 (m, 5H), 2.15-2.05 (m, 2H), 1.93-1.85 (m, 2H), 1.84-1.73 (m, 2H), 1.38 (s, 3H). LCMS [M+H]$^+$=527.1.

Example 98: Compounds 350, 351

Figure 95:
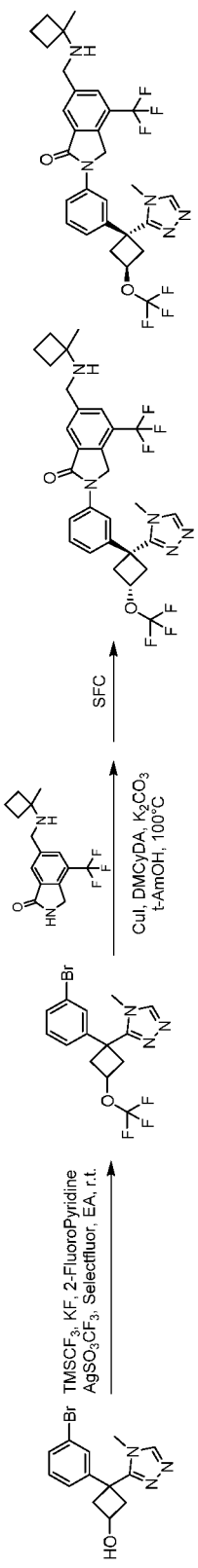

Compound 350 (2-(3-((1s,3s)-1-(4-methyl-4H-1,2,4-triazol-3-yl)-3-(trifluoromethoxy)cyclobutyl)phenyl)-6-(((1 methylcyclobutyl)amino)methyl)-4-(trifluoromethyl)isoindolin-1-one), and
Compound 351 (2-(3-((1r,3r)-1-(4-methyl-4H-1,2,4-triazol-3-yl)-3-(trifluoromethoxy)cyclobutyl)phenyl)-6-(((1-methylcyclobutyl)amino)methyl)-4-(trifluoromethyl)isoindolin-1-one), can be synthesized according to Scheme 95 (FIG. 95).

Intermediate 2: 3-(1-(3-bromophenyl)-3-(trifluoromethoxy)cyclobutyl)-4-methyl-4H-1,2,4-triazole To a solution of 3-(3-bromophenyl)-3-(4-methyl-4H-1,2,4-triazol-3-yl)cyclobutan-1-ol (300 mg, 1 mmol) in ethyl acetate (6 mL) was added silver(I) trifluoromethanesulfonate (1000 mg, 4 mmol), 1-(chloromethyl)-4-fluoro-1,4-diazabicyclo[2.2.2]octane-1,4-diium tetrafluoroborate (517 mg, 1.5 mmol), fluoropotassium (226 mg, 4 mmol), 2-fluoropyridine (0.34 mL, 4 mmol) and trimethyl(trifluoromethyl)silane (346 mg, 2.5 mmol). The mixture was stirred at 25° C. for 24 h then diluted with ethyl acetate (20 mL), washed with brine (20 mL), dried over sodium sulfate and concentrated to dryness, purified by silica gel chromatography (mobile phase: methyl alcohol/dichloromethane, gradient 0% to 5%) to give 3-(1-(3-bromophenyl)-3-(trifluoromethoxy)cyclobutyl)-4-methyl-4H-1,2,4-triazole (260 mg, 68% yield) as a yellow oil. LCMS [M+H]$^+$=376.1 and 378.1.

Compounds 350, 351
To a solution of 3-(1-(3-bromophenyl)-3-(trifluoromethoxy)cyclobutyl)-4-methyl-4H-1,2,4-triazole (140 mg, 0.37 mmol), 6-[[(1-methylcyclobutyl)amino]methyl]-4-(trifluoromethyl)isoindolin-1-one (133 mg, 0.45 mmol) and potassium carbonate (128 mg, 0.9 mmol) in tert-amyl alcohol (3 mL) was added (1 S,2S)—N$^1$,N$^2$-dimethylcyclohexane-1,2-diamine (21 mg, 0.15 mmol) and copper(I) iodide (28 mg, 0.15 mmol). The mixture was stirred at 100° C. for 2 h under nitrogen atmosphere. The reaction mixture was diluted with dichloromethane (50 mL), washed with brine (3×30 mL) and washed with ammonia solution, dried over sodium sulfate, filtered and concentrated to dryness. The residue was purified by RP-HPLC (water (NH$_3$H$_2$O+ NH$_4$HCO$_3$)-ACN 54% to 84%) to afford:

2-(3-((1s,3s)-1-(4-methyl-4H-1,2,4-triazol-3-yl)-3-(trifluoromethoxy)cyclobutyl)phenyl)-6-(((1 methylcyclobutyl)

amino)methyl)-4-(trifluoromethyl)isoindolin-1-one (Peak 2, retention time=5.355 min)(28 mg, 13% yield). $^1$H NMR (400 MHz, methanol-d$_4$) δ 8.34 (s, 1H), 8.12 (s, 1H), 8.08-8.03 (m, 2H), 7.75-7.71 (m, 1H), 7.56-7.50 (m, 1H), 7.29-7.24 (m, 1H), 5.18 (m, 2H), 5.04-4.94 (m, 1H), 3.97 (s, 2H), 3.39-3.36 (m, 5H), 3.28-3.20 (m, 2H), 2.25-2.11 (m, 2H), 1.99-1.90 (m, 2H), 1.90-1.80 (m, 2H), 1.45 (s, 3H). LCMS [M+Na]$^+$=616.0.

2-(3-(((1r,3r)-1-(4-methyl-4H-1,2,4-triazol-3-yl)-3-(trifluoromethoxy)cyclobutyl)phenyl)-6-(((1-methylcyclobutyl)amino)methyl)-4-(trifluoromethyl)isoindolin-1-one (Peak 1, retention time=4.599 min) (62.3 mg, 29% yield). $^1$H NMR (400 MHz, methanol-d$_4$) δ 8.40 (s, 1H), 8.09 (s, 1H), 8.02 (s, 1H), 7.95 (s, 1H), 7.68-7.75 (m, 1H), 7.48-7.55 (t, J=8.0 Hz 1H), 7.08-7.14 (m, 1H), 5.12-5.22 (m, 2H), 4.80-4.84 (m, 1H), 3.86-3.94 (m, 2H), 3.46-3.59 (m, 2H), 3.34 (s, 3H), 2.92-3.05 (m, 2H), 2.05-2.20 (m, 2H), 1.87-1.95 (m, 2H), 1.74-1.85 (m, 2H), 1.40 (s, 3H). LCMS [M+Na]$^+$=616.0.

Example 99: Compounds 352, 353

Figure 96:
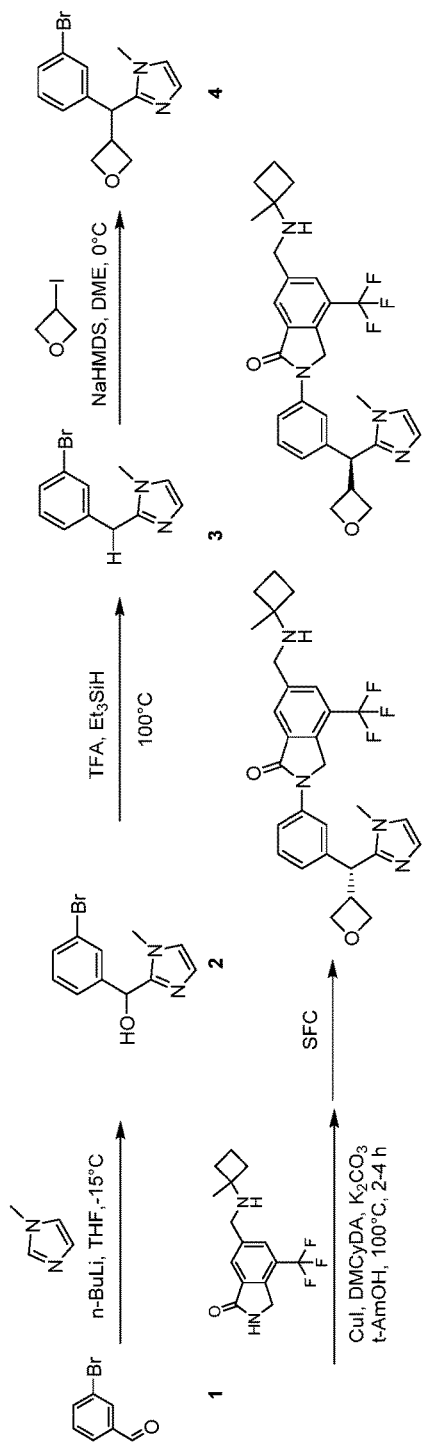

Compound 352 ((R)-2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one), and Compound 353 ((S)-2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one), can be synthesized according to Scheme 96 (FIG. 96).

Intermediate 2:
(3-bromophenyl)(1-methyl-1H-imidazol-2-yl)methanol

Under nitrogen, to a solution of 1-methyl-1H-imidazole (2.82 ml, 35.33 mmol) in tetrahydrofuran (100 mL) was added n-butyl lithium (2.5 M in hexane, 14.13 mL, 35.33 mmol) at −50° C. over 5 min. The mixture was stirred at −50° C. for 1 h then a solution of 3-bromobenzaldehyde (5.0 g, 27.14 mmol) in tetrahydrofuran (10 mL) was added dropwise. After addition, the reaction mixture was stirred at 0° C. for 1 h and then quenched with water (30 mL), extracted with dichloromethane (3×50 mL). The combined organic layers were washed with brine (50 mL), dried over sodium sulfate and concentrated. The residue was purified by silica gel chromatography (mobile phase: methanol/dichloromethane, gradient 0% to 10%) to afford (3-bromophenyl)(1-methyl-1H-imidazol-2-yl)methanol (6.1 g, 84% yield) as a yellow solid. LCMS [M+H]$^+$=267.1 and 269.1.

Intermediate 3:
2-(3-bromobenzyl)-1-methyl-1H-imidazole

A solution of (3-bromophenyl)(1-methyl-1H-imidazol-2-yl)methanol (2.0 g, 7.49 mmol) in triethylsilane (17.9 mL, 112.31 mmol) and 2,2,2-trifluoroacetic acid (8.34 mL, 112.31 mmol) was stirred at 100° C. for 16 h then concentrated. The residue was dissolved with dichloromethane (30 mL), washed with saturated sodium bicarbonate (2×10 mL) then concentrated to dryness. The residue was purified by silica gel chromatography (mobile phase: methanol/dichloromethane, gradient 0% to 10%) to afford 2-(3-bromobenzyl)-1-methyl-1H-imidazole (1.2 g, 69% yield) as a white solid. LCMS [M+H]$^+$=251.0 and 253.0.

Intermediate 4: (3-bromophenyl)(cyclobutyl)(4-methyl-4H-1,2,4-triazol-3-yl)methanol To a solution of 2-(3-bromobenzyl)-1-methyl-1H-imidazole (100 mg, 0.40 mmol) in 1,2-dimethoxyethane (2 mL) was added sodium bis(trimethylsilyl)amide (1M in tetrahydrofuran, 0.6 mL, 0.6 mmol). The mixture was stirred at 0° C. for 30 mins then 3-iodooxetane (0.06 mL, 0.71 mmol) was added, the resulting mixture was stirred at 25° C. for another 2 h then quenched with water (2 mL), extracted with dichloromethane (3×10 mL), combined the organic layers and washed with brine (10 mL), dried over sodium sulfate and concentrated. The residue was purified by silica gel chromatography (mobile phase: methanol/dichloromethane, gradient 0% to 6%) to give (3-bromophenyl)(cyclobutyl)(4-methyl-4H-1,2,4-triazol-3-yl)methanol (90 mg, 74% yield) as a yellow solid. LCMS [M+H]$^+$=307.0 and 309.0.

Compounds 352, 353

A mixture of (3-bromophenyl)(cyclobutyl)(4-methyl-4H-1,2,4-triazol-3-yl)methanol (90 mg, 0.45 mmol), copper(I) iodide (22.3 mg, 0.12 mmol), tert-butyl (1-methylcyclobutyl)((3-oxo-7-(trifluoromethyl)isoindolin-5-yl)methyl)carbamate (87.4 mg, 0.29 mmol), (1 S,2S)—N$^1$,N$^2$-dimethylcyclohexane-1,2-diamine (16.7 mg, 0.11 mmol) and potassium carbonate (121.5 mg, 0.88 mmol) in tert-amyl alcohol (1 mL) was heated at 100° C. was stirred 2 h under N$_2$. After cooled, the reaction was diluted with water (15 mL) and extracted with dichloromethane (3×25 mL). The combined organic phases were washed with brine (2×15 mL), dried over sodium sulfate, filtered and concentrated to dryness. The residue was purified by preparative TLC (solvent gradient: 10% methanol in dichloromethane) to afford 2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one (75 mg, 0.14 mmol). LCMS [M+H]$^+$=525.2.

The above mixture was purified by chiral SFC (Column=Daicel Chiralpak AS; Column dimensions=250 mm×30 mm×10 μm; Detection wavelength=220 nM; Flow rate=80 mL/min; Mobile phase: A: CO$_2$ B: ethanol; Isocratic: 40% B with 0.1% ammonium hydroxide) to afford tentatively assigned:

(R)-2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one (Peak 1, retention time=1.679 min) (20 mg, 27% yield). 1H NMR (400 MHz, DMSO-d$_6$) δ 8.05 (s, 1H), 8.00 (s, 1H), 7.90 (s, 1H), 7.81 (d, J=8.8, Hz, 1H), 7.37 (t, J=8.0 Hz, 1H), 7.04-6.97 (m, 2H), 6.83 (s, 1H), 5.16 (s, 2H), 4.75-4.63 (m, 2H), 4.52-4.45 (m, 2H), 4.24 (d, J=12.4 Hz, 1H), 3.88-3.79 (m, 3H), 3.42 (s, 3H), 2.04-1.94 (m, 2H), 1.77-1.63 (m, 4H), 1.24 (s, 3H). LCMS [M+H]$^+$=525.2.

(S)-2-(3-((1-methyl-1H-imidazol-2-yl)(oxetan-3-yl)methyl)phenyl)-6-(((1-methylcyclobutyl)amino)methyl)-4-(trifluoromethyl)isoindolin-1-one (Peak 2, retention time=1.919 min) (21 mg, 28% yield). 1H NMR (400 MHz, DMSO-d$_6$) δ 8.07 (m, 1H), 8.04 (d, J=6.8 Hz, 1H), 7.89 (d, J=6.8 Hz, 1H), 7.81 (d, J=8.4 Hz, 1H), 7.37 (t, J=8.0 Hz, 1H), 7.04-6.97 (m, 2H), 6.81 (s, 1H), 5.19 (s, 2H), 4.75-4.62 (m, 2H), 4.51-4.46 (m, 2H), 4.24 (t, J=12.8 Hz, 1H), 3.89-3.77 (m, 3H), 3.42 (s, 3H), 2.05-1.94 (m, 2H), 1.77-1.65 (m, 4H), 1.24 (s, 3H). LCMS [M+H]$^+$=525.2.

Example 100: Compounds 354, 355, 356, 357

Figure 97:
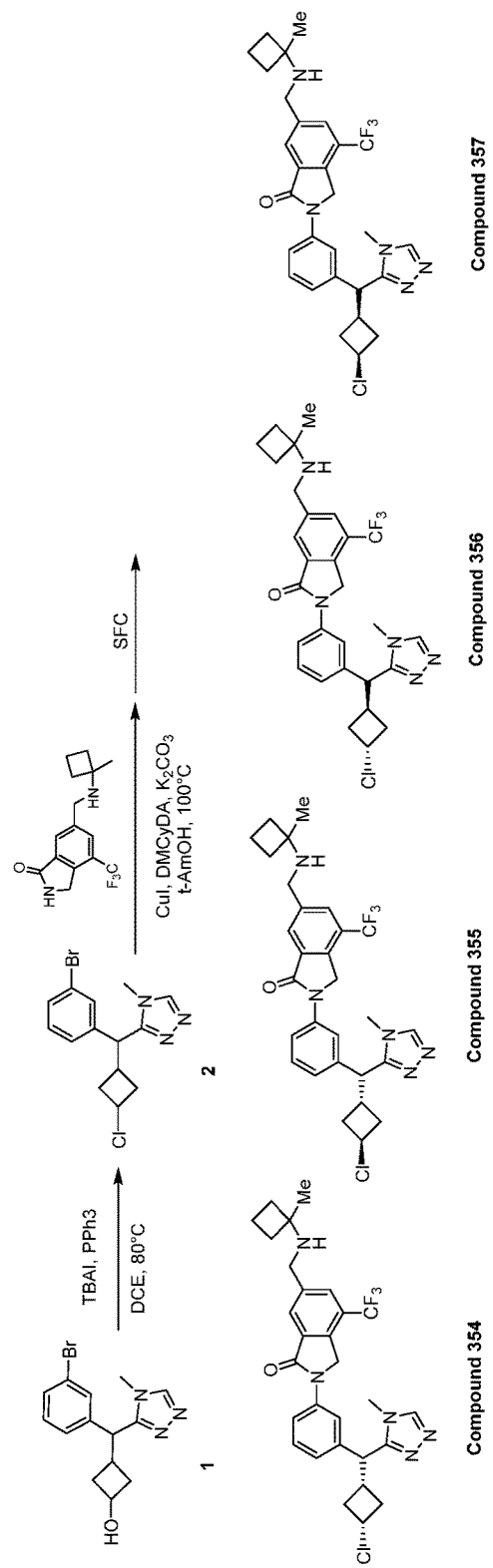

Compound 354 (2-(3-((S)-((1s,3R)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one), Compound 355 (2-(3-((S)-((1r,3S)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one), Compound 356 (2-(3-((R)-((1r,3R)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one), and Compound 357 (2-(3-((R)-((1s,3S)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 97 (FIG. 97).

Intermediate 2: 3-((3-bromophenyl)(3-chlorocyclobutyl)methyl)-4-methyl-4H-1,2,4-triazole A solution of 3-((3-bromophenyl)(4-methyl-4H-1,2,4-triazol-3-yl)methyl)cyclobutan-1-ol (200 mg, 0.62 mmol), triphenylphosphine (569.8 mg, 2.17 mmol), tetrabutylammonium iodide (802.4 mg, 2.17 mmol) in 1,2-Dichloroethane (10 mL) was stirred at 80° C. for 8 h then diluted with dichloromethane (50 mL), washed with water (2×10 mL), brine (20 mL), dried over sodium sulfate and concentrated under vacuum. The residue was purified by silica gel chromatography (mobile phase: methanol/dichloro-methane, gradient 0% to 10%) to afford a crude product which was residue was purified by RP-HPLC (0.2% $NH_3H_2O$ in water/ACN 42% to 72%) to afford 3-((3-bromophenyl)(3-chlorocyclobutyl)methyl)-4-methyl-4H-1,2,4-triazole (150 mg, 71% yield) as a yellow oil.

Compounds 354, 355, 356, 357

In a glove box, a mixture of 3-((3-bromophenyl)(3-chlorocyclobutyl)methyl)-4-methyl-4H-1,2,4-triazole (150 mg, 0.44 mmol), 6-(((1-methylcyclobutyl)amino)methyl)-4-(trifluoromethyl)isoindolin-1-one (144 mg, 0.48 mmol), copper (I) iodide (33 mg, 0.17 mmol), (1S,2S)—$N^1,N^2$-dimethylcyclohexane-1,2-diamine (25 mg, 0.17 mmol) and potassium carbonate (182 mg, 1.32 mmol) in tert-amyl alcohol (4 mL) was heated at 100° C. in sealed vial for 2 h and concentrated to dryness. The residue was purified by RP-HPLC (0.2% $NH_3·H_2O$ in water/ACN 60% to 90%) to afford 2-(3-((3-chlorocyclobutyl)(4-methyl-4H-1,2,4-triazol-3-yl)methyl)phenyl)-6-(((1-methylcyclobutyl)amino)methyl)-4-(trifluoromethyl)-isoindolin-1-one (150 mg, 61% yield).

The above mixture was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 45% B with 0.1% ammonium hydroxide) to afford product A and product B.

The product A was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 45% B with 0.1% ammonium hydroxide) to afford tentatively assigned:

2-(3-((S)-((1s,3R)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=4.678 min) (17.9 mg, 26% yield). $^1$H NMR (400 MHz, methanol-$d_4$) δ 8.37 (s, 1H), 8.09 (s, 1H), 8.01 (s, 1H), 7.89 (s, 1H), 7.78 (dd, J=2.0, 7.6 Hz, 1H), 7.45 (t, J=8.0 Hz, 1H), 7.10 (d, J=8.0 Hz, 1H), 5.15 (s, 2H), 4.61-4.57 (m, 1H), 4.36 (d, J=11.2 Hz, 1H), 3.87 (s, 2H), 3.57-3.54 (m, 1H), 3.52 (s, 3H), 2.59-2.52 (m, 2H), 2.40-2.39 (m, 1H), 2.30-2.20 (m, 1H), 2.11-2.07 (m, 2H), 1.91-1.78 (m, 4H), 1.39 (s, 3H). LCMS [M+H]$^+$=558.3.

2-(3-((S)-((1r,3S)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=4.478 min) (27.1 mg, 39% yield). $^1$H NMR (400 MHz, methanol-$d_4$) δ 8.38 (s, 1H), 8.08 (s, 1H), 8.01 (s, 1H), 7.85 (s, 1H), 7.78 (d, J=8.4 Hz, 1H), 7.44 (t, J=7.6 Hz, 1H), 7.08 (d, J=7.6 Hz, 1H), 5.14 (s, 2H), 4.37-4.32 (m, 2H), 3.86 (s, 2H), 3.50 (s, 3H), 3.09-2.96 (m, 1H), 2.88-2.80 (m, 1H), 2.49-2.45 (m, 1H), 2.24-2.04 (m, 4H), 1.91-1.75 (m, 4H), 1.38 (s, 3H). LCMS [M+H]$^+$=558.3.

The product B was purified by chiral SFC (Column=Daicel Chiralpak IG; Column dimensions=250 mm×30 mm×10 μm; Detection wavelength=220 nM; Flow rate=60 mL/min; Mobile phase: A: $CO_2$ B: ethanol; Isocratic: 20% B with 0.1% ammonium hydroxide) to afford tentatively assigned:

2-(3-((R)-((1r,3R)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=2.386 min) (23.2 mg, 33% yield). $^1$H NMR (400 MHz, methanol-$d_4$) δ 8.38 (s, 1H), 8.09 (s, 1H), 8.01 (s, 1H), 7.85 (s, 1H), 7.78 (d, J=8.0 Hz, 1H), 7.44 (t, J=8.0 Hz, 1H), 7.08 (d, J=7.2 Hz, 1H), 5.14 (s, 2H), 4.40-4.28 (m, 2H), 3.86 (s, 2H), 3.50 (s, 3H), 3.09-2.97 (m, 1H), 2.92-2.82 (m, 1H), 2.51-2.43 (m, 1H), 2.25-2.05 (m, 4H), 1.92-1.76 (m, 4H), 1.38 (s, 3H). 1.38 (s, 3H). LCMS [M+H]$^+$=558.3.

2-(3-((R)-((1s,3S)-3-chlorocyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=2.581 min) (13.9 mg, 20% yield). $^1$H NMR (400 MHz, methanol-$d_4$) δ 8.37 (s, 1H), 8.09 (s, 1H), 8.01 (s, 1H), 7.89 (s, 1H), 7.78 (d, J=8.4 Hz, 1H), 7.44 (t, J=8.0 Hz, 1H), 7.10 (d, J=8.0 Hz, 1H), 5.15 (s, 2H), 4.60-4.58 (m, 1H), 4.36 (d, J=11.2 Hz, 1H), 3.86 (s, 2H), 3.55-3.54 (m, 1H), 3.52 (s, 3H), 2.57-2.53 (m, 2H), 2.48-2.40 (m, 1H), 2.13-2.07 (m, 1H), 2.14-2.06 (m, 2H), 1.91-1.77 (m, 4H), 1.38 (s, 3H). LCMS [M+H]$^+$=558.3.

Example 101: Compounds 358, 359

Figure 98:
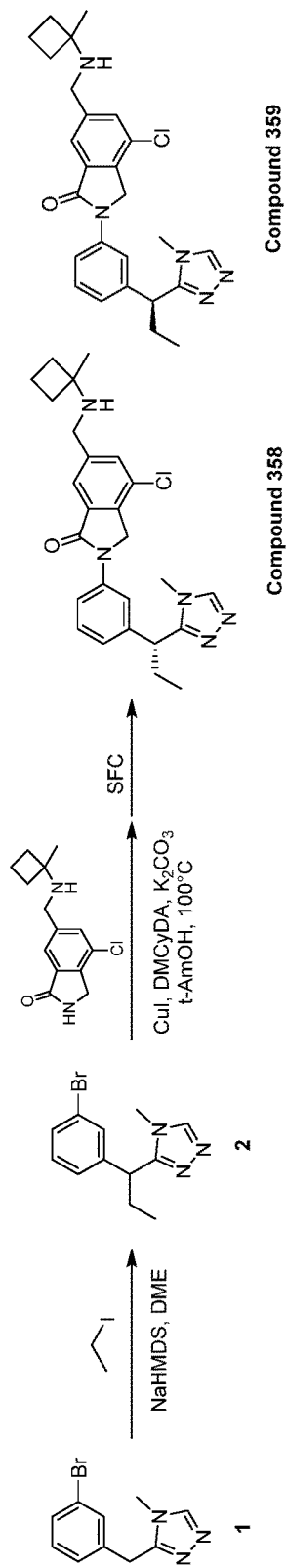

Compound 358 ((R)-4-chloro-2-(3-(1-(4-methyl-4H-1,2,4-triazol-3-yl)propyl)phenyl)-6-(((1-methylcyclobutyl)amino)methyl)isoindolin-1-one, and Compound 359 ((S)-4-chloro-2-(3-(1-(4-methyl-4H-1,2,4-triazol-3-yl)propyl)phenyl)-6-(((1-methylcyclobutyl)amino)methyl)isoindolin-1-one), can be synthesized according to Scheme 98 (FIG. 98).

Intermediate 2: 3-(1-(3-bromophenyl)propyl)-4-methyl-4H-1,2,4-triazole

To a solution of 3-(3-bromobenzyl)-4-methyl-4H-1,2,4-triazole (300.0 mg, 1.19 mmol) in 1,2-dimethoxyethane (DME) (5 mL) was added sodium bis(trimethylsilyl)azanide (1M in tetrahydrofuran, 1.31 mL, 1.31 mmol) at 0° C., then stirred at 0° C. for 30 mins. Iodoethane (0.12 mL, 1.55 mmol) was added and the mixture was stirred at 25° C. for another 2 h. The reaction was quenched by water (10 mL), extracted with dichloromethane (3×30 mL), combined the organic phase and washed with brine (20 mL), dried over sodium sulfate, filtrated and concentrated to dryness. The residue was purified by silica gel chromatography (mobile phase: methanol/dichloromethane, gradient 0% to 6%) to give 3-[1-(3-bromophenyl)propyl]-4-methyl-1,2,4-triazole (200 mg, 60% yield) as a white solid.

Compounds 358, 359

In a glove box, a mixture of 3-(1-(3-bromophenyl)propyl)-4-methyl-4H-1,2,4-triazole (200 mg, 0.71 mmol), 4-chloro-6-(((1-methylcyclobutyl)amino)methyl)isoindolin-1-one (208 mg, 0.79 mmol), copper(I) iodide (41 mg, 0.21 mmol), (1S,2S)—$N^1,N^2$-dimethylcyclohexane-1,2-diamine (30 mg, 0.21 mmol) and potassium carbonate (296 mg, 2.14 mmol) in tert-amyl alcohol (8 mL) was heated at 100° C. in sealed vial for 2 h and concentrated to dryness. The residue was dissolved with dichloromethane (20 mL), washed with 5% ammonia aqueous (10 mL), brine (10 mL), then the organic phase was concentrated to dryness. The residue was purified by RP-HPLC (water(NH$_3$·H$_2$O+NH$_4$HCO$_3$)/ACN 25% to 55%) to afford 4-chloro-2-(3-(1-(4-methyl-4H-1,2,4-triazol-3-yl)propyl)phenyl)-6-(((1-methylcyclobutyl)amino)methyl)isoindolin-1-one (120 mg, 36% yield).

The above mixture was purified by chiral SFC (Column=Phenomenex-Cellulose-2; Column dimensions=250 mm×30 mm×10 μm; Detection wavelength=220 nM; Flow rate=65 mL/min; Mobile phase: A: CO$_2$ B: ethanol; Isocratic: 60% B with 0.1% ammonium hydroxide) to afford tentatively assigned:

(R)-4-chloro-2-(3-(1-(4-methyl-4H-1,2,4-triazol-3-yl)propyl)phenyl)-6-(((1-methylcyclobutyl)amino)methyl)isoindolin-1-one (Peak 1, retention time=2.581 min) (36.2 mg, 30% yield). $^1$H NMR (400 MHz, methanol-d$_4$) δ 8.39 (s, 1H), 7.85 (s, 1H), 7.89-7.78 (m, 2H), 7.74 (s, 1H), 7.45 (t, J=8.0 Hz, 1H), 7.12 (d, J=8.0 Hz, 1H), 4.98 (s, 2H), 4.18 (t, J=8.0 Hz, 1H), 3.80 (s, 2H), 3.55 (s, 3H), 2.46-2.00 (m, 4H), 1.94-1.69 (m, 4H), 1.39 (s, 3H), 1.02 (t, J=7.4 Hz, 3H). LCMS [M+H]$^+$=464.3.

and (S)-4-chloro-2-(3-(1-(4-methyl-4H-1,2,4-triazol-3-yl)propyl)phenyl)-6-(((1-methylcyclobutyl)amino)methyl)isoindolin-1-one (Peak 2, retention time=3.627 min) (22.1 mg, 18% yield). $^1$H NMR (400 MHz, methanol-d$_4$) δ 8.39 (s, 1H), 7.83 (s, 1H), 7.79 (d, J=8.0 Hz, 1H), 7.73 (s, 1H), 7.68 (s, 1H), 7.42 (t, J=8.0 Hz, 1H), 7.11 (d, J=7.6 Hz, 1H), 5.04 (s, 2H), 4.18 (t, J=7.2 Hz, 1H), 3.75 (s, 2H), 3.55 (s, 3H), 2.45-2.32 (m, 1H), 2.23-2.03 (m, 3H), 1.95-1.65 (m, 4H), 1.37 (s, 3H), 1.01 (t, J=7.2 Hz, 3H). LCMS [M+H]$^+$=464.3.

Example 102: Compounds 360, 361

Figure 99:
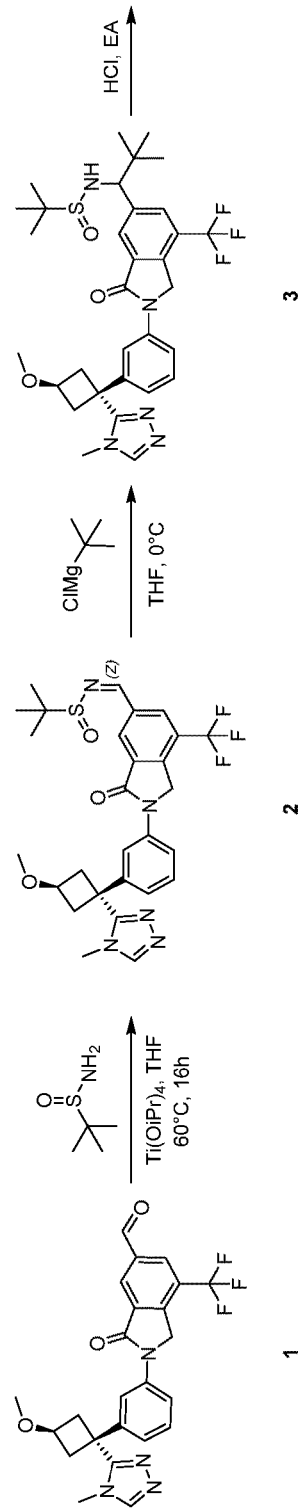

Compound 360 (6-((R)-1-amino-2,2-dimethylpropyl)-2-(3-((1r,3R)-3-methoxy-1-(4-methyl-4H-1,2,4-triazol-3-yl)cyclobutyl)phenyl)-4-(trifluoromethyl)isoindolin-1-one), and Compound 361 (6-((S)-1-amino-2,2-dimethylpropyl)-2-(3-((1r,3S)-3-methoxy-1-(4-methyl-4H-1,2,4-triazol-3-yl)cyclobutyl)phenyl)-4-(trifluoromethyl)isoindolin-1-one), can be synthesized according to Scheme 99 (FIG. 99).

Intermediate 2: N—((Z)-(2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methylene)-2-methylpropane-2-sulfinamide A mixture of 2-(3-(3-methoxy-1-(4-methyl-4H-1,2,4-triazol-3-yl)cyclobutyl)phenyl)-3-oxo-7-(trifluoromethyl)isoindoline-5-carbaldehyde (0.5 g, 1.06 mmol), 2-methylpropane-2-sulfinamide (0.1 g, 1.28 mmol) and titanium(IV) isopropoxide (3.5 mL, 3.19 mmol) in tetrahydrofuran (5 mL) was at 60° C. for 16 h under N$_2$ then diluted with ethyl ester (30 mL), washed with brine (10 mL), dried over sodium sulfate, filtered and concentrated to dryness. The residue was purified by silica gel chromatography (mobile phase: methanol/dichloro-methane, gradient 0% to 10%) to afford N—((Z)-(2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methylene)-2-methylpropane-2-sulfinamide (410 mg, 67% yield) as a pale oil. $^1$H NMR (400 MHz, DMSO-d$_6$) δ 8.83 (s, 1H), 8.57 (d, J=7.6 Hz, 2H), 8.40 (s, 1H), 7.93 (s, 1H), 7.71 (d, J=8.0 Hz, 1H), 7.44 (t, J=8.0 Hz, 1H), 6.99 (d, J=8.4 Hz, 1H), 5.31 (s, 2H), 3.89-3.81 (m, 1H), 3.30 (s, 4H), 3.25 (s, 3H), 3.18 (s, 3H), 1.23 (s, 9H). LCMS [M+H]$^+$574.1.

Intermediate 3: N-(1-(2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)-2,2-dimethylpropyl)-2-methylpropane-2-sulfinamide To a solution of N—((Z)-(2-(3-((1r,3r)-3-methoxy-1-(4-methyl-4H-1,2,4-triazol-3-yl)cyclobutyl)phenyl)-3-oxo-7-(trifluoromethyl)isoindolin-5-yl)methylene)-2-methylpropane-2-sulfinamide (400 mg, 0.70 mmol) in tetrahydrofuran (5 mL) was added tert-butyl magnesium (1.7 M in tetrahydrofuran, 0.8 mL, 1.39 mmol) at 0° C. The reaction mixture was stirred for 2.5 h. The reaction mixture was diluted with water (20 mL), extracted with ethyl acetate (3×20 mL), the organic layer was dried over anhydrous sodium sulfate, filtered and concentrated to dryness. The residue was purified by silica gel chromatography (mobile phase: methanol/dichloromethane, gradient 0% to 10%) to afford N-(1-(2-(3-((1r,3r)-3-methoxy-1-(4-methyl-4H-1,2,4-triazol-3-yl)cyclobutyl)phenyl)-3-oxo-7-(trifluoromethyl)-isoindolin-5-yl)-2,2-dimethylpropyl)-2-methylpropane-2-sulfinamide (110 mg, 25% yield) as a pale oil. LCMS [M+H]$^+$632.3.

Compounds 360, 361

To a solution of hydrochloric acid (0.2 mL, 0.82 mmol) in ethyl acetate (1 mL) was added (R)—N—((S)-1-(2-(3-(3-methoxy-1-(4-methyl-4H-1,2,4-triazol-3-yl)cyclobutyl)phenyl)-3-oxo-7-(trifluoromethyl)isoindolin-5-yl)-2,2-dimethylpropyl)-2-methylpropane-2-sulfinamide in ethyl acetate (1 mL) at 0° C. The reaction mixture was stirred for 3 h and concentrated to dryness, the residue was purified by preparative TLC (solvent gradient: 10% methanol in dichloromethane) to afford 6-(1-amino-2,2-dimethylpropyl)-2-(3-((1r,3r)-3-methoxy-1-(4-methyl-4H-1,2,4-triazol-3-yl)cyclobutyl)phenyl)-4-(trifluoromethyl)isoindolin-1-one (40 mg, 53% yield). LCMS [M+H]$^+$528.3.

The above product was purified by chiral SFC (Column=Daicel Chiralcel OD-H; Column dimensions=250 mm×30 mm×10 μm; Detection wavelength=220 nM; Flow rate=80 mL/min; Mobile phase: A: CO$_2$ B: ethanol; Isocratic: 35% B with 0.1% ammonium hydroxide) to afford tentatively assigned:

6-((R)-1-amino-2,2-dimethylpropyl)-2-(3-((1r,3R)-3-methoxy-1-(4-methyl-4H-1,2,4-triazol-3-yl)cyclobutyl)phenyl)-4-(trifluoromethyl)isoindolin-1-one (Peak 1, retention time=1.704 min) (4.7 mg, 11% yield). $^1$H NMR (400 MHz, acetonitrile-d$_3$) δ 8.08 (s, 1H), 7.96 (s, 1H), 7.88 (s, 1H), 7.85 (s, 1H), 7.68 (d, J=8.4 Hz, 1H), 7.42 (t, J=8.0 Hz, 1H), 7.02 (d, J=7.6 Hz, 1H), 5.04 (s, 2H), 3.96-3.88 (m, 2H), 3.38-3.35 (m, 2H), 3.23 (s, 3H), 3.22 (s, 3H), 2.54 (m, 2H), 0.89 (s, 9H). LCMS [M+H]$^+$=528.3.

6-((S)-1-amino-2,2-dimethylpropyl)-2-(3-((1r,3S)-3-methoxy-1-(4-methyl-4H-1,2,4-triazol-3-yl)cyclobutyl)phenyl)-4-(trifluoromethyl)isoindolin-1-one (Peak 2, retention time=1.898 min) (9 mg, 22% yield). $^1$H NMR (400 MHz, acetonitrile-d$_3$) δ 8.08 (s, 1H), 7.96 (s, 1H), 7.88 (s, 1H), 7.85 (t, J=2.0 Hz, 1H), 7.70-7.65 (m, 1H), 7.42 (t, J=8.0 Hz, 1H), 7.02 (d, J=7.6 Hz, 1H), 5.04 (s, 2H), 3.96-3.87 (m, 2H), 3.36 (m, 2H), 3.23 (d, J=4.4 Hz, 6H), 2.57-2.51 (m, 2H), 0.89 (s, 9H). LCMS [M+H]⁺=528.3.

Example 103: Compounds 362, 363, 364, 365

Figure 100:
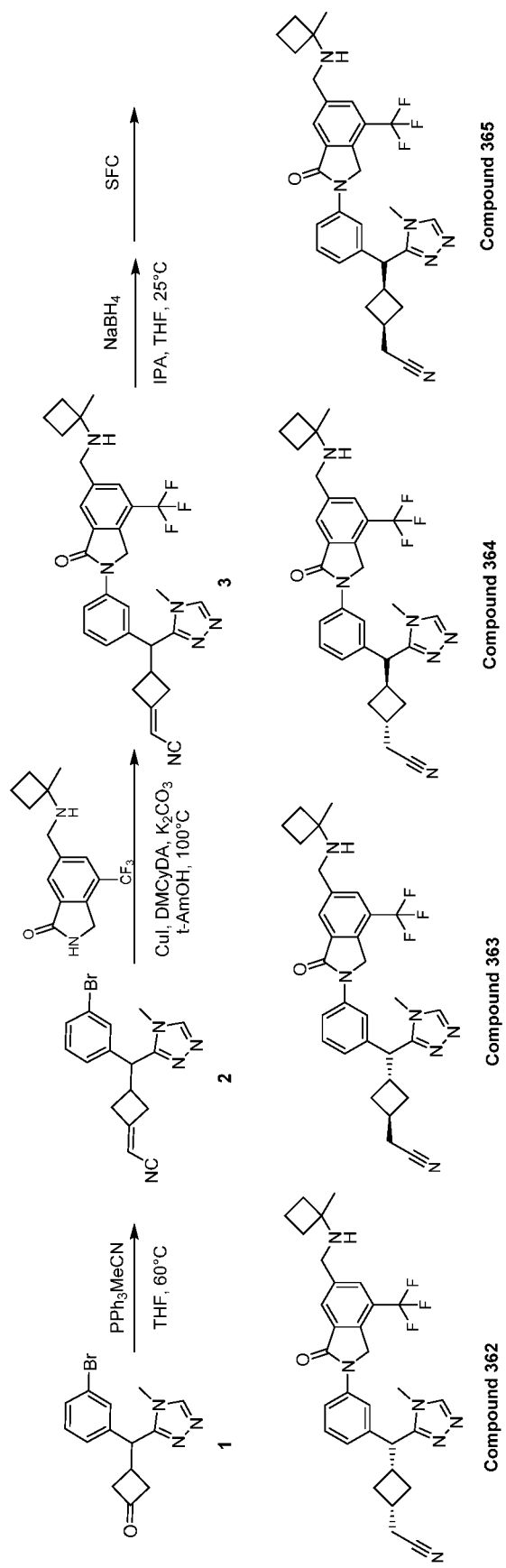

Compound 362 (2-((1R,3s)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)-cyclobutyl)acetonitrile),
Compound 363 2-((1 S,3r)-3-((S)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)-cyclobutyl)acetonitrile),
Compound 364 2-((1R,3r)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)-cyclobutyl)acetonitrile), and
Compound 365 2-((1 S,3s)-3-((R)-(4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)-cyclobutyl)acetonitrile), can be synthesized according to Scheme 100 (FIG. 100).

Intermediate 2: 2-(3-((3-bromophenyl)(4-methyl-4H-1,2,4-triazol-3-yl)methyl)cyclobutylidene)acetonitrile A solution of triphenylphosphine acetonitrile (1.51 g, 5 mmol), 3-((3-bromophenyl)(4-methyl-4H-1,2,4-triazol-3-yl)methyl)cyclobutan-1-one (400 mg, 1.25 mmol) in tetrahydrofuran (8 mL) was stirred at 70° C. for 12 h under $N_2$ then concentrated to dryness. The residue was purified by silica gel chromatography (mobile phase: methanol/dichloromethane, gradient 0% to 10%) to afford 2-(3-((3-bromophenyl)(4-methyl-4H-1,2,4-triazol-3-yl)methyl)cyclobutylidene)acetonitrile (400 mg, 93% yield) as a white solid. LCMS [M+H]⁺=343.0 and 345.0.

Intermediate 3: 2-(3-((4-methyl-4H-1,2,4-triazol-3-yl)(3-(6-(((1-methylcyclobutyl)amino)methyl)-1-oxo-4-(trifluoromethyl)isoindolin-2-yl)phenyl) methyl)cyclobutylidene)acetonitrile A solution of 2-(3-((3-bromophenyl)(4-methyl-4H-1,2,4-triazol-3-yl)methyl)-cyclobutylidene)acetonitrile (380 mg, 1.1 mmol), 6-[[(1-methylcyclobutyl)amino]methyl]-4-(trifluoromethyl)isoindolin-1-one (282 mg, 1.2 mmol), copper (I) iodide (84 mg, 0.44 mmol), potassium carbonate (230 mg, 1.66 mmol) and (1S,2S)—$N^1$,$N^2$-dimethylcyclohexane-1,2-diamine (48 mg, 0.34 mmol) in tert-amyl alcohol (4 mL) was stirred at 100 C for 2 h under nitrogen atmosphere then concentrated to dryness. The residue was purified by silica gel chromatography (mobile phase: methanol/dichloromethane, gradient 0% to 10%) to afford 2-(3-((4-methyl-4H-1,2, 4-triazol-3-yl)(3-(6-(((1-methylcyclobutyl)amino)methyl)-1-oxo-4-(trifluoromethyl)isoindolin-2-yl)phenyl)methyl) cyclobutylidene)acetonitrile (474 mg, 90% yield) as a white solid. LCMS [M+H]⁺=561.4.

Compounds 362, 363, 364, 365

To a solution of 2-(3-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutylidene) acetonitrile (474 mg, 0.45 mmol) in tetrahydrofuran (5 mL), isopropanol (1 mL) and methanol (1 mL) was added sodium borohydride (380 mg, 10.04 mmol). The mixture was stirred at 25° C. for 12 h then quenched by water (20 mL), extracted with dichloromethane (2×30 mL). combined the organic layers and dried over sodium sulfate, filtered and concentrated to dryness, the residue was purified by silica gel chromatography (mobile phase: methanol/dichloromethane, gradient 0% to 10%) to afford 2-(3-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)cyclobutyl)acetonitrile (180 mg, 38% yield). LCMS [M+H]⁺= 563.3.

The above mixture was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 35% B with 0.1% ammonium hydroxide) to afford product A and product B.

The product A was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 45% B with 0.1% ammonium hydroxide) to afford tentatively assigned:

2-((1R,3s)-3-((S)-(4-methyl-4H-1,2,4-triazol-3-yl)(3-(6-(((1-methylcyclobutyl)amino)-methyl)-1-oxo-4-(trifluoromethyl)isoindolin-2-yl)phenyl)methyl)cyclobutyl)acetonitrile. (Peak 1, retention time=4.551 min) (25.4 mg, 32% yield). ¹H NMR (400 MHz, methanol-$d_4$) δ 8.37 (s, 1H), 8.08 (s, 1H), 8.00 (s, 1H), 7.87 (s, 1H), 7.79-7.74 (m, 1H), 7.44 (t, J=8.0 Hz, 1H), 7.11 (d, J=8.0 Hz, 1H), 5.14 (s, 2H), 4.35 (d, J=11.2 Hz, 1H), 3.86 (s, 2H), 3.53 (s, 3H), 3.41-3.36 (m, 1H), 2.71-2.66 (m, 1H), 2.65-2.62 (m, 2H), 2.22-2.14 (m, 2H), 2.13-2.06 (m, 2H), 2.04-2.11 (m, 1H), 1.89-1.75 (m, 5H), 1.38 (s, 3H). LCMS [M+H]⁺=563.1.

2-((1 S,3r)-3-((S)-(4-methyl-4H-1,2,4-triazol-3-yl)(3-(6-(((1-methylcyclobutyl)-amino)methyl)-1-oxo-4-(trifluoromethyl)isoindolin-2-yl)phenyl)methyl)-cyclobutyl)acetonitrile (Peak 2, retention time=4.579 min) (4.5 mg, 6% yield). ¹H NMR (400 MHz, methanol-$d_4$) δ 8.38 (s, 1H), 8.09 (s, 1H), 8.01 (s, 1H), 7.85 (s, 1H), 7.77 (d, J=7.6 Hz, 1H), 7.44 (t, J=8.0 Hz, 1H), 7.09 (d, J=8.0 Hz, 1H), 5.14 (s, 2H), 4.21 (d, J=10.8 Hz, 1H), 3.86 (s, 2H), 3.52 (s, 3H), 3.21-3.12 (m, 1H), 2.54 (s, 3H), 2.15-2.10 (m, 3H), 1.96-1.65 (m, 6H), 1.63-1.55 (m, 1H), 1.38 (s, 3H). LCMS [M+H]⁺=563.1.

The product B was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 45% B with 0.1% ammonium hydroxide) to afford tentatively assigned:

2-((1R,3r)-3-((R)-(4-methyl-4H-1,2,4-triazol-3-yl)(3-(6-(((1-methylcyclobutyl)-amino)methyl)-1-oxo-4-(trifluoromethyl)isoindolin-2-yl)phenyl)methyl)cyclobutyl)-acetonitrile (Peak 1, retention time=4.765 min) (6.6 mg, 8% yield). ¹H NMR (400 MHz, methanol-$d_4$) δ 8.38 (s, 1H), 8.09 (s, 1H), 8.01 (s, 1H), 7.86 (s, 1H), 7.77 (d, J=8.4 Hz, 1H), 7.47-7.40 (m, 1H), 7.09 (d, J=7.6 Hz, 1H), 5.14 (s, 2H), 4.25-4.14 (m, 1H), 3.86 (s, 2H), 3.52 (s, 3H), 3.20-3.11 (m, 1H), 2.55 (s, 3H), 2.14-2.06 (m, 3H), 1.92-1.69 (m, 6H), 1.38 (s, 3H). LCMS [M+H]⁺=563.1.

2-((1 S,3s)-3-((R)-(4-methyl-4H-1,2,4-triazol-3-yl)(3-(6-(((1-methylcyclobutyl)-amino)methyl)-1-oxo-4-(trifluoromethyl)isoindolin-2-yl)phenyl)methyl)cyclobutyl)-acetonitrile (Peak 2, retention time=4.55 min) (29.3 mg, 38% yield). ¹H NMR (400 MHz, methanol-$d_4$) δ 8.37 (s, 1H), 8.08 (s, 1H), 8.00 (s, 1H), 7.87 (t, J=2.0 Hz, 1H), 7.77 (m, 1H), 7.44 (t, J=7.6 Hz, 1H), 7.11 (d, J=8.0 Hz, 1H), 5.14 (s, 2H), 4.35 (d, J=11.2 Hz, 1H), 3.86 (s, 2H), 3.53 (s, 3H), 3.40-3.35 (m, 1H), 2.69-2.58 (m, 3H), 2.21-2.14 (m, 2H), 2.12-2.05 (m, 2H), 2.04-1.96 (m, 1H), 1.90-1.75 (m, 5H), 1.38 (s, 3H). LCMS [M+H]$^+$=563.1.

Example 104: Compounds 366, 367, 368, 369

Compound 366 (2-(3-((S)-((1r,3S)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one),
Compound 367 (2-(3-((S)-((1s,3R)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one),
Compound 368 (2-(3-((R)-((1s,3S)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one), and
Compound 369 (2-(3-((R)-((1r,3R)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 101 (FIG. 101).

Intermediate 2: 1-((3-bromophenyl)(4-methyl-4H-1,2,4-triazol-3-yl)methyl)-3-methoxycyclobutan-1-ol Under nitrogen atmosphere, to a solution of 3-(3-bromobenzyl)-4-methyl-4H-1,2,4-triazole (500 mg, 1.98 mmol) in tetrahydrofuran (10 mL) was added lithium diisopropylamide (2 M in tetrahydrofuran, 1.2 mL, 2.4 mmol) at −50° c. The mixture was at −50° C. for 30 mins, 3-methoxycyclobutanone (297.8 mg, 2.97 mmol) was added and the mixture was stirred at −50° C. for 1.5 h then quenched by water (20 mL), extracted with dichloromethane (3×50 mL), the combined organic layers were dried over sodium sulfate, filtered and concentrated to dryness. The residue was purified by silica gel chromatography (mobile phase: methanol/dichloromethane, gradient 0% to 10%) to afford 1-((3-bromophenyl)(4-methyl-4H-1,2,4-triazol-3-yl)methyl)-3-methoxycyclobutan-1-ol (500 mg, 71% yield) as a yellow solid. LCMS [M+H]$^+$=354.1.

Compounds 366, 367, 368, 369

A solution of 1-((3-bromophenyl)(4-methyl-4H-1,2,4-triazol-3-yl)methyl)-3-methoxycyclobutan-1-ol (290 mg, 0.82 mmol), 6-[[(1-methylcyclobutyl)amino]methyl]-4-(trifluoromethyl)isoindolin-1-one (270.2 mg, 0.91 mmol), copper (I) iodide (62.7 mg, 0.33 mmol), potassium carbonate (227.6 mg, 1.65 mmol) and (1S,2S)—N$^1$,N$^2$-dimethyl-cyclohexane-1,2-diamine (35.1 mg, 0.25 mmol) in tert-amyl alcohol (4 mL) was stirred at 100 C for 1 hour under nitrogen atmosphere then concentrated to dryness. The residue was dissolved with dichloromethane (40 mL), washed with water (10 mL), dried over sodium sulfate, filtered and concentrated under vacuum. The residue was purified by silica gel chromatography (mobile phase: methanol/dichloromethane, gradient 0% to 10%) to afford crude product which was further purified by RP-HPLC (water(NH$_3$H$_2$O+NH$_4$HCO$_3$)-ACN 38% to 68%) to afford 2-(3-((1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (100 mg, 21% yield). LCMS [M+H]$^+$=570.3.

The above mixture was purified by chiral SFC (Column=Daicel Chiralpak IG; Column dimensions=250 mm×30 mm×10 μm; Detection wavelength=220 nM; Flow rate=70 mL/min; Mobile phase: A: CO$_2$ B: ethanol; Isocratic: 35% B with 0.1% ammonium hydroxide) to afford product A and product B.

The product A was purified by chiral SFC (Column=Daicel Chiralpak IG; Column dimensions=250 mm×30 mm×10 μm; Detection wavelength=220 nM; Flow rate=60 mL/min; Mobile phase: A: CO$_2$ B: methanol; Isocratic: 20% B with 0.1% ammonium hydroxide) to afford tentatively assigned:

2-(3-((S)-((1r,3S)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one. (Peak 1, retention time=4.353 min) (1.0 mg, 2% yield). LCMS [M+H]$^+$=570.3.

2-(3-((S)-((1s,3R)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=4.269 min) (12.6 mg, 30% yield). $^1$H NMR (400 MHz, methanol-d$_4$) δ 8.38 (s, 1H), 8.08 (s, 1H), 8.01 (s, 1H), 7.97 (s, 1H), 7.80 (d, J=8.4 Hz, 1H), 7.45 (t, J=8.0 Hz, 1H), 7.26 (d, J=7.9 Hz, 1H), 5.15 (s, 2H), 4.36 (s, 1H), 3.87 (s, 2H), 3.65-3.55 (m, 1H), 3.48 (s, 3H), 3.21 (s, 3H), 2.85-2.75 (m, 1H), 2.70-2.60 (m, 1H), 2.20-2.05 (m, 3H), 2.05-1.95 (m, 1H), 1.90-1.86 (m, 2H), 1.82-1.79 (m, 2H), 1.39 (s, 3H) LCMS [M+H]$^+$=570.3.

The product B was purified by chiral SFC (Column=Daicel Chiralpak IG; Column dimensions=250 mm×30 mm×10 μm; Detection wavelength=220 nM; Flow rate=60 mL/min; Mobile phase: A: CO$_2$ B: ethanol; Isocratic: 20% B with 0.1% ammonium hydroxide) to afford tentatively assigned:

2-(3-((R)-((1s,3S)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=4.342 min) (3.2 mg, 7% yield). $^1$H NMR (400 MHz, methanol-d$_4$) δ 8.39 (s, 1H), 8.08 (s, 1H), 8.00 (s, 1H), 7.88 (s, 1H), 7.80 (d, J=8.0 Hz, 1H), 7.44 (t, J=8.0 Hz, 1H), 7.16 (d, J=8.0 Hz, 1H), 5.14 (d, J=6.8 Hz, 2H), 4.53 (s, 1H), 4.11 (t, J=6.4 Hz, 1H), 3.85 (s, 2H), 3.47 (s, 3H), 3.24 (s, 3H), 2.53-2.45 (m, 1H), 2.31-2.24 (m, 1H), 2.22-2.16 (m, 1H), 2.14-2.06 (m, 3H), 1.90-1.85 (m, 2H), 1.82-1.75 (m, 2H), 1.37 (s, 3H). LCMS [M+H]$^+$=570.3.

2-(3-((R)-((1r,3R)-1-hydroxy-3-methoxycyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=4.251 min) (15.7 mg, 38% yield). $^1$H NMR (400 MHz, methanol-d$_4$) δ 8.38 (s, 1H), 8.08 (s, 1H), 8.00 (s, 1H), 7.97 (s, 1H), 7.83-7.78 (m, 1H), 7.45 (t, J=8.0 Hz, 1H), 7.26 (d, J=8.0 Hz, 1H), 5.14 (s, 2H), 4.36 (s, 1H), 3.86 (s, 2H), 3.60 (t, J=6.8 Hz, 1H), 3.48 (s, 3H), 3.21 (s, 3H), 2.86-2.78 (m, 1H), 2.68-2.59 (m, 1H), 2.18-2.07 (m, 3H), 2.02-1.95 (m, 1H), 1.90-1.84 (m, 2H), 1.83-1.74 (m, 2H), 1.38 (s, 3H). LCMS [M+H]$^+$=570.3.

Example 105: Compound 370

Compound 370 (2-(3-((1s,3s)-3-(fluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to Scheme 102 (FIG. 102).

Intermediates 2 and 2A: (3-((1s,3s)-1-(3-bromophenyl)-3-(fluoromethoxy)cyclobutyl)-4-methyl-4H-1,2,4-triazole, and 3-((1r,3r)-1-(3-bromophenyl)-3-(fluoromethoxy)cyclobutyl)-4-methyl-4H-1,2,4-triazole To a solution of 3-(3-bromophenyl)-3-(4-methyl-4H-1,2,4-triazol-3-yl)cyclobutan-1-ol (300.0 mg, 0.97 mmol) in tetrahydrofuran (5 mL) was added sodium hydride (60%, 35 mg, 1.46 mmol) and stirred for 30 min at 0° C., then fluoro(iodo)methane (311 mg, 1.95 mmol) was added and the resulting mixture was stirred at 25° C. for another 1 h. The reaction was quenched with water (25 mL) and extracted with ethyl acetate (3×25 mL). The combined organic phase was washed with brine (2×25 mL), dried over sodium sulfate, filtered and concentrated. The resulting residue was purified by reverse phase chromatography (water($NH_3H_2O+NH_4HCO_3$)-ACN 45%-75%) to afford 3-((1s,3s)-1-(3-bromophenyl)-3-(fluoromethoxy)cyclobutyl)-4-methyl-4H-1,2,4-triazole (110 mg, 33% yield) and 3-((1r,3r)-1-(3-bromophenyl)-3-(fluoromethoxy)cyclobutyl)-4-methyl-4H-1,2,4-triazole (140 mg, 42% yield) both as white solid. LCMS $[M+H]^+$=340.0 and 342.0.

Compound 370

A mixture of 3-((1s,3s)-1-(3-bromophenyl)-3-(fluoromethoxy)cyclobutyl)-4-methyl-4H-1,2,4-triazole (100.0 mg, 0.29 mmol), (1S,2S)—$N^1,N^2$-dimethylcyclohexane-1,2-diamine (16.73 mg, 0.12 mmol), potassium carbonate (121.9 mg, 0.88 mmol), 6-(((1-methylcyclobutyl)amino)methyl)-4-(trifluoromethyl)isoindolin-1-one (96.5 mg, 0.32 mmol) and copper(I) iodide (22.39 mg, 0.12 mmol) in tert-amyl alcohol (5 mL) was stirred at 100° C. for 1 h then concentrated. The residue was dissolved with ethyl acetate (15 mL), washed with water (5 mL), brine (2×5 mL), dried over sodium sulfate, filtered and concentrated. The resulting residue was purified by RP-HPLC (water($NH_3H_2O+NH_4HCO_3$)-ACN 50-80%) to afford 2-(3-((1s,3s)-3-(fluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one (27.9 mg, 16% yield). $^1$H NMR (400 MHz, methanol-$d_4$) δ 8.36 (s, 1H), 8.11 (s, 1H), 8.09 (s, 1H), 8.04 (s, 1H), 7.73 (d, J=8.0 Hz, 1H), 7.53 (t, J=7.6 Hz, 1H), 7.55-7.50 (m, 1H), 7.26 (d, J=8.0 Hz, 1H), 5.28 (d, J=56.0 Hz, 2H), 5.18 (s, 2H), 4.60-4.55 (m, 1H), 3.90 (s, 2H), 3.38 (s, 3H), 3.28-3.26 (m, 2H), 3.11-3.02 (m, 2H), 2.16-2.03 (m, 2H), 1.94-1.80 (m, 4H), 1.41 (s, 3H). LCMS $[M+H]^+$=558.2.

Example 106: Compound 371

Compound 371 (2-(3-((1r,3r)-3-(fluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to the following steps.

A mixture of 3-((1r,3r)-1-(3-bromophenyl)-3-(fluoromethoxy)cyclobutyl)-4-methyl-4H-1,2,4-triazole (150 mg, 0.44 mmol), (1S,2S)—$N^1,N^2$-dimethylcyclohexane-1,2-diamine (24.3 mg, 0.17 mmol), potassium carbonate (176.7 mg, 1.28 mmol), 6-(((1-methyl-cyclobutyl)amino)methyl)-4-(trifluoromethyl)isoindolin-1-one (cf. Scheme 1; 139.9 mg, 0.47 mmol) and copper(I) iodide (32.5 mg, 0.17 mmol) in tert-amyl alcohol (5.0 mL) was stirred at 100° C. for 1 h under $N_2$ then concentrated. The residue was dissolved with ethyl acetate (15 mL), washed with water (5 mL), brine (2×5 mL), dried over sodium sulfate, filtered and concentrated. The resulting residue was purified by RP-HPLC (water($NH_3H_2O+NH_4HCO_3$)-ACN 56-86%) to afford 2-(3-((1r,3r)-3-(fluoromethoxy)-1-(4-methyl-4H-1,2,4-triazol-3-yl)cyclobutyl)phenyl)-6-(((1-methylcyclobutyl)amino)methyl)-4-(trifluoromethyl)isoindolin-1-one (80.5 mg, 31% yield). $^1$H NMR (400 MHz, methanol-$d_4$) δ 8.47 (s, 1H), 8.10 (s, 1H), 8.03 (s, 1H), 7.95 (s, 1H), 7.70 (d, J=8.0 Hz, 1H), 7.51 (t, J=8.0 Hz, 1H), 7.12 (d, J=7.6 Hz, 1H), 5.28 (d, J=56.0 Hz, 2H), 5.21-5.13 (m, 1H), 5.18 (s, 2H), 4.41- 4.38 (m, 1H), 3.89 (s, 2H), 3.51-3.40 (m, 2H), 3.37 (s, 3H), 2.93-2.72 (m, 2H), 2.19-2.08 (m, 2H), 1.94 1.75 (m, 4H), 1.41 (s, 3H). LCMS $[M+H]^+$=558.3

Example 107: Compound 372, 373

Figure 103:
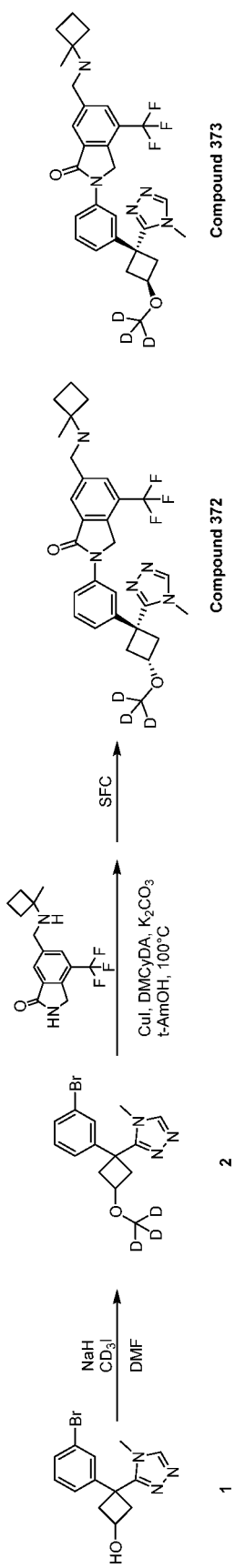

Compound 372 (2-(3-((1S,3S)-3-(methoxy-$d_3$)-1-(4-methyl-4H-1,2,4-triazol-3-yl)cyclobutyl)phenyl)-6-(((1-methylcyclobutyl)amino)methyl)-4-(trifluoromethyl)isoindolin-1-one),
and Compound 373 (2-(3-((1R,3R)-3-(methoxy-$d_3$)-1-(4-methyl-4H-1,2,4-triazol-3-yl)cyclobutyl)phenyl)-6-(((1-methylcyclobutyl)amino)methyl)-4-(trifluoromethyl)isoindolin-1-one), can be synthesized according to Scheme 103 (FIG. 103).

Intermediate 2: 3-(1-(3-bromophenyl)-3-(methoxy-$d_3$)cyclobutyl)-4-methyl-4H-1,2,4-triazole To a solution of 3-(3-bromophenyl)-3-(4-methyl-4H-1,2,4-triazol-3-yl)cyclobutan-1-ol (300 mg, 0.9 mmol) in N,N-dimethylformamide (5 mL) was added sodium hydride (60%, 58.4 mg, 1.4 mmol) and iodomethane-$d_3$ (0.09 mL, 1.4 mmol). The mixture was stirred at 25° C. for 1 hour under $N_2$ then quenched with water (10 mL), extracted with ethyl acetate (2×40 mL), the organic phase was washed with brine (3×50 mL), dried over sodium sulfate and concentrated to give a crude product which was used for next step directly. LCMS $[M+H]^+$=325.1 and 327.1.

Compounds 372, 373

To a solution of 3-(1-(3-bromophenyl)-3-(methoxy-$d_3$) cyclobutyl)-4-methyl-4H-1,2,4-triazole (300 mg, 0.9 mmol) in tert-amyl alcohol (3 mL) was added 6-(((1-methylcyclobutyl)amino)methyl)-4-(trifluoromethyl)isoindolin-1-one (320 mg, 1 mmol), copper(I) iodide (70.2 mg, 0.3 mmol), (1S,2S)—$N^1,N^2$-dimethylcyclohexane-1,2-diamine (0.06 mL, 0.3 mmol) and potassium carbonate (382 mg, 2.7 mmol), the solution was stirred at 100° C. for 2 h under $N_2$ then concentrated. The residue was dissolved with dichloromethane (30 mL), washed with 5% ammonia aqueous (2×10 mL), brine (10 mL), dried over sodium sulfate, filtered and concentrated. The residue was purified by RP-HPLC (water ($NH_3H_2O+NH_4HCO_3$)-ACN 53% to 83%) to afford 2-(3-(3-(methoxy-$d_3$)-1-(4-methyl-4H-1,2,4-triazol-3-yl)cyclobutyl)phenyl)-6-(((1-methylcyclobutyl)amino)methyl)-4-(trifluoromethyl)isoindolin-1-one. LCMS $[M+Na]^+$=565.1.

The above mixture was further purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 40% B with 0.1% ammonium hydroxide) to afford:

2-(3-((1 S,3S)-3-(methoxy-$d_3$)-1-(4-methyl-4H-1,2,4-triazol-3-yl)cyclobutyl)phenyl)-6-(((1-methylcyclobutyl) amino)methyl)-4-(trifluoromethyl)isoindolin-1-one (peak 2, retention time=2.167 min) (76 mg, 15% yield). $^1$H NMR (400 MHz, methanol-$d_4$) δ 8.32 (s, 1H), 8.09 (s, 1H), 8.06 (s, 1H), 8.01 (s, 1H), 7.69 (d, J=6.8 Hz, 1H), 7.49 (t, J=8.0 Hz 1H), 7.21 (d, J=7.6 Hz, 1H), 5.16 (s, 2H), 4.21-4.19 (m, 1H), 3.86 (m, 2H), 3.36 (s, 3H), 3.24-3.15 (m, 2H), 2.94-2.83 (m, 2H), 2.15-2.04 (m, 2H), 1.93-1.84 (m, 2H), 1.83-1.74 (m, 2H), 1.38 (s, 3H). LCMS $[M+Na]^+$=565.1.

2-(3-((1R,3R)-3-(methoxy-$d_3$)-1-(4-methyl-4H-1,2,4-triazol-3-yl)cyclobutyl)phenyl)-6-(((1-methylcyclobutyl) amino)methyl)-4-(trifluoromethyl)isoindolin-1-one (peak 1, retention time=1.786 min)(120 mg, 24% yield). $^1$H NMR (400 MHz, methanol-$d_4$) δ 8.39 (s, 1H), 8.08 (s, 1H), 8.01

(s, 1H), 7.92 (s, 1H), 7.69 (d, J=8.0 Hz, 1H), 7.48 (t, J=8.0 Hz, 1H), 7.08 (dd, J=1.2, 8.0 Hz, 1H), 5.15 (s, 2H), 4.03-3.94 (m, 1H), 3.86 (s, 2H), 3.42-3.36 (m, 2H), 3.35 (s, 3H), 2.71-2.58 (m, 2H), 2.15-2.04 (m, 2H), 1.92-1.85 (m, 2H), 1.83-1.76 (m, 2H), 1.38 (s, 3H). LCMS [M+Na]$^+$=565.1.

Example 108: Compounds 374, 375

Figure 104:
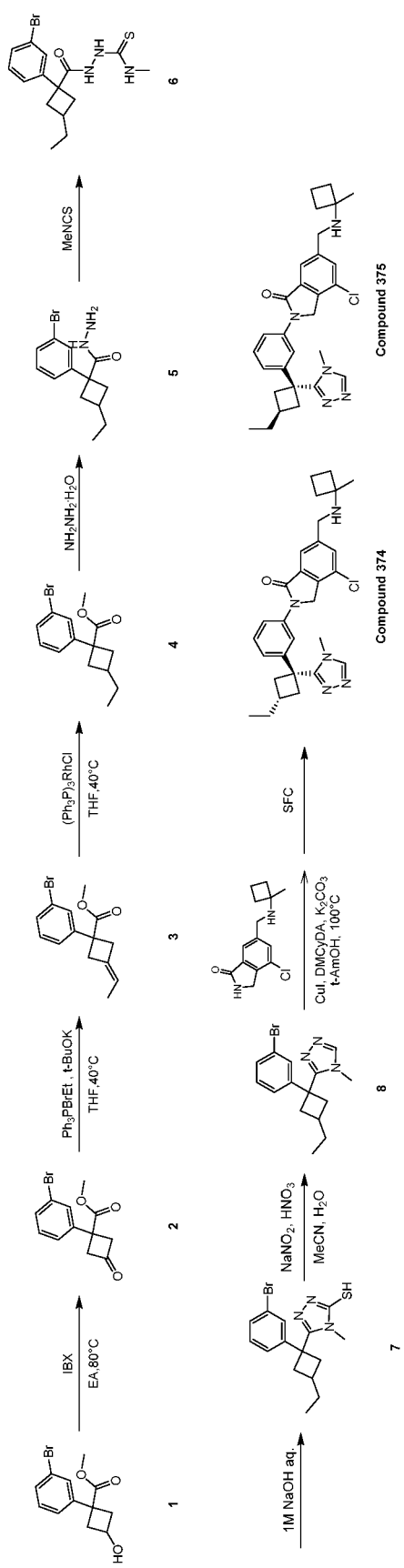

Compound 374 (4-chloro-2-(3-((1r,3s)-3-ethyl-1-(4-methyl-4H-1,2,4-triazol-3-yl)cyclobutyl)phenyl)-6-(((1-methylcyclobutyl)amino)methyl)isoindolin-1-one) and
Compound 375 (4-chloro-2-(3-((1s,3r)-3-ethyl-1-(4-methyl-4H-1,2,4-triazol-3-yl)cyclobutyl)phenyl)-6-(((1-methylcyclobutyl)amino)methyl)isoindolin-1-one), can be synthesized according to Scheme 104 (FIG. 104).

Intermediate 2: methyl 1-(3-bromophenyl)-3-oxocyclobutane-1-carboxylate

To a solution of methyl 1-(3-bromophenyl)-3-hydroxycyclobutane-1-carboxylate (5.0 g, 17.5 mmol) in ethyl acetate (70 mL) was added 1-2-iodoxybenzoic acid (14.73 g, 52.6 mmol) in portions. The mixture was stirred at 80° C. for 16 h and filtered through a pad of Celite. The filtrate was concentrated to dryness and the residue was purified by silica gel chromatography (mobile phase: ethyl acetate/petroleum ether, gradient 0% to 15%) to afford methyl 1-(3-bromophenyl)-3-oxocyclobutane-1-carboxylate (4.0 g, 80% yield) as a yellow solid. $^1$H NMR (400 MHz, CDCl$_3$) δ 7.45-7.32 (m, 4H), 3.98-3.90 (m, 2H), 3.72 (s, 3H), 3.64-3.57 (m, 2H).

Intermediate 3: methyl 1-(3-bromophenyl)-3-ethylidenecyclobutane-1-carboxylate

Under nitrogen, to a solution of ethyl triphenyl phosphonium bromide (8.08 g, 22.6 mmol) in tetrahydrofuran (80 mL) was added potassium t-butoxide (1.0 M in tetrahydrofuran, 21.19 mL, 21.19 mmol) at 0° C. The mixture was stirred at 40° C. for 1 h, and then a solution of methyl 1-(3-bromophenyl)-3-oxocyclobutane-1-carboxylate (2.0 g, 7.06 mmol) in tetrahydrofuran (10 ml) was added. The mixture was stirred at 40° C. for another 5 h and quenched with water (100 mL). The resulting solution was extracted with ethyl acetate (3×50 mL). The combined organic layers were washed with brine (2×50 mL), dried over sodium sulfate, filtered and concentrated to dryness. The residue was purified by silica gel chromatography (mobile phase: ethyl acetate/petroleum ether, gradient 0% to 2%) to afford methyl 1-(3-bromophenyl)-3-ethylidenecyclobutane-1-carboxylate (1 g, 50% yield) as yellow oil.

Intermediate 4: methyl 1-(3-bromophenyl)-3-ethylcyclobutane-1-carboxylate

To a solution of methyl 1-(3-bromophenyl)-3-ethylidenecyclobutane-1-carboxylate (1.0 g, 3.39 mmol) in tetrahydrofuran (10 mL) was added tris(triphenylphosphine)rhodium (I) chloride (0.5 g, 0.54 mmol). The mixture was stirred at 40° C. for 10 h under 15 psi hydrogen. Filtered and the filtrate was concentrated to afford methyl 1-(3-bromophenyl)-3-ethylcyclobutane-1-carboxylate (0.85 g, 84% yield) as a yellow solid.

Intermediate 5: 1-(3-bromophenyl)-3-ethylcyclobutane-1-carbohydrazide

To a solution of methyl 1-(3-bromophenyl)-3-ethylcyclobutane-1-carboxylate (0.89 g, 2.99 mmol) in methanol (10 mL) was added hydrazine hydrate (5.5 mL, 89.68 mmol). The reaction mixture was stirred at 80° C. for 2 h and concentrated to afford 1-(3-bromophenyl)-3-ethylcyclobutane-1-carbohydrazide (0.88 g, 99% yield) as a white solid which was used directly without further purification.

Intermediate 6: 2-(1-(3-bromophenyl)-3-ethylcyclobutane-1-carbonyl)-N-methylhydrazine-1-carbothioamide To a solution of 1-(3-bromophenyl)-3-ethylcyclobutane-1-carbohydrazide (0.88 g, 2.96 mmol) in tetrahydrofuran (10 mL) was added methyl isothiocyanate (433.0 mg, 5.92 mmol). The solution was stirred at 25° C. for 1 h and concentrated under vacuum to afford crude 2-(1-(3-bromophenyl)-3-ethylcyclobutane-1-carbonyl)-N-methylhydrazine-1-carbothioamide (1.0 g, 91% yield) as a white solid.

Intermediate 7: 5-(1-(3-bromophenyl)-3-ethylcyclobutyl)-4-methyl-4H-1,2,4-triazole-3-thiol A mixture of 2-(1-(3-bromophenyl)-3-ethylcyclobutane-1-carbonyl)-N-methylhydrazine-1-carbothioamide (0.85 g, 2.48 mmol) in aqueous sodium hydroxide (1.0 M, 12.42 mL, 12.42 mmol) was stirred at 25° C. for 2 h and then adjusted to pH=5 with aqueous hydrochloric acid (1.0 M). The precipitate was filtered and the cake was washed with water (20 mL) and dried under vacuum to give 5-(1-(3-bromophenyl)-3-ethylcyclobutyl)-4-methyl-4H-1,2,4-triazole-3-thiol (0.8 g, 99% yield) as a light yellow solid.

Intermediate 8: 3-(1-(3-bromophenyl)-3-ethylcyclobutyl)-4-methyl-4H-1,2,4-triazole To a solution of 5-(1-(3-bromophenyl)-3-ethylcyclobutyl)-4-methyl-4H-1,2,4-triazole-3-thiol (0.8 g, 2.27 mmol) in water (4 mL) and acetonitrile (4 mL) was added sodium nitrite (1.57 g, 22.71 mmol) and nitric acid (1 M, 27.25 mL, 27.25 mmol) at 0° c. The reaction mixture was stirred for 2 h at 20° C. then diluted with dichloromethane (40 mL), washed with saturated sodium bicarbonate (30 mL), brine (30 mL), dried over sodium sulfate, filtered and concentrated. The residue was purified by silica gel chromatography (mobile phase: methanol/dichloromethane, gradient 0% to 10%) to afford 3-(1-(3-bromophenyl)-3-ethylcyclobutyl)-4-methyl-4H-1,2,4-triazole (700 mg, 96% yield) as a white solid. LCMS [M+H]$^+$=320.0 and 322.0.
Compounds 374, 375
A mixture of 3-(1-(3-bromophenyl)-3-ethylcyclobutyl)-4-methyl-4H-1,2,4-triazole (150.0 mg, 0.47 mmol), 4-chloro-6-(((1-methylcyclobutyl)amino)methyl)isoindolin-1-one (124.0 mg, 0.47 mmol), copper(I) iodide (17.8 mg, 0.09 mmol), (1S,2S)—N$^1$,N$^2$-dimethylcyclohexane-1,2-diamine (26.7 mg, 0.19 mmol) and potassium carbonate (194.2 mg, 1.41 mmol) in tert-amyl alcohol (2 mL) was stirred at 100° C. for 10 h under N$_2$ then concentrated, the residue was dissolved with dichloromethane (25 mL), washed with 5% ammonia aqueous (20 mL), brine (20 mL), dried over sodium sulfate, filtered and concentrated to dryness. The residue was purified by RP-HPLC (water(NH$_3$H$_2$O+NH$_4$HCO$_3$)-ACN 60% to 90%) to afford 4-chloro-2-(3-(3-ethyl-1-(4-methyl-4H-1,2,4-triazol-3-yl)cyclobutyl)phenyl)-6-(((1-methylcyclobutyl)amino)methyl)isoindolin-1-one (70 mg, 39% yield). LCMS [M+H]$^+$=504.2 and 506.2.
The above mixture was further purified by chiral SFC (Column=Daicel Chiralpak AS; Column dimensions=250 mm×30 mm×10 μm; Detection wavelength=220 nM; Flow rate=100 mL/min; Mobile phase: A: $CO_2$ B: ethanol; Isocratic: 25% B with 0.1% ammonium hydroxide) to afford:

4-chloro-2-(3-((1r,3s)-3-ethyl-1-(4-methyl-4H-1,2,4-triazol-3-yl)cyclobutyl)phenyl)-6-(((1-methylcyclobutyl)amino)methyl)isoindolin-1-one (Peak 1, retention time=4.198 min) (24 mg, 69% yield). $^1$H NMR (400 MHz, methanol-$d_4$) δ 8.32 (s, 1H), 8.09 (s, 1H), 7.78 (s, 1H), 7.73-7.71 (m, 2H), 7.50 (t, J=8.0 Hz, 1H), 7.25 (d, J=8.0 Hz, 1H), 4.97 (s, 2H), 3.79 (s, 2H), 3.36 (s, 3H), 2.98-2.93 (m, 2H), 2.66-2.60 (m, 2H), 2.54-2.48 (m, 1H), 2.14-2.07 (m, 2H), 1.92-1.87 (m, 2H), 1.85-1.79 (m, 2H), 1.56-1.49 (m, 2H), 1.39 (s, 3H), 0.90 (t, J=7.6 Hz, 3H). LCMS [M+H]$^+$=504.3.

4-chloro-2-(3-((1s,3r)-3-ethyl-1-(4-methyl-4H-1,2,4-triazol-3-yl)cyclobutyl)phenyl)-6-(((1-methylcyclobutyl)amino)methyl)isoindolin-1-one (Peak 2, retention time=4.303 min) (9 mg, 26% yield). $^1$H NMR (400 MHz, methanol-$d_4$) δ 8.39 (s, 1H), 7.93 (s, 1H), 7.81 (s, 1H), 7.75 (s, 1H), 7.69-7.67 (m, 1H), 7.47 (t, J=8.0 Hz, 1H), 7.08 (d, J=7.6 Hz, 1H), 4.99 (s, 2H), 3.82 (s, 2H), 3.38 (s, 3H), 2.44-2.39 (m, 2H), 2.36-2.30 (m, 1H), 2.16-2.09 (m, 2H), 1.93-1.88 (m, 2H), 1.86-1.78 (m, 2H), 1.58-1.50 (m, 2H), 1.40 (s, 3H), 1.35-1.31 (m, 2H), 0.90 (t, J=7.6 Hz, 3H). LCMS [M+H]$^+$=504.2.

Example 109: Compounds 376, 377, 378, 379

Compound 376 (2-(3-((S)-(4-methyl-4H-1,2,4-triazol-3-yl)((1r,3S)-3-methylcyclobutyl)methyl)phenyl)-6-(((1-methylcyclobutyl)amino)methyl)-4-(trifluoromethyl)isoindolin-1-one),
Compound 377 (2-(3-((S)-(4-methyl-4H-1,2,4-triazol-3-yl)((1s,3R)-3-methylcyclobutyl)methyl)phenyl)-6-(((1-methylcyclobutyl)amino)methyl)-4-(trifluoromethyl)isoindolin-1-one),
Compound 378 (2-(3-((R)-(4-methyl-4H-1,2,4-triazol-3-yl)((1r,3R)-3-methylcyclobutyl)methyl)phenyl)-6-(((1-methylcyclobutyl)amino)methyl)-4-(trifluoromethyl)isoindolin-1-one), and
Compound 379 (2-(3-((R)-(4-methyl-4H-1,2,4-triazol-3-yl)((1s,3S)-3-methylcyclobutyl)methyl)phenyl)-6-(((1-methylcyclobutyl)amino)methyl)-4-(trifluoromethyl)isoindolin-1-one), can be synthesized according to Scheme 105 (FIG. 105).

Intermediate 2: 1-((3-bromophenyl)(4-methyl-4H-1,2,4-triazol-3-yl)methyl)-3-methylcyclobutanol To a solution of 3-(3-bromobenzyl)-4-methyl-4H-1,2,4-triazole (Intermediate D; 600.0 mg, 2.4 mmol) in tetrahydrofuran (8 mL) was added lithium diisopropylamide (2.0 M in tetrahydrofuran and n-hexane, 1.4 mL, 2.8 mmol) at −40° C. The mixture was stirred at −40° C. for 30 min, and 3-methylcyclobutanone (257.1 mg, 3.1 mmol) in tetrahydrofuran (2 mL) was added. The resulting mixture was stirred at 0° C. for 2 h and quenched by water (10 mL), extracted with dichloromethane (3×20 mL), combined the organic phase and washed with brine (20 mL), dried over sodium sulfate, filtered and concentrated under vacuum. The residue was purified by silica gel chromatography (mobile phase: methanol/dichloro-methane, gradient 0% to 10%) to afford 1-((3-bromophenyl)(4-methyl-4H-1,2,4-triazol-3-yl)methyl)-3-methylcyclobutanol (600 mg, 75% yield). LCMS [M+H]$^+$=336.1 and 338.1.

Intermediate 3: 3-((3-bromophenyl)(3-methylcyclobutylidene)methyl)-4-methyl-4H-1,2,4-triazole To a solution of 1-((3-bromophenyl)(4-methyl-4H-1,2,4-triazol-3-yl)methyl)-3-methylcyclobutanol (720.0 mg, 2.2 mmol) in dichloromethane (20 mL) was added diethylaminosulphur trifluoride (0.6 mL, 4.4 mmol) at 0° C., the mixture was stirred at 0° C. for 2 hours then quenched with water (10 mL), extracted with dichloromethane (3×20 mL). The combined organic layers were washed with brine (20 mL), dried over sodium sulfate, filtered and concentrated to dryness. The crude was purified by silica gel chromatography (mobile phase: methanol/dichloromethane, gradient 0% to 10%) to afford 3-((3-bromophenyl)(3-methylcyclobutylidene)methyl)-4-methyl-4H-1,2,4-triazole (450 mg, 62% yield) white solid. LCMS [M+H]$^+$=318.1 and 320.1.

Intermediate 4: tert-butyl ((2-(3-((4-methyl-4H-1,2,4-triazol-3-yl)(3-methylcyclobutylidene)methyl)phenyl)-3-oxo-7-(trifluoromethyl)isoindolin-5-yl)methyl)(1-methylcyclobutyl)carbamate A mixture of tert-butyl (1-methylcyclobutyl)((3-oxo-7-(trifluoromethyl)isoindolin-5-yl)methyl)carbamate (Intermediate A; 619.8 mg, 1.6 mmol), 3-((3-bromophenyl)(3-methylcyclobutylidene)methyl)-4-methyl-4H-1,2,4-triazole (450.0 mg, 1.4 mmol), (1 S,2S)—$N^1,N^2$-dimethylcyclohexane-1,2-diamine (80.5 mg, 0.5 mmol), potassium carbonate (586.4 mg, 4.2 mmol) and copper(I) iodide (107.7 mg, 0.5 mmol) in tert-amyl alcohol (8 mL) was stirred at 100° C. for 2 h under nitrogen and concentrated. The residue was dissolved with dichloromethane (50 mL), washed with 5% ammonia aqueous (2×30 mL), dried over sodium sulfate, filtered and concentrated to dryness. The residue was purified by silica gel chromatography (mobile phase: methanol/dichloromethane, gradient 0% to 10%) to afford tert-butyl ((2-(3-((4-methyl-4H-1,2,4-triazol-3-yl)(3-methylcyclobutylidene)methyl)phenyl)-3-oxo-7-(trifluoromethyl)isoindolin-5-yl)methyl)(1-methylcyclobutyl)carbamate (800 mg, 89% yield) as a white solid. LCMS [M+H]$^+$=636.3.

Intermediate 5: tert-butyl ((2-(3-((4-methyl-4H-1,2,4-triazol-3-yl)(3-methylcyclobutyl)methyl)phenyl)-3-oxo-7-(trifluoromethyl)isoindolin-5-yl)methyl)(1-methylcyclobutyl)carbamate A mixture of tert-butyl ((2-(3-((4-methyl-4H-1,2,4-triazol-3-yl)(3-methylcyclobutylidene)methyl)phenyl)-3-oxo-7-(trifluoromethyl)isoindolin-5-yl)methyl)(1-methylcyclobutyl)carbamate (800.0 mg, 1.3 mmol) in methanol (10 mL) was added Palladium (10% on carbon, 266.8 mg), the mixture was stirred 16 h at 25° C. under $H_2$ at 15 Psi. The mixture was filtered and the filtrate was concentrated. The residue was purified by silica gel chromatography (mobile phase: methanol/dichloromethane, gradient 0% to 10%) to afford tert-butyl ((2-(3-((4-methyl-4H-1,2,4-triazol-3-yl)(3-methylcyclobutyl)methyl)phenyl)-3-oxo-7-(trifluoromethyl)isoindolin-5-yl)methyl)(1-methylcyclobutyl)carbamate (480 mg, 60% yield) as a yellow solid. LCMS [M+H]$^+$=638.3.

Compounds 376, 377, 378, 379

To a solution of tert-butyl ((2-(3-((4-methyl-4H-1,2,4-triazol-3-yl)(3-methylcyclobutyl)methyl)phenyl)-3-oxo-7-(trifluoromethyl)isoindolin-5-yl)methyl)(1-methylcyclobutyl)carbamate (480.0 mg, 0.8 mmol) in dichloromethane (10 mL) was added trifluoroacetic acid (1.0 mL, 0.8 mmol). The reaction was stirred at 25° C. for 3 h and concentrated. The residue was purification by RP-HPLC (water($NH_3H_2O+NH_4HCO_3$)-ACN 55% to 85%) to afford 2-(3-((4-methyl-4H-1,2,4-triazol-3-yl)(3-methylcyclobutyl)

methyl)-phenyl)-6-(((1-methylcyclobutyl)amino)methyl)-4-(trifluoromethyl)isoindolin-1-one (200 mg, 49% yield).

The above mixture was purified by chiral SFC (Column=Daicel Chiralpak IC; Column dimensions=250 mm×30 mm×10 μm; Detection wavelength=220 nM; Flow rate=80 mL/min; Mobile phase: A: $CO_2$ B: ethanol; Isocratic: 60% B with 0.1% ammonium hydroxide) to afford product A and product B.

The product A was purified by chiral SFC (Column=Daicel Chiralpak AD; Column dimensions=250 mm×30 mm×10 μm; Detection wavelength=220 nM; Flow rate=80 mL/min; Mobile phase: A: $CO_2$ B: methanol; Isocratic: 40% B with 0.1% ammonium hydroxide) to afford tentatively assigned:

2-(3-((S)-(4-methyl-4H-1,2,4-triazol-3-yl)((1r,3S)-3-methylcyclobutyl)methyl)phenyl)-6-(((1-methylcyclobutyl)amino)methyl)-4-(trifluoromethyl)isoindolin-1-one (Peak 1, retention time=5.672 min) (10.1 mg, 13% yield). $^1$H NMR (400 MHz, methanol-$d_4$) δ 8.35 (s, 1H), 8.08 (s, 1H), 8.00 (s, 1H), 7.85 (s, 1H), 7.75 (d, J=8.0 Hz, 1H), 7.42 (t, J=8.0 Hz, 1H), 7.11 (d, J=7.6 Hz, 1H), 5.13 (s, 2H), 4.28 (d, J=11.6 Hz, 1H), 3.87 (s, 2H), 3.54 (s, 3H), 2.50-2.40 (m, 1H), 2.17-2.01 (m, 3H), 1.95-1.74 (m, 6H), 1.63-1.51 (m, 1H), 1.38 (s, 3H), 1.30-1.28 (m, 1H), 1.16 (d, J=6.8 Hz, 3H). LCMS [M+H]$^+$=538.3.

2-(3-((S)-(4-methyl-4H-1,2,4-triazol-3-yl)((1s,3R)-3-methylcyclobutyl)methyl)phenyl)-6-(((1-methylcyclobutyl)amino)methyl)-4-(trifluoromethyl)isoindolin-1-one (Peak 2, retention time=6.073 min) (44.5 mg, 56% yield). $^1$H NMR (400 MHz, methanol-$d_4$) δ 8.35 (s, 1H), 8.08 (s, 1H), 8.00 (s, 1H), 7.83 (s, 1H), 7.75 (d, J=8.0 Hz, 1H), 7.42 (t, J=8.0 Hz, 1H), 7.08 (d, J=8.0 Hz, 1H), 5.13 (s, 2H), 4.14 (d, J=10.4 Hz, 1H), 3.86 (s, 2H), 3.52 (s, 3H), 3.12-3.00 (m, 1H), 2.45-2.36 (m, 1H), 2.30-2.20 (m, 1H), 2.14-2.01 (m, 3H), 1.92-1.85 (m, 2H), 1.84-1.76 (m, 2H), 1.52-1.44 (m, 1H), 1.38 (s, 3H), 1.34-1.31 (m, 1H), 1.06 (d, J=6.8 Hz, 3H). LCMS [M+H]$^+$=538.4.

The product B was purified by chiral SFC (Column=Daicel Chiralpak OJ; Column dimensions=250 mm×30 mm×10 μm; Detection wavelength=220 nM; Flow rate=60 mL/min; Mobile phase: A: $CO_2$ B: ethanol; Isocratic: 15% B with 0.1% ammonium hydroxide) to afford tentatively assigned:

2-(3-((R)-(4-methyl-4H-1,2,4-triazol-3-yl)((1r,3R)-3-methylcyclobutyl)methyl)phenyl)-6-(((1-methylcyclobutyl)amino)methyl)-4-(trifluoromethyl)isoindolin-1-one (Peak 1, retention time=2.669 min) (34.4 mg, 43% yield). $^1$H NMR (400 MHz, methanol-$d_4$) δ 8.35 (s, 1H), 8.08 (s, 1H), 8.00 (s, 1H), 7.83 (s, 1H), 7.75 (d, J=8.0 Hz, 1H), 7.42 (t, J=8.0 Hz, 1H), 7.08 (d, J=8.0 Hz, 1H), 5.13 (s, 2H), 4.14 (d, J=11.2 Hz, 1H), 3.86 (s, 2H), 3.52 (s, 3H), 3.10-3.01 (m, 1H), 2.46-2.36 (m, 1H), 2.31-2.19 (m, 1H), 2.13-2.01 (m, 3H), 1.92-1.85 (m, 2H), 1.83-1.75 (m, 2H), 1.52-1.44 (m, 1H), 1.38 (s, 3H), 1.34-1.31 (m, 1H), 1.06 (d, J=6.4 Hz, 3H). LCMS [M+H]$^+$=538.3.

2-(3-((R)-(4-methyl-4H-1,2,4-triazol-3-yl)((1s,3S)-3-methylcyclobutyl)methyl)phenyl)-6-(((1-methylcyclobutyl)amino)methyl)-4-(trifluoromethyl)isoindolin-1-one (Peak 2, retention time=2.761 min) (9.6 mg, 12% yield). $^1$H NMR (400 MHz, methanol-$d_4$) δ 8.35 (s, 1H), 8.09 (s, 1H), 8.01 (s, 1H), 7.85 (s, 1H), 7.75 (d, J=7.6 Hz, 1H), 7.42 (t, J=8.0 Hz, 1H), 7.11 (d, J=7.6 Hz, 1H), 5.14 (s, 2H), 4.28 (d, J=11.6 Hz, 1H), 3.87 (s, 2H), 3.54 (s, 3H), 2.50-2.40 (m, 1H), 2.14-2.04 (m, 3H), 1.92-1.76 (m, 6H), 1.57 (s, 1H), 1.39 (s, 3H), 1.30-1.28 (m, 1H), 1.16 (d, J=6.8 Hz, 3H). LCMS [M+H]$^+$=538.4.

Example 110: Compounds 380, 381

Compound 380 ((R)-2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one), and Compound 381 ((S)-2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to the following steps.

First intermediate: 3-((3-bromophenyl)(4-methyl-4H-1,2,4-triazol-3-yl)methyl)oxetan-3-ol To a solution of 3-[(3-bromophenyl)methyl]-4-methyl-1,2,4-triazole (Intermediate D; 500.0 mg, 2.0 mmol) in tetrahydrofuran (8 mL) was added lithium diisopropylamide (2.0 M in tetrahydrofuran and n-hexane, 1.4 mL, 2.8 mmol) at −40° C. The mixture was stirred at −40° C. for 30 min, and oxetan-3-one (214.4 mg, 3.0 mmol) in tetrahydrofuran (2 mL) was added. The resulting mixture was stirred at 0° C. for 2 h and quenched by water (10 mL), extracted with dichloromethane (3×20 mL), combined the organic layers were dried over sodium sulfate, filtered and concentrated under vacuum. The residue was purified by silica gel chromatography (mobile phase: methanol/dichloromethane, gradient 0% to 10%) to afford 3-((3-bromophenyl)(4-methyl-4H-1,2,4-triazol-3-yl)methyl)oxetan-3-ol (560 mg, 87% yield) as a white solid. LCMS [M+H]$^+$=324.0 and 326.0.

Second Intermediate: 3-((3-bromophenyl)(3-fluorooxetan-3-yl)methyl)-4-methyl-4H-1,2,4-triazole To a solution of 3-((3-bromophenyl)(4-methyl-4H-1,2,4-triazol-3-yl)methyl)oxetan-3-ol (360.0 mg, 1.1 mmol) in dichloromethane (10 mL) was added diethylaminosulphur trifluoride (0.3 mL, 2.2 mmol) at 0° C., the mixture was stirred at 0° C. for 2 h then quenched with water (10 mL), extracted with dichloromethane (3×20 mL). combined the organic layers and washed with brine (20 mL), dried over sodium sulfate, filtered and concentrated to dryness. The residue was purified by silica gel chromatography (mobile phase: methanol/dichloromethane, gradient 0% to 10%) to afford 3-((3-bromophenyl)(3-fluorooxetan-3-yl)methyl)-4-methyl-4H-1,2,4-triazole (50 mg, 15% yield) as a white solid. $^1$H NMR (400 MHz, methanol-$d_4$) δ 8.34 (s, 1H), 7.51-7.46 (m, 1H), 7.30-7.23 (m, 2H), 7.06 (d, J=8.0 Hz, 1H), 6.36-6.20 (m, 1H), 5.43 (d, J=6.4 Hz, 1H), 5.28 (d, J=6.4 Hz, 1H), 5.16 (dd, J=2.0, 6.8 Hz, 1H), 4.95 (dd, J=4.4, 6.4 Hz, 1H), 3.21 (s, 3H). LCMS [M+H]$^+$=326.0 and 328.0.

Compounds 380, 381

A mixture of 6-(((1-methylcyclobutyl)amino)methyl)-4-(trifluoromethyl)isoindolin-1-one (cf. Scheme 1; 35.2 mg, 0.1 mmol), 3-((3-bromophenyl)(3-fluorooxetan-3-yl)methyl)-4-methyl-4H-1,2,4-triazole (35.0 mg, 0.1 mmol), (1S,2S)—$N^1,N^2$-dimethylcyclohexane-1,2-diamine (6.1 mg, 0.04 mmol), potassium carbonate (44.5 mg, 0.3 mmol) and copper(I) iodide (8.2 mg, 0.04 mmol) in tert-amyl alcohol (1 mL) was stirred at 100° C. for 2 h under nitrogen. The mixture was added dichloromethane (10 mL), washed with 5% ammonium aqueous (3×5 mL), dried over sodium sulfate, filtered and concentrated to dryness. The residue was purified by preparative TLC (solvent gradient: 10% methanol in dichloromethane) to afford 2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one (50 mg, 86% yield).

The above mixture was further purified by chiral SFC (Column=Daicel Chiralpak OD; Column dimensions=250 mm×30 mm×10 μm; Detection wavelength=220 nM; Flow rate=100 mL/min; Mobile phase: A: $CO_2$ B: ethanol; Isocratic: 40% B with 0.1% ammonium hydroxide) to afford tentatively assigned:

(R)-2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=3.695 min) (11.6 mg, 23% yield) $^1$H NMR (400 MHz, methanol-$d_4$) δ 8.28 (s, 1H), 8.08 (s, 1H), 8.01 (s, 1H), 7.80 (d, J=8.4 Hz, 1H), 7.53 (s, 1H), 7.43 (t, J=8.0 Hz, 1H), 6.92 (d, J=7.6 Hz, 1H), 6.39-6.22 (m, 1H), 5.48 (d, J=6.0 Hz, 1H), 5.32 (d, J=6.0 Hz, 1H), 5.22 (d, J=5.2 Hz, 1H), 5.09 (s, 2H), 5.05-5.00 (m, 1H), 3.86 (s, 2H), 3.12 (s, 3H), 2.16-2.03 (m, 2H), 1.92-1.75 (m, 4H), 1.37 (s, 3H). LCMS [M+H]$^+$=544.3.

(S)-2-(3-((3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=4.162 min) (11.3 mg, 23% yield). $^1$H NMR (400 MHz, methanol-$d_4$) δ 8.28 (s, 1H), 8.08 (s, 1H), 8.01 (s, 1H), 7.80 (d, J=8.4 Hz, 1H), 7.53 (s, 1H), 7.43 (t, J=8.0 Hz, 1H), 6.92 (d, J=8.0 Hz, 1H), 6.39-6.22 (m, 1H), 5.48 (d, J=6.8 Hz, 1H), 5.32 (d, J=6.4 Hz, 1H), 5.22 (d, J=5.2 Hz, 1H), 5.09 (s, 2H), 5.05-5.00 (m, 1H), 3.86 (s, 2H), 3.12 (s, 3H), 2.10-2.08 (m, 2H), 1.91-1.77 (m, 4H), 1.38 (s, 3H). LCMS [M+H]$^+$=544.3.

Example 111: Compounds 382, 383, 384, 385

Compound 382 (2-(3-((R)-((1r,3R)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one)

Compound 383 (2-(3-((S)-((1s,3R)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one)

Compound 384 (2-(3-((S)-((1r,3S)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one) and Compound 385 (2-(3-((R)-((1s,3S)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to the following steps.

Intermediate: 1-(3-((3-bromophenyl)(4-methyl-4H-1,2,4-triazol-3-yl)methyl)cyclobutyl)ethan-1-one To a solution of 3-((3-bromophenyl)(4-methyl-4H-1,2,4-triazol-3-yl)methyl)-cyclobutane-1-carbonitrile (150 mg, 0.45 mmol) in tetrahydrofuran (2.5 mL) was added methyl magnesium bromide (3M in diethyl ether, 0.60 mL, 1.81 mmol) at 0° C., the mixture was stirred at 25° C. for 1 h and quenched by water (5 mL). The resulting mixture was extracted with dichloromethane (3×20 mL), combined the organic layers and washed with brine (50 mL), dried over sodium sulfate, filtered and concentrated under vacuum. The residue was purified by silica gel chromatography (mobile phase: methanol/dichloro-methane, gradient 0% to 10%) to afford 1-(3-((3-bromophenyl)(4-methyl-4H-1,2,4-triazol-3-yl)methyl)cyclobutyl)ethan-1-one (110 mg, 70% yield) as a white solid.

Compounds 382, 383, 384, 385

In a glove box, a mixture of 1-(3-((3-bromophenyl)(4-methyl-4H-1,2,4-triazol-3-yl)methyl)cyclobutyl)ethan-1-one (110 mg, 0.31 mmol), 6-(((1-methylcyclobutyl)-amino)methyl)-4-(trifluoromethyl)isoindolin-1-one (cf. Scheme 1; 103 mg, 0.34 mmol), copper(I) iodide (24 mg, 0.12 mmol), (1 S,2S)—$N^1,N^2$-dimethylcyclohexane-1,2-diamine (18 mg, 0.12 mmol) and potassium carbonate (130 mg, 0.94 mmol) in tert-amyl alcohol (3 mL) was heated at 100° C. in sealed vial for 2 h and concentrated to dryness. The residue was purified by silica gel chromatography (mobile phase: methanol/dichloromethane, gradient 0% to 10%) to afford 2-(3-((3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one (110 mg, 62% yield).

The above mixture was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 40% B with 0.1% ammonium hydroxide) to afford tentatively assigned:

2-(3-((R)-((1r,3R)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=5.525 min) (18.6 mg, 17% yield). $^1$H NMR (400 MHz, methanol-$d_4$) δ 8.37 (s, 1H), 8.09 (s, 1H), 8.01 (s, 1H), 7.86-7.83 (m, 1H), 7.80 (dd, J=2.4, 8.0 Hz, 1H), 7.43 (d, J=8.0 Hz, 1H), 7.09 (d, J=7.6 Hz, 1H), 5.14 (s, 2H), 4.42-4.08 (m, 1H), 3.86 (s, 2H), 3.51 (s, 3H), 3.25-3.21 (m, 1H), 2.56-2.44 (m, 1H), 2.14-2.02 (m, 7H), 1.96-1.68 (m, 6H), 1.38 (s, 3H). LCMS [M+H]$^+$=566.3.

2-(3-((S)-((1s,3R)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=6.213 min) (5.0 mg, 4% yield). $^1$H NMR (400 MHz, methanol-$d_4$) δ 8.37 (s, 1H), 8.09 (s, 1H), 8.01 (s, 1H), 7.89 (s, 1H), 7.79-7.73 (m, 1H), 7.47-7.41 (m, 1H), 7.13 (d, J=7.2 Hz, 1H), 5.15 (s, 2H), 4.39-4.33 (m, 1H), 3.86 (s, 2H), 3.59-3.53 (m, 1H), 3.50 (s, 3H), 2.69-2.48 (m, 1H), 2.44-2.13 (m, 3H), 2.13-1.94 (m, 5H), 1.92-1.74 (m, 5H), 1.38 (s, 3H) LCMS [M+H]$^+$=566.3.

2-(3-((S)-((1r,3S)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 3, retention time=6.648 min) (15.2 mg, 14% yield). $^1$H NMR (400 MHz, methanol-$d_4$) δ 8.36 (s, 1H), 8.09 (s, 1H), 8.01 (s, 1H), 7.88-7.83 (m, 1H), 7.77 (d, J=8.0 Hz, 1H), 7.44 (t, J=7.6 Hz, 1H), 7.12 (d, J=7.2 Hz, 1H), 5.14 (s, 2H), 4.39-4.11 (m, 1H), 3.86 (s, 2H), 3.55-3.50 (m, 3H), 3.26-3.21 (m, 1H), 2.58-2.45 (m, 1H), 2.30-2.18 (m, 1H), 2.13-2.00 (m, 7H), 1.92-1.74 (m, 5H), 1.38 (s, 3H). LCMS [M+H]$^+$=566.3.

2-(3-((R)-((1s,3S)-3-acetylcyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 4, retention time=7.542 min) (13.8 mg, 21% yield). $^1$H NMR (400 MHz, methanol-$d_4$) δ 8.37 (s, 1H), 8.09 (s, 1H), 8.01 (s, 1H), 7.88-7.81 (m, 1H), 7.77 (d, J=8.0 Hz, 1H), 7.43 (t, J=8.0 Hz, 1H), 7.10 (d, J=7.2 Hz, 1H), 5.14 (s, 2H), 4.38-4.12 (m, 1H), 3.87 (s, 2H), 3.54-3.48 (m, 3H), 3.25-3.22 (m, 1H), 2.53-2.47 (m, 1H), 2.12-2.04 (m, 7H), 1.96-1.75 (m, 6H), 1.39 (s, 3H). LCMS [M+H]$^+$=566.3.

Example 112: Compound 386

Compound 386 ((R)-2-(3-((4-methyl-4H-1,2,4-triazol-3-yl)(oxetan-3-yl)methyl)phenyl)-6-(1-propylazetidin-3-yl)-

4-(trifluoromethyl)isoindolin-1-one), can be synthesized according to Scheme 106 (FIG. 106), wherein "PMB" is short for paramethoxybenzyl.

Intermediate 2: tert-butyl 3-(2-(4-methoxybenzyl)-3-oxo-7-(trifluoromethyl)-isoindolin-5-yl)azetidine-1-carboxylate A mixture of tert-butyl 3-bromoazetidine-1-carboxylate (118.0 mg, 0.5 mmol), 6-bromo-2-(4-methoxybenzyl)-4-(trifluoromethyl)isoindolin-1-one (100.0 mg, 0.25 mmol) in 1,2-dimethoxyethane (4 mL) was added hydroxylithium (15 mg, 0.6 mmol), [Ir(dF-CF$_3$-ppy)$_2$(dtbpy)](PF$_6$) (CAS: 870987-63-6) (2.8 mg, 0.01 mmol) and tris(trimethylsilyl) silane (74.6 mg, 0.3 mmol). The solution nickel chloride dimethoxyethane adduct (5.5 mg, 0.02 mmol) and 4,4'-di-tert-butyl-2,2'-dipyridyl (10.1 mg, 0.04 mmol) in 1,2-dimethoxyethane (1 mL) was added the mixture in glove box at 20° C. The reaction mixture was stirred under a Lumidox Screen Kit for 20 h at 20° C. The reaction mixture was quenched with water (10 mL) and then extracted with dichloromethane (3×15 mL). The combined organic layers were washed with brine (20 mL), dried over sodium sulfate, filtered and concentrated to dryness. The mixture was then concentrated to dryness and the residue was purified by preparative TLC (solvent gradient: 10% methanol in dichloromethane) to afford tert-butyl 3-(2-(4-methoxybenzyl)-3-oxo-7-(trifluoromethyl)isoindolin-5-yl)azetidine-1-carboxylate (100.0 mg, 84%) as a yellow solid. $^1$H NMR (400 MHz, CDCl$_3$) δ 8.12-8.05 (m, 1H), 7.68 (s, 1H), 7.26 (s, 2H), 6.90 (d, J=8.4 Hz, 2H), 4.78 (s, 2H), 4.46-4.39 (m, 4H), 4.08-3.97 (m, 3H), 3.90 (d, J=6.8 Hz, 1H), 3.82 (s, 3H), 3.65-3.59 (m, 2H), 1.50 (s, 9H). LCMS [M+H−56]$^+$=421.1.

Intermediate 3: 6-(azetidin-3-yl)-2-(4-methoxybenzyl)-4-(trifluoromethyl)-isoindolin-1-one To a mixture of tert-butyl 3-(2-(4-methoxybenzyl)-3-oxo-7-(trifluoromethyl)isoindolin-5-yl)azetidine-1-carboxylate (310.0 mg, 0.7 mmol) in dichloromethane (2 mL) was added trifluoroacetic acid (0.2 mL, 2.6 mmol), the mixture was stirred for 2 h and then concentrated to dryness to afford 6-(azetidin-3-yl)-2-(4-methoxybenzyl)-4-(trifluoromethyl) isoindolin-1-one (240 mg, 98% yield) as a yellow solid. LCMS [M+H]$^+$=377.0.

Intermediate 4: 2-(4-methoxybenzyl)-6-(1-propylazetidin-3-yl)-4-(trifluoromethyl)isoindolin-1-one To a solution of 6-(azetidin-3-yl)-2-(4-methoxybenzyl)-4-(trifluoromethyl)isoindolin-1-one (240 mg, 0.6 mmol) in dichloromethane (3 mL) was added propanal (0.09 mL, 1.3 mmol) and sodium triacetoxyborohydride (202.9 mg, 0.9 mmol), the mixture was stirred at 25° C. for 2 h then quenched with water (10 mL), extracted with dichloromethane (3×15 mL). The combined organic layers were washed with brine (20 mL), dried over sodium sulfate, filtered and concentrated to dryness. The residue was purified by preparative TLC (solvent gradient: 10% methanol in dichloromethane) to afford 2-(4-methoxybenzyl)-6-(1-propylazetidin-3-yl)-4-(trifluoromethyl)isoindolin-1-one (250 mg, 93%) as a yellow solid. LCMS [M+H]$^+$=419.2.

Intermediate 5: 6-(1-propylazetidin-3-yl)-4-(trifluoromethyl)isoindolin-1-one

To a solution of 2-(4-methoxybenzyl)-6-(1-propylazetidin-3-yl)-4-(trifluoromethyl)isoindolin-1-one (200.0 mg, 0.5 mmol) in acetonitrile (5 mL) was added a solution of Diammonium cerium(IV) nitrate (786.1 mg, 1.4 mmol) in water (1 mL) at 0° C. The mixture was stirred at 0° C. for 2 h then diluted with water (10 mL), extracted with dichloromethane (3×15 mL), combined the organic layers and washed with brine (20 mL), dried over sodium sulfate, filtered and concentrated to dryness. The residue was purified by preparative TLC (solvent gradient: 10% methanol in dichloromethane) to afford 6-(1-propylazetidin-3-yl)-4-(trifluoromethyl)isoindolin-1-one (50 mg, 35% yield) as a white solid. LCMS [M+H]$^+$=299.1.

Compound 386

A mixture of 6-(1-propylazetidin-3-yl)-4-(trifluoromethyl)isoindolin-1-one (50.0 mg, 0.2 mmol), (R)-3-((3-bromophenyl)(oxetan-3-yl)methyl)-4-methyl-4H-1,2,4-triazole (56.7 mg, 0.2 mmol), (1S,2S)—N$^1$,N$^2$-dimethylcyclohexane-1,2-diamine (9.5 mg, 0.07 mmol), potassium carbonate (69.3 mg, 0.5 mmol) and copper(I) iodide (12.7 mg, 0.07 mmol) in tert-amyl alcohol (1 mL) was stirred at 100° C. for 2 h under nitrogen. The mixture was diluted with dichloromethane (10 mL), washed with 5% ammonia aqueous (3×5 mL), dried over sodium sulfate, filtered and concentrated to dryness. The residue was purified by RP-HPLC (water(NH$_3$H$_2$O+NH$_4$HCO$_3$)-ACN 35% to 65%) to afford (R)-2-(3-((4-methyl-4H-1,2,4-triazol-3-yl)(oxetan-3-yl) methyl)phenyl)-6-(1-propylazetidin-3-yl)-4-(trifluoromethyl)isoindolin-1-one (9.3 mg, 11% yield). $^1$H NMR (400 MHz, methanol-d$_4$) δ 8.39 (s, 1H), 8.06 (s, 1H), 7.90 (s, 2H), 7.79 (dd, J=1.2, 8.0 Hz, 1H), 7.46 (t, J=7.6 Hz, 1H), 7.11 (d, J=8.4 Hz, 1H), 5.14 (s, 2H), 4.98-4.94 (m, 1H), 4.79 (d, J=10.8 Hz, 1H), 4.68-4.64 (m, 2H), 4.43 (t, J=6.4 Hz, 1H), 4.05-3.93 (m, 2H), 3.86 (t, J=8.0 Hz, 2H), 3.50 (s, 3H), 3.34 (s, 2H), 2.58-2.53 (m, 2H), 1.52-1.41 (m, 2H), 0.96 (t, J=7.6 Hz, 3H). LCMS [M+H]$^+$=526.3.

Example 113 Compounds 387, 388, 389, 390

Figure 107:
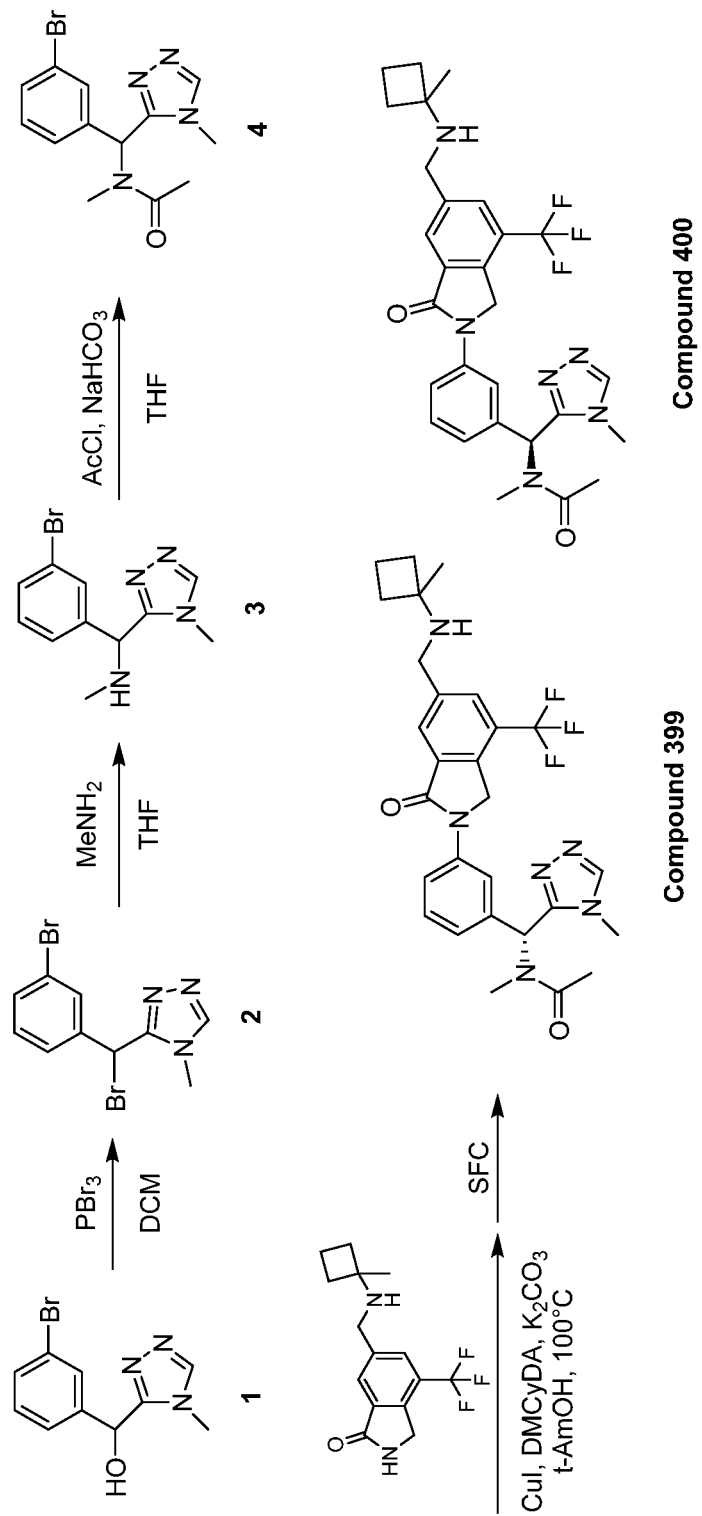

Compound 387 (2-(3-((R)-((1r,3R)-3-(difluoromethoxy) cyclobutyl)(4-methyl-4H-1,2,4-triazol-3-yl)methyl)phenyl)-6-(((1-methylcyclobutyl)amino)methyl)-4-(trifluoromethyl)isoindolin-1-one), Compound 388 (2-(3-((R)-((1s,3S)-3-(difluoromethoxy) cyclobutyl)(4-methyl-4H-1,2,4-triazol-3-yl)methyl)phenyl)-6-(((1-methylcyclobutyl)amino)methyl)-4-(trifluoromethyl)isoindolin-1-one), Compound 389 (2-(3-((S)-((1r,3S)-3-(difluoromethoxy) cyclobutyl)(4-methyl-4H-1,2,4-triazol-3-yl)methyl)phenyl)-6-(((1-methylcyclobutyl)amino)methyl)-4-(trifluoromethyl)isoindolin-1-one), Compound 390 (2-(3-((S)-((1s,3R)-3-(difluoromethoxy) cyclobutyl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 107 (FIG. 107).

Intermediate 2: 3-((3-bromophenyl)(3-(difluoromethoxy)cyclobutyl)methyl)-4-methyl-4H-1,2,4-triazole To a solution of 3-((3-bromophenyl)(4-methyl-4H-1,2,4-triazol-3-yl)methyl)-cyclobutan-1-ol (such as may be obtained from the first starting material in Scheme 62; 500 mg, 1.55 mmol) in acetonitrile (10 mL) was added copper(I) iodide (59.1 mg, 0.31 mmol) at 25° C., then the mixture was heated to 50° C. and difluoro(fluorosulfonyl)acetic acid (414.5 mg, 2.33 mmol) was added. The resulting mixture was stirred at 50° C. for another 1 h then quenched by water (10 mL), extracted with dichloromethane (3×50 mL). The combined organic layers were washed with brine (50 mL), dried over sodium sulfate, filtered and concentrated to dryness. The residue was purified by silica gel chromatography (mobile phase: methanol/dichloromethane, gradient 0% to 10%) to afford 3-((3-bromophenyl)(3-(difluoromethoxy)cyclobutyl)methyl)-4-methyl-4H-1,2,4-triazole (230 mg, 40% yield) as a white solid.

Compounds 387, 388, 389, 390

In a glove box, a mixture of 3-((3-bromophenyl)(3-(difluoromethoxy)cyclobutyl)-methyl)-4-methyl-4H-1,2,4-triazole (230 mg, 0.61 mmol), 6-(((1-methylcyclobutyl)amino)-methyl)-4-(trifluoromethyl)isoindolin-1-one (cf. Scheme 1; 203 mg, 0.68 mmol), copper(I) iodide (47 mg, 0.25 mmol), (1S,2S)—$N^1,N^2$-dimethylcyclohexane-1,2-diamine (35 mg, 0.25 mmol) and potassium carbonate (256 mg, 1.85 mmol) in tert-amyl alcohol (3 mL) was heated at 100° C. in sealed vial for 2 h and concentrated to dryness. The residue was purified by silica gel chromatography (mobile phase: methanol/dichloromethane, gradient 0% to 10%) to afford a crude which was residue was purified by RP-HPLC (0.2% $NH_3 \cdot H_2O$ in water/ACN 58% to 88%) to afford 2-(3-(3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one (110 mg, 30% yield).

The above mixture was purified by chiral SFC (Column=Daicel Chiralpak IG; Column dimensions=250 mm×30 mm×10 μm; Detection wavelength=220 nM; Flow rate=100 mL/min; Mobile phase: A: $CO_2$ B: ethanol; Isocratic: 35% B with 0.1% ammonium hydroxide) to afford product A and product B.

The product A was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 35% B with 0.1% ammonium hydroxide) to afford tentatively assigned:

2-(3-((R)-((1r,3R)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=1.749 min) (10.8 mg, 22% yield). $^1$H NMR (400 MHz, methanol-$d_4$) δ 8.37 (s, 1H), 8.09 (s, 1H), 8.01 (s, 1H), 7.89 (s, 1H), 7.77 (d, J=8.4 Hz, 1H), 7.45 (t, J=8.0 Hz, 1H), 7.12 (d, J=8.0 Hz, 1H), 6.30 (t, J=75.6 Hz, 1H), 5.15 (s, 2H), 4.33 (d, J=11.2 Hz, 1H), 3.86 (s, 2H), 3.52 (s, 3H), 3.38-3.36 (m, 1H), 2.51-2.49 (m, 1H), 2.28-2.15 (m, 1H), 2.13-2.03 (m, 5H), 1.91-1.76 (m, 4H), 1.38 (s, 3H). LCMS $[M+H]^+$=590.3.

2-(3-((R)-((1s,3S)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=2.266 min) (13.6 mg, 27% yield). $^1$H NMR (400 MHz, methanol-$d_4$) δ 8.38 (s, 1H), 8.09 (s, 1H), 8.01 (s, 1H), 7.85 (s, 1H), 7.77 (d, J=8.0 Hz, 1H), 7.44 (t, J=8.0 Hz, 1H), 7.09 (d, J=7.6 Hz, 1H), 6.29 (t, J=76.0 Hz, 1H), 5.14 (s, 2H), 4.54-4.48 (m, 1H), 4.26 (d, J=10.8 Hz, 1H), 3.86 (s, 2H), 3.51 (s, 3H), 2.91-2.80 (m, 1H), 2.70-2.62 (m, 1H), 2.33-2.22 (m, 1H), 2.14-2.00 (m, 3H), 1.94-1.76 (m, 5H), 1.38 (s, 3H). LCMS $[M+H]^+$=590.3.

The product B was purified by chiral SFC (Column=Daicel Chiralpak IG; Column dimensions=250 mm×30 mm×10 μm; Detection wavelength=220 nM; Flow rate=80 mL/min; Mobile phase: A: $CO_2$ B: ethanol; Isocratic: 48% B with 0.1% ammonium hydroxide) to afford:

2-(3-((S)-((1r,3S)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one. (Peak 1, retention time=3.933 min) (10.4 mg, 21% yield). $^1$H NMR (400 MHz, methanol-$d_4$) δ 8.38 (s, 1H), 8.08 (s, 1H), 8.01 (s, 1H), 7.85 (s, 1H), 7.77 (d, J=7.6 Hz, 1H), 7.44 (t, J=8.0 Hz, 1H), 7.09 (d, J=7.6 Hz, 1H), 6.29 (t, J=76.0 Hz, 1H), 5.14 (s, 2H), 4.51 (t, J=8.0 Hz, 1H), 4.26 (d, J=10.8 Hz, 1H), 3.86 (s, 2H), 3.51 (s, 3H), 2.89-2.81 (m, 1H), 2.67-2.63 (m, 1H), 2.29-2.24 (m, 1H), 2.14-2.02 (m, 3H), 1.92-1.75 (m, 5H), 1.38 (s, 3H). LCMS $[M+H]^+$=590.3.

2-(3-((S)-((1s,3R)-3-(difluoromethoxy)cyclobutyl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=4.838 min) (8.7 mg, 17% yield). $^1$H NMR (400 MHz, methanol-$d_4$) δ 8.38 (s, 1H), 8.09 (s, 1H), 8.01 (s, 1H), 7.89 (s, 1H), 7.77 (d, J=8.4 Hz, 1H), 7.45 (t, J=8.0 Hz, 1H), 7.12 (d, J=8.0 Hz, 1H), 6.30 (t, J=75.6 Hz, 1H), 5.14 (s, 2H), 4.33 (d, J=11.2 Hz, 1H), 3.86 (s, 2H), 3.52 (s, 3H), 2.51-2.49 (m, 1H), 2.27-2.26 (m, 1H), 2.24-2.00 (m, 5H), 1.91-1.76 (m, 4H), 1.38 (s, 3H). LCMS $[M+H]^+$=590.3.

Example 114: Compounds 391, 392

Compound 391 ((S)-2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one; and Compound 392 (R)-2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one), can be synthesized according to the following steps. First intermediate: (3-bromophenyl)(4-methyl-4H-1,2,4-triazol-3-yl)methanone A solution of (3-bromophenyl)(4-methyl-4H-1,2,4-triazol-3-yl)methanol (1.5 g, 5.64 mmol) and 2-iodoxybenzoic acid (3.2 g, 11.27 mmol) in ethyl acetate (50 mL) was stirred at 80° C. for 16 h. After cooled, the solution was filtered and the filtration was concentrated. The residue was purified by silica gel chromatography (mobile phase: methanol/dichloro-methane, gradient 0% to 3%) to afford (3-bromophenyl)(4-methyl-4H-1,2,4-triazol-3-yl)methanone (1.2 g, 80% yield) as a white solid. LCMS $[M+H]^+$=265.8 and 267.8.

Second Intermediate: 1-(3-bromophenyl)-1-(4-methyl-4H-1,2,4-triazol-3-yl)propan-1-ol To a solution of (3-bromophenyl)(4-methyl-4H-1,2,4-triazol-3-yl)methanone (800 mg, 3.01 mmol) in tetrahydrofuran (20 mL) was added ethyl magnesium bromide (3M in diethyl ether, 1.5 mL, 4.5 mmol) at 0° C. The reaction was stirred at 0° C. for 2 h then quenched with saturated ammonium chloride solution (10 mL), extracted with ethyl acetate (2×20 mL). The organic layer was dried with anhydrous sodium sulfate, filtered and concentrated to dryness. The residue was purified by silica gel chromatography (mobile phase: methanol/dichloromethane, gradient 0% to 5%) to give 1-(3-bromophenyl)-1-(4-methyl-4H-1,2,4-triazol-3-yl)propan-1-ol (700 mg, 79% yield) as a white solid. $^1$H NMR (400 MHz, DMSO-$d_6$) δ 8.35 (s, 1H), 7.47-7.44 (m, 2H), 7.30 (t, J=8.0 Hz, 1H), 7.15 (d, J=8.0 Hz, 1H), 6.24 (s, 1H), 3.30 (s, 3H), 2.42-2.21 (m, 2H), 0.75 (t, J=7.2 Hz, 1H). LCMS $[M+H]^+$=295.8 and 297.7.

Compounds 391, 392

To a solution of 1-(3-bromophenyl)-1-(4-methyl-4H-1,2,4-triazol-3-yl)propan-1-ol (200 mg, 0.68 mmol) in 2-methyl-2-butanol (4 mL), was added 6-(((1-methylcyclobutyl)-amino)methyl)-4-(trifluoromethyl)isoindolin-1-one (cf. Scheme 1; 241 mg, 0.81 mmol), copper(I) iodide (51 mg, 0.27 mmol), potassium carbonate (280 mg, 2.03 mmol) and (1 S,2S)—N$^1$,N$^2$-dimethylcyclohexane-1,2-diamine (0.04 mL, 0.27 mmol). The solution was stirred at 100° C. under N$_2$ for 3 h then concentrated. The residue was dissolved with dichloromethane (25 mL), washed with 5% ammonia aqueous (15 mL), brine (15 mL), dried over sodium sulfate, filtered and concentrated to dryness. The residue was purified by preparative TLC (solvent gradient: 10% methanol in dichloromethane) to afford the desired product of 2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one (80 mg, 21% yield).

The above product was purified by chiral SFC (Column=Daicel Chiralcel OD-H; Column dimensions=250 mm×30 mm×5 μm; Detection wavelength=220 nM; Flow rate=80 mL/min; Mobile phase: A: CO$_2$ B: ethanol; Isocratic: 35% B with 0.1% ammonium hydroxide) to afford tentatively assigned:

(S)-2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one (Peak 1, retention time=3.471 min) (16.7 mg, 20% yield). $^1$H NMR (400 MHz, methanol-d$_4$) δ 8.33 (s, 1H), 8.08 (s, 1H), 7.80 (s, 1H), 7.95 (s, 1H), 7.78 (dd, J=1.2, 8.0 Hz, 1H), 7.45 (t, J=8.0 Hz, 1H), 7.14 (d, J=8.0 Hz, 1H), 5.13 (s, 2H), 3.86 (s, 2H), 3.48 (s, 3H), 2.57-2.39 (m, 2H), 2.13-2.06 (m, 2H), 1.91-1.76 (m, 4H), 1.38 (s, 3H), 0.90 (t, J=7.2 Hz, 3H). LCMS [M+H]$^+$=514.2.

(R)-2-(3-(1-hydroxy-1-(4-methyl-4H-1,2,4-triazol-3-yl)propyl)phenyl)-6-(((1-methylcyclobutyl)amino)methyl)-4-(trifluoromethyl)isoindolin-1-one (Peak 2, retention time=3.773 min) (16.0 mg, 20% yield). $^1$H NMR (400 MHz, methanol-d$_4$) δ 8.33 (s, 1H), 8.08 (s, 1H), 8.00 (s, 1H), 7.95 (s, 1H), 7.78 (dd, J=1.2, 7.6 Hz, 1H), 7.45 (t, J=8.0 Hz, 1H), 7.14 (d, J=8.0 Hz, 1H), 5.14 (s, 2H), 3.86 (s, 2H), 3.48 (s, 3H), 2.55-2.39 (m, 2H), 2.13-2.06 (m, 2H), 1.90-1.76 (m, 4H), 1.38 (s, 3H), 0.90 (t, J=7.2 Hz, 3H). LCMS [M+H]$^+$=514.2.

Example 115: Compounds 393, 394

Compound 393 ((S)-2-(3-(1-fluoro-1-(4-methyl-4H-1,2,4-triazol-3-yl)propyl)phenyl)-6-(((1-methylcyclobutyl)amino)methyl)-4-(trifluoromethyl)isoindolin-1-one); and Compound 394 ((R)-2-(3-(1-fluoro-1-(4-methyl-4H-1,2,4-triazol-3-yl)propyl)phenyl)-6-(((1-methylcyclobutyl)amino)methyl)-4-(trifluoromethyl)isoindolin-1-one), can be synthesized according to the following steps.

Intermediate: 3-(1-(3-bromophenyl)-1-fluoropropyl)-4-methyl-4H-1,2,4-triazole

A solution of 1-(3-bromophenyl)-1-(4-methyl-4H-1,2,4-triazol-3-yl)propan-1-ol (cf. Example 114 for a preparative route; 200 mg, 0.68 mmol) and diethylaminosulfur trifluoride (178 uL, 1.35 mmol) in dichloromethane (10 mL) was stirred at 0° C. for 2 h. The reaction mixture was quenched by saturated sodium bicarbonate solution, extracted with ethyl acetate (3×20 mL), combined the organic phase then washed with brine (2×10 mL), dried over sodium sulfate, filtered and concentrated to dryness. The residue was purified by preparative TLC (solvent gradient: 10% methanol in dichloromethane) to afford 3-(1-(3-bromophenyl)-1-fluoropropyl)-4-methyl-4H-1,2,4-triazole (130 mg, 65% yield) as a white solid. LCMS [M+H]$^+$=297.9 and 300.0.

Compounds 393, 394

To a solution of 3-(1-(3-bromophenyl)-1-fluoropropyl)-4-methyl-4H-1,2,4-triazole (130 mg, 0.44 mmol) in tert-amyl alcohol (4 mL) was added 6-(((1-methylcyclobutyl)amino)methyl)-4-(trifluoromethyl)isoindolin-1-one (cf. Scheme 1; 156 mg, 0.52 mmol), copper(I) iodide (33 mg, 0.17 mmol), potassium carbonate (180 mg, 1.31 mmol) and (1 S,2S)—N$^1$,N$^2$-dimethylcyclohexane-1,2-diamine (24 mg, 0.17 mmol). The reaction was stirred at 100° C. under N$_2$ for 3 h then concentrated. The residue was dissolved with dichloromethane (30 mL), washed with brine (2×25 mL), dried over sodium sulfate, filtered and concentrated to dryness. The residue was purified by preparative TLC (solvent gradient: 10% methanol in dichloromethane) to afford 2-(3-(1-fluoro-1-(4-methyl-4H-1,2,4-triazol-3-yl)propyl)phenyl)-6-(((1-methylcyclobutyl)amino)methyl)-4-(trifluoromethyl)-isoindolin-1-one (60 mg, 27% yield).

The above mixture was further purified by chiral SFC (Column=Daicel Chiralpak IG; Column dimensions=250 mm×30 mm×10 μm; Detection wavelength=220 nM; Flow rate=80 mL/min; Mobile phase: A: CO$_2$; B: ethanol; Isocratic: 45% B with 0.1% ammonium hydroxide) to afford tentatively assigned:

(S)-2-(3-(1-fluoro-1-(4-methyl-4H-1,2,4-triazol-3-yl)propyl)phenyl)-6-(((1-methylcyclobutyl)amino)methyl)-4-(trifluoromethyl)isoindolin-1-one (Peak 1, retention time=3.911 min) (23.4 mg, 39% yield). $^1$H NMR (400 MHz, methanol-d$_4$) δ 8.45 (s, 1H), 8.08 (s, 1H), 8.01 (s, 1H), 8.00 (s, 1H), 7.80 (dd, J=1.2, 8.0 Hz, 1H), 7.53 (t, J=8.0 Hz, 1H), 7.11 (d, J=8.0 Hz, 1H), 5.16 (s, 2H), 3.86 (s, 2H), 3.51 (d, J=1.6 Hz, 3H), 2.79-2.46 (m, 2H), 2.14-2.06 (m, 2H), 1.91-1.77 (m, 4H), 1.38 (s, 3H), 1.03 (t, J=7.2 Hz, 3H). LCMS [M+Na]$^+$=538.2.

(R)-2-(3-(1-fluoro-1-(4-methyl-4H-1,2,4-triazol-3-yl)propyl)phenyl)-6-(((1-methylcyclobutyl)amino)methyl)-4-(trifluoromethyl)isoindolin-1-one (Peak 2, retention time=4.393 min) (21.1 mg, 35% yield). $^1$H NMR (400 MHz, methanol-d$_4$) δ 8.45 (s, 1H), 8.08 (s, 1H), 8.01 (s, 1H), 8.00 (s, 1H), 7.80 (dd, J=1.2, 8.0 Hz, 1H), 7.53 (t, J=7.6 Hz, 1H), 7.11 (d, J=8.4 Hz, 1H), 5.16 (s, 2H), 3.86 (s, 2H), 3.50 (d, J=1.2 Hz, 3H), 2.78-2.46 (m, 2H), 2.14-2.07 (m, 2H), 1.91-1.77 (m, 4H), 1.38 (s, 3H), 1.03 (t, J=7.6 Hz, 3H). LCMS [M+Na]$^+$=538.3.

Example 116: Compounds 395, 396, 397, 398

Compound 395 (2-(3-((R)-(4-methyl-4H-1,2,4-triazol-3-yl)((1r,3R)-3-(trifluoromethoxy)cyclobutyl)methyl)phenyl)-6-(((1-methylcyclobutyl)amino)methyl)-4-(trifluoromethyl)isoindolin-1-one), Compound 396 (2-(3-((S)-(4-methyl-4H-1,2,4-triazol-3-yl)((1s,3R)-3-(trifluoromethoxy)cyclobutyl)methyl)phenyl)-6-(((1-methylcyclobutyl)amino)methyl)-4-(trifluoromethyl)isoindolin-1-one), Compound 397 (2-(3-((S)-(4-methyl-4H-1,2,4-triazol-3-yl)((1r,3S)-3-(trifluoromethoxy)cyclobutyl)methyl)phenyl)-6-(((1-methylcyclobutyl)amino)methyl)-4-(trifluoromethyl)isoindolin-1-one), and Compound 398 (2-(3-((R)-(4-methyl-4H-1,2,4-triazol-3-yl)((1s,3S)-3-(trifluoromethoxy)cyclobutyl)methyl)phenyl)-6-(((1-methylcyclobutyl)amino)methyl)-4-(trifluoromethyl)isoindolin-1-one), can be synthesized according to the following steps.

Intermediate: 3-((3-bromophenyl)(3-(trifluoromethoxy)cyclobutyl)methyl)-4-methyl-4H-1,2,4-triazole To a solution of 3-(3-bromophenyl)-3-(4-methyl-4H-1,2,4-triazol-3-yl)cyclobutan-1-ol (such as may be obtained from the first starting material in Scheme 62; 300 mg, 1 mmol) in ethyl acetate (6 mL) was added silver(I) trifluoromethanesulfonate (957 mg, 3.7 mmol), 1-(chloromethyl)-4-fluoro-1,4-diazabicyclo[2.2.2]octane-1,4-diium tetrafluoroborate (Selectfluor™; 495 mg, 1.4 mmol), fluoropotassium (216 mg, 3.7 mmol), 2-fluoropyridine (0.32 mL, 3.7 mmol) and trimethyl(trifluoromethyl)silane (331 mg, 2.3 mmol) at room temperature. The reaction mixture was stirred at 50° C. for 24 h then diluted with ethyl acetate (100 mL) and filtered. The filtrate was washed with brine (3×50 mL), dried over sodium sulfate, filtered and concentrated to dryness. The crude was purified by silica gel chromatography (mobile phase: methyl alcohol/dichloromethane, gradient 0% to 5%) to give 3-((3-bromophenyl) (3-(trifluoromethoxy)cyclobutyl)methyl)-4-methyl-4H-1,2,4-triazole (350 mg, 96% yield) as a yellow oil. LCMS [M+H]$^+$=390.0 and 392.0.

Compounds 395, 396, 397, 398

To a solution of 3-((3-bromophenyl)(3-(trifluoromethoxy) cyclobutyl)methyl)-4-methyl-4H-1,2,4-triazole (Intermediate 2; 350 mg, 0.9 mmol) in tert-amyl alcohol (6 mL) was added 6-(((1-methylcyclobutyl)amino)methyl)-4-(trifluoromethyl)isoindolin-1-one (cf. Scheme 1; 321 mg, 1.1 mmol), copper(I) iodide (68 mg, 0.36 mmol), (1S,2S)—N$^1$, N$^2$-dimethyl-cyclohexane-1,2-diamine (51 mg, 0.36 mmol), potassium carbonate (372 mg, 2.7 mmol). The solution was stirred at 100° C. for 4 hr under N$_2$ then concentrated, the residue was dissolved with dichloromethane (30 mL), washed with 5% ammonia aqueous (15 mL) and brine (15 mL), dried over sodium sulfate, filtered and concentrated, the residue was purified by RP-HPLC (0.05% FA in water/ ACN 19% to 49%) to afford 2-(3-((4-methyl-4H-1,2,4-triazol-3-yl)(3-(trifluoromethoxy)cyclobutyl)methyl)phenyl)-6-(((1-methylcyclobutyl)-amino)methyl)-4-(trifluoromethyl)isoindolin-1-one. LCMS [M+Na]$^+$=630.2.

The above mixture was further purified by chiral SFC (Column=Daicel Chiralpak IG; Column dimensions=250 mm×30 mm×10 µm; Detection wavelength=220 nM; Flow rate=80 mL/min; Mobile phase: A: CO$_2$ B: ethanol; Isocratic: 40% B with Neu-ethanol) to afford product A and product B.

Product A was assigned as 2-(3-((R)-(4-methyl-4H-1,2,4-triazol-3-yl)((1r,3R)-3-(trifluoromethoxy)cyclobutyl) methyl)phenyl)-6-(((1-methylcyclobutyl)amino)methyl)-4-(trifluoromethyl)isoindolin-1-one (peak 1, retention time=3.113 min) (32 mg, 16% yield) as a white solid. $^1$H NMR (400 MHz, methanol-d$_4$) δ 8.38 (s, 1H), 8.19 (m, 1H), 8.01 (s, 1H), 7.85 (s, 1H), 7.81-7.75 (m, 1H), 7.45 (t, J=8.0 Hz, 1H), 7.12-7.07 (m, 1H), 5.14 (s, 2H), 4.71-4.63 (m, 1H), 4.33-4.26 (m, 1H), 3.87 (m, 2H), 3.50 (s, 3H), 2.95-2.82 (m, 1H), 2.78-2.65 (m, 1H), 2.38-2.26 (m, 1H), 2.19-2.06 (m, 1H), 2.05-1.95 (m, 1H), 1.94-1.85 (m, 2H), 1.84-1.74 (m, 2H), 1.41-1.36 (m, 3H). LCMS [M+Na]$^+$=630.2.

Product B was further purified by chiral SFC (Column=Daicel Chiralpak IG; Column dimensions=250 mm×30 mm×10 µm; Detection wavelength=220 nM; Flow rate=80 mL/min; Mobile phase: A: CO$_2$ B: IPA; Isocratic: 40% B with Neu-IPA) to afford product C and product D:

Product D was assigned as 2-(3-((S)-(4-methyl-4H-1,2,4-triazol-3-yl)((1s,3R)-3-(trifluoromethoxy)cyclobutyl) methyl)phenyl)-6-(((1-methylcyclobutyl)amino)methyl)-4-(trifluoromethyl)isoindolin-1-one (peak 4, retention time=4.845 min) (30 mg, 15% yield) as a white solid. $^1$H NMR (400 MHz, methanol-d$_4$) δ 8.37 (s, 1H), 8.09 (s, 1H), 8.01 (s, 1H), 7.90 (s, 1H), 7.81-7.75 (m, 1H), 7.45 (t, J=8.0 Hz, 1H), 7.14-7.09 (m, 1H), 5.15 (s, 2H), 4.33-4.38 (m, 1H), 3.86 (s, 2H), 3.52 (s, 3H), 2.66-2.55 (m, 1H), 2.39-2.27 (m, 2H), 2.25-2.04 (m, 4H), 1.98-1.67 (m, 5H), 1.38 (s, 3H). LCMS [M+Na]$^+$=630.2.

Product C was further purified by chiral SFC (Column=Daicel Chiralpak IG; Column dimensions=250 mm×30 mm×10 µm; Detection wavelength=220 nM; Flow rate=80 mL/min; Mobile phase: A: hexane B: ethanol; Isocratic: 40% B with 0.1% ammonium hydroxide) to afford tentatively assigned:

2-(3-((R)-(4-methyl-4H-1,2,4-triazol-3-yl)((1s,3S)-3-(trifluoromethoxy)cyclobutyl)methyl)phenyl)-6-(((1-methylcyclobutyl)amino)methyl)-4-(trifluoromethyl)isoindolin-1-one (peak 2, retention time=3.194 min) (23 mg, 12% yield). $^1$H NMR (400 MHz, methanol-d$_4$) δ 8.37 (s, 1H), 8.9 (s, 1H), 8.00 (s, 1H), 7.90-7.89 (m, 1H), 7.80-7.75 (m, 1H), 7.45 (t, J=8.0 Hz, 1H), 7.12 (d, J=8.0 Hz, 1H), 5.15 (s, 2H), 4.99-4.95 (m, 1H), 4.36 (d, J=11.6 Hz 1H), 3.87 (s, 2H), 3.52 (s, 3H), 2.66-2.54 (m, 1H), 2.40-2.00 (m, 6H), 1.94-1.84 (m, 2H), 1.84-1.73 (m, 2H), 1.38 (s, 3H). LCMS [M+H]$^+$=608.3.

2-(3-((S)-(4-methyl-4H-1,2,4-triazol-3-yl)((1r,3S)-3-(trifluoromethoxy)-cyclobutyl)methyl)phenyl)-6-(((1-methylcyclobutyl)amino)methyl)-4-(trifluoro-methyl)isoindolin-1-one (peak 3, retention time=2.818 min) (18 mg, 9% yield). $^1$H NMR (400 MHz, methanol-d$_4$) δ 8.38 (s, 1H), 8.09 (s, 1H), 8.00 (s, 1H), 7.80 (s, 1H), 7.81-7.75 (m, 1H), 7.45 (t, J=8.0 Hz, 1H), 7.09 (d, J=7.6 Hz, 1H), 5.14 (s, 2H), 4.70-4.63 (m, 1H), 4.29 (d, J=12.0 Hz, 1H), 3.87 (s, 2H), 3.50 (s, 3H), 2.95-2.80 (m, 1H), 2.76-2.66 (m, 1H), 2.36-2.28 (m, 1H), 2.19-2.07 (m, 3H), 2.06-1.98 (m, 1H), 1.92-1.85 (m, 2H), 1.83-1.74 (m, 2H), 1.38 (s, 3H). LCMS [M+H]$^+$=608.3.

Example 117: Compounds 399, 400

Compound 399 ((R)—N-methyl-N-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)acetamide), Compound 400 (S)—N-methyl-N-((4-methyl-4H-1,2,4-triazol-3-yl)(3-(6-(((1-methylcyclobutyl)amino)methyl)-1-oxo-4-(trifluoromethyl)isoindolin-2-yl)phenyl)-methyl)acetamide), can be synthesized according to Scheme 107 (FIG. 107).

Intermediate 2: 3-(bromo(3-bromophenyl)methyl)-4-methyl-4H-1,2,4-triazole

To a solution of (3-bromophenyl)(4-methyl-4H-1,2,4-triazol-3-yl)methanol (cf. Scheme 5; 600 mg, 2.24 mmol) in dichloromethane (10 mL) was added tribromophosphane (0.07 mL, 0.74 mmol) at 0° C. The reaction mixture was stirred at 25° C. for 2 h then concentrated to give 3-(bromo (3-bromophenyl)methyl)-4-methyl-4H-1,2,4-triazole (700 mg, 94% yield) as a yellow solid which was used directly for next step without further purification. LCMS [M+H]$^+$= 331.9.

Intermediate 3: 1-(3-bromophenyl)-N-methyl-1-(4-methyl-4H-1,2,4-triazol-3-yl)methanamine To a mixture of 3-(bromo(3-bromophenyl)methyl)-4-methyl-4H-1,2,4-triazole (500.0 mg, 1.51 mmol) in tetrahydrofuran (5 mL) was added monomethylamine (2 M in ethanol, 2 mL, 4.0 mmol) at 25° C. The reaction mixture was stirred at 25° C. for 3 h then concentrated to give 1-(3-bromophenyl)-N-methyl-1-(4-methyl-4H-1,2,4-triazol-3-yl)

methanamine (400 mg, 94% yield) as a green oil which was used directly for next step. LCMS [M+H]⁺=281.1 and 283.1.

Intermediate 4: N-((3-bromophenyl)(4-methyl-4H-1,2,4-triazol-3-yl)methyl)-N-methylacetamide To the mixture of 1-(3-bromophenyl)-N-methyl-1-(4-methyl-4H-1,2,4-triazol-3-yl)methanamine (400.0 mg, 1.42 mmol) in saturated potassium carbonate solution (2.0 mL) and tetrahydrofuran (6 mL) was added acetyl chloride (0.19 mL, 2.13 mmol) at 0° C. The reaction mixture was stirred at 25° C. for 1 h then diluted with ethyl acetate (50 mL), washed with brine (3×20 mL), dried over sodium sulfate, filtered and concentrated to dryness. The residue was purified by silica gel chromatography (mobile phase: methanol/dichloro-methane, gradient 0% to 5%) to afford N-[(3-bromophenyl)-(4-methyl-1,2,4-triazol-3-yl)methyl]-N-methyl-acetamide (60 mg, 13% yield) as a yellow solid. $^1$H NMR (400 MHz, methanol-$d_4$) δ 8.53 (s, 1H), 7.57 (d, J=8.4 Hz, 1H), 7.46 (s, 1H), 7.36 (t, J=8.0 Hz, 1H), 7.27-7.23 (m, 1H), 7.21 (s, 1H), 3.64 (s, 3H), 2.96 (s, 3H), 2.25 (s, 3H). LCMS [M+H]⁺=322.9 and 324.7.

Compounds 399, 400

A mixture of 3-(3-bromophenyl)-3-(4-methyl-4H-1,2,4-triazol-3-yl)thietane 1-oxide (60.0 mg, 0.18 mmol), 6-(((1-methylcyclobutyl)amino)methyl)-4-(trifluoromethyl)isoindolin-1-one (cf. Scheme 1; 55.2 mg, 0.18 mmol), copper(I) iodide (14.1 mg, 0.07 mmol), (1S,2S)—N$^1$,N$^2$-dimethylcyclohexane-1,2-diamine (10.6 mg, 0.07 mmol) and potassium carbonate (51.3 mg, 0.36 mmol) in tert-amyl alcohol (3 mL) was stirred at 100° C. for 10 h under N$_2$ and concentrated. The residue was dissolved with dichloromethane ("DCM"; 25 mL) and washed with brine (25 mL), dried over sodium sulfate, filtered and concentrated to dryness. The residue was purified by preparative TLC (solvent gradient: 10% methanol in DCM) to afford N-methyl-N-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)acetamide (60.0 mg, 59% yield).

The above product was further purified by chiral SFC (Column=Daicel Chiralpak AD; Column dimensions=250 mm×30 mm×10 μm; Detection wavelength=220 nM; Flow rate=80 mL/min; Mobile phase: A: CO$_2$ B: ethanol; Isocratic: 55% B with 0.1% ammonium hydroxide) to afford tentatively assigned:

(R)—N-methyl-N-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)acetamide (Peak 1, Retention time=2.665 min) (15.4 mg, 25% yield). $^1$H NMR (400 MHz, DMSO-$d_6$) δ 8.55 (s, 1H), 8.06 (s, 1H), 8.00 (s, 1H), 7.93 (s, 1H), 7.81 (d, J=6.8 Hz, 1H), 7.47 (t, J=8.0 Hz, 1H), 7.14 (s, 1H), 7.07 (d, J=7.2 Hz, 1H), 5.18 (s, 2H), 3.82 (s, 2H), 3.55 (s, 3H), 2.89 (s, 3H), 2.15 (s, 3H), 2.02-1.96 (m, 2H), 1.74-1.64 (m, 4H), 1.23 (s, 3H). LCMS [M+H]⁺=541.3.

(S)—N-methyl-N-((4-methyl-4H-1,2,4-triazol-3-yl)(3-(6-(((1-methylcyclobutyl)amino)-methyl)-1-oxo-4-(trifluoromethyl)isoindolin-2-yl)phenyl)methyl)acetamide (Peak 2, Retention time=2.642 min) (21.9 mg, 32% yield). $^1$H NMR (400 MHz, DMSO-$d_6$) δ 8.55 (s, 1H), 8.06 (s, 1H), 8.00 (s, 1H), 7.93 (s, 1H), 7.81 (d, J=6.8 Hz, 1H), 7.54-7.43 (m, 1H), 7.14 (s, 1H), 7.07 (d, J=7.6 Hz, 1H), 5.17 (s, 2H), 3.82 (s, 2H), 3.55 (s, 3H), 2.89 (s, 3H), 2.15 (s, 3H), 2.03-1.93 (m, 2H), 1.75-1.64 (m, 4H), 1.23 (s, 3H). LCMS [M+H]⁺=541.3.

Example 118: Compounds 401, 402

Figure 108:
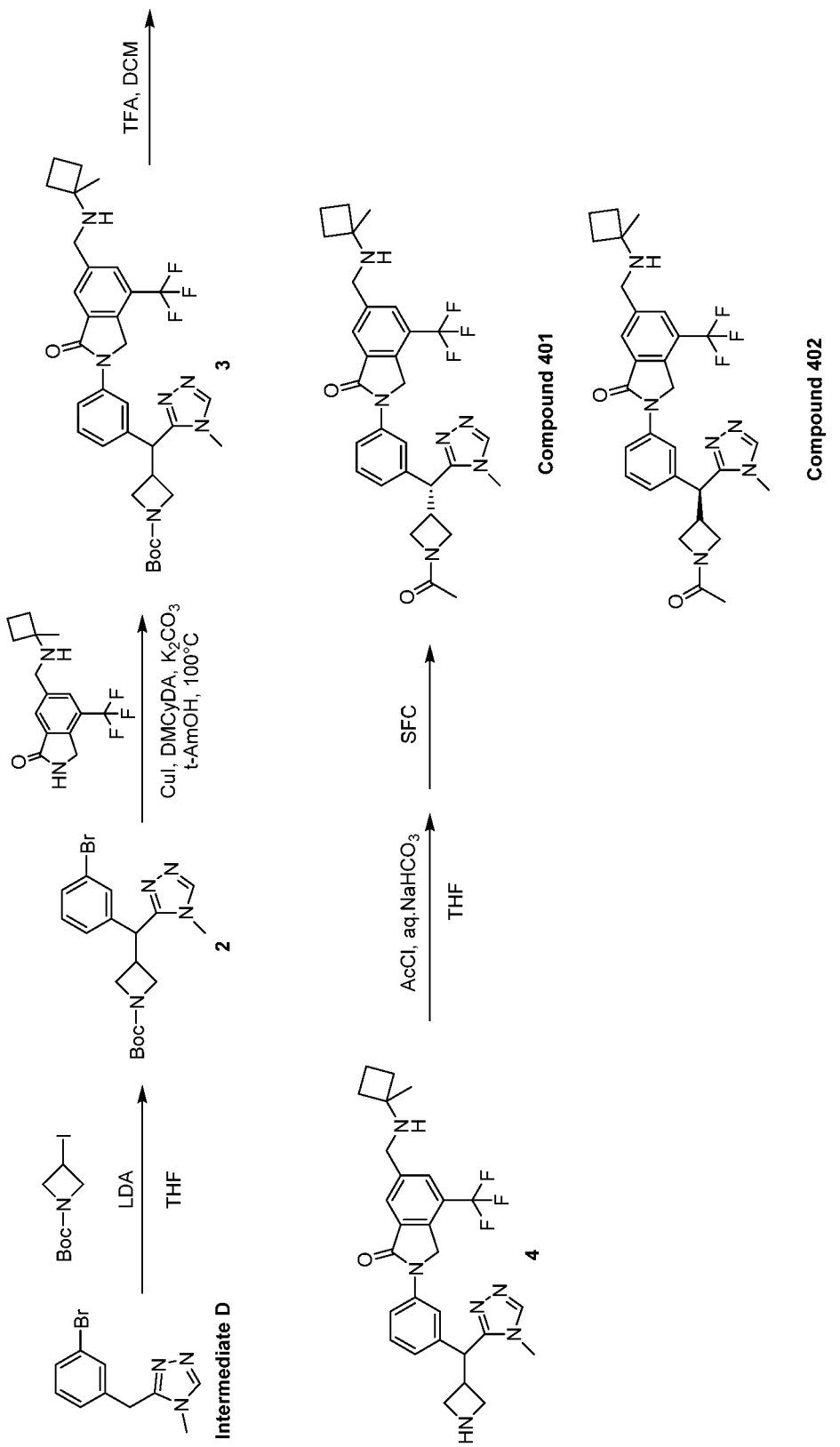

Compound 401 ((R)-2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one), Compound 402 (S)-2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 108 (FIG. 108).

Intermediate 2: tert-butyl 3-((3-bromophenyl)(4-methyl-4H-1,2,4-triazol-3-yl)methyl)azetidine-1-carboxylate To a mixture of 3-(3-bromobenzyl)-4-methyl-4H-1,2,4-triazole (Intermediate D; 500.0 mg, 1.98 mmol) in N,N-dimethylformamide (7 mL) was added sodium hydride (60%, 87.3 mg, 2.18 mmol) at 0° C., the mixture was stirred at 0° C. for 30 min. Then tert-butyl 3-iodoazetidine-1-carboxylate (673.4 mg, 2.38 mmol) was added and the resulting mixture was stirred at 60° C. for another 2 h. Quenched by addition of water (20 mL) and extracted with ethyl acetate (3×20 mL), the combined organic layers were washed with brine (20 mL), dried over sodium sulfate, filtered and concentrated to dryness. The residue was purified by silica gel chromatography (mobile phase: methanol/dichloromethane, gradient 0% to 0.5%) to afford tert-butyl 3-((3-bromophenyl)(4-methyl-4H-1,2,4-triazol-3-yl)methyl)azetidine-1-carboxylate (370 mg, 43% yield) as a yellow oil which was used for next step directly. LCMS [M+H]⁺=407.1.

Intermediate 3: tert-butyl 3-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)azetidine-1-carboxylate A mixture of 3-((3-bromophenyl)(4-methyl-4H-1,2,4-triazol-3-yl)methyl)azetidine-1-carboxylate (180 mg, 0.44 mmol), 6-(((1-methylcyclobutyl)amino)methyl)-4-(trifluoromethyl)isoindolin-1-one (cf. Scheme 1; 158 mg, 0.53 mmol), (1S,2S)—N$^1$,N$^2$-dimethylcyclohexane-1,2-diamine (67 mg, 0.46 mmol), potassium carbonate (208 mg, 1.5 mmol) and copper(I) iodide (86 mg, 0.46 mmol) in tert-amyl alcohol (4 mL) was heated at 100° C. for 2 h under nitrogen atmosphere and concentrated to dryness. The residue was purified by silica gel chromatography (mobile phase: methanol/dichloromethane, gradient 0% to 1%) to afford tert-butyl 3-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)azetidine-1-carboxylate (160.0 mg, 58% yield) as a white solid. LCMS [M+H]⁺=625.7.

Intermediate 4: 2-(3-(azetidin-3-yl(4-methyl-4H-1,2,4-triazol-3-yl)methyl)phenyl)-6-(((1-methylcyclobutyl)amino)methyl)-4-(trifluoromethyl)isoindolin-1-one To a solution of tert-butyl 3-((4-methyl-4H-1,2,4-triazol-3-yl)(3-(6-(((1-methylcyclobutyl)amino)methyl)-1-oxo-4-(trifluoromethyl)isoindolin-2-yl)phenyl)methyl)azetidine-1-carboxylate (Intermediate 3; 100.0 mg, 0.16 mmol) in dichloromethane (1 mL) was added trifluoroacetic acid (0.5 mL, 0.49 mmol). The mixture was stirred at 25° C. for 2 h and concentrated to give 2-(3-(azetidin-3-yl(4-methyl-4H-1,2,4-triazol-3-yl)methyl)phenyl)-6-(((1-methylcyclobutyl)amino)methyl)-4-(trifluoromethyl)isoindolin-1-one trifluoroacetate (120.0 mg, 0.16 mmol) as a yellow oil. LCMS [M+H]⁺=525.0.

Compounds 401, 402

To a solution of 2-(3-(azetidin-3-yl(4-methyl-4H-1,2,4-triazol-3-yl)methyl)phenyl)-6-(((1-methylcyclobutyl)amino)methyl)-4-(trifluoromethyl)isoindolin-1-one trifluoroacetate (120.0 mg, 0.16 mmol) in tetrahydrofuran (3 mL) was added triethylamine (0.1 mL, 0.64 mmol) and acetic anhydride (0.02 mL, 0.19 mmol) at 25° C. The mixture was stirred at 25° C. for 5 h then concentrated. The residue was purified by silica gel chromatography (mobile phase: methanol/dichloromethane, gradient 0% to 9%) to afford 2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one (50.0 mg, 55% yield) as a yellow oil. LCMS [M+H]$^+$=567.3.

The above product was further purified by chiral SFC (Column=Daicel Chiralcel OD-H; Column dimensions=250 mm×30 mm×5 μm; Detection wavelength=220 nM; Flow rate=80 mL/min; Mobile phase: A: $CO_2$ B: ethanol; Isocratic: 40% B with 0.1% ammonium hydroxide) to afford tentatively assigned:

(R)-2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=3.837 min) (4.7 mg, 9% yield). $^1$H NMR (400 MHz, methanol-$d_4$) δ 8.40 (s, 1H), 8.09 (s, 1H), 8.01 (s, 1H), 7.93 (d, J=6.8 Hz, 1H), 7.83-7.80 (m, 1H), 7.48 (t, J=7.6 Hz, 1H), 7.13 (d, J=7.6 Hz, 1H), 5.15 (s, 2H), 4.62-4.58 (m, 2H), 4.50-4.23 (m, 1H), 4.19-4.09 (m, 1H), 3.95-3.89 (m, 1H), 3.86 (s, 2H), 3.71-3.63 (m, 1H), 3.50 (s, 3H), 2.14-2.07 (m, 2H), 1.90-1.88 (m, 2H), 1.85 (d, J=3.2 Hz, 3H), 1.81-1.75 (m, 2H), 1.38 (s, 3H). LCMS [M+H]$^+$=567.3.

(S)-2-(3-((1-acetylazetidin-3-yl)(4-methyl-4H-1,2,4-triazol-3-yl)methyl)phenyl)-6-(((1-methylcyclobutyl)amino)methyl)-4-(trifluoromethyl)isoindolin-1-one (Peak 2, retention time=3.844 min) (4.8 mg, 10% yield). $^1$H NMR (400 MHz, methanol-$d_4$) δ 8.41 (s, 1H), 8.09 (s, 1H), 8.01 (s, 1H), 7.93 (d, J=7.6 Hz, 1H), 7.81-7.78 (m, 1H), 7.48 (t, J=8.0 Hz, 1H), 7.15 (d, J=7.6 Hz, 1H), 5.15 (s, 2H), 4.50-4.58 (m, 2H), 4.27-4.23 (m, 1H), 4.19-4.12 (m, 1H), 3.95-3.91 (m, 1H), 3.87 (s, 2H), 3.69-3.64 (m, 1H), 3.50 (s, 3H), 2.14-2.06 (m, 2H), 1.91-1.88 (m, 2H), 1.85 (d, J=3.6 Hz, 3H), 1.81-1.76 (m, 2H), 1.38 (s, 3H). LCMS [M+H]$^+$=567.2.

Example 119: Compounds 403, 404

Figure 109:
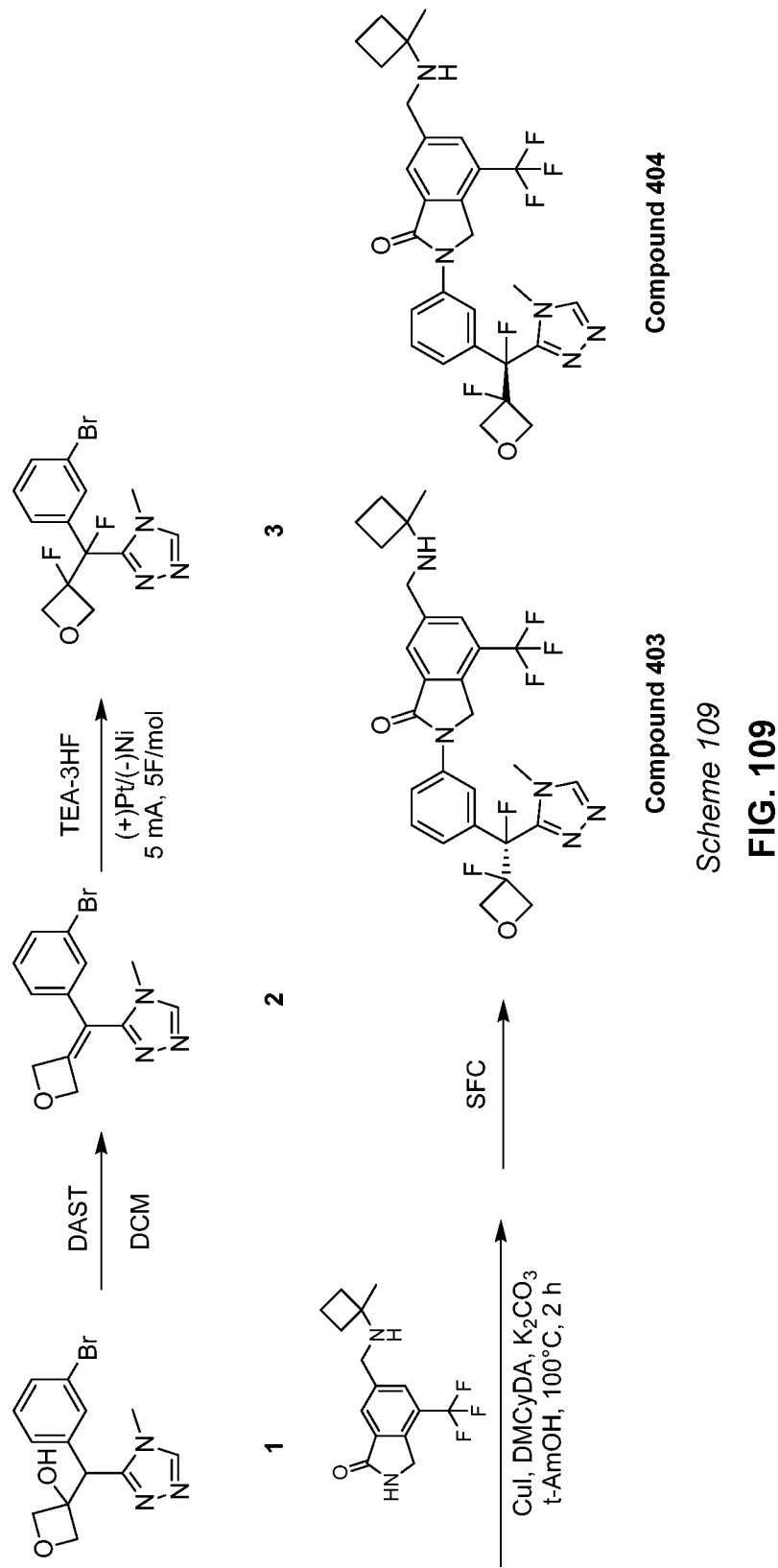

Compound 403 ((S)-2-(3-(fluoro(3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one, Compound 404 ((R)-2-(3-(fluoro(3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one), can be synthesized according to Scheme 109 (FIG. 109).

Intermediate 2: 3-((3-bromophenyl)(oxetan-3-ylidene)methyl)-4-methyl-4H-1,2,4-triazole To a solution of 3-((3-bromophenyl)(4-methyl-4H-1,2,4-triazol-3-yl)methyl)oxetan-3-ol (Intermediate 1, 500.0 mg, 1.5 mmol) in dichloromethane (10 mL) was added diethylaminosulphur trifluoride (0.3 mL, 2.3 mmol) at 0° C., the mixture was stirred at 0° C. for 2 h then quenched with water (10 mL), extracted with dichloromethane (3×20 mL). The combined organic layers were washed with brine (20 mL), dried over sodium sulfate, filtered and concentrated to dryness. The crude was purified by silica gel chromatography (mobile phase: methanol/dichloromethane, gradient 0% to 10%) to afford 3-((3-bromophenyl)(oxetan-3-ylidene)methyl)-4-methyl-4H-1,2,4-triazole (400 mg, 85% yield) as a white solid. $^1$H NMR (400 MHz, methanol-$d_4$) δ 8.53 (s, 1H), 7.54 (d, J=8.0 Hz, 1H), 7.37 (t, J=8.0 Hz, 1H), 7.22 (t, J=1.6 Hz, 1H), 7.08 (d, J=8.0 Hz, 1H), 5.65-5.59 (m, 2H), 5.41-5.35 (m, 2H). LCMS [M+H]$^+$=306.0 and 308.0.

Intermediate 3: 3-((3-bromophenyl)fluoro(3-fluorooxetan-3-yl)methyl)-4-methyl-4H-1,2,4-triazole The reaction was performed in an IKA ElectraSym 2.0 using an IKA Ni electrode as a cathode and Pt as an anode. A 10 mL IKA ElectraSym 2.0 vial was equipped with a stir bar and charged with 3-((3-bromophenyl)(oxetan-3-ylidene)methyl)-4-methyl-4H-1,2,4-triazole (Intermediate 2, 200.0 mg, 0.6 mmol) and triethylamine trihydrofluoride ("TEA-3HF", 4 mL, 24.5 mmol). The electrolysis was initiated with a constant current of 5 mA and 800 rpm stirring speed. After 5 F/mol of charge had been passed, the reaction mixture was diluted with dichloromethane (15 mL), washed with saturated sodium bicarbonate solution (3×10 mL), dried over sodium sulfate, filtered and concentrated to dryness. The residue was purified by silica gel chromatography (mobile phase: methanol/dichloromethane, gradient 0% to 10%) to afford 3-((3-bromophenyl)fluoro(3-fluorooxetan-3-yl)methyl)-4-methyl-4H-1,2,4-triazole (140 mg, 62% yield) as a yellow solid. $^1$H NMR (400 MHz, $CDCl_3$) δ 8.19-8.14 (m, 1H), 7.63 (d, J=7.6 Hz, 1H), 7.58-7.53 (m, 1H), 7.37-7.31 (m, 1H), 7.26 (s, 1H), 5.25-5.00 (m, 3H), 4.80-4.62 (m, 1H), 3.42-3.30 (m, 3H). LCMS [M+H]$^+$=344.0 and 346.0.

Compounds 403, 404

A mixture of 6-(((1-methylcyclobutyl)amino)methyl)-4-(trifluoromethyl)isoindolin-1-one (133.8 mg, 0.5 mmol), 3-((3-bromophenyl)fluoro(3-fluorooxetan-3-yl)methyl)-4-methyl-4H-1,2,4-triazole (cf. Scheme 1; 140.0 mg, 0.4 mmol), (1S,2S)—$N^1$,$N^2$-dimethylcyclohexane-1,2-diamine ("DMCyDA", 140.0 mg, 0.4 mmol), potassium carbonate (168.7 mg, 1.2 mmol) and copper(I) iodide (31.0 mg, 0.2 mmol) in tert-amyl alcohol (4 mL) was stirred at 100° C. for 2 h under nitrogen then concentrated. The residue was dissolved with dichloromethane (20 mL), washed with 5% ammonia aqueous (3×10 mL), dried over sodium sulfate, filtered and concentrated to dryness. The residue was purified by RP-HPLC (water($NH_3H_2O+NH_4HCO_3$)-ACN 35% to 65%) to afford 2-(3-(fluoro(3-fluorooxetan-3-yl)(4-methyl-4H-1,2,4-triazol-3-yl)methyl)phenyl)-6-(((1-methylcyclobutyl)amino)methyl)-4-(trifluoromethyl)-isoindolin-1-one (40 mg, 21% yield)

The above mixture was further purified by chiral SFC (Column=Daicel Chiralpak AD; Column dimensions=250 mm×30 mm×10 μm; Detection wavelength=220 nM; Flow rate=70 mL/min; Mobile phase: A: $CO_2$ B: ethanol; Isocratic: 25% B with 0.1% ammonium hydroxide) to afford tentatively assigned:

(S)-2-(3-(fluoro(3-fluorooxetan-3-yl)(4-methyl-4H-1,2,4-triazol-3-yl)methyl)phenyl)-6-(((1-methylcyclobutyl)amino)methyl)-4-(trifluoromethyl)isoindolin-1-one (Peak 1, retention time=1.501 min) (11.6 mg, 29% yield). $^1$H NMR (400 MHz, methanol-$d_4$) δ 8.55 (s, 1H), 8.18 (s, 1H), 8.08 (s, 1H), 8.02 (s, 1H), 7.86 (dd, J=1.6, 8.4 Hz, 1H), 7.60 (t, J=8.0 Hz, 1H), 7.16 (d, J=7.6 Hz, 1H), 5.24-5.15 (m, 3H), 5.11-5.03 (m, 2H), 4.72-4.68 (m, 1H), 3.86 (s, 2H), 3.39 (s, 3H), 2.14-2.06 (m, 2H), 1.91-1.85 (m, 2H), 1.85-1.76 (m, 2H), 1.38 (s, 3H). LCMS [M+H]$^+$=562.3.

(R)-2-(3-(fluoro(3-fluorooxetan-3-yl)(4-methyl-4H-1,2,4-triazol-3-yl)methyl)phenyl)-6-(((1-methylcyclobutyl)

amino)methyl)-4-(trifluoromethyl)isoindolin-1-one (Peak 2, retention time=1.661 min) (11.3 mg, 28% yield). $^1$H NMR (400 MHz, methanol-$d_4$) δ 8.55 (s, 1H), 8.18 (s, 1H), 8.09 (s, 1H), 8.02 (s, 1H), 7.86 (dd, J=2.0, 8.4 Hz, 1H), 7.60 (t, J=8.4 Hz, 1H), 7.16 (d, J=8.0 Hz, 1H), 5.19-5.18 (m, 3H), 5.10-5.04 (m, 2H), 4.71-4.68 (m, 1H), 3.86 (s, 2H), 3.39 (s, 3H), 2.14-2.07 (m, 2H), 1.92-1.86 (m, 2H), 1.83-1.76 (m, 2H), 1.38 (s, 3H). LCMS [M+H]$^+$=562.3.

Additional iso-indolinone compounds can be synthesized according to the methods described herein.

Example 120: Quantitative Data for Isoindolinone Compounds

Quantitative data for examples of iso-indolone compounds according to Formula (I) are shown in Table 2.

TABLE 2

| Compound # | $^1$H NMR | LCMS$^a$ |
|---|---|---|
| 44 | $^1$H NMR (400 MHz, DMSO-d6) δ 8.45 (s, 1H), 8.06 (d, J = 4.8 Hz, 2H), 8.00 (s, 1H), 7.82 (d, J = 8.0 Hz, 1H), 7.48 (t, J = 8.0 Hz, 1H), 7.20 (d, J = 7.6 Hz, 1H), 5.94 (s, 1H), 5.18 (s, 2H), 3.83 (s, 2H), 3.57 (s, 3H), 3.40-3.36 (m, 1H), 2.03-1.92 (m, 2H), 1.79-1.61 (m, 4H), 1.24 (s, 3H), 0.73-0.65 (m, 1H), 0.64-0.57 (m, 1H), 0.55-0.42 (m, 2H). | 526.3 |
| 45 | $^1$H NMR (400 MHz, DMSO-d6) δ 8.45 (s, 1H), 8.06 (s, 2H), 8.00 (s, 1H), 7.82 (d, J = 8.0 Hz, 1H), 7.48 (t, J = 8.0 Hz, 1H), 7.20 (d, J = 8.0 Hz, 1H), 5.94 (s, 1H), 5.18 (s, 2H), 3.82 (s, 2H), 3.57 (s, 3H), 3.39-3.37 (m, 1H), 2.04-1.93 (m, 2H), 1.76-1.62 (m, 4H), 1.23 (s, 3H), 0.74-0.65 (m, 1H), 0.64-0.57 (m, 1H), 0.55-0.42 (m, 2H) | 526.3 |
| 46 | $^1$H NMR (400 MHz, DMSO-d6) δ 8.44 (s, 1H), 8.13 (s, 1H), 8.07 (s, 1H), 8.04 (s, 1H), 7.82 (d, J = 9.2 Hz, 1H), 7.48 (t, J = 8.0 Hz, 1H), 7.20 (d, J = 7.6 Hz, 1H), 5.84 (s, 1H), 5.20 (s, 2H), 4.06-4.01 (m, 1H), 3.97 (s, 2H), 3.58 (s, 3H), 2.18-1.84 (m, 6H), 1.82-1.68 (m, 4H), 1.66-1.58 (m, 1H), 1.47-1.38 (m, 1H), 1.33 (s, 3H). | 540.3 |
| 47 | $^1$H NMR (400 MHz, DMSO-d6) δ 8.44 (s, 1H), 8.10 (s, 1H), 8.04 (s, 2H), 7.81 (d, J = 8.8 Hz, 1H), 7.47 (t, J = 8.0 Hz, 1H), 7.19 (d, J = 7.2 Hz, 1H), 5.84 (s, 1H), 5.19 (s, 2H), 4.04-4.00 (m, 1H), 3.89 (s, 2H), 3.58 (s, 3H), 2.16-1.83 (m, 6H), 1.80-1.57 (m, 5H), 1.48-1.35 (m, 1H), 1.28 (s, 3H) | 540.3 |
| 48 | $^1$H NMR (400 MHz, DMSO-d6) δ 8.41 (s, 1H), 8.12-8.02 (m, 2H), 7.67 (s, 1H), 7.24 (d, J = 5.2 Hz, 1H), 6.01 (s, 1H), 5.16 (s, 2H), 4.15-4.00 (m, 1H), 3.92 (s, 2H), 3.28 (s, 3H), 3.07 (t, J = 9.0 Hz, 2H), 3.03-2.87 (m, 2H), 2.70-2.53 (m, 2H), 2.42-2.28 (m, 1H), 2.18 (t, J = 9.8 Hz, 2H), 2.13-1.99 (m, 2H), 1.84-1.63 (m, 4H), 1.30 (s, 3H), 1.11 (d, J = 6.4 Hz, 3H). | 630.5 |
| 49 | $^1$H NMR (400 MHz, DMSO-d6) δ 8.35 (s, 1H), 8.20-8.03 (m, 2H), 7.80 (s, 1H), 7.26 (d, J = 5.2 Hz, 1H), 6.16 (s, 1H), 5.19 (s, 2H), 4.24-3.74 (m, 3H), 3.24 (s, 3H), 3.03-2.90 (m, 2H), 2.81-2.71 (m, 2H), 2.69-2.53 (m, 6H), 2.29-2.02 (m, 1H), 1.90-1.65 (m, 4H), 1.37 (s, 3H), 1.09 (d, J = 5.4 Hz, 3H. | 630.4 |
| 50 | $^1$H NMR (400 MHz, CD$_3$OD) δ 8.40 (s, 1H), 8.08 (s, 1H), 8.01 (s, 1H), 7.64 (d, J = 1.1 Hz, 1H), 5.98 (d, J = 1.1 Hz, 1H), 5.22 (s, 2H), 3.89 (s, 2H), 3.73-3.63 (m, 1H), 3.39 (s, 3H), 3.11-3.03 (m, 2H), 2.54-2.41 (m, 1H), 2.33 (td, J = 9.4, 2.2 Hz, 2H), 2.17-2.01 (m, 4H), 1.95-1.76 (m, 7H), 1.69 (d, J = 13.1 Hz, 1H), 1.47-1.36 (m, 5H), 1.32-1.20 (m, 4H), 1.17 (d, J = 6.5 Hz, 3H). | 623.1 |
| 51 | $^1$H NMR (400 MHz, CD$_3$OD) δ 8.34 (s, 1H), 8.07 (s, 1H), 8.00 (s, 1H), 7.80 (s, 1H), 6.10 (s, 1H), 5.22 (s, 2H), 3.85 (s, 2H), 3.75-3.63 (m, 1H), 3.37 (s, 3H), 2.94-2.85 (m, 2H), 2.79-2.68 (m, 1H), 2.57 (t, J = 10.4 Hz, 2H), 2.14-2.01 (m, 4H), 1.92-1.62 (m, 8H), 1.48-1.33 (m, 5H), 1.32-1.20 (m, 4H), 1.16 (d, J = 6.5 Hz, 3H). | 623.1 |
| 52 | $^1$H NMR (400 MHz, DMSO-d6) δ 8.34 (s, 1H), 8.00 (d, J = 7.9 Hz, 2H), 7.70 (s, 1H), 6.71 (d, J = 5.8 Hz, 1H), 6.13 (s, 1H), 5.15 (s, 2H), 4.03 (d, J = 5.9 Hz, 1H), 3.81 (s, 2H), 3.24 (s, 3H), 2.73 (d, J = 9.7 Hz, 2H), 2.53 (d, J = 9.6 Hz, 3H), 2.03-1.89 (m, 4H), 1.70 (ddd, J = 19.8, 9.8, 4.8 Hz, 6H), 1.59-1.42 (m, 4H), 1.23 (s, 3H), 1.08 (d, J = 6.0 Hz, 3H). | 609.1 |
| 53 | $^1$H NMR (400 MHz, DMSO-d6) δ 8.41 (s, 1H), 8.00 (d, J = 9.6 Hz, 2H), 7.57 (s, J = 0.9 Hz, 1H), 6.71 (d, J = 5.9 Hz, 1H), 5.99 (s, 1H), 5.14 (s, 2H), 4.03 (dt, J = 12.1, 6.0 Hz, 1H), 3.81 (s, 2H), 3.28 (s, 3H), 3.06 (td, J = 8.6, 1.9 Hz, 2H), 2.40-2.29 (m, 1H), 2.17 (t, J = 10.4 Hz, 2H), 2.02-1.88 (m, 4H), 1.77-1.61 (m, 6H), 1.60-1.41 (m, 4H), 1.22 (s, 3H), 1.11 (d, J = 6.6 Hz, 3H). | 609.1 |
| 54 | $^1$H NMR (400 MHz, CD$_3$OD) δ 8.42 (s, 1H), 8.10 (s, 1H), 8.02 (d, J = 1.1 Hz, 2H), 6.31 (d, J = 1.2 Hz, 1H), 5.42-5.36 (m, 1H), 5.25 (s, 2H), 3.87 (s, 2H), 3.37 (s, 3H), 3.16-3.09 (m, 2H), 2.56-2.44 (m, 1H), 2.36 (td, J = 9.5, 2.4 Hz, 2H), 2.16-1.97 (m, 4H), 1.94-1.74 (m, 9H), 1.73-1.63 (m, 2H), 1.39 (s, 3H), 1.18 (d, J = 6.5 Hz, 3H). | 610.1 |

TABLE 2-continued

| Compound # | ¹H NMR | LCMS[a] |
|---|---|---|
| 55 | ¹H NMR (400 MHz, CD₃OD) δ 8.35 (s, 1H), 8.18 (d, J = 1.2 Hz, 1H), 8.10 (s, 1H), 8.03 (s, 1H), 6.44 (d, J = 1.3 Hz, 1H), 5.44-5.36 (m, 1H), 5.27 (s, 2H), 3.88 (s, 2H), 3.35 (s, 3H), 2.97-2.88 (m, 2H), 2.80-2.68 (m, 1H), 2.62 (t, J = 10.5 Hz, 2H), 2.16-2.00 (m, 4H), 1.94-1.75 (m, 9H), 1.71-1.64 (m, 2H), 1.40 (s, 3H), 1.17 (d, J = 6.4 Hz, 3H). | 610.1 |
| 56 | ¹H NMR (400 MHz, methanol-d₄) δ 8.36 (s, 1H), 8.13 (s, 1H), 8.10 (s, 1H), 8.02 (s, 1H), 7.85 (dd, J = 1.2, 8.0 Hz, 1H), 7.50 (t, J = 7.6 Hz, 1H), 7.35 (d, J = 7.6 Hz, 1H), 5.19-5.14 (m, 3H), 3.87 (s, 2H), 3.79-3.68 (m, 4H), 3.68 (s, 3H), 2.12-2.07 (m, 2H), 1.92-1.78 (m, 4H), 1.38 (s, 3H). | 561.1 |
| 57 | ¹H NMR (400 MHz, methanol-d₄) δ 8.36 (s, 1H), 8.13 (s, 1H), 8.10 (s, 1H), 8.02 (s, 1H), 7.84 (dd, J = 1.6, 7.6 Hz, 1H), 7.50 (t, J = 8.0 Hz, 1H), 7.35 (d, J = 8.0 Hz, 1H), 5.18-5.15 (m, 3H), 3.88 (s, 2H), 3.79-3.68 (m, 4H), 3.68 (s, 3H), 2.12-2.09 (m, 2H), 1.91-1.78 (m, 4H), 1.39 (s, 3H). | 561.1 |
| 58 | ¹H NMR (400 MHz, methanol-d₄) δ 8.49 (s, 1H), 8.08 (s, 1H), 8.04-8.01 (m, 2H), 7.78-7.74 (m, 1H), 7.56 (t, J = 8.0 Hz, 1H), 7.22 (d, J = 9.2 Hz, 1H), 5.51 (d, J = 6.0 Hz, 2H), 5.21-5.17 (m, 4H), 3.86 (s, 2H), 3.37 (s, 3H), 2.15-2.05 (m, 2H), 1.90-1.75 (m, 4H), 1.38 (s, 3H) | 512.2 |
| 59 | ¹H NMR (400 MHz, methanol-d₄) δ 8.44 (s, 1H), 8.38 (d, J = 1.6 Hz, 1H), 8.09 (s, 1H), 8.02 (s, 1H), 7.00 (s, 1H), 5.28 (s, 2H), 3.86 (s, 2H), 3.77-3.72 (m, 2H), 3.48-3.44 (m, 2H), 3.42 (s, 3H), 2.86-2.79 (m, 2H), 2.12-2.08 (m, 2H), 1.90-1.86 (m, 2H), 1.81-1.79 (m, 2H), 1.38 (s, 3H), 1.31 (t, J = 7.6 Hz, 3H). | 575.3 |
| 60 | ¹H NMR (400 MHz, methanol-d₄) δ 8.44 (s, 1H), 8.38 (s, 1H), 8.10 (s, 1H), 8.02 (s, 1H), 7.01 (s, 1H), 5.27 (s, 2H), 3.84 (s, 2H), 3.76-3.69 (m, 2H), 3.50-3.43 (m, 2H), 3.41 (s, 3H), 2.54 (s, 3H), 2.15-2.07 (m, 2H), 1.90-1.77 (m, 4H), 1.38 (s, 3H). | 561.2 |
| 61 | ¹H NMR (400 MHz, methanol-d₄) δ 8.40 (s, 1H), 8.08 (s, 1H), 8.00 (s, 2H), 7.74-7.71 (m, 1H), 7.51 (t, J = 8.0 Hz, 1H), 7.21 (d, J = 7.6 Hz, 1H), 5.16 (s, 2H), 3.87 (s, 2H), 3.74-3.66 (m, 2H), 3.51-3.44 (m, 2H), 3.41 (s, 3H), 2.12-2.08 (m, 2H), 1.90-1.77 (m, 4H), 1.38 (s, 3H). | 546.2 |
| 62 | ¹H NMR (400 MHz, methanol-d₄) δ 8.43 (s, 1H), 8.07 (s, 1H), 8.00 (s, 1H), 7.69 (s, 1H), 6.11 (d, J = 1.2 Hz, 1H), 5.22 (s, 2H), 3.85 (s, 2H), 3.72-3.65 (m, 2H), 3.44 (s, 3H), 3.41-3.33 (m, 4H), 2.12-2.08 (m, 2H), 1.90-1.77 (m, 4H), 1.38 (s, 3H), 1.23 (t, J = 7.2 Hz, 3H) | 590.3 |
| 63 | ¹H NMR (400 MHz, DMSO-d₆) δ 8.43 (s, 1H), 7.99 (s, 1H), 7.92 (s, 1H), 7.88 (t, J = 1.6 Hz, 1H), 7.77 (t, J = 9.2 Hz, 1H), 7.46 (t, J = 8.0 Hz, 1H), 7.04 (d, J = 8.8 Hz, 1H), 5.21 (s, 2H), 4.41 (d, J = 14.4 Hz, 1H), 3.41-3.37 (m, 4H), 3.23 (s, 3H), 3.10-2.90 (m, 2H), 2.61-2.50 (m, 2H), 2.32-2.19 (m, 4H), 2.14 (s, 3H), 1.95-1.91 (m, 2H), 0.92 (d, J = 6.8 Hz, 3H), 0.87 (d, J = 6.4 Hz, 3H). | 592.3 |
| 64 | ¹H NMR (400 MHz, methanol-d₄) δ 8.37 (s, 1H), 8.09 (s, 1H), 8.01 (s, 1H), 7.95 (s, 1H), 7.76 (d, J = 9.2 Hz, 1H), 7.53 (t, J = 8.0 Hz, 1H), 7.23 (d, J = 7.2 Hz, 1H), 5.16 (s, 3H), 4.34 (d, J = 14.0 Hz, 1H), 3.42-3.37 (m, 2H), 3.35 (s, 5H), 3.28-3.23 (m, 2H), 2.80 (d, J = 11.6 Hz, 1H), 2.75-2.65 (m, 2H), 2.38-2.33 (m, 3H), 2.30 (s, 5H), 2.16-2.10 (m, 1H), 1.02 (d, J = 6.4 Hz, 3H), 0.98 (d, J = 6.4 Hz, 3H) | 592.3 |
| 65 | ¹H NMR (400 MHz, DMSO) δ 8.35 (s, 1H), 8.05 (s, 1H), 8.00 (s, 1H), 7.90 (t, J = 2.1 Hz, 1H), 7.70 (dd, J = 7.9, 2.1 Hz, 1H), 7.42 (t, J = 8.0 Hz, 1H), 7.00-6.93 (m, 1H), 5.18 (s, 2H), 4.58 (s, 2H), 4.48 (s, 2H), 3.82 (s, 2H), 3.25 (d, J = 2.2 Hz, 1H), 3.23 (s, 4H), 2.97-2.89 (m, 2H), 2.04-1.90 (m, 2H), 1.78-1.61 (m, 4H), 1.23 (s, 3H). | 552.2 |
| 66 | ¹H NMR (400 MHz, DMSO) δ 8.35 (s, 1H), 7.97 (s, 1H), 7.92 (d, J = 2.4 Hz, 2H), 7.67 (dd, J = 8.1, 2.1 Hz, 1H), 7.42 (t, J = 8.0 Hz, 1H), 6.98 (d, J = 7.8 Hz, 1H), 5.18 (s, 2H), 4.58 (s, 2H), 4.48 (s, 2H), 3.65 (s, 2H), 3.24 (d, J = 11.0 Hz, 5H), 2.93 (d, J = 12.7 Hz, 2H), 2.71 (t, J = 9.6 Hz, 2H), 2.01-1.85 (m, 1H), 1.63 (td, J = 17.6, 17.0, 6.9 Hz, 5H), 1.48 (q, J = 12.2 Hz, 1H), 0.82 (d, J = 5.9 Hz, 3H). | 566.2 |
| 67 | ¹H NMR (400 MHz, dmso) δ 8.41 (s, 1H), 8.00 (d, J = 7.9 Hz, 2H), 7.59 (s, 1H), 6.97 (d, J = 6.3 Hz, 1H), 5.93 (s, 1H), 5.13 (s, 2H), 4.29-4.03 (m, 1H), 3.81 (s, 2H), 3.27 (s, 2H), 3.10-3.01 (m, 2H), 2.40-2.21 (m, 3H), 2.21-2.10 (m, 2H), 2.04-1.84 (m, 4H), 1.79-1.57 (m, 6H), 1.23 (s, 3H), 1.10 (d, J = 6.6 Hz, 3H). Missing two protons | 594.4 |
| 68 | ¹H NMR (400 MHz, dmso) δ 8.32 (s, 1H), 8.02 (d, J = 5.2 Hz, 2H), 7.69 (s, 1H), 6.96 (d, J = 6.4 Hz, 1H), 6.05 (s, 1H), | 594.4 |

TABLE 2-continued

| Compound # | ¹H NMR | LCMS$^a$ |
|---|---|---|
| | 5.13 (s, 2H), 4.23-4.12 (m, 1H), 3.86 (s, 2H), 3.23-3.18 (m, 3H), 3.06-2.97 (m, 2H), 2.75-2.67 (m, 2H), 2.35-2.17 (m, 3H), 2.09-1.97 (m, 3H), 1.96-1.81 (m, 2H), 1.80-1.60 (m, 6H), 1.26 (s, 3H), 1.06 (d, J = 5.8 Hz, 3H). | |
| 69 | ¹H NMR (400 MHz, dmso) δ 8.41 (s, 1H), 8.02-7.94 (m, 2H), 7.52 (d, J = 1.1 Hz, 1H), 6.72 (d, J = 5.9 Hz, 1H), 5.98 (s, 1H), 5.12 (s, 2H), 4.06-3.96 (m, 3H), 3.84-3.73 (m, 3H), 3.28-3.19 (m, 5H), 3.15 (s, 3H), 2.40-2.32 (m, 1H), 2.06-1.85 (m, 5H), 1.73-1.60 (m, 6H), 1.58-1.39 (m, 4H), 1.20 (s, 3H). | 624.5 |
| 70 | ¹H NMR (400 MHz, dmso) δ 8.36 (s, 1H), 8.03-7.98 (m, 2H), 7.63 (s, 1H), 6.75 (d, J = 5.9 Hz, 1H), 6.12 (s, 1H), 5.15 (s, 2H), 4.15-3.99 (m, 1H), 3.81 (s, 2H), 3.27 (s, 2H), 3.17 (s, 3H), 2.98-2.89 (m, 2H), 2.81-2.78 (m, 2H), 2.08 (d, J = 8.7 Hz, 1H), 2.02-1.81 (m, 4H), 1.76-1.62 (m, 6H), 1.60-1.41 (m, 5H), 1.23 (s, 3H). | 624.5 |
| 71 | ¹H NMR (400 MHz, dmso) δ 8.49-8.36 (m, 1H), 8.01-7.86 (m, 2H), 7.64-7.53 (m, 1H), 7.06-6.95 (m, 1H), 6.37 (s, 1H), 5.98-5.88 (m, 1H), 5.20-4.85 (m, 2H), 4.27-4.06 (m, 2H), 3.70-3.58 (m, 2H), 3.35-3.16 (m, 4H), 2.75-2.57 (m, 2H), 2.36-2.07 (m, 9H), 2.02-1.64 (m, 9H), 0.97-0.82 (m, 6H). | 649.6 |
| 72 | ¹H NMR (400 MHz, dmso) δ 8.63 (s, 1H), 7.99 (s, 1H), 7.93 (s, 1H), 7.82 (s, 1H), 6.76 (d, J = 10.1 Hz, 1H), 6.37 (s, 1H), 5.32 (dt, J = 9.2, 3.1 Hz, 1H), 5.20 (s, 2H), 4.21 (d, J = 14.6 Hz, 1H), 3.39 (s, 3H), 2.61 (t, J = 10.7 Hz, 2H), 2.23 (dt, J = 18.1, 7.7 Hz, 4H), 2.14 (s, 3H), 2.03-1.87 (m, 5H), 1.82-1.56 (m, 7H), 1.02 (d, J = 6.6 Hz, 6H), 0.93 (d, J = 6.6 Hz, 3H), 0.87 (d, J = 6.6 Hz, 3H). | 666.7 |
| 73 | ¹H NMR (400 MHz, dmso) δ 8.41 (s, 1H), 7.98 (s, 1H), 7.93 (s, 1H), 7.86 (d, J = 1.1 Hz, 1H), 6.37 (d, J = 1.1 Hz, 1H), 5.35-5.26 (m, 1H), 5.19 (s, 2H), 4.21 (d, J = 14.5 Hz, 1H), 3.26 (s, 3H), 3.09 (t, J = 9.5 Hz, 2H), 2.61 (t, J = 11.2 Hz, 2H), 2.30-2.18 (m, 5H), 2.14 (s, 3H), 2.05-1.86 (m, 5H), 1.83-1.57 (m, 7H), 1.10 (d, J = 6.5 Hz, 3H), 0.93 (d, J = 6.7 Hz, 3H), 0.87 (d, J = 6.6 Hz, 3H). | 666.7 |
| 74 | ¹H NMR (400 MHz, dmso) δ 8.34 (s, 1H), 7.97 (s, 1H), 7.90 (s, 1H), 7.71 (s, 1H), 6.72 (d, J = 5.9 Hz, 1H), 6.12 (s, 1H), 5.16 (s, 2H), 4.21 (d, J = 14.5 Hz, 1H), 4.02 (dd, J = 12.5, 6.3 Hz, 1H), 3.24 (s, 3H), 2.77-2.71 (m, 2H), 2.65 (d, J = 13.3 Hz, 1H), 2.59 (d, J = 11.1 Hz, 3H), 2.55 (s, 1H), 2.34-2.17 (m, 4H), 2.14 (s, 3H), 1.92 (d, J = 11.0 Hz, 4H), 1.66 (d, J = 6.3 Hz, 2H), 1.59-1.44 (m, 5H), 1.08 (d, J = 5.9 Hz, 3H), 0.93 (d, J = 6.6 Hz, 3H), 0.88 (d, J = 6.6 Hz, 3H). | 665.8 |
| 75 | ¹H NMR (400 MHz, dmso) δ 8.41 (s, 1H), 7.97 (s, 1H), 7.90 (s, 1H), 7.57 (d, J = 1.0 Hz, 1H), 6.71 (d, J = 5.9 Hz, 1H), 5.99 (s, 1H), 5.15 (s, 2H), 4.21 (d, J = 14.3 Hz, 1H), 4.01 (dd, J = 12.9, 6.7 Hz, 1H), 3.28 (s, 3H), 3.06 (t, J = 9.7 Hz, 2H), 2.69-2.62 (m, 1H), 2.62-2.56 (m, 2H), 2.39-2.24 (m, 2H), 2.24-2.15 (m, 4H), 2.14 (s, 3H), 1.98-1.88 (m, 4H), 1.70-1.64 (m, 2H), 1.59-1.44 (m, 5H), 1.11 (d, J = 6.6 Hz, 3H), 0.93 (d, J = 6.7 Hz, 3H), 0.88 (d, J = 6.6 Hz, 3H). | 665.8 |
| 76 | ¹H NMR (400 MHz, dmso) δ 8.34 (s, 1H), 8.02 (s, 1H), 8.00 (s, 1H), 7.93 (s, 1H), 6.57 (s, 1H), 5.17 (s, 2H), 4.34 (q, J = 7.0 Hz, 2H), 4.08 (p, J = 7.2 Hz, 1H), 3.79 (s, 2H), 3.23 (s, 3H), 3.15 (s, 3H), 3.06-2.98 (m, 2H), 2.83-2.75 (m, 2H), 2.01-1.90 (m, 2H), 1.75-1.59 (m, 4H), 1.35 (t, J = 7.0 Hz, 3H), 1.20 (s, 3H). | 585.5 |
| 77 | ¹H NMR (400 MHz, dmso) δ 8.34 (s, 1H), 8.02 (s, 1H), 8.00 (s, 1H), 7.93 (s, 1H), 6.57 (s, 1H), 5.17 (s, 2H), 4.34 (q, J = 7.0 Hz, 2H), 4.08 (p, J = 7.2 Hz, 1H), 3.79 (s, 2H), 3.23 (s, 3H), 3.15 (s, 3H), 3.06-2.98 (m, 2H), 2.83-2.75 (m, 2H), 2.01-1.90 (m, 2H), 1.75-1.59 (m, 4H), 1.35 (t, J = 7.0 Hz, 3H), 1.20 (s, 3H). | 585.5 |
| 78 | ¹H NMR (400 MHz, dmso) δ 8.41 (s, 1H), 8.01 (s, 1H), 8.00 (s, 1H), 7.85 (d, J = 1.1 Hz, 1H), 6.35 (d, J = 1.1 Hz, 1H), 5.32-5.25 (m, 1H), 5.17 (s, 2H), 3.89-3.76 (m, 3H), 3.30-3.26 (m, 2H), 3.25 (s, 3H), 3.16 (s, 3H), 2.47-2.42 (m, 2H), 2.03-1.90 (m, 4H), 1.81-1.53 (m, 10H), 1.20 (s, 3H). | 625.6 |
| 79 | 1H NMR (400 MHz, dmso) δ 8.34 (s, 1H), 8.02 (s, 1H), 8.00 (s, 1H), 7.92 (s, 1H), 6.52 (s, 1H), 5.32-5.26 (m, 1H), 5.17 (s, 2H), 4.08 (p, J = 7.3 Hz, 1H), 3.79 (s, 2H), 3.24 (s, 3H), 3.15 (s, 3H), 3.05-2.98 (m, 2H), 2.83-2.74 (m, 2H), 2.05-1.90 (m, 4H), 1.82-1.55 (m, 10H), 1.21 (s, 3H). | 625.6 |
| 80 | ¹H NMR (400 MHz, dmso) δ 8.41 (s, 1H), 7.99 (s, 1H), 7.97 (s, 1H), 7.52 (d, J = 0.9 Hz, 1H), 6.69 (t, J = 5.2 Hz, 1H), 5.98 (d, J = 0.9 Hz, 1H), 5.13 (s, 2H), 3.86-3.75 (m, 3H), 3.28-3.19 (m, 7H), 3.16 (s, 3H), 2.43-2.34 (m, 2H), 2.01- | 584.4 |

TABLE 2-continued

| Compound # | ¹H NMR | LCMS$^a$ |
|---|---|---|
| | 1.91 (m, 2H), 1.75-1.59 (m, 4H), 1.21 (s, 3H), 1.13 (t, J = 7.1 Hz, 3H). | |
| 81 | ¹H NMR (400 MHz, dmso) δ 8.34 (s, 1H), 8.00 (s, 1H), 7.98 (s, 1H), 7.63 (s, 1H), 6.70 (t, J = 5.2 Hz, 1H), 6.09 (s, 1H), 5.13 (s, 2H), 4.08 (p, J = 7.2 Hz, 1H), 3.79 (s, 2H), 3.28-3.20 (m, 5H), 3.16 (s, 3H), 2.96-2.88 (m, 2H), 2.82-2.73 (m, 2H), 2.01-1.91 (m, 2H), 1.76-1.60 (m, 4H), 1.21 (s, 3H), 1.13 (t, J = 7.1 Hz, 3H). | 584.5 |
| 82 | ¹H NMR (400 MHz, CD₃CN) δ 8.12 (s, 1H), 7.99 (s, 1H), 7.93-7.85 (m, 2H), 6.33 (s, 1H), 5.47-5.30 (m, 1H), 5.18 (s, 2H), 4.24 (d, J = 13.9 Hz, 1H), 3.95-3.85 (m, 1H), 3.37-3.16 (m, 9H), 2.77-2.47 (m, 7H), 2.17-2.01 (m, 6H), 1.86-1.55 (m, 7H), 1.33-1.21 (m, 1H), 0.96-0.91 (m, 6H). | 682.6 |
| 83 | ¹H NMR (400 MHz, dmso) δ 8.36 (s, 1H), 8.02-7.87 (m, 3H), 6.53 (s, 1H), 5.36-5.29 (m, 1H), 5.19 (s, 2H), 4.24-4.05 (m, 2H), 3.45-3.30 (m, 1H), 3.25 (s, 3H), 3.17 (s, 3H), 3.06-2.96 (m, 2H), 2.84-2.76 (m, 2H), 2.67-2.55 (m, 2H), 2.36-2.06 (m, 7H), 2.06-1.83 (m, 4H), 1.83-1.53 (m, 6H), 0.99-0.83 (m, 6H). | 682.7 |
| 84 | ¹H NMR (400 MHz, dmso) δ 8.43 (s, 1H), 8.28 (s, 1H), 8.00-7.88 (m, 2H), 7.54 (s, 1H), 6.74 (s, 1H), 6.01 (s, 1H), 5.15 (s, 2H), 4.25-4.16 (m, 1H), 4.04-3.96 (m, 1H), 3.87-3.78 (m, 1H), 3.42-3.13 (m, 8H), 2.62-2.59 (m, 2H), 2.30-2.36 (m, 2H) 2.31-2.10 (m, 6H), 2.00-1.87 (m, 4H), 1.74-1.42 (m, 6H), 1.24-1.03 (m, 1H), 0.90 (m, 6H). | 681.9 |
| 85 | ¹H NMR (400 MHz, dmso) δ 8.36 (s, 1H), 7.97 (s, 1H), 7.90 (s, 1H), 7.64 (s, 1H), 7.05-6.71 (m, 1H), 6.10 (s, 1H), 5.15 (s, 2H), 4.27-3.97 (m, 3H), 3.42-3.34 (m, 1H), 3.27 (s, 3H), 3.17 (s, 3H), 2.97-2.87 (m, 2H), 2.84-2.74 (m, 2H), 2.69-2.58 (m, 2H), 2.34-2.07 (m, 6H), 2.02-1.86 (m, 4H), 1.77-1.43 (m, 6H), 1.21-1.02 (m, 1H), 0.96-0.84 (m, 6H). | 681.9 |
| 86 | ¹H NMR (400 MHz, CD₃OD) δ 8.53 (s, 1H), 8.42 (s, 1H), 8.12 (s, qH), 8.05 (s, 1H), 7.72 (s, 1H), 6.16 (s, 1H), 5.30 (s, 2H), 4.01 (s, 3H), 3.68 (s, 2H), 3.39 (s, 3H), 2.82 (s, 2H), 2.60 (s, 2H), 2.20 (s, 2H), 1.98-1.89 (m, 4H), 1.47 (s, 3H), 1.30 (s, 1H) | 609.5 |
| 87 | ¹H NMR (400 MHz, CD₃OD) δ 8.53 (s, 1H), 8.37 (s, 1H), 8.13 (s, 1H), 8.06 (s, 1H), 7.85 (s, 1H), 6.22 (s, 1H), 5.30 (s, 2H), 4.03 (s, 1H), 3.68 (s, 2H), 3.39 (dd, J = 4.2, 2.6 HZ, 3H), 3.11 (s, 3H), 2.94-2.76 (m, 5H), 2.21 (s, 2H), 1.97-1.88 (m, 4H), 1.48 (s, 3H), 1.29 (s, 1H). | 609.5 |
| 170 | ¹H NMR (400 MHz, DMSO) δ 8.36 (s, 1H), 8.05 (s, 1H), 8.00 (s, 1H), 7.87 (t, J = 2.0 Hz, 1H), 7.83-7.76 (m, 1H), 7.39 (t, J = 7.9 Hz, 1H), 6.98 (dd, J = 7.9, 1.4 Hz, 1H), 5.16 (s, 2H), 4.42 (q, J = 7.1 Hz, 1H), 3.82 (s, 2H), 3.40 (s, 3H), 2.04-1.90 (m, 2H), 1.78-1.60 (m, 7H), 1.23 (s, 3H). | 484.2 |
| 171 | ¹H NMR (400 MHz, DMSO) δ 8.36 (s, 1H), 8.05 (s, 1H), 8.00 (s, 1H), 7.87 (t, J = 2.0 Hz, 1H), 7.83-7.76 (m, 1H), 7.39 (t, J = 7.9 Hz, 1H), 6.98 (dd, J = 7.7, 1.5 Hz, 1H), 5.16 (s, 2H), 4.42 (q, J = 7.0 Hz, 1H), 3.82 (s, 2H), 3.40 (s, 3H), 2.04-1.90 (m, 2H), 1.74 (td, J = 5.2, 4.8, 2.1 Hz, 1H), 1.74-1.61 (m, 7H), 1.23 (s, 3H). | 484.2 |
| 172 | ¹H NMR (400 MHz, methanol-d₄) δ 8.33 (s, 1H), 8.09 (s, 1H), 8.06-8.03 (m, 1H), 7.95 (s, 1H), 7.72-7.67 (m, 1H), 7.50 (t, J = 8.0 Hz, 1H), 7.22 (d, J = 7.8 Hz, 1H), 5.16 (s, 2H), 4.34 (d, J = 14.8 Hz, 1H), 4.25-4.15 (m, 1H), 3.39-3.34 (m, 4H), 3.29 (s, 3H), 3.23-3.16 (m, 2H), 2.92-2.85 (m, 2H), 2.80 (d, J = 11.0 Hz, 1H), 2.76-2.65 (m, 2H), 2.40-2.32 (m, 2H), 2.29 (s, 4H), 2.20-2.06 (m, 2H), 1.04-0.95 (m, 6H). | 597.4 |
| 173 | ¹H NMR (400 MHz, methanol-d₄) δ 8.38 (s, 1H), 8.10 (s, 1H), 8.04 (s, 1H), 7.99 (t, J = 2.0 Hz, 1H), 7.71 (dd, J = 8.0, 1.6 Hz, 1H), 7.50 (t, J = 8.0, 1H), 7.20 (dd, J = 8.0, 1.6 Hz, 1H), 5.13 (s, 2H), 4.18-4.31 (m, 1H), 3.75-3.65 (m, 2H), 3.50-3.43 (m, 2H), 3.40 (s, 3H), 2.02-1.97 (m, 1H), 1.88-1.80 (m, 1H), 1.78-1.68 (m, 1H), 1.68-1.55 (m, 2H), 1.44-1.36 (m, 4H), 1.21 (s, 3H). | 560.2 |
| 174 | ¹H NMR (400 MHz, methanol-d₄) δ 8.39 (s, 1H), 8.10 (s, 1H), 8.04 (s, 1H), 7.98 (t, J = 2.0 Hz, 1H), 7.71 (dd, J = 8.0, 1.6 Hz, 1H), 7.50 (t, J = 8.0 Hz, 1H), 7.19 (dd, J = 8.0, 1.6 Hz, 1H), 5.13 (s, 2H), 4.19-4.13 (m, 1H), 4.18-4.13 (m, 2H), 3.49-3.43 (m, 2H), 3.39 (s, 3H), 2.05-1.97 (m, 1H), 1.87-1.80 (m, 1H), 1.78-1.68 (m, 1H), 1.67-1.55 (m, 2H), 1.43-1.36 (m, 4H), 1.22 (s, 3H). | 560.1 |
| 175 | ¹H NMR (400 MHz, methanol-d₄) δ 8.33 (s, 1H), 8.13 (s, 1H), 8.07 (s, 1H), 8.05 (t, J = 1.6 Hz, 1H), 7.69 (dd, J = 8.0, 1.2 Hz, 1H), 7.49 (t, J = 8.0 Hz, 1H), 7.22 (dd, J = 8.0, 1.2 Hz, 1H), 5.16 (s, 2H), 4.24-4.15 (m, 2H), 3.36 (s, 3H), 3.30 (s, | 554.2 |

TABLE 2-continued

| Compound # | ¹H NMR | LCMS$^a$ |
|---|---|---|
| | 3H), 3.22-3.18 (m, 2H), 2.90-2.86 (m, 2H), 2.09-2.02 (m, 1H), 1.90-1.83 (m, 1H), 1.82-1.72 (m, 1H), 1.70-1.57 (m, 2H), 1.47-1.39 (m, 4H), 1.26 (s, 3H). | |
| 176 | ¹H NMR (400 MHz, methanol-d$_4$) δ 8.31 (s, 1H), 8.10 (s, 1H), 8.05-8.04 (m, 2H), 7.68 (dd, J = 8.0, 1.2 Hz, 1H), 7.48 (t, J = 8.0, 1H), 7.20 (dd, J = 8.0, 1.2 Hz, 1H), 5.14 (s, 2H), 4.22-4.12 (m, 2H), 3.36 (s, 3H), 3.28 (s, 3H), 3.21-3.16 (m, 2H), 3.00-2.84 (m, 2H), 2.04-1.97 (m, 1H), 1.87-1.80 (m, 1H), 1.77-1.70 (m, 1H), 1.68-1.57 (m, 2H), 1.42-1.36 (m, 4H), 1.22 (s, 3H). | 554.2 |
| 177 | ¹H NMR (400 MHz, methanol-d$_4$) δ 8.29 (s, 1H), 8.07 (s, 1H), 8.00 (s, 1H), 7.15 (s, 1H), 7.01 (s, 1H), 6.43 (s, 1H), 5.09 (s, 2H), 3.88 (s, 2H), 3.78-3.71 (m, 1H), 3.36 (s, 3H), 2.96-2.89 (m, 2H), 2.74-2.63 (m, 1H), 2.58-2.50 (m, 2H), 2.16-2.09 (m, 2H), 2.02-1.94 (m, 2H), 1.92-1.85 (m, 2H), 1.83-1.70 (m, 4H), 1.66-1.57 (m, 2H), 1.53-1.46 (m, 2H), 1.39 (s, 3H), 1.14 (d, J = 7.6 Hz, 3H). | 607.3 |
| 178 | ¹H NMR (400 MHz, methanol-d$_4$) δ 8.32 (s, 1H), 8.09 (s, 1H), 8.07-8.06 (m, 1H), 8.01 (s, 1H), 7.69 (m, 1H), 7.49 (m, 1H), 7.22 (m, 1H), 5.16 (s, 2H), 4.30-4.24 (m, 1H), 3.86 (s, 2H), 3.49 (m, 2H), 3.36 (s, 3H), 3.20 (m, 2H), 2.92-2.86 (m, 2H), 2.12-2.06 (m, 2H), 1.90-1.78 (m, 4H), 1.38 (s, 3H), 1.18 (m, 3H). | 554.3 |
| 179 | ¹H NMR (400 MHz, methanol-d$_4$) δ 8.39 (s, 1H), 8.08 (s, 1H), 8.00 (s, 1H), 7.92-7.90 (m 1H), 7.69 (d, J = 8.4 Hz, 1H), 7.47 (t, J = 8.0 Hz, 1H), 7.08 (d, J = 8.8 Hz, 1H), 5.15 (s, 2H), 4.08 (t, J = 7.6 Hz, 1H), 3.86 (s, 2H), 3.52-3.47 (m, 2H), 3.39-3.37 (m, 2H), 3.34 (s, 3H), 2.69-2.64 (m, 2H), 2.14-2.07 (m, 2H), 1.90-1.78 (m, 4H), 1.38 (s, 3H), 1.19 (t, J = 6.8 Hz, 3H). | 554.3 |
| 180 | ¹H NMR (400 MHz, CDCl$_3$) δ 8.09 (s, 1H), 8.05 (s, 1H), 7.94-7.91 (m, 1H), 7.84 (s, 1H), 7.58-7.54 (m, 1H), 7.41 (t, J = 8.0 Hz, 1H), 7.04 (d, J = 8.0 Hz, 1H), 4.98 (s, 2H), 4.28 (d, J = 14.4 Hz, 1H), 4.12-4.04 (m, 1H), 3.45-3.39 (m, 2H), 3.32 (s, 3H), 3.29 (s, 3H), 3.24 (d, J = 14.0 Hz, 1H), 2.74-2.59 (m, 5H), 2.36-2.31 (m, 1H), 2.29 (s, 3H), 2.28-2.22 (m, 2H), 2.12-2.05 (m, 1H), 2.04-1.97 (m, 1H), 1.00 (d, J = 6.8 Hz, 3H), 0.97 (d, J = 6.8 Hz, 3H). | 597.7 |
| 181 | ¹H NMR (400 MHz, methanol-d$_4$) δ 8.30 (s, 1H), 8.08 (s, 1H), 8.01 (s, 1H), 7.51 (s, 1H), 7.39 (d, J = 2.0 Hz, 1H), 6.75 (s, 1H), 5.13 (s, 2H), 4.09-4.03 (m, 2H), 3.87 (s, 2H), 3.35 (s, 3H), 3.01-2.91 (m, 2H), 2.72-2.63 (m, 1H), 2.62-2.50 (m, 2H), 2.15-2.06 (m, 2H), 1.91-1.76 (m, 4H), 1.41-1.37 (m, 6H), 1.15 (d, J = 6.0 Hz, 3H). | 568.3 |
| 182 | ¹H NMR (400 MHz, methanol-d$_4$) δ 8.46 (s, 1H), 8.12-8.09 (m, 2H), 8.04 (s, 1H), 6.53 (s, 1H), 5.28 (s, 2H), 4.48-4.42 (m, 2H), 3.88 (s, 2H), 3.79-3.68 (m, 2H), 3.51-3.39 (m, 5H), 2.16-2.08 (m, 2H), 1.92-1.86 (m, 2H), 1.85-1.76 (m, 2H), 1.46-1.39 (m, 6H). | 591.3 |
| 183 | ¹H NMR (400 MHz, methanol-d$_4$) δ 8.36 (s, 1H), 8.07 (s, 1H), 7.99 (s, 1H), 7.00-6.95 (m, 2H), 6.27 (s, 1H), 5.08 (s, 2H), 3.87 (s, 2H), 3.75-3.73 (m, 1H), 3.38 (s, 3H), 3.14-3.06 (m, 2H), 2.51-2.41 (m, 1H), 2.36 (d, J = 11.2 Hz, 2H), 2.14-2.07 (m, 2H), 1.97-1.96 (m, 2H), 1.91-1.86 (m, 2H), 1.83-1.77 (m, 2H), 1.76-1.71 (m, 2H), 1.66-1.59 (m, 2H), 1.47 (m, 2H), 1.39 (s, 3H), 1.16 (d, J = 6.4 Hz, 3H) | 607.5 |
| 184 | ¹H NMR (400 MHz, methanol-d$_4$) δ 8.38 (s, 1H), 8.10 (s, 1H), 8.05 (s, 1H), 7.89 (t, J = 2.0 Hz, 1H), 7.68 (dd, J = 8.0, 1.2 Hz, 1H), 7.68 (t, J = 8.0 Hz, 1H), 7.07 (dd, J = 8.0, 1.2 Hz, 1H), 5.13 (s, 2H), 4.18-4.13 (m, 1H), 4.02-3.95 (m, 1H), 3.39-3.63 (m, 2H), 3.34 (s, 3H), 3.24 (s, 3H), 2.67-2.62 (m, 2H), 2.05-2.00 (m, 1H), 1.88-1.83 (m, 1H), 1.79-1.72 (m, 1H), 1.68-1.62 (m, 2H), 1.45-1.39 (m, 4H), 1.22 (s, 3H). | 554.1 |
| 185 | ¹H NMR (400 MHz, methanol-d$_4$) δ 8.39 (s, 1H), 8.11 (s, 1H), 8.06 (s, 1H), 7.91 (t, J = 2.0 Hz, 1H), 7.68 (dd, J = 8.0, 1.2 Hz, 1H), 7.47 (t, J = 8.0 Hz, 1H), 7.07 (dd, J = 8.0, 1.2 Hz, 1H) 5.14 (s, 2H), 4.18-4.14 (m, 1H), 4.03-3.96 (m, 1H), 3.40-3.67 (m, 2H), 3.35 (s, 3H), 3.30 (s, 3H), 2.68-2.63 (m, 2H), 2.06-1.98 (m, 1H), 1.88-1.83 (m, 1H), 1.80-1.72 (m, 1H), 1.69-1.59 (m, 2H), 1.46-1.40 (m, 4H), 1.23 (s, 3H). | 554.5 |
| 186 | ¹H NMR (400 MHz, methanol-d$_4$) δ 8.31 (s, 1H), 8.08 (s, 1H), 8.01 (s, 1H), 7.49 (s, 1H), 7.40 (s, 1H), 6.70 (s, 1H), 5.13 (s, 2H), 4.82 (s, 2H), 3.87 (s, 2H), 3.35 (s, 3H), 2.97-2.93 (m, 2H), 2.71-2.67 (m, 1H), 2.60-2.55 (m, 2H), 2.14-2.08 (m, 2H), 1.95-1.77 (m, 10H), 1.65 (s, 2H), 1.39 (s, 3H), 1.16 (d, 3H). | 608.4 |
| 187 | ¹H NMR (400 MHz, methanol-d$_4$) δ 8.39 (s, 1H), 8.08 (s, 1H), 8.00 (s, 1H), 7.79 (s, 1H), 6.04 (d, J = 1.8 Hz, 1H), 5.25 | 621.3 |

TABLE 2-continued

| Compound # | ¹H NMR | LCMS[a] |
|---|---|---|
| | (s, 2H), 4.79 (s, 2H), 4.65 (s, 2H), 3.85 (s, 2H), 3.67-3.64 (m, 2H), 3.38 (s, 3H), 3.27-3.23 (m, 2H), 3.02-3.00 (m, 2H), 2.80 (t, J = 4.8 Hz, 2H), 2.13-2.03 (m, 2H), 1.91-1.75 (m, 4H), 1.38 (s, 3H). | |
| 188 | ¹H NMR (400 MHz, methanol-$d_4$) δ 8.38 (s, 1H), 8.07 (s, 1H), 7.99 (s, 1H), 7.70 (s, 1H), 5.94 (s, 1H), 5.21 (s, 2H), 4.79 (s, 2H), 4.64 (s, 2H), 4.12-4.05 (m, 2H), 3.85 (s, 2H), 3.38 (s, 3H), 3.26-3.22 (m, 2H), 3.02-2.99 (m, 2H), 2.14-1.97 (m, 4H), 1.92-1.70 (m, 6H), 1.65-1.60 (m, 2H), 1.55-1.47 (m, 2H), 1.29 (s, 3H). | 636.4 |
| 189 | ¹H NMR (400 MHz, methanol-$d_4$) δ 8.37 (s, 1H), 8.08 (s, 1H), 8.01 (s, 1H), 7.36 (m, 2H), 6.58 (s, 1H), 5.12 (s, 2H), 4.05 (m, 2H), 3.87 (s, 2H), 3.37 (s, 3H), 3.15-3.10 (m, 2H), 2.52-2.42 (m, 1H), 2.40-2.33 (m, 2H), 2.15-2.07 (m, 2H), 1.92-1.86 (m, 2H), 1.84-1.77 (m, 2H), 1.40-1.37 (m, 6H), 1.16 (m, 3H). | 568.4 |
| 190 | ¹H NMR (400 MHz, DMSO-$d_6$) δ 8.31 (s, 1H), 8.10-8.01 (m, 3H), 7.79 (t, J = 7.6 Hz, 1H), 7.70 (dd, J = 7.6, 1.2 Hz, 1H), 7.44 (t, J = 8.0 Hz, 1H), 7.12 (d, J = 7.6 Hz, 1H), 5.23 (s, 2H), 4.12-4.03 (m, 1H), 3.24 (s, 3H), 3.17 (s, 3H), 3.11-3.04 (m, 2H), 2.84-2.77 (m, 2H). | 443.2 |
| 191 | ¹H NMR (400 MHz, methanol-$d_4$) δ 8.35 (s, 1H), 8.19 (d, J = 8.0 Hz, 1H), 8.00 (t, J = 2.0 Hz, 1H), 7.97 (d, J = 8.0 Hz, 1H), 7.77 (t, J = 8.0 Hz, 1H), 7.66 (dd, J = 8.0, 1.2 Hz, 1H), 7.46 (t, J = 8.0 Hz, 1H), 7.09 (dd, J = 8.0, 1.2 Hz, 1H), 5.17 (s, 2H), 4.71 (s, 2H), 4.65 (s, 2H), 3.34 (s, 3H), 3.27 (s, 2H), 3.09-3.06 (m, 2H). | 455.2 |
| 192 | ¹H NMR (400 MHz, methanol-$d_4$) δ 8.38 (s, 1H), 8.07 (s, 1H), 7.99 (s, 1H), 7.77 (d, J = 1.6 Hz, 1H), 6.02 (d, J = 1.2 Hz, 1H), 5.24 (s, 2H), 4.78 (s, 2H), 4.64 (s, 2H), 4.31-4.28 (m, 1H), 3.84 (s, 2H), 3.84 (s, 3H), 3.25-3.22 (m, 2H), 3.01-2.98 (m, 2H), 2.90-2.75 (m, 2H), 2.12-2.05 (m, 2H), 1.89-1.84 (m, 4H), 1.40-1.33 (m, 6H). | 635.3 |
| 193 | ¹H NMR (400 MHz, methanol-$d_4$) δ 8.38 (s, 1H), 8.07 (s, 1H), 8.03 (s, 1H), 7.99 (s, 1H), 6.26 (s, 1H), 5.38-5.35 (m, 1H), 5.22 (s, 2H), 4.75 (s, 2H), 4.62 (s, 2H), 3.83 (s, 2H), 3.34 (s, 3H), 3.24 (s, 2H), 3.03-3.00 (m, 2H), 2.11-1.98 (m, 4H), 1.88-1.75 (m, 8H), 1.66-1.63 (m, 2H), 1.36 (s, 3H). | 637.3 |
| 194 | ¹H NMR (400 MHz, methanol-$d_4$) δ 8.37 (s, 1H), 8.05 (s, 1H), 7.98 (s, 1H), 7.76 (s, 1H), 6.01 (s, 1H), 5.22 (s, 2H), 4.62 (s, 2H), 4.30-4.25 (m, 2H), 3.82 (s, 1H), 3.35-3.28 (m, 2H), 3.24 (s, 3H), 3.22 (d, J = 8.0 Hz, 2H), 2.98 (d, J = 8.0 Hz, 2H), 2.89-2.74 (m, 2H), 2.11-2.04 (m, 2H), 1.88-1.73 (m, 4H), 1.37-1.36 (m, 6H). | 635.3 |
| 195 | ¹H NMR (400 MHz, methanol-$d_4$) δ 8.38 (s, 1H), 8.13 (s, 1H), 8.06 (s, 1H), 7.37 (s, 1H), 7.31 (s, 1H), 6.56 (s, 1H), 5.15 (s, 2H), 4.84-4.79 (m, 1H), 4.04 (m, 2H), 3.38 (s, 3H), 3.15-3.09 (m, 2H), 2.52-2.42 (m, 1H), 2.40-2.32 (m, 2H), 2.28-2.17 (m, 2H), 2.01-1.85 (m, 6H), 1.84-1.73 (m, 4H), 1.71-1.59 (m, 2H), 1.49 (s, 3H), 1.16 (d, J = 6.4 Hz, 3H). | 608.4 |
| 196 | ¹H NMR (400 MHz, DMSO-$d_6$) δ 8.39 (s, 1H), 8.10-8.03 (m, 2H), 7.93 (s, 1H), 7.80 (t, J = 7.6 Hz, 1H), 7.69 (dd, J = 8.4, 1.6 Hz, 1H), 7.43 (t, J = 8.0 Hz, 1H), 6.97 (d, J = 7.6 Hz, 1H), 5.23 (s, 2H), 3.91-3.82 (m, 1H), 3.25 (s, 3H), 3.19 (s, 3H), 2.60-2.52 (m, 4H). | 443.1 |
| 197 | ¹H NMR (400 MHz, methanol-$d_4$) δ 8.34 (s, 1H), 7.99 (t, J = 2.0 Hz, 1H), 7.96 (s, 1H), 7.82 (s, 1H), 7.65 (dd, J = 8.0, 1.2 Hz, 1H), 7.45 (t, J = 8.0 Hz, 1H), 7.30 (d, J = 10.8 Hz, 1H), 7.06 (dd, J = 8.0, 1.2 Hz, 1H), 7.03 (s, 1H), 5.10 (s, 2H), 4.70 (s, 2H), 4.55 (s, 2H), 3.81 (s, 2H), 3.33 (s, 3H), 3.25 (s, 2H), 3.13-3.04 (m, 2H), 2.12-2.05 (m, 2H), 1.90-1.76 (m, 4H), 1.37 (s, 3H). | 534.3 |
| 198 | ¹H NMR (400 MHz, methanol-$d_4$) δ 8.70 (s, 1H), 8.44 (s, 2H), 8.02 (s, 1H), 7.99 (s, 1H), 7.93 (dd, J = 8.4, 1.6 Hz, 1H), 7.82 (s, 1H), 7.62 (t, J = 8.0 Hz, 1H), 7.28 (d, J = 8.0 Hz, 1H), 7.22-6.89 (m, 1H), 5.28-5.10 (m, 2H), 4.55 (s, 2H), 4.38-4.30 (m, 1H), 3.77 (s, 2H), 3.41-3.31 (m, 2H), 3.24-3.16 (m, 1H), 3.14 (s, 3H), 2.91-2.87 (m, 1H), 2.87-2.77 (m, 4H), 2.76 (s, 3H), 2.74-2.67 (m, 2H), 2.59-2.52 (m, 1H), 2.50-2.37 (m, 2H), 1.04 (d, J = 6.8 Hz, 3H), 1.00 (d, J = 6.8 Hz, 3H). | 591.3 |
| 199 | ¹H NMR (400 MHz, methanol-$d_4$) δ 8.35 (s, 1H), 8.09 (s, 1H), 8.02 (d, J = 3.2 Hz, 2H), 7.67 (d, J = 8.2 Hz, 1H), 7.47 (t, J = 8.0 Hz, 1H), 7.11 (d, J = 7.6 Hz, 1H), 5.15 (s, 2H), 4.69 (t, J = 6.8 Hz, 2H), 4.45-4.38 (m, 2H), 3.87 (s, 2H), 3.78-3.68 (m, 1H), 3.39-3.35 (m, 5H), 3.30 (s, 2H), 3.23 | 607.3 |

TABLE 2-continued

| Compound # | ¹H NMR | LCMS$^a$ |
|---|---|---|
|  | (d, J = 12.4 Hz, 2H), 3.02 (d, J = 12.8 Hz, 2H), 2.16-2.06 (m, 2H), 1.93-1.76 (m, 4H), 1.39 (s, 3H) |  |
| 200 | ¹H NMR (400 MHz, methanol-d$_4$) δ 8.33 (s, 1H), 8.08 (s, 1H), 8.01 (s, 1H), 7.52 (s, 1H), 7.45-7.37 (m, 1H), 6.74 (s, 1H), 5.15 (s, 2H), 4.21-4.14 (m, 1H), 3.86 (s, 2H), 3.83 (s, 3H), 3.38 (s, 3H), 3.28 (s, 3H), 3.21-3.16 (m, 2H), 2.90-2.81 (m, 2H), 2.14-2.06 (m, 2H), 1.92-1.85 (m, 2H), 1.84-1.76 (m, 2H), 1.38 (s, 3H) | 570.3 |
| 201 | ¹H NMR (400 MHz, methanol-d$_4$) δ 8.39 (s, 1H), 8.10 (s, 1H), 8.02 (s, 1H), 7.41 (d, J = 2.0 Hz, 1H), 7.36 (s, 1H), 6.62 (s, 1H), 5.15 (s, 2H), 4.02-3.91 (m, 3H), 3.82 (s, 3H), 3.38-3.33 (m, 5H), 3.30 (s, 3H), 2.68-2.58 (m, 2H), 2.21-2.09 (m, 2H), 1.96-1.77 (m, 4H), 1.42 (s, 3H) | 570.2 |
| 202 | ¹H NMR (400 MHz, methanol-d$_4$) δ 8.41 (s, 1H), 8.09 (s, 1H), 8.02 (s, 1H), 7.42 (t, J = 2.0 Hz, 1H), 7.36 (s, 1H), 6.60 (t, J = 2.0 Hz, 1H), 5.14 (s, 2H), 4.11-4.03 (m, 2H), 4.03-3.94 (m, 1H), 3.88 (s, 2H), 3.39 (s, 3H), 3.38-3.35 (m, 2H), 3.31 (s, 3H), 2.69-2.60 (m, 2H), 2.16-2.07 (m, 2H), 1.94-1.86 (m, 2H), 1.85-1.77 (m, 2H), 1.43-1.38 (m, 6H). | 584.2 |
| 203 | ¹H NMR (400 MHz, methanol-d$_4$) δ 8.32 (s, 1H), 8.08 (s, 1H), 8.01 (s, 1H), 7.50 (s, 1H), 7.40 (s, 1H), 6.72 (s, 1H), 5.14 (s, 2H), 4.18 (m, 1H), 4.06 (m, 2H), 3.86 (s, 2H), 3.38 (s, 3H), 3.28 (s, 3H), 3.18 (m, 2H), 2.88-2.82 (m, 2H), 2.14-2.06 (m, 2H), 1.91-1.85 (m, 2H), 1.84-1.76 (m, 2H), 1.43-1.38 (m, 3H), 1.38 (s, 3H). | 584.3 |
| 204 | ¹H NMR (400 MHz, methanol-d$_4$) δ 8.38 (s, 1H), 7.96 (t, J = 2.0 Hz, 1H), 7.76 (s, 1H), 7.67 (dd, J = 8.0, 1.2 Hz, 1H), 7.65 (s, 1H), 7.44 (t, J = 8.0, 1H), 7.05 (dd, J = 8.0, 1.2 Hz, 1H), 4.95 (s, 2H), 4.70 (s, 2H), 4.63 (s, 2H), 4.25 (d, J = 9.8 Hz, 1H), 3.33 (s, 3H), 3.25 (s, 2H), 3.20 (d, J = 9.8 Hz, 1H), 3.07-3.04 (m, 2H), 2.78-2.75 (m, 1H), 2.76-2.70 (m, 1H), 2.67-2.64 (m, 1H), 2.33-2.26 (m, 2H), 2.24 (s, 3H), 2.24-2.21 (m, 1H), 2.14-2.02 (m, 2H), 0.99 (d, J = 4.8 Hz, 3H), 0.96 (d, J = 4.8 Hz, 3H). | 575.3 |
| 205 | ¹H NMR (400 MHz, methanol-d$_4$) δ 8.33 (s, 1H), 8.09 (s, 1H), 8.01 (s, 1H), 7.53 (s, 1H), 7.43 (t, J = 2.0 Hz, 1H), 6.75 (t, J = 2.0 Hz, 1H), 6.11-5.97 (m, 1H), 5.40 (dd, J = 17.2, 1.6 Hz, 1H), 5.26 (dd, J = 10.8, 1.6 Hz, 1H), 5.14 (s, 2H), 4.59 (d, J = 5.2 Hz, 2H), 4.23-4.13 (m, 1H), 3.86 (s, 2H), 3.38 (s, 3H), 3.29 (s, 3H), 3.21-3.15 (m, 2H), 2.89-2.82 (m, 2H), 2.15-2.05 (m, 2H), 1.93-1.83 (m, 2H), 1.83-1.74 (m, 2H), 1.38 (s, 3H). | 596.3 |
| 206 | ¹H NMR (400 MHz, methanol-d$_4$) δ 8.32 (s, 1H), 8.09 (s, 1H), 8.02 (s, 1H), 7.47 (s, 1H), 7.42 (m, 1H), 6.70 (m, 1H), 5.15 (s, 2H), 4.66-4.61 (m, 1H), 4.17 (m, 1H), 3.89 (s, 2H), 3.39 (s, 3H), 3.29 (s, 3H), 3.18 (m, 2H), 2.88-2.82 (m, 2H), 2.16-2.09 (m, 2H), 1.93-1.87 (m, 2H), 1.85-1.76 (m, 2H), 1.40 (s, 3H), 1.32 (s, 3H), 1.31 (s, 3H). | 598.3 |
| 207 | ¹H NMR (400 MHz, methanol-d$_4$) δ 8.40 (s, 1H), 8.09 (s, 1H), 8.01 (s, 1H), 7.42 (s, 1H), 7.31 (s, 1H), 6.56 (s, 1H), 5.14 (s, 2H), 4.65-4.60 (m, 3H), 3.99-3.97 (m, 1H), 3.89 (s, 3H), 3.38 (s, 3H), 2.65-2.60 (m, 2H), 2.13-2.11 (m, 2H), 2.04-1.87 (m, 3H), 1.83-1.75 (m, 3H), 1.40 (s, 3H), 1.31 (d, J = 6.0 Hz, 6H) | 598.4 |
| 208 | ¹H NMR (400 MHz, methanol-d$_4$) δ 8.33 (s, 1H), 8.10 (s, 1H), 8.03 (s, 1H), 7.49-7.39 (m, 2H), 6.68 (s, 1H), 5.15 (s, 2H), 4.82 (s, 1H), 4.18 (t, J = 7.2 Hz, 1H), 3.92 (s, 2H), 3.39 (s, 3H), 3.29 (s, 3H), 3.22-3.13 (m, 2H), 2.86 (d, J = 10.2 Hz, 2H), 2.14 (d, J = 8.4 Hz, 2H), 1.99-1.87 (m, 4H), 1.79 (s, 6H), 1.65 (s, 2H), 1.42 (s, 3H). | 624.4 |
| 209 | ¹H NMR (400 MHz, methanol-d$_4$) δ 8.38 (s, 1H), 8.13 (s, 1H), 8.06 (s, 1H), 7.02 (s, 1H), 6.96 (s, 1H), 6.28 (s, 1H), 5.12 (s, 2H), 4.09 (s, 2H), 4.00-3.92 (m, 1H), 3.78-3.72 (m, 1H), 3.38 (s, 3H), 3.29 (s, 3H), 2.63-2.57 (m, 2H), 2.31-2.23 (m, 2H), 2.05-1.86 (m, 7H), 1.81-1.56 (m, 5H), 1.54-1.46 (m, 5H). | 623.4 |
| 210 | ¹H NMR (400 MHz, methanol-d$_4$) δ 8.38 (s, 1H), 8.07 (s, 1H), 8.00 (s, 1H), 7.00 (s, 2H), 6.28 (s, 1H), 5.09 (s, 2H), 3.96 (q, J = 7.2 Hz, 1H), 3.90-3.85 (m, 1H), 3.88 (s, 1H), 3.38 (s, 3H), 3.29 (s, 5H), 3.11 (q, J = 7.2 Hz, 2H), 2.65-2.55 (m, 2H), 2.17-2.05 (m, 2H), 1.94-1.75 (m, 4H), 1.39 (s, 3H), 1.22 (t, J = 7.2 Hz, 3H) | 583.2 |
| 211 | ¹H NMR (400 MHz, methanol-d$_4$) δ 8.38 (s, 1H), 8.08 (s, 1H), 8.01 (s, 1H), 6.99 (d, J = 8.0 Hz, 2H), 6.20 (s, 1H), 5.09 (s, 2H), 3.99-3.84 (m, 4H), 3.37 (s, 3H), 3.29 (s, 5H), 2.64-2.56 (m, 2H), 2.37 (d, J = 7.4 Hz, 2H), 2.19-2.11 (m, 2H), 1.94-1.78 (m, 8H), 1.42 (s, 3H) | 609.2 |

TABLE 2-continued

| Compound # | ¹H NMR | LCMS$^a$ |
|---|---|---|
| 212 | ¹H NMR (400 MHz, methanol-d₄) δ 8.41 (s, 1H), 8.18 (s, 1H), 8.11 (s, 1H), 7.42 (s, 1H), 7.32 (s, 1H), 6.58 (s, 1H), 5.19 (s, 2H), 4.85-4.80 (m, 1H), 4.19 (s, 2H), 4.04-3.93 (m, 1H), 3.39 (s, 3H), 3.38-3.34 (m, 3H), 2.68-2.59 (m, 2H), 2.39-2.29 (m, 2H), 2.09-1.89 (m, 7H), 1.87-1.75 (m, 5H), 1.72-1.63 (m, 2H), 1.58 (s, 3H). | 624.5 |
| 213 | ¹H NMR (400 MHz, methanol-d₄) δ 8.33 (s, 1H), 8.10 (s, 1H), 8.02 (s, 1H), 7.52 (s, 1H), 7.41 (s, 1H), 6.72 (s, 1H), 5.93-5.81 (m, 1H), 5.73-5.63 (m, 1H), 5.14 (s, 2H), 4.51 (d, J = 5.6 Hz, 2H), 4.22-4.12 (m, 1H), 3.89 (s, 2H), 3.38 (s, 3H), 3.29 (s, 3H), 3.21-3.14 (m, 2H), 2.89-2.81 (m, 2H), 2.16-2.09 (m, 2H), 1.93-1.78 (m, 4H), 1.74 (d, J = 6.4 Hz, 3H), 1.40 (s, 3H). | 610.3 |
| 214 | ¹H NMR (400 MHz, methanol-d₄) δ 8.40 (s, 1H), 8.10 (s, 1H), 8.02 (s, 1H), 7.18 (s, 1H), 7.07 (s, 1H), 6.44 (s, 1H), 5.12 (s, 2H), 4.02-3.93 (m, 1H), 3.90 (s, 2H), 3.40 (s, 3H), 3.37-3.34 (m, 2H), 3.31 (s, 3H), 2.67-2.59 (m, 2H), 2.41-2.34 (m, 1H), 2.18-2.08 (m, 2H), 1.95-1.77 (m, 4H), 1.41 (s, 3H), 0.77-0.69 (m, 2H), 0.48-0.42 (m, 2H). | 595.2 |
| 215 | ¹H NMR (400 MHz, methanol-d₄) δ 8.38 (s, 1H), 8.07 (s, 1H), 8.00 (s, 1H), 7.01 (s, 1H), 6.97 (s, 1H), 6.26 (s, 1H), 5.09 (s, 2H), 3.98-3.92 (m, 1H), 3.87 (s, 2H), 3.60-3.58 (m, 1H), 3.38 (s, 3H), 3.31-3.26 (m, 5H), 2.63-2.57 (m, 2H), 2.12-2.09 (m, 2H), 1.90-1.76 (m, 4H), 1.39 (s, 3H), 1.17 (d, J = 6.4 Hz, 6H). | 597.3 |
| 216 | ¹H NMR (400 MHz, methanol-d₄) δ 8.40 (s, 1H), 8.09 (s, 1H), 8.02 (s, 1H), 7.08 (d, J = 6.4 Hz, 2H), 6.36 (s, 1H), 5.13 (s, 2H), 3.98 (t, J = 7.2 Hz, 1H), 3.89 (s, 2H), 3.48 (t, J = 6.4 Hz, 2H), 3.40 (s, 3H), 3.31-3.25 (m, 5H), 2.72 (t, J = 6.4 Hz, 2H), 2.67-2.61 (m, 2H), 2.17-2.09 (m, 2H), 1.93-1.79 (m, 4H), 1.41 (s, 3H) | 608.2 |
| 217 | ¹H NMR (400 MHz, methanol-d₄) δ 8.32 (s, 1H), 8.07 (s, 1H), 8.00 (s, 1H), 7.16 (s, 1H), 6.96 (s, 1H), 6.32 (s, 1H), 5.09 (s, 2H), 4.19-4.14 (m, 1H), 3.91-3.85 (m, 3H), 3.38 (s, 3H), 3.28 (s, 3H), 3.16-3.10 (m, 2H), 2.84-2.78 (m, 2H), 2.37-2.35 (m, 2H), 2.14-2.06 (m, 2H), 1.90-1.77 (m, 8H), 1.38 (s, 3H) | 609.3 |
| 218 | ¹H NMR (400 MHz, methanol-d₄) δ 8.32 (s, 1H), 8.07 (s, 1H), 8.00 (s, 1H), 7.13 (s, 1H), 7.00 (s, 1H), 6.38 (s, 1H), 5.09 (s, 2H), 4.22-4.14 (m, 1H), 3.87 (s, 2H), 3.77-3.71 (m, 1H), 3.39 (s, 3H), 3.28 (s, 3H), 3.16-3.11 (m, 2H), 2.84-2.78 (m, 2H), 2.15-2.07 (m, 2H), 2.00-1.93 (m, 2H), 1.92-1.86 (m, 2H), 1.83-1.70 (m, 4H), 1.66-1.58 (m, 2H), 1.50-1.45 (m, 2H), 1.39 (s, 3H) | 623.3 |
| 219 | ¹H NMR (400 MHz, methanol-d₄) δ 8.38 (s, 1H), 8.06 (s, 1H), 7.99 (s, 1H), 7.05 (s, 1H), 7.00 (s, 1H), 6.24 (s, 1H), 5.77-5.68 (m, 1H), 5.15-4.99 (m, 4H), 3.97-3.86 (m, 4H), 3.35 (s, 3H), 3.29-3.24 (m, 5H), 2.64-2.54 (m, 2H), 2.14-2.07 (m, 2H), 1.90-1.77 (m, 4H), 1.39 (s, 3H), 1.28 (d, J = 6.8 Hz, 3H). | 609.2 |
| 220 | ¹H NMR (400 MHz, methanol-d₄) δ 8.38 (s, 1H), 8.07 (s, 1H), 8.00 (s, 1H), 7.05 (s, 1H), 7.00 (s, 1H), 6.24 (s, 1H), 5.77-5.68 (m, 1H), 5.18-4.98 (m, 4H), 3.97-3.86 (m, 4H), 3.35 (s, 3H), 3.29-3.24 (m, 5H), 2.64-2.53 (m, 2H), 2.16-2.07 (m, 2H), 1.91-1.76 (m, 4H), 1.39 (s, 3H), 1.28 (d, J = 6.8 Hz, 3H) | 609.2 |
| 221 | ¹H NMR (400 MHz, methanol-d₄) δ 8.40 (s, 1H), 8.09 (s, 1H), 8.01 (s, 1H), 7.09 (s, 1H), 7.05 (s, 1H), 6.36 (s, 1H), 5.12 (s, 2H), 4.03-3.90 (m, 3H), 3.88 (s, 2H), 3.40 (s, 3H), 3.31 (s, 3H), 2.77-2.58 (m, 5H), 2.17-2.05 (m, 2H), 1.94-1.76 (m, 4H), 1.40 (s, 3H), 1.37 (d, J = 6.4 Hz, 3H). | 622.5 |
| 222 | ¹H NMR (400 MHz, methanol-d₄) δ 8.34 (s, 1H), 8.11 (s, 2H), 8.03 (s, 1H), 7.71 (dd, J = 8.0, 1.2 Hz, 1H), 7.51 (t, J = 8.0 Hz, 1H), 7.28-7.19 (m, 1H), 5.18 (s, 2H), 4.38-4.36 (m, 1H), 3.88 (s, 2H), 3.74-3.70 (m, 1H), 3.38 (s, 3H), 3.25-3.20 (m, 2H), 2.94-2.87 (m, 2H), 2.18-2.07 (m, 2H), 1.92-1.78 (m, 4H), 1.40 (s, 3H), 1.17 (s, 3H), 1.16 (s, 3H). | 568.3 |
| 223 | ¹H NMR (400 MHz, methanol-d₄) δ 8.31 (s, 1H), 8.07 (s, 1H), 8.00 (s, 1H), 7.13 (s, 1H), 6.99 (s, 1H), 6.39 (s, 1H), 5.10 (s, 2H), 4.21-4.14 (m, 1H), 3.87 (s, 2H), 3.62-3.55 (m, 1H), 3.39 (s, 3H), 3.28 (s, 3H), 3.17-3.11 (m, 2H), 2.84-2.78 (m, 2H), 2.15-2.07 (m, 2H), 1.91-1.76 (m, 4H), 1.39 (s, 3H), 1.17 (d, J = 6.0 Hz, 6H) | 597.3 |
| 224 | ¹H NMR (400 MHz, methanol-d₄) δ 8.31 (s, 1H), 8.08 (s, 1H), 8.01 (s, 1H), 7.21 (s, 1H), 7.06 (s, 1H), 6.47 (s, 1H), 5.12 (s, 2H), 4.22-1.14 (m, 1H), 3.88 (s, 2H), 3.47 (t, J = 6.4 Hz, 2H), 3.39 (s, 3H), 3.28 (s, 3H), 3.19-3.12 (m, 2H), | 608.2 |

TABLE 2-continued

| Compound # | ¹H NMR | LCMS$^a$ |
|---|---|---|
| | 2.86-2.79 (m, 2H), 2.70 (t, J = 6.4 Hz, 2H), 2.15-2.07 (m, 2H), 1.91-1.77 (m, 4H), 1.39 (s, 3H) | |
| 225 | ¹H NMR (400 MHz, methanol-d$_4$) δ 8.38 (s, 1H), 8.07 (s, 1H), 8.00 (s, 1H), 7.07 (s, 1H), 7.04 (s, 1H), 6.34 (s, 1H), 5.11 (s, 2H), 3.98-3.86 (m, 4H), 3.38 (s, 3H), 3.29 (s, 5H), 2.70-2.58 (m, 4H), 2.15-2.07 (m, 2H), 1.91-1.77 (m, 4H), 1.38 (s, 3H), 1.35 (d, J = 6.4 Hz, 3H) | 622.3 |
| 226 | ¹H NMR (400 MHz, methanol-d$_4$) δ 8.39 (s, 1H), 8.07 (s, 1H), 8.00 (s, 1H), 7.60 (m, 1H), 7.43-7.41 (m, 1H), 6.79 (s, 1H), 5.14 (s, 2H), 4.01-3.95 (m, 1H), 3.86 (s, 2H), 3.35 (s, 3H), 3.29 (s, 3H), 2.65-2.59 (m, 2H), 2.18-2.03 (m, 3H), 1.99-1.78 (m, 6H), 1.38 (s, 3H), 1.03-0.98 (m, 2H), 0.74-0.69 (m, 2H). | 580.3 |
| 227 | ¹H NMR (400 MHz, methanol-d$_4$) δ 8.31 (s, 1H), 8.08 (s, 1H), 8.00 (s, 1H), 7.16 (s, 1H), 6.98 (s, 1H), 6.40 (s, 1H), 5.10 (s, 2H), 4.22-4.14 (m, 1H), 3.88 (s, 2H), 3.39 (s, 3H), 3.28 (s, 3H), 3.16-3.07 (m, 4H), 2.85-2.78 (m, 2H), 2.16-2.07 (m, 2H), 1.91-1.78 (m, 4H), 1.39 (s, 3H), 1.22 (t, J = 7.2 Hz, 3H) | 583.4 |
| 228 | ¹H NMR (400 MHz, methanol-d$_4$) δ 8.33 (s, 1H), 8.10 (s, 1H), 8.03 (s, 1H), 7.21 (s, 1H), 7.07 (s, 1H), 6.48 (s, 1H), 5.14 (s, 2H), 4.24-4.16 (m, 1H), 3.96-3.88 (m, 3H), 3.41 (s, 3H), 3.30 (s, 3H), 3.20-3.15 (m, 2H), 2.88-2.80 (m, 2H), 2.73-2.64 (m, 2H), 2.17-2.09 (m, 2H), 1.94-1.80 (m, 4H), 1.41 (s, 3H), 1.37 (d, J = 6.4 Hz, 3H) | 622.3 |
| 229 | ¹H NMR (400 MHz, methanol-d$_4$) δ 8.34 (s, 1H), 8.09 (s, 1H), 8.01 (s, 2H), 7.66 (d, J = 8.0 Hz, 1H), 7.46 (t, J = 8.0 Hz, 1H), 7.13 (d, J = 8.0 Hz, 1H), 5.15 (s, 2H), 3.89 (s, 2H), 3.85-3.78 (m, 1H), 3.36 (s, 3H), 3.20-3.14 (m, 4H), 3.06-3.01 (m, 1H), 2.95-2.87 (m, 2H), 2.42-2.27 (m, 2H), 2.16-2.08 (m, 2H), 2.02-1.74 (m, 6H), 1.39 (s, 3H). | 580.4 |
| 230 | ¹H NMR (400 MHz, methanol-d$_4$) δ 8.38 (s, 1H), 8.07 (s, 1H), 8.00 (s, 1H), 7.70 (s, 1H), 7.51 (s, 1H), 6.90 (s, 1H), 5.13 (s, 2H), 4.01-3.98 (m, 1H), 3.86 (s, 2H), 3.38-3.33 (m, 5H), 3.29 (s, 3H), 2.63 (m, 2H), 2.38 (s, 3H), 2.14-2.03 (m, 2H), 1.91-1.77 (m, 4H), 1.38 (s, 3H). | 554.2 |
| 231 | ¹H NMR (400 MHz, methanol-d$_4$) δ 8.32 (s, 1H), 8.07 (s, 1H), 8.00 (s, 1H), 7.21 (s, 1H), 7.15 (s, 1H), 6.54 (s, 1H), 5.09 (s, 2H), 4.19 (q, J = 7.2 Hz, 1H), 3.86 (s, 2H), 3.39 (s, 3H), 3.28 (s, 3H), 3.18-3.11 (m, 2H), 2.82 (t, J = 9.8 Hz, 2H), 2.40-2.33 (m, 1H), 2.15-2.05 (m, 2H), 1.91-1.76 (m, 4H), 1.38 (s, 3H), 0.75-0.68 (m, 2H), 0.43 (d, J = 2.4 Hz, 2H) | 595.3 |
| 232 | ¹H NMR (400 MHz, methanol-d$_4$) δ 8.38 (s, 1H), 8.06 (s, 1H), 7.99 (s, 1H), 7.04 (s, 1H), 7.01 (s, 1H), 6.26 (s, 1H), 5.96-5.80 (m, 1H), 5.24-5.20 (m, 1H), 5.13-5.06 (m, 3H), 3.97-3.91 (m, 1H), 3.86 (s, 2H), 3.74 (d, J = 4.8 Hz, 2H), 3.36 (s, 3H), 3.29 (s, 4H), 3.29-3.25 (m, 1H), 2.62-2.57 (m, 2H), 2.15-2.05 (m, 2H), 1.91-1.76 (m, 4H), 1.38 (s, 3H) | 595.3 |
| 233 | ¹H NMR (400 MHz, methanol-d$_4$) δ 8.31 (s, 1H), 8.08 (s, 1H), 8.01 (s, 1H), 7.19 (s, 1H), 7.05 (s, 1H), 6.47 (s, 1H), 5.12 (s, 2H), 4.24-4.13 (m, 1H), 3.95-3.84 (m, 3H), 3.39 (s, 3H), 3.28 (s, 3H), 3.22-3.10 (m, 2H), 2.87-2.78 (m, 2H), 2.74-2.60 (m, 2H), 2.15-2.04 (m, 2H), 1.91-1.77 (m, 4H), 1.39 (s, 3H), 1.35 (d, J = 6.4 Hz, 3H). | 622.3 |
| 234 | ¹H NMR (400 MHz, methanol-d$_4$) δ 8.39 (s, 1H), 8.07 (s, 1H), 8.00 (s, 1H), 7.04 (s, 1H), 6.96 (s, 1H), 6.18 (s, 1H), 5.09 (s, 2H), 4.95 (t, J = 6.4 Hz, 2H), 4.66-4.60 (m, 1H), 4.55-4.49 (m, 2H), 4.00-3.91 (m, 1H), 3.86 (s, 2H), 3.37 (s, 3H), 3.35 (s, 3H), 3.29 (s, 2H), 2.60 (t, J = 9.6 Hz, 2H), 2.14-2.06 (m, 2H), 1.91-1.76 (m, 4H), 1.38 (s, 3H) | 611.4 |
| 235 | ¹H NMR (400 MHz, methanol-d$_4$) δ 8.32 (s, 1H), 8.09 (s, 1H), 8.01 (s, 1H), 7.85 (s, 1H), 7.56 (s, 1H), 7.06 (s, 1H), 5.16 (s, 2H), 4.17 (m, 1H), 3.87 (s, 2H), 3.37 (s, 3H), 3.29 (s, 3H), 3.20 (m, 2H), 2.86 (m, 2H), 2.73-2.67 (m, 2H), 2.16-2.06 (m, 2H), 1.88 (m, 2H), 1.85-1.75 (m, 2H), 1.39 (s, 3H), 1.25 (m, 3H). | 568.2 |
| 236 | ¹H NMR (400 MHz, methanol-d$_4$) δ 8.39 (s, 1H), 8.08 (s, 1H), 8.01 (s, 1H), 7.69 (m, 1H), 7.56 (s, 1H), 6.93 (s, 1H), 5.15 (s, 2H), 3.98 (m, 1H), 3.87 (s, 2H), 3.38-3.34 (m, 5H), 3.29 (s, 3H), 2.72-2.62 (m, 4H), 2.14-2.07 (m, 2H), 1.92-1.86 (m, 2H), 1.84-1.74 (m, 2H), 1.38 (s, 3H), 1.26-1.22 (m, 1H), 1.24 (m, 2H). | 568.3 |
| 237 | ¹H NMR (400 MHz, methanol-d$_4$) δ 8.32 (s, 1H), 8.09 (s, 1H), 8.01 (s, 1H), 7.86 (s, 1H), 7.52 (s, 1H), 7.04 (s, 1H), 5.15 (s, 2H), 4.17 (m, 1H), 3.87 (s, 2H), 3.37 (s, 3H), 3.28 (s, 3H), 3.18 (m, 2H), 2.90-2.81 (m, 2H), 2.40 (s, 3H), | 554.2 |

TABLE 2-continued

| Compound # | ¹H NMR | LCMS$^a$ |
|---|---|---|
| | 2.16-2.06 (m, 2H), 1.93-1.85 (m, 2H), 1.84-1.74 (m, 2H), 1.38 (s, 3H). | |
| 238 | ¹H NMR (400 MHz, methanol-d$_4$) δ 8.31 (s, 1H), 8.07 (s, 1H), 8.00 (s, 1H), 7.18 (s, 1H), 6.96 (s, 1H), 6.39 (s, 1H), 5.10 (s, 2H), 4.22-4.18 (m, 1H), 3.86 (s, 2H), 3.39 (s, 3H), 3.28 (s, 3H), 3.17-3.12 (m, 2H), 2.85-2.76 (m, 5H), 2.14-2.05 (m, 2H), 1.92-1.77 (m, 4H), 1.38 (s, 3H) | 569.2 |
| 239 | ¹H NMR (400 MHz, methanol-d$_4$) δ 8.38 (s, 1H), 8.07 (s, 1H), 8.00 (s, 1H), 7.01 (s, 1H), 6.98 (s, 1H), 6.27 (s, 1H), 5.10 (s, 2H), 3.96 (t, J = 7.2 Hz, 1H), 3.87 (s, 2H), 3.38 (s, 3H), 3.29 (s, 5H), 2.76 (s, 3H), 2.64-2.58 (m, 2H), 2.15-2.07 (m, 2H), 1.92-1.78 (m, 4H), 1.39 (s, 3H). | 569.3 |
| 240 | ¹H NMR (400 MHz, methanol-d$_4$) δ 8.31 (s, 1H), 8.07 (s, 1H), 8.00 (s, 1H), 7.19 (s, 1H), 6.99 (s, 1H), 6.39 (s, 1H), 5.95-5.81 (m, 1H), 5.28-5.10 (m, 2H), 5.08 (s, 2H), 4.18 (t, J = 7.2 Hz, 1H), 3.86 (s, 2H), 3.74 (d, J = 4.8 Hz, 2H), 3.37 (s, 3H), 3.28 (s, 3H), 3.15-3.10 (m, 2H), 2.84-2.78 (m, 2H), 2.15-2.06 (m, 2H), 1.91-1.77 (m, 4H), 1.38 (s, 3H). | 595.3 |
| 241 | ¹H NMR (400 MHz, methanol-d$_4$) δ 8.33 (s, 1H), 8.09 (s, 1H), 8.01 (s, 1H), 7.52 (s, 1H), 7.32 (s, 1H), 6.58 (s, 1H), 5.33-5.29 (m, 1H), 5.14 (s, 2H), 5.00 (t, J = 6.8 Hz, 2H), 4.69-4.65 (m, 2H), 4.20-4.12 (m, 1H), 3.87 (s, 2H), 3.38 (s, 3H), 3.28 (s, 3H), 3.21-3.15 (m, 2H), 2.89-2.83 (m, 2H), 2.15-2.07 (m, 2H), 1.91-1.77 (m, 4H), 1.38 (s, 3H). | 612.3 |
| 242 | ¹H NMR (400 MHz, methanol-d$_4$) δ 8.42 (s, 1H), 8.09 (s, 1H), 8.03 (s, 1H), 7.39-7.34 (m, 2H), 6.46 (s, 1H), 5.31-5.29 (m, 1H), 5.14 (s, 2H), 5.01 (t, J = 6.8 Hz, 2H), 4.70-4.67 (m, 2H), 4.00-3.97 (m, 1H), 3.88 (s, 2H), 3.40-3.35 (m, 5H), 3.32 (s, 3H), 2.66-2.61 (m, 2H), 2.16-2.08 (m, 2H), 1.92-1.79 (m, 4H), 1.40 (s, 3H). | 612.3 |
| 243 | ¹H NMR (400 MHz, methanol-d$_4$) δ 8.32 (s, 1H), 8.08 (s, 1H), 8.00 (s, 1H), 7.21 (s, 1H), 6.94 (s, 1H), 6.30 (s, 1H), 5.10 (s, 2H), 4.95 (t, J = 6.4 Hz, 2H), 4.63 (t, J = 6.4 Hz, 1H), 4.54-4.50 (m, 2H), 4.17 (t, J = 7.2 Hz, 1H), 3.87 (s, 2H), 3.38 (s, 3H), 3.28 (s, 3H), 3.17-3.11 (m, 2H), 2.85-2.79 (m, 2H), 2.15-2.06 (m, 2H), 1.91-1.77 (m, 4H), 1.38 (s, 3H). | 611.3 |
| 244 | 1H NMR (400 MHz, methanol-d4) δ 8.38 (s, 1H), 8.09 (s, 1H), 8.01 (s, 1H), 7.85 (s, 1H), 7.78 (d, J = 8.4 Hz, 1H), 7.44 (t, J = 8.0 Hz, 1H), 7.07 (d, J = 7.2 Hz, 1H), 5.15 (s, 2H), 4.78-4.74 (m, 1H), 4.57-4.54 (m, 1H), 4.49 (t, J = 6.4 Hz, 1H), 4.28-4.18 (m, 2H), 3.86 (s, 2H), 3.48 (s, 3H), 3.16-3.09 (m, 1H), 2.73-2.52 (m, 2H), 2.16-2.04 (m, 2H), 1.93-1.74 (m, 4H), 1.38 (s, 3H) | 540.3 |
| 245 | 1H NMR (400 MHz, methanol-d4) δ 8.38 (s, 1H), 8.09 (s, 1H), 8.01 (s, 1H), 7.85 (s, 1H), 7.62 (dd, J = 2.0, 8.0 Hz, 1H), 7.45 (t, J = 8.0 Hz, 1H), 7.07 (d, J = 7.6 Hz, 1H), 5.15 (s, 2H), 4.78-4.74 (m, 1H), 4.57-4.54 (m, 1H), 4.50 (t, J = 6.4 Hz, 1H), 4.27-4.18 (m, 2H), 3.86 (s, 2H), 3.48 (s, 3H), 3.20-3.06 (m, 1H), 2.73-2.53 (m, 2H), 2.16-2.04 (m, 2H), 1.91-1.74 (m, 4H), 1.38 (s, 3H) | 540.3 |
| 246 | 1H NMR (400 MHz, methanol-d4) δ 8.36 (s, 1H), 8.02 (t, J = 1.6 Hz, 1H), 7.78 (s, 1H), 7.77-7.69 (m, 2H), 7.49 (t, J = 8.0 Hz, 1H), 7.18 (dd, J = 1.2, 7.6 Hz, 1H), 5.43-5.19 (m, 1H), 4.98 (s, 2H), 3.78 (s, 2H), 3.37 (s, 3H), 3.36-3.27 (m, 2H), 3.27-3.12 (m, 2H), 2.16-2.02 (m, 2H), 1.93-1.72 (m, 4H), 1.37 (s, 3H) | 494.1 |
| 247 | 1H NMR (400 MHz, methanol-d4) δ 8.33 (s, 1H), 8.01 (s, 1H), 7.95 (s, 1H), 7.82 (s, 1H), 7.69 (dd, J = 1.2, 8.0 Hz, 1H), 7.47 (t, J = 8.0 Hz, 1H), 7.17 (d, J = 4.4 Hz, 1H), 7.03 (t, J = 55.2 Hz, 1H), 5.40-5.17 (m, 1H), 5.10 (s, 2H), 3.81 (s, 2H), 3.36 (s, 3H), 3.34-3.31 (m, 1H), 3.28-3.24 (m, 1H), 3.22-3.11 (m, 2H), 2.14-2.03 (m, 2H), 1.90-1.73 (m, 4H), 1.37 (s, 3H). | 510.4 |
| 248 | 1H NMR (400 MHz, methanol-d4) δ 8.36 (s, 1H), 8.09 (s, 1H), 8.01 (s, 1H), 7.90 (s, 1H), 7.74 (d, J = 8.0 Hz, 1H), 7.44 (t, J = 8.0 Hz, 1H), 7.14 (d, J = 8.4 Hz, 1H), 5.14 (s, 2H), 4.29 (d, J = 8.0 Hz, 1H), 3.86 (s, 2H), 3.54 (s, 3H), 2.40-2.29 (m, 1H), 2.24-2.03 (m, 2H), 1.98-1.83 (m, 3H), 1.83-1.59 (m, 6H), 1.59-1.43 (m, 2H), 1.38 (s, 3H), 1.31-1.16 (m, 2H). | 552.4 |
| 249 | 1H NMR (400 MHz, methanol-d4) δ 8.36 (s, 1H), 8.09 (s, 1H), 8.01 (s, 1H), 7.90 (s, 1H), 7.74 (d, J = 8.4 Hz, 1H), 7.44 (t, J = 8.0 Hz, 1H), 7.14 (d, J = 8.0 Hz, 1H), 5.14 (s, 2H), 4.28 (d, J = 8.0 Hz, 1H), 3.86 (s, 2H), 3.54 (s, 3H), 2.40-2.30 (m, 1H), 2.23-2.02 (m, 3H), 1.97-1.84 (m, 3H), 1.84-1.72 (m, 3H), 1.72-1.59 (m, 3H), 1.59-1.44 (m, 2H), 1.38 (s, 3H), 1.32-1.16 (m, 2H). | 552.4 |

TABLE 2-continued

| Compound # | 1H NMR | LCMS$^a$ |
|---|---|---|
| 250 | 1H NMR (400 MHz, methanol-d4) δ 8.33 (s, 1H), 8.09 (s, 1H), 8.01 (s, 1H), 7.87 (s, 1H), 7.78 (d, J = 7.6 Hz, 1H), 7.42 (t, J = 8.0 Hz, 1H), 7.21 (d, J = 8.4 Hz, 1H), 5.15 (s, 2H), 3.94 (d, J = 10.4 Hz, 1H), 3.86 (s, 2H), 3.61 (s, 3H), 2.47-2.34 (m, 1H), 2.15-2.04 (m, 2H), 1.93-1.63 (m, 8H), 1.52-1.40 (m, 2H), 1.38 (s, 3H), 1.30-1.18 (m, 2H), 1.13-0.95 (m, 2H). | 552.4 |
| 251 | 1H NMR (400 MHz, methanol-d4) δ 8.33 (s, 1H), 8.09 (s, 1H), 8.01 (s, 1H), 7.87 (s, 1H), 7.78 (d, J = 6.8 Hz, 1H), 7.42 (t, J = 8.0 Hz, 1H), 7.21 (d, J = 8.4 Hz, 1H), 5.15 (s, 2H), 3.94 (d, J = 10.4 Hz, 1H), 3.87 (s, 2H), 3.61 (s, 3H), 2.47-2.35 (m, 1H), 2.16-2.04 (m, 2H), 1.94-1.64 (m, 8H), 1.51-1.40 (m, 2H), 1.38 (s, 3H), 1.35-1.18 (m, 2H), 1.14-0.93 (m, 2H). | 552.4 |
| 252 | 1H NMR (400 MHz, methanol-d4) δ 8.37 (s, 1H), 8.10 (s, 1H), 8.02 (s, 1H), 7.89 (s, 1H), 7.75 (d, J = 6.8 Hz, 1H), 7.45 (t, J = 8.0 Hz, 1H), 7.13 (d, J = 7.6 Hz, 1H), 5.15 (s, 2H), 4.42 (t, J = 8.0 Hz, 1H), 3.96-3.85 (m, 4H), 3.54 (s, 3H), 2.36-2.25 (m, 1H), 2.20-2.02 (m, 3H), 1.96-1.75 (m, 6H), 1.65-1.50 (m, 3H), 1.41 (s, 3H), 1.39-1.26 (m, 2H). | 568.4 |
| 253 | 1H NMR (400 MHz, methanol-d4) δ 8.37 (s, 1H), 8.10 (s, 1H), 8.02 (s, 1H), 7.89 (s, 1H), 7.75 (d, J = 8.4 Hz, 1H), 7.44 (t, J = 8.0 Hz, 1H), 7.13 (d, J = 7.6 Hz, 1H), 5.15 (s, 2H), 4.42 (t, J = 8.0 Hz, 1H), 3.96-3.85 (m, 4H), 3.54 (s, 3H), 2.36-2.26 (m, 1H), 2.17-2.03 (m, 3H), 1.94-1.75 (m, 6H), 1.66-1.51 (m, 3H), 1.39 (s, 3H), 1.37-1.27 (m, 2H). | 568.4 |
| 254 | 1H NMR (400 MHz, methanol-d4) δ 8.37 (s, 1H), 8.11 (s, 1H), 8.03 (s, 1H), 7.96 (s, 1H), 7.76 (d, J = 6.8 Hz, 1H), 7.45 (t, J = 8.0 Hz, 1H), 7.19 (d, J = 7.6 Hz, 1H), 5.16 (d, J = 4.8 Hz, 1H), 4.62-4.55 (m, 1H), 4.43-4.36 (m, 1H), 4.24 (d, J = 5.6 Hz, 1H), 4.03-3.93 (m, 2H), 3.92 (s, 2H), 3.53 (s, 3H), 2.74-2.58 (m, 2H), 2.20-2.08 (m, 2H), 1.96-1.77 (m, 4H), 1.49 (s, 3H), 1.41 (s, 3H). | 554.4 |
| 255 | 1H NMR (400 MHz, methanol-d4) δ 8.36 (s, 1H), 8.10 (s, 1H), 8.02 (s, 1H), 7.96 (s, 1H), 7.75 (d, J = 8.4 Hz, 1H), 7.45 (t, J = 8.0 Hz, 1H), 7.19 (d, J = 6.0 Hz, 1H), 5.16 (d, J = 4.8 Hz, 1H), 4.61-4.54 (m, 1H), 4.42-4.36 (m, 1H), 4.24 (d, J = 6.0 Hz, 1H), 4.02-3.93 (m, 2H), 3.90 (s, 2H), 3.53 (s, 3H), 2.73-2.59 (m, 2H), 2.18-2.06 (m, 2H), 1.95-1.76 (m, 4H), 1.49 (s, 3H), 1.40 (s, 3H). | 554.4 |
| 256 | 1H NMR (400 MHz, methanol-d4) δ 8.33 (s, 1H), 8.08 (s, 1H), 8.01 (s, 1H), 7.88 (s, 1H), 7.77 (d, J = 7.6 Hz, 1H), 7.42 (t, J = 8.0 Hz, 1H), 7.20 (d, J = 7.6 Hz, 1H), 5.17 (s, 2H), 4.00 (d, J = 10.8 Hz, 1H), 3.86 (s, 2H), 3.59 (s, 3H), 3.00-2.88 (m, 1H), 2.16-1.96 (m, 3H), 1.93-1.84 (m, 2H), 1.83-1.64 (m, 5H), 1.60-1.47 (m, 2H), 1.38 (s, 3H), 1.35-1.26 (m, 1H), 1.25-1.12 (m, 1H). | 538.4 |
| 257 | 1H NMR (400 MHz, methanol-d4) δ 8.33 (s, 1H), 8.08 (s, 1H), 8.00 (s, 1H), 7.89 (s, 1H), 7.77 (d, J = 8.0 Hz, 1H), 7.42 (t, J = 6.0 Hz, 1H), 7.21 (d, J = 7.2 Hz, 1H), 5.14 (s, 2H), 4.00 (d, J = 10.8 Hz, 1H), 3.86 (s, 2H), 3.59 (s, 3H), 3.02-2.88 (m, 1H), 2.15-2.05 (m, 2H), 2.05-1.95 (m, 1H), 1.93-1.84 (m, 2H), 1.84-1.74 (m, 2H), 1.74-1.63 (m, 3H), 1.63-1.44 (m, 2H), 1.38 (s, 3H), 1.35-1.25 (m, 1H), 1.25-1.12 (m, 1H) | 538.4 |
| 258 | 1H NMR (400 MHz, methanol-d4) δ 8.36 (s, 1H), 8.09 (s, 1H), 8.01 (s, 1H), 7.84 (s, 1H), 7.76 (d, J = 8.4 Hz, 1H), 7.42 (t, J = 8.0 Hz, 1H), 7.10 (d, J = 7.6 Hz, 1H), 5.13 (s, 2H), 4.24 (d, J = 11.2 Hz, 1H), 3.87 (s, 2H), 3.53 (s, 3H), 2.32-2.21 (m, 1H), 2.16-2.04 (m, 2H), 2.02-1.85 (m, 7H), 1.85-1.72 (m, 3H), 1.38 (s, 3H) | 524.4 |
| 259 | 1H NMR (400 MHz, methanol-d4) δ 8.36 (s, 1H), 8.08 (s, 1H), 8.01 (s, 1H), 7.84 (s, 1H), 7.76 (d, J = 8.0 Hz, 1H), 7.42 (t, J = 8.0 Hz, 1H), 7.10 (d, J = 7.6 Hz, 1H), 5.13 (s, 2H), 4.24 (d, J = 11.2 Hz, 1H), 3.86 (s, 2H), 3.53 (s, 3H), 2.32-2.21 (m, 1H), 2.15-2.04 (m, 2H), 1.98-1.72 (m, 10H), 1.38 (s, 3H) | 524.4 |
| 260 | 1H NMR (400 MHz, methanol-d4) δ 8.37 (s, 1H), 8.09 (s, 1H), 8.01 (s, 1H), 7.85 (s, 1H), 7.77 (d, J = 9.6 Hz, 1H), 7.43 (t, J = 8.0 Hz, 1H), 7.10 (d, J = 7.2 Hz, 1H), 5.89 (t, J = 55.2 Hz, 1H), 5.14 (s, 2H), 4.22 (d, J = 10.4 Hz, 1H), 4.04-3.93 (m, 1H), 3.87 (s, 2H), 3.57 (td, J = 4.0, 14.4 Hz, 1H), 3.51 (s, 3H), 2.85-2.73 (m, 1H), 2.67-2.57 (m, 1H), 2.29-2.17 (m, 1H), 2.16-2.05 (m, 2H), 1.94-1.65 (m, 6H), 1.39 (s, 3H). | 604.3 |
| 261 | 1H NMR (400 MHz, methanol-d4) δ 8.36 (s, 1H), 8.10 (s, 1H), 8.02 (s, 1H), 7.88 (s, 1H), 7.77 (d, J = 8.4 Hz, 1H), 7.44 (t, J = 8.0 Hz, 1H), 7.12 (d, J = 8.0 Hz, 1H), 6.05-5.75 (m, 1H), 5.15 (s, 2H), 4.27 (d, J = 11.2 Hz, 1H), 3.90 (s, 1H), | 604.3 |

TABLE 2-continued

| Compound # | 1H NMR | LCMS$^a$ |
|---|---|---|
| | 3.87 (s, 2H), 3.64-3.54 (m, 2H), 3.53 (s, 3H), 2.40-2.30 (m, 1H), 2.23-2.09 (m, 3H), 2.09-1.97 (m, 3H), 1.94-1.76 (m, 4H), 1.40 (s, 3H). | |
| 262 | 1H NMR (400 MHz, methanol-d4) δ 8.37 (s, 1H), 8.08 (s, 1H), 8.00 (s, 1H), 7.84 (s, 1H), 7.77 (d, J = 8.0 Hz, 1H), 7.43 (t, J = 8.0 Hz, 1H), 7.09 (d, J = 8.0 Hz, 1H), 5.89 (tt, J = 4.0, 55.6 Hz, 1H), 5.13 (s, 2H), 4.22 (d, J = 10.8 Hz, 1H), 4.04-3.93 (m, 1H), 3.85 (s, 2H), 3.57 (td, J = 4.0, 14.4 Hz, 1H), 3.53 (s, 3H), 2.88-2.73 (m, 1H), 2.68-2.56 (m, 1H), 2.29-2.18 (m, 1H), 2.15-2.03 (m, 2H), 1.93-1.64 (m, 6H), 1.38 (s, 3H). | 604.4 |
| 263 | 1H NMR (400 MHz, methanol-d4) δ 8.36 (s, 1H), 8.10 (s, 1H), 8.02 (s, 1H), 7.88 (s, 1H), 7.77 (d, J = 8.4 Hz, 1H), 7.44 (t, J = 8.0 Hz, 1H), 7.12 (d, J = 8.4 Hz, 1H), 6.05-5.75 (m, 1H), 5.15 (s, 2H), 4.27 (d, J = 12.0 Hz, 1H), 3.89 (s, 1H), 3.87 (s, 2H), 3.61-3.47 (m, 2H), 3.53 (s, 3H), 2.41-2.30 (m, 1H), 2.25-2.10 (m, 3H), 2.10-1.96 (m, 3H), 1.95-1.75 (m, 4H), 1.40 (s, 3H). | 604.4 |
| 264 | 1H NMR (400 MHz, methanol-d4) δ 8.37 (s, 1H), 8.09 (s, 1H), 8.01 (s, 1H), 7.84 (s, 1H), 7.77 (d, J = 8.0 Hz, 1H), 7.43 (t, J = 8.0 Hz, 1H), 7.09 (d, J = 8.0 Hz, 1H), 5.14 (s, 2H), 4.20 (d, J = 10.4 Hz, 1H), 3.95-3.88 (m, 1H), 3.87 (s, 2H), 3.51 (s, 3H), 3.42 (q, J = 6.8 Hz, 2H), 2.88-2.75 (m, 1H), 2.65-2.55 (m, 1H), 2.27-2.16 (m, 1H), 2.16-2.05 (m, 2H), 1.94-1.85 (m, 2H), 1.85-1.74 (m, 3H), 1.70-1.60 (m, 1H), 1.38 (s, 3H), 1.16 (t, J = 6.8 Hz, 3H) | 568.4 |
| 265 | 1H NMR (400 MHz, methanol-d4) δ 8.37 (s, 1H), 8.09 (s, 1H), 8.01 (s, 1H), 7.84 (s, 1H), 7.77 (d, J = 8.4 Hz, 1H), 7.43 (d, J = 8.0 Hz, 1H), 7.09 (d, J = 8.0 Hz, 1H), 5.14 (s, 2H), 4.20 (d, J = 10.4 Hz, 1H), 3.93-3.88 (m, 1H), 3.88 (s, 2H), 3.51 (s, 3H), 3.42 (q, J = 7.2 Hz, 2H), 2.86-2.75 (m, 1H), 2.66-2.54 (m, 1H), 2.25-2.17 (m, 1H), 2.17-2.05 (m, 2H), 1.94-1.85 (m, 2H), 1.85-1.74 (m, 3H), 1.70-1.60 (m, 1H), 1.39 (s, 3H), 1.16 (t, J = 7.2 Hz, 3H) | 568.4 |
| 266 | 1H NMR (400 MHz, methanol-d4) δ 8.36 (s, 1H), 8.09 (s, 1H), 8.01 (s, 1H), 7.88 (s, 1H), 7.77 (d, J = 6.8 Hz, 1H), 7.44 (t, J = 8.0 Hz, 1H), 7.12 (d, J = 8.4 Hz, 1H), 5.15 (s, 2H), 4.28 (d, J = 10.8 Hz, 1H), 4.22-4.15 (m, 1H), 3.88 (s, 2H), 3.53 (s, 3H), 3.45-3.36 (m, 2H), 2.35-1.74 (m, 11H), 1.39 (s, 3H), 1.17 (t, J = 7.2 Hz, 3H) | 568.4 |
| 267 | 1H NMR (400 MHz, methanol-d4) δ 8.36 (s, 1H), 8.09 (s, 1H), 8.01 (s, 1H), 7.88 (s, 1H), 7.77 (d, J = 8.4 Hz, 1H), 7.44 (t, J = 8.0 Hz, 1H), 7.13 (d, J = 8.4 Hz, 1H), 5.15 (s, 2H), 4.28 (d, J = 11.6 Hz, 1H), 4.22-4.14 (m, 1H), 3.88 (s, 2H), 3.53 (s, 3H), 3.45-3.36 (m, 2H), 2.37-1.75 (m, 11H), 1.39 (s, 3H), 1.17 (t, J = 7.2 Hz, 3H) | 568.4 |
| 268 | 1H NMR (400 MHz, methanol-d4) δ 8.35 (s, 1H), 8.09 (s, 1H), 8.01 (s, 1H), 7.86 (s, 1H), 7.75 (d, J = 7.6 Hz, 1H), 7.43 (t, J = 8.0 Hz, 1H), 7.10 (d, J = 7.2 Hz, 1H), 5.14 (s, 2H), 4.17 (t, J = 8.0 Hz, 1H), 3.87 (s, 2H), 3.52 (s, 3H), 2.46-2.35 (m, 1H), 2.35-2.19 (m, 2H), 2.17-2.03 (m, 3H), 2.00-1.60 (m, 9H), 1.38 (s, 3H) | 538.4 |
| 269 | 1H NMR (400 MHz, methanol-d4) δ 8.35 (s, 1H), 8.09 (s, 1H), 8.01 (s, 1H), 7.85 (s, 1H), 7.75 (d, J = 7.6 Hz, 1H), 7.43 (t, J = 8.0 Hz, 1H), 7.10 (d, J = 7.6 Hz, 1H), 5.14 (s, 2H), 4.17 (t, J = 8.0 Hz, 1H), 3.87 (s, 2H), 3.52 (s, 3H), 2.48-2.36 (m, 1H), 2.36-2.20 (m, 2H), 2.17-2.03 (m, 3H), 1.98-1.63 (m, 9H), 1.38 (s, 3H) | 538.4 |
| 270 | 1H NMR (400 MHz, methanol-d4) δ 8.40 (s, 1H), 7.91 (t, J = 2.0 Hz, 1H), 7.82-7.76 (m, 2H), 7.73 (s, 1H), 7.45 (t, J = 8.0 Hz, 1H), 7.08 (d, J = 2.8 Hz, 1H), 5.00-4.90 (m, 3H), 4.78 (d, J = 11.2 Hz, 1H), 4.70-4.60 (m, 2H), 4.47-4.40 (m, 1H), 4.07-3.95 (m, 1H), 3.79 (s, 2H), 3.50 (s, 3H), 2.15-2.02 (m, 2H), 1.95-1.73 (m, 4H), 1.37 (s, 3H) | 492.3 |
| 271 | 1H NMR (400 MHz, methanol-d4) δ 8.40 (s, 1H), 7.92-7.87 (m, 2H), 7.85 (s, 1H), 7.79 (d, J = 8.0 Hz, 1H), 7.47 (t, J = 8.0 Hz, 1H), 7.15 (d, J = 8.0 Hz, 1H), 5.04 (s, 2H), 5.00-4.92 (m, 1H), 4.79 (d, J = 11.2 Hz, 1H), 4.68-4.58 (m, 2H), 4.48-4.40 (m, 1H), 4.19 (s, 2H), 4.07-3.94 (m, 1H), 3.51 (s, 3H), 2.46-2.35 (m, 2H), 2.13-1.91 (m, 4H), 1.62 (s, 3H). | 492.4 |
| 272 | 1H NMR (400 MHz, methanol-d4) δ 8.47 (s, 1H), 8.02 (t, J = 1.6 Hz, 1H), 7.78 (s, 1H), 7.77-7.69 (m, 2H), 7.49 (t, J = 8.0 Hz, 1H), 7.18 (dd, J = 1.2, 7.6 Hz, 1H), 5.43-5.19 (m, 1H), 4.98 (s, 2H), 3.78 (s, 2H), 3.37 (s, 3H), 3.36-3.27 (m, 2H), 3.27-3.12 (m, 2H), 2.16-2.02 (m, 2H), 1.93-1.72 (m, 4H), 1.37 (s, 3H) | 510.4 |
| 273 | 1H NMR (400 MHz, methanol-d4) δ 8.47 (s, 1H), 8.11 (s, 1H), 7.97 (s, 1H), 7.93 (s, 1H), 7.71 (dd, J = 1.6, 8.0 Hz, | 510.4 |

TABLE 2-continued

| Compound # | ¹H NMR | LCMS$^a$ |
|---|---|---|
| | 1H), 7.53 (t, J = 8.0 Hz, 1H), 7.22-7.16 (m, 1H), 7.13 (t, J = 55.2 Hz, 1H), 5.20 (s, 2H), 5.10 (dt, J = 6.8, 55.6 Hz, 1H), 4.32 (s, 2H), 3.55-3.45 (m, 1H), 3.35 (s, 3H), 3.02-2.88 (m, 2H), 2.52-2.40 (m, 2H), 2.17-1.95 (m, 4H), 1.68 (s, 3H) | |
| 274 | 1H NMR (400 MHz, methanol-d4) δ 8.34 (s, 1H), 7.98 (s, 1H), 7.83 (d, J = 3.2 Hz, 1H), 7.06 (t, J = 55.2 Hz, 1H), 6.12 (s, 1H), 5.23 (s, 2H), 3.89 (s, 2H), 3.40-3.33 (m, 5H), 2.94-2.86 (m, 2H), 2.79-2.68 (m, 1H), 2.63-2.54 (m, 2H), 2.21-2.10 (m, 2H), 1.96-1.78 (m, 4H), 1.43 (s, 3H), 1.22 (t, J = 7.2 Hz, 3H), 1.16 (d, J = 6.4 Hz, 3H) | 550.4 |
| 275 | 1H NMR (400 MHz, methanol-d4) δ 8.38 (s, 1H), 8.09 (s, 1H), 8.01 (s, 1H), 7.91 (s, 1H), 7.78 (d, J = 7.6 Hz, 1H), 7.46 (t, J = 8.0 Hz, 1H), 7.14 (d, J = 8.0 Hz, 1H), 5.16 (s, 2H), 4.30 (t, J = 8.0 Hz, 1H), 3.90-3.82 (m, 3H), 3.78-3.66 (m, 2H), 3.53 (s, 3H), 3.40-3.34 (m, 1H), 2.46-2.36 (m, 1H), 2.33-2.24 (m, 1H), 2.24-2.04 (m, 4H), 1.93-1.84 (m, 2H), 1.84-1.75 (m, 2H), 1.75-1.62 (m, 1H), 1.39 (s, 3H) | 554.3 |
| 276 | 1H NMR (400 MHz, methanol-d4) δ 8.38 (s, 1H), 8.09 (s, 1H), 8.02 (s, 1H), 7.90 (s, 1H), 7.78 (d, J = 9.6 Hz, 1H), 7.46 (t, J = 8.0 Hz, 1H), 7.14 (d, J = 8.0 Hz, 1H), 5.16 (s, 2H), 4.31 (t, J = 8.0 Hz, 1H), 3.98-3.93 (m, 1H), 3.90-3.81 (m, 3H), 3.73-3.66 (m, 1H), 3.54 (s, 3H), 3.50-3.44 (m, 1H), 2.50-2.40 (m, 1H), 2.30-2.17 (m, 2H), 2.17-2.05 (m, 2H), 2.03-1.94 (m, 1H), 1.94-1.85 (m, 2H), 1.85-1.74 (m, 2H), 1.67-1.58 (m, 1H), 1.39 (s, 3H) | 554.3 |
| 277 | 1H NMR (400 MHz, methanol-d4) δ 8.38 (s, 1H), 8.10 (s, 1H), 8.02 (s, 1H), 7.91 (s, 1H), 7.77 (d, J = 8.8 Hz, 1H), 7.46 (t, J = 8.0 Hz, 1H), 7.14 (d, J = 7.6 Hz, 1H), 5.17 (s, 2H), 4.34-4.27 (m, 1H), 3.88 (s, 2H), 3.88-3.82 (m, 1H), 3.78-3.66 (m, 2H), 3.53 (s, 3H), 3.41-3.34 (m, 1H), 2.47-2.37 (m, 1H), 2.32-2.25 (m, 1H), 2.25-2.15 (m, 2H), 2.15-2.05 (m, 2H), 1.95-1.85 (m, 2H), 1.85-1.75 (m, 2H), 1.73-1.65 (m, 1H), 1.39 (s, 3H) | 554.4 |
| 278 | 1H NMR (400 MHz, methanol-d4) δ 8.38 (s, 1H), 8.10 (s, 1H), 8.02 (s, 1H), 7.90 (s, 1H), 7.80-7.75 (m, 1H), 7.48-7.42 (m, 1H), 7.16-7.11 (m, 1H), 5.16 (s, 2H), 4.32-4.26 (m, 1H), 3.99-3.94 (m, 1H), 3.90-3.81 (m, 3H), 3.73-3.66 (m, 1H), 3.54 (s, 3H), 3.50-3.43 (m, 1H), 2.50-2.39 (m, 1H), 2.30-2.18 (m, 2H), 2.18-2.05 (m, 2H), 2.05-1.95 (m, 1H), 1.95-1.85 (m, 2H), 1.85-1.75 (m, 2H), 1.66-1.57 (m, 1H), 1.39 (s, 3H) | 554.4 |
| 279 | 1H NMR (400 MHz, methanol-d4) δ 8.36 (s, 1H), 8.09 (s, 1H), 8.03-7.98 (m, 2H), 7.68 (dd, J = 1.6, 8.0 Hz, 1H), 7.48 (t, J = 8.0 Hz, 1H), 7.17 (d, J = 8.0 Hz, 1H), 5.15 (s, 2H), 3.86 (s, 2H), 3.33 (s, 3H), 3.07-2.96 (m, 2H), 2.86-2.77 (m, 2H), 2.21-2.05 (m, 4H), 1.92-1.75 (m, 4H), 1.38 (s, 3H) | 510.4 |
| 280 | 1H NMR (400 MHz, CDCl3) δ 8.20 (s, 1H), 8.10 (s, 1H), 8.00 (s, 1H), 7.91 (s, 1H), 7.52 (d, J = 8.4 Hz, 1H), 7.44 (d, J = 8.0 Hz, 1H), 7.13 (d, J = 7.6 Hz, 1H), 4.99 (s, 2H), 4.44 (quint, J = 7.2 Hz, 1H), 4.23 (s, 2H), 3.88 (s, 2H), 3.32 (s, 3H), 3.29-3.20 (m, 2H), 3.19-3.08 (m, 2H), 2.04-1.95 (m, 2H), 1.95-1.87 (m, 2H), 1.83-1.74 (m, 2H), 1.34 (s, 3H) | 565.4 |
| 281 | 1H NMR (400 MHz, CDCl3) δ 8.09 (s, 1H), 8.06 (s, 1H), 7.95 (s, 1H), 7.91 (s, 1H), 7.56 (dd, J = 1.6, 8.0 Hz, 1H), 7.42 (t, J = 8.0 Hz, 1H), 7.03 (d, J = 8.0 Hz, 1H), 4.98 (s, 2H), 4.33 (quint, J = 7.2 Hz, 1H), 4.22 (s, 2H), 3.87 (s, 2H), 3.55-3.46 (m, 2H), 3.31 (s, 3H), 2.84-2.74 (m, 2H), 2.05-1.94 (m, 2H), 1.94-1.84 (m, 2H), 1.83-1.72 (m, 2H), 1.34 (s, 3H) | 565.5 |
| 282 | 1H NMR (400 MHz, methanol-d4) δ 8.36 (s, 1H), 8.19 (s, 1H), 8.12 (s, 1H), 7.96 (t, J = 1.7 Hz, 1H), 7.69 (dd, J = 1.6, 8.0 Hz, 1H), 7.51 (t, J = 8.0 Hz, 1H), 7.16 (dd, J = 0.8, 8.0 Hz, 1H), 5.21 (s, 2H), 4.25 (s, 2H), 3.95-3.89 (m, 2H), 3.87-3.78 (m, 2H), 3.29 (s, 3H), 2.62 (d, J = 14.0 Hz, 2H), 2.45-2.34 (m, 4H), 2.10-1.93 (m, 4H), 1.61 (s, 3H) | 540.4 |
| 283 | 1H NMR (400 MHz, methanol-d4) δ 8.44 (br s, 1H), 8.08 (s, 1H), 8.01 (s, 1H), 7.80 (t, J = 2.0 Hz, 1H), 7.64 (dd, J = 1.6, 8.0 Hz, 1H), 7.43 (t, J = 8.0 Hz, 1H), 7.01 (d, J = 8.8 Hz, 1H), 5.14 (s, 2H), 3.86 (s, 2H), 3.60 (s, 3H), 2.15-2.03 (m, 2H), 1.93-1.84 (m, 2H), 1.84-1.74 (m, 2H), 1.64-1.53 (m, 4H), 1.38 (s, 3H) | 496.2 |
| 284 | 1H NMR (400 MHz, DMSO-d6) δ 8.36 (s, 1H), 8.10 (s, 1H), 8.07 (s, 1H), 7.90 (s, 1H), 7.82 (dd, J = 2.0, 8.0 Hz, 1H), 7.40 (t, J = 8.0 Hz, 1H), 7.01 (d, J = 8.0 Hz, 1H), 5.15 (s, 2H), 4.78-4.72 (m, 2H), 4.51-4.46 (m, 2H), 4.29 (t, J = | 540.1 |

TABLE 2-continued

| Compound # | ¹H NMR | LCMS$^a$ |
|---|---|---|
| | 6.0 Hz, 1H), 4.12-4.03 (m, 1H), 3.94-3.85 (m, 1H), 3.38 (s, 3H), 1.94-1.64 (m, 4H), 1.57-1.49 (m, 2H), 1.44-1.38 (m, 1H), 1.27 (d, J = 6.8 Hz, 3H), 1.06 (s, 3H) | |
| 285 | 1H NMR (400 MHz, DMSO-d6) δ 8.37 (s, 1H), 8.10 (s, 1H), 8.07 (s, 1H), 7.90 (s, 1H), 7.82 (d, J = 8.4 Hz, 1H), 7.40 (t, J = 8.0 Hz, 1H), 7.01 (d, J = 7.2 Hz, 1H), 5.15 (s, 2H), 4.78-4.72 (m, 2H), 4.52-4.46 (m, 2H), 4.29 (t, J = 6.4 Hz, 1H), 4.13-4.05 (m, 1H), 3.92-3.84 (m, 1H), 3.38 (s, 3H), 1.88-1.69 (m, 4H), 1.56-1.50 (m, 2H), 1.43-1.38 (m, 1H), 1.27 (d, J = 6.4 Hz, 3H), 1.06 (s, 3H) | 540.2 |
| 286 | 1H NMR (400 MHz, methanol-d4) δ 8.38 (s, 1H), 8.09 (s, 1H), 8.01 (s, 1H), 7.90 (s, 1H), 7.76 (dd, J = 2.0, 8.0 Hz, 1H), 7.45 (t, J = 8.0 Hz, 1H), 7.10 (d, J = 8.0 Hz, 1H), 5.15 (s, 2H), 4.40 (t, J = 8.0 Hz, 1H), 3.86 (s, 2H), 3.53 (s, 3H), 3.14-2.97 (m, 4H), 2.44-2.30 (m, 2H), 2.17-2.05 (m, 4H), 1.96-1.77 (m, 6H), 1.73-1.60 (m, 1H), 1.38 (s, 3H) | 616.4 |
| 287 | 1H NMR (400 MHz, methanol-d4) δ 8.38 (s, 1H), 8.09 (s, 1H), 8.01 (s, 1H), 7.90 (s, 1H), 7.76 (dd, J = 1.2, 8.4 Hz, 1H), 7.45 (t, J = 8.0 Hz, 1H), 7.10 (d, J = 7.6 Hz, 1H), 5.15 (s, 2H), 4.40 (t, J = 8.0 Hz, 1H), 3.86 (s, 2H), 3.53 (s, 3H), 3.14-2.98 (m, 4H), 2.41-2.33 (m, 2H), 2.17-2.07 (m, 4H), 1.95-1.83 (m, 4H), 1.83-1.77 (m, 2H), 1.72-1.63 (m, 1H), 1.38 (s, 3H) | 616.3 |
| 288 | 1H NMR (400 MHz, methanol-d4) δ 8.34 (s, 1H), 8.01 (s, 1H), 7.81 (s, 1H), 7.77 (s, 1H), 7.73 (dd, J = 1.2, 8.4 Hz, 1H), 7.49 (t, J = 8.0 Hz, 1H), 7.17 (d, J = 7.6 Hz, 1H), 5.41-5.19 (m, 1H), 4.97 (s, 2H), 4.06 (q, J = 6.8 Hz, 1H), 3.37 (s, 3H), 3.35-3.27 (m, 2H), 3.25-3.11 (m, 2H), 2.01 (q, J = 9.2 Hz, 1H), 1.90-1.80 (m, 1H), 1.80-1.70 (m, 1H), 1.69-1.56 (m, 2H), 1.48-1.40 (m, 1H), 1.38 (d, J = 6.8 Hz, 3H), 1.24 (s, 3H) | 508.3 |
| 289 | 1H NMR (400 MHz, methanol-d4) δ 8.34 (s, 1H), 8.00 (s, 1H), 7.81 (s, 1H), 7.77 (s, 1H), 7.73 (dd, J = 1.2, 8.0 Hz, 1H), 7.49 (t, J = 8.0 Hz, 1H), 7.17 (d, J = 8.0 Hz, 1H), 5.41-5.19 (m, 1H), 4.97 (s, 2H), 4.06 (q, J = 6.8 Hz, 1H), 3.37 (s, 3H), 3.36-3.27 (m, 2H), 3.24-3.12 (m, 2H), 2.01 (q, J = 10.0 Hz, 1H), 1.89-1.81 (m, 1H), 1.80-1.70 (m, 1H), 1.69-1.57 (m, 2H), 1.47-1.41 (m, 1H), 1.38 (d, J = 6.8 Hz, 3H), 1.24 (s, 3H) | 508.3 |
| 290 | 1H NMR (400 MHz, methanol-d4) δ 8.36 (s, 1H), 8.09 (s, 1H), 8.01 (s, 1H), 7.88 (s, 1H), 7.80 (d, J = 8.8 Hz, 1H), 7.44 (t, J = 8.0 Hz, 1H), 7.21 (d, J = 7.2 Hz, 1H), 5.15 (s, 2H), 4.02 (d, J = 10.4 Hz, 1H), 3.97-3.85 (m, 4H), 3.60 (s, 3H), 3.54-3.45 (m, 1H), 3.44-3.35 (m, 1H), 2.72-2.58 (m, 1H), 2.16-2.05 (m, 2H), 1.95-1.74 (m, 4H), 1.39 (s, 3H), 1.38-1.25 (m, 4H) | 554.3 |
| 291 | 1H NMR (400 MHz, methanol-d4) δ 8.51 (br s, 1H), 8.35 (s, 1H), 8.16 (s, 1H), 8.08 (s, 1H), 7.88 (s, 1H), 7.79 (d, J = 8.0 Hz, 1H), 7.45 (t, J = 8.0 Hz, 1H), 7.23 (d, J = 7.6 Hz, 1H), 5.18 (s, 2H), 4.13 (s, 2H), 4.02 (d, J = 10.4 Hz, 1H), 3.98-3.85 (m, 2H), 3.60 (s, 3H), 3.55-3.45 (m, 1H), 3.44-3.35 (m, 1H), 2.73-2.59 (m, 1H), 2.40-2.22 (m, 2H), 2.07-1.95 (m, 2H), 1.95-1.86 (m, 2H), 1.86-1.75 (m, 1H), 1.54 (s, 3H), 1.46-1.25 (m, 3H) | 554.3 |
| 292 | 1H NMR (400 MHz, methanol-d4) δ 8.35 (s, 1H), 8.08 (s, 1H), 8.01 (s, 1H), 7.95 (t, J = 1.6 Hz, 1H), 7.64 (dd, J = 1.2, 9.6 Hz, 1H), 7.45 (t, J = 8.0 Hz, 1H), 7.05 (d, J = 7.6 Hz, 1H), 5.14 (s, 2H), 3.86 (s, 2H), 3.31 (s, 3H), 2.63-2.50 (m, 2H), 2.47-2.35 (m, 2H), 2.15-2.00 (m, 2H), 1.95-1.83 (m, 6H), 1.83-1.70 (m, 2H), 1.38 (s, 3H) | 524.4 |
| 293 | 1H NMR (400 MHz, methanol-d4) δ 8.38 (s, 1H), 8.08 (s, 1H), 8.01 (s, 1H), 7.97 (t, J = 2.0 Hz, 1H), 7.72 (d, J = 8.4 Hz, 1H), 7.47 (t, J = 8.0 Hz, 1H), 7.22-7.15 (m, 1H), 5.15 (s, 2H), 3.98-3.88 (m, 4H), 3.87 (s, 2H), 3.47-3.40 (m, 2H), 3.40 (s, 3H), 3.22-3.15 (m, 2H), 2.16-2.05 (m, 2H), 1.94-1.74 (m, 4H), 1.38 (s, 3H) | 568.3 |
| 294 | 1H NMR (400 MHz, methanol-d4) δ 8.37 (s, 1H), 8.09 (s, 1H), 8.01 (s, 1H), 7.92 (s, 1H), 7.78 (d, J = 1.6, 8.0 Hz, 1H), 7.47 (t, J = 8.0 Hz, 1H), 7.10 (d, J = 7.6 Hz, 1H), 5.25-5.08 (m, 2H), 3.87 (s, 2H), 3.85-3.78 (m, 1H), 3.70-3.53 (m, 4H), 3.49 (s, 3H), 3.40-3.33 (m, 3H), 2.31-2.20 (m, 2H), 2.16-2.05 (m, 2H), 1.95-1.73 (m, 4H), 1.39 (s, 3H) | 570.3 |
| 295 | 1H NMR (400 MHz, methanol-d4) δ 8.41 (s, 1H), 8.09 (s, 1H), 7.85 (s, 1H), 7.78 (d, J = 8.0 Hz, 1H), 7.44 (t, J = 8.0 Hz, 1H), 7.11 (d, J = 8.0 Hz, 1H), 5.15 (s, 2H), 3.89 (s, 2H), 3.85-3.75 (m, 2H), 3.68-3.60 (m, 2H), 3.60-3.35 (m, 6H), 2.55-2.45 (m, 1H), 2.16-2.06 (m, 2H), 2.00-1.75 (m, 6H), 1.39 (s, 3H) | 570.3 |

TABLE 2-continued

| Compound # | １H NMR | LCMS$^a$ |
|---|---|---|
| 296 | 1H NMR (400 MHz, methanol-d4) δ 8.41 (s, 1H), 8.09 (s, 1H), 8.01 (s, 1H), 7.85 (s, 1H), 7.78 (d, J = 8.4 Hz, 1H), 7.44 (t, J = 8.0 Hz, 1H), 7.11 (d, J = 8.0 Hz, 1H), 5.15 (s, 2H), 3.89 (s, 2H), 3.86-3.73 (m, 2H), 3.69-3.60 (m, 2H), 3.60-3.37 (m, 6H), 2.55-2.45 (m, 1H), 2.18-2.05 (m, 2H), 2.02-1.74 (m, 6H), 1.40 (s, 3H) | 570.3 |
| 297 | 1H NMR (400 MHz, methanol-d4) δ 8.37 (s, 1H), 8.09 (s, 1H), 8.01 (s, 1H), 7.92 (s, 1H), 7.78 (d, J = 8.0 Hz, 1H), 7.47 (t, J = 8.0 Hz, 1H), 7.10 (d, J = 7.6 Hz, 1H), 5.25-5.08 (m, 2H), 3.87 (s, 2H), 3.85-3.78 (m, 1H), 3.72-3.53 (m, 4H), 3.49 (s, 3H), 3.45-3.34 (m, 3H), 2.31-2.19 (m, 2H), 2.16-2.05 (m, 2H), 1.95-1.74 (m, 4H), 1.39 (s, 3H) | 570.3 |
| 298 | 1H NMR (400 MHz, methanol-d4) δ 8.32 (s, 1H), 8.08 (s, 1H), 8.00 (s, 1H), 7.94 (s, 1H), 7.65 (dd, J = 1.6, 7.6 Hz, 1H), 7.45 (t, J = 8.0 Hz, 1H), 7.08 (d, J = 8.0 Hz, 1H), 5.13 (s, 2H), 3.86 (s, 2H), 3.30 (s, 3H), 2.61 (d, J = 13.6 Hz, 2H), 2.24-2.14 (m, 2H), 2.14-2.05 (m, 2H), 1.93-1.64 (m, 10H), 1.38 (s, 3H) | 538.3 |
| 299 | 1H NMR (400 MHz, methanol-d4) δ 8.37 (s, 1H), 8.10 (s, 1H), 8.02 (s, 1H), 7.89 (s, 1H), 7.85-7.81 (m, 1H), 7.46 (t, J = 8.0 Hz, 1H), 7.20 (d, J = 7.6 Hz, 1H), 5.15 (s, 2H), 4.18 (d, J = 10.0 Hz, 1H), 3.89 (s, 2H), 3.58 (s, 3H), 3.28-3.10 (m, 2H), 3.09-2.93 (m, 2H), 2.28 (d, J = 14.4 Hz, 1H), 2.24-2.00 (m, 4H), 2.00-1.74 (m, 6H), 1.39 (s, 3H) | 602.3 |
| 300 | 1H NMR (400 MHz, methanol-d4) δ 8.37 (s, 1H), 8.11 (s, 1H), 8.03 (s, 1H), 7.89 (s, 1H), 7.83 (d, J = 8.0 Hz, 1H), 7.46 (t, J = 8.0 Hz, 1H), 7.20 (d, J = 8.0 Hz, 1H), 5.16 (s, 2H), 4.18 (d, J = 10.0 Hz, 1H), 3.92 (s, 2H), 3.58 (s, 3H), 3.30-3.10 (m, 2H), 3.10-2.93 (m, 2H), 2.29 (d, J = 12.4 Hz, 1H), 2.24-2.10 (m, 4H), 2.10-1.75 (m, 6H), 1.41 (s, 3H) | 602.3 |
| 301 | 1H NMR (400 MHz, DMSO-d6) δ 8.36 (s, 1H), 8.02 (s, 1H), 7.97 (s, 1H), 7.96 (s, 1H), 7.71 (d, J = 8.4 Hz, 1H), 7.43 (t, J = 8.0 Hz, 1H), 7.03 (d, J = 7.6 Hz, 1H), 5..67 (d, J = 4.8 Hz, 1H), 5.20 (s, 2H), 4.86 (t, J = 6.0 Hz, 1H), 4.81-4.74 (m, 1H), 3.62-3.53 (m, 1H), 3.53-3.44 (m, 1H), 3.31 (s, 3H), 3.01-2.90 (m, 2H), 2.74-2.63 (m, 2H), 2.08-1.93 (m, 2H) | 473.0 |
| 302 | 1H NMR (400 MHz, DMSO-d6) δ 8.36 (s, 1H), 8.02 (s, 1H), 7.97 (d, J = 3.6 Hz, 1H), 7.70 (dd, J = 1.6, 8.4 Hz, 1H), 7.43 (t, J = 8.0 Hz, 1H), 7.03 (d, J = 7.6 Hz, 1H), 5.67 (d, J = 4.8 Hz, 1H), 5.20 (s, 2H), 4.86 (d, J = 5.6 Hz, 1H), 4.81-4.74 (m, 1H), 3.62-3.53 (m, 1H), 3.52-3.44 (m, 1H), 3.23 (s, 3H), 2.99-2.90 (m, 2H), 2.72-2.65 (m, 2H), 2.05-1.96 (m, 2H) | 473.0 |
| 303 | 1H NMR (400 MHz, methanol-d4) δ 8.39 (s, 1H), 7.98 (s, 1H), 7.91 (s, 1H), 7.83 (s, 1H), 7.78 (d, J = 8.4 Hz, 1H), 7.45 (t, J = 8.0 Hz, 1H), 7.09 (d, J = 8.0 Hz, 1H), 7.05 (t, J = 55.6 Hz, 1H), 5.11 (s, 2H), 5.00-4.92 (m, 1H), 4.78 (d, J = 11.2 Hz, 1H), 4.70-4.63 (m, 2H), 4.43 (t, J = 6.0 Hz, 1H), 4.04-3.96 (m, 1H), 3.84 (s, 2H), 3.50 (s, 3H), 2.16-2.05 (m, 2H), 1.95-1.73 (m, 4H), 1.39 (s, 3H) | 508.3 |
| 304 | 1H NMR (400 MHz, methanol-d4) δ 8.39 (s, 1H), 7.97 (s, 1H), 7.91 (t, J = 1.6 Hz, 1H), 7.83 (s, 1H), 7.78 (dd, J = 1.2, 8.4 Hz, 1H), 7.45 (t, J = 8.0 Hz, 1H), 7.09 (d, J = 8.0 Hz, 1H), 7.05 (t, J = 55.2 Hz, 1H), 5.11 (s, 2H), 5.00-4.93 (m, 1H), 4.78 (d, J = 11.2 Hz, 1H), 4.69-4.62 (m, 2H), 4.43 (t, J = 6.0 Hz, 1H), 4.05-3.94 (m, 1H), 3.82 (s, 2H), 3.50 (s, 3H), 2.15-2.03 (m, 2H), 1.93-1.72 (m, 4H), 1.38 (s, 3H) | 508.2 |
| 305 | 1H NMR (400 MHz, methanol-d4) δ 8.37 (s, 1H), 8.08 (s, 1H), 8.03-7.97 (m, 2H), 7.78 (dd, J = 1.6, 8.0 Hz, 1H), 7.45 (t, J = 8.0 Hz, 1H), 7.14 (d, J = 8.4 Hz, 1H), 5.15 (s, 2H), 3.86 (s, 2H), 3.47 (s, 3H), 2.15-2.06 (m, 2H), 2.04 (s, 3H), 1.94-1.73 (m, 4H), 1.38 (s, 3H) | 500.1 |
| 306 | 1H NMR (400 MHz, methanol-d4) δ 8.37 (s, 1H), 8.08 (s, 1H), 8.02-7.97 (m, 2H), 7.78 (dd, J = 1.2, 8.0 Hz, 1H), 7.45 (t, J = 8.0 Hz, 1H), 7.14 (d, J = 8.4 Hz, 1H), 5.19 (s, 2H), 3.86 (s, 2H), 3.47 (s, 3H), 2.16-2.06 (m, 2H), 2.04 (s, 3H) 1.92-1.72 (m, 4H), 1.38 (s, 3H) | 500.1 |
| 307 | 1H NMR (400 MHz, methanol-d4) δ 8.48 (s, 1H), 8.15 (s, 1H), 8.08 (s, 1H), 8.01 (s, 1H), 7.90 (dd, J = 1.2, 9.6 Hz, 1H), 7.53 (t, J = 8.0 Hz, 1H), 7.24 (d, J = 8.0 Hz, 1H), 5.16 (s, 2H), 3.86 (s, 2H), 3.40 (s, 3H), 2.15-2.04 (m, 2H), 1.93-1.73 (m, 4H), 1.38 (s, 3H) | 554.0 |
| 308 | 1H NMR (400 MHz, methanol-d4) δ 8.48 (s, 1H), 8.15 (s, 1H), 8.09 (s, 1H), 8.02 (s, 1H), 7.91 (dd, J = 1.6, 8.4 Hz, 1H), 7.54 (t, J = 8.0 Hz, 1H), 7.24 (d, J = 7.6 Hz, 1H), 5.17 (s, 2H), 3.88 (s, 2H), 3.41 (s, 3H), 2.16-2.06 (m, 2H), 1.94-1.74 (m, 4H), 1.39 (s, 3H) | 554.0 |

TABLE 2-continued

| Compound # | ¹H NMR | LCMS$^a$ |
|---|---|---|
| 309 | 1H NMR (400 MHz, methanol-d4) δ 8.30 (s, 1H), 8.08 (s, 1H), 8.00 (s, 1H), 7.96 (s, 1H), 7.78 (dd, J = 1.6, 8.4 Hz, 1H), 7.43 (t, J = 8.0 Hz, 1H), 7.18 (d, J = 8.4 Hz, 1H), 5.13 (s, 2H), 3.86 (s, 2H), 3.53 (s, 3H), 3.00 (quint, J = 8.0 Hz, 1H), 2.15-2.05 (m, 2H), 1.93-1.75 (m, 4H), 1.38 (s, 3H), 1.18 (d, J = 6.4 Hz, 3H), 0.76 (d, J = 6.8 Hz, 3H) | 528.1 |
| 310 | 1H NMR (400 MHz, methanol-d4) δ 8.30 (s, 1H), 8.08 (s, 1H), 8.01 (s, 1H), 7.96 (s, 1H), 7.78 (d, J = 8.0 Hz, 1H), 7.44 (t, J = 8.0 Hz, 1H), 7.18 (d, J = 8.0 Hz, 1H), 5.14 (s, 2H), 3.88 (s, 2H), 3.53 (s, 3H), 3.03-2.92 (m, 1H), 2.18-2.05 (m, 2H), 1.95-1.73 (m, 4H), 1.39 (s, 3H), 1.18 (d, J = 6.8 Hz, 3H), 0.76 (d, J = 6.8 Hz, 3H) | 528.1 |
| 311 | 1H NMR (400 MHz, methanol-d4) δ 8.39 (s, 1H), 7.92 (t, J = 2.0 Hz, 1H), 7.80 (s, 1H), 7.77 (s, 1H), 7.22 (d, J = 8.4 Hz, 1H), 7.49 (t, J = 8.0 Hz, 1H), 7.11 (d, J = 8.0 Hz, 1H), 5.20-5.00 (m, 1H), 4.97 (s, 2H), 4.10-4.03 (m, 1H), 3.54-3.44 (m, 2H), 3.34 (s, 3H), 3.01-2.87 (m, 2H), 2.07-1.95 (m, 1H), 1.90-1.80 (m, 1H), 1.80-1.70 (m, 1H), 1.70-1.55 (m, 2H), 1.46-1.40 (m, 1H), 1.38 (d, J = 6.8 Hz, 3H), 1.24 (s, 3H) | 508.0 |
| 312 | 1H NMR (400 MHz, methanol-d4) δ 8.39 (s, 1H), 7.92 (t, J = 1.6 Hz, 1H), 7.80 (d, J = 1.2 Hz, 1H), 7.77 (d, J = 0.8 Hz, 1H), 7.21 (dd, J = 1.2, 6.4 Hz, 1H), 7.49 (t, J = 8.0 Hz, 1H), 7.11 (dd, J = 0.8, 8.0 Hz, 1H), 5.21-4.99 (m, 1H), 4.97 (s, 2H), 4.06 (q, J = 6.8 Hz, 1H), 3.54-3.43 (m, 2H), 3.34 (s, 3H), 3.02-2.88 (m, 2H), 2.07-1.96 (m, 1H), 1.89-1.80 (m, 1H), 1.80-1.70 (m, 1H), 1.70-1.56 (m, 2H), 1.47-1.40 (m, 1H), 1.38 (d, J = 6.8 Hz, 3H), 1.24 (s, 3H) | 508.0 |
| 313 | 1H NMR (400 MHz, methanol-d4) δ 8.39 (s, 1H), 8.08 (s, 1H), 8.02 (s, 1H), 7.91 (s, 1H), 7.78 (dd, J = 1.2, 8.0 Hz, 1H), 7.46 (t, J = 8.0 Hz, 1H), 7.10 (d, J = 8.0 Hz, 1H), 5.14 (s, 2H), 4.98-4.94 (m, 1H), 4.79 (d, J = 11.2 Hz, 1H), 4.70-4.64 (m, 2H), 4.44 (t, J = 6.4 Hz, 1H), 4.06-3.95 (m, 1H), 3.90-3.84 (m, 1H), 3.50 (s, 3H), 2.05-1.94 (m, 1H), 1.90-1.81 (m, 2H), 1.77-1.56 (m, 4H), 1.43-1.34 (m, 1H), 1.19 (s, 3H), 0.77 (t, J = 7.2 Hz, 3H) | 554.2 |
| 314 | 1H NMR (400 MHz, methanol-d4) δ 8.39 (s, 1H), 8.08 (s, 1H), 8.02 (s, 1H), 7.91 (s, 1H), 7.78 (d, J = 8.4 Hz, 1H), 7.46 (t, J = 8.0 Hz, 1H), 7.10 (d, J = 8.0 Hz, 1H), 5.14 (s, 2H), 4.99-4.93 (m, 1H), 4.79 (d, J = 11.2 Hz, 1H), 4.70-4.63 (m, 2H), 4.43 (t, J = 6.4 Hz, 1H), 4.06-3.95 (m, 1H), 3.92-3.84 (m, 1H), 3.50 (s, 3H), 2.05-1.95 (m, 1H), 1.90-1.80 (m, 2H), 1.78-1.55 (m, 4H), 1.43-1.34 (m, 1H), 1.19 (s, 3H), 0.77 (t, J = 7.2 Hz, 3H) | 554.2 |
| 315 | 1H NMR (400 MHz, methanol-d4) δ 8.40 (s, 1H), 8.22 (s, 1H), 8.14 (s, 1H), 7.90 (s, 1H), 7.79 (d, J = 8.0 Hz, 1H), 7.48 (t, J = 8.0 Hz, 1H), 7.16 (d, J = 7.2 Hz, 1H), 5.21 (s, 2H), 5.00-4.93 (m, 1H), 4.83-4.76 (m, 1H), 4.70-4.62 (m, 2H), 4.44 (t, J = 6.4 Hz, 1H), 4.41-4.33 (m, 1H), 4.07-3.95 (m, 1H), 3.51 (s, 3H), 2.40-2.26 (m, 1H), 2.15-1.92 (m, 3H), 1.92-1.72 (m, 3H), 1.50 (s, 3H), 1.46-1.35 (m, 1H), 0.80 (t, J = 7.2 Hz, 3H) | 554.2 |
| 316 | 1H NMR (400 MHz, methanol-d4) δ 8.40 (s, 1H), 8.25 (s, 1H), 8.16 (s, 1H), 7.90 (s, 1H), 7.79 (d, J = 8.4 Hz, 1H), 7.49 (t, J = 8.0 Hz, 1H), 7.16 (d, J = 8.0 Hz, 1H), 5.21 (s, 2H), 5.00-4.94 (m, 1H), 4.84-4.77 (m, 1H), 4.70-4.62 (m, 2H), 4.50-4.45 (m, 1H), 4.44 (t, J = 6.4 Hz, 1H), 4.07-3.95 (m, 1H), 3.51 (s, 3H), 2.46-2.35 (m, 1H), 2.21-1.97 (m, 3H), 1.97-1.75 (m, 3H), 1.54 (s, 3H), 1.45-1.35 (m, 1H), 0.80 (t, J = 7.2 Hz, 3H) | 554.2 |
| 317 | 1H NMR (400 MHz, methanol-d4) δ 8.37 (s, 1H), 7.88 (s, 1H), 7.81-7.75 (m, 2H), 7.73 (s, 1H), 7.44 (t, J = 8.0 Hz, 1H), 7.10 (d, J = 8.0 Hz, 1H), 5.29-5.07 (m, 1H), 4.97 (s, 2H), 4.25 (d, J = 11.6 Hz, 1H), 3.78 (s, 2H), 3.52 (s, 3H), 3.45-3.35 (m, 1H), 2.62-2.45 (m, 1H), 2.35-2.02 (m, 5H), 1.93-1.74 (m, 4H), 1.37 (s, 3H) | 508.2 |
| 318 | 1H NMR (400 MHz, methanol-d4) δ 8.38 (s, 1H), 7.85 (s, 1H), 7.82-7.75 (m, 2H), 7.73 (s, 1H), 7.44 (t, J = 8.0 Hz, 1H), 7.09 (d, J = 8.0 Hz, 1H), 4.96 (s, 2H), 4.89-4.81 (m, 1H), 4.26 (d, J = 10.0 Hz, 1H), 3.79 (s, 2H), 3.51 (s, 3H), 2.79-2.62 (m, 2H), 2.36-2.25 (m, 1H), 2.15-1.95 (m, 4H), 1.95-1.72 (m, 4H), 1.38 (s, 3H) | 508.2 |
| 319 | 1H NMR (400 MHz, methanol-d4) δ 8.38 (s, 1H), 7.85 (s, 1H), 7.82-7.75 (m, 2H), 7.73 (s, 1H), 7.44 (t, J = 8.0 Hz, 1H), 7.08 (d, J = 8.0 Hz, 1H), 4.96 (s, 2H), 4.94-4.79 (m, 0.5H), 4.26 (d, J = 10.0 Hz, 1H), 3.79 (s, 2H), 3.51 (s, 3H), 2.79-2.63 (m, 2H), 2.35-2.25 (m, 1H), 2.15-1.96 (m, 4H), 1.96-1.72 (m, 4H), 1.38 (s, 3H) | 508.2 |

TABLE 2-continued

| Compound # | ¹H NMR | LCMS$^a$ |
|---|---|---|
| 320 | 1H NMR (400 MHz, methanol-d4) δ 8.37 (s, 1H), 7.88 (s, 1H), 7.82-7.75 (m, 2H), 7.73 (s, 1H), 7.44 (t, J = 8.0 Hz, 1H), 7.10 (d, J = 7.6 Hz, 1H), 5.29-5.06 (m, 1H), 4.97 (s, 2H), 4.25 (d, J = 11.6 Hz, 1H), 3.79 (s, 2H), 3.52 (s, 3H), 3.46-3.35 (s, 1H), 2.61-2.44 (m, 1H), 2.37-2.02 (m, 5H), 1.93-1.73 (m, 4H), 1.37 (s, 3H) | 508.3 |
| 321 | 1H NMR (400 MHz, methanol-d4) δ 8.58 (s, 1H), 8.02 (s, 1H), 7.87 (d, J = 7.6 Hz, 1H), 7.77 (s, 1H), 7.73 (s, 1H), 7.53 (t, J = 8.0 Hz, 1H), 7.50-7.42 (m, 3H), 7.35-7.26 (m, 2H), 7.09 (d, J = 8.0 Hz, 1H), 4.97 (s, 2H), 3.81 (s, 2H), 3.58 (s, 3H), 2.16-2.05 (m, 2H), 1.95-1.73 (m, 4H), 1.39 (s, 3H) | 530.1 |
| 322 | 1H NMR (400 MHz, methanol-d4) δ 8.58 (s, 1H), 8.02 (s, 1H), 7.87 (d, J = 8.4 Hz, 1H), 7.76 (s, 1H), 7.72 (s, 1H), 7.52 (t, J = 8.0 Hz, 1H), 7.49-7.41 (m, 3H), 7.34-7.24 (m, 2H), 7.08 (d, J = 8.0 Hz, 1H), 4.96 (s, 2H), 3.77 (s, 2H), 3.57 (s, 3H), 2.14-1.98 (m, 2H), 1.93-1.70 (m, 4H), 1.36 (s, 3H) | 530.1 |
| 405 | ¹H NMR (400 MHz, methanol-d$_4$) δ 8.34 (s, 1H), 8.08 (s, 1H), 8.01 (s, 1H), 8.00 (s, 1H), 7.70 (d, J = 8.0 Hz, 1H), 7.48 (t, J = 8.0 Hz 1H), 7.21 (d, J = 8.0 Hz, 1H), 5.68 (t, J = 56.0 Hz, 1H), 4.93 (s, 2 H), 3.86 (s, 2H), 3.46 (s, 3H), 3.29 (s, 2H), 3.20-3.11 (m, 2 H), 2.15-2.10 (m, 2H), 1.96-1.85 (m, 2H), 1.84-1.74 (m, 2H), 1.38 (s, 3H). | 576.3 |
| 406 | ¹H NMR (400 MHz, methanol-d$_4$) δ 8.39 (s, 1H), 8.00 (s, 1H), 7.90 (s, 1H), 7.88 (s, 1H), 7.78 (d, J = 6.8 Hz, 1H), 7.46 (t, J = 8.0 Hz, 1H), 7.09 (d, J = 8.0 Hz, 1H), 7.04 (t, J = 55.2 Hz, 1H), 5.11 (s, 2H), 4.66-4.55 (m, 4H), 4.43 (t, J = 6.4 Hz, 1H), 4.13 (d, J = 7.0 Hz, 1H), 4.06-3.90 (m, 1H), 3.50 (s, 3H), 2.12-1.96 (m, 1H), 1.90-1.80 (m, 1H), 1.79-1.54 (m, 4H), 1.41 (d, J = 6.8 Hz, 3H), 1.25 (s, 3H). | 522.3 |
| 407 | ¹H NMR (400 MHz, methanol-d$_4$) δ 8.39 (s, 1H), 8.00 (s, 1H), 7.91 (s, 1H), 7.88 (s, 1H), 7.78 (d, J = 7.6 Hz, 1H), 7.46 (t, J = 8.0 Hz, 1H), 7.09 (d, J = 8.0 Hz, 1H), 7.04 (t, J = 55.2 Hz, 1H), 5.11 (s, 2H), 4.65-4.54 (m, 4H), 4.43 (t, J = 6.4 Hz, 1H), 4.13 (d, J = 6.8 Hz, 1H), 4.01-3.99 (m, 1H), 3.50 (s, 3H), 2.04-2.02 (m, 1H), 1.90-1.80 (m, 1H), 1.78-1.48 (m, 4H), 1.40 (d, J = 6.8 Hz, 3H), 1.24 (s, 3H). | 522.3 |
| 408 | ¹H NMR (400 MHz, methanol-d$_4$) δ 8.41 (s, 1H), 8.09 (s, 1H), 8.04-8.00 (m, 2H), 7.80 (d, J = 1.6 Hz, 1H), 7.12 (d, J = 1.6 Hz, 1H), 5.15 (s, 2H), 4.70-4.63 (m, 3H), 4.59-4.50 (m, 1H), 4.41 (t, J = 6.4 Hz, 1H), 4.05-3.94 (m, 1H), 3.86 (s, 2H), 3.54 (s, 3H), 2.13-2.06 (m, 2H), 1.91-1.79 (m, 4H), 1.38 (s, 3H) | 560.0 |
| 409 | ¹H NMR (400 MHz, methanol-d$_4$) δ 8.41 (s, 1H), 8.09 (s, 1H), 8.02 (d, J = 2.0 Hz, 2H), 7.80 (s, 1H), 7.12 (s, 1H), 5.15 (s, 2H), 4.70-4.62 (m, 3H), 4.60-4.52 (m, 1H), 4.41 (t, J = 6.4 Hz, 1H), 4.05-3.94 (m, 1H), 3.86 (s, 2H), 3.54 (s, 3H), 2.14-2.05 (m, 2H), 1.91-1.77 (m, 4H), 1.37 (s, 3H). | 560.0 |
| 410 | ¹H NMR (400 MHz, methanol-d$_4$) δ 8.46 (s, 1H), 7.97-7.95 (m, 1H), 7.85 (d, J = 6.4 Hz, 1H), 7.78 (d, J = 2.0 Hz, 1H), 7.72 (d, J = 2.0 Hz, 1H), 7.44 (t, J = 7.2 Hz, 1H), 7.40-7.34 (m, 5H), 7.13 (d, J = 6.4 Hz, 1H), 4.95 (d, J = 3.2 Hz, 2H), 3.83-3.78 (m, 2H), 3.57 (s, 3H), 2.14-2.08 (m, 2H), 1.91-1.77 (m, 4H), 1.38 (s, 3H). | 528.2 |
| 411 | ¹H NMR (400 MHz, methanol-d$_4$) δ 8.45 (s, 1H), 7.95 (s, 1H), 7.84 (d, J = 8.4 Hz, 1H), 7.75 (s, 1H), 7.70 (s, 1H), 7.45-7.40 (m, 1H), 7.39-7.31 (m, 5H), 7.12 (d, J = 8.0 Hz, 1H), 4.92 (s, 2H), 3.76 (s, 2H), 3.56 (s, 3H), 2.13-2.02 (m, 2H), 1.89-1.75 (m, 4H), 1.36 (s, 3H). | 528.2 |
| 412 | ¹H NMR (400 MHz, methanol-d$_4$) δ 8.40 (s, 1H), 8.01 (s, 1H), 7.91 (s, 1H), 7.88 (s, 1H), 7.78 (d, J = 8.0 Hz, 1H), 7.46 (t, J = 8.0 Hz, 1H), 7.09 (d, J = 8.0 Hz, 1H), 7.05 (t, J = 55.2 Hz, 1H), 5.11 (s, 2H), 4.71-4.56 (m, 4H), 4.43 (t, J = 6.4 Hz, 1H), 4.13 (q, J = 6.8 Hz, 1H), 4.05-3.96 (m, 1H), 3.51 (s, 3H), 2.10-2.00 (m, 1H), 1.92-1.82 (m, 1H), 1.81-1.42 (m, 4H), 1.41 (d, J = 6.8 Hz, 3H), 1.24 (s, 3H). | 522.3 |
| 413 | ¹H NMR (400 MHz, methanol-d$_4$) δ 8.39 (s, 1H), 8.00 (s, 1H), 7.91 (s, 1H), 7.88 (s, 1H), 7.78 (d, J = 8.4 Hz, 1H), 7.46 (t, J = 8.0 Hz, 1H), 7.09 (d, J = 8.0 Hz, 1H), 7.04 (t, J = 55.2 Hz, 1H), 5.11 (s, 2H), 4.69-4.54 (m, 4H), 4.43 (t, J = 6.4 Hz, 1H), 4.13 (q, J = 6.8 Hz, 1H), 4.05-3.93 (m, 1H), 3.50 (s, 3H), 2.10-2.02 (m, 1H), 1.90-1.80 (m, 1H), 1.79-1.45 (m, 4H), 1.40 (d, J = 6.8 Hz, 3H), 1.24 (s, 3H). | 522.3 |
| 414 | | 526.3 |
| 415 | | 526.2 |
| 416 | ¹H NMR (400 MHz, DMSO-d$_6$) δ 8.40 (s, 1H), 8.03 (s, 1H), 7.99 (s, 1H), 7.91 (s, 1H), 7.71 (d, J = 8.0 Hz, 1H), 7.43 (t, J = 8.0 Hz, 1H), 6.96 (d, J = 7.6 Hz, 1H), 5.20 (s, 2H), 3.90 (s, 2H), 3.89-3.81 (m, 1H), 3.41-3.38 (m, 2H), 3.32 (s, | 540.3 |

TABLE 2-continued

| Compound # | ¹H NMR | LCMS$^a$ |
|---|---|---|
| | 1H), 3.25 (s, 3H), 3.19 (s, 3H), 2.59-2.55 (m, 4H), 2.44-2.37 (m, 1H), 2.04-1.95 (m, 2H), 1.87-1.75 (m, 2H), 1.69-1.59 (m, 2H). | |
| 417 | | 542.2 |
| 418 | | 526.3 |
| 419 | ¹H NMR (400 MHz, DMSO-d$_6$) δ 8.40 (s, 1H), 8.20 (s, 1H), 8.08 (s, 1H), 8.04 (s, 1H), 7.89 (s, 1H), 7.72 (dd, J = 1.6, 8.0 Hz, 1H), 7.43 (t, J = 8.0 Hz, 1H), 6.97 (d, J = 7.6 Hz, 1H), 5.21 (s, 2H), 3.99 (s, 2H), 3.92-3.82 (m, 1H), 3.37-3.31 (m, 2H), 3.25 (s, 3H), 3.19 (s, 3H), 2.87-2.78 (m, 1H), 2.57-2.53 (m, 2H), 1.07 (d, J = 6.0 Hz, 6H). | 514.2 |
| 420 | | 540.3 |
| 421 | ¹H NMR (400 MHz, methanol-d$_4$) δ 8.39 (s, 1H), 8.06 (s, 1H), 8.00 (s, 1H), 7.91 (s, 1H), 7.68 (d, J = 7.2 Hz, 1H), 7.47 (t, J = 8.0 Hz, 1H), 7.08 (d, J = 8.0 Hz, 1H), 5.15 (s, 2H), 3.99-3.97 (m, 1H), 3.95 (s, 2H), 3.40-3.37 (m, 2H), 3.35 (s, 3H), 3.25 (s, 3H), 2.68-2.62 (m, 2H), 2.42-2.40 (m, 2H), 1.85-1.79 (m, 1H), 0.94 (d, J = 6.4 Hz, 6H). | 528.3 |
| 422 | | 528.3 |
| 423 | | 538.3 |
| 424 | | 596.3 |
| 425 | | 572.2 |
| 426 | | 588.3 |
| 427 | | 588.3 |
| 428 | ¹H NMR (400 MHz, methanol-d$_4$) δ 8.38 (s, 1H), 8.07 (s, 1H), 8.00 (s, 1H), 7.92 (s, 1H), 7.80 (d, J = 8.0 Hz, 1H), 7.43 (t, J = 8.0 Hz, 1H), 7.24 (d, J = 7.6 Hz, 1H), 5.13 (d, J = 5.2 Hz, 2H), 4.57 (s, 1H), 3.86 (s, 2H), 3.50 (s, 3H), 2.34-2.42 (m, 1H), 2.19-2.23 (m, 2H), 2.06-2.14 (m, 2H), 1.96-2.20 (m, 1H), 1.85-1.90 (m, 3H), 1.72-1.83 (m, 3H), 1.38 (s, 3H). | 540.2 |
| 429 | ¹H NMR (400 MHz, methanol-d$_4$) δ 8.38 (s, 1H), 8.07 (s, 1H), 8.00 (s, 1H), 7.92 (s, 1H), 7.80 (d, J = 8.0 Hz, 1H), 7.43 (t, J = 7.6 Hz, 1H), 7.24 (d, J = 7.6 Hz, 1H), 5.13 (d, J = 5.6 Hz, 2H), 4.57 (s, 1H), 3.86 (s, 2H), 3.49 (s, 3H), 2.34-2.42 (m, 1H), 2.19-2.23 (m, 2H), 2.06-2.14 (m, 2H), 1.98-2.20 (m, 1H), 1.85-1.91 (m, 3H), 1.72-1.81 (m, 3H), 1.38 (s, 3H). | 540.2 |
| 430 | ¹H NMR (400 MHz, methanol-d$_4$) δ 8.39 (s, 1H), 8.10 (s, 1H), 8.08 (s, 1H), 7.91 (s, 1H), 7.78 (d, J = 8.0 Hz, 1H), 7.46 (t, J = 8.0 Hz, 1H), 7.10 (d, J = 7.6 Hz, 1H), 5.14 (s, 2H), 4.97-4.94 (m, 1H), 4.80-4.77 (m, 1H), 4.67-4.65 (m, 2H), 4.45-4.41 (m, 1H), 4.06-3.95 (m, 1H), 3.50 (s, 3H), 3.16 (d, J = 8.8 Hz, 1H), 2.03-1.94 (m, 1H), 1.88-1.77 (m, 2H), 1.67-1.62 (m, 2H), 1.54-1.47 (m, 1H), 1.15-1.11 (m, 1H), 1.11 (s, 3H), 0.75-0.66 (m, 1H), 0.46-0.39 (m, 2H), 0.33-0.25 (m, 1H). | 566.4 |
| 431 | ¹H NMR (400 MHz, methanol-d$_4$) δ 8.39 (s, 1H), 8.09 (s, 1H), 8.08 (s, 1H), 7.90 (s, 1H), 7.78 (d, J = 8.0 Hz, 1H), 7.46 (t, J = 8.0 Hz, 1H), 7.09 (d, J = 8.0 Hz, 1H), 5.14 (s, 2H), 4.97-4.93 (m, 1H), 4.80-4.76 (m, 1H), 4.69-4.64 (m, 2H), 4.45-4.40 (m, 1H), 4.06-3.95 (m, 1H), 3.50 (s, 3H), 3.15 (d, J = 9.2 Hz, 1H), 2.01-1.94 (m, 1H), 1.88-1.77 (m, 2H), 1.68-1.60 (m, 2H), 1.54-1.47 (m, 1H), 1.10 (s, 3H), 1.10-1.06 (m, 1H), 0.75-0.67 (m, 1H), 0.47-0.38 (m, 2H), 0.33-0.24 (m, 1H). | 566.3 |
| 432 | ¹H NMR (400 MHz, methanol-d$_4$) δ 8.38 (s, 1H), 8.05 (s, 1H), 8.00 (s, 1H), 7.88 (s, 1H), 7.75 (dd, J = 1.6, 8.0 Hz, 1H), 7.44 (t, J = 8.0 Hz, 1H), 7.08 (d, J = 7.6 Hz, 1H), 5.11 (s, 2H), 4.96-4.94 (m, 1H), 4.78-4.75 (m, 1H), 4.65-4.63 (m, 2H), 4.43-4.39 (m, 1H), 4.05-3.93 (m, 1H), 3.81 (d, J = 9.2 Hz, 1H), 3.49 (s, 3H), 2.53-2.38 (m, 1H), 2.26-2.14 (m, 1H), 1.94-1.79 (m, 4H), 1.79-1.62 (m, 4H), 1.62-1.58 (m, 1H), 1.55-1.41 (m, 2H), 1.07 (s, 3H). | 580.3 |
| 433 | ¹H NMR (400 MHz, methanol-d$_4$) δ 8.38 (s, 1H), 8.06 (s, 1H), 8.01 (s, 1H), 7.89 (s, 1H), 7.76 (dd, J = 1.6, 8.0 Hz, 1H), 7.45 (t, J = 8.0 Hz, 1H), 7.09 (d, J = 7.6 Hz, 1H), 5.12 (s, 2H), 4.95-4.93 (m, 1H), 4.79-4.76 (m, 1H), 4.66-4.64 (m, 2H), 4.44-4.39 (m, 1H), 4.03-3.95 (m, 1H), 3.82 (d, J = 9.6 Hz, 1H), 3.49 (s, 3H), 2.51-2.43 (m, 1H), 2.25-2.16 (m, 1H), 1.95-1.80 (m, 4H), 1.80-1.63 (m, 4H), 1.63-1.60 (m, 1H), 1.57-1.41 (m, 2H), 1.08 (s, 3H). | 580.3 |
| 434 | ¹H NMR (400 MHz, methanol-d$_4$) δ 8.39 (s, 1H), 8.06 (s, 1H), 8.01 (s, 1H), 7.90 (s, 1H), 7.77 (dd, J = 1.6, 8.0 Hz, 1H), 7.45 (t, J = 8.0 Hz, 1H), 7.09 (d, J = 7.6 Hz, 1H), 5.12 (s, 2H), 4.98-4.93 (m, 1H), 4.80-4.76 (m, 1H), 4.67-4.64 (m, 2H), 4.45-4.40 (m, 1H), 4.04-3.96 (m, 1H), 3.83 (d, J = 10.0 Hz, 1H), 3.50 (s, 3H), 2.52-2.44 (m, 1H), 2.25-2.17 (m, 1H), 1.95-1.83 (m, 4H), 1.82-1.67 (m, 4H), 1.65-1.62 (m, 1H), 1.57-1.44 (m, 2H), 1.09 (s, 3H). | 580.2 |

TABLE 2-continued

| Compound # | ¹H NMR | LCMS$^a$ |
|---|---|---|
| 435 | ¹H NMR (400 MHz, methanol-d$_4$) δ 8.39 (s, 1H), 8.07 (s, 1H), 8.02 (s, 1H), 7.90 (s, 1H), 7.78 (dd, J = 1.6, 8.0 Hz, 1H), 7.46 (t, J = 8.0 Hz, 1H), 7.10 (d, J = 7.6 Hz, 1H), 5.13 (s, 2H), 4.98-4.94 (m, 1H), 4.80-4.77 (m, 1H), 4.69-4.63 (m, 2H), 4.45-4.41 (m, 1H), 4.04-3.97 (m, 1H), 3.83 (d, J = 9.6 Hz, 1H), 3.51 (s, 3H), 2.52-2.43 (m, 1H), 2.26-2.18 (m, 1H), 1.96-1.83 (m, 4H), 1.82-1.66 (m, 4H), 1.66-1.61 (m, 1H), 1.58-1.44 (m, 2H), 1.09 (s, 3H). | 580.2 |
| 436 | ¹H NMR (400 MHz, methanol-d$_4$) δ 8.12 (s, 1H), 8.10 (s, 1H), 8.04 (s, 1H), 8.03 (s, 1H), 7.85 (d, J = 8.0 Hz, 1H), 7.77 (s, 1H), 7.52 (t, J = 10.8 Hz, 1H), 7.27 (d, J = 7.6 Hz, 1H), 6.30 (d, J = 10.8 Hz, 1H), 5.19 (s, 2H), 4.82-4.78 (m, 2H), 4.59-4.55 (m, 2H), 4.38-4.34 (m, 1H), 3.89 (s, 2H), 2.16-2.09 (m, 2H), 1.92-1.80 (m, 4H), 1.40 (s, 3H). | 512.1 |
| 437 | ¹H NMR (400 MHz, methanol-d$_4$) δ 7.99 (d, J = 7.2 Hz, 2H), 7.90 (d, J = 8.6 Hz, 2H), 7.73 (d, J = 10.0 Hz, 1H), 7.65 (s, 1H), 7.40 (t, J = 8.0 Hz, 1H), 7.15 (d, J = 8.0 Hz, 1H), 6.18 (d, J = 11.2 Hz, 1H), 5.07 (s, 2H), 4.70-4.66 (m, 2H), 4.47-4.43 (m, 2H), 4.26-4.20 (m, 1H), 3.77 (s, 2H), 2.04-1.97 (m, 2H), 1.80-1.69 (m, 4H), 1.29 (s, 3H). | 512.1 |
| 438 | ¹H NMR (400 MHz, methanol-d$_4$) δ 8.37 (s, 1H), 8.09 (s, 1H), 8.01 (s, 1H), 7.92 (s, 1H), 7.84 (dd, J = 1.2, 8.0 Hz, 1H), 7.49 (t, J = 7.6 Hz, 1H), 7.19 (d, J = 8.0 Hz, 1H), 5.15 (s, 2H), 4.37 (d, J = 10.4 Hz, 1H), 3.86 (s, 2H), 3.56-3.55 (m, 1H), 3.53 (s, 3H), 3.52-3.49 (m, 1H), 3.26-3.20 (m, 1H), 3.13-3.05 (m, 1H), 2.98-2.94 (m, 1H), 2.14-2.05 (m, 2H), 2.04-1.96 (m, 2H), 1.91-1.86 (m, 2H), 1.84-1.76 (m, 2H), 1.38 (s, 3H). | 588.3 |
| 439 | ¹H NMR (400 MHz, methanol-d$_4$) δ 8.37 (s, 1H), 8.09 (s, 1H), 8.01 (s, 1H), 7.92 (d, J = 1.6 Hz, 1H), 7.84 (dd, J = 1.6, 8.0 Hz, 1H), 7.49 (t, J = 8.0 Hz, 1H), 7.19 (d, J = 8.0 Hz, 1H), 5.15 (s, 2H), 4.37 (d, J = 10.4 Hz, 1H), 3.86 (s, 2H), 3.56-3.55 (m, 1H), 3.53 (s, 3H), 3.52-3.49 (m, 1H), 3.26-3.20 (m, 1H), 3.13-3.05 (m, 1H), 2.98-2.90 (m, 1H), 2.14-2.07 (m, 2H), 2.04-1.96 (m, 2H), 1.91-1.86 (m, 2H), 1.84-1.76 (m, 2H), 1.38 (s, 3H). | 588.3 |
| 440 | ¹H NMR (400 MHz, methanol-d$_4$) δ 8.27 (s, 1H), 8.10 (s, 1H), 8.02 (s, 1H), 7.92-7.89 (m, 1H), 7.80-7.74 (m, 1H), 7.43 (t, J = 8.0 Hz, 1H), 7.18 (d, J = 8.0 Hz, 1H), 5.17 (s, 2H), 4.76-4.68 (m, 2H), 4.65-4.60 (m, 1H), 4.54 (t, J = 6.4 Hz, 1H), 4.46 (t, J = 6.4 Hz, 1H), 4.06-3.96 (m, 1H), 3.88 (s, 2H), 2.17-2.08 (m, 2H), 1.94-1.86 (m, 2H), 1.85-1.76 (m, 2H), 1.40 (s, 3H) | 512.3 |
| 441 | ¹H NMR (400 MHz, methanol-d$_4$) δ 8.26 (s, 1H), 8.10 (s, 1H), 8.02 (s, 1H), 7.90 (s, 1H), 7.79-7.75 (m, 1H), 7.42 (t, J = 8.0 Hz, 1H), 7.18 (d, J = 8.0 Hz, 1H), 5.16 (s, 2H), 4.75-4.67 (m, 2H), 4.65-4.60 (s, 1H), 4.53 (t, J = 6.4 Hz, 1H), 4.45 (t, J = 6.4 Hz, 1H), 4.04-3.96 (m, 1H), 3.91 (s, 2H), 2.18-2.10 (m, 2H), 1.95-1.88 (m, 2H), 1.86-1.76 (m, 2H), 1.41 (s, 3H) | 512.3 |
| 442 | ¹H NMR (400 MHz, methanol-d$_4$) δ 8.39 (s, 1H), 8.11 (s, 1H), 8.06 (s, 1H), 7.91 (s, 1H), 7.78 (d, J = 8.0 Hz, 1H), 7.46 (t, J = 8.0 Hz, 1H), 7.10 (d, J = 7.6 Hz, 1H), 5.14 (s, 2H), 4.98-4.93 (m, 1H), 4.81-4.77 (m, 1H), 4.68-4.64 (m, 2H), 4.45-4.41 (m, 1H), 4.18-4.13 (m, 1H), 4.04-3.96 (m, 1H), 3.50 (s, 3H), 2.04-1.98 (m, 1H), 1.88-1.80 (m, 1H), 1.77-1.70 (m, 1H), 1.67-1.58 (m, 2H), 1.40 (d, J = 6.8 Hz, 3H), 1.34-1.29 (m, 1H), 1.23 (s, 3H). | 540.3 |
| 443 | ¹H NMR (400 MHz, methanol-d$_4$) δ 8.39 (s, 1H), 8.11 (s, 1H), 8.06 (s, 1H), 7.91 (s, 1H), 7.78 (dd, J = 1.6, 8.0 Hz, 1H), 7.46 (t, J = 8.0 Hz, 1H), 7.10 (d, J = 7.6 Hz, 1H), 5.13 (s, 2H), 4.98-4.93 (m, 1H), 4.81-4.76 (m, 1H), 4.68-4.63 (m, 2H), 4.45-4.40 (m, 1H), 4.19-4.13 (m, 1H), 4.05-3.96 (m, 1H), 3.50 (s, 3H), 2.06-1.97 (m, 1H), 1.88-1.81 (m, 1H), 1.79-1.70 (m, 1H), 1.68-1.58 (m, 2H), 1.45-1.41 (m, 1H), 1.40 (d, J = 6.8 Hz, 3H), 1.22 (s, 3H). | 540.3 |
| 444 | ¹H NMR (400 MHz, methanol-d$_4$) δ 8.39 (s, 1H), 8.11 (s, 1H), 8.06 (s, 1H), 7.91 (s, 1H), 7.78 (dd, J = 1.6, 8.0 Hz, 1H), 7.46 (t, J = 8.0 Hz, 1H), 7.10 (d, J = 7.6 Hz, 1H), 5.14 (s, 2H), 4.98-4.94 (m, 1H), 4.80-4.77 (m, 1H), 4.67-4.64 (m, 2H), 4.45-4.41 (m, 1H), 4.19-4.13 (m, 1H), 4.05-3.95 (m, 1H), 3.50 (s, 3H), 2.06-1.97 (m, 1H), 1.89-1.81 (m, 1H), 1.79-1.70 (m, 1H), 1.69-1.58 (m, 2H), 1.45-1.42 (m, 1H), 1.40 (d, J = 6.8 Hz, 3H), 1.23 (s, 3H). | 540.3 |
| 445 | ¹H NMR (400 MHz, methanol-d$_4$) δ 8.39 (s, 1H), 8.11 (s, 1H), 8.06 (s, 1H), 7.91 (s, 1H), 7.78 (dd, J = 1.6, 8.0 Hz, 1H), 7.46 (t, J = 8.0 Hz, 1H), 7.10 (d, J = 7.6 Hz, 1H), 5.14 (s, 2H), 4.98-4.94 (m, 1H), 4.81-4.77 (m, 1H), 4.69-4.63 | 540.3 |

TABLE 2-continued

| Compound # | ¹H NMR | LCMS$^a$ |
|---|---|---|
| | (m, 2H), 4.45-4.41 (m, 1H), 4.19-4.13 (m, 1H), 4.05-3.95 (m, 1H), 3.50 (s, 3H), 2.06-1.98 (m, 1H), 1.89-1.81 (m, 1H), 1.79-1.70 (m, 1H), 1.69-1.58 (m, 2H), 1.44-1.42 (m, 1H), 1.40 (d, J = 6.8 Hz, 3H), 1.23 (s, 3H). | |
| 446 | ¹H NMR (400 MHz, methanol-d$_4$) δ 8.40 (s, 1H), 7.96 (s, 1H), 7.94 (s, 1H), 7.83 (s, 1H), 7.72-7.68 (m, 1H), 7.53-7.46 (m, 1H), 7.19-6.89 (m, 2H), 5.12 (s, 2H), 4.57-4.47 (m, 1H), 3.82 (s, 2H), 3.68-3.61 (m, 2H), 3.34 (s, 3H), 3.08-2.98 (m, 2H), 2.15-2.05 (m, 2H), 1.92-1.84 (m, 2H), 1.84-1.75 (m, 2H), 1.38 (s, 3H). | 526.1 |
| 447 | ¹H NMR (400 MHz, methanol-d$_4$) δ 8.40 (s, 1H), 7.96 (s, 1H), 7.94 (s, 1H), 7.83 (s, 1H), 7.72-7.68 (m, 1 H), 7.53-7.46 (m, 1H), 7.19-6.89 (m, 2 H), 5.12 (s, 2H), 4.57-4.47 (m, 1H), 3.82 (s, 2H), 3.68-3.61 (m, 2H), 3.34 (s, 3H), 3.08-2.98 (m, 2H), 2.15-2.05 (m, 2H), 1.92-1.84 (m, 2H), 1.84-1.75 (m, 2H), 1.38 (s, 3H) | 526.1 |
| 448 | ¹H NMR (400 MHz, methanol-d$_4$) δ 8.32 (s, 1H), 8.05 (s, 1H), 7.83 (s, 1H), 7.71-7.67 (m, 2H), 7.63-7.58 (m, 1H), 7.47 (t, J = 8.0 Hz, 1H), 7.17 (d, J = 8.0 Hz, 1H), 4.97 (s, 2H), 4.20 (m, 1H), 3.78 (s, 2H), 3.36 (s, 3H), 3.29 (s, 3H), 3.19 (m, 2H), 2.91-2.85 (m, 2H), 2.13-2.05 (m, 2H), 1.91-1.86 (m, 2H), 1.84-1.75 (m, 2H), 1.38 (s, 3H). | 472.3 |
| 449 | ¹H NMR (400 MHz, methanol-d$_4$) δ 8.38 (s, 1H), 7.89 (t, J = 1.6 Hz, 1H), 7.82 (s, 1H), 7.68 (d, J = 8.0 Hz, 2H), 7.61-7.58 (m, 1H), 7.45 (t, J = 8.0 Hz, 1H), 7.05 (d, J = 8.0 Hz, 1H), 4.95 (s, 2H), 3.99 (m, 1H), 3.77 (s, 2H), 3.40-3.35 (m, 2H), 3.35 (s, 3H), 3.29 (s, 3H), 2.68-2.60 (m, 2H), 2.13-2.04 (m, 2H), 1.91-1.85 (m, 2H), 1.83-1.75 (m, 2H), 1.38 (s, 3H). | 472.3 |
| 450 | ¹H NMR (400 MHz, CDCl$_3$) δ 8.08 (s, 1H), 8.06 (s, 1H), 7.90 (s, 1H), 7.86 (s, 1H), 7.59 (d, J = 8.4 Hz, 1H), 7.40 (t, J = 8.0 Hz, 1H), 7.03 (d, J = 7.6 Hz, 1H), 4.97 (s, 2H), 4.30-4.26 (m, 1H), 3.87 (s, 2H), 3.47-3.38 (m, 2H), 3.31 (s, 3H), 3.29-3.21 (m, 1H), 2.77-2.63 (m, 2H), 2.07-1.86 (m, 4H), 1.84-1.77 (m, 2H), 1.35 (s, 3H), 0.58-0.54(m, 2H), 0.49-0.43 (m, 2H). | 566.3 |
| 451 | ¹H NMR (400 MHz, methanol-d$_4$) δ 8.40 (s, 1 H), 7.92 (s, 1 H), 7.78 (s, 1 H), 7.69-7.75 (m, 2 H), 7.46-7.53 (m, 1 H), 7.09 (d, J = 7.6 Hz, 1 H), 4.98 (s, 2 H), 4.47-4.57 (m, 1 H), 3.80 (s, 2 H), 3.62-3.68 (m, 2 H), 3.34 (s, 3 H), 3.00-3.06 (m, 2 H), 2.08-2.16 (m, 2 H), 1.86-1.92 (m, 2 H), 1.76-1.83 (m, 2 H), 1.39 (s, 3 H) | 510.0 |
| 452 | ¹H NMR (400 MHz, methanol-d$_4$) δ 8.34 (s, 1 H), 8.04 (s, 1 H), 7.79 (s, 1 H), 7.72-7.77 (m, 2 H), 7.48-7.53 (m, 1 H), 7.21 (d, J = 7.6 Hz, 1 H), 4.99 (s, 2 H), 4.71-4.75 (m, 1 H), 3.81 (s, 2 H), 3.44-3.50 (m, 2 H), 3.35 (s, 3 H), 3.24-3.28 (m, 2 H), 2.07-2.15 (m, 2 H), 1.77-1.91 (m, 4 H), 1.39 (s, 3 H) | 510.0 |
| 453 | ¹H NMR (400 MHz, methanol-d$_4$) δ 8.37 (s, 1H), 8.18 (s, 1H), 8.11 (s, 1H), 7.99 (s, 1H), 7.68 (d, J = 8.0 Hz, 1H), 7.48 (t, J = 8.0 Hz, 1H), 7.16 (d, J = 8.0 Hz, 1H), 5.16 (s, 2H), 4.57-4.50 (m, 1H), 4.46-4.30 (m, 2H), 3.34 (s, 3H), 3.05-2.95 (m, 2H), 2.87-2.73 (m, 2H), 2.32-2.19 (m, 2 H), 2.03-1.98 (m, 1H), 1.80-1.75 (m, 2 H), 1.70-1.60 (m, 2 H), 1.59-1.51 (m, 1H) 1.20 (s, 3H). | 542.2 |
| 454 | ¹H NMR (400 MHz, methanol-d$_4$) δ 8.32 (s, 1H), 8.10 (s, 1H), 8.09 (s, 1H), 8.03 (s, 1H), 7.71-7.68 (m, 1H), 7.51 (t, J = 7.6 Hz, 1H), 7.27 (d, J = 8.0 Hz, 1H), 5.17 (s, 2H), 3.89 (s, 2H), 3.36 (s, 3H), 2.98-2.93 (m, 2H), 2.66-2.61 (m, 2H), 2.55-2.46 (m, 1H), 2.16-2.09 (m, 2H), 1.94-1.88 (m, 2H), 1.86-1.80 (m, 2H), 1.56-1.49 (m, 2H), 1.40 (s, 3H), 0.90 (t, J = 7.2 Hz, 3H). | 538.3 |
| 455 | ¹H NMR (400 MHz, methanol-d$_4$) δ 8.38 (s, 1H), 8.09 (s, 1H), 8.01 (s, 1H), 7.92 (s, 1H), 7.65-7.63 (m, 1H), 7.46 (t, J = 8.0 Hz, 1H), 7.08 (d, J = 8.4 Hz, 1H), 5.15 (s, 2H), 3.88 (s, 2H), 3.36 (s, 3H), 2.42-2.37 (m, 2H), 2.34-2.25 (m, 1H), 2.15-2.07 (m, 2H), 1.90-1.86 (m, 2H), 1.84-1.77 (m, 2H), 1.54-1.50 (m, 2H), 1.39 (s, 3H), 1.30 (s, 2H), 0.88 (t, J = 7.6 Hz, 3H). | 538.3 |
| 456 | ¹H NMR (400 MHz, methanol-d$_4$) δ 8.39 (s, 1H), 8.10 (s, 1H), 8.08 (s, 1H), 7.91 (s, 1H), 7.78 (d, J = 8.0 Hz, 1H), 7.46 (t, J = 8.0 Hz, 1H), 7.10 (d, J = 7.6 Hz, 1H), 5.14 (s, 2H), 4.97-4.93 (m, 1H), 4.80-4.77 (m, 1H), 4.67-4.65 (m, 2H), 4.48-4.36 (m, 1H), 4.04-3.96 (m, 1H), 3.51 (s, 3H), 3.17-3.13 (m, 1H), 2.00-1.95 (m, 1H), 1.88-1.79 (m, 2H), 1.67-1.63 (m, 2H), 1.53-1.49 (m, 1H), 1.10 (s, 3H), 1.09-1.06 (m, 1H), 0.74-0.68 (m, 1H), 0.46-0.41 (m, 2H), 0.31-0.27 (m, 1H). | 566.3 |
| 457 | ¹H NMR (400 MHz, methanol-d$_4$) δ 8.39 (s, 1H), 8.10 (s, 1H), 8.08 (s, 1H), 7.91 (s, 1H), 7.78 (d, J = 8.0 Hz, 1H), 7.46 | 566.3 |

TABLE 2-continued

| Compound # | ¹H NMR | LCMS$^a$ |
|---|---|---|
|  | (t, J = 8.0 Hz, 1H), 7.10 (d, J = 7.6 Hz, 1H), 5.14 (s, 2H), 4.97-4.93 (m, 1H), 4.80-4.77 (m, 1H), 4.67-4.63 (m, 2H), 4.47-4.39 (m, 1H), 4.06-3.94 (m, 1H), 3.51 (s, 3H), 3.21-3.11 (m, 1H), 2.04-1.94 (m, 1H), 1.91-1.77 (m, 2H), 1.71-1.60 (m, 2H), 1.55-1.44 (m, 1H), 1.11 (s, 3H), 1.08-1.03 (m, 1H), 0.78-0.65 (m, 1H), 0.50-0.37 (m, 2H), 0.34-0.23 (m, 1H). |  |
| 458 | ¹H NMR (400 MHz, methanol-d$_4$) δ 8.38 (s, 1H), 7.97 (s, 1H), 7.85 (s, 1H), 7.83 (s, 1H), 7.78 (d, J = 8.0 Hz, 1H), 7.44 (t, J = 8.0 Hz, 1H), 7.08 (d, J = 7.6 Hz, 1H), 7.05 (t, J = 55.2 Hz, 1H), 5.11 (s, 2H), 4.98-4.95 (m, 1H), 4.27 (d, J = 10.4 Hz, 1H), 3.82 (s, 2H), 3.51 (s, 3H), 2.78-2.65 (m, 2H), 2.35-2.25 (m, 1H), 2.14-2.04 (m, 3H), 2.04-1.93 (m, 1H), 1.91-1.77 (m, 4H), 1.38 (s, 3H). | 524.4 |
| 459 | ¹H NMR (400 MHz, methanol-d$_4$) δ 8.37 (s, 1H), 7.96 (s, 1H), 7.88 (s, 1H), 7.82 (s, 1H), 7.77 (dd, J = 2.0, 8.0 Hz, 1H), 7.43 (t, J = 8.0 Hz, 1H), 7.10 (d, J = 8.0 Hz, 1H), 7.04 (t, J = 55.2 Hz, 1H), 5.27-5.11 (m, 1H), 5.10 (s, 2H), 4.26 (d, J = 11.2 Hz, 1H), 3.82 (s, 2H), 3.52 (s, 3H), 3.44-3.35 (m, 1H), 2.60-2.46 (m, 1H), 2.35-2.15 (m, 3H), 2.13-2.06 (m, 2H), 1.92-1.76 (m, 4H), 1.38 (s, 3H). | 524.3 |
| 460 | ¹H NMR (400 MHz, methanol-d$_4$) δ 8.38 (s, 1H), 7.97 (s, 1H), 7.85 (s, 1H), 7.83 (s, 1H), 7.77 (dd, J = 1.6, 8.0 Hz, 1H), 7.44 (t, J = 8.0 Hz, 1H), 7.10 (d, J = 8.0 Hz, 1H), 7.04 (t, J = 55.2 Hz, 1H), 5.10 (s, 2H), 5.02-4.96 (m, 1H), 4.27 (d, J = 10.0 Hz, 1H), 3.82 (s, 2H), 3.51 (s, 3H), 2.78-2.64 (m, 2H), 2.34-2.25 (m, 1H), 2.13-2.03 (m, 3H), 2.02-1.91 (m, 1H), 1.91-1.76 (m, 4H), 1.38 (s, 3H). | 524.4 |
| 461 | ¹H NMR (400 MHz, methanol-d$_4$) δ 8.38 (s, 1H), 7.97 (s, 1H), 7.89 (s, 1H), 7.83 (s, 1H), 7.78 (d, J = 8.4 Hz, 1H), 7.44 (t, J = 8.0 Hz, 1H), 7.11 (d, J = 7.6 Hz, 1H), 7.05 (t, J = 55.2 Hz, 1H), 5.29-5.12 (m, 1H), 5.11 (s, 2H), 4.27 (d, J = 11.6 Hz, 1H), 3.82 (s, 2H), 3.53 (s, 3H), 3.45-3.35 (m, 1H), 2.61-2.47 (m, 1H), 2.36-2.15 (m, 3H), 2.14-2.06 (m, 2H), 1.92-1.78 (m, 4H), 1.38 (s, 3H). | 524.4 |
| 462 | ¹H NMR (400 MHz, methanol-d$_4$) δ 8.43 (s, 1H), 8.11 (s, 1H), 8.06-8.03 (m, 2H), 7.89 (d, J = 8.0 Hz, 1H), 7.50 (t, J = 8.0 Hz, 1H), 7.29 (d, J = 8.0 Hz, 1H), 5.26-5.23 (m, 1H), 5.17 (s, 2H), 3.88 (s, 2H), 3.86-3.73 (m, 1H), 3.62-3.55 (m, 1H), 3.53 (s, 3H), 3.52-3.38 (m, 2H), 2.18-2.06 (m, 2H), 1.93-1.76 (m, 4H), 1.40 (s, 3H). | 560.3 |
| 463 | ¹H NMR (400 MHz, methanol-d$_4$) δ 8.39 (s, 1H), 8.08 (s, 1H), 8.01 (s, 1H), 7.91 (s, 1H), 7.78 (d, J = 8.0 Hz, 1H), 7.46 (t, J = 8.0 Hz, 1H), 7.10 (d, J = 7.6 Hz, 1H), 5.14 (s, 2H), 4.99-4.93 (m, 1H), 4.79 (d, J = 11.2 Hz, 1H), 4.69-4.63 (m, 2H), 4.43 (t, J = 6.4 Hz, 1H), 4.06-3.94 (m, 3H), 3.51 (s, 3H), 2.70 (d, J = 19.6 Hz, 2H), 1.38 (d, J = 20.0 Hz, 6H). | 532.2 |
| 464 | ¹H NMR (400 MHz, methanol-d$_4$) δ 8.39 (s, 1H), 8.07 (s, 1H), 8.00 (s, 1H), 7.91 (s, 1H), 7.78 (dd, J = 1.6, 8.4 Hz, 1H), 7.46 (t, J = 8.0 Hz, 1H), 7.10 (d, J = 8.0 Hz, 1H), 5.14 (s, 2H), 4.98-4.94 (m, 1H), 4.80-4.77 (m, 1H), 4.68-4.63 (m, 2H), 4.42 (t, J = 6.4 Hz, 1H), 4.06-3.98 (m, 1H), 3.96 (s, 2H), 3.50 (s, 3H), 2.43 (d, J = 7.2 Hz, 2H), 1.83-1.80 (m, 1H), 0.94 (d, J = 6.4 Hz, 6H). | 514.3 |
| 465 | ¹H NMR (400 MHz, methanol-d$_4$) δ 8.39 (s, 1H), 8.08 (s, 1H), 8.01 (s, 1H), 7.91 (t, J = 1.6, 1H), 7.79 (dd, J = 1.6, 8.0 Hz, 1H), 7.46 (t, J = 8.0 Hz, 1H), 7.10 (d, J = 8.4 Hz, 1H), 5.14 (s, 2H), 4.98-4.93 (m, 1H), 4.79 (d, J = 10.8 Hz, 1H), 4.68-4.64 (m, 2H), 4.43 (t, J = 6.4 Hz, 1H), 4.05-3.95 (m, 3H), 3.50 (s, 3H), 2.46 (s, 2H), 1.15 (s, 3H), 0.37-0.28 (m, 4H). | 526.3 |
| 466 | ¹H NMR (400 MHz, methanol-d$_4$) δ 8.39 (s, 1H), 8.06 (s, 1H), 7.97 (s, 1H), 7.91 (s, 1H), 7.80-7.75 (m, 1H), 7.46 (t, J = 8.0 Hz, 1H), 7.10 (d, J = 8.0 Hz, 1H), 5.14 (s, 2H), 4.98-4.92 (m, 2H), 4.79 (d, J = 11.2 Hz, 1H), 4.67-4.64 (m, 2H), 4.43 (t, J = 6.4 Hz, 1H), 4.01 (s, 2H), 3.50 (s, 3H), 1.36 (s, 3H), 0.67-0.61 (m, 2H), 0.44-0.39 (m, 2H). | 512.2 |
| 467 | ¹H NMR (400 MHz, methanol-d$_4$) δ 8.39 (s, 1H), 8.07 (s, 1H), 8.01 (s, 1H), 7.91 (s, 1H), 7.69 (d, J = 8.0 Hz, 1H), 7.48 (t, J = 8.0 Hz, 1H), 7.09 (d, J = 8.0 Hz, 1H), 5.16 (s, 2H), 4.04-3.97 (m, 2H), 3.95-3.89 (m, 1H), 3.41-3.36 (m, 2H), 3.35 (s, 3H), 3.30 (s, 3H), 2.65 (m, 2H), 2.61-2.54 (m, 1H), 2.35-2.24 (m, 1H), 2.14-1.97 (m, 2H), 1.91-1.68 (m, 4H), 1.01 (d, J = 6.4 Hz, 3H). | 554.3 |
| 468 | ¹H NMR (400 MHz, methanol-d$_4$) δ 8.42 (s, 1H), 8.10 (s, 1H), 8.03 (s, 1H), 7.93 (t, J = 2.0 Hz, 1H), 7.80 (d, J = 8.4 Hz, 1H), 7.48 (t, J = 8.0 Hz 1H), 7.12 (d, J = 8.0 Hz 1H), 5.16 (s, 2H), 5.00-4.80 (m, 1H), 4.79-4.69 (m, 1H), 4.66- | 528.3 |

TABLE 2-continued

| Compound # | ¹H NMR | LCMS$^a$ |
|---|---|---|
|  | 4.70 (m, 2H), 4.43-4.48 (t, J = 6.4 Hz, 1H), 3.96-4.07 (m, 3H), 3.50-3.55 (m, 3H), 2.35 (s, 2H), 0.96 (s, 9H). |  |
| 469 | ¹H NMR (400 MHz, methanol-d$_4$) δ 8.37 (s, 1H), 7.99 (s, 1H), 7.94 (s, 1H), 7.91 (s, 1H), 7.84 (d, J = 8.4 Hz, 1H), 7.40 (t, J = 8.0 Hz, 1 H), 7.01 (d, J = 7.6 Hz, 1H), 5.16 (s, 2H), 4.78-4.72 (m, 2H), 4.51-4.46 (m, 2H), 4.28 (t, J = 6.4 Hz, 1 H), 3.92-3.85 (m, 1H), 3.78 (s, 2H), 3.38 (s, 3H), 3.20-3.17 (m, 1H), 1.97-1.95 (m, 2H), 1.59-1.56 (m, 2H), 1.23-1.21 (m, 2H), 0.77-0.75 (m, 1H), 0.44-0.39 (m, 1H). | 538.3 |
| 470 | ¹H NMR (400 MHz, methanol-d$_4$) δ 8.39 (s, 1H), 8.06 (s, 1H), 8.00 (s, 1H), 7.91 (t, J = 1.6 Hz, 1H), 7.68 (dd, J = 1.6, 8.0 Hz, 1H), 7.47 (t, J = 8.0 Hz, 1H), 7.08 (d, J = 8.0 Hz, 1H), 5.15 (s, 2H), 4.02-3.96 (m, 2H), 3.94-3.89 (m, 1H), 3.40-3.36 (m, 2H), 3.35 (s, 3H), 3.30 (s, 3H), 2.65 (m, 2H), 2.60-2.53 (m, 1H), 2.33-2.25 (m, 1H), 2.12-1.96 (m, 2H), 1.90-1.75 (m, 2H), 1.74-1.67 (m, 2H), 1.00 (d, J = 6.4 Hz, 3H). | 554.3 |
| 471 | ¹H NMR (400 MHz, methanol-d$_4$) δ 8.39 (s, 1H), 8.06 (s, 1H), 7.99 (s, 1H), 7.92 (s, 1H), 7.69 (d, J = 8.4 Hz, 1H), 7.47 (t, J = 8.0 Hz, 1H), 7.08 (d, J = 7.6 Hz, 1H), 5.15 (s, 2H), 3.99 (t, J = 7.6 Hz, 1H), 3.93 (s, 2H), 3.41-3.36 (m, 2H), 3.35 (s, 3H), 3.30 (s, 3H), 2.67-2.61 (m, 4H), 2.57-2.49 (m, 2H), 1.45 (s, 3H). | 576.2 |
| 472 | ¹H NMR (400 MHz, methanol-d$_4$) δ 8.39 (s, 1H), 8.05 (s, 1H), 7.96 (s, 1H), 7.91 (s, 1H), 7.78 (dd, J = 1.6, 8.4 Hz, 1H), 7.45 (t, J = 8.0 Hz, 1H), 7.10 (d, J = 7.6 Hz, 1H), 5.14 (s, 2H), 4.98-4.93 (m, 1H), 4.80-4.77 (m, 1H), 4.67-4.63 (m, 2H), 4.44-4.40 (m, 1H), 4.05-3.98 (m, 1H), 3.97 (s, 2H), 3.78 (d, J = 8.4 Hz, 2H), 3.65 (d, J = 8.4 Hz, 2H), 3.50 (s, 3H), 1.94-1.91 (m, 1H), 1.72-1.70 (m, 2H). | 540.2 |
| 473 |  | 542.3 |
| 474 |  | 540.3 |
| 475 |  | 526.3 |
| 476 |  | 528.3 |
| 477 |  | 512.2 |
| 478 |  | 542.3 |
| 479 |  | 542.5 |
| 480 |  | 512.5 |
| 481 | ¹H NMR (400 MHz, DMSO-d$_6$) δ 8.40 (s, 1H), 8.05 (s, 1H), 8.01 (s, 1H), 7.92 (s, 1H), 7.70 (d, J = 8.4 Hz, 1H), 7.43 (t, J = 8.0 Hz, 1H), 6.96 (d, J = 7.6 Hz, 1H), 5.20 (s, 2H), 3.93 (s, 2H), 3.91-3.83 (m, 1H), 3.25 (s, 3H), 3.19 (s, 3H), 2.60-2.50 (m, 2H), 2.50-2.40 (m, 2H), 2.23 (s, 2H), 0.89 (s, 9H). | 542.5 |
| 482 | ¹H NMR (400 MHz, DMSO-d$_6$) δ 8.40 (s, 1H), 8.04 (s, 1H), 8.01 (s, 1H), 7.90 (s, 1H), 7.71 (d, J = 8.0 Hz, 1H), 7.43 (t, J = 8.0 Hz, 1H), 6.96 (d, J = 8.4 Hz, 1H), 5.21 (s, 2H), 3.94 (s, 2H), 3.91-3.85 (m, 1H), 3.37-3.33 (m, 1H), 3.25 (s, 3H), 3.19 (s, 3H), 2.67-2.66 (m, 1H), 2.60-2.58 (m, 2H), 2.45-2.33 (m, 2H), 1.95-1.85 (m, 1H), 1.56-1.52 (m, 1H), 1.21-1.16 (m, 1H). | 562.3 |
| 483 |  | 546.2 |
| 484 |  | 556.3 |
| 485 |  | 538.2 |
| 486 |  | 544.5 |
| 487 |  | 556.2 |
| 488 |  | 554.3 |
| 489 |  | 570.3 |
| 490 |  | 554.3 |
| 491 |  | 566.2 |
| 492 |  | 554.2 |
| 493 |  | 584.3 |
| 494 |  | 576.3 |
| 495 |  | 570.3 |
| 496 |  | 558.3 |
| 497 |  | 558.1 |
| 498 |  | 552.3 |
| 499 |  | 590.3 |
| 500 | ¹H NMR (400 MHz, DMSO-d$_6$) δ 8.40 (s, 1H), 8.04 (s, 1H), 7.99 (s, 1H), 7.90 (s, 1H), 7.71 (d, J = 8.4 Hz, 1H), 7.43 (t, J = 8.0 Hz, 1H), 6.96 (d, J = 8.0 Hz, 1H), 5.20 (s, 1H), 4.21 (s, 1H), 3.90 (s, 2H), 3.90-3.85 (m, 1H), 3.50-3.47 (m, 1H), 3.25 (s, 3H), 3.20-3.15 (m, 4H), 2.79-2.76 (m, 1H), 2.70-2.50 (m, 3H), 2.50-2.45 (m, 2H), 1.84-1.74 (m, 2H), 1.42-1.39 (m, 1H), 1.24-1.20 (m, 1H). | 568.3 |
| 501 |  | 576.3 |
| 502 |  | 526.3 |
| 503 |  | 576.3 |
| 504 |  | 570.3 |
| 505 |  | 551.3 |

TABLE 2-continued

| Compound # | $^1$H NMR | LCMS$^a$ |
|---|---|---|
| 506 | | 576.3 |
| 507 | $^1$H NMR (400 MHz, DMSO-d$_6$) δ 8.40 (s, 1H), 8.07 (s, 1H), 8.02 (s, 1H), 7.91 (s, 1H), 7.71 (d, J = 8.4 Hz, 1H), 7.43 (t, J = 8.0 Hz, 1H), 6.96 (d, J = 7.6 Hz, 1H), 5.21 (s, 2H), 4.44 (d, J = 48.0 Hz, 2H), 3.93 (s, 2H), 3.93-3.75 (m, 1H), 3.25 (s, 3H), 3.15 (s, 3H), 2.75-2.50 (m, 4H), 2.50-2.30 (m, 2H), 1.95-1.70 (m, 6H). | 572.3 |
| 508 | $^1$H NMR (400 MHz, DMSO-d$_6$) δ 8.39 (s, 1H), 8.00 (s, 1H), 7.96 (s, 1H), 7.89 (s, 1H), 7.70 (d, J = 8.4 Hz, 1H), 7.42 (t, J = 8.0 Hz, 1H), 6.95 (d, J = 8.0 Hz, 1H), 5.19 (s, 2H), 3.94 (s, 2H), 3.90-3.82 (m, 1H), 3.38-3.33 (m, 2H), 3.24 (s, 3H), 3.18 (s, 3H), 2.55-2.51 (m, 2H), 2.48-2.46 (m, 1H), 1.79-1.65 (m, 3H), 1.60-1.44 (m, 2H), 1.16-1.02 (m, 2H), 0.55-0.49 (m, 1H), 0.45-0.42 (m, 1H). | 552.3 |
| 509 | | 596.3 |
| 510 | | 588.3 |
| 511 | $^1$H NMR (400 MHz, methanol-d$_4$) δ 8.39 (s, 1H), 8.06 (s, 1H), 7.99 (s, 1H), 7.91 (t, J = 2.0 Hz, 1H), 7.69 (dd, J = 1.6, 8.4 Hz, 1H), 7.47 (t, J = 8.0 Hz, 1H), 7.08 (d, J = 8.0 Hz, 1H), 5.15 (s, 2H), 4.03-4.00 (m, 1H), 3.95 (s, 2H), 3.38-3.36 (m, 2H), 3.35 (s, 3H), 3.29 (s, 3H), 2.68-2.64 (m, 2H), 2.63-2.55 (m, 2H), 1.63-1.53 (m, 2H), 0.95 (t, J = 7.6 Hz, 3H). | 514.3 |

$^a$[M + H]$^+$ or [M − H]$^−$.

Example 121: Cbl-b and C-Cbl LCK Ub TR-FRET Assay

Compounds were 3-fold serially diluted in DMSO in a 384-well polypropylene plate (#P-05525-BC; Labcyte) to generate a source plate with 10 concentrations of each compound, top concentration=2 mM. 80 nL of DMSO or compounds were transferred to each well of a black 384-well ProxiPlate (#6008260; PerkinElmer) using a Labcyte Echo. 1× assay buffer (50 mM HEPES pH7.0, 100 mM NaCl, 0.01% BSA, 0.01% Triton-X100, 1 mM DTT), 2× enzyme solution (16 nM Biotin-Cbl-b or 12 nM Biotin-c-Cbl in 1× assay buffer), 2× kinase mixture (120 nM His-LCK, 1 mM ATP, 10 mM MgCl$_2$ in assay buffer) and 2.33× detection mixture (4.66× solution 1: 163 nM Anti-HA-D2 antibody (#610HADAB; PerkinElmer), 27.96 nM Streptavidin-EU (#AD0062; PerkinElmer), 1.398 mM EDTA in 1× assay buffer+4.66× solution 2: 2.796 μM UBE2D2/Methylated-HA-Ubiquitin thioester adduct (BostonBiochem) in 1× assay buffer) were prepared. 4 μL of 2× enzyme solution was added to each well containing compound, briefly centrifuged to mix, and incubated for 60 min at room temperature. 4 μL of 2× kinase mixture was added, briefly centrifuged to mix, and incubated for 90 min. at room temperature. 6 μL of detection mixture was added to all wells and briefly centrifuged before incubating for 20 min at room temperature. Plates were read for TR-FRET using an Envision at excitation 340 nm, emission at 615 and 665 nm, 4 flashes per well. IC$_{50}$ was generated using no LCK as the low control and DMSO as the high control.

LCK assay data for representative compounds of formula (I) herein are shown in Table 3.

TABLE 3

Cbl-b and C-Cbl Selectivity of Isoindolin-1-one Compounds

| Compound | Cbl-b Lck HTRF IC$_{50}$ (μM) | C-cbl Lck HTRF IC$_{50}$ (μM) | (fold-selectivity) |
|---|---|---|---|
| 1 | 8.3 | 14.1 | (1.7x) |
| 2 | 0.016 | 0.024 | (1.5x) |
| 3 | 0.0036 | 0.0025 | (0.69x) |
| 4 | 0.0066 | 0.0060 | (0.91x) |
| 5 | 0.0071 | 0.0045 | (0.64x) |
| 6 | 0.011 | 0.0062 | (0.56x) |
| 7 | 0.027 | 0.025 | (0.93x) |
| 8 | 0.011 | 0.043 | 3.9x |
| 9 | 0.011 | 0.118 | 8.4x |
| 10 | 0.012 | 0.024 | (2.0x) |
| 11 | 5.1 | 20 | (3.9x) |
| 12 | 0.012 | 0.018 | (1.5x) |
| 13 | 0.20 | 0.54 | (2.7x) |
| 14 | 0.63 | 1.0 | (1.6x) |
| 15 | 1.9 | 4.9 | (1.6x) |
| 16 | 0.0069 | 0.0052 | (0.75x) |
| 17 | 0.0055 | 0.0051 | (0.93x) |
| 18 | 0.0079 | 0.0077 | (0.97x) |
| 19 | 0.088 | 0.176 | (2.0x) |
| 20 | 0.17 | 0.39 | (2.3x) |
| 21 | 0.018 | 0.041 | (2.3x) |
| 22 | 0.042 | 0.122 | (2.9x) |
| 23 | 0.010 | 0.029 | (2.9x) |
| 24 | 0.013 | 0.023 | (1.8x) |
| 25 | 0.014 | 0.036 | (2.6x) |
| 26 | 0.030 | 0.099 | (3.3x) |
| 27 | 0.17 | 0.51 | (3.0x) |
| 28 | 0.013 | 0.035 | (2.7x) |
| 29 | 0.083 | 0.166 | (2.0x) |
| 30 | 0.017 | 0.027 | (1.6x) |
| 31 | 0.015 | 0.033 | (2.2x) |
| 32 | 3.8 | 20 | (5.3x) |
| 33 | 0.15 | 0.72 | (4.8x) |
| 34 | 0.012 | 0.011 | (0.94x) |
| 35 | 0.0091 | 0.0088 | (0.97x) |
| 36 | 0.011 | 0.012 | (1.1x) |
| 37 | 0.0066 | 0.0099 | (1.5x) |
| 38 | 0.011 | 0.032 | (2.9x) |
| 39 | 0.0072 | 0.017 | (2.4x) |
| 40 | 0.0089 | 0.028 | (3.2x) |
| 41 | 0.021 | 0.059 | (2.8x) |
| 42 | 0.18 | 0.27 | (1.5x) |
| 43 | 0.47 | 0.56 | (1.2x) |
| 44 | 4.2 | 10.0 | (2.4x) |
| 45 | 0.29 | 0.41 | (1.4x) |
| 46 | 20 | 20 | (1.0x) |
| 47 | 1.2 | 2.3 | (1.9x) |

TABLE 3-continued

Cbl-b and C-Cbl Selectivity of Isoindolin-1-one Compounds

| Compound | Cbl-b Lck HTRF IC$_{50}$ (µM) | C-cbl Lck HTRF IC$_{50}$ (µM) | (fold-selectivity) |
|---|---|---|---|
| 48 | 0.010 | 0.015 | (1.5x) |
| 49 | 0.014 | 0.0196 | (1.4x) |
| 50 | 0.031 | 0.053 | (1.7x) |
| 51 | 0.038 | 0.061 | (1.6x) |
| 52 | 0.0072 | 0.0094 | (1.3x) |
| 53 | 0.0057 | 0.0063 | (1.1x) |
| 54 | 0.0082 | 0.115 | (1.4x) |
| 55 | 0.0067 | 0.0094 | (1.4x) |
| 56 | 1.0 | 6.7 | (6.7x) |
| 57 | 10 | 19 | (1.9x) |
| 58 | 0.28 | 0.56 | (2.0x) |
| 59 | 0.018 | 0.017 | (0.96x) |
| 60 | 0.11 | 0.080 | (0.73x) |
| 61 | 0.015 | 0.0255 | (1.7x) |
| 62 | 0.0055 | 0.0051 | (0.93x) |
| 63 | 0.0079 | 0.0142 | (1.8x) |
| 64 | 0.024 | 0.070 | (2.9x) |
| 65 | 0.020 | 0.062 | (3.1x) |
| 66 | 0.025 | 0.0625 | (2.5x) |
| 67 | 0.0065 | 0.0059 | (0.9x) |
| 68 | 0.0085 | 0.0071 | (0.8x) |
| 69 | 0.011 | 0.054 | (4.9x) |
| 70 | 0.017 | 0.158 | (9.3x) |
| 71 | 0.014 | 0.0168 | (1.2x) |
| 72 | 2.4 | 5.3 | (2.4x) |
| 73 | 0.022 | 0.035 | (1.6x) |
| 74 | 0.015 | 0.023 | (1.5x) |
| 75 | 0.017 | 0.022 | (1.3x) |
| 76 | 0.0064 | 0.0064 | (1.0x) |
| 77 | 0.0082 | 0.0082 | (1.0x) |
| 78 | 0.014 | 0.070 | (5.0x) |
| 79 | 0.032 | 0.237 | (7.4x) |
| 88 | 0.012 | 0.012 | 1.0x |
| 89 | 0.041 | 0.098 | 2.4x |
| 90 | 0.0078 | 0.0066 | 0.83x |
| 91 | 0.010 | 0.008 | 0.8x |
| 92 | 0.013 | 0.029 | 2.2x |
| 93 | 0.12 | 0.90 | 7.3x |
| 94 | 0.021 | 0.12 | 6.0x |
| 95 | 0.012 | 0.021 | 1.7x |
| 96 | 4.5 | 16 | 3.7x |
| 97 | 5.2 | 16 | 3.1x |
| 98 | 1.3 | 7.5 | 5.8x |
| 99 | 0.086 | 0.32 | 3.7x |
| 100 | 0.025 | 0.086 | 3.5x |
| 101 | 0.0091 | 0.0098 | 1.1x |
| 102 | 0.0072 | 0.011 | 1.5x |
| 103 | 0.014 | 0.026 | 1.7x |
| 104 | 0.013 | 0.017 | 1.4x |
| 105 | 0.015 | 0.054 | 3.7x |
| 106 | 0.023 | 0.081 | 3.5x |
| 107 | 0.30 | 1.8 | 6.0x |
| 108 | 0.017 | 0.16 | 9.2x |
| 109 | 0.047 | 0.22 | 4.6x |
| 110 | 1.4 | 9.4 | 6.5x |
| 111 | 4.9 | 20 | 4.1x |
| 112 | 20 | 20 | 1.0x |
| 113 | 3.5 | 18 | 5.3x |
| 114 | 0.36 | 0.77 | 2.1 |
| 115 | 0.010 | 0.023 | 2.3x |
| 116 | 0.025 | 0.15 | 6.0x |
| 117 | 0.012 | 0.060 | 5.0x |
| 118 | 20 | 20 | 1.0x |
| 119 | 3.6 | 13 | 3.6x |
| 120 | 0.36 | 1.8 | 4.8 |
| 121 | 11 | 20 | 1.7x |
| 122 | 1.4 | 2.1 | 1.6x |
| 123 | 0.068 | 0.23 | 3.4x |
| 124 | 0.056 | 0.10 | 1.9x |
| 125 | 0.41 | 2.3 | 5.7x |
| 126 | 0.075 | 0.25 | 3.4 |
| 127 | 0.41 | 2.0 | 4.1x |
| 128 | 0.24 | 1.3 | 4.9x |
| 129 | 0.011 | 0.039 | 3.5x |
| 130 | 0.0055 | 0.0057 | 1.0x |
| 131 | 0.74 | 5.6 | 7.4x |
| 132 | 0.60 | 4.8 | 8.0x |
| 133 | 0.15 | 0.73 | 4.9x |
| 134 | 0.0098 | 0.017 | 1.8x |
| 135 | 0.037 | 0.069 | 1.9x |
| 136 | 20 | 20 | 1.0x |
| 137 | 0.0061 | 0.0085 | 1.4x |
| 138 | 0.0041 | 0.0042 | 1.0x |
| 139 | 0.35 | 1.3 | 3.6x |
| 140 | 0.83 | 1.5 | 1.9x |
| 141 | 0.0076 | 0.012 | 1.6x |
| 142 | 0.20 | 0.35 | 1.8x |
| 143 | 0.062 | 0.19 | 3.1x |
| 144 | 4.5 | 8.2 | 1.6x |
| 145 | 0.076 | 0.18 | 2.4x |
| 146 | 4.0 | 9.2 | 2.3x |
| 147 | 0.013 | 0.029 | 2.2x |
| 148 | 0.0099 | 0.044 | 4.4x |
| 149 | 0.0049 | 0.0041 | 0.82x |
| 150 | 0.0091 | 0.013 | 1.4x |
| 151 | 3.8 | 7.9 | 2.1x |
| 152 | 0.018 | 0.052 | 2.9x |
| 153 | 2.7 | 8.3 | 2.9x |
| 154 | 20 | 20 | 1.0x |
| 155 | 10 | 10 | 2.0x |
| 156 | 7.7 | 18 | 2.4x |
| 157 | 20 | 20 | 1.0 |
| 158 | 1.4 | 5.0 | 3.6 |
| 159 | 20 | 20 | 1.0x |
| 160 | 1.3 | 5.3 | 3.9x |
| 161 | 0.60 | 4.3 | 7.2x |
| 162 | 9.1 | 20 | 2.1x |
| 163 | 20 | 20 | 1.0x |
| 164 | 0.0089 | 0.018 | 2.0x |
| 165 | 3.9 | 10 | 2.3 |
| 166 | 1.9 | 7.2 | 3.8x |
| 167 | 1.4 | 6.4 | 4.7x |
| 168 | 0.023 | 0.034 | 1.5x |
| 169 | 0.072 | 0.34 | 4.8x |
| 170 | 0.012 | 0.012 | 1.0x |
| 171 | 1.1 | 2.3 | 2.0x |
| 172 | 0.088 | 0.29 | 3.4x |
| 173 | 0.020 | 0.045 | 2.2x |
| 174 | 0.0085 | 0.0068 | 0.80x |
| 175 | 0.0096 | 0.0097 | 1.0x |
| 176 | 0.062 | 0.22 | 3.4x |
| 177 | 0.059 | 0.18 | 2.8x |
| 178 | 0.033 | 0.085 | 2.5x |
| 179 | 0.030 | 0.11 | 3.4x |
| 180 | 0.018 | 0.074 | 3.7x |
| 181 | 0.0098 | 0.0083 | 0.85x |
| 182 | 0.011 | 0.011 | 1.0x |
| 183 | 0.018 | 0.058 | 3.4x |
| 184 | 0.0076 | 0.0083 | 1.1x |
| 185 | 0.023 | 0.15 | 6.7x |
| 186 | 0.035 | 0.10 | 2.9x |
| 187 | 0.011 | 0.022 | 1.0x |
| 188 | 0.016 | 0.18 | 11x |
| 189 | 0.0072 | 0.0041 | 0.56x |
| 190 | 7.8 | 16 | 2.0x |
| 191 | 5.7 | 9.7 | 1.7x |
| 192 | 0.013 | 0.0092 | 0.7x |
| 193 | 0.036 | 0.42 | 11x |
| 194 | 0.013 | 0.034 | 2.5x |
| 195 | 0.036 | 0.084 | 2.4x |
| 196 | 1.5 | 8.3 | 5.6x |
| 197 | 0.037 | 0.16 | 4.5x |
| 198 | 0.046 | 0.20 | 4.4x |
| 199 | 15 | 20 | 1.4x |
| 200 | 0.024 | 0.040 | 1.7x |
| 201 | 0.012 | 0.018 | 1.5x |
| 202 | 0.011 | 0.021 | 1.8x |
| 203 | 0.018 | 0.038 | 2.1x |
| 204 | 0.013 | 0.029 | 2.3x |
| 205 | 0.063 | 0.24 | 3.8x |

TABLE 3-continued

Cbl-b and C-Cbl Selectivity of Isoindolin-1-one Compounds

| Compound | Cbl-b Lck HTRF IC$_{50}$ (µM) | C-cbl Lck HTRF IC$_{50}$ (µM) | (fold-selectivity) |
|---|---|---|---|
| 206 | 0.034 | 0.082 | 2.4x |
| 207 | 0.024 | 0.052 | 2.2x |
| 208 | 0.45 | 2.2 | 4.8x |
| 209 | 0.044 | 0.32 | 7.2x |
| 210 | 0.009 | 0.012 | 1.3x |
| 211 | 0.015 | 0.060 | 4.0x |
| 212 | 0.15 | 0.39 | 2.6x |
| 213 | 0.24 | 0.44 | 1.9x |
| 214 | 0.0093 | 0.0090 | 0.97x |
| 215 | 0.0094 | 0.012 | 1.3x |
| 216 | 0.014 | 0.061 | 4.2x |
| 217 | 0.018 | 0.097 | 5.5x |
| 218 | 0.081 | 0.81 | 10x |
| 219 | 0.013 | 0.036 | 2.7x |
| 220 | 0.013 | 0.039 | 3.0x |
| 221 | 0.011 | 0.016 | 1.5x |
| 222 | 0.064 | 0.27 | 4.2x |
| 223 | 0.015 | 0.021 | 1.4x |
| 224 | 0.020 | 0.10 | 5.0x |
| 225 | 0.018 | 0.072 | 4.0x |
| 226 | 0.011 | 0.010 | 0.99x |
| 227 | 0.010 | 0.016 | 1.6x |
| 228 | 0.016 | 0.021 | 1.3x |
| 229 | 0.23 | 1.4 | 5.9x |
| 230 | 0.19 | 0.29 | 1.5x |
| 231 | 0.011 | 0.017 | 1.5x |
| 232 | 0.013 | 0.035 | 2.6x |
| 233 | 0.040 | 0.20 | 5.0x |
| 234 | 0.025 | 0.14 | 5.6x |
| 235 | 0.078 | 0.11 | 1.4x |
| 236 | 0.038 | 0.065 | 1.7x |
| 237 | 0.34 | 0.39 | 1.2x |
| 238 | 0.012 | 0.014 | 1.1x |
| 239 | 0.013 | 0.013 | 1.0x |
| 240 | 0.014 | 0.051 | 3.7x |
| 241 | 0.13 | 0.53 | 4.0x |
| 242 | 0.056 | 0.22 | 4.0x |
| 243 | 0.064 | 0.29 | 4.4x |
| 244 | 3.1 | 3.6 | 1.2x |
| 245 | 0.049 | 0.11 | 2.2x |
| 246 | 0.0086 | 0.015 | 1.7x |
| 247 | 0.0098 | 0.018 | 1.9x |
| 248 | 1.4 | 2.1 | 1.6x |
| 249 | 0.10 | 0.50 | 5.0x |
| 250 | 3.1 | 3.6 | 1.2x |
| 251 | 0.88 | 0.89 | 1.0x |
| 252 | 9.1 | 13 | 1.4x |
| 253 | 0.12 | 0.14 | 1.1x |
| 254 | 20 | 20 | 1.0x |
| 255 | 0.76 | 0.99 | 1.3x |
| 256 | 0.21 | 1.4 | 6.5x |
| 257 | 0.022 | 0.027 | 1.2x |
| 258 | 0.17 | 0.97 | 5.8x |
| 259 | 0.016 | 0.016 | 1.0x |
| 260 | 0.45 | 2.4 | 5.4x |
| 261 | 1.3 | 4.5 | 3.5x |
| 262 | 0.038 | 0.27 | 7.1x |
| 263 | 0.010 | 0.018 | 1.8x |
| 264 | 5.1 | 20 | 3.9x |
| 265 | 0.31 | 3.4 | 11x |
| 266 | 6.7 | 20 | 3.0x |
| 267 | 0.037 | 0.17 | 4.5x |
| 268 | 1.7 | 2.7 | 1.6x |
| 269 | 0.076 | 0.30 | 4.0x |
| 270 | 0.011 | 0.027 | 2.3x |
| 271 | 1.8 | 4.3 | 2.6x |
| 272 | 0.015 | 0.025 | 1.7x |
| 273 | 0.0085 | 0.016 | 2.0x |
| 274 | 0.0075 | 0.0069 | 0.91x |
| 275 | 20 | 20 | 1.0x |
| 276 | 20 | 20 | 1.0x |
| 277 | 3.6 | 8.6 | 2.3x |
| 278 | 5.0 | 8.9 | 1.8x |
| 279 | 0.0066 | 0.0093 | 1.4x |
| 280 | 0.0068 | 0.011 | 1.6x |
| 281 | 0.0067 | 0.0095 | 1.3x |
| 282 | 0.41 | 2.8 | 6.5x |
| 283 | 0.081 | 0.22 | 2.7x |
| 284 | 0.51 | 3.7 | 7.3x |
| 285 | 0.0060 | 0.0065 | 1.1x |
| 286 | 20 | 20 | 1.0x |
| 287 | 20 | 20 | 1.0x |
| 288 | 0.0053 | 0.0049 | 0.92x |
| 289 | 0.018 | 0.043 | 2.4x |
| 290 | 13 | 20 | 1.5x |
| 291 | 0.011 | 0.047 | 4.3x |
| 292 | 0.0098 | 0.023 | 2.4x |
| 293 | 0.064 | 0.19 | 3.0x |
| 294 | 0.40 | 0.66 | 1.6x |
| 295 | 20 | 20 | 1.0x |
| 296 | 8 | 16 | 2.0x |
| 297 | 1.3 | 2.3 | 1.8x |
| 298 | 0.66 | 1.5 | 2.3x |
| 299 | 2.5 | 3.8 | 1.5x |
| 300 | 8.7 | 17 | 2.0x |
| 301 | 0.30 | 0.59 | 2.0x |
| 302 | 0.41 | 0.88 | 2.1x |
| 303 | 0.011 | 0.026 | 2.3x |
| 304 | 7.8 | 20 | 2.6x |
| 305 | 20 | 20 | 1.0x |
| 306 | 0.14 | 0.23 | 1.6x |
| 307 | 7.6 | 12 | 1.5x |
| 308 | 0.027 | 0.041 | 1.5x |
| 309 | 5.3 | 20 | 3.8x |
| 310 | 0.024 | 0.11 | 4.7x |
| 311 | 0.0040 | 0.0043 | 1.1x |
| 312 | 0.0078 | 0.027 | 3.5x |
| 313 | 0.0064 | 0.0044 | 0.68x |
| 314 | 0.011 | 0.051 | 4.5x |
| 315 | 6.8 | 20 | 2.0x |
| 316 | 0.27 | 3.1 | 11x |
| 317 | 0.17 | 1.1 | 6.5x |
| 318 | 0.28 | 1.6 | 5.6x |
| 319 | 0.012 | 0.041 | 3.5x |
| 320 | 0.0056 | 0.0075 | 1.3x |
| 321 | 20 | 20 | 1.0x |
| 322 | 10 | 20 | 2.0x |
| 323 | 0.0050 | 0.0071 | 1.4x |
| 324 | 0.0048 | 0.0071 | 1.5x |
| 325 | 11 | 20 | 1.9x |
| 326 | 16 | 20 | 1.2x |
| 327 | 0.19 | 0.55 | 2.9x |
| 328 | 0.10 | 0.38 | 3.8x |
| 329 | 0.011 | 0.019 | 1.8x |
| 330 | 0.20 | 0.39 | 1.9x |
| 331 | 0.029 | 0.11 | 3.8x |
| 332 | 16 | 20 | 1.3x |
| 333 | 0.039 | 0.041 | 1.0x |
| 334 | 0.0059 | 0.014 | 2.5x |
| 335 | 0.0088 | 0.026 | 3.0x |
| 336 | 0.0074 | 0.0091 | 1.2x |
| 337 | 0.0062 | 0.0078 | 1.2x |
| 338 | 3.8 | 6.0 | 1.6x |
| 339 | 0.0056 | 0.0063 | 1.1x |
| 340 | 0.11 | 1.1 | 10x |
| 341 | 0.013 | 0.10 | 8.4x |
| 342 | 0.0056 | 0.0066 | 1.2x |
| 343 | 0.29 | 0.61 | 2.1x |
| 344 | 20 | 20 | 1x |
| 345 | 2.4 | 11 | 4.4x |
| 346 | 0.040 | 0.19 | 4.6x |
| 347 | 0.010 | 0.030 | 3x |
| 348 | 0.14 | 0.50 | 3.5x |
| 349 | 20 | 20 | 1x |
| 350 | 0.016 | 0.077 | 4.8x |
| 351 | 0.0064 | 0.020 | 6.4x |
| 352 | 0.069 | 0.28 | 4.1x |
| 353 | 9.6 | 20 | 2.1x |
| 354 | 0.070 | 0.58 | 8.3x |
| 355 | 0.15 | 2.0 | 13x |

TABLE 3-continued

Cbl-b and C-Cbl Selectivity of Isoindolin-1-one Compounds

| Compound | Cbl-b Lck HTRF IC$_{50}$ (μM) | C-cbl Lck HTRF IC$_{50}$ (μM) | (fold-selectivity) |
|---|---|---|---|
| 356 | 0.029 | 0.18 | 6.1x |
| 357 | 0.0052 | 0.0071 | 1.4x |
| 358 | 0.14 | 0.48 | 3.5x |
| 359 | 0.0048 | 0.0041 | 0.85x |
| 360 | 0.092 | 0.59 | 6.4x |
| 361 | 0.0081 | 0.036 | 4.4x |
| 362 | 0.0060 | 0.038 | 6.3x |
| 363 | 0.061 | 0.14 | 2.3x |
| 364 | 0.0025 | 0.0033 | 1.3x |
| 365 | 0.0048 | 0.0059 | 1.2x |
| 367 | 7.1 | 12 | 1.7x |
| 368 | 4.0 | 6.4 | 1.6x |
| 369 | 0.24 | 1.0 | 4.3x |
| 370 | 0.013 | 0.042 | 3.2x |
| 371 | 0.0083 | 0.042 | 5.0x |
| 372 | 0.014 | 0.070 | 5.0x |
| 373 | 0.0072 | 0.027 | 3.8x |
| 374 | 0.0066 | 0.014 | 2.0x |
| 375 | 0.0064 | 0.016 | 2.5x |
| 376 | 0.055 | 0.49 | 9.0x |
| 377 | 0.24 | 2.5 | 11x |
| 378 | 0.0094 | 0.056 | 6.0x |
| 379 | 0.0068 | 0.0095 | 1.6x |
| 380 | 0.006 | 0.0071 | 1.2x |
| 381 | 0.0088 | 0.016 | 1.9x |
| 382 | 0.15 | 0.45 | 3.0x |
| 383 | 0.019 | 0.024 | 1.3x |
| 384 | 0.024 | 0.066 | 2.8x |
| 385 | 0.26 | 0.72 | 2.8x |
| 386 | 0.11 | 0.29 | 2.6x |
| 387 | 0.13 | 1.0 | 7.8x |
| 388 | 0.12 | 0.87 | 7.6x |
| 389 | 0.0051 | 0.0089 | 1.7x |
| 390 | 0.0055 | 0.0055 | 1.0x |
| 391 | 0.85 | 0.86 | 1.0x |
| 392 | 0.010 | 0.014 | 1.4x |
| 393 | 0.19 | 0.46 | 2.4x |
| 394 | 0.0046 | 0.0038 | 0.8x |
| 395 | 0.075 | 0.16 | 2.1x |
| 396 | 0.10 | 0.17 | 1.7x |
| 397 | 0.0064 | 0.0048 | 0.8x |
| 398 | 0.0058 | 0.0065 | 1.1x |
| 399 | 0.53 | 6.0 | 12x |
| 400 | 20 | 20 | 1.0x |
| 401 | 8.5 | 13 | 1.6 |
| 402 | 0.58 | 2.5 | 4.3x |
| 403 | 0.75 | 0.96 | 1.3x |
| 404 | 0.0048 | 0.0049 | 1.0x |
| 405 | 0.015 | 0.077 | 5.3x |
| 406 | 9.9 | 20 | 2.0x |
| 407 | 0.39 | 5.7 | 14x |
| 408 | 0.54 | 0.78 | 1.4 |
| 409 | 0.052 | 0.057 | 1.1x |
| 410 | 4.5 | 15 | 3.4x |
| 411 | 20 | 20 | 1.0x |
| 412 | 0.014 | 0.059 | 4.2x |
| 413 | 0.0045 | 0.0071 | 1.6x |
| 414 | 0.0094 | 0.050 | 5.2x |
| 415 | 0.011 | 0.048 | 4.2x |
| 416 | 0.0075 | 0.011 | 1.5x |
| 417 | 0.48 | 3.2 | 6.6x |
| 418 | 0.18 | 1.4 | 7.3x |
| 419 | 0.029 | 0.19 | 6.7x |
| 420 | 0.10 | 0.72 | 7.2x |
| 421 | 0.0065 | 0.017 | 2.6x |
| 422 | 0.22 | 1.6 | 7.2x |
| 423 | 0.10 | 0.50 | 5.0x |
| 424 | 0.23 | 1.5 | 6.5x |
| 425 | 0.13 | 0.88 | 6.8x |
| 426 | 0.013 | 0.060 | 4.6x |
| 427 | 0.0070 | 0.022 | 3.1x |
| 428 | 5.3 | 20 | 3.8x |
| 429 | 0.037 | 0.20 | 5.1x |
| 430 | 0.019 | 0.091 | 4.7x |
| 431 | 0.0053 | 0.0058 | 1.1x |
| 432 | 0.0055 | 0.0071 | 1.3x |
| 433 | 0.017 | 0.078 | 4.7x |
| 434 | 0.16 | 0.51 | 3.1x |
| 435 | 8.5 | 20 | 2.4x |
| 436 | 0.57 | 2.4 | 4.2x |
| 437 | 20 | 20 | 1.0x |
| 438 | 3.0 | 20 | 6.8x |
| 439 | 14 | 20 | 1.4 |
| 440 | 0.066 | 0.4 | 6.0x |
| 441 | 6.3 | 20 | 3.2x |
| 442 | 0.26 | 2.8 | 11x |
| 443 | 3.3 | 5.7 | 1.7x |
| 444 | 0.0041 | 0.0045 | 1.1x |
| 445 | 0.0097 | 0.030 | 3.1x |
| 446 | 0.0068 | 0.011 | 1.7x |
| 447 | 0.0045 | 0.0062 | 1.4x |
| 448 | 0.73 | 3.9 | 5.5x |
| 449 | 0.22 | 1.2 | 5.4x |
| 450 | 0.0058 | 0.023 | 4.0x |
| 451 | 0.0042 | 0.0066 | 1.6x |
| 452 | 0.0055 | 0.0056 | 1.0x |
| 453 | 0.0066 | 0.011 | 1.7x |
| 454 | 0.0065 | 0.016 | 2.4x |
| 455 | 0.0087 | 0.020 | 2.3x |
| 456 | 0.36 | 2.4 | 6.5x |
| 457 | 7.1 | 11 | 1.6x |
| 458 | 0.014 | 0.043 | 3.1x |
| 459 | 0.0059 | 0.0063 | 1.1x |
| 460 | 0.61 | 3.9 | 6.4x |
| 461 | 0.36 | 3.2 | 8.8 |
| 462 | 0.013 | 0.024 | 1.9x |
| 463 | 0.0065 | 0.012 | 1.9x |
| 464 | 0.0065 | 0.0071 | 1.1x |
| 465 | 0.0066 | 0.012 | 1.8x |
| 466 | 0.0062 | 0.0086 | 1.4x |
| 467 | 0.022 | 0.086 | 4.0x |
| 468 | 0.0052 | 0.0075 | 1.4x |
| 469 | 0.0053 | 0.0045 | 0.85x |
| 470 | 0.0044 | 0.0045 | 1.0x |
| 471 | 0.0083 | 0.036 | 4.3x |
| 472 | 0.013 | 0.042 | 3.2x |
| 473 | 0.014 | 0.050 | 3.6x |
| 474 | 0.011 | 0.051 | 4.8x |
| 475 | 0.0087 | 0.023 | 3.3x |
| 476 | 0.082 | 0.57 | 7.1x |
| 477 | 0.017 | 0.093 | 5.6x |
| 478 | 0.13 | 0.84 | 6.4x |
| 479 | 0.029 | 0.25 | 8.6x |
| 480 | 0.034 | 0.28 | 7.9x |
| 481 | 0.0062 | 0.025 | 4.0x |
| 482 | 0.0053 | 0.020 | 3.7x |
| 483 | 0.010 | 0.058 | 5.8x |
| 484 | 0.026 | 0.26 | 10x |
| 485 | 0.013 | 0.067 | 5.2x |
| 486 | 0.018 | 0.11 | 6.0x |
| 487 | 0.019 | 0.15 | 7.4x |
| 488 | 0.0058 | 0.014 | 2.4x |
| 489 | 0.014 | 0.074 | 5.3x |
| 490 | 0.055 | 0.27 | 5.0 |
| 491 | 0.0084 | 0.036 | 4.3x |
| 492 | 0.014 | 0.087 | 6.2x |
| 493 | 0.028 | 0.23 | 8.5x |
| 494 | 0.0083 | 0.025 | 3.1x |
| 495 | 0.018 | 0.11 | 6.7x |
| 496 | 0.017 | 0.087 | 5.2x |
| 497 | 0.0052 | 0.024 | 4.7x |
| 498 | 0.0041 | 0.015 | 3.6x |
| 499 | 0.016 | 0.078 | 5.0x |
| 500 | 0.016 | 0.085 | 5.3x |
| 501 | 0.011 | 0.052 | 4.8x |
| 502 | 0.0094 | 0.039 | 4.1x |
| 503 | 0.0085 | 0.026 | 3.0x |
| 504 | 0.013 | 0.068 | 5.1x |
| 505 | 0.0073 | 0.030 | 4.1x |
| 506 | 0.022 | 0.18 | 8.0x |

TABLE 3-continued

Cbl-b and C-Cbl Selectivity of Isoindolin-1-one Compounds

| Compound | Cbl-b Lck HTRF IC$_{50}$ (µM) | C-cbl Lck HTRF IC$_{50}$ (µM) | (fold-selectivity) |
|---|---|---|---|
| 507 | 0.0093 | 0.042 | 4.5x |
| 508 | 0.0062 | 0.024 | 3.8x |
| 509 | 0.016 | 0.075 | 4.7x |
| 510 | 0.012 | 0.051 | 4.2x |
| 511 | 0.012 | 0.061 | 5.0x |

Cbl-b Lck HTRF data in Table 3 is measured according to Example 121 herein; C-cbl Lck HTRF data is measured according to Example 1001 herein.

Example 122: PBMC IL-2 Assay

Immune response to compounds described herein can be assessed via a PBMC IL-2 assay, conducted according to the following protocol. PBMCs (#A19K379053, A19K261022; TPCS) are thawed into complete medium: 1640 medium (#2085568; Gibco), 10% FBS (#SH30084.03; HyClone), and 1× pen/strep. Compounds are 3-fold serially diluted in DMSO in a 384-well polypropylene plate (#P-05525-BC; Labcyte) using the Tecan EVO to generate a source plate with 10 concentrations of each compound, top concentration=4 mM. Compounds are dispensed into a 96-well plate (#6005680; PerkinElmer) using a Labcyte Echo; final dispensed volume of each control and compound is 1000 nL (final DMSO=0.5%). After recovery overnight, cells are seeded at 2×10$^5$ cells/well into 96-well plates containing compounds and incubated at 37° C., 5% $CO_2$ for 30 min. Cells are stimulated by adding 20 µL/well 1/10 TransAct (#130-111-160; Miltenyi) diluted in complete medium, placed on a shaker for 2 min at 600 rpm, and incubated for 24 h at 37° C., 5% $CO_2$. Plates are centrifuged at 1200 rpm for 5 min and 120 µL cell supernatant collected. Supernatants are diluted 10-fold and IL-2 concentrations of each sample are determined using the IL-2 MSD kit (#K151AHB-4; MSD) per the manufacturer's instructions.

Example 123: Liver Microsomes Metabolic Stability Assays

Metabolic stability of test compounds was evaluated in pooled rat, mouse, dog, and cynomolgus monkey liver microsomes (BD Biosciences, San Jose, Calif.). The incubation conditions were as follows: 1 µM of the tested compound, 1 mM NADPH, 0.5 mg/mL microsomal protein in 0.1 M potassium phosphate buffer (pH 7.4). Following a 5-minute pre-incubation period, the enzymatic reactions were initiated by the addition of NADPH and test compound to the microsomes diluted in phosphate buffered saline. The mixtures were incubated at 37° C. for 0, 20, 40, and 60 min. Compound concentrations were assessed by LC-MS/MS. Intrinsic clearance based upon microsomal stability data was determined using a substrate depletion method and scaled to hepatic clearance using the well-stirred model (Obach, R. S.; Baxter, J. G.; Liston, T. E.; Silber, B. M.; Jones, B. C.; MacIntyre, F.; Rance, D. J.; Wastall, P., "The Prediction of Human Pharmacokinetic Parameters from Preclinical and in vitro Metabolism Data", J. Pharmacol. Exp. Ther., (1997), 283 (1), 46-58).

Example 124: Hepatocyte Metabolic Stability Assays

Metabolic stability assays of test compounds were evaluated in cryopreserved pooled rat, mouse, dog, and cynomolgus monkey hepatocytes (CellzDirect; Durham, N.C., USA). Membrane integrity of the cells was assessed by trypan blue exclusion. Test compounds (1.0 µM with 0.1% dimethylsulfoxide) were incubated with cells (0.5 million cells/mL) at 37° C. in a 95% air/5% $CO_2$ atmosphere for 0, 20, 40, or 60 minutes. Concentrations of test compounds in hepatocyte incubations were determined by LC/MS/MS. Intrinsic clearance was determined using a substrate depletion method and scaled to hepatic clearance using the well-stirred model as described above for the liver microsomes metabolic stability assays.

Example 125: In Vitro Plasma Protein Binding

In vitro plasma protein binding (n=2) was determined in pooled mouse, rat, and human plasma (Bioreclamation, Inc., Hicksville, N.Y.) by equilibrium dialysis using a Rapid Equilibrium Dialysis (RED) device (Pierce Biotechnology/Thermo Fisher Scientific; Rockford, Ill.) with a molecular weight cut-off of 8000 Daltons. Test compounds were added to plasma. Plasma samples were equilibrated with phosphate-buffered saline at 37° C. for 4 hours. Compound concentrations in post-dialysis plasma and buffer samples were measured by LC-MS/MS. The percent unbound fraction in plasma for each compound was calculated by dividing the compound concentration in the post-dialysis buffer by that measured in the post-dialysis plasma and multiplying by 100%.

Example 126: In Vitro Permeability Assay in gMDCK (Madin-Darby Canine Kidney) Cells The permeability of test compounds was determined in gMDCK cells (American Type Culture Collection; Manassas, Va.), which establishes that these compounds have significantly improved permeability than those previously known. Four days prior to use, MDCK cells were seeded at a density of 2.5×10$^5$ cells/mL in 24 well plates. Compounds were dissolved in transport buffer consisting of Hank's Balanced Salt Solution with 10 mM HEPES (Invitrogen Corporation, Grand Island, N.Y.) at a concentration of 10 µM, and permeability was assessed in the apical to basolateral (A-B) and basolateral to apical (B-A) directions following a 3 hour incubation. Lucifer Yellow (Sigma Aldrich, St. Louis, Mo.) was used as the cell monolayer integrity marker. Test compound concentrations in the donor and receiving compartments were determined by LC-MS/MS. The apparent permeability ($P_{app}$) of test compounds was determined as follows:

$$P_{app} = (dQ/dt) * (1/AC_0)$$

Where dQ/dt is the rate of compound appearance in the receiver compartment, Q is the quantity of compound), $C_0$ is the concentration in the donor compartment and A is the surface area of the insert. Efflux ratio was calculated as $P_{app, B-A}/P_{app, A-B}$.

Example 127: Reversible CYP Inhibition

Reversible CYP inhibition by compounds described herein can be measured by protocols described by Halladay, J. S.; Delarosa, E. M.; Tran, D.; Wang, L.; Wong, S.; Khojasteh, S. C., "High-Throughput, 384-Well, LC-MS/MS CYP Inhibition Assay Using Automation, Cassette-Analysis Technique, and Streamlined Data Analysis", *Drug. Metab. Lett.* 2011, 5 (3), 220-230, incorporated herein by reference.

Example 128: CYP3A Time-Dependent Inhibition (TDI)

Time-dependent inhibition by compounds described herein can be measured by various methods. Exemplary such protocols for CYP3A automated AUC shift dilution TDI assay and definitive Ki/Kinact TDI assay are described by Kenny, J. R.; Mukadam, S.; Zhang, C.; Tay, S.; Collins, C.; Galetin, A.; Khojasteh, S. C., "Drug-Drug Interaction Potential of Marketed Oncology Drugs: in vitro Assessment of Time-Dependent Cytochrome P450 Inhibition, Reactive Metabolite Formation and Drug-Drug Interaction Prediction," *Pharm. Res.* 2012, 29 (7), 1960-1976.

Example 129: In Vivo Pharmacokinetics (PK)

The pharmacokinetics of test compounds were evaluated following a single intravenous bolus (IV) of solution at a dose of 0.2-1 mg/kg and oral administration (PO) of solution/suspension at doses of 1-5 mg/kg in male cynomolgus monkey, beagle dogs, or Sprague Dawley rats using a parallel study design. Blood samples for the IV dose group were collected prior to administration (predose) and at 0.033, 0.083, 0.25, 0.5, 1, 3, 6, 9 and 24 hours post dose. Blood samples for PO dose groups were collected prior to administration (predose) and at 0.083, 0.25, 0.5, 1, 3, 6, 9 and 24 hours post dose. For the IV group, urine was collected from each animal at predose and from 0-6 and 6-24 hours post dose. The vehicle used for IV dose groups was a combination of PEG400 with citrate buffer (pH 5.0) or PEG400/Cremphor with DMSO/$H_2O$, and for PO groups was MCT.

Plasma and urine concentrations were quantitated at Genentech Inc. using a non-validated LC/MS/MS method. The lower limit of quantitation (LLOQ) of the plasma and urine assays was 0.005 μM. PK parameters were determined by non-compartmental methods using WinNonlin (version 5.2, Pharsight Corporation, Mountain View, Calif.).

Example 130: Pharmacodynamics (PD) Study; Enhancement of CD4 and CD8 T Cell Activation in Response to Systemic Anti-CD3 Administration in the Presence of Cbl-b Inhibitor Female C57BL/6 or Balb/c mice are administered with anti-CD3 antibody (2 ug/mouse, clone 2C11) or an isotype control (2 μg/mouse, hamster IgG) is administered by tail vein injection. A Cbl-b inhibitor is administered PO starting at time 0 (immediately before anti-CD3 administration) and again 8 hrs later. Four hours after anti-CD3 administration, mice are bled and cytokines are quantified in serum via Luminex. Twenty-four hours after anti-CD3 administration, mice are euthanized and activation of CD4 and CD8 T cells quantified in spleens and blood. Expression of 4-1 BB, CD25, CD40L, and CD69 as well as cell surface TCR levels will be quantified by flow cytometry. Serum are collected for cytokine analysis via Luminex.

Example 131: Tumor PD/Efficacy Study; Evaluation of Tumor Growth and Immune Cell Infiltration in Mice with Syngeneic Tumors Treated Prophylactically or Therapeutically with Cbl-b Inhibitor Female C57Bl/6 mice age 6-12 weeks are inoculated subcutaneously in the 5th mammary fat pad with 0.1 million E0771 cells in 100 microliters of HBSS+matrigel under manual restraint. For prophylactic studies, a Cbl-b inhibitor is administered PO BID×3 weeks starting 1 hr prior to tumor inoculation. Three weeks after tumor inoculation, mice are euthanized and tumor, spleen, blood and draining lymph node are harvested and immune cell infiltrate and phenotype are assessed by flow cytometry. Serum are obtained at various time points for cytokine analysis via Luminex. For therapeutic efficacy assessment, tumors are inoculated as described above and allowed to grow until tumors reach a median volume of 120-250 $mm^3$. Dosing with a Cbl-b inhibitor is then be initiated as above and continued until end of study. Tumor volumes and mouse body weight and condition are recorded twice weekly or more as needed until end of study. Efficacy of a Cbl-b inhibitor can also be assessed in additional syngeneic tumor models, including CT26 and TC-1.

Example 132: Cbl-b and c-Cbl SPR Assay

Affinity of binding to Cbl-b and c-Cbl for compounds described herein was assessed by surface plasmon resonance (SPR) according to the following protocol. All experiments were recorded on a Biacore™ 8K or Biacore™ 8K+ (Cytiva) with both surface preparation and experimental measurements performed at 20° C. in an assay buffer consisting of 50 mM HEPES, pH 7.5, 0.15 M NaCl, 0.001% (v/v) Tween® 20, 0.2 mM tris(2-carboxyethyl)phosphine, 0.025% (w/v) carboxymethylated dextran (average MW 10 kDa), 0.2% (w/v) PEG 3350, and 2% DMSO.

Human Cbl-b (residues 40-426) or c-Cbl (residues 47-435) were irreversibly captured to a Series S sensor chip SA (Cytiva 29104992) via an N-terminal avi-tag, biotinylated by co-expression in *E. coli* with BirA. A surface capture range of 1300-1500 RU of protein was used for both isoforms.

For SPR measurements, 6 concentrations with 2 fold serial dilution were measured with blanks flanking each series for double referencing. Initial concentrations between 20 and 0.5 μM were used depending on the anticipated affinity of the tested compound. SPR sensorgrams were recorded in multi-cycle kinetics format, with a contact time of 60 seconds and a flow rate of 40 μl/min, the dissociation time was varied between 120-1200 seconds aiming for 4-5 half-lives of the measured interaction.

Kinetic and affinity parameters were extracted from the multicycle kinetics data fitting to a 1:1 binding model using the Biacore™ Incyte evaluation software (Cytiva).

Multi-Point Chaser SPR Assay Variation

For the purposes of this type of experiment the term "chaser compound" refers to a low affinity analogue of the compound under investigation which binds close to saturation at the used concentration and fully dissociates within 120 seconds. For the studies presented here the chaser compound is (Example 254 of WO2022169997).

Affinity of binding to Cbl-b and c-Cbl for potent compounds described herein ($K_d$<10 nM) were assessed by surface plasmon resonance (SPR) using a "Chaser" assay format.

Chaser assay utilize a single cycle kinetics SPR experiment with a contact time of 120 seconds, a flow rate of 50 μl/min and a dissociation time of 450 seconds. Single cycle kinetics titration utilized an initial blank injection and 5 concentrations with 2 fold serial dilution with a maximum concentration of 500 nM, blanked to a preceding 6 point blank single cycle kinetics injection for double referencing.

In the case of potent compounds, the protein-compound half-life cannot be accurately measured using routine fitting of the single cycle titration data. The $k_d$ is measured independently by determining the percentage unoccupied compound binding site over time by measuring the binding of a chaser compound measured by SPR.

Chaser binding was measured by a multicycle kinetics SPR experiment using a contact time of 20 seconds, a flow rate of 30 μl/min, and a dissociation time of 120 seconds. 7 injections of a single chaser concentration of 15 μM with a preceding blank injection, were recorded spaced out between 674 and 30,263 seconds after the last single cycle kinetics titration injection. The % compound bound at a given time was determined by comparison to a single injection of chaser preceding the single cycle kinetics titration defined below.

% Compound Bound=(1−(RUT/RUT0))*100

Where RUT is the observed SPR signal for chaser injection at time T, and RUT0 is the observed SPR signal for chaser injected prior to the titration of compound under investigation.

The % compound bound is plotted against time in seconds and fit to a single exponential, where the exponent represents the kd of the compound-protein complex. The single cycle kinetics experiment of the compound is then fit with a fixed kd determined using the chaser.

SPR and the LCK biochemical assay are orthogonal assays: SPR is a protein binding assay while the LCK assay is an enzyme activity assay. SPR measures compound binding affinity to CBL-B/C-CBL, whereas LCK assay measures compound inhibition of CBL-B/C-CBL ubiquitin transfer activity.

Cbl-b Lck SPR and C-cbl Lck SPR data for selected compounds (as numbered herein) are shown in Table 4, and are both measured according to Example 132 herein.

TABLE 4

| Example | Cbl-b SPR Kd (uM) | C-cbl SPR Kd (uM) | Fold of selectivity |
|---|---|---|---|
| 2 | 0.0023 | 0.029 | 13× |
| 7 | 0.0013 | 0.0057 | 4.4× |
| 8 | 0.0033 | 0.023 | 6.9× |
| 9 | 0.011 | 0.22 | 20× |
| 12 | 0.0025 | 0.012 | 5× |
| 13 | 0.12 | 0.49 | 4.1× |
| 14 | 0.63 | 5.5 | 8.8× |
| 15 | 0.77 | 11 | 14× |
| 16 | 0.00025 | 0.00034 | 1.3× |
| 17 | 0.00037 | 0.0011 | 3.2× |
| 18 | 0.0015 | 0.0056 | 3.7× |
| 19 | 0.040 | 0.20 | 5.0× |
| 20 | 0.080 | 0.35 | 4.4× |
| 21 | 0.0041 | 0.022 | 5.3× |
| 22 | 0.0027 | 0.067 | 25× |
| 23 | 0.0026 | 0.036 | 14× |
| 24 | 0.0017 | 0.015 | 8.4× |
| 25 | 0.0040 | 0.022 | 5.4× |
| 26 | 0.010 | 0.090 | 9.0× |
| 27 | 0.060 | 0.43 | 7.2× |
| 28 | 0.0025 | 0.013 | 5.5× |
| 29 | 0.059 | 0.17 | 2.8× |
| 30 | 0.0026 | 0.0098 | 3.8× |
| 31 | 0.0023 | 0.016 | 6.6× |
| 34 | 0.0040 | 0.0023 | 0.6× |
| 35 | 0.0005 | 0.0017 | 3.4× |
| 36 | 0.0013 | 0.0080 | 6.1× |
| 37 | 0.00080 | 0.0038 | 4.8× |
| 38 | 0.0034 | 0.024 | 6.4× |
| 39 | 0.0010 | 0.0075 | 7.5× |
| 40 | 0.0021 | 0.020 | 9.5× |
| 41 | 0.0057 | 0.078 | 14× |
| 48 | 0.0038 | 0.011 | 3.0× |
| 49 | 0.0022 | 0.016 | 7.0× |
| 50 | 0.0065 | 0.020 | 3.0× |
| 52 | 0.00095 | 0.011 | 11× |
| 53 | 0.0007 | 0.0065 | 9.2× |
| 54 | 0.0013 | 0.015 | 11× |
| 58 | 0.14 | 0.44 | 3.1× |
| 61 | 0.0037 | 0.020 | 5.2× |
| 62 | 0.00037 | 0.0011 | 3.2× |
| 63 | 0.0037 | 0.019 | 5.1× |
| 64 | 0.016 | 0.081 | 5.1× |
| 65 | 0.0037 | 0.068 | 19× |
| 66 | 0.016 | 0.081 | 5.0× |
| 67 | 0.00036 | 0.00053 | 1.5× |
| 68 | 0.00024 | 0.0010 | 4.3× |
| 69 | 0.0033 | 0.023 | 6.9× |
| 70 | 0.011 | 0.22 | 20× |
| 71 | 0.0037 | 0.034 | 9.1× |
| 72 | 0.0004 | 0.0018 | 4.5× |
| 73 | 0.001 | 0.003 | 3.0× |
| 74 | 0.0083 | 0.072 | 8.7× |
| 75 | 0.031 | 0.23 | 7.7× |
| 88 | 0.021 | 0.087 | 4.1× |
| 89 | 0.0006 | 0.004 | 6.6× |
| 90 | 0.0002 | 0.0004 | 2.0× |
| 91 | 0.0003 | 0.0009 | 3.0× |
| 92 | 0.0013 | 0.012 | 11× |
| 93 | 0.066 | 0.71 | 11× |
| 94 | 0.0074 | 0.14 | 19× |
| 95 | 0.002 | 0.015 | 7.5× |
| 96 | 4.3 | 18 | 4.1× |
| 99 | 0.048 | 0.23 | 4.8× |
| 100 | 0.0058 | 0.072 | 12× |
| 101 | 0.00085 | 0.0042 | 4.9× |
| 102 | 0.00083 | 0.0039 | 4.7× |
| 103 | 0.0016 | 0.012 | 7.8× |
| 104 | 0.0016 | 0.015 | 9.1× |
| 105 | 0.0031 | 0.020 | 6.5× |
| 106 | 0.0072 | 0.057 | 7.9× |
| 107 | 0.25 | 1.7 | 6.8× |
| 108 | 0.0052 | 0.12 | 21× |
| 109 | 0.021 | 0.14 | 7.0× |
| 110 | 1.1 | 7.6 | 7.2× |
| 111 | 3.6 | 31 | 8.6× |
| 113 | 2.7 | 34 | 13× |
| 114 | 0.29 | 0.61 | 2.1× |
| 115 | 0.0018 | 0.0089 | 5.2× |
| 116 | 0.0081 | 0.11 | 15× |
| 117 | 0.0032 | 0.053 | 16× |
| 119 | 0.78 | 2.3 | 3.0× |
| 120 | 0.18 | 1.4 | 6.8× |
| 123 | 0.021 | 0.13 | 6.1× |
| 124 | 0.017 | 0.067 | 3.9× |
| 125 | 0.13 | 1.5 | 11× |
| 126 | 0.012 | 0.13 | 6.0× |
| 127 | 0.36 | 4.8 | 13× |
| 128 | 0.23 | 3.0 | 13× |
| 129 | 0.0036 | 0.043 | 13× |
| 130 | 0.0003 | 0.0016 | 5.3× |
| 131 | 0.28 | 4.5 | 16× |
| 132 | 0.36 | 5.6 | 15× |
| 133 | 0.083 | 0.66 | 7.7× |
| 134 | 0.0019 | 0.013 | 6.6× |
| 135 | 0.013 | 0.063 | 4.9× |
| 137 | 0.00027 | 0.0021 | 8.4× |
| 138 | 0.00075 | 0.0042 | 5.6× |
| 139 | 0.22 | 1.0 | 4.6× |
| 140 | 0.98 | 0.85 | 0.88× |
| 141 | 0.0019 | 0.0094 | 5.1× |
| 142 | 0.37 | 1.3 | 3.8× |
| 143 | 0.058 | 0.22 | 4.3× |
| 145 | 0.019 | 0.29 | 14× |
| 147 | 0.0036 | 0.042 | 9.6× |
| 148 | 0.0093 | 0.063 | 6.7× |
| 149 | 0.0003 | 0.0014 | 4.7× |
| 150 | 0.0029 | 0.028 | 8.5× |

TABLE 4-continued

| Example | Cbl-b SPR Kd (uM) | C-cbl SPR Kd (uM) | Fold of selectivity |
|---|---|---|---|
| 152 | 0.0087 | 0.059 | 6.5× |
| 160 | 1.3 | 1.0 | 0.76× |
| 161 | 0.46 | 3.0 | 6.6× |
| 164 | 0.0019 | 0.014 | 7.0× |
| 166 | 0.71 | 3.8 | 5.3× |
| 167 | 0.91 | 5.2 | 5.8× |
| 169 | 0.066 | 0.18 | 2.7× |
| 170 | 0.0049 | 0.015 | 2.8× |
| 171 | 0.80 | 1.7 | 2.1× |
| 172 | 0.067 | 0.31 | 4.7× |
| 173 | 0.0079 | 0.049 | 6.3× |
| 174 | 0.0004 | 0.0011 | 2.8× |
| 175 | 0.00095 | 0.0060 | 6.4× |
| 176 | 0.041 | 0.28 | 6.8× |
| 177 | 0.0099 | 0.099 | 10× |
| 178 | 0.0058 | 0.030 | 4.6× |
| 179 | 0.0046 | 0.058 | 13× |
| 180 | 0.0035 | 0.036 | 10.2× |
| 181 | 0.00037 | 0.00074 | 2.0× |
| 182 | 0.00035 | 0.00085 | 2.7× |
| 183 | 0.0032 | 0.018 | 5.8× |
| 184 | 0.00042 | 0.0025 | 6.3× |
| 185 | 0.0032 | 0.097 | 29× |
| 186 | 0.013 | 0.072 | 5.2× |
| 187 | 0.00095 | 0.015 | 15× |
| 188 | 0.0047 | 0.10 | 22× |
| 189 | 0.00030 | 0.001 | 3.3× |
| 190 | 5.2 | 11 | 2.2× |
| 192 | 0.00030 | 0.0017 | 5.7× |
| 193 | 0.012 | 0.32 | 27× |
| 194 | 0.0019 | 0.016 | 8.3× |
| 195 | 0.015 | 0.11 | 7.6× |
| 196 | 1.8 | 9.9 | 5.5× |
| 197 | 0.012 | 0.11 | 9.2× |
| 198 | 0.029 | 0.12 | 5.1× |
| 200 | 0.008 | 0.019 | 2.4× |
| 201 | 0.003 | 0.011 | 3.6× |
| 202 | 0.0033 | 0.017 | 5.2× |
| 203 | 0.0064 | 0.021 | 3.3× |
| 204 | 0.0037 | 0.015 | 4.1× |
| 205 | 0.046 | 0.13 | 2.8× |
| 206 | 0.012 | 0.030 | 2.4× |
| 207 | 0.0093 | 0.024 | 2.6× |
| 208 | 0.25 | 1.5 | 6.0× |
| 209 | 0.017 | 0.20 | 12× |
| 210 | 0.0015 | 0.0067 | 4.7× |
| 211 | 0.0035 | 0.049 | 14× |
| 212 | 0.11 | 0.53 | 4.8× |
| 213 | 0.16 | 0.30 | 1.8× |
| 214 | 0.00090 | 0.0042 | 4.7× |
| 215 | 0.0017 | 0.0070 | 4.1× |
| 216 | 0.0047 | 0.051 | 11× |
| 217 | 0.0075 | 0.091 | 13× |
| 218 | 0.077 | 0.77 | 10× |
| 219 | 0.0045 | 0.029 | 6.5× |
| 220 | 0.0027 | 0.034 | 13× |
| 221 | 0.0013 | 0.0076 | 5.8× |
| 222 | 0.014 | 0.20 | 13× |
| 223 | 0.0029 | 0.022 | 7.5× |
| 224 | 0.0095 | 0.10 | 10× |
| 225 | 0.0069 | 0.039 | 5.6× |
| 226 | 0.0013 | 0.0042 | 3.2× |
| 227 | 0.0017 | 0.011 | 6.5× |
| 228 | 0.0019 | 0.016 | 8.7× |
| 229 | 0.11 | 0.76 | 7.0× |
| 230 | 0.075 | 0.17 | 2.3× |
| 231 | 0.0015 | 0.0081 | 5.4× |
| 232 | 0.0014 | 0.013 | 9.2× |
| 233 | 0.021 | 0.15 | 7.1× |
| 234 | 0.0074 | 0.076 | 10× |
| 235 | 0.036 | 0.11 | 2.9× |
| 236 | 0.019 | 0.047 | 2.5× |
| 238 | 0.0022 | 0.0058 | 2.6× |
| 239 | 0.0010 | 0.0044 | 4.4× |
| 240 | 0.0023 | 0.027 | 12× |
| 241 | 0.034 | 0.27 | 8.6× |
| 242 | 0.023 | 0.13 | 5.5× |
| 243 | 0.011 | 0.15 | 14× |
| 246 | 0.0042 | 0.0085 | 2.1× |
| 247 | 0.0022 | 0.012 | 5.5× |
| 249 | 0.049 | 0.30 | 6.9× |
| 256 | 0.18 | 2.5 | 14× |
| 257 | 0.00065 | 0.0037 | 5.7× |
| 258 | 0.17 | 2.2 | 13× |
| 259 | 0.00022 | 0.0011 | 5.5× |
| 260 | 0.59 | 2.2 | 8.8× |
| 262 | 0.013 | 0.15 | 12× |
| 263 | 0.0019 | 0.010 | 5.4× |
| 265 | 0.18 | 1.3 | 7.5× |
| 267 | 0.025 | 0.19 | 7.6× |
| 270 | 0.0026 | 0.016 | 5.9× |
| 272 | 0.0014 | 0.011 | 7.6× |
| 273 | 0.00090 | 0.0059 | 6.7× |
| 274 | 0.00010 | 0.00020 | 2.0× |
| 277 | 1.4 | 7.7 | 5.3× |
| 278 | 1.8 | 8.6 | 4.8× |
| 279 | 0.0018 | 0.012 | 6.4× |
| 280 | 0.0011 | 0.0072 | 7.0× |
| 281 | 0.0011 | 0.0070 | 6.3× |
| 282 | 0.23 | 2.3 | 10× |
| 283 | 0.043 | 0.22 | 5.3× |
| 285 | 0.00070 | 0.00080 | 1.1× |
| 288 | 0.00010 | 0.00035 | 3.5× |
| 289 | 0.0046 | 0.037 | 8.5× |
| 291 | 0.062 | 0.13 | 2.1× |
| 292 | 0.0050 | 0.031 | 6.3× |
| 293 | 0.053 | 0.20 | 4.0× |
| 294 | 0.53 | 0.72 | 1.3× |
| 297 | 2.8 | 5.8 | 2.0× |
| 298 | 0.48 | 2.6 | 5.9× |
| 301 | 0.56 | 1.4 | 2.8× |
| 302 | 0.41 | 1.6 | 4.0× |
| 303 | 0.0033 | 0.028 | 8.2× |
| 306 | 0.14 | 0.28 | 2.0× |
| 308 | 0.037 | 0.056 | 1.5× |
| 310 | 0.030 | 0.11 | 3.7× |
| 311 | 0.00010 | 0.00025 | 2.5× |
| 312 | 0.0020 | 0.028 | 14× |
| 313 | 0.00020 | 0.00080 | 4.0× |
| 314 | 0.0051 | 0.028 | 5.5× |
| 316 | 0.17 | 1.3 | 7.5× |
| 317 | 0.10 | 1.5 | 15× |
| 318 | 0.25 | 2.3 | 9.6× |
| 319 | 0.0064 | 0.053 | 8.0× |
| 320 | 0.00040 | 0.0022 | 5.5× |
| 323 | 0.00047 | 0.0052 | 12× |
| 324 | 0.00057 | 0.0057 | 10× |
| 327 | 0.21 | 0.98 | 4.7× |
| 328 | 0.067 | 0.32 | 4.8× |
| 329 | 0.0032 | 0.019 | 5.7× |
| 330 | 0.11 | 1.2 | 11× |
| 331 | 0.015 | 0.12 | 8× |
| 333 | 0.026 | 0.056 | 2.2× |
| 334 | 0.00085 | 0.022 | 26× |
| 335 | 0.0026 | 0.045 | 17× |
| 336 | 0.0032 | 0.013 | 4.1× |
| 337 | 0.0019 | 0.0065 | 3.4× |
| 339 | 0.0017 | 0.0042 | 2.5× |
| 340 | 0.082 | 1.9 | 24× |
| 341 | 0.011 | 0.12 | 11× |
| 342 | 0.00050 | 0.0012 | 2.4× |
| 343 | 0.44 | 2.8 | 6.4× |
| 345 | 1.3 | 4.1 | 3× |
| 346 | 0.035 | 0.20 | 5.4× |
| 347 | 0.003 | 0.033 | 11× |
| 348 | 0.075 | 0.63 | 8.4× |
| 351 | 0.0012 | 0.019 | 16× |
| 352 | 0.034 | 0.27 | 7.6× |
| 356 | 0.019 | 0.21 | 11× |
| 357 | 0.00040 | 0.0022 | 5.5× |
| 359 | 0.00040 | 0.00082 | 2.1× |
| 360 | 0.084 | 0.84 | 10× |
| 361 | 0.004 | 0.084 | 21× |
| 362 | 0.0029 | 0.059 | 21× |

TABLE 4-continued

| Example | Cbl-b SPR Kd (uM) | C-cbl SPR Kd (uM) | Fold of selectivity |
|---|---|---|---|
| 363 | 0.078 | 0.28 | 3.6× |
| 364 | 0.00055 | 0.0024 | 4.4× |
| 365 | 0.00085 | 0.0072 | 6× |
| 369 | 0.21 | 1.5 | 7.2× |
| 370 | 0.0042 | 0.039 | 9× |
| 371 | 0.048 | 0.38 | 7.8× |
| 372 | 0.063 | 0.080 | 13× |
| 373 | 0.0021 | 0.038 | 19× |
| 374 | 0.00095 | 0.010 | 11× |
| 375 | 0.001 | 0.011 | 11× |
| 376 | 0.046 | 0.79 | 16× |
| 377 | 0.24 | 2.6 | 11× |
| 378 | 0.0069 | 0.096 | 14× |
| 379 | 0.00090 | 0.006 | 6.7× |
| 380 | 0.00080 | 0.0040 | 5.0× |
| 381 | 0.0027 | 0.016 | 6.0× |
| 382 | 0.19 | 0.15 | 0.8× |
| 383 | 0.0026 | 0.020 | 7.7× |
| 384 | 0.007 | 0.039 | 5.6× |
| 385 | 0.56 | 0.39 | 0.7× |
| 386 | 0.11 | 0.32 | 2.4× |
| 387 | 0.20 | 1.9 | 9.5× |
| 388 | 0.10 | 0.97 | 9.7× |
| 389 | 0.0029 | 0.013 | 4.4× |
| 390 | 0.0006 | 0.0017 | 3.0× |
| 392 | 0.0075 | 0.038 | 5.1× |
| 393 | 0.15 | 0.54 | 3.5× |
| 394 | 0.00065 | 0.0014 | 2.4× |
| 395 | 0.13 | 0.92 | 7.1× |
| 397 | 0.0013 | 0.0046 | 3.5× |
| 398 | 0.002 | 0.009 | 4.5× |
| 399 | 0.49 | 8.1 | 17× |
| 402 | 0.89 | 2.8 | 3.4× |
| 403 | 2.5 | 2.4 | 1.0× |
| 404 | 0.00085 | 0.0022 | 2.6× |
| 405 | 0.0094 | 0.075 | 7.7× |
| 407 | 0.27 | 4.3 | 16× |
| 408 | 0.44 | 0.77 | 1.8× |
| 409 | 0.062 | 0.090 | 1.4× |
| 412 | 0.0052 | 0.082 | 16× |
| 413 | 0.0003 | 0.0016 | 5.3× |
| 414 | 0.010 | 0.077 | 7.7× |
| 415 | 0.0050 | 0.063 | 13× |
| 416 | 0.00087 | 0.012 | 13× |
| 417 | 1.1 | 8.6 | 7.2× |
| 418 | 0.14 | 1.2 | 8.7× |
| 419 | 0.032 | 0.24 | 8.2× |
| 421 | 0.0017 | 0.024 | 14× |
| 422 | 0.34 | 1.8 | 5.3× |
| 423 | 0.096 | 0.84 | 8.7× |
| 425 | 0.17 | 1.9 | 11× |
| 426 | 0.0066 | 0.0099 | 15× |
| 427 | 0.0026 | 0.037 | 14× |
| 429 | 0.042 | 0.17 | 4.8× |
| 430 | 0.0059 | 0.074 | 14× |
| 431 | 0.0004 | 0.0013 | 3.1× |
| 432 | 0.0004 | 0.0015 | 3.6× |
| 433 | 0.0085 | 0.086 | 10× |
| 434 | 0.19 | 2.5 | 13× |
| 436 | 0.60 | 3.5 | 5.3× |
| 442 | 0.18 | 3.3 | 18× |
| 444 | 0.0004 | 0.0007 | 1.8× |
| 445 | 0.0048 | 0.023 | 4.7× |
| 446 | 0.0013 | 0.0066 | 5.1× |
| 447 | 0.0003 | 0.0016 | 5.3× |
| 448 | 0.42 | 2.5 | 5.8× |
| 449 | 0.12 | 0.92 | 8.0× |
| 450 | 0.0026 | 0.019 | 7.2× |
| 451 | 0.00025 | 0.0015 | 6.0× |
| 452 | 0.0007 | 0.0024 | 3.3× |
| 453 | 0.0017 | 0.0048 | 2.8× |
| 454 | 0.00085 | 0.0092 | 11× |
| 455 | 0.0014 | 0.015 | 11× |
| 456 | 0.23 | 4.1 | 18× |
| 458 | 0.0057 | 0.057 | 10× |
| 459 | 0.0005 | 0.0032 | 6.1× |
| 461 | 0.19 | 3.4 | 18× |
| 462 | 0.0020 | 0.021 | 10× |
| 463 | 0.0032 | 0.017 | 5.2× |
| 464 | 0.0011 | 0.0036 | 3.3× |
| 466 | 0.0025 | 0.0091 | 3.6× |
| 467 | 0.016 | 0.12 | 7.6× |
| 468 | 0.0016 | 0.012 | 7× |
| 470 | 0.00035 | 0.0015 | 2.9× |
| 471 | 0.0083 | 0.091 | 11× |
| 473 | 0.0076 | 0.085 | 11× |
| 474 | 0.0048 | 0.068 | 14× |
| 475 | 0.0036 | 0.045 | 13× |
| 476 | 0.095 | 1.1 | 11× |
| 477 | 0.011 | 0.13 | 11× |
| 478 | 0.12 | 1.1 | 8.7× |
| 480 | 0.045 | 0.49 | 11× |
| 481 | 0.0015 | 0.027 | 18× |
| 482 | 0.0019 | 0.030 | 15× |
| 483 | 0.0046 | 0.084 | 18× |
| 484 | 0.013 | 0.20 | 13× |
| 485 | 0.0074 | 0.11 | 14× |
| 486 | 0.0082 | 0.098 | 11× |
| 487 | 0.0049 | 0.21 | 41× |
| 488 | 0.0010 | 0.013 | 13× |
| 489 | 0.0062 | 0.048 | 7.8× |
| 490 | 0.032 | 0.48 | 14× |
| 491 | 0.0029 | 0.048 | 17× |
| 492 | 0.012 | 0.18 | 15× |
| 493 | 0.018 | 0.14 | 7.8× |
| 494 | 0.0018 | 0.020 | 11× |
| 495 | 0.0085 | 0.11 | 12× |
| 496 | 0.0061 | 0.073 | 12× |
| 497 | 0.0019 | 0.0266 | 14× |
| 498 | 0.0008 | 0.013 | 16× |
| 499 | 0.0037 | 0.079 | 19× |
| 500 | 0.010 | 0.12 | 12× |
| 501 | 0.0046 | 0.081 | 16× |
| 502 | 0.0050 | 0.069 | 14× |
| 503 | 0.0020 | 0.044 | 22× |
| 504 | 0.0057 | 0.090 | 16× |
| 505 | 0.0047 | 0.064 | 12× |
| 506 | 0.055 | 0.45 | 8.1× |
| 507 | 0.0035 | 0.052 | 15× |
| 508 | 0.0017 | 0.024 | 14× |
| 509 | 0.006 | 0.075 | 13× |
| 510 | 0.0034 | 0.060 | 18× |
| 511 | 0.0050 | 0.065 | 13× |

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:

1. A compound of formula (I),

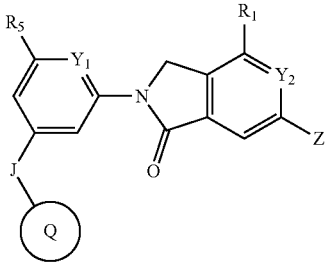

wherein:

Q is a 5-membered heteroaryl, optionally substituted by one or more alkyl, cycloalkyl, hydroxyalkyl, or haloalkyl groups;

$Y_1$ and $Y_2$ are independently CH, CF, or N;

J is $C(R_3)(R_4)$, wherein:

$R_3$, $R_4$ are independently selected from: H, halogen, CN, OH, amino, and $LR_{2a}$, wherein L is O, $NR_0$, $CHR_0$, C(=O), or a bond, wherein Ro is H or alkyl, and $R_{2a}$ is selected from alkyl, alkenyl, alkynyl, alkylcarboxy, cyanoalkyl, aminoalkyl, hydroxyalkyl, haloalkyl, and a 3-14 membered ring moiety, wherein at least one of $R_3$ and $R_4$ is not H; or $R_3$ and $R_4$ together with the carbon atom to which they are both bonded form a 3-14 membered ring moiety, wherein, if either of $R_3$ or $R_4$ is alkyl, haloalkyl, or hydroxyalkyl, $R_3$ or $R_4$ is optionally substituted by a 3-14 membered ring moiety;

and wherein, if either of $R_3$ or $R_4$ is, or is substituted by, a 3-14 membered ring moiety, or $R_3$ and $R_4$ together are a 3-14 membered ring moiety, the ring moiety is selected from:

a monocyclic ring, a fused bicyclic ring system, a bridged bicyclic ring system, and a spirocyclic ring system, and wherein the ring moiety:

is optionally substituted by one or more groups independently selected from halogen, CN, amino, oxo, carbenyl, OH, or $L_0R_{2b}$, wherein $L_0$ is $CH_2$, C(=O), NH, O, S, S(=O), S(=O)$_2$, or a bond, and $R_{2b}$ is alkyl, cycloalkyl, heterocyclyl, alkenvyl, alkoxy, hydroxyalkyl, haloalkyl, cyanoalkyl, and aminoalkyl;

is saturated, or contains 1 or 2 in-ring double bonds, or is aryl;

is carbocyclic, heterocyclic, or heteroaryl; and when the ring moiety is heterocyclic or heteroaryl, it comprises 1, 2 or 3 ring atoms that are independently selected from O, N, and S;

$R_5$ is selected from: H, halo, or $L_1$-$R_{10}$, wherein $L_1$ is —N($R_{11}$)—, —C(=O) N ($R_{11}$), O, S, carbonyl, or a bond, and wherein Rio and $R_{11}$ are independently H, alkyl, cycloalkyl, alkenyl, alkynyl, aryl, heteroaryl, or heterocyclyl, and when either of Rio and $R_{11}$ are not H, $R_{10}$ or $R_{11}$ is optionally substituted by one or more groups selected from: halo, CN, amino, oxo, OH, alkoxy, alkyl, perhaloalkyl, haloalkyl, heterocyclyl, aryl, and heteroaryl, or $R_{10}$ and $R_{11}$ together form a cycloalkyl or heterocyclyl ring, a spirocyclic ring, a fused bicyclic ring, or a bridged bicyclic ring, wherein the ring formed by $R_{10}$ and $R_{11}$ together is optionally substituted by one or more groups selected from halo, CN, amino, oxo, carbenyl, OH, alkoxy, alkyl, perhaloalkyl, or haloalkyl;

$R_1$ is H, halo, haloalkyl, or cycloalkyl; and

Z is —$L_{2a}NR_7R_8$, wherein:

$L_{2a}$ is —C(H) $R_{6a}$;

$R_{6a}$=H, alkyl, cycloalkyl, haloalkyl or hydroxyalkyl;

$R_7$ is H; and $R_8$ is $L_3R_9$, wherein:

$L_3$=—(C(H)$R_{10}$)$_n$—, —(C(H)$R_{10}$)$_n$O—, or a bond, wherein n=1 or 2;

$R_{10}$ is selected from H and alkyl;

$R_9$ is selected from alkyl, haloalkyl, perhaloalkyl, hydroxyalkyl, aminoalkyl, cycloalkyl, hydroxyalkyl, alkoxyalkyl, alkyl alkanoate, heterocyclyl, spirocyclyl ring system, fused ring system, bicyclyl ring system, a 5 or 6 member heteroaromatic ring, or a 3-10 member fused heteroaromatic ring system, and a bridged bicyclyl ring;

and wherein, $R_8$ is cycloalkyl, heterocyclyl, spirocyclyl, a fused bicyclyl, a bridged bicyclic ring, a 5 or 6 member heteroaromatic ring, or a 3-10 member fused heteroaromatic ring system, said ring or ring system is optionally substituted with one or more groups selected from: sulfonyl, halo, hydroxyl, alkoxy, alkyl, cycloalkyl, alkoxyalkyl, carbenyl, alkenyl, hydroxyalkyl, cyano, carboxyalkyl, or haloalkyl;

or an enantiomer, diastereomer or a pharmaceutically acceptable salt or solvate thereof.

2. The compound of claim 1 wherein $R_5$ is H.

3. The compound of claim 1, wherein $R_5$ is selected from: alkyl, alkoxy, alkylamino, cycloalkylamino, cycloalkyl, and cycloalkyloxy, any of which is optionally substituted by one or more groups independently selected from: halo, alkyl, cyano, hydroxyl, amino, and alkoxy.

4. The compound of claim 1, wherein $Y_1$ and $Y_2$ are CH.

5. The compound of claim 1, wherein $Y_1$ is N.

6. The compound of claim 1, wherein $R_1$ is CF3.

7. The compound of claim 1, wherein Q is 2-methyl triazol-1-yl or imidazolyl.

8. The compound of claim 1, wherein Q is 2-methyl triazol-1-yl.

9. The compound of claim 1, wherein Z is —C(H) $R_{6a}NR_7R_8$, and:

$R_{6a}$ is H or methyl.

10. The compound of claim 1, wherein Z is —C(H) $R_{6a}NR_7R_8$, and wherein:

$R_{6a}$ is H or methyl;

$R_7$ is H; and $R_8$ is cyclobutyl, optionally substituted with alkyl.

11. The compound of claim 1, wherein $R_3$ is H or OH, and $R_4$ is selected from cyclobut-1-amino, 3-oxetanyl, cyclopropyloxy, cyclobutyloxy, and methoxy, and wherein $R_4$ is optionally substituted by one or more groups selected from: halo, alkyl, hydroxyl, and alkoxyl.

12. The compound of claim 1, wherein $R_3$ and $R_4$ together with the carbon atom to which they are both bonded form a 3-8 membered ring moiety selected from: cyclobutyl, oxetanyl, cyclobutenyl, spiro [3.3] hept-2-yl, and 2-oxaspiro [3.3] hept-6-yl, wherein the ring moiety is optionally substituted by one or more groups independently selected from: halo, carbenyl, oxo, hydroxyl, cyano, alkyl, and alkoxy.

13. The compound of claim 1, wherein $R_3$ and $R_4$ together with the carbon atom to which they are both bonded form an oxetan-3-yl ring or a cyclobutyl ring.

14. The compound of claim 1, wherein R₃ and R₄ together with the carbon atom to which they are both bonded form a cycloalkyl ring substituted by one or more instances of methyl, ethyl, methoxy, acetyl, chloro, fluoro, fluromethyl, difluoromethoxy, trifluoromethoxy, methoxy-d3, cyanomethyl, or cyano.

15. A compound selected from the group consisting of:
(S)-2-(3-(cyclobutyl (hydroxy) (4-methyl-4H-1,2,4-triazol-3-yl)methyl)phenyl)-6-(((1-methylcyclobutyl) amino)methyl)-4-(trifluoromethyl) isoindolin-1-one (Compound 2);
2-(6-(cyclopentylamino)-4-((1r,3r)-3-methoxy-1-(4-methyl-4H-1,2,4-triazol-3-yl)cyclobutyl) pyridin-2-yl)-6-(((1-methylcyclobutyl)amino)methyl)-4-(trifluoromethyl) isoindolin-1-one (Compound 9);
2-(3-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 22);
2-(3-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 23);
(1r,3r)-3-(4-methyl-4H-1,2,4-triazol-3-yl)-3-(3-(6-(((1-methylcyclobutyl)amino)methyl)-1-oxo-4-(trifluoromethyl) isoindolin-2-yl)phenyl)cyclobutanecarbonitrile (Compound 24);
2-(3-((1r,3r)-3-fluoro-1-(4-methyl-4H-1,2,4-triazol-3-yl) cyclobutyl)phenyl)-6-(((1-methylcyclobutyl)amino) methyl)-4-(trifluoromethyl) isoindolin-1-one (Compound 36);
(S)-6-((2-isopropyl-4-methylpiperazin-1-yl)methyl)-2-(3-(6-(4-methyl-4H-1,2,4-triazol-3-yl)-2-oxaspiro [3.3] heptan-6-yl)phenyl)-4-(trifluoromethyl) isoindolin-1-one (Compound 41);
2-(6-(cyclopentylamino)-4-((1r,3r)-3-methyl-1-(4-methyl-4H-1,2,4-triazol-3-yl)cyclobutyl) pyridin-2-yl)-6-(((1-methylcyclobutyl)amino)methyl)-4-(trifluoromethyl) isoindolin-1-one (Compound 52);
2-(6-(cyclopentyloxy)-4-((1s,3s)-3-methyl-1-(4-methyl-4H-1,2,4-triazol-3-yl)cyclobutyl) pyridin-2-yl)-6-(((1-methylcyclobutyl)amino)methyl)-4-(trifluoromethyl) isoindolin-1-one (Compound 54);
2-(3-(6-(4-methyl-4H-1,2,4-triazol-3-yl)-2-oxaspiro [3.3] heptan-6-yl)phenyl)-6-(((1-methylcyclobutyl)amino) methyl)-4-(trifluoromethyl) isoindolin-1-one (Compound 65);
2-(6-(cyclopentylamino)-4-((1R,3R)-3-methoxy-1-(4-methyl-4H-1,2,4-triazol-3-yl)cyclobutyl) pyridin-2-yl)-6-(((1-methylcyclobutyl)amino)methyl)-4-(trifluoromethyl) isoindolin-1-one (Compound 70);
2-(3-(2-(4-methyl-4H-1,2,4-triazol-3-yl)-6-oxospiro [3.3] heptan-2-yl)phenyl)-6-(((1-methylcyclobutyl)amino) methyl)-4-(trifluoromethyl) isoindolin-1-one (Compound 92);
2-(3-(6,6-difluoro-2-(4-methyl-4H-1,2,4-triazol-3-yl) spiro [3.3] heptan-2-yl)phenyl)-6-(((1-methylcyclobutyl)amino)methyl)-4-(trifluoromethyl) isoindolin-1-one (Compound 94);
2-(3-((1s,3s)-3-fluoro-1-(4-methyl-4H-1,2,4-triazol-3-yl) cyclobutyl)phenyl)-6-(((1-methylcyclobutyl)amino) methyl)-4-(trifluoromethyl) isoindolin-1-one (Compound 95);
2-(3-((1r,3r)-3-(fluoromethyl)-1-(4-methyl-4H-1,2,4-triazol-3-yl)cyclobutyl)phenyl)-6-(((1-methylcyclobutyl) amino)methyl)-4-(trifluoromethyl) isoindolin-1-one (Compound 101);
2-(3-((1s,3s)-3-(fluoromethyl)-1-(4-methyl-4H-1,2,4-triazol-3-yl)cyclobutyl)phenyl)-6-(((1-methylcyclobutyl) amino)methyl)-4-(trifluoromethyl) isoindolin-1-one (Compound 102);
(S)-2-(3-(3,3-difluoro-1-(4-methyl-4H-1,2,4-triazol-3-yl) cyclopentyl)phenyl)-6-(((1-methylcyclobutyl)amino) methyl)-4-(trifluoromethyl) isoindolin-1-one (Compound 106);
2-(3-((4r,6r)-6-(4-methyl-4H-1,2,4-triazol-3-yl)-1-oxaspiro [3.3] heptan-6-yl)phenyl)-6-(((1-methylcyclobutyl)amino)methyl)-4-(trifluoromethyl) isoindolin-1-one (Compound 108);
4-(difluoromethyl)-2-(3-((1r,3r)-3-methoxy-1-(4-methyl-4H-1,2,4-triazol-3-yl)cyclobutyl)phenyl)-6-(((1-methylcyclobutyl)amino)methyl) isoindolin-1-one (Compound 117);
2-(3-((R)-((1r,3R)-3-fluorocyclobutyl) (4-methyl-4H-1,2,4-triazol-3-yl)methyl)phenyl)-6-(((1-methylcyclobutyl)amino)methyl)-4-(trifluoromethyl) isoindolin-1-one (Compound 129);
2-(3-((R)-((1s,3S)-3-fluorocyclobutyl) (4-methyl-4H-1,2,4-triazol-3-yl)methyl)phenyl)-6-(((1-methylcyclobutyl)amino)methyl)-4-(trifluoromethyl) isoindolin-1-one (Compound 130);
2-(3-((1r,3r)-3-chloro-1-(4-methyl-4H-1,2,4-triazol-3-yl) cyclobutyl)phenyl)-6-(((1-methylcyclobutyl)amino) methyl)-4-(trifluoromethyl) isoindolin-1-one (Compound 137);
2-(3-((1s,3s)-3-chloro-1-(4-methyl-4H-1,2,4-triazol-3-yl) cyclobutyl)phenyl)-6-(((1-methylcyclobutyl)amino) methyl)-4-(trifluoromethyl) isoindolin-1-one (Compound 138);
(R)-2-(3-(fluoro (4-methyl-4H-1,2,4-triazol-3-yl) (oxetan-3-yl)methyl)phenyl)-6-(((1-methylcyclobutyl) amino)methyl)-4-(trifluoro-methyl) isoindolin-1-one (Compound 150);
(R)-2-(3-((4-methyl-4H-1,2,4-triazol-3-yl) (oxetan-3-yl) methyl)phenyl)-6-(((1-methylcyclobutyl)amino) methyl)-4-(trifluoromethyl) isoindolin-1-one (Compound 164);
(R)-2-(3-(1-(4-methyl-4H-1,2,4-triazol-3-yl)ethyl)phenyl)-6-(((1-methylcyclobutyl)amino)methyl)-4-(trifluoromethyl) isoindolin-1-one (Compound 170);
2-(3-((1r,3S)-3-methoxy-1-(4-methyl-4H-1,2,4-triazol-3-yl)cyclobutyl)phenyl)-6-((S)-1-((1-methylcyclobutyl) amino)ethyl)-4-(trifluoromethyl) isoindolin-1-one (Compound 185);
(R)-4-chloro-2-(3-((4-methyl-4H-1,2,4-triazol-3-yl) (oxetan-3-yl)methyl)phenyl)-6-(((1-methylcyclobutyl) amino)methyl) isoindolin-1-one (Compound 270);
4-(difluoromethyl)-2-(3-((1r,3r)-3-fluoro-1-(4-methyl-4H-1,2,4-triazol-3-yl)cyclobutyl)phenyl)-6-(((1-methylcyclobutyl)amino)methyl) isoindolin-1-one (Compound 272);
4-chloro-2-(3-((1r,3r)-3-fluoro-1-(4-methyl-4H-1,2,4-triazol-3-yl)cyclobutyl)phenyl)-6-(((1-methylcyclobutyl) amino)methyl) isoindolin-1-one (Compound 273);
4-chloro-2-(3-((1r,3S)-3-fluoro-1-(4-methyl-4H-1,2,4-triazol-3-yl)cyclobutyl)phenyl)-6-((S)-1-((1-methylcyclobutyl)amino)ethyl) isoindolin-1-one (Compound 312);
4-chloro-2-(3-((S)-((1r,3S)-3-fluorocyclobutyl) (4-methyl-4H-1,2,4-triazol-3-yl)methyl)phenyl)-6-(((1-methylcyclobutyl)amino)methyl) isoindolin-1-one (Compound 320);

2-(3-((1r,3r)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 334);

2-(3-((1s,3s)-3-(difluoromethoxy)-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 335);

(R)-2-(3-(cyclopropyl (4-methyl-4H-1,2,4-triazol-3-yl)methyl)phenyl)-6-(((1-methylcyclobutyl)amino)methyl)-4-(trifluoromethyl) isoindolin-1-one (Compound 342);

2-(3-((1r,3r)-3-acetyl-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 347);

2-(3-((1r,3r)-1-(4-methyl-4H-1,2,4-triazol-3-yl)-3-(trifluoromethoxy)cyclobutyl)phenyl)-6-(((1-methylcyclobutyl)amino)methyl)-4-(trifluoromethyl) isoindolin-1-one (Compound 351;

(S)-4-chloro-2-(3-(1-(4-methyl-4H-1,2,4-triazol-3-yl)propyl)phenyl)-6-(((1-methylcyclobutyl)amino)methyl) isoindolin-1-one (Compound 359);

6-((S)-1-amino-2,2-dimethylpropyl)-2-(3-((1r,3S)-3-methoxy-1-(4-methyl-4H-1,2,4-triazol-3-yl)cyclobutyl)phenyl)-4-(trifluoromethyl) isoindolin-1-one (Compound 361);

2-((1R,3s)-3-((S)-(4-methyl-4H-1,2,4-triazol-3-yl) (3-(6-(((1-methylcyclobutyl)amino)methyl)-1-oxo-4-(trifluoromethyl) isoindolin-2-yl)phenyl)methyl)cyclobutyl) acetonitrile (Compound 362);

2-((1R,3r)-3-((R)-(4-methyl-4H-1,2,4-triazol-3-yl) (3-(6-(((1-methylcyclobutyl)amino)methyl)-1-oxo-4-(trifluoromethyl) isoindolin-2-yl)phenyl)methyl)cyclobutyl) acetonitrile (Compound 364);

2-((1S,3s)-3-((R)-(4-methyl-4H-1,2,4-triazol-3-yl) (3-(6-(((1-methylcyclobutyl)amino)methyl)-1-oxo-4-(trifluoromethyl) isoindolin-2-yl)phenyl)methyl)cyclobutyl) acetonitrile (Compound 365);

2-(3-((1S,3S)-3-(methoxy-d3)-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 372);

2-(3-((1R,3R)-3-(methoxy-d3)-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 373);

4-chloro-2-(3-((1r,3s)-3-ethyl-1-(4-methyl-4H-1,2,4-triazol-3-yl)cyclobutyl)phenyl)-6-(((1-methylcyclobutyl)amino)methyl) isoindolin-1-one (Compound 374);

4-chloro-2-(3-((1s,3r)-3-ethyl-1-(4-methyl-4H-1,2,4-triazol-3-yl)cyclobutyl)phenyl)-6-(((1-methylcyclobutyl)amino)methyl) isoindolin-1-one (Compound 375);

(R)-2-(3-((3-fluorooxetan-3-yl) (4-methyl-4H-1,2,4-triazol-3-yl)methyl)phenyl)-6-(((1-methylcyclobutyl)amino)methyl)-4-(trifluoromethyl) isoindolin-1-one (Compound 380);

(R)-2-(3-(fluoro (3-fluorooxetan-3-yl) (4-methyl-4H-1,2,4-triazol-3-yl)methyl)phenyl)-6-(((1-methylcyclobutyl)amino)methyl)-4-(trifluoromethyl) isoindolin-1-one (Compound 404);

6-(((cyclobutylmethyl)amino)methyl)-2-(3-((1r3r)-3-methoxy-1-(4-methyl-4H-1,2,4-triazol-3-yl)cyclobutyl)phenyl)-4-(trifluoromethyl) isoindolin-1-one (Compound 416);

6-((isobutylamino)methyl)-2-(3-((1r 3r)-3-methoxy-1-(4-methyl-4H-1,2,4-triazol-3-yl)cyclobutyl)phenyl)-4-(trifluoromethyl)isoindolin-1-one(Compound 421);

6-(((1,1-difluorospiro[2.3]hexan-5-yl)amino)methyl)-2-(3-((1r 3r)-3-methoxy-1-(4-methyl-4H-1,2,4-triazol-3-yl)cyclobutyl)phenyl)-4-(trifluoromethyl) isoindolin-1-one
(Compound 426);

6-(((6,6-difluorobicyclo[3.1.0] hexan-3-yl)amino)methyl)-2-(3-((1r3r)-3-methoxy-1-(4-methyl-4H-1,2,4-triazol-3-yl)cyclobutyl)phenyl)-4-(trifluoromethyl) isoindolin-1-one
(Compound 427);

2-(3-((1s,3s)-3-chloro-1-(4-methyl-4H-1,2,4-triazol-3-yl)cyclobutyl)phenyl)-4-(difluoromethyl)-6-(((1-methylcyclobutyl)amino)methyl) isoindolin-1-one (Compound 446);

2-(3-((1r,3r)-3-chloro-1-(4-methyl-4H-1,2,4-triazol-3-yl)cyclobutyl)phenyl)-4-(difluoromethyl)-6-(((1-methylcyclobutyl)amino)methyl) isoindolin-1-one (Compound 447);

4-chloro-2-(3-((1r,3r)-3-chloro-1-(4-methyl-4H-1,2,4-triazol-3-yl)cyclobutyl)phenyl)-6-(((1-methylcyclobutyl)amino)methyl) isoindolin-1-one (Compound 451);

2-(3-((1r,3s)-3-ethyl-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 454);

2-(3-((1s,3r)-3-ethyl-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 455); and 4-(difluoromethyl)-2-(3-((R)-((1s,3S)-3-fluorocyclobutyl) (4-methyl-4H-1,2,4-triazol-3-yl)methyl)phenyl)-6-(((1-methylcyclobutyl)amino)methyl) isoindolin-1-one (Compound 459);

or a pharmaceutically acceptable salt thereof.

16. A method of treating a cancer, comprising administering to a subject in need thereof, a compound according to claim 1.

17. The compound of claim 1, selected from the group consisting of:

2-(3-((1s,3s)-3-methoxy-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 22);

2-(3-((1r,3r)-3-methoxy-1-(4-methyl-4H-1,2,4-triazol-3-yl)cyclobutyl)phenyl)-6-(((1-methylcyclobutyl)amino)methyl)-4-(trifluoromethyl) isoindolin-1-one (Compound 23); and (R)-2-(3-((5-methyl-1H-1,2,3-triazol-1-yl) (oxetan-3-yl)methyl)phenyl)-6-(((1-methylcyclobutyl)amino)methyl)-4-(trifluoromethyl) isoindolin-1-one (Compound 135);

or a pharmaceutically acceptable salt thereof.

18. A pharmaceutical composition comprising a compound of claim 1, or a pharmaceutically acceptable salt thereof, and a pharmaceutically acceptable carrier or excipient.

19. A pharmaceutical composition comprising a compound of claim 15, or a pharmaceutically acceptable salt thereof, and a pharmaceutically acceptable carrier or excipient.

20. A pharmaceutical composition comprising a compound of claim 17, or a pharmaceutically acceptable salt thereof, and a pharmaceutically acceptable carrier or excipient.

* * * * *